(12) United States Patent
Bair et al.

(10) Patent No.: US 10,272,072 B2
(45) Date of Patent: Apr. 30, 2019

(54) COMPOUNDS AND COMPOSITIONS FOR THE INHIBITION OF NAMPT

(71) Applicants: Forma TM, LLC, Watertown, MA (US); Genentech, Inc., South San Francisco, CA (US)

(72) Inventors: Kenneth W. Bair, Wellesley, MA (US); Timm R. Baumeister, Watertown, MA (US); Alexandre Joseph Buckmelter, Acton, MA (US); Karl H. Clodfelter, Watertown, MA (US); Peter Dragovich, South San Francisco, CA (US); Francis Gosselin, South San Francisco, CA (US); Bingsong Han, North Haven, CT (US); Jian Lin, Acton, MA (US); Dominic J. Reynolds, Watertown, MA (US); Bruce Roth, South San Francisco, CA (US); Chase C. Smith, Rutland, MA (US); Zhongguo Wang, Lexington, MA (US); Po-Wai Yuen, Beijing (CN); Xiaozhang Zheng, Lexington, MA (US)

(73) Assignees: Forma TM, LLC, Watertown, MA (US); Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/352,184

(22) Filed: Nov. 15, 2016

(65) Prior Publication Data
US 2017/0368039 A1 Dec. 28, 2017

Related U.S. Application Data

(63) Continuation of application No. 13/820,497, filed as application No. PCT/US2011/050321 on Sep. 2, 2011, now abandoned.

(60) Provisional application No. 61/379,789, filed on Sep. 3, 2010, provisional application No. 61/379,796, filed on Sep. 3, 2010, provisional application No. 61/386,023, filed on Sep. 24, 2010, provisional application No. 61/386,028, filed on Sep. 24, 2010,
(Continued)

(51) Int. Cl.
| | | |
|---|---|---|
| A61K 31/4353 | (2006.01) |
| A61K 31/497 | (2006.01) |
| A61K 31/5377 | (2006.01) |
| A61K 31/4355 | (2006.01) |
| C07D 471/04 | (2006.01) |
| C07D 491/04 | (2006.01) |
| C07D 495/04 | (2006.01) |
| A61K 31/4365 | (2006.01) |
| A61K 31/437 | (2006.01) |
| A61K 31/496 | (2006.01) |
| A61K 31/519 | (2006.01) |
| A61K 31/55 | (2006.01) |
| A61K 45/06 | (2006.01) |
| C07D 487/04 | (2006.01) |
| C07D 491/048 | (2006.01) |

(52) U.S. Cl.
CPC ........ *A61K 31/4355* (2013.01); *A61K 31/437* (2013.01); *A61K 31/4365* (2013.01); *A61K 31/496* (2013.01); *A61K 31/497* (2013.01); *A61K 31/519* (2013.01); *A61K 31/5377* (2013.01); *A61K 31/55* (2013.01); *A61K 45/06* (2013.01); *C07D 471/04* (2013.01); *C07D 487/04* (2013.01); *C07D 491/04* (2013.01); *C07D 491/048* (2013.01); *C07D 495/04* (2013.01)

(58) Field of Classification Search
CPC .............. A61K 31/4353; A61K 31/497; A61K 31/5377; C07D 491/04; C07D 487/04; C07D 471/04
USPC .......................................................... 546/121
See application file for complete search history.

(56) References Cited

U.S. PATENT DOCUMENTS 4,031,068 A    6/1977    Cantor
5,206,259 A *    4/1993    Shuto ..................... A01N 43/56
                                                                                514/236.5

(Continued)

FOREIGN PATENT DOCUMENTS

CN            1057258 A      12/1991
EP            1193256 A1      4/2002
(Continued)

OTHER PUBLICATIONS

Beauparlant, P. et al., Preclinical development of the nicotinamide phosphoribosyl transferase inhibitor prodrug GMX1777, Anti-Cancer Drugs, 20(5):346-354 (2009).
(Continued)

*Primary Examiner* — Niloofar Rahmani
(74) *Attorney, Agent, or Firm* — Choate, Hall & Stewart LLP; John P. Rearick; Michael A. Shinall

(57) ABSTRACT

The present invention relates to compounds and compositions for the inhibition of NAMPT, their synthesis, applications and antidotes. An illustrative compound of the invention is shown below:

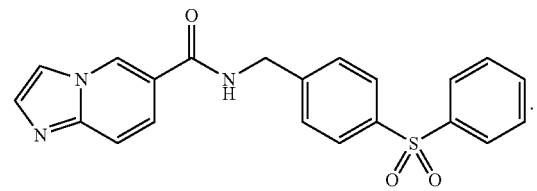

19 Claims, No Drawings

Related U.S. Application Data provisional application No. 61/475,813, filed on Apr. 15, 2011, provisional application No. 61/483,242, filed on May 6, 2011.

(56) References Cited

U.S. PATENT DOCUMENTS

| | | | |
|---|---|---|---|
| 5,264,448 | A | 11/1993 | Shuto et al. |
| 6,716,844 | B2 | 4/2004 | Freskos et al. |
| 7,329,755 | B2 | 2/2008 | Dai et al. |
| 7,417,058 | B2 | 8/2008 | Halazy et al. |
| 7,491,827 | B2 | 2/2009 | Dai et al. |
| 7,872,039 | B2 | 1/2011 | Dorsch et al. |
| 7,879,873 | B2 * | 2/2011 | Cook ............... C07D 471/04 514/303 |
| 8,017,628 | B2 | 9/2011 | Arkinstall et al. |
| 8,450,348 | B2 | 5/2013 | Murthi et al. |
| 8,933,024 | B2 | 1/2015 | Petry et al. |
| 9,169,209 | B2 | 10/2015 | Bair et al. |
| 9,458,172 | B2 | 10/2016 | Bair et al. |
| 9,555,039 | B2 | 1/2017 | Bair et al. |
| 9,676,721 | B2 | 6/2017 | Bair et al. |
| 9,822,129 | B2 | 11/2017 | Bair et al. |
| 2004/0053917 | A1 | 3/2004 | Halazy et al. |
| 2004/0127538 | A1 | 7/2004 | Oinuma et al. |
| 2004/0132785 | A1 | 7/2004 | Turpin et al. |
| 2004/0138255 | A1 | 7/2004 | Huang et al. |
| 2004/0209948 | A1 | 10/2004 | Guan et al. |
| 2004/0224978 | A1 | 11/2004 | Dai et al. |
| 2005/0085518 | A1 | 4/2005 | Dai et al. |
| 2008/0153810 | A1 | 6/2008 | Ronsheim et al. |
| 2008/0200523 | A1 | 8/2008 | Murthi et al. |
| 2008/0255222 | A1 | 10/2008 | Halazy et al. |
| 2009/0005426 | A1 | 1/2009 | Arkinstall et al. |
| 2009/0054494 | A1 | 2/2009 | Keil et al. |
| 2009/0325923 | A1 | 12/2009 | Leo et al. |
| 2013/0273034 | A1 | 10/2013 | Bair et al. |
| 2013/0295051 | A1 | 11/2013 | Bair et al. |
| 2014/0248240 | A1 | 9/2014 | Bair et al. |
| 2014/0275057 | A1 | 9/2014 | Bair et al. |
| 2014/0294805 | A1 | 10/2014 | Bair et al. |
| 2015/0104384 | A1 * | 4/2015 | Bair ............... C07D 471/04 424/1.53 |
| 2015/0175621 | A1 | 6/2015 | Bair et al. |
| 2016/0002266 | A1 | 1/2016 | Bair et al. |
| 2016/0355514 | A1 | 12/2016 | Bair et al. |
| 2017/0137441 | A1 | 5/2017 | Bair et al. |
| 2017/0216262 | A1 | 8/2017 | Bair et al. |

FOREIGN PATENT DOCUMENTS

| | | |
|---|---|---|
| EP | 1343434 A1 | 9/2003 |
| EP | 1380576 A1 | 1/2004 |
| EP | 1657238 A1 | 5/2006 |
| JP | 2003527395 A | 9/2003 |
| JP | 2008502610 A | 1/2008 |
| JP | 2008524294 A | 7/2008 |
| JP | 2010513493 A | 4/2010 |
| WO | WO-91/17983 A1 | 11/1991 |
| WO | WO-97/48397 A1 | 12/1997 |
| WO | WO-97/48695 A1 | 12/1997 |
| WO | WO-97/48696 A1 | 12/1997 |
| WO | WO-99/31060 A2 | 6/1999 |
| WO | WO-99/31063 A1 | 6/1999 |
| WO | WO-99/31064 A1 | 6/1999 |
| WO | WO-99/31087 A1 | 6/1999 |
| WO | WO-00/50399 A1 | 8/2000 |
| WO | WO-01/68652 A1 | 9/2001 |
| WO | WO-03/80054 A1 | 10/2003 |
| WO | WO-2004/058709 A1 | 7/2004 |
| WO | WO-2005/123688 A2 | 12/2005 |
| WO | WO-2006/083673 A2 | 8/2006 |
| WO | WO-2008/079277 A1 | 7/2008 |
| WO | WO-2008/082487 A2 | 7/2008 |
| WO | WO-2009/134666 A1 | 11/2009 |
| WO | WO-2009/136175 A1 | 11/2009 |
| WO | WO-2010/036632 A1 | 4/2010 |
| WO | WO-2010/096722 A1 | 8/2010 |
| WO | WO-2010/097410 A1 | 9/2010 |
| WO | WO-2010/109115 A1 | 9/2010 |
| WO | WO-2010/109122 A1 | 9/2010 |
| WO | WO-2011/157827 A1 | 12/2011 |
| WO | WO-2012/031197 A1 | 3/2012 |
| WO | WO-2012/061926 A1 | 5/2012 |
| WO | WO-2013/126856 A1 | 8/2013 |
| WO | WO-2013/127268 A1 | 9/2013 |
| WO | WO-2013/130935 A1 | 9/2013 |
| WO | WO-2013/130943 A1 | 9/2013 |

OTHER PUBLICATIONS

Bruzzone, S. et al., Catastrophic NAD+ depletion in activated T lymphocytes through Nampt inhibition reduces demyelination and disability in EAE, PLoS ONE, 4(11):e7897 (2009).

Cook, B.N. et al., CA 152:429699, Preparation of arylazaindolecarboxamides as chemotactic cytokine receptor 1 (CCR1) antagonists, Boehringer Ingelheim International GMBH, Germany, 5 pages (2010).

Crowley, C.L. et al., The NAD+ precursors, nicotinic acid and nicotinamide protect cells against apoptosis induced by multiple stress inducer, deoxycholate, Cell Death and Differentiation, 7:314-326 (2000).

Database Zregistry [Online], Chemical abstracts services, Columbus, Ohio, US; Aug. 18, 2011, XP002667032, retrieved from STN Database accession No. 1319707-58-8 (RN) abstract & Aug. 16, 2011, Chemical Library, FCH group.

Database Zregistry [Online], Chemical abstracts services, Columbus, Ohio, US; May 2, 2011, XP002667031, retrieved from STN Database accession No. 1288921-97-0 (RN) abstract & May 2, 2011, Chemical Library, FCH group.

Database Zregistry [Online], Chemical abstracts services, Columbus, Ohio, US; May 24, 2011, XP002667033, retrieved from STN Database accession No. 1299197-68-4 (RN) abstract & May 24, 2011, Chemical Library, FCH library.

Database Zregistry [Online], Chemical abstracts services, Columbus, Ohio, US; Nov. 10, 2010, XP002667030, retrieved from STN Database accession No. 1252408-80-2 (RN) abstract & Nov. 10, 2010, Chemical Library, Enamine.

Database Zregistry, Chemical abstracts services, Columbus, Ohio, US; May 12, 2011, XP002667024, retrieved from STN Database accession No. 1293791-24-8 (RN) abstract & May 12, 2011, Chemical Library, Enamine.

Drevs, J. et al., Antiangiogenic potency of FK866/K22.175, a new inhibitor of intracellular NAD biosynthesis, in murine renal cell carcinoma, Anticancer Res., 23:4853-4858 (2003).

Dvir-Ginzberg, M. et al., Regulation of cartilage-specific gene expression in human chondrocytes by SirT1 and nicotinamide phosphoribosyltransferase, J Biol Chem, 283(52):36300-36310 (2008).

Ekelund, S. et al., Early stimulation of acidification rate by novel cytotoxic pyridyl cyanoguanidines in human tumor cells: comparison with m-iodobenzylguanidine, Biochem Pharmacol, 60(6):839-849 (2000).

Feng, J. et al., CA 153:359036, Preparation of oxodihydrotriazolopyridine derivatives for use as soluble epoxide hydrolase inhibitors, Takeda Pharmaceutical Company Limited, Japan, 3 pages (2010).

Formentini, L. et al., Detection and pharmacological modulation of nicotinamide mononucleotide (NMN) in vitro and in vivo, Biochem Pharmacol, 77(10):1612-1620 (2009).

Friberg, L.E. et al., Pharmacokinetic-pharmacodynamic modelling of the schedule-dependent effect of the anti-cancer agent CHS 828 in a rat hollow fibre model, Eur. J. Pharmaceutical Sci., 25:163-173 (2005).

Fuchs, D. et al., Metronomic administration of the drug GMX1777, a cellular NAD synthesis inhibitor, results in neuroblastoma regression and vessel maturation without inducing drug resistance, Int J Cancer, 126(12):2773-2789 (2010).

(56) References Cited

OTHER PUBLICATIONS

Fuchs, D. et al., Regression of orthotopic neuroblastoma in mice by to geting the endothelial and tumor cell compartments, J. Transl. Med., 7:16-27 (2009).
Galli, J. et al., Synthesis and biological evaluation of isosteric analogues of FK866, an inhibitor of NAD salvage, ChemMedChem, 3:771-779 (2008).
Galli, M. et al., The Nicotinamide Phosphoribosyltransferase: A Molecular Link between Metabolism, Inflammation, and Cancer, Cancer Res., 70(1):8-11 (2009).
Hasmann, M. and Schemainda, I., FK866, a highly specific non-competitive inhibitor of nicotinamide phosphoribosyltransferase represents a novel mechanism for induction of tumor cell apoptosis, Cancer Res., 63(21):7436-7442 (2003).
Hassan, S.B. et al., Model for time dependency of cytotoxic effect of CHS 828 in vitro suggests two different mechanisms of action, J Pharmacol Exp Ther, 299(3):1140-1147 (2001).
Hjarnaa, P.V. et al., CHS828, a Novel Pyridyl Cyanoguanidine with Potent Antitumor Activity in Vitro and in Vivo, Cancer Res., 59:5751-5757 (1999).
Holen, K. et al., The pharmacokinetics, toxicities, and biologic effects of FK866, a nicotinamide adenine dinucleotide biosynthesis inhibitor, Invest New Drugs, 26:45-51 (2008).
Hovstadius, P. et al., A Phase I study of CHS 828 in patients with solid tumor malignancy, Clin Cancer Res, 8:2843-2850 (2002).
Hsu, C.P. et al., Nicotinamide phosphoribosyltransferase regulates cell survival through NAD+ synthesis in cardiac myocytes, Circ Res, 105(5):481-491 (2009).
Imai, S. et al., "Clocks" in the NAD World: NAD as a metabolic oscillator for the regulation of metabolism and aging, Biochimica et Biophysica Acta (BBA)—Proteins and Proteomics, 1804(8):1584-1590 (2010).
Improper Markush, Fed. Reg. 76(27) p. 7162-7175, slide 1, 64-67 (2011).
International Search Report for PCT/US11/50321, issued by ISA/EPO, 4 pages (dated Feb. 16, 2012).
Jacobson, E.L. et al., Mapping the role of NAD metabolism in prevention and treatment of carcinogenesis, Mol Cell Biochem., 193(1-2):69-74 (1999).
Jonsson, E. et al., In vivo activity of CHS 828 on hollow-fibre cultures of primary human tumour cells from patients, Cancer Lett., 162(2):193-200 (2001).
Kato, et al., Efficacy of combining GMX1777 with radiation therapy for human head and neck carcinoma, Clin Cancer Res., 16:898-911 (2010).
Khan, J.A. et al., Nicotinamide adenine dinucleotide metabolism as an attractive target for drug discovery, Expert Opin. Ther. Targets, 11:695-705 (2007).
Lindsley, C.W. et al., CA 159:426465, Preparation of substituted 5-aminothieno [2,3-c]pyridazine-6-carboxamide analogs as positive allosteric modulators of the muscarinic acetylcholine receptor M4, Vanderbilt University, USA, 3 pages (2013).
Lockman, J.W. et al., Analogues of 4-[(7-Bromo-2-methyl-4-oxo-3H-quinazolin-6-yl)methylprop-2-ynylamino]-N-(3-pyridylmethyl)benzamide (CB-30865) as potent inhibitors of nicotinamide phosphoribosyltransferase (Nampt)., J Med Chem., 53(24):8734-8746 (2010).
Lovborg, H. et al., Action of a novel anticancer agent, CHS 828, on mouse fibroblasts: increased sensitivity of cells lacking poly (ADP-Ribose) polymerase-1, Cancer Res, 62:4206-4211 (2002).
Lovborg, H. et al., Modulation of pyridyl cyanoguanidine (CHS 828) induced cytotoxicity by 3-aminobenzamide in U-937 GTB cells, Biochem Pharmacol, 63(8):1491-1498 (2002).
Lovborg, H. et al., Multiparametric evaluation of apoptosis: effects of standard cytotoxic agents and the cyanoguanidine CHS 828, Mol Cancer Ther., 3(5):521-526 (2004).
Lovborg, H. et al., Structure-activity relationship analysis of cytotoxic cyanoguanidines: selection of CHS 828 as candidate drug, BMC Res Notes, 2:114, 7 pages (2009).
Martinsson, P. et al., Cell death with atypical features induced by the novel antitumoral drug CHS 828, in human U-937 GTB cells, Eur. J. Pharmacol., 417(3):181-7 (2001).
Martinsson, P. et al., Temporal effects of the novel antitumour pyridyl cyanoguanidine (CHS 828) on human lymphoma cells, Eur. J. Cancer, 37:260-267 (2001).
Martinsson, P. et al., The combination of the antitumoural pyridyl cyanoguanidine CHS 828 and etoposide in vitro—from cytotoxic synergy to complete inhibition of apoptosis, Br J Pharmacol., 137:568-573 (2002).
Olesen, U.H. et al., Anticancer agent CHS-828 inhibits cellular synthesis of NAD, Biochem Biophys Res Commun., 367(4):799-804 (2008).
Pajouhesh, H. et al., CA 156:666176, Preparation of arylsulfone derivatives for use as calcium channel blockers, Zalicus Pharmaceuticals Ltd., Can., 3 pages (2012).
Petry, S. et al., CA 156:74422, Azolopyridin-3-one derivatives as inhibitors of lipases and phospholipases and their preparation, Sanofi, Fr., 3 pages (2011).
Pogrebniak, A. et al., Chemopotentiating effects of a novel NAD biosynthesis inhibitor, FK866, in combination with antineoplastic agents, Eur J Med Res., 11(8):313-321 (2006).
Ravaud, A. et al., Phase I study and pharmacokinetic of CHS-828, a guanidino-containing compound, administered orally as a single dose every 3 weeks in solid tumours: an ECSG/EORTC study, Eur J Cancer, 41(5):702-707 (2005).
Revollo, J.R. et al., Nampt/PBEF/Visfatin regulates insulin secretion in beta cells as a systemic NAD biosynthetic enzyme, Cell Metabolism, 6(5):363-375 (2007).
Rongvaux, A., et al. Nicotinamide Phosphoribosyl Transferase/Pre-B Cell Colony-Enhancing Factor Nisfatin Is Required for Lymphocyte Development and Cellular Resistance to Genotoxic Stress, J. Immunol.,181:4685-4695 (2008).
Von Heiderman, A. et al., Safety and efficacy of NAD depleting cancer drugs: results of a phase I clinical trial of CHS 828 and overview of published data, Cancer Chemother Pharmacol, 65(6):1165-1172 (2010).
Wang, T. et al., Structure of Nampt/PBEF/visfatin, a mammalian NAD+ biosynthetic enzyme, Nat Struct Mol Biol., 13(7):661-662 (2006).
Watson, M. et al., The small molecule GMX1778 is a potent inhibitor of NAD+ biosynthesis: strategy for enhanced therapy in nicotinic acid phosphoribosyltransferase 1-deficient tumors, Mol Cell Biol, 29(21):5872-5888 (2009).
Wosikowski, K. et al., WK175, a novel antitumor agent, decreases the intracellular nicotinamide adenine dinucleotide concentration and induces the apoptotic cascade in human leukemia cells, Cancer Res., 62:1057-1062 (2002).
Yang, H. et al., Nutrient-sensitive mitochondrial NAD+ levels dictate cell survival, Cell, 130(6):1095-1107 (2007).
You, H. et al., Design, synthesis and X-ray crystallographic study of NAmPRTase inhibitors as anti-cancer agents, Eur J Med Chem., 46(4):1153-1164 (2011).

\* cited by examiner

COMPOUNDS AND COMPOSITIONS FOR THE INHIBITION OF NAMPT

PRIORITY CLAIM

This is a continuation application of U.S. non-provisional application Ser. No. 13/820,497, filed on May 15, 2014, which is the U.S. National Stage Application of PCT/US2011/050321, which was filed on Sep. 2, 2011 and claims priority from U.S. provisional application Ser. No. 61/379,789 and 61/379,796 filed Sep. 3, 2010, U.S. provisional application Ser. Nos. 61/386,023 and 61/386,028 filed Sep. 24, 2010, U.S. provisional application Ser. No. 61/475,813 filed on Apr. 15, 2011, and U.S. provisional application Ser. No. 61/483,242 filed on May 6, 2011, the contents of which are fully incorporated herein by reference in their entirety.

FIELD OF THE INVENTION

The present invention relates to compounds and composition for inhibition of Nicotinamide phosphoribosyltransferase ("NAMPT"), their synthesis, applications and antidote.

BACKGROUND OF THE INVENTION

Nicotinamide adenine dinucleotide (NAD) plays fundamental roles in both cellular energy metabolism and cellular signaling. In energy metabolism, the chemistry of the pyridine ring allows NAD to readily accept and donate electrons in hydride transfer reactions catalyzed by numerous dehydrogenases.

The preparation of a class of compounds, comprising several subclasses, which act as inhibitors of the formation of nicotinamide adenyl nucleotide, and their use thereof as anti-tumour agents, is already described in the patent applications WO00/50399, WO97/48695, WO97/48696, WO97/48397, WO99/31063, WO99/31060, WO99/31087, WO99/31064, WO00/50399, and WO03/80054.

One of these inhibitors, (E)-N-[4-(1-benzoylpiperidin-4-yl)butyl]-3-(pyridine-3-yl)-acrylamide also known as APO866, FK866, WK175, or WK22.175 and hereinafter referred to as FK866 [International Non-proprietary Name], is especially described in the literature as an anticancer agent. FK866 may be used for treatment of diseases implicating deregulated apoptosis such as cancer. It has been demonstrated in the prior art that FK866 interferes with nicotinamide adenine dinucleotide (also known and hereinafter referred to as NAD) biosynthesis and induces apoptotic cell death without any DNA damaging effects.

Additionally, FK866 ((E)-N-[4-(1-benzoylpiperidin-4-yl)butyl]-3-(pyridin-3-yl)acrylamide) induces apoptosis in HepG2 cells without having primary effects on cellular energy metabolism. (Hasmann M, Schemainda I. FK866, a Highly Specific Noncompetitive Inhibitor of Nicotinamide Phosphoribosyltransferase, Represents a Novel Mechanism for Induction of Tumor Cell Apoptosis. Cancer Res 2003; 63:7436-7442. [PubMed: 14612543]) Instead of causing immediate cytotoxicity, it inhibits NAMPT and depletes the cells of NAD, suggesting that FK866 could be a promising agent against cancer cells that rely on nicotinamide to synthesize NAD. The crystal structure of the NAMPT-FK866 complex reveals that the compound binds at the nicotinamide-binding site of NAMPT to inhibit its activity. FK866 has been tested in a murine renal cell carcinoma model and shown to display anti-tumor, antimetastatic, and anti-angiogenic activities (Drevs J, et al. Antiangiogenic potency of FK866/K22.175, a new inhibitor of intracellular NAD biosynthesis, in murine renal cell carcinoma. Anticancer Res 2003; 23:4853-4858. [PubMed:14981935]).

In a mouse mammary carcinoma model, FK866 also induces a delay in tumor growth and an enhancement in tumor radiosensitivity accompanied with dose-dependent decreases in NAD levels, pH, and energy status. A chemo-sensitizing effect of FK866 has also been observed on anti-neoplastic 1-methyl-3-nitro-1-nitrosoguanidinium (MNNG)-induced cell death in THP-1 and K562 leukemia cell lines (Pogrebniak A, et al. Chemopotentiating effects of a novel NAD biosynthesis inhibitor, FK866, in combination with antineoplastic agents. Eur J Med Res 2006; 11:313-321. [PubMed: 17052966]).

The efficacy of GMX1777 was evaluated in xenograft models and the pharmacokinetic profile of GMX1778 and its effect on nicotinamide adenine dinucleotide cellular levels was measured by liquid chromatography/mass spectrometry. (Beauparlant P., et al. Preclinical development of the nicotinamide phosphoribosyl transferase inhibitor prodrug GMX1777. Anticancer Drugs. 2009 June; 20(5):346-54).

GMX1777 is a water-soluble intravenously administered prodrug of GMX1778 that Gemin X in-licensed from LEO Pharma (LEO numbers: EB 1627 and CHS828, respectively). These compounds and other substituted cyanoguanidines have the structures of Table 1. None of the compounds of the present invention are cyanoguanidines.

TABLE 1

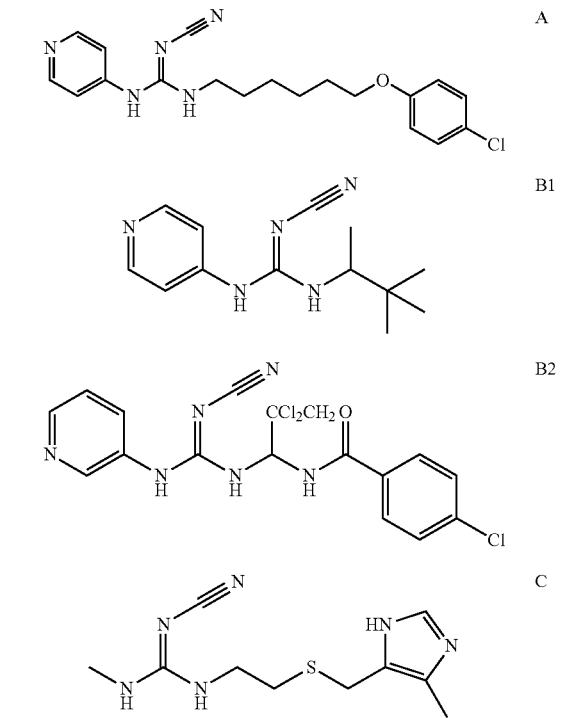

Substituted Cyanoguanidines with Defined Pharmacological Effects:
A Cytotoxic CHS 828;
B Potassium channel openers pinacidil (B1) and 12 g of compound as described in Perez-Medrano et al (B2); and
C Histamine-II receptor antagonist cimetidine. (from Lövborg et al. *BMC Research Notes* 2009 2:114 doi: 10.1186/1756-0500-2-114)

More recently, CHS-828 has been identified as a NAMPT inhibitor (Olesen U H, et al. Anticancer agent CHS-828 inhibits cellular synthesis of NAD. Biochem Biophys Res Commun 2008; 367:799-804. [PubMed: 18201551]). CHS-828 has been shown to potently inhibit cell growth in a broad range of tumor cell lines, although the detailed mechanism for this inhibitory effect of CHS-828 remains undetermined (Ravaud A, et al. Phase I study and guanidine kinetics of CHS-828, a guanidine-containing compound, administered orally as a single dose every 3 weeks in solid tumors: an ECSG/EORTC study. Eur J Cancer 2005; 41:702-707. [PubMed: 15763645]). Both FK866 and CHS-828 are currently in clinical trials for cancer treatments.

There are numerous uses for drugs which inhibit NAMPT.

Lack of NAMPT expression strongly affects development of both T and B lymphocytes. By using mutant forms of this protein and a well-characterized pharmacological inhibitor (FK866), authors demonstrated that the ability of the NAMPT to regulate cell viability during genotoxic stress requires its enzymatic activity. Collectively, these data demonstrate that NAMPT participates in cellular resistance to genotoxic/oxidative stress, and it may confer to cells of the immune system the ability to survive during stressful situations such as inflammation. (Rongvaux, A., et al. *The Journal of Immunology*, 2008, 181: 4685-4695).

NAMPT may also have effects on endothelium (EC) in relation to high glucose levels, oxidative stress and on aging. It is also believed that NAMPT may enable proliferating human EC to resist the oxidative stress of aging and of high glucose, and to productively use excess glucose to support replicative longevity and angiogenic activity.

SUMMARY OF THE INVENTION

One aspect of this invention is the provision of compounds, compositions, kits, and antidotes for the NAMPT pathway in mammals having a compound of the Formula I:

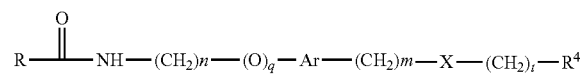

wherein:
R is an aryl, heteroaryl, $C_3$-$C_8$ cycloalkyl, $C_3$-$C_8$ cycloalkenyl, heterocycloalkyl, arylalkyl-, (heteroaryl)alkyl-, ($C_3$-$C_8$ cycloalkyl)alkyl-, ($C_3$-$C_8$ cycloalkenyl)alkyl-, (heterocycloalkyl)alkyl-, (aryloxy)alkyl-, (heteroaryloxy)alkyl-, ($C_3$-$C_8$ cycloalkyloxy)alkyl-, ($C_3$-$C_8$ cycloalkenyloxy)alkyl- or (heterocycloalkyloxy)alkyl-, wherein the heteroatom of each of said heteroaryl and heterocycloalkyl numbers 1, 2 or 3, and is independently selected from N, S or O, further wherein each of said aryl, heteroaryl and heterocycloalkyl may independently be either substituted or fused with an aryl or heteroaryl, still further wherein any of said aryl, heteroaryl and heterocycloalkyl is either unsubstituted or optionally independently substituted with one or more substituents which can be the same or different and are independently selected from the group consisting of deuterium, halo, cyano, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, -alkyl, -alkenyl, -alkynyl, -alkoxy, hydroxyl, alkyl hydroxy, hydroxyl, alkyl hydroxy, or (alkoxyalkyl)amino-, —N($R^3$)—C(O)-alkyl, —N($R^3$)—C(O)-aryl, -cycloalkyl, -heterocycloalkyl, -aryl, and heteroaryl, with the proviso that no two adjacent ring heteroatoms are both S or both O;
Ar is aryl, heteroaryl, heterocycloalkyl or $C_3$ to $C_8$ cycloalkyl, with each of said aryl, heteroaryl, heterocycloalkyl and cycloalkyl being either unsubstituted or optionally independently substituted with 1, 2, 3 or 4 substituents which can be the same or different and are independently selected from the group consisting of deuterium, halo, cyano, amino, aminoalkyl-, (amino)alkoxy-, —$CONH_2$, —C(O)NH(alkyl), —C(O)N(alkyl)$_2$, —C(O) NH(aryl), —C(O)N(aryl)$_2$, —$CH_zF_{3-z}$, —$OCH_zF_{3-z}$, -alkyl, -alkenyl, -alkynyl, -alkoxy, hydroxyl, -alkyl hydroxyl, aryloxy-, (alkoxyalkyl)amino-, —N($R^3$)—C(O)-alkyl, —N($R^3$)—C(O)-aryl, -cycloalkyl, -heterocycloalkyl, -aryl, and -heteroaryl;
$R^4$ is cycloalkyl, —$CH_zF_{3-z}$, aryl, heterocycloalkyl, heteroaryl, alkyl, -alkenyl, -alkynyl, (aryl)alkyl-, (heteroaryl)alkyl- or (heterocycloalkyl)alkyl-, or

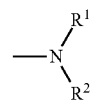

(i)

wherein each of said cycloalkyl, aryl, heterocycloalkyl, heteroaryl and alkyl is either unsubstituted or optionally substituted with 1, 2, 3, 4 or 5 substituents which can be the same or different and are independently selected from the group consisting of deuterium, halo, cyano, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, -alkyl, alkoxy-, -alkenyl, -alkynyl, aryloxy-, (alkoxyalkyl)amino-, -cycloalkyl, -heterocycloalkyl, (heterocycloalkyl)alkyl-, -aryl, (aryl)alkyl-, -heteroaryl, (heteroaryl)alkyl-, —S(O)$_2$-alkyl, —S(O)$_2$-aryl, —S(O)$_2$—$CF_3$, —C(O)N(alkyl)$_2$, —C(O)alkyl, —N($R^3$)—C(O)-alkyl, —N($R^3$)—C(O)-aryl, —S(O$_2$)NH$_2$, —S(O$_2$)NH(alkyl), —S(O$_2$)N(alkyl)$_2$, —N(H)S(O$_2$)(alkyl), —C(O)N(H)(alkyl), and methylenedioxy, (ii) further wherein each of said cycloalkyl, aryl, heterocycloalkyl, and heteroaryl may optionally additionally be fused with independently selected aryl, heteroaryl, heterocycloalkyl or cycloalkyl;
$R^3$ is H, alkyl or arylalkyl-;
X is S, S(O), S(O)$_2$, O or C(O);
n is 1, 2, 3 or 4;
m is 0, 1, 2, 3 or 4;
q is 0 or 1;
t is 0, 1 or 2; and
z is 0, 1 or 2;
and pharmaceutically acceptable salts, solates, esters, prodrugs and isomers thereof.

Another aspect of the invention are the compounds of Formula I, where q=0, m=0, t=0, A=Ar, X=Q and $R^4$ is

and the formula is now Formula IB

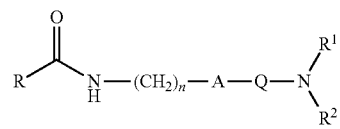

IB where:
R and $R^3$ are as defined in Formula I;
$R^1$ and $R^2$ are the same or they are different, and are independently selected from H, a straight or branched $C_1$ to $C_7$ alkyl, straight or branched $C_1$ to $C_7$ alkoxy, straight or branched $C_1$ to $C_4$ hydroxyalkyl, aryl, heteroaryl, heterocycloalkyl and cycloalkyl, and wherein heteroatoms of said heteroaryl and heterocycloalkyl are independently selected from one or more N, O and S, with the proviso that no two adjacent ring heteroatoms are both S or both O, further wherein R¹ and R² can be either unsubstituted or optionally independently substituted with one or more substituents which can be the same or different and are independently selected from the group consisting of deuterium, halo, cyano, amino, aminoalkyl-, (amino)alkoxy-, —CONH₂, —C(O)NH(alkyl), —C(O)N(alkyl)₂, —C(O)NH(aryl), —C(O)N(aryl)₂, —CH$_z$F$_{3-z}$, —OCH$_z$F$_{3-z}$, -alkyl, -alkenyl, -alkynyl, hydroxyalkyl-, -alkoxy, hydroxyl, alkyl hydroxy, carboxy, (alkoxyalkyl) amino-, -alkylamine, aminocarbonyl-, —CHO, —N(R³)—C(O)-alkyl, —N(R³)—C(O)-aryl, -cycloalkyl, -heterocycloalkyl, -aryl, and heteroaryl;

A is aryl, heteroaryl, heterocycloalkyl or C₃ to C₈ cycloalkyl, with each of said aryl, heteroaryl, heterocycloalkyl and cycloalkyl being either unsubstituted or optionally independently substituted with 1, 2, 3 or 4 substituents which can be the same or different and are independently selected from the group consisting of deuterium, halo, cyano, amino, aminoalkyl-, (amino)alkoxy-, —CONH₂, —C(O)NH(alkyl), —C(O)N(alkyl)₂, —C(O)NH(aryl), —C(O)N(aryl)₂, —CH$_z$F$_{3-z}$, —OCH$_z$F$_{3-z}$, -alkyl, -alkenyl, -alkynyl, -alkoxy, hydroxyl, -alkyl hydroxyl, aryloxy-, (alkoxyalkyl)amino-, —N(R³)—C(O)-alkyl, —N(R³)—C(O)-aryl, -cycloalkyl, -heterocycloalkyl, -aryl, and -heteroaryl;

Q is C(O), S(O), S(O)₂, —N(H)—C(O)—, —S(O₂)—NH—, or —N(H)—S(O₂)—;

n is 0, 1, 2, 3 or 4; and z is 0, 1 or 2;

and pharmaceutically acceptable salts, solvates, esters, prodrugs or isomers thereof.

Another aspect of this invention is the provision of compounds, compositions, kits, and antidotes for the NAMPT pathway in mammals having a compound derived from Formula I where q=0, m=0 and t=0, whereby the formula becomes Formula II or pharmaceutically acceptable salts thereof:

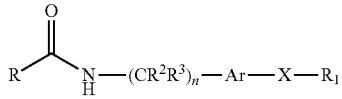

II where:

R is heteroaryl comprising 1, 2, 3 or 4 heteroatom(s) independently selected from N, S or O, wherein said heteroaryl may be substituted by one or more substituents selected from the group consisting of amino, oxo, and halo; and wherein said heteroaryl can comprise one or more N-oxide(s) formed with a N atom member of said heteroaryl;

Ar is aryl or heteroaryl comprising 1, 2, 3 or 4 heteroatom(s) independently selected from N, S or O;

X is S(O)₂ or SO;

R¹ is —NHR⁴ where R⁴ is cycloalkyl, heterocycloalkyl, aryl or heteroaryl;

cycloalkyl;

aryl;

heterocycloalkyl; or heteroaryl; wherein:

(i) each of said cycloalkyl, aryl, or heteroaryl is unsubstituted or substituted with 1, 2, 3, 4 or 5 substituents which can be the same or different and are independently selected from the group consisting of:

deuterium, halo, hydroxy, hydroxyalkyl, cyano, —(CH₂)$_m$NR$^a$R$^b$, oxo, alkyl, cyanoalkyl, haloalkyl, alkoxy, haloalkoxy, alkoxyalkyl-, alkenyl, alkynyl, alkynylalkoxy, —CONH₂, —S-alkyl, —C(O)NH(alkyl), —C(O)N(alkyl)₂, —C(O)NH(cycloalkyl), —C(O)NH(aryl), —C(O)N(aryl)₂, arylalkyl-, arylalkoxy-, aryloxy-, cycloalkyl, heterocycloalkyl, aryl, (heterocycloalkyl)alkyl-, (heterocycloalkyl)alkoxy-, —C(O)heterocycloalkyl, heteroaryl, (heteroaryl)alkyl-, —S(O)₂-alkyl, —S(O)₂-aryl, —S(O)₂—CH$_z$F$_{3-z}$, —C(O)alkyl, —N(R⁵)—C(O)-alkyl, —N(R⁵)—C(O)-aryl, —S(O₂)NH₂, —S(O₂)NH(alkyl), —S(O₂)N(alkyl)₂, —N(H)(SO₂)(alkyl), and methylenedioxy, wherein each of said cycloalkyl, heterocycloalkyl, aryl or heteroaryl may be substituted by one or more halo, cyano, alkyl or alkoxy and;

(ii) each of said cycloalkyl, heterocycloalkyl, aryl, or heteroaryl may optionally additionally be fused with independently selected aryl, heteroaryl, heterocycloalkyl or cycloalkyl to from a bicyclic or tricyclic group that may be substituted by one or more halo, cyano, alkyl or alkoxy;

R² and R³ can be independently selected from the group consisting of H and deuterium;

R⁵ is H, alkyl or arylalkyl-;

R$^a$ and R$^b$ are independently selected from the group consisting of H, alkyl, alkoxy, alkoxyalkyl and haloalkyl;

m is 0, 1, 2, 3, 4, 5 or 6; and n is 0 or 1.

Another aspect of this invention are compounds Formula II or pharmaceutically acceptable salts thereof where X=SO₂, and the formula is:

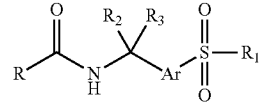

IIA where:

R is heteroaryl comprising 1, 2, 3 or 4 heteroatom(s) independently selected from N, S or O, wherein said heteroaryl may be substituted by one or more substituents selected from the group consisting of amino, oxo, and halo; and wherein said heteroaryl can comprise one or more N-oxide(s) formed with a N atom member of said heteroaryl;

Ar is aryl or 5 or 6 membered heteroaryl comprising 1, 2, 3 or 4 heteroatom(s) independently selected from N, S or O;

R¹ is —NHR⁴ and R⁴ is cycloalkyl, heterocycloalkyl, aryl or heteroaryl;

cycloalkyl;

aryl; or heteroaryl; wherein:

each of said cycloalkyl, aryl, or heteroaryl is unsubstituted or substituted with 1, 2, 3, 4 or 5 substituents which can be the same or different and are independently selected from the group consisting of:

deuterium, halo, hydroxy, hydroxyalkyl, cyano, —(CH₂)$_m$NR$^a$R$^b$, oxo, alkyl, cyanoalkyl, haloalkyl, alkoxy, haloalkoxy, alkoxyalkyl-, alkenyl, alkynyl, alkynylalkoxy, —CONH₂, —S-alkyl, —C(O)NH(alkyl), —C(O)N(alkyl)₂, —C(O)NH(cycloalkyl), —C(O)NH(aryl), —C(O)N(aryl)₂, arylalkyl-, arylalkoxy-, aryloxy-, cycloalkyl, heterocycloalkyl, aryl, (heterocycloalkyl)alkyl-, (heterocycloalkyl)alkoxy-, —C(O)heterocycloalkyl, heteroaryl, (heteroaryl)alkyl-, —S(O)$_2$-alkyl, —S(O)$_2$-aryl, —S(O)$_2$—CH$_z$F$_{3-z}$, —C(O)alkyl, —N(R$^5$)—C(O)-alkyl, —N(R$^5$)—C(O)-aryl, —S(O$_2$)NH$_2$, —S(O$_2$)NH(alkyl), —S(O$_2$)N(alkyl)$_2$, —N(H)(SO$_2$)(alkyl), and methylenedioxy, wherein each of said cycloalkyl, heterocycloalkyl, aryl or heteroaryl may be substituted by one or more halo, cyano, alkyl or alkoxy and;

each of said cycloalkyl, heterocycloalkyl, aryl, or heteroaryl may optionally additionally be fused with independently selected aryl, heteroaryl, heterocycloalkyl or cycloalkyl to from a bicyclic or tricyclic group that may be substituted by one or more halo, cyano, alkyl or alkoxy;

R$^2$ and R$^3$ can be independently selected from the group consisting of H and deuterium;

R$^5$ is H, alkyl or arylalkyl-;

R$^a$ and R$^b$ are independently selected from the group consisting of H, alkyl, alkoxy, alkoxyalkyl and haloalkyl; and m is 0, 1, 2, 3, 4, 5 or 6.

Yet another aspect of the invention is compounds of Formula II A, where Ar=phenyl, whereby the formula becomes Formula II B: We claim:

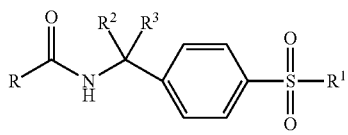

IIB where:

R is bicyclic heteroaryl comprising 1, 2, 3 or 4 heteroatom(s) independently selected from N, S or O, wherein said heteroaryl may be substituted by one or more substituents selected from the group consisting of amino, oxo, and halo; and wherein said heteroaryl can comprise one or more N-oxide(s) formed with a N atom member of said heteroaryl;

R$^1$ is —NHR$^4$ and R$^4$ is cycloalkyl, heterocycloalkyl, aryl or heteroaryl;

cycloalkyl;

aryl; or heteroaryl; wherein:

each of said cycloalkyl, aryl, or heteroaryl is unsubstituted or substituted with 1, 2, 3, 4 or 5 substituents which can be the same or different and are independently selected from the group consisting of:

deuterium, halo, hydroxy, hydroxyalkyl, cyano, —(CH$_2$)$_m$NR$^a$R$^b$, oxo, alkyl, cyanoalkyl, haloalkyl, alkoxy, haloalkoxy, alkoxyalkyl-, alkenyl, alkynyl, alkynylalkoxy, —CONH$_2$, —S-alkyl, —C(O)NH(alkyl), —C(O)N(alkyl)$_2$, —C(O)NH(cycloalkyl), —C(O)NH(aryl), —C(O)N(aryl)$_2$, arylalkyl-, arylalkoxy-, aryloxy-, cycloalkyl, heterocycloalkyl, aryl, (heterocycloalkyl)alkyl-, (heterocycloalkyl)alkoxy-, —C(O)heterocycloalkyl, heteroaryl, (heteroaryl)alkyl-, —S(O)$_2$-alkyl, —S(O)$_2$-aryl, —S(O)$_2$—CH$_z$F$_{3-z}$, —C(O)alkyl, —N(R$^5$)—C(O)-alkyl, —N(R$^5$)—C(O)-aryl, —S(O$_2$)NH$_2$, —S(O$_2$)NH(alkyl), —S(O$_2$)N(alkyl)$_2$, —N(H)(SO$_2$)(alkyl), and methylenedioxy, wherein each of said cycloalkyl, heterocycloalkyl, aryl or heteroaryl may be substituted by one or more halo, cyano, alkyl or alkoxy and;

each of said cycloalkyl, heterocycloalkyl, aryl, or heteroaryl may optionally additionally be fused with independently selected aryl, heteroaryl, heterocycloalkyl or cycloalkyl to from a bicyclic or tricyclic group that may be substituted by one or more halo, cyano, alkyl or alkoxy;

R$^2$ and R$^3$ can be independently selected from the group consisting of H and deuterium;

R$^5$ is H, alkyl or arylalkyl-;

R$^a$ and R$^b$ are independently selected from the group consisting of H, alkyl, alkoxy, alkoxyalkyl and haloalkyl;

m is 0, 1, 2, 3, 4, 5 or 6;

z is 0, 1 or 2.

Another aspect of this invention is the provision of methods of treating a disease via the inhibition of NAMPT in a subject (e.g., a human) in need thereof by administering to the subject an effective amount of the compound or the pharmaceutical formulation of the present invention.

Still another aspect of this invention is to provide a method for treating, preventing, inhibiting or eliminating a disease or condition in a patient by inhibiting NAMPT in said patient by administering a therapeutically effective amount of at least one compound of this disclosure, wherein said disease or condition is selected from the group consisting of cancer, ovarian cancer, breast cancer, uterine cancer, colon cancer, cervical cancer, lung cancer, prostate cancer, skin cancer, bladder cancer, pancreatic cancer, leukemia, lymphoma, Hodgkin's disease, viral infections, Human Immunodeficiency Virus, hepatitis virus, herpes virus, herpes simplex, inflammatory disorders, irritable bowel syndrome, inflammatory bowel disease, rheumatoid arthritis, asthma, chronic obstructive pulmonary disease, osteoarthritis, osteoporosis, dermatitis, atoptic dermatitis, psoriasis, systemic lupus erythematosis, multiple sclerosis, psoriatic arthritis, ankylosing spodylitis, graft-versus-host disease, Alzheimer's disease, cerebrovascular accident, atherosclerosis, diabetes, glomerulonephiritis, metabolic syndrome, non-small cell lung cancer, small cell lung cancer, multiple myeloma, leukemias, lymphomas, squamous cell cancers, kidney cancer, uretral and bladder cancers, cancers of head and neck, cancers of the brain and central nervous system.

Another preferred embodiment is a pharmaceutical formulation comprising a pharmaceutically acceptable compound of the present invention, which provides, upon administration to a human, a decrease in tumor burden and/or metastases. The pharmaceutical formulation can be administered by oral means or other suitable means.

Yet another embodiment is a method of treating ovarian cancer in a subject (e.g., a human) in need thereof by administering to the subject an effective amount of the compound or the pharmaceutical formulation of the present invention.

Yet another embodiment is a method of treating colon cancer in a subject (e.g., a human) in need thereof by administering to the subject an effective amount of the compound or the pharmaceutical formulation of the present invention.

Yet another embodiment is a method of treating breast cancer in a subject (e.g., a human) in need thereof by administering to the subject an effective amount of the pharmaceutical formulation of the present invention.

Yet another embodiment is a method of treating leukemia in a subject (e.g., a human) in need thereof by administering to the subject an effective amount of the compound or the pharmaceutical formulation of the present invention.

Yet another embodiment is a method of treating colon cancer before or after surgical resection and/or radiation therapy, in a subject (e.g., a human) in need thereof by administering to the subject an effective amount of the compound or the pharmaceutical formulation of the present invention.

Yet another embodiment is a method of treating cancer before or after surgical resection and/or radiation therapy, in a subject (e.g., a human) in need thereof by administering to the subject an effective amount of the compound or the pharmaceutical formulation of the present invention, including adjunctive therapy to treat nausea, with or without dexamethasone.

Yet another embodiment is a method of treating cancer before or after surgical resection and or radiation therapy, in a subject (e.g., a human) in need thereof by administering to the subject an effective amount of the compound or the pharmaceutical formulation of the present invention, including adjunctive therapy with one or more additional therapeutic agents, or their pharmaceutically acceptable salts. Non-limiting examples of such additional therapeutic agents include cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil or 5-FU); anti-metabolites (such as methoxtrexate); alkylating agents (such as temozolomide, cyclophosphamide); Farnesyl protein transferase inhibitors (such as, SARASAR™.(4-[2-[4-[(11R)-3,10-dibromo-8-chloro-6,11-dihydro-5H-benzo[5,-6]cyclohepta[1,2-b]pyridin-11-yl-]-1-piperidinyl]-2-oxoehtyl]-1-piperidine-carboxamide, or SCH 66336), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa® (from Astra Zeneca Pharmaceuticals, England), Tarceva® (EGFR kinase inhibitors), antibodies to EGFR (e.g., C225), GLEEVEC® (C-abl kinase inhibitor from Novartis Pharmaceuticals, East Hanover, N.J.); interferons such as, for example, Intron® (from Merck & Company), Peg-Intron® (from Merck & Company); hormonal therapy combinations; aromatase combinations; ara-C, adriamycin, cytoxan, and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN® from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade®, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Ifosfomide, Rituximab, C225, and Campath, 5-fluorouracil and leucovorin, with or without a 5-HT$_3$ receptor inhibitor (e.g., dolansetron, granisetron, ondansetron) with or without dexamethasone.

If formulated as a fixed dose, such combination products employ the compounds of this invention within the dosage range described herein (or as known to those skilled in the art) and the other pharmaceutically active agents or treatments within its dosage range. For example, the CDC2 inhibitor olomucine has been found to act synergistically with known cytotoxic agents in inducing apoptosis (J. Cell Sci., (1995) 108, 2897). The compounds of the invention may also be administered sequentially with known anticancer or cytotoxic agents when a combination formulation is inappropriate. In any combination treatment, the invention is not limited in the sequence of administration; compounds of the disclosed Formulas may be administered either prior to or after administration of the known anticancer or cytotoxic agent. For example, the cytotoxic activity of the cyclin-dependent kinase inhibitor flavopiridol is affected by the sequence of administration with anticancer agents. Cancer Research, (1997) 57, 3375. Such techniques are within the skills of persons skilled in the art as well as attending physicians.

Any of the aforementioned methods may be augmented by administration of fluids (such as water), loop diuretics, one or more of a chemotherapeutic or antineoplastic agent, such as leucovorin and fluorouracil, and an adjunctive chemotherapeutic agent (such as filgrastim and erythropoietin), or any combination of the foregoing.

Yet another embodiment is a method for administering a compound of the instant invention to a subject (e.g., a human) in need thereof by administering to the subject the pharmaceutical formulation of the present invention.

Yet another embodiment is a method of preparing a pharmaceutical formulation of the present invention by mixing at least one pharmaceutically acceptable compound of the present invention, and, optionally, one or more pharmaceutically acceptable additives or excipients.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 500 mg, more preferably from about 1 mg to about 250 mg, still more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Definitions

As used above, and throughout this disclosure, the following terms, unless otherwise indicated, shall be understood to have the following meanings. If a definition is missing, convention definition as known to one skilled in the art controls.

"Patient" includes both human and animals.

"Mammal" means humans and other mammalian animals.

The term "inhibitor" refers to a molecule such as a compound, a drug, an enzyme activator or a hormone that blocks or otherwise interferes with a particular biologic activity.

The terms "effective amount" or "therapeutically effective amount" refer to a sufficient amount of the agent to provide the desired biological result. That result can be reduction and/or alleviation of the signs, symptoms, or causes of a disease, or any other desired alteration of a biological system. For example, an "effective amount" for therapeutic use is the amount of the composition comprising a compound as disclosed herein required to provide a clinically significant decrease in a disease. An appropriate "effective" amount in any individual case may be determined by one of ordinary skill in the art using routine experimentation. Thus, the expression "effective amount" generally refers to the quantity for which the active substance has therapeutic effects. In the present case the active substance is the inhibitor of the formation of Nicotinamide phosphoribosyltransferase (NAMPT).

As used herein, the terms "treat" or "treatment" are synonymous with the term "prevent" and are meant to indicate a postponement of development of diseases, preventing the development of diseases, and/or reducing severity of such symptoms that will or are expected to develop. Thus, these terms include ameliorating existing disease symptoms, preventing additional symptoms, ameliorating or preventing the underlying metabolic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

By "pharmaceutically acceptable" or "pharmacologically acceptable" is meant a material which is not biologically or otherwise substantially undesirable, i.e., the material may be administered to an individual without causing any substantially undesirable biological effects or interacting in a substantially deleterious manner with any of the components of the composition in which it is contained. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

"Carrier materials" or what are also referred to as "excipients" include any commonly used excipients in pharmaceutics and should be selected on the basis of compatibility and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may comprise, e.g., acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, and the like. See, e.g., Hoover, John E., *Remington's Pharmaceutical Sciences*, Mack Publishing Co., Easton, Pa. 1975.

As used herein, the term "subject" encompasses mammals and non-mammals. Examples of mammals include, but are not limited to, any member of the Mammalian class:

humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the present invention, the mammal is a human.

As used herein, "alkyl" means a straight chain or branched saturated chain having from 1 to 10 carbon atoms. Representative saturated alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl and the like, and longer alkyl groups, such as heptyl, and octyl and the like. An alkyl group can be unsubstituted or substituted. Alkyl groups containing three or more carbon atoms may be straight, branched or cyclized. As used herein, "lower alkyl" means an alkyl having from 1 to 6 carbon atoms.

As used herein, an "alkenyl group" includes an unbranched or branched hydrocarbon chain having one or more double bonds therein. The double bond of an alkenyl group can be unconjugated or conjugated to another unsaturated group. Illustrative alkenyl groups include, but are not limited to, ($C_2$-$C_8$) alkenyl groups, such as ethylenyl, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl and the like. An alkenyl group can be unsubstituted or substituted.

The term "hydroxyalkyl" denotes an alkyl group as defined above wherein at least one of the hydrogen atoms of the alkyl group is replaced by a hydroxy group. Examples of hydroxyalkyl include, but are not limited to, methyl, ethyl, propyl, isopropyl, isobutyl, sec-butyl, tert-butyl, pentyl or n-hexyl wherein one or more hydrogen atoms are replaced by OH, as well as those hydroxyalkyl groups specifically illustrated by the examples herein below.

The term "cyanoalkyl" denotes an alkyl group as defined above wherein at least one of the hydrogen atoms of the alkyl group is replaced by a cyano (—CN) group.

As used herein, "alkynyl group" includes an unbranched or branched hydrocarbon chain having one or more triple bonds therein. The triple bond of an alkynyl group can be unconjugated or conjugated to another unsaturated group. Suitable alkynyl groups include, but are not limited to, ($C_2$-$C_6$) alkynyl groups, such as ethynyl, propynyl, butynyl, pentynyl, hexynyl, methylpropynyl, 4-methyl-1-butynyl, 4-propyl-2-pentynyl, 4-butyl-2-hexynyl and the like. An alkynyl group can be unsubstituted or substituted.

The term "haloalkyl" denotes an alkyl group as defined above wherein at least one of the hydrogen atoms of the alkyl group is replaced by a halogen atom, preferably fluoro or chloro, most preferably fluoro. Examples of haloalkyl include, but are not limited to, methyl, ethyl, propyl, isopropyl, isobutyl, sec-butyl, tert-butyl, pentyl or n-hexyl wherein one or more hydrogen atoms are replaced by Cl, F, Br or I atom(s), as well as those haloalkyl groups specifically illustrated by the examples herein below. Among the preferred haloalkyl groups are monofluoro-, difluoro- or trifluoro-methyl, -ethyl or -propyl, for example 3,3,3-trifluoropropyl, 2-fluoroethyl, 2,2,2-trifluoroethyl, fluoromethyl, trifluoromethyl.

The terms "trifluoromethyl," "sulfonyl," and "carboxyl" include $CF_3$, $SO_2$, and $CO_2H$, respectively.

The term "oxo" means =O-group;

The term "hydroxy" means an OH group;

The term "alkoxy" as used herein includes —O-(alkyl), wherein alkyl is defined above.

The term "aminoalkyl" as used herein means a group having one or more nitrogen atoms and one or more alkyl groups as defined above on the nitrogen.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Heteroarylalkyl" means a heteroaryl moiety as defined herein linked via an alkyl moiety (defined above) to a parent core. Non-limiting examples of suitable heteroaryls include 2-pyridinylmethyl, quinolinylmethyl and the like.

"Heterocyclylalkyl" means a heterocyclyl moiety as defined herein linked via an alkyl moiety (defined above) to a parent core. Non-limiting examples of suitable heterocyclylalkyls include piperidinylmethyl, piperazinylmethyl and the like.

The term "bicyclic heteroaryl" means a structure having atoms arranged in two rings fused together with at least two atoms common to each ring, and at least one of the rings being a heteroaryl ring. Non limiting examples of bicyclic heteroaryl comprise bicyclic heteroaryl groups comprising 1, 2, 3 or 4 heteroatom(s) independently selected from N, S or O.

It should also be noted that any carbon as well as heteroatom with unsatisfied valences in the text, schemes, examples and Tables herein is assumed to have the sufficient number of hydrogen atom(s) to satisfy the valences.

When any variable (e.g., aryl, heterocycle, $R^2$, etc.) occurs more than one time in any constituent or in the Formulas, its definition on each occurrence is independent of its definition at every other occurrence.

The term "N-oxide(s) formed with a N atom member of said heteroaryl" denotes a heterorayl group containing a nitrogen atom that forms a N-oxide. Illustrative and non limiting examples of such N-oxides are:

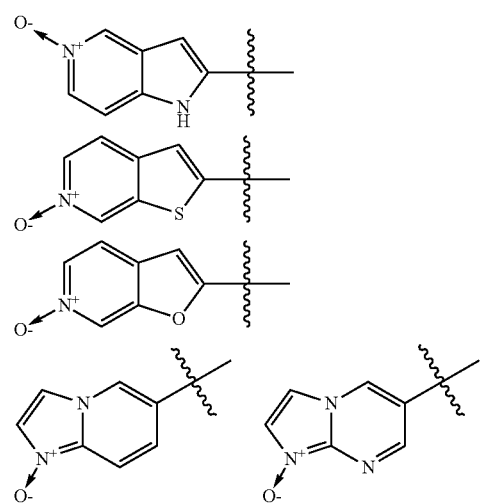

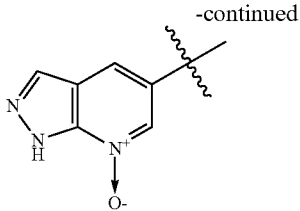

As used herein, the term "composition" is intended to encompass a product comprising the specified ingredients in the specified amounts, as well as any product which results, directly or indirectly, from combination of the specified ingredients in the specified amounts.

The term "deuterium" as used herein means a stable isotope of hydrogen having odd numbers of protons and neutrons.

The term "halo" as used herein means a substituent having at least one halogen selected from fluorine, chlorine, bromine, and iodine.

The term "cyano" as used herein means a substituent having a carbon atom joined to a nitrogen atom by a triple bond.

The term "amino" as used herein means a substituent containing at least one nitrogen atom.

The term "(amino)alkoxy" as used herein means a substituent having at least one amino group and at least one alkoxy group.

The term "aryloxy" as used herein means a substituent of the form Ar—O— where Ar is an aryl group as defined herein.

The term "methylenedioxy" as used herein means a functional group with the structural formula —O—CH$_2$—O— which is connected to the molecule by two chemical bonds via the oxygens.

As used herein, "alkoxyalkyl" means -(alkyl)-O-(alkyl), wherein each "alkyl" is independently an alkyl group defined above.

The term "(alkoxyalkyl)amino" as used herein means a substituent having at least one alkoxyalkyl group as defined above and at least one amino group as defined above.

The term "spiroheterocycloalkyl" as used herein means a spiro group (containing no heteroatom) linked in a spiro manner to a heterocycloalkyl group. A non-limiting example would be the moiety shown below:

The term "heterospiroheterocycloalkyl" as used herein means a spiro group (containing a hetero atom such O, N or S) linked in a spiro manner to a heterocycloalkyl group. A non-limiting example would be the moiety shown below:

"Aryl" means a monovalent aromatic hydrocarbon radical of 6-20 carbon atoms (C$_6$-C$_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein. Illustrative examples of aryl groups include, but are not limited to phenyl, naphthalene and the following moieties:

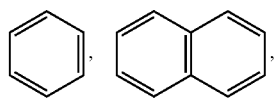

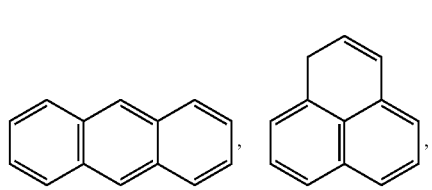

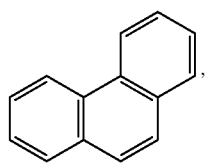

and the like.

Illustrative substituted aryls include:

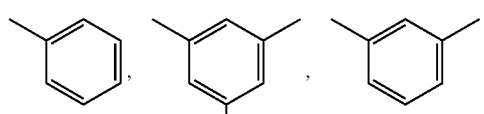

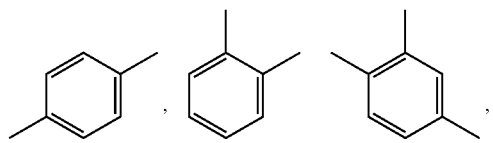

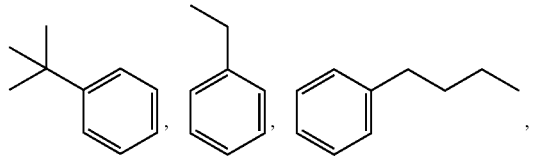

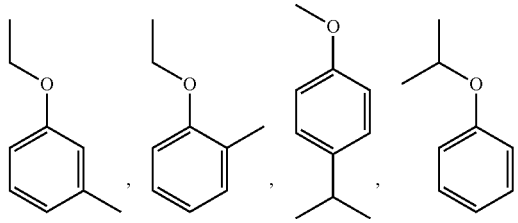

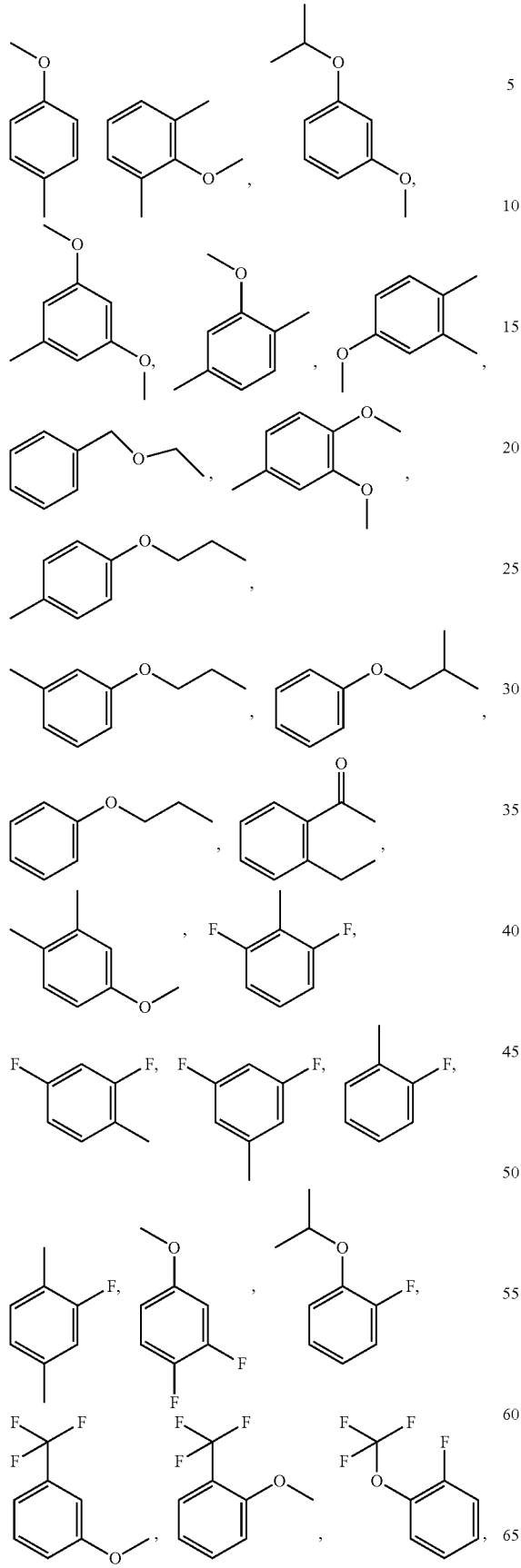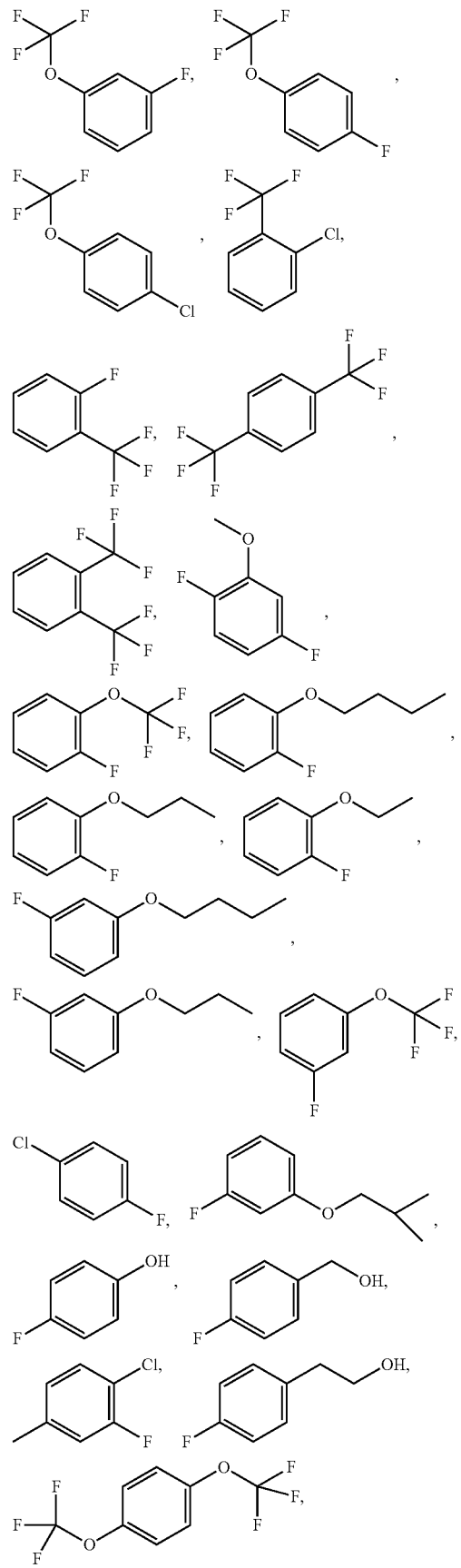

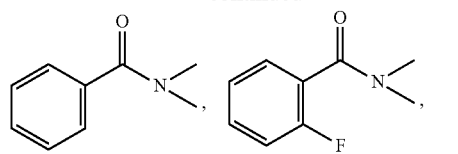
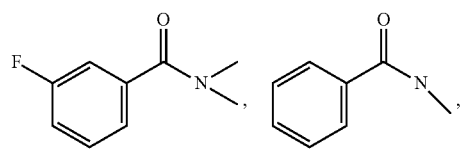
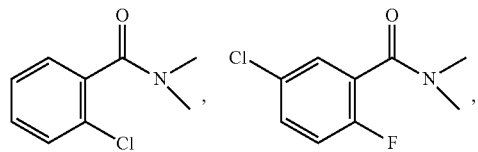
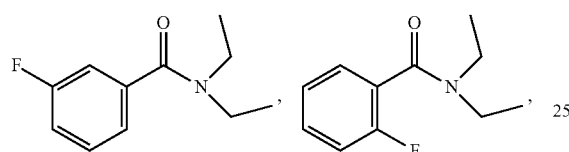
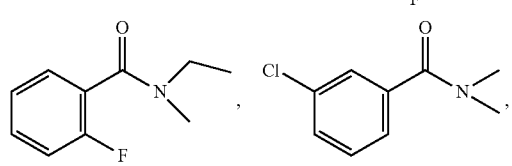
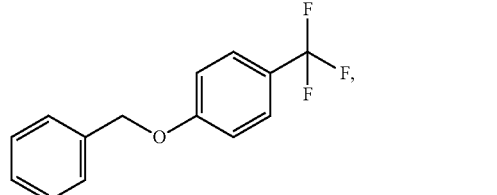
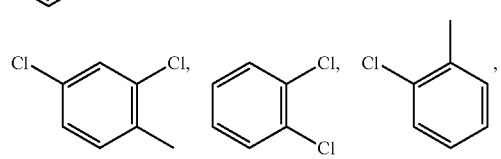
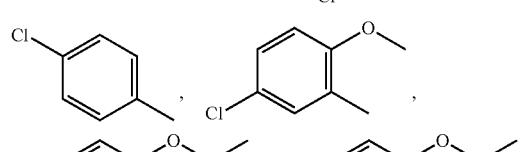
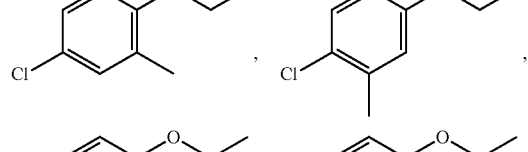
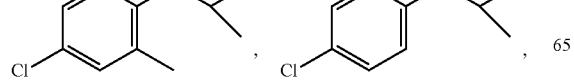
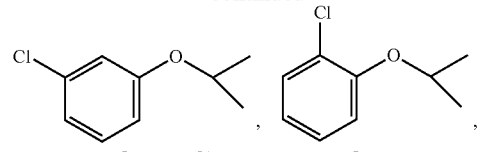
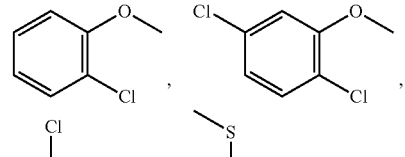
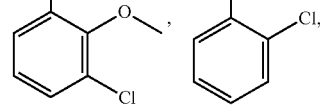
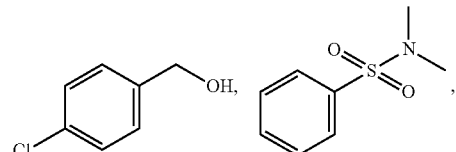
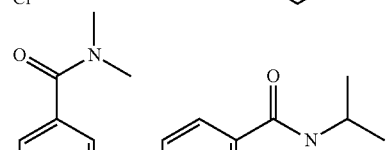
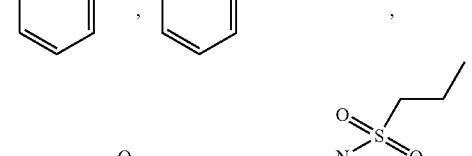
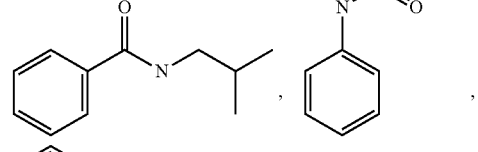
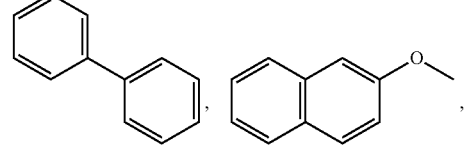
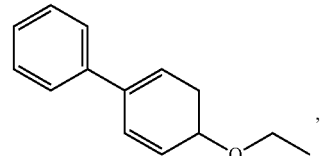
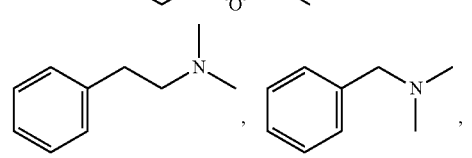
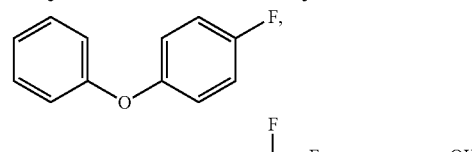
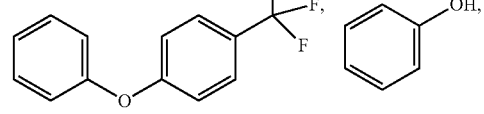

21
-continued
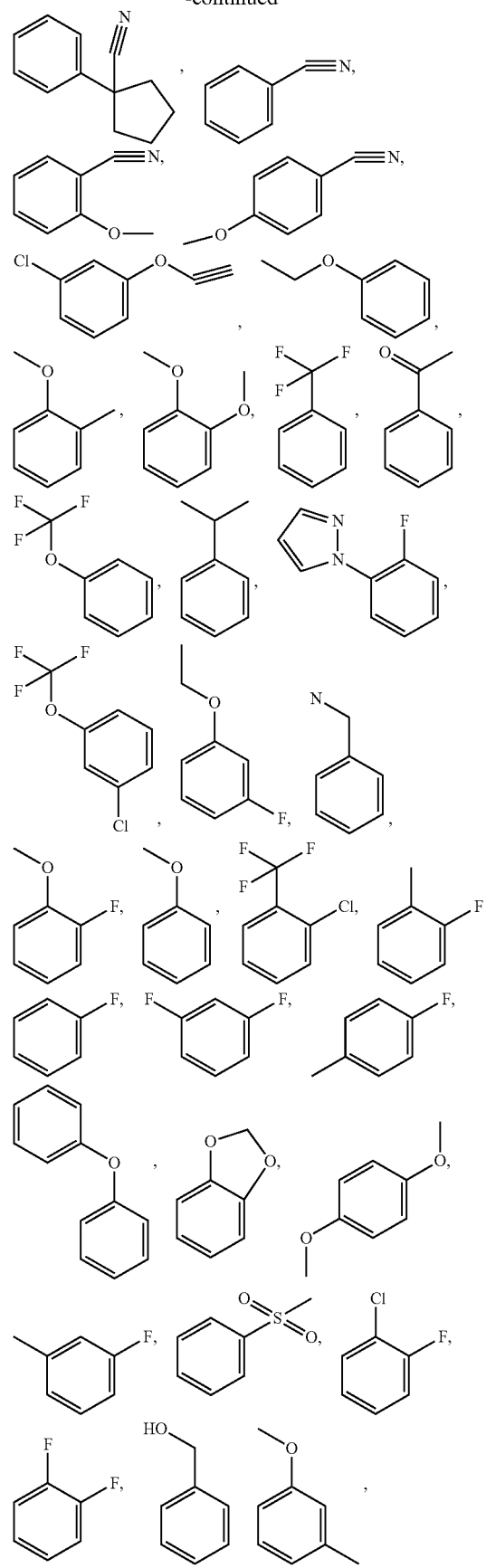
22
-continued
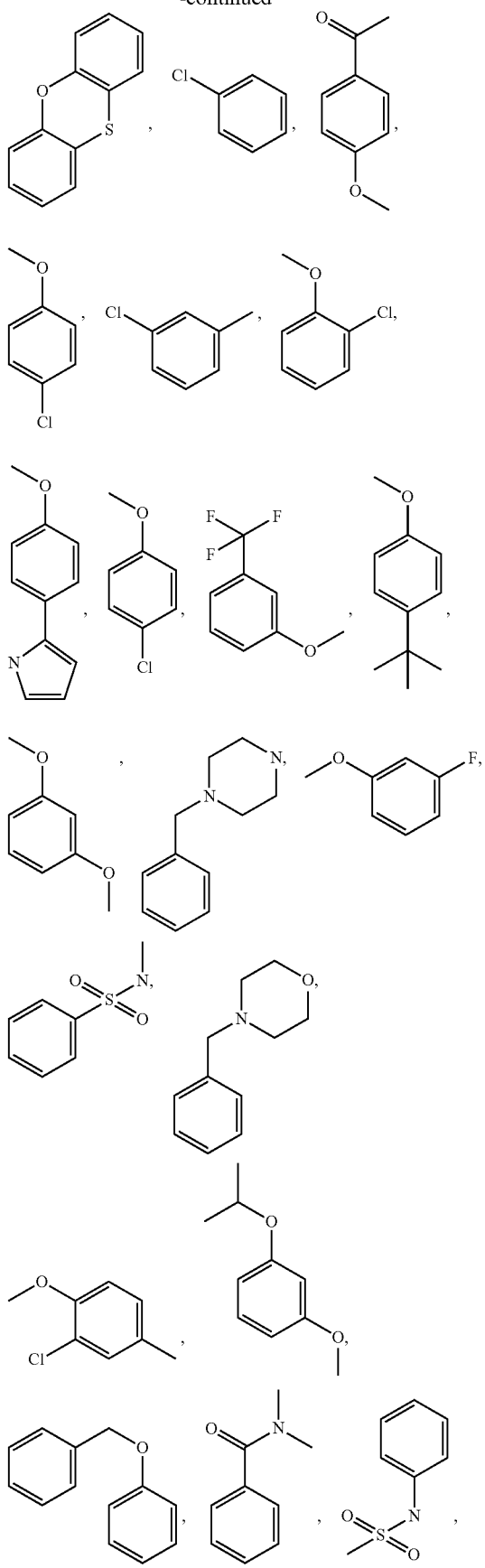

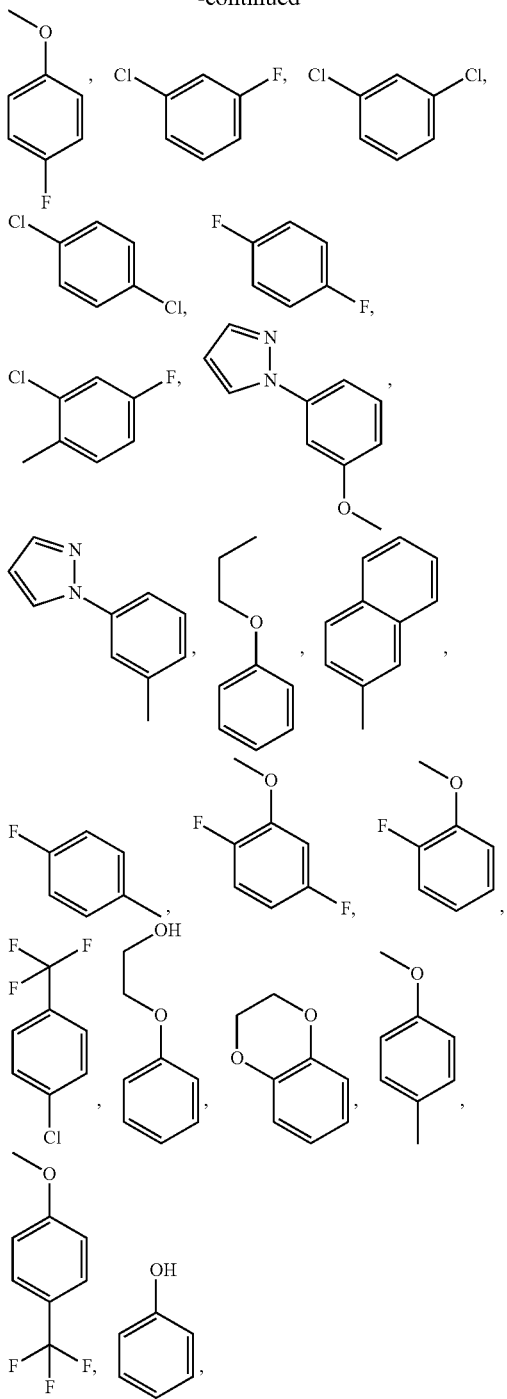

and the like.

As used herein, the term "heteroaryl" refers to a monocyclic, or fused polycyclic, aromatic heterocycle (ring structure having ring atoms selected from carbon atoms as well as nitrogen, oxygen, and/or sulfur atoms) having from 3 to 24 ring atoms per ring. The term "heteroaryl" as used herein also includes a monovalent aromatic radical of a 5-, 6-, or 7-membered ring and includes fused ring systems (at least one of which is aromatic) of 5-10 atoms containing at least one heteroatom independently selected from nitrogen, oxygen, and sulfur. Examples of heteroaryl groups include, but are not limited to pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups may be optionally substituted independently with one or more substituents described herein. 5 or 6 membered heteroaryl can be selected from the group consisting of optionally substituted pyridinyl, pyrimidinyl, thiazolyl, imidazolyl, oxazolyl, isoxazolyl, pyrazolyl, pyridinone and benzimidazolyl. In a certain embodiment, heteroaryl is bicyclic heteroaryl selected from benzothiazole, dihydronaphthyridine, dihydropyridopyrimidine, dihydropyrrolopyridine, furopyridine, imidazopyrazine, imidazopyrazole imidazopyridine, imidazopyrimidine, indazole, indole, isoquinoline, naphthyridine, pyrazolopyridine, pyrrolopyridine, tetrazolopyridine, tetrahydroimidazopyridine, tetrahydropyrazolopyridine, thiazolopyridine and thienopyridine. In a another embodiment, heteroaryl is bicyclic heteroaryl selected from 1H-pyrazolo [3,4-b]pyridine; 1,4,6,7-Tetrahydro-pyrazolo[4,3-c]pyridine; 7,8-Dihydro-5H-pyrido[4,3-d]pyrimidine; 5,7-Dihydro-pyrrolo[3,4-b]pyridine; 7,8-Dihydro-5H-[1,6] naphthyridine; 1,4,6,7-Tetrahydro-imidazo[4,5-c]pyridine; 1,8a-dihydroimidazo[1,2-a]pyridine; thieno[3,2-c]pyridine; 1H-imidazo[1,2-b]pyrazole; 1H-pyrazolo[3,4-b]pyridine; furo[2,3-c]pyridine; 1H-pyrazolo[3,4-b]pyridine; 1H-pyrrolo[3,2-c]pyridine; thieno[2,3-b]pyridine; imidazo[1,2-a] pyrimidine; furo[2,3-c]pyridine; isoquinoline; 1H-indazole; imidazo[1,2-a]pyridine; thieno[2,3-c]pyridine; furo[2,3-c] pyridine; 1H-pyrrolo[2,3-c]pyridine; imidazo[1,2-a]pyrazine; 1,3-benzothiazole; benzo[d]thiazole; 1H-pyrrolo[2,3-b]pyridine; [1,3]thiazolo[5,4-c]pyridine; [1,2,3,4]tetrazolo [1,5-a]pyridine; 1,5-naphthyridine; 1H-indole; 1H-imidazo [4,5-c]pyridine; and 1,6-naphthyridine.

By way of example and not limitation, carbon bonded heterocycles and heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Further examples of carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles and heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of an isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

The term "bicyclic heteroaryl" means a structure having atoms arranged in two rings fused together with at least two atoms common to each ring, and at least one of the rings being a heteroaryl ring. Illustrative examples of bicyclic heteroaryls include but are not limited to:

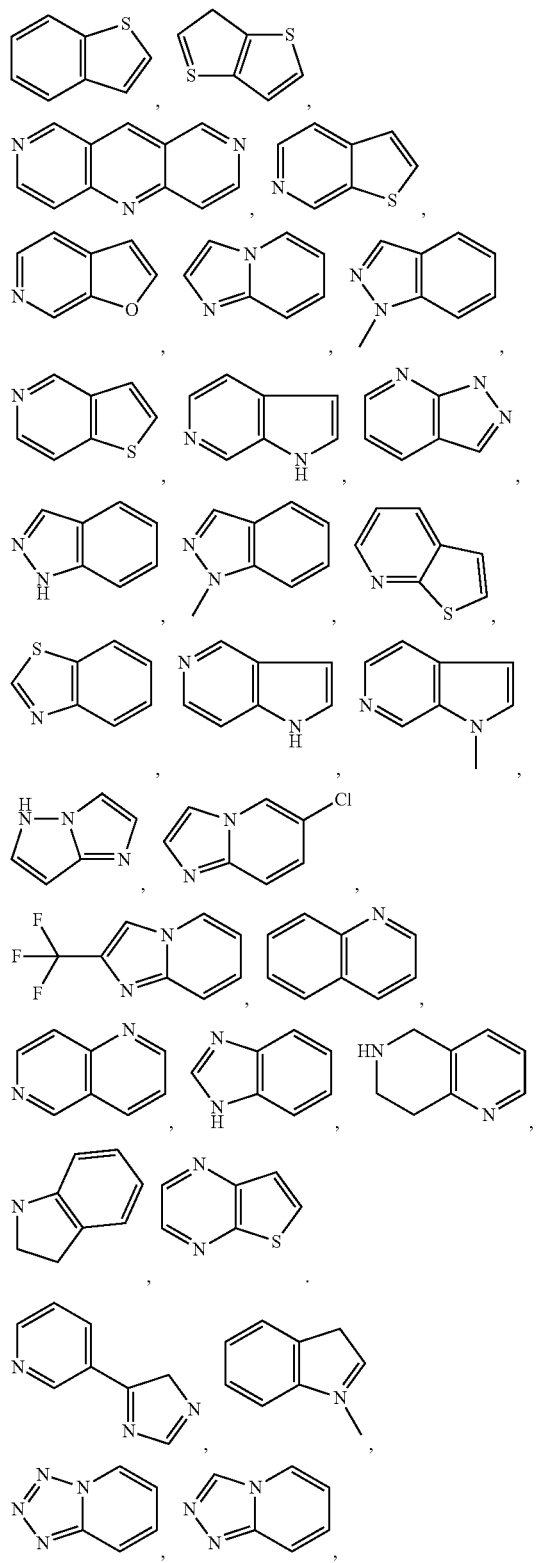

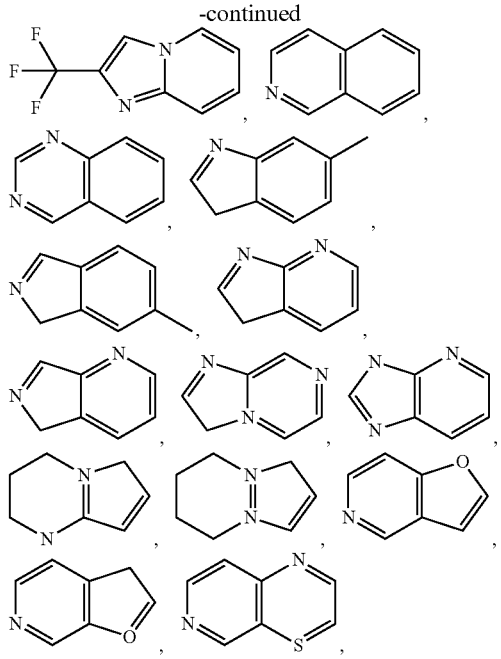

and the like.

Further examples of bicyclic heteroaryls include but are not limited to:

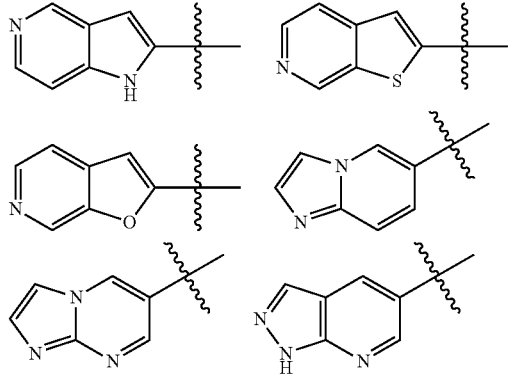

These bicyclic heteroaryl groups can be substituted as defined for R herein.

As used herein, the terms "cycloalkyl" and "cycloalkenyl" refers to a saturated or partially saturated, monocyclic or fused or spiro polycyclic, carbocycle having from 3 to 24 ring atoms per ring. Illustrative examples of cycloalkyl and "cycloalkenyl" groups include, but are not limited to, the following moieties:

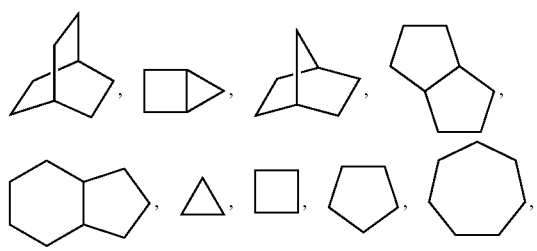

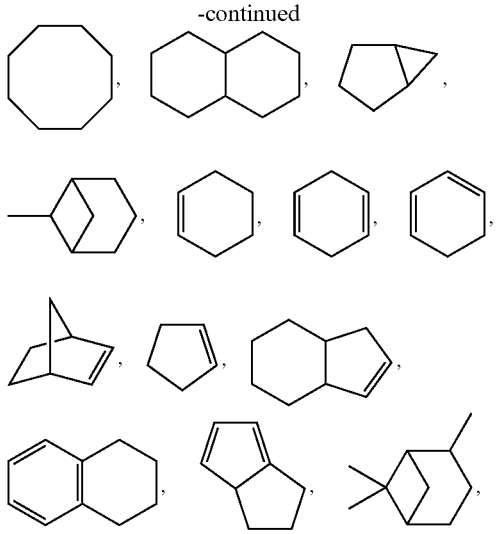

and the like.

As used herein, the term "heterocycloalkyl" refers to a monocyclic, or fused or spiro, polycyclic, ring structure that is saturated or partially saturated and has from 3 to 24 ring atoms per ring selected from C atoms and N, O, and/or S atoms. Illustrative examples of heterocycloalkyl and substituted heterocycloalkyl groups include, but are not limited to:

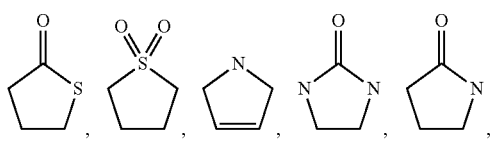

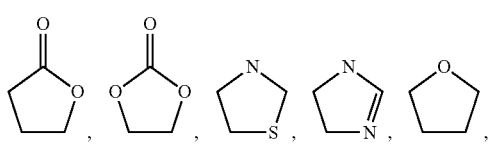

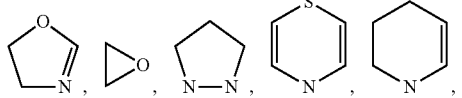

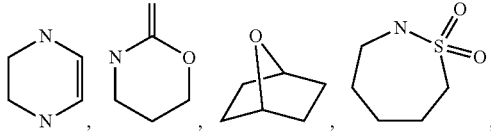

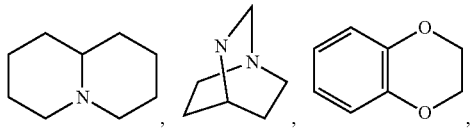

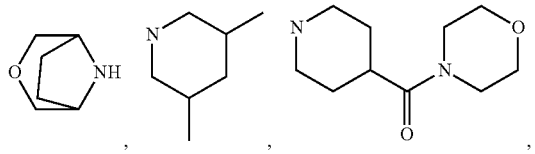

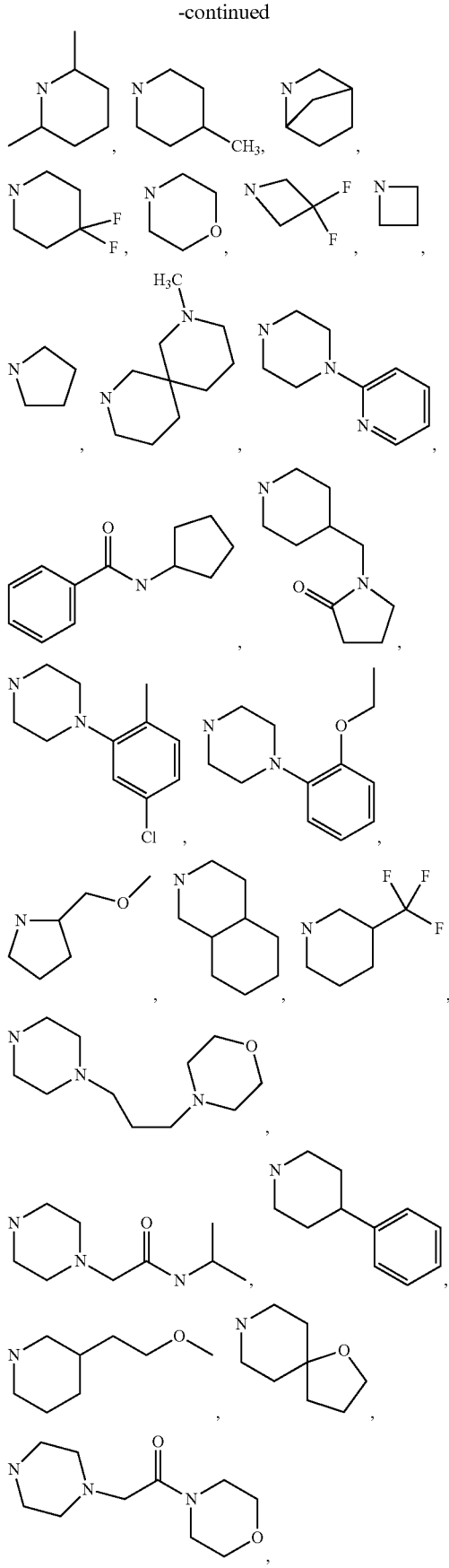

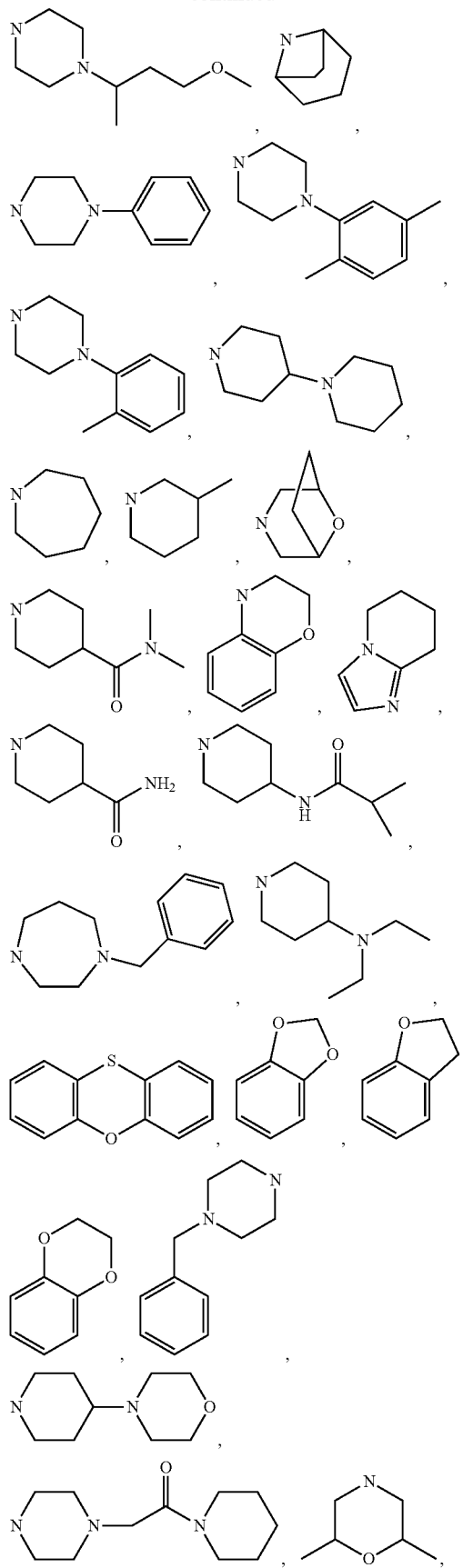
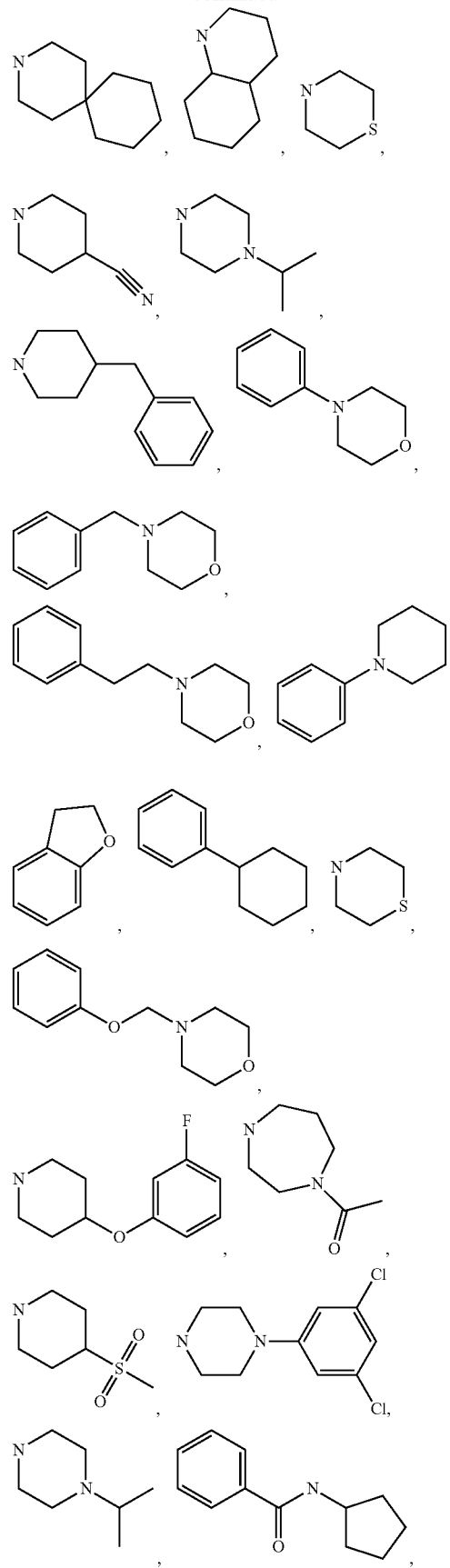

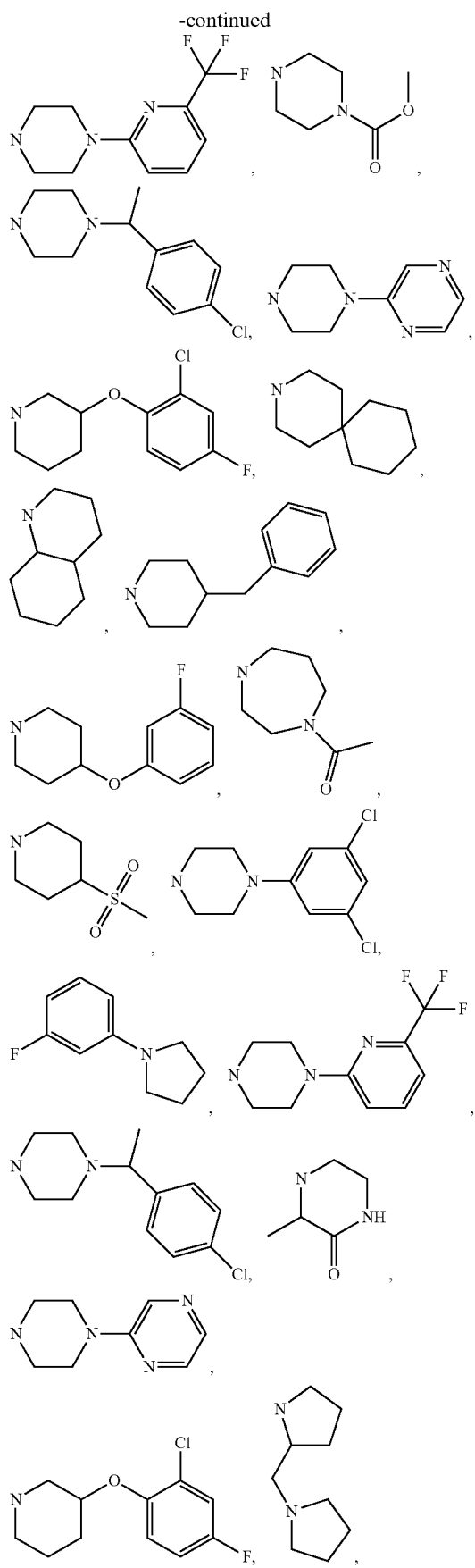
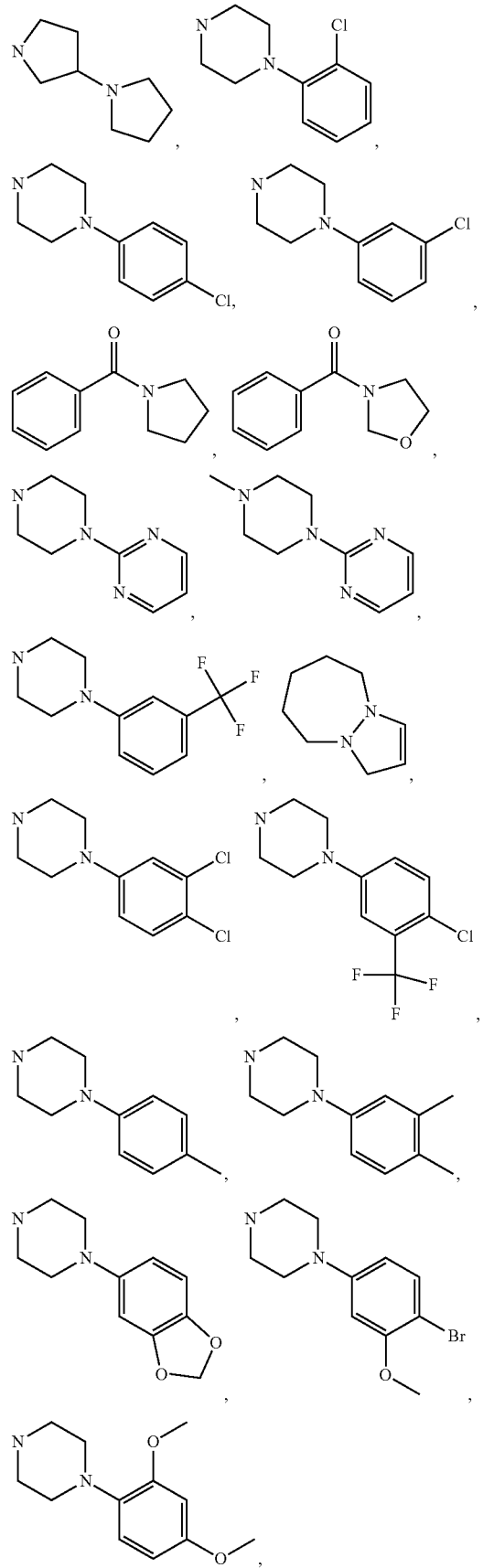

-continued

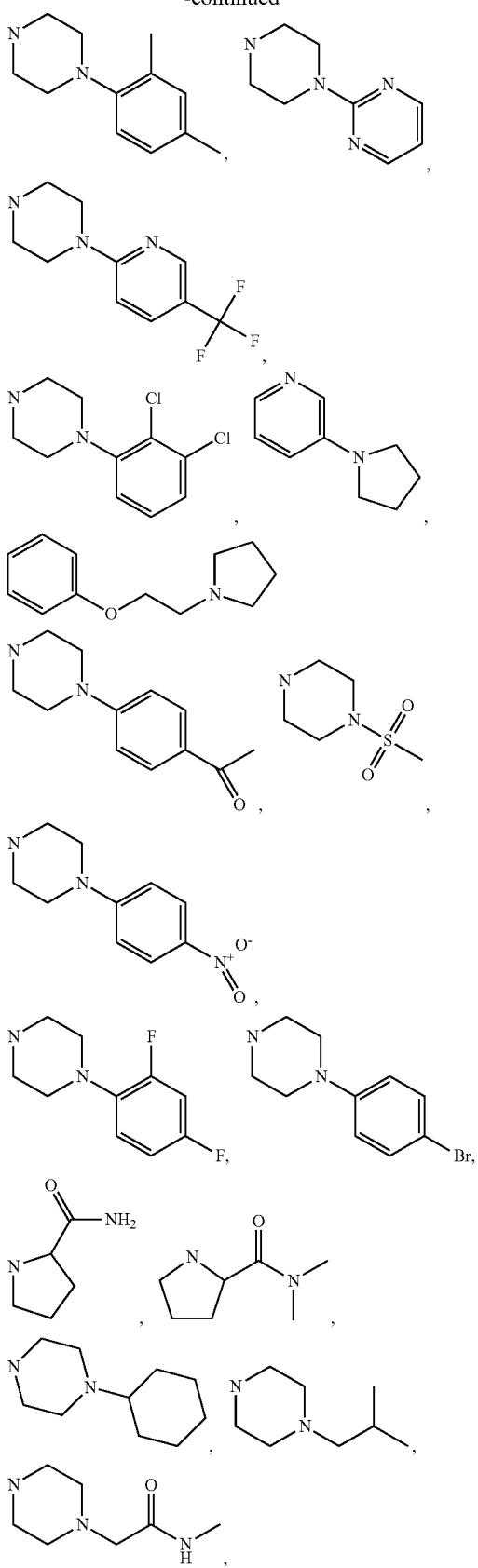

and the like.

Numerical ranges, as used herein, are intended to include sequential whole numbers. For example, a range expressed as "from 0 to 4" would include 0, 1, 2, 3 and 4.

As used herein, the term "substituted" means that the specified group or moiety bears one or more suitable substituents.

As used herein, the term "unsubstituted" means that the specified group bears no substituents.

As used herein, the term "optionally substituted" means that the specified group is unsubstituted or substituted by one or more substituents.

When a multifunctional moiety is shown, the point of attachment to the core is indicated by a line. For e.g. (cycloalkyloxy)alkyl- refers to alkyl being the point of attachment to the core while cycloalkyl is attached to alkyl via the oxy group.

The expression "adjunctive chemotherapeutic agent" generally refers to agents which treat, alleviate, relieve, or ameliorate the side effects of chemotherapeutic agents. Such agents include those which modify blood cell growth and maturation. Examples of adjunctive chemotherapeutic agents include, but are not limited to, filgrastim and erythropoietin. Other such adjunctive chemotherapeutic agents include those which inhibit nausea associated with administration of the chemotherapeutic agents, such as a 5-HT$_3$ receptor inhibitor (e.g., dolansetron, granisetron, or ondansetron), with or without dexamethasone.

The terms "chemotherapeutic agent" and "antineoplastic agent" generally refer to agents which treat, prevent, cure, heal, alleviate, relieve, alter, remedy, ameliorate, improve, or affect malignancies and their metastasis. Examples of such agents (also known as "antineoplastic agents") include, but are not limited to, prednisone, fluorouracil (e.g., 5-fluorouracil (5-FU)), anastrozole, bicalutamide, carboplatin, cisplatin, chlorambucil, cisplatin, carboplatin, docetaxel, doxorubicin, flutamide, interferon-alpha, letrozole, leuprolide, megestrol, mitomycin, oxaliplatin, paclitaxel, plicamycin (Mithracin™), tamoxifen, thiotepa, topotecan, valrubicin, vinblastine, vincristine, and any combination of any of the foregoing. Additional such agents are described later.

"Nicotinamide phosphoribosyltransferase" also named NAMPT, NMPRT, NMPRTase or NAmPRTase, (International nomenclature: E.C. 2.4.2.12) is a key enzyme in nicotinamide adenyl dinucleotide (NAD) biosynthesis from the natural precursor nicotinamide.

It must be noted that, as used in the specification and the appended claims, the singular forms "a," "an" and "the" include plural referents unless the context clearly dictates otherwise.

When used as a therapeutic agent the inhibitors of the formation of nicotinamide phosphoribosyltransferase (NAMPT) described herein may be administered with one or more physiologically acceptable excipients. A physiologically acceptable carrier or excipient is a formulation to which the compound can be added to dissolve it or otherwise facilitate its administration.

The dosage forms of the present invention, may contain a mixture of one or more compounds of this invention, and may include additional materials known to those skilled in the art as pharmaceutical excipients. Such pharmaceutical excipients include, for example, the following: Stabilizing additives may be incorporated into the delivery agent solution. With some drugs, the presence of such additives promotes the stability and dispersibility of the agent in solution. The stabilizing additives may be employed at a concentration ranging from about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. The preferred stabilizing additives are gum acacia, gelatin and methyl cellulose.

Acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Aerosol propellants (butane, dichlorodifluoro-methane, dichlorotetrafluoroethane, isobutane, propane, trichloromonofluoromethane); Air displacements (carbon dioxide, nitrogen); Alcohol denaturants (denatonium benzoate, methyl isobutyl ketone, sucrose octacetate); Alkalizing agents (strong ammonia solution, ammonium carbonate, diethanolamine, diisopropanolamine, potassium hydroxide, sodium bicarbonate, sodium borate, sodium carbonate, sodium hydroxide, trolamine); Anticaking agents (see glidant); Antifoaming agents (dimethicone, simethicone); Antimicrobial preservatives (benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Antioxidants (ascorbic acid, acorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Capsule lubricants (see tablet and capsule lubricant); Chelating agents (edetate disodium, ethylenediaminetetraacetic acid and salts, edetic acid); Coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcystalline wax, zein); Colorants (caramel, red, yellow, black or blends, ferric oxide); Complexing agents (ethylenediaminetetraacetic acid and salts (EDTA), edetic acid, gentisic acid ethanolmaide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, soritan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); Glidants and/or anticaking agents (calcium silicate, magnesium silicate, colloidal silicon dioxide, talc); Humectants (glycerin, hexylene glycol, propylene glycol, sorbitol); Plasticizers (castor oil, diacetylated monoglycerides, diethyl phthalate, glycerin, mono- and di-acetylated monoglycerides, polyethylene glycol, propylene glycol, triacetin, triethyl citrate); Polymers (e.g., cellulose acetate, alkyl celloloses, hydroxyalkylcelloloses, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methycellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); Tablet disintegrants (alginic acid, microcrystalline cellulose, croscarmellose sodium, corspovidone, polacrilin potassium, sodium starch glycolate, starch, pregelatinized starch); Tablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, seame oil, soybean oil, squalane); Vehicle: solid carrier (sugar spheres); Vehicle: sterile (bacteriostatic water for injection, bacteriostatic sodium chloride injection); Viscosity-increasing (see suspending agent); Water repelling agent (cyclomethicone, dimethicone, simethicone); and Wetting and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol). This list is not meant to be exclusive, but instead merely representative of the classes of excipients and the particular excipients which may be used in dosage forms of the present invention.

The compounds of the disclosed Formulas can form salts which are also within the scope of this invention. Reference to a compound of the Formulas herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the Formulas contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formulas may be formed, for example, by reacting a compound of Formulas with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, MD, on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the compounds of the invention are also considered to be part of the invention. Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$) acyl glycerol.

Prodrugs and solvates of the compounds of the invention are also contemplated herein. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g, a drug precursor) that is transformed in vivo to yield a compound of the instant Formulas or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the instant Formulas or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl) amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholine ($C_2$-$C_3$)alkyl, and the like.

Similarly, if a compound of the instant Formulas contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)

alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, $—P(O)(O(C_1-C_6)alkyl)_2$ or glycosyl (the radical resulting from the removal of a hydroxyl group of the hemiacetal form of a carbohydrate), and the like.

If a compound of the instant Formulas incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, $—C(OH)C(O)OY^1$ wherein $Y^1$ is H, $(C_1-C_6)$alkyl or benzyl, $—C(OY^2)Y^3$ wherein $Y^2$ is $(C_1-C_4)$ alkyl and $Y^3$ is $(C_1-C_6)$alkyl, carboxy$(C_1-C_6)$alkyl, amino$(C_1-C_4)$alkyl or mono-N— or di-N,N—$(C_1-C_6)$alkylaminoalkyl, $—C(Y^4)Y^5$ wherein $Y^4$ is H or methyl and $Y^5$ is mono-N— or di-N,N—$(C_1-C_6)$ alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, J. Pharmaceutical Sci., 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, AAPS Pharm Sci Tech., 5(1), article 12 (2004); and A. L. Bingham et al, Chem. Commun., 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Compounds of the various Formulas, and salts, solvates, esters and prodrugs thereof, may exist in their tautomeric form (for example, as an amide or imino ether). All such tautomeric forms are contemplated herein as part of the present invention.

The compounds of the various Formulas may contain asymmetric or chiral centers, and, therefore, exist in different stereoisomeric forms. It is intended that all stereoisomeric forms of the compounds of the various Formulas as well as mixtures thereof, including racemic mixtures, form part of the present invention. In addition, the present invention embraces all geometric and positional isomers. For example, if a compound of the various Formulas incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the various Formulas may be atropisomers (e.g., substituted biaryls) and are considered as part of this invention. Enantiomers can also be separated by use of chiral HPLC column.

It is also possible that the compounds of the various Formulas may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of the various Formulas incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of the various Formulas (e.g., those labelled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of the various Formulas can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of the various Formulas, and of the salts, solvates, esters and prodrugs of the compounds of the various Formulas, are intended to be included in the present invention.

Benefits of the present invention include oral administration of an optimal amount of a nicotinamide phosphoribosyltransferase biosynthesis inhibitor.

Benefits of the present invention include intravenous administration of an optimal amount of a nicotinamide phosphoribosyltransferase biosynthesis inhibitor.

Benefits of the present invention include intraperitoneal administration of an optimal amount of a nicotinamide phosphoribosyltransferase biosynthesis inhibitor.

Benefits of the present invention include intramural administration of an optimal amount of a nicotinamide phosphoribosyltransferase biosynthesis inhibitor.

Benefits of the present invention include intramuscular administration of an optimal amount of a nicotinamide phosphoribosyltransferase biosynthesis inhibitor.

Benefits of the present invention include subcutaneous administration of an optimal amount of a nicotinamide phosphoribosyltransferase biosynthesis inhibitor.

Benefits of the present invention include intra-tumor administration of an optimal amount of a nicotinamide phosphoribosyltransferase biosynthesis inhibitor.

Benefits of the present invention include intrathecal administration of an optimal amount of a nicotinamide phosphoribosyltransferase biosynthesis inhibitor.

Benefits of the present invention include subdural administration of an optimal amount of a nicotinamide phosphoribosyltransferase biosynthesis inhibitor.

Benefits of the present invention include periorbital administration of an optimal amount of a nicotinamide phosphoribosyltransferase biosynthesis inhibitor.

Based on these results, the present invention has important implications for the design of novel treatment strategies for patients with cancer, including leukemias and solid tumors, inflammatory diseases, osteoporosis, atherosclerosis; irritable bowel syndrome and other conditions disclosed herein or that are known to those skilled in the art.

DESCRIPTION OF THE PREFERRED EMBODIMENTS

An aspect of the present invention concerns compounds disclosed herein.

An aspect of the present invention concerns compounds which are or can be inhibitors of the formation of nicotinamide phosphoribosyltransferase.

An aspect of the present invention concerns the use of an inhibitor of the formation of nicotinamide phosphoribosyltransferase for the preparation of a medicament used in the treatment, prevention, inhibition or elimination of tumors.

An aspect of the present invention concerns the use of an inhibitor of the formation of nicotinamide phosphoribosyltransferase for the preparation of a medicament used in the treatment, prevention, inhibition or elimination of cancer.

An aspect of the present invention concerns the use of an inhibitor of the formation of nicotinamide phosphoribosyltransferase for the preparation of a medicament used in the treatment, prevention, inhibition or elimination of cancer, where the cancer is selected from leukemia, lymphoma, ovarian cancer, breast cancer, uterine cancer, colon cancer, cervical cancer, lung cancer, prostate cancer, skin cancer, CNS cancer, bladder cancer, pancreatic cancer and Hodgkin's disease.

The present invention also describes one or more methods of synthesizing the compounds of the present invention.

The invention also describes one or more uses of the compounds of the present invention.

The invention also describes one or more uses of the compounds of the present invention with an adjunctive agent such as use with TNF, GCSF, or other chemotherapeutic agents The invention also describes one or more uses of the pharmaceutical compositions of the present invention.

An aspect of the present invention concerns the use as an inhibitor of the formation of nicotinamide phosphoribosyltransferase for the preparation of a medicament used in the treatment of inflammatory diseases.

An aspect of the present invention concerns the use as an inhibitor of the formation of nicotinamide phosphoribosyltransferase for the preparation of a medicament used in the treatment of inflammatory diseases, such as Irritable Bowel Syndrome or Inflammatory Bowel Disease.

An aspect of the present invention concerns the use as an inhibitor of the formation of nicotinamide phosphoribosyltransferase for the preparation of a medicament used in the treatment of disease of the bone such as osteoporosis.

An aspect of the present invention concerns the use as an inhibitor of the formation of nicotinamide phosphoribosyltransferase for the preparation of a medicament used in the treatment of disease of the cardiovascular system, such as atherosclerosis.

An aspect of the present invention concerns the use as an inhibitor of the formation of nicotinamide phosphoribosyltransferase for the preparation of a medicament used in the treatment of disease or a condition caused by an elevated level of NAMPT.

Such disease or condition is one or more selected from the group consisting of cancer, ovarian cancer, breast cancer, uterine cancer, colon cancer, cervical cancer, lung cancer, prostate cancer, skin cancer, bladder cancer, pancreatic cancer, leukemia, lymphoma, Hodgkin's disease, viral infections, Human Immunodeficiency Virus, hepatitis virus, herpes virus, herpes simplex, inflammatory disorders, irritable bowel syndrome, inflammatory bowel disease, rheumatoid arthritis, asthma, chronic obstructive pulmonary disease, osteoarthritis, osteoporosis, dermatitis, atoptic dermatitis, psoriasis, systemic lupus erythematosis, multiple sclerosis, psoriatic arthritis, ankylosing spodylitis, graft-versus-host disease, Alzheimer's disease, cerebrovascular accident, atherosclerosis, diabetes, glomerulonephiritis, metabolic syndrome, non-small cell lung cancer, small cell lung cancer, multiple myeloma, leukemias, lymphomas, squamous cell cancers, kidney cancer, uretral and bladder cancers, cancers of head and neck, cancers of the brain and central nervous system (CNS).

The inventive compounds can be useful in the therapy of proliferative diseases such as, but not limited to cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease.

More specifically, the compounds can be useful in the treatment of a variety of cancers, including (but not limited to) the following: carcinoma, including that of the bladder, breast, colon, kidney, liver, lung, including small cell lung cancer, non-small cell lung cancer, head and neck, esophagus, gall bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

The compounds of the invention may induce or inhibit apoptosis.

The compounds of the invention may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

A further aspect of the invention is a method of inhibiting a NAMPT pathway in an animal, said method comprising administering to said animal a pharmaceutically acceptable amount of a compound of the invention to an animal in need thereof.

A further aspect of the invention is a pharmaceutical formulation comprising a compound of the invention.

Another embodiment of the invention comprises a pharmaceutical formulation of the invention, wherein the pharmaceutical formulation, upon administration to a human, results in a decrease in tumor burden.

Still another embodiment of the invention is a pharmaceutical formulation, further comprising one or more of an antineoplastic agent, a chemotherapeutic agent, or an adjunctive chemotherapeutic agent.

The pharmaceutical formulations of the invention may further comprise a therapeutic effective amount of an adjunctive chemotherapeutic agent.

The adjunctive chemotherapeutic agent may be an agent which modifies blood cell growth and maturation. Non-limiting examples of adjunctive chemotherapeutic agent are filgrastim, pegfilgrastim and erythropoietin.

The invention is also directed to a method of treating or preventing a disorder associated with excessive rate of growth of cells in a mammal comprising administering to the mammal an effective amount of the pharmaceutical formulation of the invention. Non-limiting examples of disorder include cancer or metastasis from malignant tumors.

Another aspect of the invention is a method of inhibiting tumor cell growth and rate of division in a mammal with cancer, or other disorder associated with abnormally dividing cells comprising administering to the mammal an effective amount of the pharmaceutical formulation of this invention.

Another embodiment of the invention is a method of treating bone pain due to excessive growth of a tumor or metastasis to bone in a mammal in need thereof comprising administering to the mammal an effective amount of the pharmaceutical formulation of this invention.

Still another embodiment of the invention is a method for administering a NAMPT-inhibitor-containing compound to a mammal in need thereof comprising administering to the mammal the pharmaceutical formulation of the invention. In one embodiment, the mammal is a human.

A further embodiment of the invention is a method of preparing a pharmaceutical formulation comprising mixing at least one pharmaceutically acceptable compound of the present invention, and, optionally, one or more pharmaceutically acceptable excipients or additives.

The invention is also directed to methods of synthesizing compounds of the present invention.

Compounds of the Invention

The invention is directed to compounds as described herein and pharmaceutically acceptable salts, solvates, esters, prodrugs or isomers thereof, and pharmaceutical compositions comprising one or more compounds as described herein and pharmaceutically acceptable salts or isomers thereof. The invention further relates to molecules which are useful in inhibiting the enzyme nicotinamide phosphoribosyltransferase (NAMPT) and pharmaceutically acceptable salts, solvates, esters, prodrugs or isomers thereof.

An aspect of this invention is the provision of compounds, compositions, kits, and antidotes for the NAMPT pathway in mammals having a compound of the Formula I:

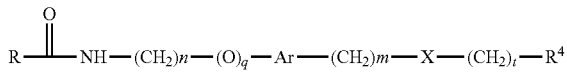

I wherein R is an aryl, heteroaryl, $C_3$-$C_8$ cycloalkyl, $C_3$-$C_8$ cycloalkenyl, heterocycloalkyl, arylalkyl-, (heteroaryl)alkyl-, ($C_3$-$C_8$ cycloalkyl)alkyl-, ($C_3$-$C_8$ cycloalkenyl)alkyl-, (heterocycloalkyl)alkyl-, (aryloxy)alkyl-, (heteroaryloxy)alkyl-, ($C_3$-$C_8$ cycloalkyloxy)alkyl-, ($C_3$-$C_8$ cycloalkenyloxy)alkyl- or (heterocycloalkyloxy)alkyl-, wherein the heteroatom of each of said heteroaryl and heterocycloalkyl numbers 1, 2 or 3, and is independently selected from N, S or O, further wherein each of said aryl, heteroaryl and heterocycloalkyl may independently be either substituted or fused with an aryl or heteroaryl, still further wherein any of said aryl, heteroaryl and heterocycloalkyl is either unsubstituted or optionally independently substituted with one or more substituents which can be the same or different and are independently selected from the group consisting of deuterium, halo, cyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, -alkyl, -alkenyl, -alkynyl, -alkoxy, hydroxyl, alkyl hydroxy, hydroxyl, alkyl hydroxy, or (alkoxyalkyl) amino-, —N(R$^3$)—C(O)-alkyl, —N(R$^3$)—C(O)-aryl, -cycloalkyl, -heterocycloalkyl, -aryl, and heteroaryl, with the proviso that no two adjacent ring heteroatoms are both S or both O;

Ar is aryl, heteroaryl, heterocycloalkyl or $C_3$ to $C_8$ cycloalkyl, with each of said aryl, heteroaryl, heterocycloalkyl and cycloalkyl being either unsubstituted or optionally independently substituted with 1, 2, 3 or 4 substituents which can be the same or different and are independently selected from the group consisting of deuterium, halo, cyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, -alkyl, -alkenyl, -alkynyl, -alkoxy, hydroxyl, -alkyl hydroxyl, aryloxy-, (alkoxyalkyl)amino-, —N(R$^3$)—C(O)-alkyl, —N(R$^3$)—C(O)-aryl, -cycloalkyl, -heterocloalkyl, -aryl, and -heteroaryl;

R$^4$ is cycloalkyl, —CH$_z$F$_{3-z}$, aryl, heterocycloalkyl, heteroaryl, alkyl, -alkenyl, -alkynyl, (aryl)alkyl-, (heteroaryl)alkyl- or (heterocycloalkyl)alkyl-, or

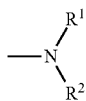

(i)

wherein each of said cycloalkyl, aryl, heterocycloalkyl, heteroaryl and alkyl is either unsubstituted or optionally substituted with 1, 2, 3, 4 or 5 substituents which can be the same or different and are independently selected from the group consisting of deuterium, halo, cyano, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, -alkyl, alkoxy-, -alkenyl, -alkynyl, aryloxy-, (alkoxyalkyl)amino-, -cycloalkyl, -heterocloalkyl, (heterocycloalkyl)alkyl-, -aryl, (aryl)alkyl-, -heteroaryl, (heteroaryl)alkyl-, —S(O)$_2$-alkyl, —S(O)$_2$-aryl, —S(O)$_2$—CF$_3$, —C(O)N(alkyl)$_2$, —C(O)alkyl, —N(R$^3$)—C(O)-alkyl, —N(R$^3$)—C(O)-aryl, —S(O$_2$)NH$_2$, —S(O$_2$)NH(alkyl), —S(O$_2$)N(alkyl)$_2$, —N(H)S(O$_2$)(alkyl), —C(O)N(H)(alkyl), and methylenedioxy, (ii) further wherein each of said cycloalkyl, aryl, heterocycloalkyl, and heteroaryl may optionally additionally be fused with independently selected aryl, heteroaryl, heterocycloalkyl or cycloalkyl;

R$^3$ is H, alkyl or arylalkyl-;
X is S, S(O), S(O)$_2$, O or C(O);
n is 1, 2, 3 or 4;
m is 0, 1, 2, 3 or 4;
q is 0 or 1;
t is 0, 1 or 2; and
z is 0, 1 or 2;
and pharmaceutically acceptable salts, solates, esters, prodrugs and isomers thereof.

In the compounds of Formula I, the various moieties are independently selected.

The following embodiments are directed to Formula I, as applicable. For any moieties that are not specifically defined, the previous definitions control. Further, the moieties aryl, heteroaryl, and heterocycloalkyl in these embodiments can be independently unsubstituted or optionally substituted or optionally fused as described earlier. Any one or more of the embodiments relating to Formula I below can be combined with one or more other embodiments of Formula I.

An embodiment of the invention is the provision of a compound of Formula I, where the various moieties are independently selected, R is aryl, and n, m, q, t, z, Ar, X, R$^4$ and R$^3$ are as defined.

An embodiment of the invention is the provision of a compound of Formula I, where the various moieties are independently selected, R is heteroaryl, and n, m, q, t, z, Ar, X, R$^4$ and R$^3$ are as defined.

An embodiment of the invention is the provision of a compound of Formula I where the various moieties are independently selected, Ar is aryl, and R, n, m, q, t, z, X, R$^4$ and R$^3$ are as defined.

An embodiment of the invention is the provision of a compound of Formula I, where the various moieties are independently selected, Ar is heteroaryl, and R, n, m, q, t, z, X, R$^4$ and R$^3$ are as defined.

An embodiment of the invention is the provision of a compound of Formula I, where the various moieties are independently selected, Ar, R, n, m, q, t, z, R$^4$ and R$^3$ are as defined and X is S.

An embodiment of the invention is the provision of a compound of Formula I, where the various moieties are independently selected, Ar, R, n, m, q, t, z, R$^4$ and R$^3$ are as defined and X is S(O).

An embodiment of the invention is the provision of a compound of Formula I, where the various moieties are independently selected, Ar, R, n, m, q, t, z, R$^4$ and R$^3$ are as defined and X is S(O$_2$).

An embodiment of the invention is the provision of a compound of Formula I, where the various moieties are independently selected, Ar, R, n, m, q, t, z, R$^4$ and R$^3$ are as defined and X is O.

An embodiment of the invention is the provision of a compound of Formula I, where the various moieties are independently selected, Ar, R, n, m, q, t, z, R$^4$ and R$^3$ are as defined and X is C(O).

An embodiment of the invention is the provision of a compound of Formula I, where the various moieties are independently selected, Ar, R, n, m, q, t, z, R$^4$ and R$^3$ are as defined and X is C(O).

An embodiment of the invention is the provision of a compound of Formula I, where the various moieties are independently selected, Ar, R, n, m, q, t, z, R$^4$ and X are as defined and R$^3$ is H.

An embodiment of the invention is the provision of a compound of Formula I, where the various moieties are independently selected, Ar, R, n, m, q, t, z, R$^4$ and X are as defined and R$^3$ is alkyl.

An embodiment of the invention is the provision of a compound of Formula I, where the various moieties are independently selected, Ar, R, n, m, q, t, z, R$^4$ and X are as defined and R$^3$ is arylalkyl.

An embodiment of the invention is the provision of a compound of Formula I, where the various moieties are independently selected, Ar, R, n, m, q, t, z, R$^3$ and X are as defined and R$^4$ is aryl.

An embodiment of the invention is the provision of a compound of Formula I, where the various moieties are independently selected, Ar, R, n, m, q, t, z, R$^3$ and X are as defined and R$^4$ is heteroaryl.

An embodiment of the invention is the provision of a compound of Formula I, where the various moieties are independently selected, Ar, R, n, m, q, t, z, R$^3$ and X are as defined and R$^4$ is heterocycloalkyl.

An embodiment of the invention is the provision of a compound of Formula I, where the various moieties are independently selected, R is aryl, R$^4$ is heteroaryl, and n, m, q, t, z, Ar, R$^3$ and X are as defined.

An embodiment of the invention is the provision of a compound of Formula I, where the various moieties are independently selected, R is aryl, R$^4$ is aryl, and n, m, q, t, z, Ar, R$^3$ and X are as defined.

An embodiment of the invention is the provision of a compound of Formula I, where the various moieties are independently selected, R is heteroaryl, $R^4$ is heteroaryl, and n, m, q, t, z, Ar, $R^3$ and X are as defined.

An embodiment of the invention is the provision of a compound of Formula I, where the various moieties are independently selected, R is heteroaryl, $R^4$ is aryl, and n, m, q, t, z, Ar, $R^3$ and X are as defined.

An embodiment of the invention is the provision of a compound of Formula I, where the various moieties are independently selected, R is phenyl, $R^1$ is heteroaryl, and n, m, q, t, z, Ar, $R^3$ and X are as defined.

An embodiment of the invention is the provision of a compound of Formula I, where the various moieties are independently selected, R is phenyl, $R^4$ is aryl, and n, m, q, t, $R^1$, $R^3$ z, and Ar are as defined.

An embodiment of the invention is the provision of a compound of Formula I, where the various moieties are independently selected, R is heteroaryl, $R^4$ is phenyl, and n, m, q, t, z, Ar, $R^3$ and X are as defined.

An embodiment of the invention is the provision of a compound of Formula I, where the various moieties are independently selected, R is pyrrolopyridinyl, $R^4$ is phenyl, and n, m, q, t, Ar, z, $R^3$ and X are as defined.

An embodiment of the invention is the provision of a compound of Formula I, where the various moieties are independently selected, R is oxadiazolyl, $R^4$ is phenyl, and n, m, q, t, Ar, z, $R^3$ and X are as defined.

An embodiment of the invention is the provision of a compound of Formula I, where the various moieties are independently selected, R is oxadiazolyl (substituted with pyridinyl), $R^4$ is phenyl, and n, m, q, t, z, Ar, $R^3$ and X are as defined.

An embodiment of the invention is the provision of a compound of Formula I, where the various moieties are independently selected, R is pyrazolyl, $R^4$ is phenyl, and n, m, q, t, z, Ar, $R^3$ and X are as defined.

An embodiment of the invention is the provision of a compound of Formula I, where the various moieties are independently selected, R is pyrazolyl (substituted with pyridinyl), $R^4$ is phenyl, and n, m, q, t, z, Ar, $R^3$ and X are as defined.

An embodiment of the invention is the provision of a compound of Formula I, where the various moieties are independently selected, R is imidazolyl, $R^4$ is phenyl, and n, m, q, t, Ar, z, $R^3$ and X are as defined.

An embodiment of the invention is the provision of a compound of Formula I, where the various moieties are independently selected, R is triazolopyridinyl, $R^4$ is phenyl, and n, m, q, t, z, Ar, $R^3$ and X are as defined.

An embodiment of the invention is the provision of a compound of Formula I, where the various moieties are independently selected, R is naphthyridinyl, $R^4$ is phenyl, and n, m, q, t, z, Ar, $R^3$ and X are as defined.

An embodiment of the invention is the provision of a compound of Formula I, where the various moieties are independently selected, R is tetrazolopyridinyl, $R^4$ is phenyl, and n, m, q, t, z, Ar, $R^3$ and X are as defined.

An embodiment of the invention is the provision of a compound of Formula I, where the various moieties are independently selected, R is isoquinolinyl, $R^4$ is phenyl, and n, m, q, t, Ar, $R^3$ z, and X are as defined.

An embodiment of the invention is the provision of a compound of Formula I, where the various moieties are independently selected, R is quinolinyl, $R^4$ is phenyl, and n, m, q, t, Ar, z, $R^3$ and X are as defined.

An embodiment of the invention is the provision of a compound of Formula I, where the various moieties are independently selected, R is imidazopyrazinyl, $R^4$ is phenyl, and n, m, q, t, z, Ar, $R^3$ and X are as defined.

An embodiment of the invention is the provision of a compound of Formula I, where the various moieties are independently selected, R is quinazolinyl, $R^4$ is phenyl, and n, m, q, t, z, Ar, $R^3$ and X are as defined.

An embodiment of the invention is the provision of a compound of Formula I, where the various moieties are independently selected, R is benzothiazolyl, $R^4$ is phenyl, and n, m, q, t, z, Ar, $R^3$ and X are as defined.

An embodiment of the invention is the provision of a compound of Formula I, where the various moieties are independently selected, R is thienopyridinyl, $R^4$ is phenyl, and n, m, q, t, z, Ar, $R^3$ and X are as defined.

An embodiment of the invention is the provision of a compound of Formula I, where the various moieties are independently selected, R is pyrrolopyridinyl, $R^4$ is thiophenyl, and n, m, q, z, t, Ar, $R^3$ and X are as defined.

An embodiment of the invention is the provision of a compound of Formula I, where the various moieties are independently selected, R is oxadiazolyl, $R^4$ is naphthalinyl, and n, m, q, t, z, Ar, $R^3$ and X are as defined.

An embodiment of the invention is the provision of a compound of Formula I, where the various moieties are independently selected, R is oxadiazolyl (substituted with pyridinyl), $R^4$ is quinolinyl, and n, m, q, z, t, Ar, $R^3$ and X are as defined.

An embodiment of the invention is the provision of a compound of Formula I, where the various moieties are independently selected, R is pyrazolyl, $R^4$ is isoquinolinyl, and n, m, q, t, z, Ar, $R^3$ and X are as defined.

An embodiment of the invention is the provision of a compound of Formula I, where the various moieties are independently selected, R is pyrazolyl (substituted with pyridinyl), $R^4$ is benzodioxinyl, and n, m, q, t, z, Ar, $R^3$ and X are as defined.

An embodiment of the invention is the provision of a compound of Formula I, where the various moieties are independently selected, R is imidazolyl, $R^4$ is phenoxathiinyl, and n, m, q, t, z, Ar, $R^3$ and X are as defined.

An embodiment of the invention is the provision of a compound of Formula I, where the various moieties are independently selected, R is pyrrolopyridinyl, $R^4$ is phenyl, Ar is phenyl, and n, m, q, t, z, $R^3$ and X are as defined.

An embodiment of the invention is the provision of a compound of Formula I, where the various moieties are independently selected, R is oxadiazolyl, $R^4$ is phenyl, Ar is phenyl, and n, m, q, t, z, $R^3$ and X are as defined.

An embodiment of the invention is the provision of a compound of Formula I d, where the various moieties are independently selected, R is oxadiazolyl (substituted with pyridinyl), $R^4$ is phenyl, Ar is phenyl, and n, m, z, q, t, $R^3$ and X are as defined.

An embodiment of the invention is the provision of a compound of Formula I, where the various moieties are independently selected, R is pyrazolyl, $R^4$ is phenyl, Ar is phenyl, and n, m, q, t, z, $R^3$ and X are as defined.

An embodiment of the invention is the provision of a compound of Formula I, where the various moieties are independently selected, R is pyrazolyl (substituted with pyridinyl), $R^4$ is phenyl, Ar is phenyl, and n, m, q, z, t, $R^3$ and X are as defined.

An embodiment of the invention is the provision of a compound, where the various moieties are independently selected, R is imidazolyl, $R^4$ is phenyl, Ar is phenyl, and n, m, q, t, z, $R^3$ and X are as defined.

An embodiment of the invention is the provision of a compound of Formula I, where the various moieties are independently selected, R is triazolopyridinyl, $R^4$ is phenyl, Ar is phenyl, and n, m, q, t, z, $R^3$ and X are as defined.

An embodiment of the invention is the provision of a compound of Formula I, where the various moieties are independently selected, R is naphthyridinyl, $R^4$ is phenyl, Ar is phenyl, and n, m, q, t, z, $R^3$ and X are as defined.

An embodiment of the invention is the provision of a compound of Formula I, where the various moieties are independently selected, R is tetrazolopyridinyl, $R^4$ is phenyl, Ar is phenyl, and n, m, q, t, z, $R^3$ and X are as defined.

An embodiment of the invention is the provision of a compound of Formula I, where the various moieties are independently selected, R is isoquinolinyl, $R^4$ is phenyl, Ar is phenyl, and n, m, q, t, z, $R^3$ and X are as defined.

An embodiment of the invention is the provision of a compound of Formula I, where the various moieties are independently selected, R is quinolinyl, $R^4$ is phenyl, Ar is phenyl, and n, m, q, t, z, $R^3$ and X are as defined.

An embodiment of the invention is the provision of a compound of Formula I, where the various moieties are independently selected, R is imidazopyrazinyl, $R^4$ is phenyl, Ar is phenyl, and n, m, q, t, z, $R^3$ and X are as defined.

An embodiment of the invention is the provision of a compound of Formula I, where the various moieties are independently selected, R is quinazolinyl, $R^4$ is phenyl, Ar is phenyl, and n, m, q, t, z, $R^3$ and X are as defined.

An embodiment of the invention is the provision of a compound of Formula I, where the various moieties are independently selected, R is benzothiazolyl, $R^4$ is phenyl, Ar is phenyl, and n, m, q, t, z, $R^3$ and X are as defined.

An embodiment of the invention is the provision of a compound of Formula I, where the various moieties are independently selected, R is thienopyridinyl, $R^4$ is phenyl, Ar is phenyl, and n, m, q, t, z, $R^3$ and X are as defined.

An embodiment of the invention is the provision of a compound of Formula I, where the various moieties are independently selected, R is pyrrolopyridinyl, $R^4$ is phenyl, Ar is phenyl, n is 1, m is 1, q is 0, t is 0, z is 0, $R^3$ and X are as defined.

An embodiment of the invention is the provision of a compound of Formula I, where the various moieties are independently selected, R is oxadiazolyl, $R^4$ is phenyl, Ar is phenyl, n is 1, m is 1, q is 0, t is 0, z is 0, $R^3$ and X are as defined.

An embodiment of the invention is the provision of a compound of Formula I, where the various moieties are independently selected, R is oxadiazolyl (substituted with pyridinyl), $R^4$ is phenyl, Ar is phenyl, n is 1, m is 1, q is 0, t is 0, z is 0, $R^3$ and X are as defined.

An embodiment of the invention is the provision of a compound of Formula I, where the various moieties are independently selected, R is pyrazolyl, $R^4$ is phenyl, Ar is phenyl, n is 1, m is 1, q is 0, t is 0, z is 0, $R^3$ and X are as defined.

An embodiment of the invention is the provision of a compound of Formula I where the various moieties are independently selected, R is pyrazolyl (substituted with pyridinyl), $R^4$ is phenyl, Ar is phenyl, n is 1, m is 1, q is 0, t is 0, z is 0, $R^3$ and X are as defined.

An embodiment of the invention is the provision of a compound of Formula I, where the various moieties are independently selected, R is imidazolyl, $R^4$ is phenyl, Ar is phenyl, n is 1, m is 1, q is 0, t is 0, z is 0, $R^3$ and X are as defined.

An embodiment of the invention is the provision of a compound of Formula I, where the various moieties are independently selected, R is triazolopyridinyl, $R^4$ is phenyl, Ar is phenyl, n is 1, m is 1, q is 0, t is 0, z is 0, $R^3$ and X are as defined.

An embodiment of the invention is the provision of a compound of Formula I, where the various moieties are independently selected, R is naphthyridinyl, $R^4$ is phenyl, Ar is phenyl, n is 1, m is 1, q is 0, t is 0, z is 0, $R^3$ and X are as defined.

An embodiment of the invention is the provision of a compound of Formula I, where the various moieties are independently selected, R is tetrazolopyridinyl, $R^4$ is phenyl, Ar is phenyl, n is 1, m is 1, q is 0, t is 0, z is 0, $R^3$ and X are as defined.

An embodiment of the invention is the provision of a compound of Formula I, where the various moieties are independently selected, R is isoquinolinyl, $R^4$ is phenyl, Ar is phenyl, n is 1, m is 1, q is 0, t is 0, z is 0, $R^3$ and X are as defined.

An embodiment of the invention is the provision of a compound of Formula I, where the various moieties are independently selected, R is quinolinyl, $R^4$ is phenyl, Ar is phenyl, n is 1, m is 1, q is 0, t is 0, z is 0, $R^3$ and X are as defined.

An embodiment of the invention is the provision of a compound of Formula I, where the various moieties are independently selected, R is imidazopyrazinyl, $R^4$ is phenyl, Ar is phenyl, n is 1, m is 1, q is 0, t is 0, z is 0, $R^3$ and X are as defined.

An embodiment of the invention is the provision of a compound of Formula I, where the various moieties are independently selected, R is quinazolinyl, $R^4$ is phenyl, Ar is phenyl, n is 1, m is 1, q is 0, t is 0, z is 0, $R^3$ and X are as defined.

An embodiment of the invention is the provision of a compound of Formula I, where the various moieties are independently selected, R is benzothiazolyl, $R^4$ is phenyl, Ar is phenyl, n is 1, m is 1, q is 0, t is 0, z is 0, $R^3$ and X are as defined.

An embodiment of the invention is the provision of a compound of Formula I, where the various moieties are independently selected, R is thienopyridinyl, $R^4$ is phenyl, Ar is phenyl, n is 1, m is 1, q is 0, t is 0, z is 0, $R^3$ and X are as defined.

Another aspect of the invention are the compounds of Formula I, where q=0, m=0, t=0, Ar=A, X=Q and R4 is

and the formula is now Formula IB

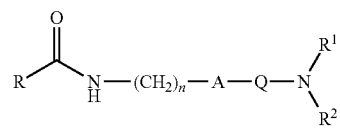

IB wherein
R and $R^3$ are as defined in Formula I;
$R^1$ and $R^2$ are the same or they are different, and are independently selected from H, a straight or branched $C_1$ to $C_7$ alkyl, straight or branched $C_1$ to $C_7$ alkoxy, straight or branched $C_1$ to $C_4$ hydroxyalkyl, aryl, heteroaryl, heterocycloalkyl and cycloalkyl, and wherein heteroatoms of said heteroaryl and heterocycloalkyl are independently selected from one or more N, O and S, with the proviso that no two adjacent ring heteroatoms are both S or both O, further wherein $R^1$ and $R^2$ can be either unsubstituted or optionally independently substituted with one or more substituents which can be the same or different and are independently selected from the group consisting of deuterium, halo, cyano, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, -alkyl, -alkenyl, -alkynyl, hydroxyalkyl-, -alkoxy, hydroxyl, alkyl hydroxy, carboxy, (alkoxyalkyl) amino-, -alkylamine, aminocarbonyl-, —CHO, —N($R^3$)—C(O)-alkyl, —N($R^3$)—C(O)-aryl, -cycloalkyl, -heterocycloalkyl, -aryl, and heteroaryl;

A is aryl, heteroaryl, heterocycloalkyl or $C_3$ to $C_8$ cycloalkyl, with each of said aryl, heteroaryl, heterocycloalkyl and cycloalkyl being either unsubstituted or optionally independently substituted with 1, 2, 3 or 4 substituents which can be the same or different and are independently selected from the group consisting of deuterium, halo, cyano, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, -alkyl, -alkenyl, -alkynyl, -alkoxy, hydroxyl, -alkyl hydroxyl, aryloxy-, (alkoxyalkyl)amino-, —N($R^3$)—C(O)-alkyl, —N($R^3$)—C(O)-aryl, -cycloalkyl, -heterocycloalkyl, -aryl, and -heteroaryl;

Q is C(O), S(O), S(O)$_2$, —N(H)—C(O)—, —S(O$_2$)—NH—, or —N(H)—S(O$_2$)—;

n is 0, 1, 2, 3 or 4; and z is 0, 1 or 2;

and pharmaceutically acceptable salts, solvates, esters, prodrugs or isomers thereof.

Another embodiment of Formula IB are compounds of Formula IC

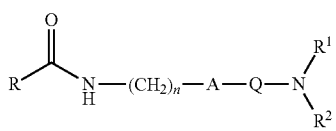

IC wherein

R, A, Q, $R^3$, z and n are as defined in Formula IB, and $R^1$ and $R^2$ are joined together to form, along with the N they are shown attached to in the formula, a $C_3$-$C_8$ heterocycloalkyl, a $C_3$-$C_8$ heterocycloalkenyl, a fused bicyclic heterocycloalkyl, a fused tricyclic heterocycloalkyl, spiroheterocycloalkyl, or a heterospiroheterocycloalkyl, wherein each of said heterocycloalkyl, heterocycloalkenyl, spiroheterocycloalkyl, and heterospiroheterocycloalkyl can optionally contain one or more heteroatoms in addition to the N atom they are shown attached to in the formula, said heteroatoms being selected from N, S and O, with the proviso that no two adjacent ring heteroatoms are both S or both O, further wherein each of said heterocycloalkyl and heterocycloalkenyl can be either unsubstituted or optionally independently substituted with one or more substituents which can be the same or different and are independently selected from the group consisting of deuterium, halo, cyano, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, -alkyl, -alkenyl, -alkynyl, hydroxyalkyl, -alkoxy, hydroxyl, -alkyl hydroxy, carboxy, (alkoxyalkyl) amino-, -alkylamine, aminocarbonyl-, —CHO, —N($R^3$)—C(O)-alkyl, —N($R^3$)—C(O)-aryl, -cycloalkyl, -heterocycloalkyl, -aryl, and heteroaryl;

and pharmaceutically acceptable salts thereof.

In the compounds of Formulas IB and C the various moieties are independently selected.

The following embodiments are directed to Formula IB and C, as applicable. For any moieties that are not specifically defined, the previous definitions control. Further, the moieties aryl, heteroaryl, heterocycloalkyl, cycloalkyl, cycloalkenyl and heterocycloalkenyl in these embodiments can be independently unsubstituted or optionally substituted or optionally fused as described earlier. Any one or more of the embodiments relating to Formula IB and IC below can be combined with one or more other embodiments for Formula IB and IC.

An embodiment of the invention is the provision of a compound of Formulas IB and IC, where the various moieties are independently selected, R is aryl, and n, A, Q and $R^1$ and $R^2$ are as defined.

Another embodiment of the invention is the provision of a compound of Formulas IB and IC where the various moieties are independently selected, R is heteroaryl, and n, A, Q and $R^1$ and $R^2$ are as defined.

Another embodiment of the invention is the provision of a compound of Formulas IB and IC, the various moieties are independently selected, R is $C_3$-$C_8$ cycloalkyl, and n, A, Q and R1 and $R^2$ are as defined.

Another embodiment of the invention is the provision of a compound of Formula IB and IC, where the various moieties are independently selected, R is $C_3$-$C_8$ cycloalkenyl, and n, A, Q and $R^1$ and $R^2$ are as defined.

Another embodiment of the invention is the provision of a compound of Formula IB and IC, where the various moieties are independently selected, R is heterocycloalkyl, and n, A, Q and $R^1$ and $R^2$ are as defined.

Another embodiment of the invention is the provision of a compound of Formula IB and IC, where the various moieties are independently selected, R is arylalkyl, and n, A, Q and $R^1$ and $R^2$ are as defined.

Another embodiment of the invention is the provision of a compound of Formula IB and IC, where the various moieties are independently selected, R is (heteroaryl)alkyl, and n, A, Q and $R^1$ and $R^2$ are as defined.

Another embodiment of the invention is the provision of a compound of Formula IB and IC where the various moieties are independently selected, R is ($C_3$-$C_8$ cycloalkyl) alkyl, and n, A, Q and $R^1$ and $R^2$ are as defined.

Another embodiment of the invention is the provision of a compound of Formula IB and IC, where the various moieties are independently selected, R is ($C_3$-$C_8$ cycloalkenyl)alkyl, and n, A, Q and $R^1$ and $R^2$ are as defined.

Another embodiment of the invention is the provision of a compound of Formula IB and IC, where the various moieties are independently selected, R is (heterocycloalkyl) alkyl, and n, A, Q and $R^1$ and $R^2$ are as defined.

Another embodiment of the invention is the provision of a compound of Formula IB and IC, where the various moieties are independently selected, R is (aryloxy)alkyl, and n, A, Q and $R^1$ and $R^2$ are as defined.

Another embodiment of the invention is the provision of a compound of Formula IB and IC, where the various moieties are independently selected, R is (heteroaryloxy) alkyl, and n, A, Q and $R^1$ and $R^2$ are as defined.

Another embodiment of the invention is the provision of a compound of Formula IB and IC, where the various moieties are independently selected, R is ($C_3$-$C_8$ cycloalkyloxy)alkyl, and n, A, Q and $R^1$ and $R^2$ are as defined.

Another embodiment of the invention is the provision of a compound of Formula IB, where the various moieties are independently selected, R is ($C_3$-$C_8$ cycloalkenyloxy)alkyl, and n, A, Q and $R^1$ and $R^2$ are as defined.

Another embodiment of the invention is the provision of a compound of Formula IB and IC, where the various moieties are independently selected, R is (heterocycloalkyloxy)alkyl, and n, A, Q and $R^1$ and $R^2$ are as defined.

Another embodiment of the invention is the provision of a compound of Formula IB and IC, where the various moieties are independently selected, R, n, Q and R1 and $R^2$ are as defined and A is aryl.

Another embodiment of the invention is the provision of a compound of Formula IB and IC, where he various moieties are independently selected, R, n, Q and G are as defined and A is heteroaryl.

Another embodiment of the invention is the provision of a compound of Formula IB and IC, where the various moieties are independently selected, R, n, Q and R1 and $R^2$ are as defined and A is heterocycloalkyl.

Another embodiment of the invention is the provision of a compound of Formula IB and IC, where the various moieties are independently selected, R, n, Q and R1 and $R^2$ are as defined and A is $C_3$-$C_8$ cycloalkyl.

Another embodiment of the invention is the provision of a compound of Formula IB and IC, where he various moieties are independently selected, R, A, Q and R1 and $R^2$ are as defined and n is 0.

Another embodiment of the invention is the provision of a compound of Formula I B and IC, where the various moieties are independently selected, R, A, Q and R1 and $R^2$ are as defined and n is 1.

Another embodiment of the invention is the provision of a compound of Formula IB and IC, where the various moieties are independently selected, R, A, Q and R1 and $R^2$ are as defined and n is 2.

Another embodiment of the invention is the provision of a compound of Formula IB and IC, where the various moieties are independently selected, R, A, Q and R1 and $R^2$ are as defined and n is 3.

Another embodiment of the invention is the provision of a compound of Formula IB and IC, where the various moieties are independently selected, R, A, Q and R1 and $R^2$ are as defined and n is 4.

Another embodiment of the invention is the provision of a compound of Formula IB, where the various moieties are independently selected, R, A, n and R1 and $R^2$ are as defined and Q is C(O).

Another embodiment of the invention is the provision of a compound of Formula IB and IC, where the various moieties are independently selected, R, A, n and $R^1$ and $R^2$ are as defined and Q is S(O).

Another embodiment of the invention is the provision of a compound of Formula IB and IC, where the various moieties are independently selected, R, A, n and $R^1$ and $R^2$ are as defined and Q is $S(O_2)$.

Another embodiment of the invention is the provision of a compound of Formula IB and IC, where the various moieties are independently selected, R, A, n and $R^1$ and $R^2$ are as defined and Q is —N(H)—$S(O_2)$—.

Another embodiment of the invention is the provision of a compound of Formula IB and IC, where the various moieties are independently selected, R, A, n and $R^1$ and $R^2$ are as defined and Q is —$S(O_2)$—N(H)—.

Another embodiment of the invention is the provision of a compound of Formula IB and IC, where the various moieties are independently selected, R, A, n and $R^1$ and $R^2$ are as defined and Q is —N(H)—C(O)—.

An embodiment of the invention is the provision of a compound of Formula IB and IC, where the various moieties are independently selected, R is phenyl, and n, A, Q and $R^1$ and $R^2$ are as defined.

An embodiment of the invention is the provision of a compound of Formula IB and IC, where the various moieties are independently selected, R is naphthyl, and n, A, Q and $R^1$ and $R^2$ are as defined.

An embodiment of the invention is the provision of a compound of Formula IB and IC, where the various moieties are independently selected, R is pyridyl, and n, A, Q and $R^1$ and $R^2$ are as defined.

An embodiment of the invention is the provision of a compound, where Formulas IB and IC the various moieties are independently selected, R is a pyrrolopyridinyl group, and n, A, Q and $R^1$ and $R^2$ are as defined.

An embodiment of the invention is the provision of a compound of Formula IB and IC, where the various moieties are independently selected, R is a thienopyridinyl group, and n, A, Q and R1 and $R^2$ are as defined.

An embodiment of the invention is the provision of a compound of Formula IB and IC, where the various moieties are independently selected, R is an indazolyl group, and n, A, Q and $R^1$ and $R^2$ are as defined.

An embodiment of the invention is the provision of a compound of Formula IB and IC, where the various moieties are independently selected, R is a pyrazolopyridinyl group, and n, A, Q and R1 and $R^2$ are as defined.

An embodiment of the invention is the provision of a compound of Formula IB and IC, where the various moieties are independently selected, R is an imidazopyridinyl group, and n, A, Q and $R^1$ and $R^2$ are as defined.

An embodiment of the invention is the provision of a compound of Formula IB and IC, where the various moieties are independently selected, R is an imidazopyrazolyl group, and n, A, Q and $R^1$ and $R^2$ are as defined.

An embodiment of the invention is the provision of a compound of Formula IB and IC, where the various moieties are independently selected, R is a tetrazolopyridinyl group, and n, A, Q and $R^1$ and $R^2$ are as defined.

An embodiment of the invention is the provision of a compound of Formula IB and IC, where the various moieties are independently selected, R is a naphthyridinyl group, and n, A, Q and $R^1$ and $R^2$ are as defined.

An embodiment of the invention is the provision of a compound of Formula IB and IC, where the various moieties are independently selected, R is a benzodiazolyl group, and n, A, Q and $R^1$ and $R^2$ are as defined.

An embodiment of the invention is the provision of a compound of Formula IB and IC, where the various moieties are independently selected, R is a benzothiazolyl group, and n, A, Q and R1 and $R^2$ are as defined.

An embodiment of the invention is the provision of a compound of Formula IB and IC, where the various moieties are independently selected, R is a furopyridinyl group, and n, A, Q and R1 and $R^2$ are as defined.

An embodiment of the invention is the provision of a compound of Formula IB and I C, where the various moieties are independently selected, R is a (pyridinyloxy)methyl group, and n, A, Q and $R^1$ and $R^2$ are as defined.

Another embodiment of the invention is the provision of a compound of Formula IB and IC, where the various moieties are independently selected, R is (pyridinyl)alkyl, and n, A, Q and $R^1$ and $R^2$ are as defined.

Another embodiment of the invention is the provision of a compound of Formula IB and IC, where the various moieties are independently selected, R is (pyridinyl)ethyl, and n, A, Q and $R^1$ and $R^2$ are as defined.

Another embodiment of the invention is the provision of a compound of Formula IB and IC, where the various moieties are independently selected, R is (pyrrolopyridinyl)methyl, and n, A, Q and R1 and $R^2$ are as defined.

Another embodiment of the invention is the provision of a compound of Formula IB and IC, where the various moieties are independently selected, R, n, Q and R1 and $R^2$ are as defined and A is phenyl.

Another embodiment of the invention is the provision of a compound of Formula IB and IC, where the various moieties are independently selected, R, n, Q and R1 and $R^2$ are as defined and A is piperidinyl.

Another embodiment of the invention is the provision of a compound of Formula IB and IC, where the various moieties are independently selected, R, A, n, $R^2$, and Q are as defined, and $R^1$ is H.

Another embodiment of the invention is the provision of a compound of Formula IB, where the various moieties are independently selected, R, A, n, $R^1$, and Q are as defined, and —$R^2$ is piperidinyl.

Another embodiment of the invention is the provision of a compound of Formula IB, where the various moieties are independently selected, R, A, n, $R^1$, and Q are as defined, and —$R^2$ is quinolinyl.

Another embodiment of the invention is the provision of a compound of Formula IB, where the various moieties are independently selected, R, A, n, $R^1$, and Q are as defined, R1 is H and —$R^2$ is morpholinyl.

Another embodiment of the invention is the provision of a compound of Formula IB, where the various moieties are independently selected, R, A, n, $R^1$, and Q are as defined, $R^1$ is H and —$R^2$ is piperidinyl.

Another embodiment of the invention is the provision of a compound of Formula IB, where the various moieties are independently selected, R, A, n, $R^1$, and Q are as defined, R1 is H and —$R^2$ is quinolinyl.

Another embodiment of the invention is the provision of a compound of Formula IB, where the various moieties are independently selected, R, A, n, $R^1$, and Q are as defined, and —$R^2$ is morpholinyl.

Another embodiment of the invention is the provision of a compound of Formula IB and IC, where the various moieties are independently selected, n, $R^1$, $R^2$, and Q are as defined, both A and R are aryl.

Another embodiment of the invention is the provision of a compound of Formula IB and IC, where the various moieties are independently selected, n, $R^1$, $R^2$, and Q are as defined, both A and R are heteroaryl.

Another embodiment of the invention is the provision of a compound of Formula IB and IC, where the various moieties are independently selected, n, $R^1$, $R^2$, and Q are as defined, R is heteroaryl and A is aryl.

Another embodiment of the invention is the provision of a compound of Formula IB and IC, where the various moieties are independently selected, n, $R^1$, $R^2$, and Q are as defined, R is (heteroaryl)alkyl and A is aryl.

Another embodiment of the invention is the provision of a compound of Formula IB and IC, where the various moieties are independently selected, n, $R^1$, $R^2$, and Q are as defined, R is (heteroaryloxy)alkyl and A is aryl.

Another embodiment of the invention is the provision of a compound of Formula IB and IC, where the various moieties are independently selected, n, $R^1$, $R^2$, and Q are as defined, R is aryl and A is heteroaryl.

Another embodiment of the invention is the provision of a compound of Formula IB and IC, where the various moieties are independently selected, n, $R^1$, $R^2$ are as defined, both A and R are aryl and Q is $S(O_2)$.

Another embodiment of the invention is the provision of a compound of Formula IB and IC, where the various moieties are independently selected, n, $R^1$, $R^2$ are as defined, both A and R are heteroaryl and Q is $S(O_2)$.

Another embodiment of the invention is the provision of a compound of Formula IB and IC, where the various moieties are independently selected, n, $R^1$, $R^2$ are as defined, A is aryl, R is heteroaryl and Q is $S(O_2)$.

Another embodiment of the invention is the provision of a compound of Formula IB and IC, where the various moieties are independently selected, n, $R^1$, $R^2$ are as defined, A is aryl, R is (heteroaryl)alkyl and Q is $S(O_2)$.

Another embodiment of the invention is the provision of a compound of Formula IB and IC, where the various moieties are independently selected, n, $R^1$, $R^2$ are as defined, A is aryl, R is (heteroaryloxy)alkyl and Q is $S(O_2)$.

Another aspect of the invention is compounds derived from Formula I where q=0, m=0 and t=0, whereby the formula becomes Formula II or pharmaceutically acceptable salts thereof:

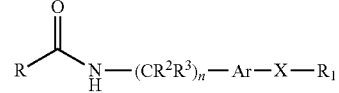

III wherein:
R is heteroaryl comprising 1, 2, 3 or 4 heteroatom(s) independently selected from N, S or O, wherein said heteroaryl may be substituted by one or more substituents selected from the group consisting of amino, oxo, and halo; and wherein said heteroaryl can comprise one or more N-oxide(s) formed with a N atom member of said heteroaryl;

Ar is aryl or heteroaryl comprising 1, 2, 3 or 4 heteroatom(s) independently selected from N, S or O;

X is $S(O)_2$ or S=O;

$R^1$ is —$NHR^4$ and $R^4$ is cycloalkyl, heterocycloalkyl, aryl or heteroaryl;
cycloalkyl;
aryl;
heterocycloalkyl; or
heteroaryl; wherein:
each of said cycloalkyl, aryl, or heteroaryl is unsubstituted or substituted with 1, 2, 3, 4 or 5 substituents which can be the same or different and are independently selected from the group consisting of:
deuterium, halo, hydroxy, hydroxyalkyl, cyano, —$(CH_2)_mNR^aR^b$, oxo, alkyl, cyanoalkyl, haloalkyl, alkoxy, haloalkoxy, alkoxyalkyl-, alkenyl, alkynyl, alkynylalkoxy, —$CONH_2$, —S-alkyl, —C(O)NH(alkyl), —C(O)N(alkyl)$_2$, —C(O)NH(cycloalkyl), —C(O)NH(aryl), —C(O)N(aryl)$_2$, arylalkyl-, arylalkoxy-, aryloxy-, cycloalkyl, heterocycloalkyl, aryl, (heterocycloalkyl)alkyl-, (heterocycloalkyl)alkoxy-, —C(O)heterocycloalkyl, heteroaryl, (heteroaryl)alkyl-, —S(O)₂-alkyl, —S(O)₂-aryl, —S(O)₂—CH$_z$F$_{3-z}$, —C(O)alkyl, —N(R⁵)—C(O)-alkyl, —N(R⁵)—C(O)-aryl, —S(O₂)NH₂, —S(O₂)NH(alkyl), —S(O₂)N(alkyl)₂, —N(H)(SO₂)(alkyl), and methylenedioxy, wherein each of said cycloalkyl, heterocycloalkyl, aryl or heteroaryl may be substituted by one or more halo, cyano, alkyl or alkoxy and;

each of said cycloalkyl, heterocycloalkyl, aryl, or heteroaryl may optionally additionally be fused with independently selected aryl, heteroaryl, heterocycloalkyl or cycloalkyl to from a bicyclic or tricyclic group that may be substituted by one or more halo, cyano, alkyl or alkoxy;

R² and R³ can be independently selected from the group consisting of H and deuterium;

R⁵ is H, alkyl or arylalkyl-;

Rᵃ and Rᵇ are independently selected from the group consisting of H, alkyl, alkoxy, alkoxyalkyl and haloalkyl;

m is 0, 1, 2, 3, 4, 5 or 6; and n is 0 or 1;

An embodiment of Formula II of this invention is the provision of compounds compositions, kits and andtidotes for the NAMPT pathway in mammals where X is S(O)₂ and n=1, the formula now becoming the Formula II A:

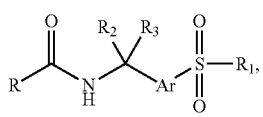  IIA wherein:

R is heteroaryl comprising 1, 2, 3 or 4 heteroatom(s) independently selected from N, S or O, wherein said heteroaryl may be substituted by one or more substituents selected from the group consisting of amino, oxo, and halo; and wherein said heteroaryl can comprise one or more N-oxide(s) formed with a N atom member of said heteroaryl;

Ar is aryl or 5 or 6 membered heteroaryl comprising 1, 2, 3 or 4 heteroatom(s) independently selected from N, S or O;

R¹ is —NHR⁴ where R⁴ is cycloalkyl, heterocycloalkyl, aryl or heteroaryl;

cycloalkyl;

aryl; or heteroaryl; wherein:

each of said cycloalkyl, aryl, or heteroaryl is unsubstituted or substituted with 1, 2, 3, 4 or 5 substituents which can be the same or different and are independently selected from the group consisting of:

deuterium, halo, hydroxy, hydroxyalkyl, cyano, —(CH₂)$_m$NRᵃRᵇ, oxo, alkyl, cyanoalkyl, haloalkyl, alkoxy, haloalkoxy, alkoxyalkyl-, alkenyl, alkynyl, alkynylalkoxy, —CONH₂, —S-alkyl, —C(O)NH(alkyl), —C(O)N(alkyl)₂, —C(O)NH(cycloalkyl), —C(O)NH(aryl), —C(O)N(aryl)₂, arylalkyl-, arylalkoxy-, aryloxy-, cycloalkyl, heterocycloalkyl, aryl, (heterocycloalkyl)alkyl-, (heterocycloalkyl)alkoxy-, —C(O)heterocycloalkyl, heteroaryl, (heteroaryl)alkyl-, —S(O)₂-alkyl, —S(O)₂-aryl, —S(O)₂—CH$_z$F$_{3-z}$, —C(O)alkyl, —N(R⁵)—C(O)-alkyl, —N(R⁵)—C(O)-aryl, —S(O₂)NH₂, —S(O₂)NH(alkyl), —S(O₂)N(alkyl)₂, —N(H)(SO₂)(alkyl), and methylenedioxy, wherein each of said cycloalkyl, heterocycloalkyl, aryl or heteroaryl may be substituted by one or more halo, cyano, alkyl or alkoxy and;

each of said cycloalkyl, heterocycloalkyl, aryl, or heteroaryl may optionally additionally be fused with independently selected aryl, heteroaryl, heterocycloalkyl or cycloalkyl to from a bicyclic or tricyclic group that may be substituted by one or more halo, cyano, alkyl or alkoxy;

R² and R³ can be independently selected from the group consisting of H and deuterium;

R⁵ is H, alkyl or arylalkyl-;

Rᵃ and Rᵇ are independently selected from the group consisting of H, alkyl, alkoxy, alkoxyalkyl and haloalkyl; and m is 0, 1, 2, 3, 4, 5 or 6.

In the compounds of Formulas II, and IIA, the various moieties are independently selected.

The following embodiments are directed to Formulas II, and IIA as applicable. For any moieties that are not specifically defined, the previous definitions control. Further, the moieties aryl, heteroaryl, heterocycloalkyl, cycloalkyl, cycloalkenyl and heterocycloalkenyl in these embodiments can be independently unsubstituted or optionally substituted or optionally fused as described earlier. Any one or more of the embodiments relating to Formula II or IIA below can be combined with one or more other embodiments for Formula II or IIA.

An embodiment of the invention is the provision of a compound of Formula II or II A where the various moieties are independently selected and Ar is aryl.

An embodiment of the invention is the provision of a compound of Formula II or IIA where the various moieties are independently selected and Ar is phenyl.

Another embodiment of the invention is the provision of a compound of Formula II or IIA where the various moieties are independently selected and Ar has the formula of:

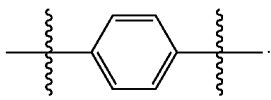

Another embodiment of the invention is the provision of a compound of Formula II or IIA where the various moieties are independently selected and Ar is 5 or 6 membered heteroaryl.

Another embodiment of the invention is the provision of a compound of Formula II or IIA where the various moieties are independently selected and Ar is pyridine.

Another embodiment of the invention is the provision of a compound of Formula II or IIA where the various moieties are independently selected and R is a bicyclic heteroaryl.

Another embodiment of the invention is the provision of a compound of Formula II or IIA where the various moieties are independently selected and R is a 9 to 10 membered bicyclic heteroaryl containing 1, 2, 3, or 4 heteroatoms independently selected from N, S or O.

Another embodiment of the invention is the provision of a compound of Formula II or IIA where the various moieties are independently selected and R is selected from benzothiazole, dihydronaphthyridine, dihydropyridopyrimidine, dihydropyrrolopyridine, furopyridine, imidazopyrazine, imidazopyrazole imidazopyridine, imidazopyrimidine, indazole, indole, isoquinoline, naphthyridine, pyrazolopyridine, pyrrolopyridine, tetrazolopyridine, tetrahydroimidazopyridine, tetrahydropyrazolopyridine, thiazolopyridine and thienopyridine.

Another embodiment of the invention is the provision of a compound of Formula II or IIA where the various moieties are independently selected and R is selected from 1H-pyrazolo[3,4-b]pyridine; 1,4,6,7-Tetrahydro-pyrazolo[4,3-c]pyridine; 7,8-Dihydro-5H-pyrido[4,3-d]pyrimidine; 5,7-Dihydro-pyrrolo[3,4-b]pyridine; 7,8-Dihydro-5H-[1,6]naphthyridine; 1,4,6,7-Tetrahydro-imidazo[4,5-c]pyridine; 1,8a-dihydroimidazo[1,2-a]pyridine; thieno[3,2-c]pyridine; 1H-imidazo[1,2-b]pyrazole; 1H-pyrazolo[3,4-b]pyridine; furo[2,3-c]pyridine; 1H-pyrazolo[3,4-b]pyridine; 1H-pyrrolo[3,2-c]pyridine; thieno[2,3-b]pyridine; imidazo[1,2-a]pyrimidine; furo[2,3-c]pyridine; isoquinoline; 1H-indazole; imidazo[1,2-a]pyridine; thieno[2,3-c]pyridine; furo[2,3-c]pyridine; 1H-pyrrolo[2,3-c]pyridine; imidazo[1,2-a]pyrazine; 1,3-benzothiazole; benzo[d]thiazole; 1H-pyrrolo[2,3-b]pyridine; [1,3]thiazolo[5,4-c]pyridine; [1,2,3,4]tetrazolo[1,5-a]pyridine; 1,5-naphthyridine; 1H-indole; 1H-imidazo[4,5-c]pyridine; and 1,6-naphthyridine.

Another embodiment of the invention is the provision of compounds of Formula II or IIA wherein R is selected from the group consisting of:

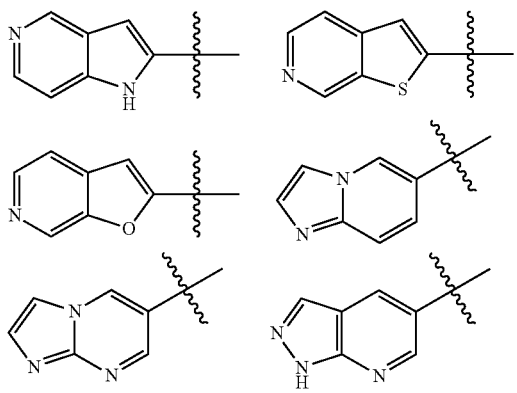

Another embodiment of the invention is the provision of a compound of Formula II or IIA where the various moieties are independently selected, Ar is aryl and R is a 9 to 10 membered bicyclic heteroaryl containing 1, 2, 3, or 4 heteroatoms independently selected from N, S or O.

Another embodiment of the invention is the provision of a compound of Formula II or IIA where the various moieties are independently selected, Ar is phenyl and R is a 9 to 10 membered bicyclic heteroaryl containing 1, 2, 3, or 4 heteroatoms independently selected from N, S or O.

Another embodiment of the invention is the provision of a compound of Formula II or IIA where the various moieties are independently selected, Ar is phenyl and R is selected from benzothiazole, dihydronaphthyridine, dihydropyridopyrimidine, dihydropyrrolopyridine, furopyridine, imidazopyrazine, imidazopyrazole imidazopyridine, imidazopyrimidine, indazole, indole, isoquinoline, naphthyridine, pyrazolopyridine, pyrrolopyridine, tetrazolopyridine, tetrahydroimidazopyridine, tetrahydropyrazolopyridine, thiazolopyridine and thienopyridine.

Another embodiment of the invention is the provision of a compound of Formula II or IIA where the various moieties are independently selected and Ar is 5 or 6 membered heteroaryl and R is a 9 to 10 membered bicyclic heteroaryl containing 1, 2, 3, or 4 heteroatoms independently selected from N, S or O.

Another embodiment of the invention is the provision of a compound of Formula II or IIA where the various moieties are independently selected, Ar is pyridine and R is a 9 to 10 membered bicyclic heteroaryl containing 1, 2, 3, or 4 heteroatoms independently selected from N, S or O.

Another embodiment of the invention is the provision of a compound of Formula II or IIA where the various moieties are independently selected and R is substituted at a position adjacent to a nitrogen atom on its cycle.

Another embodiment of the invention is the provision of a compound of Formula II or IIA where the various moieties are independently selected, Ar is aryl and R is substituted at a position adjacent to a nitrogen atom on its cycle.

Another embodiment of the invention is the provision of a compound of Formula II or IIA where the various moieties are independently selected, Ar is phenyl and R is substituted at a position adjacent to a nitrogen atom on its cycle.

Another embodiment of the invention is the provision of a compound of Formula II or IIA where the various moieties are independently selected, Ar is 5 or 6 membered heteroaryl and R is substituted at a position adjacent to a nitrogen atom on its cycle.

Another embodiment of the invention is the provision of a compound of Formula II or IIA where the various moieties are independently selected, Ar is pyridine and R is substituted at a position adjacent to a nitrogen atom on its cycle.

Another embodiment of the invention is the provision of a compound of Formula II or IIA where the various moieties are independently selected, $R^1$ is —$NHR^4$ and $R^4$ is cycloalkyl, heterocycloalkyl, aryl or heteroaryl.

Another embodiment of the invention is the provision of a compound of Formula III or IIIA where the various moieties are independently selected, Ar is aryl, $R^1$ is —$NHR^4$ and $R^4$ is cycloalkyl, heterocycloalkyl, aryl or heteroaryl.

Another embodiment of the invention is the provision of a compound of Formula II or IIA where the various moieties are independently selected, Ar is phenyl, $R^1$ is —$NHR^4$ and $R^4$ is cycloalkyl, heterocycloalkyl, aryl or heteroaryl.

Another embodiment of the invention is the provision of a compound of Formula II or IIA where the various moieties are independently selected, Ar is 5 or 6 membered heteroaryl, $R^1$ is —$NHR^4$ and $R^4$ is cycloalkyl, heterocycloalkyl, aryl or heteroaryl.

Another embodiment of the invention is the provision of a compound of Formula II or IIA where the various moieties are independently selected, Ar is pyridine, $R^1$ is —$NHR^4$ and $R^4$ is cycloalkyl, heterocycloalkyl, aryl or heteroaryl.

Another embodiment of the invention is the provision of a compound of Formula II or IIA where the various moieties are independently selected and R is a 9 to 10 membered bicyclic heteroaryl containing 1, 2, 3, or 4 heteroatoms independently selected from N, S or O, Ar is phenyl and $R^1$ is —$NHR^4$ and $R^4$ is cycloalkyl, heterocycloalkyl, aryl or heteroaryl.

Another embodiment of the invention is the provision of a compound of Formula II or IIA where the various moieties are independently selected and R is a 9 to 10 membered bicyclic heteroaryl containing 1, 2, 3, or 4 heteroatoms independently selected from N, S or O, Ar is pyridine and $R^1$ is —$NHR^4$ and $R^4$ is cycloalkyl, heterocycloalkyl, aryl or heteroaryl.

Another embodiment of the invention is the provision of a compound of Formula II or IIA where the various moieties are independently selected and R¹ is unsubstituted or substituted C₃-C₁₀ cycloalkyl.

Another embodiment of the invention is the provision of a compound of Formula II or IIA where the various moieties are independently selected, Ar is aryl, and R¹ is unsubstituted or substituted C₃-C₁₀ cycloalkyl.

Another embodiment of the invention is the provision of a compound of Formula II or IIA where the various moieties are independently selected, Ar is phenyl, and R¹ is unsubstituted or substituted C₃-C₁₀ cycloalkyl.

Another embodiment of the invention is the provision of a compound of Formula II or IIA where the various moieties are independently selected, Ar is 5 or 6 membered heteroaryl, and R¹ is unsubstituted or substituted C₃-C₁₀ cycloalkyl.

Another embodiment of the invention is the provision of a compound of Formula II or IIA where the various moieties are independently selected, Ar is pyridine, and R¹ is unsubstituted or substituted C₃-C₁₀ cycloalkyl.

Another embodiment of the invention is the provision of a compound of Formula II or IIA where the various moieties are independently selected and R¹ is unsubstituted or substituted aryl.

Another embodiment of the invention is the provision of a compound of Formula II or IIA where the various moieties are independently selected and R¹ is unsubstituted or substituted 5 to 11 membered monocyclic or bicyclic heterocycloalkyl comprising 1, 2, 3, or 4 heteroatom(s) selected from N, S or O.

Another embodiment of the invention is the provision of a compound of Formula II or IIA where the various moieties are independently selected, Ar is aryl and R¹ is unsubstituted or substituted 5 to 11 membered monocyclic or bicyclic heterocycloalkyl comprising 1, 2, 3, or 4 heteroatom(s) selected from N, S or O.

Another embodiment of the invention is the provision of a compound of Formula II or IIA where the various moieties are independently selected, Ar is phenyl and R¹ is unsubstituted or substituted 5 to 11 membered monocyclic or bicyclic heterocycloalkyl comprising 1, 2, 3, or 4 heteroatom(s) selected from N, S or O.

Another embodiment of the invention is the provision of a compound of Formula II or IIA where the various moieties are independently selected, Ar is 5 or 6 membered heteroaryl and R¹ is unsubstituted or substituted 5 to 11 membered monocyclic or bicyclic heterocycloalkyl comprising 1, 2, 3, or 4 heteroatom(s) selected from N, S or O.

Another embodiment of the invention is the provision of a compound of Formula II or IIA where the various moieties are independently selected, Ar is pyridine and R¹ is unsubstituted or substituted 5 to 11 membered monocyclic or bicyclic heterocycloalkyl comprising 1, 2, 3, or 4 heteroatom(s) selected from N, S or O.

Another embodiment of the invention is the provision of a compound of Formula II or IIA where the various moieties are independently selected, R¹ is unsubstituted or substituted 5 to 11 membered monocyclic or bicyclic heterocycloalkyl containing at least one N-heteroatom from which the heterocycloalkyl is attached to the rest of the compound of Formula II or IIA.

Another embodiment of the invention is the provision of a compound of Formula II or IIA where the various moieties are independently selected, Ar is aryl and R¹ is unsubstituted or substituted 5 to 11 membered monocyclic or bicyclic heterocycloalkyl containing at least one N-heteroatom from which the heterocycloalkyl is attached to the rest of the compound of Formula II or IIA.

Another embodiment of the invention is the provision of a compound of Formula II or IIA where the various moieties are independently selected, Ar is phenyl and R¹ is unsubstituted or substituted 5 to 11 membered monocyclic or bicyclic heterocycloalkyl containing at least one N-heteroatom from which the heterocycloalkyl is attached to the rest of the compound of Formula II or IIA.

Another embodiment of the invention is the provision of a compound of Formula II or IIA where the various moieties are independently selected, Ar is 5 or 6 membered heterocyclic aryl and R¹ is unsubstituted or substituted 5 to 11 membered monocyclic or bicyclic heterocycloalkyl containing at least one N-heteroatom from which the heterocycloalkyl is attached to the rest of the compound of Formula II or IIA.

Another embodiment of the invention is the provision of a compound of Formula II or IIA where the various moieties are independently selected, Ar is pyridine and R¹ is unsubstituted or substituted 5 to 11 membered monocyclic or bicyclic heterocycloalkyl containing at least one N-heteroatom from which the heterocycloalkyl is attached to the rest of the compound of Formula II or IIA.

One embodiment of Formula IIA are compounds where Ar is phenyl and the formula becomes Formula IIB

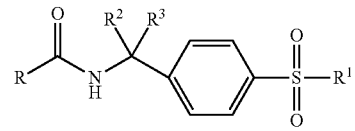

wherein:

R is bicyclic heteroaryl comprising 1, 2, 3 or 4 heteroatom(s) independently selected from N, S or O, wherein said heteroaryl may be substituted by one or more substituents selected from the group consisting of amino, oxo, and halo; and wherein said heteroaryl can comprise one or more N-oxide(s) formed with a N atom member of said heteroaryl;

R¹ is —NHR⁴ and R⁴ is cycloalkyl, heterocycloalkyl, aryl or heteroaryl;

cycloalkyl;

aryl; or heteroaryl; wherein:

each of said cycloalkyl, aryl, or heteroaryl is unsubstituted or substituted with 1, 2, 3, 4 or 5 substituents which can be the same or different and are independently selected from the group consisting of:

deuterium, halo, hydroxy, hydroxyalkyl, cyano, —(CH₂)$_m$NRᵃRᵇ, oxo, alkyl, cyanoalkyl, haloalkyl, alkoxy, haloalkoxy, alkoxyalkyl-, alkenyl, alkynyl, alkynylalkoxy, —CONH₂, —S-alkyl, —C(O)NH (alkyl), —C(O)N(alkyl)₂, —C(O)NH(cycloalkyl), —C(O)NH(aryl), —C(O)N(aryl)₂, arylalkyl-, arylalkoxy-, aryloxy-, cycloalkyl, heterocycloalkyl, aryl, (heterocycloalkyl)alkyl-, (heterocycloalkyl)alkoxy-, —C(O)heterocycloalkyl, heteroaryl, (heteroaryl) alkyl-, —S(O)₂-alkyl, —S(O)₂-aryl, —S(O)₂—CH$_z$F$_{3-z}$, —C(O)alkyl, —N(R⁵)—C(O)-alkyl, —N(R⁵)—C(O)-aryl, —S(O)₂NH₂, —S(O)₂NH (alkyl), —S(O)₂N(alkyl)₂, —N(H)(SO₂)(alkyl), and methylenedioxy, wherein each of said cycloalkyl, heterocycloalkyl, aryl or heteroaryl may be substituted by one or more halo, cyano, alkyl or alkoxy and;

each of said cycloalkyl, heterocycloalkyl, aryl, or heteroaryl may optionally additionally be fused with independently selected aryl, heteroaryl, heterocycloalkyl or cycloalkyl to from a bicyclic or tricyclic group that may be substituted by one or more halo, cyano, alkyl or alkoxy;

$R^2$ and $R^3$ can be independently selected from the group consisting of H and deuterium;

$R^5$ is H, alkyl or arylalkyl-;

$R^a$ and $R^b$ are independently selected from the group consisting of H, alkyl, alkoxy, alkoxyalkyl and haloalkyl;

m is 0, 1, 2, 3, 4, 5 or 6;

z is 0, 1 or 2.

An embodiment of the invention are compounds of Formula II B where R is selected from 9 to 10 membered bicyclic heteroaryl groups containing 1, 2, 3 or 4 heteroatoms independently selected from N, S, and O.

Another embodiment of the invention are compounds of Formula IIB, where R is selected from: benzothiazole, dihydronaphthyridine, dihydropyridopyrimidine, dihydropyrrolopyridine, furopyridine, imidazopyrazine, imidazopyrazole imidazopyridine, imidazopyrimidine, indazole, indole, isoquinoline, naphthyridine, pyrazolopyridine, pyrrolopyridine, tetrazolopyridine, tetrahydroimidazopyridine, tetrahydropyrazolopyridine, thiazolopyridine and thienopyridine.

Another embodiment of the invention are compounds of Formula IIB, where R is selected from: 1H-pyrazolo[3,4-b]pyridine; 1,4,6,7-Tetrahydro-pyrazolo[4,3-c]pyridine; 7,8-Dihydro-5H-pyrido[4,3-d]pyrimidine; 5,7-Dihydro-pyrrolo[3,4-b]pyridine; 7,8-Dihydro-5H-[1,6]naphthyridine; 1,4,6,7-Tetrahydro-imidazo[4,5-c]pyridine; 1,8a-dihydroimidazo[1,2-a]pyridine; thieno[3,2-c]pyridine; 1H-imidazo[1,2-b]pyrazole; 1H-pyrazolo[3,4-b]pyridine; furo[2,3-c]pyridine; 1H-pyrazolo[3,4-b]pyridine; 1H-pyrrolo[3,2-c]pyridine; thieno[2,3-b]pyridine; imidazo[1,2-a]pyrimidine; furo[2,3-c]pyridine; isoquinoline; 1H-indazole; imidazo[1,2-a]pyridine; thieno[2,3-c]pyridine; furo[2,3-c]pyridine; 1H-pyrrolo[2,3-c]pyridine; imidazo[1,2-a]pyrazine; 1,3-benzothiazole; benzo[d]thiazole; 1H-pyrrolo[2,3-b]pyridine; [1,3]thiazolo[5,4-c]pyridine; [1,2,3,4]tetrazolo[1,5-a]pyridine; 1,5-naphthyridine; 1H-indole; 1H-imidazo[4,5-c]pyridine; and 1,6-naphthyridine.

Another embodiment of the invention is compounds of Formula IIB where R is substituted at a position adjacent to a nitrogen atom on its cycle.

Another embodiment of the invention si compounds of Formula IIB wherein R is selected from the group consisting of:

Still another embodiment of the invention is compounds of Formula IIB where $R^1$ is —$NHR^4$, $R^4$ is cycloalkyl, heterocycloalkyl, aryl or heteroaryl.

Yet another embodiment of the invention is compounds of Formula IIB, where $R^4$ is unsubstituted or substituted cycloalkyl.

Another embodiment of the invention is compounds of Formula IIB, where $R^4$ is unsubstituted or substituted heterocycloalkyl.

Another embodiment of the invention is compounds of Formula IIB, where $R^4$ is unsubstituted or substituted aryl.

Yet another embodiment of the invention is compounds of Formula IIB, where $R^4$ is unsubstituted or substituted heteroaryl.

Still another embodiment of the invention is compounds of Formula IIB, where $R^1$ is unsubstituted or substituted $C_3$-$C_{10}$-cycloalkyl.

Another embodiment of the invention is compounds of Formula IIB, where $R^1$ is unsubstituted or substituted aryl.

One embodiment of the invention is compounds of Formula IIB, where R1 is unsubstituted or substituted 5 to 10 membered monocyclic or bicyclic heteroaryl comprising 1, 2, 3 or 4 heteroatom(s) selected from N, S or O.

Another embodiment of the invention is compounds of Formula IIB, where $R^1$ or $R^4$ is selected from the group consisting of: 6-methoxypyridine; 2-ethoxy-4-fluorophenyl; 3,4-difluorophenyl; 3,4-dimethoxyphenyl; 3,4-dimethoxyphenyl; 3-chloro-5-fluorophenyl; 3-fluoro-4-methoxyphenyl; 4-chloro-2-methylphenyl; 4-fluoro-2-methoxyphenyl; 4-methoxy-2,5-dimethylphenyl; 4-methylphenyl; 5-chloro-2-ethoxyphenyl; 5-fluoro-2-methoxyphenyl; 1-(3-chlorophenyl)-1H-pyrazole; 1-(4-fluorophenyl)-1H-pyrazole; 1-(propan-2-yl)-1H-pyrazole; 1,3-thiazole; 1,4-dimethyl-1H-imidazole; 1,5-dimethyl-1H-imidazole; 1-benzothiophene; 1H-indole; 1-methyl-1H-1,3-benzodiazole; 1-methyl-1H-indazole; 1-methyl-1H-indole; 1-methyl-1H-pyrazole; 1-methyl-3-(trifluoromethyl)-1H-pyrazole; 1-methyl-5-(trifluoromethyl)-1H-pyrazole; 1-propyl-1H-pyrazole; 2-(2,2,2-trifluoroethoxy)-4-(trifluoromethyl)phenyl; 2-(3-fluorophenyl)-1,3-thiazole; 2-(benzyloxy)-5-(trifluoromethyl)phenyl; 2-(benzyloxy)phenyl; 2-(dimethylamino)pyrimidine; 2-(dimethylcarbamoyl)phenyl; 2-(ethoxymethyl)phenyl; 2-(methylsulfamoyl)phenyl; 2-(morpholin-4-yl)pyridine; 2-(morpholin-4-yl)pyridine; 2-(morpholin-4-ylmethyl)phenyl; 2-(pyrrolidin-1-yl)-1,3-thiazole; 2-(trifluoromethoxy)phenyl; 2-(trifluoromethoxy) phenyl]; 2-(trifluoromethyl)imidazo[1,2-a]pyridine; 2-(trifluoromethyl)phenyl; 2-(trifluoromethyl)pyridine; 2,3,6-trimethoxyphenyl; 2,3-difluoro-6-methoxyphenyl; 2,3-difluorophenyl; 2,3-dihydro-1,4-benzodioxine; 2,3-dihydro-1-benzofuran; 2,3-dihydro-1-benzofuranphenyl; 2,3-dimethoxy-5-methylphenyl; 2,3-dimethoxyphenyl; 2,3-dimethylphenyl; 2,4,5-trimethylphenyl; 2,4-bis(trifluoromethyl)phenyl; 2,4-dichloro-3-methoxyphenyl; 2,4-difluorophenyl; 2,4-dimethoxyphenyl; 2,4-dimethylphenyl; 2,5-difluorophenyl; 2,5-dimethoxyphenyl; 2,5-dimethylphenyl; 2,6-dichloro-3-methylphenyl; 2,6-dichlorophenyl; 2,6-dimethoxy-4-methylphenyl; 2,6-dimethoxypyridine; 2,6-dimethylphenyl; 2-[ethyl(methyl)amino]-1,3-thiazole;

2-acetylphenyl; 2-butoxy-4-fluorophenyl; 2-butoxy-5-chlorophenyl; 2-butoxy-6-fluorophenyl; 2-chloro-3-(trifluoromethyl)phenyl; 2-chloro-3-fluorophenyl; 2-chloro-4-(trifluoromethyl)phenyl; 2-chloro-4-fluorophenyl; 2-chloro-4-methoxyphenyl; 2-chloro-4-methylphenyl; 2-chloro-5-(hydroxymethyl)phenyl; 2-chloro-5-(trifluoromethoxy)phenyl; 2-chloro-5-(trifluoromethyl)phenyl; 2-chloro-5-fluorophenyl; 2-chloro-5-methoxyphenyl; 2-chloro-5-methoxyphenyl; 2-chloro-5-methylphenyl; 2-chloro-6-fluorophenyl; 3-trifluoromethylphenyl; 2-chloro-6-methoxyphenyl; 2-chlorophenyl; 2-cyanophenyl; 2-ethoxy-4-fluorophenyl; 2-ethoxy-6-fluorophenyl; 2-ethoxyphenyl; 2-ethylphenyl; 2-fluoro-3-(propan-2-yloxy)phenyl; 2-fluoro-3-(trifluoromethoxy)phenyl; 2-fluoro-3-methoxyphenyl; 2-fluoro-3-methylphenyl; 2-fluoro-4-(1H-pyrazol-1-yl)phenyl; 2-fluoro-4-(trifluoromethyl)phenyl; 2-fluoro-4-methoxyphenyl; 2-fluoro-4-methylphenyl; 2-fluoro-5-methoxyphenyl; 2-fluoro-5-methylphenyl; 2-fluoro-6-methoxyphenyl; 2-fluoro-6-propoxyphenyl; 2-fluorophenyl; 2H-1,3-benzodioxole; 2-methanesulfonamidophenyl; 2-methanesulfonylphenyl; 2-methoxy-3-(trifluoromethyl)phenyl; 2-methoxy-4-(1H-pyrazol-1-yl)phenyl; 2-methoxy-4-(trifluoromethyl)phenyl; 2-methoxy-5-(propan-2-yl)phenyl; 2-methoxy-5-(trifluoromethoxy)phenyl; 2-methoxy-5-methylphenyl; 2-methoxy-6-(propan-2-yloxy)phenyl; 2-methoxyphenyl; 2-methyl-1,3-thiazole; 2-methyl-2H-indazole; 2-methyl-4-(1H-pyrazol-1-yl)phenyl; 2-methyl-4-(trifluoromethyl)phenyl; 2-methyl-4-propoxyphenyl; 2-methylphenyl; 2-methylpyridine; 2-phenoxyphenyl; 2-phenylethane; 3-(1H-pyrazol-1-yl)phenyl; 3-(2,2,2-trifluoroethoxy)phenyl; 3-(2-methylpropoxy)phenyl; 3-(3,5-dimethyl-1H-pyrazol-1-yl)phenyl; 3-(4-fluorophenoxy)phenyl; 3-(5-methyl-1,2,4-oxadiazol-3-yl)phenyl; 3-(cyclopentylcarbamoyl)phenyl; 3-(diethylcarbamoyl)-5-fluorophenyl; 3-(difluoromethoxy)phenyl; 3-(dimethylsulfamoyl)phenyl; 3-(ethanesulfonyl)phenyl; 3-(ethylcarbamoyl)phenyl; 3-(methoxymethyl)phenyl, 3-(methylcarbamoyl)phenyl; 3-(morpholin-4-yl)phenyl; 3-(piperidin-1-yl)phenyl; 3-(piperidin-1-ylmethyl)phenyl; 3-(piperidin-1-ylphenyl; 3-(propan-2-yl)phenyl; 3-(propan-2-yloxy)phenyl; 3-(propane-1-sulfonamido)phenyl; 3-(pyrimidin-2-yl)phenyl; 3-(trifluoromethoxy)phenyl; 3-(trifluoromethyl)phenyl; 3,4-dichlorophenyl; 3,4-dimethoxyphenyl; 3,4-dimethylphenyl; 3,5-dichlorophenyl; 3,5-difluorophenyl; 3,5-dimethoxyphenyl; 3,5-dimethylphenyl; 3-[(2-methylpropyl)carbamoyl]phenyl; 3-[(dimethylamino)methylphenyl; 3-[(morpholin-4-yl)carbonyl]phenyl; 3-[(propan-2-yl)carbamoyl]phenyl; 3-[2-(dimethylamino)ethoxyphenyl; 3-[2-(dimethylamino)ethyl]phenyl; 3-[2-(morpholin-4-yl)ethoxy]phenyl; 3-acetylphenyl; 3-butoxyphenyl; 3-chloro-2-(morpholin-4-yl)pyridine; 3-chloro-2-fluorophenyl; 3-chloro-2-methoxyphenyl; 3-chloro-2-methylphenyl; 3-chloro-4-(trifluoromethyl)phenyl; 3-chloro-4-methoxyphenyl; 3-chloro-4-methylphenyl; 3-chloro-4-propoxyphenyl; 3-chloro-5-(diethylcarbamoyl)phenyl; 3-chloro-5-(hydroxymethyl)phenyl; 3-chloro-5-fluorophenyl; 3-chloro-5-methoxyphenyl; 3-chloro-5-methylphenyl; 3-chlorophenyl; 3-cyanophenyl; 3-ethoxy-2-fluorophenyl; 3-ethoxy-4-fluorophenyl; 3-ethoxyphenyl; 3-ethylphenyl; 3-fluoro-2-methoxyphenyl; 3-fluoro-2-methylphenyl; 3-fluoro-2-methylphenyl; 3-fluoro-4-(1H-pyrazol-1-yl)phenyl; 3-fluoro-4-(2,2,2-trifluoroethoxy)phenyl; 3-fluoro-4-(methylsulfanyl)phenyl; 3-fluoro-4-(trifluoromethoxy)phenyl; 3-fluoro-4-(trifluoromethyl)phenyl; 3-fluoro-4-methoxyphenyl; 3-fluoro-4-methylphenyl; 3-fluoro-4-propoxyphenyl; 3-fluoro-5-(2,2,2-trifluoroethoxy)phenyl; 3-fluoro-5-(2-methylpropoxy)phenyl; 3-fluoro-5-(morpholin-4-yl)phenyl; 3-fluoro-5-(pyrrolidin-1-yl)phenyl; 3-fluoro-5-(trifluoromethyl)phenyl; 3-fluoro-5-methoxyphenyl; 3-fluoro-5-methylphenyl; 3-fluorophenyl; 3-hydroxyphenyl; 3-methanesulfonylphenyl; 3-methoxy-4-methylphenyl; 3-methoxy-5-methylphenyl; 3-methoxyphenyl; 3-methylphenyl; 3-phenylphenyl; 3-phenylpropane; 3-propoxyphenyl; 3-sulfamoylphenyl; 3-tert-butylphenyl; 4-(1-cyanocyclopentyl)phenyl; 4-(1H-imidazol-1-yl)phenyl; 4-(1H-imidazol-1-ylmethyl)phenyl; 4-(1H-pyrazol-1-yl)phenyl; 4-(2-methylpropoxy)phenyl; 4-(4-ethoxyphenyl)phenyl; 4-(4-methylpiperazin-1-yl)phenyl; 4-(difluoromethyl)-3-fluorophenyl; 4-(dimethylcarbamoyl)phenyl; 4-(ethoxymethyl)phenyl; 4-(ethylcarbamoyl)phenyl; 4-(hydroxymethyl)phenyl; 4-(morpholin-4-yl)phenyl; 4-(propan-2-yl)phenyl; 4-(propan-2-yloxy)phenyl; 4-(pyrrolidin-1-yl); 4-(pyrrolidin-1-yl)phenyl; 4-(trifluoromethoxy)phenyl; 4-(trifluoromethyl)phenyl; 4-(trifluoromethyl)pyridine; 3,5-difluorophenyl; 4,5-difluoro-2-methoxyphenyl; 4-[(1R)-1-hydroxybutylphenyl; (dimethylamino)methylphenyl; 4-[(pyrrolidin-1-yl)carbonyl]phenyl; 4-[2-(dimethylamino)ethyl]phenyl; 4-[2-(pyrrolidin-1-yl)ethoxy]phenyl; 4-acetylphenyl; 4-butoxy-2-methylphenyl; 4-butoxy-3-chlorophenyl; 4-butoxy-3-fluorophenyl; 4-butoxyphenyl; 4-butylphenyl; 4-chloro-2-(trifluoromethyl)phenyl; 4-chloro-2-ethoxyphenyl; 4-chloro-2-methoxyphenyl; 4-chloro-2-methylphenyl; 4-chloro-3-(trifluoromethyl)phenyl; 4-chloro-3-fluorophenyl; 4-chloro-3-methoxyphenyl; 4-chlorophenyl; 4-cyanophenyl; 4-cyclohexylphenyl; 4-ethoxy-2-methylphenyl; 4-ethoxy-3-fluorophenyl; 4-ethoxyphenyl; 4-ethylphenyl; 4-fluoro-2-(propan-2-yloxy)phenyl; 4-fluoro-2,5-dimethylphenyl; 4-fluoro-2-methoxyphenyl; 4-fluoro-2-methylphenyl; 4-fluoro-3-(2,2,2-trifluoroethoxy)phenyl; 4-fluoro-3-(trifluoromethyl)phenyl; 4-fluoro-3-[(propan-2-yl)carbamoyl]phenyl; 4-fluoro-3-methoxyphenyl; 4-fluoro-3-methylphenyl; 4-fluorophenyl; 4-methanesulfonylphenyl; 4-methoxy-2-(trifluoromethyl)phenyl; 4-methoxy-2,5-dimethylphenyl; 4-methoxy-2-methylphenyl; 4-methoxy-3,5-dimethylphenyl; 4-methoxy-3-methylphenyl; 4-methoxyphenyl; 4-methylphenyl; 4-methylpyridine; 4-methylthiophene; 4-phenylbutane; 4-phenylphenyl; 4-phenyl-phenyl; 4-propoxyphenyl; 3,5-difluorophenyl; 5-(diethylcarbamoyl)-2-fluorophenyl; 5-(dimethylamino)pyrazine; 5-(pyrrolidin-1-yl)pyridine; 5-(trifluoromethyl)pyridine; 5-acetyl-2-methoxyphenyl; 5-chloro-2-(2,2,2-trifluoroethoxy)phenyl; 5-chloro-2-(2,2-difluoroethoxy)phenyl; 5-chloro-2-(prop-2-yn-1-yloxy)phenyl; 5-chloro-2-(propan-2-yloxy)phenyl; 5-chloro-2-ethoxyphenyl; 5-chloro-2-hydroxyphenyl; 5-chloro-2-methoxyphenyl; 5-chloro-2-methylphenyl; 5-chloro-2-propoxyphenyl; 5-chloropyridine; 5-cyano-2-methoxyphenyl; 5-fluoro-2-(hydroxymethyl)phenyl; 5-fluoro-2-methoxyphenyl; 5-fluoro-2-methylphenyl; 5-fluoro-6-methylpyridine; 5-fluoropyridine; 5H,6H,7H,8H,9H-imidazo[1,2-a]azepine; 5H,6H,7H,8H,9H-imidazo[1,2-a]azepinephenyl; 5-hydroxy-(4-phenylphenyl); 5-hydroxy-1-methyl-1H-indazole; 5-hydroxy-2-(trifluoromethoxy)phenyl; 5-hydroxy-3-(morpholin-4-yl)phenyl; 5-hydroxy-3-(piperidin-1-ylphenyl; 5-hydroxy-3-(pyrrolidin-1-ylphenyl; 5-methoxypyridine; 5-methylpyridine; 5-methylthiophene; 5-tert-butyl-2-methoxyphenyl; 6-(1H-pyrazol-1-yl)pyridine; 6-(3,4-difluorophenyl)pyridine; 6-(4-methylpiperazin-1-yl)pyridine; 6-(dimethylamino)pyridine; 6-(morpholin-4-yl)pyridine; 6-(trifluoromethyl)pyridine; 6-amino-(3,5-difluorophenyl); 6-chloro-2-fluoro-3-methylphenyl; 6-chloroimidazo[1,2-a]pyridine; 6-chloroimidazo[1,2-a]pyridinephenyl; 6-methoxynaphthalene; 6-methoxypyridine; 6-methylpyrazine; 6-methylpyridine; 8-thiatricyclo

[7.4.0.0²,⁷]trideca-1(13),2,4,6,9,11-hexaene; b6-chloroimidazo[1,2-a]pyridine; Cyclohexane; dimethyl-1,3-thiazole; furan; isoquinoline; naphthalene; naphthalenephenyl; phenoxathiine; phenyl; pyridine and quinoline.

Another embodiment of the invention is compounds of Formula IIB, where $R^1$ is cycloalkyl, aryl or heteroaryl, wherein each of said cycloalkyl, aryl, or heteroaryl is unsubstituted or substituted with 1, 2, 3, 4 or 5 substituents which can be the same or different and are independently selected from the group consisting of: halo, hydroxy, hydroxyalkyl, cyano, alkyl, alkynyl, alkynylalkoxy, alkoxyalkyl, alkoxy, haloalkyl, haloalkoxy, —C(O)NH(alkyl), —C(O)NH(cycloalkyl), —C(O)N(alkyl)₂, arylalkoxy-, aryloxy-, cycloalkyl, heterocycloalkyl, aryl, (heterocycloalkyl)alkyl-, (heterocycloalkyl)alkoxy-, —C(O)heterocycloalkyl, heteroaryl, (heteroaryl)alkyl-, —S(O)₂-alkyl, —S-alkyl, —C(O)alkyl, —S(O₂)NH₂, —S(O₂)NH(alkyl), —S(O₂)N(alkyl)₂, —N(H)(SO₂)(alkyl), wherein each of said cycloalkyl, heterocycloalkyl, aryl or heteroaryl may be substituted by one or more halo, cyano, alkyl or alkoxy; and z is 0, 1 or 2.

Still another embodiment of the invention is compounds of Formula IIC, where $R^1$ is cycloalkyl, aryl or heteroaryl, wherein each of said cycloalkyl, aryl, or heteroaryl is unsubstituted or substituted with 1, 2, 3, 4 or 5 substituents which can be the same or different and are independently selected from the group consisting of: halo, haloalkyl and haloalkoxy.

Another embodiment of the invention is compounds of Formula IIB, where haloalkyl is —CH$_z$F$_{3-z}$, —CH$_2$CH$_z$F$_{3-z}$, and z is 0, 1 or 2.

One embodiment of the invention is compounds of Formula IIB, where haloalkoxy is —OCH$_z$F$_{3-z}$, and z is 0, 1 or 2.

Another embodiment of the invention is compounds of Formula IIB, where halo is F.

Another embodiment of the invention is compounds of Formula IIB, where R is 1H-pyrazolo[3,4-b]pyridine.

Another embodiment of the invention is compounds of Formula IIB, where R is 1,8a-dihydroimidazo[1,2-a]pyridine.

Anyone or more embodiments of Formula IIB provided above may be combined with one or more other embodiments of Formula IIB as provided above.

In another embodiment, the invention is further illustrated by the compounds shown in Table 2:

TABLE 2

| Structure | Name |
|---|---|
| 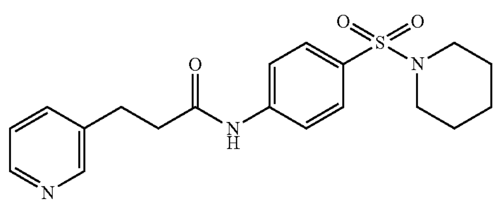 [SMILES: O=C(CCc1cccnc1)Nc1ccc(S(=O)(=O)N2CCCCC2)cc1] | N-[4-(piperidine-1-sulfonyl)phenyl]-3-(pyridin-3-yl)propanamide |
| 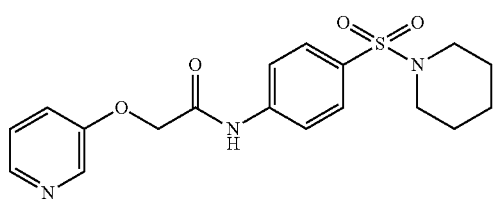 [SMILES: O=C(COc1cccnc1)Nc1ccc(S(=O)(=O)N2CCCCC2)cc1] | N-[4-(piperidine-1-sulfonyl)phenyl]-2-(pyridin-3-yloxy)acetamide |
| 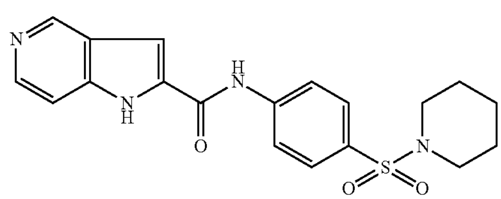 [SMILES: O=C(Nc1ccc(S(=O)(=O)N2CCCCC2)cc1)c1cc2cnccc2[nH]1] | N-[4-(piperidine-1-sulfonyl)phenyl]-1H-pyrrolo[3,2-c]pyridine-2-carboxamide |
| 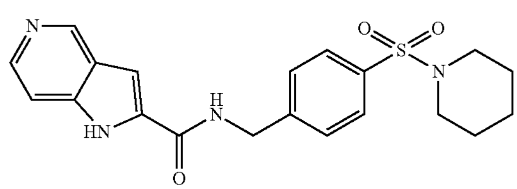 [SMILES: O=C(NCc1ccc(S(=O)(=O)N2CCCCC2)cc1)c1cc2cnccc2[nH]1] | N-{[4-(piperidine-1-sulfonyl)phenyl]methyl}-1H-pyrrolo[3,2-c]pyridine-2-carboxamide |
| 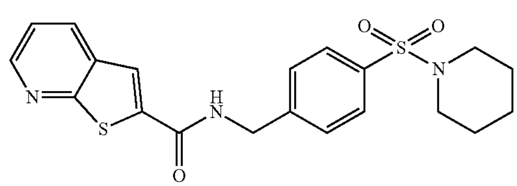 [SMILES: O=C(NCc1ccc(S(=O)(=O)N2CCCCC2)cc1)c1cc2cccnc2s1] | N-{[4-(piperidine-1-sulfonyl)phenyl]methyl}thieno[2,3-b]pyridine-2-carboxamide |

TABLE 2-continued

| Structure | Name |
|---|---|
| 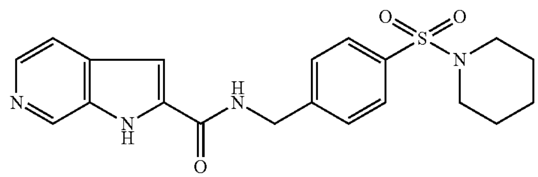 [SMILES: O=C(NCc1ccc(S(=O)(=O)N2CCCCC2)cc1)c1cc2ccncc2[nH]1] | N-{[4-(piperidine-1-sulfonyl)phenyl]methyl}-1H-pyrrolo[2,3-c]pyridine-2-carboxamide |
| 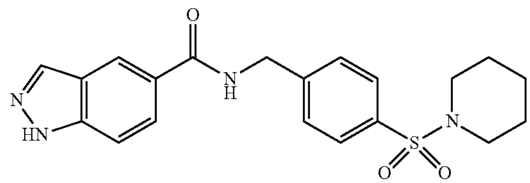 [SMILES: O=C(NCc1ccc(S(=O)(=O)N2CCCCC2)cc1)c1ccc2[nH]ncc2c1] | N-{[4-(piperidine-1-sulfonyl)phenyl]methyl}-1H-indazole-5-carboxamide |
| 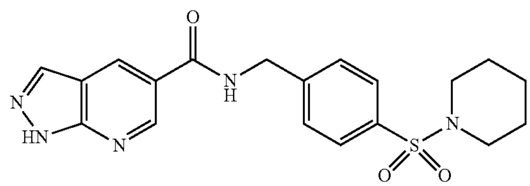 [SMILES: O=C(NCc1ccc(S(=O)(=O)N2CCCCC2)cc1)c1cnc2[nH]ncc2c1] | N-{[4-(piperidine-1-sulfonyl)phenyl]methyl}-1H-pyrazolo[3,4-b]pyridine-5-carboxamide |
| 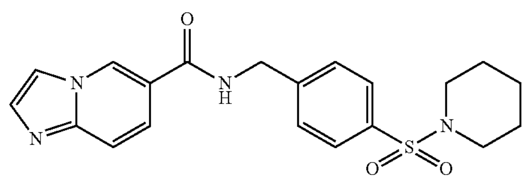 [SMILES: O=C(NCc1ccc(S(=O)(=O)N2CCCCC2)cc1)c1ccc2nccn2c1] | N-{[4-(piperidine-1-sulfonyl)phenyl]methyl}imidazo[1,2-a]pyridine-6-carboxamide |
| 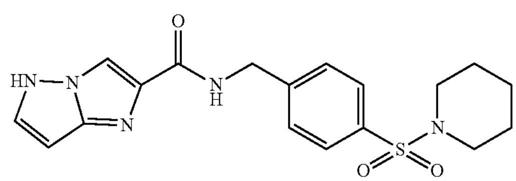 [SMILES: O=C(NCc1ccc(S(=O)(=O)N2CCCCC2)cc1)c1cn2[nH]ccc2n1] | N-{[4-(piperidine-1-sulfonyl)phenyl]methyl}-1H-imidazo[1,2-b]pyrazole-5-carboxamide |
| 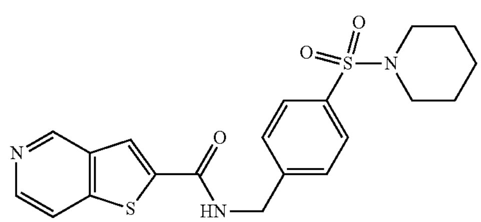 [SMILES: O=C(NCc1ccc(S(=O)(=O)N2CCCCC2)cc1)c1cc2cnccc2s1] | N-{[4-(piperidine-1-sulfonyl)phenyl]methyl}thieno[3,2-c]pyridine-2-carboxamide |
| 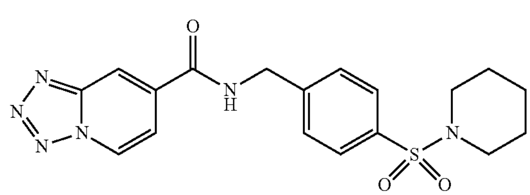 [SMILES: O=C(NCc1ccc(S(=O)(=O)N2CCCCC2)cc1)c1ccn2nnnc2c1] | N-{[4-(piperidine-1-sulfonyl)phenyl]methyl}-[1,2,3,4]tetrazolo[1,5-a]pyridine-7-carboxamide |
| 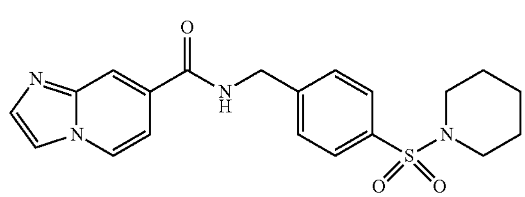 [SMILES: O=C(NCc1ccc(S(=O)(=O)N2CCCCC2)cc1)c1ccn2ccnc2c1] | N-{[4-(piperidine-1-sulfonyl)phenyl]methyl}imidazo[1,2-a]pyridine-7-carboxamide |

TABLE 2-continued

| | |
|---|---|
| 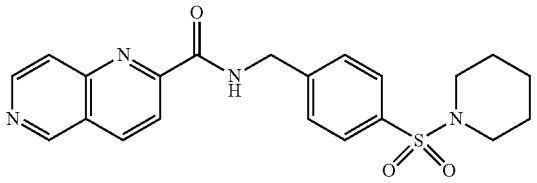 [SMILES: O=C(NCc1ccc(S(=O)(=O)N2CCCCC2)cc1)c1ccc2cnccc2n1] | N-{[4-(piperidine-1-sulfonyl)phenyl]methyl}-1,6-naphthyridine-2-carboxamide |
| 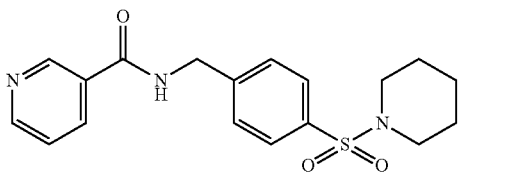 [SMILES: O=C(NCc1ccc(S(=O)(=O)N2CCCCC2)cc1)c1cccnc1] | N-{[4-(piperidine-1-sulfonyl)phenyl]methyl}pyridine-3-carboxamide |
| 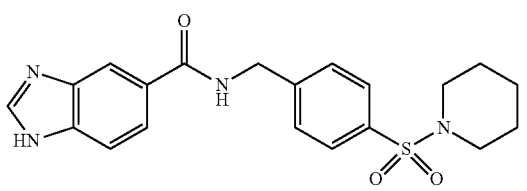 [SMILES: O=C(NCc1ccc(S(=O)(=O)N2CCCCC2)cc1)c1ccc2[nH]cnc2c1] | N-{[4-(piperidine-1-sulfonyl)phenyl]methyl}-1H-1,3-benzodiazole-5-carboxamide |
| 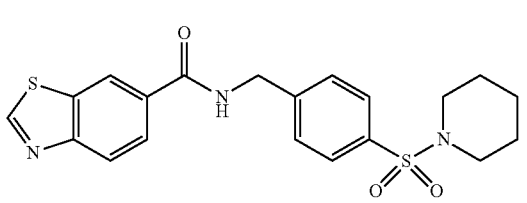 [SMILES: O=C(NCc1ccc(S(=O)(=O)N2CCCCC2)cc1)c1ccc2ncsc2c1] | N-{[4-(piperidine-1-sulfonyl)phenyl]methyl}-1,3-benzothiazole-6-carboxamide |
| 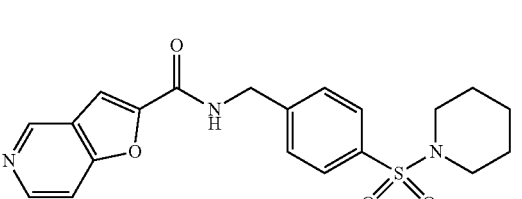 | N-{[4-(piperidine-1-sulfonyl)phenyl]methyl}furo[3,2-c]pyridine-2-carboxamide |
| 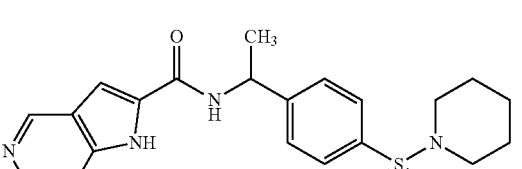 | N-{1-[4-(piperidine-1-sulfonyl)phenyl]ethyl}-1H-pyrrolo[3,2-c]pyridine-2-carboxamide |
| 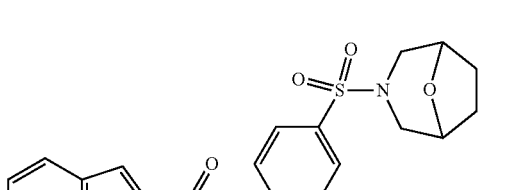 | N-[(4-{8-oxa-3-azabicyclo[3.2.1]octane-3-sulfonyl}phenyl)methyl]thieno[2,3-c]pyridine-2-carboxamide |
| 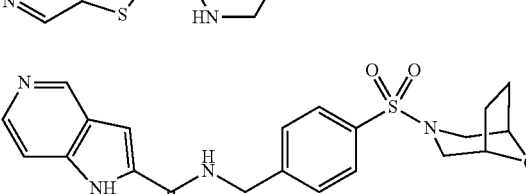 | N-[(4-{8-oxa-3-azabicyclo[3.2.1]octane-3-sulfonyl}phenyl)methyl]-1H-pyrrolo[3,2-c]pyridine-2-carboxamide |

TABLE 2-continued
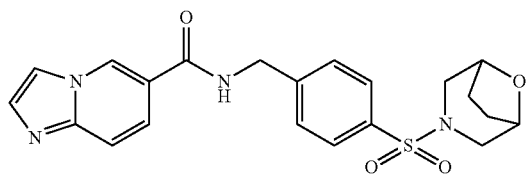 [SMILES: O=C(NCc1ccc(S(=O)(=O)N2CC3CCC(C2)O3)cc1)c1ccc2nccn2c1]
N-[(4-{8-oxa-3-azabicyclo[3.2.1]octane-3-sulfonyl}phenyl)methyl]imidazo[1,2-a]pyridine-6-carboxamide
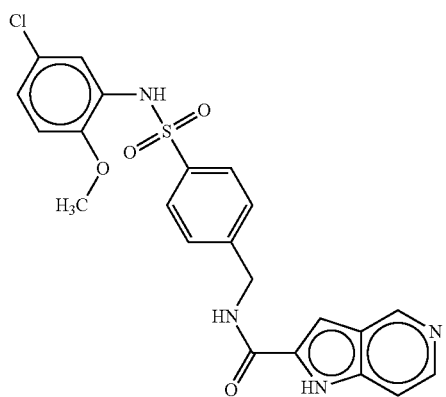
N-({4-[(5-chloro-2-methoxyphenyl)sulfamoyl]phenyl}methyl)-1H-pyrrolo[3,2-c]pyridine-2-carboxamide
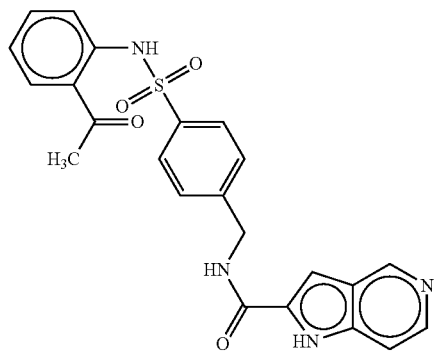
N-({4-[(2-acetylphenyl)sulfamoyl]phenyl}methyl)-1H-pyrrolo[3,2-c]pyridine-2-carboxamide
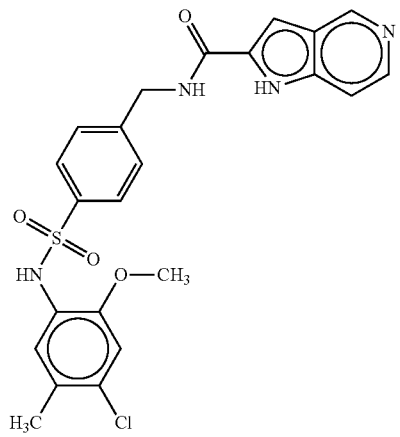
N-({4-[(4-chloro-2-methoxy-5-methylphenyl)sulfamoyl]phenyl}methyl)-1H-pyrrolo[3,2-c]pyridine-2-carboxamide TABLE 2-continued
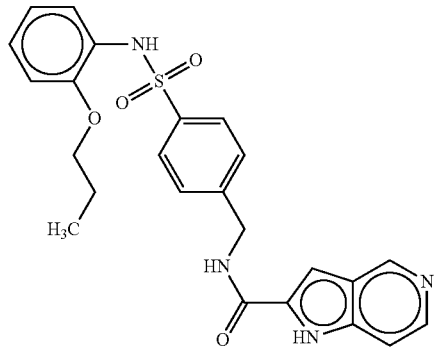
N-({4-[(2-propoxyphenyl)sulfamoyl]phenyl}methyl)-1H-pyrrolo[3,2-c]pyridine-2-carboxamide
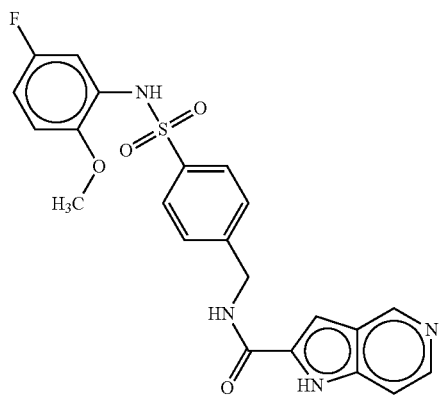
N-({4-[(5-fluoro-2-methoxyphenyl)sulfamoyl]phenyl}methyl)-1H-pyrrolo[3,2-c]pyridine-2-carboxamide
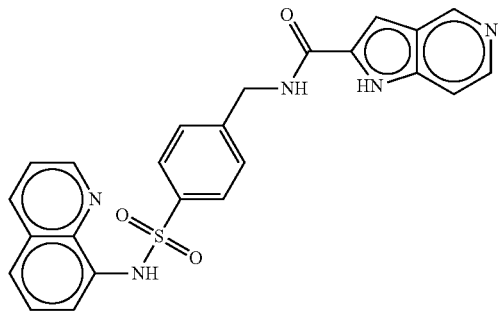
N-({4-[(quinolin-8-yl)sulfamoyl]phenyl}methyl)-1H-pyrrolo[3,2-c]pyridine-2-carboxamide
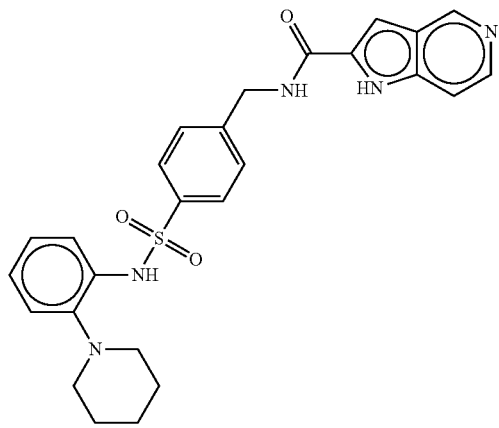
N-[(4-{[2-(piperidin-1-yl)phenyl]sulfamoyl}phenyl)methyl]-1H-pyrrolo[3,2-c]pyridine-2-carboxamide TABLE 2-continued
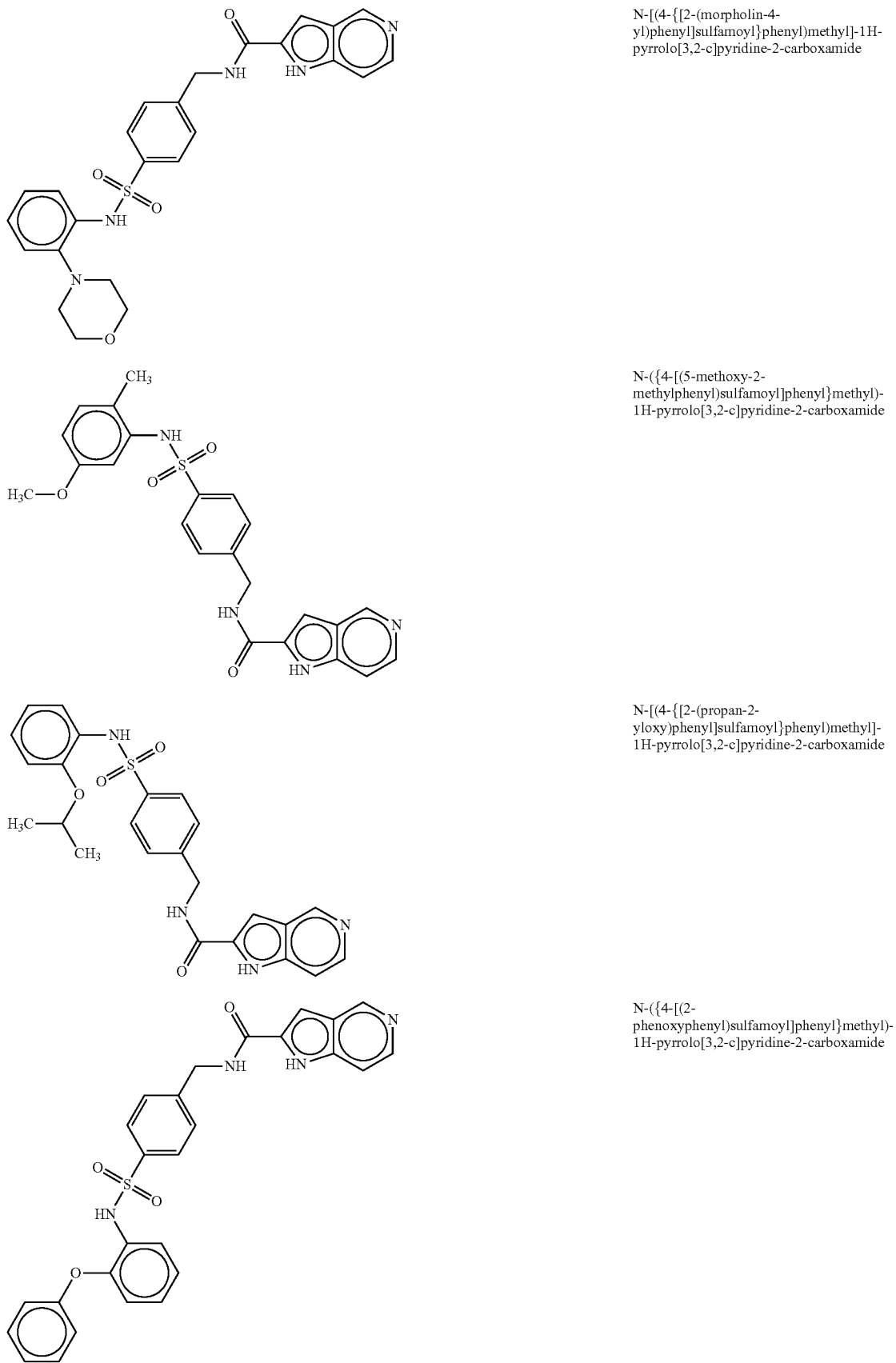
N-[(4-{[2-(morpholin-4-yl)phenyl]sulfamoyl}phenyl)methyl]-1H-pyrrolo[3,2-c]pyridine-2-carboxamide
N-({4-[(5-methoxy-2-methylphenyl)sulfamoyl]phenyl}methyl)-1H-pyrrolo[3,2-c]pyridine-2-carboxamide
N-[(4-{[2-(propan-2-yloxy)phenyl]sulfamoyl}phenyl)methyl]-1H-pyrrolo[3,2-c]pyridine-2-carboxamide
N-({4-[(2-phenoxyphenyl)sulfamoyl]phenyl}methyl)-1H-pyrrolo[3,2-c]pyridine-2-carboxamide TABLE 2-continued
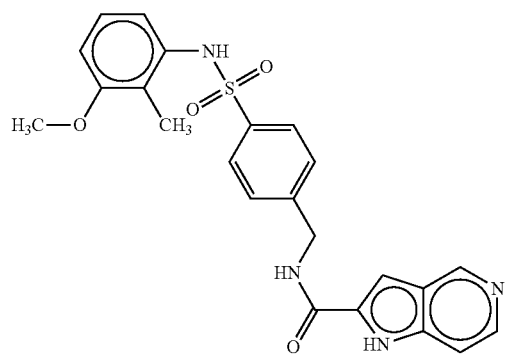
N-({4-[(3-methoxy-2-methylphenyl)sulfamoyl]phenyl}methyl)-1H-pyrrolo[3,2-c]pyridine-2-carboxamide
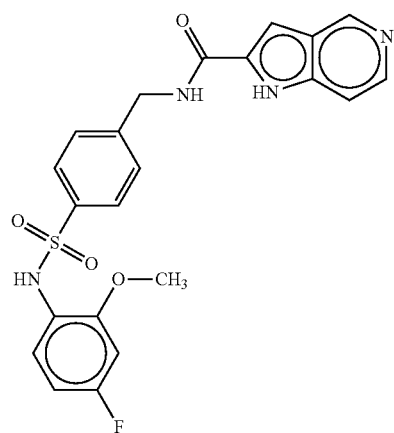
N-({4-[(4-fluoro-2-methoxyphenyl)sulfamoyl]phenyl}methyl)-1H-pyrrolo[3,2-c]pyridine-2-carboxamide
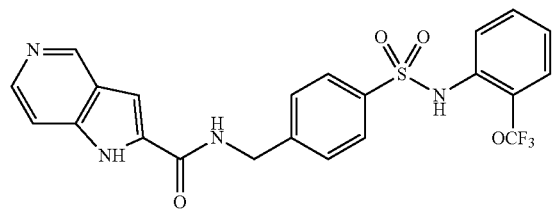 [SMILES: O=C(NCc1ccc(S(=O)(=O)Nc2ccccc2OC(F)(F)F)cc1)c1cc2cnccc2[nH]1]
N-[(4-{[2-(trifluoromethoxy)phenyl]sulfamoyl}phenyl)methyl]-1H-pyrrolo[3,2-c]pyridine-2-carboxamide
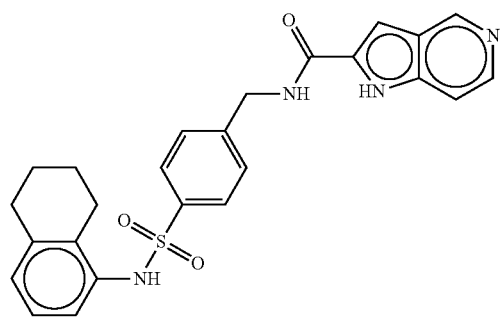
N-({4-[(5,6,7,8-tetrahydronaphthalen-1-yl)sulfamoyl]phenyl}methyl)-1H-pyrrolo[3,2-c]pyridine-2-carboxamide TABLE 2-continued
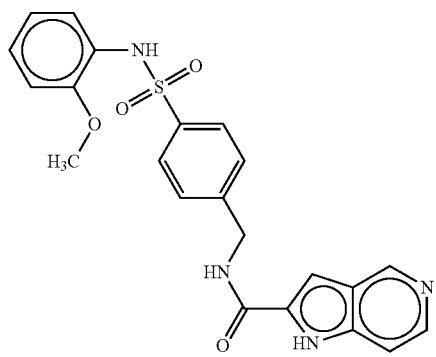
N-({4-[(2-methoxyphenyl)sulfamoyl]phenyl}methyl)-1H-pyrrolo[3,2-c]pyridine-2-carboxamide
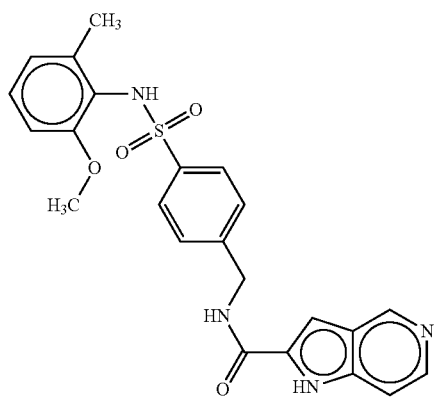
N-({4-[(2-methoxy-6-methylphenyl)sulfamoyl]phenyl}methyl)-1H-pyrrolo[3,2-c]pyridine-2-carboxamide
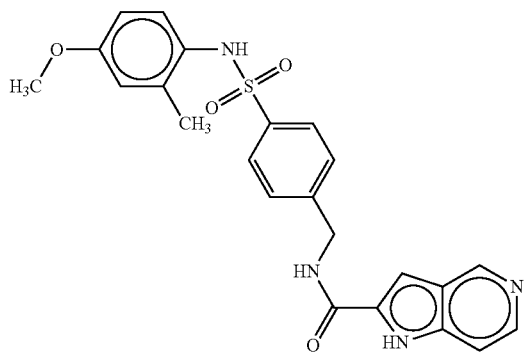
N-({4-[(4-methoxy-2-methylphenyl)sulfamoyl]phenyl}methyl)-1H-pyrrolo[3,2-c]pyridine-2-carboxamide
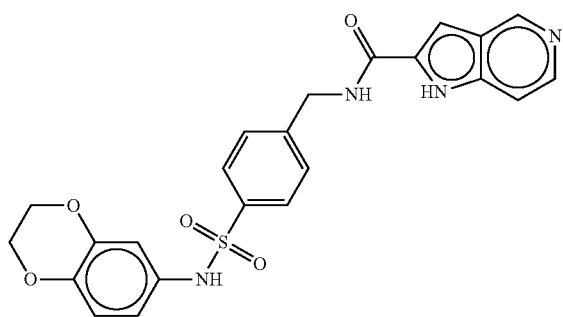
N-({4-[(2,3-dihydro-1,4-benzodioxin-6-yl)sulfamoyl]phenyl}methyl)-1H-pyrrolo[3,2-c]pyridine-2-carboxamide TABLE 2-continued
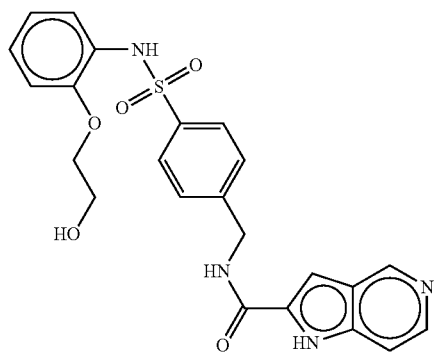
N-[(4-{[2-(2-hydroxyethoxy)phenyl]sulfamoyl}phenyl)methyl]-1H-pyrrolo[3,2-c]pyridine-2-carboxamide
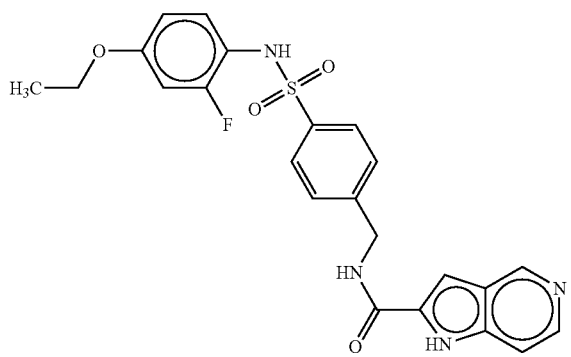
N-({4-[(4-ethoxy-2-fluorophenyl)sulfamoyl]phenyl}methyl)-1H-pyrrolo[3,2-c]pyridine-2-carboxamide
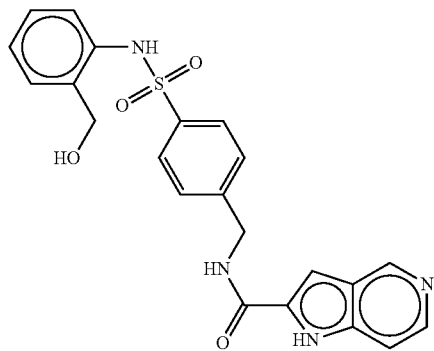
N-[(4-{[2-(hydroxymethyl)phenyl]sulfamoyl}phenyl)methyl]-1H-pyrrolo[3,2-c]pyridine-2-carboxamide
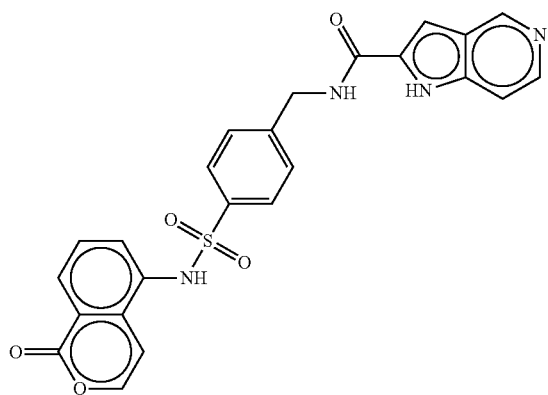
N-({4-[(1-oxo-1H-isochromen-5-yl)sulfamoyl]phenyl}methyl)-1H-pyrrolo[3,2-c]pyridine-2-carboxamide TABLE 2-continued

| | |
|---|---|
| 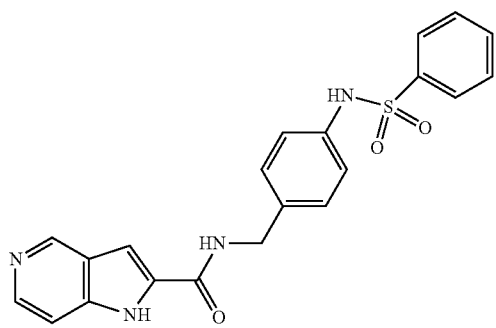 [SMILES: O=C(NCc1ccc(NS(=O)(=O)c2ccccc2)cc1)c1cc2cnccc2[nH]1] | N-[(4-benzenesulfonamidophenyl)methyl]-1H-pyrrolo[3,2-c]pyridine-2-carboxamide |
| 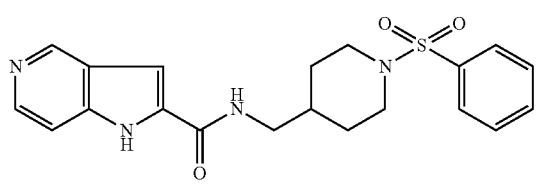 [SMILES: O=C(NCC1CCN(S(=O)(=O)c2ccccc2)CC1)c1cc2cnccc2[nH]1] | N-{[1-(benzenesulfonyl)piperidin-4-yl]methyl}-1H-pyrrolo[3,2-c]pyridine-2-carboxamide |
| 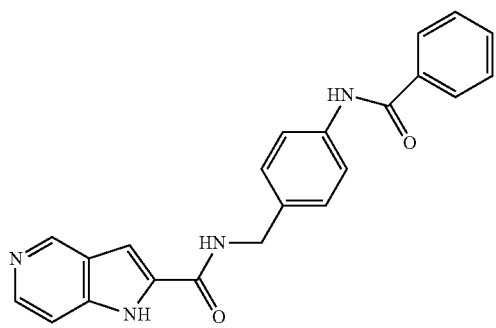 [SMILES: O=C(Nc1ccc(CNC(=O)c2cc3cnccc3[nH]2)cc1)c1ccccc1] | N-[(4-benzamidophenyl)methyl]-1H-pyrrolo[3,2-c]pyridine-2-carboxamide |
| 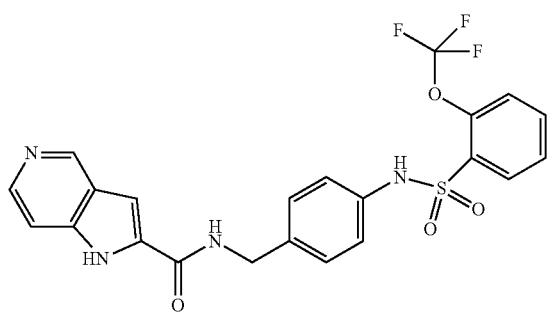 [SMILES: O=C(NCc1ccc(NS(=O)(=O)c2ccccc2OC(F)(F)F)cc1)c1cc2cnccc2[nH]1] | N-[(4-{[2-(trifluoromethoxy)benzene]sulfonamido}phenyl)methyl]-1H-pyrrolo[3,2-c]pyridine-2-carboxamide |
| 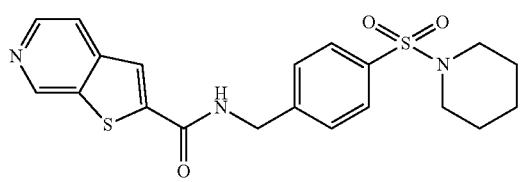 [SMILES: O=C(NCc1ccc(S(=O)(=O)N2CCCCC2)cc1)c1cc2ccncc2s1] | N-{[4-(piperidine-1-sulfonyl)phenyl]methyl}thieno[2,3-c]pyridine-2-carboxamide |

TABLE 2-continued
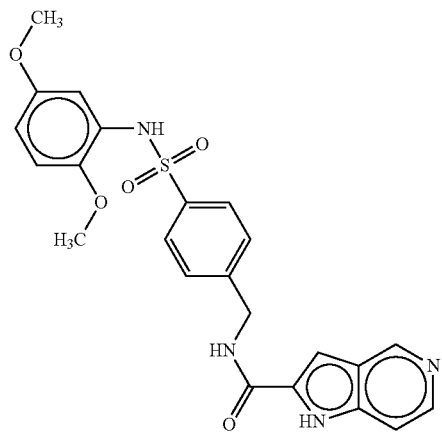
N-({4-[(2,5-dimethoxyphenyl)sulfamoyl]phenyl}methyl)-1H-pyrrolo[3,2-c]pyridine-2-carboxamide
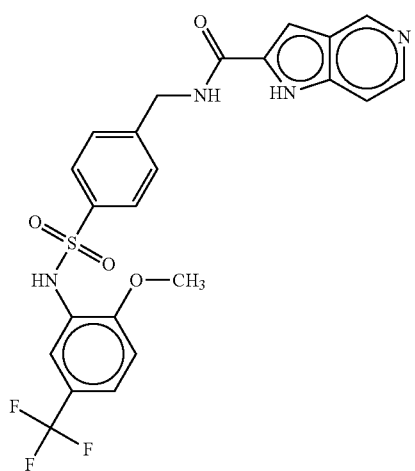
N-[(4-{[2-methoxy-5-(trifluoromethyl)phenyl]sulfamoyl}phenyl)methyl]-1H-pyrrolo[3,2-c]pyridine-2-carboxamide
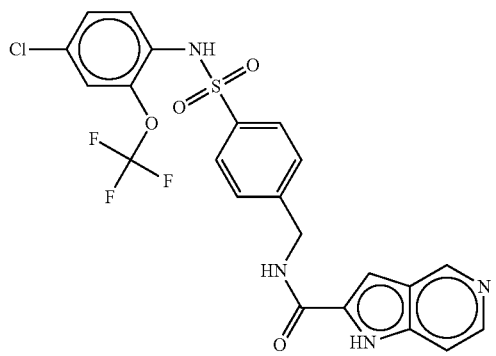
N-[(4-{[4-chloro-2-(trifluoromethoxy)phenyl]sulfamoyl}phenyl)methyl]-1H-pyrrolo[3,2-c]pyridine-2-carboxamide
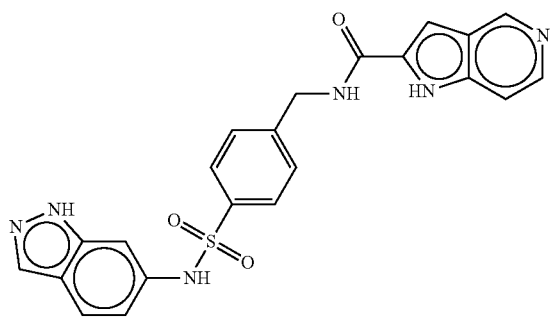
N-({4-[(1H-indazol-6-yl)sulfamoyl]phenyl}methyl)-1H-pyrrolo[3,2-c]pyridine-2-carboxamide TABLE 2-continued

| | |
|---|---|
| 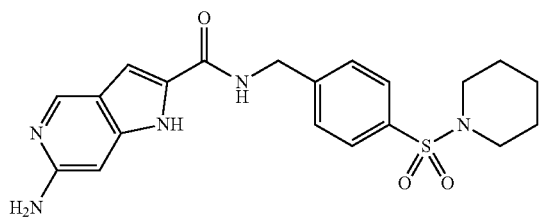 [SMILES: Nc1cc2[nH]c(C(=O)NCc3ccc(S(=O)(=O)N4CCCCC4)cc3)cc2cn1] | 6-Amino-1H-pyrrolo[3,2-c]pyridine-2-carboxylic acid 4-(piperidine-1-sulfonyl)-benzylamide |
| 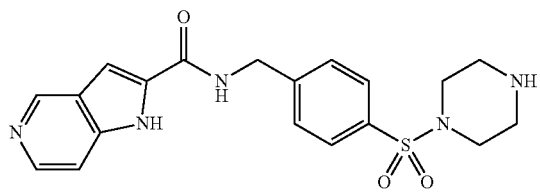 [SMILES: O=C(NCc1ccc(S(=O)(=O)N2CCNCC2)cc1)c1cc2cnccc2[nH]1] | 1H-Pyrrolo[3,2-c]pyridine-2-carboxylic acid 4-(piperazine-1-sulfonyl)-benzylamide |
| 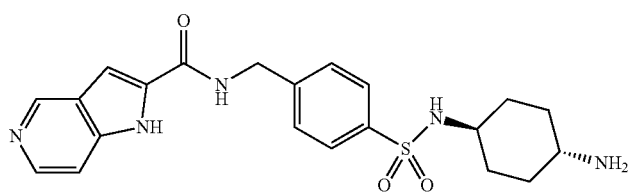 [SMILES: N[C@H]1CC[C@H](NS(=O)(=O)c2ccc(CNC(=O)c3cc4cnccc4[nH]3)cc2)CC1] | 1H-Pyrrolo[3,2-c]pyridine-2-carboxylic acid 4-(4-amino-cyclohexylsulfamoyl)-benzylamide |
| 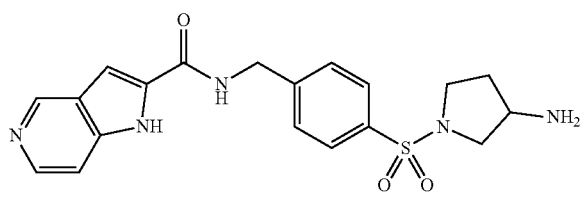 [SMILES: NC1CCN(S(=O)(=O)c2ccc(CNC(=O)c3cc4cnccc4[nH]3)cc2)C1] | 1H-Pyrrolo[3,2-c]pyridine-2-carboxylic acid 4-(3-amino-pyrrolidine-1-sulfonyl)-benzylamide |
| 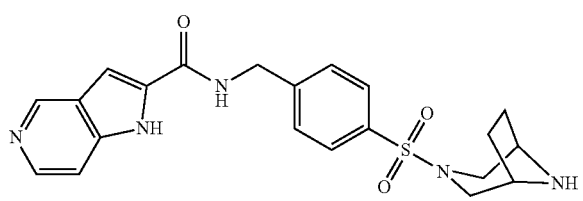 [SMILES: O=C(NCc1ccc(S(=O)(=O)N2CC3CCC(C2)N3)cc1)c1cc2cnccc2[nH]1] | 1H-Pyrrolo[3,2-c]pyridine-2-carboxylic acid 4-(3,8-diaza-bicyclo[3.2.1]octane-3-sulfonyl)-benzylamide |
| 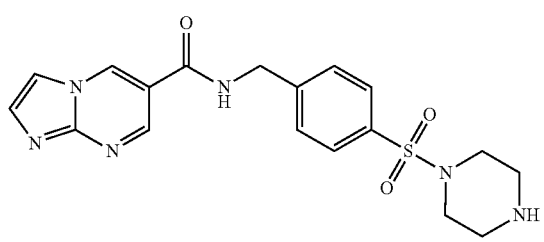 [SMILES: O=C(NCc1ccc(S(=O)(=O)N2CCNCC2)cc1)c1cnc2nccn2c1] | Imidazo[1,2-a]pyrimidine-6-carboxylic acid 4-(piperazine-1-sulfonyl)-benzylamide |
| 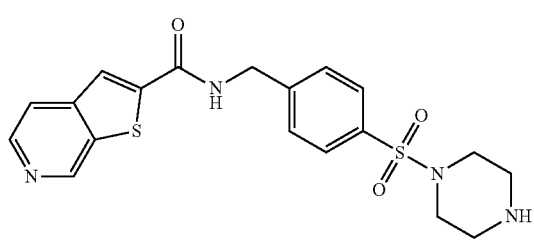 | Thieno[2,3-c]pyridine-2-carboxylic acid 4-(piperazine-1-sulfonyl)-benzylamide |

TABLE 2-continued

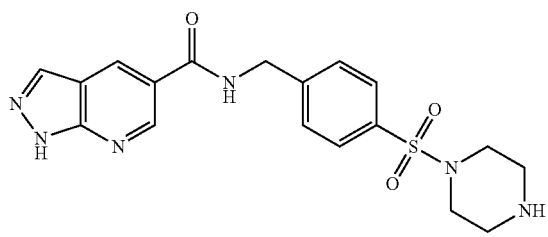 [SMILES: O=C(NCc1ccc(S(=O)(=O)N2CCNCC2)cc1)c1cnc2[nH]ncc2c1]

1H-Pyrazolo[3,4-b]pyridine-5-carboxylic acid 4-(piperazine-1-sulfonyl)-benzylamide

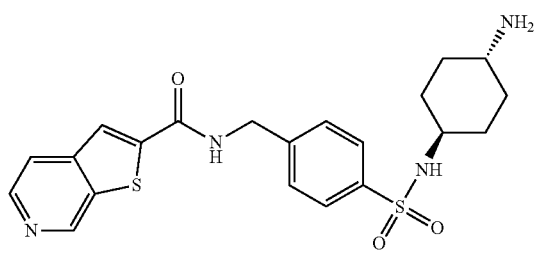 [SMILES: N[C@H]1CC[C@H](NS(=O)(=O)c2ccc(CNC(=O)c3cc4ccncc4o3)cc2)CC1]

Thieno[2,3-c]pyridine-2-carboxylic acid 4-(4-amino-cyclohexylsulfamoyl)-benzylamide

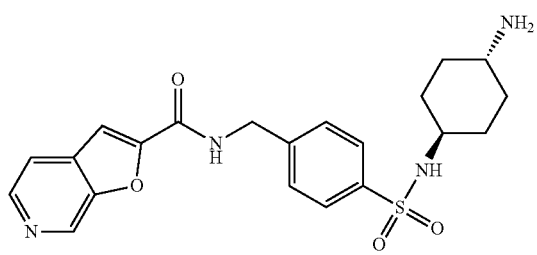

Furo[2,3-c]pyridine-2-carboxylic acid 4-(4-amino-cyclohexylsulfamoyl)-benzylamide

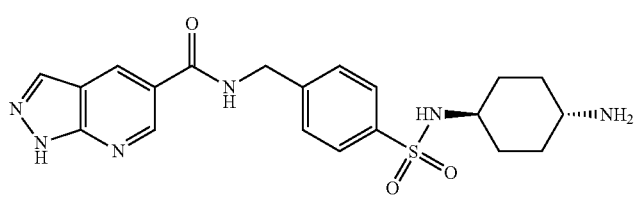 [SMILES: N[C@H]1CC[C@H](NS(=O)(=O)c2ccc(CNC(=O)c3cnc4[nH]ncc4c3)cc2)CC1]

1H-Pyrazolo[3,4-b]pyridine-5-carboxylic acid 4-(4-amino-cyclohexylsulfamoyl)-benzylamide

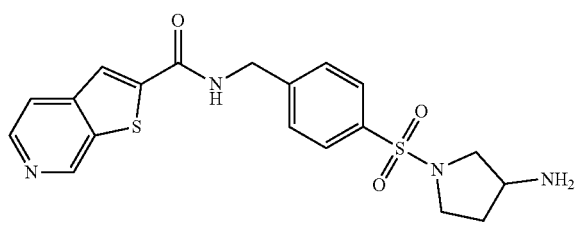 [SMILES: NC1CCN(S(=O)(=O)c2ccc(CNC(=O)c3cc4ccncc4s3)cc2)C1]

Thieno[2,3-c]pyridine-2-carboxylic acid 4-(3-amino-pyrrolidine-1-sulfonyl)-benzylamide

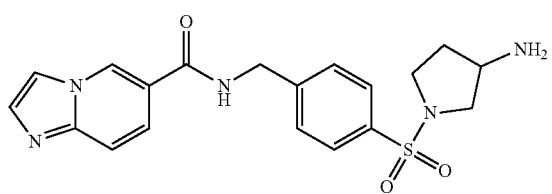 [SMILES: NC1CCN(S(=O)(=O)c2ccc(CNC(=O)c3ccc4nccn4c3)cc2)C1]

Imidazo[1,2-a]pyridine-6-carboxylic acid 4-(3-amino-pyrrolidine-1-sulfonyl)-benzylamide

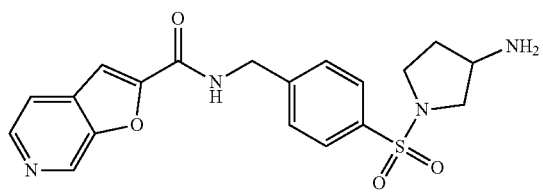 [SMILES: NC1CCN(S(=O)(=O)c2ccc(CNC(=O)c3cc4ccncc4o3)cc2)C1]

Furo[2,3-c]pyridine-2-carboxylic acid 4-(3-amino-pyrrolidine-1-sulfonyl)-benzylamide TABLE 2-continued

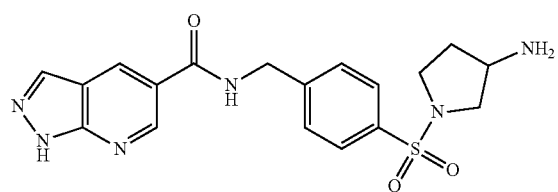 [SMILES: NC1CCN(S(=O)(=O)c2ccc(CNC(=O)c3cnc4[nH]ncc4c3)cc2)C1]

1H-Pyrazolo[3,4-b]pyridine-5-carboxylic acid 4-(3-amino-pyrrolidine-1-sulfonyl)-benzylamide

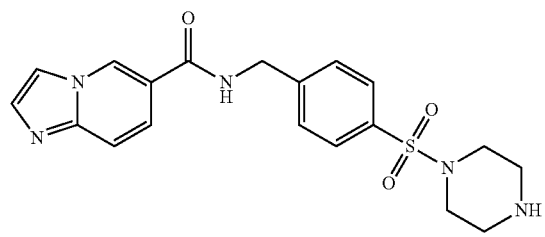 [SMILES: O=C(NCc1ccc(S(=O)(=O)N2CCNCC2)cc1)c1ccc2nccn2c1]

Imidazo[1,2-a]pyridine-6-carboxylic acid 4-(piperazine-1-sulfonyl)-benzylamide

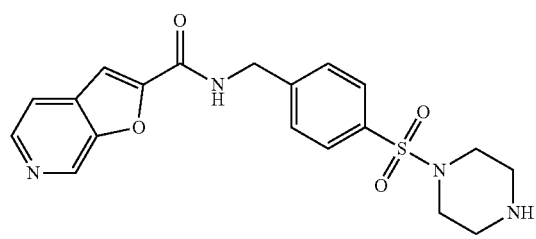

Furo[2,3-c]pyridine-2-carboxylic acid 4-(piperazine-1-sulfonyl)-benzylamide

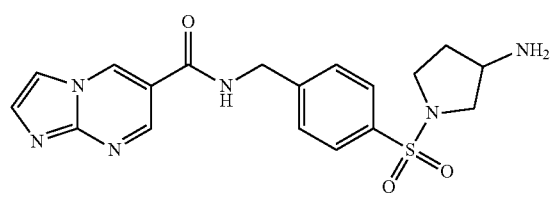 [SMILES: NC1CCN(S(=O)(=O)c2ccc(CNC(=O)c3cnc4nccn4c3)cc2)C1]

Imidazo[1,2-a]pyrimidine-6-carboxylic acid 4-(3-amino-pyrrolidine-1-sulfonyl)-benzylamide

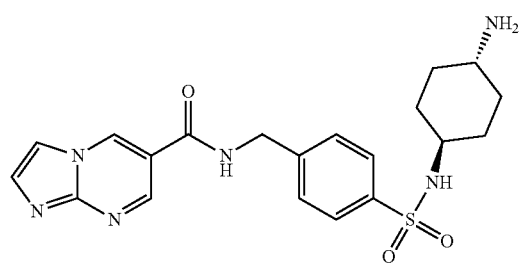 [SMILES: N[C@H]1CC[C@H](NS(=O)(=O)c2ccc(CNC(=O)c3cnc4nccn4c3)cc2)CC1]

Imidazo[1,2-a]pyrimidine-6-carboxylic acid 4-(4-amino-cyclohexylsulfamoyl)-benzylamide

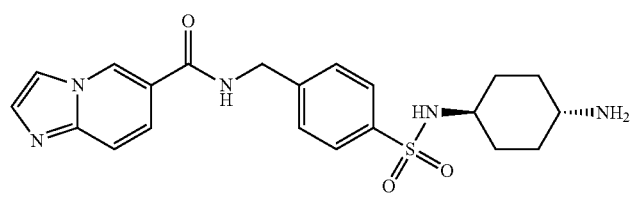 [SMILES: N[C@H]1CC[C@H](NS(=O)(=O)c2ccc(CNC(=O)c3ccc4nccn4c3)cc2)CC1]

Imidazo[1,2-a]pyridine-6-carboxylic acid 4-(4-amino-cyclohexylsulfamoyl)-benzylamide

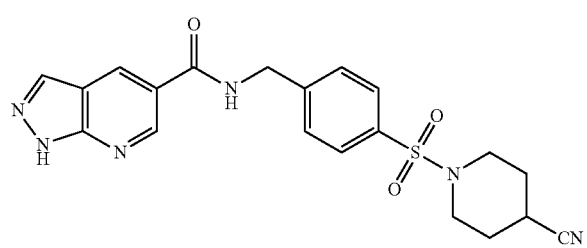 [SMILES: N#CC1CCN(S(=O)(=O)c2ccc(CNC(=O)c3cnc4[nH]ncc4c3)cc2)CC1]

1H-Pyrazolo[3,4-b]pyridine-5-carboxylic acid 4-(4-cyano-piperidine-1-sulfonyl)-benzylamide TABLE 2-continued

| Structure | Name |
|---|---|
| (structure) | 1H-Pyrazolo[3,4-b]pyridine-5-carboxylic acid 4-(4-cyanomethyl-piperidine-1-sulfonyl)-benzylamide |
| (structure) | 1H-Pyrazolo[3,4-b]pyridine-5-carboxylic acid 4-(4-methoxy-piperidine-1-sulfonyl)-benzylamide |
| (structure) | 1H-Pyrazolo[3,4-b]pyridine-5-carboxylic acid 4-(4-amino-piperidine-1-sulfonyl)-benzylamide |
| (structure) | 1H-Pyrazolo[3,4-b]pyridine-5-carboxylic acid 4-[4-(2,2,2-trifluoro-ethylamino)-piperidine-1-sulfonyl]-benzylamide |
| (structure) | N-({4-[1-(3-chlorophenyl)-1H-pyrazole-4-sulfonyl]phenyl}methyl)-1H-pyrazolo[3,4-b]pyridine-5-carboxamide |
| (structure) | N-({4-[(4-chloro-2-ethoxybenzene)sulfonyl]phenyl}methyl)-1H-pyrrolo[3,2-c]pyridine-2-carboxamide |

TABLE 2-continued

| | |
|---|---|
| 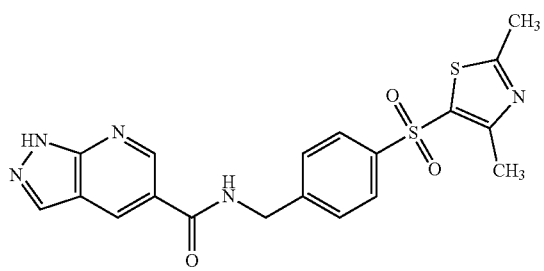 [SMILES: Cc1nc(C)c(S(=O)(=O)c2ccc(CNC(=O)c3cnc4[nH]ncc4c3)cc2)s1] | N-{[4-(dimethyl-1,3-thiazole-5-sulfonyl)phenyl]methyl}-1H-pyrazolo[3,4-b]pyridine-5-carboxamide |
| 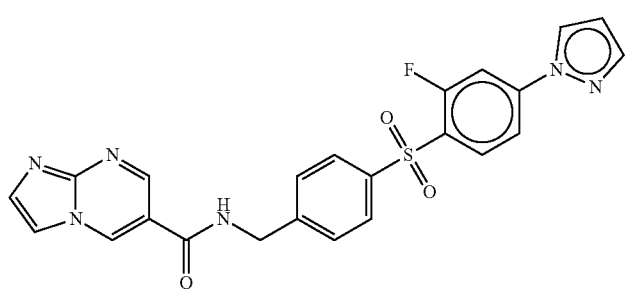 | N-[(4-{[2-fluoro-4-(1H-pyrazol-1-yl)benzene]sulfonyl}phenyl)methyl]imidazo[1,2-a]pyrimidine-6-carboxamide |
| 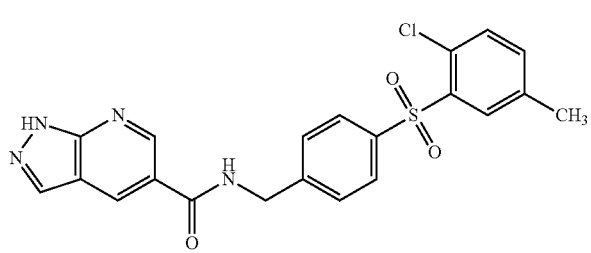 [SMILES: Cc1ccc(Cl)c(S(=O)(=O)c2ccc(CNC(=O)c3cnc4[nH]ncc4c3)cc2)c1] | N-({4-[(2-chloro-5-methylbenzene)sulfonyl]phenyl}methyl)-1H-pyrazolo[3,4-b]pyridine-5-carboxamide |
| 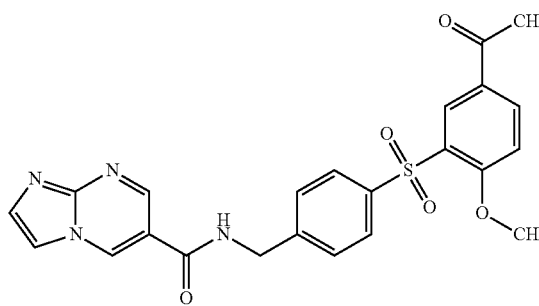 | N-({4-[(5-acetyl-2-methoxybenzene)sulfonyl]phenyl}methyl)imidazo[1,2-a]pyrimidine-6-carboxamide |
| 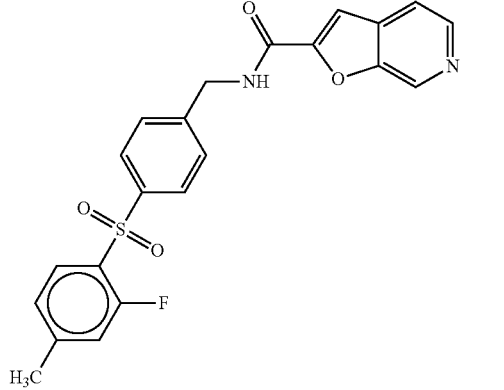 | N-({4-[(2-fluoro-4-methylbenzene)sulfonyl]phenyl}methyl)furo[2,3-c]pyridine-2-carboxamide |

TABLE 2-continued

| | |
|---|---|
| 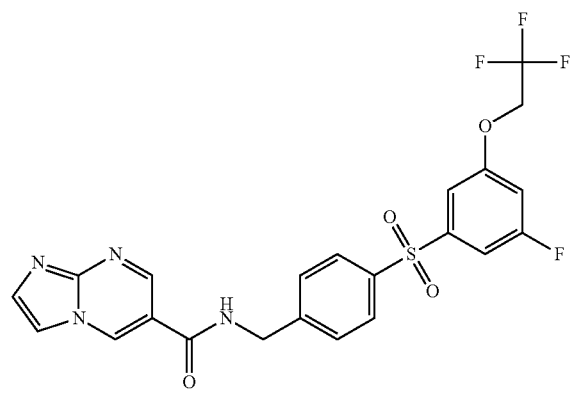 [SMILES: O=C(NCc1ccc(S(=O)(=O)c2cc(F)cc(OCC(F)(F)F)c2)cc1)c1cnc2nccn2c1] | N-[(4-{[3-fluoro-5-(2,2,2-trifluoroelhoxy)benzene]sulfonyl}phenyl)methyl]imidazo[1,2-a]pyrimidine-6-carboxamide |
| 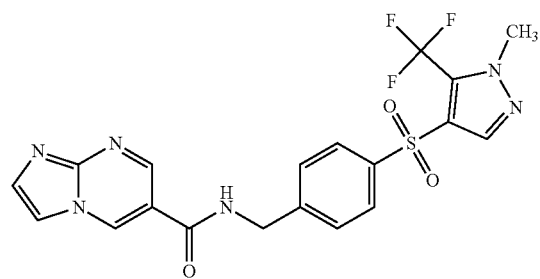 [SMILES: Cn1ncc(S(=O)(=O)c2ccc(CNC(=O)c3cnc4nccn4c3)cc2)c1C(F)(F)F] | N-({4-[1-methyl-5-(trifluoromethyl)-1H-pyrazole-4-sulfonyl]phenyl}methyl)imidazo[1,2-a]pyrimidine-6-carboxamide |
| 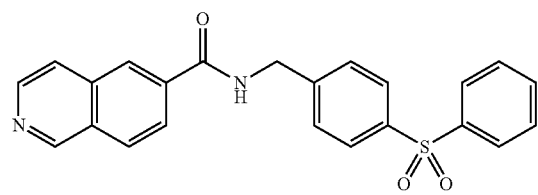 [SMILES: O=C(NCc1ccc(S(=O)(=O)c2ccccc2)cc1)c1ccc2cnccc2c1] | N-{[4-(benzenesulfonyl)phenyl]methyl}isoquinoline-6-carboxamide |
| 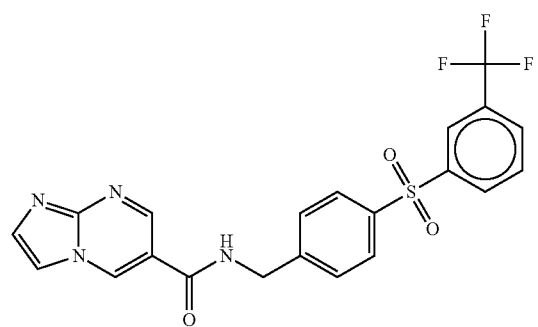 | N-[(4-{[3-(trifluoromethyl)benzene]sulfonyl}phenyl)methyl]imidazo[1,2-a]pyrimidine-6-carboxamide |
| 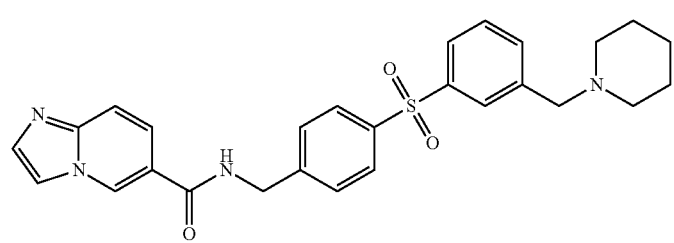 [SMILES: O=C(NCc1ccc(S(=O)(=O)c2cccc(CN3CCCCC3)c2)cc1)c1ccc2nccn2c1] | N-[(4-{[3-(piperidin-1-ylmethyl)benzene]sulfonyl}phenyl)methyl]imidazo[1,2-a]pyridine-6-carboxamide |

TABLE 2-continued
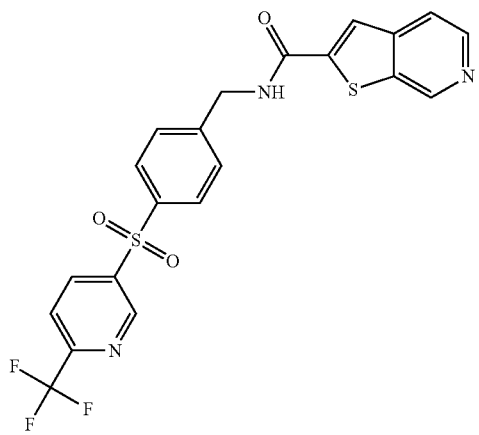 [SMILES: O=C(NCc1ccc(S(=O)(=O)c2ccc(C(F)(F)F)nc2)cc1)c1cc2ccncc2s1]
N-({4-[6-(trifluoromethyl)pyridine-3-sulfonyl]phenyl}methyl)thieno[2,3-c]pyridine-2-carboxamide
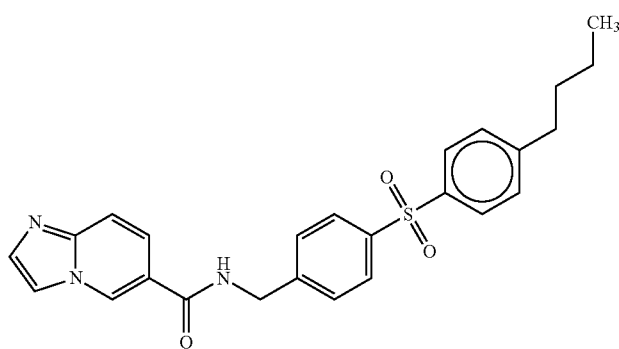
N-({4-[(4-butylbenzene)sulfonyl]phenyl}methyl)imidazo[1,2-a]pyridine-6-carboxamide
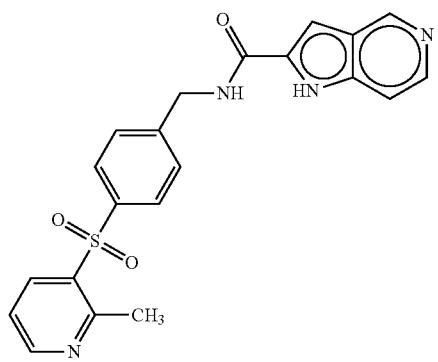
N-{[4-(2-methylpyridine-3-sulfonyl)phenyl]methyl}-1H-pyrrolo[3,2-c]pyridine-2-carboxamide
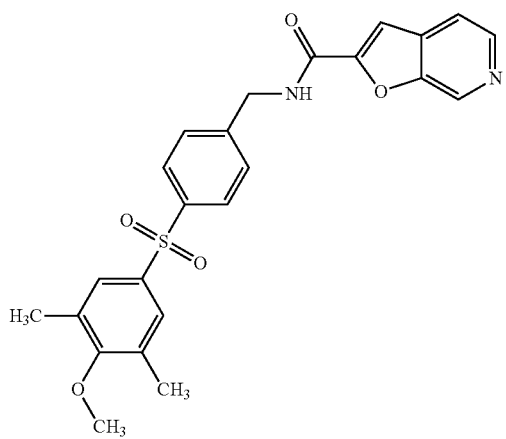 [SMILES: COc1c(C)cc(S(=O)(=O)c2ccc(CNC(=O)c3cc4ccncc4o3)cc2)cc1C]
N-({4-[(4-methoxy-3,5-dimethylbenzene)sulfonyl]phenyl}methyl)furo[2,3-c]pyridine-2-carboxamide TABLE 2-continued
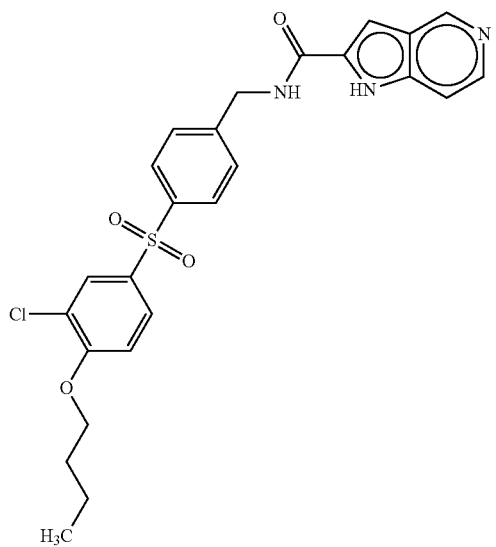
N-({4-[(4-butoxy-3-chlorobenzene)sulfonyl]phenyl}methyl)-1H-pyrrolo[3,2-c]pyridine-2-carboxamide
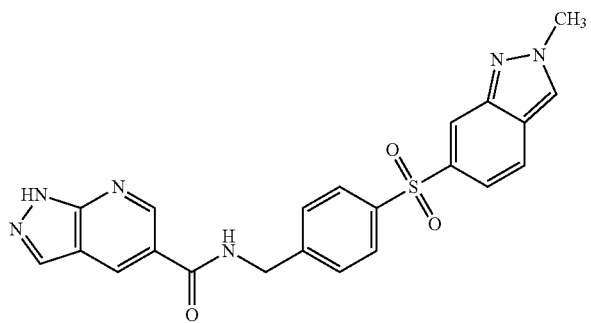 [SMILES: Cn1cc2ccc(S(=O)(=O)c3ccc(CNC(=O)c4cnc5[nH]ncc5c4)cc3)cc2n1]
N-{[4-(2-methyl-2H-indazole-6-sulfonyl)phenyl]methyl}-1H-pyrazolo[3,4-b]pyridine-5-carboxamide
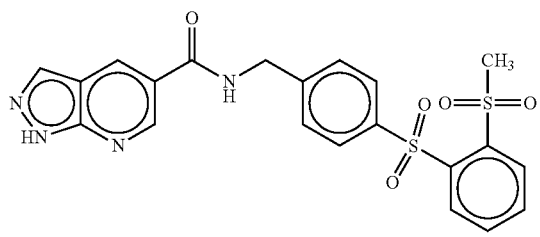
N-({4-[(2-methanesulfonylbenzene)sulfonyl]phenyl}methyl)-1H-pyrazolo[3,4-b]pyridine-5-carboxamide
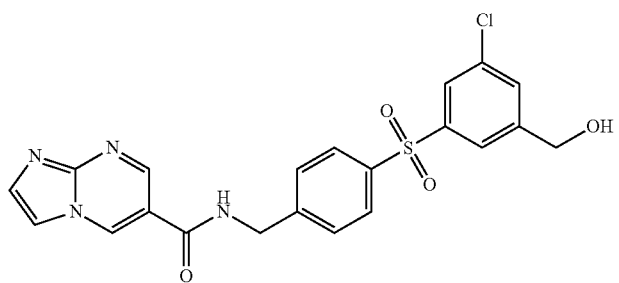 [SMILES: O=C(NCc1ccc(S(=O)(=O)c2cc(Cl)cc(CO)c2)cc1)c1cnc2nccn2c1]
N-[(4-{[3-chloro-5-(hydroxymethyl)benzene]sulfonyl}phenyl)methyl]imidazo[1,2-a]pyrimidine-6-carboxamide TABLE 2-continued
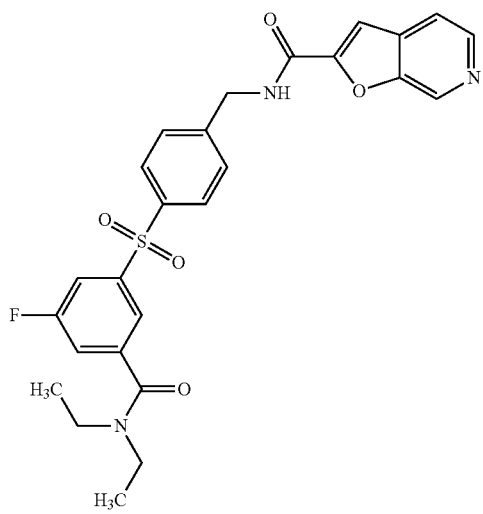 [SMILES: CCN(CC)C(=O)c1cc(F)cc(S(=O)(=O)c2ccc(CNC(=O)c3cc4ccncc4o3)cc2)c1]
N-[(4-{[3-(diethylcarbamoyl)-5-fluorobenzene]sulfonyl}phenyl)methyl]furo[2,3-c]pyridine-2-carboxamide
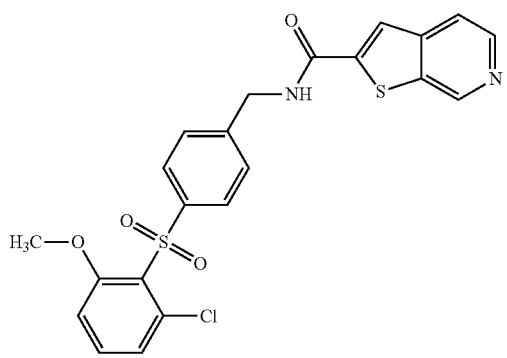 [SMILES: COc1cccc(Cl)c1S(=O)(=O)c1ccc(CNC(=O)c2cc3ccncc3s2)cc1]
N-({4-[(2-chloro-6-methoxybenzene)sulfonyl]phenyl}methyl)thieno[2,3-c]pyridine-2-carboxamide
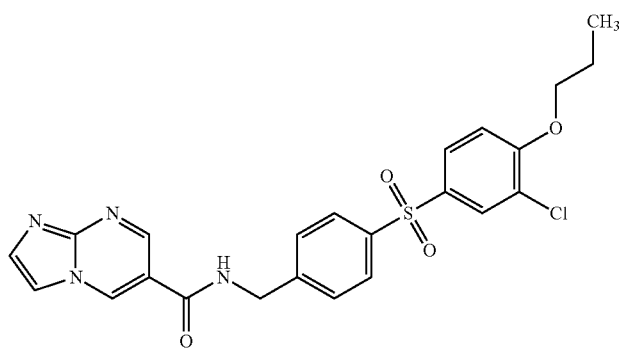
N-({4-[(3-chloro-4-propoxybenzene)sulfonyl]phenyl}methyl]imidazo[1,2-a]pyrimidine-6-carboxamide
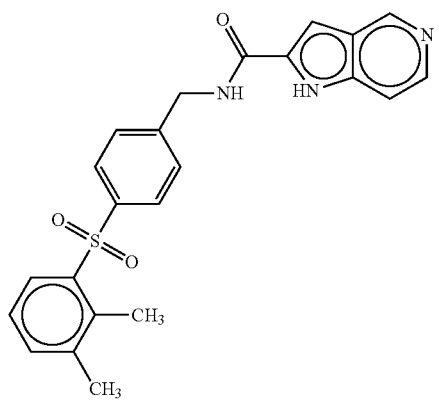
N-({4-[(2,3-dimethylbenzene)sulfonyl]phenyl}methyl)-1H-pyrrolo[3,2-c]pyridine-2-carboxamide TABLE 2-continued
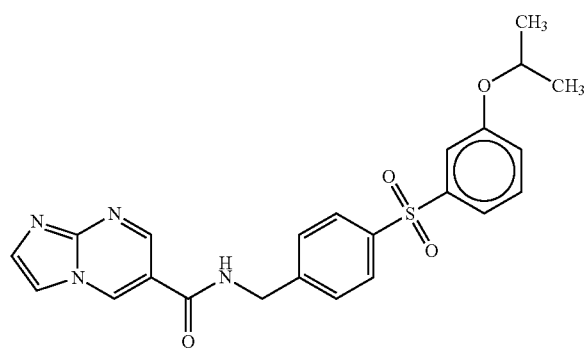
N-[(4-{[3-(propan-2-yloxy)benzene]sulfonyl}phenyl)methyl]imidazo[1,2-a]pyrimidine-6-carboxamide
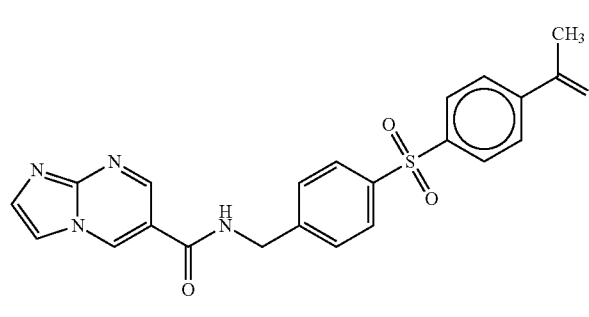
N-({4-[(4-acelylbenzene)sulfonyl]phenyl}methyl)imidazo[1,2-a]pyrimidine-6-carboxamide
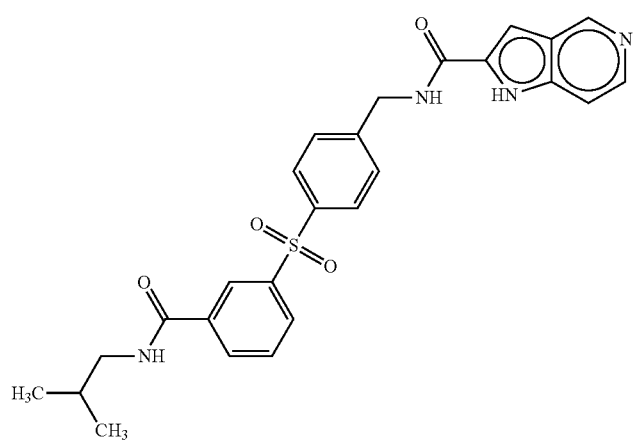
N-{[4-({3-[(2-methylpropyl)carbamoyl]benzene}sulfonyl)phenyl]methyl}-1H-pyrrolo[3,2-c]pyridine-2-carboxamide
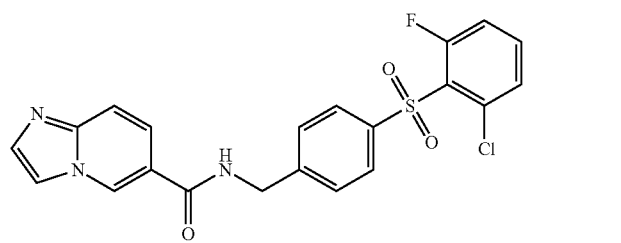
N-({4-[(2-chloro-6-fluorobenzene)sulfonyl]phenyl}methyl)imidazo[1,2-a]pyridine-6-carboxamide TABLE 2-continued
| | |
|---|---|
| 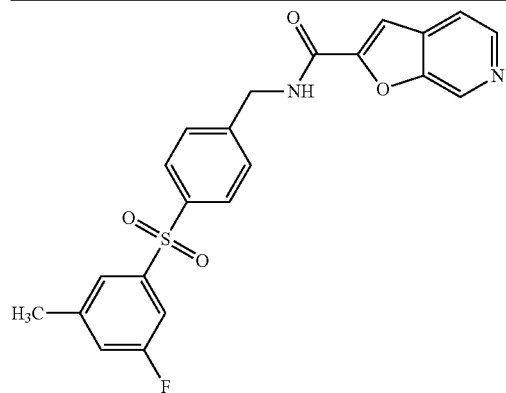 | N-({4-[(3-fluoro-5-methylbenzene)sulfonyl]phenyl}methyl)furo[2,3-c]pyridine-2-carboxamide |
| 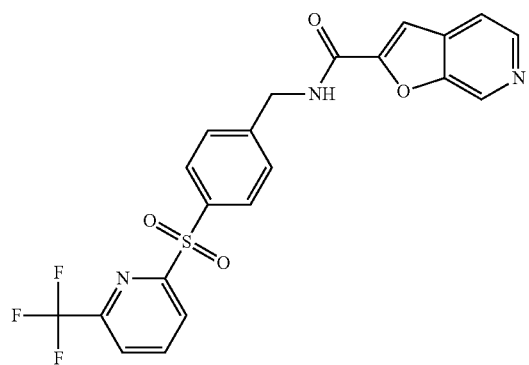 | N-({4-[6-(trifluoromethyl)pyridine-2-sulfonyl]phenyl}methyl)furo[2,3-c]pyridine-2-carboxamide |
| 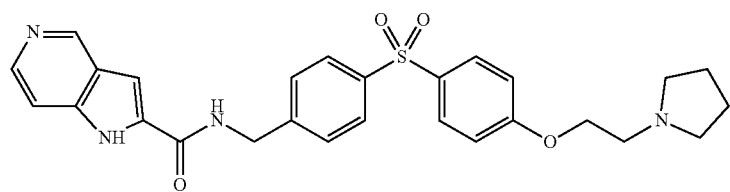 [SMILES: O=C(NCc1ccc(S(=O)(=O)c2ccc(OCCN3CCCC3)cc2)cc1)c1cc2cnccc2[nH]1] | N-{[4-({4-[2-(pyrrolidin-1-yl)ethoxy]benzene}sulfonyl)phenyl]methyl}-1H-pyrrolo[3,2-c]pyridine-2-carboxamide |
| 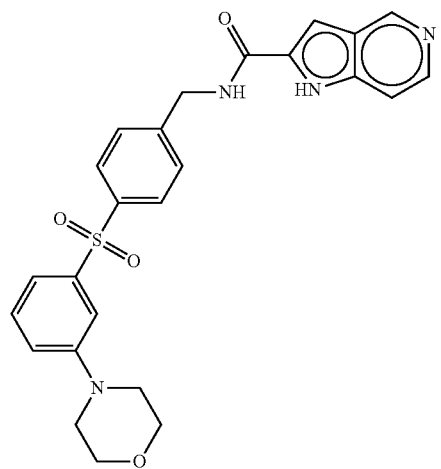 | N-[(4-{[3-(morpholin-4-yl)benzene]sulfonyl}phenyl)methyl]-1H-pyrrolo[3,2-c]pyridine-2-carboxamide |

TABLE 2-continued

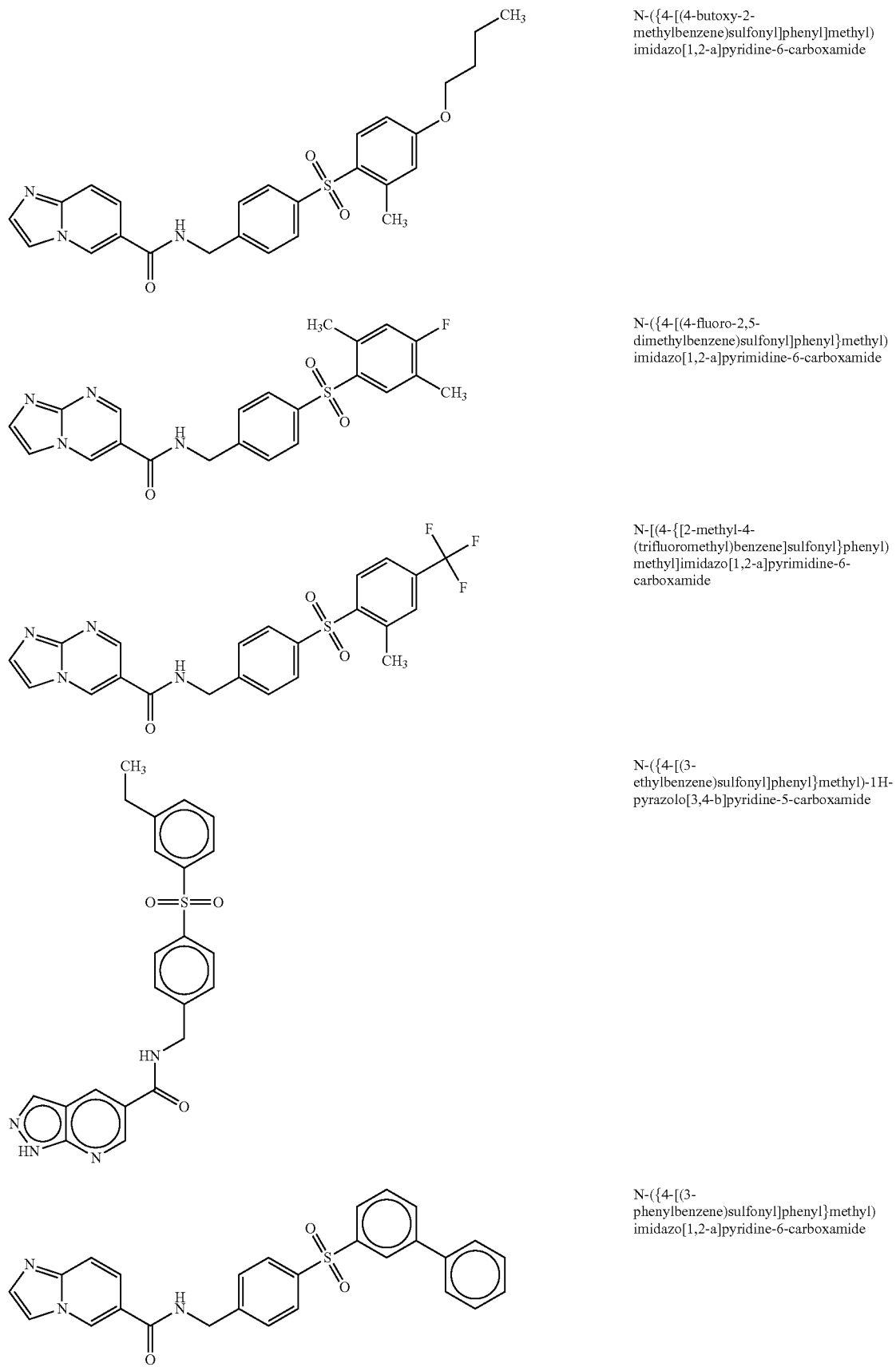

N-({4-[(4-butoxy-2-methylbenzene)sulfonyl]phenyl]methyl)imidazo[1,2-a]pyridine-6-carboxamide N-({4-[(4-fluoro-2,5-dimethylbenzene)sulfonyl]phenyl}methyl)imidazo[1,2-a]pyrimidine-6-carboxamide N-[(4-{[2-methyl-4-(trifluoromethyl)benzene]sulfonyl}phenyl)methyl]imidazo[1,2-a]pyrimidine-6-carboxamide N-({4-[(3-ethylbenzene)sulfonyl]phenyl}methyl)-1H-pyrazolo[3,4-b]pyridine-5-carboxamide N-({4-[(3-phenylbenzene)sulfonyl]phenyl}methyl)imidazo[1,2-a]pyridine-6-carboxamide TABLE 2-continued

| Structure | Name |
|---|---|
| 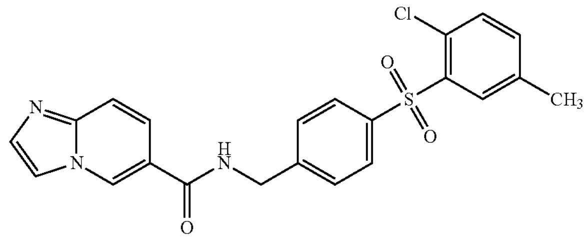 [SMILES: Cc1ccc(Cl)c(S(=O)(=O)c2ccc(CNC(=O)c3ccc4nccn4c3)cc2)c1] | N-({4-[(2-chloro-5-methylbenzene)sulfonyl]phenyl}methyl)imidazo[1,2-a]pyridine-6-carboxamide |
| 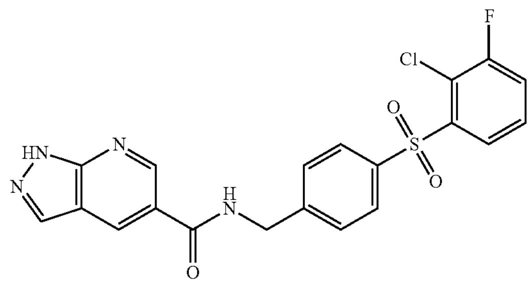 [SMILES: O=C(NCc1ccc(S(=O)(=O)c2cccc(F)c2Cl)cc1)c1cnc2[nH]ncc2c1] | N-({4-[(2-chloro-3-fluorobenzene)sulfonyl]phenyl}methyl)-1H-pyrazolo[3,4-b]pyridine-5-carboxamide |
| 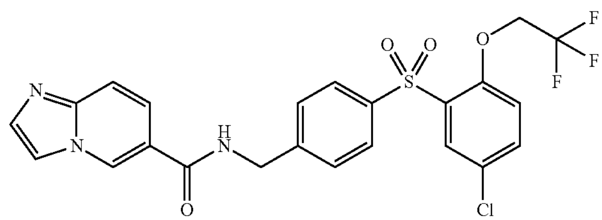 [SMILES: O=C(NCc1ccc(S(=O)(=O)c2cc(Cl)ccc2OCC(F)(F)F)cc1)c1ccc2nccn2c1] | N-[(4-{[5-chloro-2-(2,2,2-trifluoroethoxy)benzene]sulfonyl}phenyl)methyl]imidazo[1,2-a]pyridine-6-carboxamide |
| 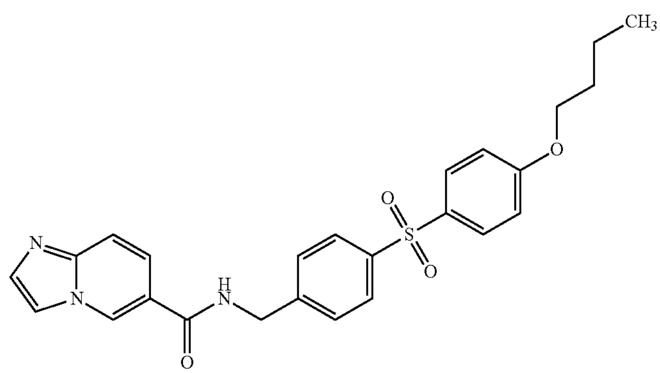 [SMILES: CCCCOc1ccc(S(=O)(=O)c2ccc(CNC(=O)c3ccc4nccn4c3)cc2)cc1] | N-({4-[(4-butoxybenzene)sulfonyl]phenyl}methyl)imidazo[1,2-a]pyridine-6-carboxamide |
| | N-({4-[6-(trifluoromethyl)pyridine-2-sulfonyl]phenyl}methyl)-1H-pyrazolo[3,4-b]pyridine-5-carboxamide |

TABLE 2-continued
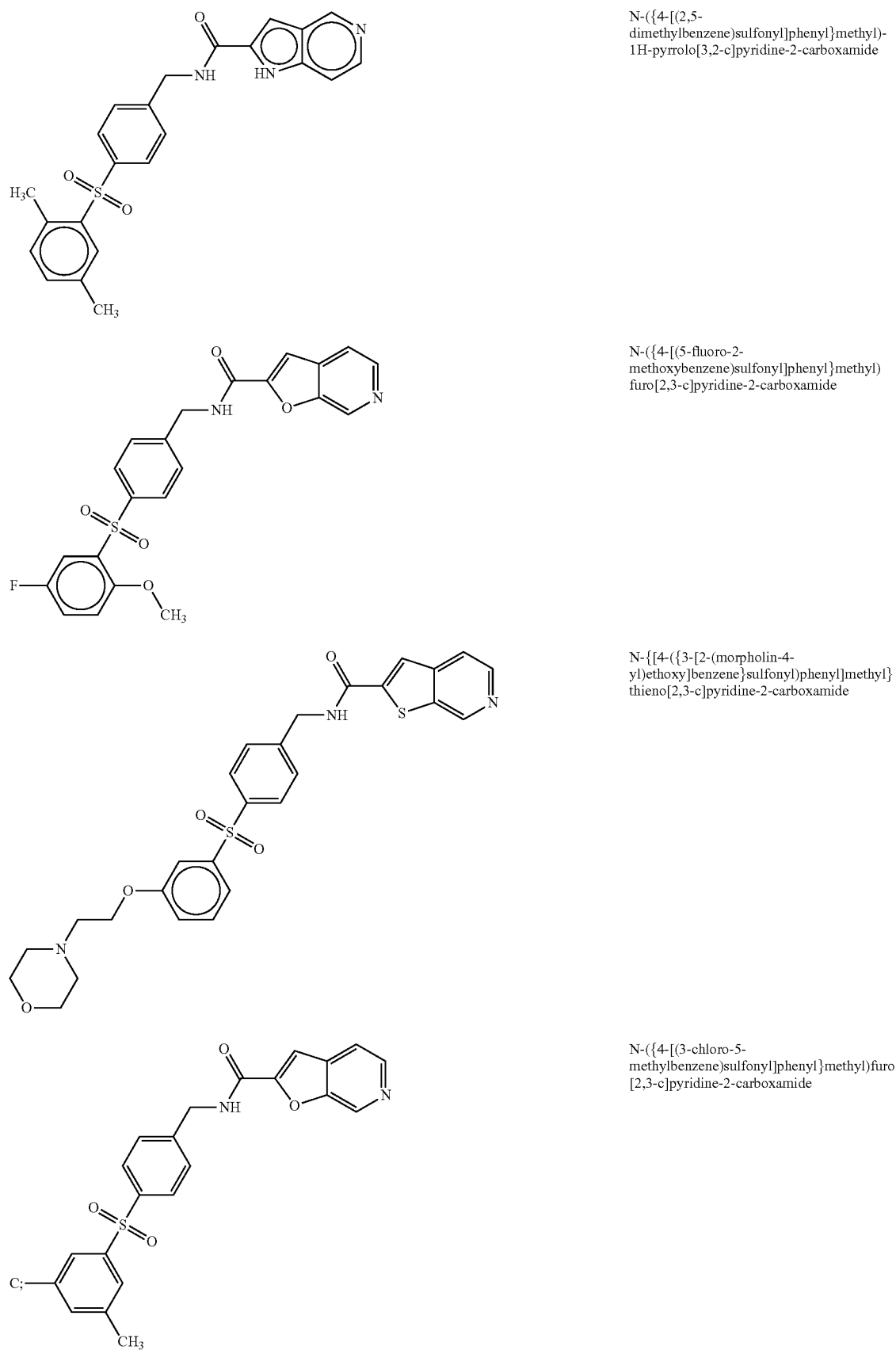
N-({4-[(2,5-dimethylbenzene)sulfonyl]phenyl}methyl)-1H-pyrrolo[3,2-c]pyridine-2-carboxamide
N-({4-[(5-fluoro-2-methoxybenzene)sulfonyl]phenyl}methyl)furo[2,3-c]pyridine-2-carboxamide
N-{[4-({3-[2-(morpholin-4-yl)ethoxy]benzene}sulfonyl)phenyl]methyl}thieno[2,3-c]pyridine-2-carboxamide
N-({4-[(3-chloro-5-methylbenzene)sulfonyl]phenyl}methyl)furo[2,3-c]pyridine-2-carboxamide TABLE 2-continued
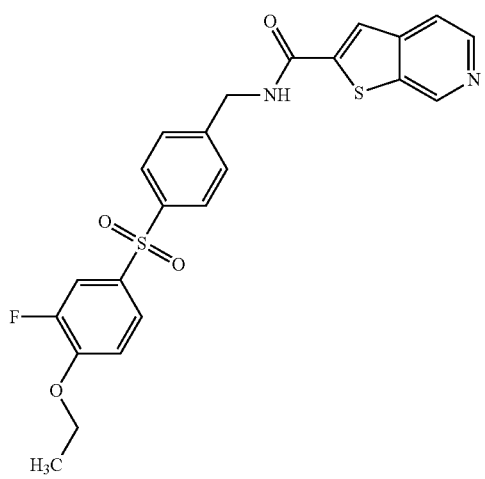 [SMILES: CCOc1ccc(S(=O)(=O)c2ccc(CNC(=O)c3cc4ccncc4s3)cc2)cc1F]
N-({4-[(4-ethoxy-3-fluorobenzene)sulfonyl]phenyl}methyl)thieno[2,3-c]pyridine-2-carboxamide
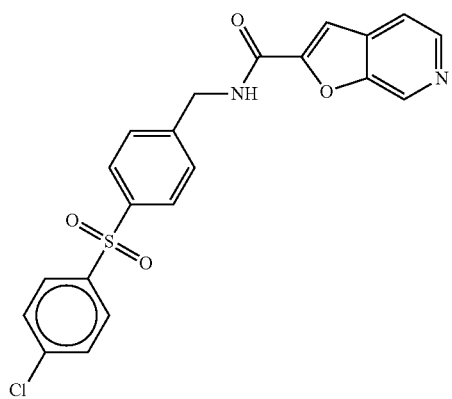
N-({4-[(4-chlorobenzene)sulfonyl]phenyl}methyl)furo[2,3-c]pyridine-2-carboxamide
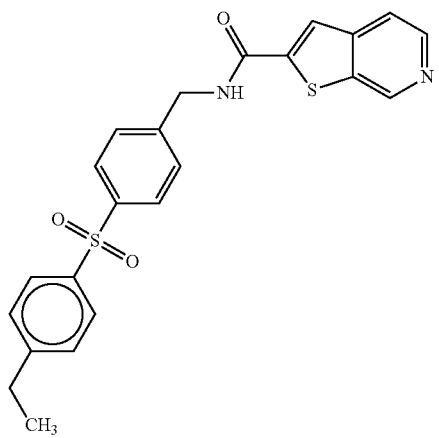
N-({4-[(4-ethylbenzene)sulfonyl]phenyl}methyl)thieno[2,3-c]pyridine-2-carboxamide
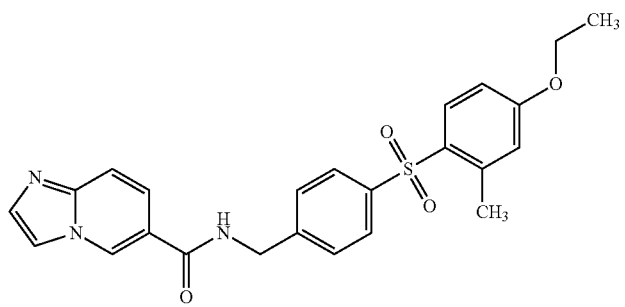 [SMILES: CCOc1ccc(S(=O)(=O)c2ccc(CNC(=O)c3ccc4nccn4c3)cc2)c(C)c1]
N-({4-[(4-ethoxy-2-methylbenzene)sulfonyl]phenyl}methyl)imidazo[1,2-a]pyridine-6-carboxamide TABLE 2-continued

| | |
|---|---|
| (structure) | N-({4-[(3-chloro-5-fluorobenzene)sulfonyl]phenyl}methyl)imidazo[1,2-a]pyridine-6-carboxamide |
| (structure) | N-[(4-{[4-(1-cyanocyclopentyl)benzene]sulfonyl}phenyl)methyl]imidazo[1,2-a]pyrimidine-6-carboxamide |
| (structure) | N-({4-[(3-propoxybenzene)sulfonyl]phenyl}methyl)thieno[2,3-c]pyridine-2-carboxamide |
| (structure) | N-[(4-{[3-fluoro-4-(trifluoromethoxy)benzene]sulfonyl}phenyl)methyl]imidazo[1,2-a]pyrimidine-6-carboxamide |

TABLE 2-continued
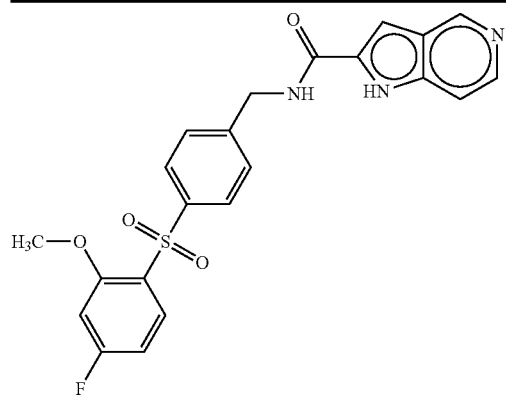
N-({4-[(4-fluoro-2-methoxybenzene)sulfonyl]phenyl}methyl)-1H-pyrrolo[3,2-c]pyridine-2-carboxamide
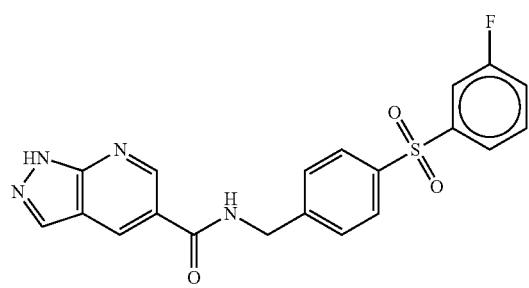
N-({4-[(3-fluorobenzene)sulfonyl]phenyl}methyl)-1H-pyrazolo[3,4-b]pyridine-5-carboxamide
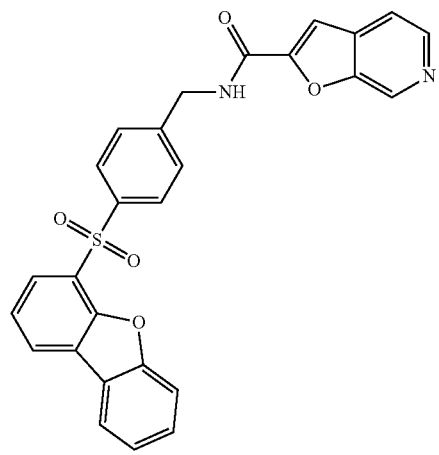 [SMILES: O=C(NCc1ccc(S(=O)(=O)c2cccc3c2oc2ccccc23)cc1)c1cc2ccncc2o1]
N-[(4-{8-thiatricyclo[7.4.0.0²,☐]trideca-1(13),2,4,6,9,11-hexaene-6-sulfonyl}phenyl)methyl]furo[2,3-c]pyridine-2-carboxamide
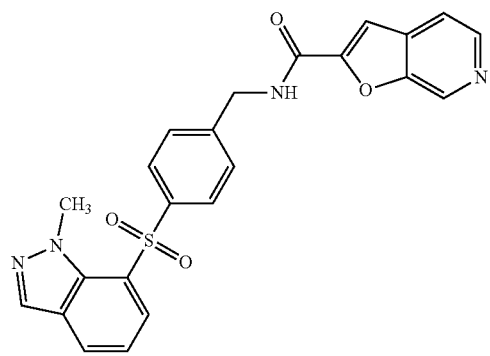 [SMILES: Cn1ncc2cccc(S(=O)(=O)c3ccc(CNC(=O)c4cc5ccncc5o4)cc3)c21]
N-{[4-(1-methyl-1H-indazole-7-sulfonyl)phenyl]methyl}furo[2,3-c]pyridine-2-carboxamide TABLE 2-continued
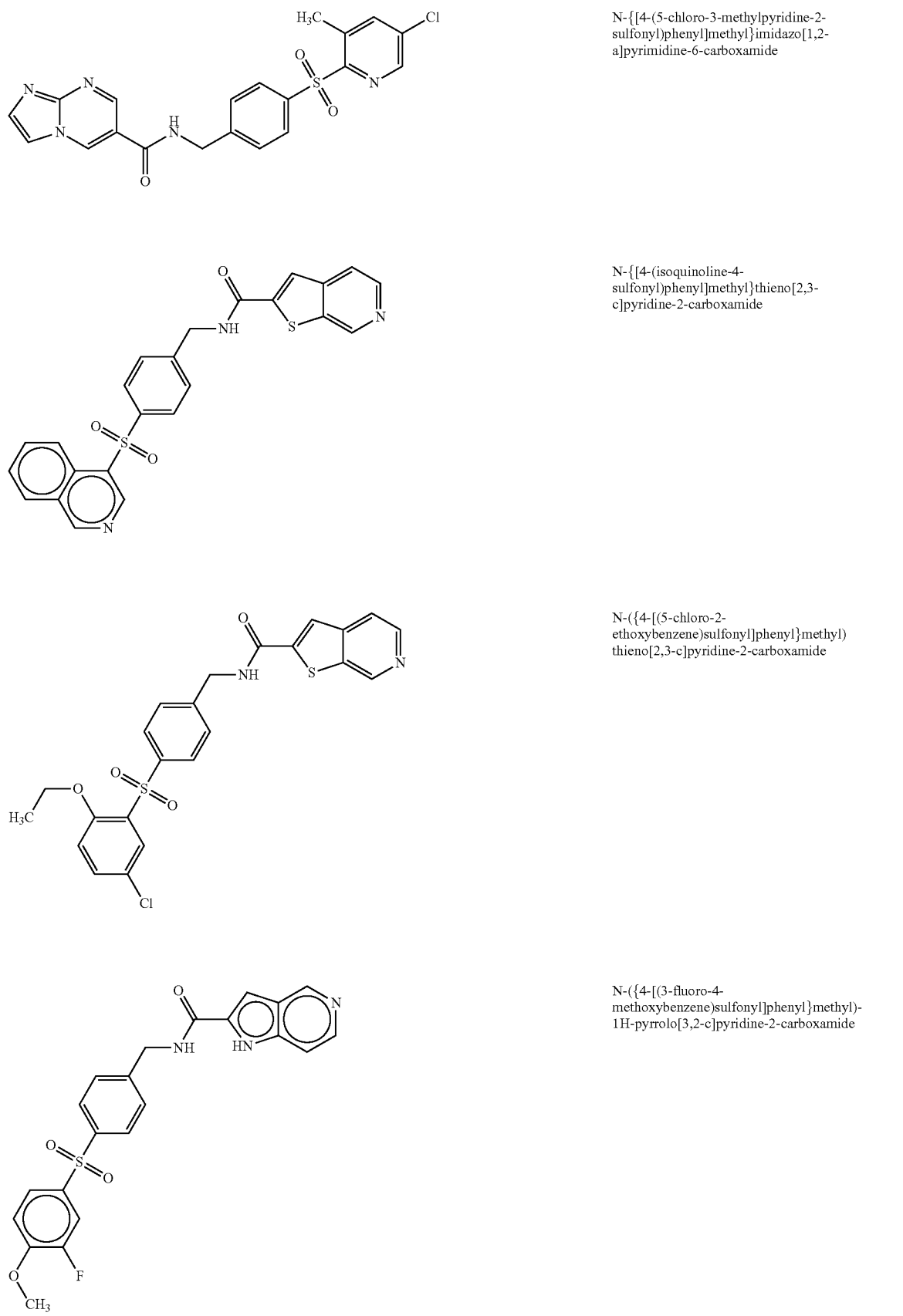
N-{[4-(5-chloro-3-methylpyridine-2-sulfonyl)phenyl]methyl}imidazo[1,2-a]pyrimidine-6-carboxamide
N-{[4-(isoquinoline-4-sulfonyl)phenyl]methyl}thieno[2,3-c]pyridine-2-carboxamide
N-({4-[(5-chloro-2-ethoxybenzene)sulfonyl]phenyl}methyl)thieno[2,3-c]pyridine-2-carboxamide
N-({4-[(3-fluoro-4-methoxybenzene)sulfonyl]phenyl}methyl)-1H-pyrrolo[3,2-c]pyridine-2-carboxamide TABLE 2-continued
| | |
|---|---|
| 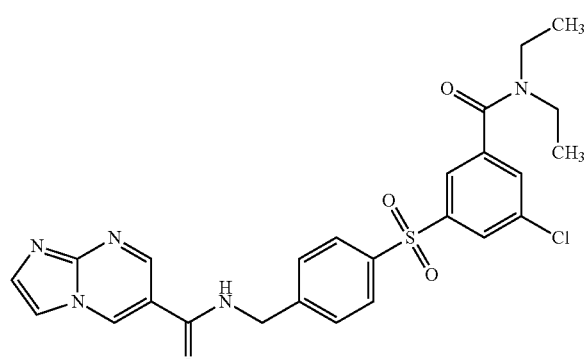 | N-[(4-{[3-chloro-5-(diethylcarbamoyl)benzene]sulfonyl}phenyl)methyl]imidazo[1,2-a]pyrimidine-6-carboxamide |
| 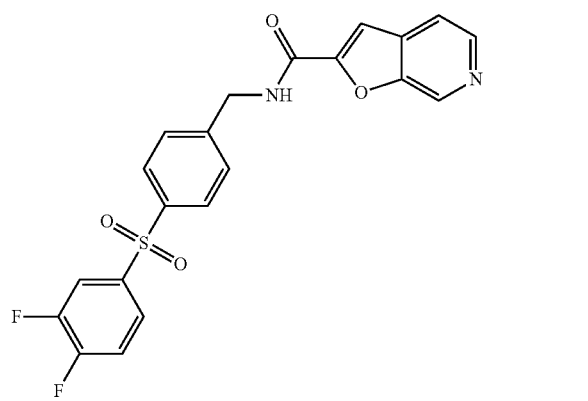 [SMILES: O=C(NCc1ccc(S(=O)(=O)c2ccc(F)c(F)c2)cc1)c1cc2ccncc2o1] | N-({4-[(3,4-difluorobenzene)sulfonyl]phenyl}methyl)furo[2,3-c]pyridine-2-carboxamide |
| 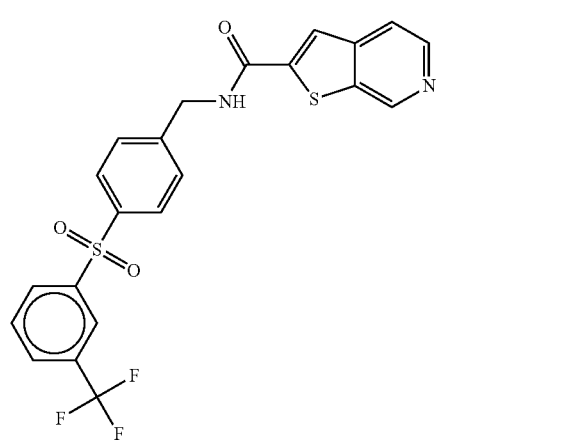 | N-[(4-{[3-(trifluoromethyl)benzene]sulfonyl}phenyl)methyl]thieno[2,3-c]pyridine-2-carboxamide |
| 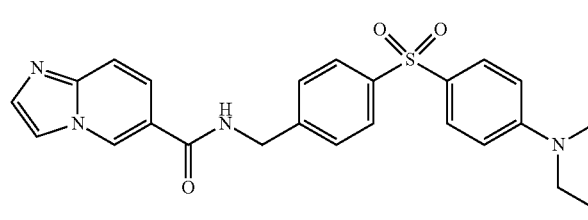 | N-[(4-{[4-(4-methylpiperazin-1-yl)benzene]sulfonyl}phenyl)methyl]imidazo[1,2-a]pyridine-6-carboxamide |

TABLE 2-continued
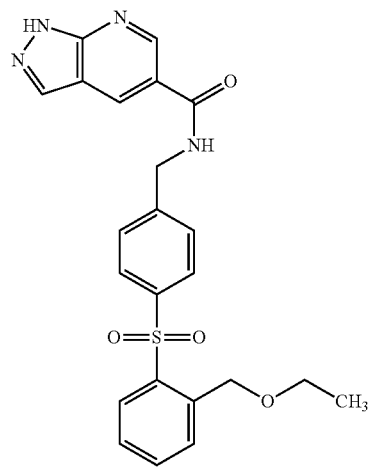 [SMILES: CCOCc1ccccc1S(=O)(=O)c1ccc(CNC(=O)c2cnc3[nH]ncc3c2)cc1]
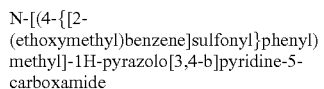
N-[(4-{[2-(ethoxymethyl)benzene]sulfonyl}phenyl)methyl]-1H-pyrazolo[3,4-b]pyridine-5-carboxamide
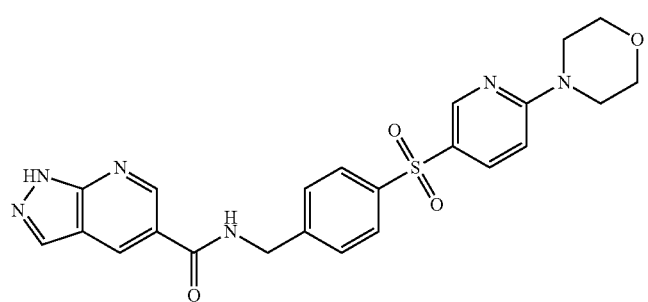 [SMILES: O=C(NCc1ccc(S(=O)(=O)c2ccc(N3CCOCC3)nc2)cc1)c1cnc2[nH]ncc2c1]
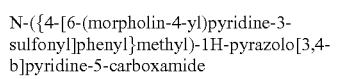
N-({4-[6-(morpholin-4-yl)pyridine-3-sulfonyl]phenyl}methyl)-1H-pyrazolo[3,4-b]pyridine-5-carboxamide
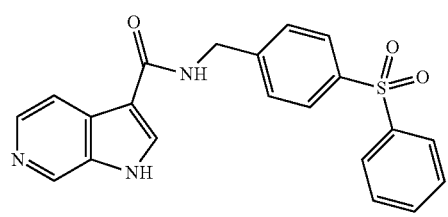 [SMILES: O=C(NCc1ccc(S(=O)(=O)c2ccccc2)cc1)c1c[nH]c2cnccc12]
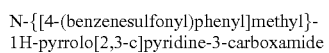
N-{[4-(benzenesulfonyl)phenyl]methyl}-1H-pyrrolo[2,3-c]pyridine-3-carboxamide
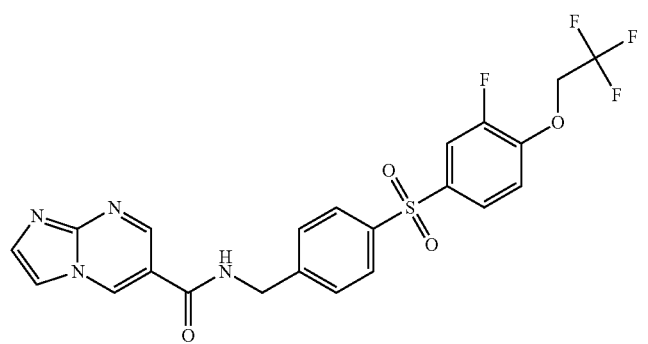 [SMILES: O=C(NCc1ccc(S(=O)(=O)c2ccc(OCC(F)(F)F)c(F)c2)cc1)c1cnc2nccn2c1]
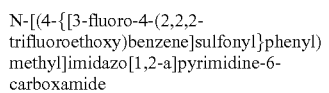
N-[(4-{[3-fluoro-4-(2,2,2-trifluoroethoxy)benzene]sulfonyl}phenyl)methyl]imidazo[1,2-a]pyrimidine-6-carboxamide TABLE 2-continued

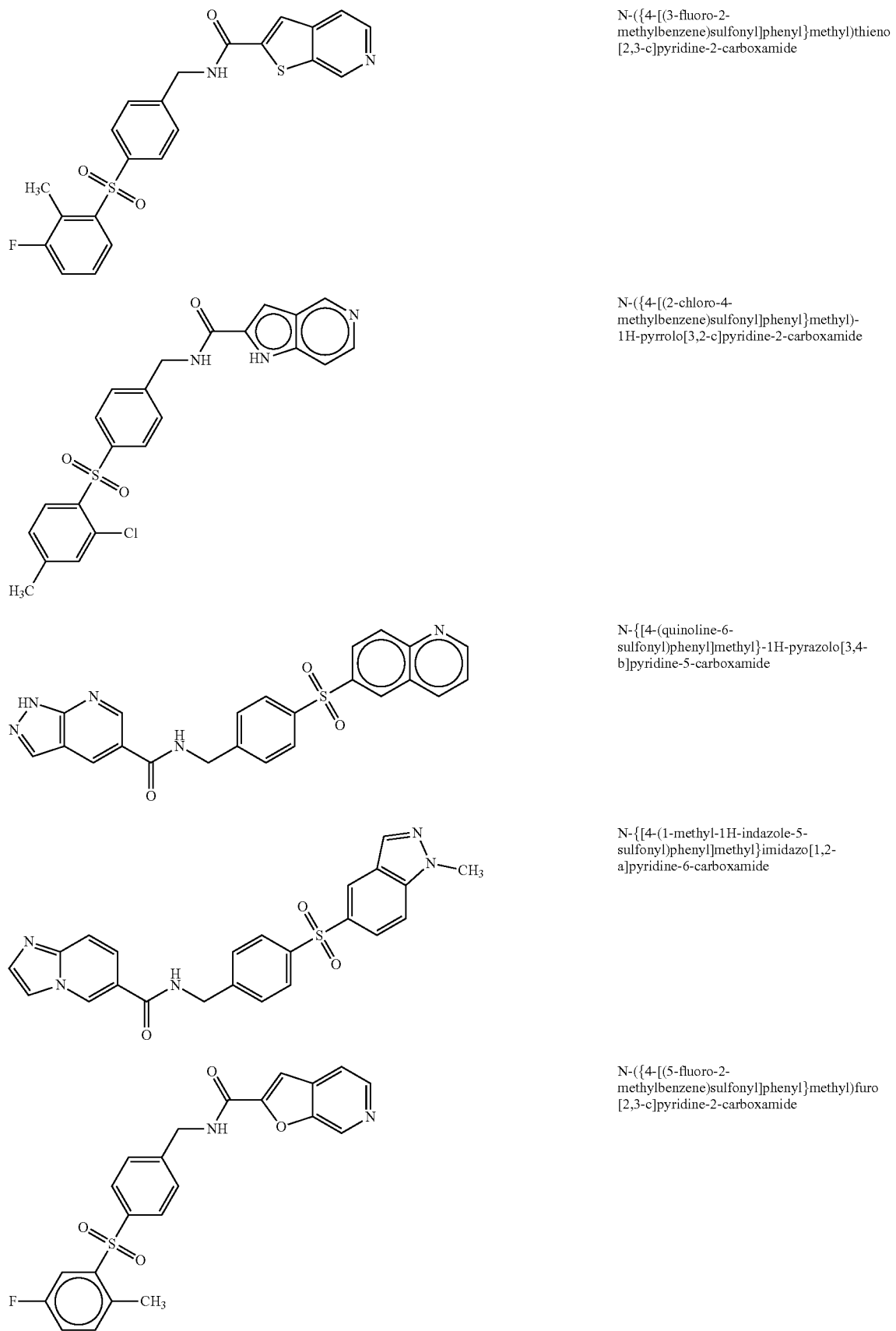

N-({4-[(3-fluoro-2-methylbenzene)sulfonyl]phenyl}methyl)thieno[2,3-c]pyridine-2-carboxamide N-({4-[(2-chloro-4-methylbenzene)sulfonyl]phenyl}methyl)-1H-pyrrolo[3,2-c]pyridine-2-carboxamide N-{[4-(quinoline-6-sulfonyl)phenyl]methyl}-1H-pyrazolo[3,4-b]pyridine-5-carboxamide N-{[4-(1-methyl-1H-indazole-5-sulfonyl)phenyl]methyl}imidazo[1,2-a]pyridine-6-carboxamide N-({4-[(5-fluoro-2-methylbenzene)sulfonyl]phenyl}methyl)furo[2,3-c]pyridine-2-carboxamide TABLE 2-continued
| | |
|---|---|
| 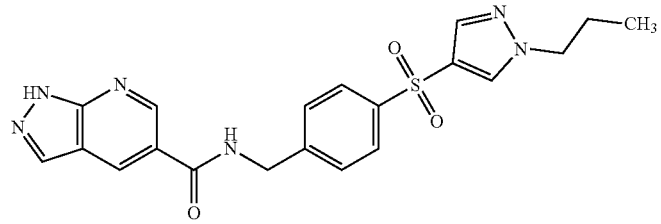 [SMILES: CCCn1cc(S(=O)(=O)c2ccc(CNC(=O)c3cnc4[nH]ncc4c3)cc2)cn1] | N-{[4-(1-propyl-1H-pyrazole-4-sulfonyl)phenyl]methyl}-1H-pyrazolo[3,4-b]pyridine-5-carboxamide |
| 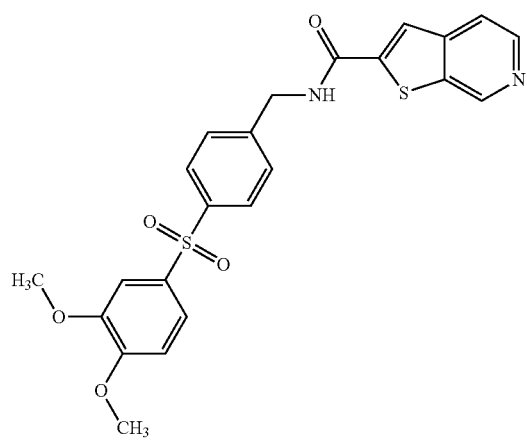 | N-({4-[(3,4-dimethoxybenzene)sulfonyl]phenyl}methyl)thieno[2,3-c]pyridine-2-carboxamide |
| 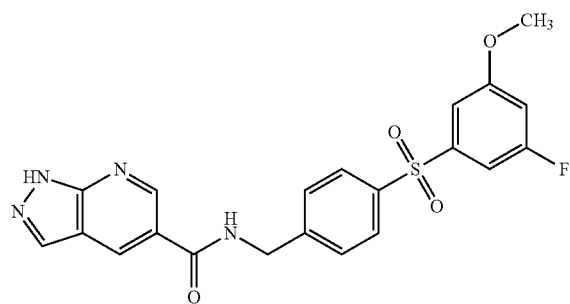 [SMILES: COc1cc(F)cc(S(=O)(=O)c2ccc(CNC(=O)c3cnc4[nH]ncc4c3)cc2)c1] | N-({4-[(3-fluoro-5-methoxybenzene)sulfonyl]phenyl}methyl)-1H-pyrazolo[3,4-b]pyridine-5-carboxamide |
| 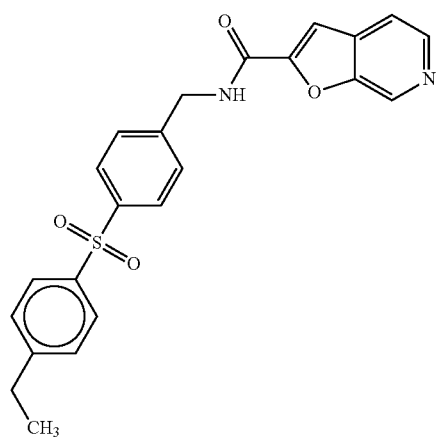 | N-({4-[(4-ethylbenzene)sulfonyl]phenyl}methyl)furo[2,3-c]pyridine-2-carboxamide |

TABLE 2-continued
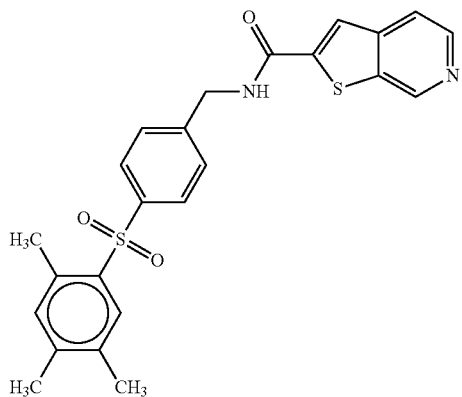
N-({4-[(2,4,5-trimethylbenzene)sulfonyl]phenyl}methyl)thieno[2,3-c]pyridine-2-carboxamide
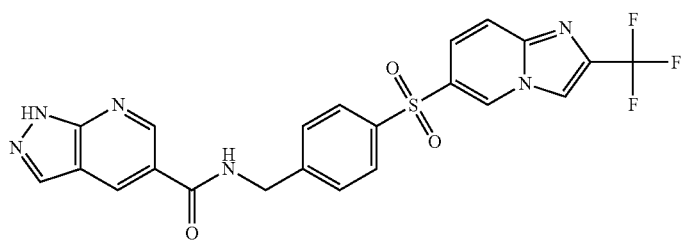 [SMILES: O=C(NCc1ccc(S(=O)(=O)c2ccc3nc(C(F)(F)F)cn3c2)cc1)c1cnc2[nH]ncc2c1]
N-({4-[2-(trifluoromethyl)imidazo[1,2-a]pyridine-6-sulfonyl]phenyl}methyl)-1H-pyrazolo[3,4-b]pyridine-5-carboxamide
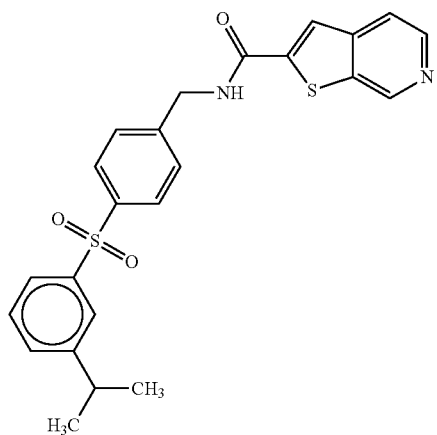
N-[(4-{[3-(propan-2-yl)benzene]sulfonyl}phenyl)methyl]thieno[2,3-c]pyridine-2-carboxamide
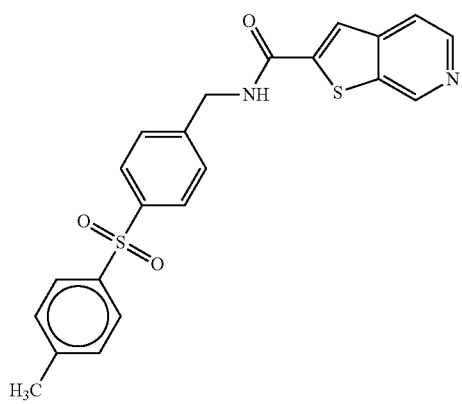
N-({4-[(4-methylbenzene)sulfonyl]phenyl}methyl)thieno[2,3-c]pyridine-2-carboxamide TABLE 2-continued
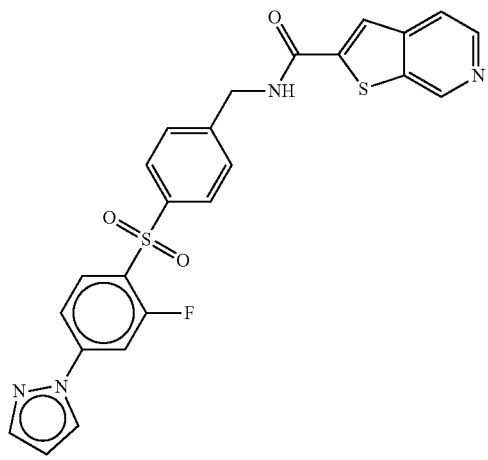
N-[(4-{[2-fluoro-4-(1H-pyrazol-1-yl)benzene]sulfonyl}phenyl)methyl]thieno[2,3-c]pyridine-2-carboxamide
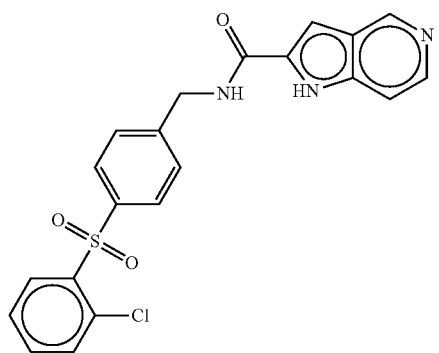
N-({4-[(2-chlorobenzene)sulfonyl]phenyl}methyl)-1H-pyrrolo[3,2-c]pyridine-2-carboxamide
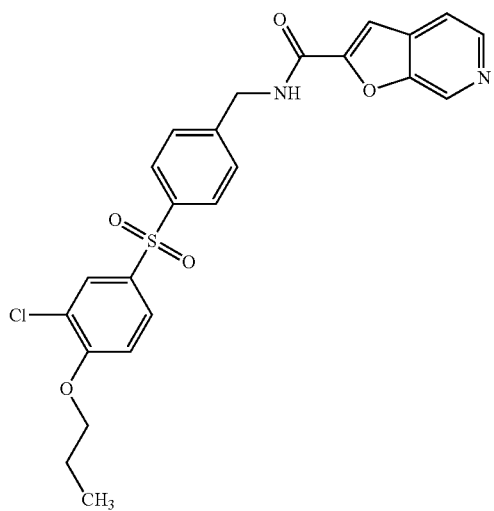 [SMILES: CCCOc1ccc(S(=O)(=O)c2ccc(CNC(=O)c3cc4ccncc4o3)cc2)cc1Cl]
N-({4-[(3-chloro-4-propoxybenzene)sulfonyl]phenyl}methyl)furo[2,3-c]pyridine-2-carboxamide

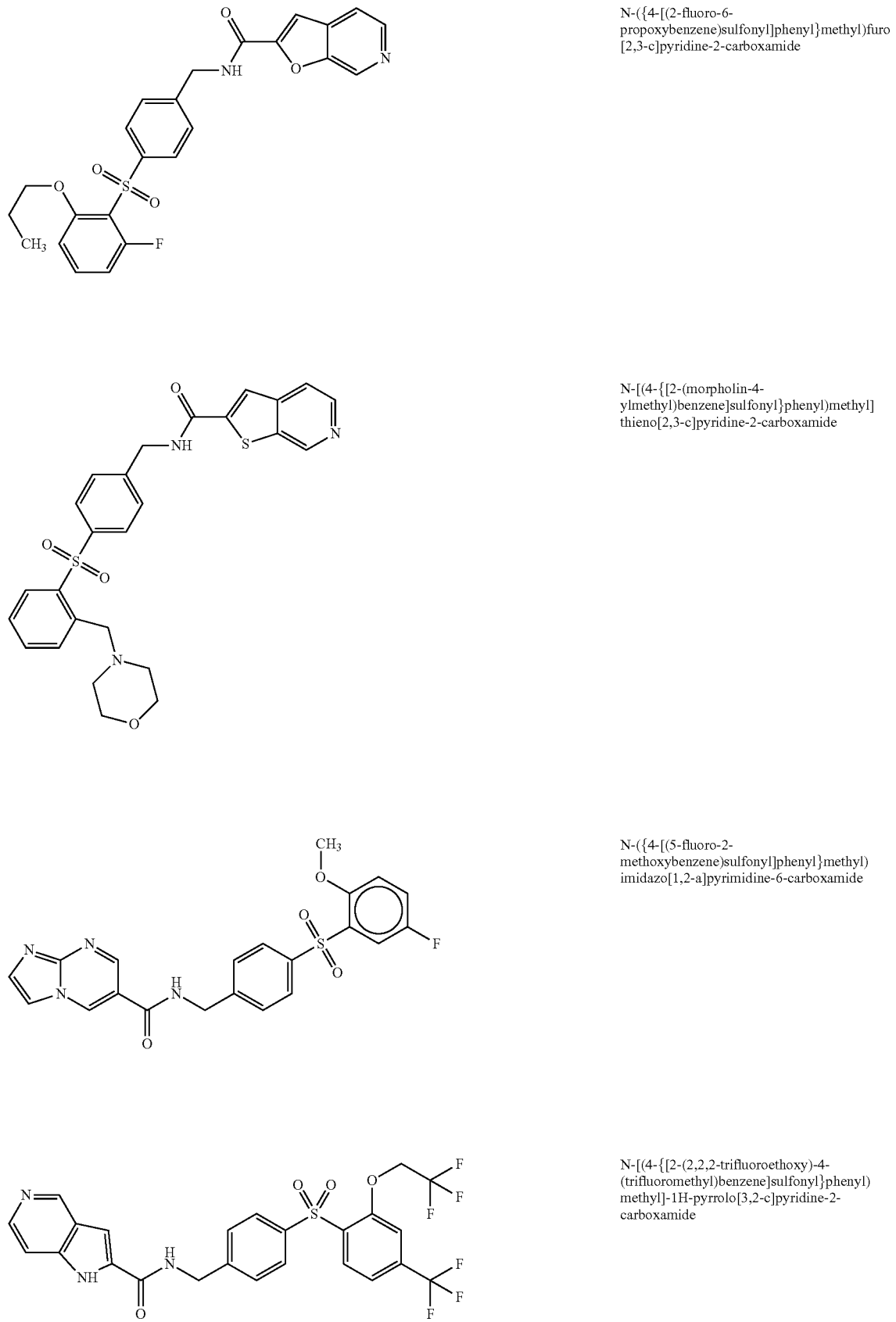
N-({4-[(2-fluoro-6-propoxybenzene)sulfonyl]phenyl}methyl)furo[2,3-c]pyridine-2-carboxamide
N-[(4-{[2-(morpholin-4-ylmethyl)benzene]sulfonyl}phenyl)methyl]thieno[2,3-c]pyridine-2-carboxamide
N-({4-[(5-fluoro-2-methoxybenzene)sulfonyl]phenyl}methyl)imidazo[1,2-a]pyrimidine-6-carboxamide
N-[(4-{[2-(2,2,2-trifluoroethoxy)-4-(trifluoromethyl)benzene]sulfonyl}phenyl)methyl]-1H-pyrrolo[3,2-c]pyridine-2-carboxamide TABLE 2-continued
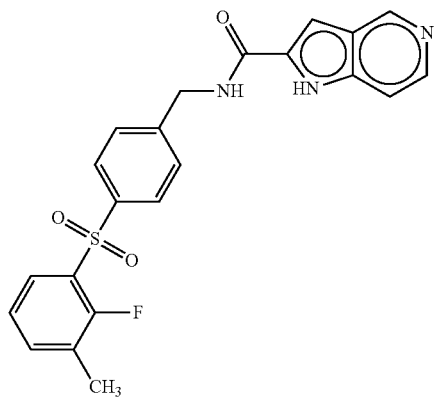
N-({4-[(2-fluoro-3-methylbenzene)sulfonyl]phenyl}methyl)-1H-pyrrolo[3,2-c]pyridine-2-carboxamide
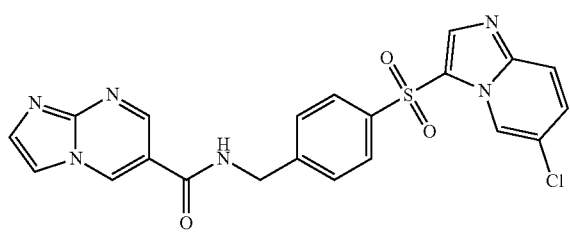 [SMILES: O=C(NCc1ccc(S(=O)(=O)c2cnc3ccc(Cl)cn23)cc1)c1cnc2nccn2c1]
N-[(4-{6-chloroimidazo[1,2-a]pyridine-3-sulfonyl}phenyl)methyl]imidazo[1,2-a]pyrimidine-6-carboxamide
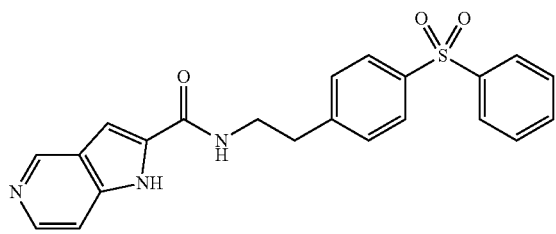 [SMILES: O=C(NCCc1ccc(S(=O)(=O)c2ccccc2)cc1)c1cc2cnccc2[nH]1]
N-{2-[4-(benzenesulfonyl)phenyl]ethyl}-1H-pyrrolo[3,2-c]pyridine-2-carboxamide
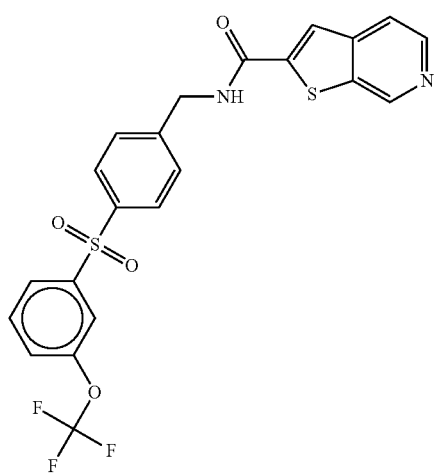
N-[(4-{[3-(trifluoromethoxy)benzene]sulfonyl}phenyl)methyl]thieno[2,3-c]pyridine-2-carboxamide TABLE 2-continued
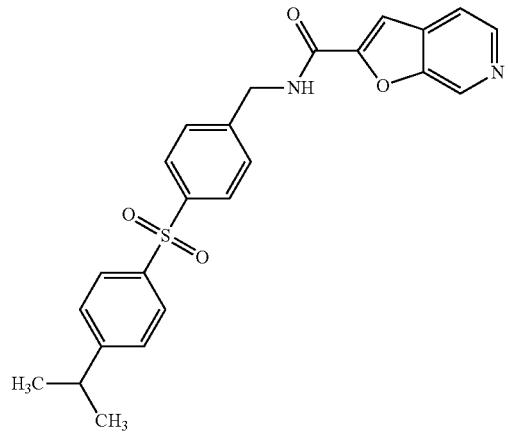
N-[(4-{[4-(propan-2-yl)benzene]sulfonyl}phenyl)methyl]furo[2,3-c]pyridine-2-carboxamide
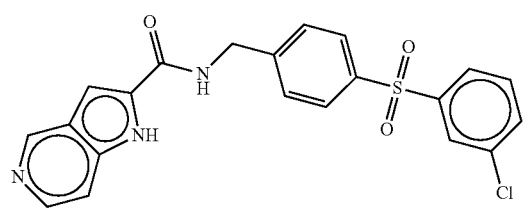
N-({4-[(3-chlorobenzene)sulfonyl]phenyl}methyl)-1H-pyrrolo[3,2-c]pyridine-2-carboxamide
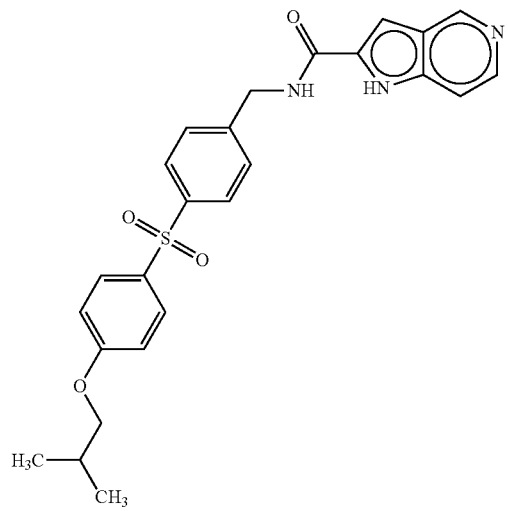
N-[(4-{[4-(2-methylpropoxy)benzene]sulfonyl}phenyl)methyl]-1H-pyrrolo[3,2-c]pyridine-2-carboxamide
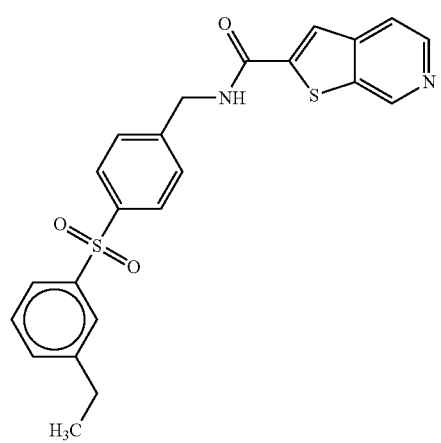
N-({4-[(3-ethylbenzene)sulfonyl]phenyl}methyl)thieno[2,3-c]pyridine-2-carboxamide TABLE 2-continued

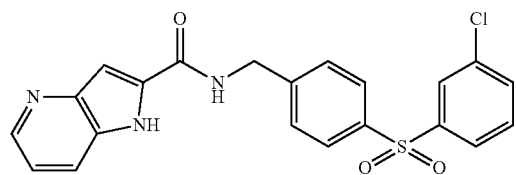 [SMILES: O=C(NCc1ccc(S(=O)(=O)c2cccc(Cl)c2)cc1)c1cc2ncccc2[nH]1]

N-({4-[(3-chlorobenzene)sulfonyl]phenyl}methyl)-1H-pyrrolo[3,2-b]pyridine-2-carboxamide

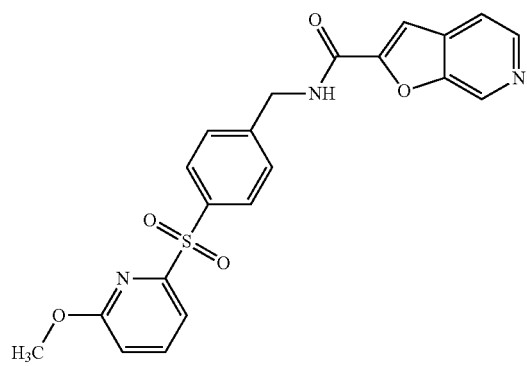 [SMILES: COc1cccc(S(=O)(=O)c2ccc(CNC(=O)c3cc4ccncc4o3)cc2)n1]

N-{[4-(6-methoxypyridine-2-sulfonyl)phenyl]methyl}furo[2,3-c]pyridine-2-carboxamide

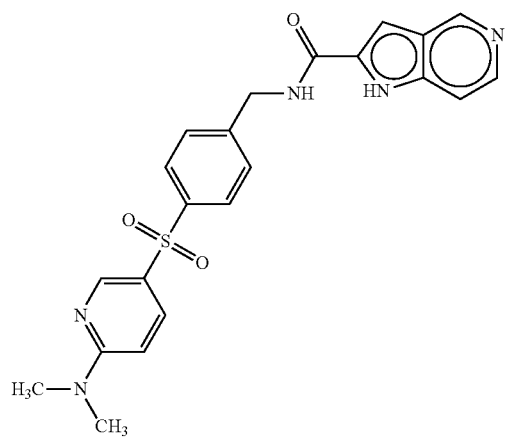

N-({4-[6-(dimethylamino)pyridine-3-sulfonyl]phenyl}methyl)-1H-pyrrolo[3,2-c]pyridine-2-carboxamide

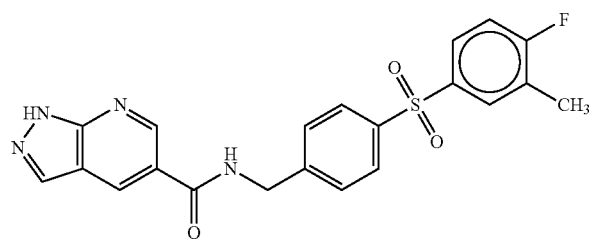

N-({4-[(4-fluoro-3-methylbenzene)sulfonyl]phenyl}methyl)-1H-pyrazolo[3,4-b]pyridine-5-carboxamide

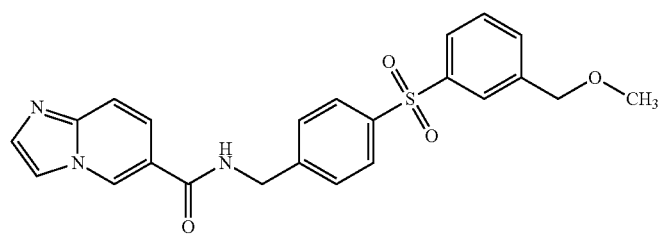 [SMILES: COCc1cccc(S(=O)(=O)c2ccc(CNC(=O)c3ccc4nccn4c3)cc2)c1]

N-[(4-{[3-(methoxymethyl)benzene]sulfonyl}phenyl)methyl]imidazo[1,2-a]pyridine-6-carboxamide TABLE 2-continued

| | |
|---|---|
| 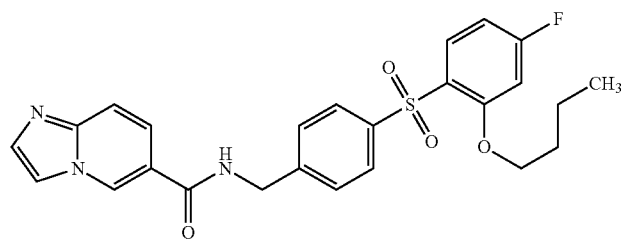 [SMILES: CCCCOc1cc(F)ccc1S(=O)(=O)c1ccc(CNC(=O)c2ccc3nccn3c2)cc1] | N-({4-[(2-butoxy-4-fluorobenzene)sulfonyl]phenyl}methyl)imidazo[1,2-a]pyridine-6-carboxamide |
| 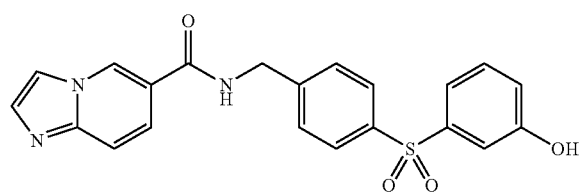 [SMILES: O=C(NCc1ccc(S(=O)(=O)c2cccc(O)c2)cc1)c1ccc2nccn2c1] | N-({4-[(3-hydroxybenzene)sulfonyl]phenyl}methyl)imidazo[1,2-a]pyridine-6-carboxamide |
| 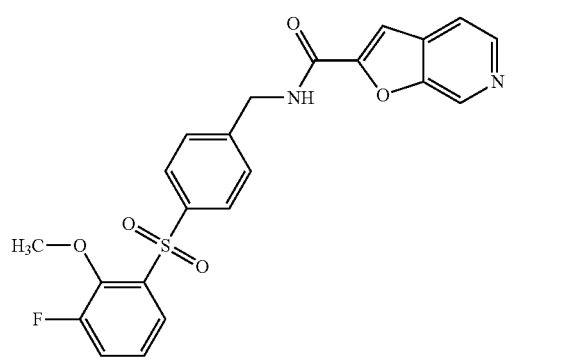 [SMILES: COc1c(F)cccc1S(=O)(=O)c1ccc(CNC(=O)c2cc3ccncc3o2)cc1] | N-({4-[(3-fluoro-2-methoxybenzene)sulfonyl]phenyl}methyl)furo[2,3-c]pyridine-2-carboxamide |
| 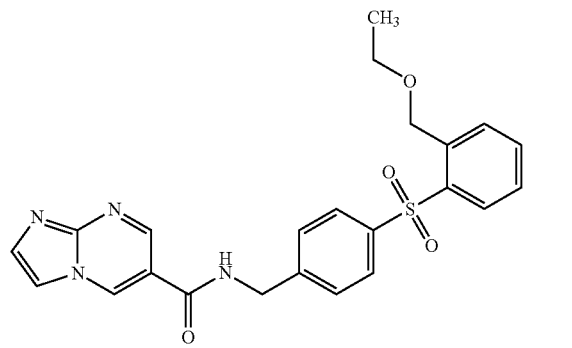 [SMILES: CCOCc1ccccc1S(=O)(=O)c1ccc(CNC(=O)c2cnc3nccn3c2)cc1] | N-[(4-{[2-(ethoxymethyl)benzene]sulfonyl}phenyl)methyl]imidazo[1,2-a]pyrimidine-6-carboxamide |
| 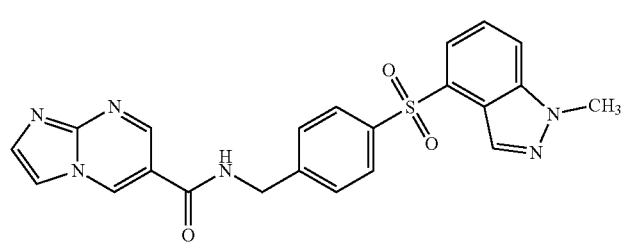 [SMILES: Cn1ncc2c(S(=O)(=O)c3ccc(CNC(=O)c4cnc5nccn5c4)cc3)cccc21] | N-{[4-(1-methyl-1H-indazole-4-sulfonyl)phenyl]methyl}imidazo[1,2-a]pyrimidine-6-carboxamide |

TABLE 2-continued
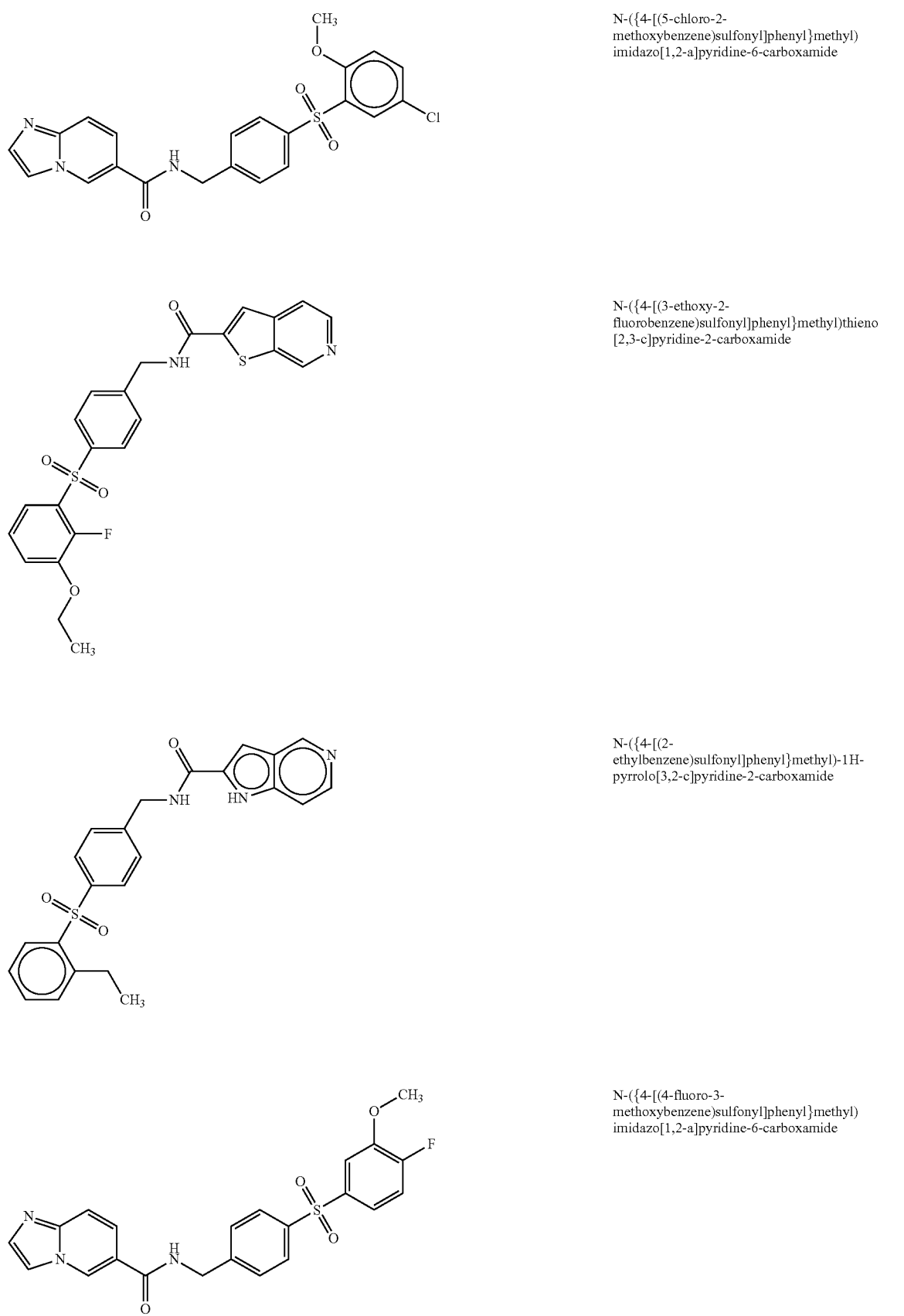
N-({4-[(5-chloro-2-methoxybenzene)sulfonyl]phenyl}methyl)imidazo[1,2-a]pyridine-6-carboxamide
N-({4-[(3-ethoxy-2-fluorobenzene)sulfonyl]phenyl}methyl)thieno[2,3-c]pyridine-2-carboxamide
N-({4-[(2-ethylbenzene)sulfonyl]phenyl}methyl)-1H-pyrrolo[3,2-c]pyridine-2-carboxamide
N-({4-[(4-fluoro-3-methoxybenzene)sulfonyl]phenyl}methyl)imidazo[1,2-a]pyridine-6-carboxamide TABLE 2-continued

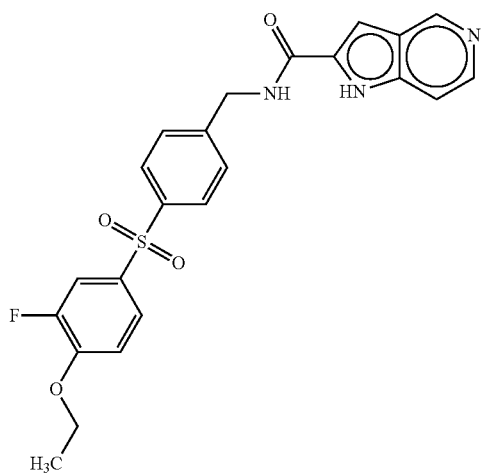

N-({4-[(4-ethoxy-3-fluorobenzene)sulfonyl]phenyl}methyl)-1H-pyrrolo[3,2-c]pyridine-2-carboxamide

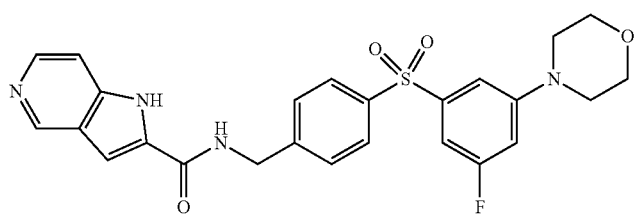 [SMILES: O=C(NCc1ccc(S(=O)(=O)c2cc(F)cc(N3CCOCC3)c2)cc1)c1cc2cnccc2[nH]1]

N-[(4-{[3-fluoro-5-(morpholin-4-yl)benzene]sulfonyl}phenyl)methyl]-1H-pyrrolo[3,2-c]pyridine-2-carboxamide

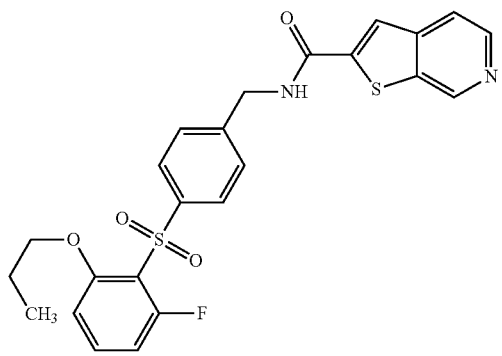 [SMILES: CCCOc1cccc(F)c1S(=O)(=O)c1ccc(CNC(=O)c2cc3ccncc3s2)cc1]

N-({4-[(2-fluoro-6-propoxybenzene)sulfonyl]phenyl}methyl)thieno[2,3-c]pyridine-2-carboxamide

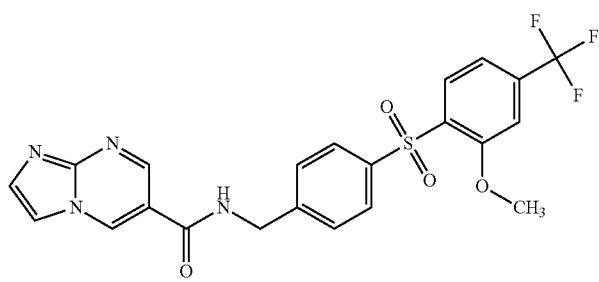

N-[(4-{[2-methoxy-4-(trifluoromethyl)benzene]sulfonyl}phenyl)methyl]imidazo[1,2-a]pyrimidine-6-carboxamide TABLE 2-continued
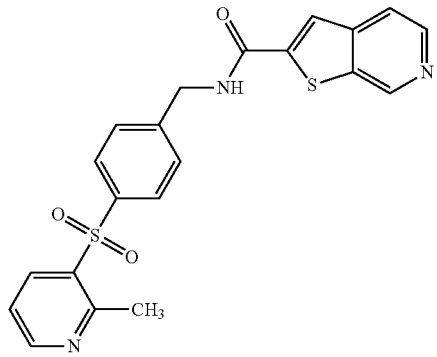 [SMILES: Cc1ncccc1S(=O)(=O)c1ccc(CNC(=O)c2cc3ccncc3s2)cc1]
N-{[4-(2-methylpyridine-3-sulfonyl)phenyl]methyl}thieno[2,3-c]pyridine-2-carboxamide
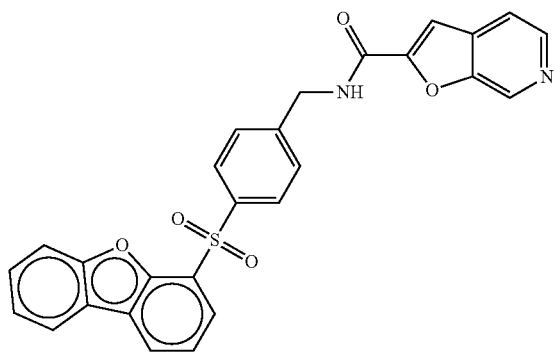
N-[(4-{8-oxatricyclo[7.4.0.0²,☐]trideca-1(13),2,4,6,9,11-hexaene-6-sulfonyl}phenyl)methyl]furo[2,3-c]pyridine-2-carboxamide
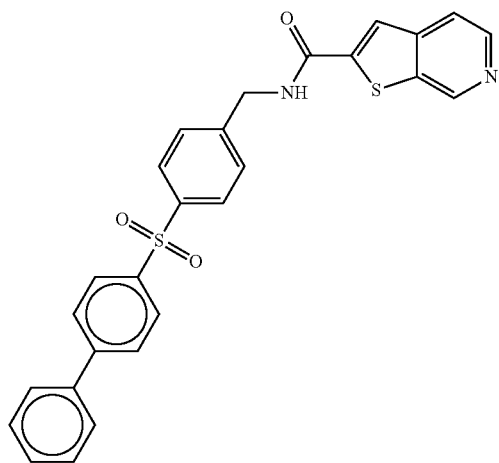
N-({4-[(4-phenylbenzene)sulfonyl]phenyl}methyl)thieno[2,3-c]pyridine-2-carboxamide
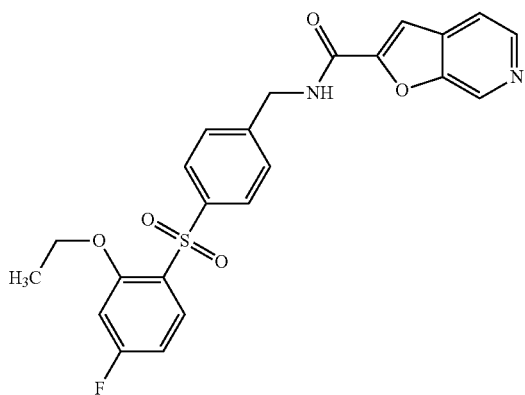 [SMILES: CCOc1cc(F)ccc1S(=O)(=O)c1ccc(CNC(=O)c2cc3ccncc3o2)cc1]
N-({4-[(2-ethoxy-4-fluorobenzene)sulfonyl]phenyl}methyl)furo[2,3-c]pyridine-2-carboxamide TABLE 2-continued
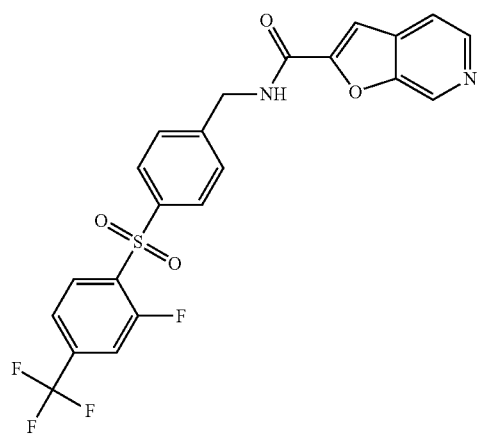 [SMILES: O=C(NCc1ccc(S(=O)(=O)c2ccc(C(F)(F)F)cc2F)cc1)c1cc2ccncc2o1]
N-[(4-{[2-fluoro-4-(trifluoromethyl)benzene]sulfonyl}phenyl)methyl]thieno[2,3-c]pyridine-2-carboxamide
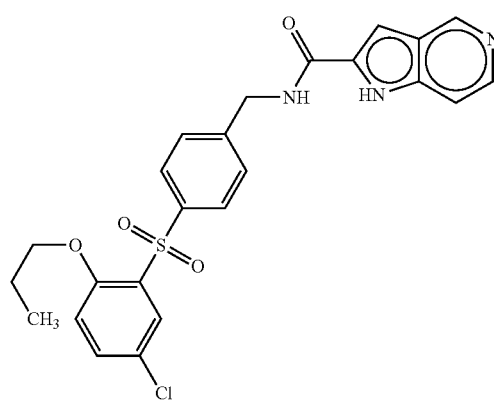
N-({4-[(5-chloro-2-propoxybenzene)sulfonyl]phenyl}methyl)-1H-pyrrolo[3,2-c]pyridine-2-carboxamide
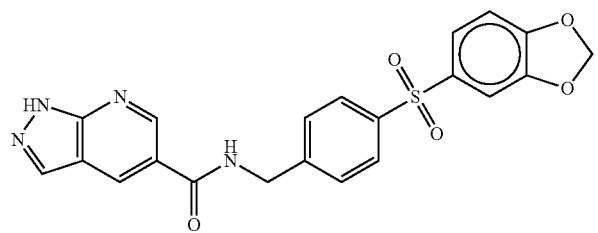
N-{[4-(2H-1,3-benzodioxole-5-sulfonyl)phenyl]methyl}-1H-pyrazolo[3,4-b]pyridine-5-carboxamide
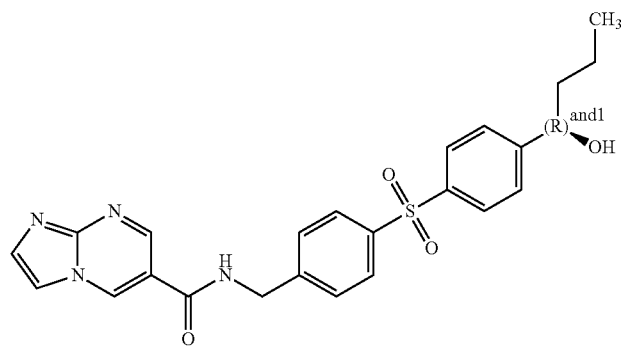
N-{[4-({4-[(1R)-1-hydroxybutyl]benzene}sulfonyl)phenyl]methyl}imidazo[1,2-a]pyrimidine-6-carboxamide TABLE 2-continued

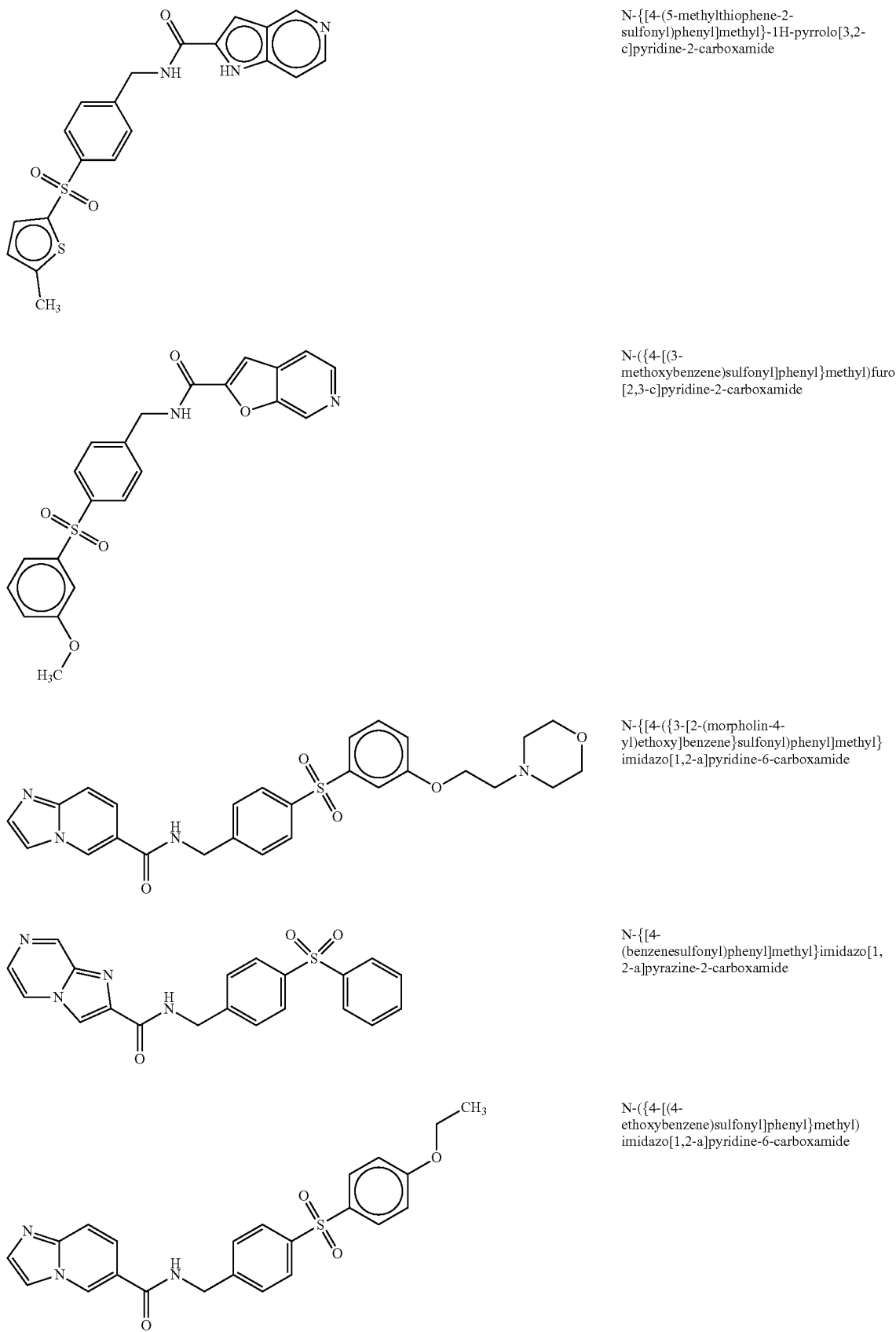

N-{[4-(5-methylthiophene-2-sulfonyl)phenyl]methyl}-1H-pyrrolo[3,2-c]pyridine-2-carboxamide N-({4-[(3-methoxybenzene)sulfonyl]phenyl}methyl)furo[2,3-c]pyridine-2-carboxamide N-{[4-({3-[2-(morpholin-4-yl)ethoxy]benzene}sulfonyl)phenyl]methyl}imidazo[1,2-a]pyridine-6-carboxamide N-{[4-(benzenesulfonyl)phenyl]methyl}imidazo[1,2-a]pyrazine-2-carboxamide N-({4-[(4-ethoxybenzene)sulfonyl]phenyl}methyl)imidazo[1,2-a]pyridine-6-carboxamide TABLE 2-continued
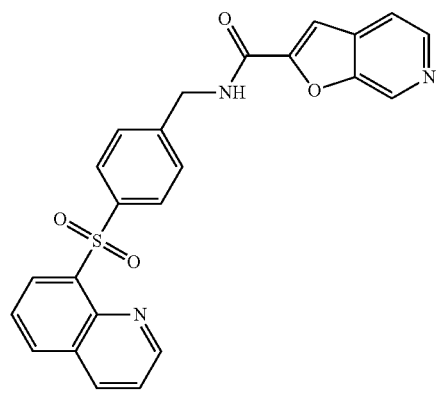
N-{[4-(quinoline-8-sulfonyl)phenyl]methyl}furo[2,3-c]pyridine-2-carboxamide
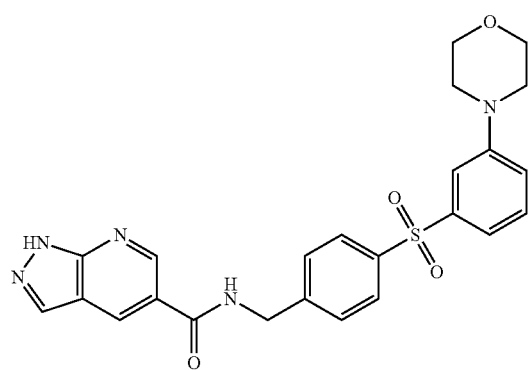 [SMILES: O=C(NCc1ccc(S(=O)(=O)c2cccc(N3CCOCC3)c2)cc1)c1cnc2[nH]ncc2c1]
N-[(4-{[3-(morpholin-4-yl)benzene]sulfonyl}phenyl)methyl]-1H-pyrazolo[3,4-b]pyridine-5-carboxamide
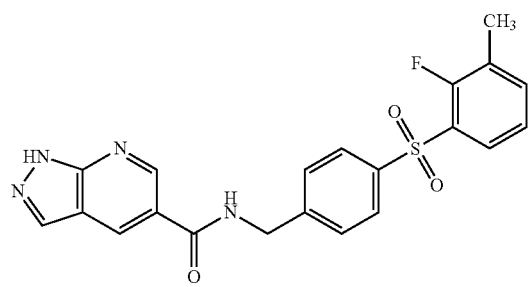 [SMILES: Cc1cccc(S(=O)(=O)c2ccc(CNC(=O)c3cnc4[nH]ncc4c3)cc2)c1F]
N-({4-[(2-fluoro-3-methylbenzene)sulfonyl]phenyl}methyl)-1H-pyrazolo[3,4-b]pyridine-5-carboxamide
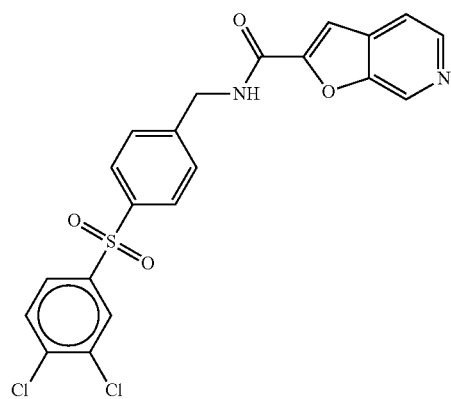
N-({4-[(3,4-dichlorobenzene)sulfonyl]phenyl}methyl)furo[2,3-c]pyridine-2-carboxamide TABLE 2-continued

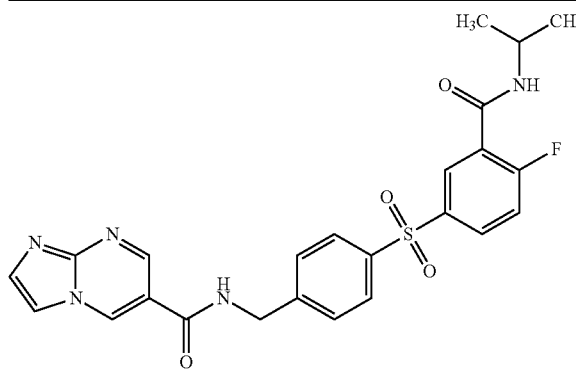

N-{[4-({4-fluoro-3-[(propan-2-yl)carbamoyl]benzene}sulfonyl)phenyl]methyl}imidazo[1,2-a]pyrimidine-6-carboxamide

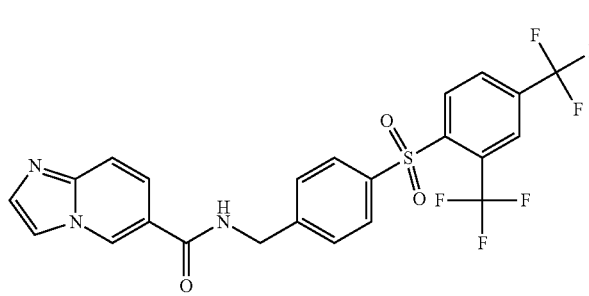

N-[(4-{[2,4-bis(trifluoromethyl)benzene]sulfonyl}phenyl)methyl]imidazo[1,2-a]pyridine-6-carboxamide

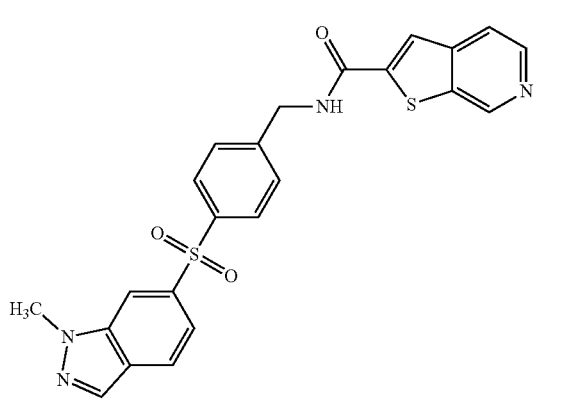

N-{[4-(1-methyl-1H-indazole-6-sulfonyl)phenyl]methyl}thieno[2,3-c]pyridine-2-carboxamide

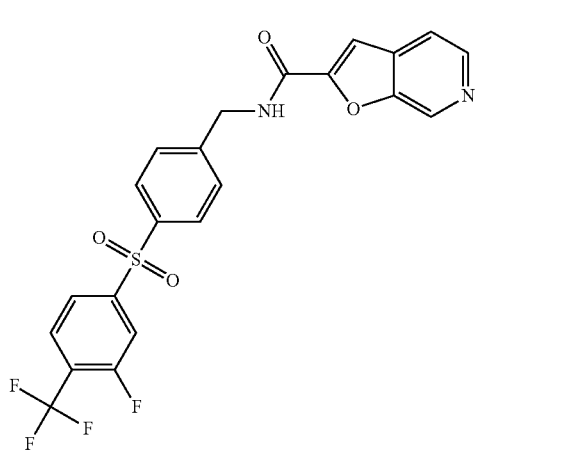 [SMILES: O=C(NCc1ccc(S(=O)(=O)c2ccc(C(F)(F)F)c(F)c2)cc1)c1cc2ccncc2o1]

N-[(4-{[3-fluoro-4-(trifluoromethyl)benzene]sulfonyl}phenyl)methyl]furo[2,3-c]pyridine-2-carboxamide TABLE 2-continued
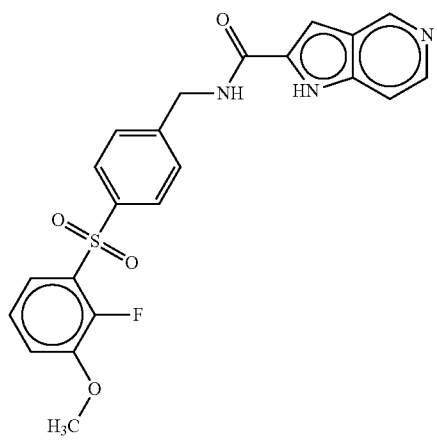
N-({4-[(2-fluoro-3-methoxybenzene)sulfonyl]phenyl}methyl)-1H-pyrrolo[3,2-c]pyridine-2-carboxamide
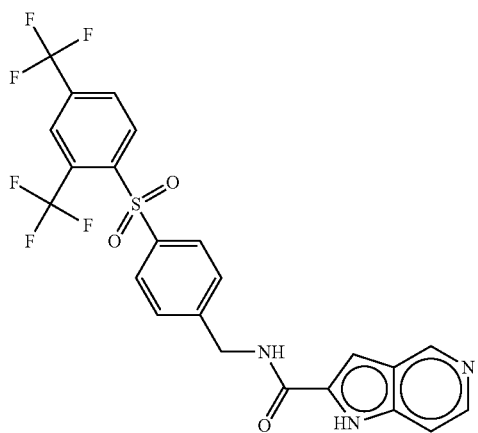
N-[(4-{[2,4-bis(trifluoromethyl)benzene]sulfonyl}phenyl)methyl]-1H-pyrrolo[3,2-c]pyridine-2-carboxamide
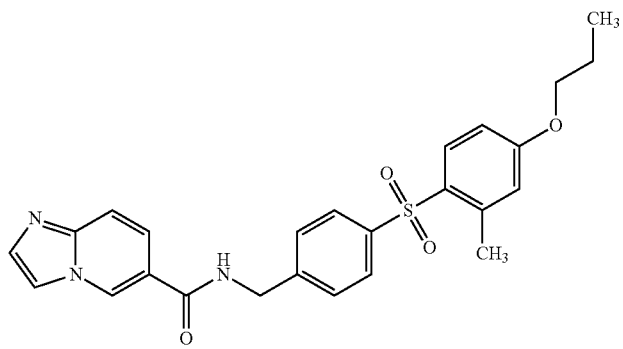
N-({4-[(2-methyl-4-propoxybenzene)sulfonyl]phenyl}methyl)imidazo[1,2-a]pyridine-6-carboxamide TABLE 2-continued
| | |
|---|---|
| 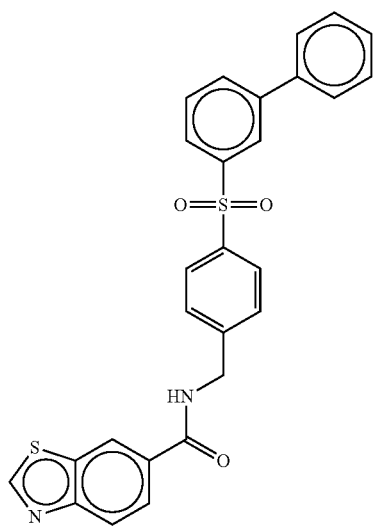 | N-({4-[(3-phenylbenzene)sulfonyl]phenyl}methyl)-1,3-benzothiazole-6-carboxamide |
| 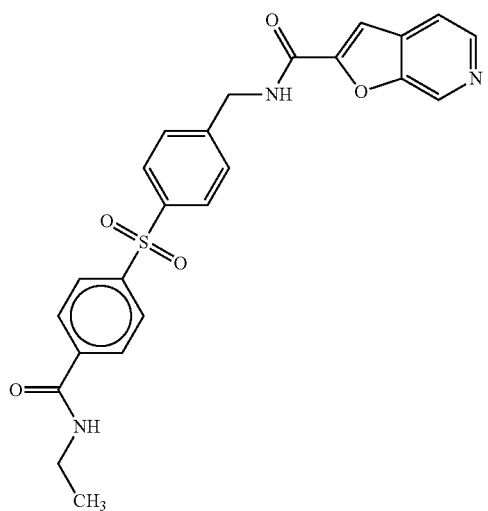 | N-[(4-{[4-(ethylcarbamoyl)benzene]sulfonyl}phenyl)methyl]furo[2,3-c]pyridine-2-carboxamide |
| 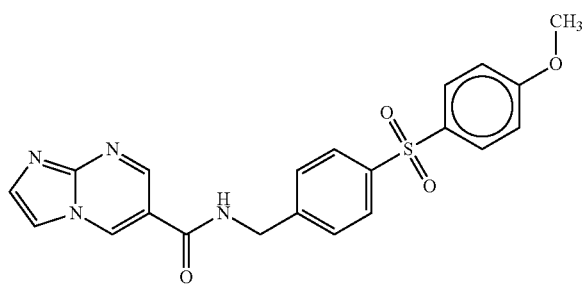 | N-({4-[(4-methoxybenzene)sulfonyl]phenyl}methyl)imidazo[1,2-a]pyrimidine-6-carboxamide |
| 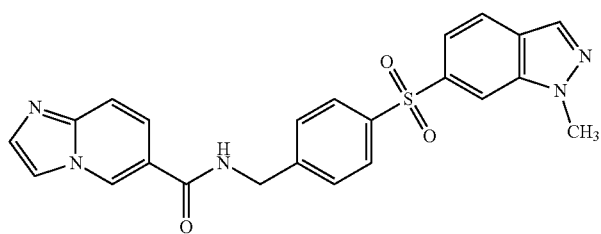 [SMILES: Cn1ncc2ccc(S(=O)(=O)c3ccc(CNC(=O)c4ccc5nccn5c4)cc3)cc21] | N-{[4-(1-methyl-1H-indazole-6-sulfonyl)phenyl]methyl}imidazo[1,2-a]pyridine-6-carboxamide |

TABLE 2-continued
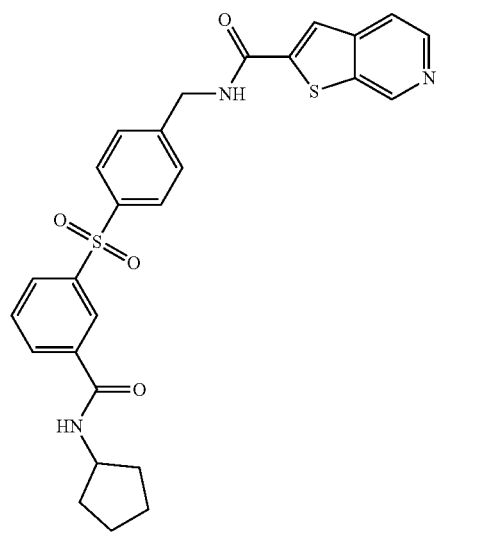
N-[(4-{[3-(cyclopentylcarbamoyl)benzene]sulfonyl}phenyl)methyl]thieno[2,3-c]pyridine-2-carboxamide
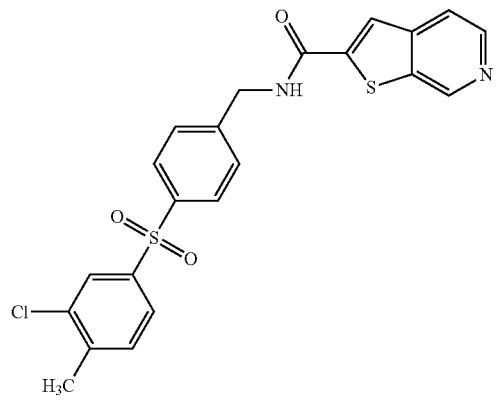 [SMILES: Cc1ccc(S(=O)(=O)c2ccc(CNC(=O)c3cc4ccncc4s3)cc2)cc1Cl]
N-({4-[(3-chloro-4-methylbenzene)sulfonyl]phenyl}methyl)thieno[2,3-c]pyridine-2-carboxamide
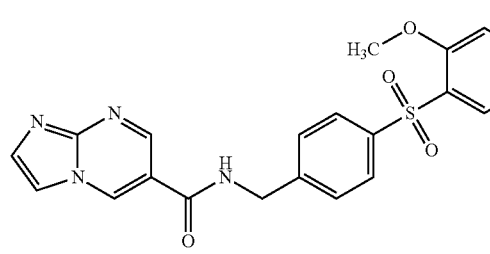
N-({4-[(4,5-difluoro-2-methoxybenzene)sulfonyl]phenyl}methyl)imidazo[1,2-a]pyrimidine-6-carboxamide
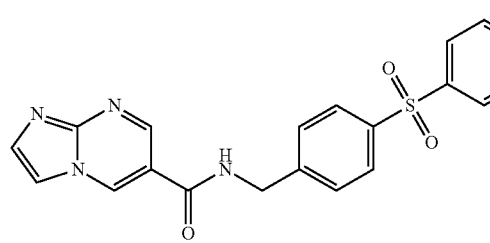
N-[(4-{[3-(methoxymethyl)benzene]sulfonyl}phenyl)methyl]imidazo[1,2-a]pyrimidine-6-carboxamide TABLE 2-continued
| | |
|---|---|
| 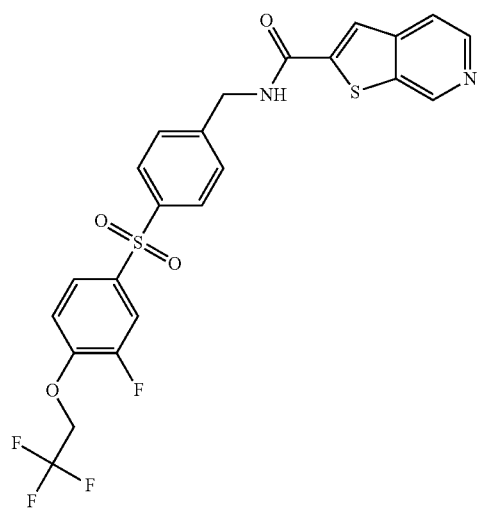 [SMILES: O=C(NCc1ccc(S(=O)(=O)c2ccc(OCC(F)(F)F)c(F)c2)cc1)c1cc2ccncc2s1] | N-[(4-{[3-fluoro-4-(2,2,2-trifluoroethoxy)benzene]sulfonyl}phenyl)methyl]thieno[2,3-c]pyridine-2-carboxamide |
| 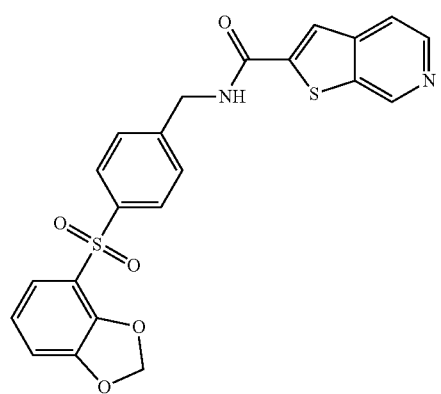 [SMILES: O=C(NCc1ccc(S(=O)(=O)c2cccc3c2OCO3)cc1)c1cc2ccncc2s1] | N-{[4-(2H-1,3-benzodioxole-4-sulfonyl)phenyl]methyl}thieno[2,3-c]pyridine-2-carboxamide |
| 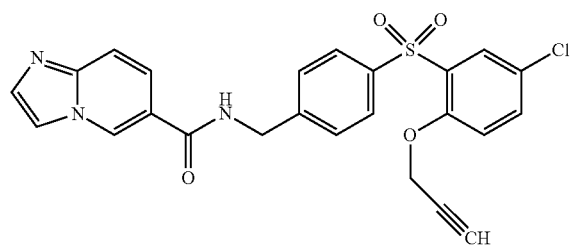 [SMILES: C#CCOc1ccc(Cl)cc1S(=O)(=O)c1ccc(CNC(=O)c2ccc3nccn3c2)cc1] | N-[(4-{[5-chloro-2-(prop-2-yn-1-yloxy)benzene]sulfonyl}phenyl)methyl]imidazo[1,2-a]pyridine-6-carboxamide |
| 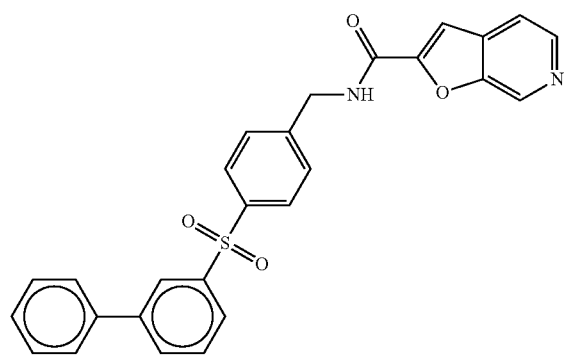 | N-({4-[(3-phenylbenzene)sulfonyl]phenyl}methyl)furo[2,3-c]pyridine-2-carboxamide |

TABLE 2-continued
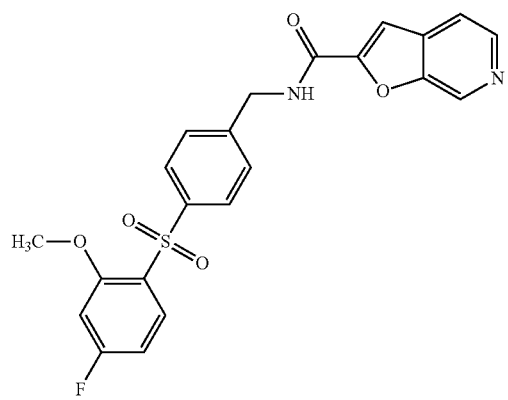
N-({4-[(4-fluoro-2-methoxybenzene)sulfonyl]phenyl}methyl)furo[2,3-c]pyridine-2-carboxamide
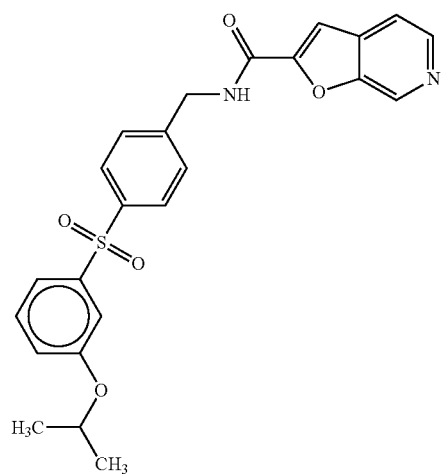
N-[(4-{[3-(propan-2-yloxy)benzene]sulfonyl}phenyl)methyl]furo[2,3-c]pyridine-2-carboxamide
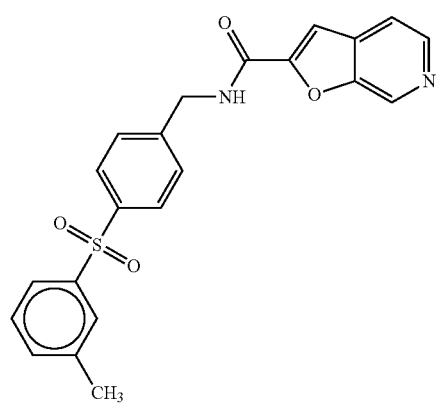
N-({4-[(3-methylbenzene)sulfonyl]phenyl}methyl)furo[2,3-c]pyridine-2-carboxamide
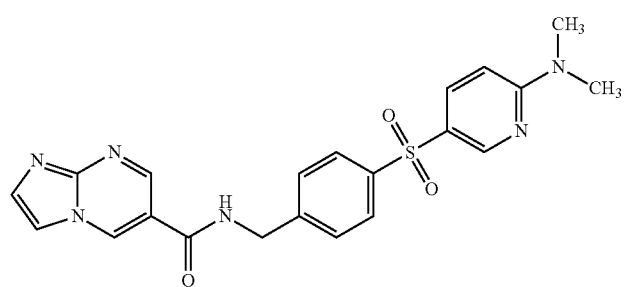 [SMILES: CN(C)c1ccc(S(=O)(=O)c2ccc(CNC(=O)c3cnc4nccn4c3)cc2)cn1]
N-({4-[6-(dimethylamino)pyridine-3-sulfonyl]phenyl}methyl)imidazo[1,2-a]pyrimidine-6-carboxamide TABLE 2-continued
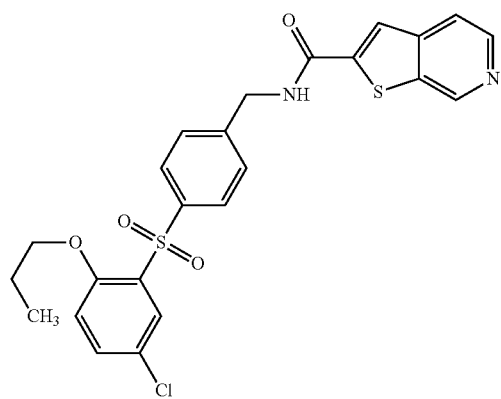
N-({4-[(5-chloro-2-propoxybenzene)sulfonyl]phenyl}merhyl)thieno[2,3-c]pyridine-2-carboxamide
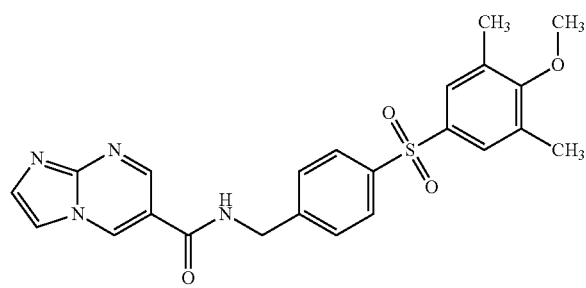 [SMILES: COc1c(C)cc(S(=O)(=O)c2ccc(CNC(=O)c3cnc4nccn4c3)cc2)cc1C]
N-({4-[(4-methoxy-3,5-dimethylbenzene)sulfonyl]phenyl}methyl)imidazo[1,2-a]pyrimidine-6-carboxamide
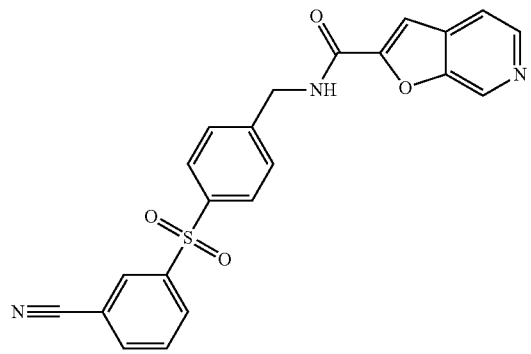
N-({4-[(3-cyanobenzene)sulfonyl]phenyl}methyl)furo[2,3-c]pyridine-2-carboxamide
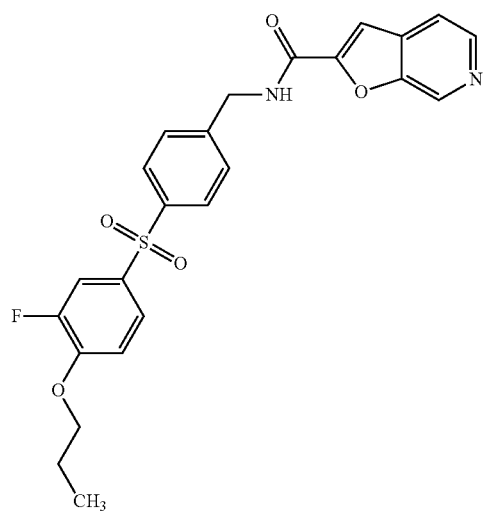 [SMILES: CCCOc1ccc(S(=O)(=O)c2ccc(CNC(=O)c3cc4ccncc4o3)cc2)cc1F]
N-({4-[(3-fluoro-4-propoxybenzene)sulfonyl]phenyl}methyl)furo[2,3-c]pyridine-2-carboxamide TABLE 2-continued
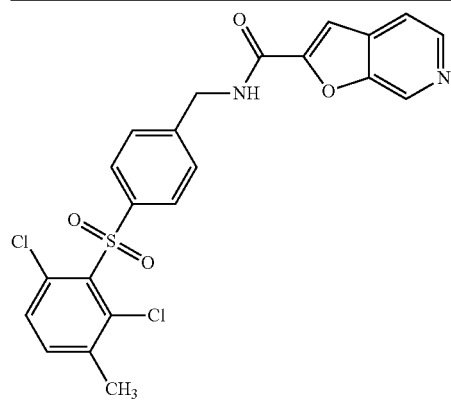
N-({4-[(2,6-dichloro-3-methylbenzene)sulfonyl]phenyl}methyl)furo[2,3-c]pyridine-2-carboxamide
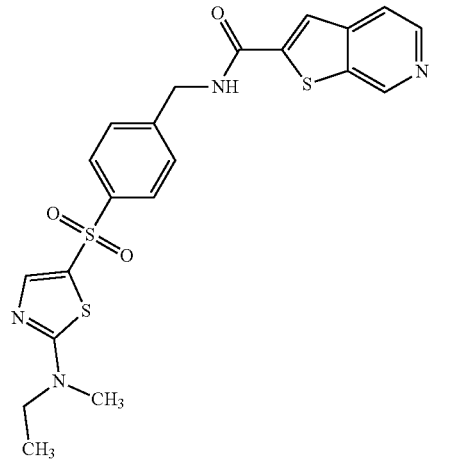 [SMILES: CCN(C)c1ncc(S(=O)(=O)c2ccc(CNC(=O)c3cc4ccncc4s3)cc2)s1]
N-[(4-{2-[ethyl(methyl)amino]-1,3-thiazole-5-sulfonyl}phenyl)methyl]thieno[2,3-c]pyridine-2-carboxamide
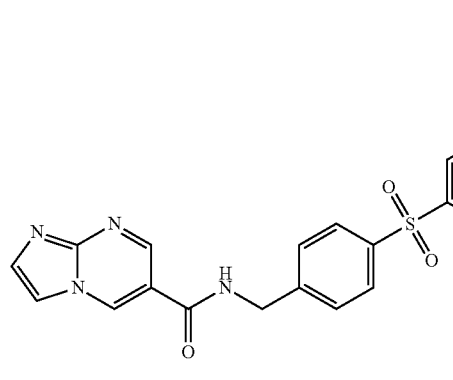
N-({4-[(3-propoxybenzene)sulfonyl]phenyl}methyl)imidazo[1,2-a]pyrimidine-6-carboxamide
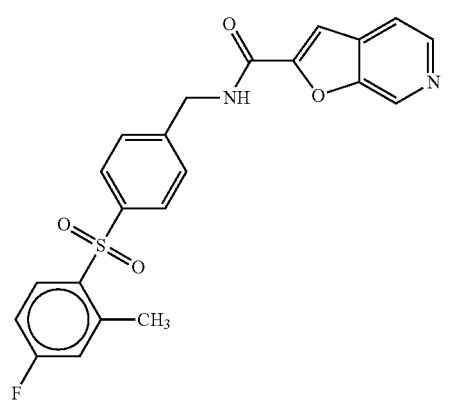
N-({4-[(4-fluoro-2-methylbenzene)sulfonyl]phenyl}methyl)furo[2,3-c]pyridine-2-carboxamide TABLE 2-continued
| | |
|---|---|
| 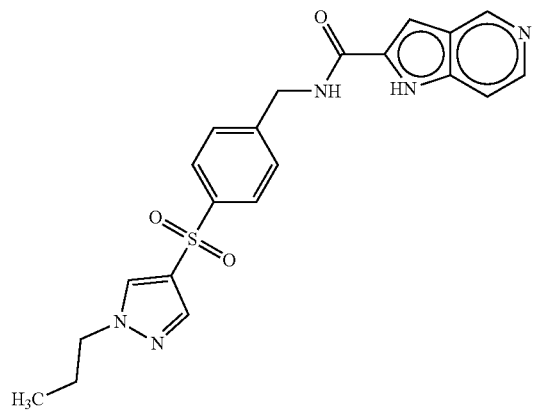 | N-{[4-(1-propyl-1H-pyrazole-4-sulfonyl)phenyl]methyl}-1H-pyrrolo[3,2-c]pyridine-2-carboxamide |
| 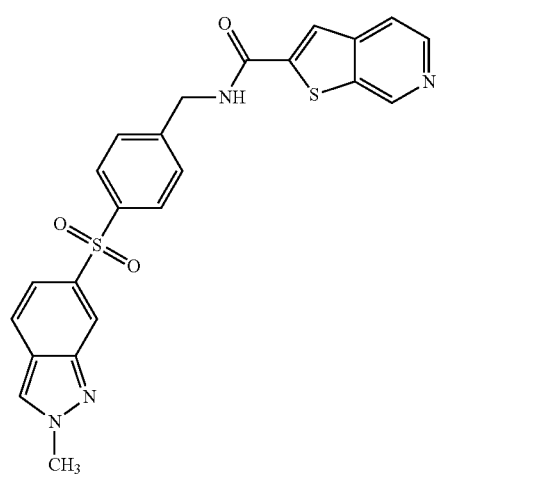 | N-{[4-(2-methyl-2H-indazole-6-sulfonyl)phenyl]methyl}thieno[2,3-c]pyridine-2-carboxamide |
| 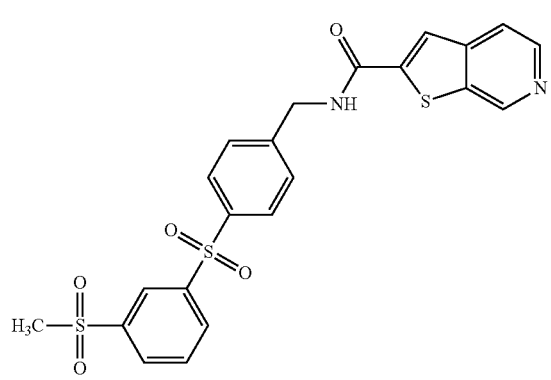 [SMILES: CS(=O)(=O)c1cccc(S(=O)(=O)c2ccc(CNC(=O)c3cc4ccncc4s3)cc2)c1] | N-({4-[(3-methanesulfonylbenzene)sulfonyl]phenyl}methyl)furo[2,3-c]pyridine-2-carboxamide |
| 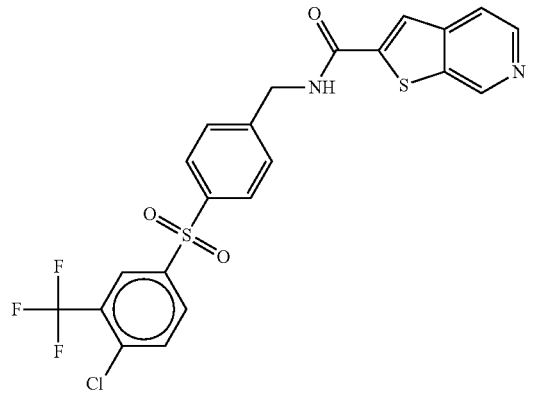 | N-[(4-{[4-chloro-3-(trifluoromethyl)benzene]sulfonyl}phenyl)methyl]thieno[2,3-c]pyridine-2-carboxamide |

TABLE 2-continued
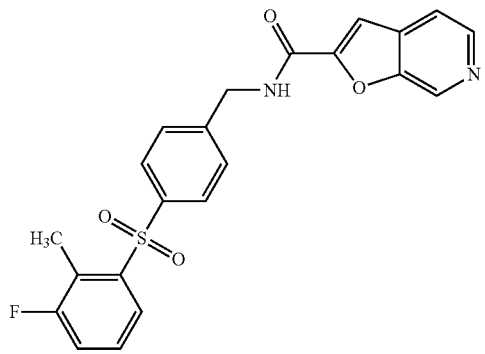 [SMILES: Cc1c(F)cccc1S(=O)(=O)c1ccc(CNC(=O)c2cc3ccncc3o2)cc1]
N-({4-[(3-fluoro-2-methylbenzene)sulfonyl]phenyl}methyl)furo[2,3-c]pyridine-2-carboxamide
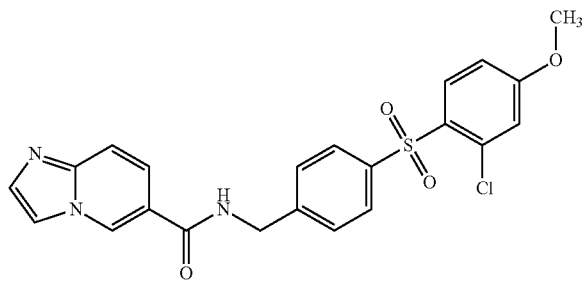 [SMILES: COc1ccc(S(=O)(=O)c2ccc(CNC(=O)c3ccc4nccn4c3)cc2)c(Cl)c1]
N-({4-[(2-chloro-4-methoxybenzene)sulfonyl]phenyl}methyl)imidazo[1,2-a]pyridine-6-carboxamide
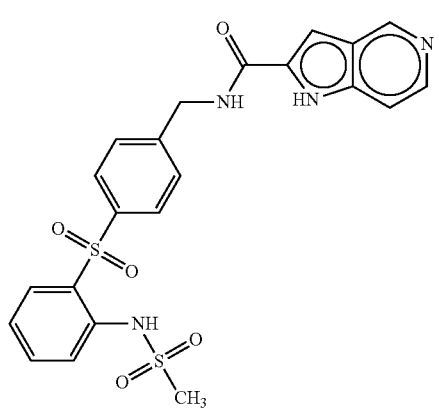
N-({4-[(2-methanesulfonamidobenzene)sulfonyl]phenyl}methyl)-1H-pyrrolo[3,2-c]pyridine-2-carboxamide
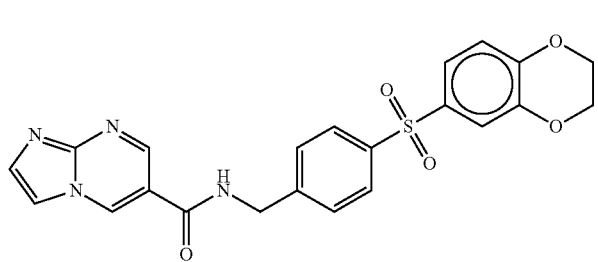
N-{[4-(2,3-dihydro-1,4-benzodioxine-6-sulfonyl)phenyl]methyl}imidazo[1,2-a]pyrimidine-6-carboxamide TABLE 2-continued
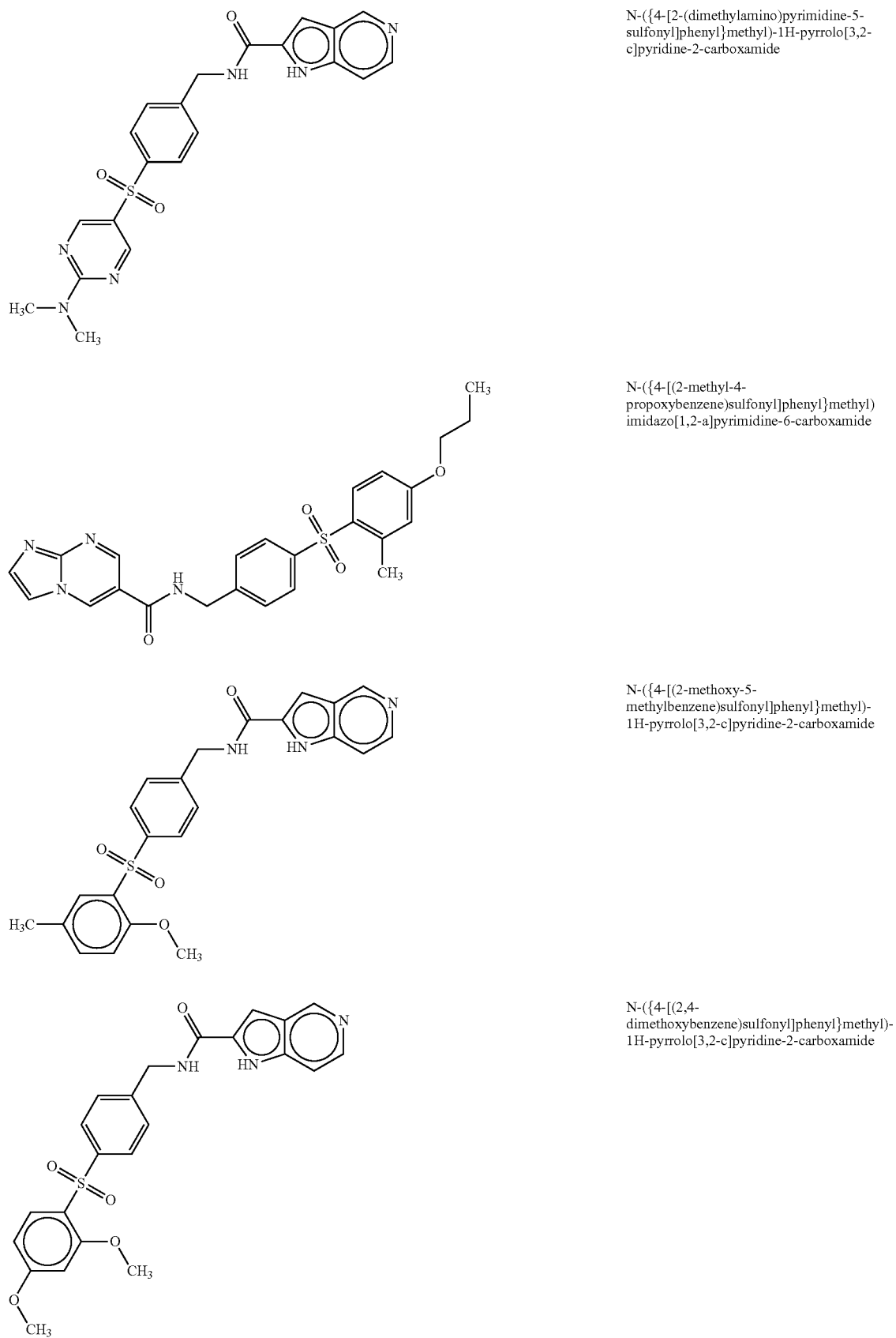
N-({4-[2-(dimethylamino)pyrimidine-5-sulfonyl]phenyl}methyl)-1H-pyrrolo[3,2-c]pyridine-2-carboxamide
N-({4-[(2-methyl-4-propoxybenzene)sulfonyl]phenyl}methyl)imidazo[1,2-a]pyrimidine-6-carboxamide
N-({4-[(2-methoxy-5-methylbenzene)sulfonyl]phenyl}methyl)-1H-pyrrolo[3,2-c]pyridine-2-carboxamide
N-({4-[(2,4-dimethoxybenzene)sulfonyl]phenyl}methyl)-1H-pyrrolo[3,2-c]pyridine-2-carboxamide TABLE 2-continued
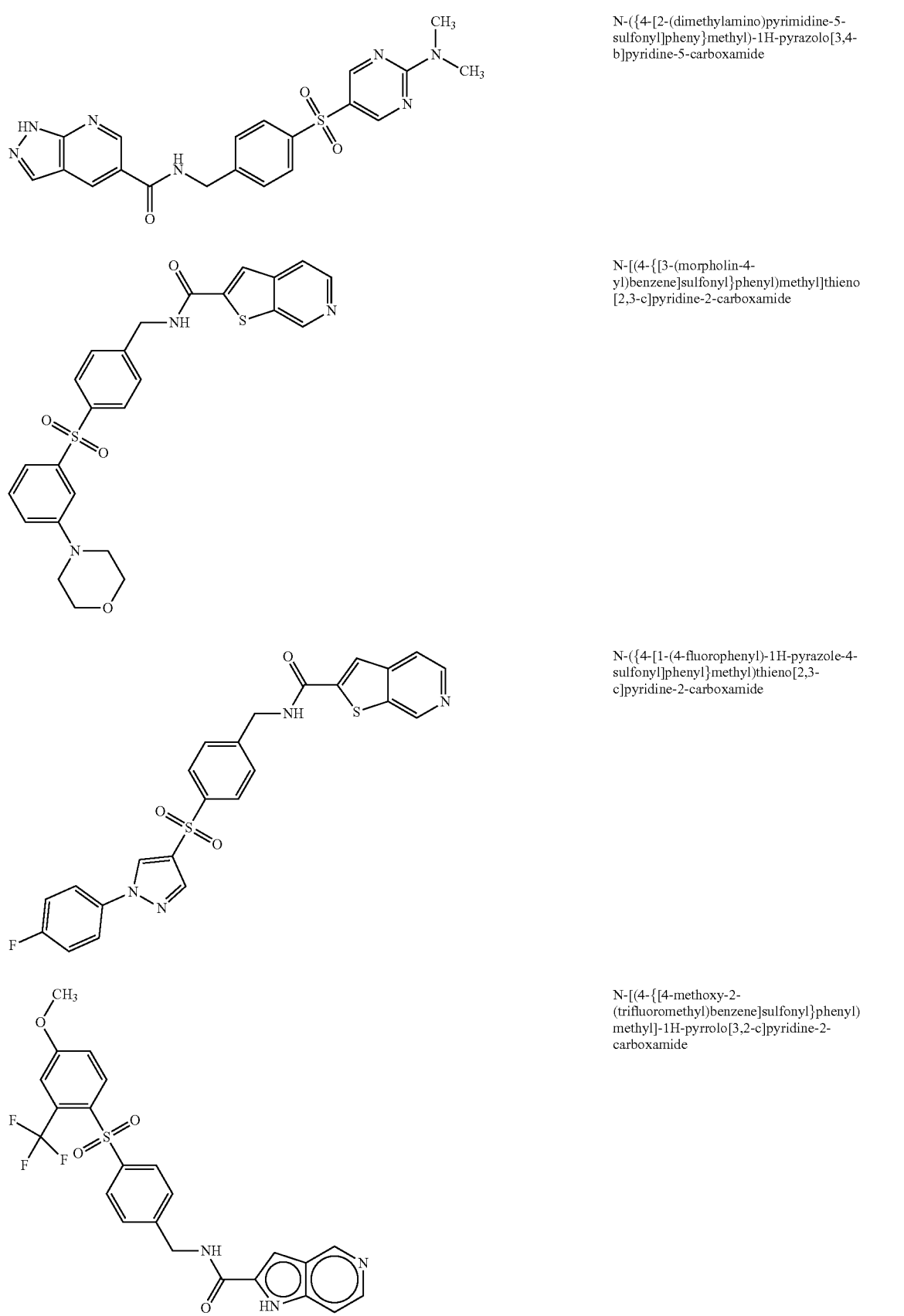
N-({4-[2-(dimethylamino)pyrimidine-5-sulfonyl]pheny}methyl)-1H-pyrazolo[3,4-b]pyridine-5-carboxamide
N-[(4-{[3-(morpholin-4-yl)benzene]sulfonyl}phenyl)methyl]thieno[2,3-c]pyridine-2-carboxamide
N-({4-[1-(4-fluorophenyl)-1H-pyrazole-4-sulfonyl]phenyl}methyl)thieno[2,3-c]pyridine-2-carboxamide
N-[(4-{[4-methoxy-2-(trifluoromethyl)benzene]sulfonyl}phenyl)methyl]-1H-pyrrolo[3,2-c]pyridine-2-carboxamide TABLE 2-continued

| | |
|---|---|
| 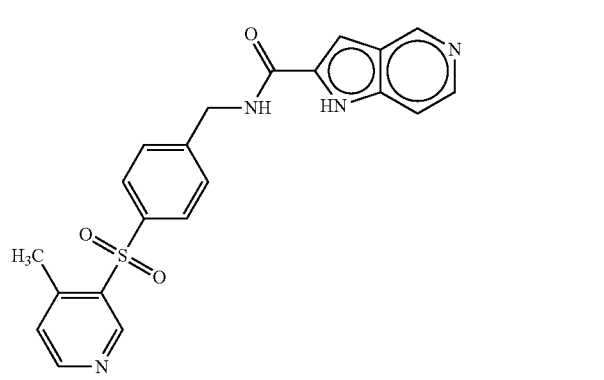 | N-({4-[(4-ethoxy-3-fluorobenzene)sulfonyl]phenyl}methyl)-1H-pyrazolo[3,4-b]pyridine-5-carboxamide |
| | N-{[4-(4-methylpyridine-3-sulfonyl)phenyl]methyl}-1H-pyrrolo[3,2-c]pyridine-2-carboxamide |
| 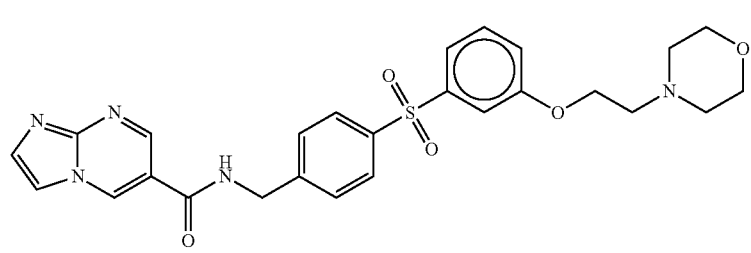 | N-{[4-({3-[2-(morpholin-4-yl)ethoxy]benzene}sulfonyl)phenyl]methyl}imidazo[1,2-a]pyrimidine-6-carboxamide |
| 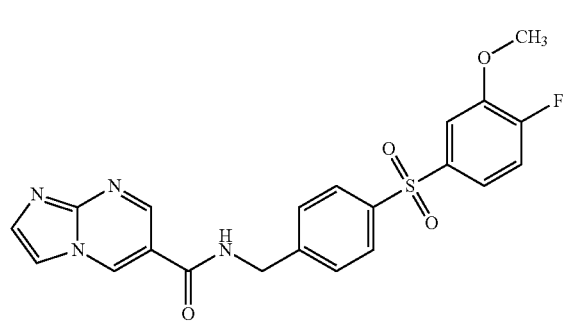 [SMILES: COc1cc(S(=O)(=O)c2ccc(CNC(=O)c3cnc4nccn4c3)cc2)ccc1F] | N-({4-[(4-fluoro-3-methoxybenzene)sulfonyl]phenyl}methyl)imidazo[1,2-a]pyrimidine-6-carboxamide |
| 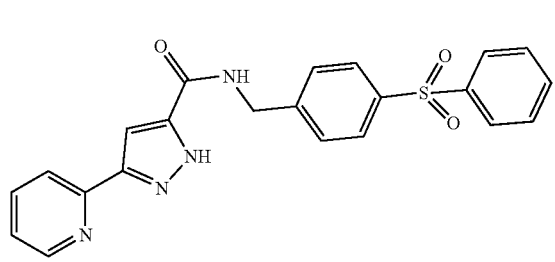 [SMILES: O=C(NCc1ccc(S(=O)(=O)c2ccccc2)cc1)c1cc(-c2ccccn2)n[nH]1] | N-{[4-(benzenesulfonyl)phenyl]methyl}-3-(pyridin-2-yl)-1H-pyrazole-5-carboxamide |

TABLE 2-continued

| | |
|---|---|
| 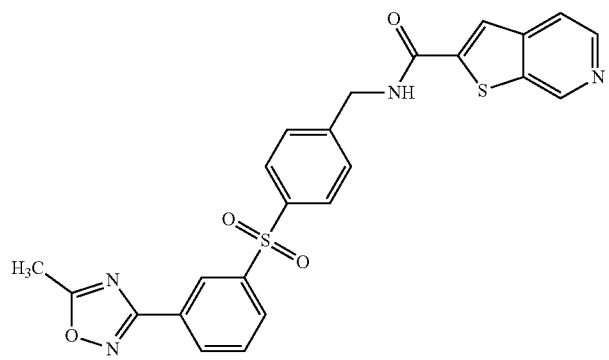 [SMILES: Cc1nc(-c2cccc(S(=O)(=O)c3ccc(CNC(=O)c4cc5ccncc5s4)cc3)c2)no1] | N-[(4-{[3-(5-methyl-1,2,4-oxadiazol-3-yl)benzene]sulfonyl}phenyl)methyl]thieno[2,3-c]pyridine-2-carboxamide |
| 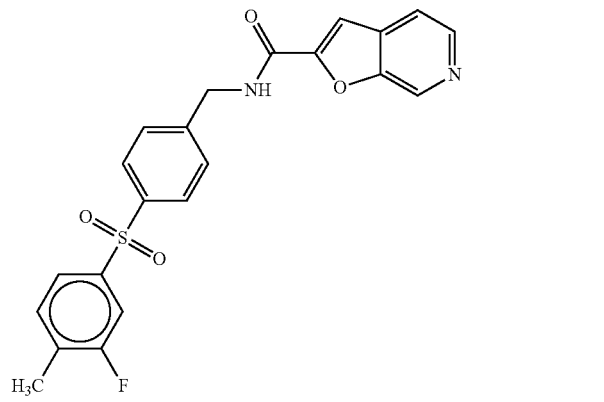 | N-({4-[(3-fluoro-4-methylbenzene)sulfonyl]phenyl}methyl)furo[2,3-c]pyridine-2-carboxamide |
| 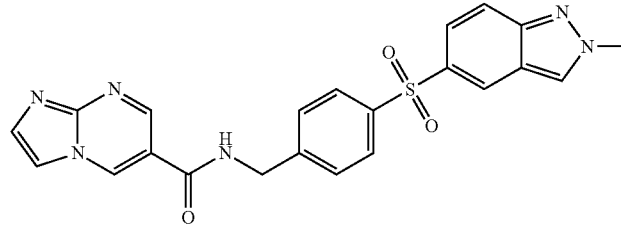 | N-{[4-(2-methyl-2H-indazole-5-sulfonyl)phenyl]methyl}imidazo[1,2-a]pyrimidine-6-carboxamide |
| 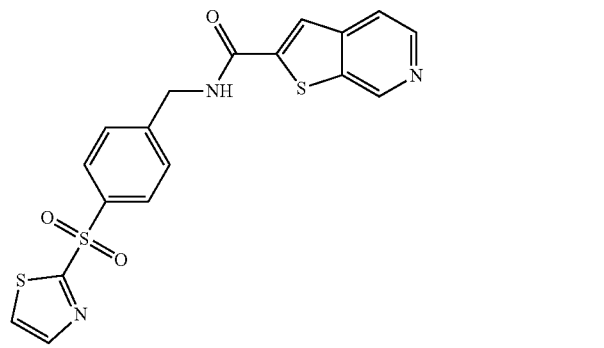 [SMILES: O=C(NCc1ccc(S(=O)(=O)c2nccs2)cc1)c1cc2ccncc2s1] | N-{[4-(1,3-thiazole-2-sulfonyl)phenyl]methyl}thieno[2,3-c]pyridine-2-carboxamide |
| 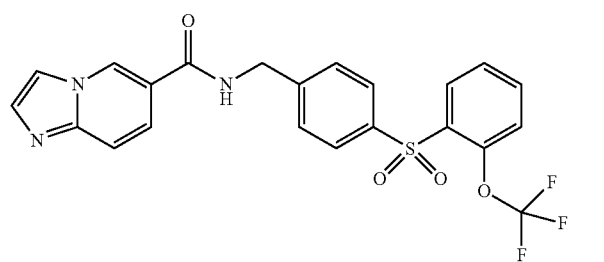 [SMILES: O=C(NCc1ccc(S(=O)(=O)c2ccccc2OC(F)(F)F)cc1)c1ccc2nccn2c1] | N-(4-(2-(trifluoromethoxy)phenylsulfonyl)benzyl)imidazo[1,2-a]pyridine-6-carboxamide |

TABLE 2-continued
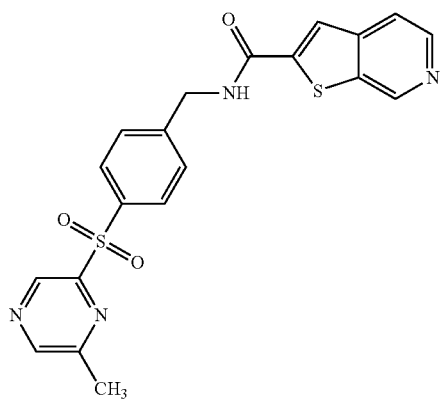 [SMILES: Cc1cncc(S(=O)(=O)c2ccc(CNC(=O)c3cc4ccncc4s3)cc2)n1]
N-{[4-(6-methylpyrazine-2-sulfonyl)phenyl]methyl}thieno[2,3-c]pyridine-2-carboxamide
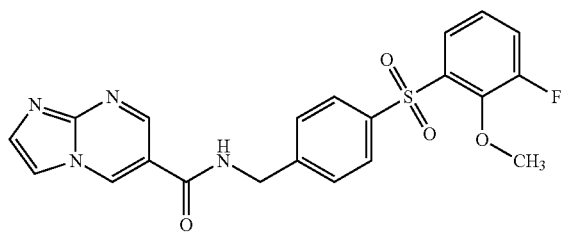 [SMILES: COc1c(F)cccc1S(=O)(=O)c1ccc(CNC(=O)c2cnc3nccn3c2)cc1]
N-({4-[(3-fluoro-2-methoxybenzene)sulfonyl]phenyl}methyl)imidazo[1,2-a]pyrimidine-6-carboxamide
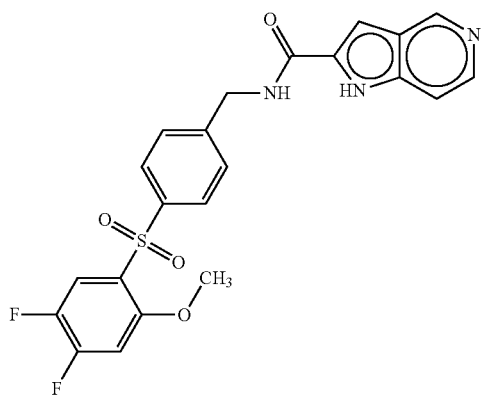
N-({4-[(4,5-difluoro-2-methoxybenzene)sulfonyl]phenyl}methyl)-1H-pyrrolo[3,2-c]pyridine-2-carboxamide
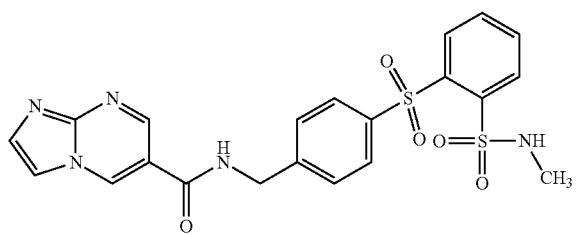 [SMILES: CNS(=O)(=O)c1ccccc1S(=O)(=O)c1ccc(CNC(=O)c2cnc3nccn3c2)cc1]
N-[(4-{[2-(methylsulfamoyl)benzene]sulfonyl}phenyl)methyl]imidazo[1,2-a]pyrimidine-6-carboxamide TABLE 2-continued
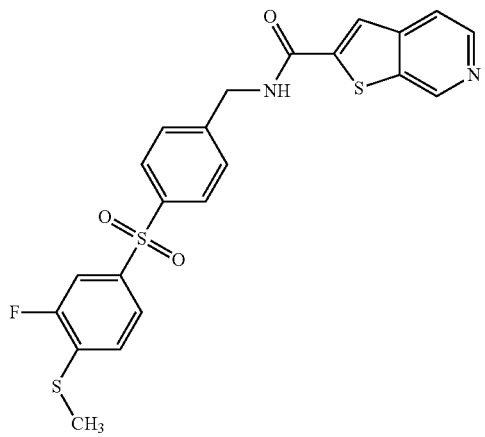 [SMILES: CSc1ccc(S(=O)(=O)c2ccc(CNC(=O)c3cc4ccncc4s3)cc2)cc1F]
N-[(4-{[3-fluoro-4-(methylsulfanyl)benzene]sulfonyl}phenyl)methyl]thieno[2,3-c]pyridine-2-carboxamide
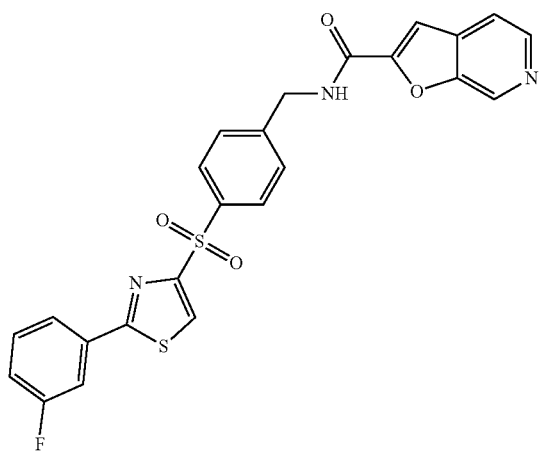
N-({4-[2-(3-fluorophenyl)-1,3-thiazole-4-sulfonyl]phenyl}methyl)furo[2,3-c]pyridine-2-carboxamide
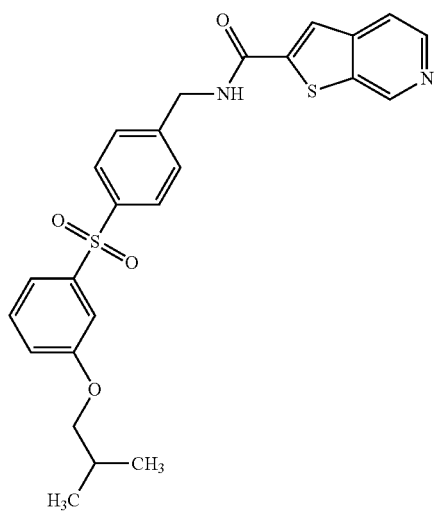 [SMILES: CC(C)COc1cccc(S(=O)(=O)c2ccc(CNC(=O)c3cc4ccncc4s3)cc2)c1]
N-[(4-{[3-(2-methylpropoxy)benzene]sulfonyl}phenyl)methyl]thieno[2,3-c]pyridine-2-carboxamide TABLE 2-continued

| | |
|---|---|
| 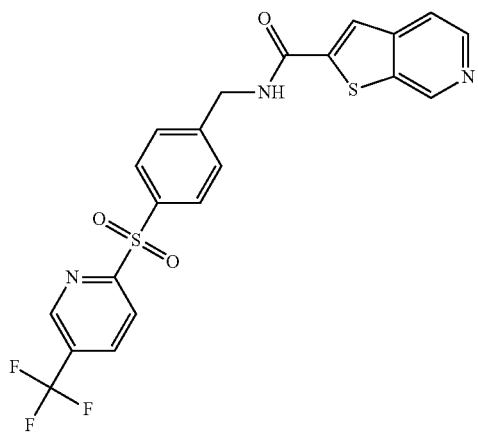 [SMILES: O=C(NCc1ccc(S(=O)(=O)c2ccc(C(F)(F)F)cn2)cc1)c1cc2ccncc2s1] | N-({4-[5-(trifluoromethyl)pyridine-2-sulfonyl]phenyl}methyl)thieno[2,3-c]pyridine-2-carboxamide |
| 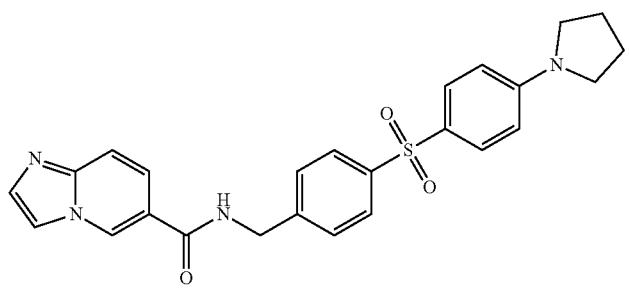 [SMILES: O=C(NCc1ccc(S(=O)(=O)c2ccc(N3CCCC3)cc2)cc1)c1ccc2nccn2c1] | N-[(4-{[4-(pyrrolidin-1-yl)benzene]sulfonyl}phenyl)methyl]imidazo[1,2-a]pyridine-6-carboxamide |
| 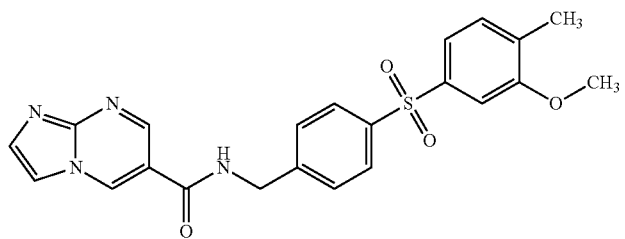 [SMILES: COc1cc(S(=O)(=O)c2ccc(CNC(=O)c3cnc4nccn4c3)cc2)ccc1C] | N-({4-[(3-methoxy-4-methylbenzene)sulfonyl]phenyl}methyl)imidazo[1,2-a]pyrimidine-6-carboxamide |
| 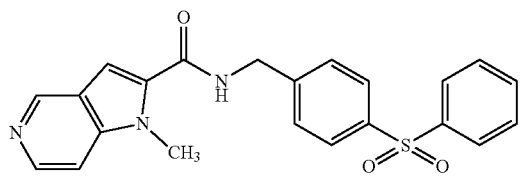 [SMILES: Cn1c(C(=O)NCc2ccc(S(=O)(=O)c3ccccc3)cc2)cc2cnccc21] | N-{[4-(benzenesulfonyl)phenyl]methyl}-1-methyl-1H-pyrrolo[3,2-c]pyridine-2-carboxamide |
| 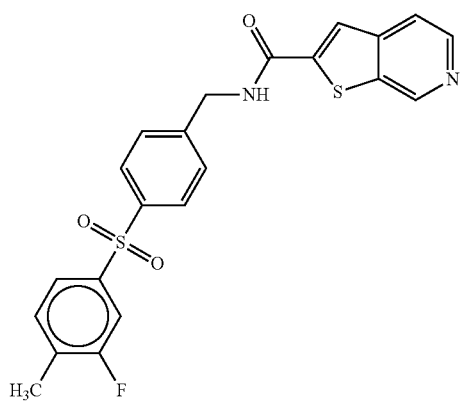 | N-({4-[(3-fluoro-4-methylbenzene)sulfonyl]phenyl}methyl)thieno[2,3-c]pyridine-2-carboxamide |

TABLE 2-continued
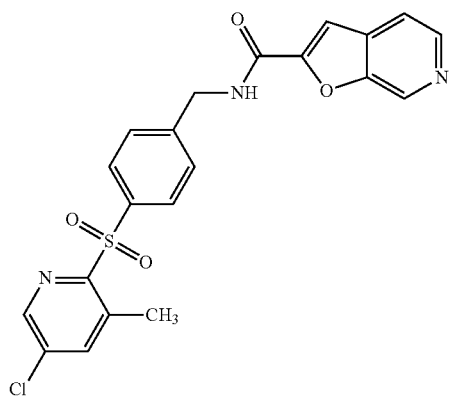 [SMILES: Cc1cc(Cl)cnc1S(=O)(=O)c1ccc(CNC(=O)c2cc3ccncc3o2)cc1]
N-{[4-(5-chloro-3-methylpyridine-2-sulfonyl)phenyl]methyl}furo[2,3-c]pyridine-2-carboxamide
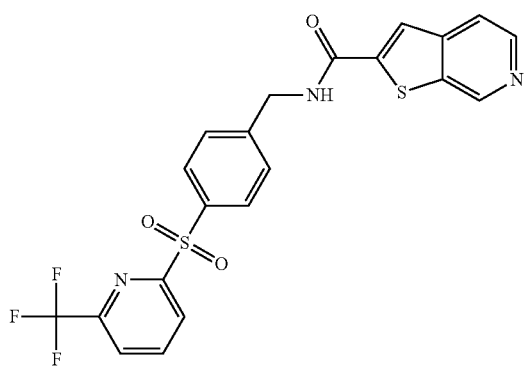 [SMILES: O=C(NCc1ccc(S(=O)(=O)c2cccc(C(F)(F)F)n2)cc1)c1cc2ccncc2s1]
N-({4-[6-(trifluoromethyl)pyridine-2-sulfonyl]phenyl}methyl)thieno[2,3-c]pyridine-2-carboxamide
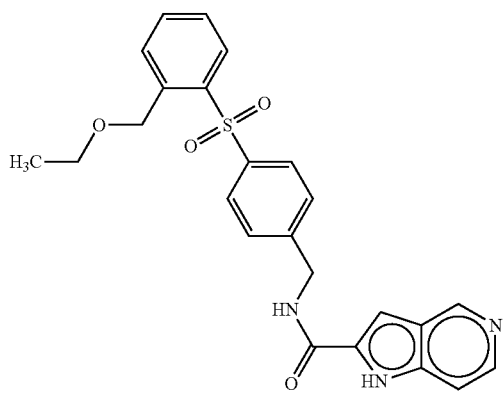
N-[(4-{[2-(ethoxymethyl)benzene]sulfonyl}phenyl)methyl]-1H-pyrrolo[3,2-c]pyridine-2-carboxamide
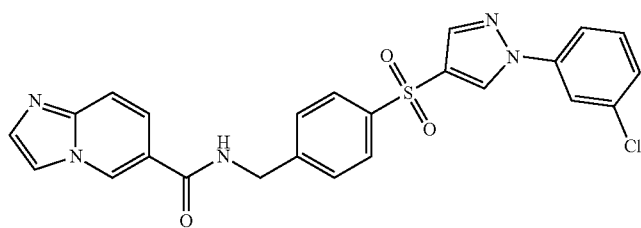 [SMILES: O=C(NCc1ccc(S(=O)(=O)c2cnn(-c3cccc(Cl)c3)c2)cc1)c1ccc2nccn2c1]
N-({4-[1-(3-chlorophenyl)-1H-pyrazole-4-sulfonyl]phenyl}methyl)imidazo[1,2-a]pyridine-6-carboxamide TABLE 2-continued

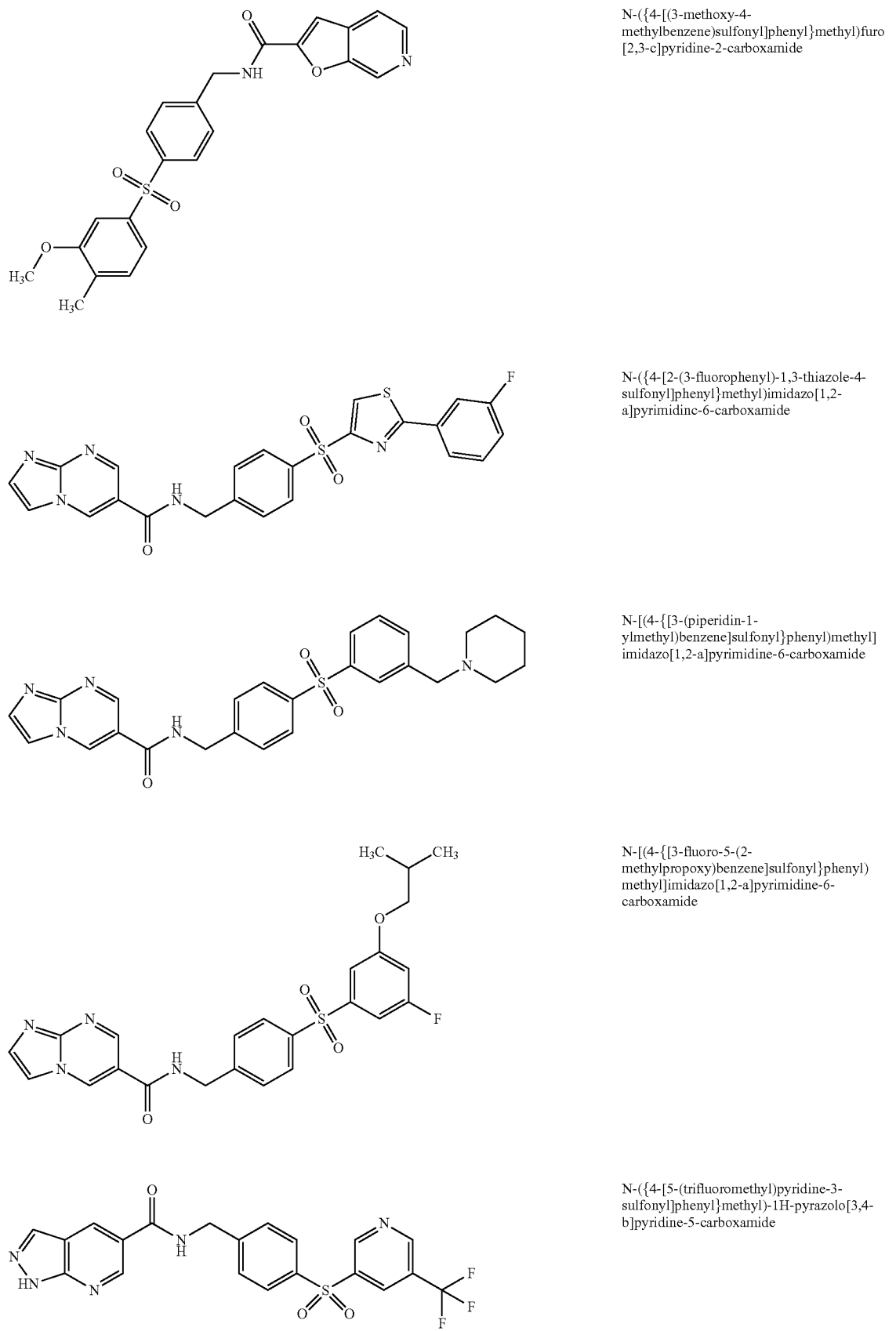

N-({4-[(3-methoxy-4-methylbenzene)sulfonyl]phenyl}methyl)furo[2,3-c]pyridine-2-carboxamide N-({4-[2-(3-fluorophenyl)-1,3-thiazole-4-sulfonyl]phenyl}methyl)imidazo[1,2-a]pyrimidine-6-carboxamide N-[(4-{[3-(piperidin-1-ylmethyl)benzene]sulfonyl}phenyl)methyl]imidazo[1,2-a]pyrimidine-6-carboxamide N-[(4-{[3-fluoro-5-(2-methylpropoxy)benzene]sulfonyl}phenyl)methyl]imidazo[1,2-a]pyrimidine-6-carboxamide N-({4-[5-(trifluoromethyl)pyridine-3-sulfonyl]phenyl}methyl)-1H-pyrazolo[3,4-b]pyridine-5-carboxamide TABLE 2-continued

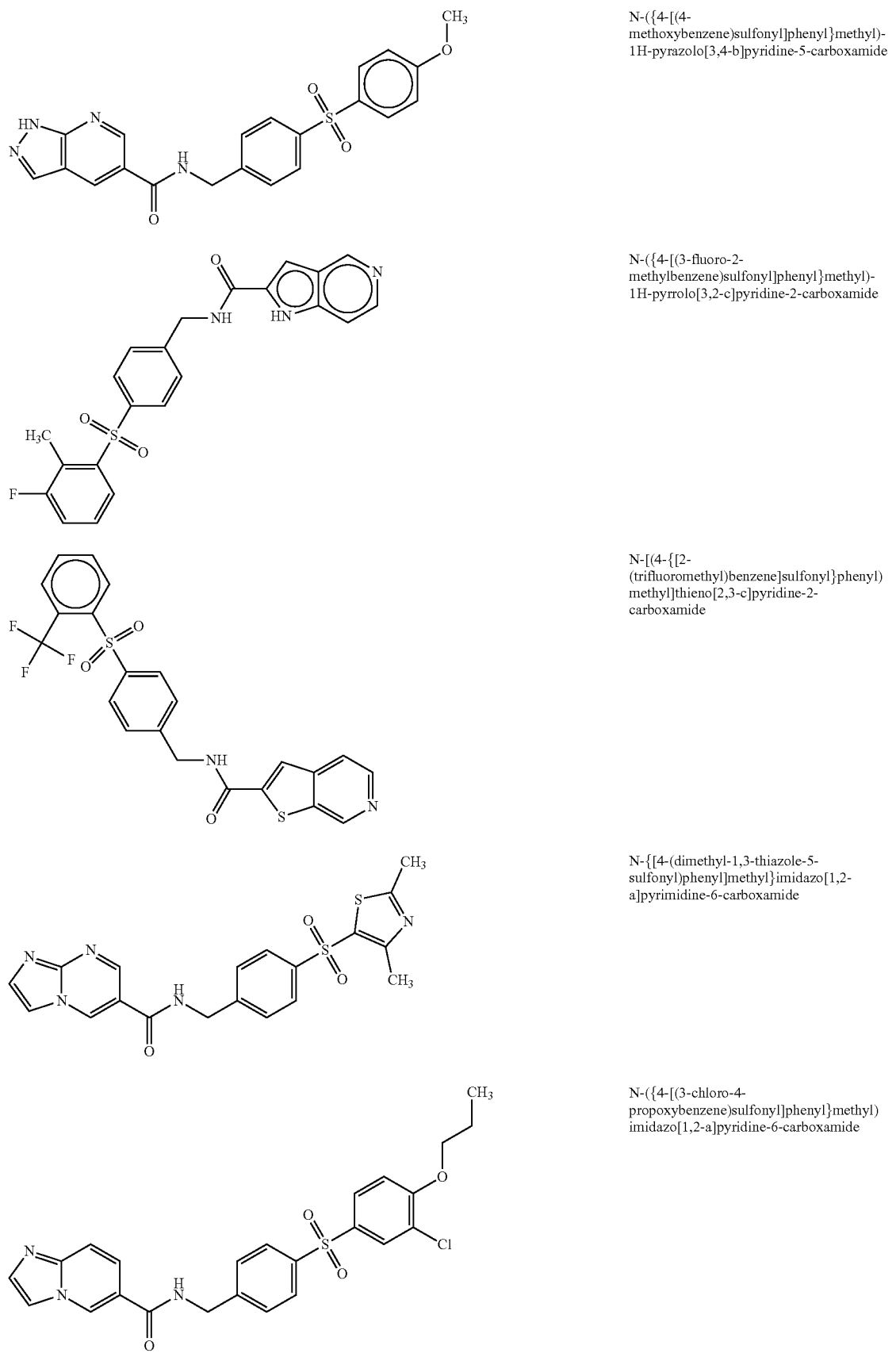

| | |
|---|---|
| | N-({4-[(4-methoxybenzene)sulfonyl]phenyl}methyl)-1H-pyrazolo[3,4-b]pyridine-5-carboxamide |
| | N-({4-[(3-fluoro-2-methylbenzene)sulfonyl]phenyl}methyl)-1H-pyrrolo[3,2-c]pyridine-2-carboxamide |
| | N-[(4-{[2-(trifluoromethyl)benzene]sulfonyl}phenyl)methyl]thieno[2,3-c]pyridine-2-carboxamide |
| | N-{[4-(dimethyl-1,3-thiazole-5-sulfonyl)phenyl]methyl}imidazo[1,2-a]pyrimidine-6-carboxamide |
| | N-({4-[(3-chloro-4-propoxybenzene)sulfonyl]phenyl}methyl)imidazo[1,2-a]pyridine-6-carboxamide |

TABLE 2-continued
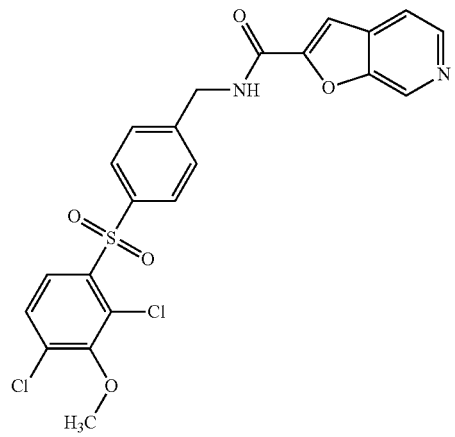 [SMILES: COc1c(Cl)ccc(S(=O)(=O)c2ccc(CNC(=O)c3cc4ccncc4o3)cc2)c1Cl]
N-({4-[(2,4-dichloro-3-methoxybenzene)sulfonyl]phenyl}methyl)furo[2,3-c]pyridine-2-carboxamide
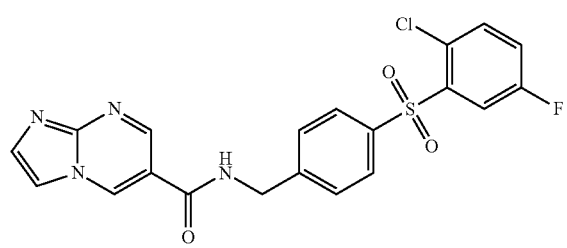 [SMILES: O=C(NCc1ccc(S(=O)(=O)c2cc(F)ccc2Cl)cc1)c1cnc2nccn2c1]
N-({4-[(2-chloro-5-fluorobenzene)sulfonyl]phenyl}methyl)imidazo[1,2-a]pyrimidine-6-carboxamide
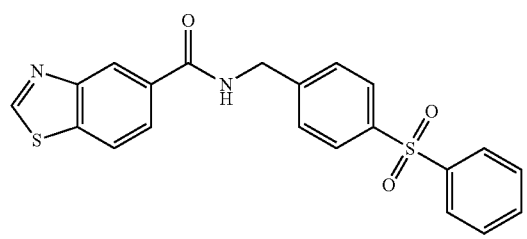 [SMILES: O=C(NCc1ccc(S(=O)(=O)c2ccccc2)cc1)c1ccc2scnc2c1]
N-(4-(phenylsulfonyl)benzyl)benzo[d]thiazole-5-carboxamide
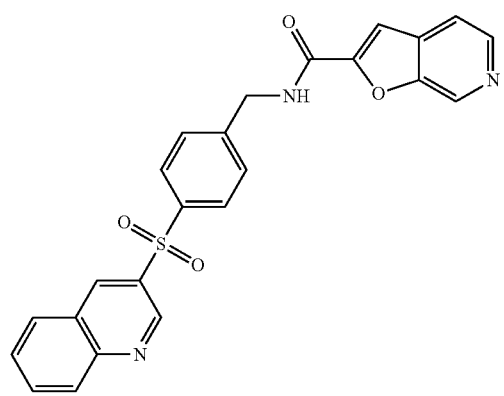 [SMILES: O=C(NCc1ccc(S(=O)(=O)c2cnc3ccccc3c2)cc1)c1cc2ccncc2o1]
N-{[4-(quinoline-3-sulfonyl)phenyl]methyl}furo[2,3-c]pyridine-2-carboxamide TABLE 2-continued
| | |
|---|---|
| 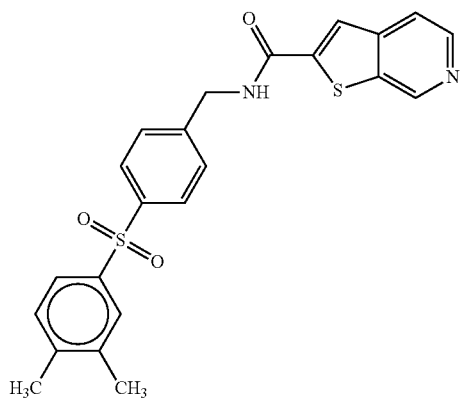 | N-({4-[(3,4-dimethylbenzene)sulfonyl]phenyl}methyl)furo[2,3-c]pyridine-2-carboxamide |
| 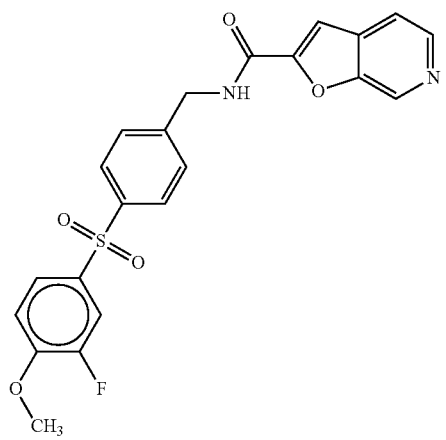 | N-({4-[(3-fluoro-4-methoxybenzene)sulfonyl]phenyl}methyl)furo[2,3-c]pyridine-2-carboxamide |
| 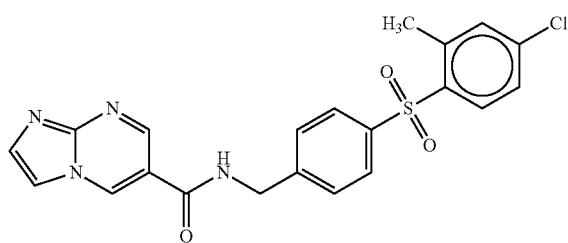 | N-({4-[(4-chloro-2-methylbenzene)sulfonyl]phenyl}methyl)imidazo[1,2-a]pyrimidine-6-carboxamide |
| 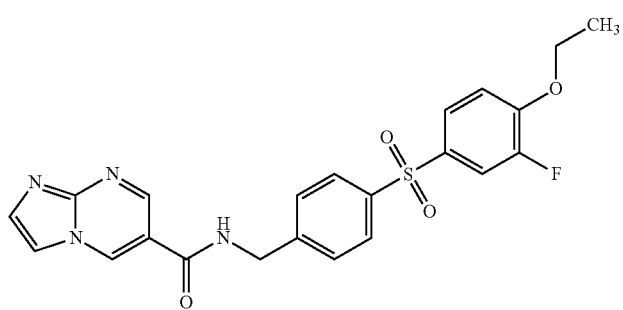 [SMILES: CCOc1ccc(S(=O)(=O)c2ccc(CNC(=O)c3cnc4nccn4c3)cc2)cc1F] | N-({4-[(4-ethoxy-3-fluorobenzene)sulfonyl]phenyl}methyl)imidazo[1,2-a]pyrimidine-6-carboxamide |

TABLE 2-continued

| | |
|---|---|
| 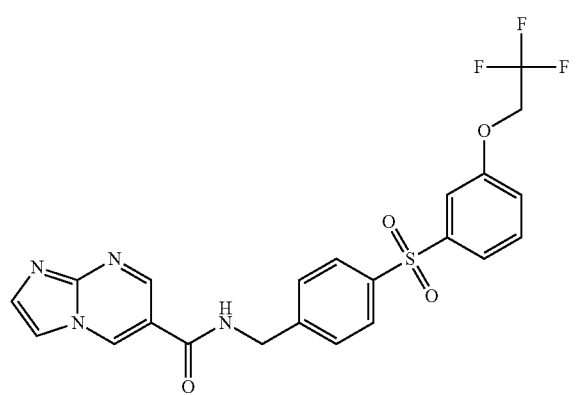 [SMILES: O=C(NCc1ccc(S(=O)(=O)c2cccc(OCC(F)(F)F)c2)cc1)c1cnc2nccn2c1] | N-[(4-{[3-(2,2,2-trifluoroethoxy)benzene]sulfonyl}phenyl)methyl]imidazo[1,2-a]pyrimidine-6-carboxamide |
| 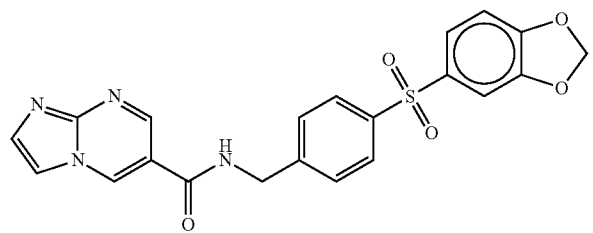 | N-{[4-(2H-1,3-benzodioxole-5-sulfonyl)phenyl]methyl}imidazo[1,2-a]pyrimidine-6-carboxamide |
| 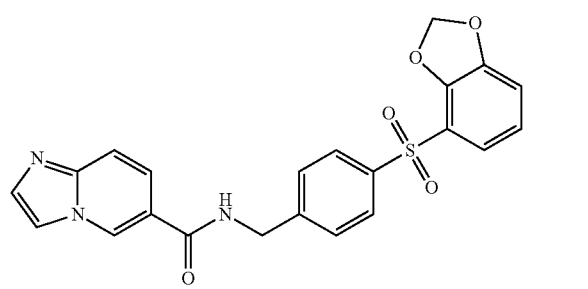 | N-{[4-(2H-1,3-benzodioxole-4-sulfonyl)phenyl]methyl}imidazo[1,2-a]pyridine-6-carboxamide |
| 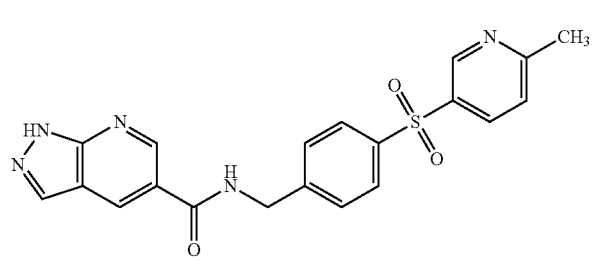 [SMILES: Cc1ccc(S(=O)(=O)c2ccc(CNC(=O)c3cnc4[nH]ncc4c3)cc2)cn1] | N-{[4-(6-methylpyridine-3-sulfonyl)phenyl]methyl}-1H-pyrazolo[3,4-b]pyridine-5-carboxamide |
| 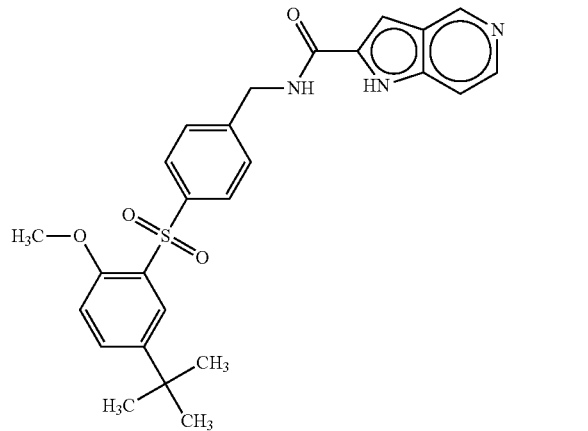 | N-({4-[(5-tert-butyl-2-methoxybenzene)sulfonyl]phenyl}methyl)-1H-pyrrolo[3,2-c]pyridine-2-carboxamide |

TABLE 2-continued
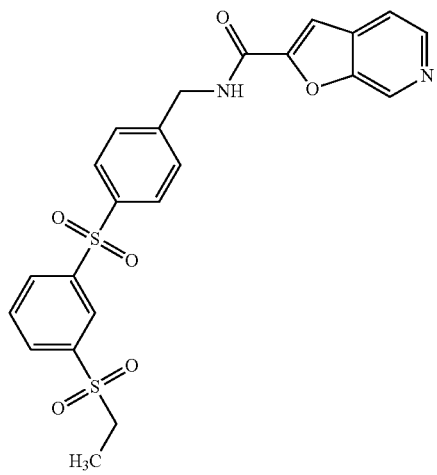
N-[(4-{[3-(ethanesulfonyl)benzene]sulfonyl}phenyl)methyl]furo[2,3-c]pyridine-2-carboxamide
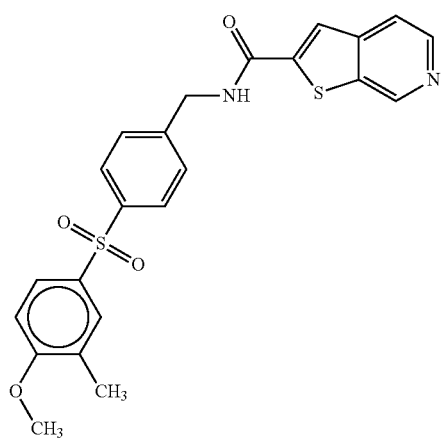
N-({4-[(4-methoxy-3-methylbenzene)sulfonyl]phenyl}methyl)thieno[2,3-c]pyridine-2-carboxamide
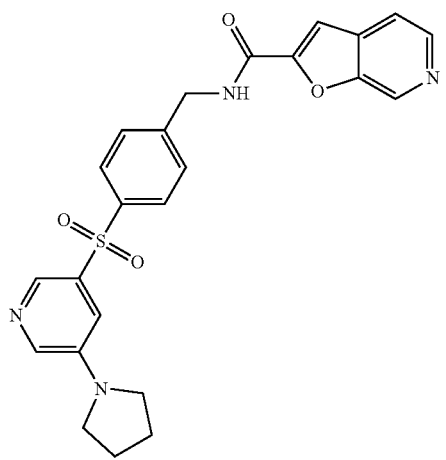 [SMILES: O=C(NCc1ccc(S(=O)(=O)c2cncc(N3CCCC3)c2)cc1)c1cc2ccncc2o1]
N-({4-[5-(pyrrolidin-1-yl)pyridine-3-sulfonyl]phenyl}methyl)furo[2,3-c]pyridine-2-carboxamide TABLE 2-continued
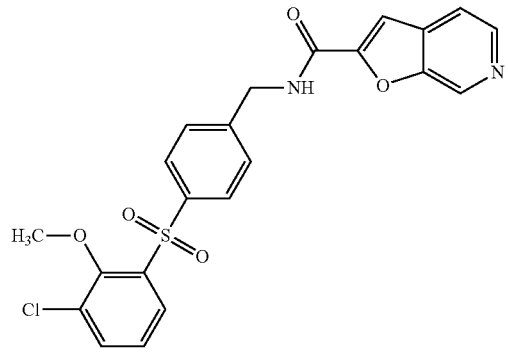
N-({4-[(3-chloro-2-methoxybenzene)sulfonyl]phenyl}methyl)furo[2,3-c]pyridine-2-carboxamide
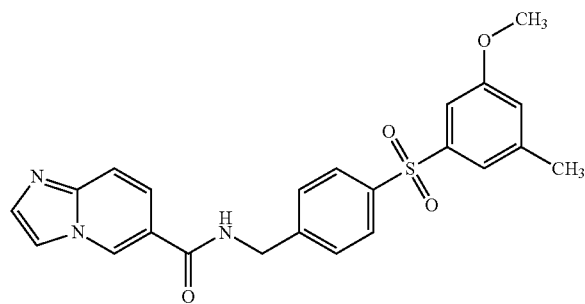 [SMILES: COc1cc(C)cc(S(=O)(=O)c2ccc(CNC(=O)c3ccc4nccn4c3)cc2)c1]
N-({4-[(3-methoxy-5-methylbenzene)sulfonyl]phenyl}methyl)imidazo[1,2-a]pyridine-6-carboxamide
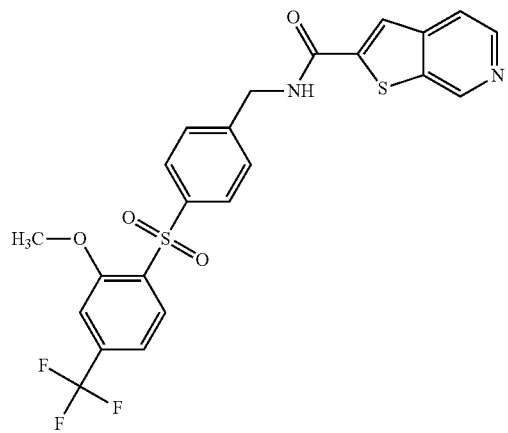 [SMILES: COc1cc(C(F)(F)F)ccc1S(=O)(=O)c1ccc(CNC(=O)c2cc3ccncc3s2)cc1]
N-[(4-{[2-methoxy-4-(trifluoromethyl)benzene]sulfonyl}phenyl)methyl]thieno[2,3-c]pyridine-2-carboxamide
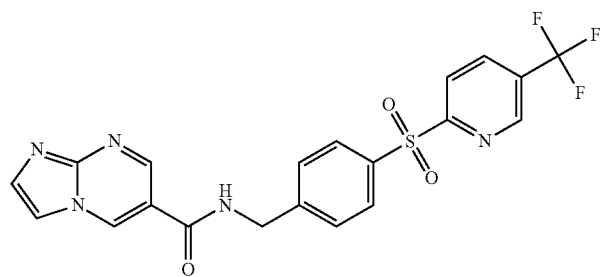 [SMILES: O=C(NCc1ccc(S(=O)(=O)c2ccc(C(F)(F)F)cn2)cc1)c1cnc2nccn2c1]
N-({4-[5-(trifluoromethyl)pyridine-2-sulfonyl]phenyl}methyl)imidazo[1,2-a]pyrimidine-6-carboxamide TABLE 2-continued
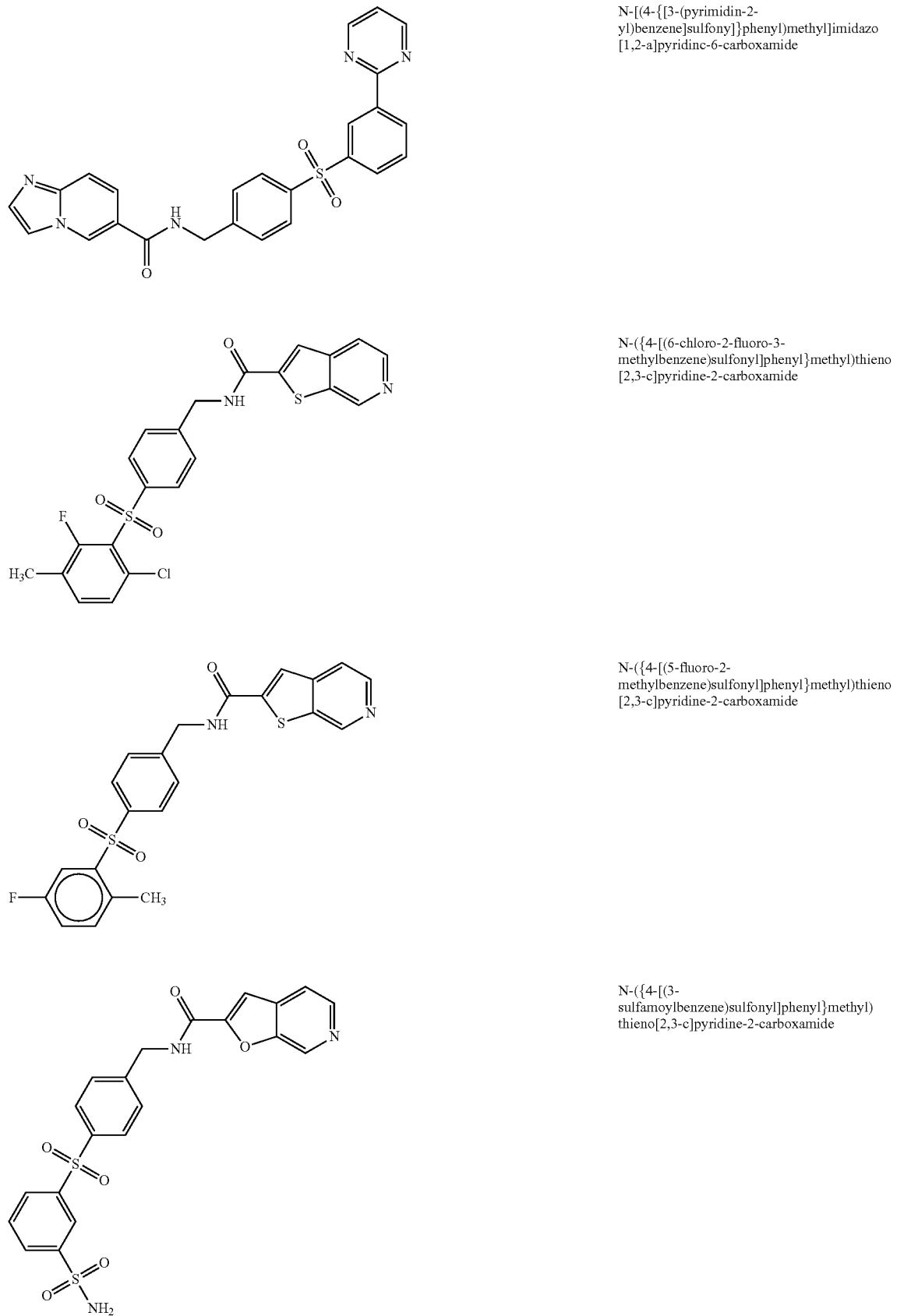
N-[(4-{[3-(pyrimidin-2-yl)benzene]sulfonyl]}phenyl)methyl]imidazo[1,2-a]pyridine-6-carboxamide
N-({4-[(6-chloro-2-fluoro-3-methylbenzene)sulfonyl]phenyl}methyl)thieno[2,3-c]pyridine-2-carboxamide
N-({4-[(5-fluoro-2-methylbenzene)sulfonyl]phenyl}methyl)thieno[2,3-c]pyridine-2-carboxamide
N-({4-[(3-sulfamoylbenzene)sulfonyl]phenyl}methyl)thieno[2,3-c]pyridine-2-carboxamide TABLE 2-continued

| Structure | Name |
|---|---|
| 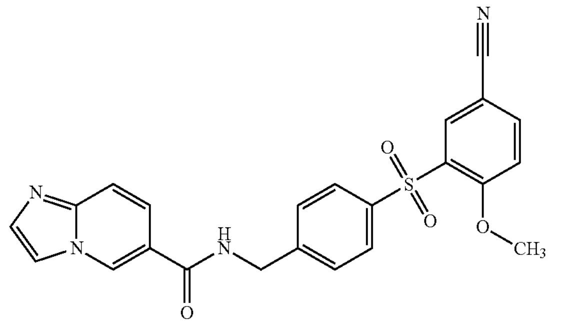 [SMILES: COc1ccc(C#N)cc1S(=O)(=O)c1ccc(CNC(=O)c2ccc3nccn3c2)cc1] | N-({4-[(5-cyano-2-methoxybenzene)sulfonyl]phenyl}methyl)imidazo[1,2-a]pyridine-6-carboxamide |
| 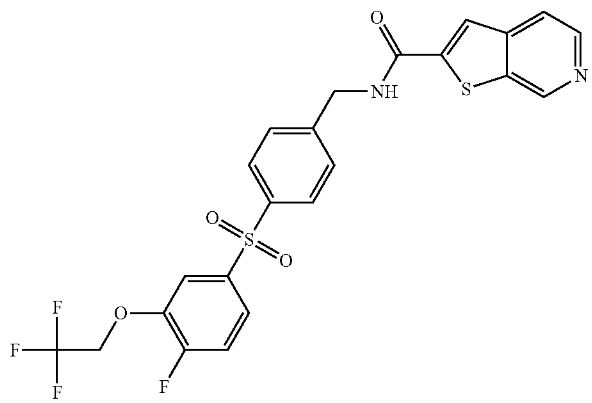 [SMILES: O=C(NCc1ccc(S(=O)(=O)c2ccc(F)c(OCC(F)(F)F)c2)cc1)c1cc2ccncc2s1] | N-[(4-{[4-fluoro-3-(2,2,2-trifluoroethoxy)benzene]sulfonyl}phenyl)methyl]furo[2,3-c]pyridine-2-carboxamide |
| 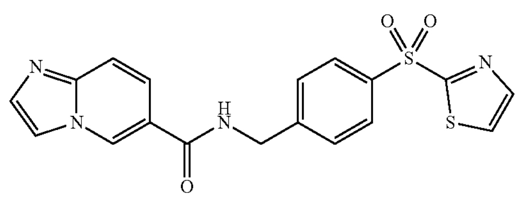 [SMILES: O=C(NCc1ccc(S(=O)(=O)c2nccs2)cc1)c1ccc2nccn2c1] | N-{[4-(1,3-thiazole-2-sulfonyl)phenyl]methyl}imidazo[1,2-a]pyridine-6-carboxamide |
| 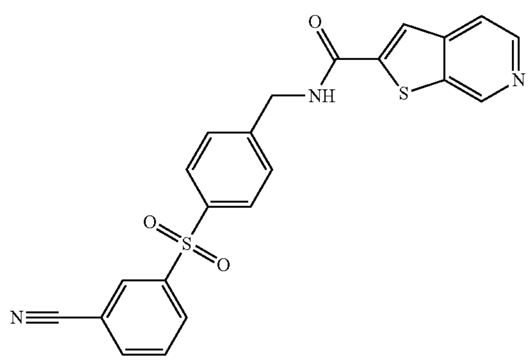 [SMILES: N#Cc1cccc(S(=O)(=O)c2ccc(CNC(=O)c3cc4ccncc4s3)cc2)c1] | N-({4-[(3-cyanobenzene)sulfonyl]phenyl}methyl)thieno[2,3-c]pyridine-2-carboxamide |
| 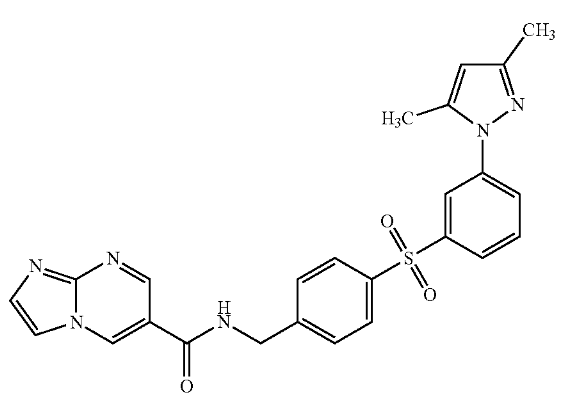 [SMILES: Cc1cc(C)n(-c2cccc(S(=O)(=O)c3ccc(CNC(=O)c4cnc5nccn5c4)cc3)c2)n1] | N-[(4-{[3-(3,5-dimethyl-1H-pyrazol-1-yl)benzene]sulfonyl}phenyl)methyl]imidazo[1,2-a]pyrimidine-6-carboxamide |

TABLE 2-continued

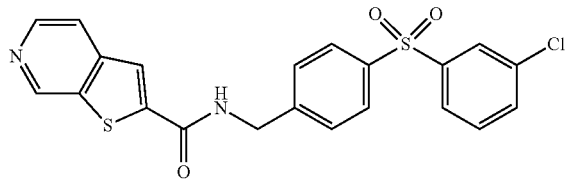 [SMILES: O=C(NCc1ccc(S(=O)(=O)c2cccc(Cl)c2)cc1)c1cc2ccncc2s1]

N-({4-[(3-chlorobenzene)sulfonyl]phenyl}methyl)thieno[2,3-c]pyridine-2-carboxamide

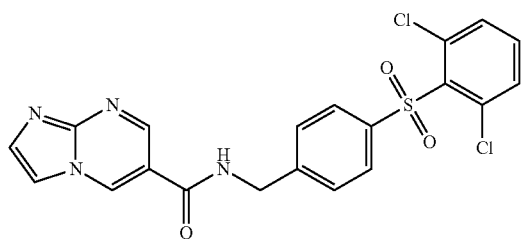 [SMILES: O=C(NCc1ccc(S(=O)(=O)c2c(Cl)cccc2Cl)cc1)c1cnc2nccn2c1]

N-({4-[(2,6-dichlorobenzene)sulfonyl]phenyl}methyl)imidazo[1,2-a]pyrimidine-6-carboxamide

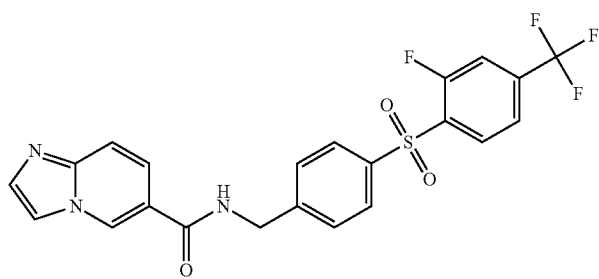 [SMILES: O=C(NCc1ccc(S(=O)(=O)c2ccc(C(F)(F)F)cc2F)cc1)c1ccc2nccn2c1]

N-[(4-{[2-fluoro-4-(trifluoromethyl)benzene]sulfonyl}phenyl)methyl]imidazo[1,2-a]pyridine-6-carboxamide

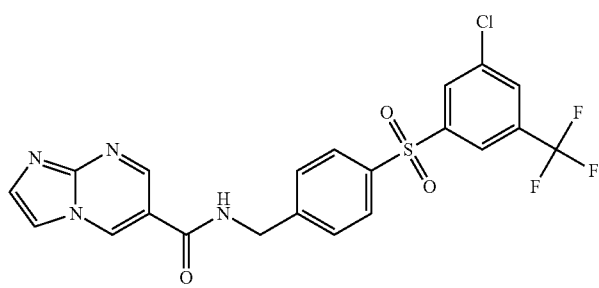

N-[(4-{[3-chloro-5-(trifluoromethyl)benzene]sulfonyl}phenyl)methyl]imidazo[1,2-a]pyrimidine-6-carboxamide

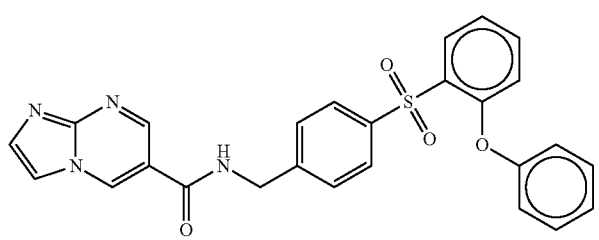

N-({4-[(2-phenoxybenzene)sulfonyl]phenyl}methyl)imidazo[1,2-a]pyrimidine-6-carboxamide

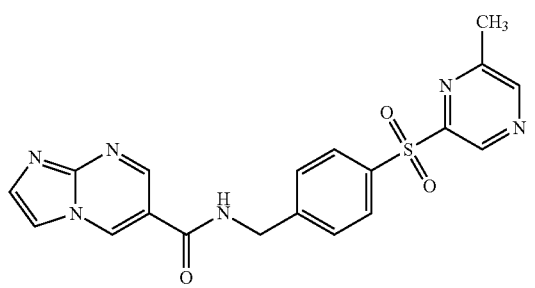 [SMILES: Cc1cncc(S(=O)(=O)c2ccc(CNC(=O)c3cnc4nccn4c3)cc2)n1]

N-{[4-(6-methylpyrazine-2-sulfonyl)phenyl]methyl}imidazo[1,2-a]pyrimidine-6-carboxamide

| | |
|---|---|
| 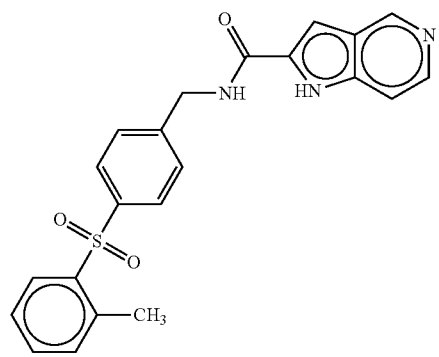 | N-({4-[(2-methylbenzene)sulfonyl]phenyl}methyl)-1H-pyrrolo[3,2-c]pyridine-2-carboxamide |
| 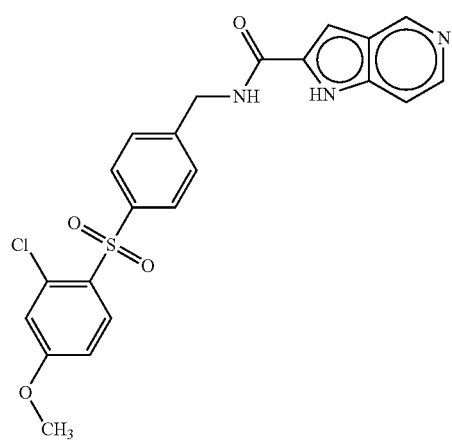 | N-({4-[(2-chloro-4-methoxybenzene)sulfonyl]phenyl}methyl)-1H-pyrrolo[3,2-c]pyridine-2-carboxamide |
| 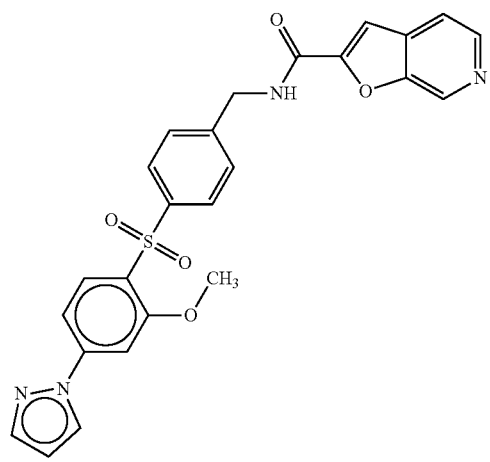 | N-[(4-{[2-methoxy-4-(1H-pyrazol-1-yl)benzene]sulfonyl}phenyl)methyl]furo[2,3-c]pyridine-2-carboxamide |

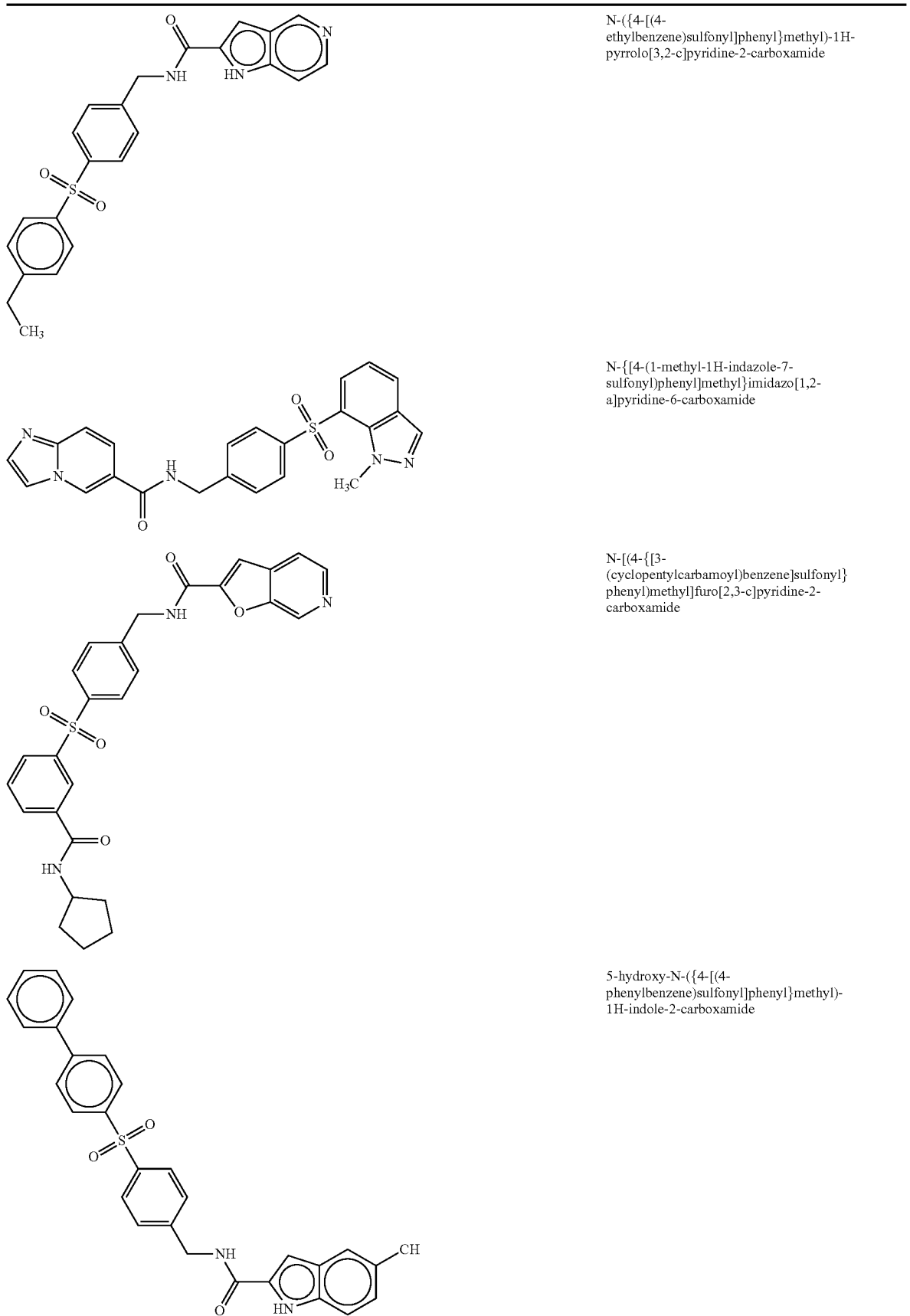
N-({4-[(4-ethylbenzene)sulfonyl]phenyl}methyl)-1H-pyrrolo[3,2-c]pyridine-2-carboxamide
N-{[4-(1-methyl-1H-indazole-7-sulfonyl)phenyl]methyl}imidazo[1,2-a]pyridine-6-carboxamide
N-[(4-{[3-(cyclopentylcarbamoyl)benzene]sulfonyl}phenyl)methyl]furo[2,3-c]pyridine-2-carboxamide
5-hydroxy-N-({4-[(4-phenylbenzene)sulfonyl]phenyl}methyl)-1H-indole-2-carboxamide TABLE 2-continued
| | |
|---|---|
| 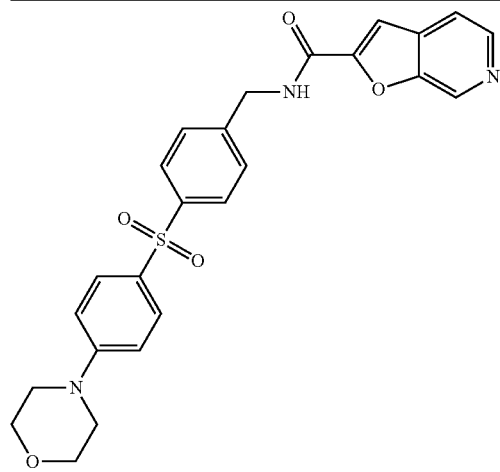 | N-[(4-{[4-(morpholin-4-yl)benzene]sulfonyl}phenyl)methyl]furo[2,3-c]pyridine-2-carboxamide |
| 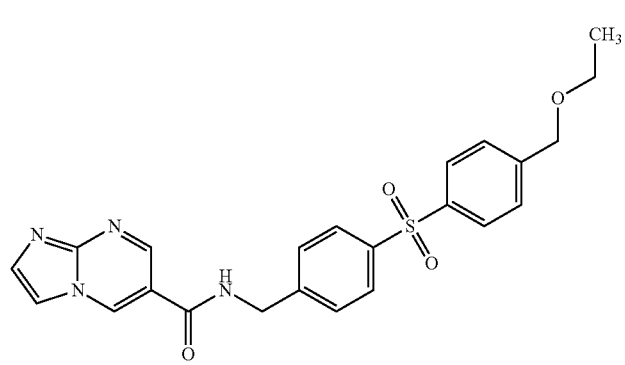 [SMILES: CCOCc1ccc(S(=O)(=O)c2ccc(CNC(=O)c3cnc4nccn4c3)cc2)cc1] | N-[(4-{[4-(ethoxymethyl)benzene]sulfonyl}phenyl)methyl]imidazo[1,2-a]pyrimidine-6-carboxamide |
| 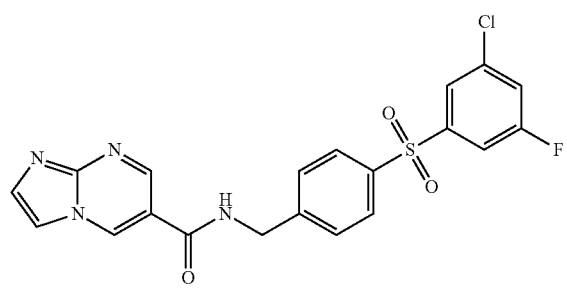 [SMILES: O=C(NCc1ccc(S(=O)(=O)c2cc(F)cc(Cl)c2)cc1)c1cnc2nccn2c1] | N-({4-[(3-chloro-5-fluorobenzene)sulfonyl]phenyl}rnethyl)imidazo[1,2-a]pyrimidine-6-carboxamide |
| 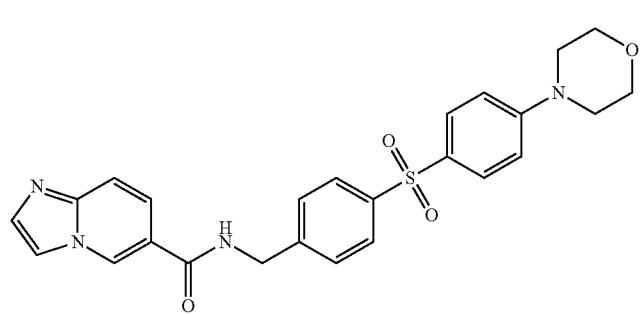 [SMILES: O=C(NCc1ccc(S(=O)(=O)c2ccc(N3CCOCC3)cc2)cc1)c1ccc2nccn2c1] | N-[(4-{[4-(morpholin-4-yl)benzene]sulfonyl}phenyl)methyl]imidazo[1,2-a]pyridine-6-carboxamide |

| | |
|---|---|
| 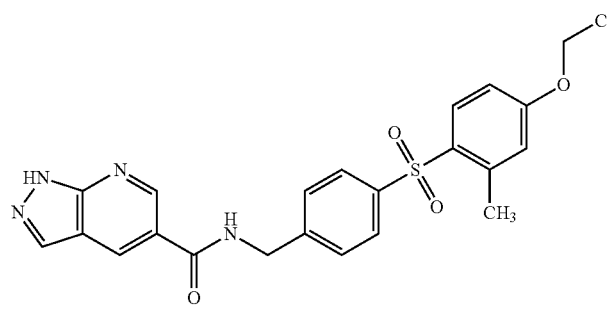 | N-({4-[(4-ethoxy-2-methylbenzene)sulfonyl]phenyl}methyl)-1H-pyrazolo[3,4-b]pyridine-5-carboxamide |
| 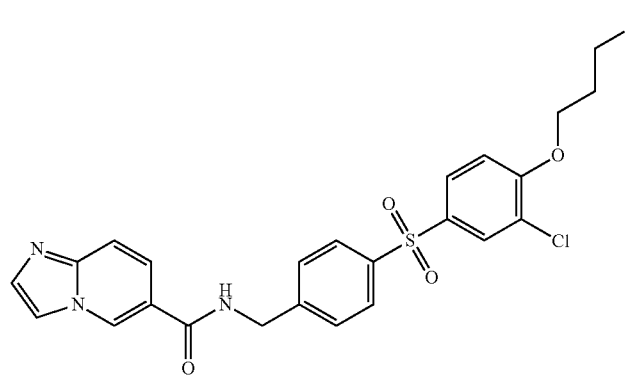 | N-({4-[(4-butoxy-3-chlorobenzene)sulfonyl]phenyl}methyl)imidazo[1,2-a]pyridine-6-carboxamide |
| 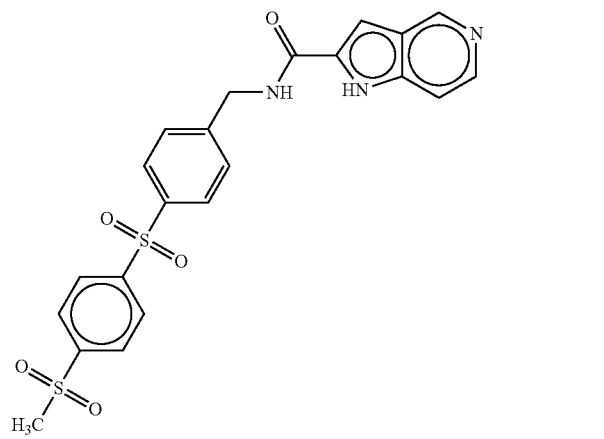 | N-({4-[(4-methanesulfonylbenzene)sulfonyl]phenyl}methyl)-1H-pyrrolo[3,2-c]pyridine-2-carboxamide |
| 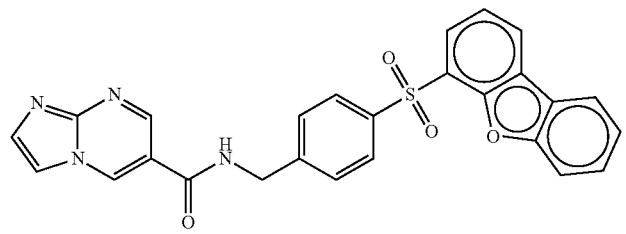 | N-[(4-{8-oxatricyclo[7.4.0.0²,□]trideca-1(13),2,4,6,9,11-hexaene-6-sulfonyl}phenyl)methyl]imidazo[1,2-a]pyrimidine-6-carboxamide |

| | |
|---|---|
| 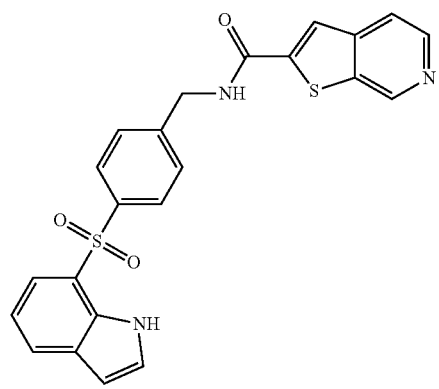 | N-{[4-(1H-indole-7-sulfonyl)phenyl]methyl}thieno[2,3-c]pyridine-2-carboxamide |
| 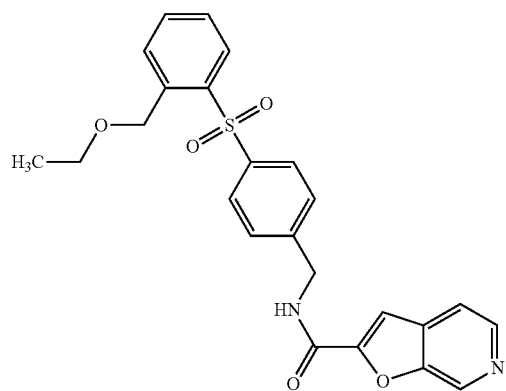 [SMILES: CCOCc1ccccc1S(=O)(=O)c1ccc(CNC(=O)c2cc3ccncc3o2)cc1] | N-[(4-{[2-(ethoxymethyl)benzene]sulfonyl}phenyl)methyl]furo[2,3-c]pyridine-2-carboxamide |
| 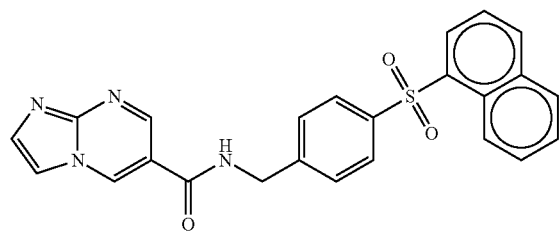 | N-{[4-(naphthalene-1-sulfonyl)phenyl]methyl}imidazo[1,2-a]pyrimidine-6-carboxamide |
| 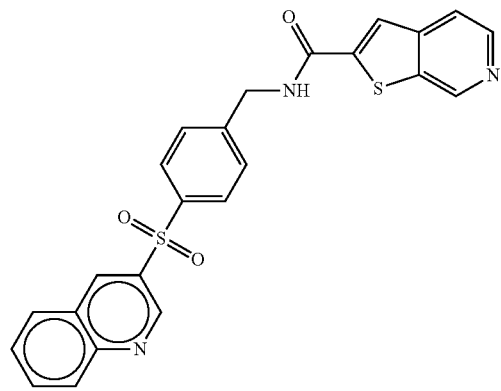 | N-{[4-(quinoline-3-sulfonyl)phenyl]methyl}thieno[2,3-c]pyridine-2-carboxamide |

TABLE 2-continued
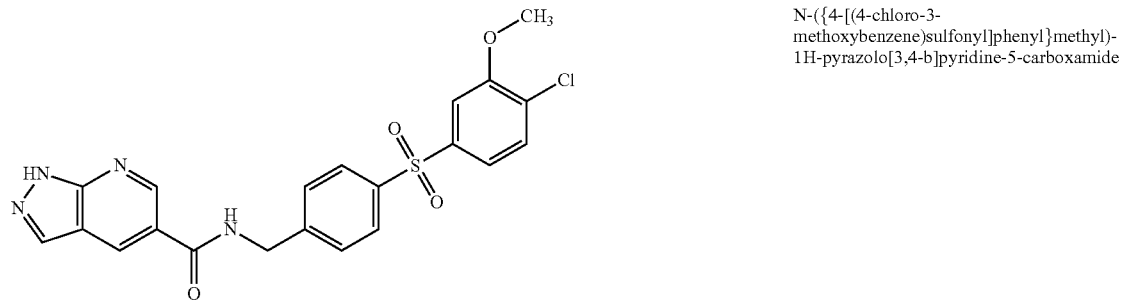
N-({4-[(4-chloro-3-methoxybenzene)sulfonyl]phenyl}methyl)-1H-pyrazolo[3,4-b]pyridine-5-carboxamide
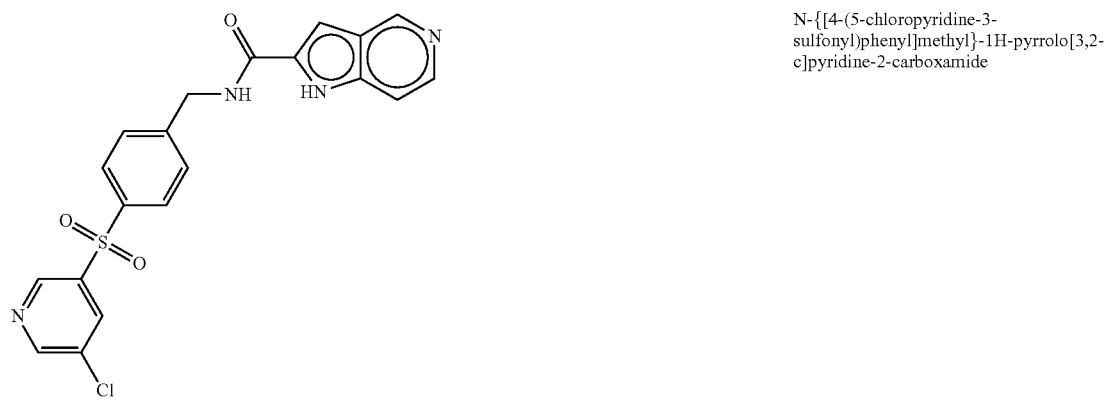
N-{[4-(5-chloropyridine-3-sulfonyl)phenyl]methyl}-1H-pyrrolo[3,2-c]pyridine-2-carboxamide
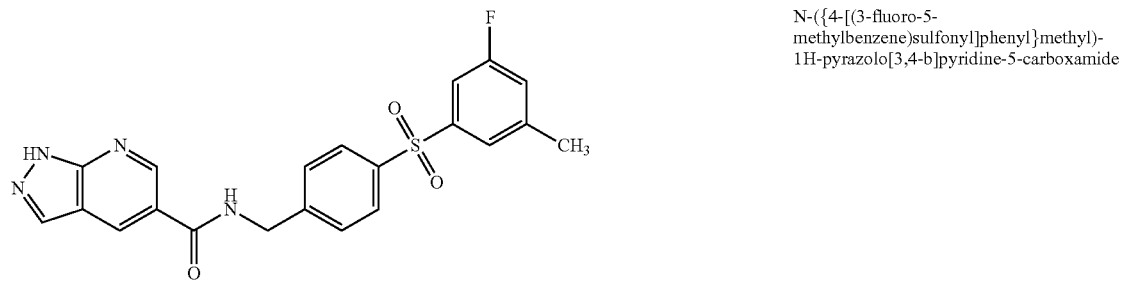
N-({4-[(3-fluoro-5-methylbenzene)sulfonyl]phenyl}methyl)-1H-pyrazolo[3,4-b]pyridine-5-carboxamide
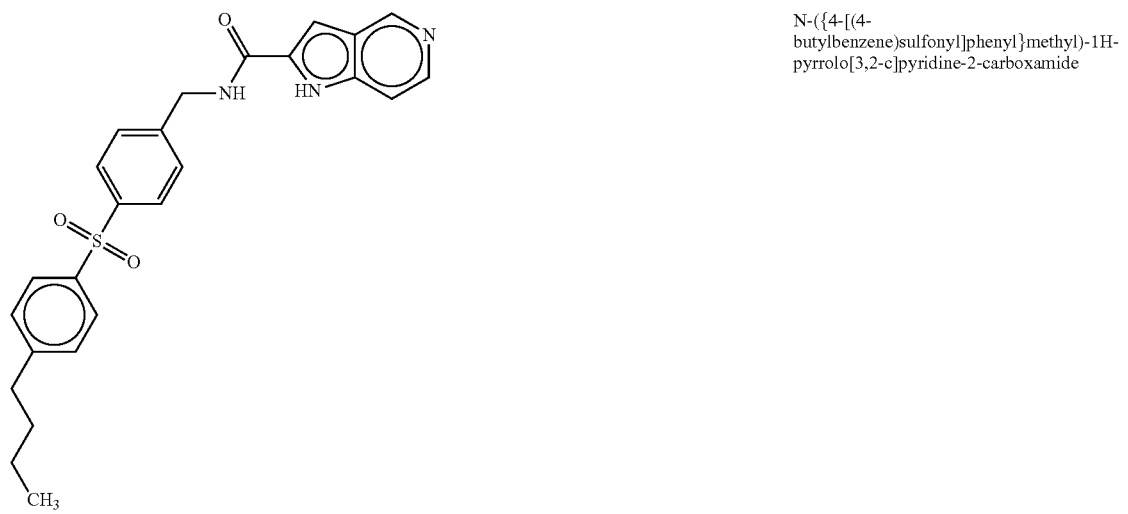
N-({4-[(4-butylbenzene)sulfonyl]phenyl}methyl)-1H-pyrrolo[3,2-c]pyridine-2-carboxamide TABLE 2-continued
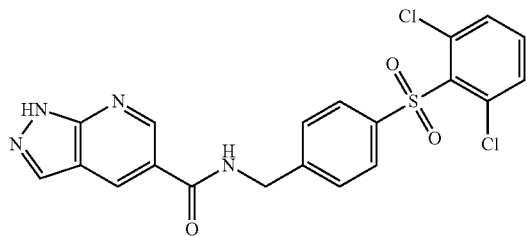 [SMILES: O=C(NCc1ccc(S(=O)(=O)c2c(Cl)cccc2Cl)cc1)c1cnc2[nH]ncc2c1]
N-({4-[(2,6-dichlorobenzene)sulfonyl]phenyl}methyl)-1H-pyrazolo[3,4-b]pyridine-5-carboxamide
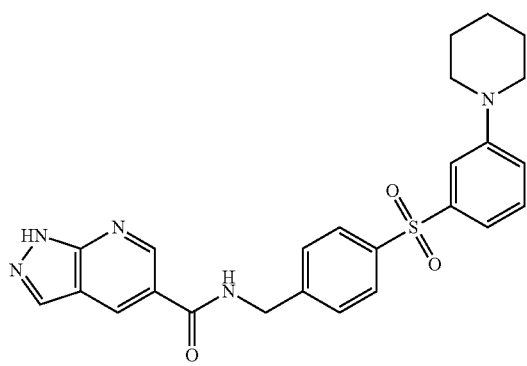 [SMILES: O=C(NCc1ccc(S(=O)(=O)c2cccc(N3CCCCC3)c2)cc1)c1cnc2[nH]ncc2c1]
N-[(4-{[3-(piperidin-1-yl)benzene]sulfonyl}phenyl)methyl]-1H-pyrazolo[3,4-b]pyridine-5-carboxamide
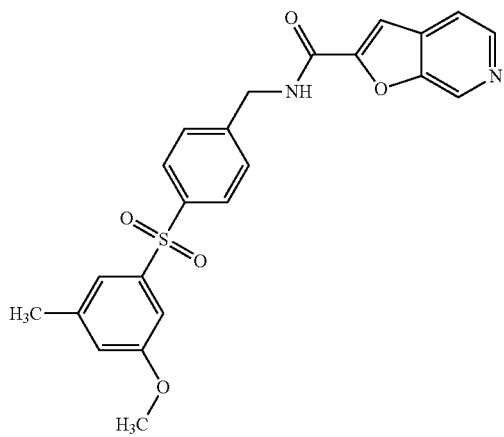 [SMILES: COc1cc(C)cc(S(=O)(=O)c2ccc(CNC(=O)c3cc4ccncc4o3)cc2)c1]
N-({4-[(3-methoxy-5-methylbenzene)sulfonyl]phenyl}methyl)furo[2,3-c]pyridine-2-carboxamide
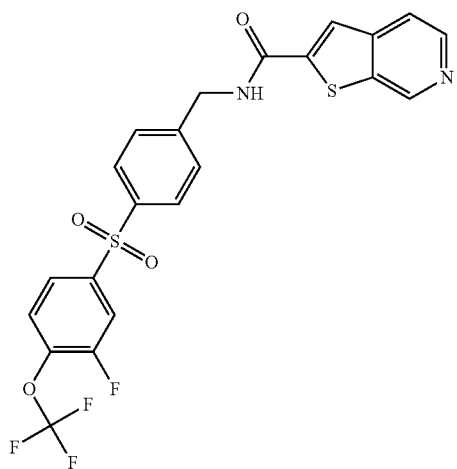 [SMILES: O=C(NCc1ccc(S(=O)(=O)c2ccc(OC(F)(F)F)c(F)c2)cc1)c1cc2ccncc2s1]
N-[(4-{[3-fluoro-4-(trifluoromethoxy)benzene]sulfonyl}phenyl)methyl]thieno[2,3-c]pyridine-2-carboxamide TABLE 2-continued
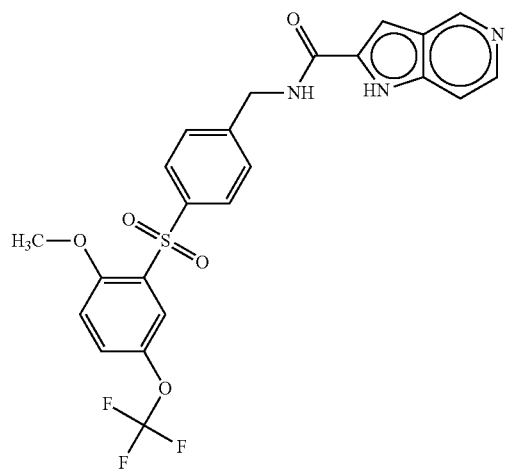
N-[(4-{[2-methoxy-5-(trifluoromethoxy)benzene]sulfonyl}phenyl)methyl]-1H-pyrrolo[3,2-c]pyridine-2-carboxamide
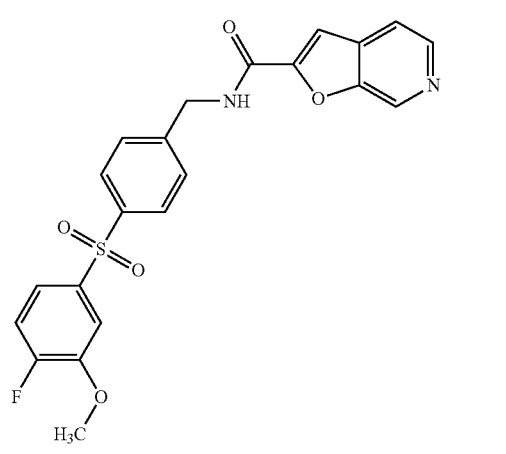
N-({4-[(4-fluoro-3-methoxybenzene)sulfonyl]phenyl}methyl)furo[2,3-c]pyridine-2-carboxamide
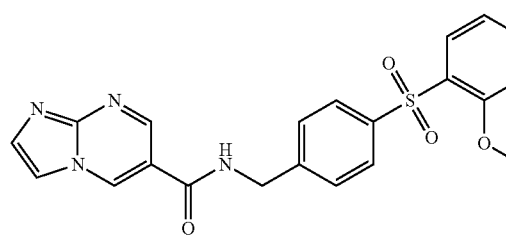
N-{[4-(phenoxathiine-4-sulfonyl)phenyl]methyl}imidazo[1,2-a]pyrimidine-6-carboxamide
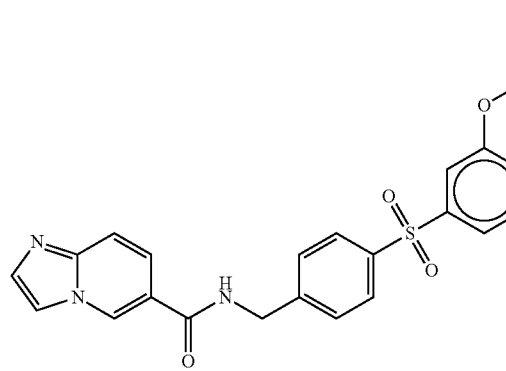
N-[(4-{[3-(4-fluorophenoxy)benzene]sulfonyl}phenyl)methyl]imidazo[1,2-a]pyridine-6-carboxamide

| | |
|---|---|
| 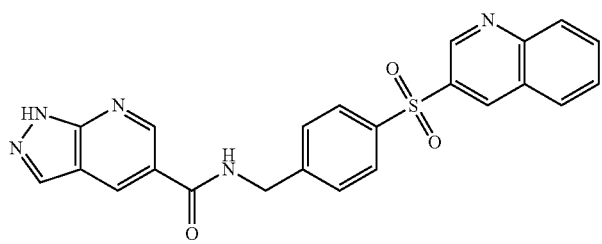 [SMILES: O=C(NCc1ccc(S(=O)(=O)c2cnc3ccccc3c2)cc1)c1cnc2[nH]ncc2c1] | N-{[4-(quinoline-3-sulfonyl)phenyl]methyl}-1H-pyrazolo[3,4-b]pyridine-5-carboxamide |
| 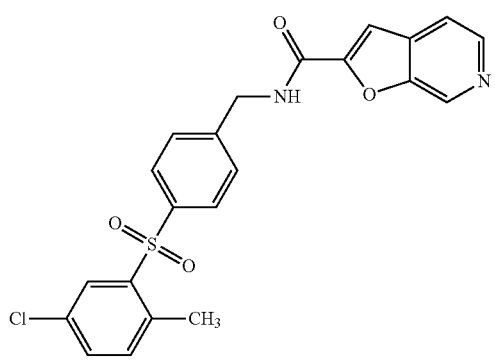 [SMILES: Cc1ccc(Cl)cc1S(=O)(=O)c1ccc(CNC(=O)c2cc3ccncc3o2)cc1] | N-({4-[(5-chloro-2-methylbenzene)sulfonyl]phenyl}methyl)furo[2,3-c]pyridine-2-carboxamide |
| 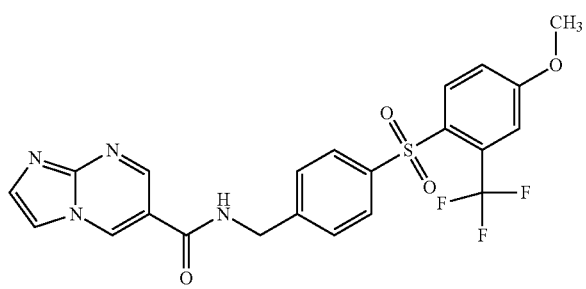 [SMILES: COc1ccc(S(=O)(=O)c2ccc(CNC(=O)c3cnc4nccn4c3)cc2)c(C(F)(F)F)c1] | N-[(4-{[4-methoxy-2-(trifluoromethyl)benzene]sulfonyl}phenyl)methyl]imidazo[1,2-a]pyrimidine-6-carboxamide |
| 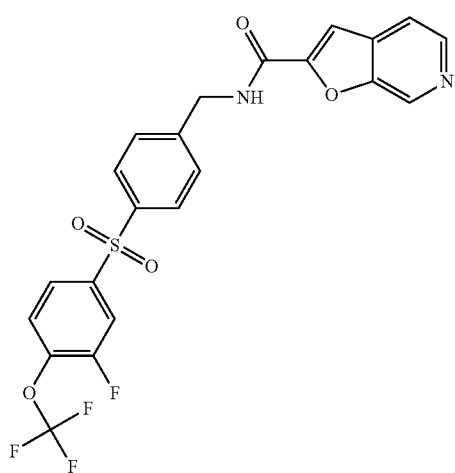 [SMILES: O=C(NCc1ccc(S(=O)(=O)c2ccc(OC(F)(F)F)c(F)c2)cc1)c1cc2ccncc2o1] | N-[(4-{[3-fluoro-4-(trifluoromethoxy)benzene]sulfonyl}phenyl)methyl]furo[2,3-c]pyridine-2-carboxamide |

TABLE 2-continued
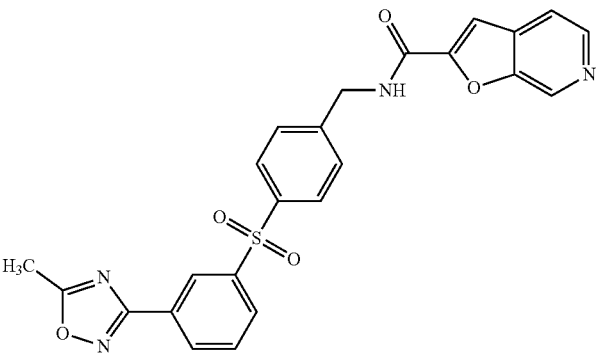
N-[(4-{[3-(5-methyl-1,2,4-oxadiazol-3-yl)benzene]sulfonyl}phenyl)methyl]furo[2,3-c]pyridine-2-carboxamide
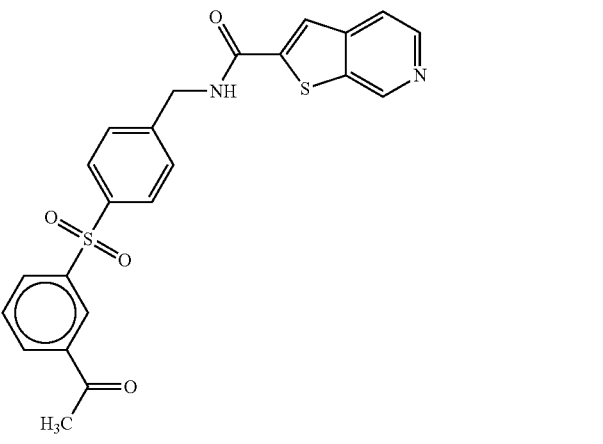
N-({4-[(3-acetylbenzene)sulfonyl]phenyl}methyl)thieno[2,3-c]pyridine-2-carboxamide
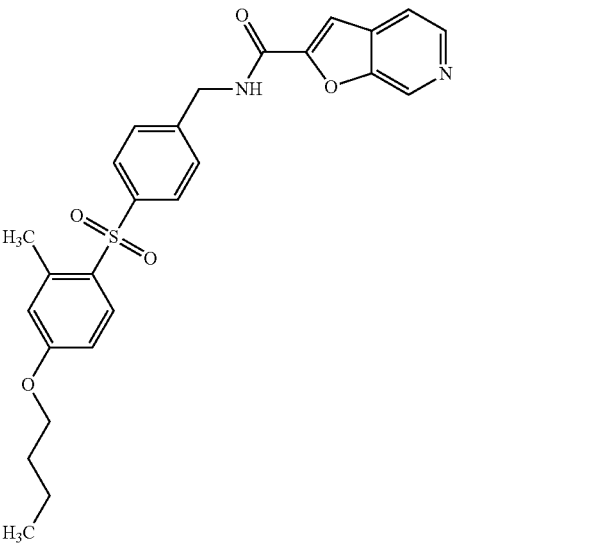 [SMILES: CCCCOc1ccc(S(=O)(=O)c2ccc(CNC(=O)c3cc4ccncc4o3)cc2)c(C)c1]
N-({4-[(4-butoxy-2-methylbenzene)sulfonyl]phenyl}methyl)furo[2,3-c]pyridine-2-carboxamide
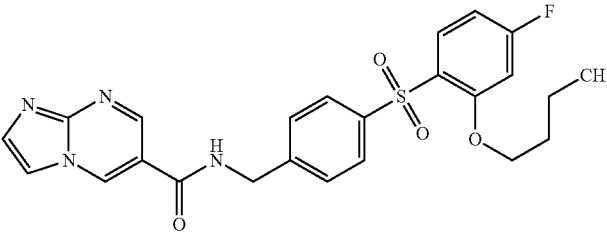
N-({4-[(2-butoxy-4-fluorobenzene)sulfonyl]phenyl}methyl)imidazo[1,2-a]pyrimidine-6-carboxamide TABLE 2-continued
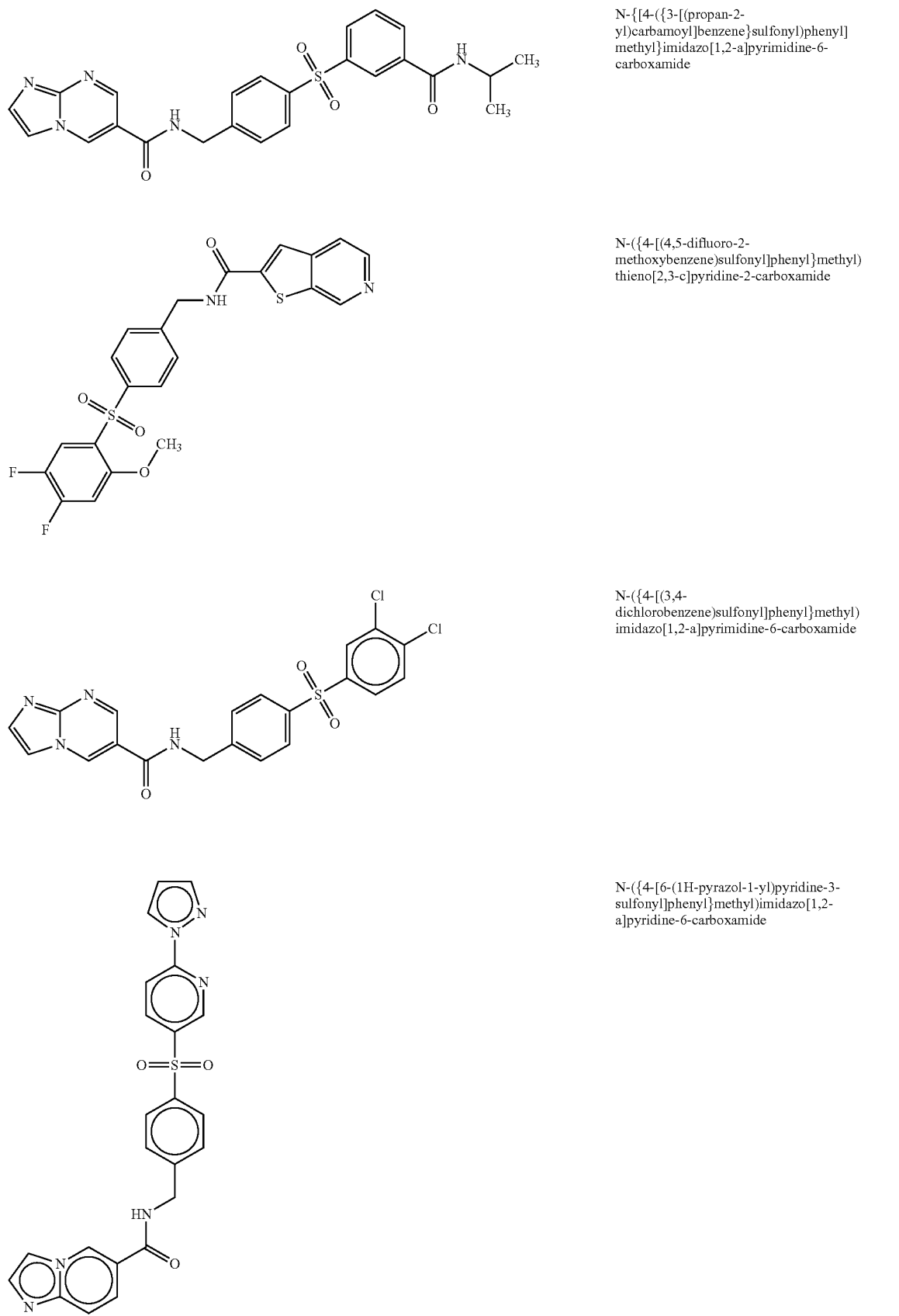
N-{[4-({3-[(propan-2-yl)carbamoyl]benzene}sulfonyl)phenyl]methyl}imidazo[1,2-a]pyrimidine-6-carboxamide
N-({4-[(4,5-difluoro-2-methoxybenzene)sulfonyl]phenyl}methyl)thieno[2,3-c]pyridine-2-carboxamide
N-({4-[(3,4-dichlorobenzene)sulfonyl]phenyl}methyl)imidazo[1,2-a]pyrimidine-6-carboxamide
N-({4-[6-(1H-pyrazol-1-yl)pyridine-3-sulfonyl]phenyl}methyl)imidazo[1,2-a]pyridine-6-carboxamide TABLE 2-continued
| | |
|---|---|
| 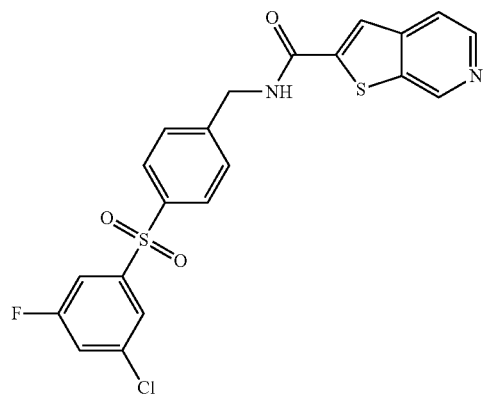 [SMILES: O=C(NCc1ccc(S(=O)(=O)c2cc(F)cc(Cl)c2)cc1)c1cc2ccncc2s1] | N-({4-[(3-chloro-5-fluorobenzene)sulfonyl]phenyl}methyl)thieno[2,3-c]pyridine-2-carboxamide |
| 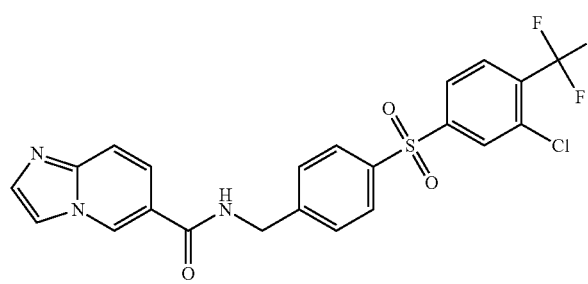 | N-[(4-{[3-chloro-4-(trifluoromethyl)benzene]sulfonyl}phenyl)methyl]imidazo[1,2-a]pyridine-6-carboxamide |
| 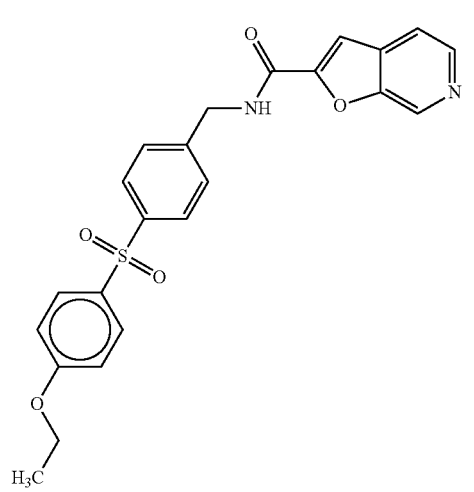 | N-({4-[(4-ethoxybenzene)sulfonyl]phenyl}methyl)furo[2,3-c]pyridine-2-carboxamide |
| 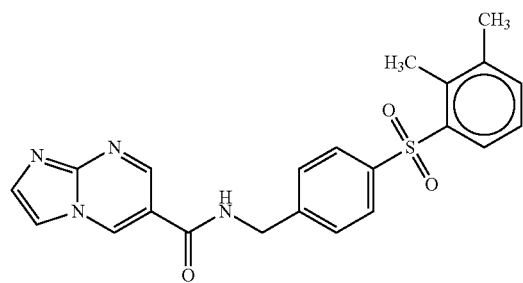 | N-({4-[(2,3-dimethylbenzene)sulfonyl]phenyl}methyl)imidazo[1,2-a]pyrimidine-6-carboxamide |

TABLE 2-continued
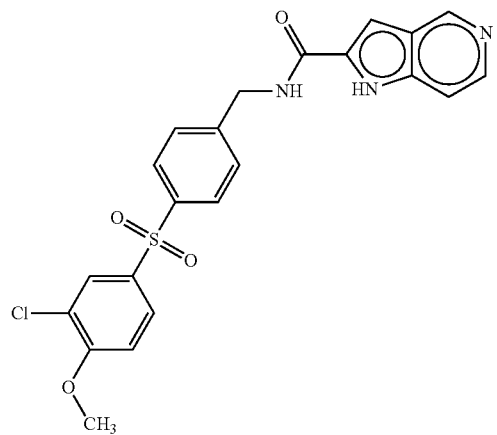
N-({4-[(3-chloro-4-methoxybenzene)sulfonyl]phenyl}methyl)-1H-pyrrolo[3,2-c]pyridine-2-carboxamide
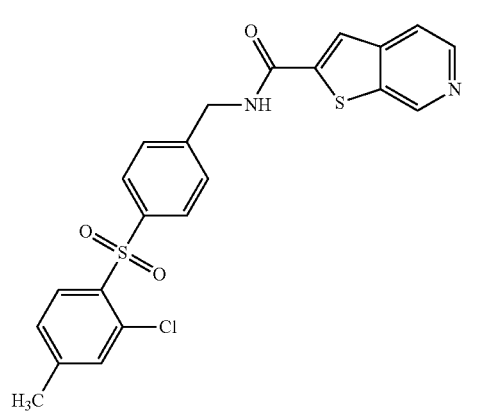 [SMILES: Cc1ccc(S(=O)(=O)c2ccc(CNC(=O)c3cc4ccncc4s3)cc2)c(Cl)c1]
N-({4-[(2-chloro-4-methylbenzene)sulfonyl]phenyl}methyl)thieno[2,3-c]pyridine-2-carboxamide
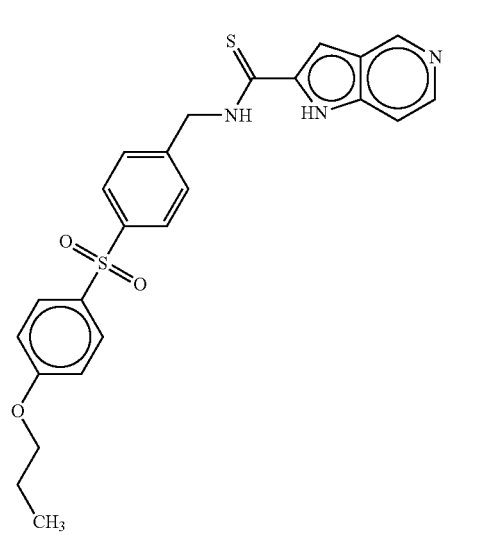
N-({4-[(4-propoxybenzene)sulfonyl]phenyl}methyl)-1H-pyrrolo[3,2-c]pyridine-2-carboxamide
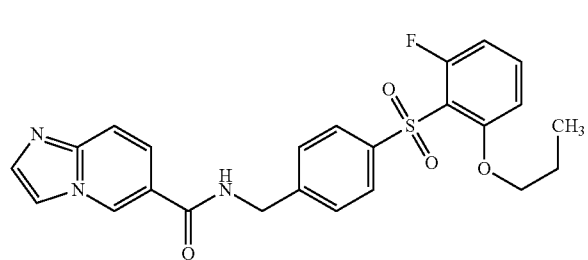
N-({4-[(2-fluoro-6-propoxybenzene)sulfonyl]phenyl}methyl)imidazo[1,2-a]pyridine-6-carboxamide TABLE 2-continued
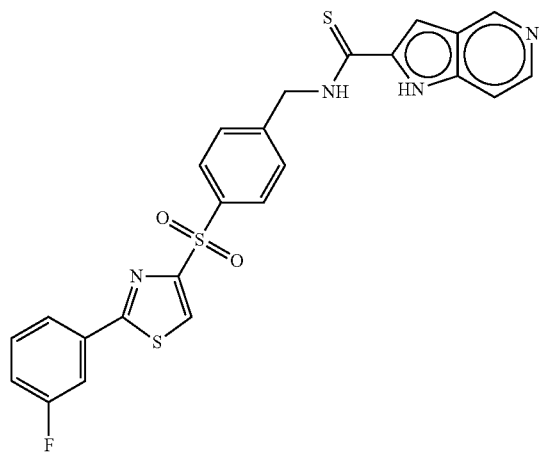
N-({4-[2-(3-fluorophenyl)-1,3-thiazole-4-sulfonyl]phenyl}methyl)-1H-pyrrolo[3,2-c]pyridine-2-carboxamide
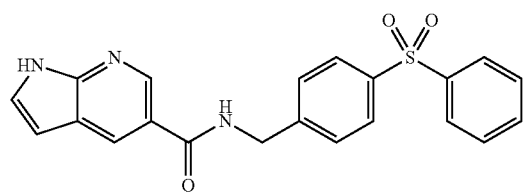 [SMILES: O=C(NCc1ccc(S(=O)(=O)c2ccccc2)cc1)c1cnc2[nH]ccc2c1]
N-{[4-(benzenesulfonyl)phenyl]methyl}-1H-pyrrolo[2,3-b]pyridine-5-carboxamide
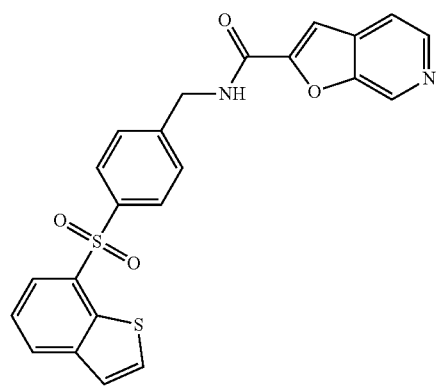 [SMILES: O=C(NCc1ccc(S(=O)(=O)c2cccc3ccsc23)cc1)c1cc2ccncc2o1]
N-{[4-(1-benzothiophene-7-sulfonyl)phenyl]methyl}furo[2,3-c]pyridine-2-carboxamide
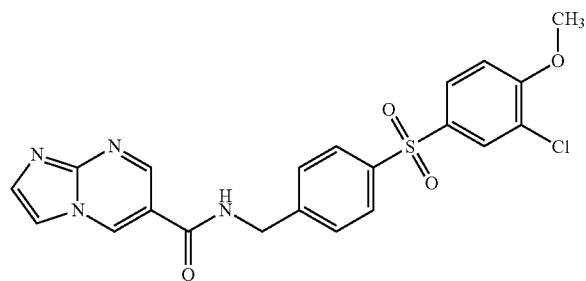 [SMILES: COc1ccc(S(=O)(=O)c2ccc(CNC(=O)c3cnc4nccn4c3)cc2)cc1Cl]
N-({4-[(3-chloro-4-methoxybenzene)sulfonyl]phenyl}methyl)imidazo[1,2-a]pyrimidine-6-carboxamide TABLE 2-continued
| | |
|---|---|
| 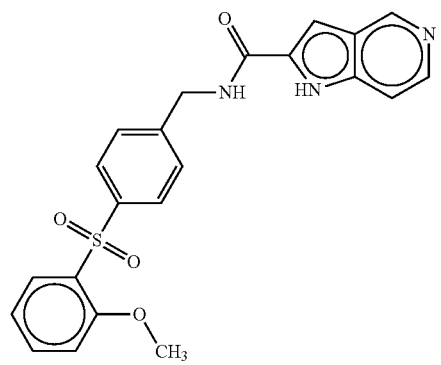 | N-({4-[(2-methoxybenzene)sulfonyl]phenyl}methyl)-1H-pyrrolo[3,2-c]pyridine-2-carboxamide |
| 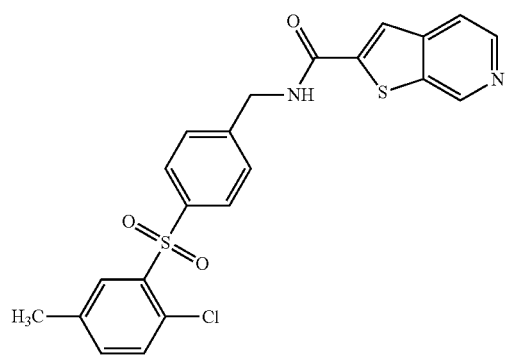 [SMILES: Cc1ccc(Cl)c(S(=O)(=O)c2ccc(CNC(=O)c3cc4ccncc4s3)cc2)c1] | N-({4-[(2-chloro-5-methylbenzene)sulfonyl]phenyl}methyl)thieno[2,3-c]pyridine-2-carboxamide |
| 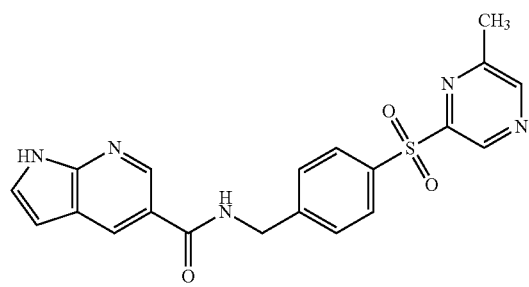 [SMILES: Cc1cncc(S(=O)(=O)c2ccc(CNC(=O)c3cnc4[nH]ccc4c3)cc2)n1] | N-{[4-(6-methylpyrazine-2-sulfonyl)phenyl]methyl}-1H-pyrazolo[3,4-b]pyridine-5-carboxamide |
| 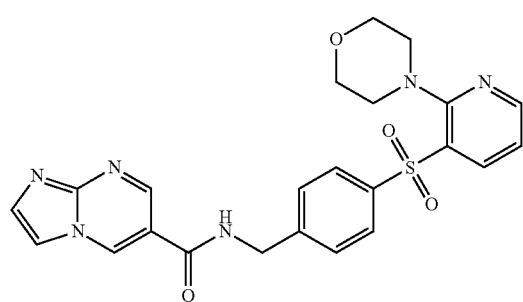 [SMILES: O=C(NCc1ccc(S(=O)(=O)c2cccnc2N2CCOCC2)cc1)c1cnc2nccn2c1] | N-({4-[2-(morpholin-4-yl)pyridine-3-sulfonyl]phenyl}methyl)imidazo[1,2-a]pyrimidine-6-carboxamide |

TABLE 2-continued
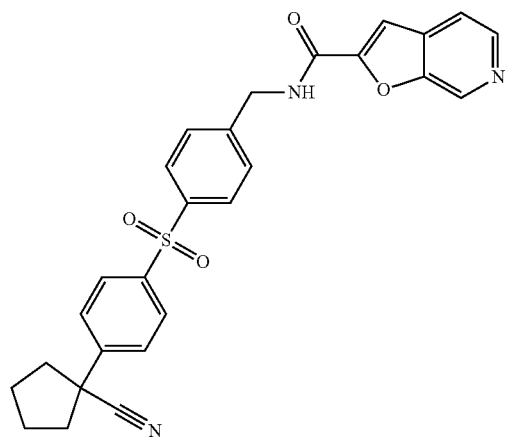 [SMILES: N#CC1(c2ccc(S(=O)(=O)c3ccc(CNC(=O)c4cc5ccncc5o4)cc3)cc2)CCCC1]
N-[(4-{[4-(1-cyanocyclopentyl)benzene]sulfonyl}phenyl)methyl]furo[2,3-c]pyridine-2-carboxamide
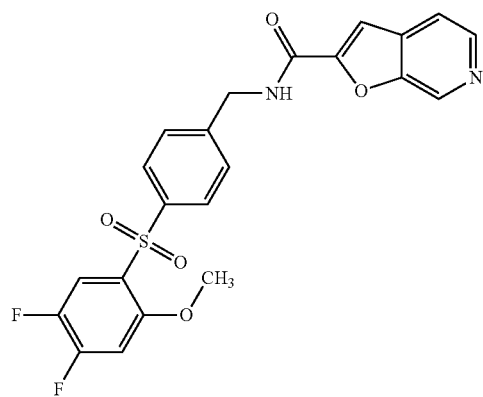
N-({4-[(4,5-difluoro-2-methoxybenzene)sulfonyl]phenyl}methyl)furo[2,3-c]pyridine-2-carboxamide
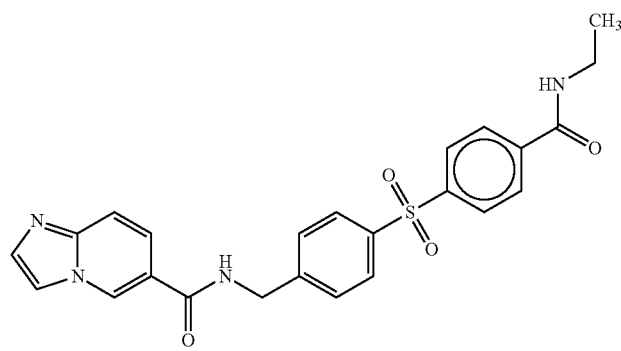
N-[(4-{[4-(ethylcarbamoyl)benzene]sulfonyl}phenyl)methyl]imidazo[1,2-a]pyridine-6-carboxamide
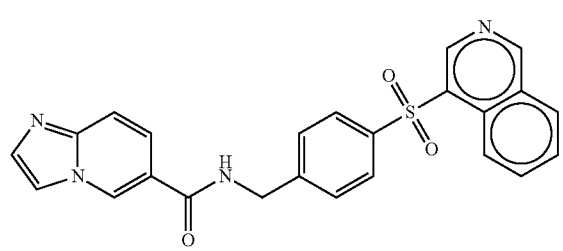
N-{[4-(isoquinoline-4-sulfonyl)phenyl]methyl}imidazo[1,2-a]pyridine-6-carboxamide TABLE 2-continued

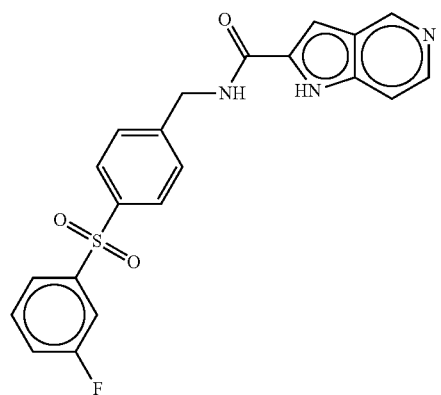 N-({4-[(3-fluorobenzene)sulfonyl]phenyl}methyl)-1H-pyrrolo[3,2-c]pyridine-2-carboxamide

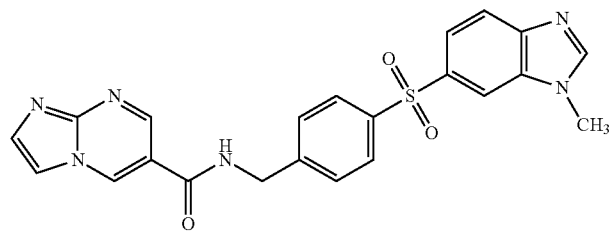 N-{[4-(1-methyl-1H-1,3-benzodiazole-6-sulfonyl)phenyl]methyl}imidazo[1,2-a]pyrimidine-6-carboxamide

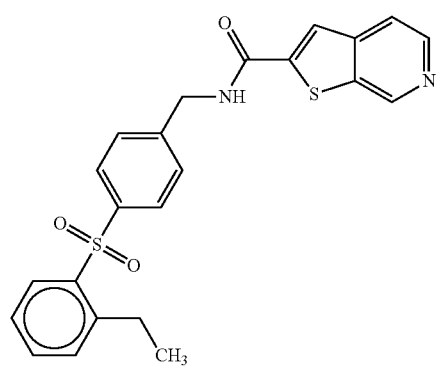 N-({4-[(2-ethylbenzene)sulfonyl]phenyl}methyl)thieno[2,3-c]pyridine-2-carboxamide

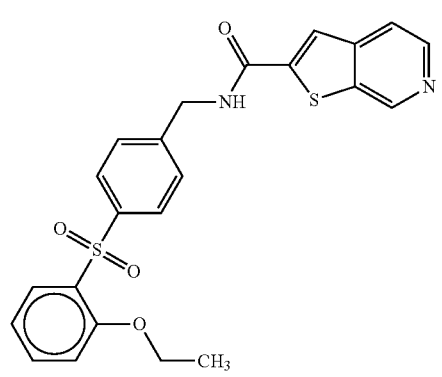 N-({4-[(2-ethoxybenzene)sulfonyl]phenyl}methyl)furo[2,3-c]pyridine-2-carboxamide

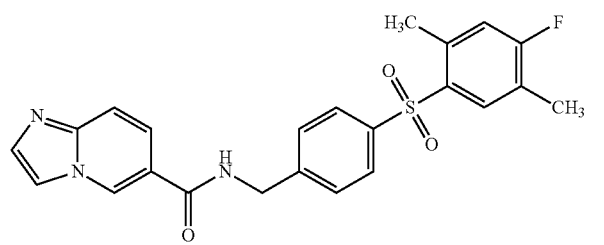 [SMILES: Cc1cc(S(=O)(=O)c2ccc(CNC(=O)c3ccc4nccn4c3)cc2)c(C)cc1F] N-({4-[(4-fluoro-2,5-dimethylbenzene)sulfonyl]phenyl}methyl)imidazo[1,2-a]pyridine-6-carboxamide TABLE 2-continued
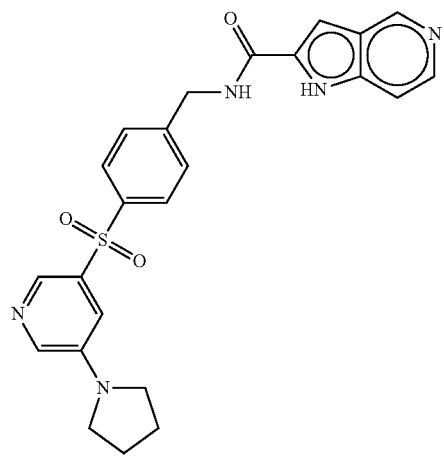
N-({4-[5-(pyrrolidin-1-yl)pyridine-3-sulfonyl]phenyl}methyl)-1H-pyrrolo[3,2-c]pyridine-2-carboxamide
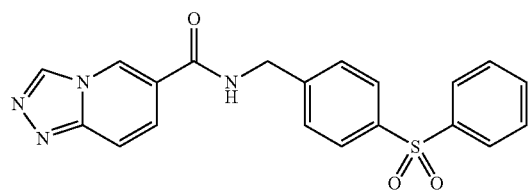 [SMILES: O=C(NCc1ccc(S(=O)(=O)c2ccccc2)cc1)c1ccc2nncn2c1]
N-{[4-(benzenesulfonyl)phenyl]methyl}-[1,2,4]triazolo[4,3-a]pyridine-6-carboxamide
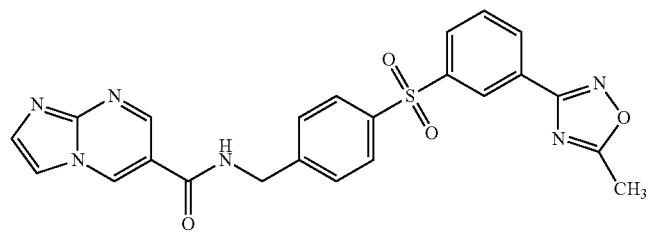 [SMILES: Cc1nc(-c2cccc(S(=O)(=O)c3ccc(CNC(=O)c4cnc5nccn5c4)cc3)c2)no1]
N-[(4-{[3-(5-methyl-1,2,4-oxadiazol-3-yl)benzene]sulfonyl}phenyl)methyl]imidazo[1,2-a]pyrimidine-6-carboxamide
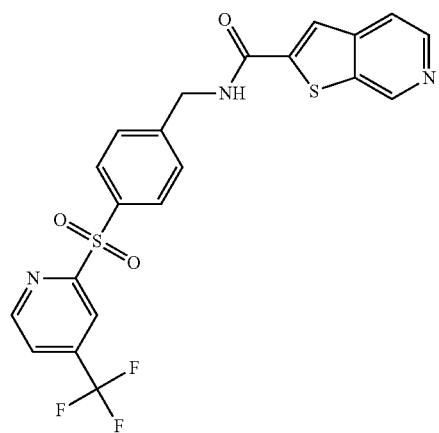
N-({4-[4-(trifluoromethyl)pyridine-2-sulfonyl]phenyl}methyl)thieno[2,3-c]pyridine-2-carboxamide TABLE 2-continued
| | |
|---|---|
| 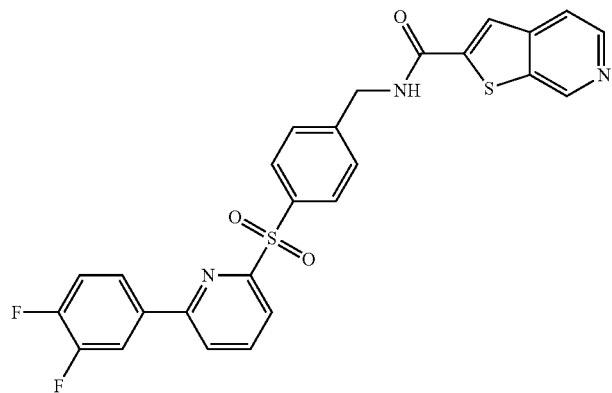 [SMILES: O=C(NCc1ccc(S(=O)(=O)c2cccc(-c3ccc(F)c(F)c3)n2)cc1)c1cc2ccncc2s1] | N-({4-[6-(3,4-difluorophenyl)pyridine-2-sulfonyl]phenyl}methyl)thieno[2,3-c]pyridine-2-carboxamide |
| 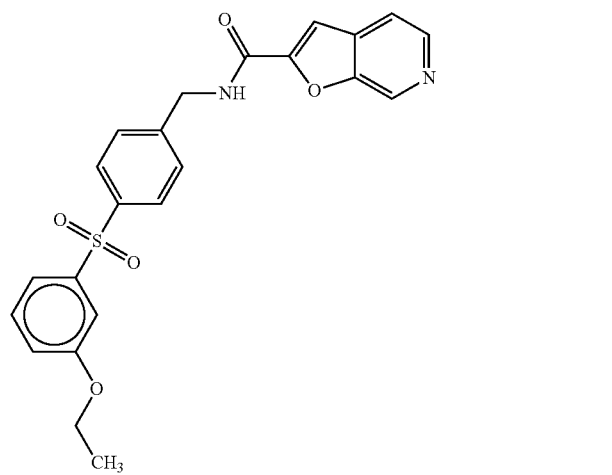 | N-({4-[(3-ethoxybenzene)sulfonyl]phenyl}methyl)furo[2,3-c]pyridine-2-carboxamide |
| 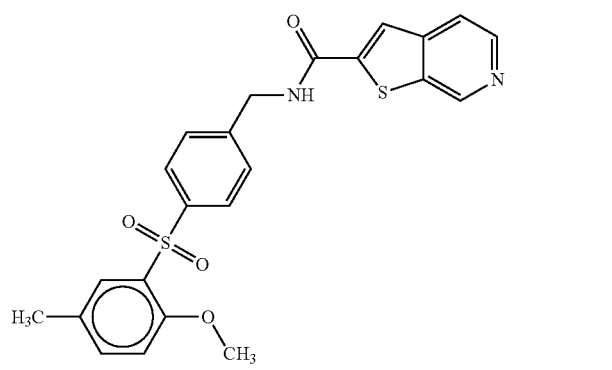 | N-({4-[(2-methoxy-5-methylbenzene)sulfonyl]phenyl}methyl)furo[2,3-c]pyridine-2-carboxamide |
| 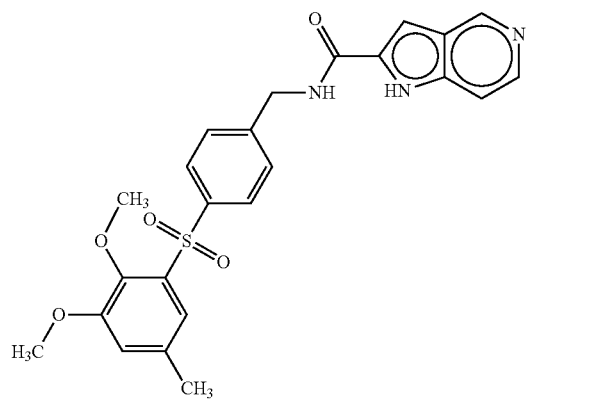 | N-({4-[(2,3-dimethoxy-5-methylbenzene)sulfonyl]phenyl}methyl)-1H-pyrrolo[3,2-c]pyridine-2-carboxamide |

TABLE 2-continued
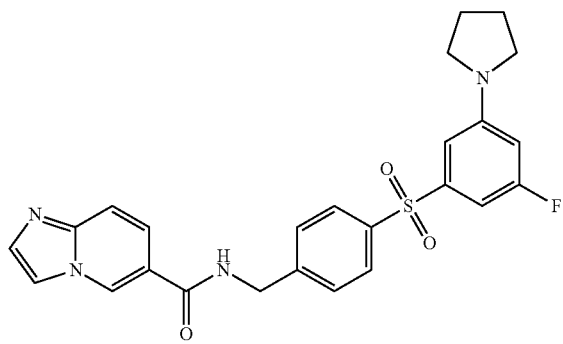 [SMILES: O=C(NCc1ccc(S(=O)(=O)c2cc(F)cc(N3CCCC3)c2)cc1)c1ccc2nccn2c1]
N-[(4-{[3-fluoro-5-(pyrrolidin-1-yl)benzene]sulfonyl}phenyl)methyl]imidazo[1,2-a]pyridine-6-carboxamide
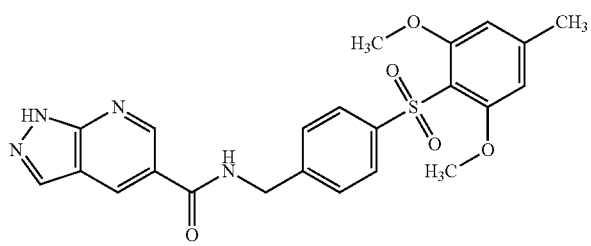 [SMILES: COc1cc(C)cc(OC)c1S(=O)(=O)c1ccc(CNC(=O)c2cnc3[nH]ncc3c2)cc1]
N-({4-[(2,6-dimethoxy-4-methylbenzene)sulfonyl]phenyl}methyl)-1H-pyrazolo[3,4-b]pyridine-5-carboxamide
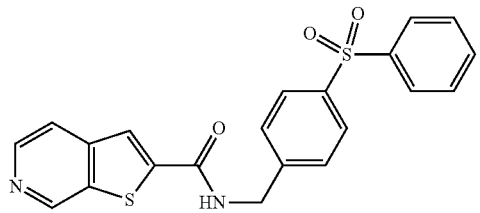 [SMILES: O=C(NCc1ccc(S(=O)(=O)c2ccccc2)cc1)c1cc2ccncc2s1]
N-{[4-(benzenesulfony])phenyl]methyl}thieno[2,3-c]pyridine-2-carboxamide
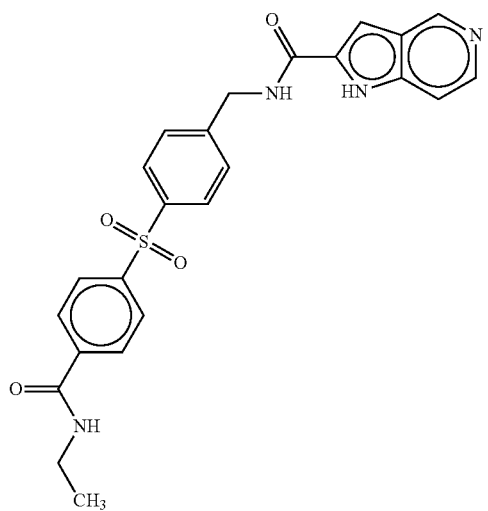
N-[(4-{[4-(ethylcarbamoyl)benzene]sulfonyl}phenyl)methyl]-1H-pyrrolo[3,2-c]pyridine-2-carboxamide TABLE 2-continued

| Structure | Name |
|---|---|
| 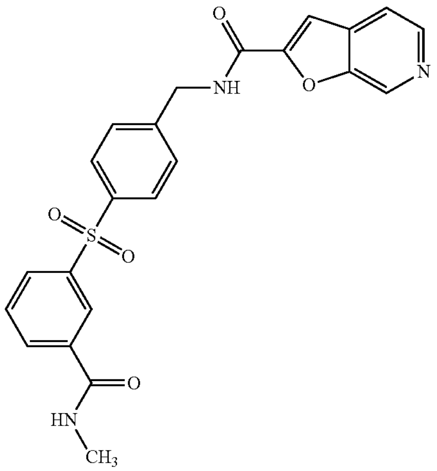 [SMILES: CNC(=O)c1cccc(S(=O)(=O)c2ccc(CNC(=O)c3cc4ccncc4o3)cc2)c1] | N-[(4-{[3-(methylcarbamoyl)benzene]sulfonyl}phenyl)methyl]furo[2,3-c]pyridine-2-carboxamide |
| 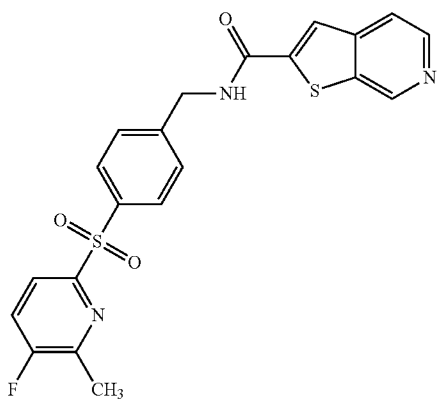 | N-{[4-(5-fluoro-6-methylpyridine-2-sulfonyl)phenyl]methyl}thieno[2,3-c]pyridine-2-carboxamide |
| 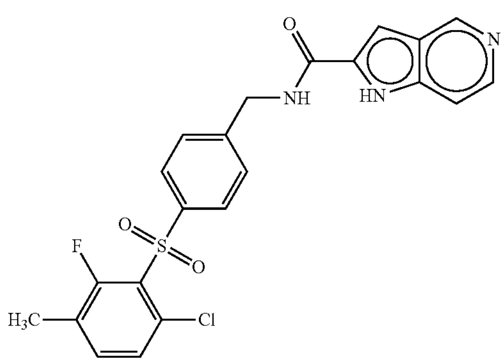 | N-({4-[(6-chloro-2-fluoro-3-methylbenzene)sulfonyl]phenyl}methyl)-1H-pyrrolo[3,2-c]pyridine-2-carboxamide |
| 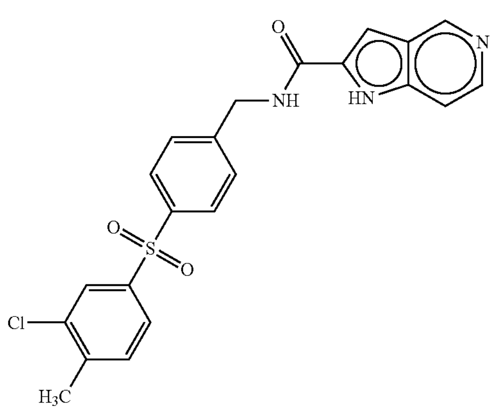 | N-({4-[(3-chloro-4-methylbenzene)sulfonyl]phenyl}methyl)-1H-pyrrolo[3,2-c]pyridine-2-carboxamide |

TABLE 2-continued

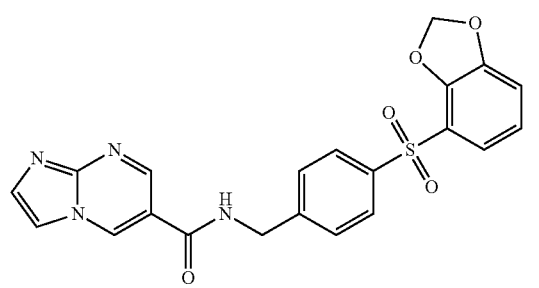 [SMILES: O=C(NCc1ccc(S(=O)(=O)c2cccc3c2OCO3)cc1)c1cnc2nccn2c1]

N-{[4-(2H-1,3-benzodioxole-4-sulfonyl)phenyl]methyl}imidazo[1,2-a]pyrimidine-6-carboxamide

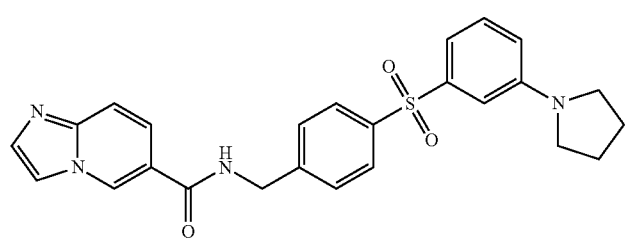 [SMILES: O=C(NCc1ccc(S(=O)(=O)c2cccc(N3CCCC3)c2)cc1)c1ccc2nccn2c1]

N-[(4-{[3-(pyrrolidin-1-yl)benzene]sulfonyl}phenyl)methyl]imidazo[1,2-a]pyridine-6-carboxamide

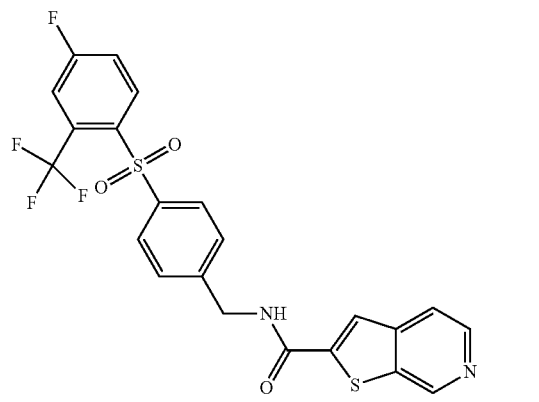 [SMILES: O=C(NCc1ccc(S(=O)(=O)c2ccc(F)cc2C(F)(F)F)cc1)c1cc2ccncc2s1]

N-[(4-{[4-fluoro-2-(trifluoromethyl)benzene]sulfonyl}phenyl)methyl]thieno[2,3-c]pyridine-2-carboxamide

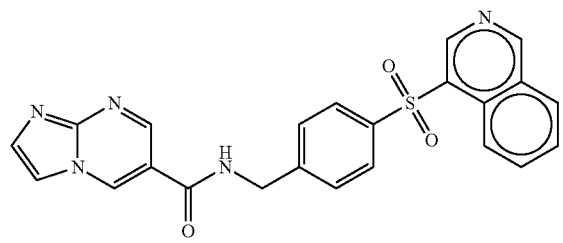

N-{[4-(isoquinoline-4-sulfonyl)phenyl]methyl}imidazo[1,2-a]pyrimidine-6-carboxamide

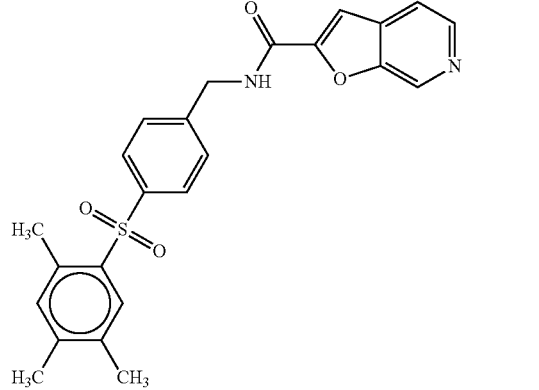

N-({4-[(2,4,5-trimethylbenzene)sulfonyl]phenyl}methyl)furo[2,3-c]pyridine-2-carboxamide TABLE 2-continued

| Structure | Name |
|---|---|
| | N-({4-[(2,4-dichloro-3-methoxybenzene)sulfonyl]phenyl}methyl)imidazo[1,2-a]pyrimidine-6-carboxamide |
| | (E)-2-cyano-3-({4-[(5-fluoro-2-methoxyphenyl)sulfamoyl]phenyl}methyl)-1-(pyridin-4-yl)guanidine |
| | N-[(4-{[2-fluoro-3-(propan-2-yloxy)benzene]sulfonyl}phenyl)methyl]thieno[2,3-c]pyridine-2-carboxamide |
| | N-({4-[(4-methoxy-3-methylbenzene)sulfonyl]phenyl}methyl)imidazo[1,2-a]pyrimidine-6-carboxamide |
| | N-({4-[6-(trifluoromethyl)pyridine-2-sulfonyl]phenyl}methyl)imidazo[1,2-a]pyrimidine-6-carboxamide |

TABLE 2-continued
| | |
|---|---|
| 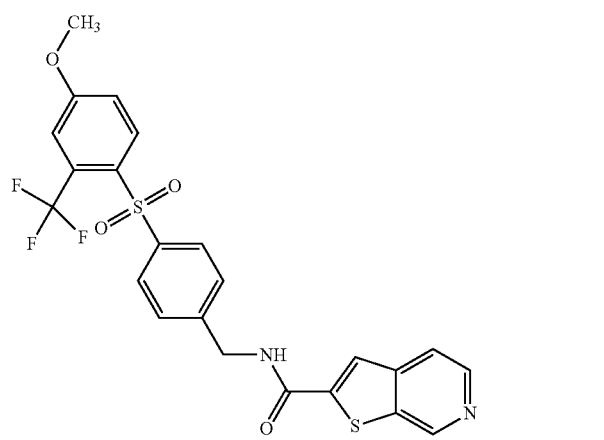 [SMILES: COc1ccc(S(=O)(=O)c2ccc(CNC(=O)c3cc4ccncc4s3)cc2)c(C(F)(F)F)c1] | N-[(4-{[4-methoxy-2-(trifluoromethyl)benzene]sulfonyl}phenyl)methyl]thieno[2,3-c]pyridine-2-carboxamide |
| 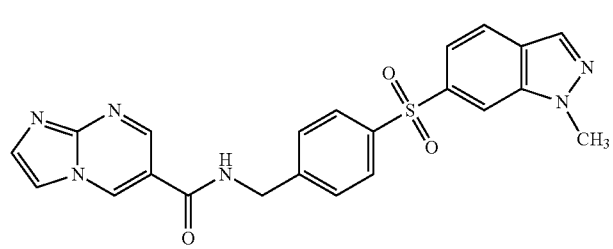 [SMILES: Cn1ncc2ccc(S(=O)(=O)c3ccc(CNC(=O)c4cnc5nccn5c4)cc3)cc21] | N-{[4-(1-methyl-1H-indazole-6-sulfonyl)phenyl]methyl}imidazo[1,2-a]pyrimidine-6-carboxamide |
| 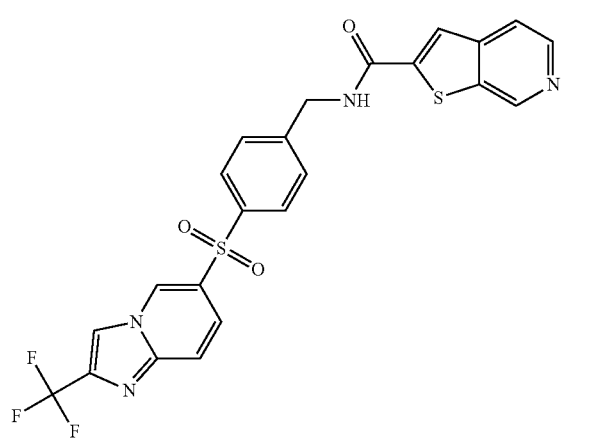 | N-({4-[2-(trifluoromethyl)imidazo[1,2-a]pyridine-6-sulfonyl]phenyl}methyl)thieno[2,3-c]pyridine-2-carboxamide |
| 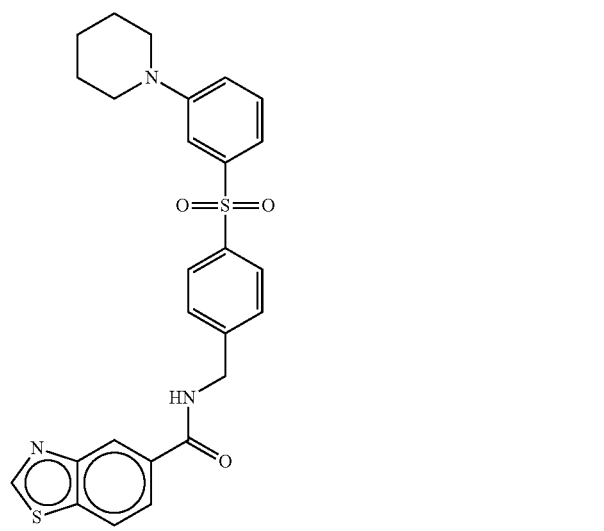 | N-[(4-{[3-(piperidin-1-yl)benzene]sulfonyl}phenyl)methyl]-1,3-benzothiazole-6-carboxamide |

TABLE 2-continued
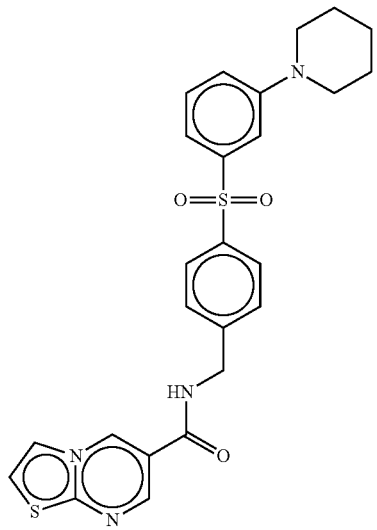
N-[(4-{[3-(piperidin-1-yl)benzene]sulfonyl}phenyl)methyl]imidazo[1,2-a]pyrimidine-6-carboxamide
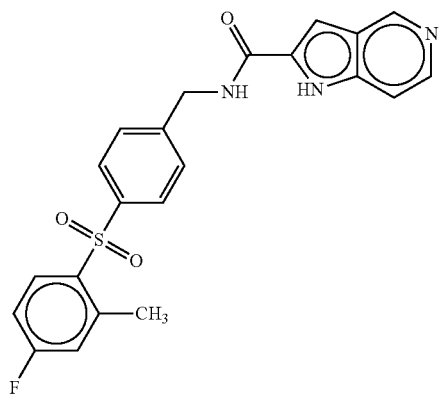
N-({4-[(4-fluoro-2-methylbenzene)sulfonyl]phenyl}methyl)-1H-pyrrolo[3,2-c]pyridine-2-carboxamide
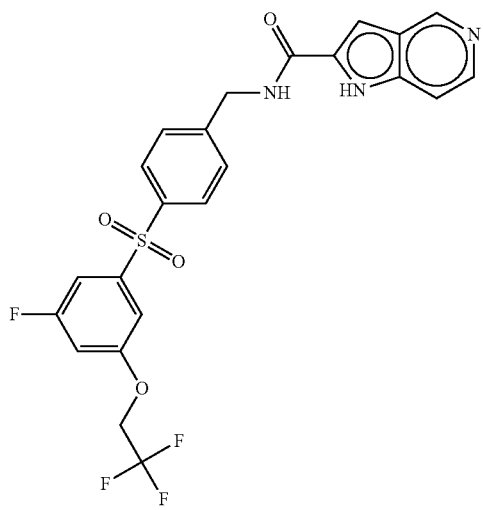
N-[(4-{[3-fluoro-5-(2,2,2-trifluoroethoxy)benzene]sulfonyl}phenyl)methyl]-1H-pyrrolo[3,2-c]pyridine-2-carboxamide
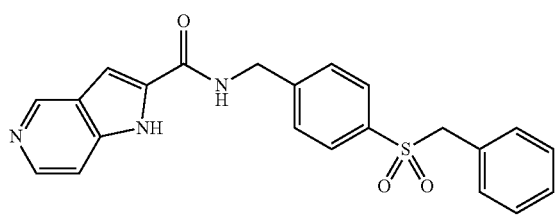 [SMILES: O=C(NCc1ccc(S(=O)(=O)Cc2ccccc2)cc1)c1cc2cnccc2[nH]1]
N-{[4-(phenylmethane)sulfonylphenyl]methyl}-1H-pyrrolo[3,2-c]pyridine-2-carboxamide TABLE 2-continued
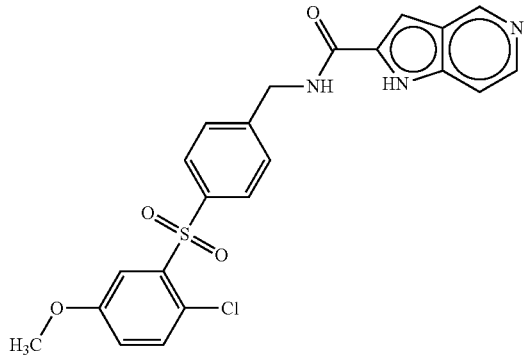
N-({4-[(2-chloro-5-methoxybenzene)sulfonyl]phenyl}methyl)-1H-pyrrolo[3,2-c]pyridine-2-carboxamide
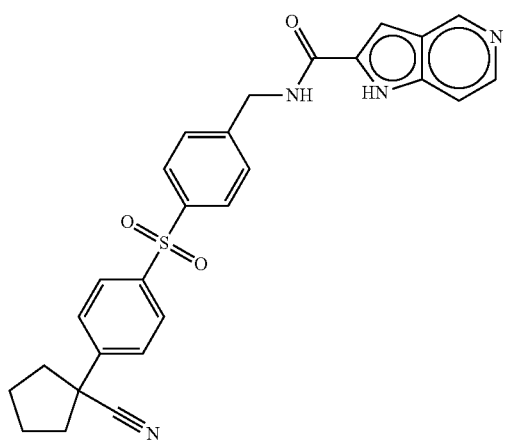
N-[(4-{[4-(1-cyanocyclopentyl)benzene]sulfonyl}phenyl)methyl]-1H-pyrrolo[3,2-c]pyridine-2-carboxamide
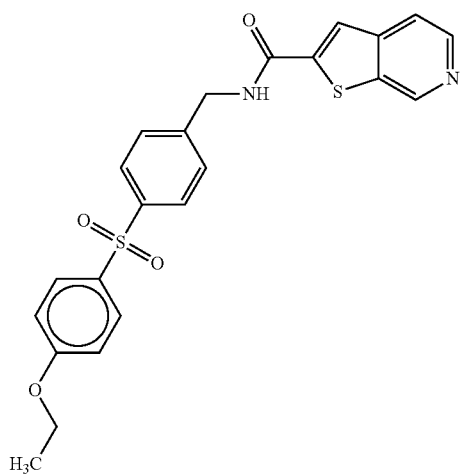
N-({4-[(4-ethoxybenzene)sulfonyl]phenyl}methyl)thieno[2,3-c]pyridine-2-carboxamide
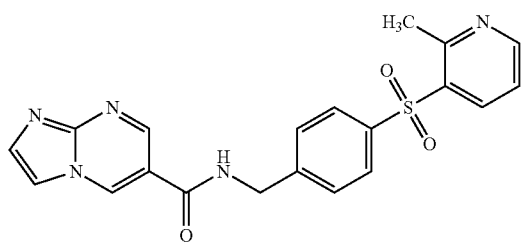 [SMILES: Cc1ncccc1S(=O)(=O)c1ccc(CNC(=O)c2cnc3nccn3c2)cc1]
N-{[4-(2-methylpyridine-3-sulfonyl)phenyl]methyl}imidazo[1,2-a]pyrimidine-6-carboxamide TABLE 2-continued

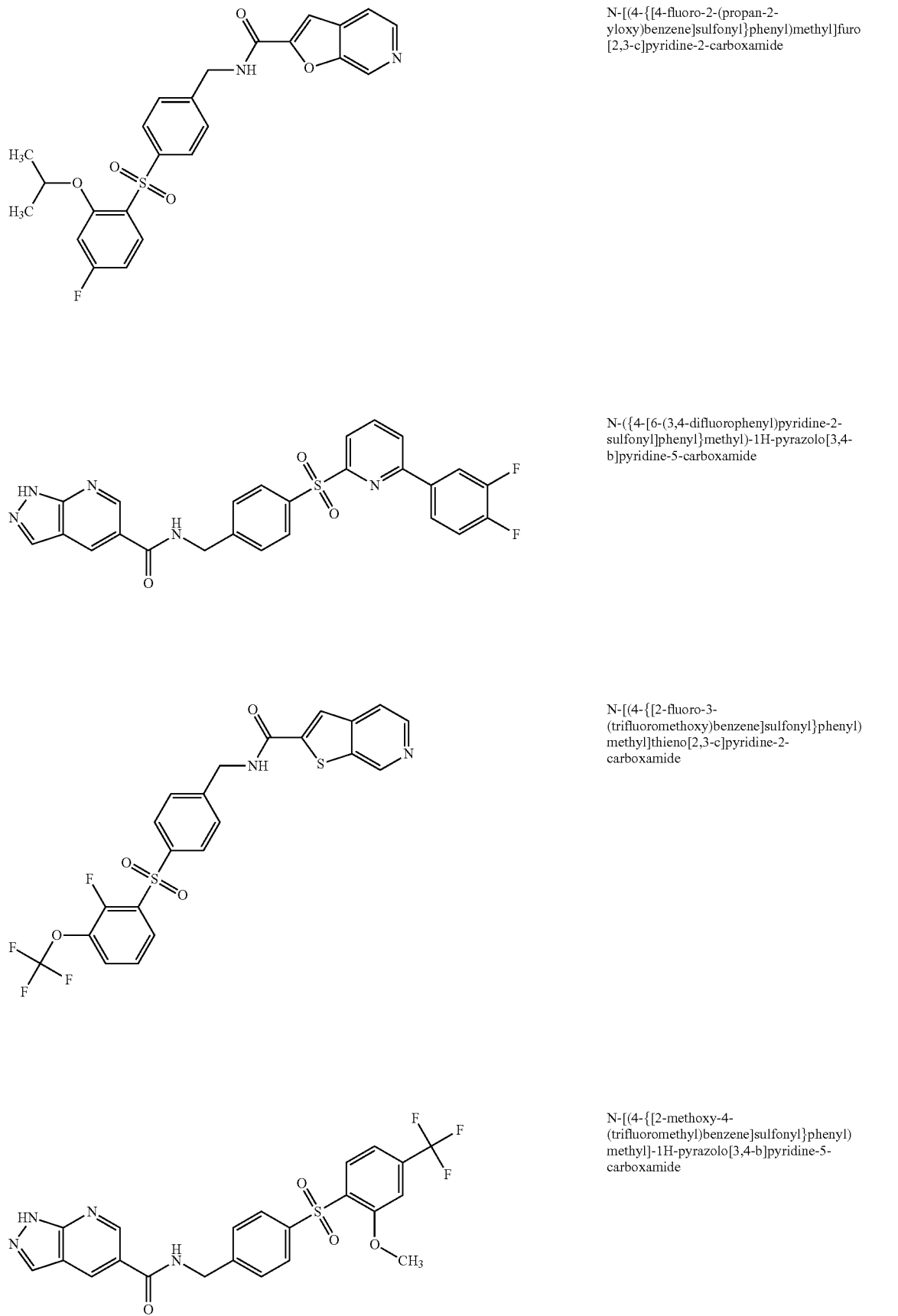

N-[(4-{[4-fluoro-2-(propan-2-yloxy)benzene]sulfonyl}phenyl)methyl]furo[2,3-c]pyridine-2-carboxamide N-({4-[6-(3,4-difluorophenyl)pyridine-2-sulfonyl]phenyl}methyl)-1H-pyrazolo[3,4-b]pyridine-5-carboxamide N-[(4-{[2-fluoro-3-(trifluoromethoxy)benzene]sulfonyl}phenyl)methyl]thieno[2,3-c]pyridine-2-carboxamide N-[(4-{[2-methoxy-4-(trifluoromethyl)benzene]sulfonyl}phenyl)methyl]-1H-pyrazolo[3,4-b]pyridine-5-carboxamide TABLE 2-continued
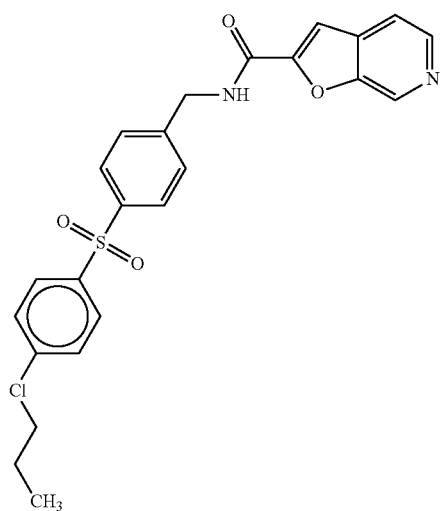
N-({4-[(4-propoxybenzene)sulfonyl]phenyl}methyl)furo[2,3-c]pyridine-2-carboxamide
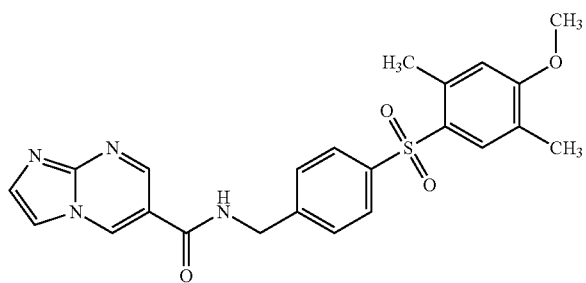
N-({4-[(4-methoxy-2,5-dimethylbenzene)sulfonyl]phenyl}methyl)imidazo[1,2-a]pyrimidine-6-carboxamide
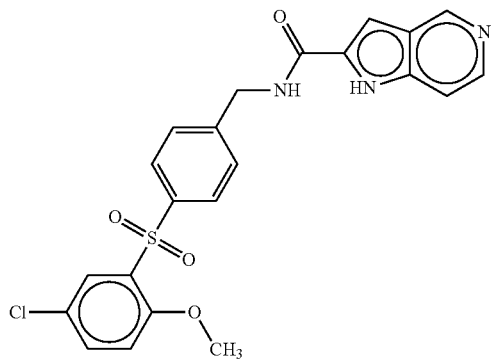
N-({4-[(5-chloro-2-methoxybenzene)sulfonyl]phenyl}methyl)-1H-pyrrolo[3,2-c]pyridine-2-carboxamide
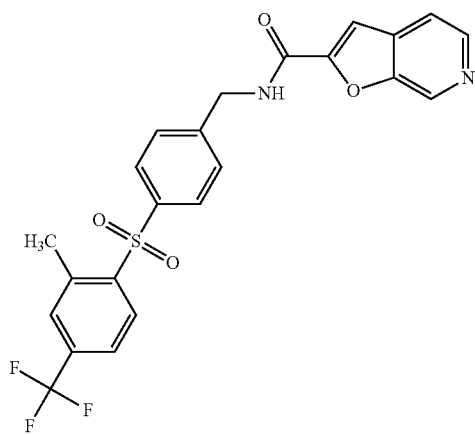 [SMILES: Cc1cc(C(F)(F)F)ccc1S(=O)(=O)c1ccc(CNC(=O)c2cc3ccncc3o2)cc1]
N-[(4-{[2-methyl-4-(trifluoromethyl)benzene]sulfonyl}phenyl)methyl]furo[2,3-c]pyridine-2-carboxamide TABLE 2-continued
| | |
|---|---|
| 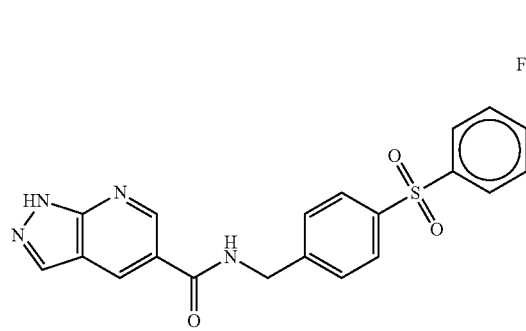 | N-[(4-{[4-(trifluoromethoxy)benzene]sulfonyl}phenyl)methyl]-1H-pyrazolo[3,4-b]pyridine-5-carboxamide |
| 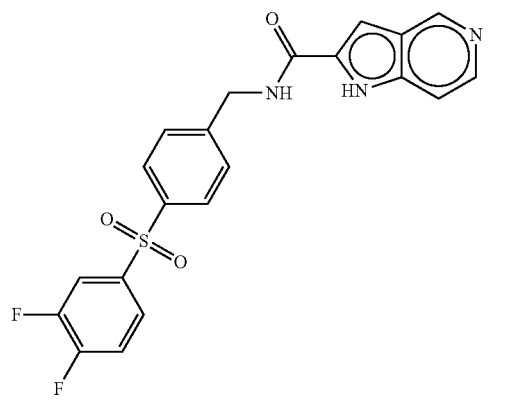 | N-({4-[(3,4-difluorobenzene)sulfonyl]phenyl}methyl)-1H-pyrrolo[3,2-c]pyridine-2-carboxamide |
| 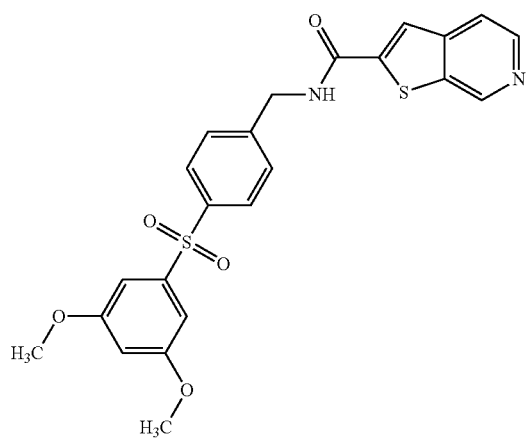 | N-({4-[(3,5-dimethoxybenzene)sulfonyl]phenyl}methyl)thieno[2,3-c]pyridine-2-carboxamide |
| 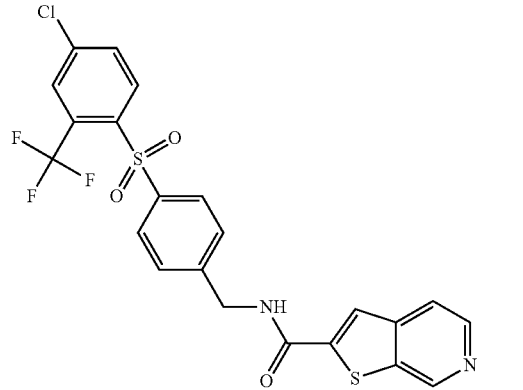 [SMILES: O=C(NCc1ccc(S(=O)(=O)c2ccc(Cl)cc2C(F)(F)F)cc1)c1cc2ccncc2s1] | N-[(4-{[4-chloro-2-(trifluoromethyl)benzene]sulfonyl}phenyl)methyl]thieno[2,3-c]pyridine-2-carboxamide |

TABLE 2-continued

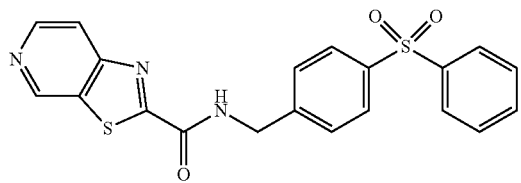 [SMILES: O=C(NCc1ccc(S(=O)(=O)c2ccccc2)cc1)c1nc2ccncc2s1]

N-{[4-(benzenesulfonyl)phenyl]methyl}-[1,3]thiazolo[5,4-c]pyridine-2-carboxamide

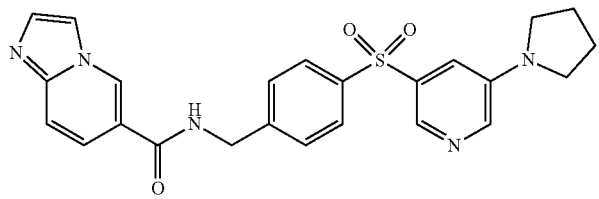 [SMILES: O=C(NCc1ccc(S(=O)(=O)c2cncc(N3CCCC3)c2)cc1)c1ccc2nccn2c1]

N-({4-[5-(pyrrolidin-1-yl)pyridine-3-sulfonyl]phenyl}methyl)imidazo[1,2-a]pyridine-6-carboxamide

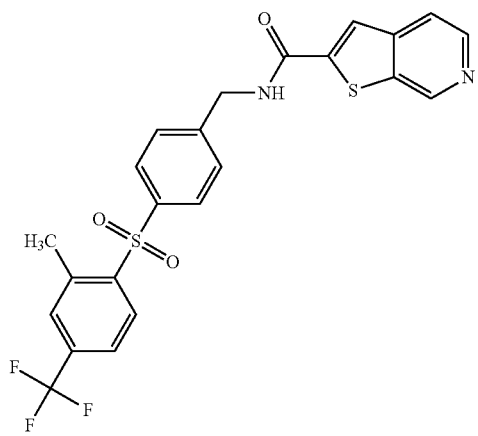 [SMILES: Cc1cc(C(F)(F)F)ccc1S(=O)(=O)c1ccc(CNC(=O)c2cc3ccncc3s2)cc1]

N-[(4-{[2-methyl-4-(trifluoromethyl)benzene]sulfonyl}phenyl)methyl]thieno[2,3-c]pyridine-2-carboxamide

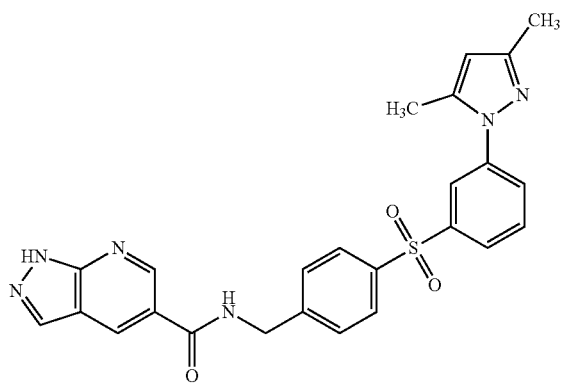 [SMILES: Cc1cc(C)n(-c2cccc(S(=O)(=O)c3ccc(CNC(=O)c4cnc5[nH]ncc5c4)cc3)c2)n1]

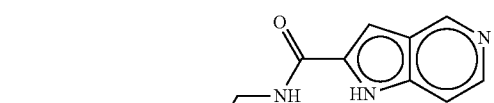

N-[(4-{[3-(3,5-dimethyl-1H-pyrazol-1-yl)benzene]sulfonyl}phenyl)methyl]-1H-pyrazolo[3,4-b]pyridine-5-carboxamide

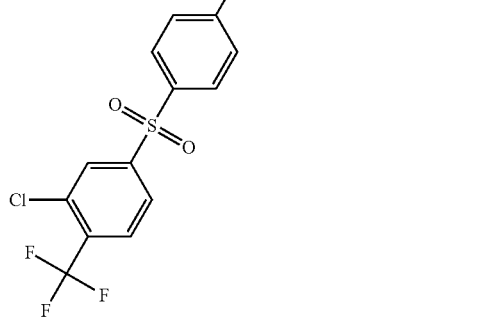

N-[(4-{[3-chloro-4-(trifluoromethyl)benzene]sulfonyl}phenyl)methyl]-1H-pyrrolo[3,2-c]pyridine-2-carboxamide TABLE 2-continued
| | |
|---|---|
| 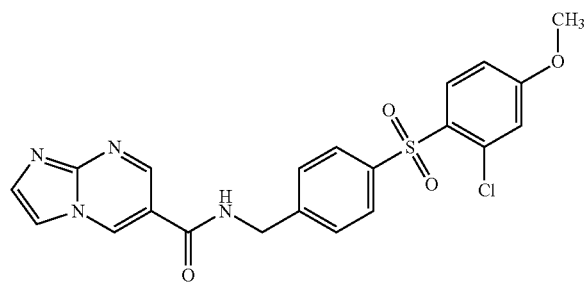 | N-({4-[(2-chloro-4-methoxybenzene)sulfonyl]phenyl}methyl)imidazo[1,2-a]pyrimidine-6-carboxamide |
| 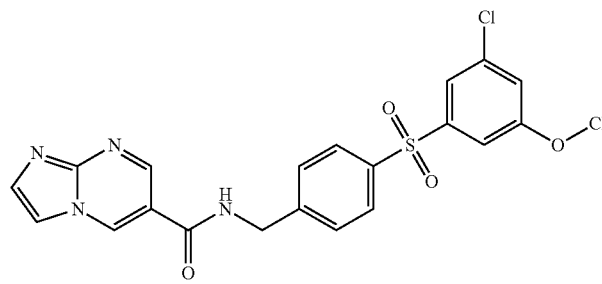 | N-({4-[(3-chloro-5-methoxybenzene)sulfonyl]phenyl}methyl)imidazo[1,2-a]pyrimidine-6-carboxamide |
| 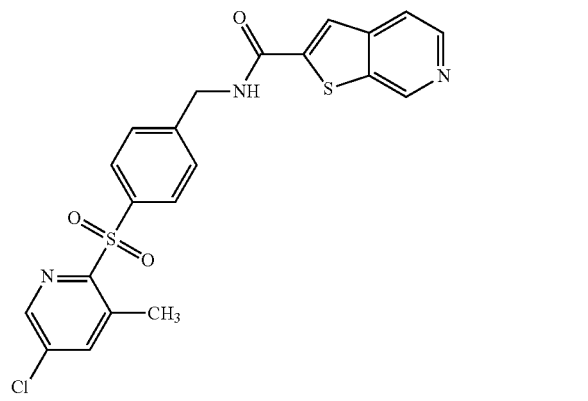 | N-{[4-(5-chloro-3-methylpyridine-2-sulfonyl)phenyl]methyl}thieno[2,3-c]pyridine-2-carboxamide |
| 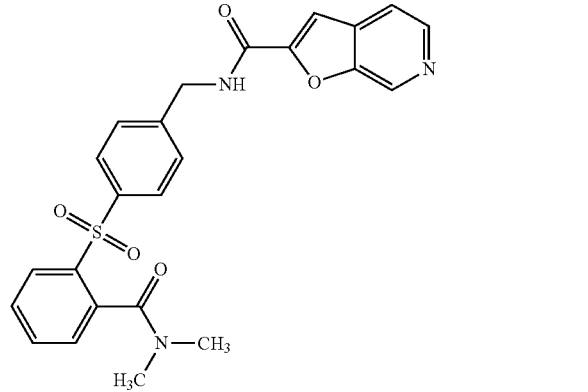 | N-[(4-{[2-(dimethylcarbamoyl)benzene]sulfonyl}phenyl)methyl]furo[2,3-c]pyridine-2-carboxamide |

TABLE 2-continued
| | |
|---|---|
| 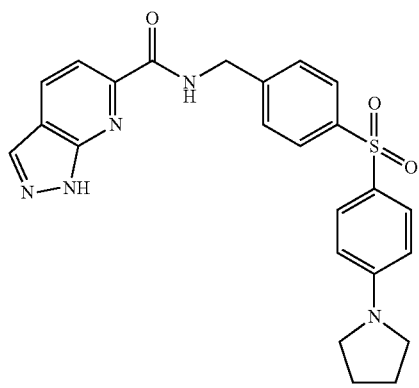 [SMILES: O=C(NCc1ccc(S(=O)(=O)c2ccc(N3CCCC3)cc2)cc1)c1ccc2cn[nH]c2n1] | N-[(4-{[4-(pyrrolidin-1-yl)benzene]sulfonyl}phenyl)methyl]-1H-pyrazolo[3,4-b]pyridine-6-carboxamide |
| 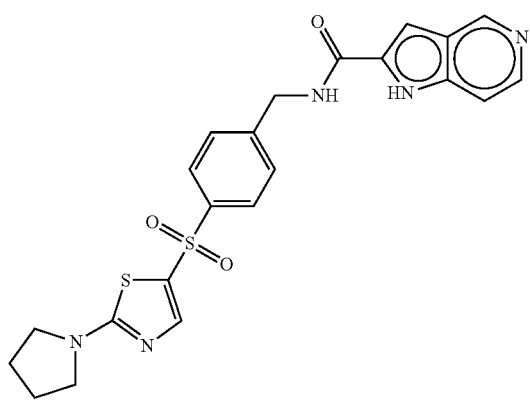 | N-({4-[2-(pyrrolidin-1-yl)-1,3-thiazole-5-sulfonyl]phenyl}methyl)-1H-pyrrolo[3,2-c]pyridine-2-carboxamide |
| 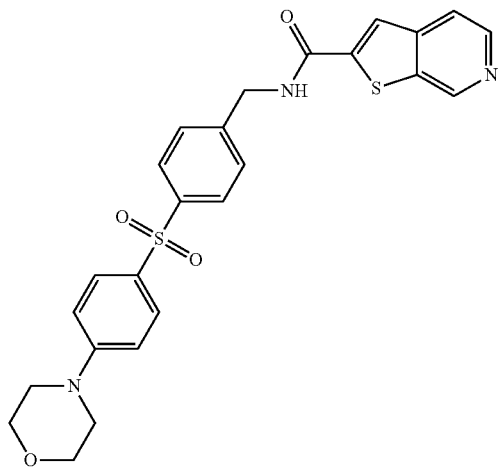 | N-[(4-{[4-(morpholin-4-yl)benzene]sulfonyl}phenyl)methyl]thieno[2,3-c]pyridine-2-carboxamide |
| 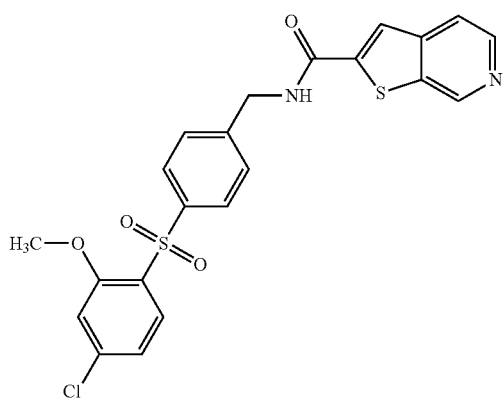 | N-({4-[(4-chloro-2-methoxybenzene)sulfonyl]phenyl}methyl)thieno[2,3-c]pyridine-2-carboxamide |

TABLE 2-continued

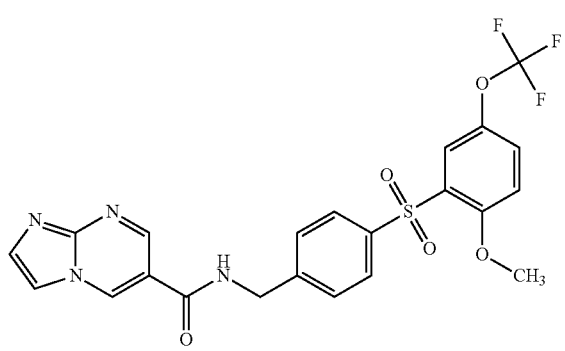 [SMILES: COc1ccc(OC(F)(F)F)cc1S(=O)(=O)c1ccc(CNC(=O)c2cnc3nccn3c2)cc1]

N-[(4-{[2-methoxy-5-(trifluoromethoxy)benzene]sulfonyl}phenyl)methyl]imidazo[1,2-a]pyrimidine-6-carboxamide

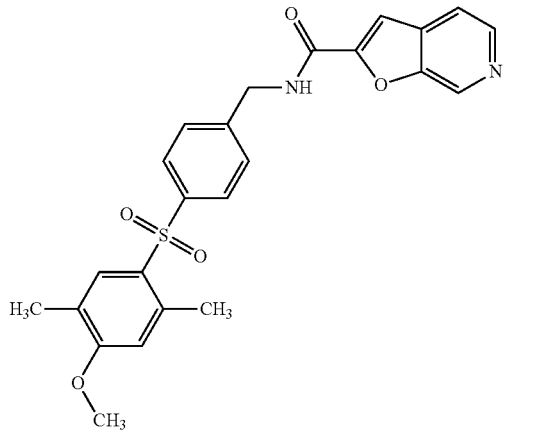 [SMILES: COc1cc(C)c(S(=O)(=O)c2ccc(CNC(=O)c3cc4ccncc4o3)cc2)cc1C]

N-({4-[(4-methoxy-2,5-dimethylbenzene)sulfonyl]phenyl}methyl)furo[2,3-c]pyridine-2-carboxamide

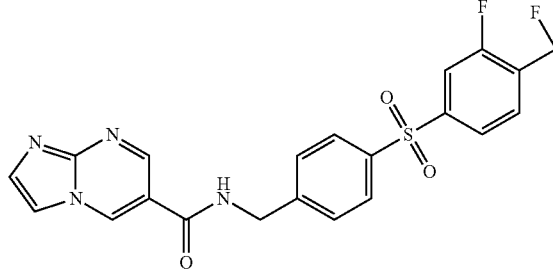

N-[(4-{[3-fluoro-4-(trifluoromethyl)benzene]sulfonyl}phenyl)methyl]imidazo[1,2-a]pyrimidine-6-carboxamide

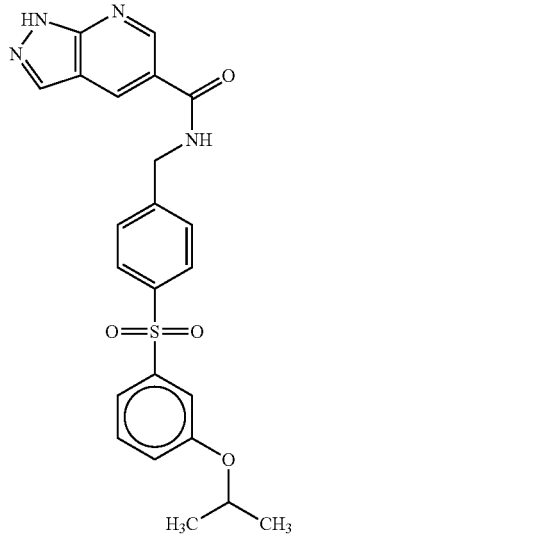

N-[(4-{[3-(propan-2-yloxy)benzene]sulfonyl}phenyl)methyl]-1H-pyrazolo[3,4-b]pyridine-5-carboxamide TABLE 2-continued

| | |
|---|---|
| 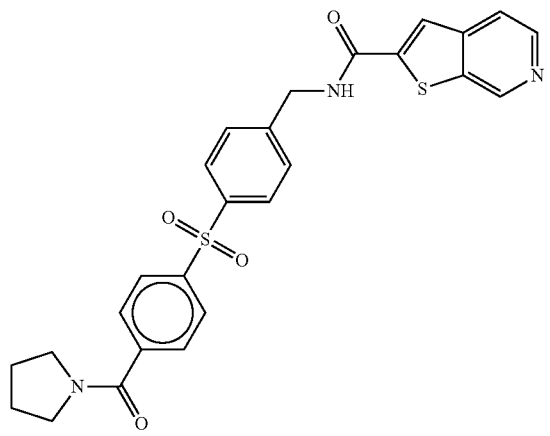 | N-{[4-({4-[(pyrrolidin-1-yl)carbonyl]benzene}sulfonyl)phenyl]methyl}thieno[2,3-c]pyridine-2-carboxamide |
| 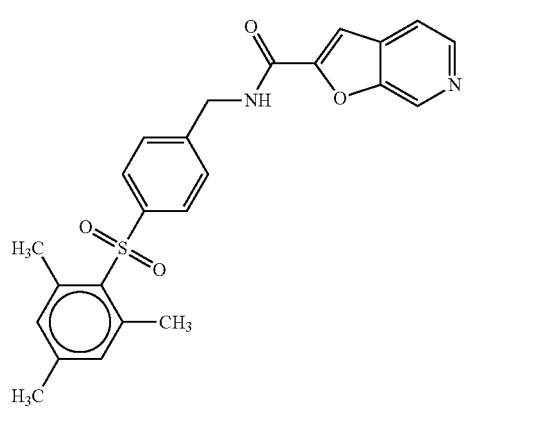 | N-({4-[(2,4,6-trimethylbenzene)sulfonyl]phenyl}methyl)furo[2,3-c]pyridine-2-carboxamide |
| 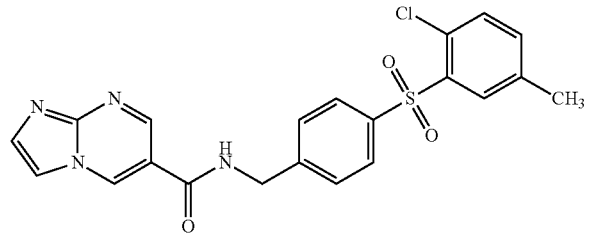 [SMILES: Cc1ccc(Cl)c(S(=O)(=O)c2ccc(CNC(=O)c3cnc4nccn4c3)cc2)c1] | N-({4-[(2-chloro-5-methylbenzene)sulfonyl]phenyl}methyl)imidazo[1,2-a]pyrimidine-6-carboxamide |
|  | N-[(4-{[2-(benzyloxy)-5-(trifluoromethyl)benzene]sulfonyl}phenyl)methyl]imidazo[1,2-a]pyrimidine-6-carboxamide |
| 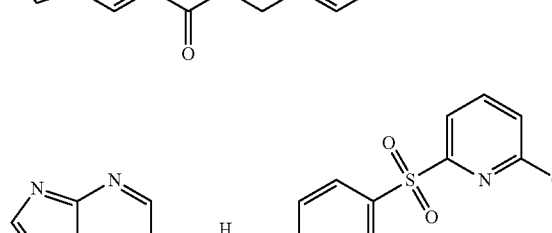 | N-{[4-(6-methoxypyridine-2-sulfonyl)phenyl]methyl}imidazo[1,2-a]pyrimidine-6-carboxamide |

TABLE 2-continued
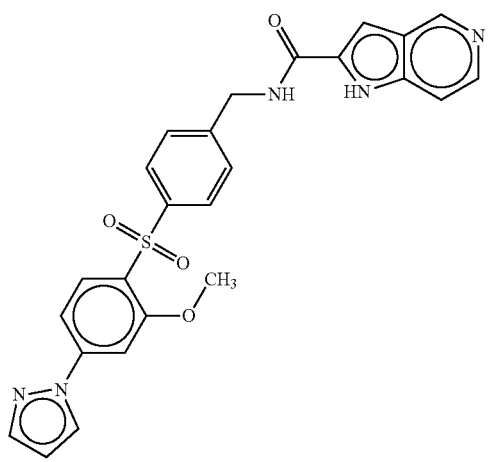
N-[(4-{[2-methoxy-4-(1H-pyrazol-1-yl)benzene]sulfonyl}phenyl)methyl]-1H pyrrolo[3,2-c]pyridine-2-carboxamide
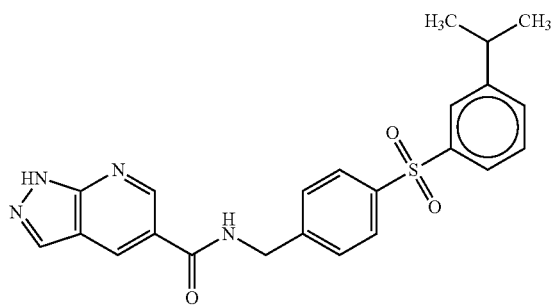
N-[(4-{[3-(propan-2-yl)benzene]sulfonyl}phenyl)methyl]-1H-pyrazolo[3,4-b]pyridine-5-carboxamide
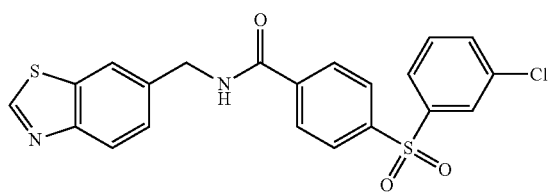 [SMILES: O=C(NCc1ccc2ncsc2c1)c1ccc(S(=O)(=O)c2cccc(Cl)c2)cc1]
N-(1,3-benzothiazol-6-ylmethyl)-4-[(3-chlorobenzene)sulfonyl]benzamide
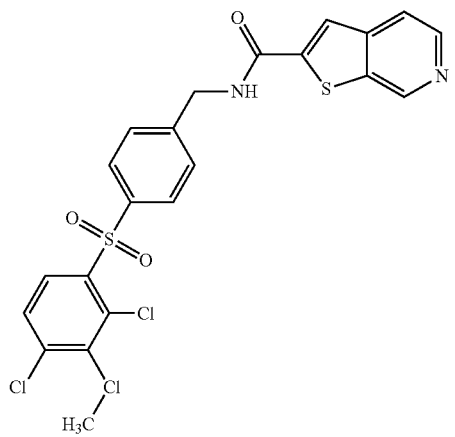
N-({4-[(2,4-dichloro-3-methoxybenzene)sulfonyl]phenyl}methyl)thieno[2,3-c]pyridine-2-carboxamide TABLE 2-continued
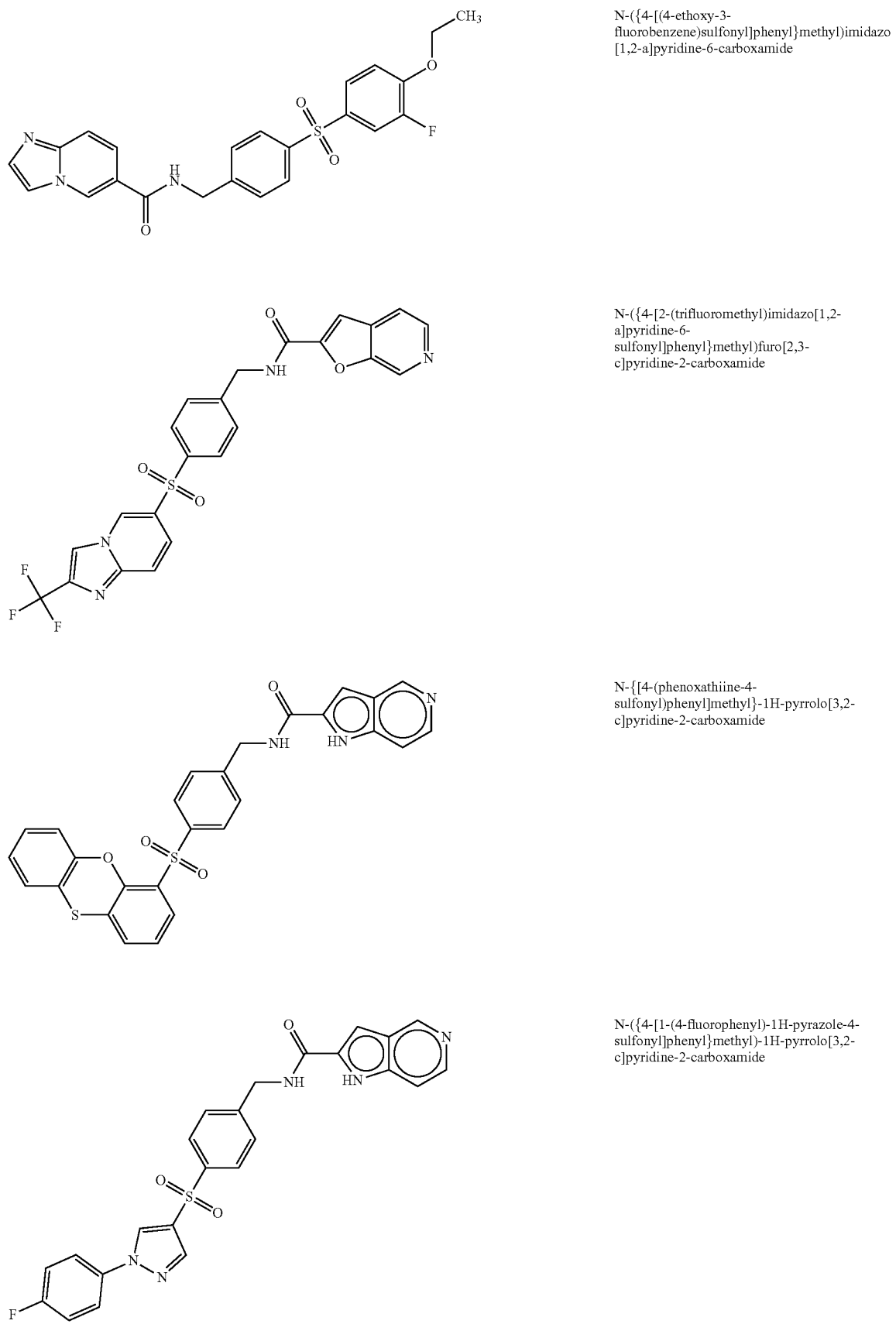
N-({4-[(4-ethoxy-3-fluorobenzene)sulfonyl]phenyl}methyl)imidazo[1,2-a]pyridine-6-carboxamide
N-({4-[2-(trifluoromethyl)imidazo[1,2-a]pyridine-6-sulfonyl]phenyl}methyl)furo[2,3-c]pyridine-2-carboxamide
N-{[4-(phenoxathiine-4-sulfonyl)phenyl]methyl}-1H-pyrrolo[3,2-c]pyridine-2-carboxamide
N-({4-[1-(4-fluorophenyl)-1H-pyrazole-4-sulfonyl]phenyl}methyl)-1H-pyrrolo[3,2-c]pyridine-2-carboxamide TABLE 2-continued
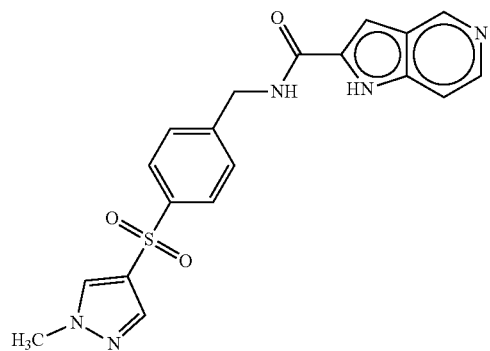
N-{[4-(1-methyl-1H-pyrazole-4-sulfonyl)phenyl]methyl}-1H-pyrrolo[3,2-c]pyridine-2-carboxamide
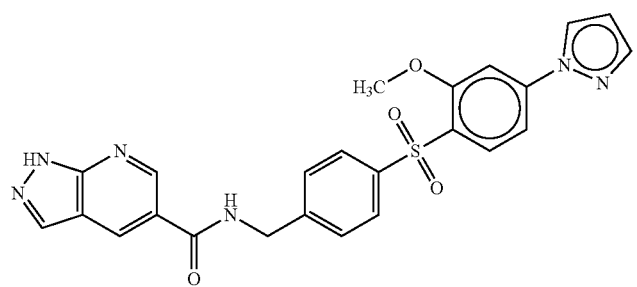
N-[(4-{[2-methoxy-4-(1H-pyrazol-1-yl)benzene]sulfonyl}phenyl)methyl]-1H-pyrazolo[3,4-b]pyridine-5-carboxamide
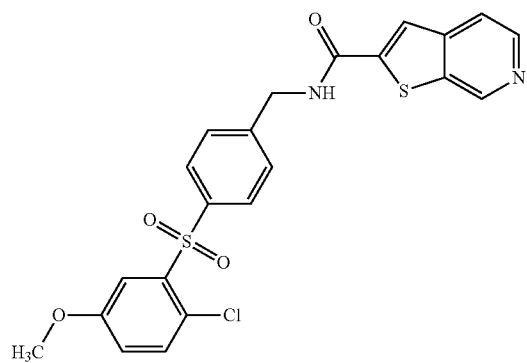
N-({4-[(2-chloro-5-methoxybenzene)sulfonyl]phenyl}methyl)thieno[2,3-c]pyridine-2-carboxamide
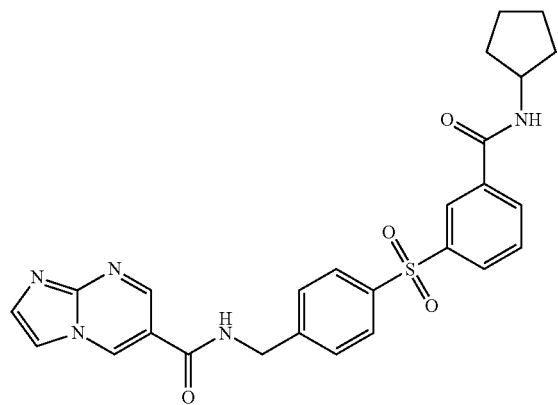 [SMILES: O=C(NCc1ccc(S(=O)(=O)c2cccc(C(=O)NC3CCCC3)c2)cc1)c1cnc2nccn2c1]
N-[(4-{[3-(cyclopentylcarbamoyl)benzene]sulfonyl}phenyl)methyl]imidazo[1,2-a]pyrimidine-6-carboxamide TABLE 2-continued
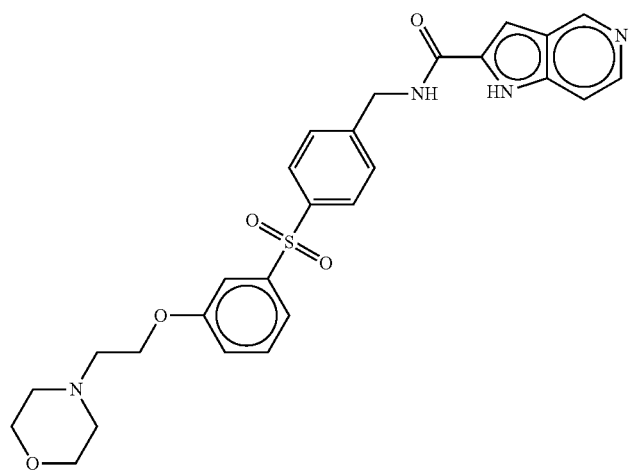
N-{[4-({3-[2-(morpholin-4-yl)ethoxy]benzene}sulfonyl)phenyl]methyl}-1H-pyrrolo[3,2-c]pyridine-2-carboxamide
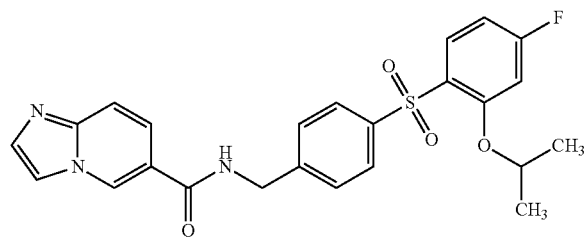 [SMILES: CC(C)Oc1cc(F)ccc1S(=O)(=O)c1ccc(CNC(=O)c2ccc3nccn3c2)cc1]
N-[(4-{[4-fluoro-2-(propan-2-yloxy)benzene]sulfonyl}phenyl)methyl]imidazo[1,2-a]pyridine-6-carboxamide
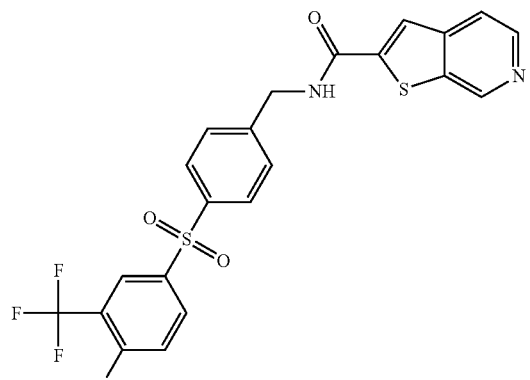
N-[(4-{[4-fluoro-3-(trifluoromethyl)benzene]sulfonyl}phenyl)methyl]thieno[2,3-c]pyridine-2-carboxamide
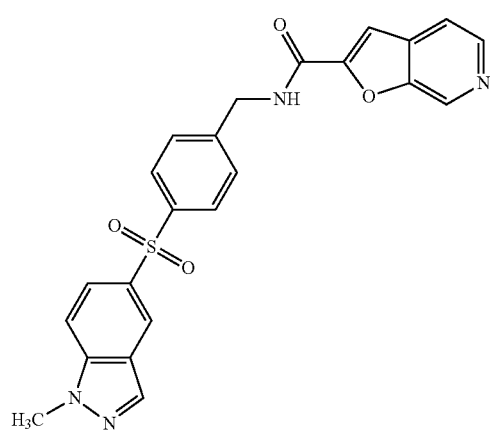 [SMILES: Cn1ncc2cc(S(=O)(=O)c3ccc(CNC(=O)c4cc5ccncc5o4)cc3)ccc21]
N-{[4-(1-methyl-1H-indazole-5-sulfonyl)phenyl]methyl}furo[2,3-c]pyridine-2-carboxamide TABLE 2-continued
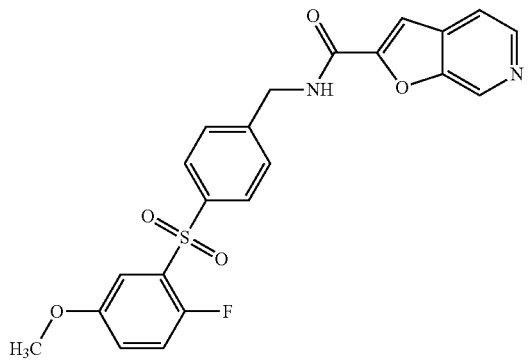
N-({4-[(2-fluoro-5-methoxybenzene)sulfonyl]phenyl}methyl)furo[2,3-c]pyridine-2-carboxamide
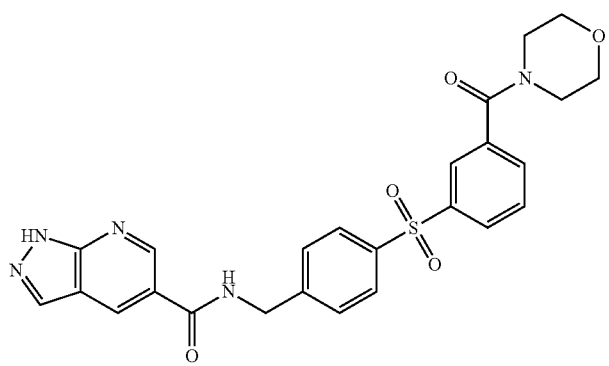 [SMILES: O=C(NCc1ccc(S(=O)(=O)c2cccc(C(=O)N3CCOCC3)c2)cc1)c1cnc2[nH]ncc2c1]
N-{[4-({3-[(morpholin-4-yl)carbonyl]benzene}sulfonyl)phenyl]methyl}-1H-pyrazolo[3,4-b]pyridine-5-carboxamide
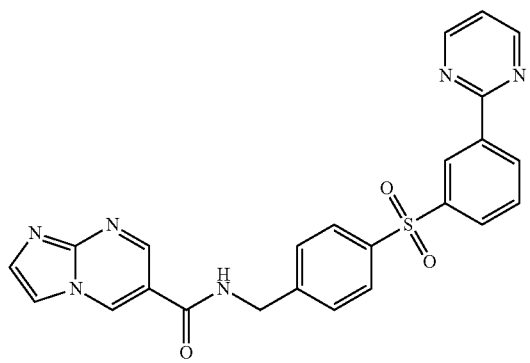 [SMILES: O=C(NCc1ccc(S(=O)(=O)c2cccc(-c3ncccn3)c2)cc1)c1cnc2nccn2c1]
N-[(4-{[3-(pyrimidin-2-yl)benzene]sulfonyl}phenyl)methyl]imidazo[1,2-a]pyrimidine-6-carboxamide
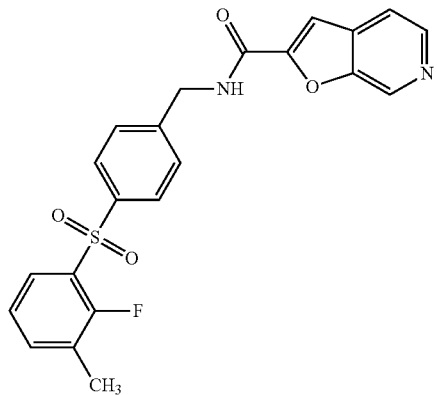 [SMILES: Cc1cccc(S(=O)(=O)c2ccc(CNC(=O)c3cc4ccncc4o3)cc2)c1F]
N-({4-[(2-fluoro-3-methylbenzene)sulfonyl]phenyl}methyl)thieno[2,3-c]pyridine-2-carboxamide TABLE 2-continued
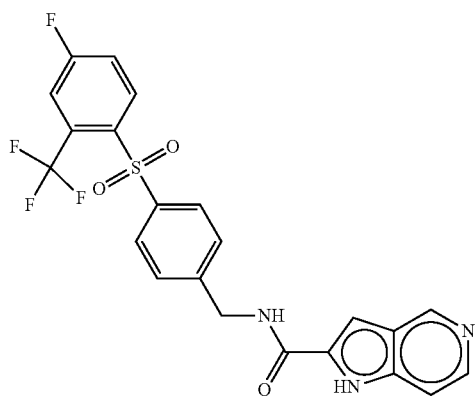
N-[(4-{[4-fluoro-2-(trifluoromethyl)benzene]sulfonyl}phenyl)methyl]-1H-pyrrolo[3,2-c]pyridine-2-carboxamide
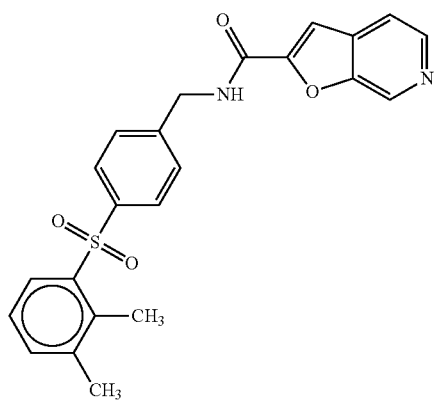
N-({4-[(2,3-dimethylbenzene)sulfonyl]phenyl}methyl)furo[2,3-c]pyridine-2-carboxamide
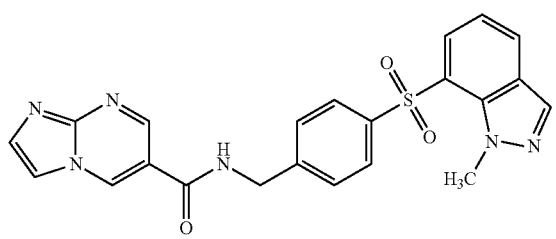 [SMILES: Cn1ncc2cccc(S(=O)(=O)c3ccc(CNC(=O)c4cnc5nccn5c4)cc3)c21]
N-{[4-(1-methyl-1H-indazole-7-sulfonyl)phenyl]methyl}imidazo[1,2-a]pyrimidine-6-carboxamide
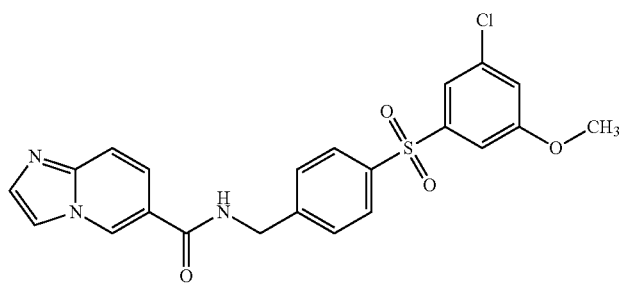 [SMILES: COc1cc(Cl)cc(S(=O)(=O)c2ccc(CNC(=O)c3ccc4nccn4c3)cc2)c1]
N-({4-[(3-chloro-5-methoxybenzene)sulfonyl]phenyl}methyl)imidazo[1,2-a]pyridine-6-carboxamide TABLE 2-continued

| | |
|---|---|
| 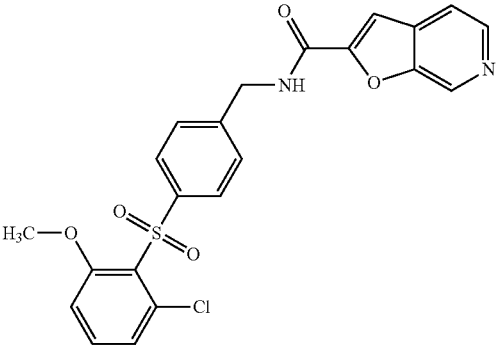 | N-({4-[(2-chloro-6-methoxybenzene)sulfonyl]phenyl}methyl)furo[2,3-c]pyridine-2-carboxamide |
| 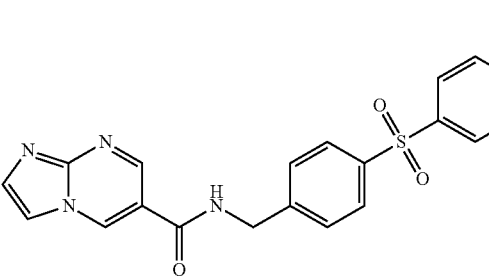 | N-({4-[(3,4-dimethoxybenzene)sulfonyl]phenyl}methyl)imidazo[1,2-a]pyrimidine-6-carboxamide |
| 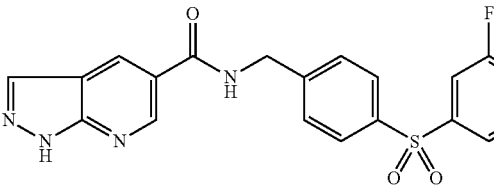 | N-({4-[(3,5-difluorobenzene)sulfonyl]phenyl}methyl)-1H-pyrazolo[3,4-b]pyridine-5-carboxamide |
| 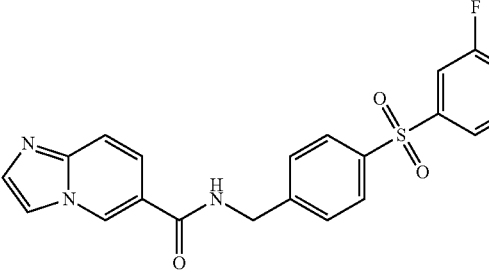 | N-[(4-{[3-fluoro-4-(trifluoromethyl)benzene]sulfonyl}phenyl)methyl]imidazo[1,2-a]pyridine-6-carboxamide |
| 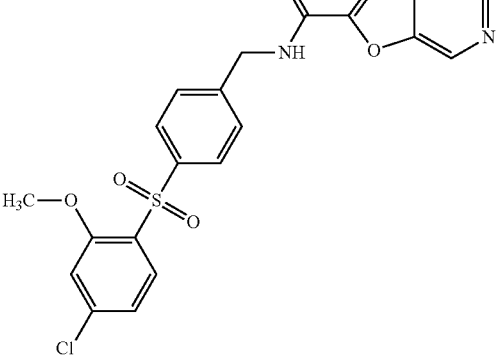 | N-({4-[(4-chloro-2-methoxybenzene)sulfonyl]phenyl}methyl)furo[2,3-c]pyridine-2-carboxamide |

TABLE 2-continued

| | |
|---|---|
| 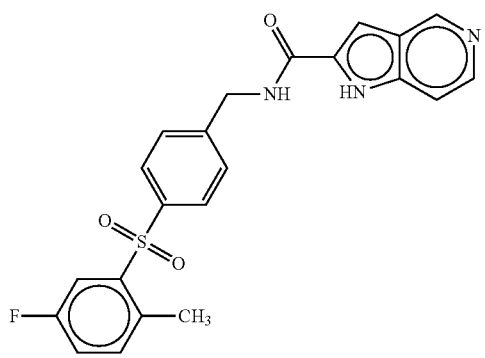 | N-({4-[(5-fluoro-2-methylbenzene)sulfonyl]phenyl}methyl)-1H-pyrrolo[3,2-c]pyridine-2-carboxamide |
| 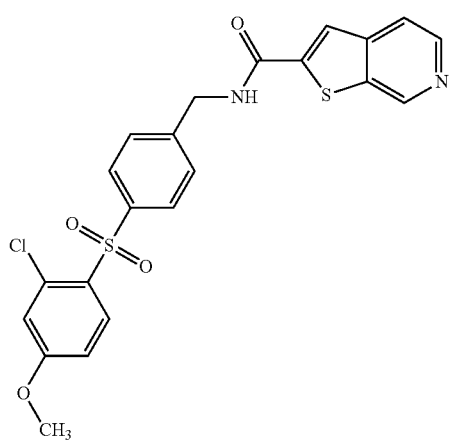 [SMILES: COc1ccc(S(=O)(=O)c2ccc(CNC(=O)c3cc4ccncc4s3)cc2)c(Cl)c1] | N-({4-[(2-chloro-4-methoxybenzene)sulfonyl]phenyl}methyl)thieno[2,3-c]pyridine-2-carboxamide |
| 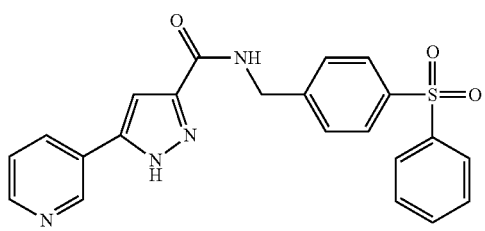 [SMILES: O=C(NCc1ccc(S(=O)(=O)c2ccccc2)cc1)c1cc(-c2cccnc2)[nH]n1] | N-{[4-(benzenesulfonyl)phenyl]methyl}-5-(pyridin-3-yl)-1H-pyrazole-3-carboxamide |
| 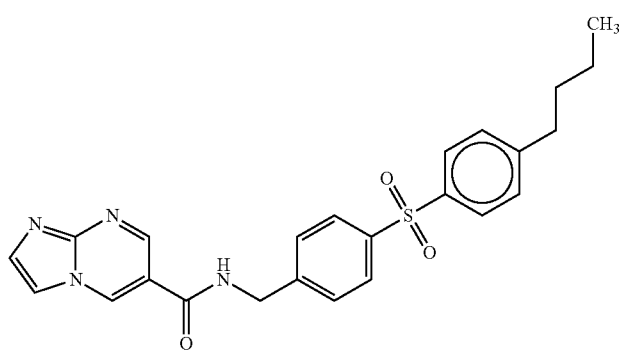 | N-({4-[(4-butylbenzene)sulfonyl]phenyl}methyl)imidazo[1,2-a]pyrimidine-6-carboxamide |
| 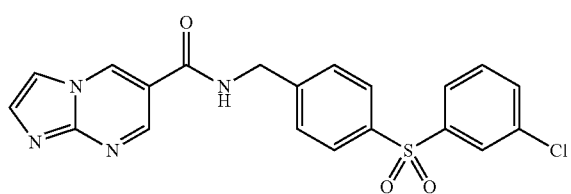 [SMILES: O=C(NCc1ccc(S(=O)(=O)c2cccc(Cl)c2)cc1)c1cnc2nccn2c1] | N-({4-[(3-chlorobenzene)sulfonyl]phenyl}methyl)imidazo[1,2-a]pyrimidine-6-carboxamide |

TABLE 2-continued
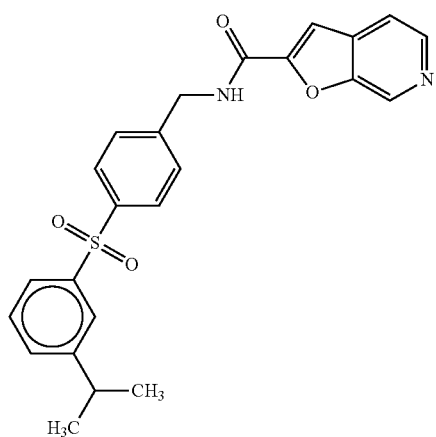
N-[(4-{[3-(propan-2-yl)benzene]sulfonyl}phenyl)methyl]furo[2,3-c]pyridine-2-carboxamide
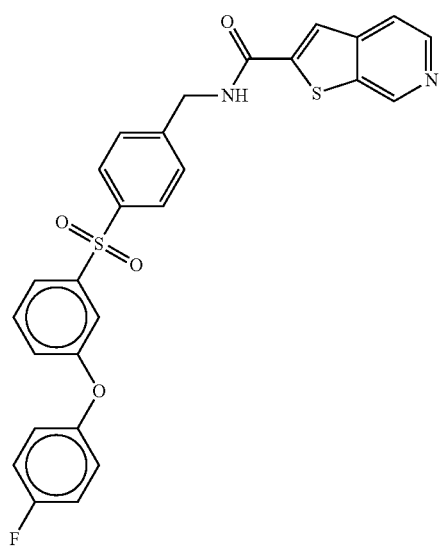
N-[(4-{[3-(4-fluorophenoxy)benzene]sulfonyl}phenyl)methyl]thieno[2,3-c]pyridine-2-carboxamide
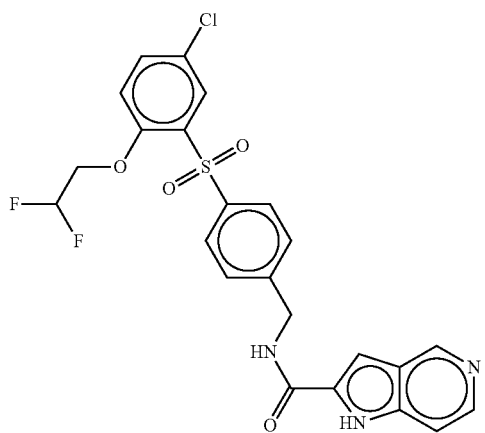
N-[(4-{[5-chloro-2-(2,2-difluoroethoxy)benzene]sulfonyl}phenyl)methyl]-1H-pyrrolo[3,2-c]pyridine-2-carboxamide TABLE 2-continued
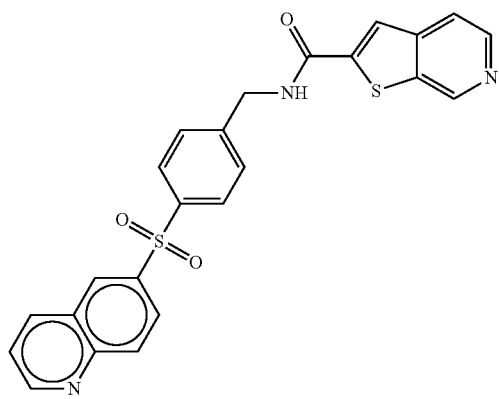
N-{[4-(quinoline-6-sulfonyl)phenyl]methyl}thieno[2,3-c]pyridine-2-carboxamide
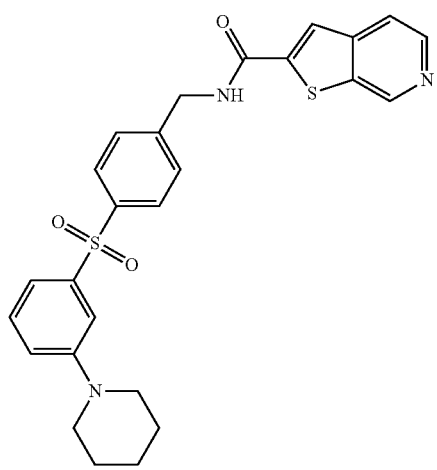 [SMILES: O=C(NCc1ccc(S(=O)(=O)c2cccc(N3CCCCC3)c2)cc1)c1cc2ccncc2s1]
N-[(4-{[3-(piperidin-1-yl)benzene]sulfonyl}phenyl)methyl]thieno[2,3-c]pyridine-2-carboxamide
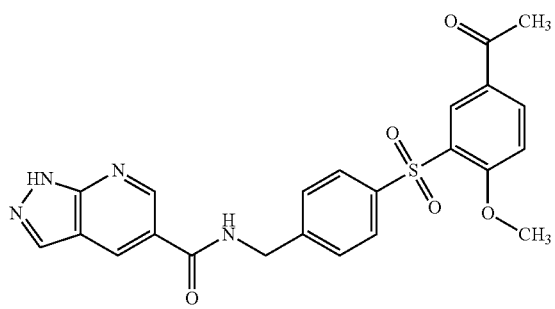 [SMILES: COc1ccc(C(C)=O)cc1S(=O)(=O)c1ccc(CNC(=O)c2cnc3[nH]ncc3c2)cc1]
N-({4-[(5-acetyl-2-methoxybenzene)sulfonyl]phenyl}methyl)-1H-pyrazolo[3,4-b]pyridine-5-carboxamide
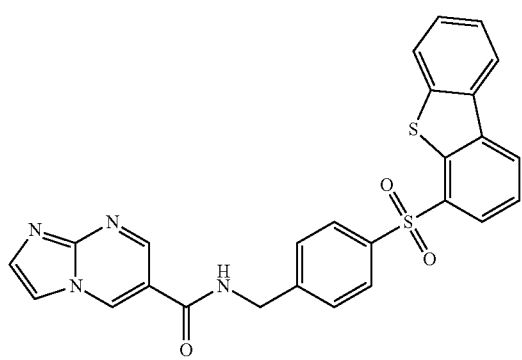 [SMILES: O=C(NCc1ccc(S(=O)(=O)c2cccc3c2sc2ccccc23)cc1)c1cnc2nccn2c1]
N-[(4-{8-thiatricyclo[7.4.0.0$^{2,}$□]trideca-1(13),2,4,6,9,11-hexaene-6-sulfonyl}phenyl)methyl]imidazo[,2-a]pyrimidine-6-carboxamide

TABLE 2-continued
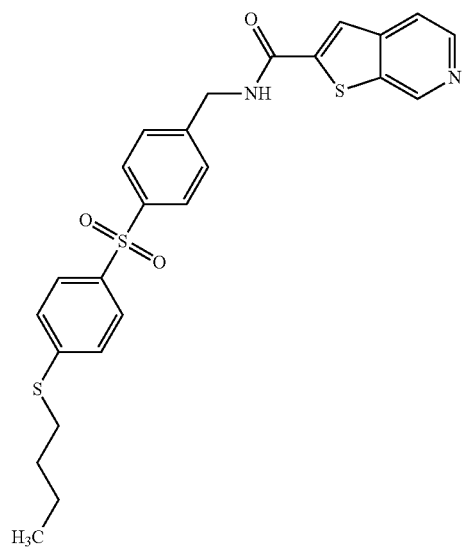 [SMILES: CCCCSc1ccc(S(=O)(=O)c2ccc(CNC(=O)c3cc4ccncc4s3)cc2)cc1]
N-({4-[(4-butoxybenzene)sulfonyl]phenyl}methyl)thieno[2,3-c]pyridine-2-carboxamide
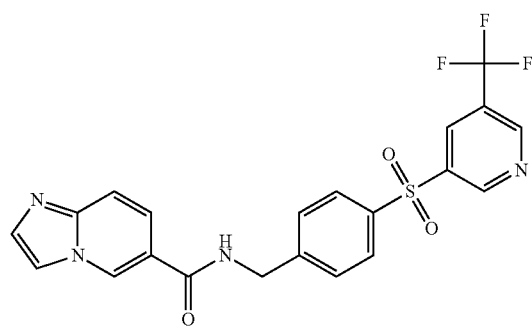
N-({4-[5-(trifluoromethyl)pyridine-3-sulfonyl]phenyl}methyl)imidazo[1,2-a]pyridine-6-carboxamide
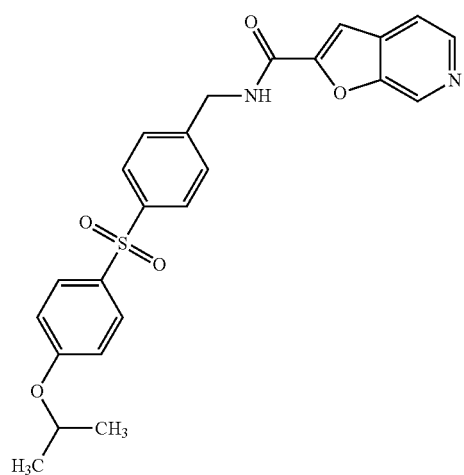 [SMILES: CC(C)Oc1ccc(S(=O)(=O)c2ccc(CNC(=O)c3cc4ccncc4o3)cc2)cc1]
N-[(4-{[4-(propan-2-yloxy)benzene]sulfonyl}phenyl)methyl]furo[2,3-c]pyridine-2-carboxamide TABLE 2-continued
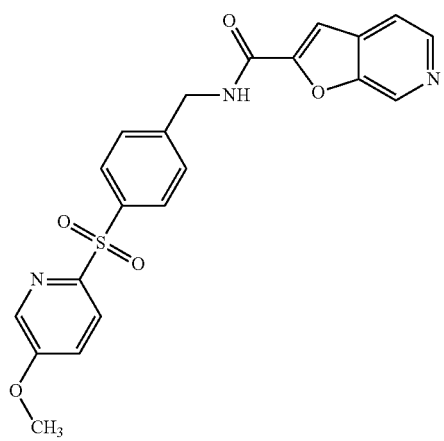 [SMILES: COc1ccc(S(=O)(=O)c2ccc(CNC(=O)c3cc4ccncc4o3)cc2)nc1]
N-{[4-(5-methoxypyridine-2-sulfonyl)phenyl]methyl}furo[2,3-c]pyridine-2-carboxamide
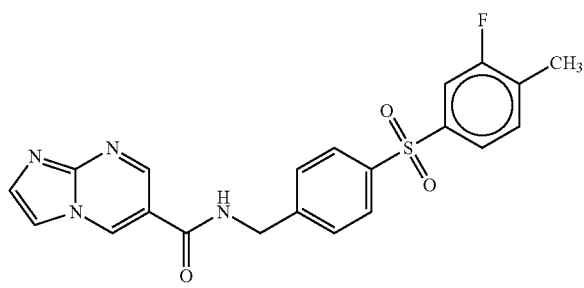
N-({4-[(3-fluoro-4-methylbenzene)sulfonyl]phenyl}methyl)imidazo[1,2-a]pyrimidine-6-carboxamide
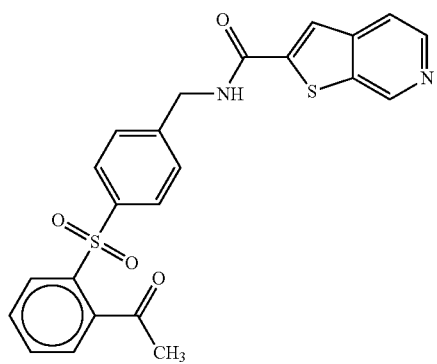
N-({4-[(2-acetylbenzene)sulfonyl]phenyl}methyl)thieno[2,3-c]pyridine-2-carboxamide
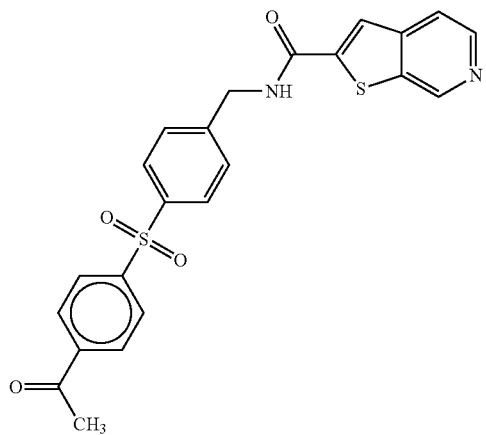
N-({4-[(4-acetylbenzene)sulfonyl]phenyl}methyl)thieno[2,3-c]pyridine-2-carboxamide TABLE 2-continued

| | |
|---|---|
| 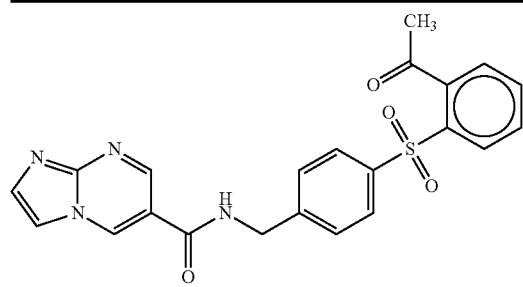 | N-({4-[(2-acetylbenzene)sulfonyl]phenyl}methyl)imidazo[1,2-a]pyrimidine-6-carboxamide |
| 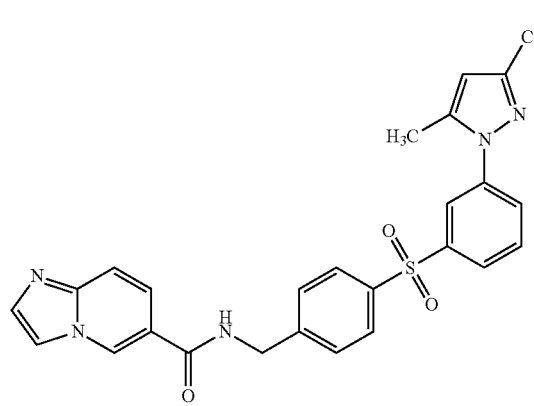 | N-[(4-{[3-(3,5-dimethyl-1H-pyrazol-1-yl)benzene]sulfonyl}phenyl)methyl]imidazo[1,2-a]pyridine-6-carboxamide |
| 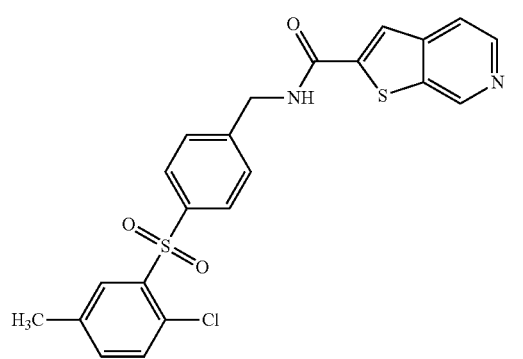 [SMILES: Cc1ccc(Cl)c(S(=O)(=O)c2ccc(CNC(=O)c3cc4ccncc4s3)cc2)c1] | N-({4-[(2-chloro-5-methylbenzene)sulfonyl]phenyl}methyl)furo[2,3-c]pyridine-2-carboxamide |
| 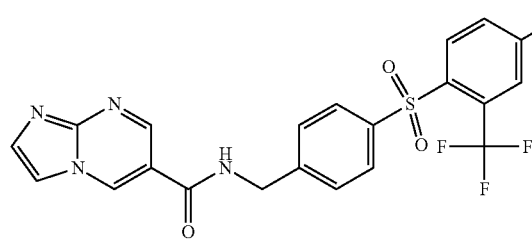 | N-[(4-{[4-chloro-2-(trifluoromethyl)benzene]sulfonyl}phenyl)methyl]imidazo[1,2-a]pyrimidine-6-carboxamide |
| 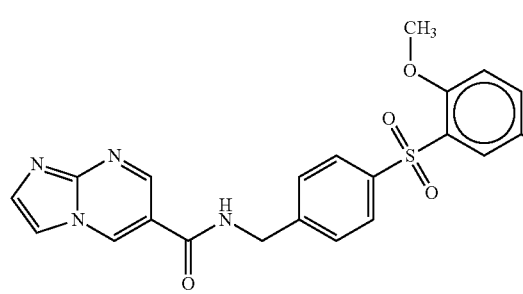 | N-({4-[(2-methoxy-5-methylbenzene)sulfonyl]phenyl}methyl)imidazo[1,2-a]pyrimidine-6-carboxamide |

TABLE 2-continued

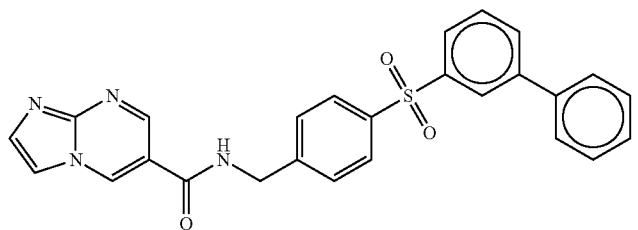

N-({4-[(3-phenylbenzene)sulfonyl]phenyl}methyl)imidazo[1,2-a]pyrimidine-6-carboxamide

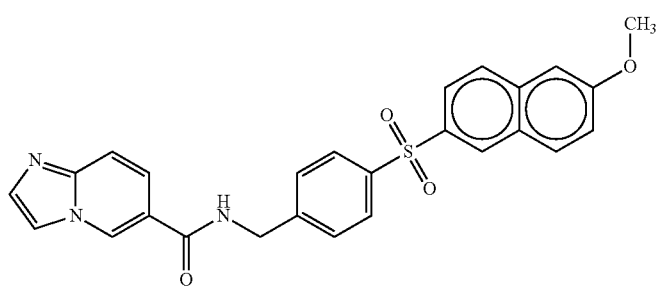

N-{[4-(6-methoxynaphthalene-2-sulfonyl)phenyl]methyl}imidazo[1,2-a]pyridine-6-carboxamide

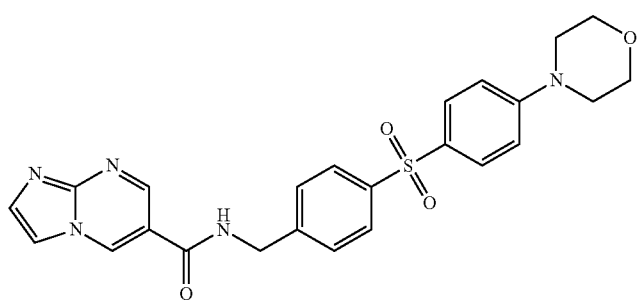 [SMILES: O=C(NCc1ccc(S(=O)(=O)c2ccc(N3CCOCC3)cc2)cc1)c1cnc2nccn2c1]

N-[(4-{[4-(morpholin-4-yl)benzene]sulfonyl}phenyl)methyl]imidazo[1,2-a]pyrimidine-6-carboxamide

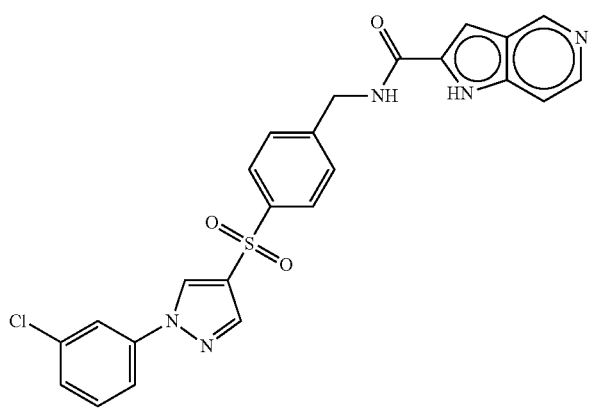

N-({4-[1-(3-chlorophenyl)-1H-pyrazole-4-sulfonyl]phenyl}methyl)-1H-pyrrolo[3,2-c]pyridine-2-carboxamide

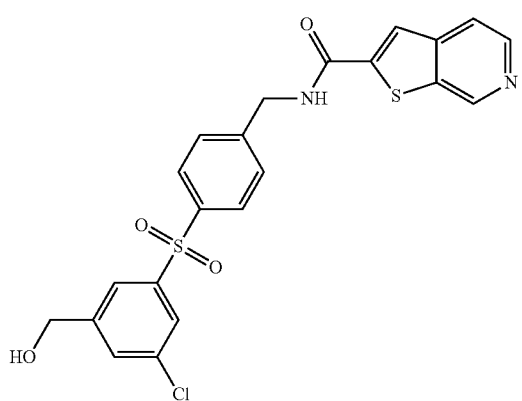 [SMILES: O=C(NCc1ccc(S(=O)(=O)c2cc(Cl)cc(CO)c2)cc1)c1cc2ccncc2s1]

N-[(4-{[3-chloro-5-(hydroxymethyl)benzene]sulfonyl}phenyl)methyl]thieno[2,3-c]pyridine-2-carboxamide TABLE 2-continued
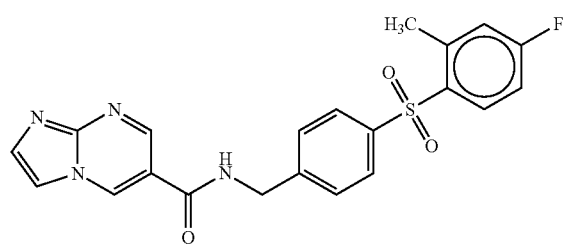
N-({4-[(4-fluoro-2-methylbenzene)sulfonyl]phenyl}methyl)imidazo[1,2-a]pyrimidine-6-carboxamide
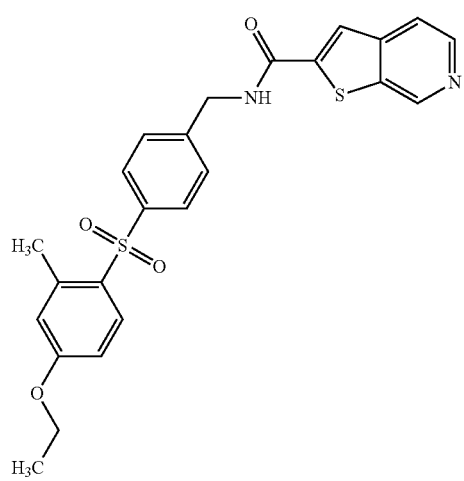 [SMILES: CCOc1ccc(S(=O)(=O)c2ccc(CNC(=O)c3cc4ccncc4s3)cc2)c(C)c1]
N-({4-[(4-ethoxy-2-methylbenzene)sulfonyl]phenyl}methyl)thieno[2,3-c]pyridine-2-carboxamide
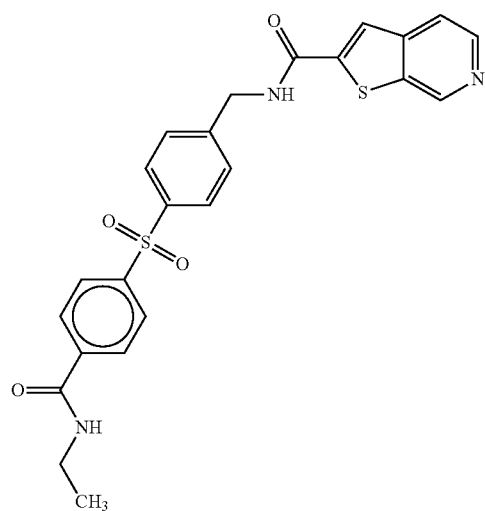
N-[(4-{4-(ethylcarbamoyl)benzene]sulfonyl}phenyl)methyl]thieno[2,3-c]pyridine-2-carboxamide TABLE 2-continued
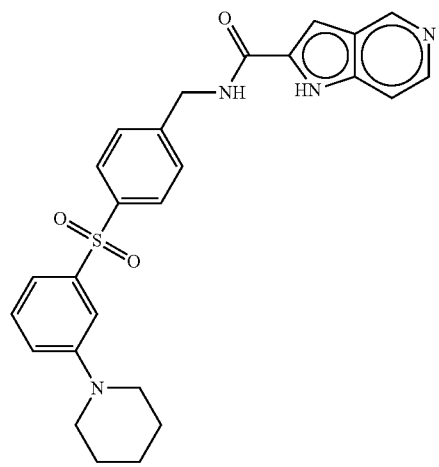
N-[(4-{[3-(piperidin-1-yl)benzene]sulfonyl}phenyl)methyl]-1H-pyrrolo[3,2-c]pyridine-2-carboxamide
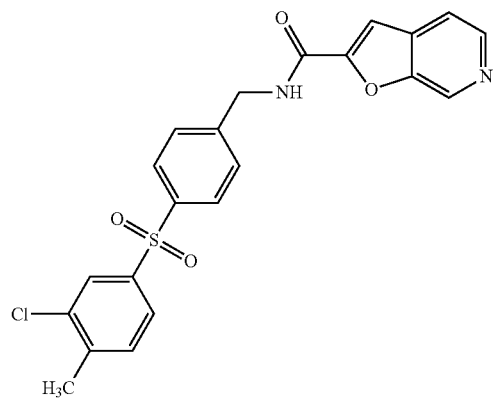
N-({4-[(3-chloro-4-methylbenzene)sulfonyl]phenyl}methyl)furo[2,3-c]pyridine-2-carboxamide
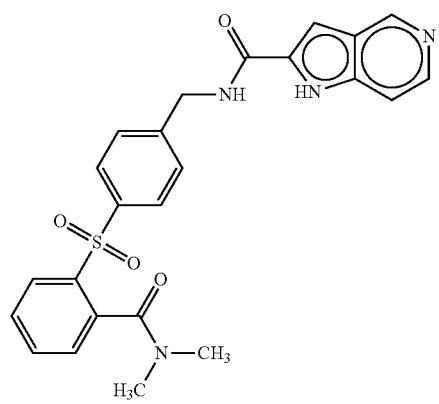
N-[(4-{[2-(dimethylcarbamoyl)benzene]sulfonyl}phenyl)methyl]-1H-pyrrolo[3,2-c]pyridine-2-carboxamide
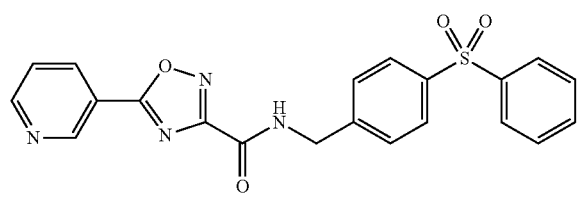 [SMILES: O=C(NCc1ccc(S(=O)(=O)c2ccccc2)cc1)c1noc(-c2cccnc2)n1]
N-{[4-(benzenesulfonyl)phenyl]methyl}-5-(pyridin-3-yl)-1,2,4-oxadiazole-3-carboxamide TABLE 2-continued

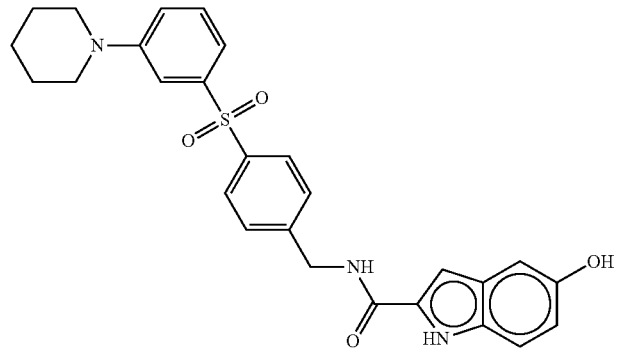

5-hydroxy-N-[(4-{[3-(piperidin-1-yl)benzene]sulfonyl}phenyl)methyl]-1H-indole-2-carboxamide

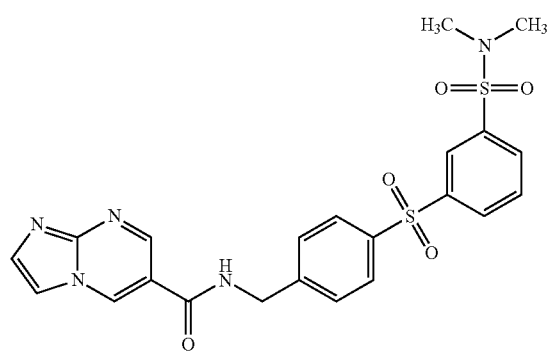 [SMILES: CN(C)S(=O)(=O)c1cccc(S(=O)(=O)c2ccc(CNC(=O)c3cnc4nccn4c3)cc2)c1]

N-[(4-{[3-(dimethylsulfamoyl)benzene]sulfonyl}phenyl)methyl]imidazo[1,2-a]pyrimidine-6-carboxamide

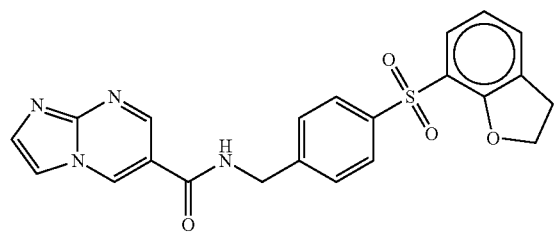

N-{[4-(2,3-dihydro-1-benzofuran-7-sulfonyl)phenyl]methyl}imidazo[1,2-a]pyridine-6-carboxamide

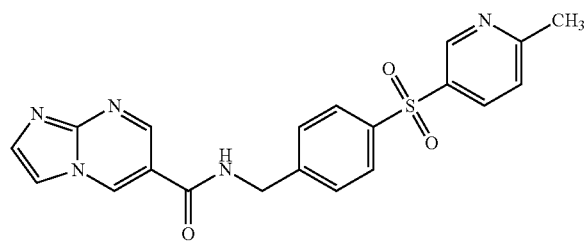 [SMILES: Cc1ccc(S(=O)(=O)c2ccc(CNC(=O)c3cnc4nccn4c3)cc2)cn1]

N-{[4-(6-methylpyridine-3-sulfonyl)phenyl]methyl}imidazo[1,2-a]pyrimidine-6-carboxamide

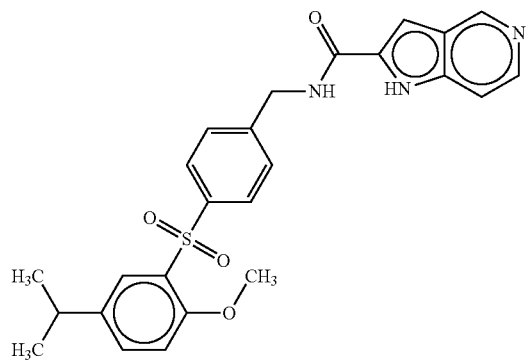

N-[(4-{[2-methoxy-5-(propan-2-yl)benzene]sulfonyl}phenyl)methyl]-1H-pyrrolo[3,2-c]pyridine-2-carboxamide TABLE 2-continued
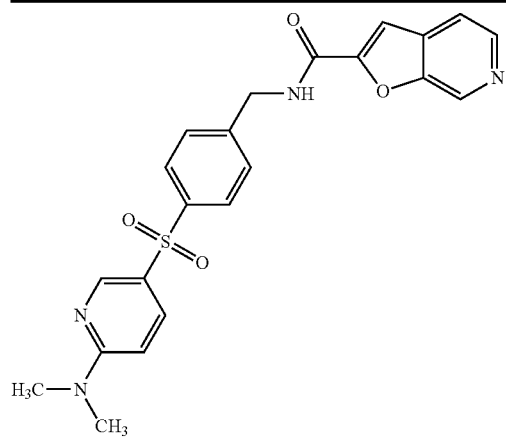
N-({4-[6-(dimethylamino)pyridine-3-sulfonyl]phenyl}methyl)furo[2,3-c]pyridine-2-carboxamide
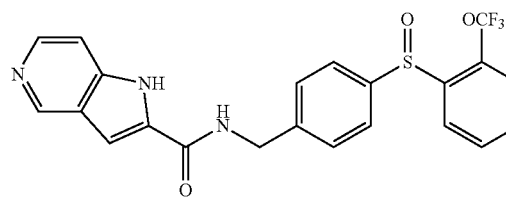
N-[(4-{[2-(trifluoromethoxy)benzene]sulfinyl}phenyl)methyl]-1H-pyrrolo[3,2-c]pyridine-2-carboxamide
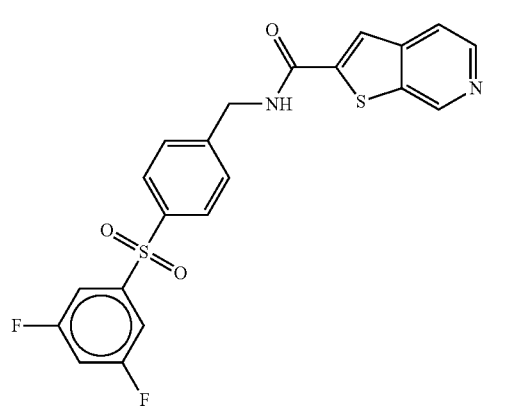
N-({4-[(3,5-difluorobenzene)sulfonyl]phenyl}methyl)thieno[2,3-c]pyridine-2-carboxamide
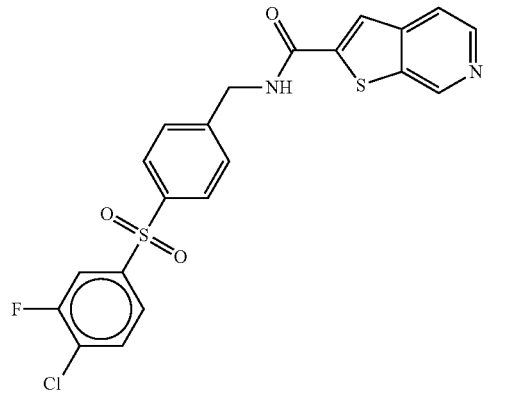
N-({4-[(4-chloro-3-fluorobenzene)sulfonyl]phenyl}methyl)thieno[2,3-c]pyridine-2-carboxamide TABLE 2-continued
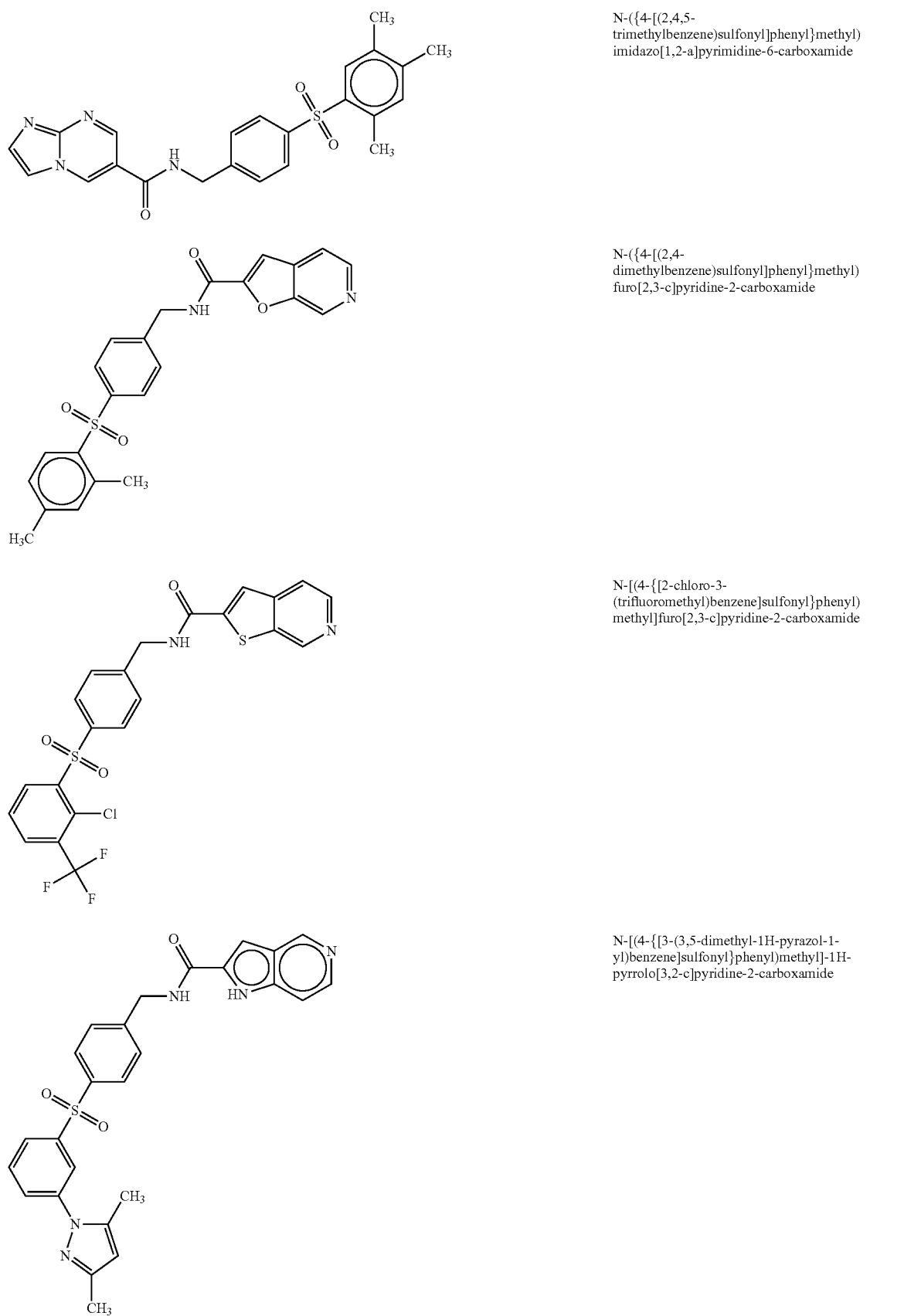
N-({4-[(2,4,5-trimethylbenzene)sulfonyl]phenyl}methyl)imidazo[1,2-a]pyrimidine-6-carboxamide
N-({4-[(2,4-dimethylbenzene)sulfonyl]phenyl}methyl)furo[2,3-c]pyridine-2-carboxamide
N-[(4-{[2-chloro-3-(trifluoromethyl)benzene]sulfonyl}phenyl)methyl]furo[2,3-c]pyridine-2-carboxamide
N-[(4-{[3-(3,5-dimethyl-1H-pyrazol-1-yl)benzene]sulfonyl}phenyl)methyl]-1H-pyrrolo[3,2-c]pyridine-2-carboxamide TABLE 2-continued
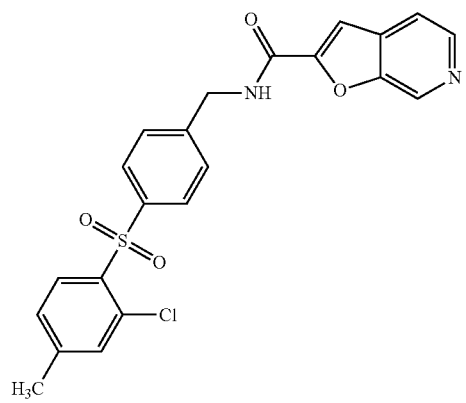
N-({4-[(2-chloro-4-methylbenzene)sulfonyl]phenyl}methyl)furo[2,3-c]pyridine-2-carboxamide
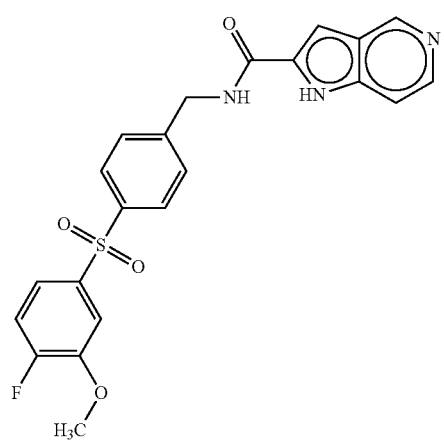
N-({4-[(4-fluoro-3-methoxybenzene)sulfonyl]phenyl}methyl)-1H-pyrrolo[3,2-c]pyridine-2-carboxamide
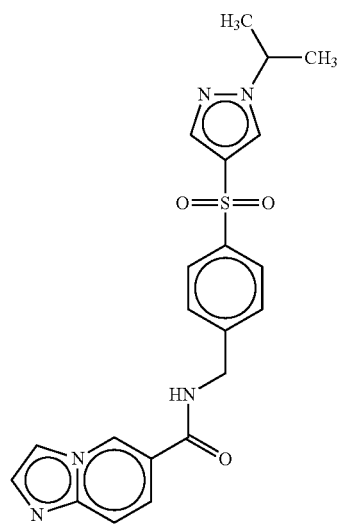
N-({4-[1-(propan-2-yl)-1H-pyrazole-4-sulfonyl]phenyl}methyl)imidazo[1,2-a]pyridine-6-carboxamide TABLE 2-continued
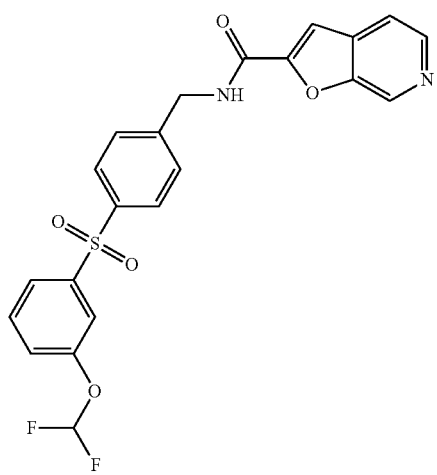 [SMILES: O=C(NCc1ccc(S(=O)(=O)c2cccc(OC(F)F)c2)cc1)c1cc2ccncc2o1]
N-[(4-{[3-(difluoromethoxy)benzene]sulfonyl}phenyl)methyl]furo[2,3-c]pyridine-2-carboxamide
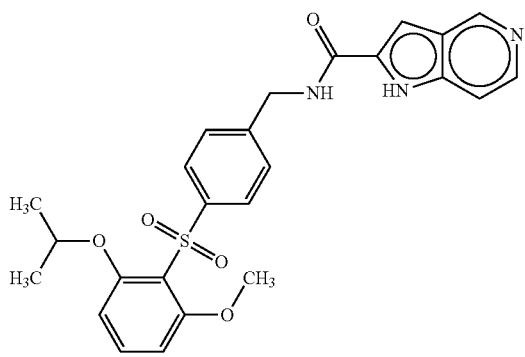
N-[(4-{[2-methoxy-6-(propan-2-yloxy)benzene]sulfonyl}phenyl)methyl]-1H-pyrrolo[3,2-c]pyridine-2-carboxamide
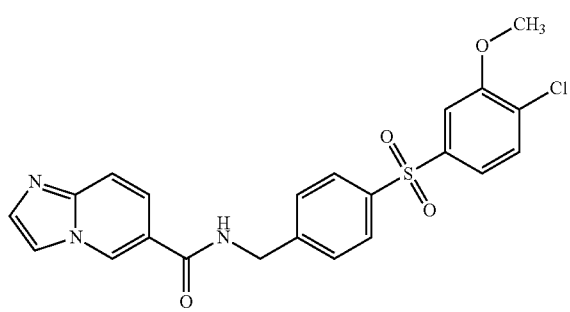 [SMILES: COc1cc(S(=O)(=O)c2ccc(CNC(=O)c3ccc4nccn4c3)cc2)ccc1Cl]
N-({4-[(4-chloro-3-methoxybenzene)sulfonyl]phenyl}methyl)imidazo[1,2-a]pyridine-6-carboxamide
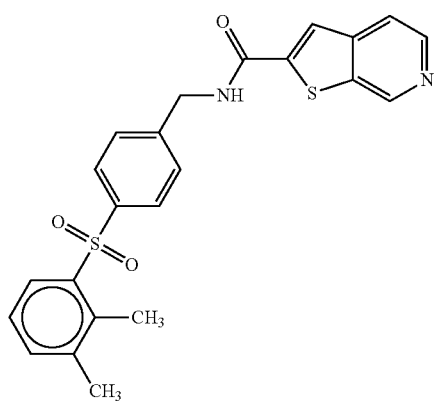
N-({4-[(2,3-dimethylbenzene)sulfonyl]phenyl}methyl)thieno[2,3-c]pyridine-2-carboxamide TABLE 2-continued
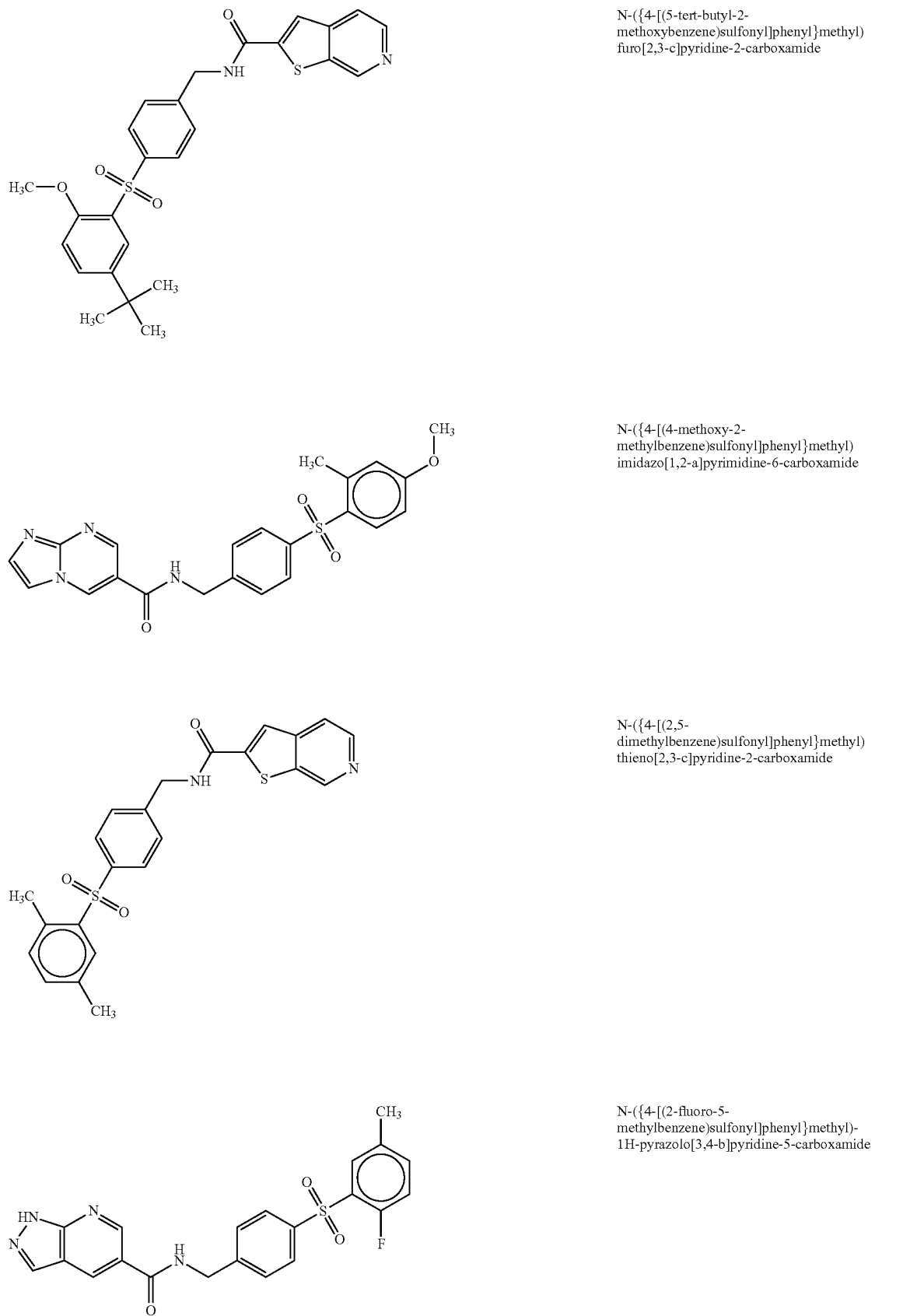
N-({4-[(5-tert-butyl-2-methoxybenzene)sulfonyl]phenyl}methyl)furo[2,3-c]pyridine-2-carboxamide
N-({4-[(4-methoxy-2-methylbenzene)sulfonyl]phenyl}methyl)imidazo[1,2-a]pyrimidine-6-carboxamide
N-({4-[(2,5-dimethylbenzene)sulfonyl]phenyl}methyl)thieno[2,3-c]pyridine-2-carboxamide
N-({4-[(2-fluoro-5-methylbenzene)sulfonyl]phenyl}methyl)-1H-pyrazolo[3,4-b]pyridine-5-carboxamide TABLE 2-continued
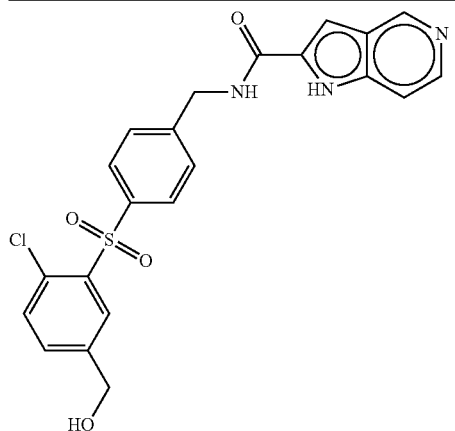
N-[(4-{[2-chloro-5-(hydroxymethyl)benzene]sulfonyl}phenyl)methyl]-1H-pyrrolo[3,2-c]pyridine-2-carboxamide
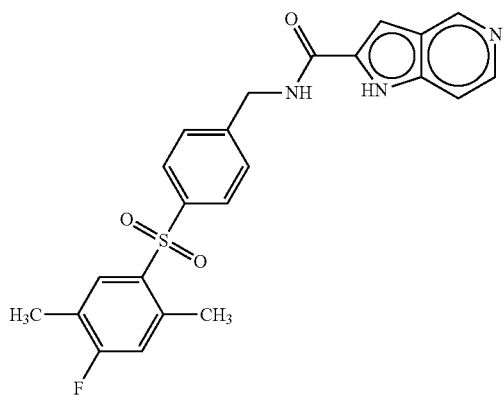
N-({4-[(4-fluoro-2,5-dimethylbenzene)sulfonyl]phenyl}methyl)-1H-pyrrolo[3,2-c]pyridine-2-carboxamide
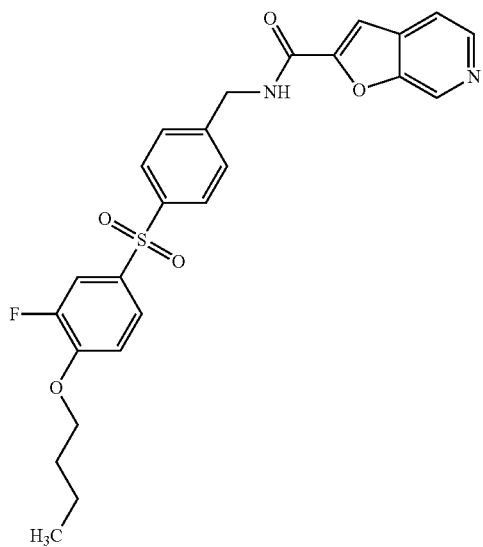 [SMILES: CCCCOc1ccc(S(=O)(=O)c2ccc(CNC(=O)c3cc4ccncc4o3)cc2)cc1F]
N-({4-[(4-butoxy-3-fluorobenzene)sulfonyl]phenyl}methyl)furo[2,3-c]pyridine-2-carboxamide
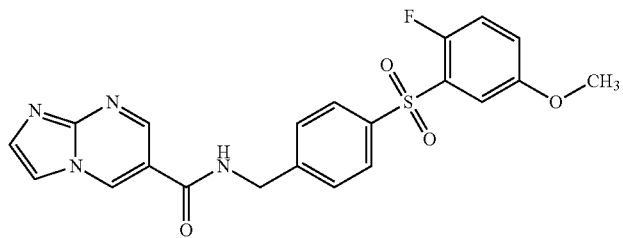
N-({4-[(2-fluoro-5-methoxybenzene)sulfonyl]phenyl}methyl)imidazo[1,2-a]pyrimidine-6-carboxamide TABLE 2-continued

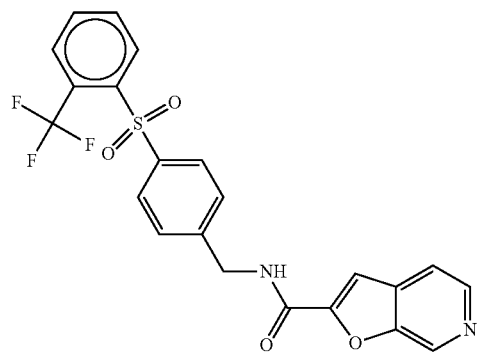

N-[(4-{[2-(trifluoromethyl)benzene]sulfonyl}phenyl)methyl]furo[2,3-c]pyridine-2-carboxamide

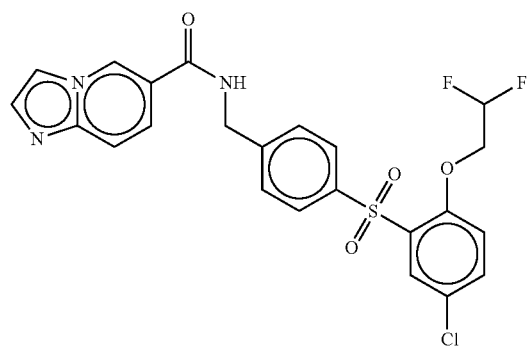

N-[(4-{[5-chloro-2-(2,2-difluoroethoxy)benzene]sulfonyl}phenyl)methyl]imidazo[1,2-a]pyridine-6-carboxamide

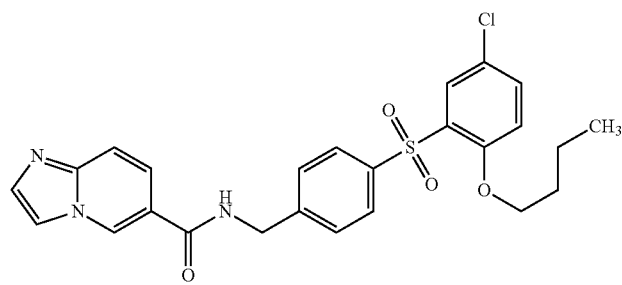

N-({4-[(2-butoxy-5-chlorobenzene)sulfonyl]phenyl}methyl)imidazo[1,2-a]pyridine-6-carboxamide

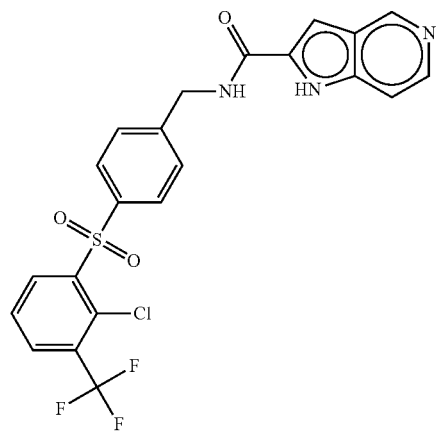

N-[(4-{[2-chloro-3-(trifluoromethyl)benzene]sulfonyl}phenyl)methyl]-1H-pyrrolo[3,2-c]pyridine-2-carboxamide TABLE 2-continued
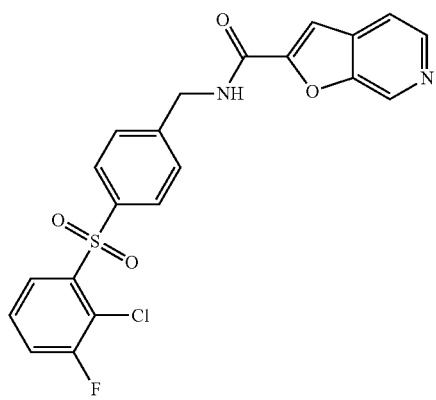 [SMILES: O=C(NCc1ccc(S(=O)(=O)c2cccc(F)c2Cl)cc1)c1cc2ccncc2o1]
N-({4-[(2-chloro-3-fluorobenzene)sulfonyl]phenyl}methyl)furo[2,3-c]pyridine-2-carboxamide
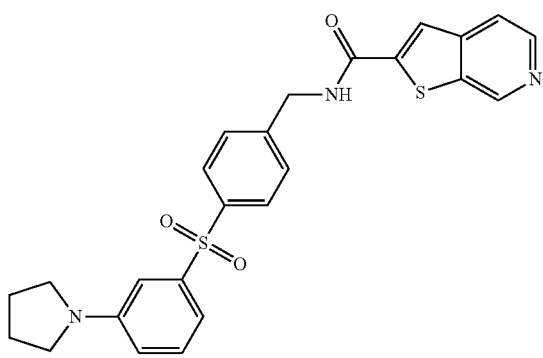 [SMILES: O=C(NCc1ccc(S(=O)(=O)c2cccc(N3CCCC3)c2)cc1)c1cc2ccncc2s1]
N-[(4-{[3-(pyrrolidin-1-yl)benzene]sulfonyl}phenyl)methyl]thieno[2,3-c]pyridine-2-carboxamide
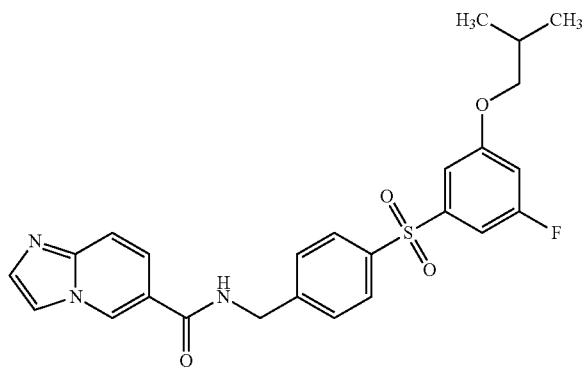 [SMILES: CC(C)COc1cc(F)cc(S(=O)(=O)c2ccc(CNC(=O)c3ccc4nccn4c3)cc2)c1]
N-[(4-{[3-fluoro-5-(2-methylpropoxy)benzene]sulfonyl}phenyl)methyl]imidazo[1,2-a]pyridine-6-carboxamide
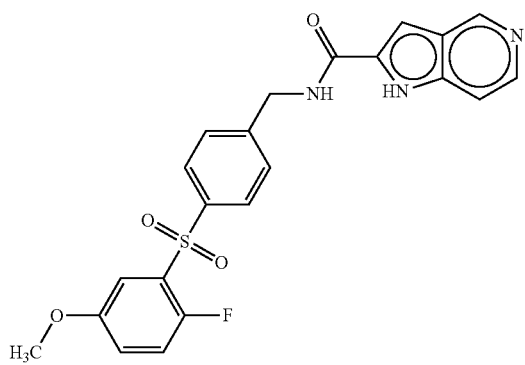
N-({4-[(2-fluoro-5-methoxybenzene)sulfonyl]phenyl}methyl)-1H-pyrrolo[3,2-c]pyridine-2-carboxamide TABLE 2-continued
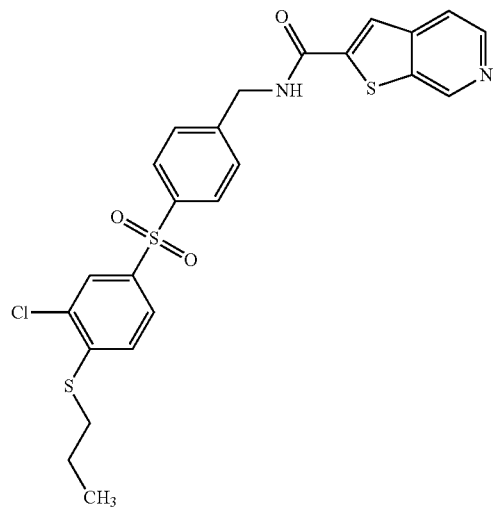
N-({4-[(3-chloro-4-propoxybenzene)sulfonyl]phenyl}methyl)thieno[2,3-c]pyridine-2-carboxamide
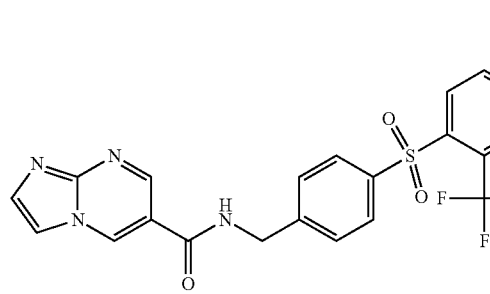
N-[(4-{[2,4-bis(trifluoromethyl)benzene]sulfonyl}phenyl)methyl]imidazo[1,2-a]pyrimidine-6-carboxamide
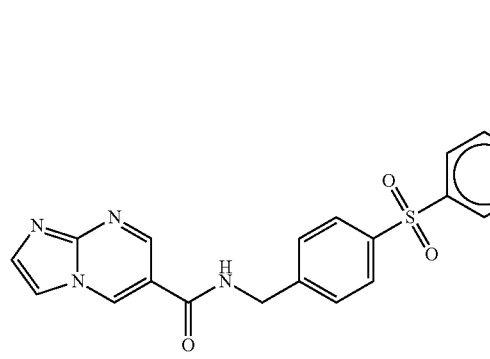
N-({4-[(4-propoxybenzene)sulfonyl]phenyl}methyl)imidazo[1,2-a]pyrimidine-6-carboxamide
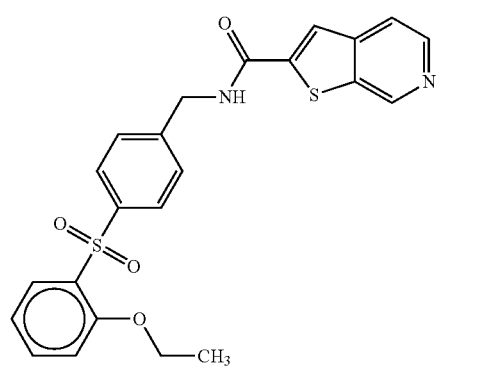
N-({4-[(2-ethoxybenzene)sulfonyl]phenyl}methyl)thieno[2,3-c]pyridine-2-carboxamide TABLE 2-continued

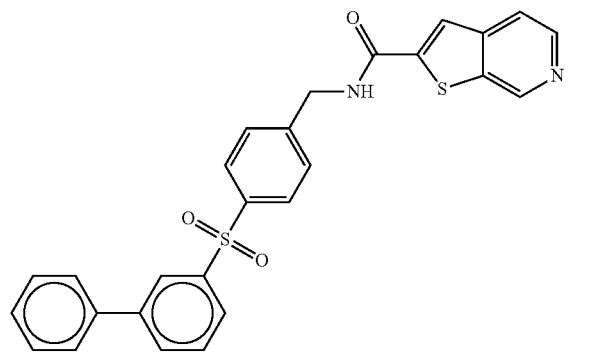
N-({4-[(3-phenylbenzene)sulfonyl]phenyl}methyl)thieno[2,3-c]pyridine-2-carboxamide

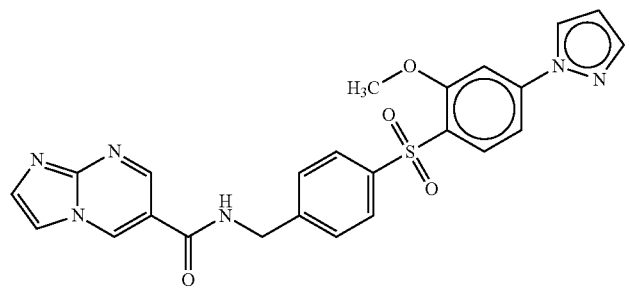
N-[(4-{[2-methoxy-4-(1H-pyrazol-1-yl)benzene]sulfonyl}phenyl)methyl]imidazo[1,2-a]pyrimidine-6-carboxamide

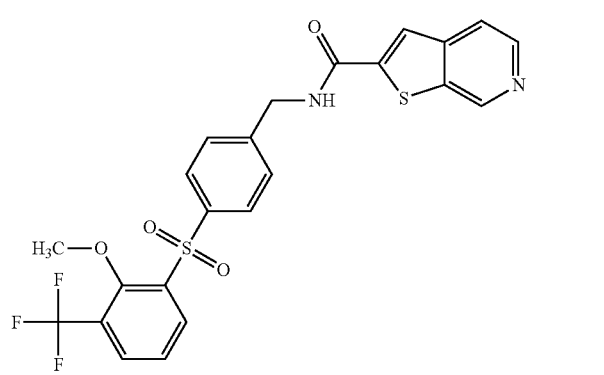 [SMILES: COc1c(C(F)(F)F)cccc1S(=O)(=O)c1ccc(CNC(=O)c2cc3ccncc3s2)cc1]
N-[(4-{[2-methoxy-3-(trifluoromethyl)benzene]sulfonyl}phenyl)methyl]thieno[2,3-c]pyridine-2-carboxamide

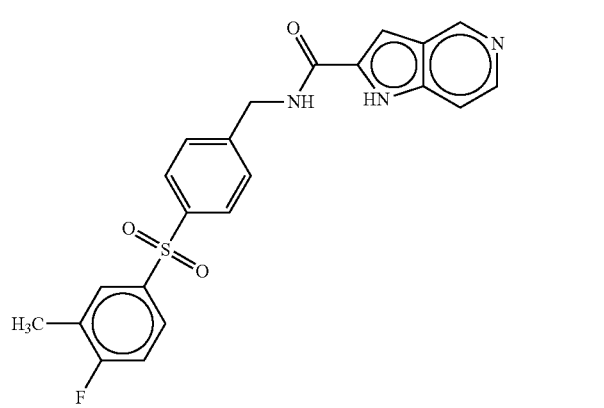
N-({4-[(4-fluoro-3-methylbenzene)sulfonyl]phenyl}methyl)-1H-pyrrolo[3,2-c]pyridine-2-carboxamide

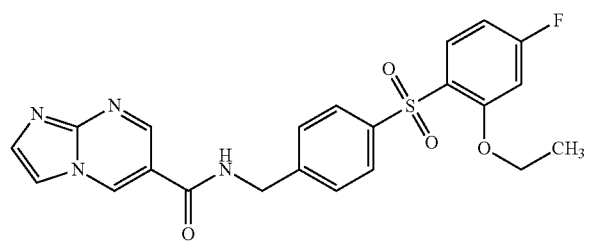 [SMILES: CCOc1cc(F)ccc1S(=O)(=O)c1ccc(CNC(=O)c2cnc3nccn3c2)cc1]
N-({4-[(2-ethoxy-4-fluorobenzene)sulfonyl]phenyl}methyl)imidazo[1,2-a]pyrimidine-6-carboxamide TABLE 2-continued
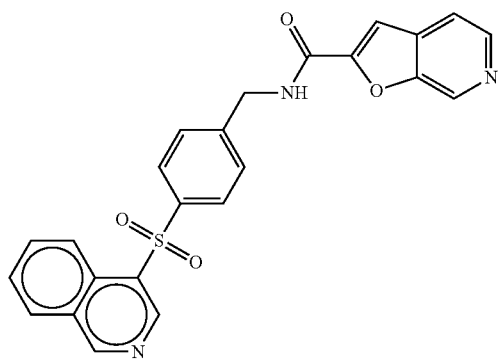
N-{[4-(isoquinoline-4-sulfonyl)phenyl]methyl}furo[2,3-c]pyridine-2-carboxamide
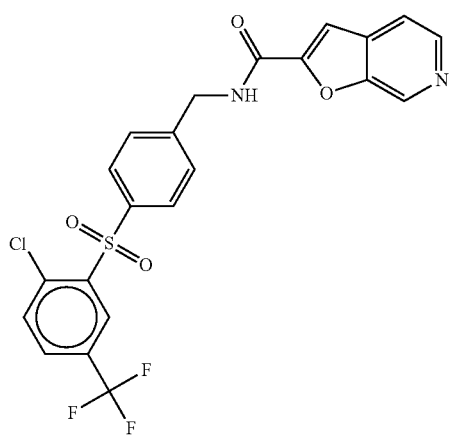
N-[(4-{[2-chloro-5-(trifluoromethyl)benzene]sulfonyl}phenyl)methyl]furo[2,3-c]pyridine-2-carboxamide
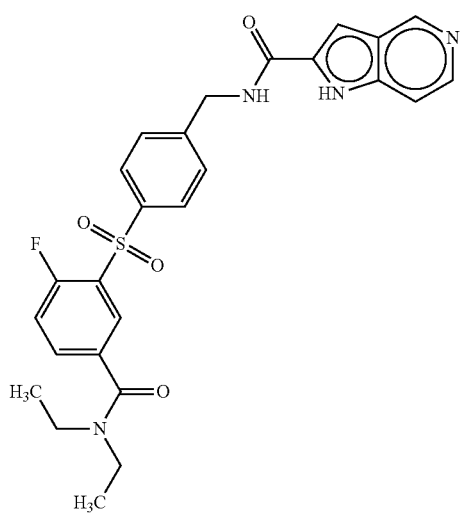
N-[(4-{[5-(diethylcarbamoyl)-2-fluorobenzene]sulfonyl}phenyl)methyl]-1H-pyrrolo[3,2-c]pyridine-2-carboxamide
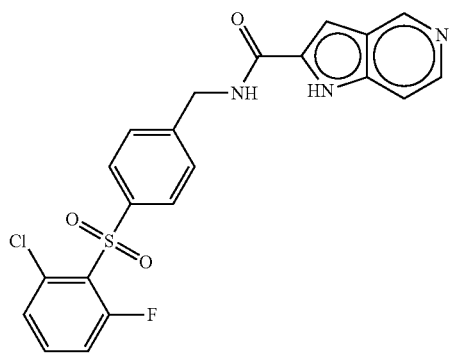
N-({4-[(2-chloro-6-fluorobenzene)sulfonyl]phenyl}methyl)-1H-pyrrolo[3,2-c]pyridine-2-carboxamide TABLE 2-continued
| | |
|---|---|
| 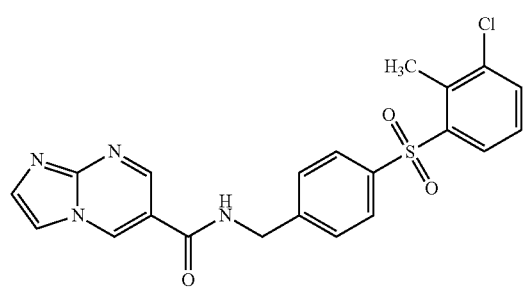 | N-({4-[(3-chloro-2-methylbenzene)sulfonyl]phenyl}methyl)imidazo[1,2-a]pyrimidine-6-carboxamide |
| 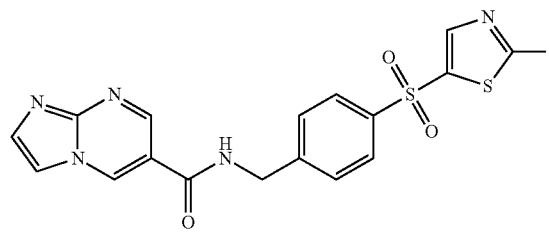 | N-({4-[2-(pyrrolidin-1-yl)-1,3-thiazole-5-sulfonyl]phenyl}methyl)imidazo[1,2-a]pyrimidine-6-carboxamide |
| 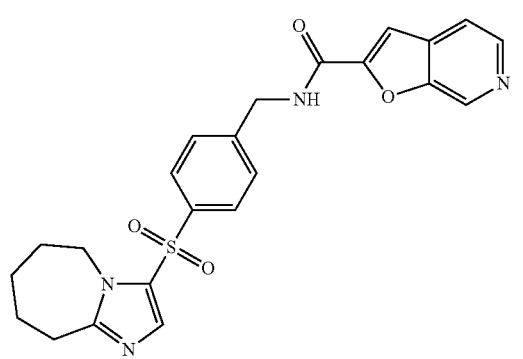 | N-[(4-{5H,6H,7H,8H,9H-imidazo[1,2-a]azepine-3-sulfonyl}phenyl)methyl]furo[2,3-c]pyridine-2-carboxamide |
| 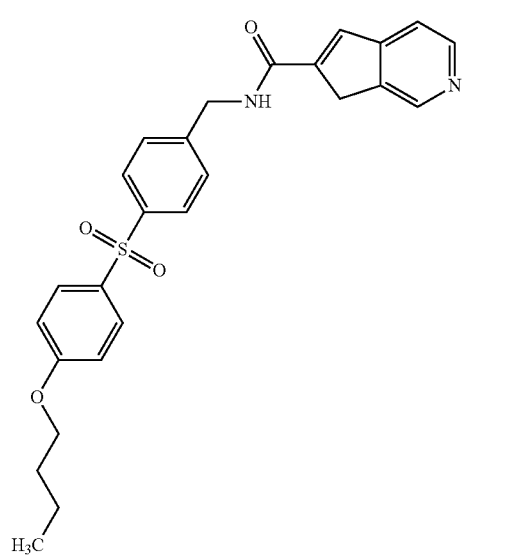 | N-({4-[(4-butoxybenzene)sulfonyl]phenyl}methyl)furo[2,3-c]pyridine-2-carboxamide |

TABLE 2-continued

| Structure | Name |
|---|---|
| (structure) | N-({4-[(3,5-dimethylbenzene)sulfonyl]phenyl}methyl)imidazo[1,2-a]pyrimidine-6-carboxamide |
| (structure) | N-({4-[(5-chloro-2-methylbenzene)sulfonyl]phenyl}methyl)imidazo[1,2-a]pyrimidine-6-carboxamide |
| (structure) | N-[(4-{[3-fluoro-4-(methylsulfanyl)benzene]sulfonyl}phenyl)methyl]furo[2,3-c]pyridine-2-carboxamide |
| (structure) | N-({4-[(4-fluoro-3-methylbenzene)sulfonyl]phenyl}methyl)imidazo[1,2-a]pyrimidine-6-carboxamide |
| (structure) | N-({4-[(3-tert-butylbenzene)sulfonyl]phenyl}methyl)furo[2,3-c]pyridine-2-carboxamide |

TABLE 2-continued

| | |
|---|---|
| 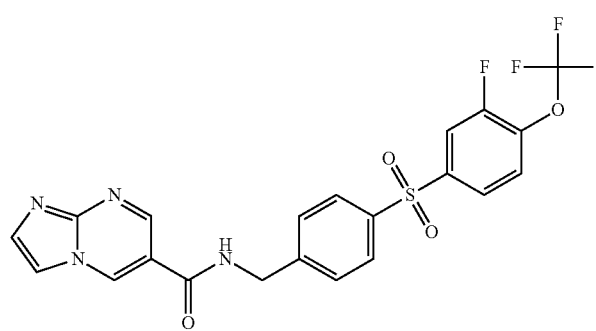 | N-[(4-{[3-fluoro-4-(trifluoromethoxy)benzene]sulfonyl}phenyl)methyl]imidazo[1,2-a]pyridine-6-carboxamide |
| 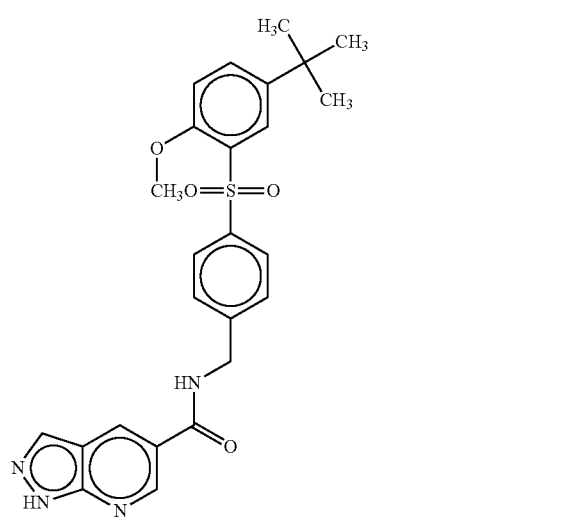 | N-({4-[(5-tert-butyl-2-methoxybenzene)sulfonyl]phenyl}methyl)-1H-pyrazolo[3,4-b]pyridine-5-carboxamide |
| 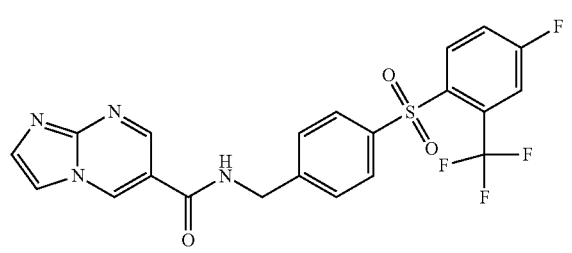 [SMILES: O=C(NCc1ccc(S(=O)(=O)c2ccc(F)cc2C(F)(F)F)cc1)c1cnc2nccn2c1] | N-[(4-{[4-fluoro-2-(trifluoromethyl)benzene]sulfonyl}phenyl)methyl]imidazo[1,2-a]pyridine-6-carboxamide |
| 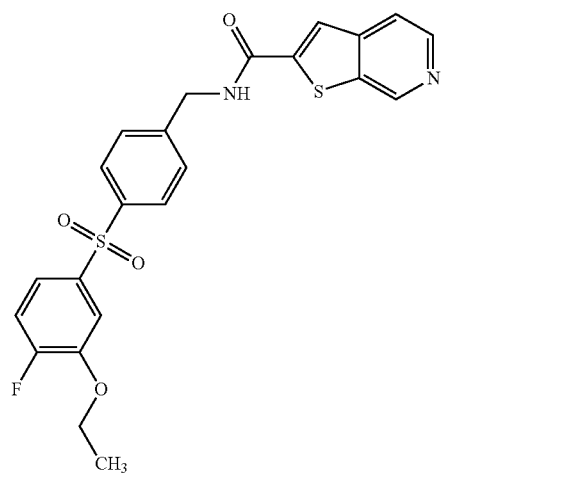 [SMILES: CCOc1cc(S(=O)(=O)c2ccc(CNC(=O)c3cc4ccncc4s3)cc2)ccc1F] | N-({4-[(3-ethoxy-4-fluorobenzene)sulfonyl]phenyl}methyl)thieno[2,3-c]pyridine-2-carboxamide |

TABLE 2-continued
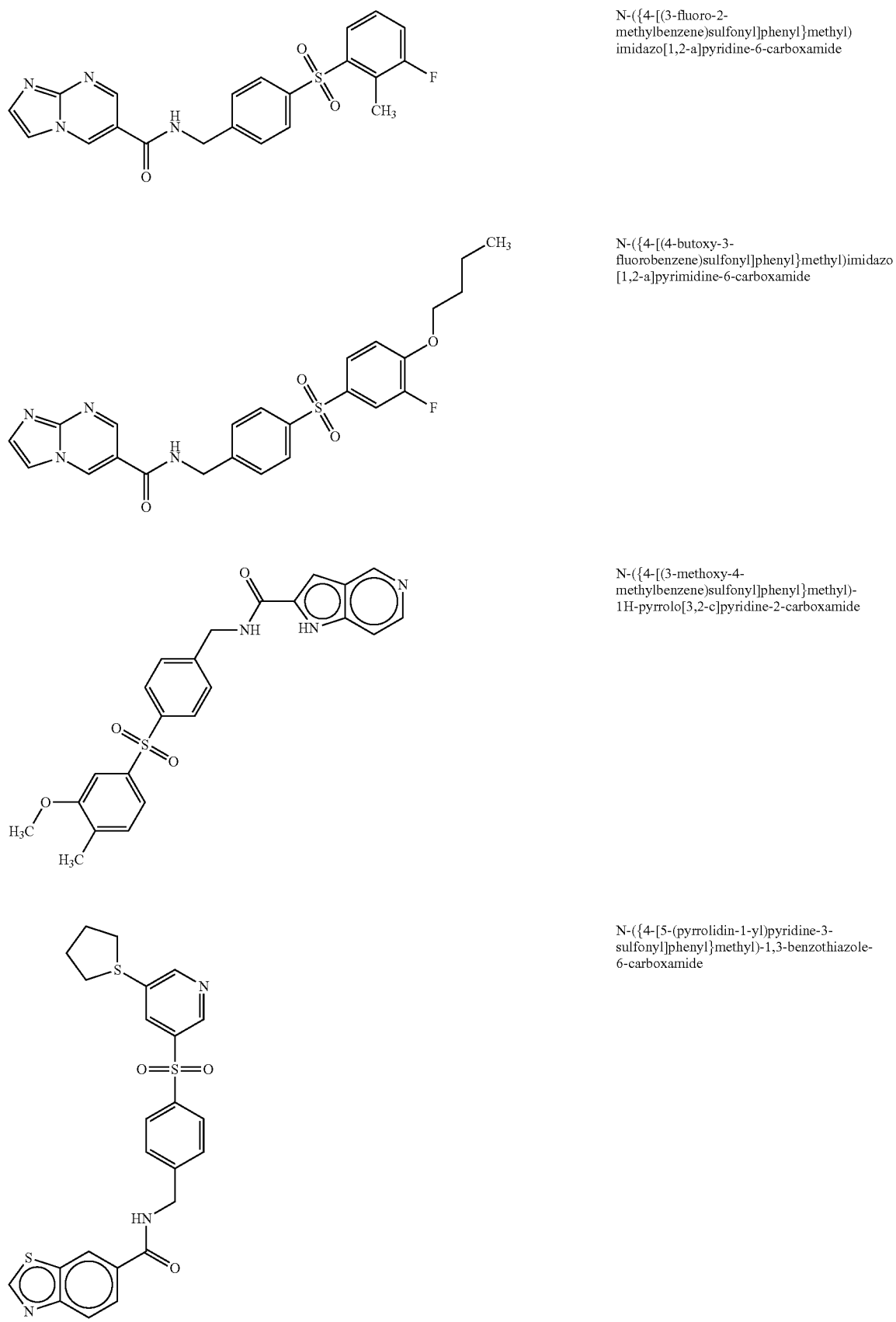
N-({4-[(3-fluoro-2-methylbenzene)sulfonyl]phenyl}methyl)imidazo[1,2-a]pyridine-6-carboxamide
N-({4-[(4-butoxy-3-fluorobenzene)sulfonyl]phenyl}methyl)imidazo[1,2-a]pyrimidine-6-carboxamide
N-({4-[(3-methoxy-4-methylbenzene)sulfonyl]phenyl}methyl)-1H-pyrrolo[3,2-c]pyridine-2-carboxamide
N-({4-[5-(pyrrolidin-1-yl)pyridine-3-sulfonyl]phenyl}methyl)-1,3-benzothiazole-6-carboxamide TABLE 2-continued
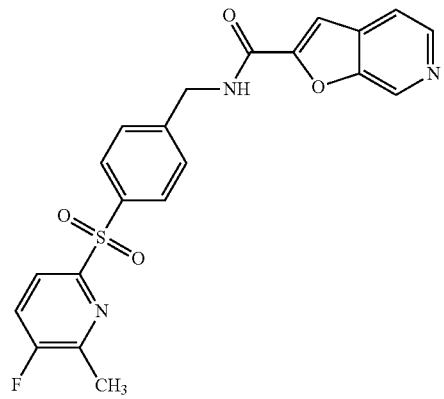 [SMILES: Cc1nc(S(=O)(=O)c2ccc(CNC(=O)c3cc4ccncc4o3)cc2)ccc1F]
N-{[4-(5-fluoro-6-methylpyridine-2-sulfonyl)phenyl]methyl}furo[2,3-c]pyridine-2-carboxamide
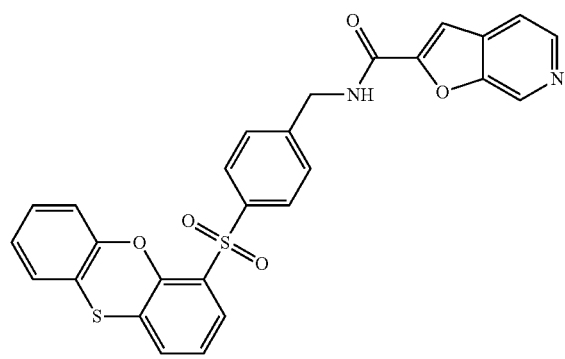 [SMILES: O=C(NCc1ccc(S(=O)(=O)c2cccc3c2Oc2ccccc2S3)cc1)c1cc2ccncc2o1]
N-{[4-(phenoxathiine-4-sulfonyl)phenyl]methyl}furo[2,3-c]pyridine-2-carboxamide
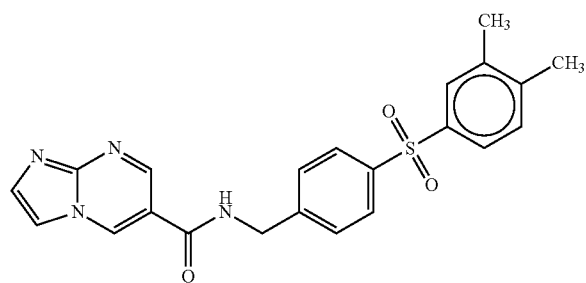
N-({4-[(3,4-dimethylbenzene)sulfonyl]phenyl}methyl)imidazo[1,2-a]pyrimidine-6-carboxamide
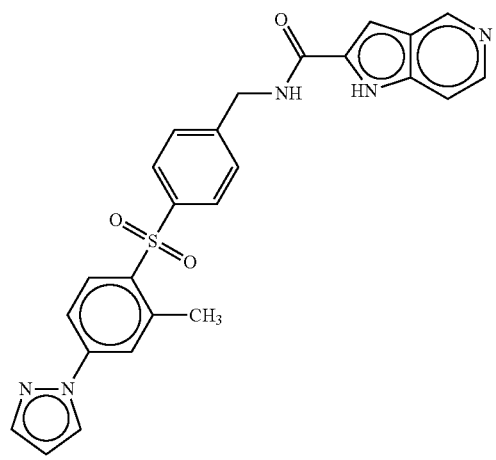
N-[(4-{[2-methyl-4-(1H-pyrazol-1-yl)benzene]sulfonyl}phenyl)methyl]-1H-pyrrolo[3,2-c]pyridine-2-carboxamide TABLE 2-continued
| | |
|---|---|
| 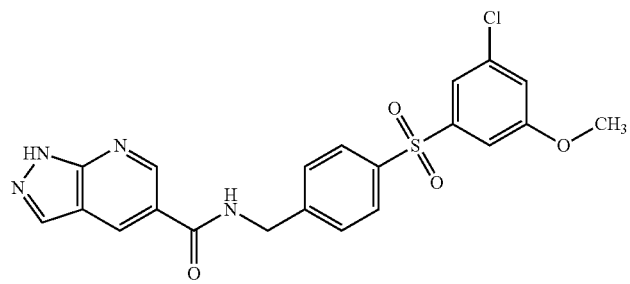 [SMILES: COc1cc(Cl)cc(S(=O)(=O)c2ccc(CNC(=O)c3cnc4[nH]ncc4c3)cc2)c1] | N-({4-[(3-chloro-5-methoxybenzene)sulfonyl]phenyl}methyl)-1H-pyrazolo[3,4-b]pyridine-5-carboxamide |
| 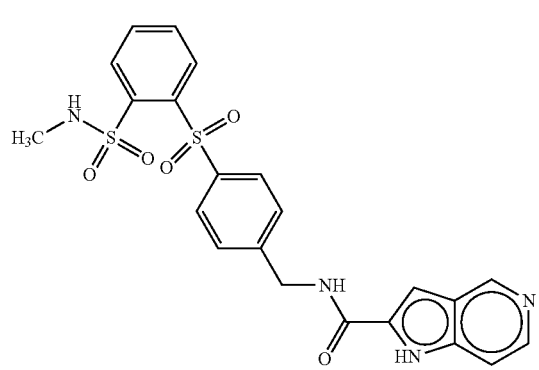 | N-[(4-{[2-(methylsulfamoyl)benzene]sulfonyl}phenyl)methyl]-1H-pyrrolo[3,2-c]pyridine-2-carboxamide |
| 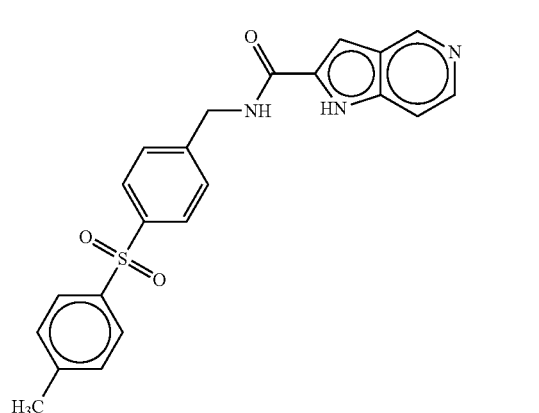 | N-({4-[(4-methylbenzene)sulfonyl]phenyl}methyl)-1H-pyrrolo[3,2-c]pyridine-2-carboxamide |
| 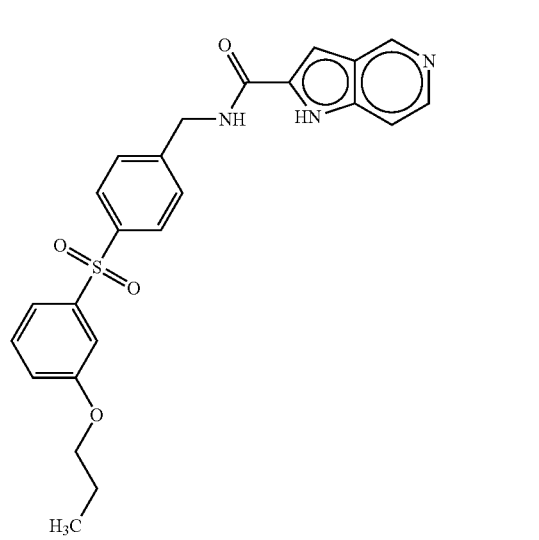 | N-({4-[(3-propoxybenzene)sulfonyl]phenyl}methyl)-1H-pyrrolo[3,2-c]pyridine-2-carboxamide |

TABLE 2-continued

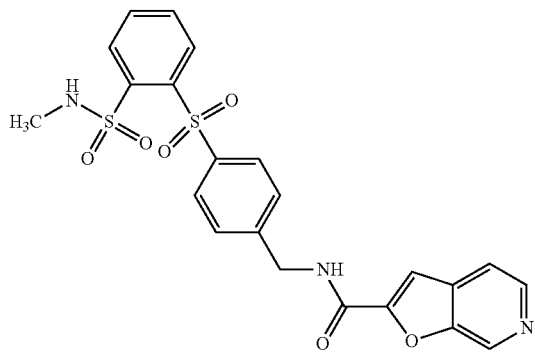 [SMILES: CNS(=O)(=O)c1ccccc1S(=O)(=O)c1ccc(CNC(=O)c2cc3ccncc3o2)cc1]
N-[(4-{[2-(methylsulfamoyl)benzene]sulfonyl}phenyl)methyl]furo[2,3-c]pyridine-2-carboxamide

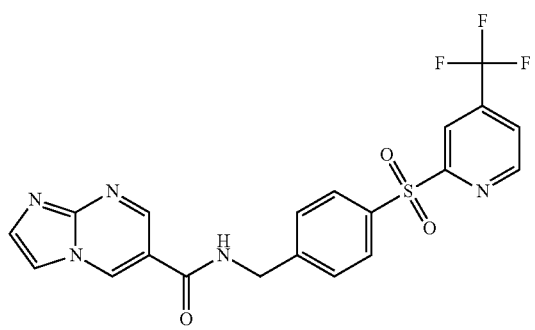
N-({4-[4-(trifluoromethyl)pyridine-2-sulfonyl]phenyl}methyl)imidazo[1,2-a]pyrimidine-6-carboxamide

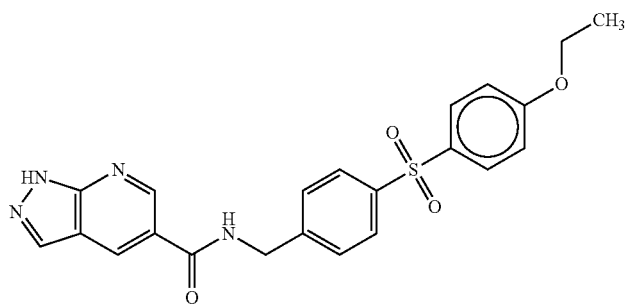
N-({4-[(4-ethoxybenzene)sulfonyl]phenyl}methyl)-1H-pyrazolo[3,4-b]pyridine-5-carboxamide

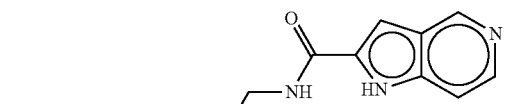
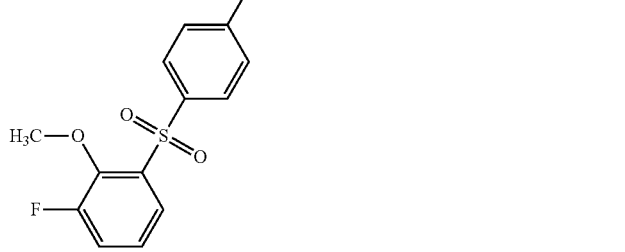
N-({4-[(3-fluoro-2-methoxybenzene)sulfonyl]phenyl}methyl)-1H-pyrrolo[3,2-c]pyridine-2-carboxamide

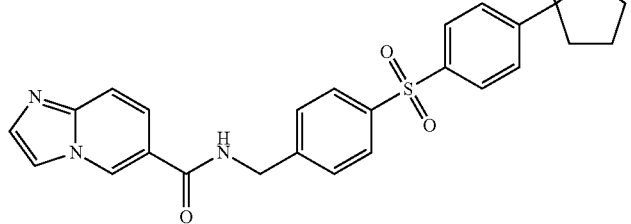
N-[(4-{[4-(1-cyanocyclopentyl)benzene]sulfonyl}phenyl)methyl]imidazo[1,2-a]pyridine-6-carboxamide TABLE 2-continued
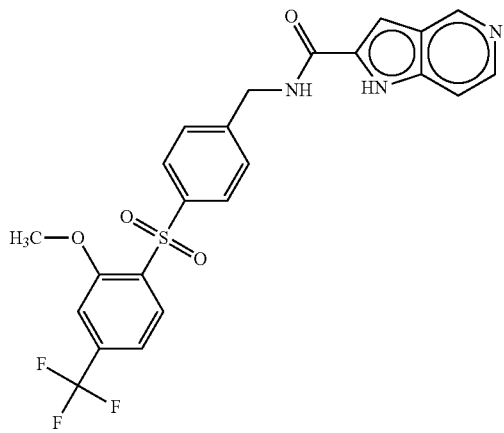
N-[(4-{[2-methoxy-4-(trifluoromethyl)benzene]sulfonyl}phenyl)methyl]-1H-pyrrolo[3,2-c]pyridine-2-carboxamide
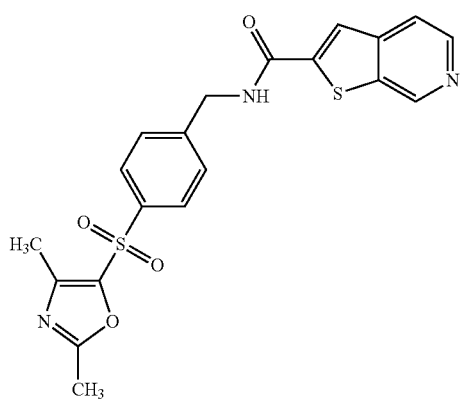 [SMILES: Cc1nc(C)c(S(=O)(=O)c2ccc(CNC(=O)c3cc4ccncc4s3)cc2)o1]
N-{[4-(dimethyl-1,3-thiazole-5-sulfonyl)phenyl]methyl}thieno[2,3-c]pyridine-2-carboxamide
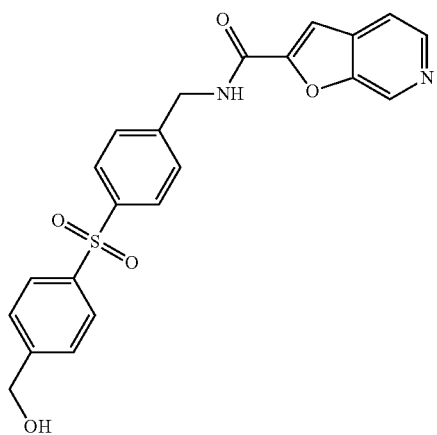 [SMILES: O=C(NCc1ccc(S(=O)(=O)c2ccc(CO)cc2)cc1)c1cc2ccncc2o1]
N-[(4-{[4-(hydroxymethyl)benzene]sulfonyl}phenyl)methyl]furo[2,3-c]pyridine-2-carboxamide
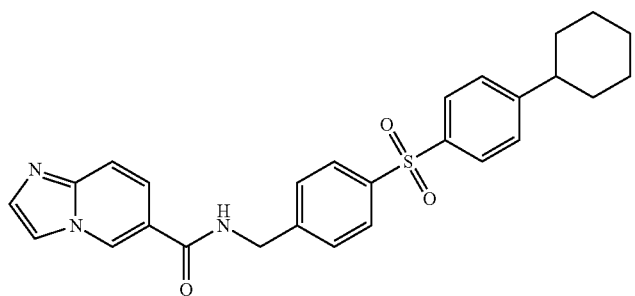
N-({4-[(4-cyclohexylbenzene)sulfonyl]phenyl}methyl)imidazo[1,2-a]pyridine-6-carboxamide TABLE 2-continued

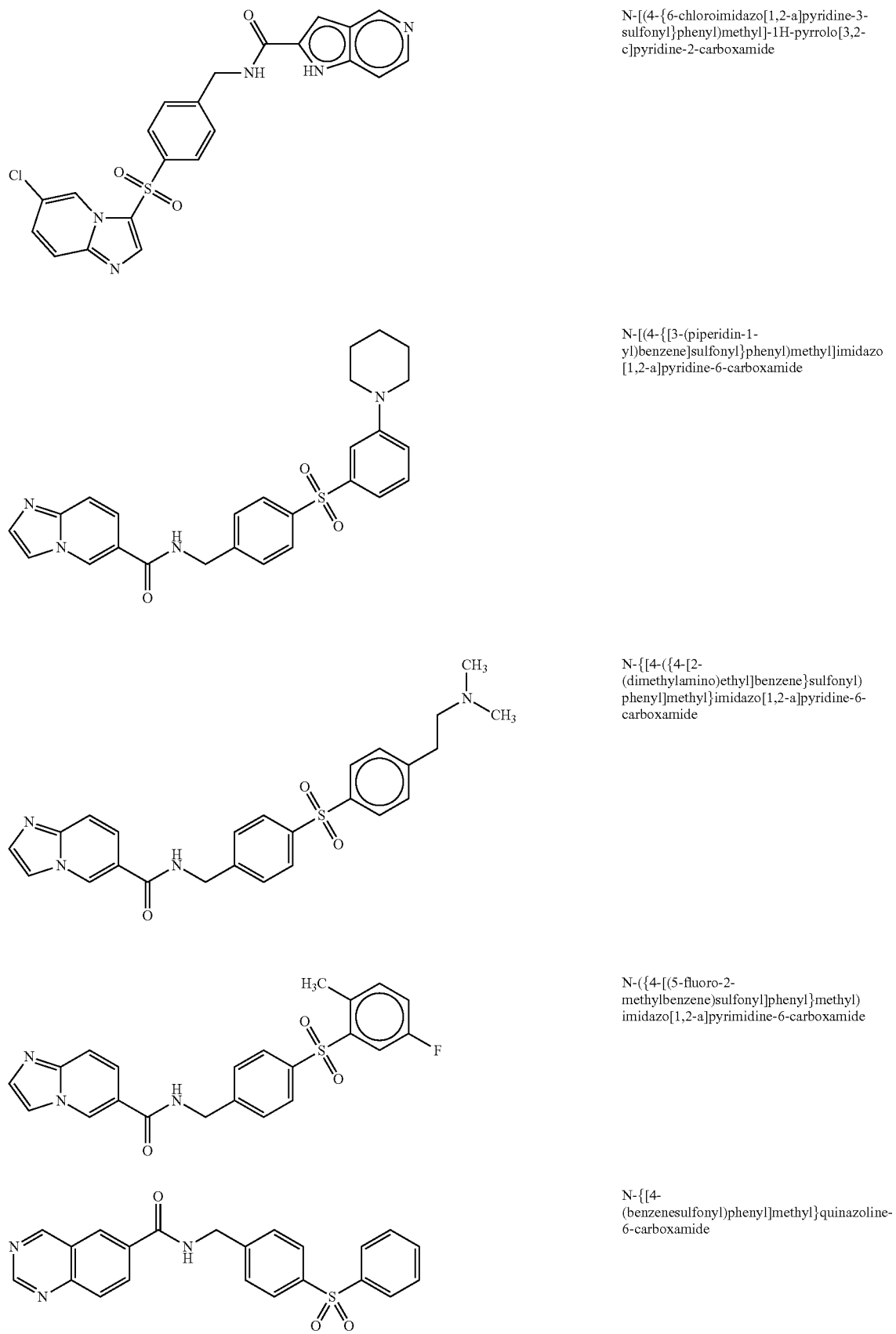

N-[(4-{6-chloroimidazo[1,2-a]pyridine-3-sulfonyl}phenyl)methyl]-1H-pyrrolo[3,2-c]pyridine-2-carboxamide N-[(4-{[3-(piperidin-1-yl)benzene]sulfonyl}phenyl)methyl]imidazo[1,2-a]pyridine-6-carboxamide N-{[4-({4-[2-(dimethylamino)ethyl]benzene}sulfonyl)phenyl]methyl}imidazo[1,2-a]pyridine-6-carboxamide N-({4-[(5-fluoro-2-methylbenzene)sulfonyl]phenyl}methyl)imidazo[1,2-a]pyrimidine-6-carboxamide N-{[4-(benzenesulfonyl)phenyl]methyl}quinazoline-6-carboxamide TABLE 2-continued
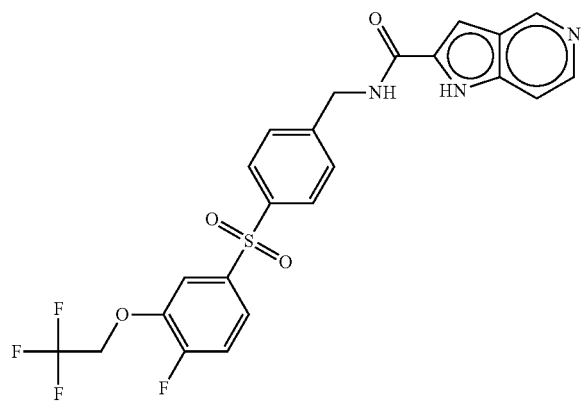
N-[(4-{[4-fluoro-3-(2,2,2-trifluoroethoxy)benzene]sulfonyl}phenyl)methyl]-1H-pyrrolo[3,2-c]pyridine-2-carboxamide
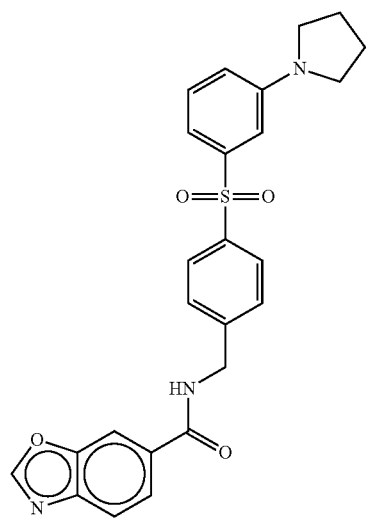
N-[(4-{[3-(pyrrolidin-1-yl)benzene]sulfonyl}phenyl)methyl]-1,3-benzothiazole-6-carboxamide
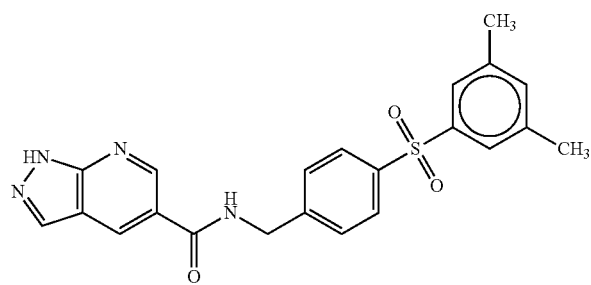
N-({4-[(3,5-dimethylbenzene)sulfonyl]phenyl}methyl)-1H-pyrazolo[3,4-b]pyridine-5-carboxamide
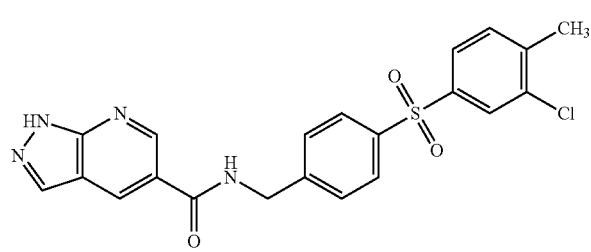 [SMILES: Cc1ccc(S(=O)(=O)c2ccc(CNC(=O)c3cnc4[nH]ncc4c3)cc2)cc1Cl]
N-({4-[(3-chloro-4-methylbenzene)sulfonyl]phenyl}methyl)-1H-pyrazolo[3,4-b]pyridine-5-carboxamide TABLE 2-continued

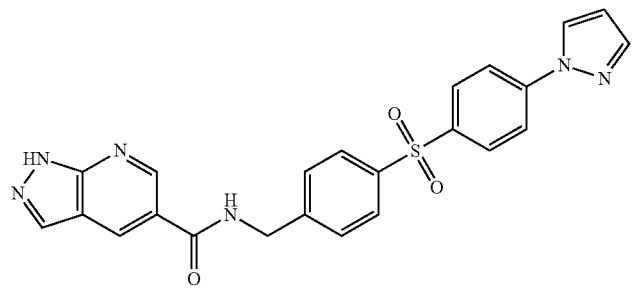 [SMILES: O=C(NCc1ccc(S(=O)(=O)c2ccc(-n3cccn3)cc2)cc1)c1cnc2[nH]ncc2c1]

N-[(4-{[4-(1H-pyrazol-1-yl)benzene]sulfonyl}phenyl)methyl]-1H-pyrazolo[3,4-b]pyridine-5-carboxamide

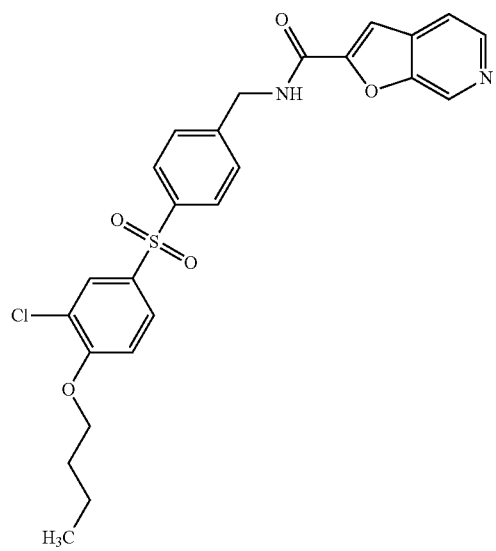

N-({4-[(4-butoxy-3-chlorobenzene)sulfonyl]phenyl}methyl)furo[2,3-c]pyridine-2-carboxamide

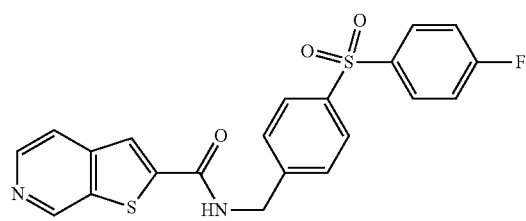 [SMILES: O=C(NCc1ccc(S(=O)(=O)c2ccc(F)cc2)cc1)c1cc2ccncc2s1]

N-({4-[(4-fluorobenzene)sulfonyl]phenyl}methyl)thieno[2,3-c]pyridine-2-carboxamide

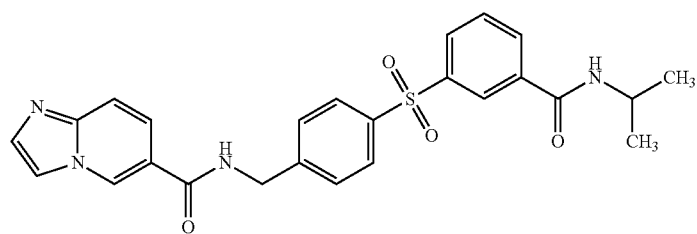 [SMILES: CC(C)NC(=O)c1cccc(S(=O)(=O)c2ccc(CNC(=O)c3ccc4nccn4c3)cc2)c1]

N-{[4-({3-[(propan-2-yl)carbamoyl]benzene}sulfonyl)phenyl]methyl}imidazo[1,2-a]pyridine-6-carboxamide

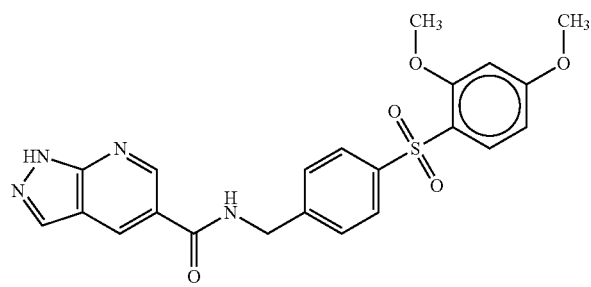

N-({4-[(2,4-dimethoxybenzene)sulfonyl]phenyl}methyl)-1H-pyrazolo[3,4-b]pyridine-5-carboxamide TABLE 2-continued
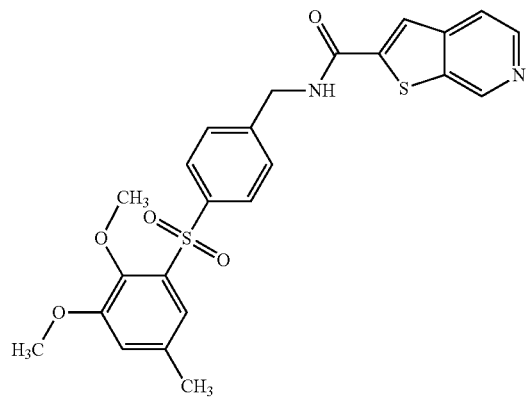 [SMILES: COc1cc(C)cc(S(=O)(=O)c2ccc(CNC(=O)c3cc4ccncc4s3)cc2)c1OC]
N-({4-[(2,3-dimethoxy-5-methylbenzene)sulfonyl]phenyl}methyl)thieno[2,3-c]pyridine-2-carboxamide
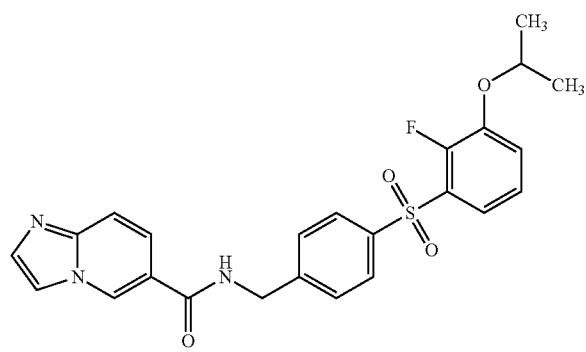 [SMILES: CC(C)Oc1cccc(S(=O)(=O)c2ccc(CNC(=O)c3ccc4nccn4c3)cc2)c1F]
N-[(4-{[2-fluoro-3-(propan-2-yloxy)benzene]sulfonyl}phenyl)methyl]imidazo[1,2-a]pyridine-6-carboxamide
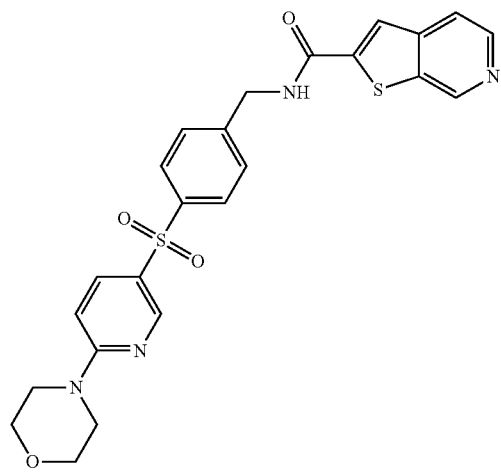
N-({4-[6-(morpholin-4-yl)pyridine-3-sulfonyl]phenyl}methyl)thieno[2,3-c]pyridine-2-carboxamide
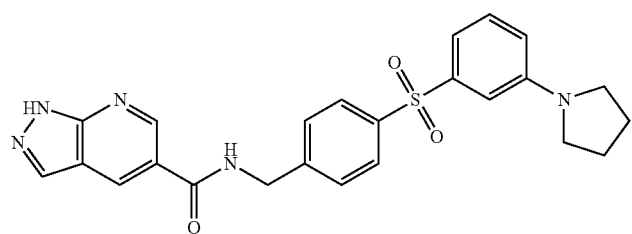 [SMILES: O=C(NCc1ccc(S(=O)(=O)c2cccc(N3CCCC3)c2)cc1)c1cnc2[nH]ncc2c1]
N-[(4-{[3-(pyrrolidin-1-yl)benzene]sulfonyl}phenyl)methyl]-1H-pyrazolo[3,4-b]pyridine-5-carboxamide TABLE 2-continued
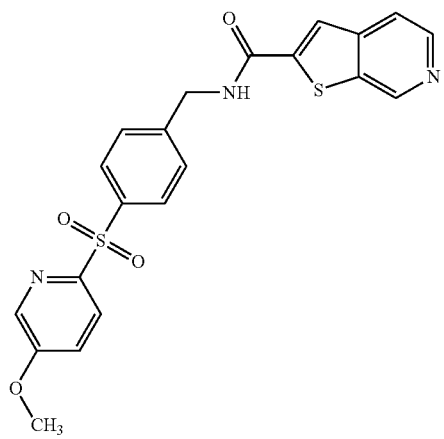 [SMILES: COc1ccc(S(=O)(=O)c2ccc(CNC(=O)c3cc4ccncc4s3)cc2)nc1]
N-{[4-(5-methoxypyridine-2-sulfonyl)phenyl]methyl}thieno[2,3-c]pyridine-2-carboxamide
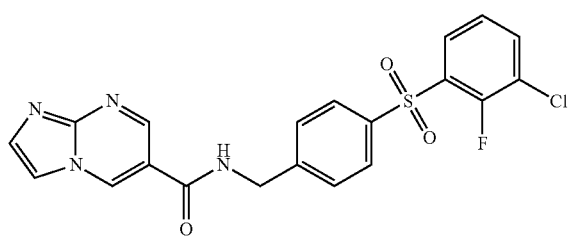 [SMILES: O=C(NCc1ccc(S(=O)(=O)c2cccc(Cl)c2F)cc1)c1cnc2nccn2c1]
N-({4-[(3-chloro-2-fluorobenzene)sulfonyl]phenyl}methyl)imidazo[1,2-a]pyrimidine-6-carboxamide
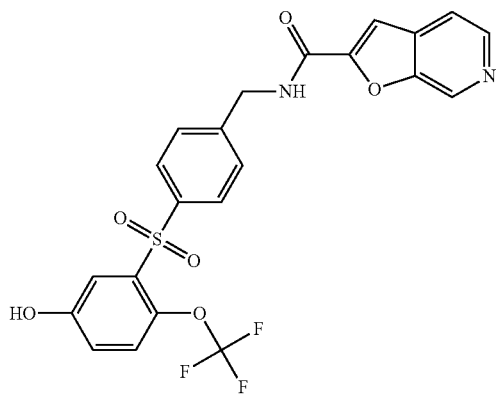 [SMILES: O=C(NCc1ccc(S(=O)(=O)c2cc(O)ccc2OC(F)(F)F)cc1)c1cc2ccncc2o1]
N-[(4-{[5-hydroxy-2-(trifluoromethoxy)benzene]sulfonyl}phenyl)methyl]furo[2,3-c]pyridine-2-carboxamide
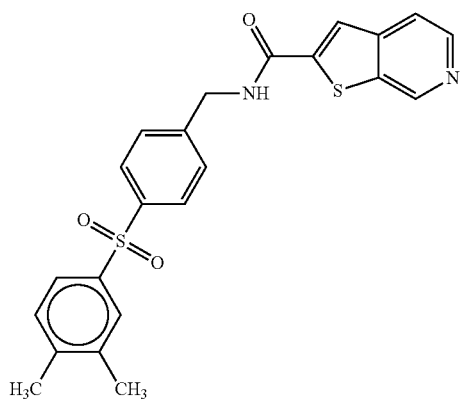
N-({4-[(3,4-dimethylbenzene)sulfonyl]phenyl}methyl)thieno[2,3-c]pyridine-2-carboxamide

| | |
|---|---|
| 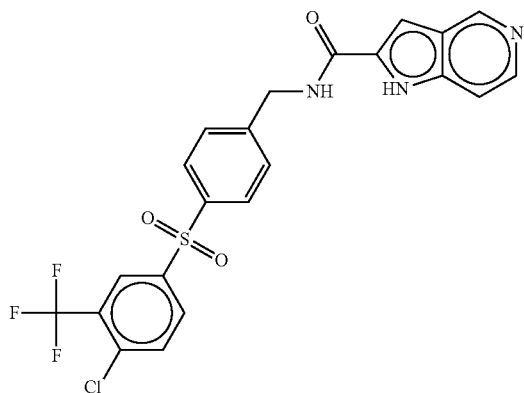 | N-[(4-{[4-chloro-3-(trifluoromethyl)benzene]sulfonyl}phenyl)methyl]-1H-pyrrolo[3,2-c]pyridine-2-carboxamide |
| 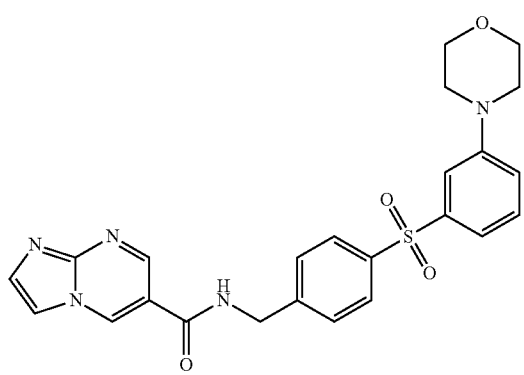 [SMILES: O=C(NCc1ccc(S(=O)(=O)c2cccc(N3CCOCC3)c2)cc1)c1cnc2nccn2c1] | N-[(4-{[3-(morpholin-4-yl)benzene]sulfonyl}phenyl)methyl]imidazo[1,2-a]pyrimidine-6-carboxamide |
| 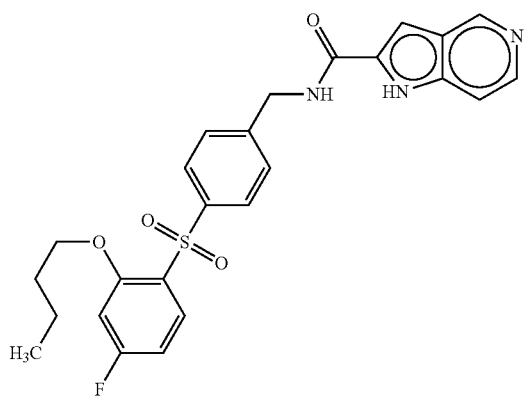 | N-({4-[(2-butoxy-4-fluorobenzene)sulfonyl]phenyl}methyl)-1H-pyrrolo[3,2-c]pyridine-2-carboxamide |

TABLE 2-continued

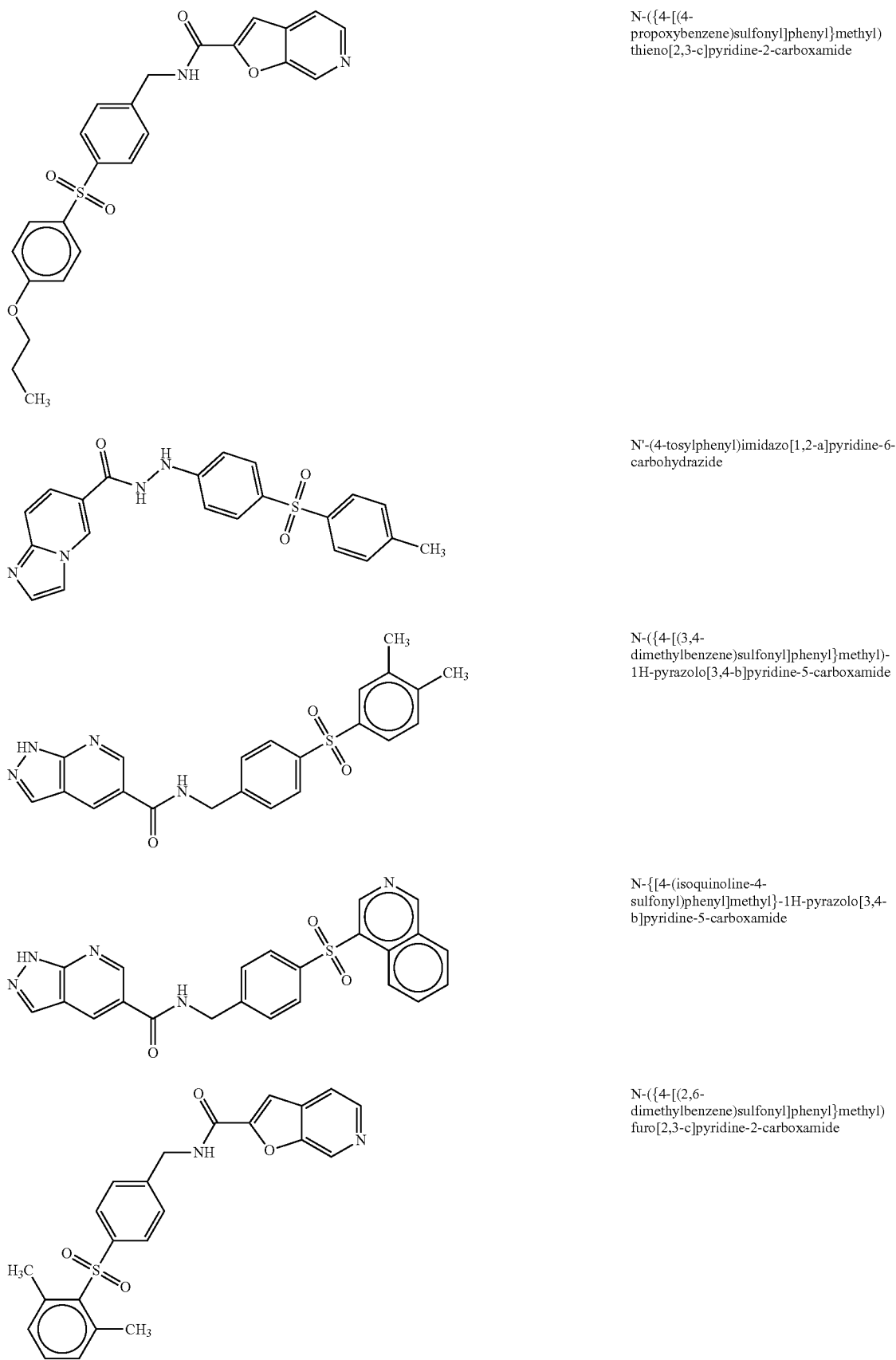

N-({4-[(4-propoxybenzene)sulfonyl]phenyl}methyl)thieno[2,3-c]pyridine-2-carboxamide N'-(4-tosylphenyl)imidazo[1,2-a]pyridine-6-carbohydrazide N-({4-[(3,4-dimethylbenzene)sulfonyl]phenyl}methyl)-1H-pyrazolo[3,4-b]pyridine-5-carboxamide N-{[4-(isoquinoline-4-sulfonyl)phenyl]methyl}-1H-pyrazolo[3,4-b]pyridine-5-carboxamide N-({4-[(2,6-dimethylbenzene)sulfonyl]phenyl}methyl)furo[2,3-c]pyridine-2-carboxamide TABLE 2-continued

| Structure | Name |
|---|---|
| 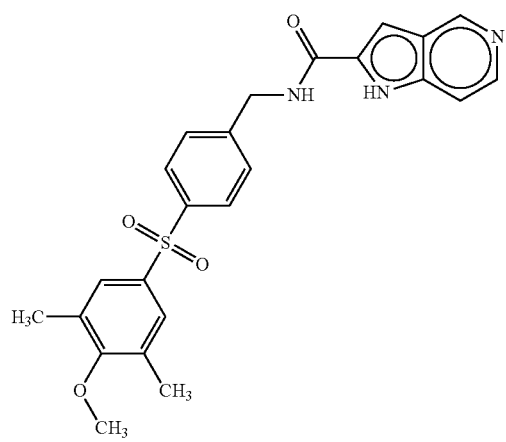 | N-({4-[(4-methoxy-3,5-dimethylbenzene)sulfonyl]phenyl}methyl)-1H-pyrrolo[3,2-c]pyridine-2-carboxamide |
| 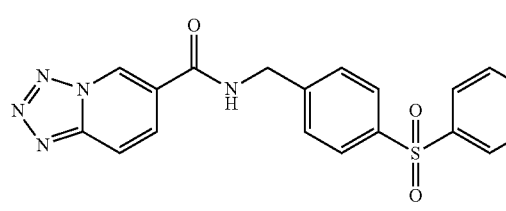 | N-{[4-(benzenesulfonyl)phenyl]methyl}-[1,2,3,4]tetrazolo[1,5-a]pyridine-6-carboxamide |
| 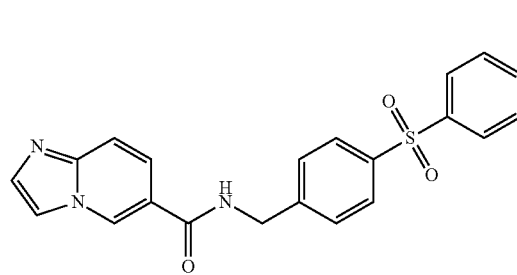 | N-({4-[(4-cyanobenzene)sulfonyl]phenyl}methyl)imidazo[1,2-a]pyridine-6-carboxamide |
| 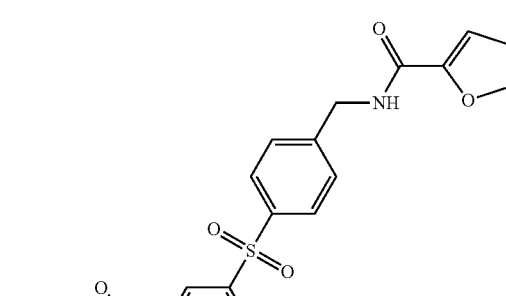 | N-{[4-({3-[(propan-2-yl)carbamoyl]benzene}sulfonyl)phenyl]methyl}furo[2,3-c]pyridine-2-carboxamide |
| 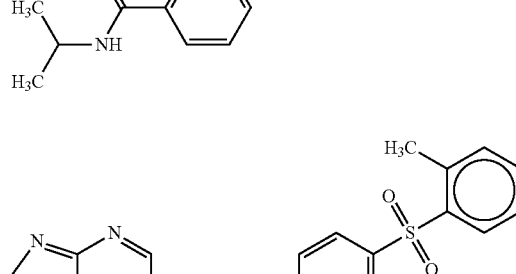 | N-({4-[(2,4-dimethylbenzene)sulfonyl]phenyl}methyl)imidazo[1,2-a]pyrimidine-6-carboxamide |

TABLE 2-continued
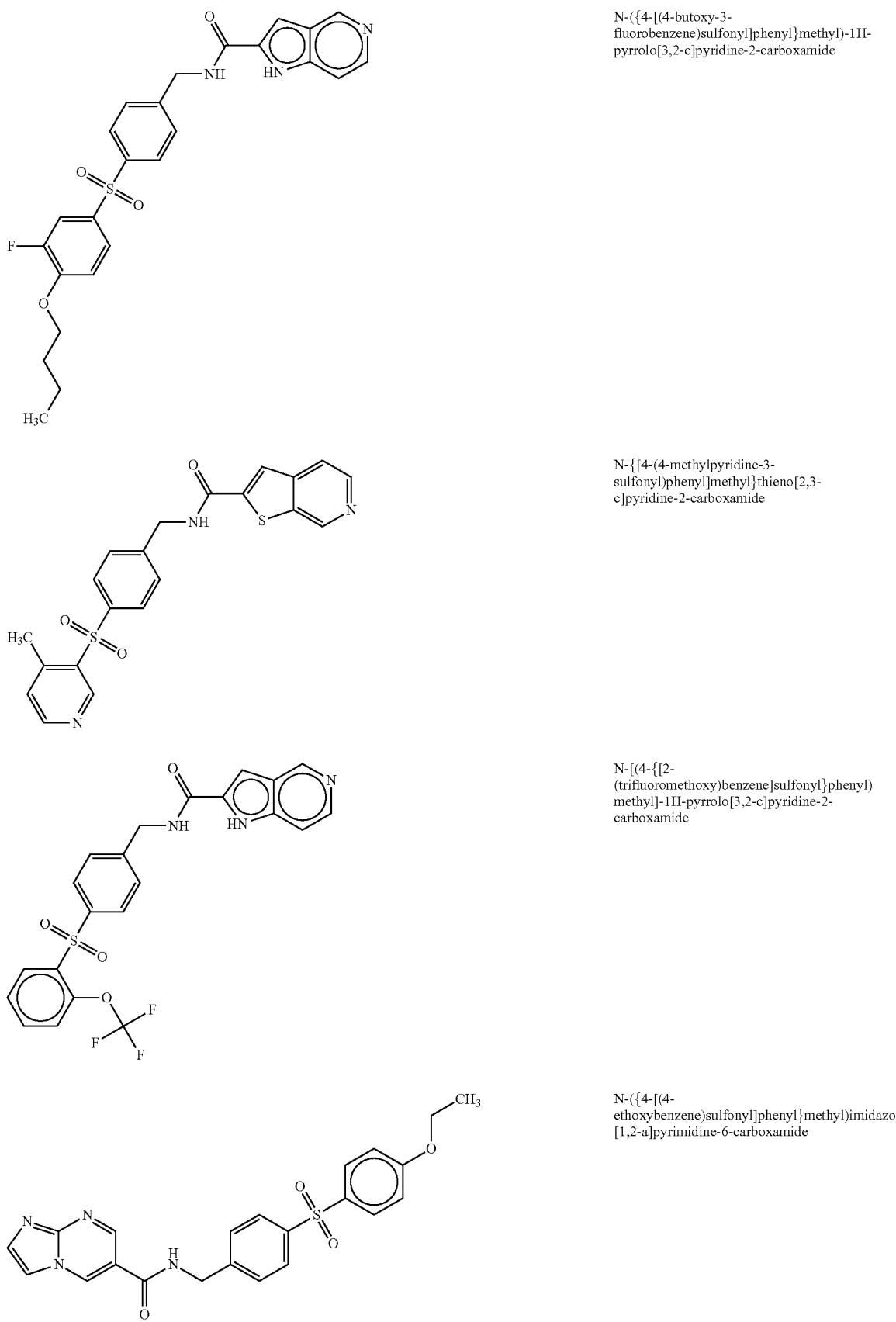
N-({4-[(4-butoxy-3-fluorobenzene)sulfonyl]phenyl}methyl)-1H-pyrrolo[3,2-c]pyridine-2-carboxamide
N-{[4-(4-methylpyridine-3-sulfonyl)phenyl]methyl}thieno[2,3-c]pyridine-2-carboxamide
N-[(4-{[2-(trifluoromethoxy)benzene]sulfonyl}phenyl)methyl]-1H-pyrrolo[3,2-c]pyridine-2-carboxamide
N-({4-[(4-ethoxybenzene)sulfonyl]phenyl}methyl)imidazo[1,2-a]pyrimidine-6-carboxamide TABLE 2-continued
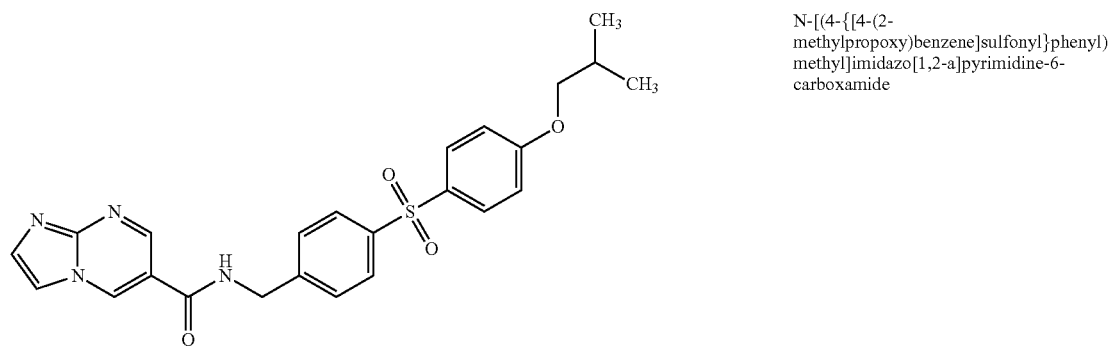
N-[(4-{[4-(2-methylpropoxy)benzene]sulfonyl}phenyl)methyl]imidazo[1,2-a]pyrimidine-6-carboxamide
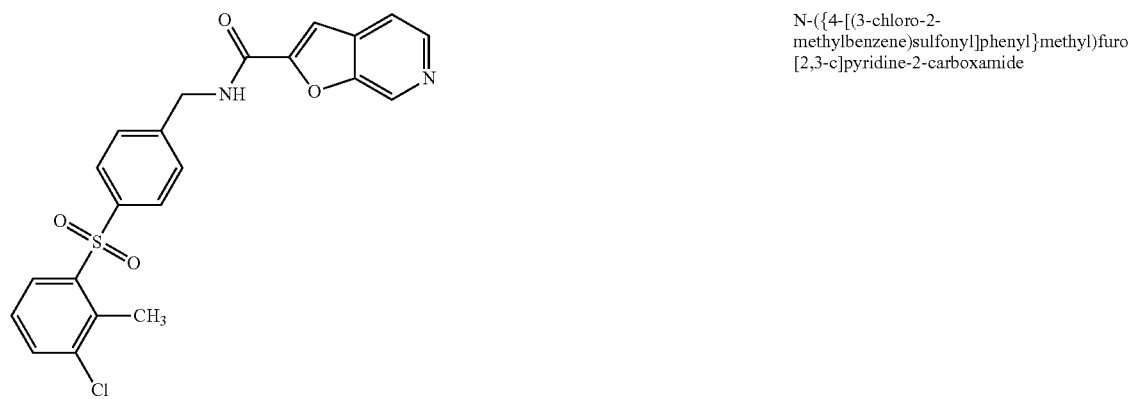
N-({4-[(3-chloro-2-methylbenzene)sulfonyl]phenyl}methyl)furo[2,3-c]pyridine-2-carboxamide
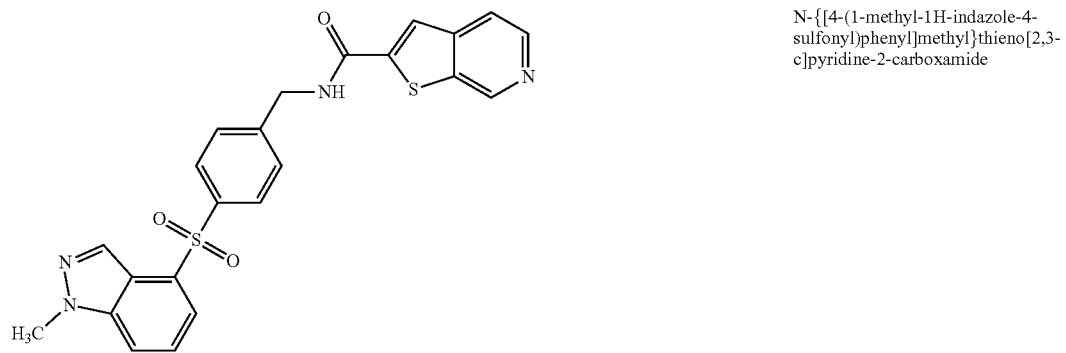
N-{[4-(1-methyl-1H-indazole-4-sulfonyl)phenyl]methyl}thieno[2,3-c]pyridine-2-carboxamide
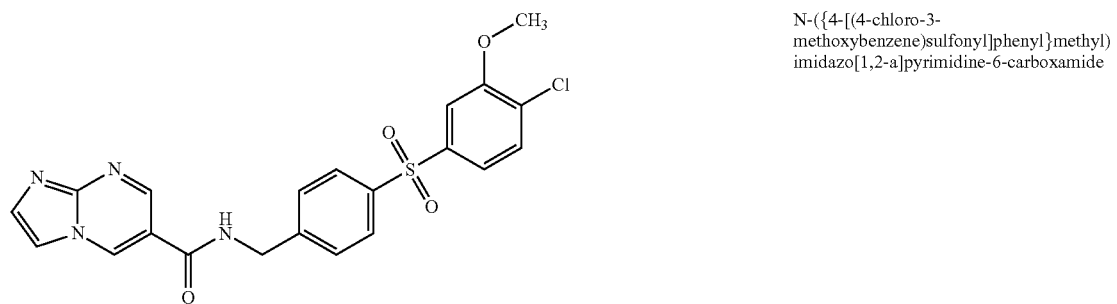
N-({4-[(4-chloro-3-methoxybenzene)sulfonyl]phenyl}methyl)imidazo[1,2-a]pyrimidine-6-carboxamide TABLE 2-continued

| | |
|---|---|
| 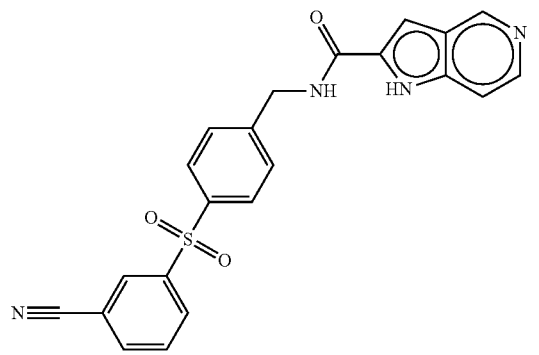 | N-({4-[(3-cyanobenzene)sulfonyl]phenyl}methyl)-1H-pyrrolo[3,2-c]pyridine-2-carboxamide |
| 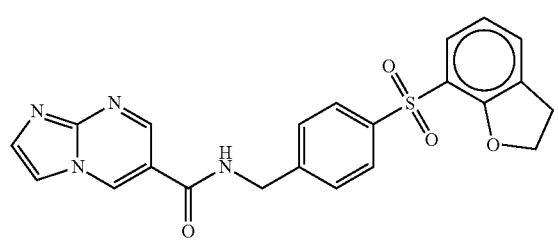 | N-{[4-(2,3-dihydro-1-benzofuran-7-sulfonyl)phenyl]methyl}imidazo[1,2-a]pyrimidine-6-carboxamide |
| 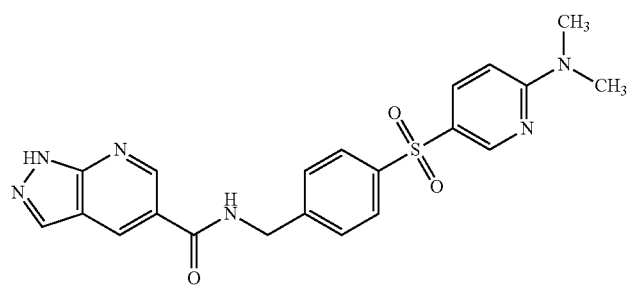 [SMILES: CN(C)c1ccc(S(=O)(=O)c2ccc(CNC(=O)c3cnc4[nH]ncc4c3)cc2)cn1] | N-({4-[6-(dimethylamino)pyridine-3-sulfonyl]phenyl}methyl)-1H-pyrazolo[3,4-b]pyridine-5-carboxamide |
| 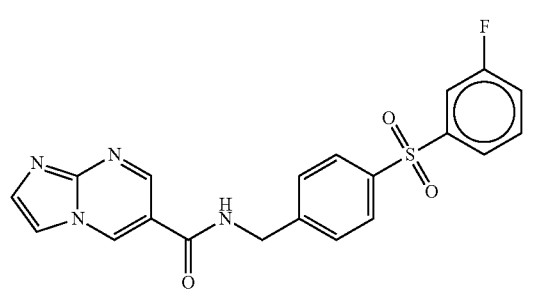 | N-({4-[(3-fluorobenzene)sulfonyl]phenyl}methyl)imidazo[1,2-a]pyrimidine-6-carboxamide |
| 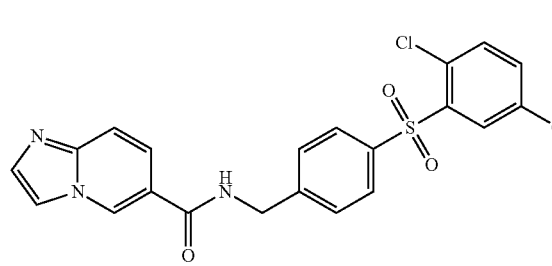 | N-({4-[(2-chloro-5-methoxybenzene)sulfonyl]phenyl}methyl)imidazo[1,2-a]pyridine-6-carboxamide |

TABLE 2-continued
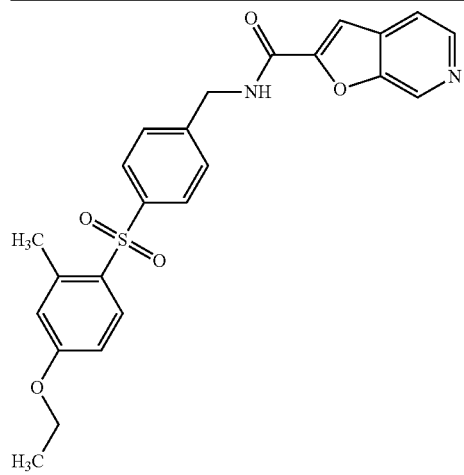
N-({4-[(4-ethoxy-2-methylbenzene)sulfonyl]phenyl}methyl)furo[2,3-c]pyridine-2-carboxamide
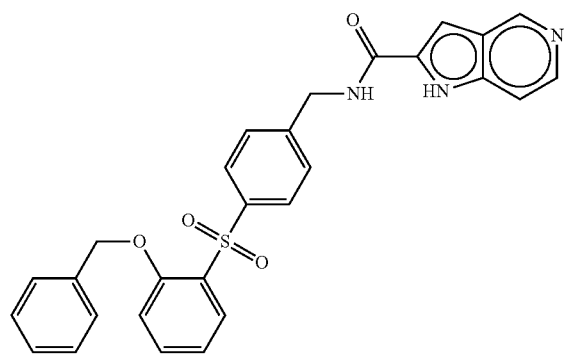
N-[(4-{[2-(benzyloxy)benzene]sulfonyl}phenyl)methyl]-1H-pyrrolo[3,2-c]pyridine-2-carboxamide
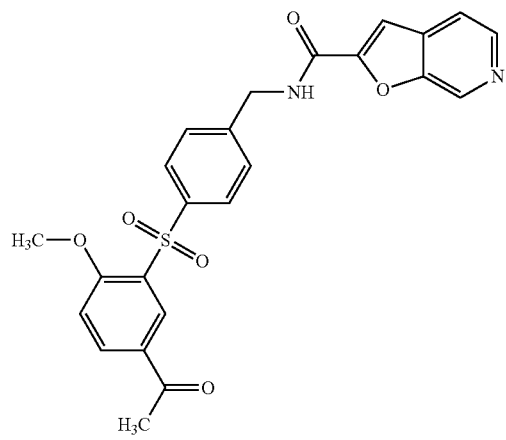 [SMILES: COc1ccc(C(C)=O)cc1S(=O)(=O)c1ccc(CNC(=O)c2cc3ccncc3o2)cc1]
N-({4-[(5-acetyl-2-methoxybenzene)sulfonyl]phenyl}methyl)furo[2,3-c]pyridine-2-carboxamide
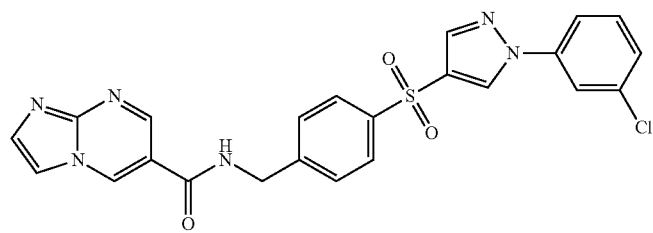 [SMILES: O=C(NCc1ccc(S(=O)(=O)c2cnn(-c3cccc(Cl)c3)c2)cc1)c1cnc2nccn2c1]
N-({4-[1-(3-chlorophenyl)-1H-pyrazole-4-sulfonyl]phenyl}methyl)imidazo[1,2-a]pyrimidine-6-carboxamide TABLE 2-continued

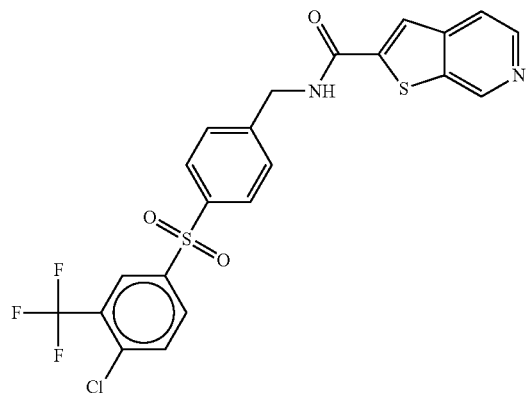

N-[(4-{[4-chloro-3-(trifluoromethyl)benzene]sulfonyl}phenyl)methyl]furo[2,3-c]pyridine-2-carboxamide

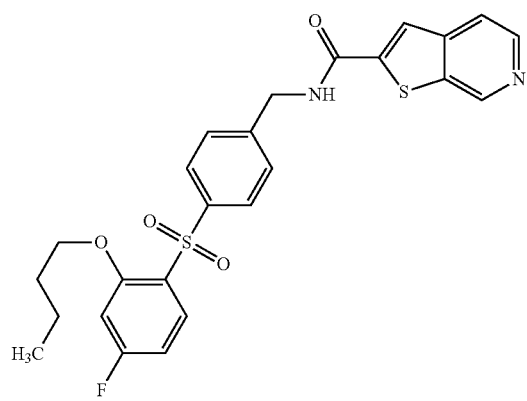

N-({4-[(2-butoxy-4-fluorobenzene)sulfonyl]phenyl}methyl)thieno[2,3-c]pyridine-2-carboxamide

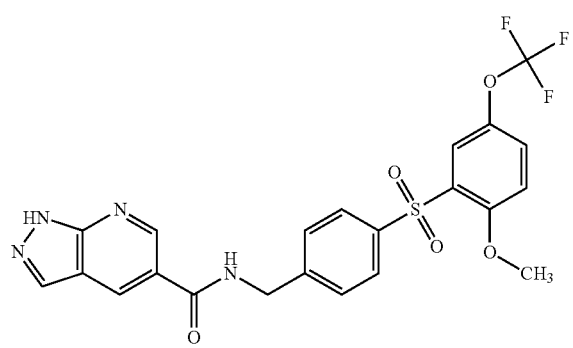 [SMILES: COc1ccc(OC(F)(F)F)cc1S(=O)(=O)c1ccc(CNC(=O)c2cnc3[nH]ncc3c2)cc1]

N-[(4-{[2-methoxy-5-(trifluoromethoxy)benzene]sulfonyl}phenyl)methyl]-1H-pyrazolo[3,4-b]pyridine-5-carboxamide

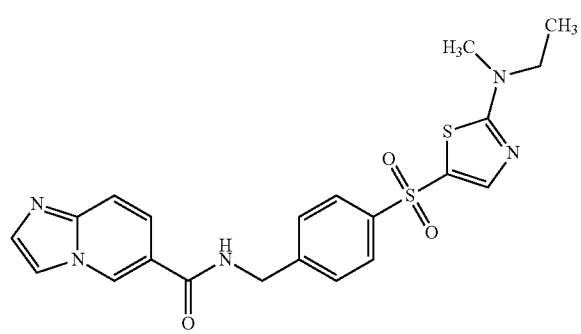 [SMILES: CCN(C)c1ncc(S(=O)(=O)c2ccc(CNC(=O)c3ccc4nccn4c3)cc2)s1]

N-[(4-{2-[ethyl(methyl)amino]-1,3-thiazole-5-sulfonyl}phenyl)methyl]imidazo[1,2-a]pyridine-6-carboxamide TABLE 2-continued

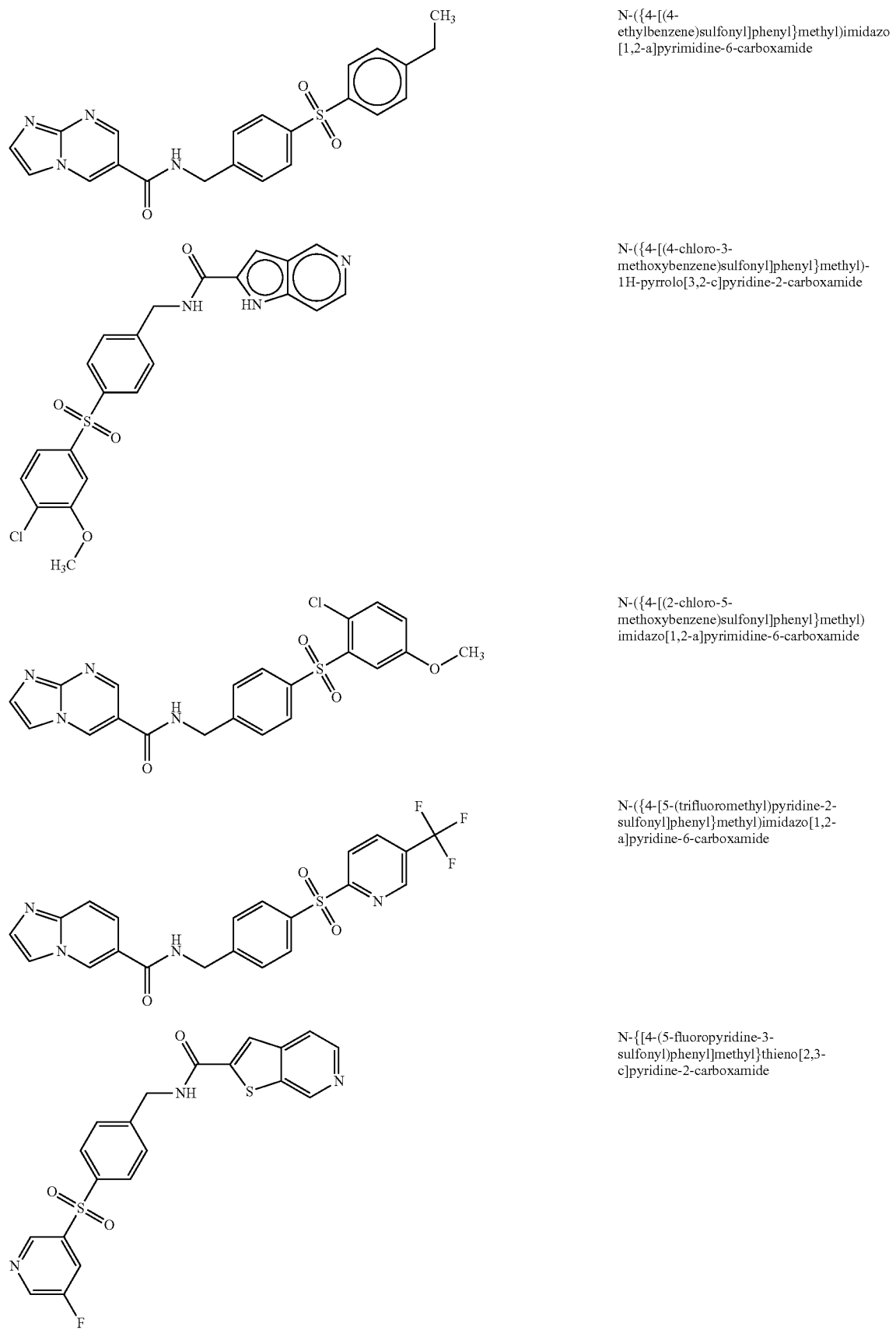

N-({4-[(4-ethylbenzene)sulfonyl]phenyl}methyl)imidazo[1,2-a]pyrimidine-6-carboxamide N-({4-[(4-chloro-3-methoxybenzene)sulfonyl]phenyl}methyl)-1H-pyrrolo[3,2-c]pyridine-2-carboxamide N-({4-[(2-chloro-5-methoxybenzene)sulfonyl]phenyl}methyl)imidazo[1,2-a]pyrimidine-6-carboxamide N-({4-[5-(trifluoromethyl)pyridine-2-sulfonyl]phenyl}methyl)imidazo[1,2-a]pyridine-6-carboxamide N-{[4-(5-fluoropyridine-3-sulfonyl)phenyl]methyl}thieno[2,3-c]pyridine-2-carboxamide TABLE 2-continued

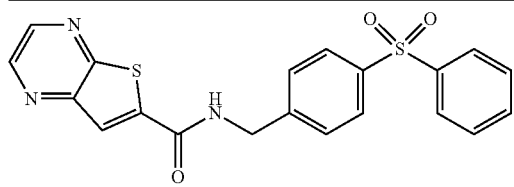

N-{[4-(benzenesulfonyl)phenyl]methyl}thieno[2,3-b]pyrazine-6-carboxamide

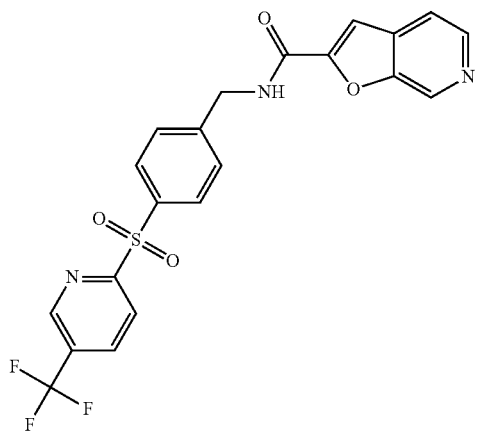 [SMILES: O=C(NCc1ccc(S(=O)(=O)c2ccc(C(F)(F)F)cn2)cc1)c1cc2ccncc2o1]

N-({4-[5-(trifluoromethyl)pyridine-2-sulfonyl]phenyl}methyl)furo[2,3-c]pyridine-2-carboxamide

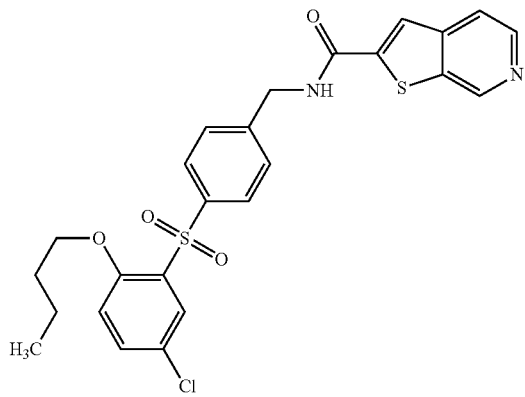 [SMILES: CCCCOc1ccc(Cl)cc1S(=O)(=O)c1ccc(CNC(=O)c2cc3ccncc3s2)cc1]

N-({4-[(2-butoxy-5-chlorobenzene)sulfonyl]phenyl}methyl)thieno[2,3-c]pyridine-2-carboxamide

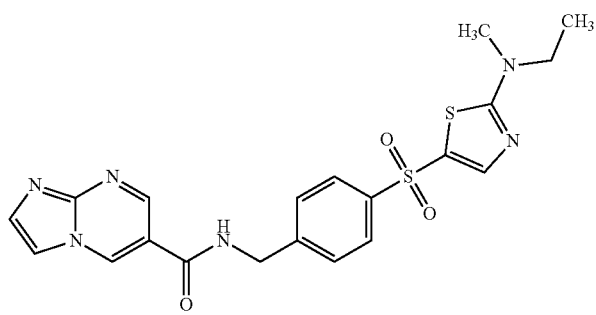 [SMILES: CCN(C)c1ncc(S(=O)(=O)c2ccc(CNC(=O)c3cnc4nccn4c3)cc2)s1]

N-[(4-{2-[ethyl(methyl)amino]-1,3-thiazole-5-sulfonyl}phenyl)methyl]imidazo[1,2-a]pyrimidine-6-carboxamide

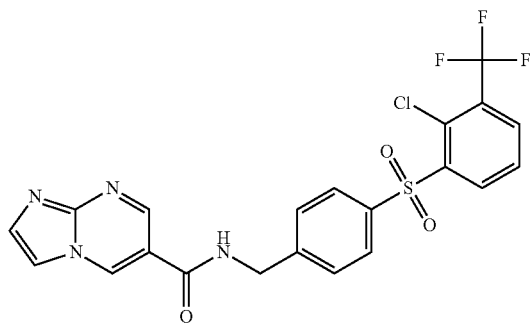 [SMILES: O=C(NCc1ccc(S(=O)(=O)c2cccc(C(F)(F)F)c2Cl)cc1)c1cnc2nccn2c1]

N-[(4-{[2-chloro-3-(trifluoromethyl)benzene]sulfonyl}phenyl)methyl]imidazo[1,2-a]pyrimidine-6-carboxamide

| | |
|---|---|
| 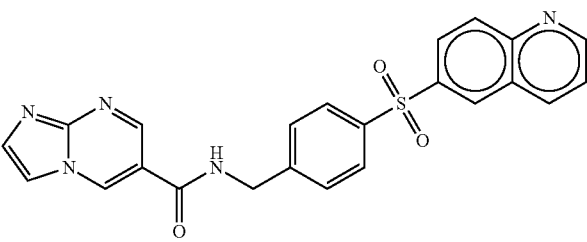 | N-{[4-(quinoline-6-sulfonyl)phenyl]methyl}imidazo[1,2-a]pyrimidine-6-carboxamide |
| 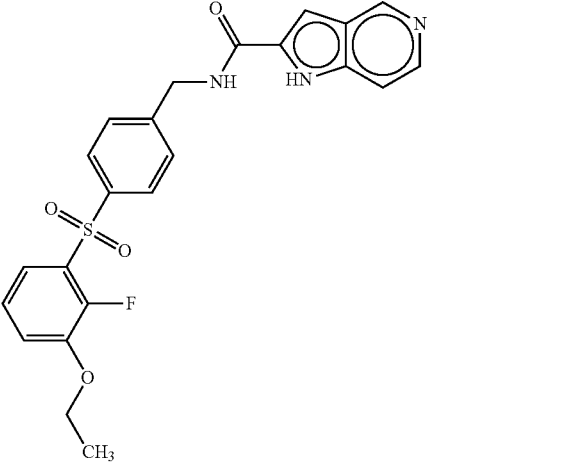 | N-({4-[(3-ethoxy-2-fluorobenzene)sulfonyl]phenyl}methyl)-1H-pyrrolo[3,2-c]pyridine-2-carboxamide |
| 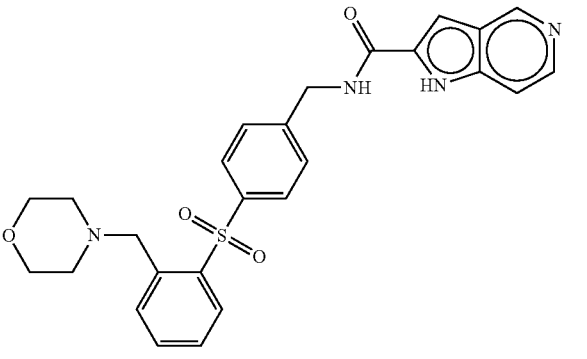 | N-[(4-{[2-(morpholin-4-ylmethyl)benzene]sulfonyl}phenyl)methyl]-1H-pyrrolo[3,2-c]pyridine-2-carboxamide |
| 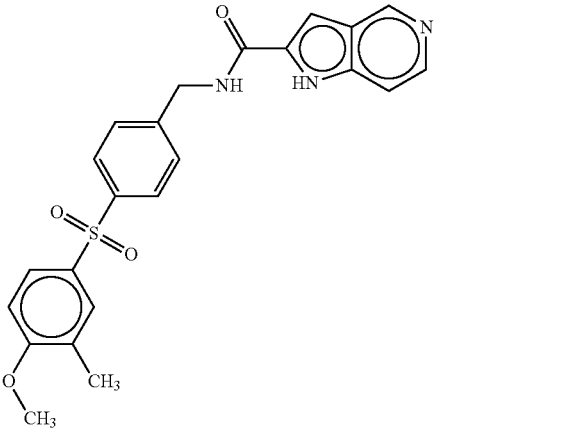 | N-({4-[(4-methoxy-3-methylbenzene)sulfonyl]phenyl}methyl)-1H-pyrrolo[3,2-c]pyridine-2-carboxamide |

TABLE 2-continued
| | |
|---|---|
| 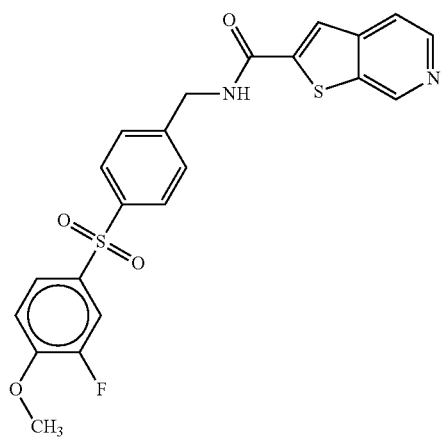 | N-({4-[(3-fluoro-4-methoxybenzene)sulfonyl]phenyl}methyl)thieno[2,3-c]pyridine-2-carboxamide |
| 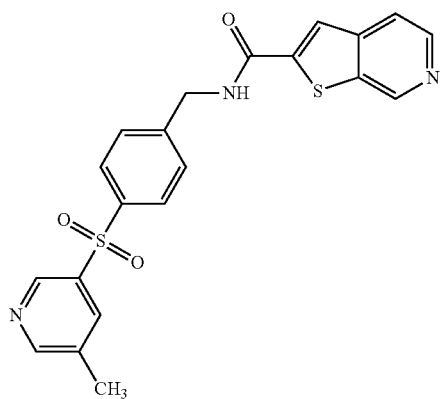 | N-{[4-(5-methylpyridine-3-sulfonyl)phenyl]methyl}thieno[2,3-c]pyridine-2-carboxamide |
| 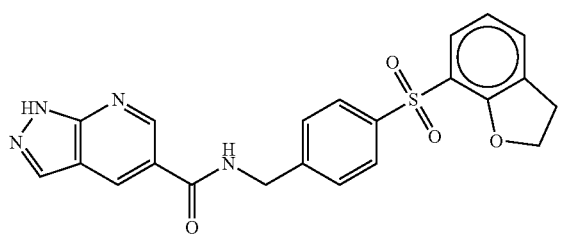 | N-{[4-(2,3-dihydro-1-benzofuran-7-sulfonyl)phenyl]methyl}-1H-pyrazolo[3,4-b]pyridine-5-carboxamide |
| 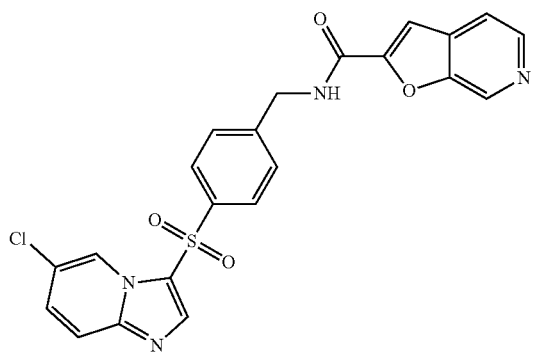 [SMILES: O=C(NCc1ccc(S(=O)(=O)c2cnc3ccc(Cl)cn23)cc1)c1cc2ccncc2o1] | N-[(4-{6-chloroimidazo[1,2-a]pyridine-3-sulfonyl}phenyl)methyl]furo[2,3-c]pyridine-2-carboxamide |

TABLE 2-continued
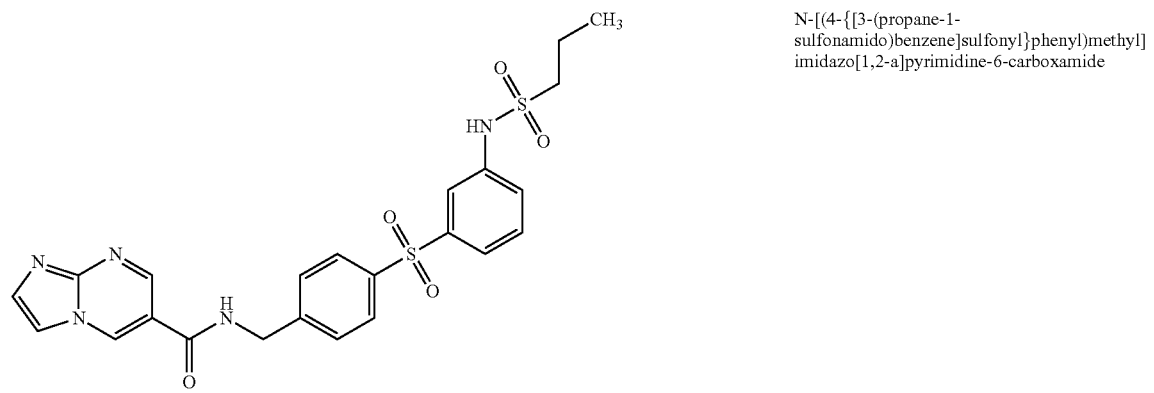
N-[(4-{[3-(propane-1-sulfonamido)benzene]sulfonyl}phenyl)methyl]imidazo[1,2-a]pyrimidine-6-carboxamide
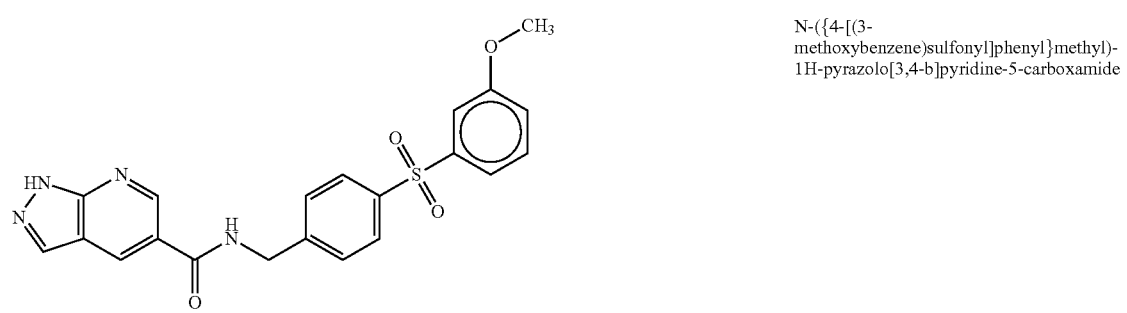
N-({4-[(3-methoxybenzene)sulfonyl]phenyl}methyl)-1H-pyrazolo[3,4-b]pyridine-5-carboxamide
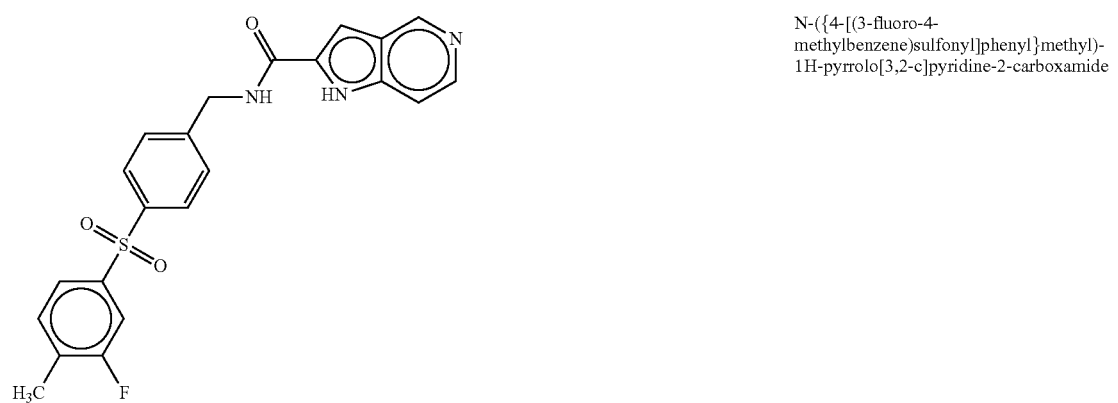
N-({4-[(3-fluoro-4-methylbenzene)sulfonyl]phenyl}methyl)-1H-pyrrolo[3,2-c]pyridine-2-carboxamide
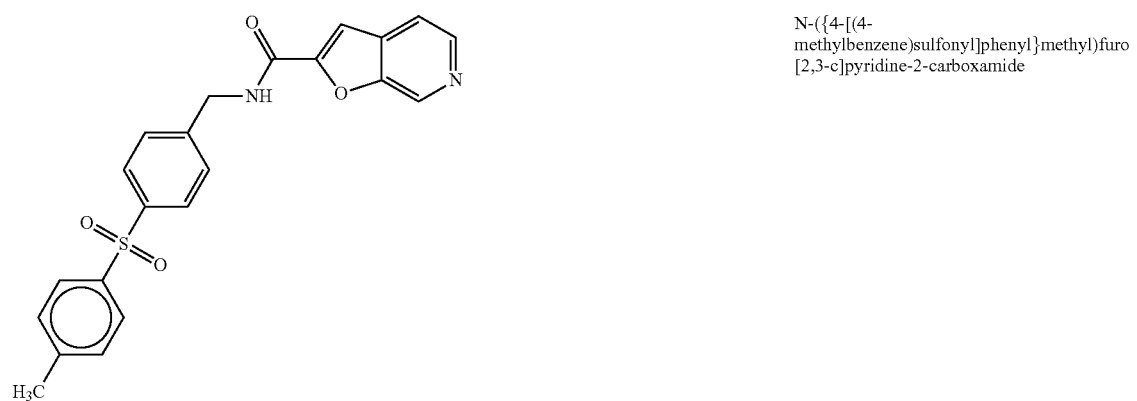
N-({4-[(4-methylbenzene)sulfonyl]phenyl}methyl)furo[2,3-c]pyridine-2-carboxamide TABLE 2-continued
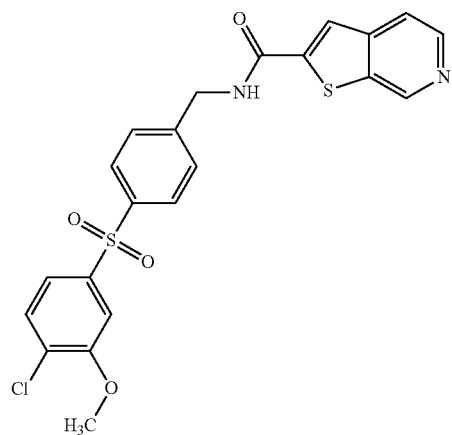 [SMILES: COc1cc(S(=O)(=O)c2ccc(CNC(=O)c3cc4ccncc4s3)cc2)ccc1Cl]
N-({4-[(4-chloro-3-methoxybenzene)sulfonyl]phenyl}methyl)thieno[2,3-c]pyridine-2-carboxamide
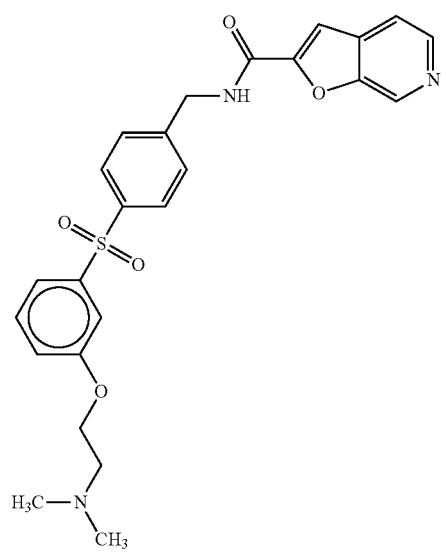
N-{[4-({3-[2-(dimethylamino)ethoxy]benzene}sulfonyl)phenyl]methyl}furo[2,3-c]pyridine-2-carboxamide
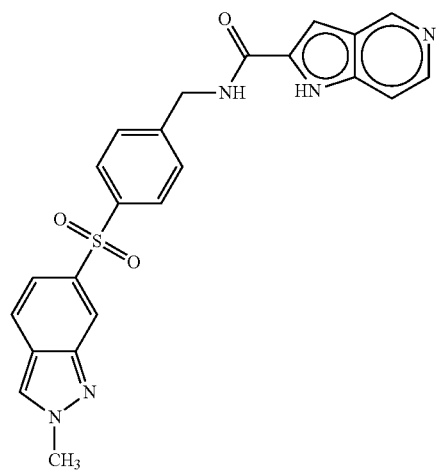
N-{[4-(2-methyl-2H-indazole-6-sulfonyl)phenyl]methyl}-1H-pyrrolo[3,2-c]pyridine-2-carboxamide TABLE 2-continued
| | |
|---|---|
| 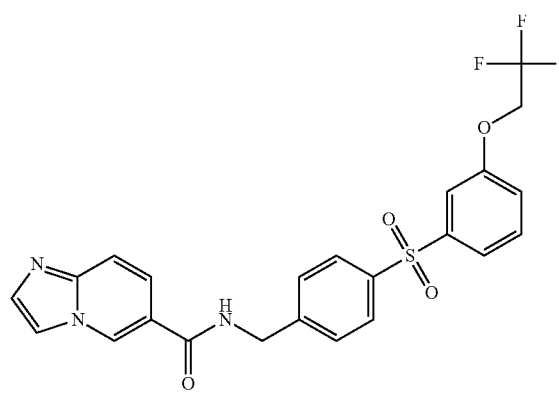 | N-[(4-{[3-(2,2,2-trifluoroethoxy)benzene]sulfonyl}phenyl)methyl]imidazo[1,2-a]pyridine-6-carboxamide |
| 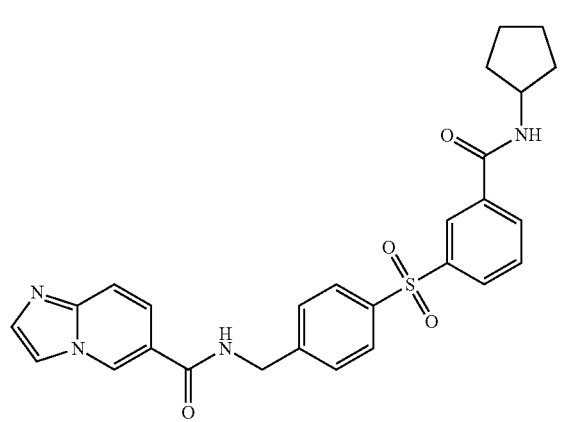 [SMILES: O=C(NCc1ccc(S(=O)(=O)c2cccc(C(=O)NC3CCCC3)c2)cc1)c1ccc2nccn2c1] | N-[(4-{[3-(cyclopentylcarbamoyl)benzene]sulfonyl}phenyl)methyl]imidazo[1,2-a]pyridine-6-carboxamide |
| 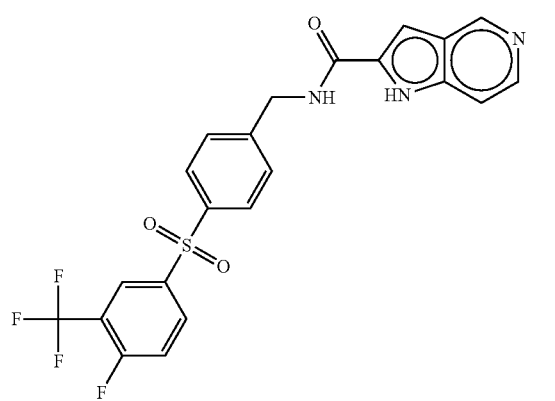 | N-[(4-{[4-fluoro-3-(trifluoromethyl)benzene]sulfonyl}phenyl)methyl]-1H-pyrrolo[3,2-c]pyridine-2-carboxamide |
| 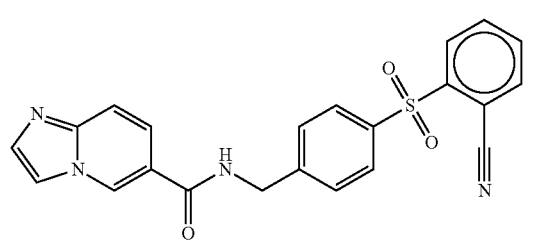 | N-({4-[(2-cyanobenzene)sulfonyl]phenyl}methyl)imidazo[1,2-a]pyridine-6-carboxamide |

TABLE 2-continued
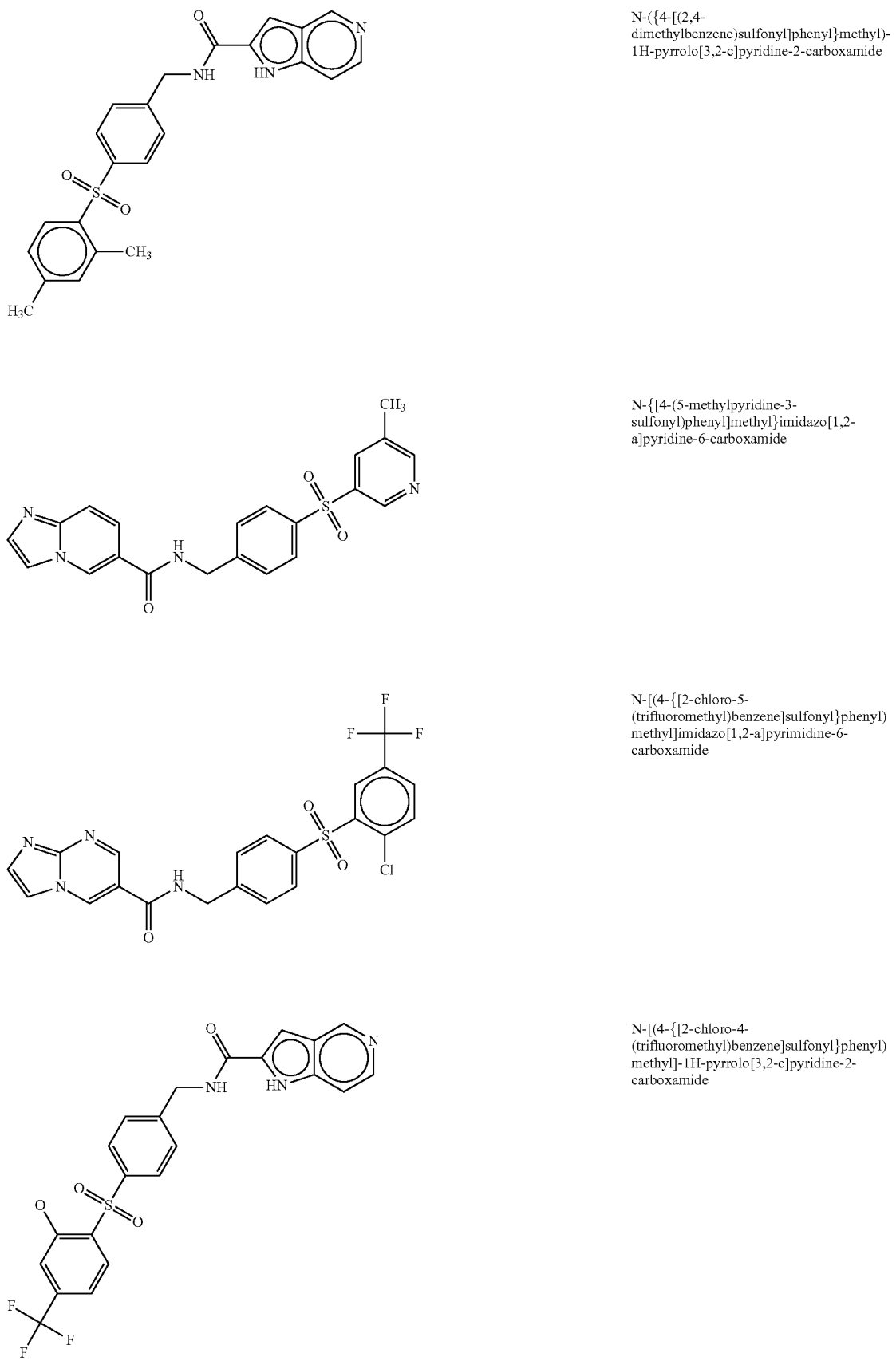
N-({4-[(2,4-dimethylbenzene)sulfonyl]phenyl}methyl)-1H-pyrrolo[3,2-c]pyridine-2-carboxamide
N-{[4-(5-methylpyridine-3-sulfonyl)phenyl]methyl}imidazo[1,2-a]pyridine-6-carboxamide
N-[(4-{[2-chloro-5-(trifluoromethyl)benzene]sulfonyl}phenyl)methyl]imidazo[1,2-a]pyrimidine-6-carboxamide
N-[(4-{[2-chloro-4-(trifluoromethyl)benzene]sulfonyl}phenyl)methyl]-1H-pyrrolo[3,2-c]pyridine-2-carboxamide TABLE 2-continued
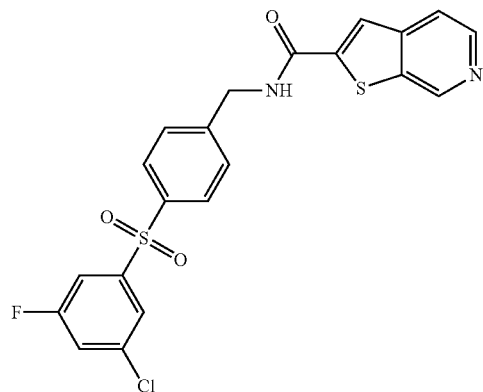 [SMILES: O=C(NCc1ccc(S(=O)(=O)c2cc(F)cc(Cl)c2)cc1)c1cc2ccncc2s1]
N-({4-[(3-chloro-5-fluorobenzene)sulfonyl]phenyl}methyl)furo[2.3-c]pyridine-2-carboxamide
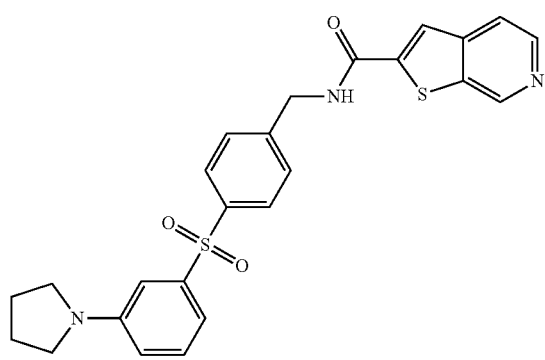 [SMILES: O=C(NCc1ccc(S(=O)(=O)c2cccc(N3CCCC3)c2)cc1)c1cc2ccncc2s1]
N-[(4-{[3-(pyrrolidin-1-yl)benzene]sulfonyl}phenyl)methyl]furo[2,3-c]pyridine-2-carboxamide
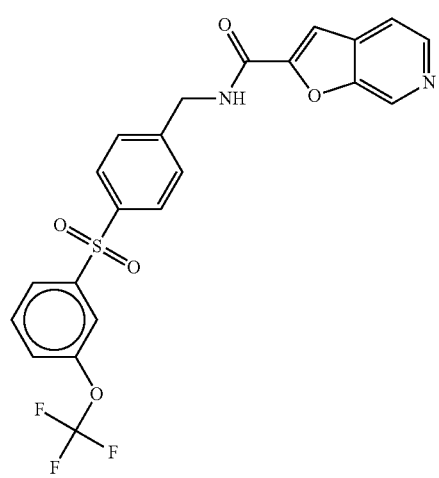
N-[(4-{[3-(trifluoromethoxy)benzene]sulfonyl}phenyl)methyl]furo[2,3-c]pyridine-2-carboxamide
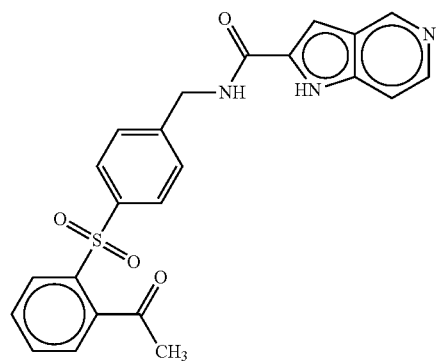
N-({4-[(2-acetylbenzene)sulfonyl]phenyl}methyl)-1H-pyrrolo[3,2-c]pyridine-2-carboxamide

| | |
|---|---|
| 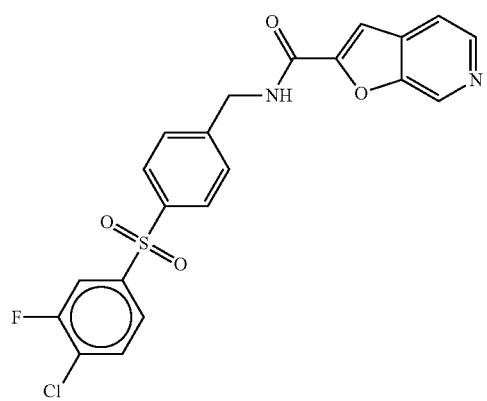 | N-({4-[(4-chloro-3-fluorobenzene)sulfonyl]phenyl}methyl)furo[2,3-c]pyridine-2-carboxamide |
| 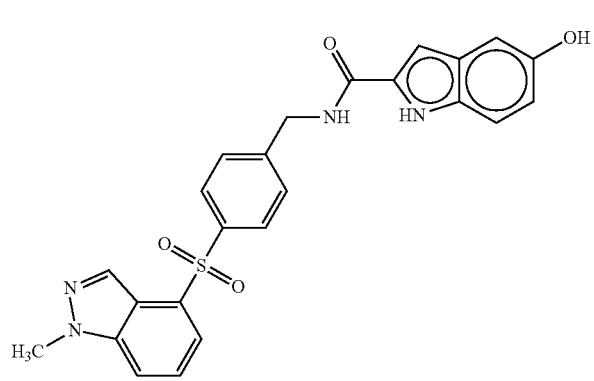 | 5-hydroxy-N-{[4-(1-methyl-1H-indazole-4-sulfonyl)phenyl]methyl}-1H-indole-2-carboxamide |
| 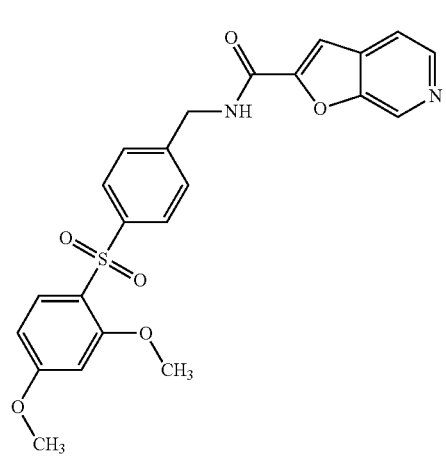 [SMILES: COc1ccc(S(=O)(=O)c2ccc(CNC(=O)c3cc4ccncc4o3)cc2)c(OC)c1] | N-{[4-(2,6-dimethoxypyridine-3-sulfonyl)phenyl]methyl}furo[2,3-c]pyridine-2-carboxamide |
| 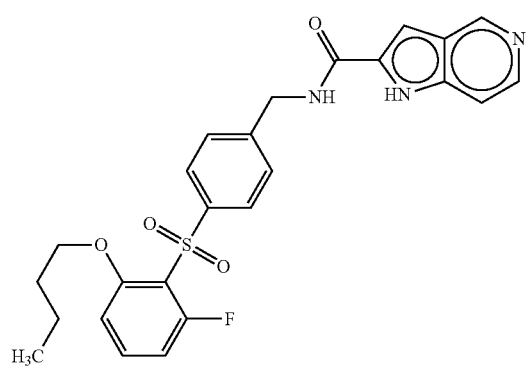 | N-({4-[(2-butoxy-6-fluorobenzene)sulfonyl]phenyl}methyl)-1H-pyrrolo[3,2-c]pyridine-2-carboxamide |

TABLE 2-continued

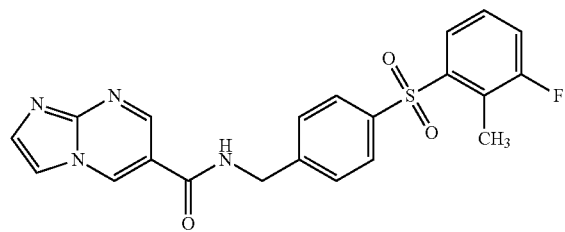 [SMILES: Cc1c(F)cccc1S(=O)(=O)c1ccc(CNC(=O)c2cnc3nccn3c2)cc1]

N-({4-[(3-fluoro-2-methylbenzene)sulfonyl]phenyl}methyl)imidazo[1,2-a]pyrimidine-6-carboxamide

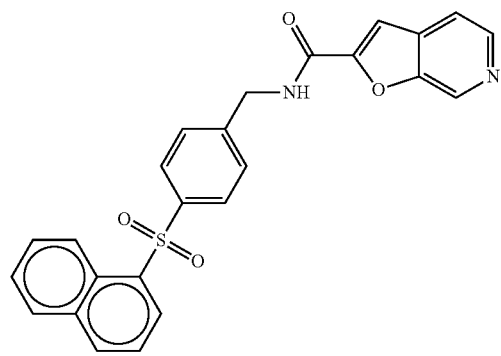

N-{[4-(naphthalene-1-sulfonyl)phenyl]methyl}furo[2,3-c]pyridine-2-carboxamide

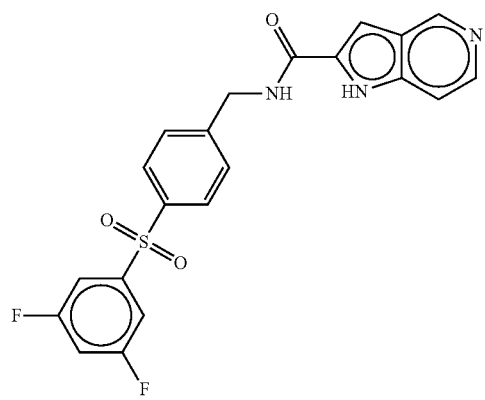

N-({4-[(3,5-difluorobenzene)sulfonyl]phenyl}methyl)-1H-pyrrolo[3,2-c]pyridine-2-carboxamide

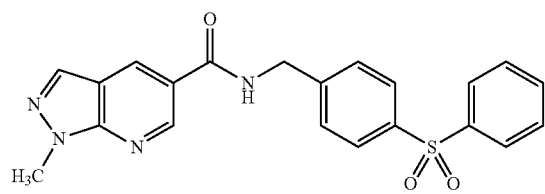 [SMILES: Cn1ncc2cc(C(=O)NCc3ccc(S(=O)(=O)c4ccccc4)cc3)cnc21]

N-{[4-(benzenesulfonyl)phenyl]methyl}-1-methyl-1H-pyrazolo[3,4-b]pyridine-5-carboxamide

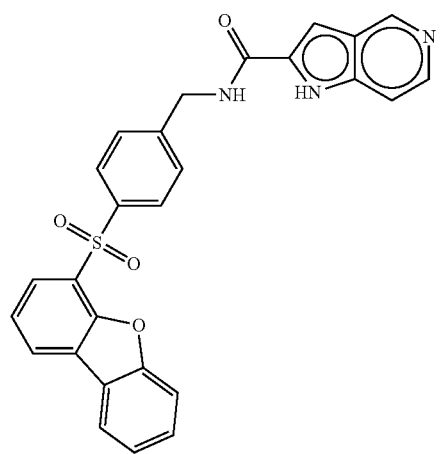

N-[(4-{S-thiatricyclo[7.4.0.0²,□]trideca-1(13),2,4,6,9,11-hexaene-6-sulfonyl}phenyl)methyl]-1H-pyrrolo[3,2-c]pyridine-2-carboxamide TABLE 2-continued
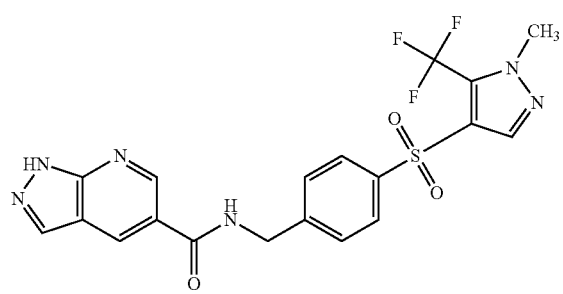 [SMILES: Cn1ncc(S(=O)(=O)c2ccc(CNC(=O)c3cnc4[nH]ncc4c3)cc2)c1C(F)(F)F]
N-({4-[1-methyl-5-(trifluoromethyl)-1H-pyrazole-4-sulfonyl]phenyl}methyl)-1H-pyrazolo[3,4-b]pyridine-5-carboxamide
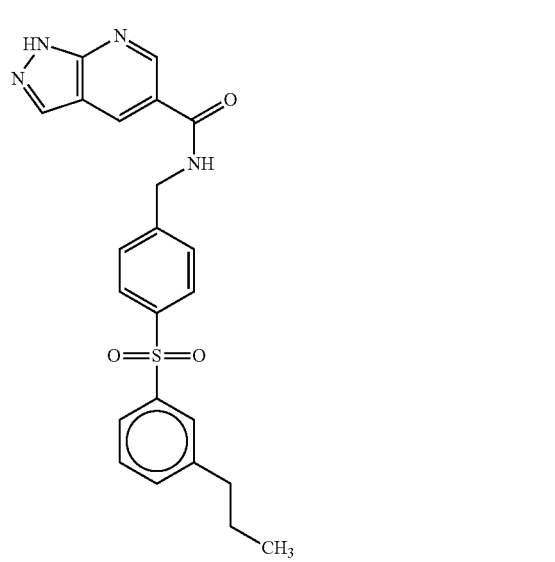
N-({4-[(3-ethoxybenzene)sulfonyl]phenyl}methyl)-1H-pyrazolo[3,4-b]pyridine-5-carboxamide
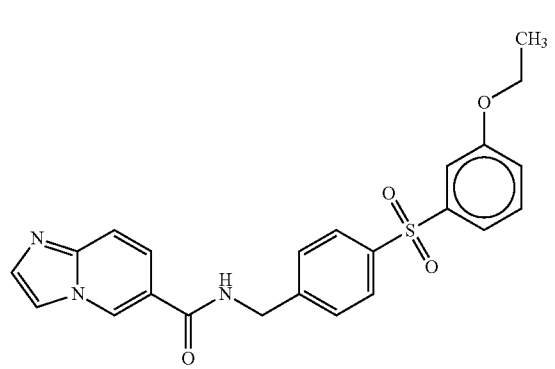
N-({4-[(3-ethoxybenzene)sulfonyl]phenyl}methyl)imidazo[1,2-a]pyridine-6-carboxamide
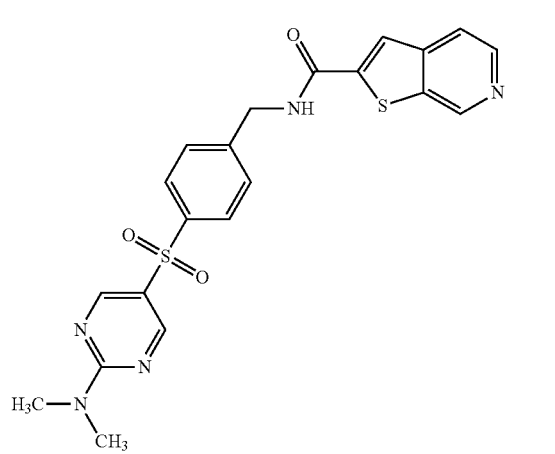 [SMILES: CN(C)c1ncc(S(=O)(=O)c2ccc(CNC(=O)c3cc4ccncc4s3)cc2)cn1]
N-({4-[2-(dimethylamino)pyrimidine-5-sulfonyl]phenyl}methyl)thieno[2,3-c]pyridine-2-carboxamide TABLE 2-continued
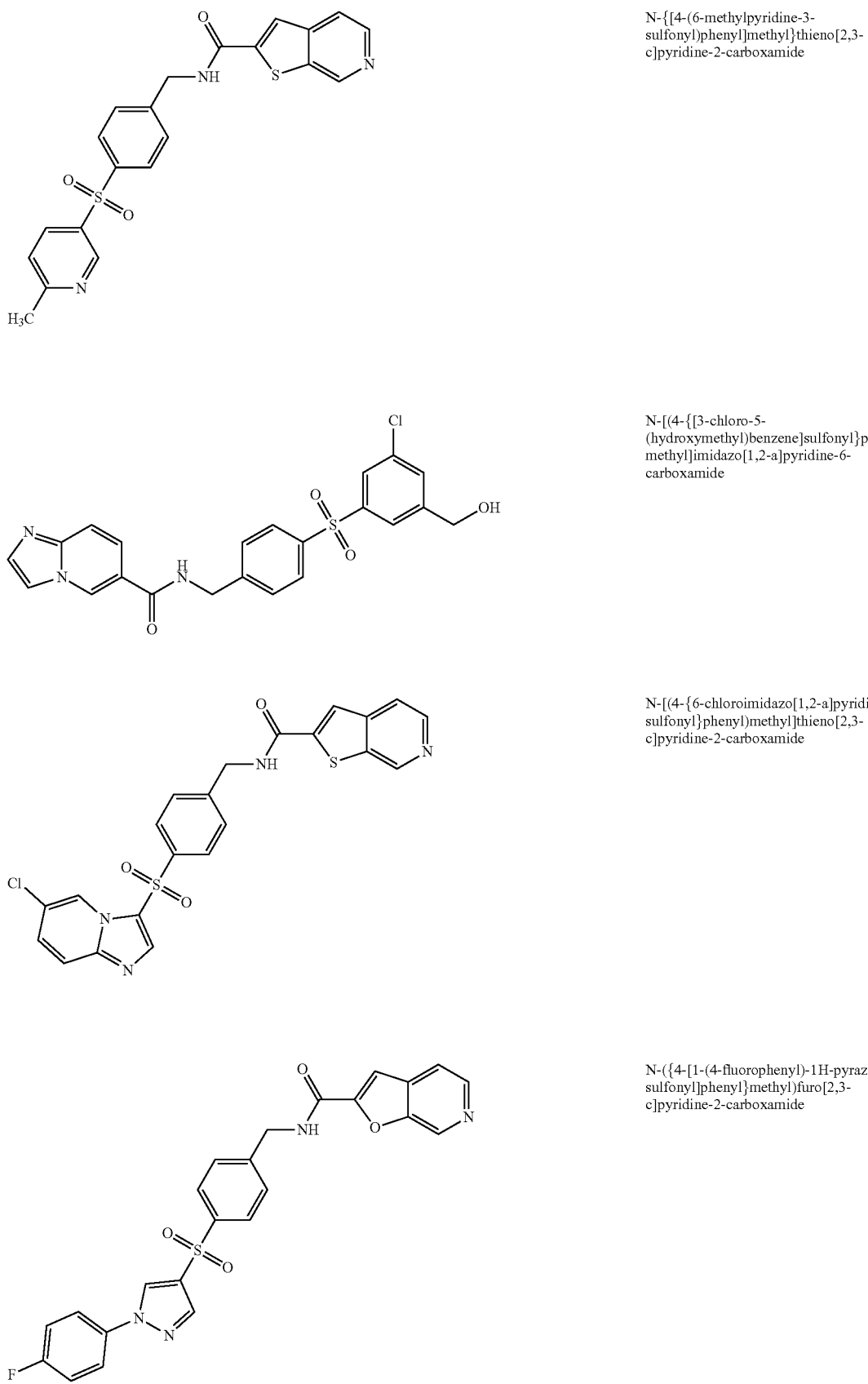
N-{[4-(6-methylpyridine-3-sulfonyl)phenyl]methyl}thieno[2,3-c]pyridine-2-carboxamide
N-[(4-{[3-chloro-5-(hydroxymethyl)benzene]sulfonyl}phenyl)methyl]imidazo[1,2-a]pyridine-6-carboxamide
N-[(4-{6-chloroimidazo[1,2-a]pyridine-3-sulfonyl}phenyl)methyl]thieno[2,3-c]pyridine-2-carboxamide
N-({4-[1-(4-fluorophenyl)-1H-pyrazole-4-sulfonyl]phenyl}methyl)furo[2,3-c]pyridine-2-carboxamide TABLE 2-continued
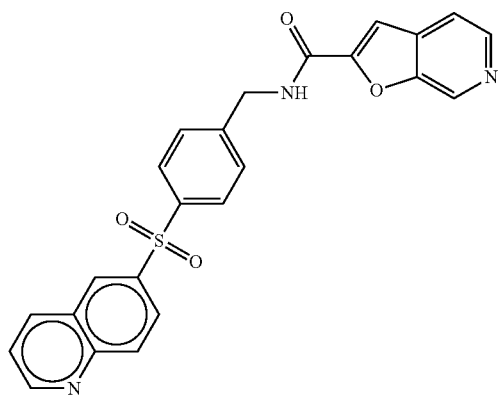
N-{[4-(quinoline-6-sulfonyl)phenyl]methyl}furo[2,3-c]pyridine-2-carboxamide
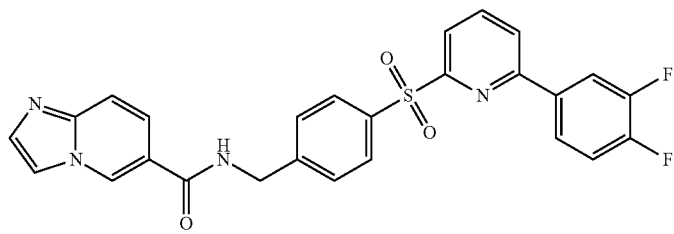 [SMILES: O=C(NCc1ccc(S(=O)(=O)c2cccc(-c3ccc(F)c(F)c3)n2)cc1)c1ccc2nccn2c1]
N-({4-[6-(3,4-difluorophenyl)pyridine-2-sulfonyl]phenyl}methyl)imidazo[1,2-a]pyridine-6-carboxamide
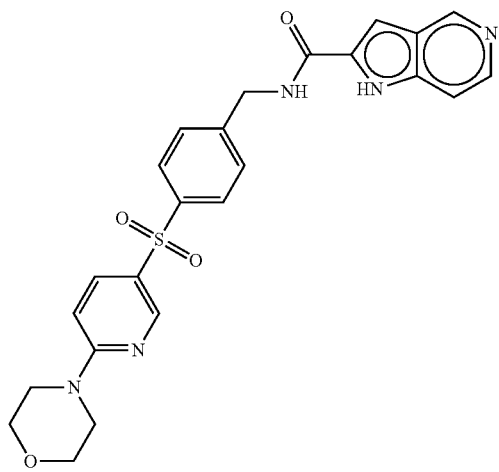
N-({4-[6-(morpholin-4-yl)pyridine-3-sulfonyl]phenyl}methyl)-1H-pyrrolo[3,2-c]pyridine-2-carboxamide
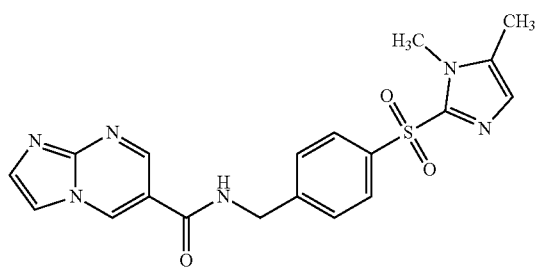 [SMILES: Cc1cnc(S(=O)(=O)c2ccc(CNC(=O)c3cnc4nccn4c3)cc2)n1C]
N-{[4-(1,5-dimethyl-1H-imidazole-2-sulfonyl)phenyl]methyl}imidazo[1,2-a]pyrimidine-6-carboxamide TABLE 2-continued
| | |
|---|---|
| 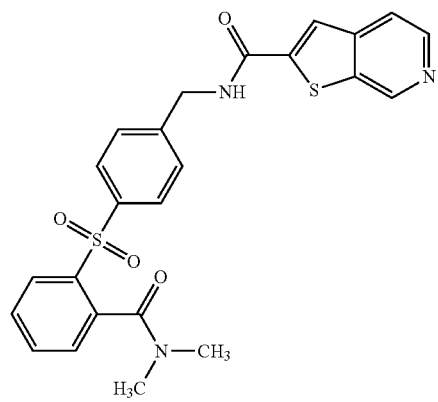 | N-[(4-{[2-(dimethylcarbamoyl)benzene]sulfonyl}phenyl)methyl]thieno[2,3-c]pyridine-2-carboxamide |
| 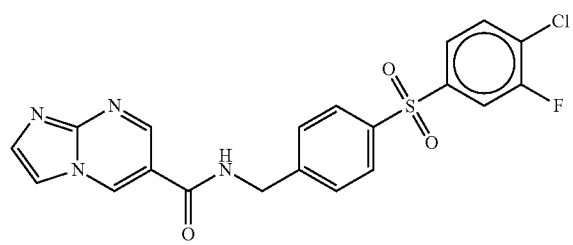 | N-({4-[(4-chloro-3-fluorobenzene)sulfonyl]phenyl}methyl)imidazo[1,2-a]pyrimidine-6-carboxamide |
| 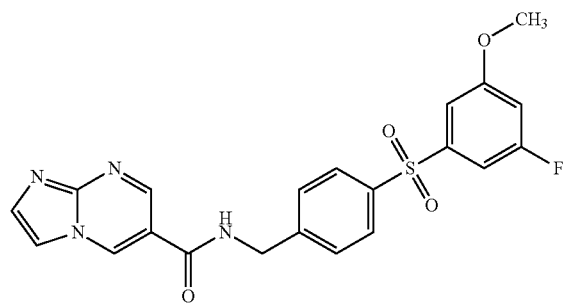 [SMILES: COc1cc(F)cc(S(=O)(=O)c2ccc(CNC(=O)c3cnc4nccn4c3)cc2)c1] | N-({4-[(3-fluoro-5-methoxybenzene)sulfonyl]phenyl}methyl)imidazo[1,2-a]pyrimidine-6-carboxamide |
| 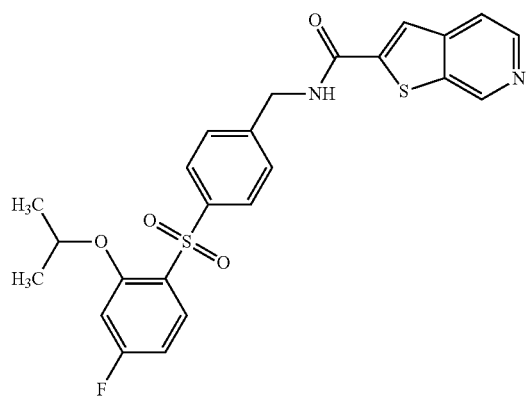 [SMILES: CC(C)Oc1cc(F)ccc1S(=O)(=O)c1ccc(CNC(=O)c2cc3ccncc3s2)cc1] | N-[(4-{[4-fluoro-2-(propan-2-yloxy)benzene]sulfonyl}phenyl)methyl]thieno[2,3-c]pyridine-2-carboxamide |

TABLE 2-continued
| | |
|---|---|
|  | N-({4-[(2,6-dichlorobenzene)sulfonyl]phenyl}methyl)-1H-pyrrolo[3,2-c]pyridine-2-carboxamide |
| 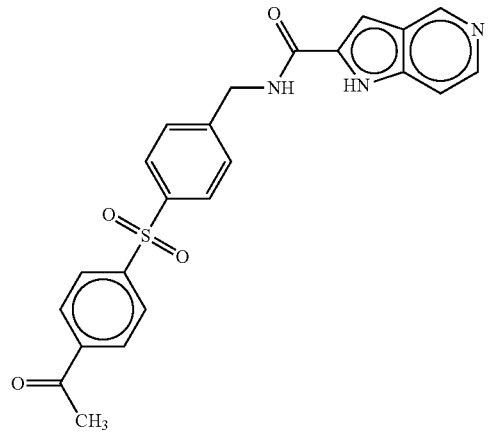 | N-({4-[(4-acetylbenzene)sulfonyl]phenyl}methyl)-1H-pyrrolo[3,2-c]pyridine-2-carboxamide |
| 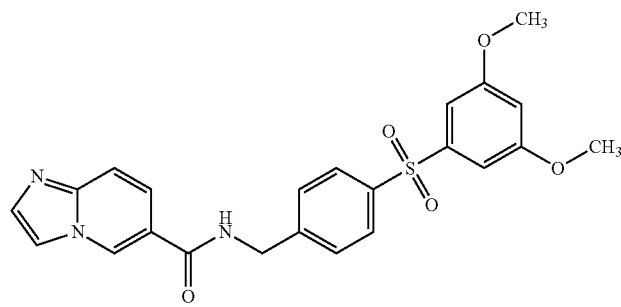 | N-({4-[(3,5-dimethoxybenzene)sulfonyl]phenyl}methyl)imidazo[1,2-a]pyridine-6-carboxamide |
| 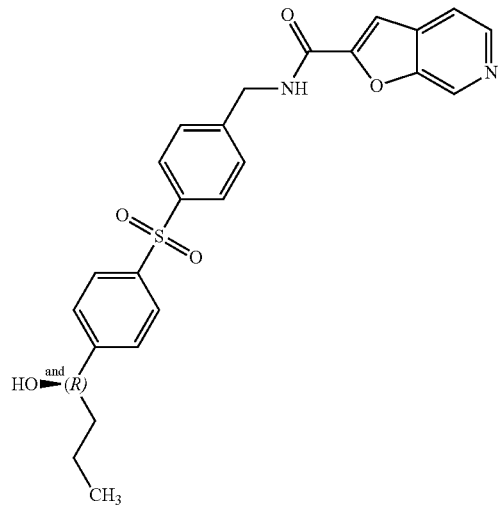 | N-{[4-({4-[(1R)-1-hydroxybutyl]benzene}sulfonyl)phenyl]methyl}furo[2,3-c]pyridine-2-carboxamide |

TABLE 2-continued
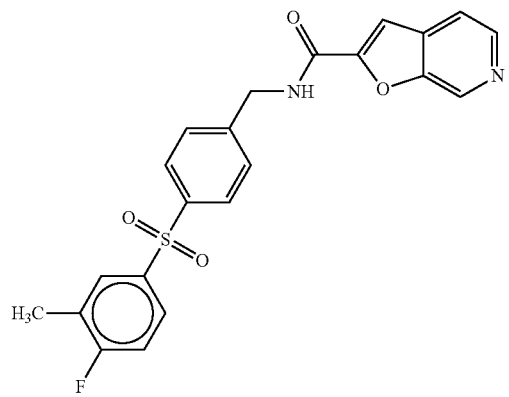
N-({4-[(4-fluoro-3-methylbenzene)sulfonyl]phenyl}methyl)furo[2,3-c]pyridine-2-carboxamide
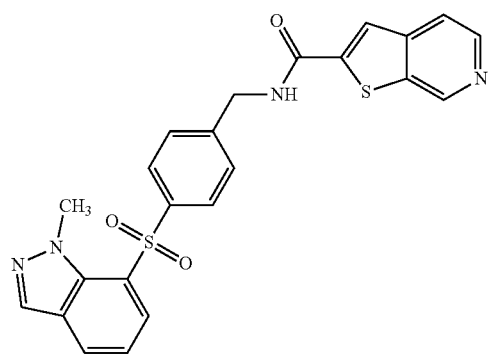 [SMILES: Cn1ncc2cccc(S(=O)(=O)c3ccc(CNC(=O)c4cc5ccncc5s4)cc3)c21]
N-{[4-(1-methyl-1H-indazole-7-sulfonyl)phenyl]methyl}thieno[2,3-c]pyridine-2-carboxamide
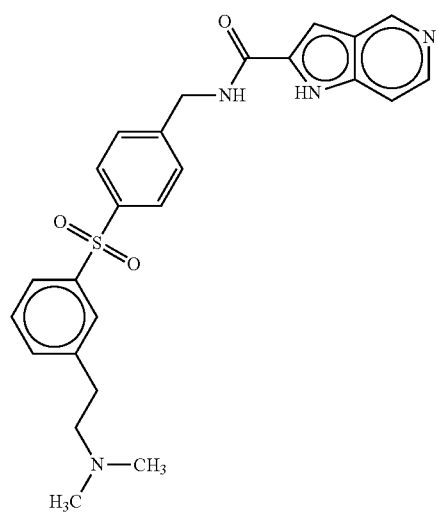
N-{[4-({3-[2-(dimethylamino)ethyl]benzene}sulfonyl)phenyl]methyl}-1H-pyrrolo[3,2-c]pyridine-2-carboxamide
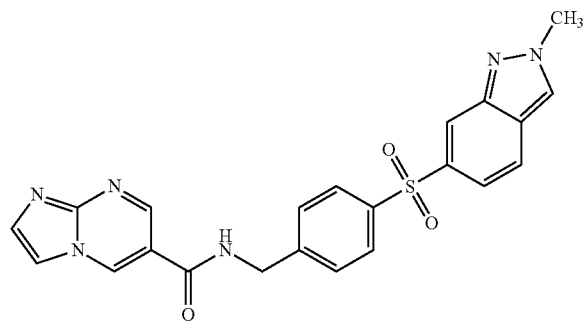 [SMILES: Cn1cc2ccc(S(=O)(=O)c3ccc(CNC(=O)c4cnc5nccn5c4)cc3)cc2n1]
N-{[4-(2-methyl-2H-indazole-6-sulfonyl)phenyl]methyl}imidazo[1,2-a]pyrimidine-6-carboxamide TABLE 2-continued
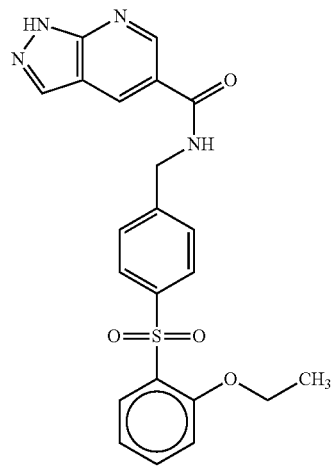
N-({4-[(2-ethoxybenzene)sulfonyl]phenyl}methyl)-1H-pyrazolo[3,4-b]pyridine-5-carboxamide
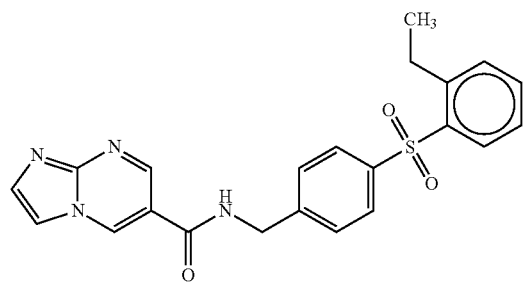
N-({4-[(2-ethylbenzene)sulfonyl]phenyl}methyl)imidazo[1,2-a]pyrimidine-6-carboxamide
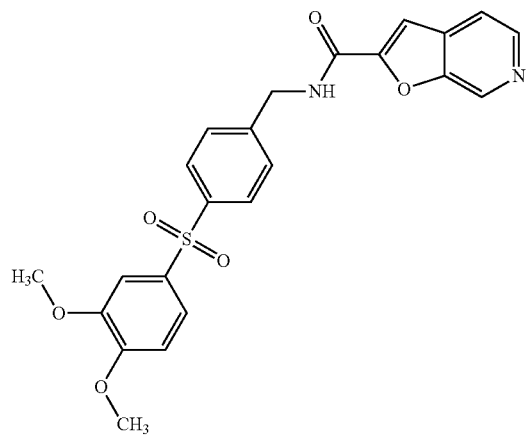 [SMILES: COc1ccc(S(=O)(=O)c2ccc(CNC(=O)c3cc4ccncc4o3)cc2)cc1OC]
N-({4-[(3,4-dimethoxybenzene)sulfonyl]phenyl}methyl)furo[2,3-c]pyridine-2-carboxamide
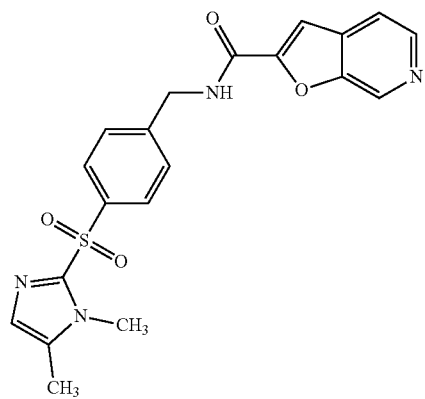 [SMILES: Cc1cnc(S(=O)(=O)c2ccc(CNC(=O)c3cc4ccncc4o3)cc2)n1C]
N-{[4-(1,5-dimethyl-1H-imidazole-2-sulfonyl)phenyl]methyl}furo[2,3-c]pyridine-2-carboxamide TABLE 2-continued
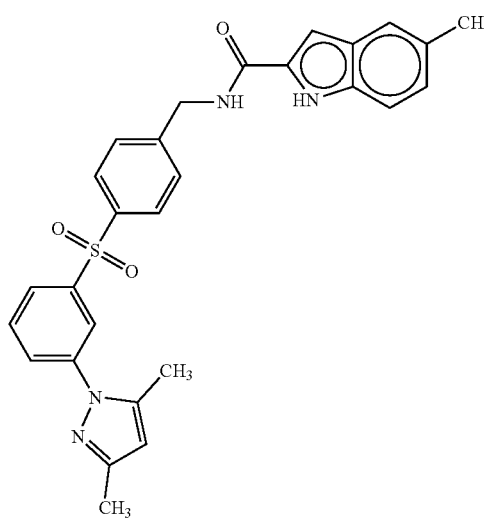
N-[(4-{[3-(3,5-dimethyl-1H-pyrazol-1-yl)benzene]sulfonyl}phenyl)methyl]-5-hydroxy-1H-indole-2-carboxamide
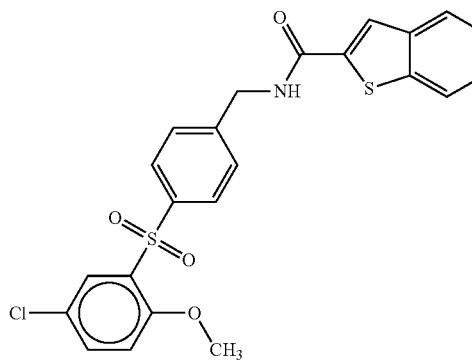
N-({4-[(5-chloro-2-methoxybenzene)sulfonyl]phenyl}methyl)thieno[2,3-c]pyridine-2-carboxamide
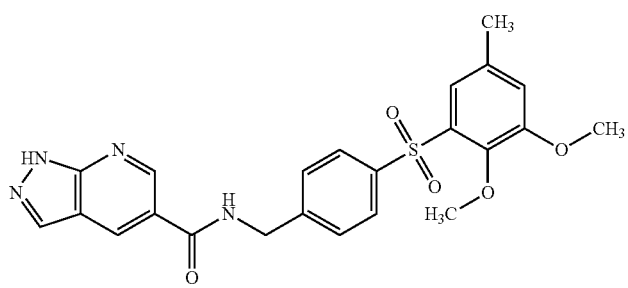 [SMILES: COc1cc(C)cc(S(=O)(=O)c2ccc(CNC(=O)c3cnc4[nH]ncc4c3)cc2)c1OC]
N-({4-[(2,3-dimethoxy-5-methylbenzene)sulfonyl]phenyl}methyl)-1H-pyrazolo[3,4-b]pyridine-5-carboxamide
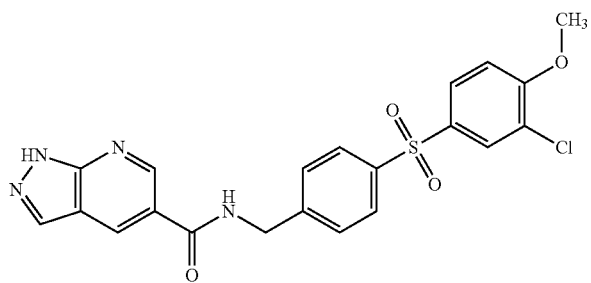 [SMILES: COc1ccc(S(=O)(=O)c2ccc(CNC(=O)c3cnc4[nH]ncc4c3)cc2)cc1Cl]
N-({4-[(3-chloro-4-methoxybenzene)sulfonyl]phenyl}methyl)-1H-pyrazolo[3,4-b]pyridine-5-carboxamide TABLE 2-continued

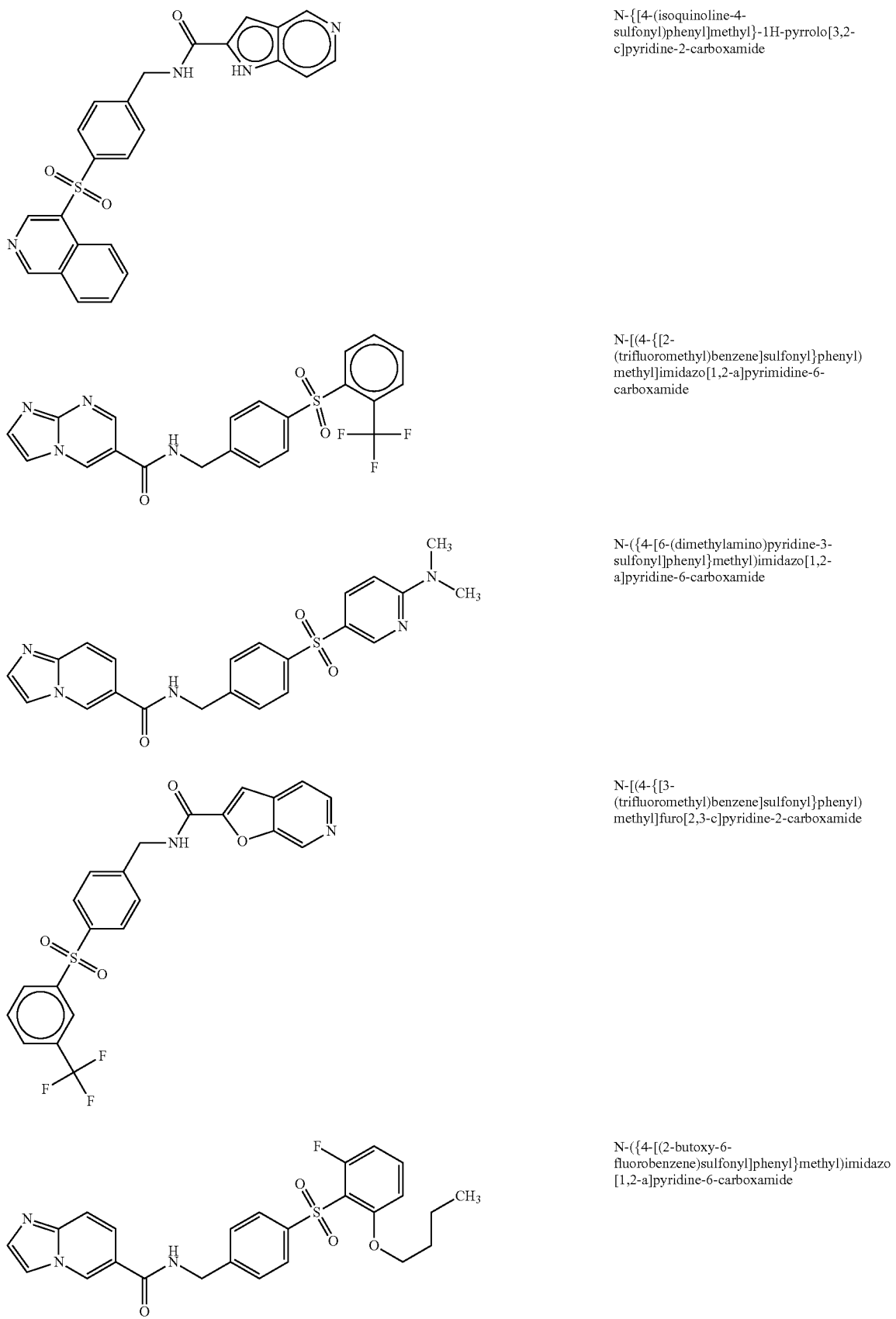

N-{[4-(isoquinoline-4-sulfonyl)phenyl]methyl}-1H-pyrrolo[3,2-c]pyridine-2-carboxamide N-[(4-{[2-(trifluoromethyl)benzene]sulfonyl}phenyl)methyl]imidazo[1,2-a]pyrimidine-6-carboxamide N-({4-[6-(dimethylamino)pyridine-3-sulfonyl]phenyl}methyl)imidazo[1,2-a]pyridine-6-carboxamide N-[(4-{[3-(trifluoromethyl)benzene]sulfonyl}phenyl)methyl]furo[2,3-c]pyridine-2-carboxamide N-({4-[(2-butoxy-6-fluorobenzene)sulfonyl]phenyl}methyl)imidazo[1,2-a]pyridine-6-carboxamide TABLE 2-continued
| | |
|---|---|
| 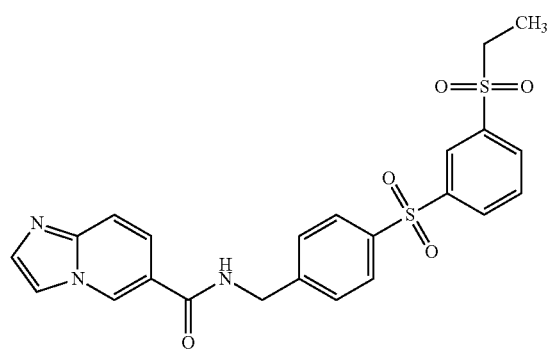 [SMILES: CCS(=O)(=O)c1cccc(S(=O)(=O)c2ccc(CNC(=O)c3ccc4nccn4c3)cc2)c1] | N-[(4-{[3-(ethanesulfonyl)benzene]sulfonyl}phenyl)methyl]imidazo[1,2-a]pyridine-6-carboxamide |
| 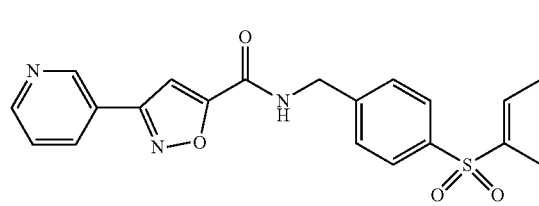 | N-{[4-(benzenesulfonyl)phenyl]methyl}-3-(pyridin-3-yl)-1,2-oxazole-5-carboxamide |
| 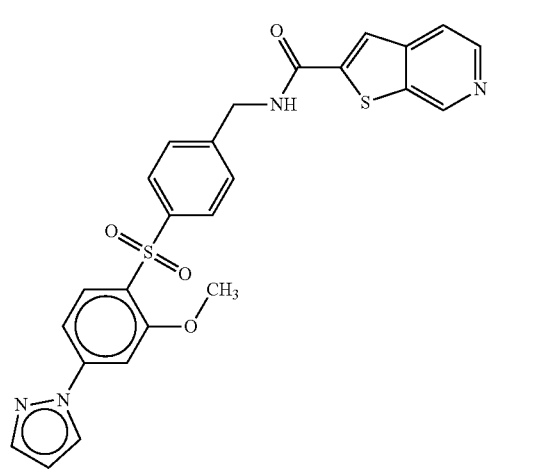 | N-[(4-{[2-methoxy-4-(1H-pyrazol-1-yl)benzene]sulfonyl}phenyl)methyl]thieno[2,3-c]pyridine-2-carboxamide |
| 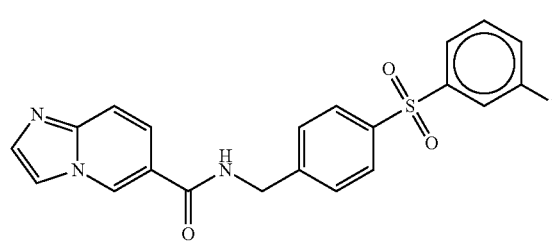 | N-[(4-{[3-(1H-pyrazol-1-yl)benzene]sulfonyl}phenyl)methyl]imidazo[1,2-a]pyridine-6-carboxamide |

TABLE 2-continued

| Structure | Name |
|---|---|
| (structure) | N-({4-[(3-chloro-4-propoxybenzene)sulfonyl]phenyl}methyl)-1H-pyrrolo[3,2-c]pyridine-2-carboxamide |
| (structure) | N-({4-[(5-chloro-2-propoxybenzene)sulfonyl]phenyl}methyl)furo[2,3-c]pyridine-2-carboxamide |
| (structure) | N-[(4-{[3-fluoro-5-(trifluoromethyl)benzene]sulfonyl}phenyl)methyl]-1H-pyrrolo[3,2-c]pyridine-2-carboxamide |
| (structure) | N-[(4-{[3-(ethylcarbamoyl)benzene]sulfonyl}phenyl)methyl]imidazo[1,2-a]pyrimidine-6-carboxamide |

TABLE 2-continued

| | |
|---|---|
| 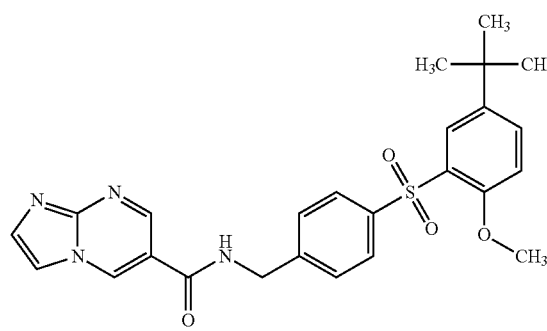 | N-({4-[(5-tert-butyl-2-methoxybenzene)sulfonyl]phenyl}methyl)imidazo[1,2-a]pyrimidine-6-carboxamide |
| 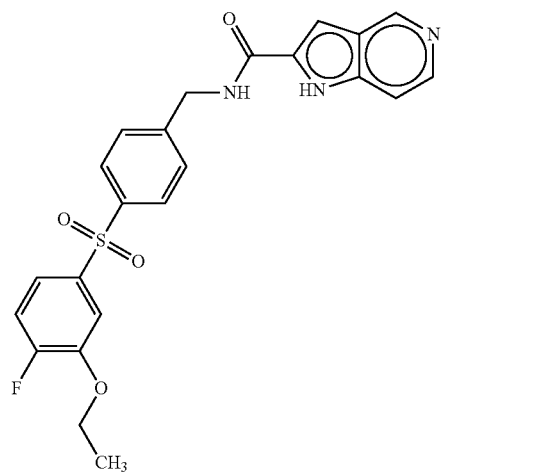 | N-({4-[(3-ethoxy-4-fluorobenzene)sulfonyl]phenyl}methyl)-1H-pyrrolo[3,2-c]pyridine-2-carboxamide |
| 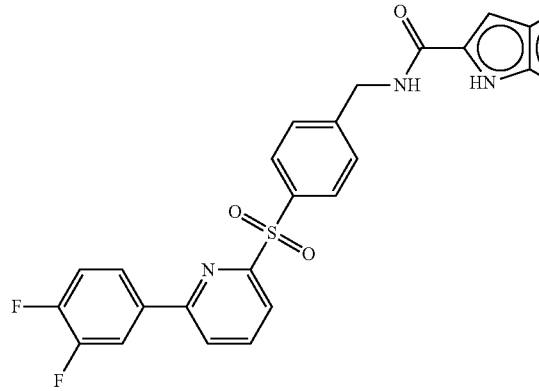 | N-({4-[6-(3,4-difluorophenyl)pyridine-2-sulfonyl]phenyl}methyl)-1H-pyrrolo[3,2-c]pyridine-2-carboxamide |
| 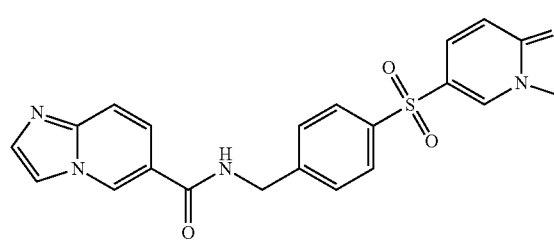 | N-({4-[2-(trifluoromethyl)imidazo[1,2-a]pyridine-6-sulfonyl]phenyl}methyl)imidazo[1,2-a]pyridine-6-carboxamide |

TABLE 2-continued
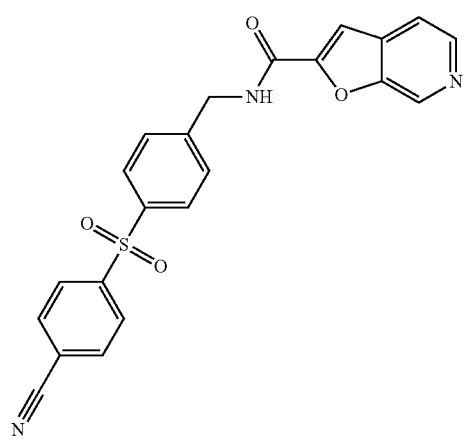 [SMILES: N#Cc1ccc(S(=O)(=O)c2ccc(CNC(=O)c3cc4ccncc4o3)cc2)cc1]
N-({4-[(4-cyanobenzene)sulfonyl]phenyl}methyl)furo[2,3-c]pyridine-2-carboxamide
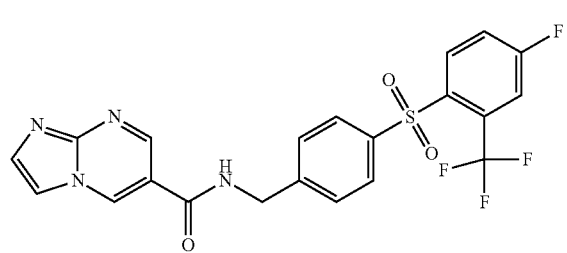 [SMILES: O=C(NCc1ccc(S(=O)(=O)c2ccc(F)cc2C(F)(F)F)cc1)c1cnc2nccn2c1]
N-[(4-{[4-fluoro-2-(trifluoromethyl)benzene]sulfonyl}phenyl)methyl]imidazo[1,2-a]pyrimidine-6-carboxamide
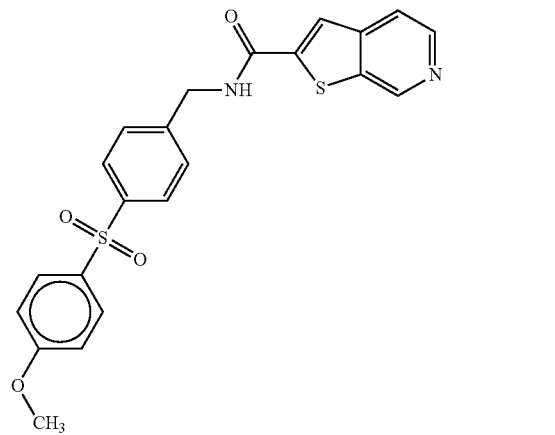
N-({4-[(4-methoxybenzene)sulfonyl]phenyl}methyl)thieno[2,3-c]pyridine-2-carboxamide
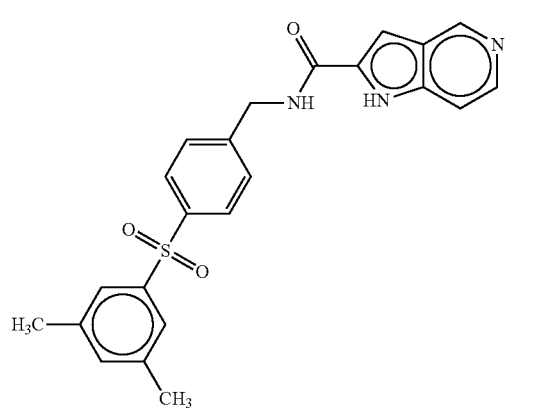
N-({4-[(3,5-dimethylbenzene)sulfonyl]phenyl}methyl)-1H-pyrrolo[3,2-c]pyridine-2-carboxamide TABLE 2-continued

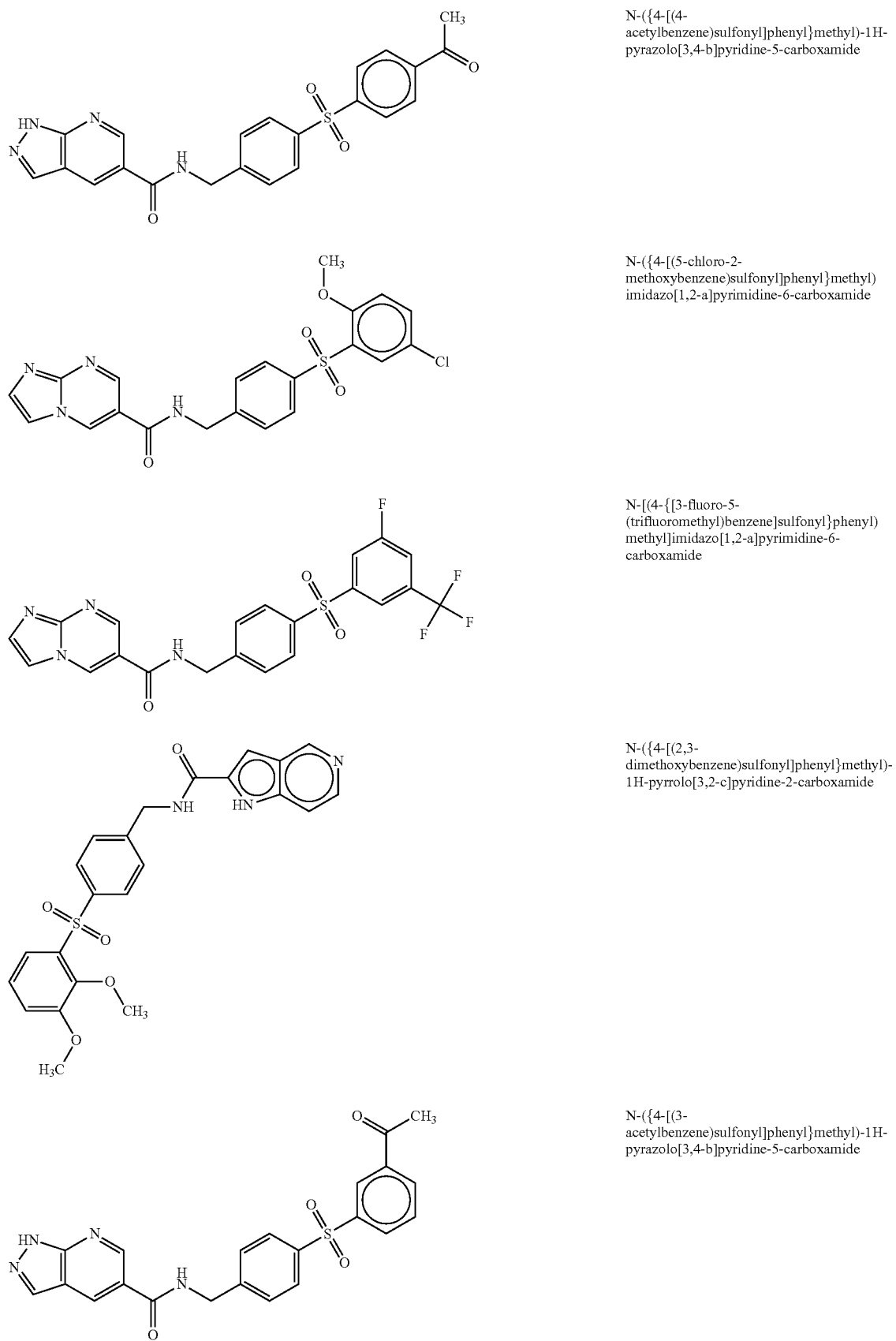

N-({4-[(4-acetylbenzene)sulfonyl]phenyl}methyl)-1H-pyrazolo[3,4-b]pyridine-5-carboxamide N-({4-[(5-chloro-2-methoxybenzene)sulfonyl]phenyl}methyl)imidazo[1,2-a]pyrimidine-6-carboxamide N-[(4-{[3-fluoro-5-(trifluoromethyl)benzene]sulfonyl}phenyl)methyl]imidazo[1,2-a]pyrimidine-6-carboxamide N-({4-[(2,3-dimethoxybenzene)sulfonyl]phenyl}methyl)-1H-pyrrolo[3,2-c]pyridine-2-carboxamide N-({4-[(3-acetylbenzene)sulfonyl]phenyl}methyl)-1H-pyrazolo[3,4-b]pyridine-5-carboxamide TABLE 2-continued
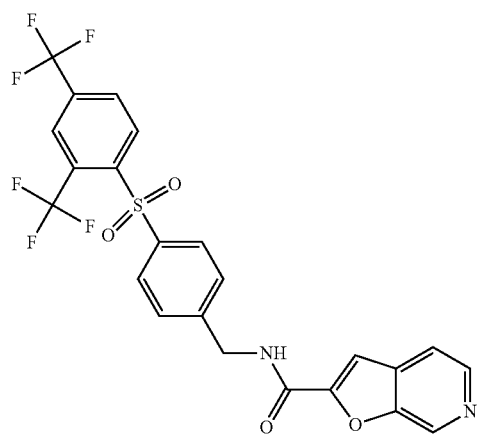 [SMILES: O=C(NCc1ccc(S(=O)(=O)c2ccc(C(F)(F)F)cc2C(F)(F)F)cc1)c1cc2ccncc2o1]
N-[(4-{[2,4-bis(trifluoromethyl)benzene]sulfonyl}phenyl)methyl]furo[2,3-c]pyridine-2-carboxamide
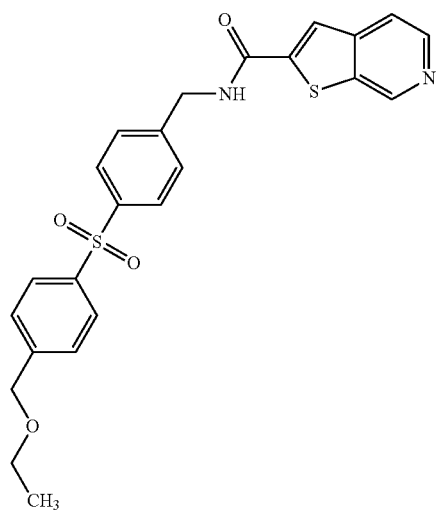 [SMILES: CCOCc1ccc(S(=O)(=O)c2ccc(CNC(=O)c3cc4ccncc4s3)cc2)cc1]
N-[(4-{[4-(ethoxymethyl)benzene]sulfonyl}phenyl)methyl]furo[2,3-c]pyridine-2-carboxamide
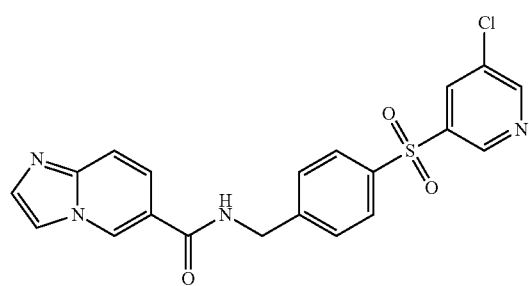 [SMILES: O=C(NCc1ccc(S(=O)(=O)c2cncc(Cl)c2)cc1)c1ccc2nccn2c1]
N-{[4-(5-chloropyridine-3-sulfonyl)phenyl]methyl}imidazo[1,2-a]pyridine-6-carboxamide
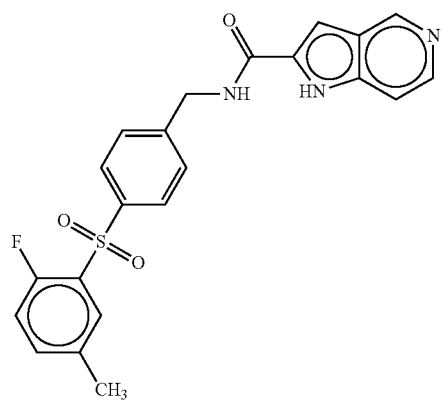
N-({4-[(2-fluoro-5-methylbenzene)sulfonyl]phenyl}methyl)-1H-pyrrolo[3,2-c]pyridine-2-carboxamide TABLE 2-continued

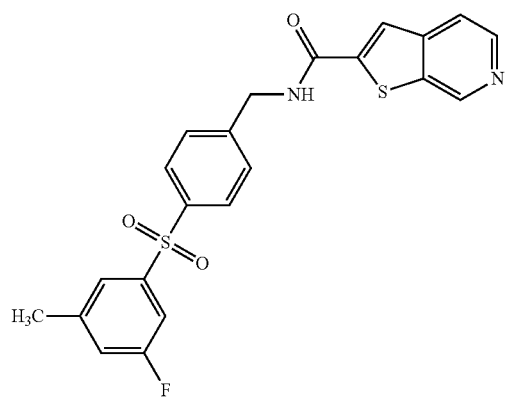
N-({4-[(3-fluoro-5-methylbenzene)sulfonyl]phenyl}methyl)thieno[2,3-c]pyridine-2-carboxamide

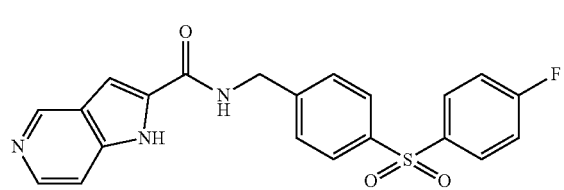 [SMILES: O=C(NCc1ccc(S(=O)(=O)c2ccc(F)cc2)cc1)c1cc2cnccc2[nH]1]
N-({4-[(4-fluorobenzene)sulfonyl]phenyl}methyl)-1H-pyrrolo[3,2-c]pyridine-2-carboxamide

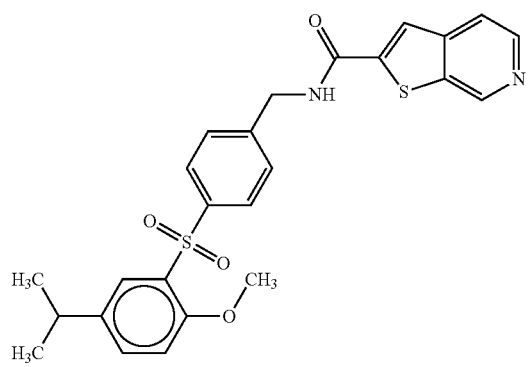
N-[(4-{[2-methoxy-5-(propan-2-yl)benzene]sulfonyl}phenyl)methyl]furo[2,3-c]pyridine-2-carboxamide

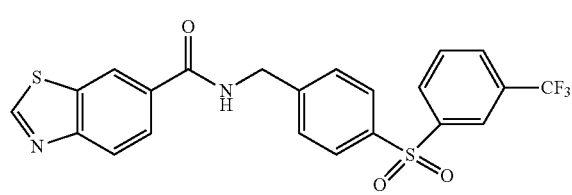 [SMILES: O=C(NCc1ccc(S(=O)(=O)c2cccc(C(F)(F)F)c2)cc1)c1ccc2ncsc2c1]
N-[(4-{[3-(trifluoromethyl)benzene]sulfonyl}phenyl)methyl]-1,3-benzothiazole-6-carboxamide

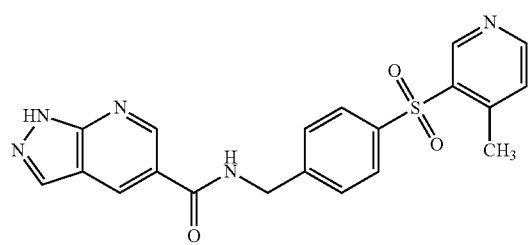 [SMILES: Cc1ccncc1S(=O)(=O)c1ccc(CNC(=O)c2cnc3[nH]ncc3c2)cc1]
N-{[4-(4-methylpyridine-3-sulfonyl)phenyl]methyl}-1H-pyrazolo[3,4-b]pyridine-5-carboxamide TABLE 2-continued
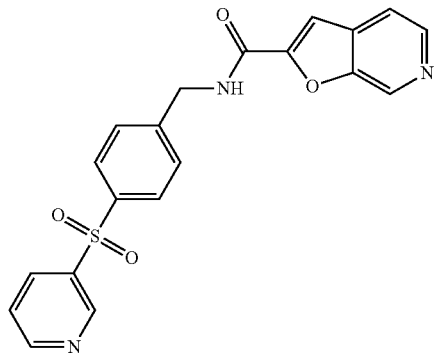 [SMILES: O=C(NCc1ccc(S(=O)(=O)c2cccnc2)cc1)c1cc2ccncc2o1]
N-{[4-(pyridine-3-sulfonyl)phenyl]methyl}furo[2,3-c]pyridine-2-carboxamide
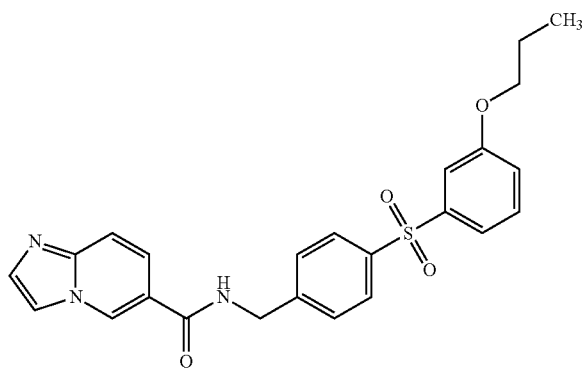 [SMILES: CCCOc1cccc(S(=O)(=O)c2ccc(CNC(=O)c3ccc4nccn4c3)cc2)c1]
N-({4-[(3-propoxybenzene)sulfonyl]phenyl}methyl)imidazo[1,2-a]pyridine-6-carboxamide
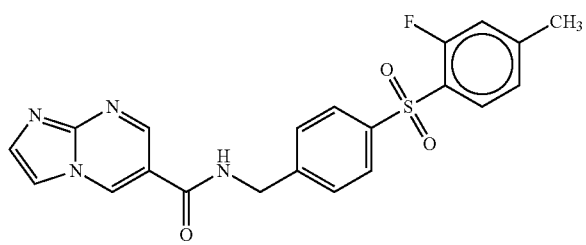
N-({4-[(2-fluoro-4-methylbenzene)sulfonyl]phenyl}methyl)imidazo[1,2-a]pyrimidine-6-carboxamide
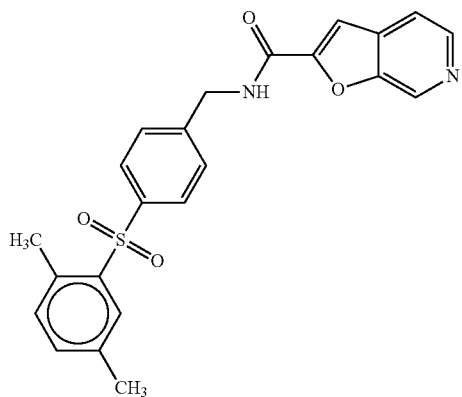
N-({4-[(2,5-dimethylbenzene)sulfonyl]phenyl}methyl)furo[2,3-c]pyridine-2-carboxamide TABLE 2-continued
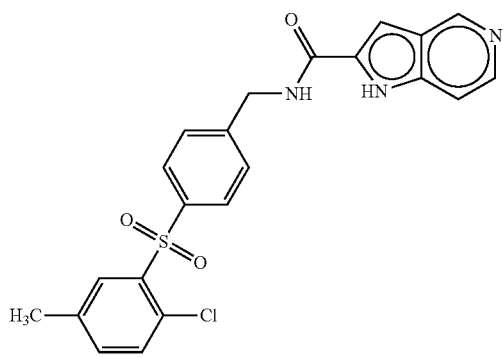
N-({4-[(2-chloro-5-methylbenzene)sulfonyl]phenyl}methyl)-1H-pyrrolo[3,2-c]pyridine-2-carboxamide
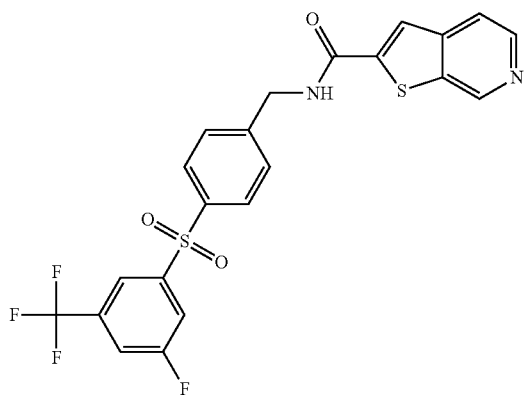 [SMILES: O=C(NCc1ccc(S(=O)(=O)c2cc(F)cc(C(F)(F)F)c2)cc1)c1cc2ccncc2s1]
N-[(4-{[3-fluoro-5-(trifluoromethyl)benzene]sulfonyl}phenyl)methyl]furo[2,3-c]pyridine-2-carboxarnide
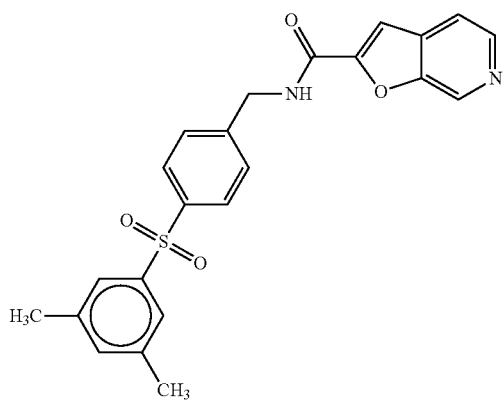
N-({4-[(3,5-dimethylbenzene)sulfonyl]phenyl}methyl)furo[2,3-c]pyridine-2-carboxamide
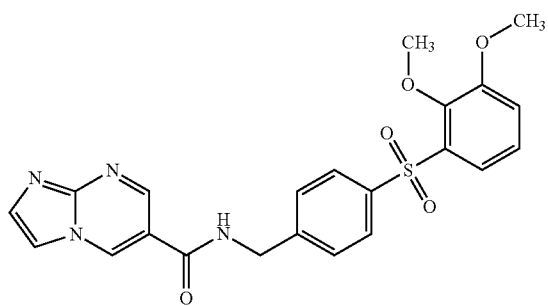 [SMILES: COc1cccc(S(=O)(=O)c2ccc(CNC(=O)c3cnc4nccn4c3)cc2)c1OC]
N-({4-[(2,3-dimethoxybenzene)sulfonyl]phenyl)methyl)imidazo[1,2-a]pyrimidine-6-carboxamide TABLE 2-continued
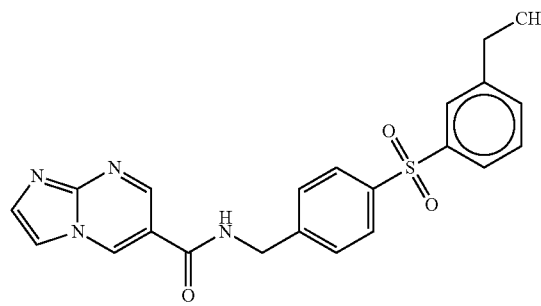
N-({4-[(3-ethylbenzene)sulfonyl]phenyl}methyl)imidazo[1,2-a]pyrimidine-6-carboxamide
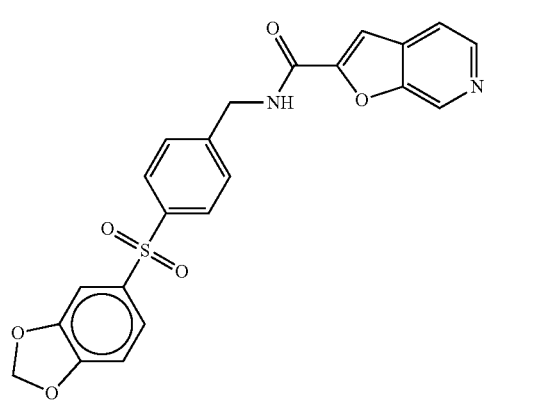
N-{[4-(2H-1,3-benzodioxole-5-sulfonyl)phenyl]methyl}furo[2,3-c]pyridine-2-carboxamide
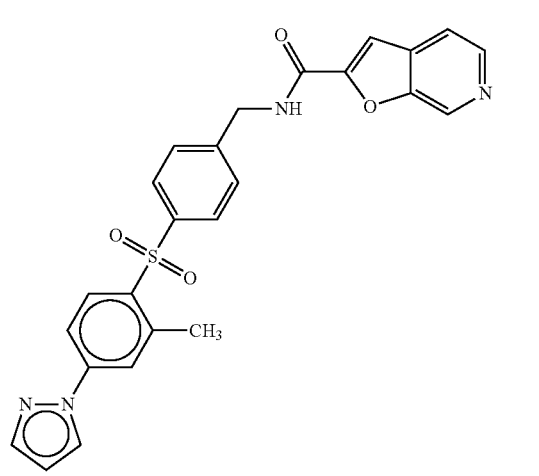
N-[(4-{[2-methyl-4-(1H-pyrazol-1-yl)benzene]sulfonyl}phenyl)methyl]thieno[2,3-c]pyridine-2-carboxamide
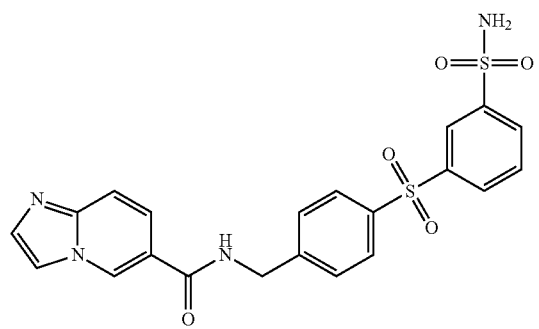 [SMILES: NS(=O)(=O)c1cccc(S(=O)(=O)c2ccc(CNC(=O)c3ccc4nccn4c3)cc2)c1]
N-({4-[(3-sulfamoylbenzene)sulfonyl]phenyl}methyl)imidazo[1,2-a]pyridine-6-carboxamide TABLE 2-continued

| | |
|---|---|
| 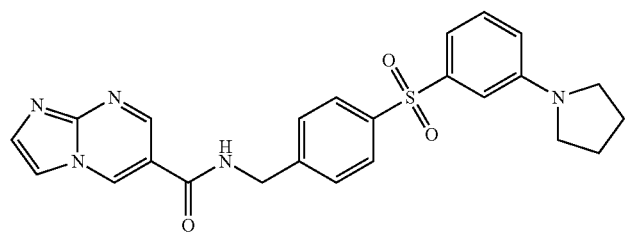 [SMILES: O=C(NCc1ccc(S(=O)(=O)c2cccc(N3CCCC3)c2)cc1)c1cnc2nccn2c1] | N-[(4-{[3-(pyrrolidin-1-yl)benzene]sulfonyl}phenyl)methyl]imidazo[1,2-a]pyrimidine-6-carboxamide |
| 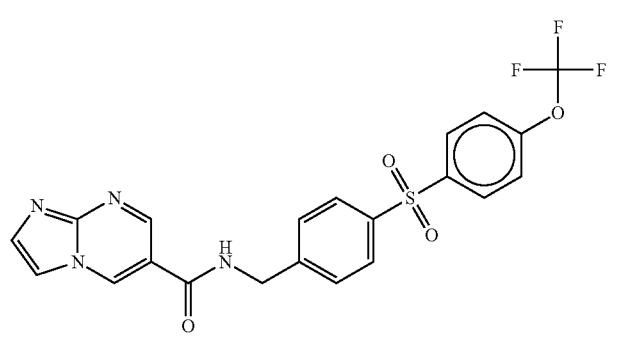 | N-[(4-{[4-(trifluoromethoxy)benzene]sulfonyl}phenyl)methyl]imidazo[1,2-a]pyrimidine-6-carboxamide |
| 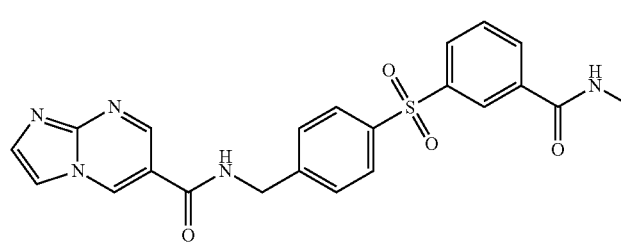 | N-{[4-({3-[(2-methylpropyl)carbamoyl]benzene}sulfonyl)phenyl]methyl}imidazo[1,2-a]pyrimidine-6-carboxamide |
| 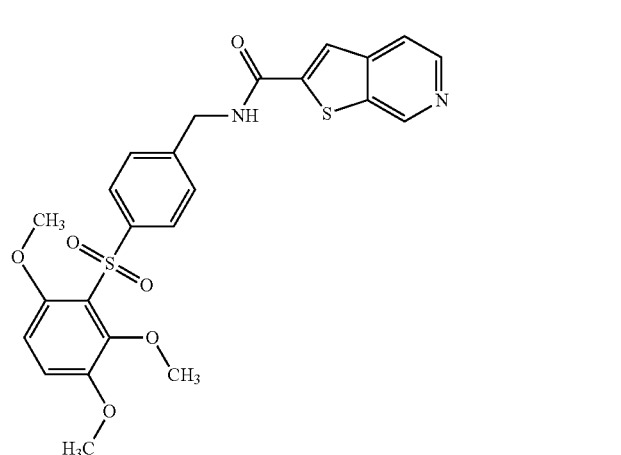 [SMILES: COc1ccc(OC)c(S(=O)(=O)c2ccc(CNC(=O)c3cc4ccncc4s3)cc2)c1OC] | N-({4-[(2,3,6-trimethoxybenzene)sulfonyl]phenyl}methyl)thieno[2,3-c]pyridine-2-carboxamide |
| 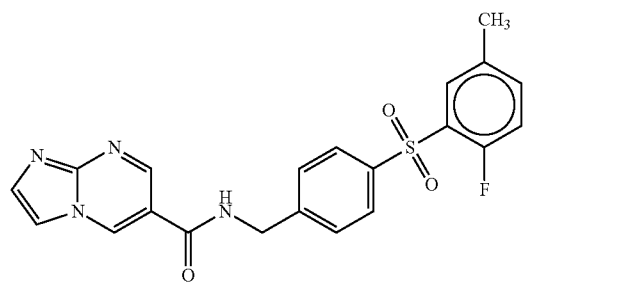 | N-({4-[(2-fluoro-5-methylbenzene)sulfonyl]phenyl}methyl)imidazo[1,2-a]pyrimidine-6-carboxamide |

TABLE 2-continued

| Structure | Name |
|---|---|
| (structure) | N-({4-[(3-methoxy-5-methylbenzene)sulfonyl]phenyl}methyl)-1H-pyrrolo[3,2-c]pyridine-2-carboxamide |
| (structure) | N-{[4-(1-methyl-1H-indazole-4-sulfonyl)phenyl]methyl}furo[2,3-c]pyridine-2-carboxamide |
| (structure) | N-{[4-(benzenesulfonyl)phenyl]methyl}imidazo[1,2-a]pyridine-6-carboxamide |
| (structure) | N-({4-[(2-chloro-4-methylbenzene)sulfonyl]phenyl}methyl)imidazo[1,2-a]pyridine-6-carboxamide |
| (structure) | N-({4-[(4-butoxy-3-chlorobenzene)sulfonyl]phenyl}methyl)-1H-pyrazolo[3,4-b]pyridine-5-carboxamide |

TABLE 2-continued

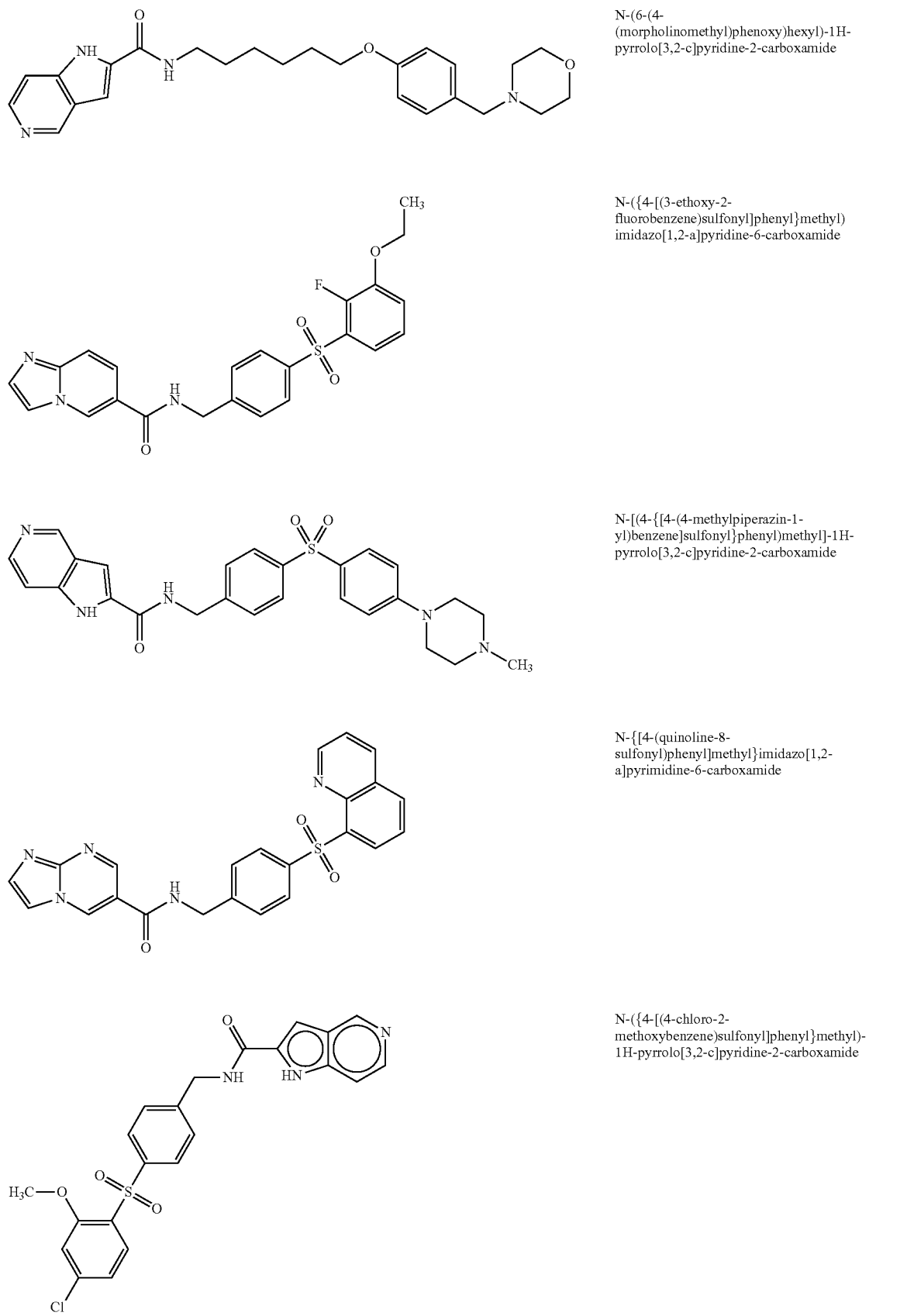

N-(6-(4-(morpholinomethyl)phenoxy)hexyl)-1H-pyrrolo[3,2-c]pyridine-2-carboxamide N-({4-[(3-ethoxy-2-fluorobenzene)sulfonyl]phenyl}methyl)imidazo[1,2-a]pyridine-6-carboxamide N-[(4-{[4-(4-methylpiperazin-1-yl)benzene]sulfonyl}phenyl)methyl]-1H-pyrrolo[3,2-c]pyridine-2-carboxamide N-{[4-(quinoline-8-sulfonyl)phenyl]methyl}imidazo[1,2-a]pyrimidine-6-carboxamide N-({4-[(4-chloro-2-methoxybenzene)sulfonyl]phenyl}methyl)-1H-pyrrolo[3,2-c]pyridine-2-carboxamide TABLE 2-continued
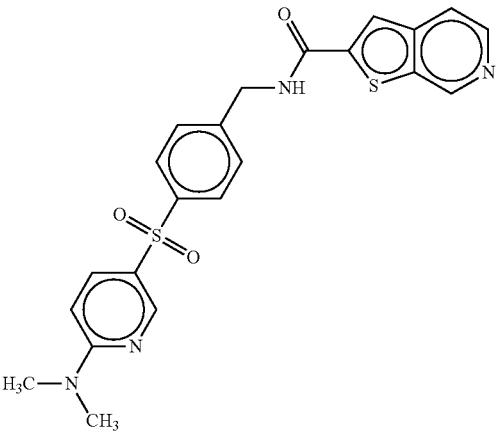
N-({4-[6-(dimethylamino)pyridine-3-sulfonyl]phenyl}methyl)thieno[2,3-c]pyridine-2-carboxamide
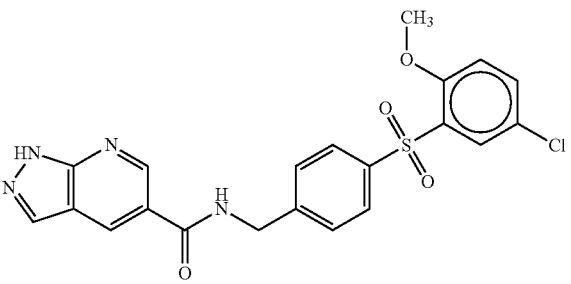
N-({4-[(5-chloro-2-methoxybenzene)sulfonyl]phenyl}methyl)-1H-pyrazolo[3,4-b]pyridine-5-carboxamide
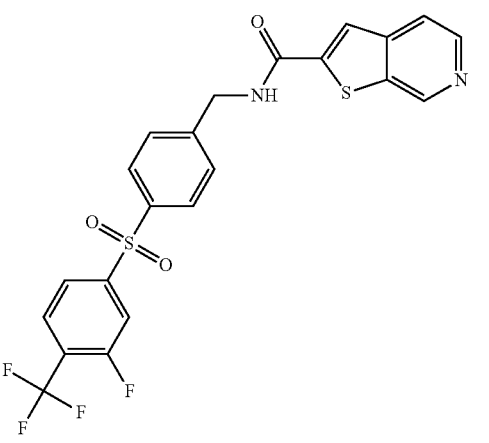
N-[(4-{[3-fluoro-4-(trifluoromethyl)benzene]sulfonyl}phenyl)methyl]thieno[2,3-c]pyridine-2-carboxamide
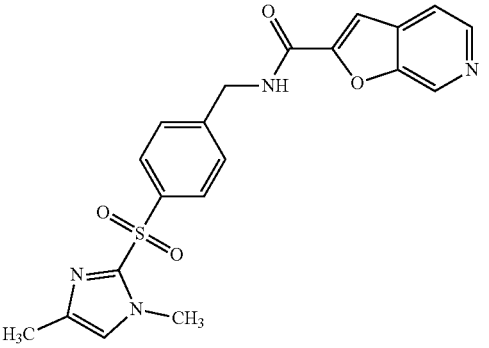 [SMILES: Cc1cn(C)c(S(=O)(=O)c2ccc(CNC(=O)c3cc4ccncc4o3)cc2)n1]
N-{[4-(1,4-dimethyl-1H-imidazole-2-sulfonyl)phenyl]methyl}furo[2,3-c]pyridine-2-carboxamide TABLE 2-continued
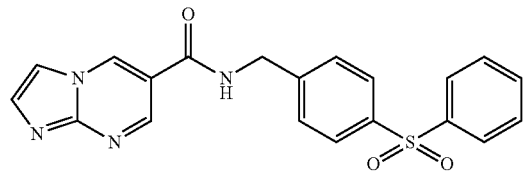 [SMILES: O=C(NCc1ccc(S(=O)(=O)c2ccccc2)cc1)c1cnc2nccn2c1]
N-{[4-(benzenesulfonyl)phenyl]methyl}imidazo[1,2-a]pyrimidine-6-carboxamide
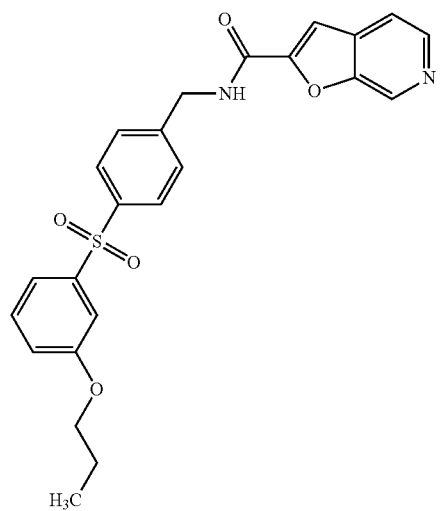
N-({4-[(3-propoxybenzene)sulfonyl]phenyl}methyl)furo[2,3-c]pyridine-2-carboxamide
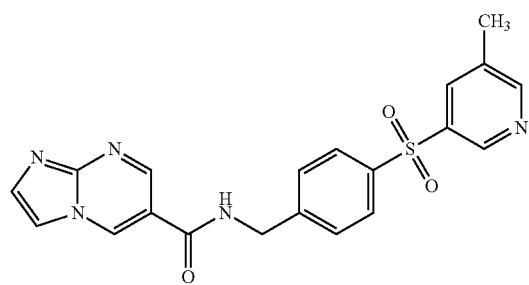
N-{[4-(5-methylpyridine-3-sulfonyl)phenyl]methyl}imidazo[1,2-a]pyrimidine-6-carboxamide
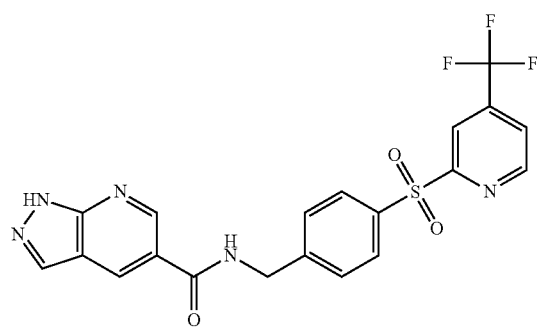 [SMILES: O=C(NCc1ccc(S(=O)(=O)c2cc(C(F)(F)F)ccn2)cc1)c1cnc2[nH]ncc2c1]
N-({4-[4-(trifluoromethyl)pyridine-2-sulfonyl]phenyl}methyl)-1H-pyrazolo[3,4-b]pyridine-5-carboxamide TABLE 2-continued
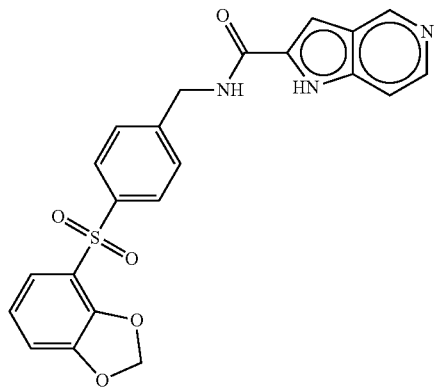
N-{[4-(2H-1,3-benzodioxole-4-sulfonyl)phenyl]methyl}-1H-pyrrolo[3,2-c]pyridine-2-carboxamide
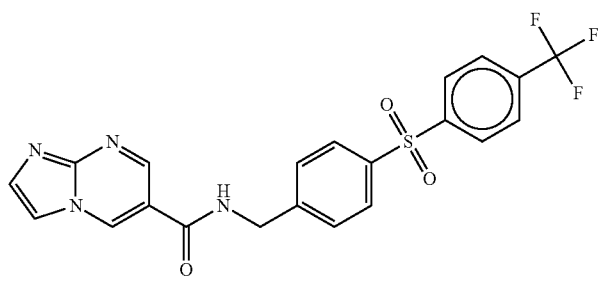
N-[(4-{[4-(trifluoromethyl)benzene]sulfonyl}phenyl)methyl]imidazo[1,2-a]pyrimidine-6-carboxamide
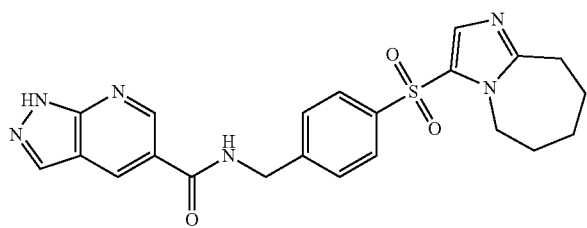 [SMILES: O=C(NCc1ccc(S(=O)(=O)c2cnc3n2CCCCC3)cc1)c1cnc2[nH]ncc2c1]
N-[(4-{5H,6H,7H,8H,9H-imidazo[1,2-a]azepine-3-sulfonyl}phenyl)methyl]-1H-pyrazolo[3,4-b]pyridine-5-carboxamide
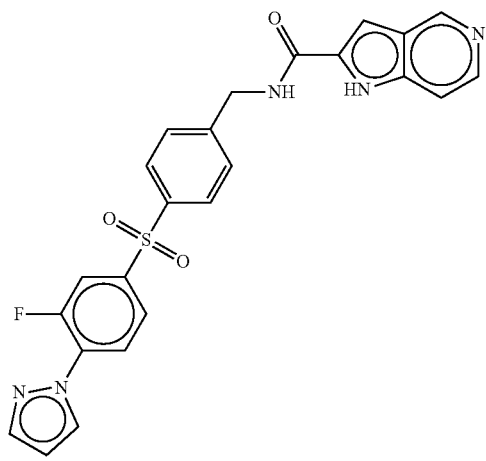
N-[(4-{[3-fluoro-4-(1H-pyrazol-1-yl)benzene]sulfonyl}phenyl)methyl]-1H-pyrrolo[3,2-c]pyridine-2-carboxamide TABLE 2-continued
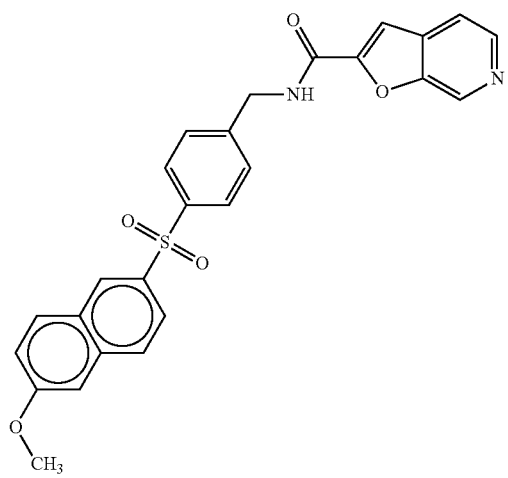
N-{[4-(6-methoxynaphthalene-2-sulfonyl)phenyl]methyl}furo[2,3-c]pyridine-2-carboxamide
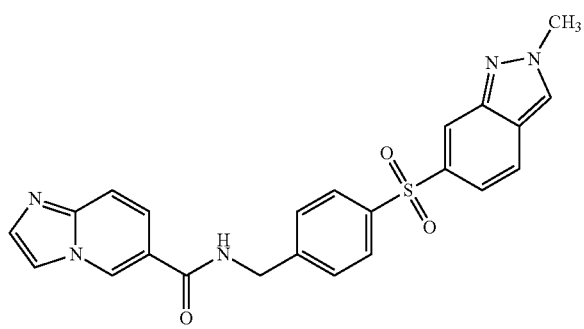 [SMILES: Cn1cc2ccc(S(=O)(=O)c3ccc(CNC(=O)c4ccc5nccn5c4)cc3)cc2n1]
N-{[4-(2-methyl-2H-indazole-6-sulfonyl)phenyl]methyl}imidazo[1,2-a]pyridine-6-carboxamide
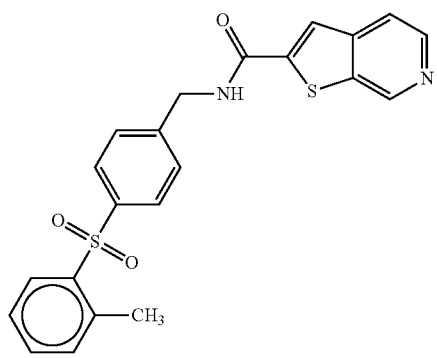
N-({4-[(2-methylbenzene)sulfonyl]phenyl}methyl)thieno[2,3-c]pyridine-2-carboxamide
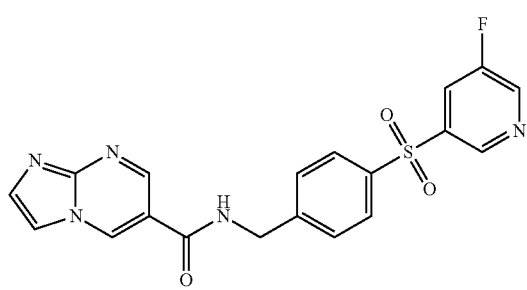 [SMILES: O=C(NCc1ccc(S(=O)(=O)c2cncc(F)c2)cc1)c1cnc2nccn2c1]
N-{[4-(5-fluoropyridine-3-sulfonyl)phenyl]methyl}imidazo[1,2-a]pyrimidine-6-carboxamide TABLE 2-continued
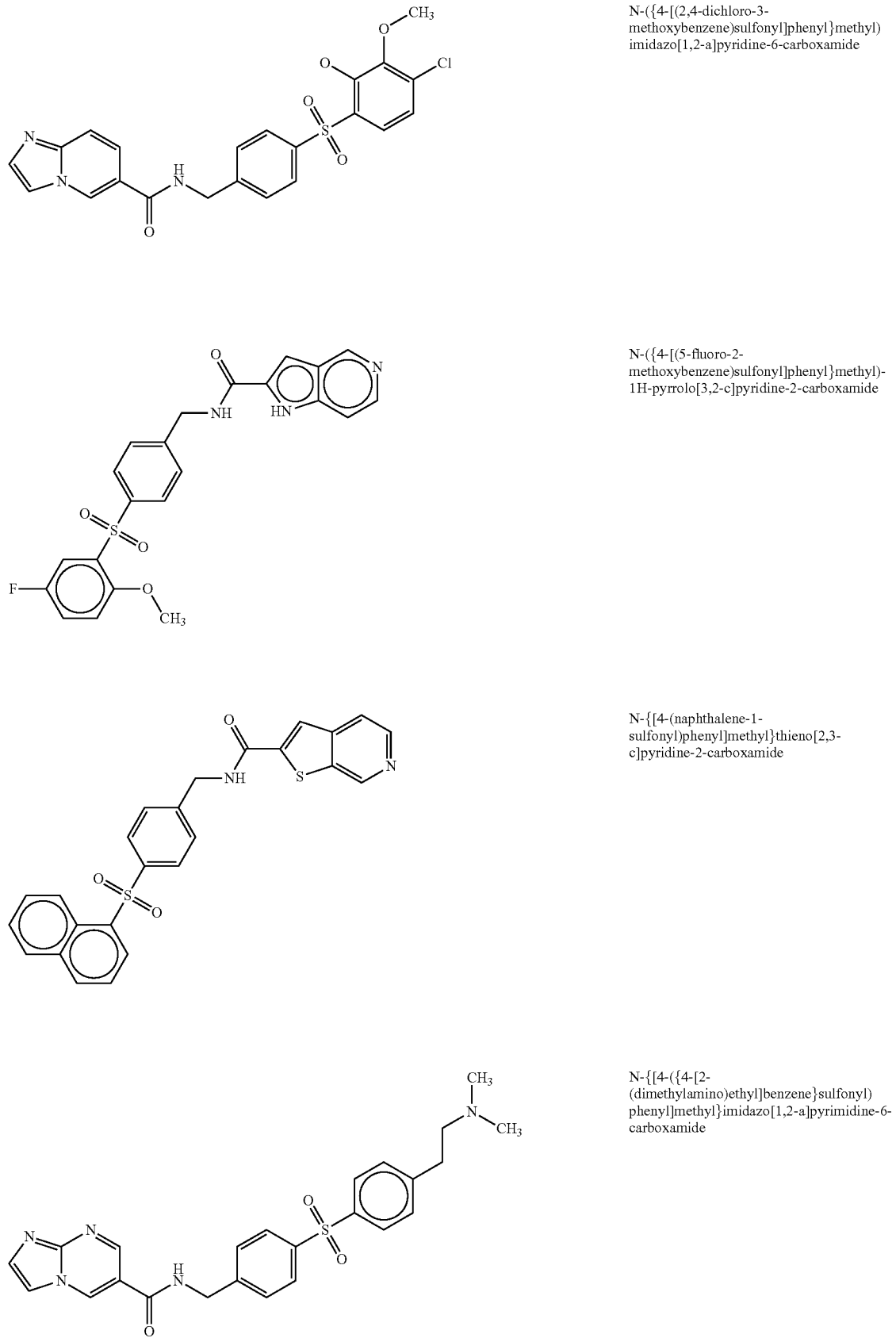
N-({4-[(2,4-dichloro-3-methoxybenzene)sulfonyl]phenyl}methyl)imidazo[1,2-a]pyridine-6-carboxamide
N-({4-[(5-fluoro-2-methoxybenzene)sulfonyl]phenyl}methyl)-1H-pyrrolo[3,2-c]pyridine-2-carboxamide
N-{[4-(naphthalene-1-sulfonyl)phenyl]methyl}thieno[2,3-c]pyridine-2-carboxamide
N-{[4-({4-[2-(dimethylamino)ethyl]benzene}sulfonyl)phenyl]methyl}imidazo[1,2-a]pyrimidine-6-carboxamide TABLE 2-continued
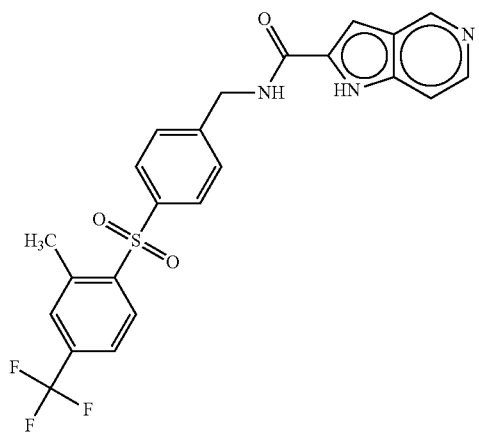
N-[(4-{[2-methyl-4-(trifluoromethyl)benzene]sulfonyl}phenyl)methyl]-1H-pyrrolo[3,2-c]pyridine-2-carboxamide
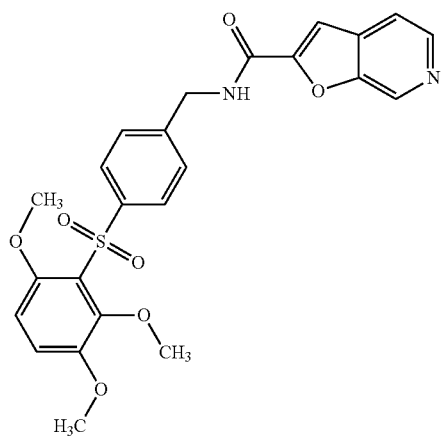 [SMILES: COc1ccc(OC)c(S(=O)(=O)c2ccc(CNC(=O)c3cc4ccncc4o3)cc2)c1OC]
N-({4-[(2,3,6-trimethoxybenzene)sulfonyl]phenyl}methyl)furo[2,3-c]pyridine-2-carboxamide
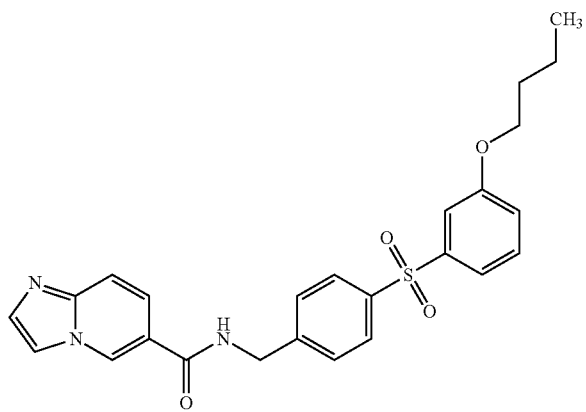 [SMILES: CCCCOc1cccc(S(=O)(=O)c2ccc(CNC(=O)c3ccc4nccn4c3)cc2)c1]
N-({4-[(3-butoxybenzene)sulfonyl]phenyl}methyl)imidazo[1,2-a]pyridine-6-carboxamide TABLE 2-continued
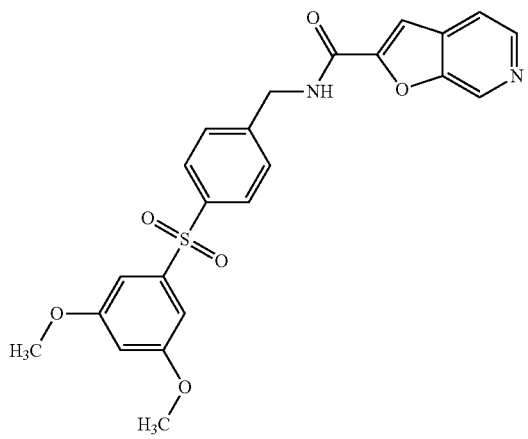
N-({4-[(3,5-dimethoxybenzene)sulfonyl]phenyl}methyl)furo[2,3-c]pyridine-2-carboxamide
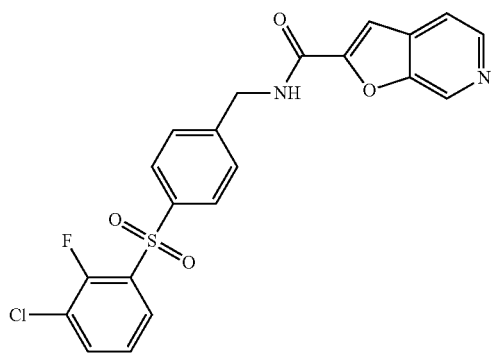 [SMILES: O=C(NCc1ccc(S(=O)(=O)c2cccc(Cl)c2F)cc1)c1cc2ccncc2o1]
N-({4-[(3-chloro-2-fluorobenzene)sulfonyl]phenyl}methyl)furo[2,3-c]pyridine-2-carboxamide
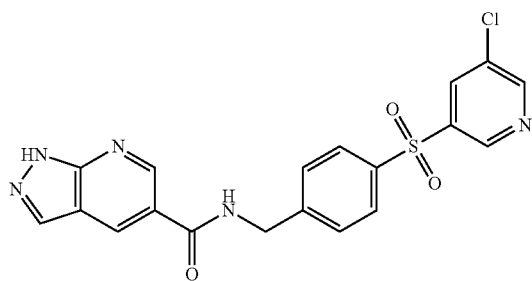 [SMILES: O=C(NCc1ccc(S(=O)(=O)c2cncc(Cl)c2)cc1)c1cnc2[nH]ncc2c1]
N-{[4-(5-chloropyridine-3-sulfonyl)phenyl]methyl}-1H-pyrazolo[3,4-b]pyridine-5-carboxamide
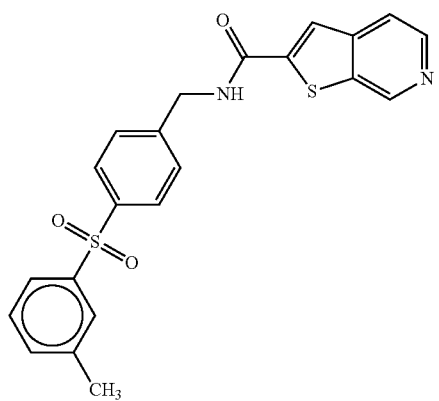
N-({4-[(3-methylbenzene)sulfonyl]phenyl}methyl)thieno[2,3-c]pyridine-2-carboxamide

TABLE 2-continued
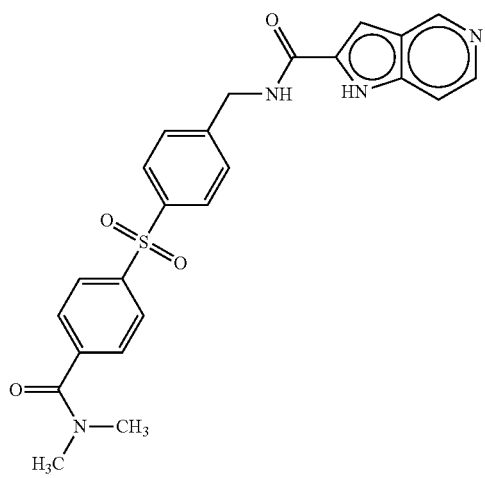
N-[(4-{[4-(dimethylcarbamoyl)benzene]sulfonyl}phenyl)methyl]-1H-pyrrolo[3,2-c]pyridine-2-carboxamide
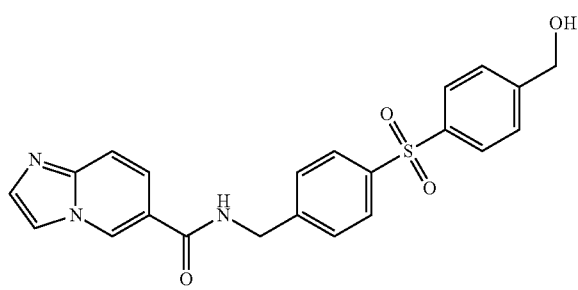 [SMILES: O=C(NCc1ccc(S(=O)(=O)c2ccc(CO)cc2)cc1)c1ccc2nccn2c1]
N-[(4-{[4-(hydroxymethyl)benzene]sulfonyl}phenyl)methyl]imidazo[1,2-a]pyridine-6-carboxamide
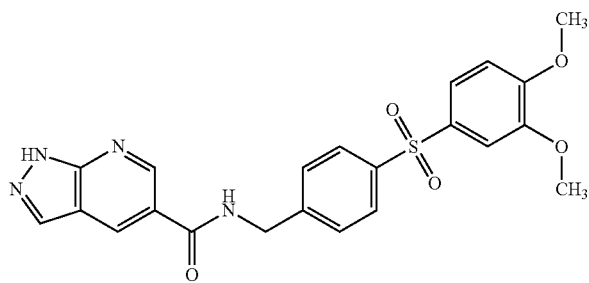 [SMILES: COc1ccc(S(=O)(=O)c2ccc(CNC(=O)c3cnc4[nH]ncc4c3)cc2)cc1OC]
N-({4-[(3,4-dimethoxybenzene)sulfonyl]phenyl}methyl)-1H-pyrazolo[3,4-b]pyridine-5-carboxamide
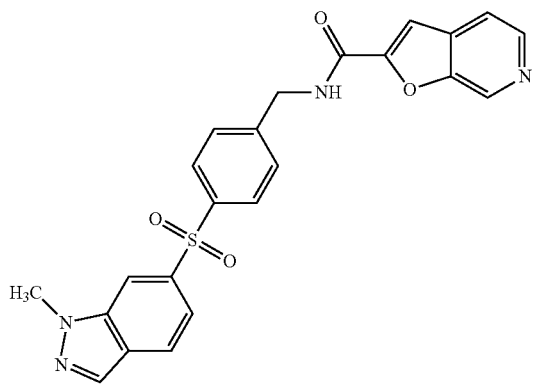 [SMILES: Cn1ncc2ccc(S(=O)(=O)c3ccc(CNC(=O)c4cc5ccncc5o4)cc3)cc21]
N-{[4-(1-methyl-1H-indazole-6-sulfonyl)phenyl]methyl)furo[2,3-c]pyridine-2-carboxamide TABLE 2-continued
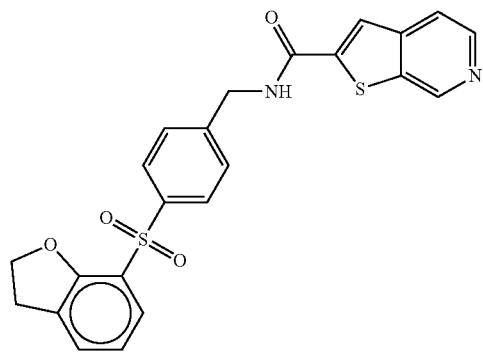
N-{[4-(2,3-dihydro-1-benzofuran-7-sulfonyl)phenyl]methyl}thieno[2,3-c]pyridine-2-carboxamide
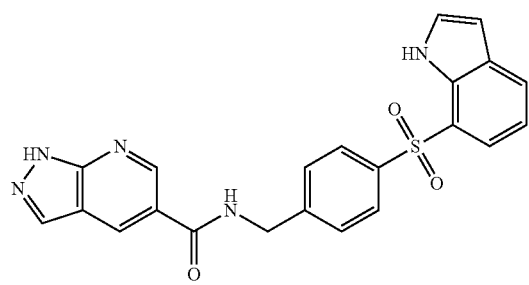 [SMILES: O=C(NCc1ccc(S(=O)(=O)c2cccc3cc[nH]c23)cc1)c1cnc2[nH]ncc2c1]
N-{[4-(1H-indole-7-sulfonyl)phenyl]methyl}-1H-pyrazolo[3,4-b]pyridine-5-carboxamide
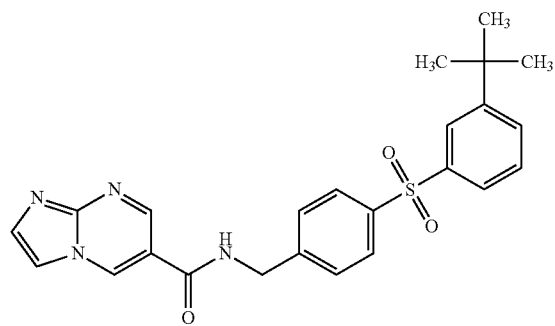 [SMILES: CC(C)(C)c1cccc(S(=O)(=O)c2ccc(CNC(=O)c3cnc4nccn4c3)cc2)c1]
N-({4-[(3-tert-butylbenzene)sulfonyl]phenyl}methyl)imidazo[1,2-a]pyrimidine-6-carboxamide
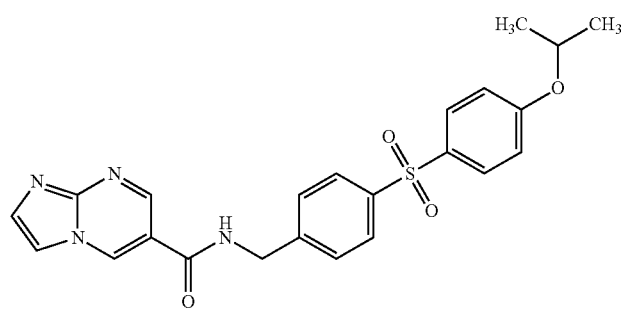 [SMILES: CC(C)Oc1ccc(S(=O)(=O)c2ccc(CNC(=O)c3cnc4nccn4c3)cc2)cc1]
N-[(4-{[4-(propan-2-yloxy)benzene]sulfonyl}phenyl)methyl]imidazo[1,2-a]pyrimidine-6-carboxamide TABLE 2-continued
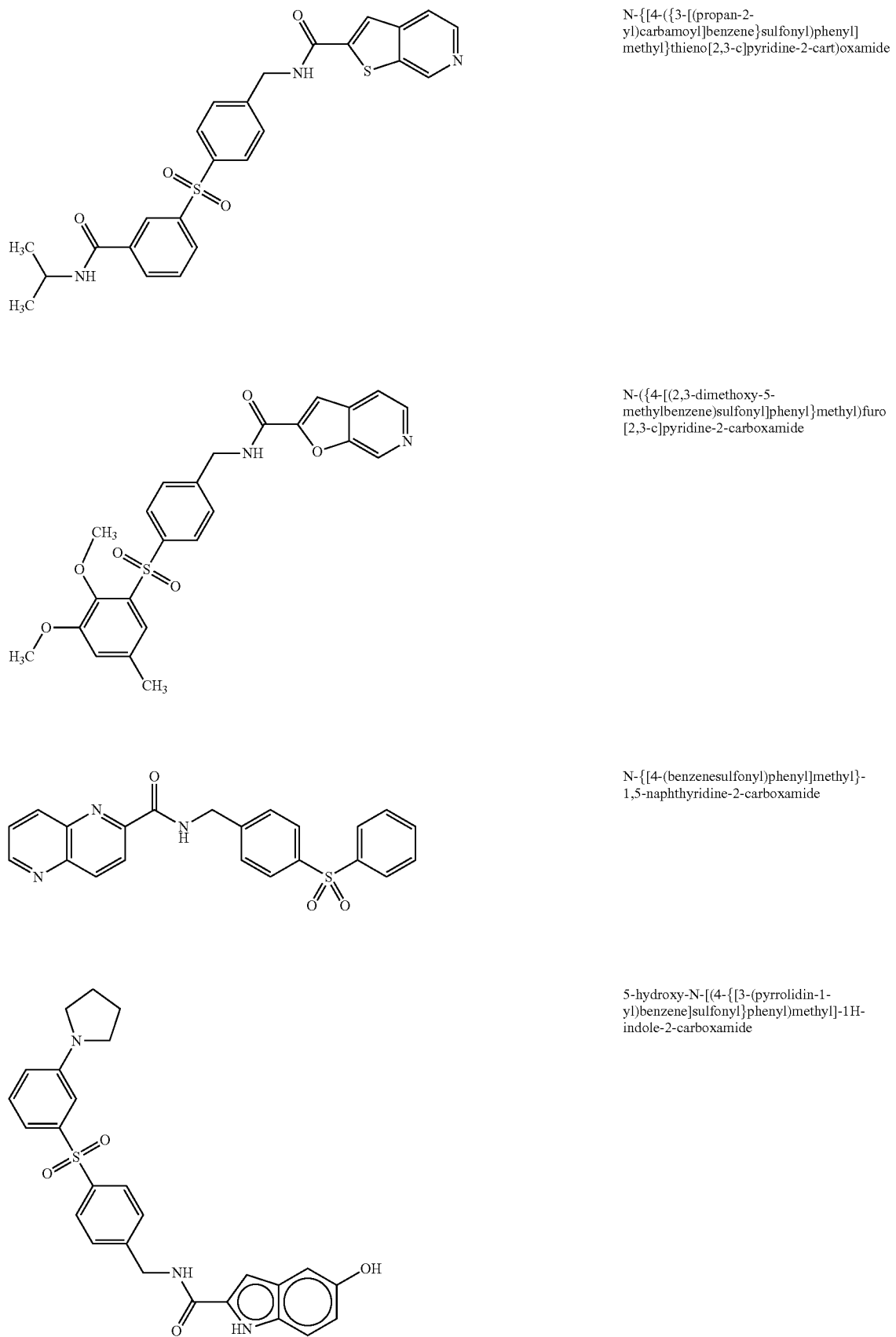
N-{[4-({3-[(propan-2-yl)carbamoyl]benzene}sulfonyl)phenyl]methyl}thieno[2,3-c]pyridine-2-cart)oxamide
N-({4-[(2,3-dimethoxy-5-methylbenzene)sulfonyl]phenyl}methyl)furo[2,3-c]pyridine-2-carboxamide
N-{[4-(benzenesulfonyl)phenyl]methyl}-1,5-naphthyridine-2-carboxamide
5-hydroxy-N-[(4-{[3-(pyrrolidin-1-yl)benzene]sulfonyl}phenyl)methyl]-1H-indole-2-carboxamide TABLE 2-continued
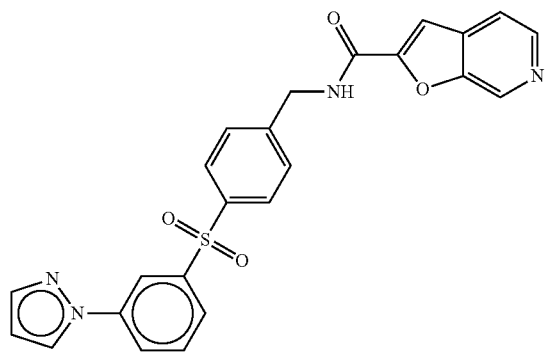
N-[(4-{[3-(1H-pyrazol-1-yl)benzene]sulfonyl}phenyl)methyl]furo[2,3-c]pyridine-2-carboxamide
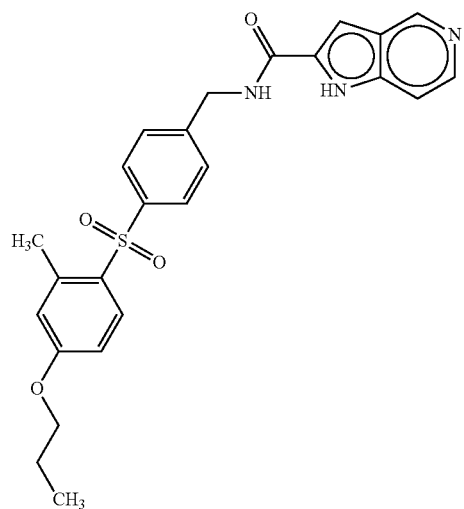
N-({4-[(2-methyl-4-propoxybenzene)sulfonyl]phenyl}methyl)-1H-pyrrolo[3,2-c]pyridine-2-carboxamide
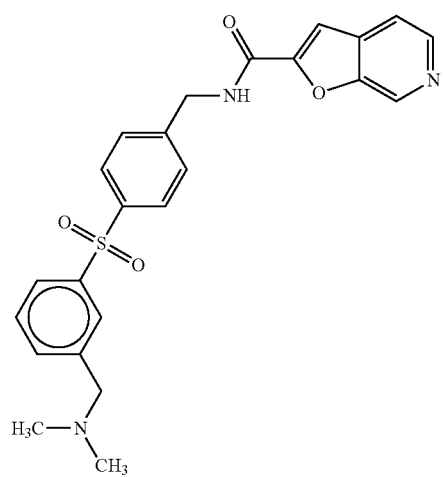
N-{[4-({3-[(dimethylamino)methyl]benzene}sulfonyl)phenyl]methyl}furo[2,3-c]pyridine-2-carboxamide TABLE 2-continued
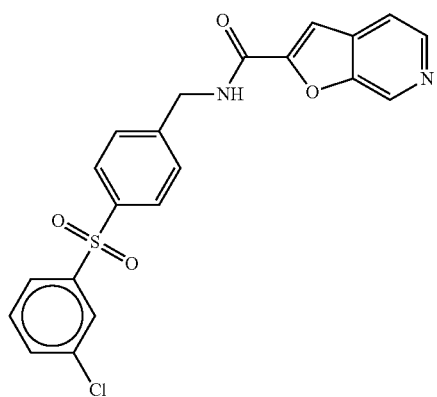
N-({4-[(3-chlorobenzene)sulfonyl]phenyl}methyl)furo[2,3-c]pyridine-2-carboxamide
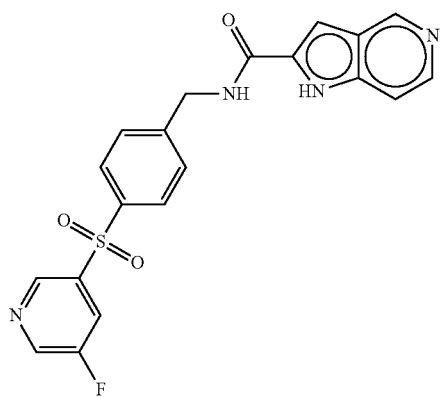
N-{[4-(5-fluoropyridine-3-sulfonyl)phenyl]methyl}-1H-pyrrolo[3,2-c]pyridine-2-carboxamide
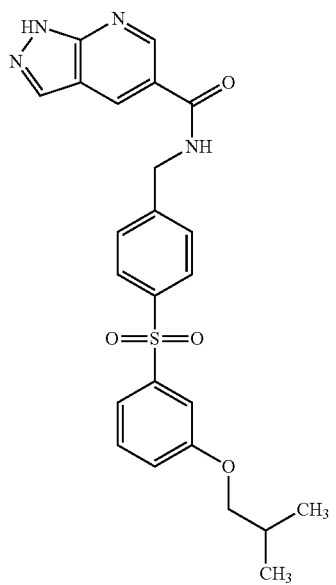 [SMILES: CC(C)COc1cccc(S(=O)(=O)c2ccc(CNC(=O)c3cnc4[nH]ncc4c3)cc2)c1]
N-[(4-{[3-(2-methylpropoxy)benzene]sulfonyl}phenyl)methyl]-1H-pyrazolo[3,4-b]pyridine-5-carboxamide

TABLE 2-continued
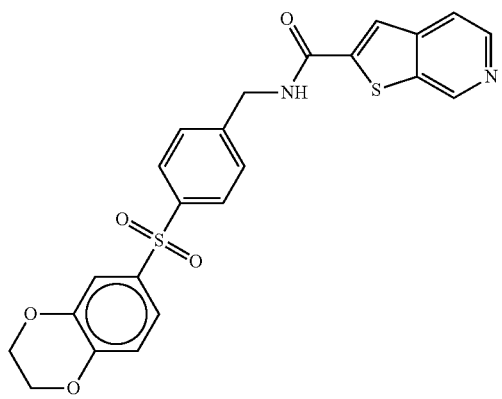 N-{[4-(2,3-dihydro-1,4-benzodioxine-6-sulfonyl)phenyl]methyl}thieno[2,3-c]pyridine-2-carboxamide
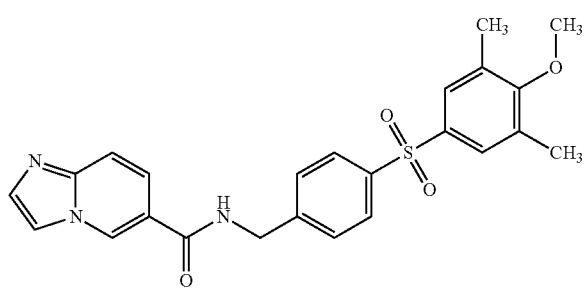 [SMILES: COc1c(C)cc(S(=O)(=O)c2ccc(CNC(=O)c3ccc4nccn4c3)cc2)cc1C] N-({4-[(4-methoxy-3,5-dimethylbenzene)sulfonyl]phenyl}methyl)imidazo[1,2-a]pyridine-6-carboxamide
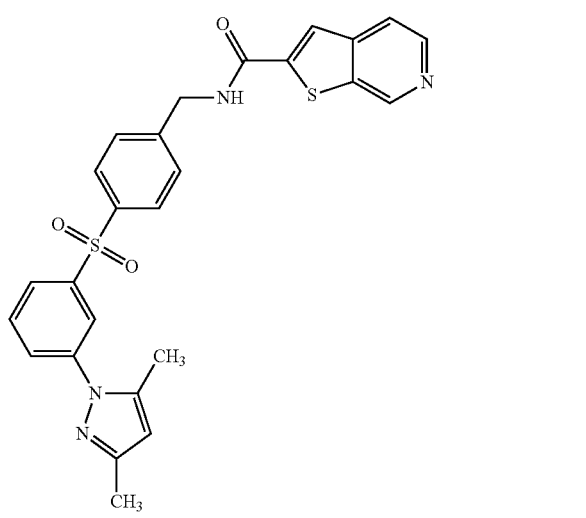 [SMILES: Cc1cc(C)n(-c2cccc(S(=O)(=O)c3ccc(CNC(=O)c4cc5ccncc5s4)cc3)c2)n1] N-[(4-{[3-(3,5-dimethyl-1H-pyrazol-1-yl)benzene]sulfonyl}phenyl)methyl]thieno[2,3-c]pyridine-2-carboxamide
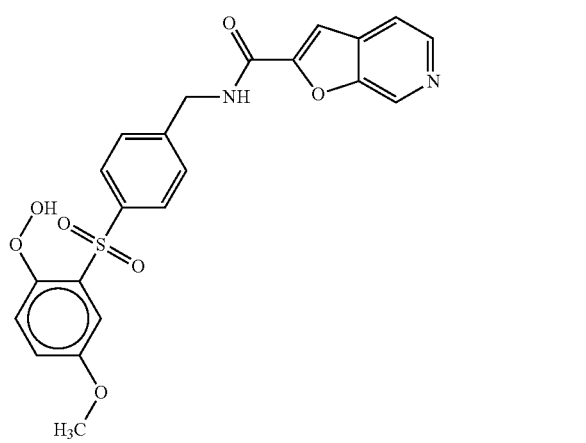 N-({4-[(2,5-dimethoxybenzene)sulfonyl]phenyl}methyl)furo[2,3-c]pyridine-2-carboxamide

| | |
|---|---|
| (structure) | N-({4-[(2,4,6-trimethylbenzene)sulfonyl]phenyl}methyl)imidazo[1,2-a]pyrimidine-6-carboxamide |
| (structure) | N-[(4-{[4-(4-methylpiperazin-1-yl)benzene]sulfonyl}phenyl)methyl]thieno[2,3-c]pyridine-2-carboxamide |
| (structure) | N-[(4-{[2-methoxy-5-(trifluoromethyl)benzene]sulfonyl}phenyl)methyl]imidazo[1,2-a]pyrimidine-6-carboxamide |
| (structure) | N-({4-[(4-chloro-2-ethoxybenzene)sulfonyl]phenyl}methyl)imidazo[1,2-a]pyrimidine-6-carboxamide |
| (structure) | N-[(4-{[3-(ethanesulfonyl)benzene]sulfonyl}phenyl)methyl]imidazo[1,2-a]pyrimidine-6-carboxamide |

TABLE 2-continued
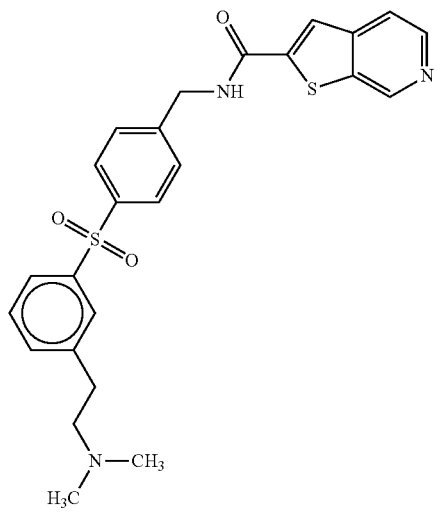
N-{[4-({3-[2-(dimethylamino)ethyl]benzene}sulfonyl)phenyl]methyl}thieno[2,3-c]pyridine-2-carboxamide
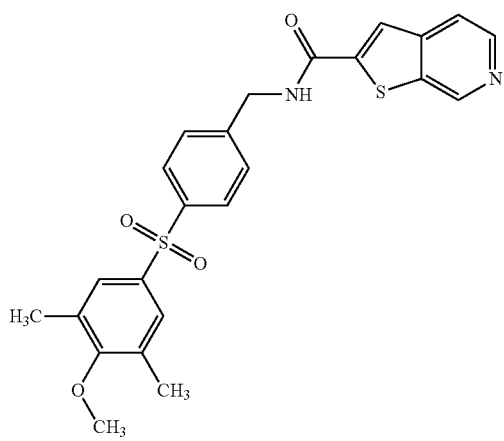
N-({4-[(4-methoxy-3,5-dimethylbenzene)sulfonyl]phenyl}methyl)thieno[2,3-c]pyridine-2-carboxamide
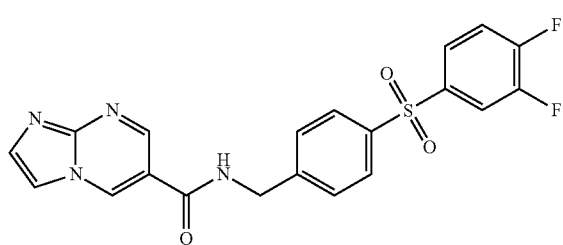 [SMILES: O=C(NCc1ccc(S(=O)(=O)c2ccc(F)c(F)c2)cc1)c1cnc2nccn2c1]
N-({4-[(3,4-difluorobenzene)sulfonyl]phenyl}methyl)imidazo[1,2-a]pyrimidine-6-carboxamide TABLE 2-continued
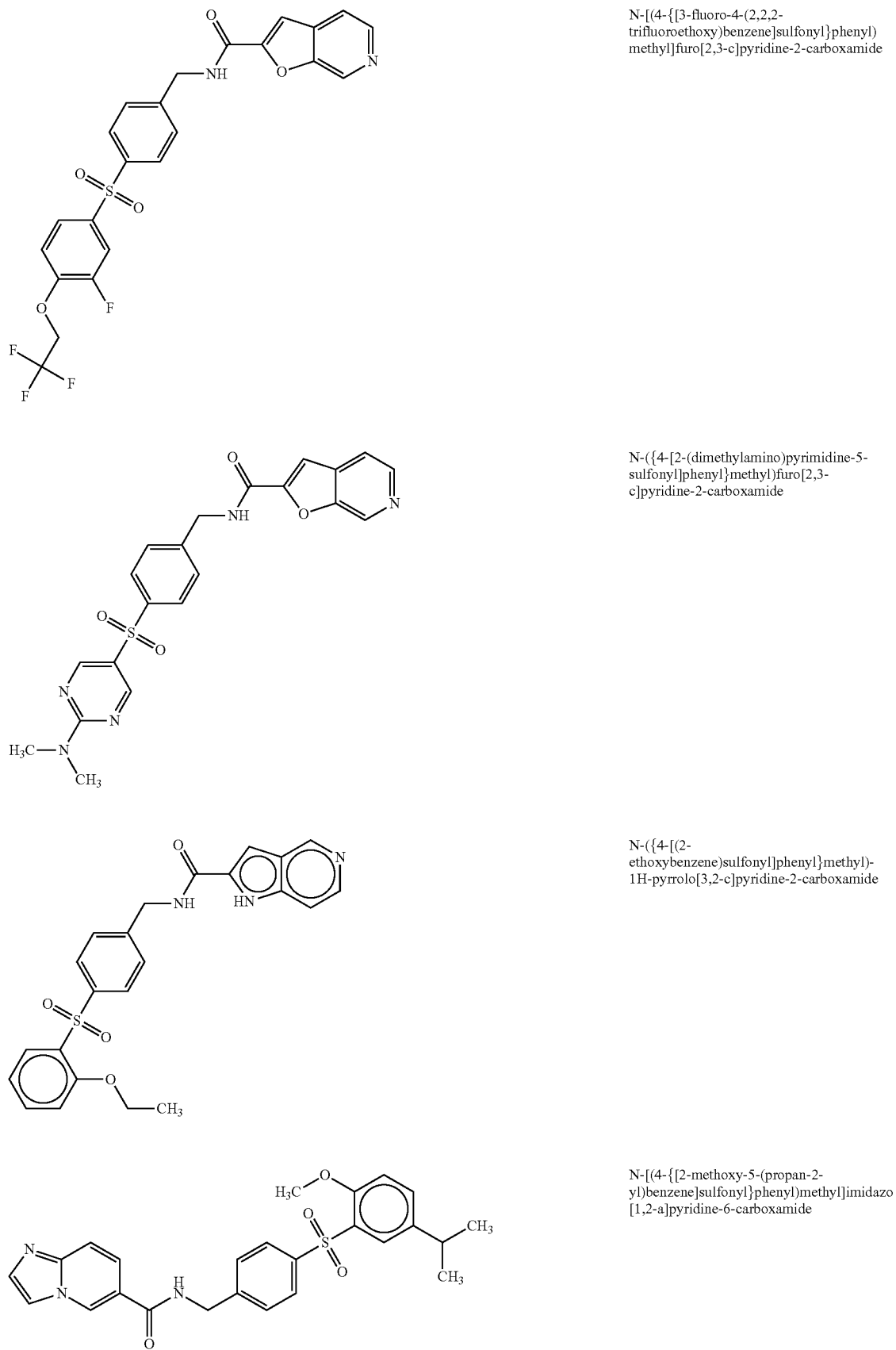
N-[(4-{[3-fluoro-4-(2,2,2-trifluoroethoxy)benzene]sulfonyl}phenyl)methyl]furo[2,3-c]pyridine-2-carboxamide
N-({4-[2-(dimethylamino)pyrimidine-5-sulfonyl]phenyl}methyl)furo[2,3-c]pyridine-2-carboxamide
N-({4-[(2-ethoxybenzene)sulfonyl]phenyl}methyl)-1H-pyrrolo[3,2-c]pyridine-2-carboxamide
N-[(4-{[2-methoxy-5-(propan-2-yl)benzene]sulfonyl}phenyl)methyl]imidazo[1,2-a]pyridine-6-carboxamide TABLE 2-continued

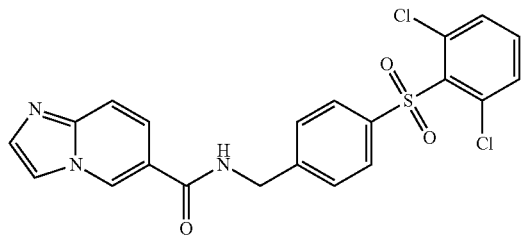 [SMILES: O=C(NCc1ccc(S(=O)(=O)c2c(Cl)cccc2Cl)cc1)c1ccc2nccn2c1]

N-({4-[(2,6-dichlorobenzene)sulfonyl]phenyl}methyl)imidazo[1,2-a]pyridine-6-carboxamide

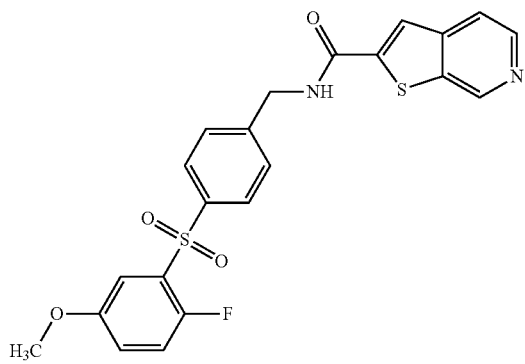

N-({4-[(2-fluoro-5-methoxybenzene)sulfonyl]phenyl}methyl)thieno[2,3-c]pyridine-2-carboxamide

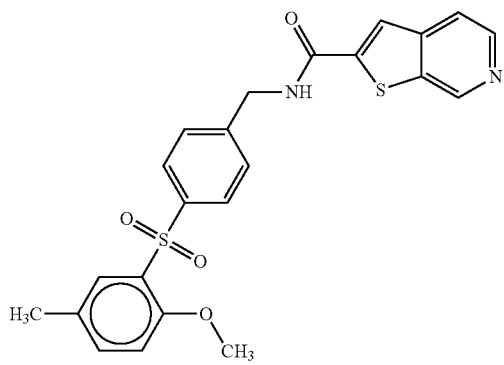

N-({4-[(2-methoxy-5-methylbenzene)sulfonyl]phenyl}methyl)thieno[2,3-c]pyridine-2-carboxamide

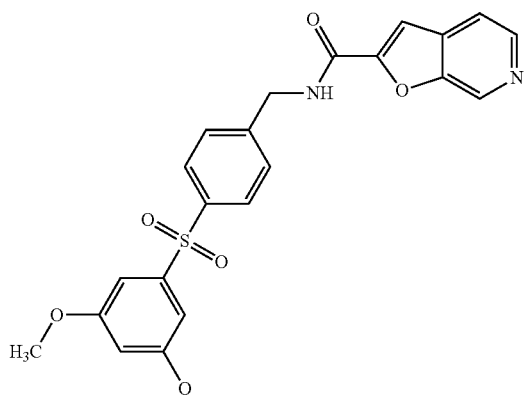

N-({4-[(3-chloro-5-methoxybenzene)sulfonyl]phenyl}methyl)furo[2,3-c]pyridine-2-carboxainide

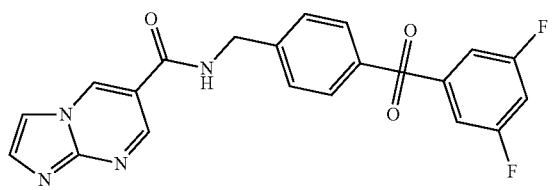

N-({4-[(3,5-difluorobenzene)sulfonyl]phenyl}methyl)imidazo[1,2-a]pyrimidine-6-carboxamide TABLE 2-continued
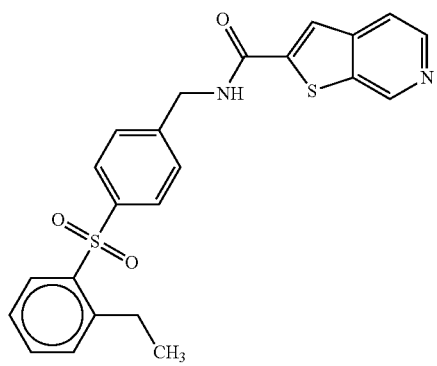
N-({4-[(2-ethylbenzene)sulfonyl]phenyl}methyl)furo[2,3-c]pyridine-2-carboxamide
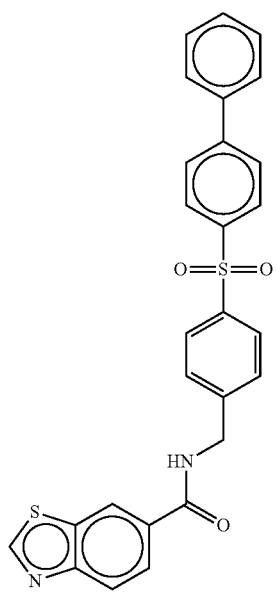
N-({4-[(4-phenylbenzene)sulfonyl]phenyl}methyl)-1,3-benzothiazole-6-carboxamide
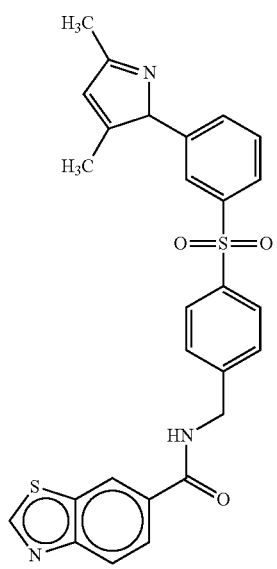
N-[(4-{[3-(3,5-dimethyl-1H-pyrazol-1-yl)benzene]sulfonyl}phenyl)methyl]-1,3-benzothiazole-6-carboxamide TABLE 2-continued
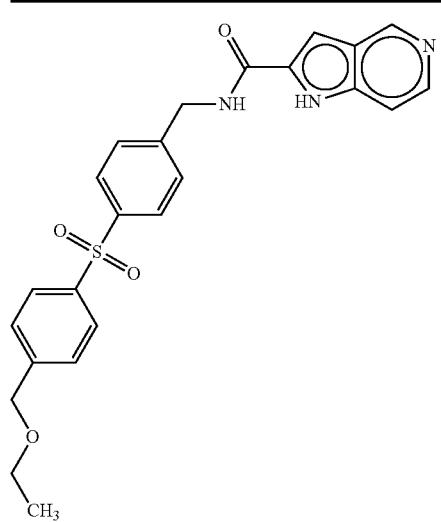
N-[(4-{[4-(ethoxymethyl)benzene]sulfonyl}phenyl)methyl]-1H-pyrrolo[3,2-c]pyridine-2-carboxamide
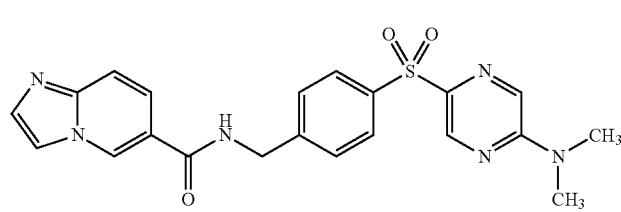 [SMILES: CN(C)c1cnc(S(=O)(=O)c2ccc(CNC(=O)c3ccc4nccn4c3)cc2)cn1]
N-({4-[5-(dimethylamino)pyrazine-2-sulfonyl]phenyl}methyl)imidazo[1,2-a]pyridine-6-carboxamide
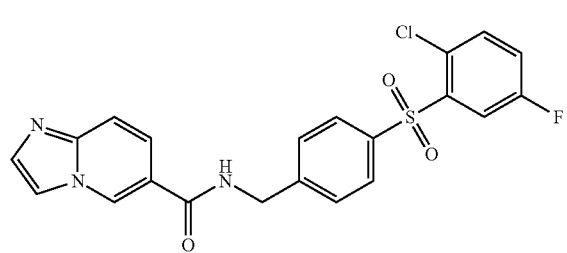 [SMILES: O=C(NCc1ccc(S(=O)(=O)c2cc(F)ccc2Cl)cc1)c1ccc2nccn2c1]
N-({4-[(2-chloro-5-fluorobenzene)sulfonyl]phenyl}methyl)imidazo[1,2-a]pyridine-6-carboxamide
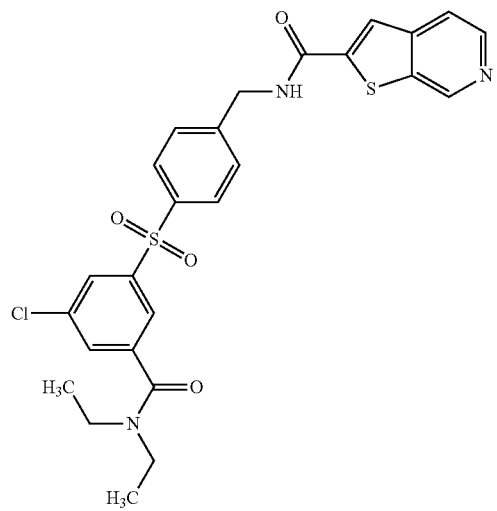 [SMILES: CCN(CC)C(=O)c1cc(Cl)cc(S(=O)(=O)c2ccc(CNC(=O)c3cc4ccncc4s3)cc2)c1]
N-[(4-{[3-chloro-5-(diethylcarbamoyl)benzene]sulfonyl}phenyl)methyl]thieno[2,3-c]pyridine-2-carboxamide TABLE 2-continued
| | |
|---|---|
| 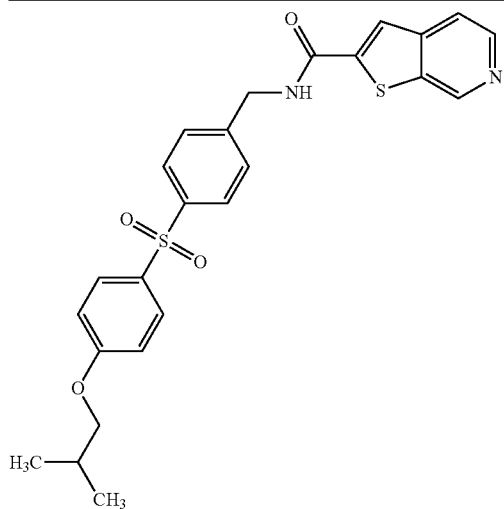 | N-[(4-{[4-(2-methylpropoxy)benzene]sulfonyl}phenyl)methyl]thieno[2,3-c]pyridine-2-carboxamide |
| 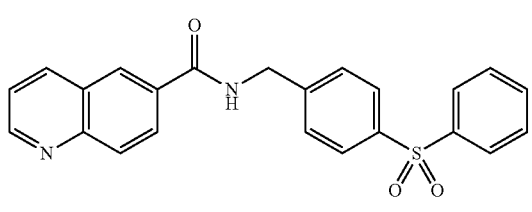 [SMILES: O=C(NCc1ccc(S(=O)(=O)c2ccccc2)cc1)c1ccc2ncccc2c1] | N-{[4-(benzenesulfonyl)phenyl]methyl}quinoline-6-carboxamide |
| 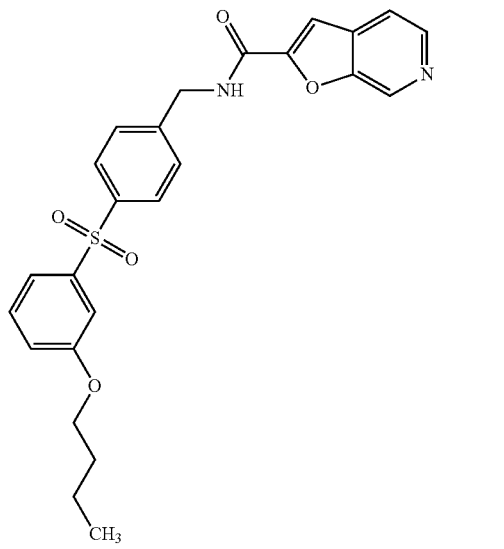 [SMILES: CCCCOc1cccc(S(=O)(=O)c2ccc(CNC(=O)c3cc4ccncc4o3)cc2)c1] | N-({4-[(3-butoxybenzene)sulfonyl]phenyl}methyl)furo[2,3-c]pyridine-2-carboxamide |
| 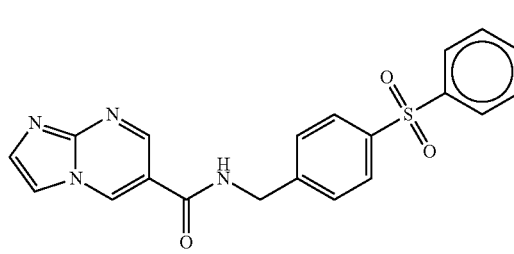 | N-({4-[(4-methylbenzene)sulfonyl]phenyl}methyl)imidazo[1,2-a]pyrimidine-6-carboxamide |

TABLE 2-continued
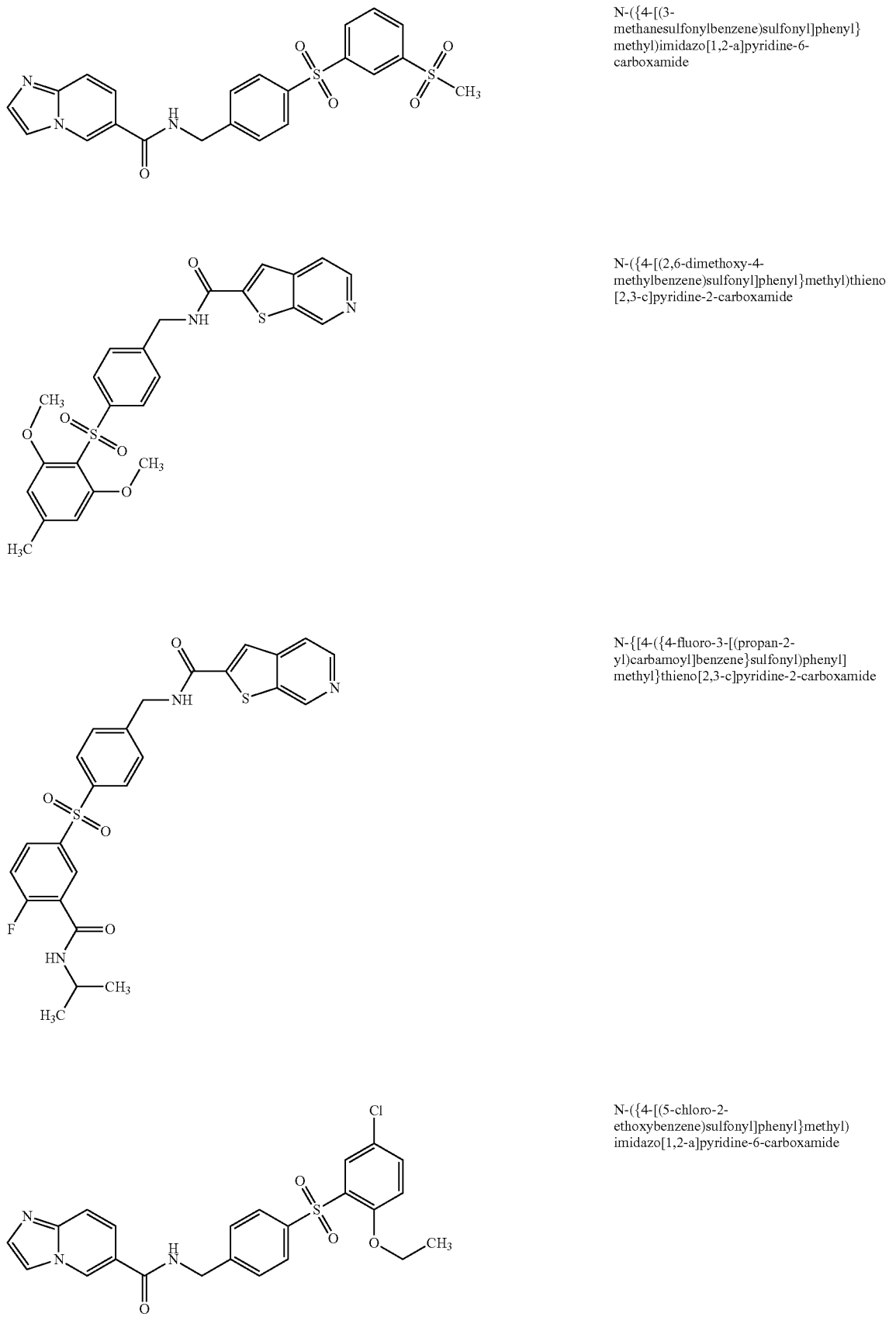
N-({4-[(3-methanesulfonylbenzene)sulfonyl]phenyl}methyl)imidazo[1,2-a]pyridine-6-carboxamide
N-({4-[(2,6-dimethoxy-4-methylbenzene)sulfonyl]phenyl}methyl)thieno[2,3-c]pyridine-2-carboxamide
N-{[4-({4-fluoro-3-[(propan-2-yl)carbamoyl]benzene}sulfonyl)phenyl]methyl}thieno[2,3-c]pyridine-2-carboxamide
N-({4-[(5-chloro-2-ethoxybenzene)sulfonyl]phenyl}methyl)imidazo[1,2-a]pyridine-6-carboxamide TABLE 2-continued

| | |
|---|---|
| 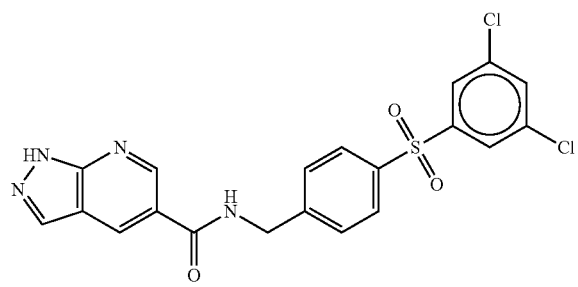 | N-({4-[(3,5-dichlorobenzene)sulfonyl]phenyl}methyl)-1H-pyrazolo[3,4-b]pyridine-5-carboxamide |
| 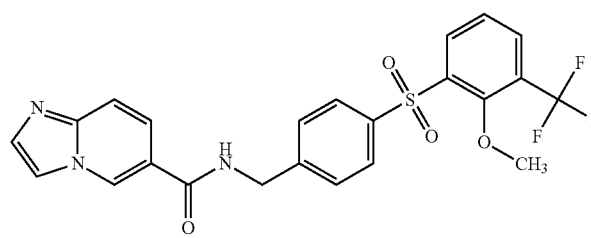 | N-[(4-{[2-methoxy-3-(trifluoromethyl)benzene]sulfonyl}phenyl)methyl]imidazo[1,2-a]pyridine-6-carboxamide |
| 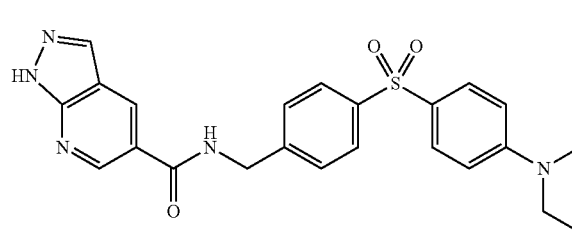 | N-[(4-{[4-(4-methylpiperazin-1-yl)benzene]sulfonyl}phenyl)methyl]-1H-pyrazolo[3,4-b]pyridine-5-carboxamide |
| 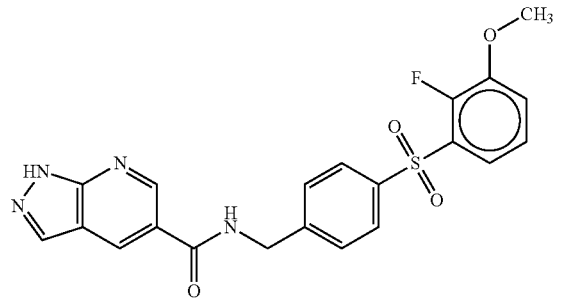 | N-({4-[(2-fluoro-3-methoxybenzene)sulfonyl]phenyl}methyl)-1H-pyrazolo[3,4-b]pyridine-5-carboxamide |
| 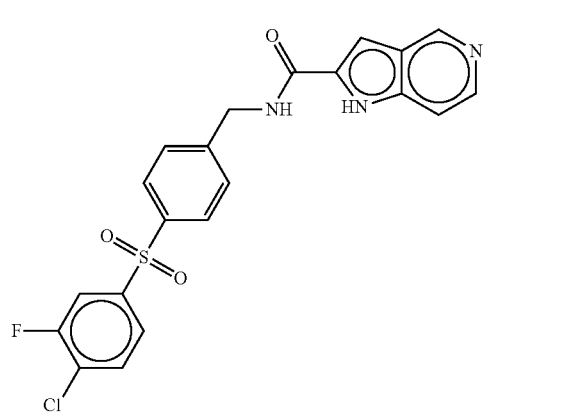 | N-({4-[(4-chloro-3-fluorobenzene)sulfonyl]phenyl}methyl)-1H-pyrrolo[3,2-c]pyridine-2-carboxamide |

TABLE 2-continued
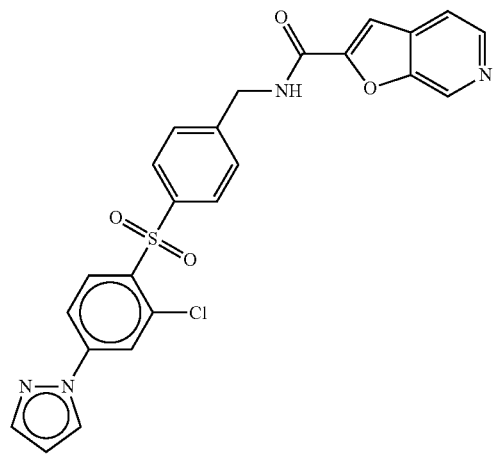
N-[(4-{[2-fluoro-4-(1H-pyrazol-1-yl)benzene]sulfonyl}phenyl)methyl]furo[2,3-c]pyridine-2-carboxamide
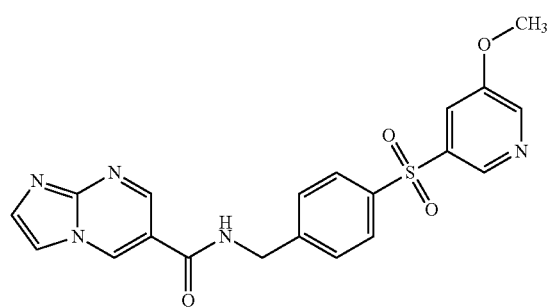 [SMILES: COc1cncc(S(=O)(=O)c2ccc(CNC(=O)c3cnc4nccn4c3)cc2)c1]
N-{[4-(5-methoxypyridine-3-sulfonyl)phenyl]methyl}imidazo[1,2-a]pyrimidine-6-carboxamide
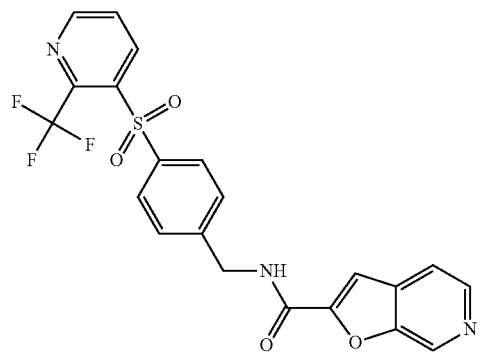 [SMILES: O=C(NCc1ccc(S(=O)(=O)c2cccnc2C(F)(F)F)cc1)c1cc2ccncc2o1]
N-({4-[2-(trifluoromethyl)pyridine-3-sulfonyl]phenyl}methyl)furo[2,3-c]pyridine-2-carboxamide
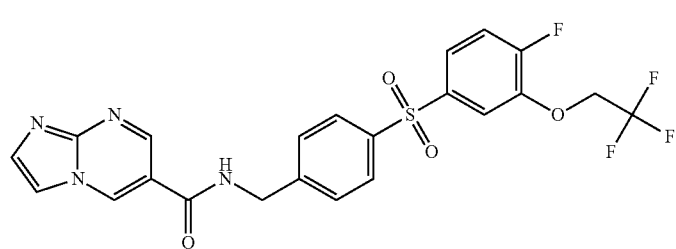 [SMILES: O=C(NCc1ccc(S(=O)(=O)c2ccc(F)c(OCC(F)(F)F)c2)cc1)c1cnc2nccn2c1]
N-[(4-{[4-fluoro-3-(2,2,2-trifluoroethoxy)benzene]sulfonyl}phenyl)methyl]inudazo[1,2-a]pyrimidine-6-carboxamide TABLE 2-continued
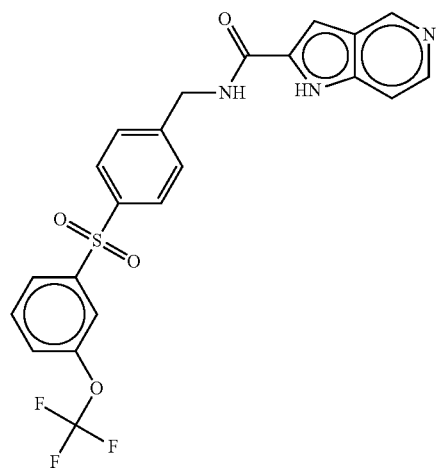
N-[(4-{[3-(trifluoromethoxy)benzene]sulfonyl}phenyl)methyl]-1H-pyrrolo[3,2-c]pyridine-2-carboxamide
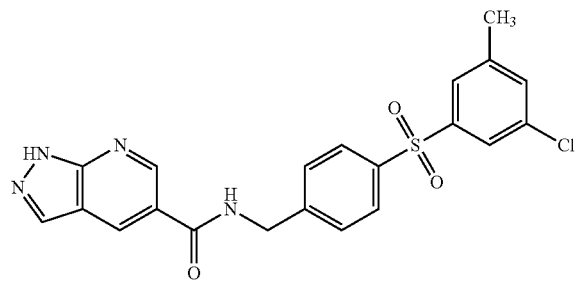 [SMILES: Cc1cc(Cl)cc(S(=O)(=O)c2ccc(CNC(=O)c3cnc4[nH]ncc4c3)cc2)c1]
N-({4-[(3-chloro-5-methylbenzene)sulfonyl]phenyl}methyl)-1H-pyrazolo[3,4-b]pyridine-5-carboxamide
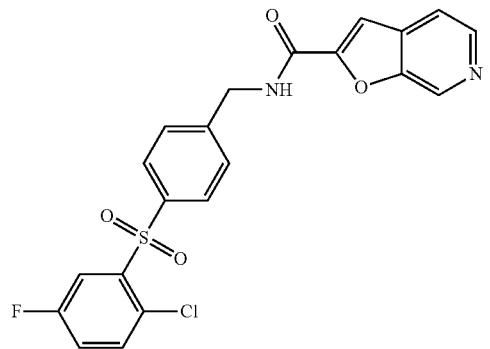
N-({4-[(2-chloro-5-fluorobenzene)sulfonyl]phenyl}methyl)furo[2,3-c]pyridine-2-carboxamide
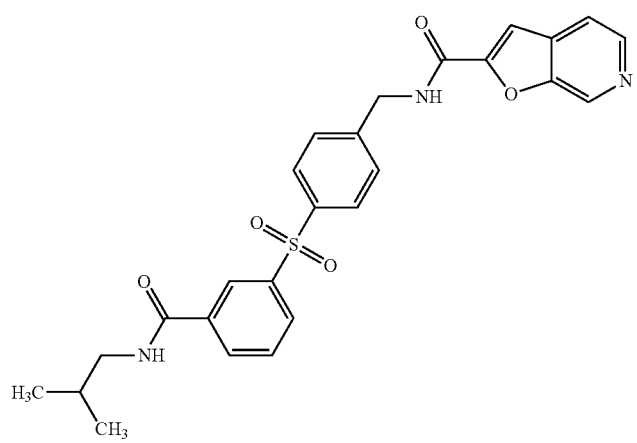
N-{[4-({3-[(2-methylpropyl)carbamoyl]benzene}sulfonyl)phenyl]methyl}furo[2,3-c]pyridine-2-carboxamide TABLE 2-continued

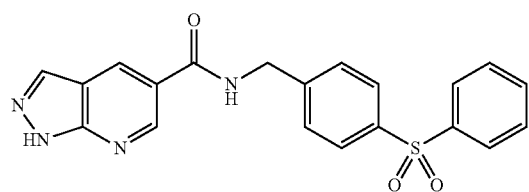 [SMILES: O=C(NCc1ccc(S(=O)(=O)c2ccccc2)cc1)c1cnc2[nH]ncc2c1]

N-{[4-(benzenesulfonyl)phenyl]methyl}-1H-pyrazolo[3,4-b]pyridine-5-carboxamide

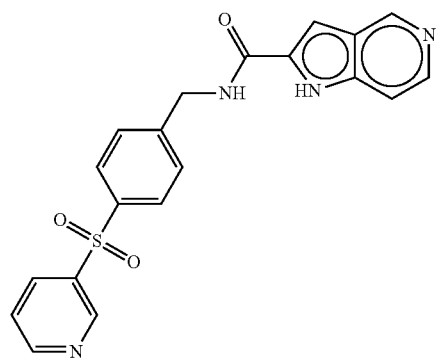

N-{[4-(pyridine-3-sulfonyl)phenyl]methyl}-1H-pyrrolo[3,2-c]pyridine-2-carboxamide

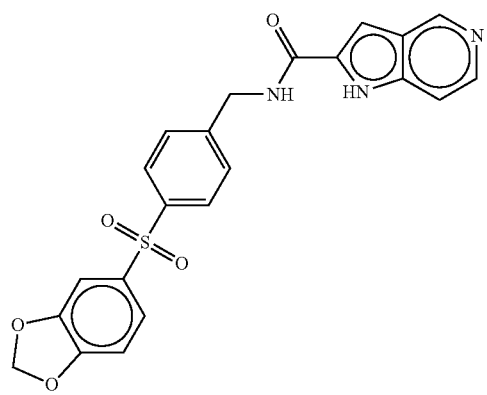

N-{[4-(2H-1,3-benzodioxole-5-sulfonyl)phenyl]methyl}-1H-pyrrolo[3,2-c]pyridine-2-carboxamide

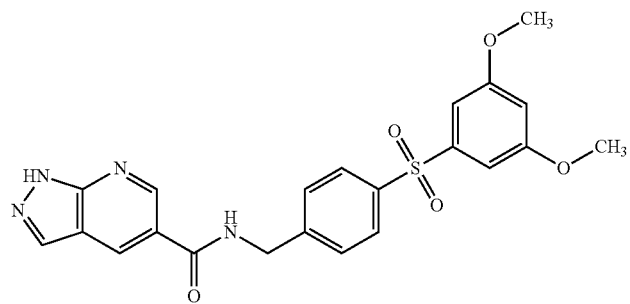 [SMILES: COc1cc(OC)cc(S(=O)(=O)c2ccc(CNC(=O)c3cnc4[nH]ncc4c3)cc2)c1]

N-({4-[(3,5-dimethoxybenzene)sulfonyl]phenyl}methyl)-1H-pyrazolo[3,4-b]pyridine-5-carboxamide

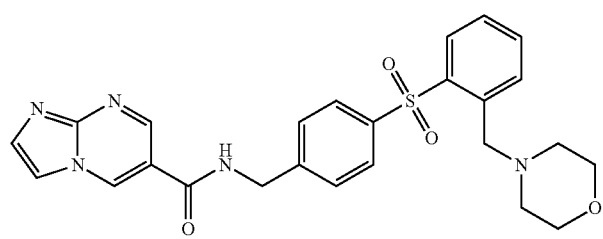 [SMILES: O=C(NCc1ccc(S(=O)(=O)c2ccccc2CN2CCOCC2)cc1)c1cnc2nccn2c1]

N-[(4-{[2-(morpholin-4-ylmethyl)benzene]sulfonyl}phenyl)methyl]imidazo[1,2-a]pyrimidine-6-carboxamide TABLE 2-continued
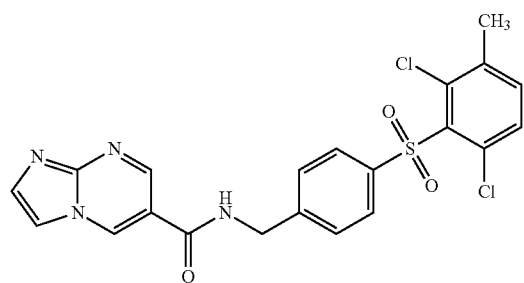 [SMILES: Cc1ccc(Cl)c(S(=O)(=O)c2ccc(CNC(=O)c3cnc4nccn4c3)cc2)c1Cl]
N-({4-[(2,6-dichloro-3-methylbenzene)sulfonyl]phenyl}methyl)imidazo[1,2-a]pyrimidine-6-carboxamide
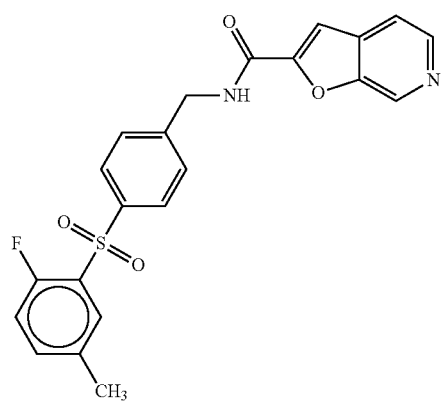
N-({4-[(2-fluoro-5-methylbenzene)sulfonyl]phenyl}methyl)furo[2,3-c]pyridine-2-carboxamide
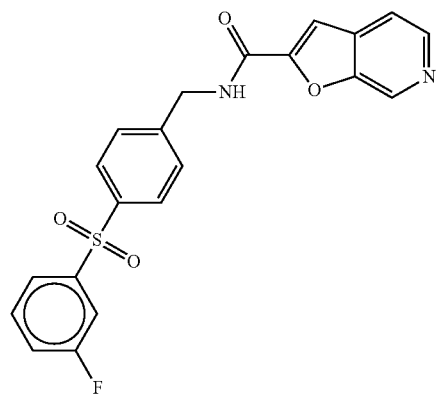
N-({4-[(3-fluorobenzene)sulfonyl]phenyl}methyl)furo[2,3-c]pyridine-2-carboxamide
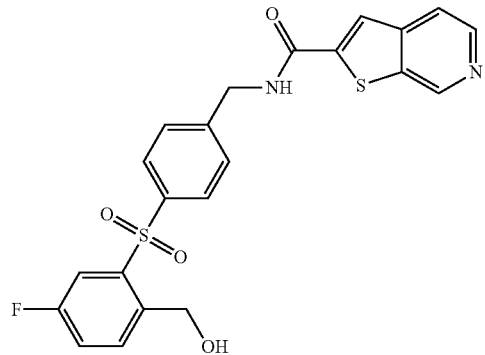
N-[(4-{[5-fluoro-2-(hydroxymethyl)benzene]sulfonyl}phenyl)methyl]thieno[2,3-c]pyridine-2-carboxamide TABLE 2-continued

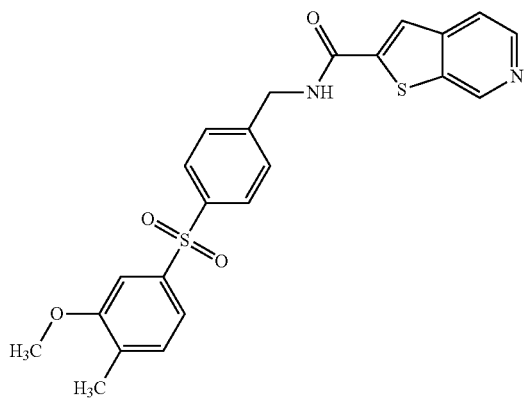

N-({4-[(3-methoxy-4-methylbenzene)sulfonyl]phenyl}methyl)thieno[2,3-c]pyridine-2-carboxamide

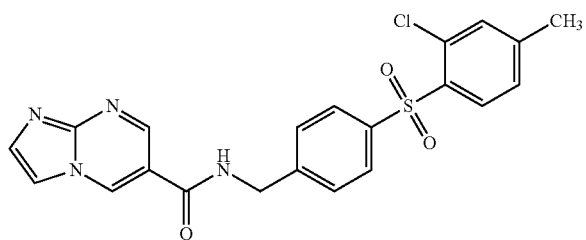 [SMILES: Cc1ccc(S(=O)(=O)c2ccc(CNC(=O)c3cnc4nccn4c3)cc2)c(Cl)c1]

N-({4-[(2-chloro-4-methylbenzene)sulfonyl]phenyl}methyl)imidazo[1,2-a]pyrimidine-6-carboxamide

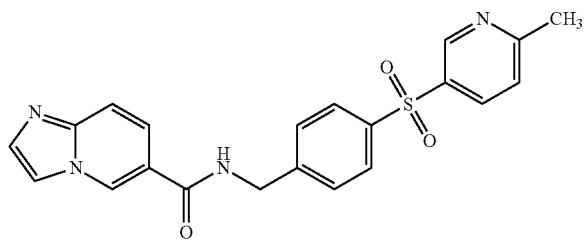 [SMILES: Cc1ccc(S(=O)(=O)c2ccc(CNC(=O)c3ccc4nccn4c3)cc2)cn1]

N-{[4-(6-methylpyridine-3-sulfonyl)phenyl]methyl}imidazo[1,2-a]pyridine-6-carboxamide

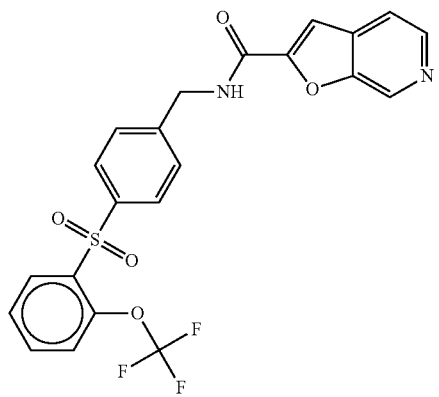

N-[(4-{[2-(trifluoromethoxy)benzene]sulfonyl}phenyl)methyl]furo[2,3-c]pyridine-2-carboxamide

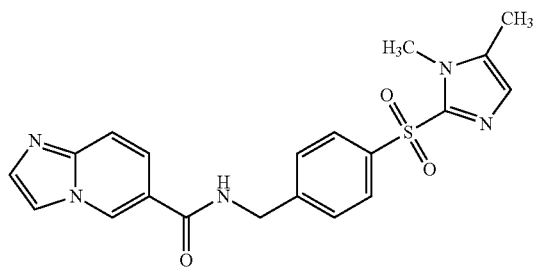 [SMILES: Cc1cnc(S(=O)(=O)c2ccc(CNC(=O)c3ccc4nccn4c3)cc2)n1C]

N-{[4-(1,5-dimethyl-1H-imidazole-2-sulfonyl)phenyl]methyl}imidazo[1,2-a]pyridine-6-carboxamide TABLE 2-continued

| | |
|---|---|
| 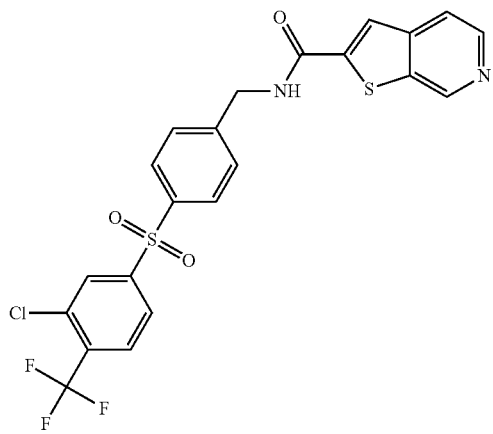 [SMILES: O=C(NCc1ccc(S(=O)(=O)c2ccc(C(F)(F)F)c(Cl)c2)cc1)c1cc2ccncc2s1] | N-[(4-{[3-chloro-4-(trifluoromethyl)benzene]sulfonyl}phenyl)methyl]thieno[2,3-c]pyridine-2-carboxamide |
| 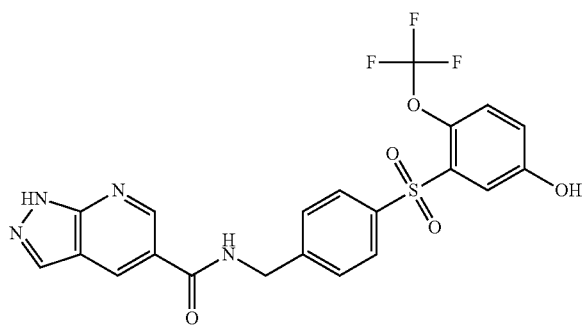 [SMILES: O=C(NCc1ccc(S(=O)(=O)c2cc(O)ccc2OC(F)(F)F)cc1)c1cnc2[nH]ncc2c1] | N-[(4-{[5-hydroxy-2-(trifluoromethoxy)benzene]sulfonyl}phenyl)methyl]-1H-pyrazolo[3,4-b]pyridine-5-carboxamide |
| 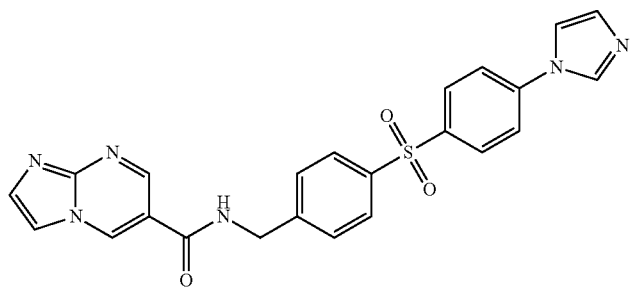 [SMILES: O=C(NCc1ccc(S(=O)(=O)c2ccc(-n3ccnc3)cc2)cc1)c1cnc2nccn2c1] | N-[(4-{[4-(1H-imidazol-1-yl)benzene]sulfonyl}phenyl)methyl]imidazo[1,2-a]pyrimidine-6-carboxamide |
| 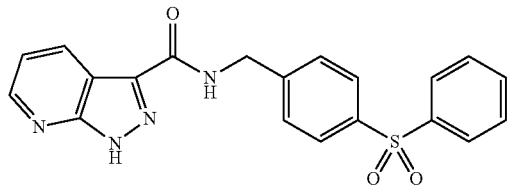 [SMILES: O=C(NCc1ccc(S(=O)(=O)c2ccccc2)cc1)c1n[nH]c2ncccc12] | N-{[4-(benzenesulfonyl)phenyl]methyl}-1H-pyrazolo[3,4-b]pyridine-3-carboxamide |
| 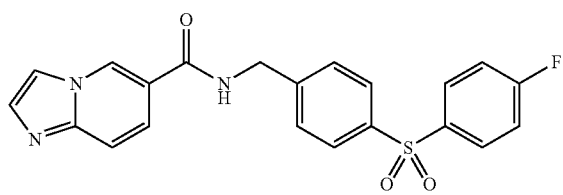 [SMILES: O=C(NCc1ccc(S(=O)(=O)c2ccc(F)cc2)cc1)c1ccc2nccn2c1] | N-({4-[(4-fluorobenzene)sulfonyl]phenyl}methyl)imidazo[1,2-a]pyridine-6-carboxamide |

TABLE 2-continued
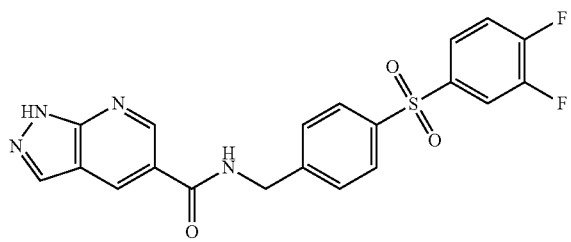 [SMILES: O=C(NCc1ccc(S(=O)(=O)c2ccc(F)c(F)c2)cc1)c1cnc2[nH]ncc2c1]
N-({4-[(3,4-difluorobenzene)sulfonyl]phenyl}methyl)-1H-pyrazolo[3,4-b]pyridine-5-carboxamide
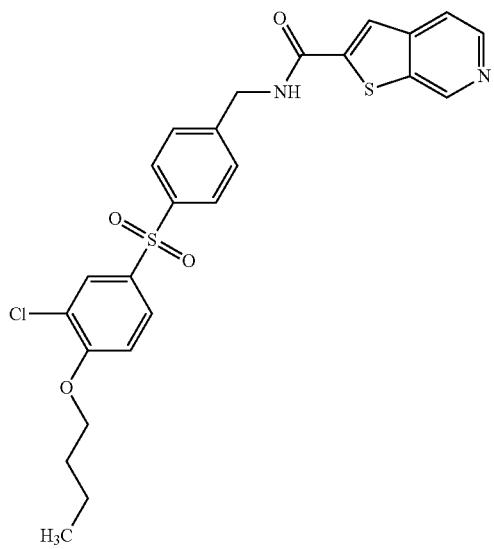
N-({4-[(4-butoxy-3-chlorobenzene)sulfonyl]phenyl}methyl)thieno[2,3-c]pyridine-2-carboxamide
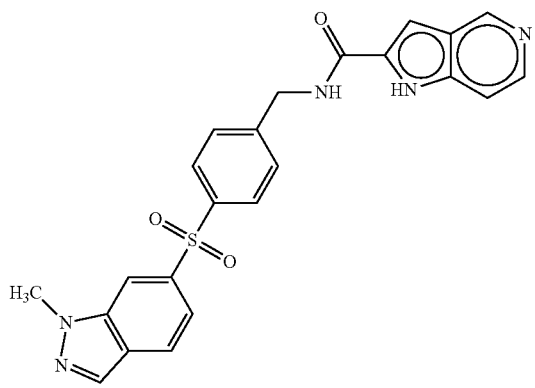
N-{[4-(1-methyl-1H-indazole-6-sulfonyl)phenyl]methyl}-1H-pyrrolo[3,2-c]pyridine-2-carboxamide
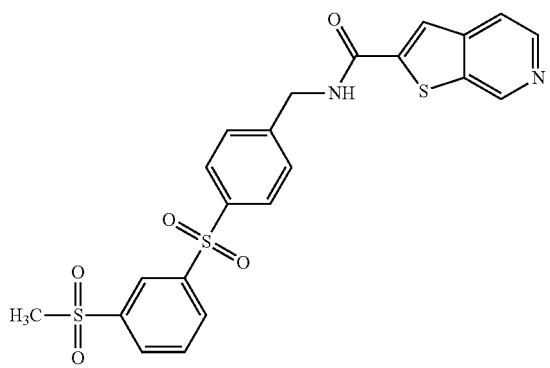 [SMILES: CS(=O)(=O)c1cccc(S(=O)(=O)c2ccc(CNC(=O)c3cc4ccncc4s3)cc2)c1]
N-({4-[(3-methanesulfonylbenzene)sulfonyl]phenyl}methyl)thieno[2,3-c]pyridine-2-carboxamide TABLE 2-continued

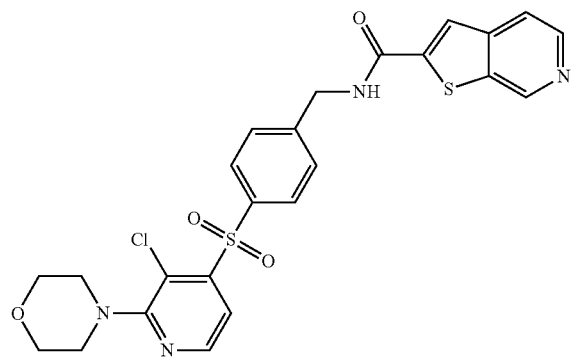 [SMILES: O=C(NCc1ccc(S(=O)(=O)c2ccnc(N3CCOCC3)c2Cl)cc1)c1cc2ccncc2s1]

N-({4-[3-chloro-2-(morpholin-4-yl)pyridine-4-sulfonyl]phenyl}methyl)thieno[2,3-c]pyridine-2-carboxamide

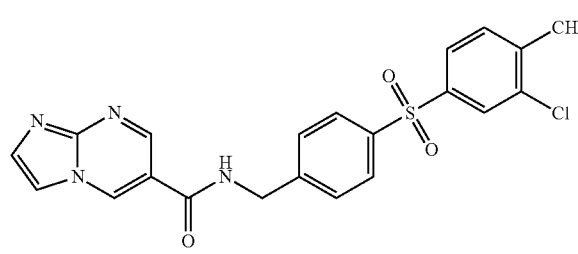

N-({4-[(3-chloro-4-methylbenzene)sulfonyl]phenyl}methyl)imidazo[1,2-a]pyrimidine-6-carboxamide

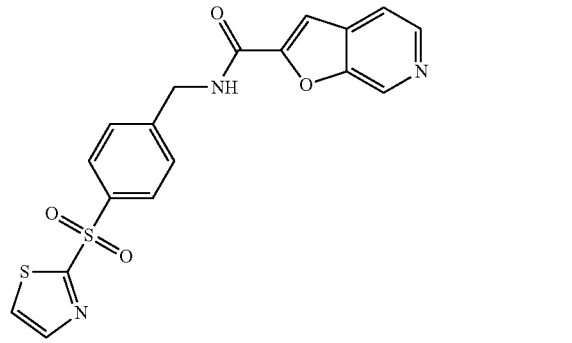 [SMILES: O=C(NCc1ccc(S(=O)(=O)c2nccs2)cc1)c1cc2ccncc2o1]

N-{[4-(1,3-thiazole-2-sulfonyl)phenyl]methyl}furo[2,3-c]pyridine-2-carboxamide

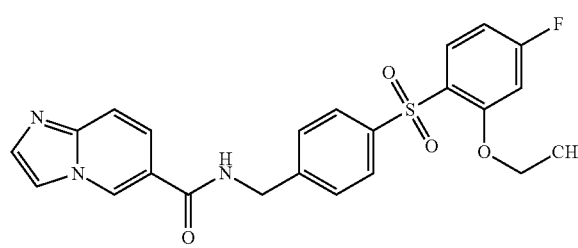

N-({4-[(2-ethoxy-4-fluorobenzene)sulfonyl]phenyl}methyl)imidazo[1,2-a]pyridine-6-carboxamide

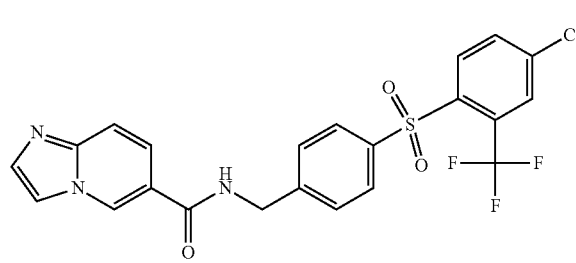

N-[(4-{[4-chloro-2-(trifluoromethyl)benzene]sulfonyl}phenyl)methyl]imidazo[1,2-a]pyridine-6-carboxamide TABLE 2-continued
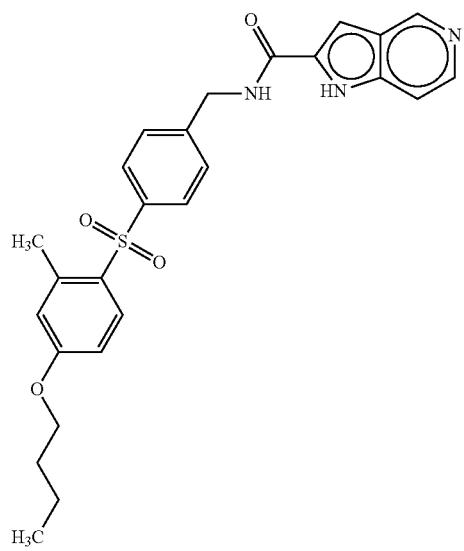
N-({4-[(4-butoxy-2-methylbenzene)sulfonyl]phenyl}methyl)-1H-pyrrolo[3,2-c]pyridine-2-carboxamide
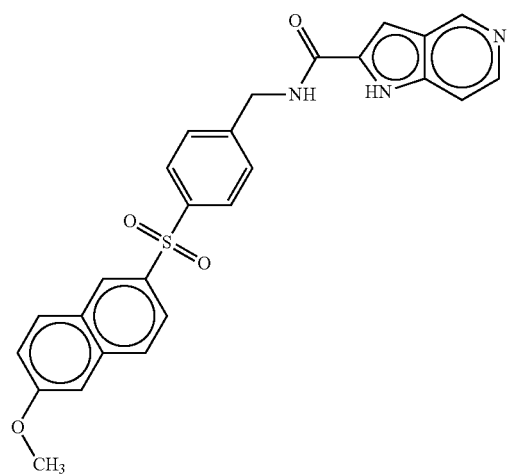
N-{[4-(6-methoxynaphthalene-2-sulfonyl)phenyl]methyl}-1H-pyrrolo[3,2-c]pyridine-2-carboxamide
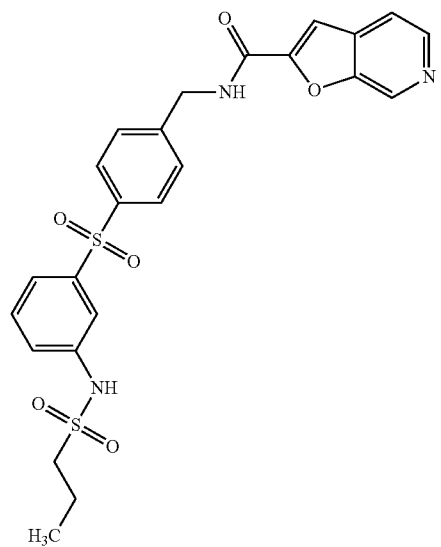 [SMILES: CCCS(=O)(=O)Nc1cccc(S(=O)(=O)c2ccc(CNC(=O)c3cc4ccncc4o3)cc2)c1]
N-[(4-{[3-(propane-1-sulfonamido)benzene]sulfonyl}phenyl)methyl]thieno[2,3-c]pyridine-2-carboxamide TABLE 2-continued

| Structure | Name |
|---|---|
| (structure) | N-[(4-{[4-chloro-3-(trifluoromethyl)benzene]sulfonyl}phenyl)methyl]imidazo[1,2-a]pyrimidine-6-carboxamide |
| (structure) | N-[(4-{[3-fluoro-5-(2-methylpropoxy)benzene]sulfonyl}phenyl)methyl]thieno[2,3-c]pyridine-2-carboxamide |
| (structure) | N-[(4-{[2-methyl-4-(1H-pyrazol-1-yl)benzene]sulfonyl}phenyl)methyl]-1H-pyrazolo[3,4-b]pyridine-5-carboxamide |
| (structure) | N-({4-[(3-chloro-5-fluorobenzene)sulfonyl]phenyl}methyl)-1H-pyrazolo[3,4-b]pyridine-5-carboxamide |
| (structure) | N-({4-[5-(trifluoromethyl)pyridine-2-sulfonyl]phenyl}methyl)-1H-pyrazolo[3,4-b]pyridine-5-carboxamide |

TABLE 2-continued

| | |
|---|---|
| 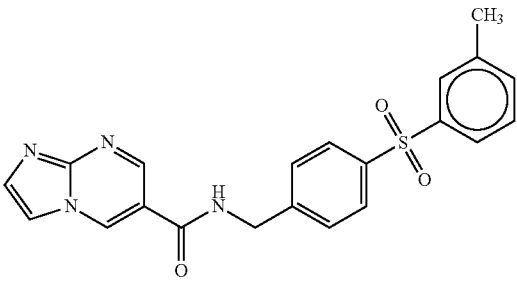 | N-({4-[(3-methylbenzene)sulfonyl]phenyl}methyl)imidazo[1,2-a]pyrimidine-6-carboxamide |
| 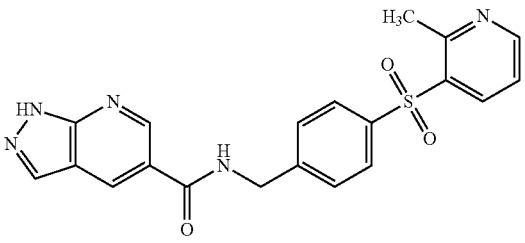 [SMILES: Cc1ncccc1S(=O)(=O)c1ccc(CNC(=O)c2cnc3[nH]ncc3c2)cc1] | N-{[4-(2-methylpyridine-3-sulfonyl)phenyl]methyl}-1H-pyrazolo[3,4-b]pyridine-5-carboxamide |
| 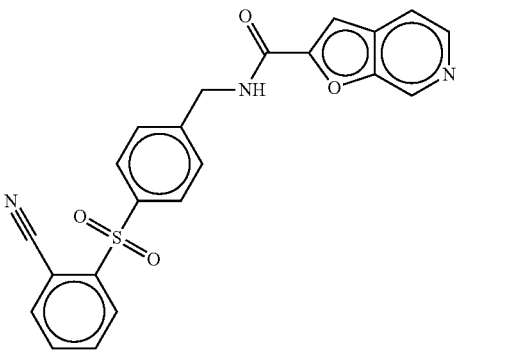 | N-({4-[(2-cyanobenzene)sulfonyl]phenyl}methyl)furo[2,3-c]pyridine-2-carboxamide |
| 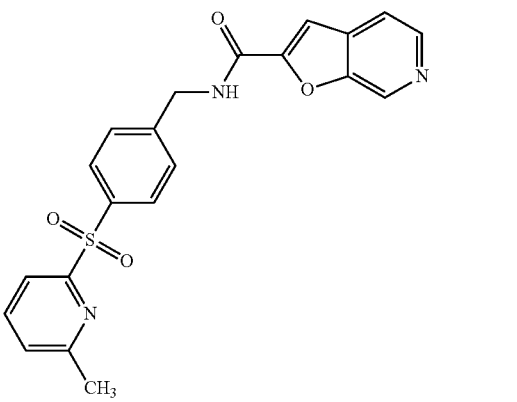 [SMILES: Cc1cccc(S(=O)(=O)c2ccc(CNC(=O)c3cc4ccncc4o3)cc2)n1] | N-{[4-(6-methylpyridine-2-sulfonyl)phenyl]methyl}furo[2,3-c]pyridine-2-carboxamide |
| 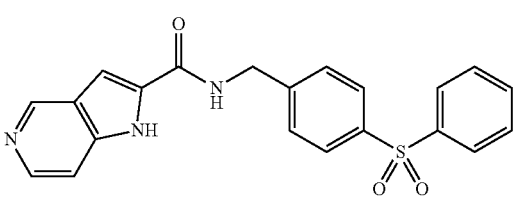 [SMILES: O=C(NCc1ccc(S(=O)(=O)c2ccccc2)cc1)c1cc2cnccc2[nH]1] | N-{[4-(benzenesulfonyl)phenyl]methyl}-1H-pyrrolo[3,2-c]pyridine-2-carboxamide |

TABLE 2-continued

| Structure | Name |
|---|---|
| 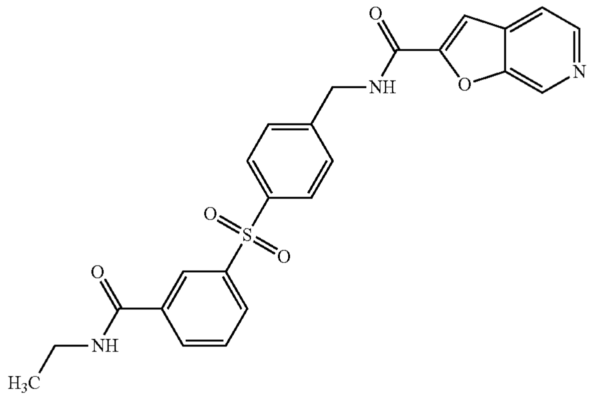 [SMILES: CCNC(=O)c1cccc(S(=O)(=O)c2ccc(CNC(=O)c3cc4ccncc4o3)cc2)c1] | N-[(4-{[3-(ethylcarbamoyl)benzene]sulfonyl}phenyl)methyl]furo[2,3-c]pyridine-2-carboxamide |
| 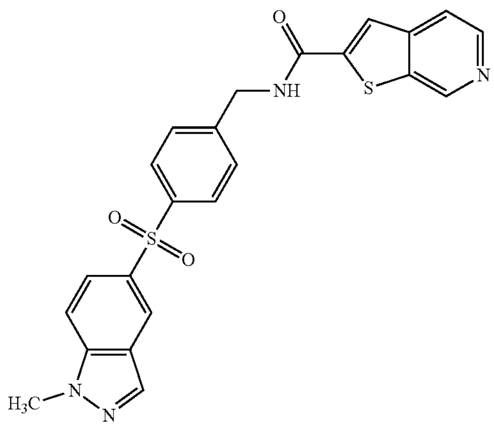 [SMILES: Cn1ncc2cc(S(=O)(=O)c3ccc(CNC(=O)c4cc5ccncc5s4)cc3)ccc21] | N-{[4-(1-methyl-1H-indazole-5-sulfonyl)phenyl]methyl}thieno[2,3-c]pyridine-2-carboxamide |
| 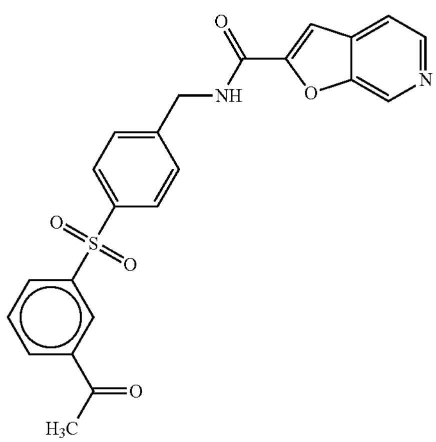 | N-({4-[(3-acetylbenzene)sulfonyl]phenyl}methyl)furo[2,3-c]pyridine-2-carboxamide |
| 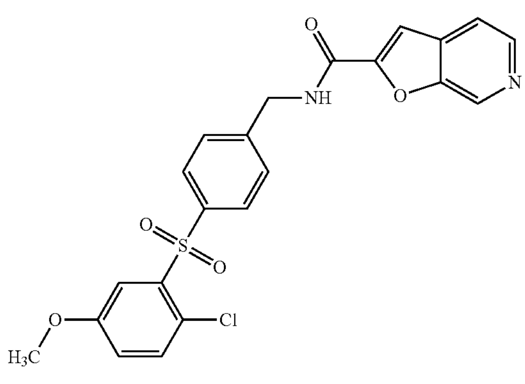 | N-({4-[(2-chloro-5-methoxybenzene)sulfonyl]phenyl}methyl)furo[2,3-c]pyridine-2-carboxamide |

TABLE 2-continued
| | |
|---|---|
| 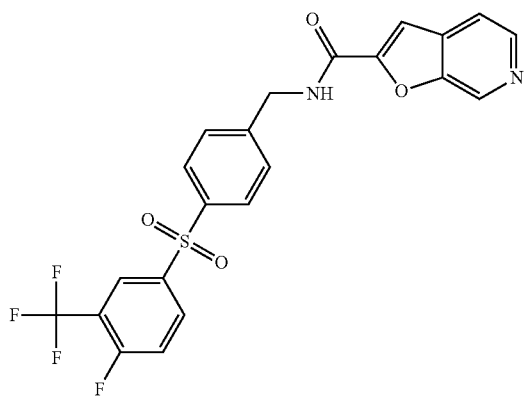 [SMILES: O=C(NCc1ccc(S(=O)(=O)c2ccc(F)c(C(F)(F)F)c2)cc1)c1cc2ccncc2o1] | N-[(4-{[4-fluoro-3-(trifluoromethyl)benzene]sulfonyl}phenyl)methyl]furo[2,3-c]pyridine-2-carboxamide |
| 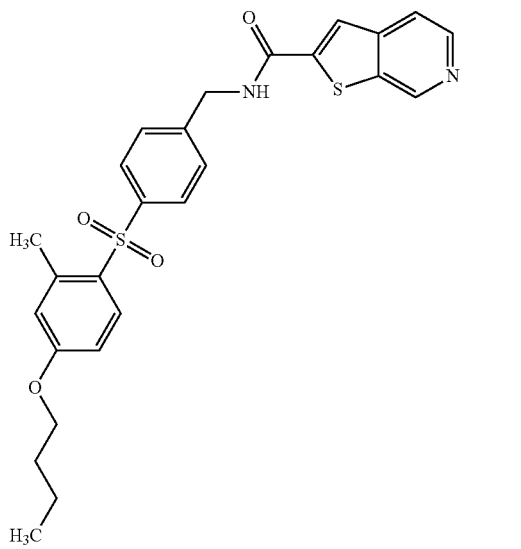 [SMILES: CCCCOc1ccc(S(=O)(=O)c2ccc(CNC(=O)c3cc4ccncc4s3)cc2)c(C)c1] | N-({4-[(4-butoxy-2-methylbenzene)sulfonyl]phenyl}methyl)thieno[2,3-c]pyridine-2-carboxamide |
| 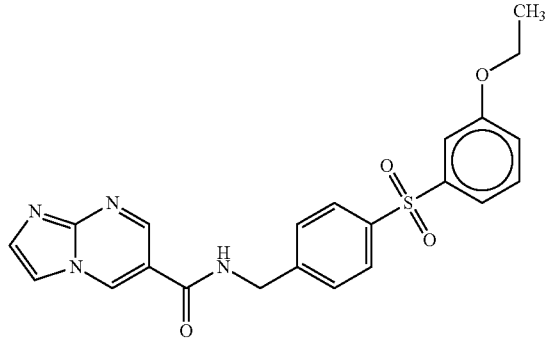 | N-({4-[(3-ethoxybenzene)sulfonyl]phenyl}methyl)imidazo[1,2-a]pyrimidine-6-carboxamide |
| 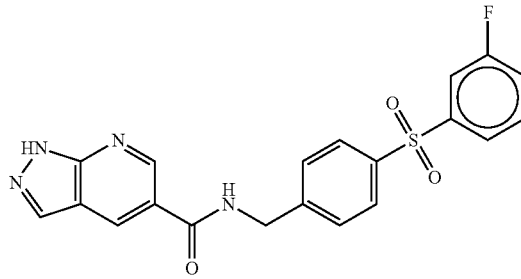 | N-({4-[(3-fluoro-4-methylbenzene)sulfonyl]phenyl}methyl)-1H-pyrazolo[3,4-b]pyridine-5-carboxamide |

TABLE 2-continued

| | |
|---|---|
| | N-({4-[4-(trifluoromethyl)pyridine-2-sulfonyl]phenyl}methyl)imidazo[1,2-a]pyridine-6-carboxamide |
| | N-[(4-{[4-chloro-2-(trifluoromethyl)benzene]sulfonyl}phenyl)methyl]furo[2,3-c]pyridine-2-carboxamide |
| | N-({4-[(4-chloro-2-ethoxybenzene)sulfonyl]phenyl}methyl)furo[2,3-c]pyridine-2-carboxamide |
| | N-{[4-(2,3-dihydro-1-benzofuran-7-sulfonyl)phenyl]methyl}furo[2,3-c]pyridine-2-carboxamide |

TABLE 2-continued
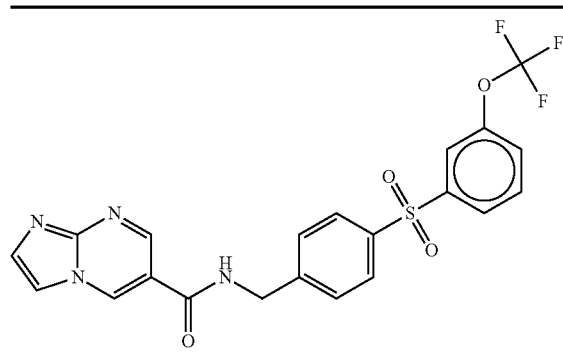
N-[(4-{[3-(trifluoromethoxy)benzene]sulfonyl}phenyl)methyl]imidazo[1,2-a]pyrimidine-6-carboxamide
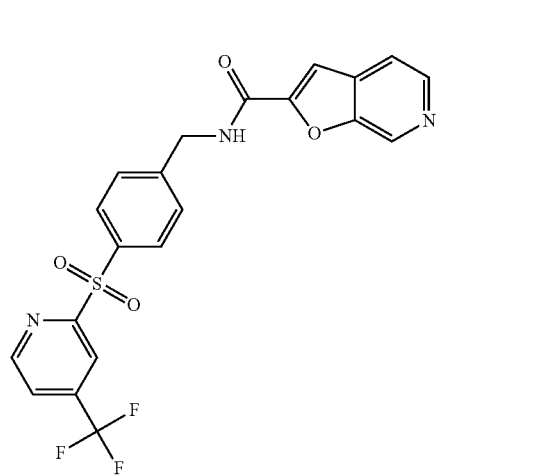 [SMILES: O=C(NCc1ccc(S(=O)(=O)c2cc(C(F)(F)F)ccn2)cc1)c1cc2ccncc2o1]
N-({4-[4-(trifluoromethyl)pyridine-2-sulfonyl]phenyl}methyl)furo[2,3-c]pyridine-2-carboxamide
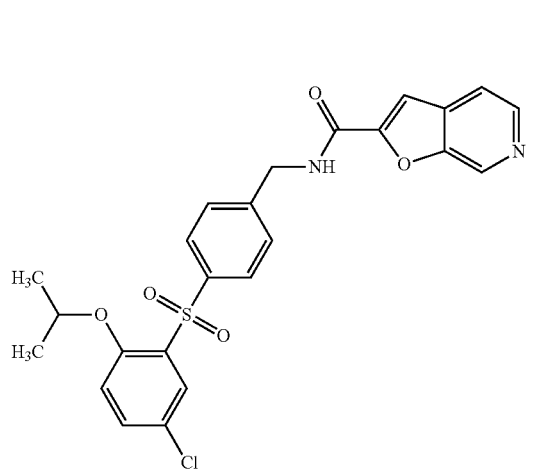 [SMILES: CC(C)Oc1ccc(Cl)cc1S(=O)(=O)c1ccc(CNC(=O)c2cc3ccncc3o2)cc1]
N-[(4-{[5-chloro-2-(propan-2-yloxy)benzene]sulfonyl}phenyl)methyl]furo[2,3-c]pyridine-2-carboxamide
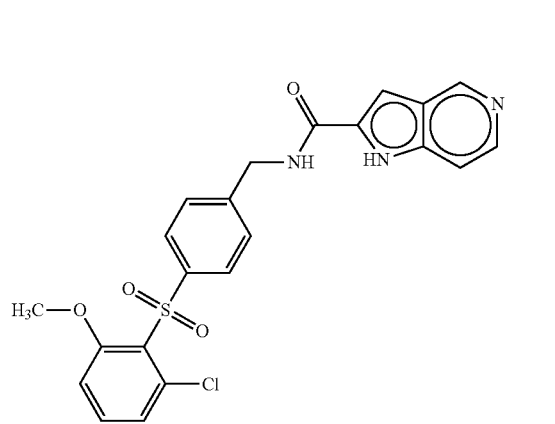
N-({4-[(2-chloro-6-methoxybenzene)sulfonyl]phenyl}methyl)-1H-pyrrolo[3,2-c]pyridine-2-carboxamide TABLE 2-continued

| | |
|---|---|
| 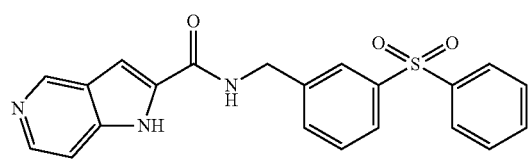 [SMILES: O=C(NCc1cccc(S(=O)(=O)c2ccccc2)c1)c1cc2cnccc2[nH]1] | N-{[3-(benzenesulfonyl)phenyl]methyl}-1H-pyrrolo[3,2-c]pyridine-2-carboxamide |
| 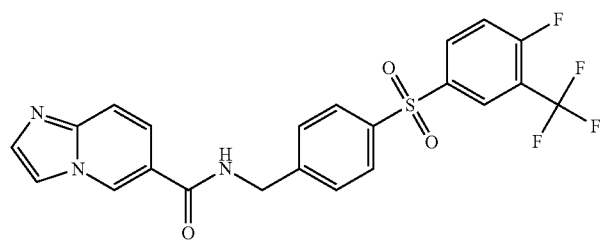 [SMILES: O=C(NCc1ccc(S(=O)(=O)c2ccc(F)c(C(F)(F)F)c2)cc1)c1ccc2nccn2c1] | N-[(4-{[4-fluoro-3-(trifluoromethyl)benzene]sulfonyl}phenyl)methyl]imidazo[1,2-a]pyridine-6-carboxamide |
| 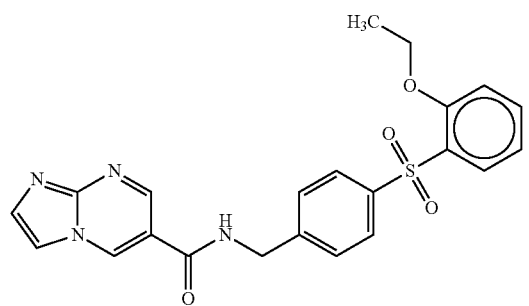 | N-({4-[(2-ethoxybenzene)sulfonyl]phenyl}methyl)imidazo[1,2-a]pyrimidine-6-carboxamide |
| 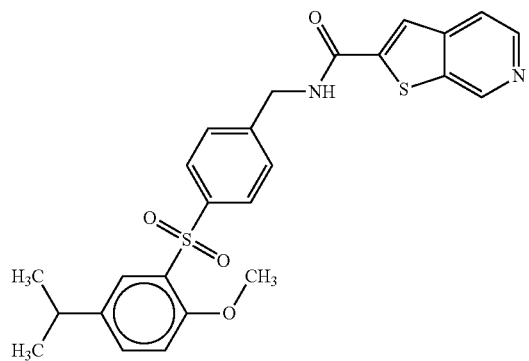 | N-[(4-{[2-methoxy-5-(propan-2-yl)benzene]sulfonyl}phenyl)methyl]thieno[2,3-c]pyridine-2-carboxamide |
| 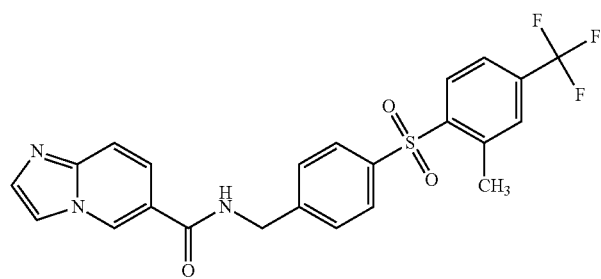 [SMILES: Cc1cc(C(F)(F)F)ccc1S(=O)(=O)c1ccc(CNC(=O)c2ccc3nccn3c2)cc1] | N-[(4-{[2-methyl-4-(trifluoromethyl)benzene]sulfonyl}phenyl)methyl]imidazo[1,2-a]pyridine-6-carboxamide |

TABLE 2-continued

| | |
|---|---|
| 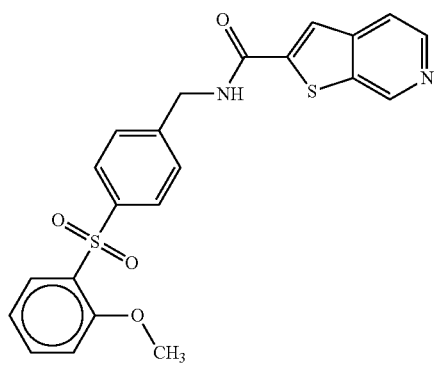 | N-({4-[(2-methoxybenzene)sulfonyl]phenyl}methyl)thieno[2,3-c]pyridine-2-carboxamide |
| 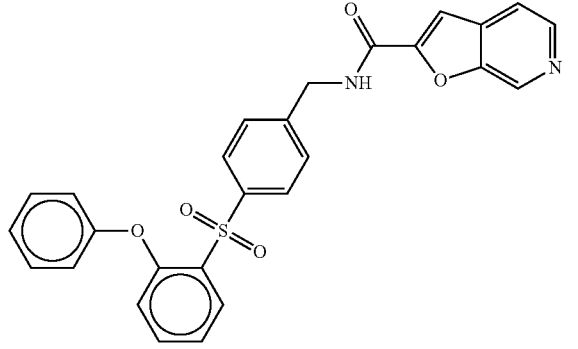 | N-({4-[(2-phenoxybenzene)sulfonyl]phenyl}methyl)furo[2,3-c]pyridine-2-carboxamide |
| 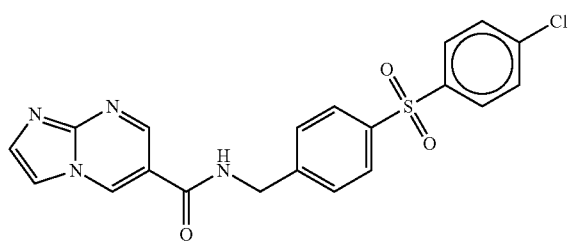 | N-({4-[(4-chlorobenzene)sulfonyl]phenyl}methyl)imidazo[1,2-a]pyrimidine-6-carboxamide |
| 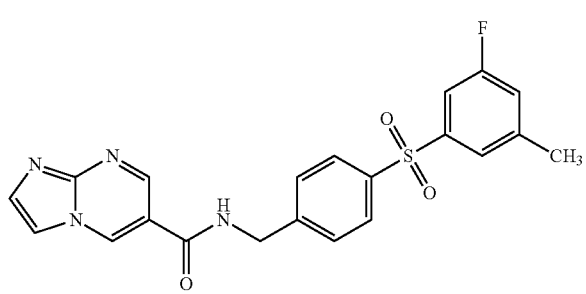 [SMILES: Cc1cc(F)cc(S(=O)(=O)c2ccc(CNC(=O)c3cnc4nccn4c3)cc2)c1] | N-({4-[(3-fluoro-5-methylbenzene)sulfonyl]phenyl}methyl)imidazo[1,2-a]pyrimidine-6-carboxamide |
| 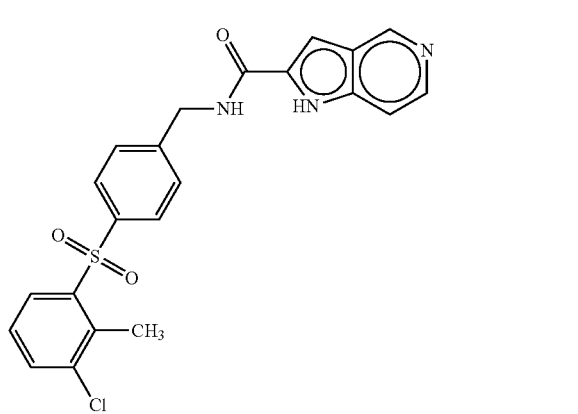 | N-({4-[(3-chloro-2-methylbenzene)sulfonyl]phenyl}methyl)-1H-pyrrolo[3,2-c]pyridine-2-carboxamide |

TABLE 2-continued

N-[(4-{[3-(trifluoromethoxy)benzene]sulfonyl}phenyl)methyl-1H-pyrazolo[3,4-b]pyridine-5-carboxamide N-({4-[(2-butoxy-5-chlorobenzene)sulfonyl]phenyl}methyl)-1H-pyrrolo[3,2-c]pyridine-2-carboxamide N-({4-[(2-ethoxy-4-fluorobenzene)sulfonyl]phenyl}methyl)-1H-pyrazolo[3,4-b]pyridine-5-carboxamide N-({4-[(2-chloro-5-fluorobenzene)sulfonyl]phenyl}methyl)thieno[2,3-c]pyridine-2-carboxamide N-({4-[(3-methoxy-5-methylbenzene)sulfonyl]phenyl}methyl)imidazo[1,2-a]pyrimidine-6-carboxamide TABLE 2-continued
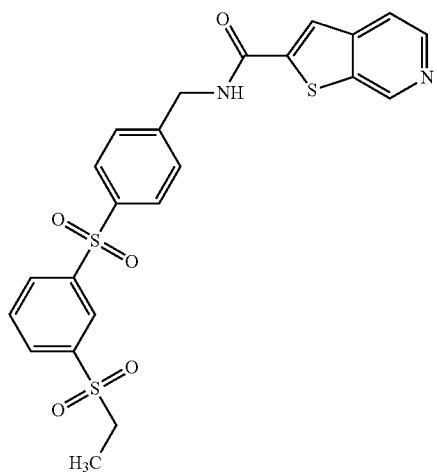
N-[(4-{[3-(ethanesulfonyl)benzene]sulfonyl}phenyl)methyl]thieno[2,3-c]pyridine-2-carboxamide
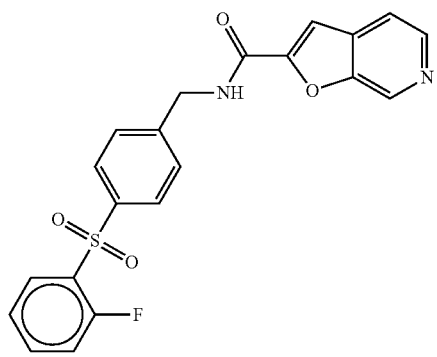
N-({4-[(2-fluorobenzene)sulfonyl]phenyl}methyl)furo[2,3-c]pyridine-2-carboxamide
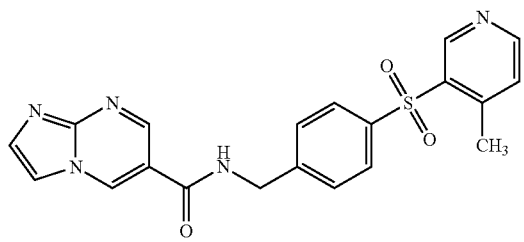 [SMILES: Cc1ccncc1S(=O)(=O)c1ccc(CNC(=O)c2cnc3nccn3c2)cc1]
N-{[4-(4-methylpyridine-3-sulfonyl)phenyl]methyl}imidazo[1,2-a]pyrimidine-6-carboxamide
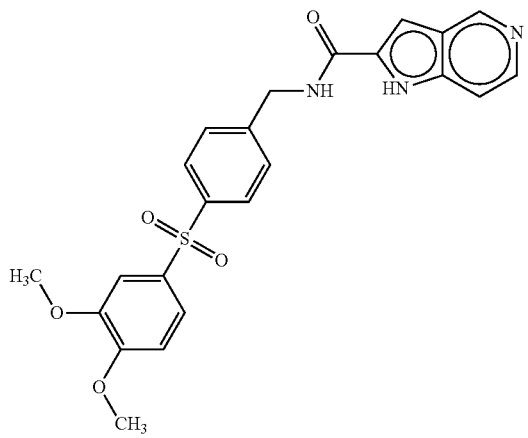
N-({4-[(3,4-dimethoxybenzene)sulfonyl]phenyl}methyl)-1H-pyrrolo[3,2-c]pyridine-2-carboxamide TABLE 2-continued

| | |
|---|---|
| 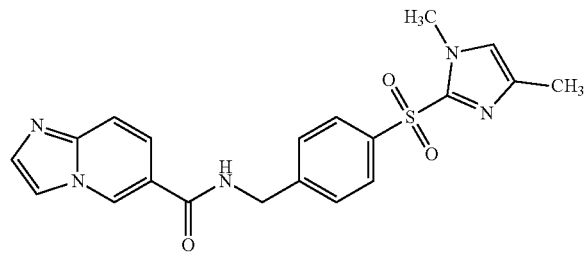 [SMILES: Cc1cn(C)c(S(=O)(=O)c2ccc(CNC(=O)c3ccc4nccn4c3)cc2)n1] | N-{[4-(1,4-dimethyl-1H-imidazole-2-sulfonyl)phenyl]methyl}imidazo[1,2-a]pyridine-6-carboxamide |
| 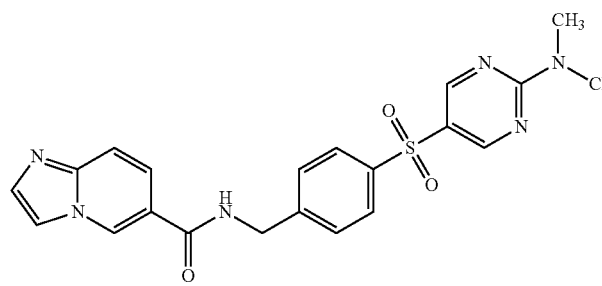 | N-({4-[2-(dimethylamino)pyrimidine-5-sulfonyl]phenyl}methyl)imidazo[1,2-a]pyridine-6-carboxamide |
| 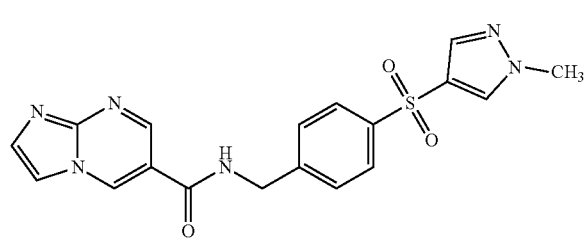 [SMILES: Cn1cc(S(=O)(=O)c2ccc(CNC(=O)c3cnc4nccn4c3)cc2)cn1] | N-{[4-(1-methyl-1H-pyrazole-4-sulfonyl)phenyl]methyl}imidazo[1,2-a]pyrimidine-6-carboxamide |
| 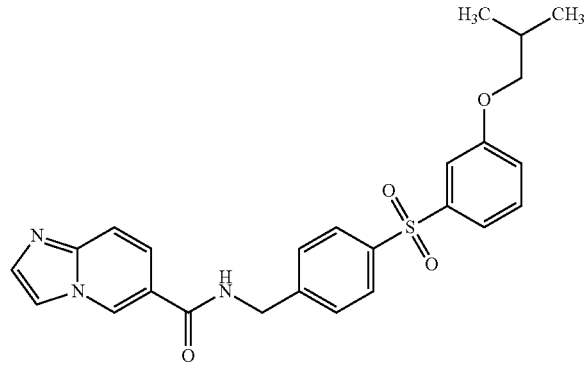 [SMILES: CC(C)COc1cccc(S(=O)(=O)c2ccc(CNC(=O)c3ccc4nccn4c3)cc2)c1] | N-[(4-{[3-(2-methylpropoxy)benzene]sulfonyl}phenyl)methyl]imidazo[1,2-a]pyridine-6-carboxamide |
| 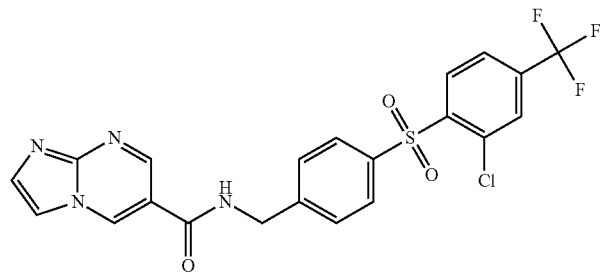 [SMILES: O=C(NCc1ccc(S(=O)(=O)c2ccc(C(F)(F)F)cc2Cl)cc1)c1cnc2nccn2c1] | N-[(4-{[2-chloro-4-(trifluoromethyl)benzene]sulfonyl}phenyl)methyl]imidazo[1,2-a]pyrimidine-6-carboxamide |

TABLE 2-continued
| | |
|---|---|
| 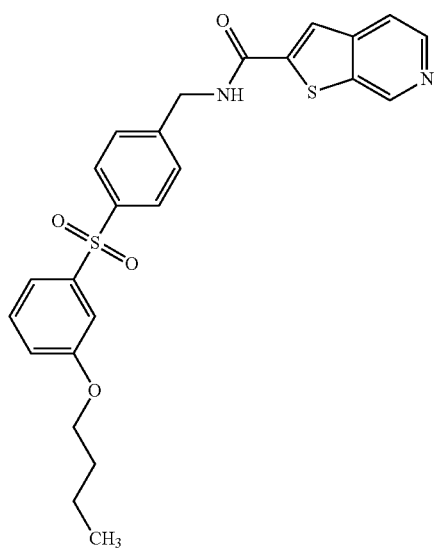 [SMILES: CCCCOc1cccc(S(=O)(=O)c2ccc(CNC(=O)c3cc4ccncc4s3)cc2)c1] | N-({4-[(3-butoxybenzene)sulfonyl]phenyl}methyl)thieno[2,3-c]pyridine-2-carboxamide |
| 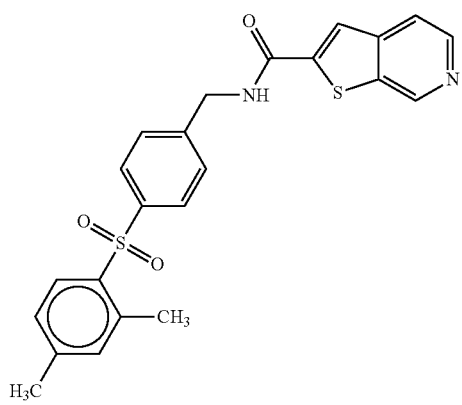 | N-({4-[(2,4-dimethylbenzene)sulfonyl]phenyl}methyl)thieno[2,3-c]pyridine-2-carboxamide |
| 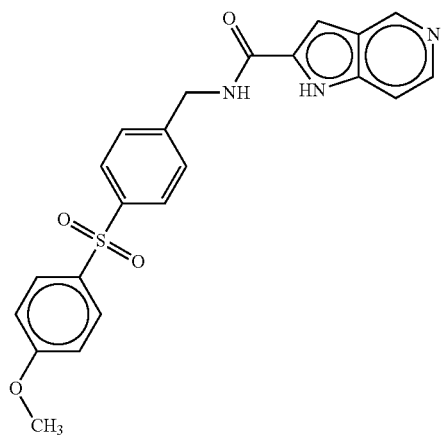 | N-({4-[(4-methoxybenzene)sulfonyl]phenyl}methyl)-1H-pyrrolo[3,2-c]pyridine-2-carboxamide |

| | |
|---|---|
| | N-[(4-{[4-(propan-2-yl)benzene]sulfonyl}phenyl)methyl]thieno[2,3-c]pyridine-2-carboxamide |
| | N-[(4-{[2-(trifluoromethyl)benzene]sulfonyl}phenyl)methyl]-1H-pyrrolo[3,2-c]pyridine-2-carboxamide |
| | N-({4-[(3-acetylbenzene)sulfonyl]phenyl}methyl)-1H-pyrrolo[3,2-c]pyridine-2-carboxamide |
| | N-({4-[(2-ethoxy-4-fluorobenzene)sulfonyl]phenyl}methyl)thieno[2,3-c]pyridine-2-carboxamide |

TABLE 2-continued

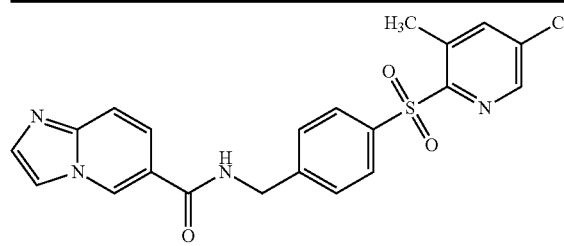 N-{[4-(5-chloro-3-methylpyridine-2-sulfonyl)phenyl]methyl}imidazo[1,2-a]pyridine-6-carboxamide

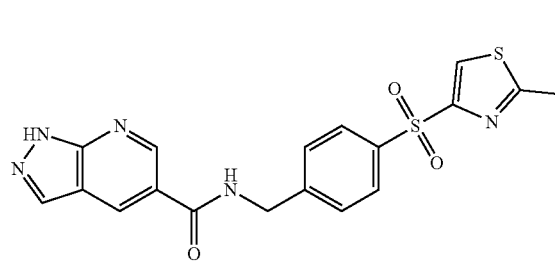 N-({4-[2-(3-fluorophenyl)-1,3-thiazole-4-sulfonyl]phenyl}methyl)-1H-pyrazolo[3,4-b]pyridine-5-carboxamide

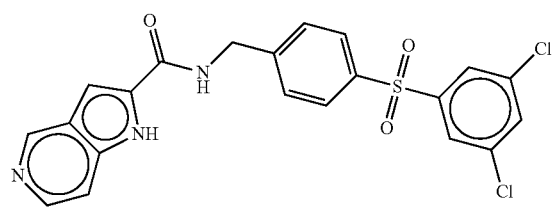 N-({4-[(3,5-dichlorobenzene)sulfonyl]phenyl}methyl)-1H-pyrrolo[3,2-c]pyridine-2-carboxamide

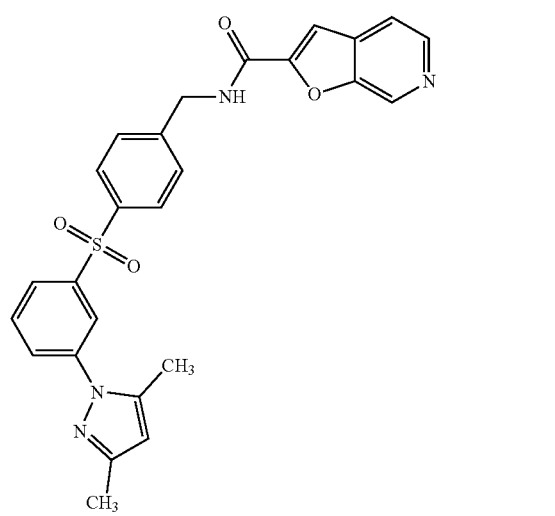 [SMILES: Cc1cc(C)n(-c2cccc(S(=O)(=O)c3ccc(CNC(=O)c4cc5ccncc5o4)cc3)c2)n1] N-[(4-{[3-(3,5-dimethyl-1H-pyrazol-1-yl)benzene]sulfonyl}phenyl)methyl]furo[2,3-c]pyridine-2-carboxamide

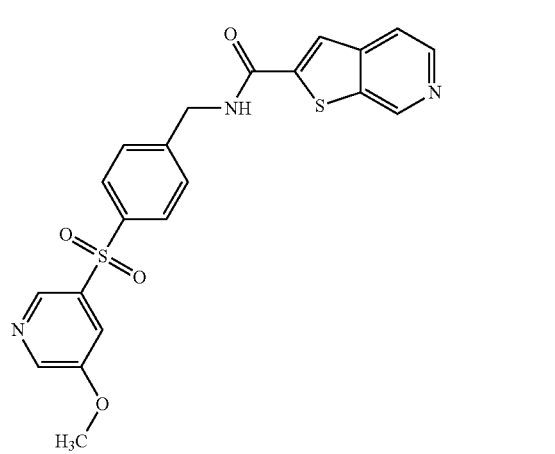 [SMILES: COc1cncc(S(=O)(=O)c2ccc(CNC(=O)c3cc4ccncc4s3)cc2)c1] N-{[4-(5-methoxypyridine-3-sulfonyl)phenyl]methyl}thieno[2,3-c]pyridine-2-carboxamide TABLE 2-continued
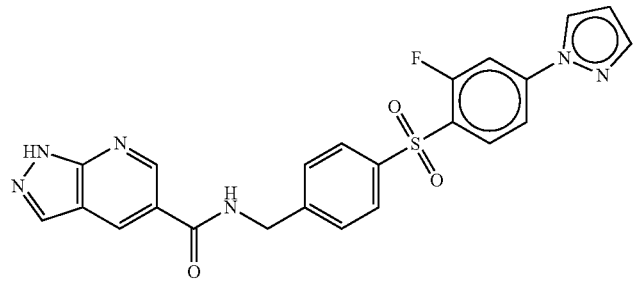
N-[(4-{[2-fluoro-4-(1H-pyrazol-1-yl)benzene]sulfonyl}phenyl)methyl]-1H-pyrazolo[3,4-b]pyridine-5-carboxamide
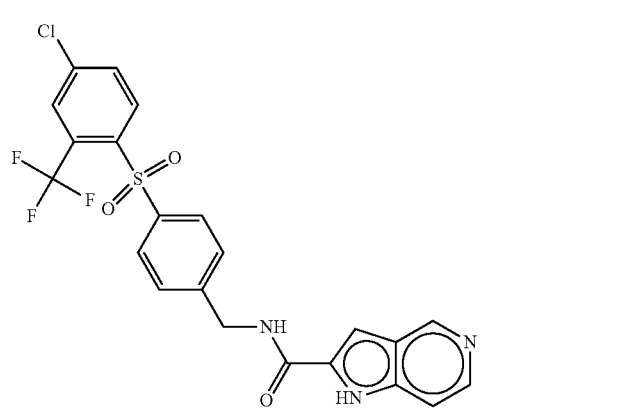
N-[(4-{[4-chloro-2-(trifluoromethyl)benzene]sulfonyl}phenyl)methyl]-1H-pyrrolo[3,2-c]pyridine-2-carboxamide
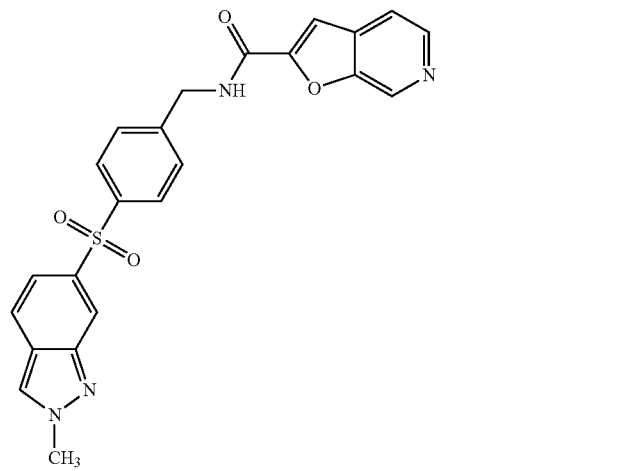 [SMILES: Cn1cc2ccc(S(=O)(=O)c3ccc(CNC(=O)c4cc5ccncc5o4)cc3)cc2n1]
N-{[4-(2-methyl-2H-indazole-6-sulfonyl)phenyl]methyl}furo[2,3-c]pyridine-2-carboxamide
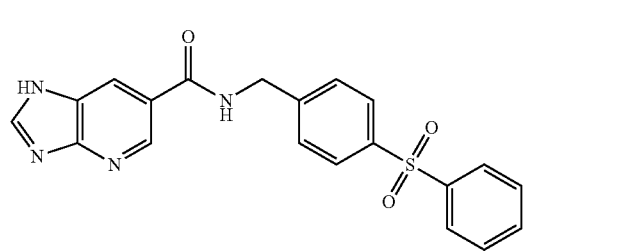 [SMILES: O=C(NCc1ccc(S(=O)(=O)c2ccccc2)cc1)c1cnc2nc[nH]c2c1]
N-(4-(phenylsulfonyl)benzyl)-1H-imidazo[4,5-b]pyridine-6-carboxamide TABLE 2-continued
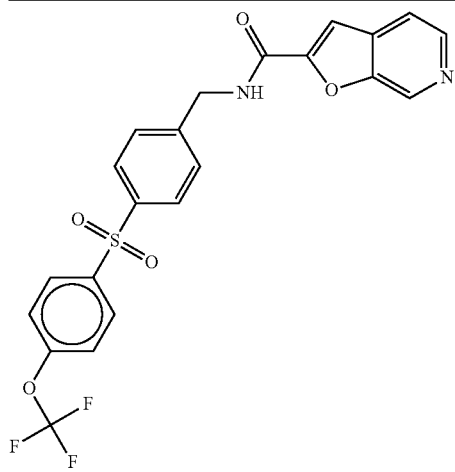
N-[(4-{[4-(trifluoromethoxy)benzene]sulfonyl}phenyl)methyl]furo[2,3-c]pyridine-2-carboxamide
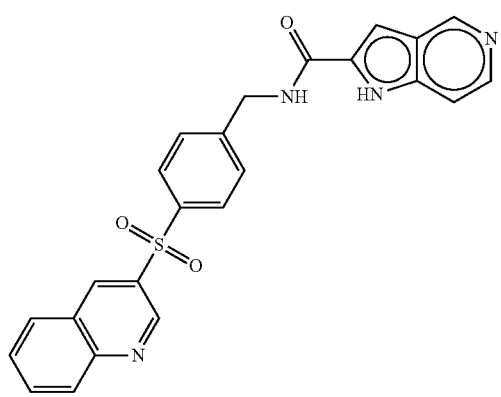
N-{[4-(quinoline-3-sulfonyl)phenyl]methyl}-1H-pyrrolo[3,2-c]pyridine-2-carboxamide
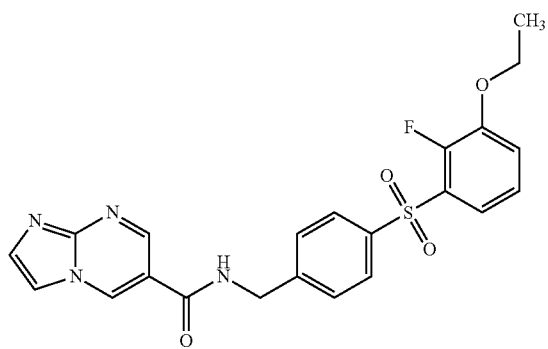 [SMILES: CCOc1cccc(S(=O)(=O)c2ccc(CNC(=O)c3cnc4nccn4c3)cc2)c1F]
N-({4-[(3-ethoxy-2-fluorobenzene)sulfonyl]phenyl}methyl)imidazo[1,2-a]pyrimidine-6-carboxamide
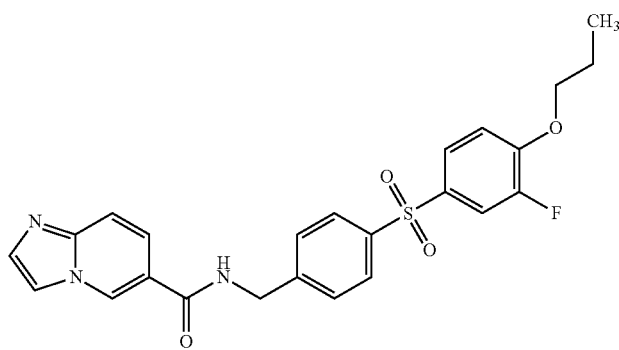 [SMILES: CCCOc1ccc(S(=O)(=O)c2ccc(CNC(=O)c3ccc4nccn4c3)cc2)cc1F]
N-({4-[(3-fluoro-4-propoxybenzene)sulfonyl]phenyl}methyl)imidazo[1,2-a]pyridine-6-carboxamide TABLE 2-continued

| Structure | Name |
|---|---|
| 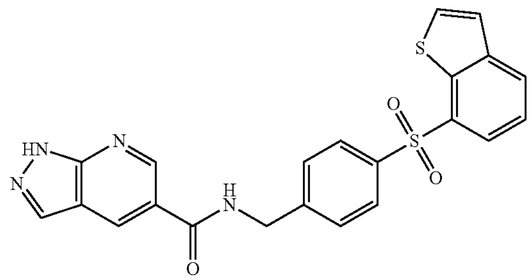 [SMILES: O=C(NCc1ccc(S(=O)(=O)c2cccc3ccsc23)cc1)c1cnc2[nH]ncc2c1] | N-{[4-(1-benzothiophene-7-sulfonyl)phenyl]methyl}-1H-pyrazolo[3,4-b]pyridine-5-carboxamide |
| 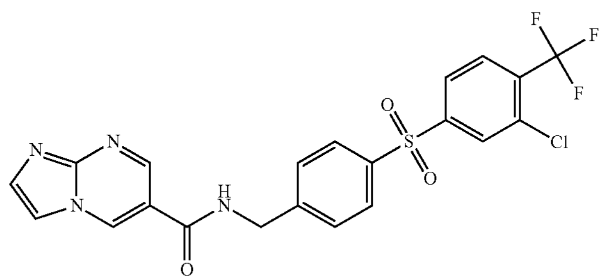 [SMILES: O=C(NCc1ccc(S(=O)(=O)c2ccc(C(F)(F)F)c(Cl)c2)cc1)c1cnc2nccn2c1] | N-[(4-{[3-chloro-4-(trifluoromethyl)benzene]sulfonyl}phenyl)methyl]imidazo[1,2-a]pyrimidine-6-carboxamide |
| 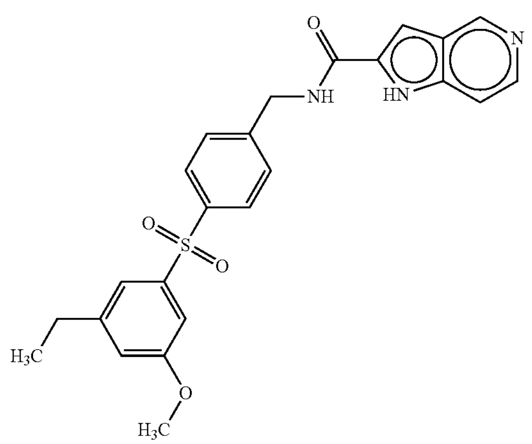 | N-({4-[(3,5-dimethoxybenzene)sulfonyl]phenyl}methyl)-1H-pyrrolo[3,2-c]pyridine-2-carboxamide |
| 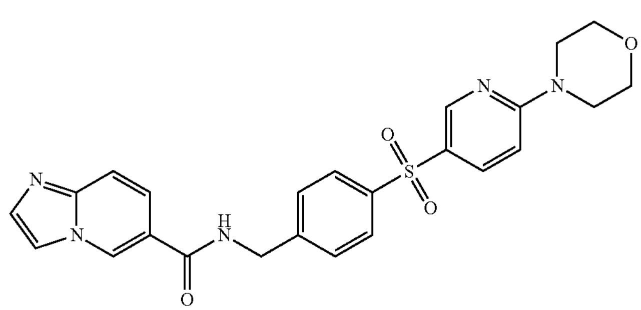 [SMILES: O=C(NCc1ccc(S(=O)(=O)c2ccc(N3CCOCC3)nc2)cc1)c1ccc2nccn2c1] | N-({4-[6-(morpholin-4-yl)pyridine-3-sulfonyl]phenyl}methyl)imidazo[1,2-a]pyridine-6-carboxamide |
| 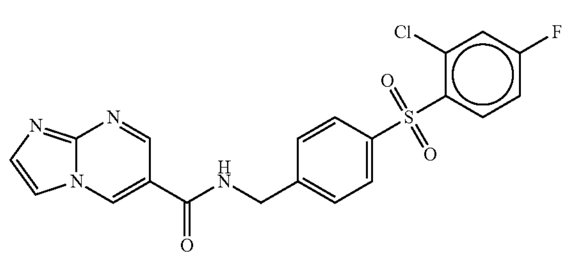 | N-({4-[(2-chloro-4-fluorobenzene)sulfonyl]phenyl}methyl)imidazo[1,2-a]pyrimidine-6-carboxamide |

TABLE 2-continued

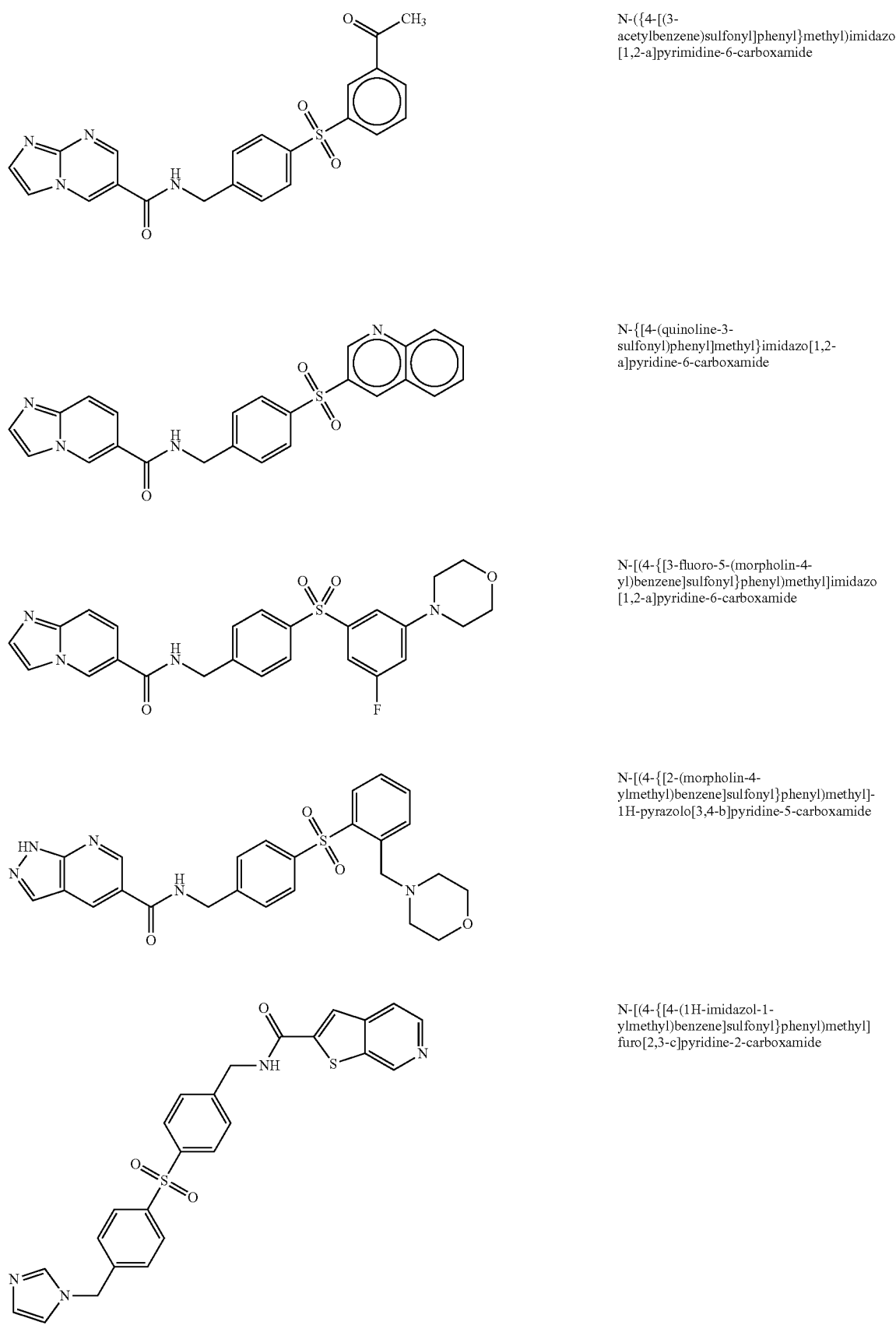

N-({4-[(3-acetylbenzene)sulfonyl]phenyl}methyl)imidazo[1,2-a]pyrimidine-6-carboxamide N-{[4-(quinoline-3-sulfonyl)phenyl]methyl}imidazo[1,2-a]pyridine-6-carboxamide N-[(4-{[3-fluoro-5-(morpholin-4-yl)benzene]sulfonyl}phenyl)methyl]imidazo[1,2-a]pyridine-6-carboxamide N-[(4-{[2-(morpholin-4-ylmethyl)benzene]sulfonyl}phenyl)methyl]-1H-pyrazolo[3,4-b]pyridine-5-carboxamide N-[(4-{[4-(1H-imidazol-1-ylmethyl)benzene]sulfonyl}phenyl)methyl]furo[2,3-c]pyridine-2-carboxamide

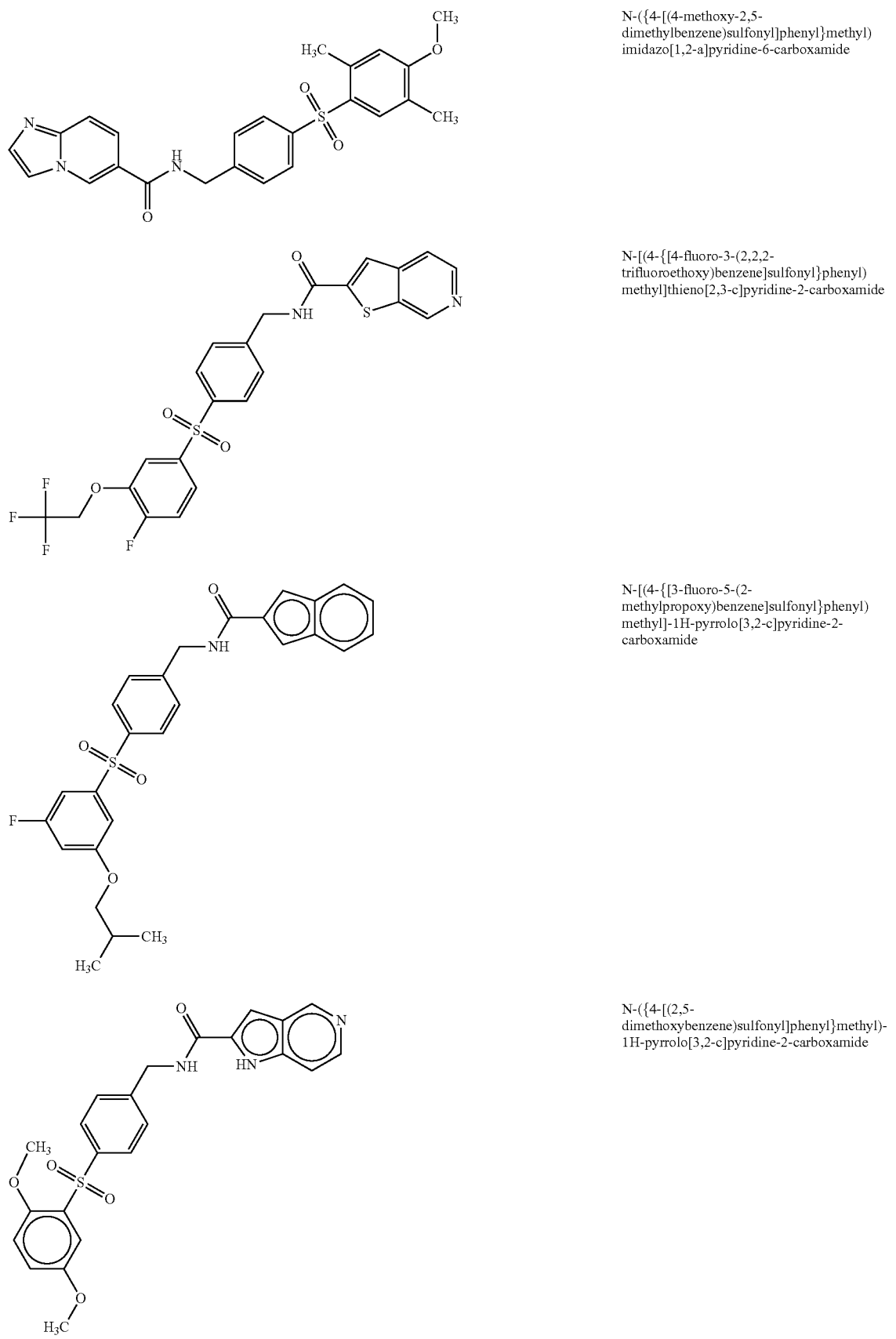
N-({4-[(4-methoxy-2,5-dimethylbenzene)sulfonyl]phenyl}methyl)imidazo[1,2-a]pyridine-6-carboxamide
N-[(4-{[4-fluoro-3-(2,2,2-trifluoroethoxy)benzene]sulfonyl}phenyl)methyl]thieno[2,3-c]pyridine-2-carboxamide
N-[(4-{[3-fluoro-5-(2-methylpropoxy)benzene]sulfonyl}phenyl)methyl]-1H-pyrrolo[3,2-c]pyridine-2-carboxamide
N-({4-[(2,5-dimethoxybenzene)sulfonyl]phenyl}methyl)-1H-pyrrolo[3,2-c]pyridine-2-carboxamide TABLE 2-continued
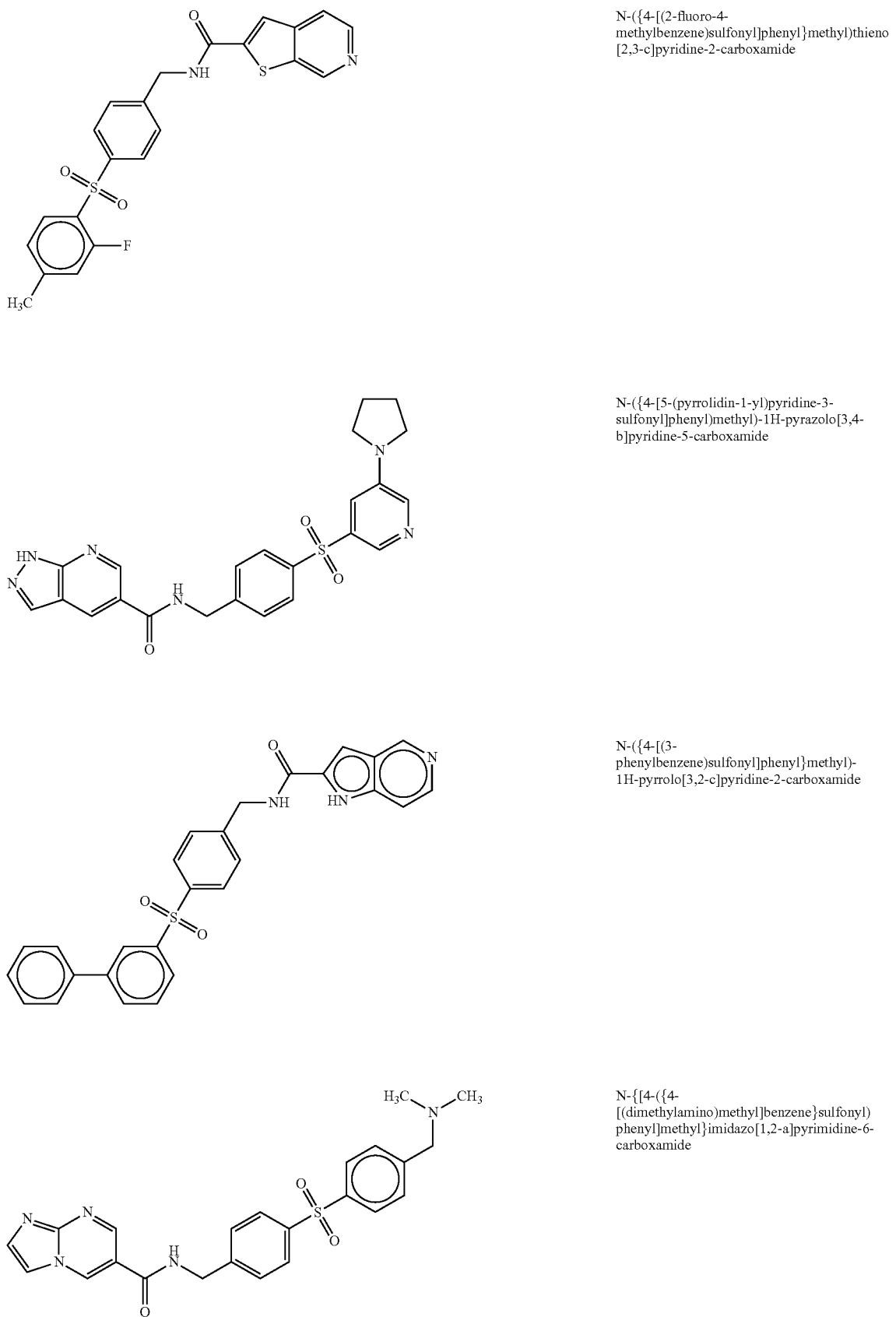
N-({4-[(2-fluoro-4-methylbenzene)sulfonyl]phenyl}methyl)thieno[2,3-c]pyridine-2-carboxamide
N-({4-[5-(pyrrolidin-1-yl)pyridine-3-sulfonyl]phenyl}methyl)-1H-pyrazolo[3,4-b]pyridine-5-carboxamide
N-({4-[(3-phenylbenzene)sulfonyl]phenyl}methyl)-1H-pyrrolo[3,2-c]pyridine-2-carboxamide
N-{[4-({4-[(dimethylamino)methyl]benzene}sulfonyl)phenyl]methyl}imidazo[1,2-a]pyrimidine-6-carboxamide TABLE 2-continued
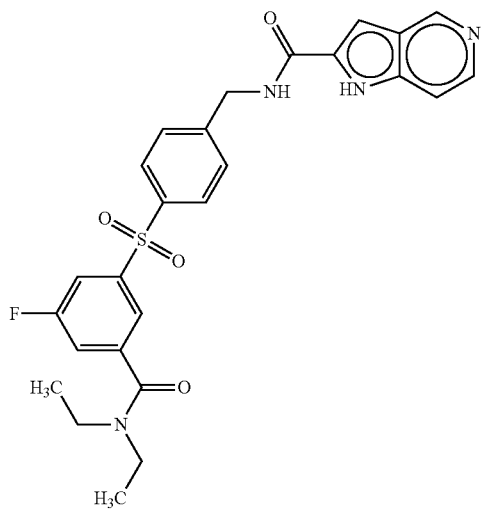
N-[(4-{[3-(diethylcarbamoyl)-5-fluorobenzene]sulfonyl}phenyl)methyl]-1H-pyrrolo[3,2-c]pyridine-2-carboxamide
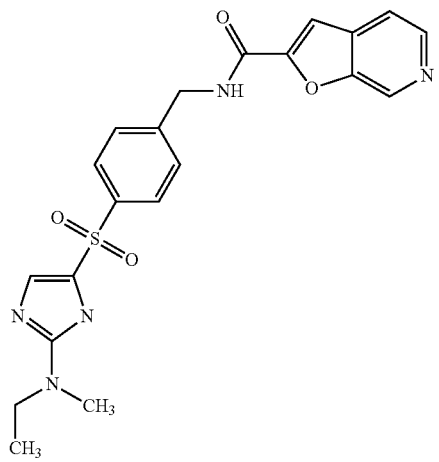 [SMILES: CCN(C)c1ncc(S(=O)(=O)c2ccc(CNC(=O)c3cc4ccncc4o3)cc2)[nH]1]
N-[(4-{2-[ethyl(methyl)amino]-1,3-thiazole-5-sulfonyl}phenyl)methyl]furo[2,3-c]pyridine-2-carboxamide
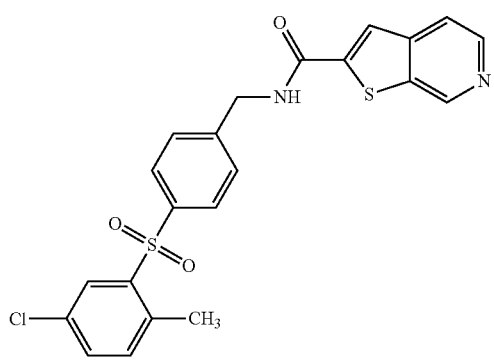 [SMILES: Cc1ccc(Cl)cc1S(=O)(=O)c1ccc(CNC(=O)c2cc3ccncc3s2)cc1]
N-({4-[(5-chloro-2-methylbenzene)sulfonyl]phenyl}methyl)thieno[2,3-c]pyridine-2-carboxamide
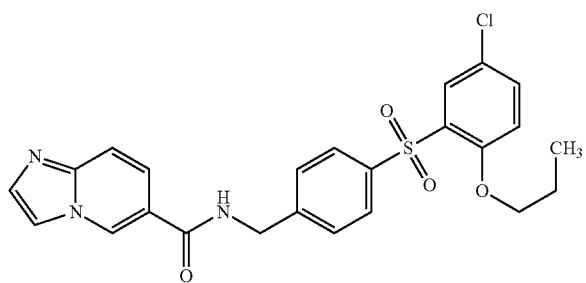 [SMILES: CCCOc1ccc(Cl)cc1S(=O)(=O)c1ccc(CNC(=O)c2ccc3nccn3c2)cc1]
N-({4-[(5-chloro-2-propoxybenzene)sulfonyl]phenyl}methyl)imidazo[1,2-a]pyridine-6-carboxamide TABLE 2-continued
N-[(4-{[4-(1H-imidazol-1-ylmethyl)benzene]sulfonyl}phenyl)methyl]thieno[2,3-c]pyridine-2-carboxamide
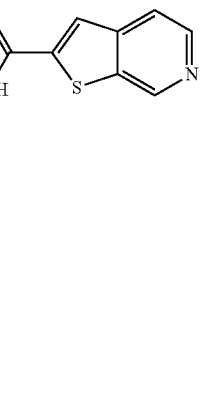
N-({4-[(4-chloro-2-ethoxybenzene)sulfonyl]phenyl}methyl)thieno[2,3-c]pyridine-2-carboxamide
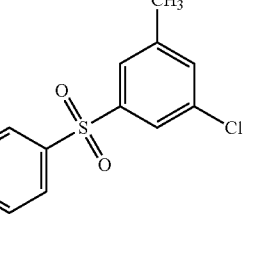
N-({4-[(3-chloro-5-methylbenzene)sulfonyl]phenyl}methyl)imidazo[1,2-a]pyrimidine-6-carboxamide
N-[(4-{[4-(2-methylpropoxy)benzene]sulfonyl}phenyl)methyl]furo[2,3-c]pyridine-2-carboxamide TABLE 2-continued
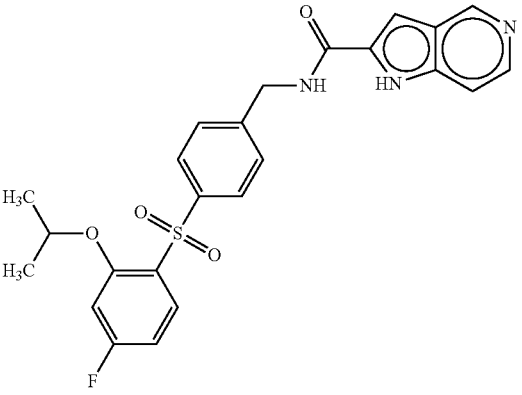
N-[(4-{[4-fluoro-2-(propan-2-yloxy)benzene]sulfonyl}phenyl)methyl]-1H-pyrrolo[3,2-c]pyridine-2-carboxamide
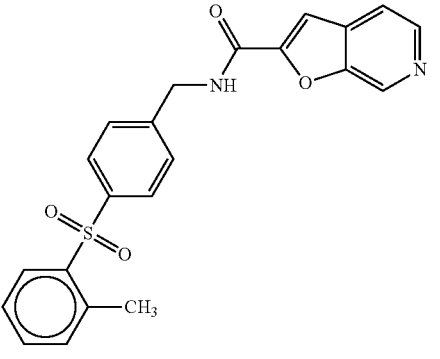
N-({4-[(2-methylbenzene)sulfonyl]phenyl}methyl)furo[2,3-c]pyridine-2-carboxamide
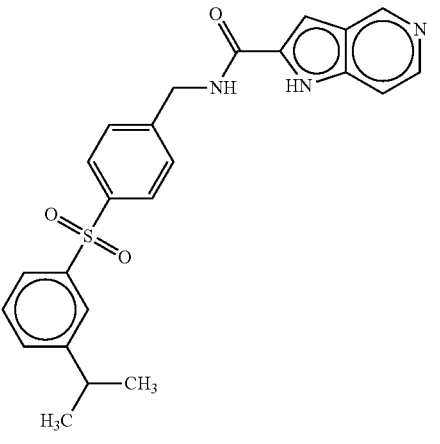
N-[(4-{[3-(propan-2-yl)benzene]sulfonyl}phenyl)methyl]-1H-pyrrolo[3,2-c]pyridine-2-carboxamide
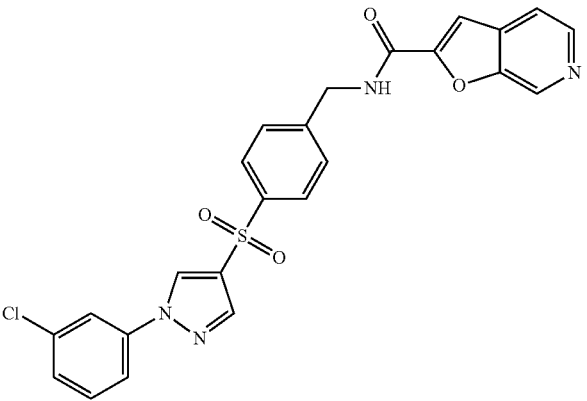 [SMILES: O=C(NCc1ccc(S(=O)(=O)c2cnn(-c3cccc(Cl)c3)c2)cc1)c1cc2ccncc2o1]
N-({4-[1-(3-chlorophenyl)-1H-pyrazole-4-sulfonyl]phenyl}methyl)furo[2,3-c]pyridine-2-carboxamide TABLE 2-continued

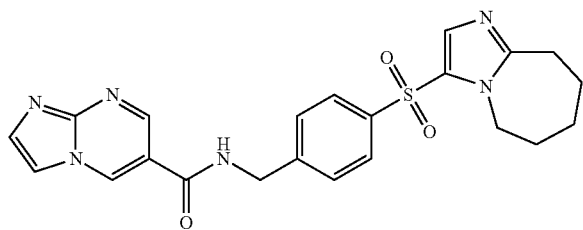 [SMILES: O=C(NCc1ccc(S(=O)(=O)c2cnc3n2CCCCC3)cc1)c1cnc2nccn2c1]

N-[(4-{5H,6H,7H,8H,9H-imidazo[1,2-a]azepine-3-sulfonyl}phenyl)methyl]imidazo[1,2-a]pyrimidine-6-carboxamide

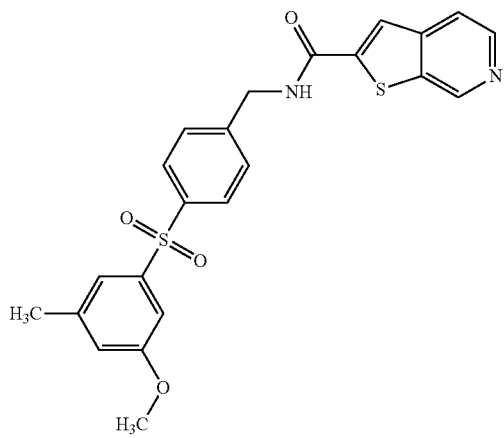 [SMILES: COc1cc(C)cc(S(=O)(=O)c2ccc(CNC(=O)c3cc4ccncc4s3)cc2)c1]

N-({4-[(3-methoxy-5-methylbenzene)sulfonyl]phenyl}methyl)thieno[2,3-c]pyridine-2-carboxamide

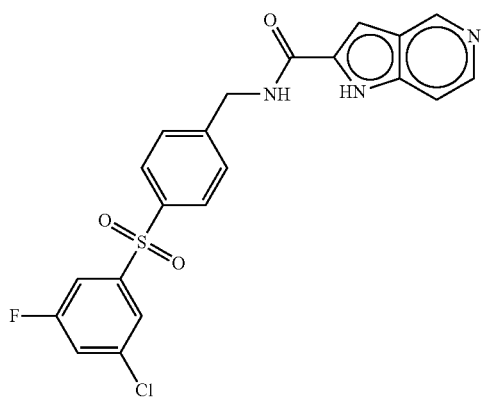

N-({4-[(3-chloro-5-fluorobenzene)sulfonyl]phenyl}methyl)-1H-pyrrolo[3,2-c]pyridine-2-carboxamide

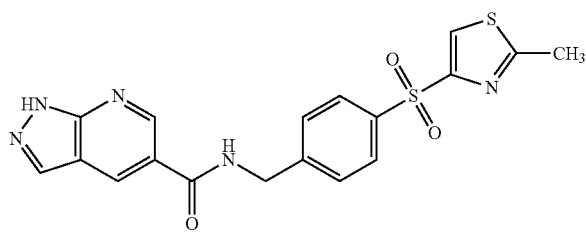 [SMILES: Cc1nc(S(=O)(=O)c2ccc(CNC(=O)c3cnc4[nH]ncc4c3)cc2)cs1]

N-{[4-(2-methyl-1,3-thiazole-4-sulfonyl)phenyl]methyl}-1H-pyrazolo[3,4-b]pyridine-5-carboxamide

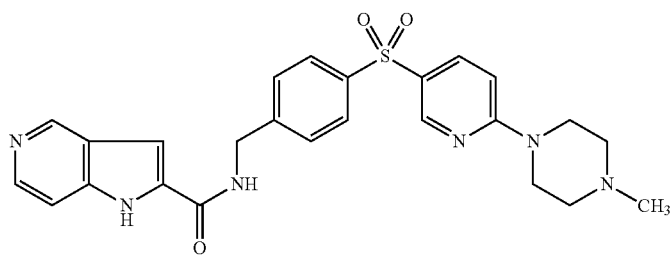 [SMILES: CN1CCN(c2ccc(S(=O)(=O)c3ccc(CNC(=O)c4cc5cnccc5[nH]4)cc3)cn2)CC1]

N-({4-[6-(4-methylpiperazin-1-yl)pyridine-3-sulfonyl]phenyl}methyl)-1H-pyrrolo[3,2-c]pyridine-2-carboxamide TABLE 2-continued
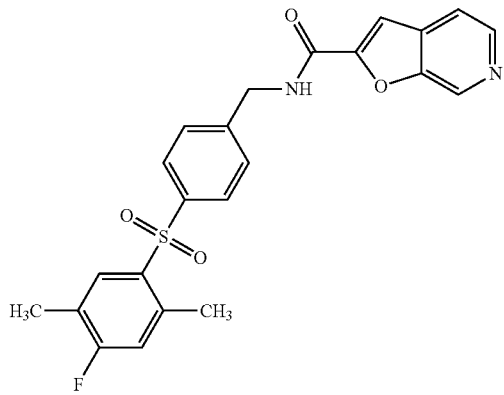 [SMILES: Cc1cc(S(=O)(=O)c2ccc(CNC(=O)c3cc4ccncc4o3)cc2)c(C)cc1F]
N-({4-[(4-fluoro-2,5-dimethylbenzene)sulfonyl]phenyl}methyl)furo[2,3-c]pyridine-2-carboxamide
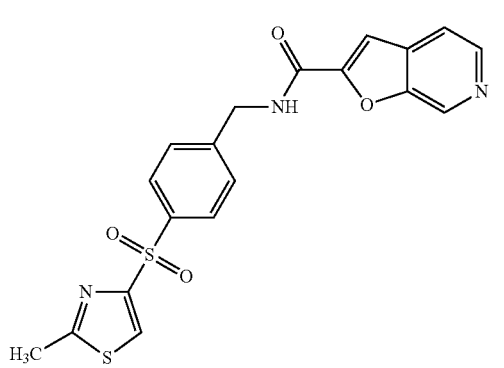 [SMILES: Cc1nc(S(=O)(=O)c2ccc(CNC(=O)c3cc4ccncc4o3)cc2)cs1]
N-{[4-(2-methyl-1,3-thiazole-4-sulfonyl)phenyl]methyl}furo[2,3-c]pyridine-2-carboxamide
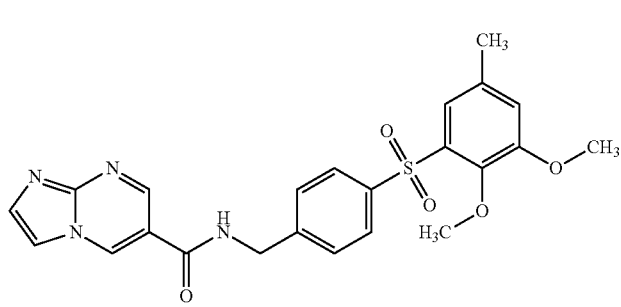 [SMILES: COc1cc(C)cc(S(=O)(=O)c2ccc(CNC(=O)c3cnc4nccn4c3)cc2)c1OC]
N-({4-[(2,3-dimethoxy-5-methylbenzene)sulfonyl]phenyl}methyl)imidazo[1,2-a]pyrimidine-6-carboxamide
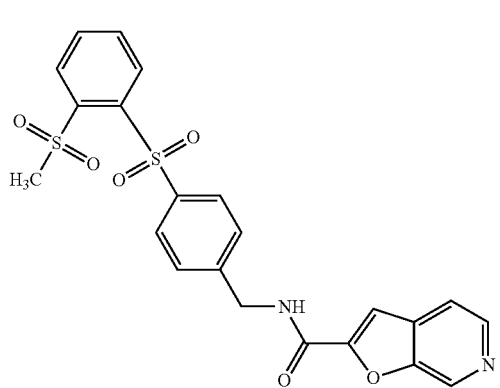 [SMILES: CS(=O)(=O)c1ccccc1S(=O)(=O)c1ccc(CNC(=O)c2cc3ccncc3o2)cc1]
N-({4-[(2-methanesulfonylbenzene)sulfonyl]phenyl}methyl)furo[2,3-c]pyridine-2-carboxamide TABLE 2-continued

| Structure | Name |
|---|---|
| 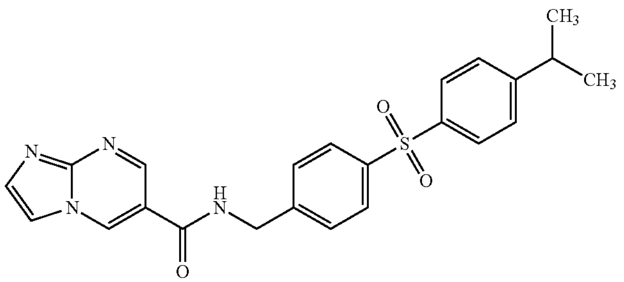 [SMILES: CC(C)c1ccc(S(=O)(=O)c2ccc(CNC(=O)c3cnc4nccn4c3)cc2)cc1] | N-[(4-{[4-(propan-2-yl)benzene]sulfonyl}phenyl)methyl]imidazo[1,2-a]pyrimidine-6-carboxamide |
| 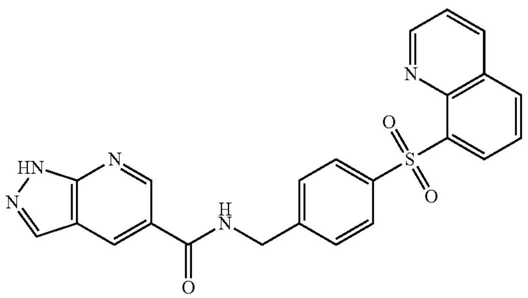 [SMILES: O=C(NCc1ccc(S(=O)(=O)c2cccc3cccnc23)cc1)c1cnc2[nH]ncc2c1] | N-{[4-(quinoline-8-sulfonyl)phenyl]methyl}-1H-pyrazolo[3,4-b]pyridine-5-carboxamide |
| 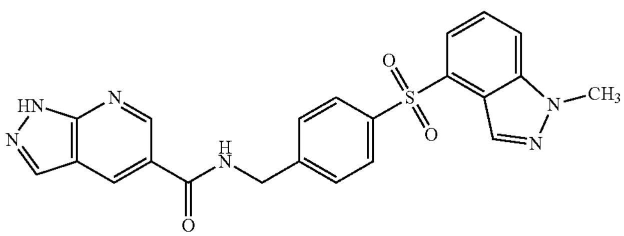 [SMILES: Cn1ncc2c(S(=O)(=O)c3ccc(CNC(=O)c4cnc5[nH]ncc5c4)cc3)cccc21] | N-{[4-(1-methyl-1H-indazole-4-sulfonyl)phenyl]methyl}-1H-pyrazolo[3,4-b]pyridine-5-carboxamide |
| 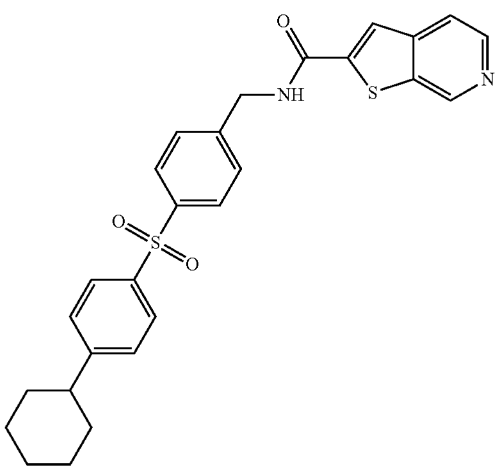 [SMILES: O=C(NCc1ccc(S(=O)(=O)c2ccc(C3CCCCC3)cc2)cc1)c1cc2ccncc2s1] | N-({4-[(4-cyclohexylbenzene)sulfonyl]phenyl}methyl)thieno[2,3-c]pyridine-2-carboxamide |
| 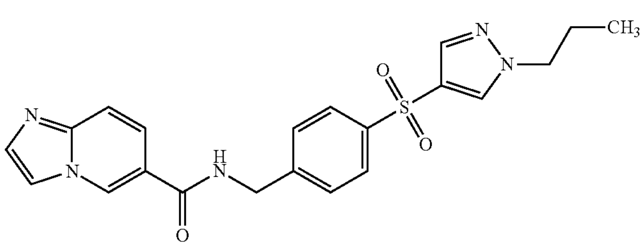 [SMILES: CCCn1cc(S(=O)(=O)c2ccc(CNC(=O)c3ccc4nccn4c3)cc2)cn1] | N-{[4-(1-propyl-1H-pyrazole-4-sulfonyl)phenyl]methyl}imidazo[1,2-a]pyridine-6-carboxamide |

TABLE 2-continued
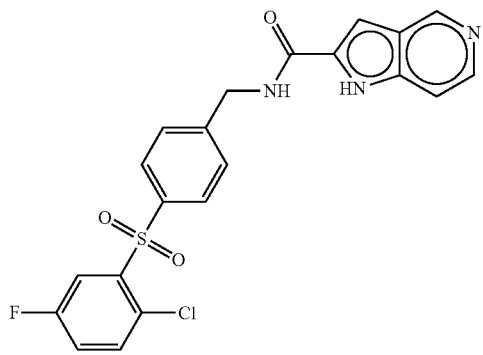
N-({4-[(2-chloro-5-fluorobenzene)sulfonyl]phenyl}methyl)-1H-pyrrolo[3,2-c]pyridine-2-carboxamide
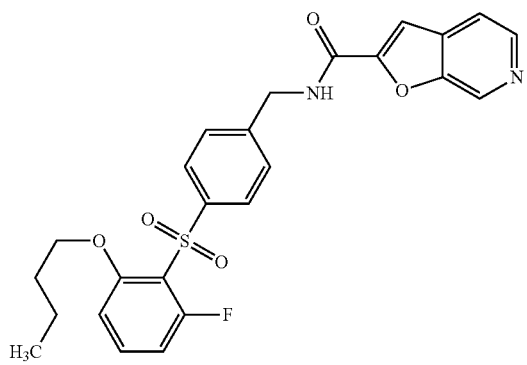 [SMILES: CCCCOc1cccc(F)c1S(=O)(=O)c1ccc(CNC(=O)c2cc3ccncc3o2)cc1]
N-({4-[(2-butoxy-6-fluorobenzene)sulfonyl]phenyl}methyl)furo[2,3-c]pyridine-2-carboxamide
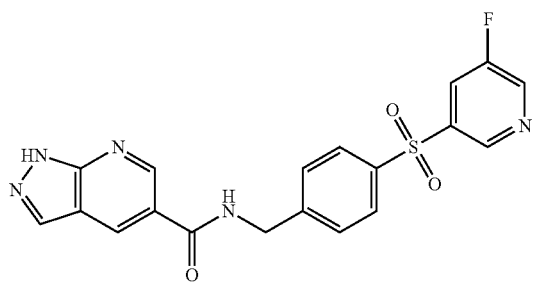 [SMILES: O=C(NCc1ccc(S(=O)(=O)c2cncc(F)c2)cc1)c1cnc2[nH]ncc2c1]
N-{[4-(5-fluoropyridine-3-sulfonyl)phenyl]methyl}-1H-pyrazolo[3,4-b]pyridine-5-carboxamide
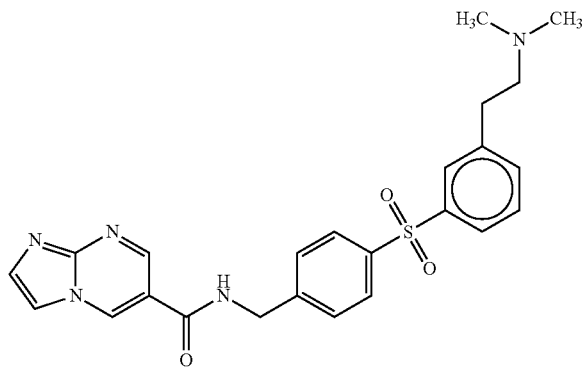
N-{[4-({3-[2-(dimethylamino)ethyl]benzene}sulfonyl)phenyl]methyl}imidazo[1,2-a]pyrimidine-6-carboxamide TABLE 2-continued N-({4-[(2,6-dimethoxy-4-methylbenzene)sulfonyl]phenyl}methyl)-1H-pyrrolo[3,2-c]pyridine-2-carboxamide N-[(4-{[3-(morpholin-4-yl)benzene]sulfonyl}phenyl)methyl]furo[2,3-c]pyridine-2-carboxamide N-[(4-{5H,6H,7H,8H,9H-imidazo[1,2-a]azepine-3-sulfonyl}phenyl)methyl]thieno[2,3-c]pyridine-2-carboxamide N-({4-[(3-tert-butylbenzene)sulfonyl]phenyl}methyl)thieno[2,3-c]pyridine-2-carboxamide TABLE 2-continued
| | |
|---|---|
| 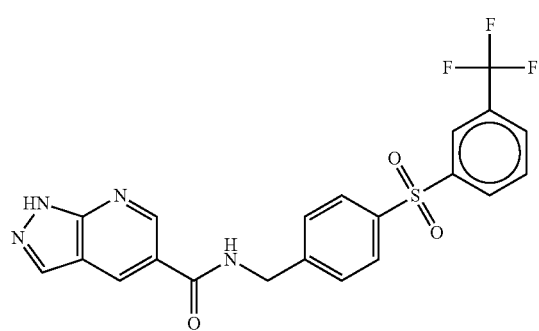 | N-[(4-{[3-(trifluoromethyl)benzene]sulfonyl}phenyl)methyl]-1H-pyrazolo[3,4-b]pyridine-5-carboxamide |
| 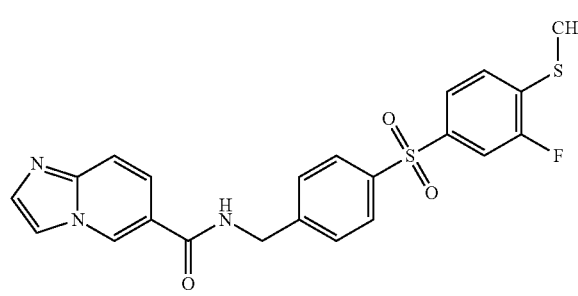 | N-[(4-{[3-fluoro-4-(methylsulfanyl)benzene]sulfonyl}phenyl)methyl]imidazo[1,2-a]pyridine-6-carboxamide |
| 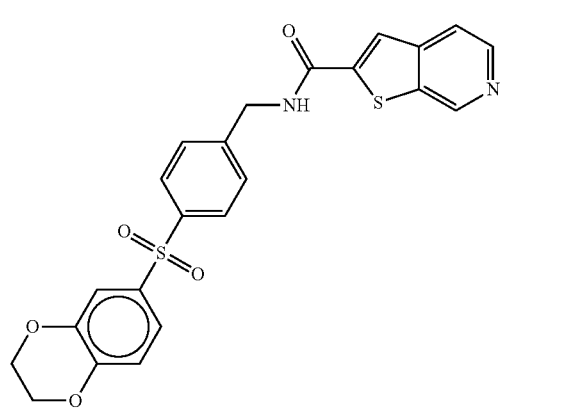 | N-{[4-(2,3-dihydro-1,4-benzodioxine-6-sulfonyl)phenyl]methyl}furo[2,3-c]pyridine-2-carboxamide |
| 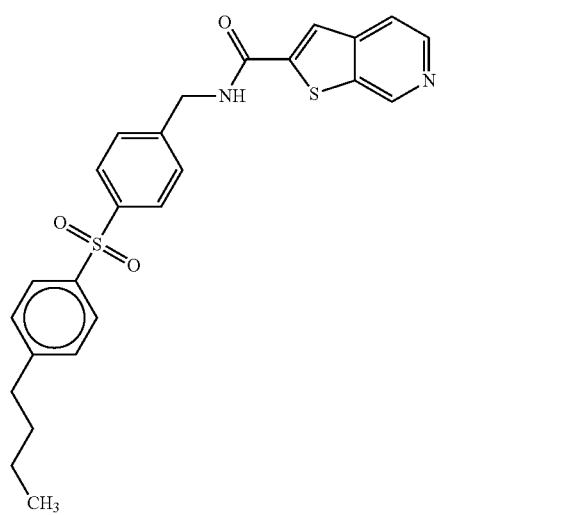 | N-({4-[(4-butylbenzene)sulfonyl]phenyl}methyl)furo[2,3-c]pyridine-2-carboxamide |

TABLE 2-continued
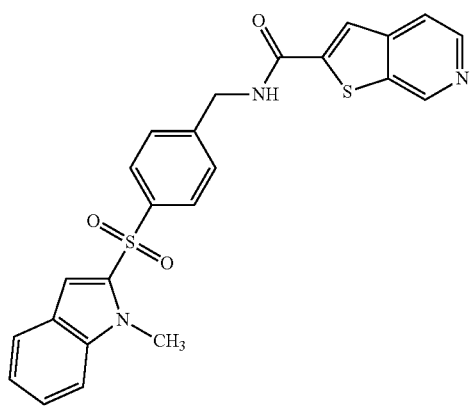 [SMILES: Cn1c(S(=O)(=O)c2ccc(CNC(=O)c3cc4ccncc4s3)cc2)cc2ccccc21]
N-{[4-(1-methyl-1H-indole-2-sulfonyl)phenyl]methyl}thieno[2,3-c]pyridine-2-carboxamide
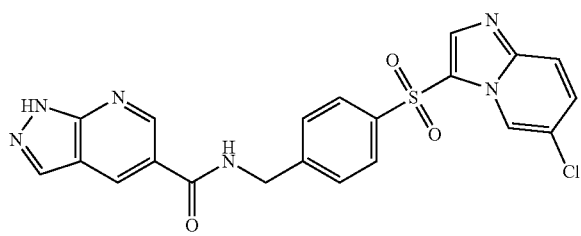 [SMILES: O=C(NCc1ccc(S(=O)(=O)c2cnc3ccc(Cl)cn23)cc1)c1cnc2[nH]ncc2c1]
N-[(4-{6-chloroimidazo[1,2-a]pyridine-3-sulfonyl}phenyl)methyl]-1H-pyrazolo[3,4-b]pyridine-5-carboxamide
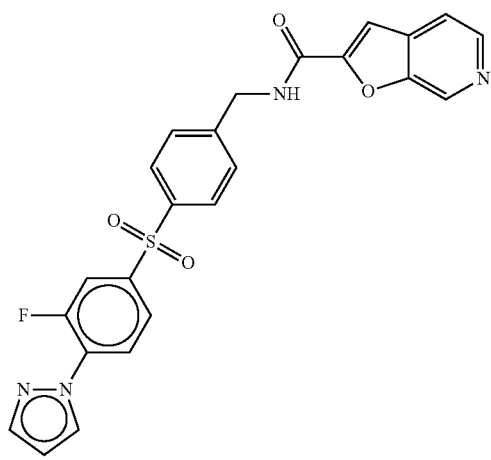
N-[(4-{[3-fluoro-4-(1H-pyrazol-1-yl)benzene]sulfonyl}phenyl)methyl]furo[2,3-c]pyridine-2-carboxamide
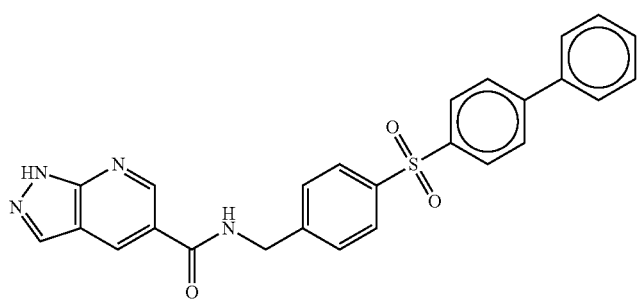
N-({4-[(4-phenylbenzene)sulfonyl]phenyl}methyl)-1H-pyrazolo[3,4-b]pyridine-5-carboxamide TABLE 2-continued
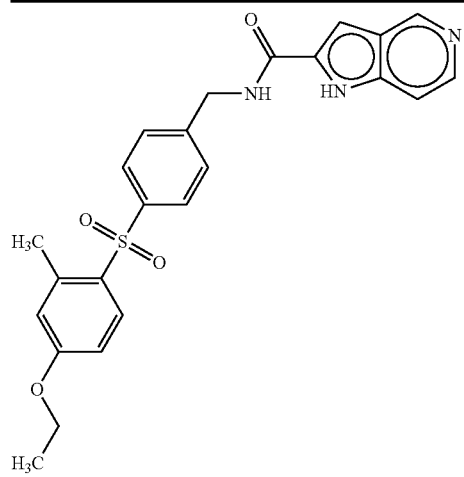
N-({4-[(4-ethoxy-2-methylbenzene)sulfonyl]phenyl}methyl)-1H-pyrrolo[3,2-c]pyridine-2-carboxamide
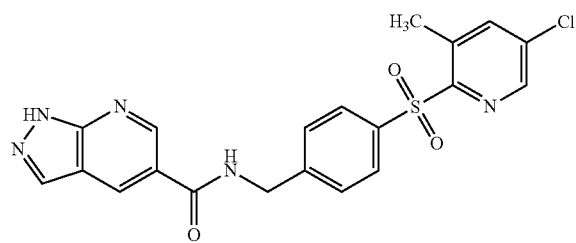 [SMILES: Cc1cc(Cl)cnc1S(=O)(=O)c1ccc(CNC(=O)c2cnc3[nH]ncc3c2)cc1]
N-{[4-(5-chloro-3-methylpyridine-2-sulfonyl)phenyl]methyl}-1H-pyrazolo[3,4-b]pyridine-5-carboxamide
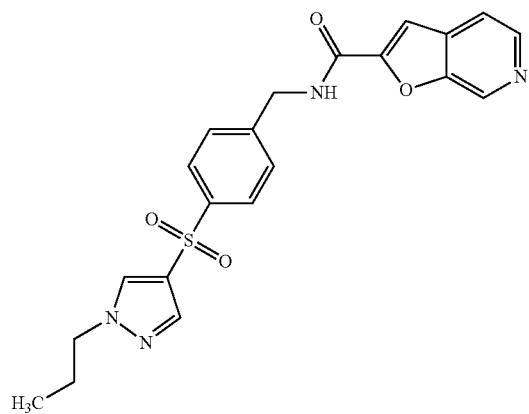 [SMILES: CCCn1cc(S(=O)(=O)c2ccc(CNC(=O)c3cc4ccncc4o3)cc2)cn1]
N-{[4-(1-propyl-1H-pyrazole-4-sulfonyl)phenyl]methyl}thieno[2,3-c]pyridine-2-carboxamide
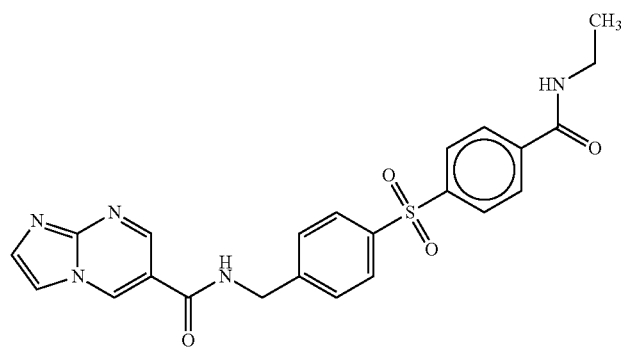
N-[(4-{[4-(ethylcarbamoyl)benzene]sulfonyl}phenyl)methyl]imidazo[1,2-a]pyrimidine-6-carboxamide TABLE 2-continued
| | |
|---|---|
| 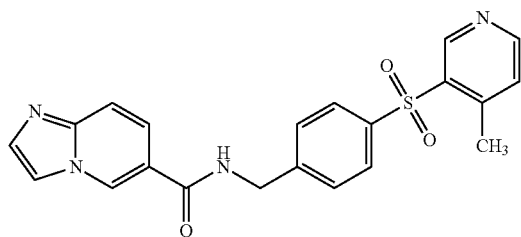 [SMILES: Cc1ccncc1S(=O)(=O)c1ccc(CNC(=O)c2ccc3nccn3c2)cc1] | N-{[4-(4-methylpyridine-3-sulfonyl)phenyl]methyl}imidazo[1,2-a]pyridine-6-carboxamide |
| 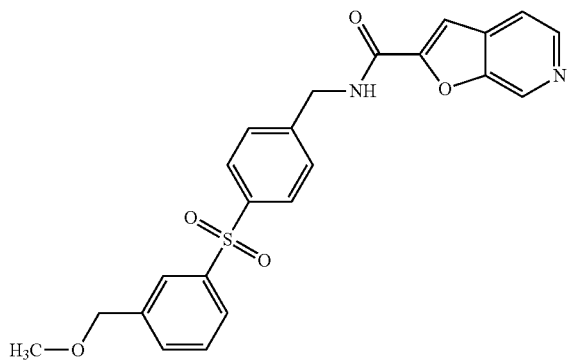 [SMILES: COCc1cccc(S(=O)(=O)c2ccc(CNC(=O)c3cc4ccncc4o3)cc2)c1] | N-[(4-{[3-(methoxymethyl)benzene]sulfonyl}phenyl)methyl]thieno[2,3-c]pyridine-2-carboxamide |
| 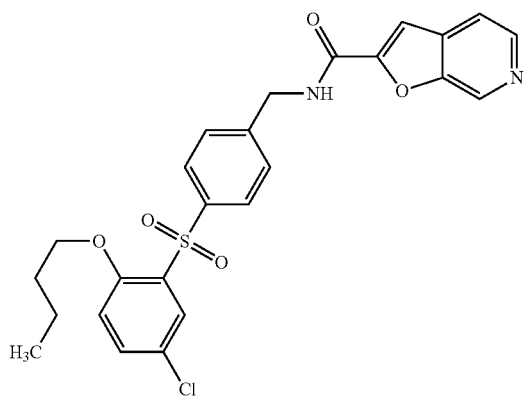 | N-({4-[(2-butoxy-5-chlorobenzene)sulfonyl]phenyl}methyl)furo[2,3-c]pyridine-2-carboxamide |
| 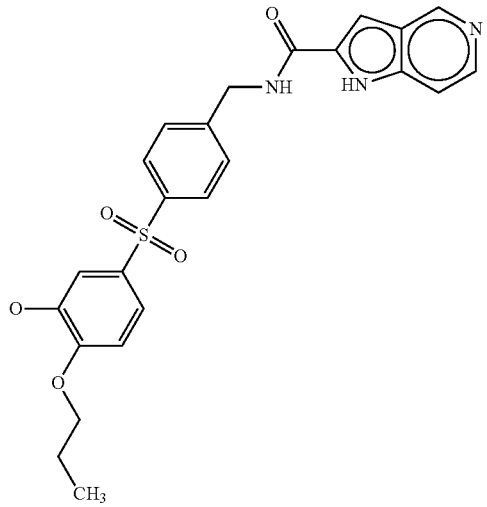 | N-({4-[(3-fluoro-4-propoxybenzene)sulfonyl]phenyl}methyl)-1H-pyrrolo[3,2-c]pyridine-2-carboxamide |

TABLE 2-continued
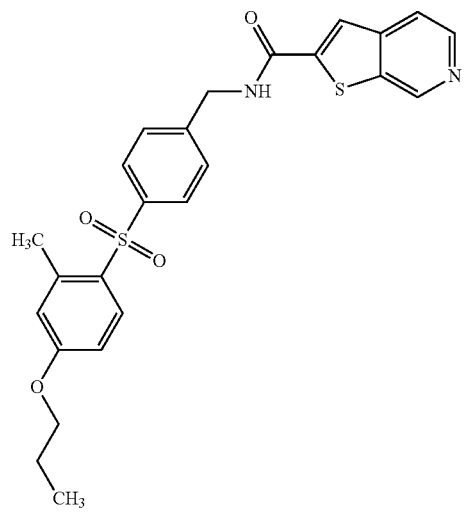 [SMILES: CCCOc1ccc(S(=O)(=O)c2ccc(CNC(=O)c3cc4ccncc4s3)cc2)c(C)c1]
N-({4-[(2-methyl-4-propoxybenzene)sulfonyl]phenyl}methyl)furo[2,3-c]pyridine-2-carboxamide
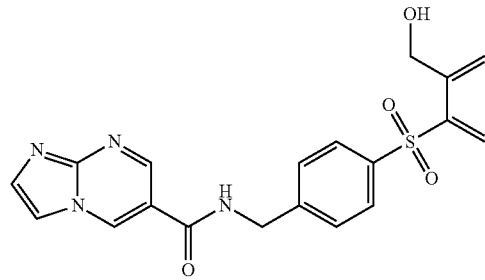
N-[(4-{[5-fluoro-2-(hydroxymethyl)benzene]sulfonyl}phenyl)methyl]imidazo[1,2-a]pyrimidine-6-carboxamide
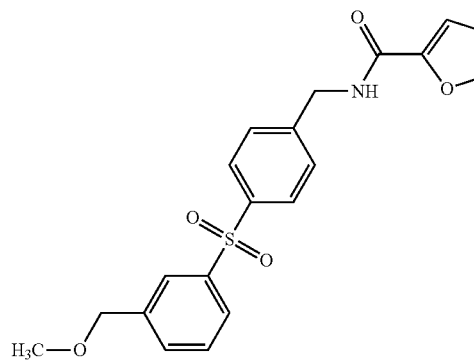
N-[(4-{[3-(methoxymethyl)benzene]sulfonyl}phenyl)methyl]furo[2,3-c]pyridine-2-carboxamide
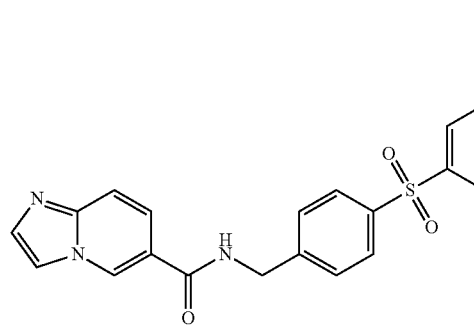
N-{[4-(5-methoxypyridine-3-sulfonyl)phenyl]methyl}imidazo[1,2-a]pyridine-6-carboxamide TABLE 2-continued

| | |
|---|---|
| 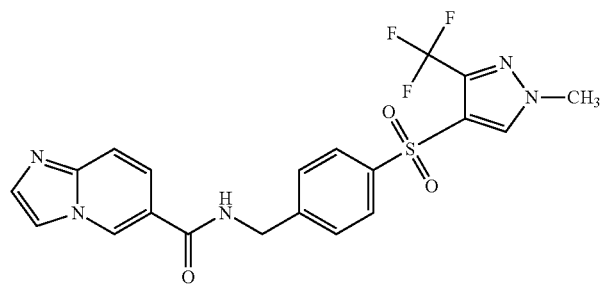 [SMILES: Cn1cc(S(=O)(=O)c2ccc(CNC(=O)c3ccc4nccn4c3)cc2)c(C(F)(F)F)n1] | N-({4-[1-methyl-3-(trifluoromethyl)-1H-pyrazole-4-sulfonyl]phenyl}methyl)imidazo[1,2-a]pyridine-6-carboxamide |
| 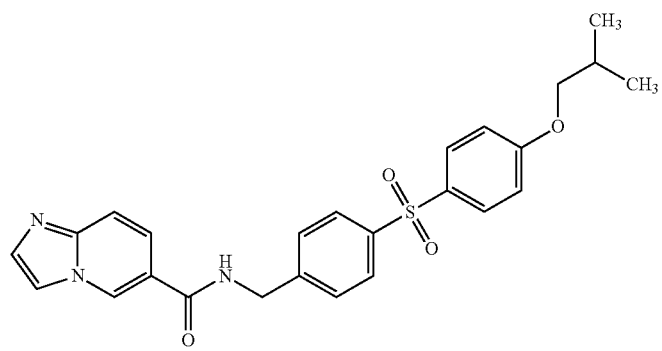 | N-[(4-{[4-(2-methylpropoxy)benzene]sulfonyl}phenyl)methyl]imidazo[1,2-a]pyridine-6-carboxamide |
| 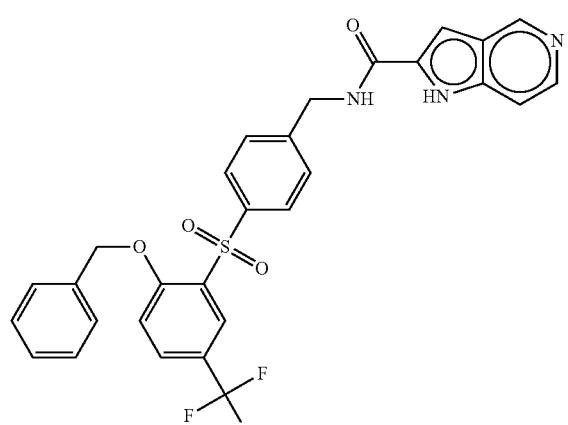 | N-[(4-{[2-(benzyloxy)-5-(trifluoromethyl)benzene]sulfonyl}phenyl)methyl]-1H-pyrrolo[3,2-c]pyridine-2-carboxamide |
| 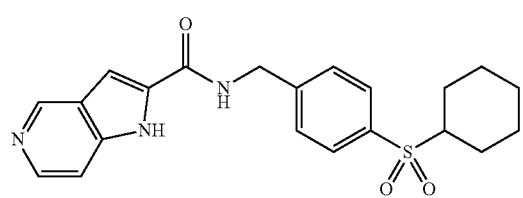 [SMILES: O=C(NCc1ccc(S(=O)(=O)C2CCCCC2)cc1)c1cc2cnccc2[nH]1] | N-{[4-(cyclohexanesulfonyl)phenyl]methyl}-1H-pyrrolo[3,2-c]pyridine-2-carboxamide |

TABLE 2-continued
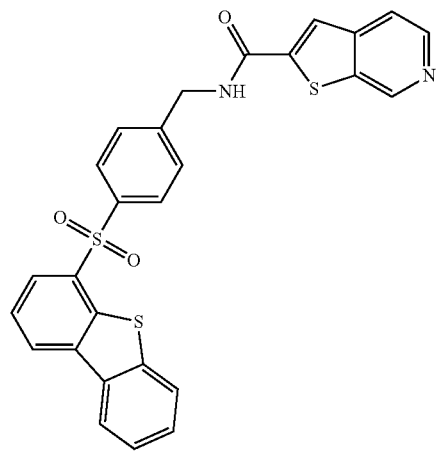
N-[(4-{8-thiatricyclo[7.4.0.0²,□]trideca-1(13),2,4,6,9,11-hexaene-6-sulfonyl}phenyl)methyl]thieno[2,3-c]pyridine-2-carboxamide
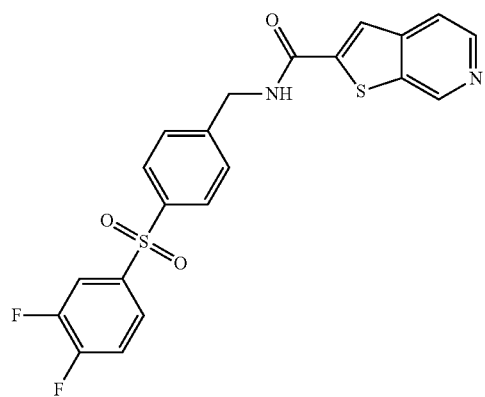
N-({4-[(3,4-difluorobenzene)sulfonyl]phenyl}methyl)thieno[2,3-c]pyridine-2-carboxamide
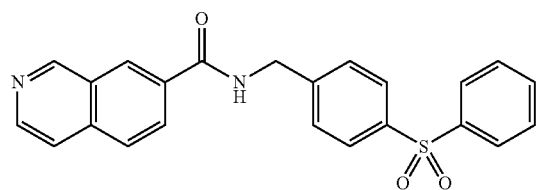 [SMILES: O=C(NCc1ccc(S(=O)(=O)c2ccccc2)cc1)c1ccc2ccncc2c1]
N-{[4-(benzenesulfonyl)phenyl]methyl}isoquinoline-7-carboxamide
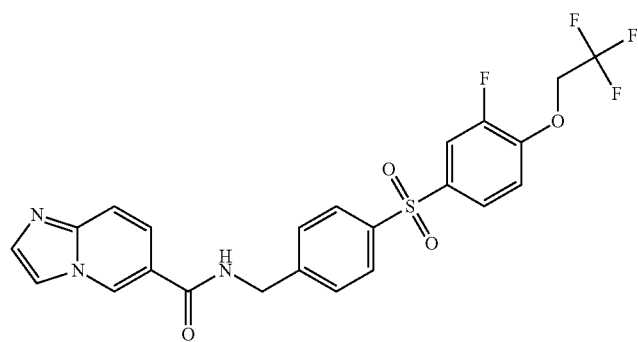 [SMILES: O=C(NCc1ccc(S(=O)(=O)c2ccc(OCC(F)(F)F)c(F)c2)cc1)c1ccc2nccn2c1]
N-[(4-{[3-fluoro-4-(2,2,2-trifluoroethoxy)benzene]sulfonyl}phenyl)methyl]imidazo[1,2-a]pyridine-6-carboxamide

| | |
|---|---|
| 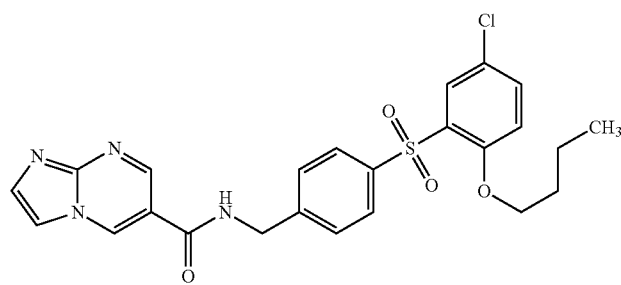 [SMILES: CCCCOc1ccc(Cl)cc1S(=O)(=O)c1ccc(CNC(=O)c2cnc3nccn3c2)cc1] | N-({4-[(2-butoxy-5-chlorobenzene)sulfonyl]phenyl}methyl)imidazo[1,2-a]pyrimidine-6-carboxamide |
| 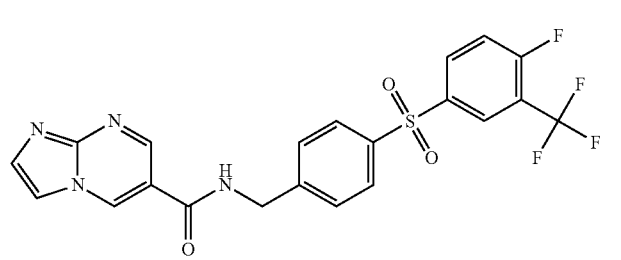 [SMILES: O=C(NCc1ccc(S(=O)(=O)c2ccc(F)c(C(F)(F)F)c2)cc1)c1cnc2nccn2c1] | N-[(4-{[4-fluoro-3-(trifluoromethyl)benzene]sulfonyl}phenyl)methyl]imidazo[1,2-a]pyrimidine-6-carboxamide |
| 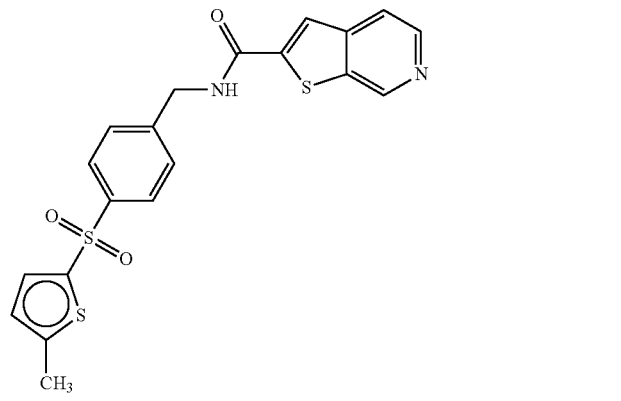 | N-{[4-(5-methylthiophene-2-sulfonyl)phenyl]methyl}thieno[2,3-c]pyridine-2-carboxamide |
| 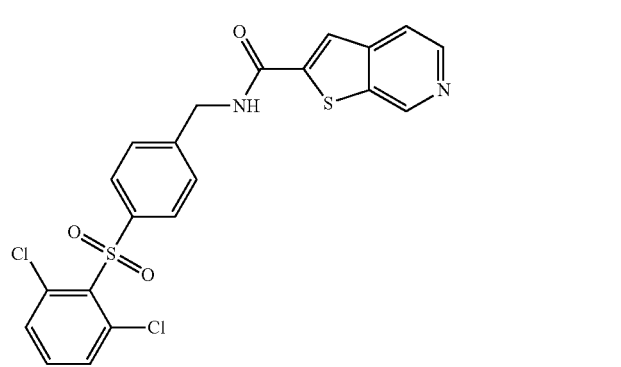 [SMILES: O=C(NCc1ccc(S(=O)(=O)c2c(Cl)cccc2Cl)cc1)c1cc2ccncc2s1] | N-({4-[(2,6-dichlorobenzene)sulfonyl]phenyl}methyl)thieno[2,3-c]pyridine-2-carboxamide |

TABLE 2-continued
| | |
|---|---|
| 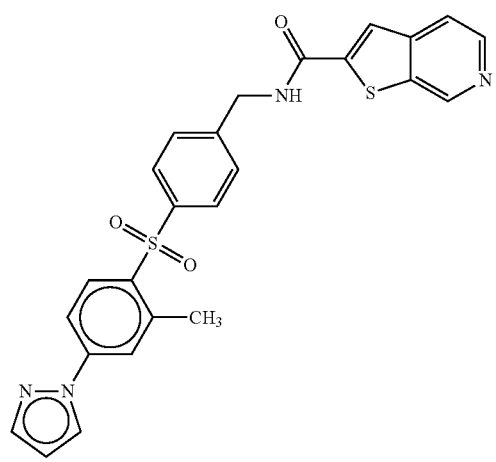 | N-[(4-{[2-methyl-4-(1H-pyrazol-1-yl)benzene]sulfonyl}phenyl)methyl]furo[2,3-c]pyridine-2-carboxamide |
| 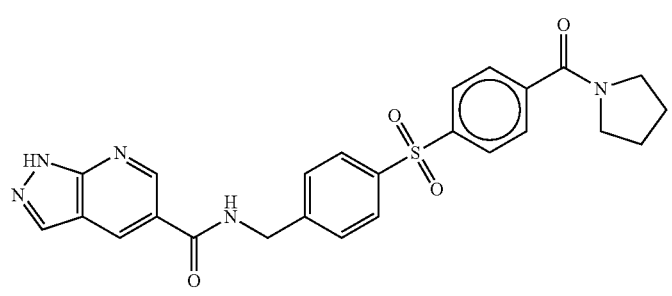 | N-{[4-({4-[(pyrrolidin-1-yl)carbonyl]benzene}sulfonyl)phenyl]methyl}-1H-pyrazolo[3,4-b]pyridine-5-carboxamide |
| 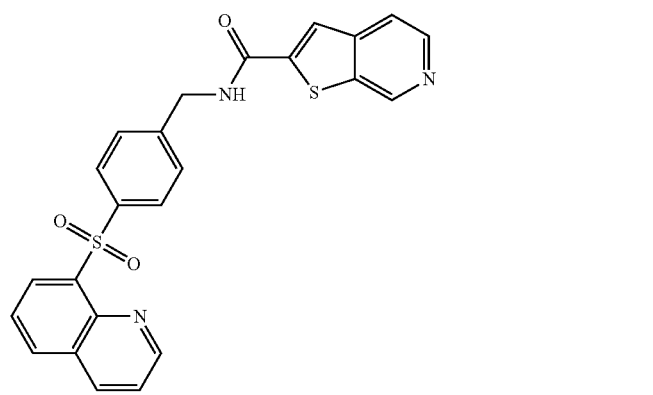 [SMILES: O=C(NCc1ccc(S(=O)(=O)c2cccc3cccnc23)cc1)c1cc2ccncc2s1] | N-{[4-(quinoline-8-sulfonyl)phenyl]methyl}thieno[2,3-c]pyridine-2-carboxamide |
| 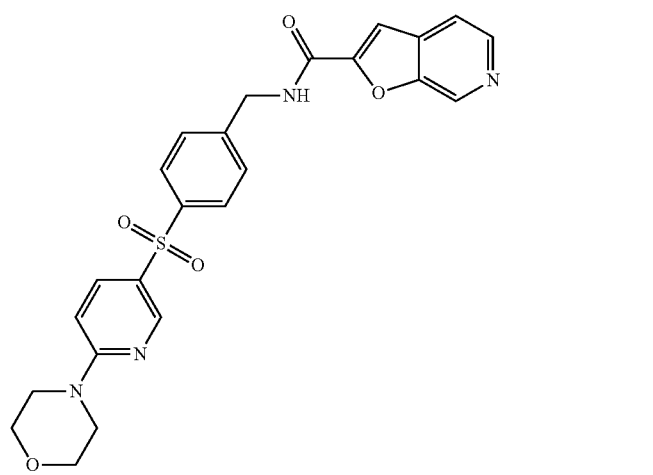 | N-({4-[6-(morpholin-4-yl)pyridine-3-sulfonyl]phenyl}methyl)furo[2,3-c]pyridine-2-carboxamide |

TABLE 2-continued
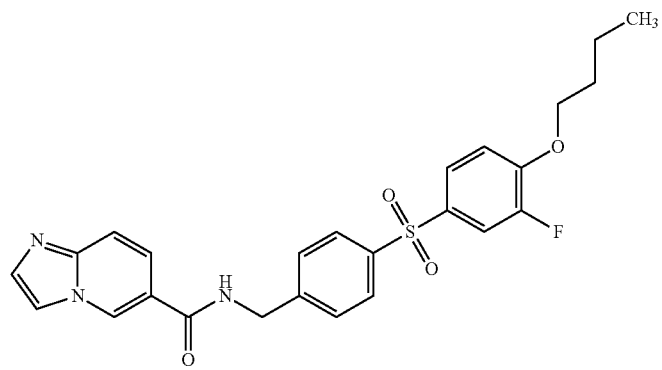 [SMILES: CCCCOc1ccc(S(=O)(=O)c2ccc(CNC(=O)c3ccc4nccn4c3)cc2)cc1F]
N-({4-[(4-butoxy-3-fluorobenzene)sulfonyl]phenyl}methyl)imidazo[1,2-a]pyridine-6-carboxamide
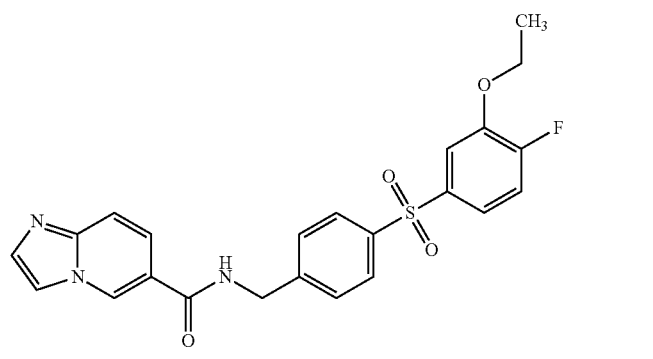 [SMILES: CCOc1cc(S(=O)(=O)c2ccc(CNC(=O)c3ccc4nccn4c3)cc2)ccc1F]
N-({4-[(3-ethoxy-4-fluorobenzene)sulfonyl]phenyl}methyl)imidazao[1,2-a]pyridine-6-carboxamide
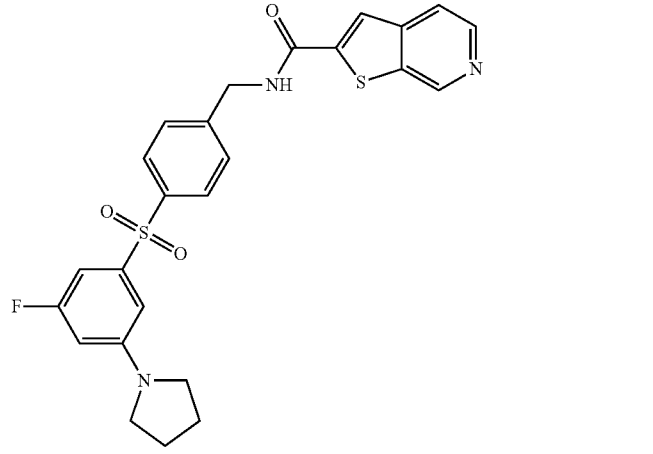 [SMILES: O=C(NCc1ccc(S(=O)(=O)c2cc(F)cc(N3CCCC3)c2)cc1)c1cc2ccncc2s1]
N-[(4-{[3-fluoro-5-(pyrrolidin-1-yl)benzene]sulfonyl}phenyl)methyl]thieno[2,3-c]pyridine-2-carboxamide
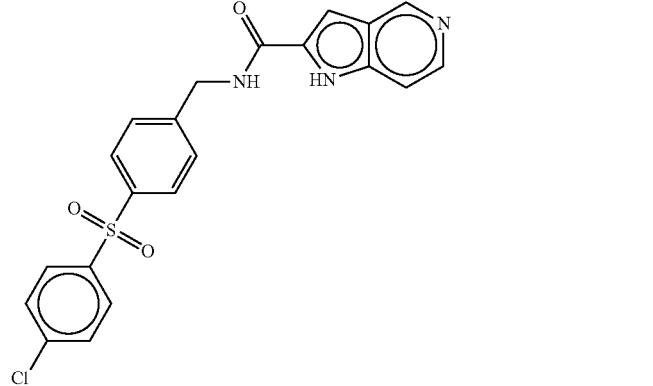
N-({4-[(4-chlorobenzene)sulfonyl]phenyl}methyl)-1H-pyrrolo[3,2-c]pyridine-2-carboxamide TABLE 2-continued
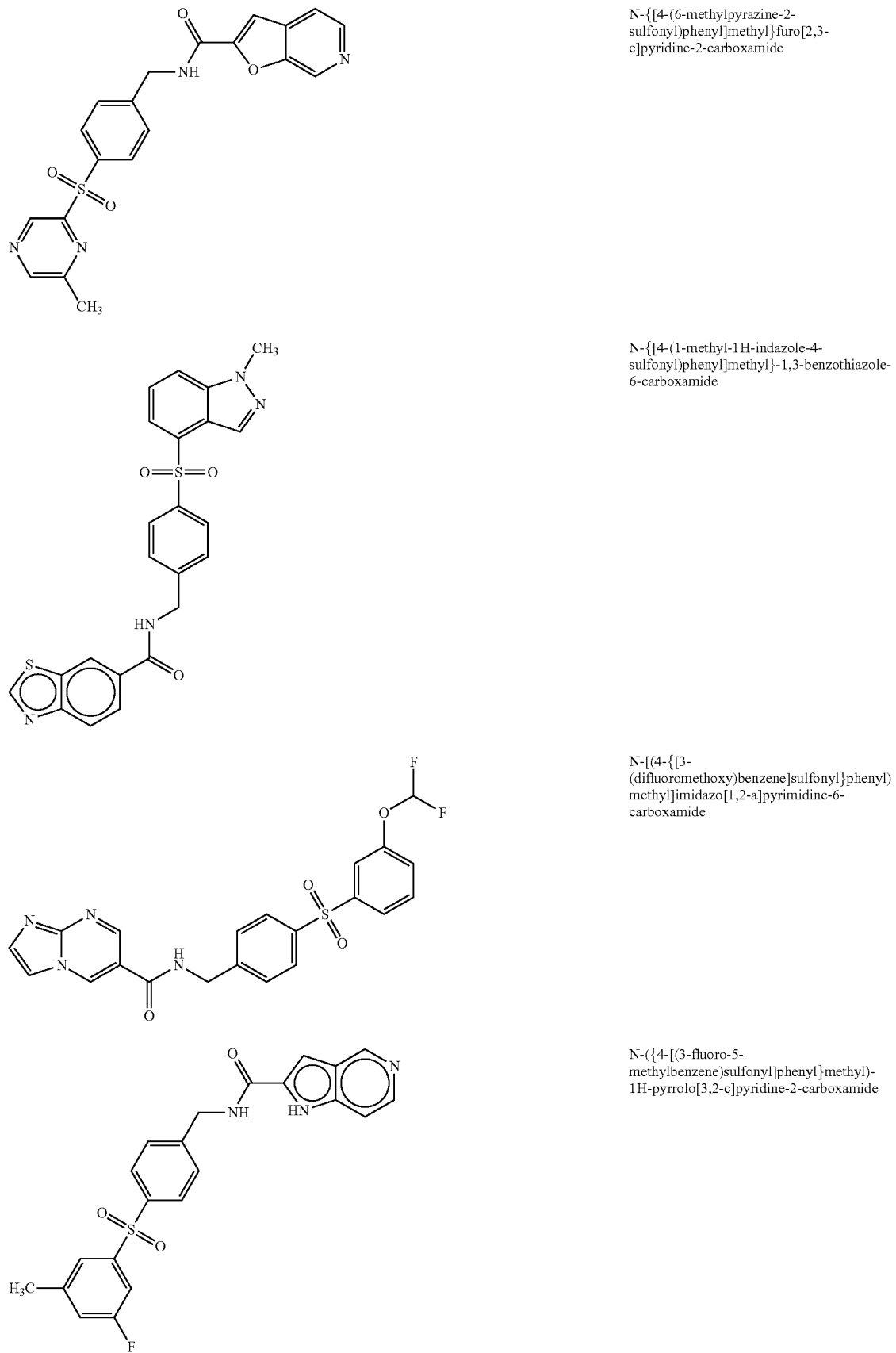
N-{[4-(6-methylpyrazine-2-sulfonyl)phenyl]methyl}furo[2,3-c]pyridine-2-carboxamide
N-{[4-(1-methyl-1H-indazole-4-sulfonyl)phenyl]methyl}-1,3-benzothiazole-6-carboxamide
N-[(4-{[3-(difluoromethoxy)benzene]sulfonyl}phenyl)methyl]imidazo[1,2-a]pyrimidine-6-carboxamide
N-({4-[(3-fluoro-5-methylbenzene)sulfonyl]phenyl}methyl)-1H-pyrrolo[3,2-c]pyridine-2-carboxamide

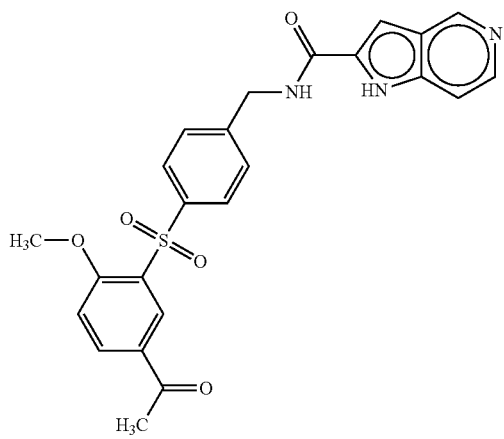
N-({4-[(5-acetyl-2-methoxybenzene)sulfonyl]phenyl}methyl)-1H-pyrrolo[3,2-c]pyridine-2-carboxamide
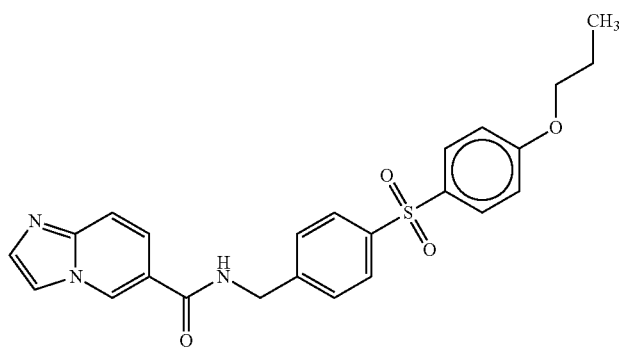
N-({4-[(4-propoxybenzene)sulfonyl]phenyl}methyl)imidazo[1,2-a]pyridine-6-carboxamide
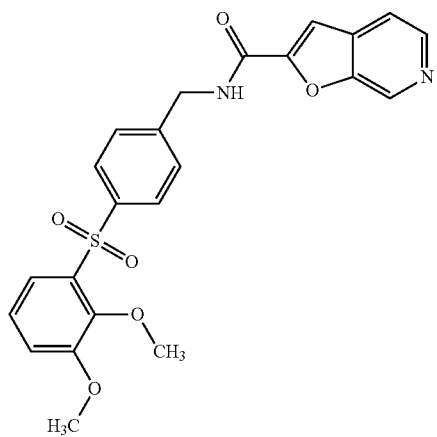 [SMILES: COc1cccc(S(=O)(=O)c2ccc(CNC(=O)c3cc4ccncc4o3)cc2)c1OC]
N-({4-[(2,3-dimethoxybenzene)sulfonyl]phenyl}methyl)furo[2,3-c]pyridine-2-carboxamide
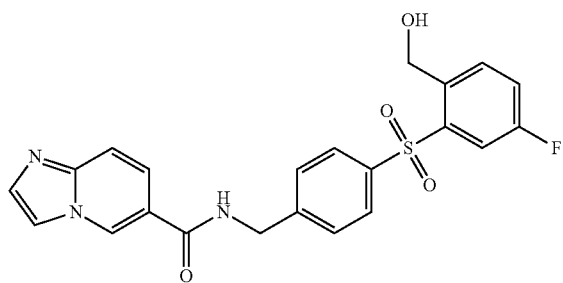 [SMILES: O=C(NCc1ccc(S(=O)(=O)c2cc(F)ccc2CO)cc1)c1ccc2nccn2c1]
N-[(4-{[5-fluoro-2-(hydroxymethyl)benzene]sulfonyl}phenyl)methyl]imidazo[1,2-a]pyridine-6-carboxamide TABLE 2-continued
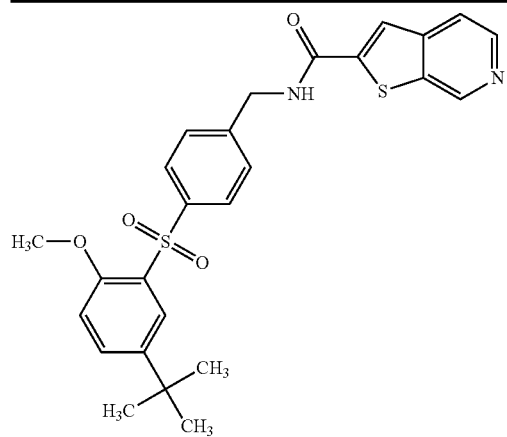
N-({4-[(5-tert-butyl-2-methoxybenzene)sulfonyl]phenyl}methyl)thieno[2,3-c]pyridine-2-carboxamide
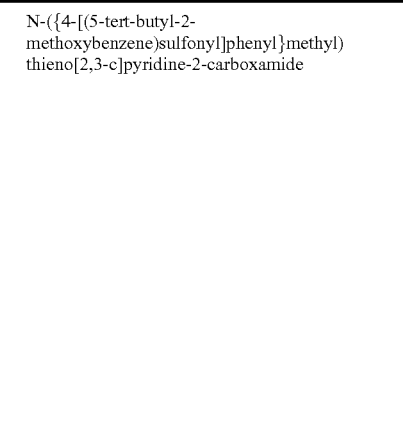
N-[(4-{[3-(pyrrolidin-1-yl)benzene]sulfonyl}phenyl)methyl]-1H-pyrrolo[3,2-c]pyridine-2-carboxamide
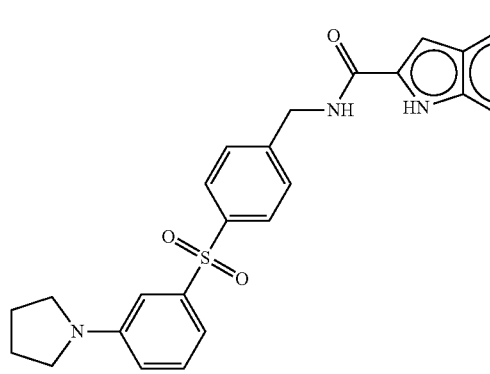
N-[(4-{[3-fluoro-4-(1H-pyrazol-1-yl)benzene]sulfonyl}phenyl)methyl]-1H-pyrazolo[3,4-b]pyridine-5-carboxamide
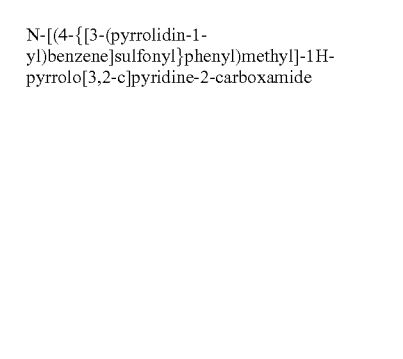
N-({4-[(2-chloro-4-fluorobenzene)sulfonyl]phenyl}methyl)furo[2,3-c]pyridine-2-carboxamide TABLE 2-continued

| Structure | Name |
|---|---|
| 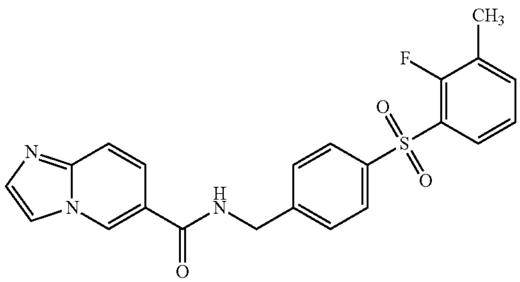 [SMILES: Cc1cccc(S(=O)(=O)c2ccc(CNC(=O)c3ccc4nccn4c3)cc2)c1F] | N-({4-[(2-fluoro-3-methylbenzene)sulfonyl]phenyl}methyl)imidazo[1,2-a]pyridine-6-carboxamide |
| 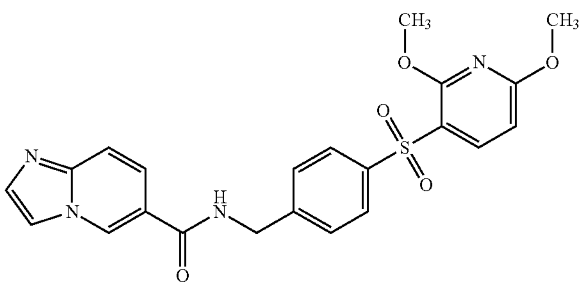 [SMILES: COc1ccc(S(=O)(=O)c2ccc(CNC(=O)c3ccc4nccn4c3)cc2)c(OC)n1] | N-{[4-(2,6-dimethoxypyridine-3-sulfonyl)phenyl]methyl}imidazo[1,2-a]pyridine-6-carboxamide |
| 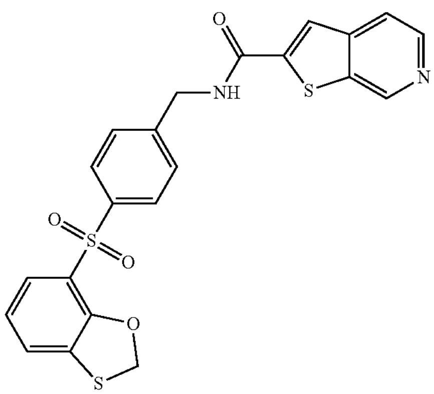 [SMILES: O=C(NCc1ccc(S(=O)(=O)c2cccc3c2OCS3)cc1)c1cc2ccncc2s1] | N-{[4-(2H-1,3-benzodioxole-4-sulfonyl)phenyl]methyl}furo[2,3-c]pyridine-2-carboxamide |
| 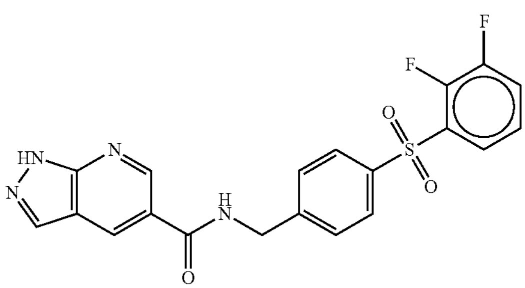 | N-({4-[(2,3-difluorobenzene)sulfonyl]phenyl}methyl)-1H-pyrazolo[3,4-b]pyridine-5-carboxamide |
| | N-[(4-{[3-(2-methylpropoxy)benzene]sulfonyl}phenyl)methyl]imidazo[1,2-a]pyrimidine-6-carboxamide |

TABLE 2-continued
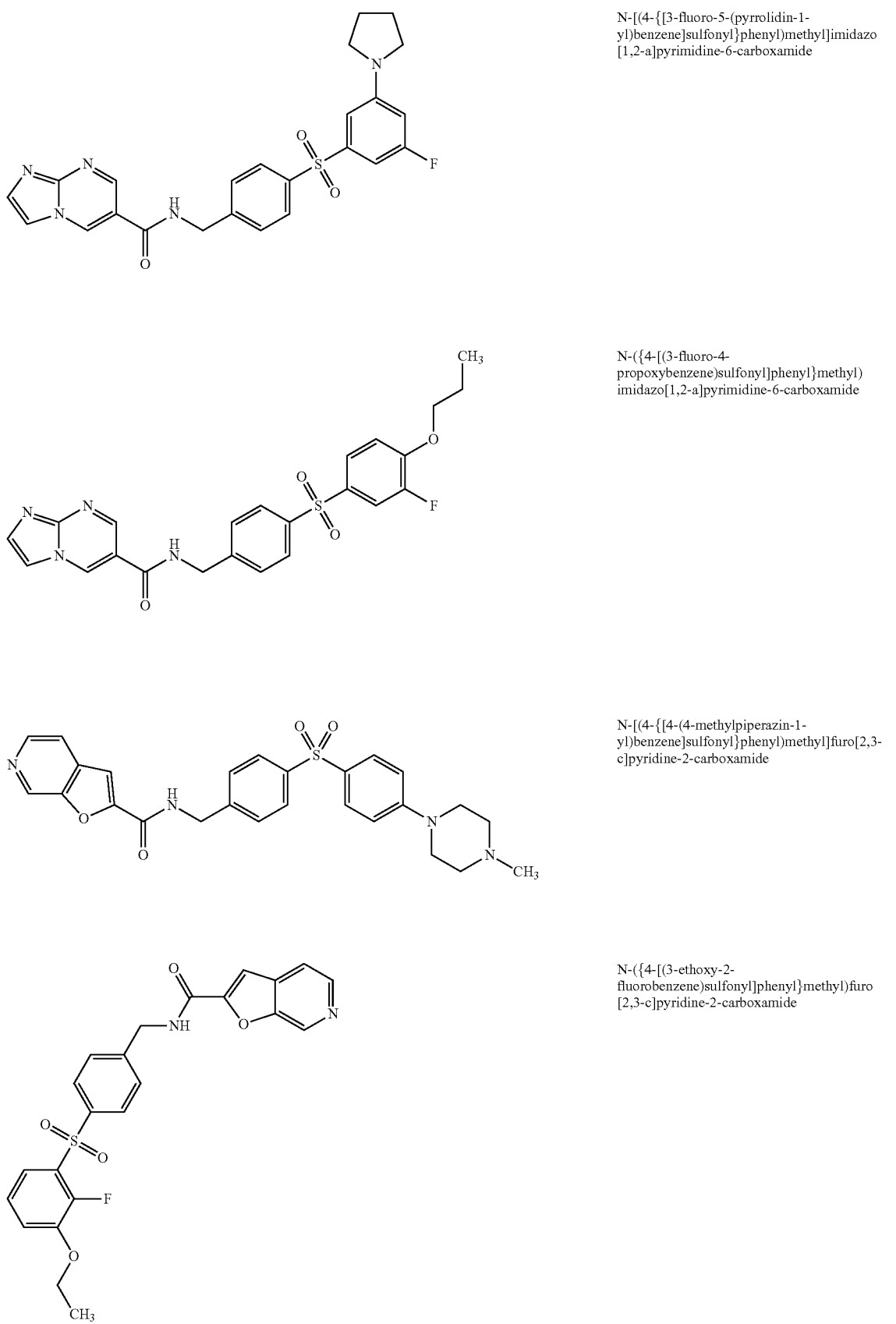
N-[(4-{[3-fluoro-5-(pyrrolidin-1-yl)benzene]sulfonyl}phenyl)methyl]imidazo[1,2-a]pyrimidine-6-carboxamide
N-({4-[(3-fluoro-4-propoxybenzene)sulfonyl]phenyl}methyl)imidazo[1,2-a]pyrimidine-6-carboxamide
N-[(4-{[4-(4-methylpiperazin-1-yl)benzene]sulfonyl}phenyl)methyl]furo[2,3-c]pyridine-2-carboxamide
N-({4-[(3-ethoxy-2-fluorobenzene)sulfonyl]phenyl}methyl)furo[2,3-c]pyridine-2-carboxamide TABLE 2-continued

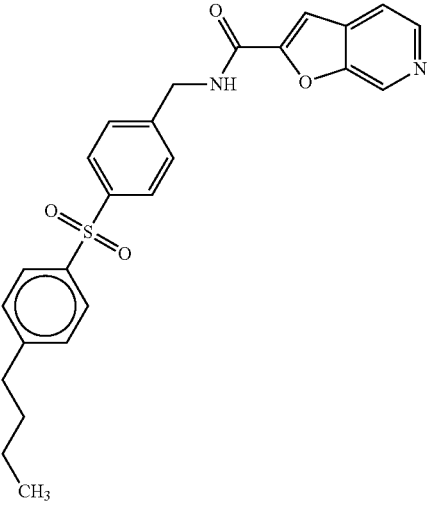
N-({4-[(4-butylbenzene)sulfonyl]phenyl}methyl)thieno[2,3-c]pyridine-2-carboxamide

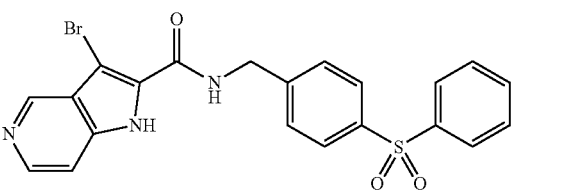 [SMILES: O=C(NCc1ccc(S(=O)(=O)c2ccccc2)cc1)c1[nH]c2ccncc2c1Br]
N-{[4-(benzenesulfonyl)phenyl]methyl}-3-bromo-1H-pyrrolo[3,2-c]pyridine-2-carboxamide

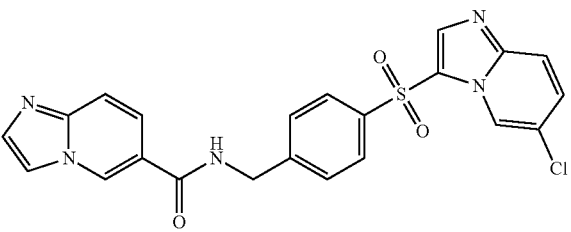 [SMILES: O=C(NCc1ccc(S(=O)(=O)c2cnc3ccc(Cl)cn23)cc1)c1ccc2nccn2c1]
N-[(4-{6-chloroimidazo[1,2-a]pyridine-3-sulfonyl}phenyl)methyl]imidazo[1,2-a]pyridine-6-carboxamide

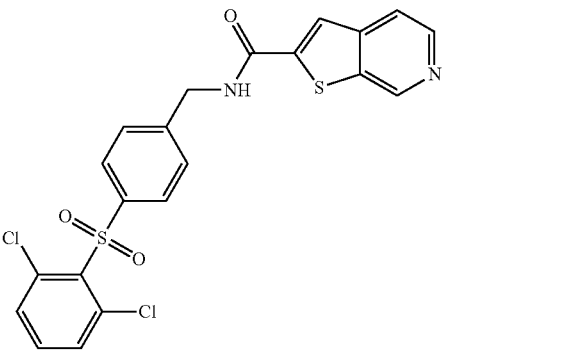 [SMILES: O=C(NCc1ccc(S(=O)(=O)c2c(Cl)cccc2Cl)cc1)c1cc2ccncc2s1]
N-({4-[(2,6-dichlorobenzene)sulfonyl]phenyl}methyl)furo[2,3-c]pyridine-2-carboxamide

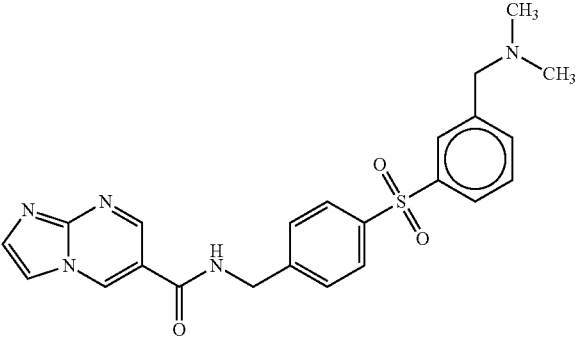
N-{[4-({3-[(dimethylamino)methyl]benzene}sulfonyl)phenyl]methyl}imidazo[1,2-a]pyrimidine-6-carboxamide TABLE 2-continued
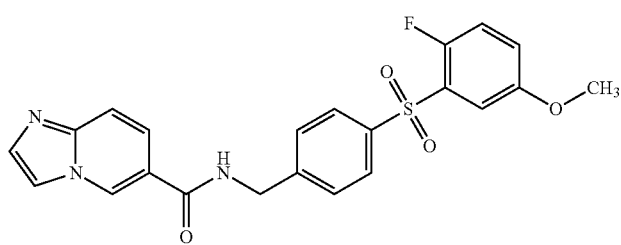 [SMILES: COc1ccc(F)c(S(=O)(=O)c2ccc(CNC(=O)c3ccc4nccn4c3)cc2)c1]
N-({4-[(2-fluoro-5-methoxybenzene)sulfonyl]phenyl}methyl)imidazo[1,2-a]pyridine-6-carboxamide
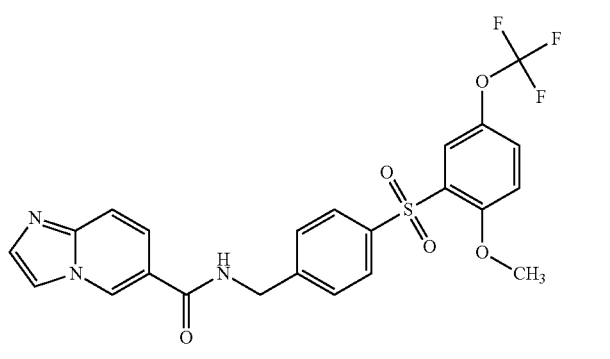 [SMILES: COc1ccc(OC(F)(F)F)cc1S(=O)(=O)c1ccc(CNC(=O)c2ccc3nccn3c2)cc1]
N-[(4-{[2-methoxy-5-(trifluoromethoxy)benzene]sulfonyl}phenyl)methyl]imidazo[1,2-a]pyridine-6-carboxamide
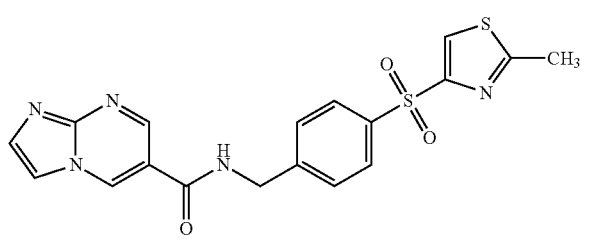 [SMILES: Cc1nc(S(=O)(=O)c2ccc(CNC(=O)c3cnc4nccn4c3)cc2)cs1]
N-{[4-(2-methyl-1,3-thiazole-4-sulfonyl)phenyl]methyl}imidazo[1,2-a]pyrimidine-6-carboxamide
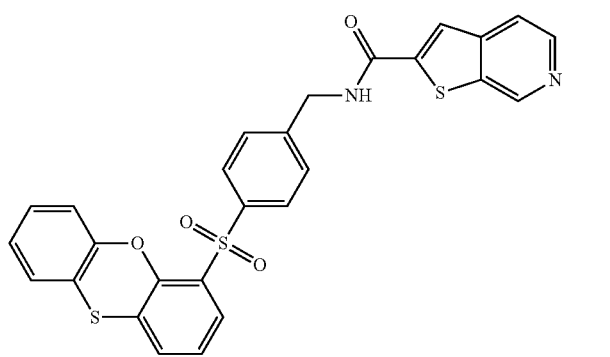 [SMILES: O=C(NCc1ccc(S(=O)(=O)c2cccc3c2Oc2ccccc2S3)cc1)c1cc2ccncc2s1]
N-{[4-(phenoxathiine-4-sulfonyl)phenyl]methyl}thieno[2,3-c]pyridine-2-carboxamide TABLE 2-continued
| | |
|---|---|
| 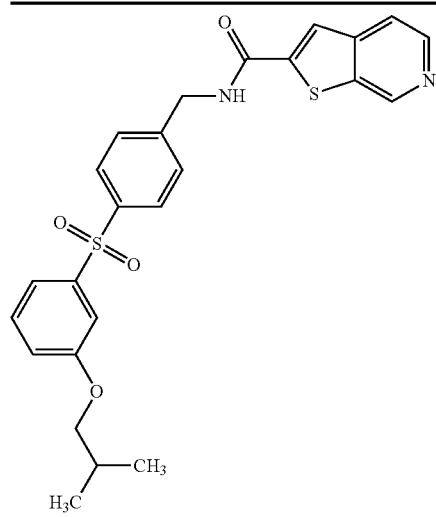 | N-[(4-{[3-(2-methylpropoxy)benzene]sulfonyl}phenyl)methyl]furo[2,3-c]pyridine-2-carboxamide |
| 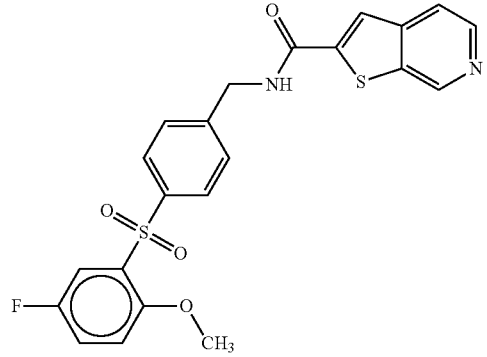 | N-({4-[(5-fluoro-2-methoxybenzene)sulfonyl]phenyl}methyl)thieno[2,3-c]pyridine-2-carboxamide |
| 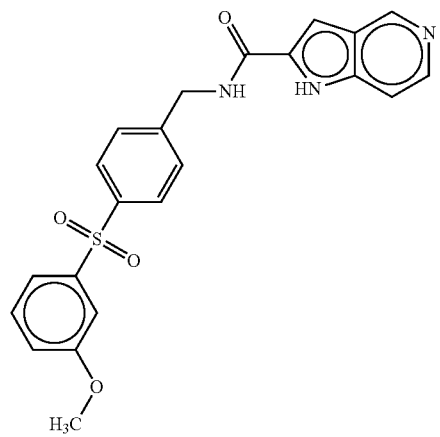 | N-({4-[(3-methoxybenzene)sulfonyl]phenyl}methyl)-1H-pyrrolo[3,2-c]pyridine-2-carboxamide |

TABLE 2-continued
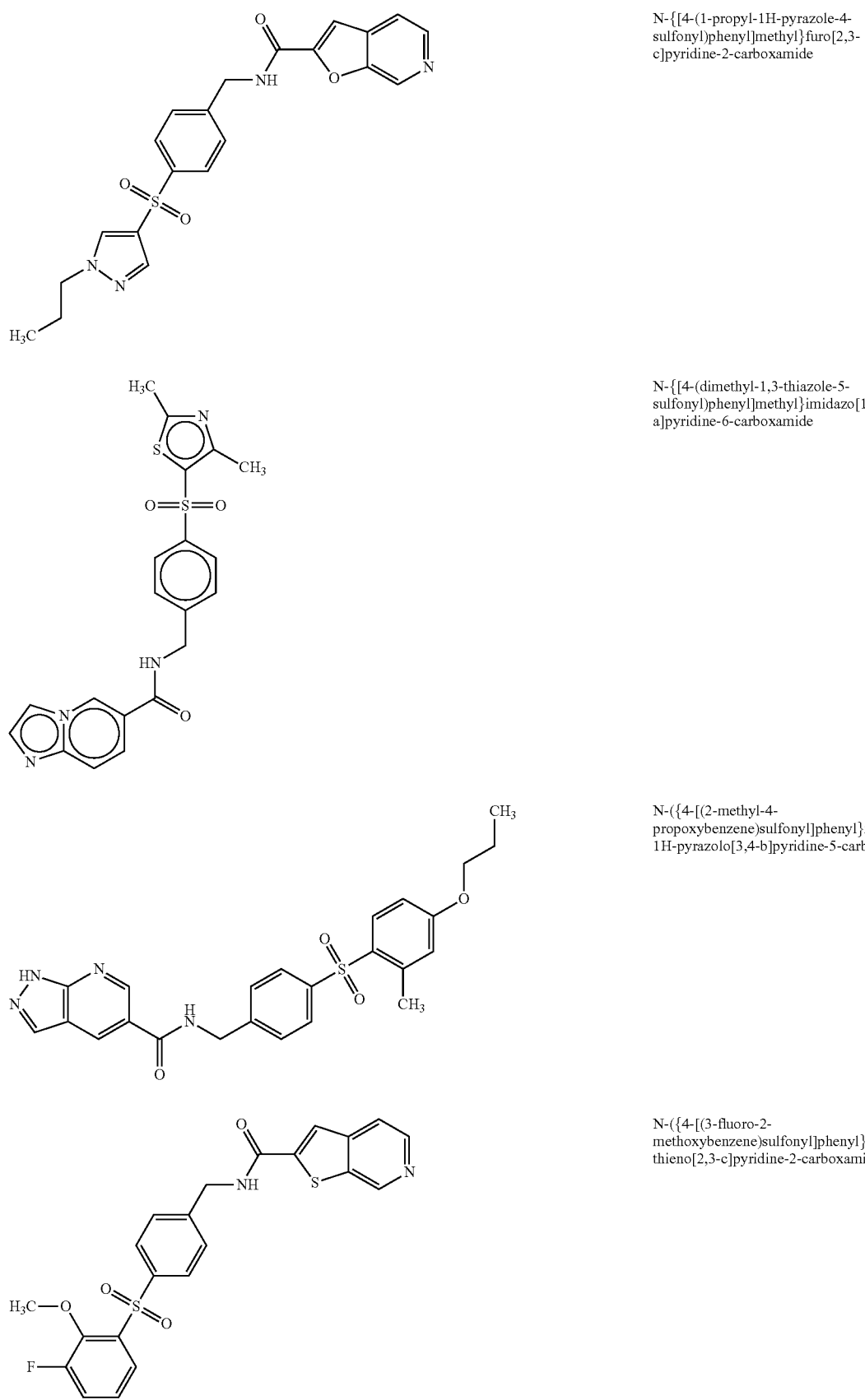
N-{[4-(1-propyl-1H-pyrazole-4-sulfonyl)phenyl]methyl}furo[2,3-c]pyridine-2-carboxamide
N-{[4-(dimethyl-1,3-thiazole-5-sulfonyl)phenyl]methyl}imidazo[1,2-a]pyridine-6-carboxamide
N-({4-[(2-methyl-4-propoxybenzene)sulfonyl]phenyl}methyl)-1H-pyrazolo[3,4-b]pyridine-5-carboxamide
N-({4-[(3-fluoro-2-methoxybenzene)sulfonyl]phenyl}methyl)thieno[2,3-c]pyridine-2-carboxamide TABLE 2-continued

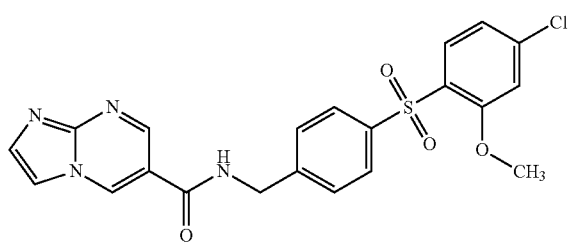

N-({4-[(4-chloro-2-methoxybenzene)sulfonyl]phenyl}methyl)imidazo[1,2-a]pyrimidine-6-carboxamide

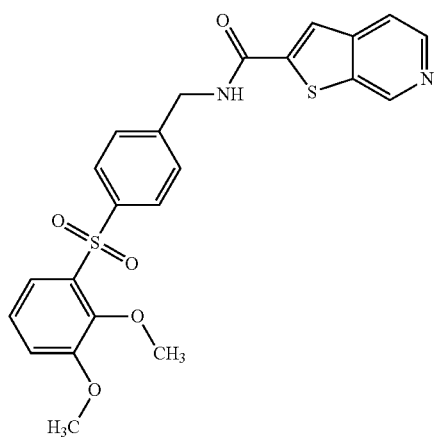

N-({4-[(2,3-dimethoxybenzene)sulfonyl]phenyl}methyl)thieno[2,3-c]pyridine-2-carboxamide

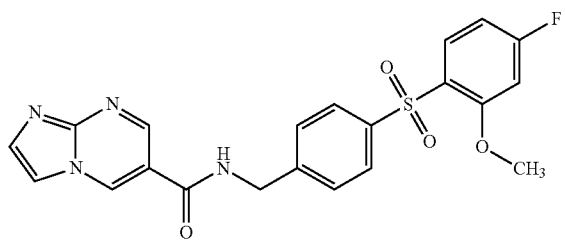 [SMILES: COc1cc(F)ccc1S(=O)(=O)c1ccc(CNC(=O)c2cnc3nccn3c2)cc1]

N-({4-[(4-fluoro-2-methoxybenzene)sulfonyl]phenyl}methyl)imidazo[1,2-a]pyrimidine-6-carboxamide

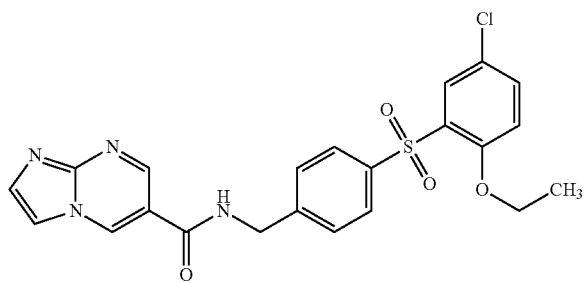 [SMILES: CCOc1ccc(Cl)cc1S(=O)(=O)c1ccc(CNC(=O)c2cnc3nccn3c2)cc1]

N-({4-[(5-chloro-2-ethoxybenzene)sulfonyl]phenyl}methyl)imidazo[1,2-a]pyrimidine-6-carboxamide

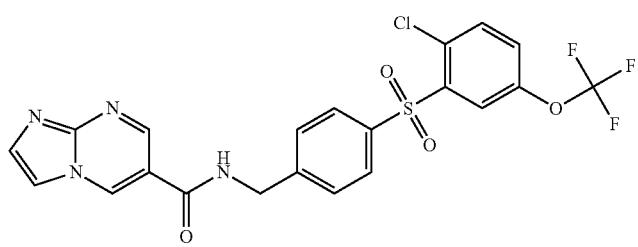 [SMILES: O=C(NCc1ccc(S(=O)(=O)c2cc(OC(F)(F)F)ccc2Cl)cc1)c1cnc2nccn2c1]

N-[(4-{[2-chloro-5-(trifluoromethoxy)benzene]sulfonyl}phenyl)methyl]imidazo[1,2-a]pyrimidine-6-carboxamide TABLE 2-continued
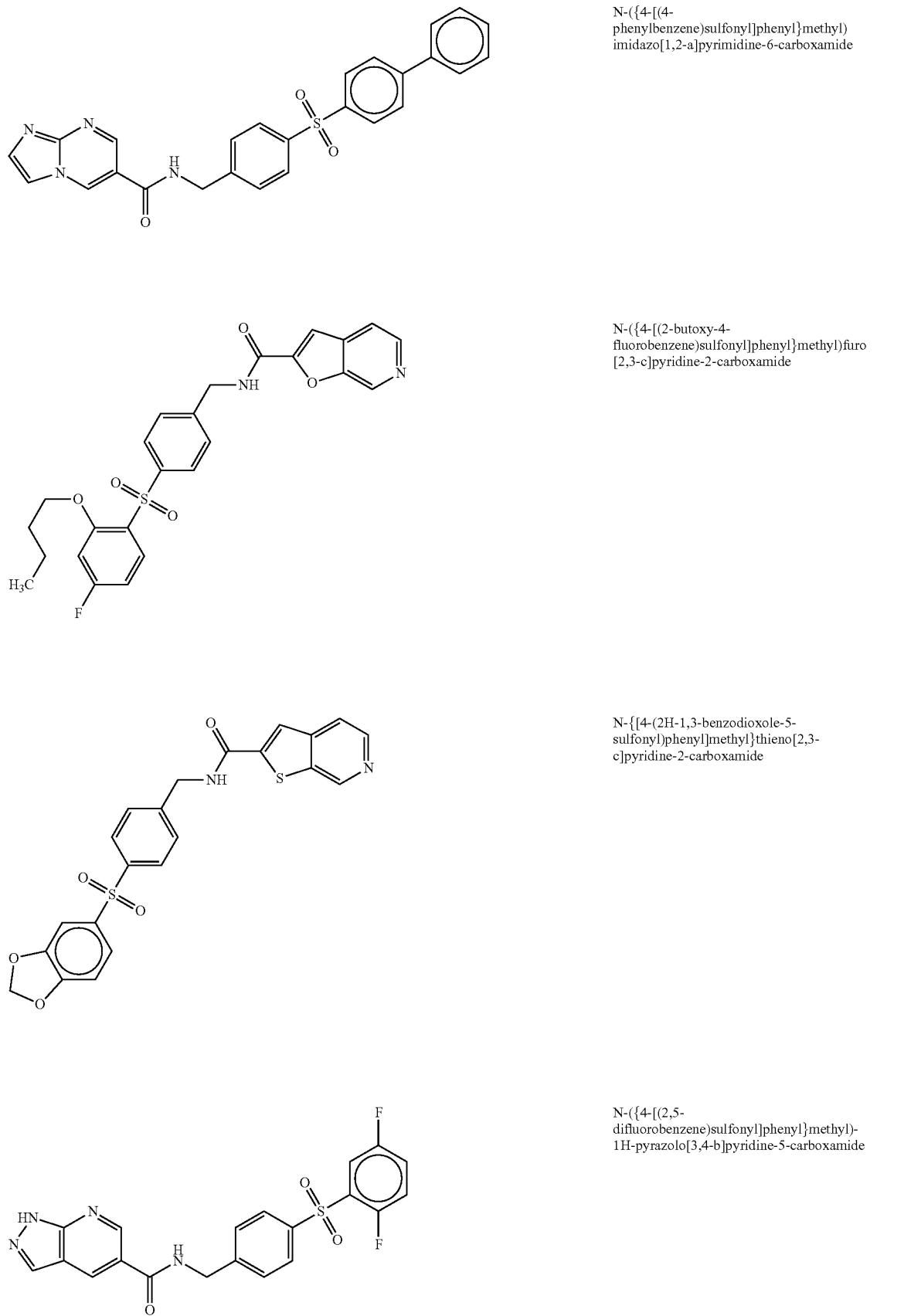
N-({4-[(4-phenylbenzene)sulfonyl]phenyl}methyl)imidazo[1,2-a]pyrimidine-6-carboxamide
N-({4-[(2-butoxy-4-fluorobenzene)sulfonyl]phenyl}methyl)furo[2,3-c]pyridine-2-carboxamide
N-{[4-(2H-1,3-benzodioxole-5-sulfonyl)phenyl]methyl}thieno[2,3-c]pyridine-2-carboxamide
N-({4-[(2,5-difluorobenzene)sulfonyl]phenyl}methyl)-1H-pyrazolo[3,4-b]pyridine-5-carboxamide TABLE 2-continued
| | |
|---|---|
| 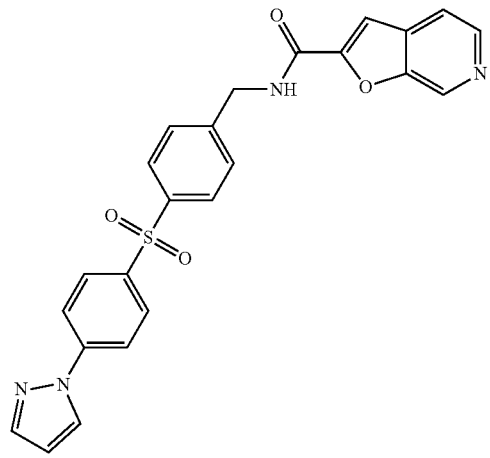 [SMILES: O=C(NCc1ccc(S(=O)(=O)c2ccc(-n3cccn3)cc2)cc1)c1cc2ccncc2o1] | N-[(4-{[4-(1H-pyrazol-1-yl)benzene]sulfonyl}phenyl)methyl]furo[2,3-c]pyridine-2-carboxamide |
| 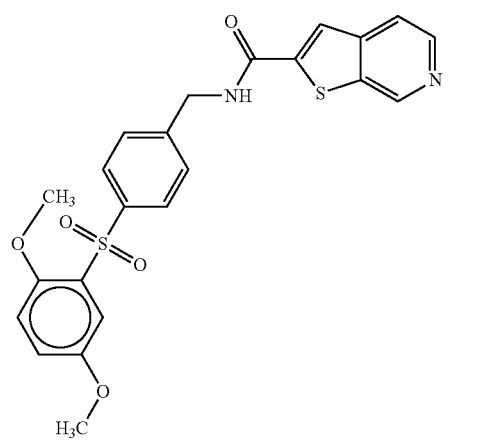 | N-({4-[(2,5-dimethoxybenzene)sulfonyl]phenyl}methyl)thieno[2,3-c]pyridine-2-carboxamide |
| 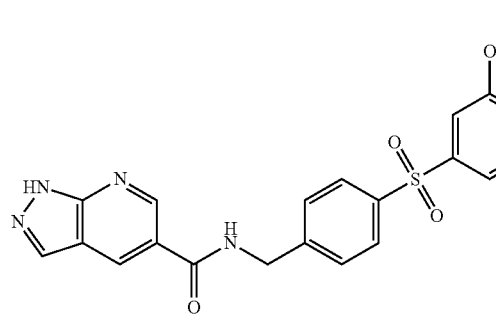 | N-{[4-(5-methoxypyridine-3-sulfonyl)phenyl]methyl}-1H-pyrazolo[3,4-b]pyridine-5-carboxamide |
| 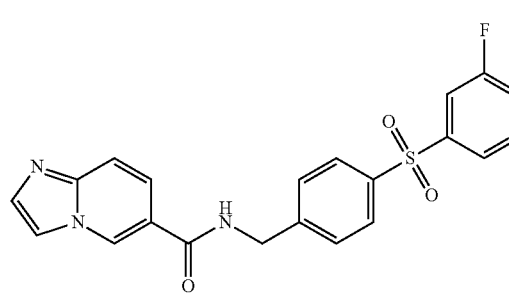 | N-{[4-(5-fluoropyridine-3-sulfonyl)phenyl]methyl}imidazo[1,2-a]pyridine-6-carboxamide |

TABLE 2-continued
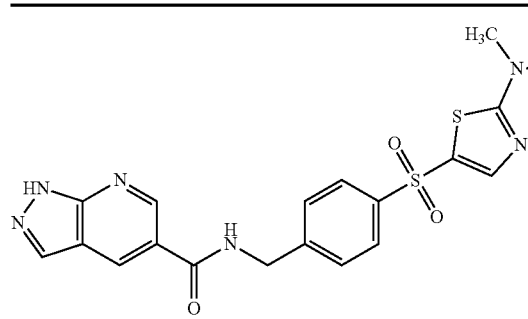
N-[(4-{2-[ethyl(methyl)amino]-1,3-thiazole-5-sulfonyl}phenyl)methyl]-1H-pyrazolo[3,4-b]pyridine-5-carboxamide
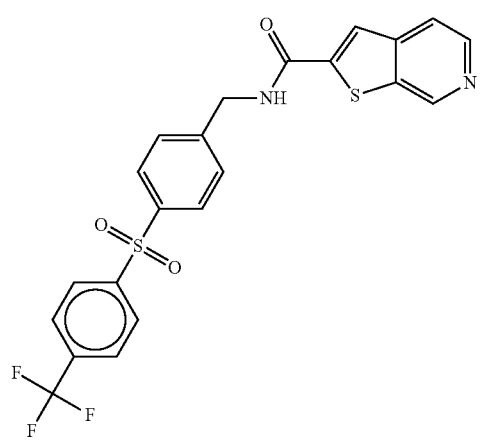
N-[(4-{[4-(trifluoromethyl)benzene]sulfonyl}phenyl)methyl]furo[2,3-c]pyridine-2-carboxamide
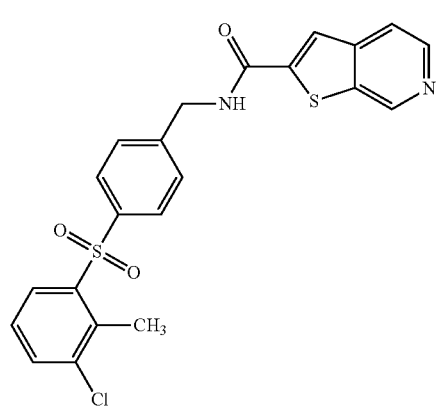
N-({4-[(3-chloro-2-methylbenzene)sulfonyl]phenyl}methyl)thieno[2,3-c]pyridine-2-carboxamide
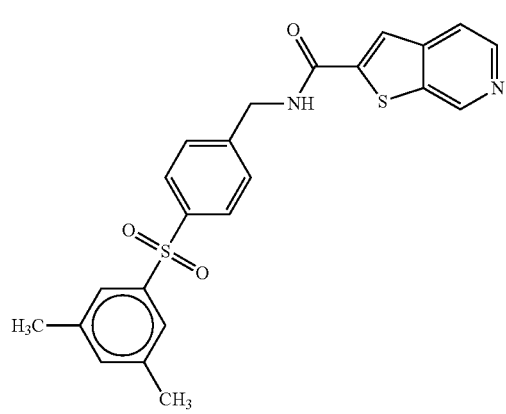
N-({4-[(3,5-dimethylbenzene)sulfonyl]phenyl}methyl)thieno[2,3-c]pyridine-2-carboxamide TABLE 2-continued
| | |
|---|---|
|  | N-[(4-{[4-(trifluoromethyl)benzene]sulfonyl}phenyl)methyl]-1H-pyrrolo[3,2-c]pyridine-2-carboxamide |
| 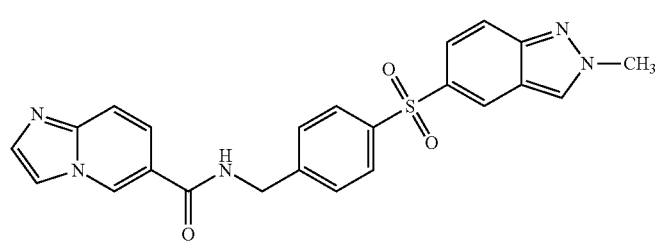 [SMILES: Cn1cc2cc(S(=O)(=O)c3ccc(CNC(=O)c4ccc5nccn5c4)cc3)ccc2n1] | N-{[4-(2-methyl-2H-indazole-5-sulfonyl)phenyl]methyl}midazo[1,2-a]pyridine-6-carboxamide |
| 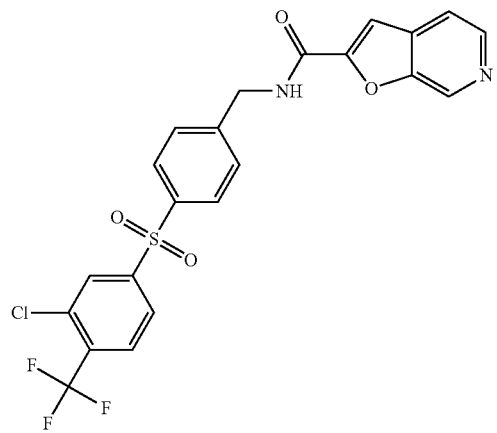 | N-[(4-{[3-chloro-4-(trifluoromethyl)benzene]sulfonyl}phenyl)methyl]furo[2,3-c]pyridine-2-carboxamide |
| 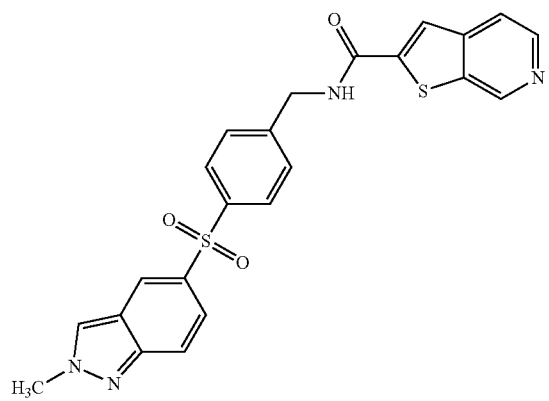 [SMILES: Cn1cc2cc(S(=O)(=O)c3ccc(CNC(=O)c4cc5ccncc5s4)cc3)ccc2n1] | N-{[4-(2-methyl-2H-indazole-5-sulfonyl)phenyl]methyl}thieno[2,3-c]pyridine-2-carboxamide |

TABLE 2-continued
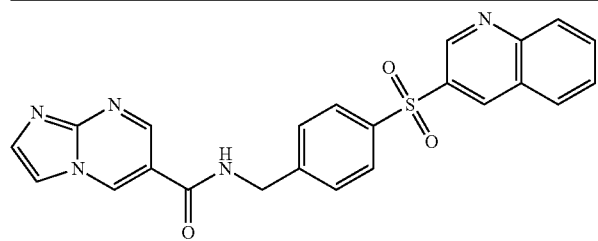
N-{[4-(quinoline-3-sulfonyl)phenyl]methyl}imidazo[1,2-a]pyrimidine-6-carboxamide
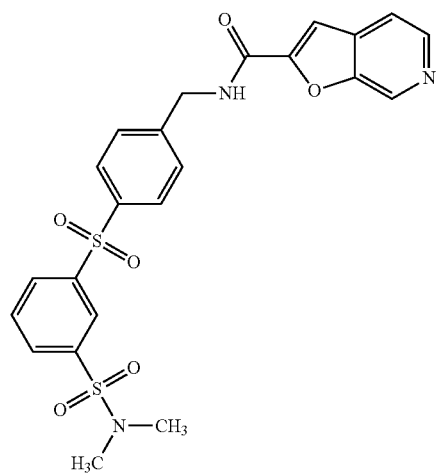 [SMILES: CN(C)S(=O)(=O)c1cccc(S(=O)(=O)c2ccc(CNC(=O)c3cc4ccncc4o3)cc2)c1]
N-[(4-{[3-(dimethylsulfamoyl)benzene]sulfonyl}phenyl)methyl]furo[2,3-c]pyridine-2-carboxamide
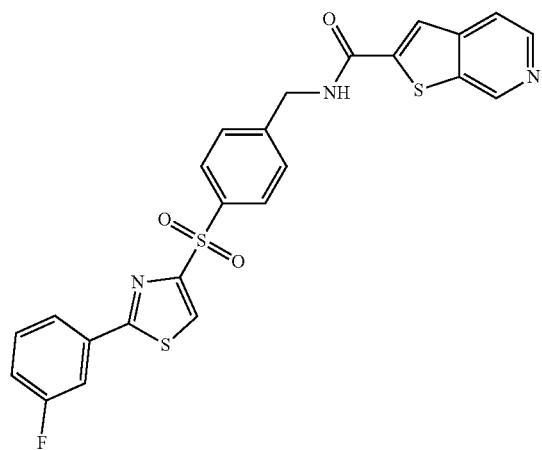 [SMILES: O=C(NCc1ccc(S(=O)(=O)c2csc(-c3cccc(F)c3)n2)cc1)c1cc2ccncc2s1]
N-({4-[2-(3-fluorophenyl)-1,3-thiazole-4-sulfonyl]phenyl}methyl)thieno[2,3-c]pyridine-2-carboxamide
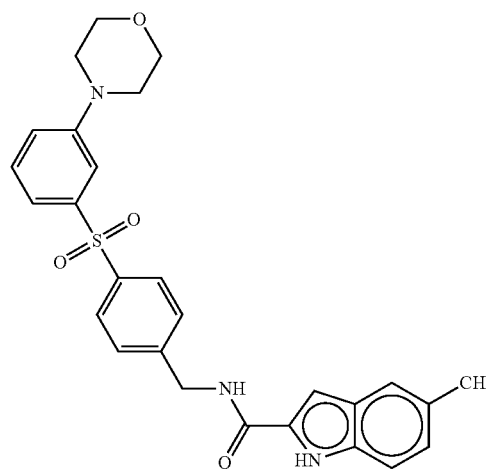
5-hydroxy-N-[(4-{[3-(morpholin-4-yl)benzene]sulfonyl}phenyl)methyl]-1H-indole-2-carboxamide TABLE 2-continued
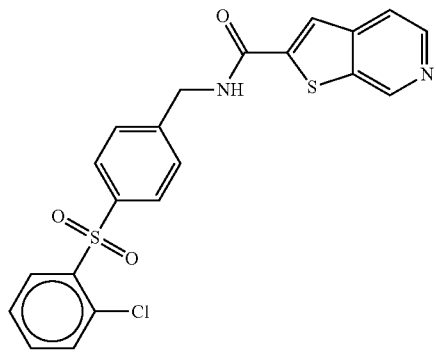
N-({4-[(2-chlorobenzene)sulfonyl]phenyl}methyl)thieno[2,3-c]pyridine-2-carboxamide
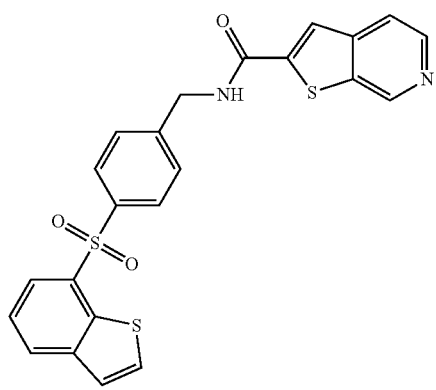
N-{[4-(1-benzothiophene-7-sulfonyl)phenyl]methyl}thieno[2,3-c]pyridine-2-carboxamide
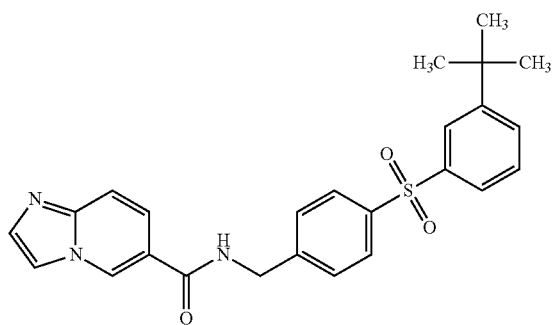
N-({4-[(3-tert-butylbenzene)sulfonyl]phenyl}methyl)imidazo[1,2-a]pyridine-6-carboxamide
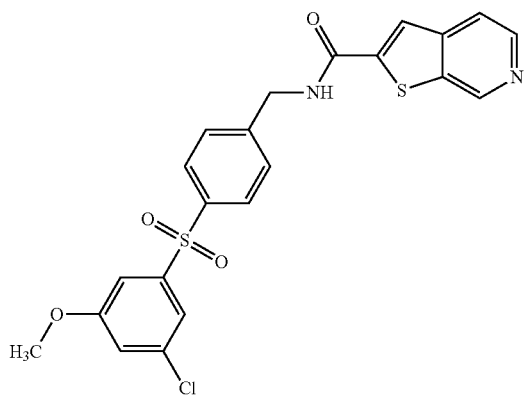 [SMILES: COc1cc(Cl)cc(S(=O)(=O)c2ccc(CNC(=O)c3cc4ccncc4s3)cc2)c1]
N-({4-[(3-chloro-5-methoxybenzene)sulfonyl]phenyl}methyl)thieno[2,3-c]pyridine-2-carboxamide TABLE 2-continued

| | |
|---|---|
| | N-[(4-{[3-(propan-2-yl)benzene]sulfonyl}phenyl)methyl]imidazo[1,2-a]pyrimidine-6-carboxamide |
| | N-({4-[(4-chloro-2-ethoxybenzene)sulfonyl]phenyl}methyl)imidazo[1,2-a]pyridine-6-carboxamide |
| | N-({4-[(3-methoxybenzene)sulfonyl]phenyl}methyl)thieno[2,3-c]pyridine-2-carboxamide |
| | N-({4-[(3-cyanobenzene)sulfonyl]phenyl}methyl)imidazo[1,2-a]pyrimidine-6-carboxamide |
| | N-({4-[2-(benzenesulfonyl)ethyl]phenyl}methyl)-1H-pyrrolo[3,2-c]pyridine-2-carboxamide |

TABLE 2-continued

| Structure | Name |
|---|---|
| 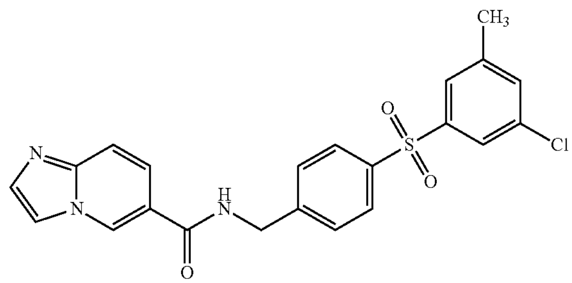 | N-({4-[(3-chloro-5-methylbenzene)sulfonyl]phenyl}methyl)imidazo[1,2-a]pyridine-6-carboxamide |
| 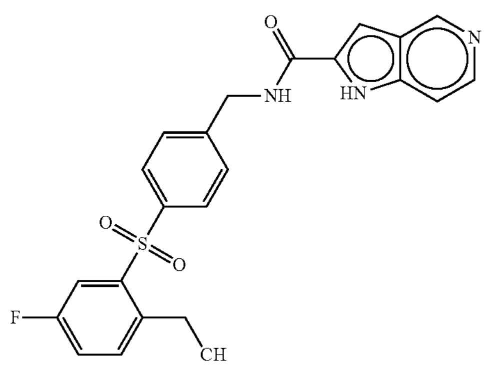 | N-[(4-{[5-fluoro-2-(hydroxymethyl)benzene]sulfonyl}phenyl)methyl]-1H-pyrrolo[3,2-c]pyridine-2-carboxamide |
| 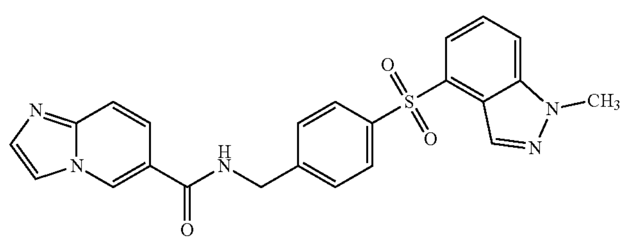 [SMILES: Cn1ncc2c(S(=O)(=O)c3ccc(CNC(=O)c4ccc5nccn5c4)cc3)cccc21] | N-{[4-(1-methyl-1H-indazole-4-sulfonyl)phenyl]methyl}imidazo[1,2-a]pyridine-6-carboxamide |
| 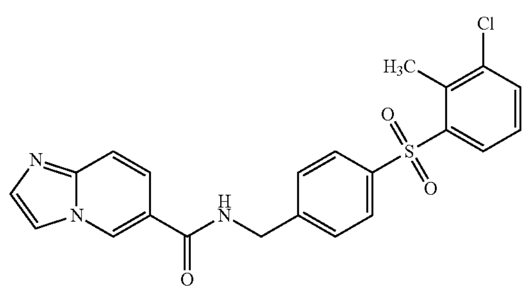 [SMILES: Cc1c(Cl)cccc1S(=O)(=O)c1ccc(CNC(=O)c2ccc3nccn3c2)cc1] | N-({4-[(3-chloro-2-methylbenzene)sulfonyl]phenyl}methyl)imidazo[1,2-a]pyridine-6-carboxamide |
| 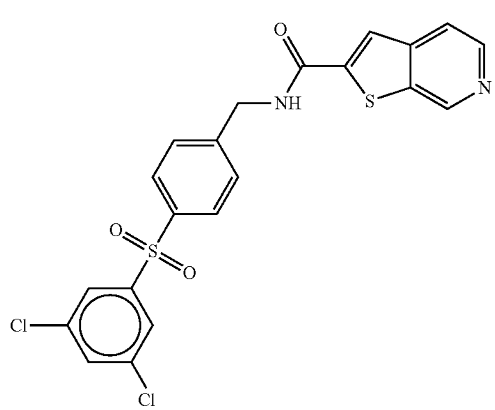 | N-({4-[(3,5-dichlorobenzene)sulfonyl]phenyl}methyl)thieno[2,3-c]pyridine-2-carboxamide |

TABLE 2-continued

| | |
|---|---|
| 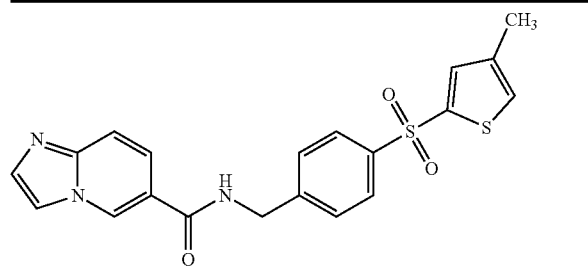 | N-{[4-(4-methylthiophene-2-sulfonyl)phenyl]methyl}imidazo[1,2-a]pyridine-6-carboxamide |
| 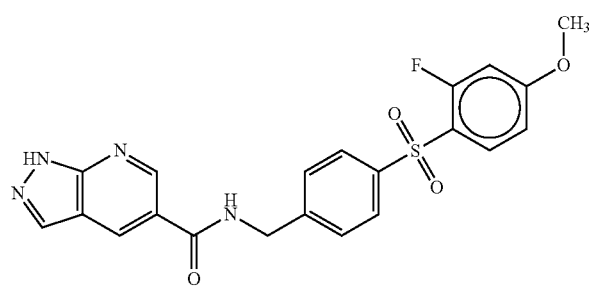 | N-({4-[(2-fluoro-4-methoxybenzene)sulfonyl]phenyl}methyl)-1H-pyrazolo[3,4-b]pyridine-5-carboxamide |
| 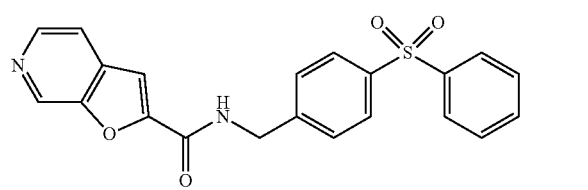 [SMILES: O=C(NCc1ccc(S(=O)(=O)c2ccccc2)cc1)c1cc2ccncc2o1] | N-{[4-(benzenesulfonyl)phenyl]methyl}furo[2,3-c]pyridine-2-carboxamide |
| 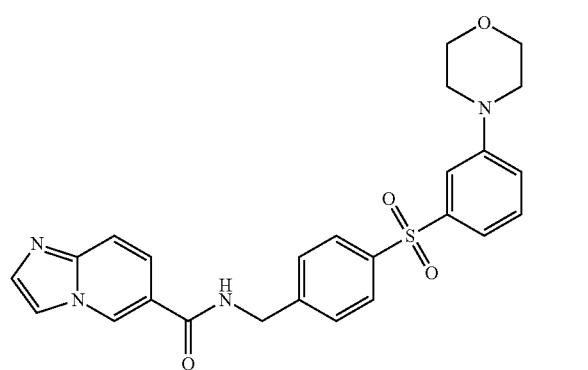 [SMILES: O=C(NCc1ccc(S(=O)(=O)c2cccc(N3CCOCC3)c2)cc1)c1ccc2nccn2c1] | N-[(4-{[3-(morpholin-4-yl)benzene]sulfonyl}phenyl)methyl]imidazo[1,2-a]pyridine-6-carboxamide |
| 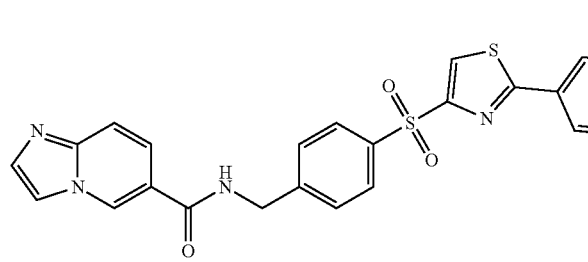 | N-({4-[2-(3-fluorophenyl)-1,3-thiazole-4-sulfonyl]phenyl}methyl)imidazo[1,2-a]pyridine-6-carboxamide |
| 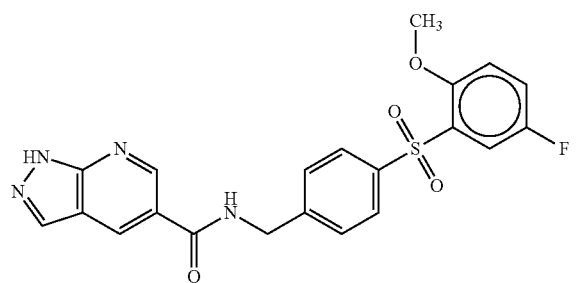 | N-({4-[(5-fluoro-2-methoxybenzene)sulfonyl]phenyl}methyl)-1H-pyrazolo[3,4-b]pyridine-5-carboxamide |

TABLE 2-continued

| | |
|---|---|
| 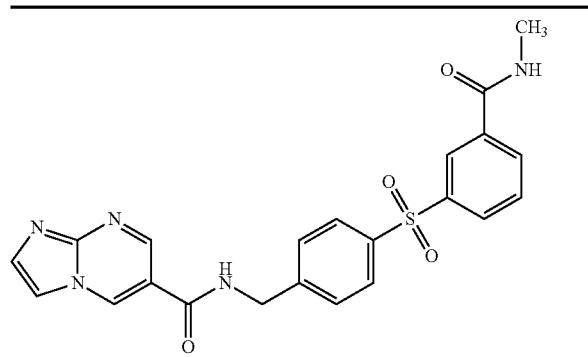 | N-[(4-{[3-(methylcarbamoyl)benzene]sulfonyl}phenyl)methyl]imidazo[1,2-a]pyrimidine-6-carboxamide |
| 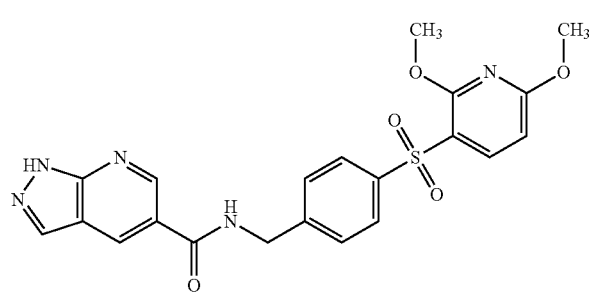 [SMILES: COc1ccc(S(=O)(=O)c2ccc(CNC(=O)c3cnc4[nH]ncc4c3)cc2)c(OC)n1] | N-{[4-(2,6-dimethoxypyridine-3-sulfonyl)phenyl]methyl}-1H-pyrazolo[3,4-b]pyridine-5-carboxamide |
| 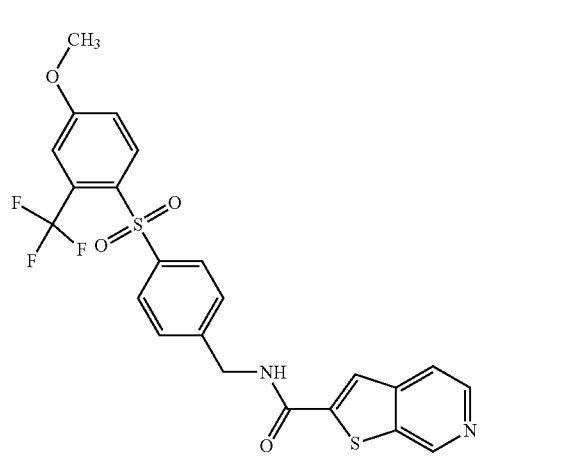 [SMILES: COc1ccc(S(=O)(=O)c2ccc(CNC(=O)c3cc4ccncc4s3)cc2)c(C(F)(F)F)c1] | N-[(4-{[4-methoxy-2-(trifluoromethyl)benzene]sulfonyl}phenyl)methyl]furo[2,3-c]pyridine-2-carboxamide |
| 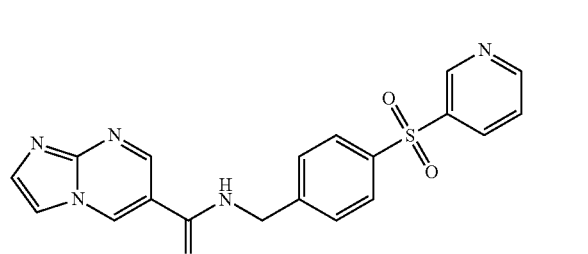 | N-{[4-(pyridine-3-sulfonyl)phenyl]methyl}imidazo[1,2-a]pyrimidine-6-carboxamide |
| 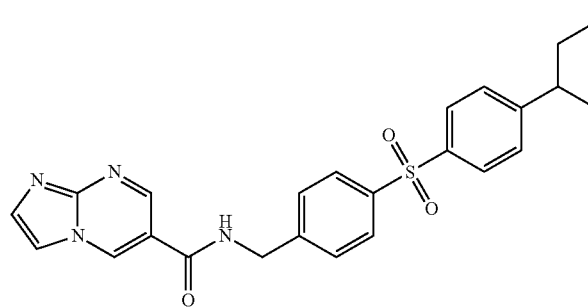 | N-({4-[(4-cyclohexylbenzene)sulfonyl]phenyl}methyl)imidazo[1,2-a]pyrimidine-6-carboxamide |

TABLE 2-continued
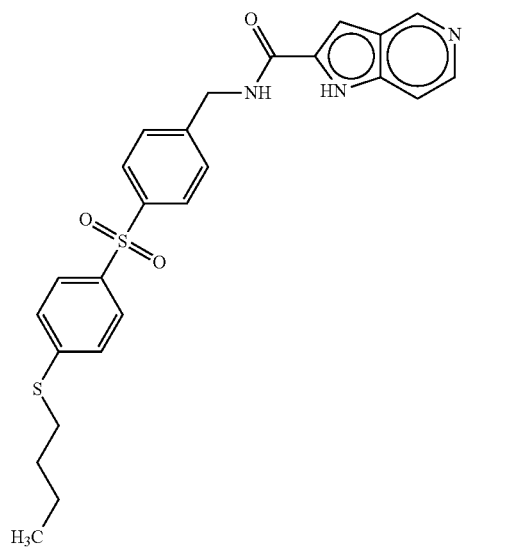
N-({4-[(4-butoxybenzene)sulfonyl]phenyl}methyl)-1H-pyrrolo[3,2-c]pyridine-2-carboxamide
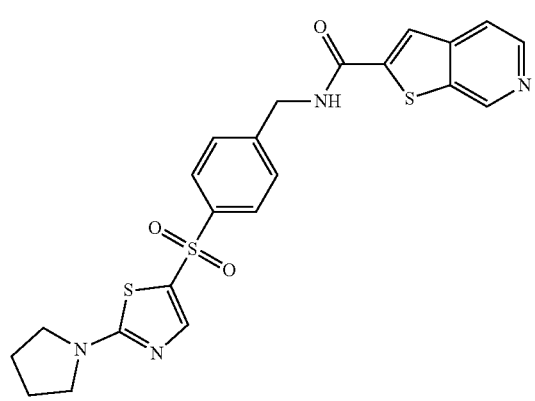 [SMILES: O=C(NCc1ccc(S(=O)(=O)c2cnc(N3CCCC3)s2)cc1)c1cc2ccncc2s1]
N-({4-[2-(pyrrolidin-1-yl)-1,3-thiazole-5-sulfonyl]phenyl}methyl)thieno[2,3-c]pyridine-2-carboxamide
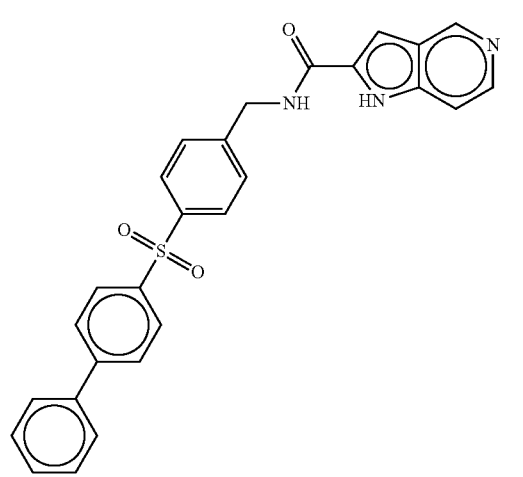
N-({4-[(4-phenylbenzene)sulfonyl]phenyl}methyl)-1H-pyrrolo[3,2-c]pyridine-2-carboxamide TABLE 2-continued

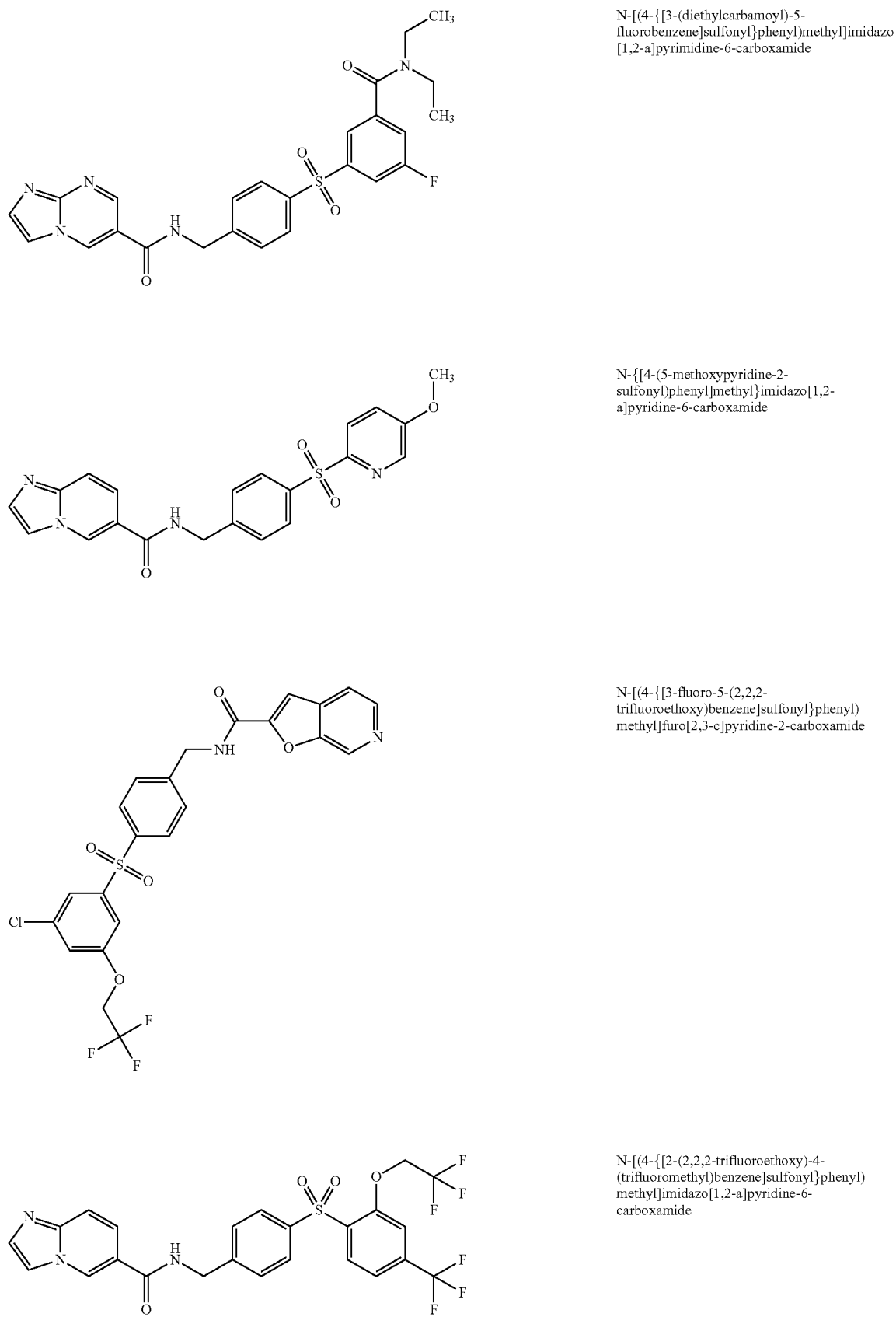

N-[(4-{[3-(diethylcarbamoyl)-5-fluorobenzene]sulfonyl}phenyl)methyl]imidazo[1,2-a]pyrimidine-6-carboxamide N-{[4-(5-methoxypyridine-2-sulfonyl)phenyl]methyl}imidazo[1,2-a]pyridine-6-carboxamide N-[(4-{[3-fluoro-5-(2,2,2-trifluoroethoxy)benzene]sulfonyl}phenyl)methyl]furo[2,3-c]pyridine-2-carboxamide N-[(4-{[2-(2,2,2-trifluoroethoxy)-4-(trifluoromethyl)benzene]sulfonyl}phenyl)methyl]imidazo[1,2-a]pyridine-6-carboxamide TABLE 2-continued

| | |
|---|---|
| | N-[(4-{[3-chloro-5-(trifluoromethyl)benzene]sulfonyl}phenyl)methyl]-1H-pyrrolo[3,2-c]pyridine-2-carboxamide |
| | N-[(4-{[4-(4-ethoxyphenyl)benzene]sulfonyl}phenyl)methyl]-1H-pyrrolo[3,2-c]pyridine-2-carboxamide |
| | N-({4-[(3-chlorobenzene)sulfonyl]phenyl}methyl)-1H-pyrazolo[3,4-b]pyridine-5-carboxamide |
| | N-({4-[(5-chloro-2-hydroxybenzene)sulfonyl]phenyl}methyl)imidazo[1,2-a]pyridine-6-carboxamide |
| | N-({4-[(3-fluoro-4-methoxybenzene)sulfonyl]phenyl}methyl)-1H-pyrazolo[3,4-b]pyridine-5-carboxamide |

TABLE 2-continued
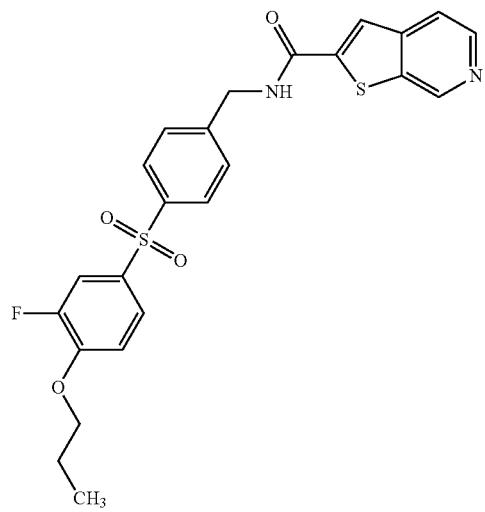
N-({4-[(3-fluoro-4-propoxybenzene)sulfonyl]phenyl}methyl)thieno[2,3-c]pyridine-2-carboxamide
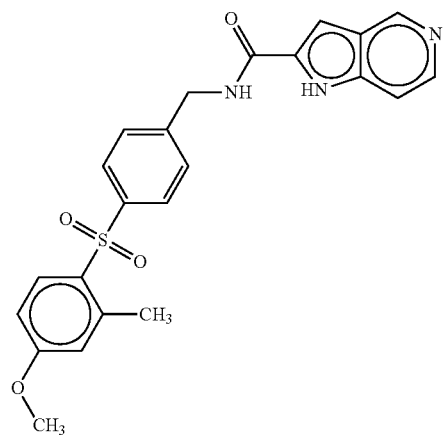
N-({4-[(4-methoxy-2-methylbenzene)sulfonyl]phenyl}methyl)-1H-pyrrolo[3,2-c]pyridine-2-carboxamide
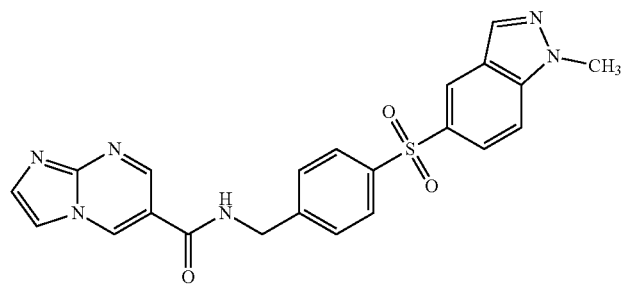 [SMILES: Cn1ncc2cc(S(=O)(=O)c3ccc(CNC(=O)c4cnc5nccn5c4)cc3)ccc21]
N-{4-(1-methyl-1H-indazole-5-sulfonyl)phenyl]methyl}imidazo[1,2-a]pyrimidine-6-carboxamide
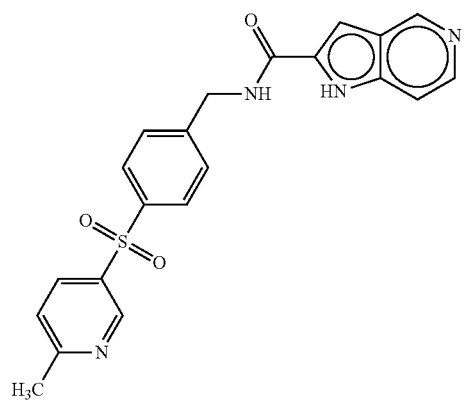
N-{[4-(6-methylpyridine-3-sulfonyl)phenyl]methyl}-1H-pyrrolo[3,2-c]pyridine-2-carboxamide TABLE 2-continued
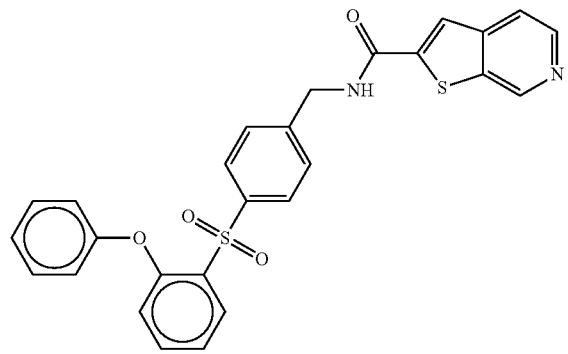
N-({4-[(2-phenoxybenzene)sulfonyl]phenyl}methyl)thieno[2,3-c]pyridine-2-carboxamide
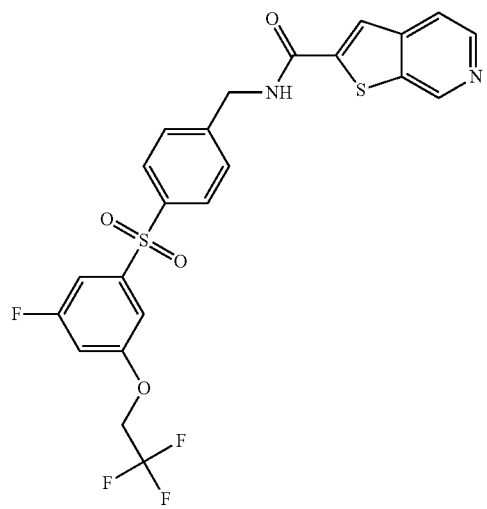 [SMILES: O=C(NCc1ccc(S(=O)(=O)c2cc(F)cc(OCC(F)(F)F)c2)cc1)c1cc2ccncc2s1]
N-[(4-{[3-fluoro-5-(2,2,2-trifluoroethoxy)benzene]sulfonyl}phenyl)methyl]thieno[2,3-c]pyridine-2-carboxamide
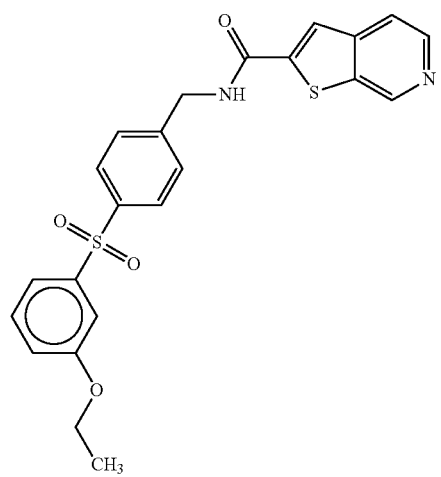
N-({4-[(3-ethoxybenzene)sulfonyl]phenyl}methyl)thieno[2,3-c]pyridine-2-carboxamide

| | |
|---|---|
| 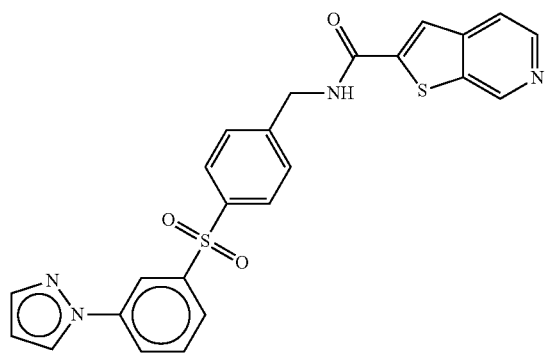 | N-[(4-{[3-(1H-pyrazol-1-yl)benzene]sulfonyl}phenyl)methyl]thieno[2,3-c]pyridine-2-carboxamide |
| 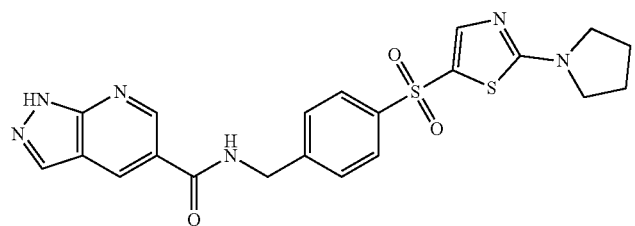 [SMILES: O=C(NCc1ccc(S(=O)(=O)c2cnc(N3CCCC3)s2)cc1)c1cnc2[nH]ncc2c1] | N-({4-[2-(pyrrolidin-1-yl)-1,3-thiazole-5-sulfonyl]phenyl}methyl)-1H-pyrazolo[3,4-b]pyridine-5-carboxamide |
| 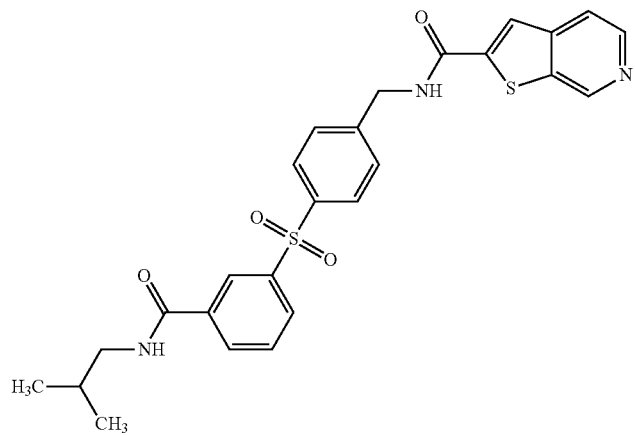 [SMILES: CC(C)CNC(=O)c1cccc(S(=O)(=O)c2ccc(CNC(=O)c3cc4ccncc4s3)cc2)c1] | N-{[4-({3-[(2-methylpropyl)carbamoyl]benzene}sulfonyl)phenyl]methyl}thieno[2,3-c]pyridine-2-carboxamide |
| 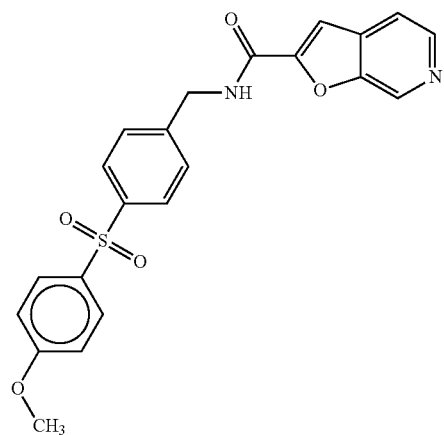 | N-({4-[(4-methoxybenzene)sulfonyl]phenyl}methyl)furo[2,3-c]pyridine-2-carboxamide |

TABLE 2-continued
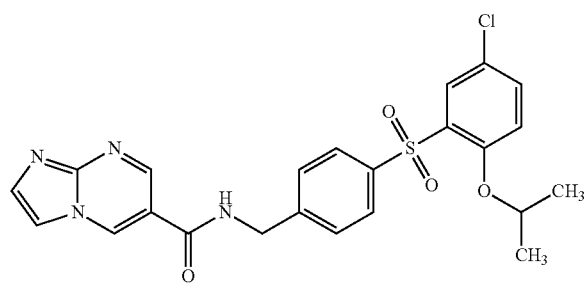 [SMILES: CC(C)Oc1ccc(Cl)cc1S(=O)(=O)c1ccc(CNC(=O)c2cnc3nccn3c2)cc1]
N-[(4-{[5-chloro-2-(propan-2-yloxy)benzene]sulfonyl}phenyl)methyl]imidazo[1,2-a]pyrimidine-6-carboxamide
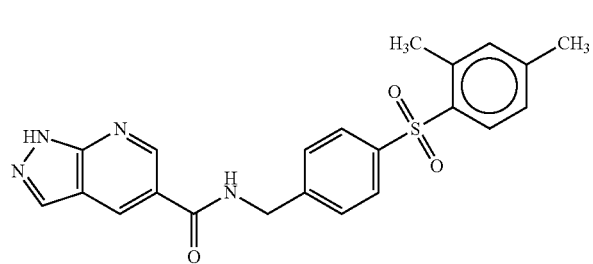
N-({4-[(2,4-dimethylbenzene)sulfonyl]phenyl}methyl)-1H-pyrazolo[3,4-b]pyridine-5-carboxamide
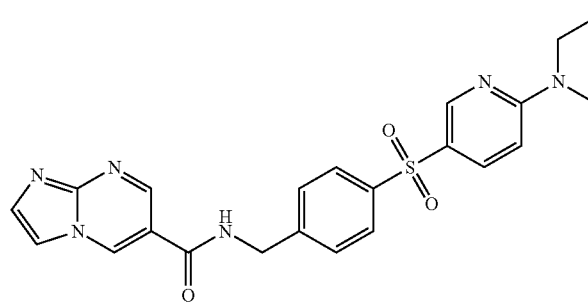
N-({4-[6-(morpholin-4-yl)pyridine-3-sulfonyl]phenyl}methyl)imidazo[1,2-a]pyrimidine-6-carboxamide
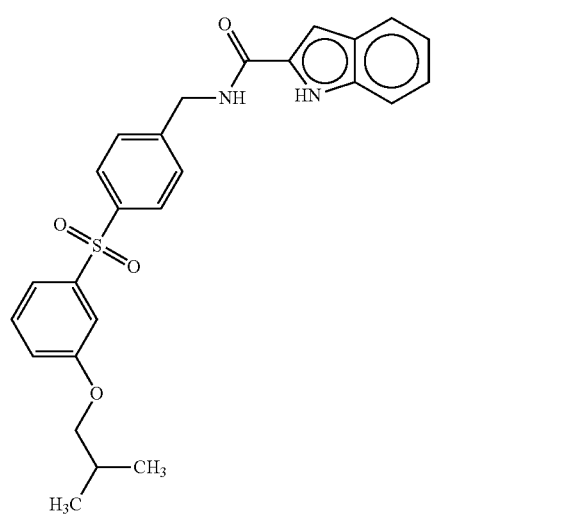
N-[(4-{[3-(2-methylpropoly)benzene]sulfonyl}phenyl)methyl]-1H-pyrrolo[3,2-c]pyridine-2-carboxamide TABLE 2-continued
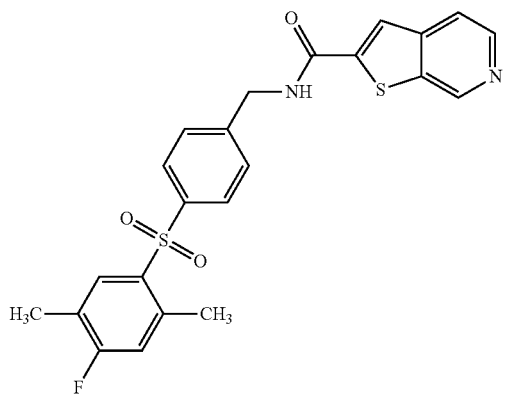 [SMILES: Cc1cc(S(=O)(=O)c2ccc(CNC(=O)c3cc4ccncc4s3)cc2)c(C)cc1F]
N-({4-[(4-fluoro-2,5-dimethylbenzene)sulfonyl]phenyl}methyl)thieno[2,3-c]pyridine-2-carboxamide
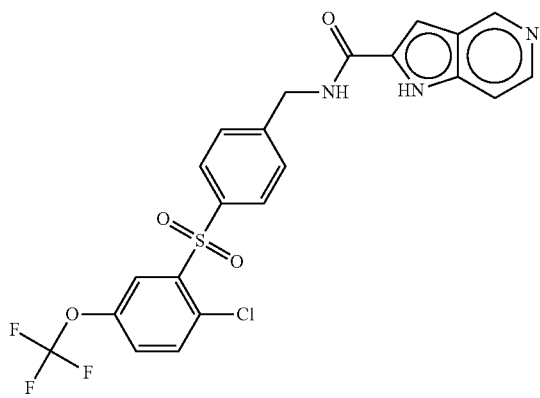
N-[(4-{[2-chloro-5-(trifluoromethoxy)benzene]sulfonyl}phenyl)methyl]-1H-pyrrolo[3,2-c]pyridine-2-carboxamide
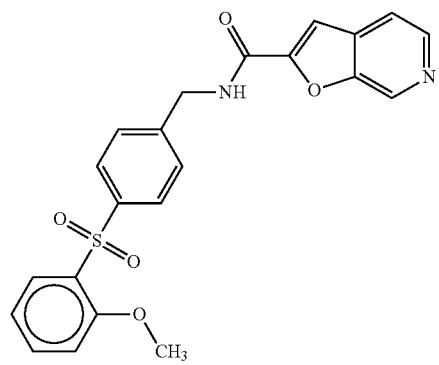
N-({4-[(2-methoxybenzene)sulfonyl]phenyl}methyl)furo[2,3-c]pyridine-2-carboxamide
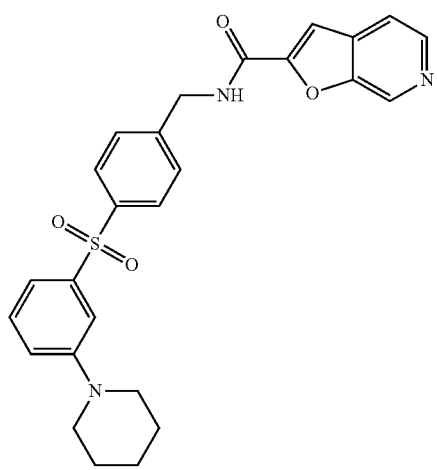
N-[(4-{[3-(piperidin-1-yl)benzene]sulfonyl}phenyl)methyl]furo[2,3-c]pyridine-2-carboxamide TABLE 2-continued
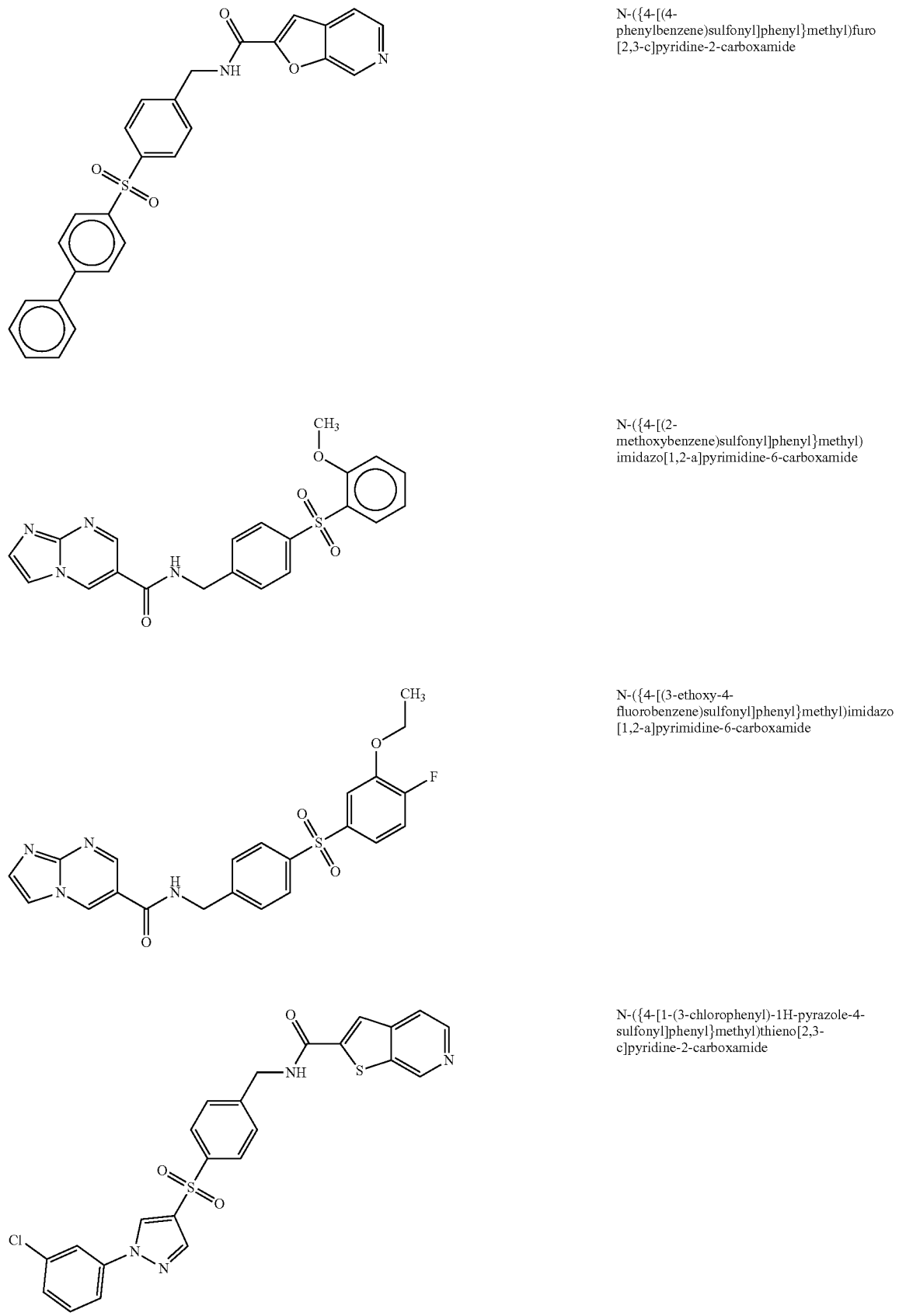
N-({4-[(4-phenylbenzene)sulfonyl]phenyl}methyl)furo[2,3-c]pyridine-2-carboxamide
N-({4-[(2-methoxybenzene)sulfonyl]phenyl}methyl)imidazo[1,2-a]pyrimidine-6-carboxamide
N-({4-[(3-ethoxy-4-fluorobenzene)sulfonyl]phenyl}methyl)imidazo[1,2-a]pyrimidine-6-carboxamide
N-({4-[1-(3-chlorophenyl)-1H-pyrazole-4-sulfonyl]phenyl}methyl)thieno[2,3-c]pyridine-2-carboxamide TABLE 2-continued
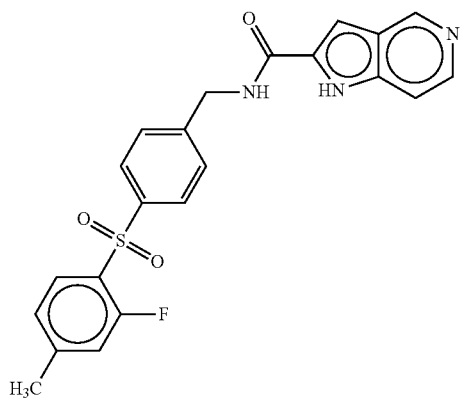
N-({4-[(2-fluoro-4-methylbenzene)sulfonyl]phenyl}methyl)-1H-pyrrolo[3,2-c]pyridine-2-carboxamide
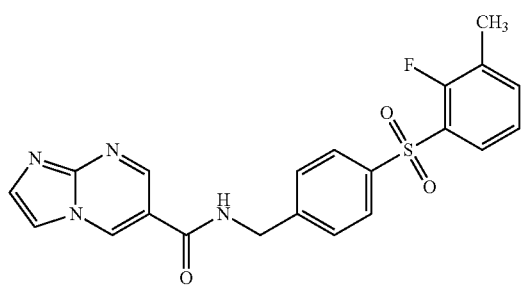 [SMILES: Cc1cccc(S(=O)(=O)c2ccc(CNC(=O)c3cnc4nccn4c3)cc2)c1F]
N-({4-[(2-fluoro-3-methylbenzene)sulfonyl]phenyl}methyl)imidazo[1,2-a]pyrimidine-6-carboxamide
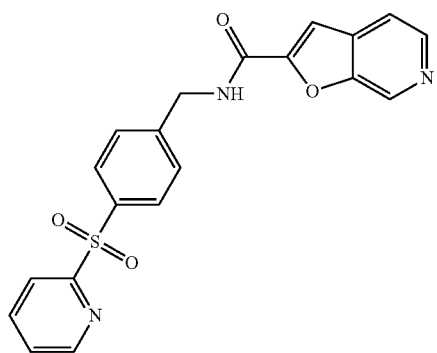 [SMILES: O=C(NCc1ccc(S(=O)(=O)c2ccccn2)cc1)c1cc2ccncc2o1]
N-{[4-(pyridine-2-sulfonyl)phenyl]methyl}furo[2,3-c]pyridine-2-carboxamide
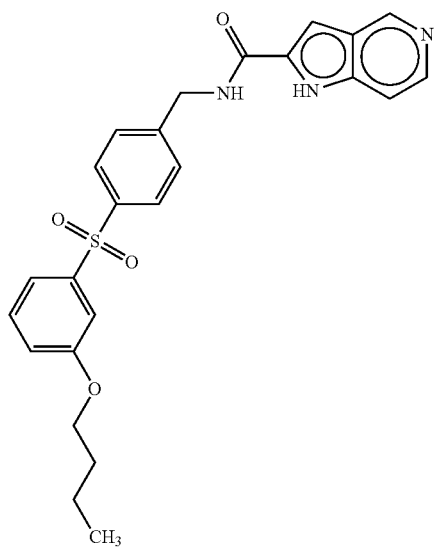
N-({4-[(3-butoxybenzene)sulfonyl]phenyl}methyl)-1H-pyrrolo[3,2-c]pyridine-2-carboxamide TABLE 2-continued
| | |
|---|---|
| 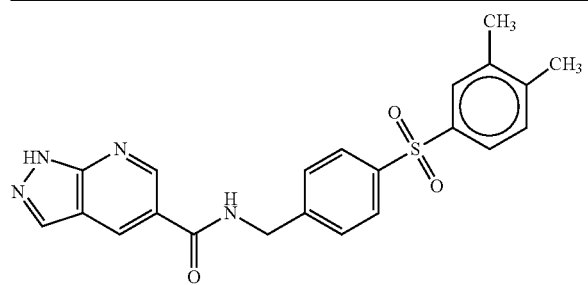 | N-({4-[(3,4-dichlorobenzene)sulfonyl]phenyl}methyl)-1H-pyrazolo[3,4-b]pyridine-5-carboxamide |
| 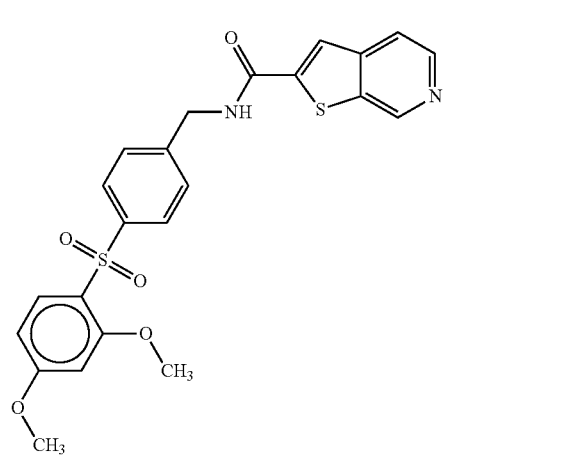 | N-({4-[(2,4-dimethoxybenzene)sulfonyl]phenyl}methyl)thieno[2,3-c]pyridine-2-carboxamide |
| 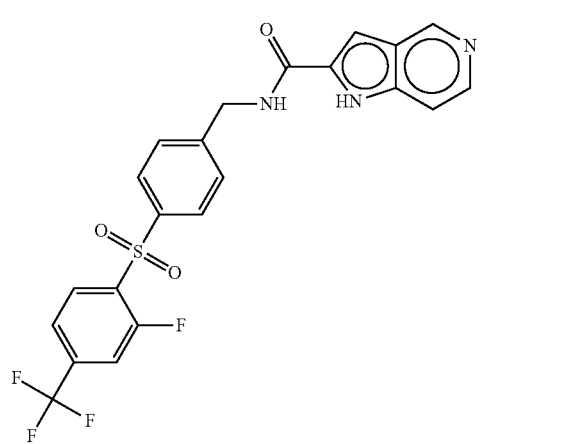 | N-[(4-{[2-fluoro-4-(trifluoromethyl)benzene]sulfonyl}phenyl)methyl]-1H-pyrrolo[3,2-c]pyridine-2-carboxamide |
| 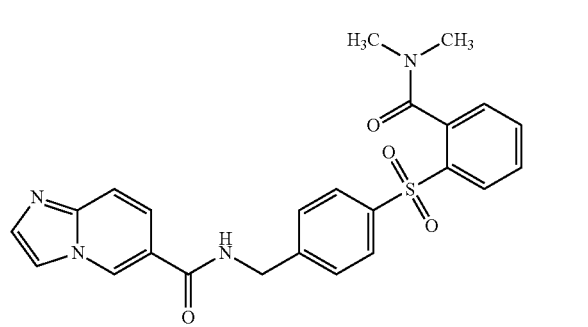 [SMILES: CN(C)C(=O)c1ccccc1S(=O)(=O)c1ccc(CNC(=O)c2ccc3nccn3c2)cc1] | N-[(4-{[2-(dimethylcarbamoyl)benzene]sulfonyl}phenyl)methyl]imidazo[1,2-a]pyridine-6-carboxamide |

TABLE 2-continued
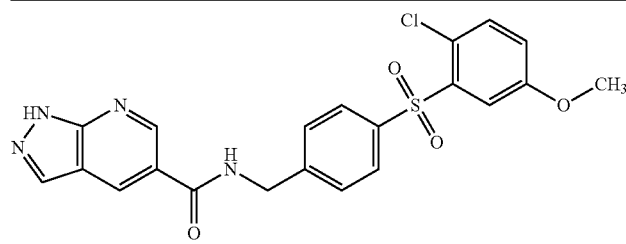
N-({4-[(2-chloro-5-methoxybenzene)sulfonyl]phenyl}methyl)-1H-pyrazolo[3,4-b]pyridine-5-carboxamide
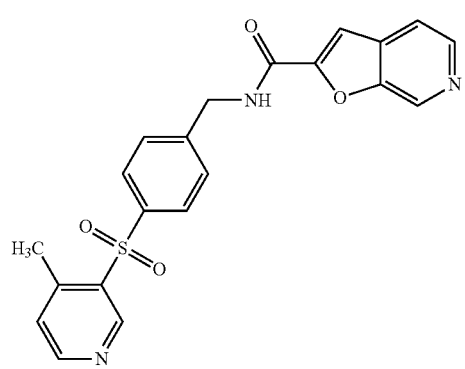 [SMILES: Cc1ccncc1S(=O)(=O)c1ccc(CNC(=O)c2cc3ccncc3o2)cc1]
N-{[4-(4-methylpyridine-3-sulfonyl)phenyl]methyl}furo[2,3-c]pyridine-2-carboxamide
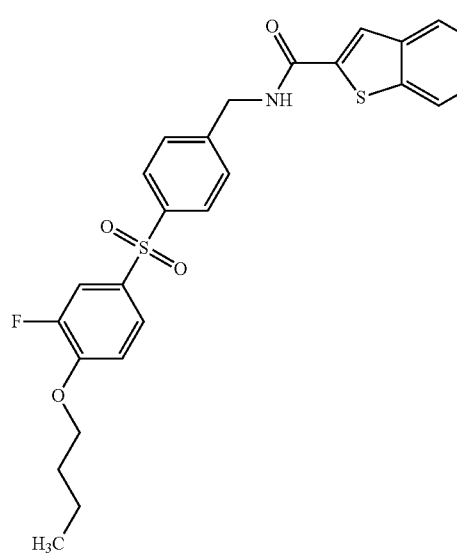
N-({4-[(4-butoxy-3-fluorobenzene)sulfonyl]phenyl}methyl)thieno[2,3-c]pyridine-2-carboxamide
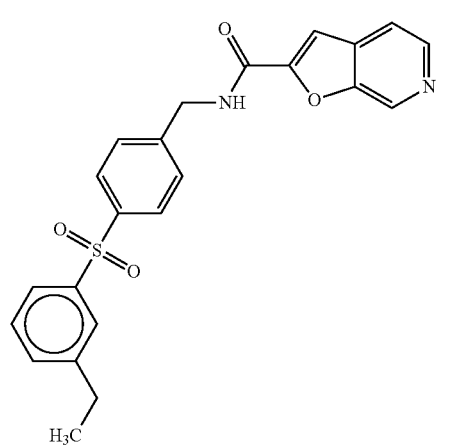
N-({4-[(3-ethylbenzene)sulfonyl]phenyl}methyl)furo[2,3-c]pyridine-2-carboxamide TABLE 2-continued
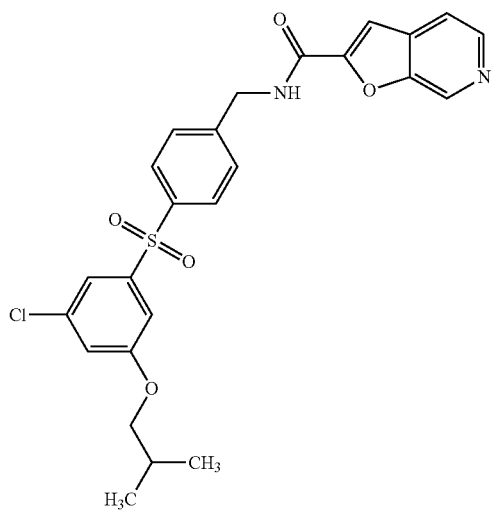 [SMILES: CC(C)COc1cc(Cl)cc(S(=O)(=O)c2ccc(CNC(=O)c3cc4ccncc4o3)cc2)c1]
N-[(4-{[3-fluoro-5-(2-methylpropoxy)benzene]sulfonyl}phenyl)methyl]furo[2,3-c]pyridine-2-carboxamide
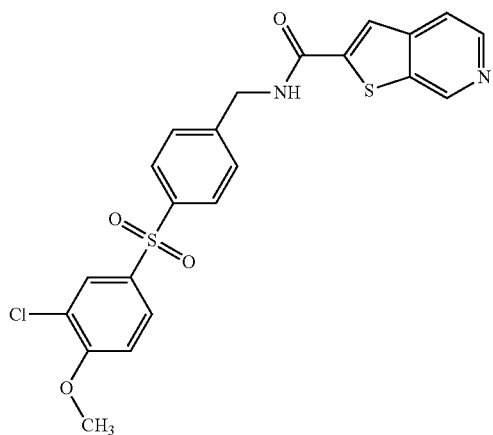
N-({4-[(3-chloro-4-methoxybenzene)sulfonyl]phenyl}methyl)thieno[2,3-c]pyridine-2-carboxamide
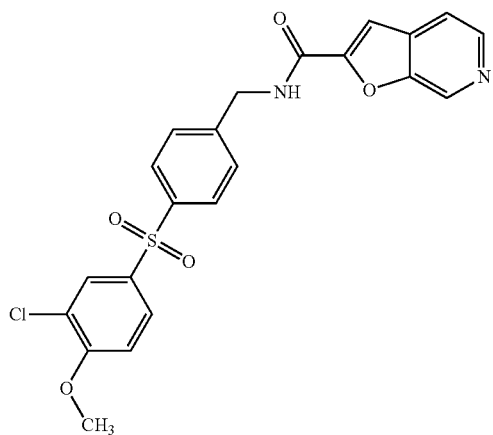 [SMILES: COc1ccc(S(=O)(=O)c2ccc(CNC(=O)c3cc4ccncc4o3)cc2)cc1Cl]
N-({4-[(3-chloro-4-methoxybenzene)sulfonyl]phenyl}methyl)furo[2,3-c]pyridine-2-carboxamide TABLE 2-continued

| Structure | Name |
|---|---|
| | N-[(4-{[2-(trifluoromethoxy)benzene]sulfonyl}phenyl)methyl]imidazo[1,2-a]pyrimidine-6-carboxamide |
| | N-({4-[(2-ethoxy-6-fluorobenzene)sulfonyl]phenyl}methyl)furo[2,3-c]pyridine-2-carboxamide |
| | N-({4-[(3,5-difluorobenzene)sulfonyl]phenyl}methyl)imidazo[1,2-a]pyridine-6-carboxamide |
| | N-[(4-{[4-fluoro-2-(propan-2-yloxy)benzene]sulfonyl}phenyl)methyl]imidazo[1,2-a]pyrimidine-6-carboxamide |
| | N-({4-[2-(morpholin-4-yl)pyridine-3-sulfonyl]phenyl}methyl)furo[2,3-c]pyridine-2-carboxamide |

TABLE 2-continued
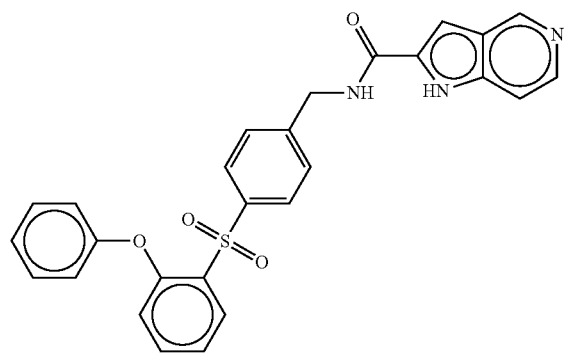
N-({4-[(2-phenoxybenzene)sulfonyl]phenyl}methyl)-1H-pyrrolo[3,2-c]pyridine-2-carboxamide
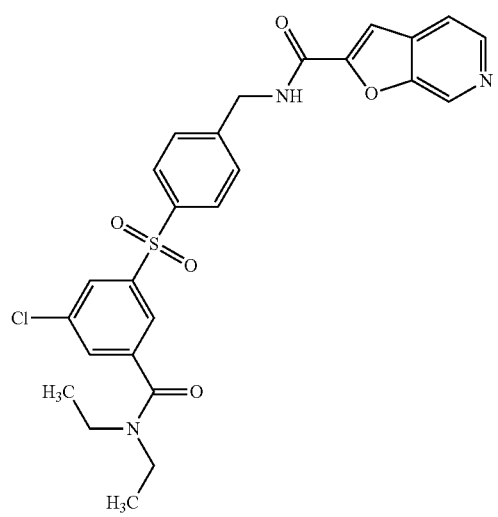
N-[(4-{[3-chloro-5-(diethylcarbamoyl)benzene]sulfonyl}phenyl)methyl]furo[2,3-c]pyridine-2-carboxamide
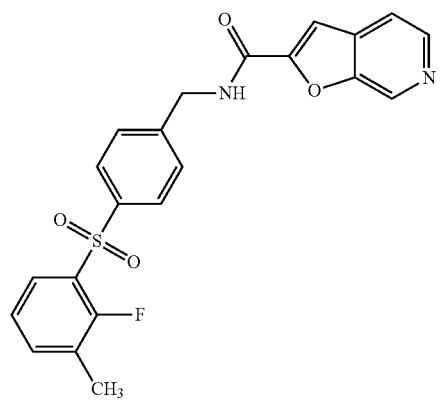 [SMILES: Cc1cccc(S(=O)(=O)c2ccc(CNC(=O)c3cc4ccncc4o3)cc2)c1F]
N-({4-[(2-fluoro-3-methylbenzene)sulfonyl]phenyl}methyl)furo[2,3-c]pyridine-2-carboxamide
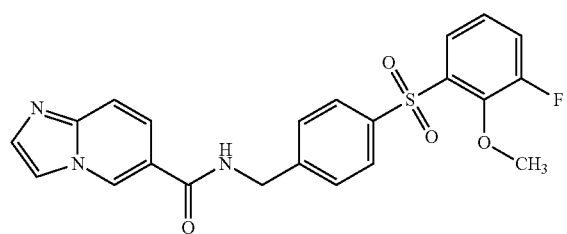 [SMILES: COc1c(F)cccc1S(=O)(=O)c1ccc(CNC(=O)c2ccc3nccn3c2)cc1]
N-({4-[(3-fluoro-2-methoxybenzene)sulfonyl]phenyl}methyl)imidazo[1,2-a]pyridine-6-carboxamide

| | |
|---|---|
| 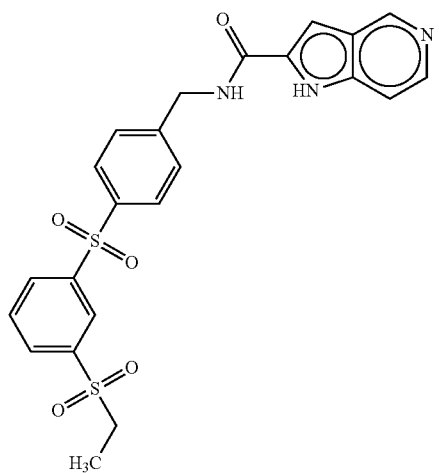 | N-[(4-{[3-(ethanesulfonyl)benzene]sulfonyl}phenyl)methyl]-1H-pyrrolo[3,2-c]pyridine-2-carboxamide |
| 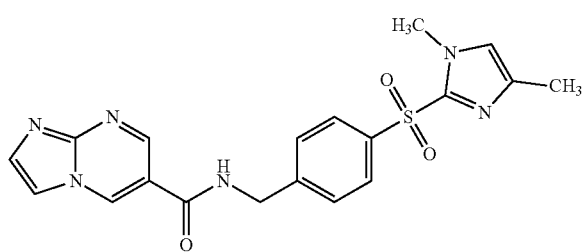 [SMILES: Cc1cn(C)c(S(=O)(=O)c2ccc(CNC(=O)c3cnc4nccn4c3)cc2)n1] | N-{[4-(1,4-dimethyl-1H-imidazole-2-sulfonyl)phenyl]methyl}imidazo[1,2-a]pyrimidine-6-carboxamide |
| 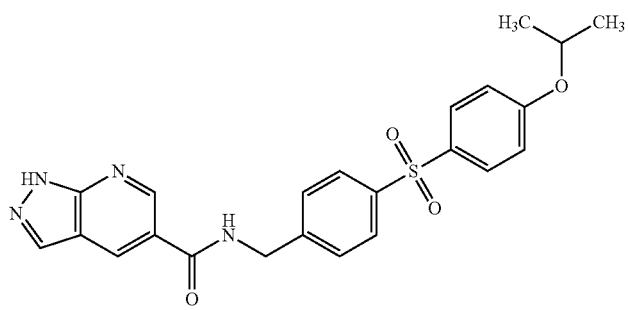 [SMILES: CC(C)Oc1ccc(S(=O)(=O)c2ccc(CNC(=O)c3cnc4[nH]ncc4c3)cc2)cc1] | N-[(4-{[4-(propan-2-yloxy)benzene]sulfonyl}phenyl)methyl]-1H-pyrazolo[3,4-b]pyridine-5-carboxamide |
| 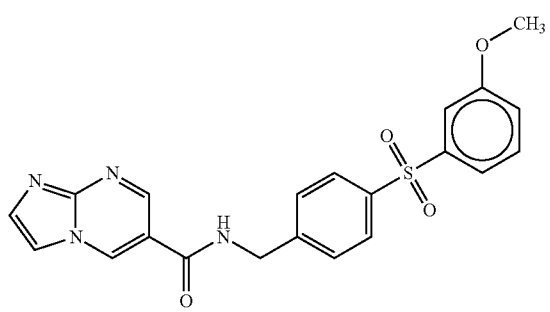 | N-({4-[(3-methoxybenzene)sulfonyl]phenyl}methyl)imidazo[1,2-a]pyrimidine-6-carboxamide |

TABLE 2-continued
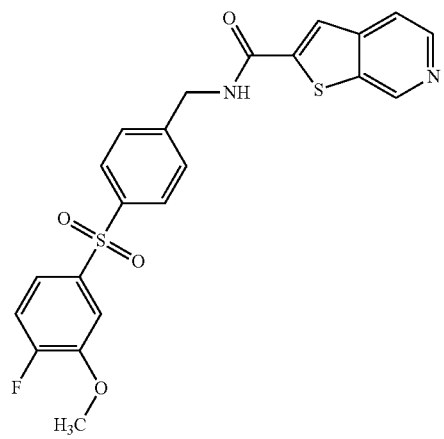 [SMILES: COc1cc(S(=O)(=O)c2ccc(CNC(=O)c3cc4ccncc4s3)cc2)ccc1F]
N-({4-[(4-fluoro-3-methoxybenzene)sulfonyl]phenyl}methyl)thieno[2,3-c]pyridine-2-carboxamide
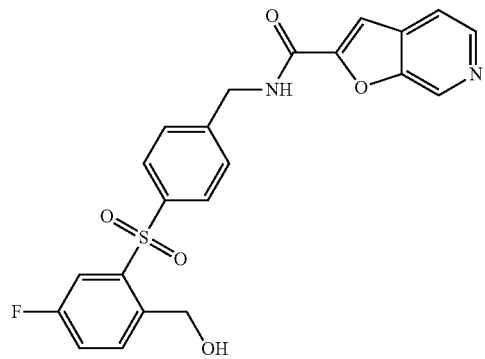 [SMILES: O=C(NCc1ccc(S(=O)(=O)c2cc(F)ccc2CO)cc1)c1cc2ccncc2o1]
N-[(4-{[5-fluoro-2-(hydroxymethyl)benzene]sulfonyl}phenyl)methyl]furo[2,3-c]pyridine-2-carboxamide
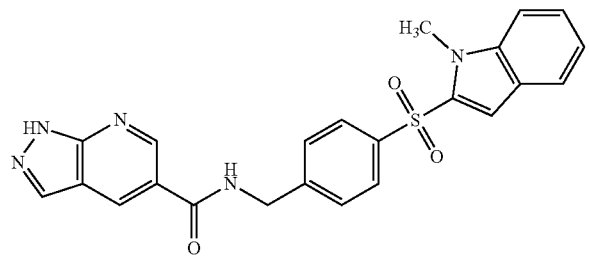 [SMILES: Cn1c(S(=O)(=O)c2ccc(CNC(=O)c3cnc4[nH]ncc4c3)cc2)cc2ccccc21]
N-{[4-(1-methyl-1H-indole-2-sulfonyl)phenyl]methyl}-1H-pyrazolo[3,4-b]pyridine-5-carboxamide
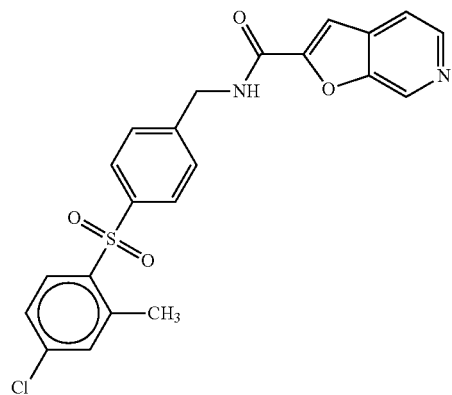
N-({4-[(4-chloro-2-methylbenzene)sulfonyl]phenyl}methyl)furo[2,3-c]pyridine-2-carboxamide TABLE 2-continued
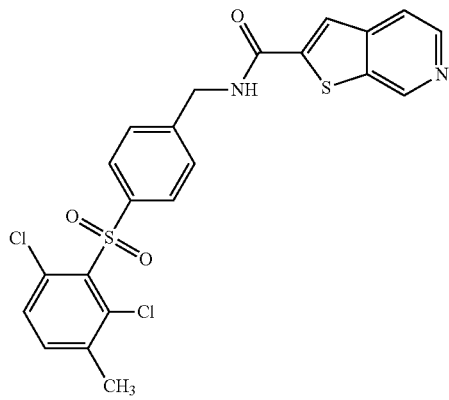 [SMILES: Cc1ccc(Cl)c(S(=O)(=O)c2ccc(CNC(=O)c3cc4ccncc4s3)cc2)c1Cl]
N-({4-[(2,6-dichloro-3-methylbenzene)sulfonyl]phenyl}methyl)thieno[2,3-c]pyridine-2-carboxamide
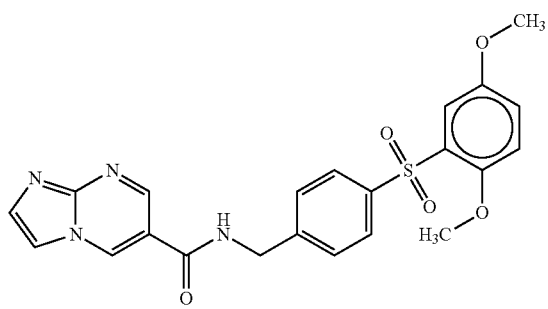
N-({4-[(2,5-dimethoxybenzene)sulfonyl]phenyl}methyl)imidazo[1,2-a]pyrimidine-6-carboxamide
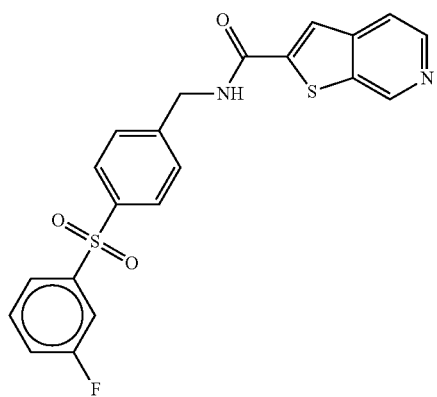
N-({4-[(3-fluorobenzene)sulfonyl]phenyl}methyl)thieno[2,3-c]pyridine-2-carboxamide
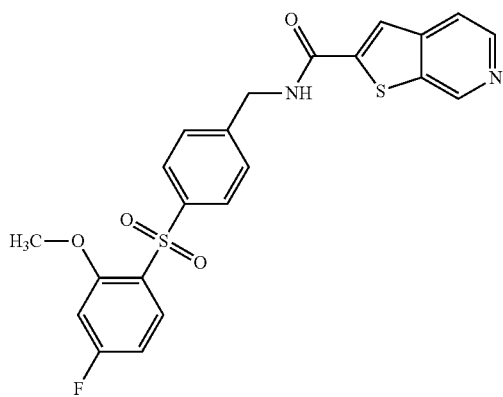
N-({4-[(4-fluoro-2-methoxybenzene)sulfonyl]phenyl}methyl)thieno[2,3-c]pyridine-2-carboxamide

| | |
|---|---|
| 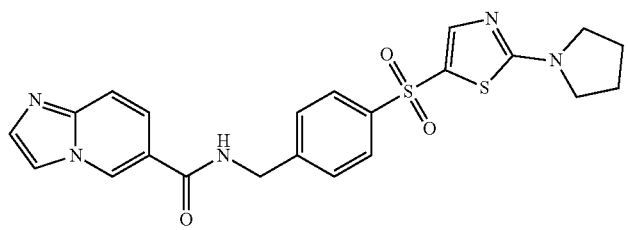 [SMILES: O=C(NCc1ccc(S(=O)(=O)c2cnc(N3CCCC3)s2)cc1)c1ccc2nccn2c1] | N-({4-[2-(pyrrolidin-1-yl)-1,3-thiazole-5-sulfonyl]phenyl}methyl)imidazo[1,2-a]pyridine-6-carboxamide |
| 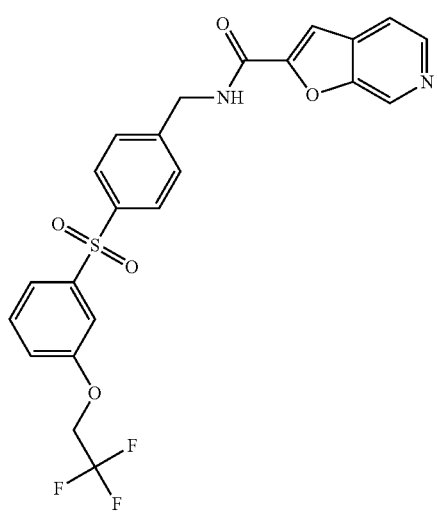 [SMILES: O=C(NCc1ccc(S(=O)(=O)c2cccc(OCC(F)(F)F)c2)cc1)c1cc2ccncc2o1] | N-[(4-{[3-(2,2,2-trifluoroethoxy)benzene]sulfonyl}phenyl)methyl]furo[2,3-c]pyridine-2-carboxamide |
| 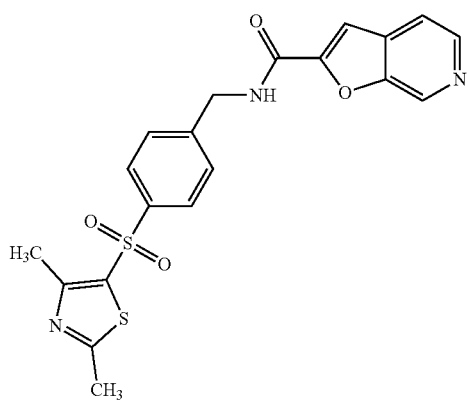 [SMILES: Cc1nc(C)c(S(=O)(=O)c2ccc(CNC(=O)c3cc4ccncc4o3)cc2)s1] | N-{[4-(dimethyl-1,3-thiazole-5-sulfonyl)phenyl]methyl}furo[2,3-c]pyridine-2-carboxamide |
| 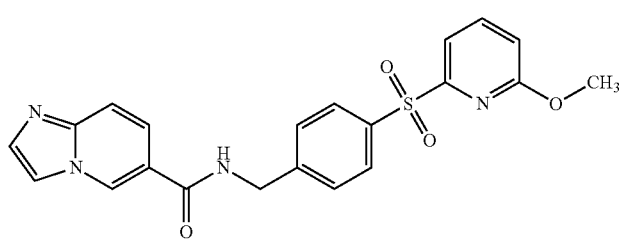 [SMILES: COc1cccc(S(=O)(=O)c2ccc(CNC(=O)c3ccc4nccn4c3)cc2)n1] | N-{[4-(6-methoxypyridine-2-sulfonyl)phenyl]methyl}imidazo[1,2-a]pyridine-6-carboxamide |

TABLE 2-continued
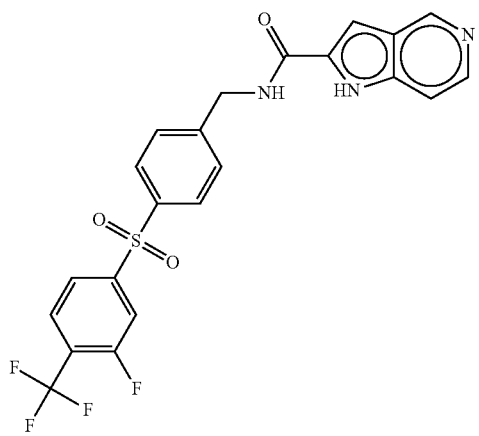
N-[(4-{[3-fluoro-4-(trifluoromethyl)benzene]sulfonyl}phenyl)methyl]-1H-pyrrolo[3,2-c]pyridine-2-carboxamide
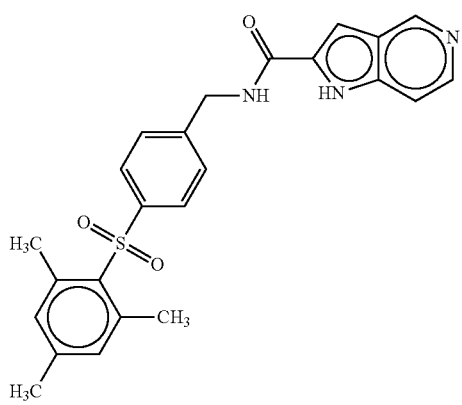
N-({4-[(2,4,6-trimethylbenzene)sulfonyl]phenyl}methyl)-1H-pyrrolo[3,2-c]pyridine-2-carboxamide
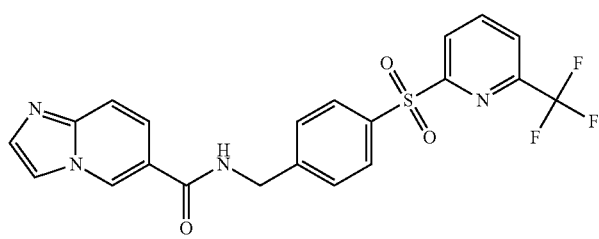
N-({4-[6-(trifluoromethyl)pyridine-2-sulfonyl]phenyl}methyl)imidazo[1,2-a]pyridine-6-carboxamide
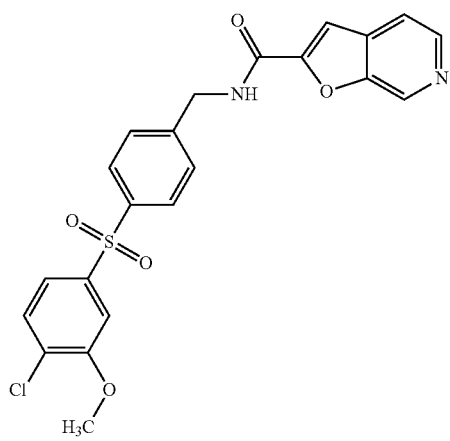
N-({4-[(4-chloro-3-methoxybenzene)sulfonyl]phenyl}methyl)furo[2,3-c]pyridine-2-carboxamide TABLE 2-continued
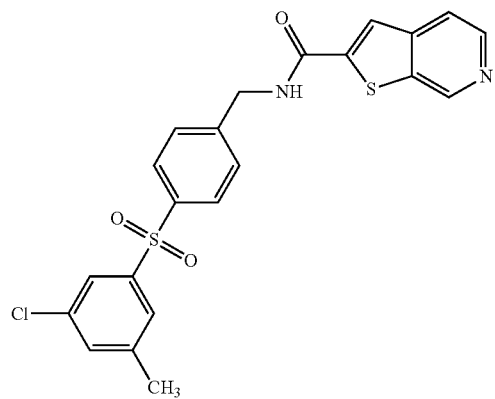
N-({4-[(3-chloro-5-methylbenzene)sulfonyl]phenyl}methyl)thieno[2,3-c]pyridine-2-carboxamide
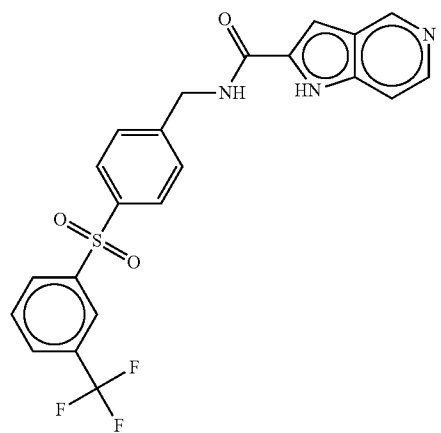
N-[(4-{[3-(trifluoromethyl)benzene]sulfonyl}phenyl)methyl]-1H-pyrrolo[3,2-c]pyridine-2-carboxamide
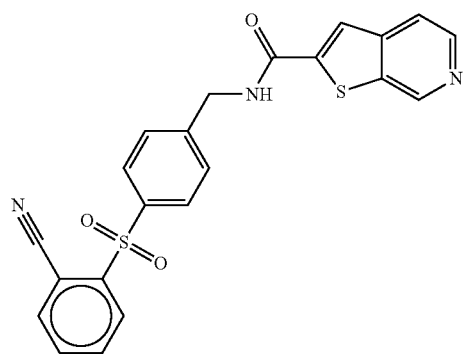
N-({4-[(2-cyanobenzene)sulfonyl]phenyl}methyl)thieno[2,3-c]pyridine-2-carboxamide
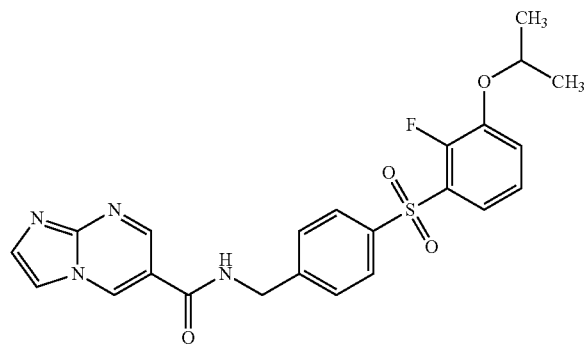 [SMILES: CC(C)Oc1cccc(S(=O)(=O)c2ccc(CNC(=O)c3cnc4nccn4c3)cc2)c1F]
N-[(4-{[2-fluoro-3-(propan-2-yloxy)benzene]sulfonyl}phenyl)methyl]imidazo[1,2-a]pyrimidine-6-carboxamide TABLE 2-continued

| | |
|---|---|
| 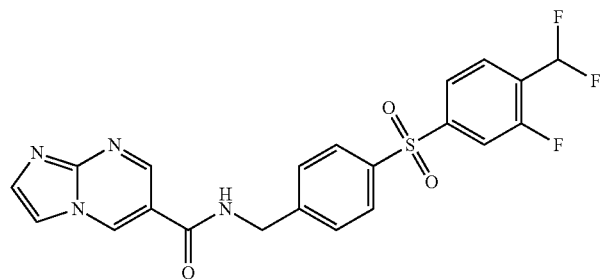 [SMILES: O=C(NCc1ccc(S(=O)(=O)c2ccc(C(F)F)c(F)c2)cc1)c1cnc2nccn2c1] | N-[(4-{[4-(difluoromethyl)-3-fluorobenzene]sulfonyl}phenyl)methyl]imidazo[1,2-a]pyrimidine-6-carboxamide |
| 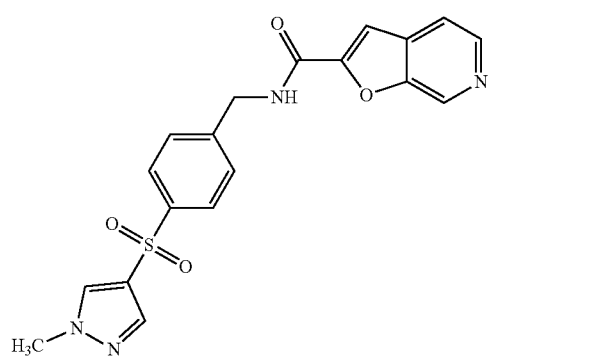 [SMILES: Cn1cc(S(=O)(=O)c2ccc(CNC(=O)c3cc4ccncc4o3)cc2)cn1] | N-{[4-(1-methyl-1H-pyrazole-4-sulfonyl)phenyl]methyl}furo[2,3-c]pyridine-2-carboxamide |
| 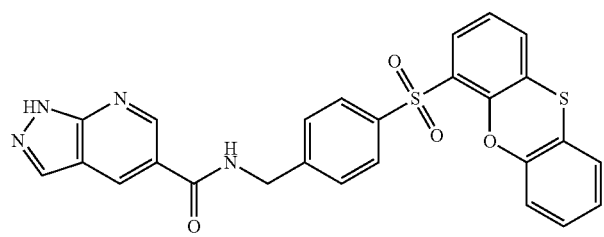 [SMILES: O=C(NCc1ccc(S(=O)(=O)c2cccc3c2Oc2ccccc2S3)cc1)c1cnc2[nH]ncc2c1] | N-{[4-(phenoxathiine-4-sulfonyl)phenyl]methyl}-1H-pyrazolo[3,4-b]pyridine-5-carboxamide |
| 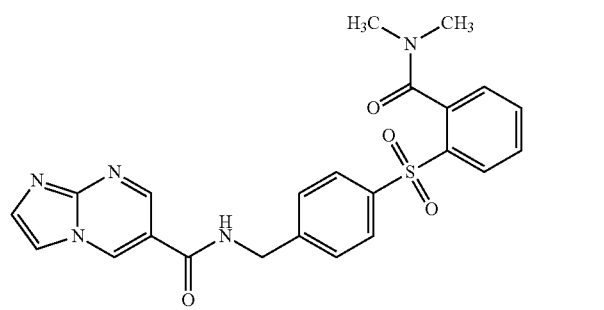 [SMILES: CN(C)C(=O)c1ccccc1S(=O)(=O)c1ccc(CNC(=O)c2cnc3nccn3c2)cc1] | N-[(4-{[2-(dimethylcarbamoyl)benzene]sulfonyl}phenyl)methyl]imidazo[1,2-a]pyrimidine-6-carboxamide |
| 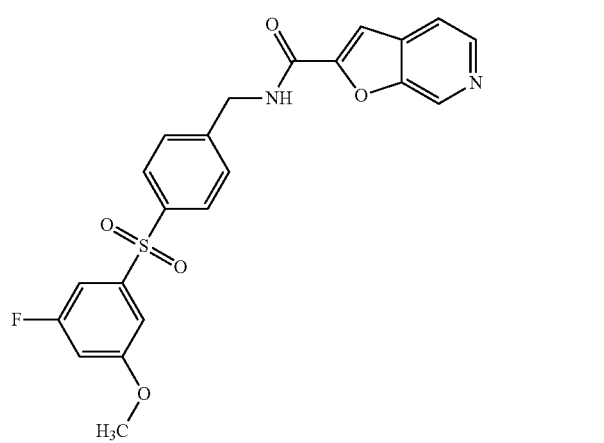 [SMILES: COc1cc(F)cc(S(=O)(=O)c2ccc(CNC(=O)c3cc4ccncc4o3)cc2)c1] | N-({4-[(3-fluoro-5-methoxybenzene)sulfonyl]phenyl}methyl)furo[2,3-c]pyridine-2-carboxamide |

| | |
|---|---|
| 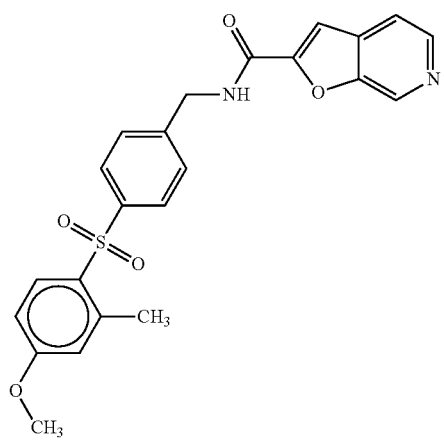 | N-({4-[(4-methoxy-2-methylbenzene)sulfonyl]phenyl}methyl)furo[2,3-c]pyridine-2-carboxamide |
| 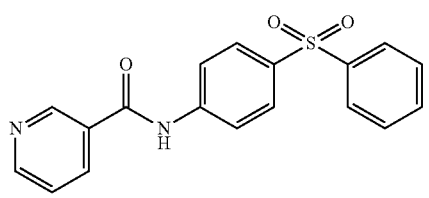 [SMILES: O=C(Nc1ccc(S(=O)(=O)c2ccccc2)cc1)c1cccnc1] | N-[4-(benzenesulfonyl)phenyl]pyridine-3-carboxamide |
| 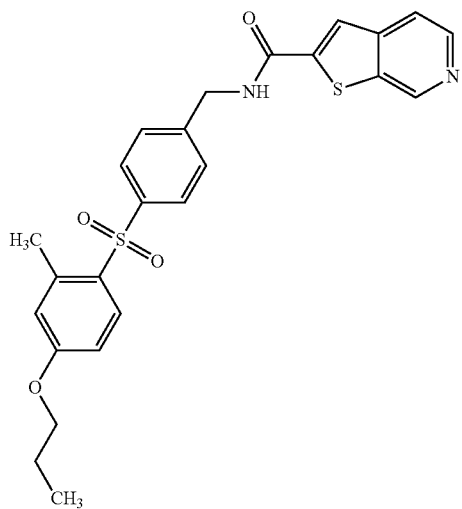 [SMILES: CCCOc1ccc(S(=O)(=O)c2ccc(CNC(=O)c3cc4ccncc4s3)cc2)c(C)c1] | N-({4-[(2-methyl-4-propoxybenzene)sulfonyl]phenyl}methyl)thieno[2,3-c]pyridine-2-carboxamide |
| 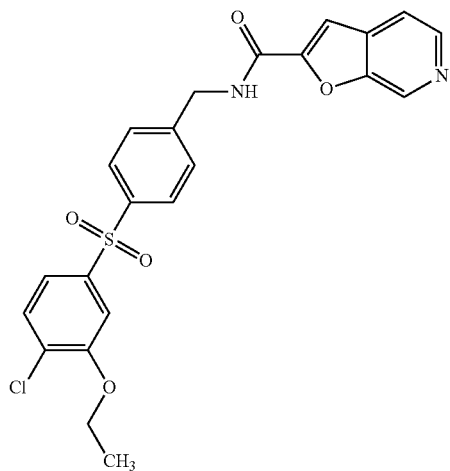 [SMILES: CCOc1cc(S(=O)(=O)c2ccc(CNC(=O)c3cc4ccncc4o3)cc2)ccc1Cl] | N-({4-[(3-ethoxy-4-fluorobenzene)sulfonyl]phenyl}methyl)furo[2,3-c]pyridine-2-carboxamide |

TABLE 2-continued
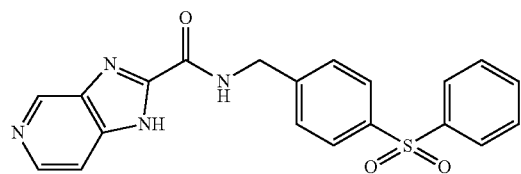 [SMILES: O=C(NCc1ccc(S(=O)(=O)c2ccccc2)cc1)c1nc2cnccc2[nH]1]
N-{[4-(benzenesulfonyl)phenyl]methyl}-1H-imidazo[4,5-c]pyridine-2-carboxamide
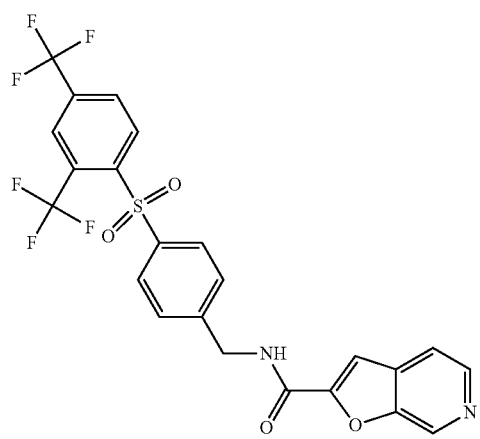 [SMILES: O=C(NCc1ccc(S(=O)(=O)c2ccc(C(F)(F)F)cc2C(F)(F)F)cc1)c1cc2ccncc2o1]
N-[(4-{[2,4-bis(trifluoromethyl)benzene]sulfonyl}phenyl)methyl]thieno[2,3-c]pyridine-2-carboxamide
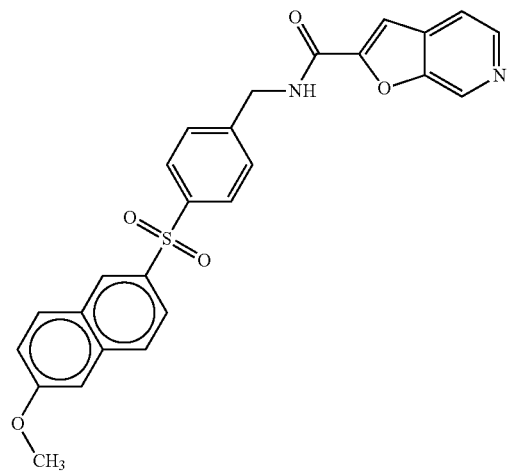
N-{[4-(6-methoxynaphthalene-2-sulfonyl)phenyl]methyl}thieno[2,3-c]pyridine-2-carboxamide
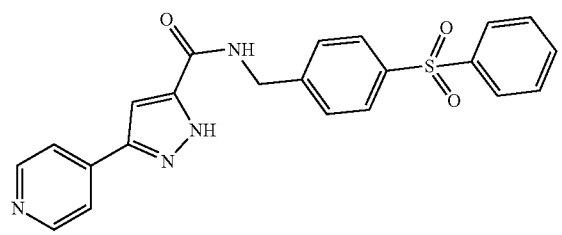 [SMILES: O=C(NCc1ccc(S(=O)(=O)c2ccccc2)cc1)c1cc(-c2ccncc2)n[nH]1]
N-{[4-(benzenesulfonyl)phenyl]methyl}-3-(pyridin-4-yl)-1H-pyrazole-5-carboxamide TABLE 2-continued
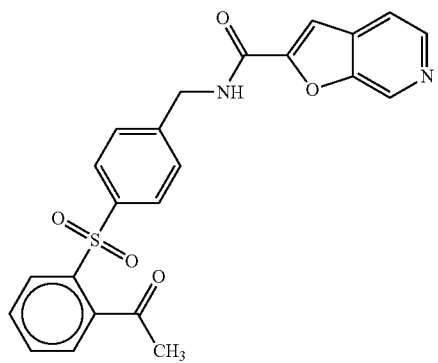
N-({4-[(2-acetylbenzene)sulfonyl]phenyl}methyl)furo[2,3-c]pyridine-2-carboxamide
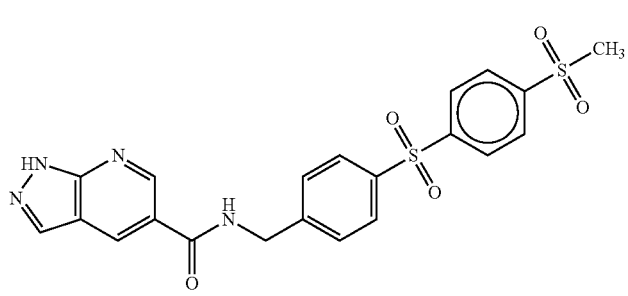
N-({4-[(4-methanesulfonylbenzene)sulfonyl]phenyl}methyl)-1H-pyrazolo[3,4-b]pyridine-5-carboxamide
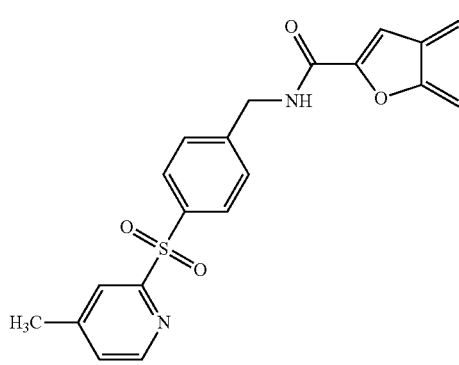
N-{[4-(4-methylpyridine-2-sulfonyl)phenyl]methyl}furo[2,3-c]pyridine-2-carboxamide
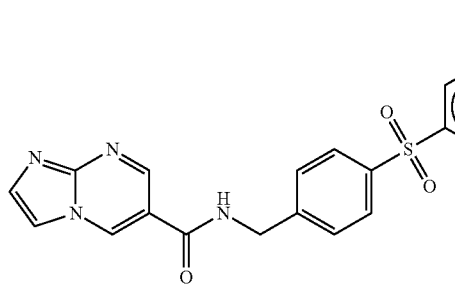
N-({4-[(3-fluoro-4-methoxybenzene)sulfonyl]phenyl}methyl)imidazo[1,2-a]pyrimidine-6-carboxamide TABLE 2-continued
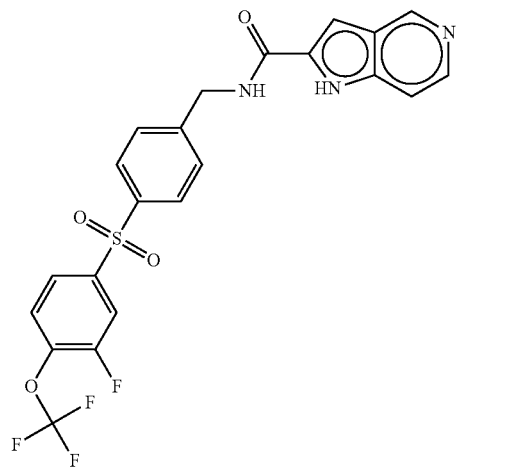
N-[(4-{[3-fluoro-4-(trifluoromethoxy)benzene]sulfonyl}phenyl)methyl]-1H-pyrrolo[3,2-c]pyridine-2-carboxamide
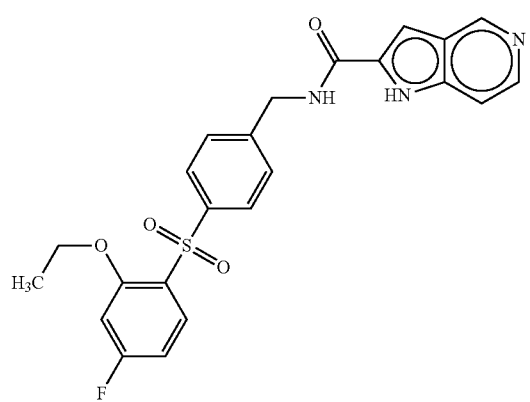
N-({4-[(2-ethoxy-4-fluorobenzene)sulfonyl]phenyl}methyl)-1H-pyrrolo[3,2-c]pyridine-2-carboxamide
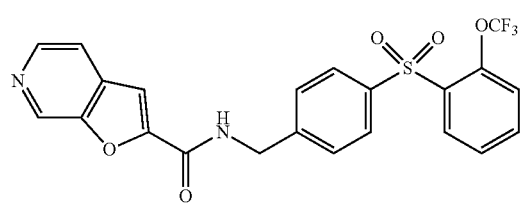 [SMILES: O=C(NCc1ccc(S(=O)(=O)c2ccccc2OC(F)(F)F)cc1)c1cc2ccncc2o1]
N-[(4-{[2-(trifluoromethoxy)benzene]sulfonyl}phenyl)methyl]thieno[2,3-c]pyridine-2-carboxamide
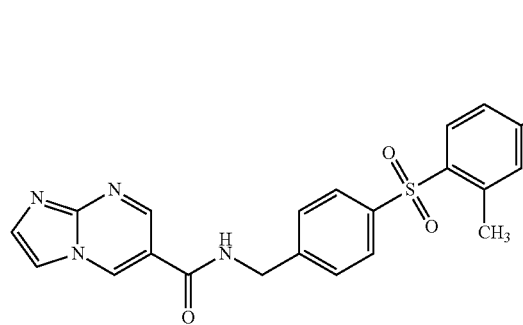
N-({4-[(4-ethoxy-2-methylbenzene)sulfonyl]phenyl}methyl)imidazo[1,2-a]pyrimidine-6-carboxamide TABLE 2-continued

| | |
|---|---|
| 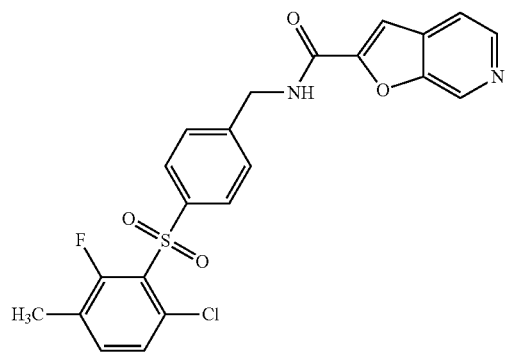 [SMILES: Cc1ccc(Cl)c(S(=O)(=O)c2ccc(CNC(=O)c3cc4ccncc4o3)cc2)c1F] | N-({4-[(6-chloro-2-fluoro-3-methylbenzene)sulfonyl]phenyl}methyl)furo[2,3-c]pyridine-2-carboxamide |
| 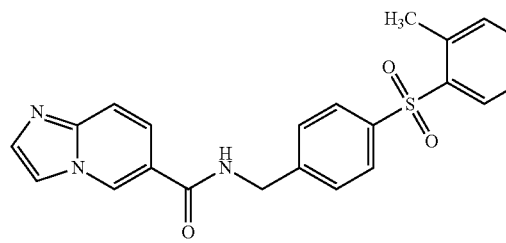 | N-({4-[(5-chloro-2-methylbenzene)sulfonyl]phenyl}methyl)imidazo[1,2-a]pyridine-6-carboxamide |
| 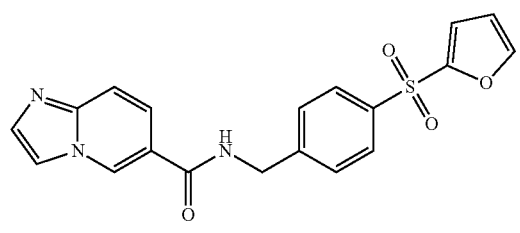 [SMILES: O=C(NCc1ccc(S(=O)(=O)c2ccco2)cc1)c1ccc2nccn2c1] | N-{[4-(furan-2-sulfonyl)phenyl]methyl}imidazo[1,2-a]pyridine-6-carboxamide |
| 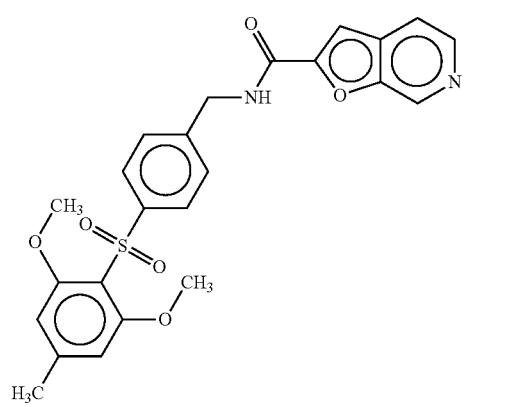 | N-({4-[(2,6-dimethoxy-4-methylbenzene)sulfonyl]phenyl}methyl)furo[2,3-c]pyridine-2-carboxamide |
| 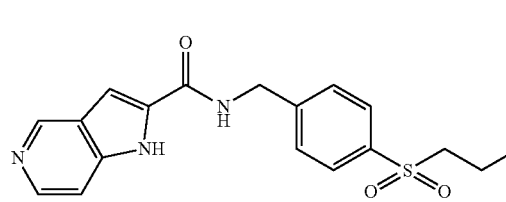 | N-({4-[(2-phenylethane)sulfonyl]phenyl}methyl)-1H-pyrrolo[3,2-c]pyridine-2-carboxamide |

TABLE 2-continued
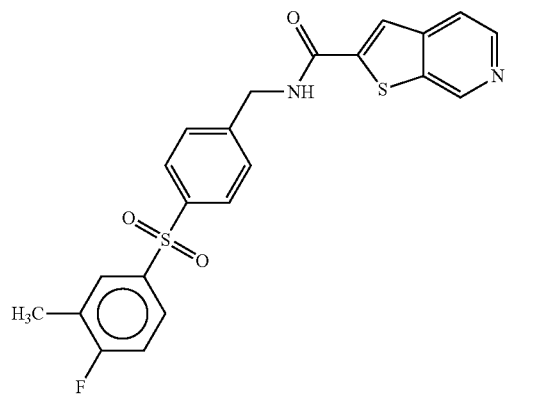
N-({4-[(4-fluoro-3-methylbenzene)sulfonyl]phenyl}methyl)thieno[2,3-c]pyridine-2-carboxamide
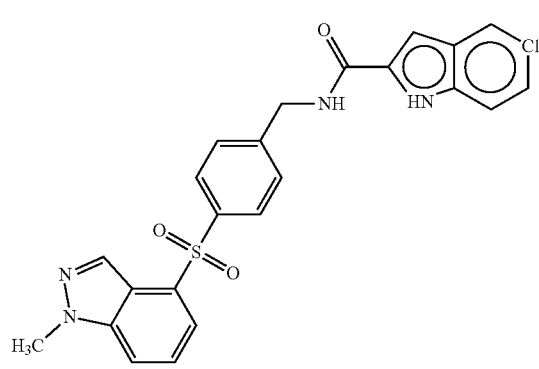
N-{[4-(1-methyl-1H-indazole-4-sulfonyl)phenyl]methyl}-1H-pyrrolo[3,2-c]pyridine-2-carboxamide
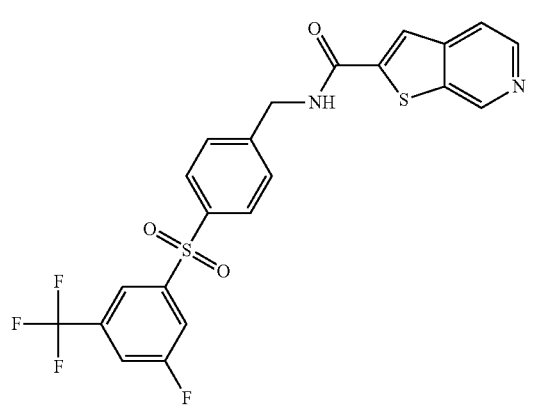 [SMILES: O=C(NCc1ccc(S(=O)(=O)c2cc(F)cc(C(F)(F)F)c2)cc1)c1cc2ccncc2s1]
N-[(4-{[3-fluoro-5-(trifluoromethyl)benzene]sulfonyl}phenyl)methyl]thieno[2,3-c]pyridine-2-carboxamide
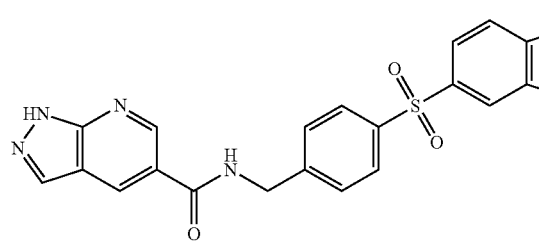
N-{[4-(1-methyl-1H-indazole-6-sulfonyl)phenyl]methyl}-1H-pyrazolo[3,4-b]pyridine-5-carboxamide TABLE 2-continued
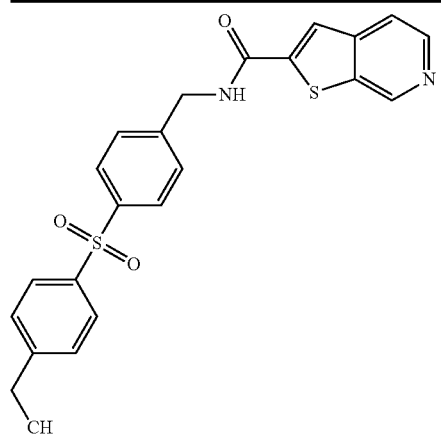
N-[(4-{[4-(hydroxymethyl)benzene]sulfonyl}phenyl)methyl]thieno[2,3-c]pyridine-2-carboxamide
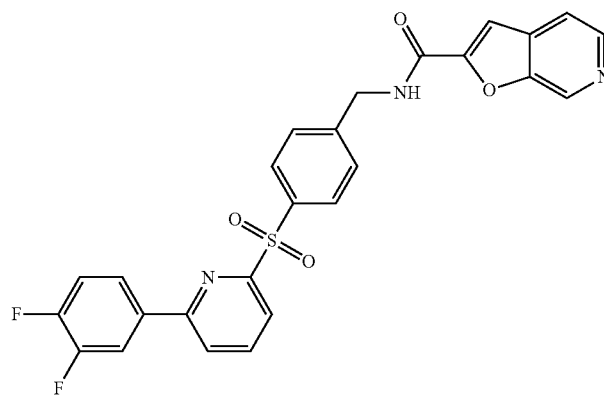
N-({4-[6-(3,4-difluorophenyl)pyridine-2-sulfonyl]phenyl}methyl)furo[2,3-c]pyridine-2-carboxamide
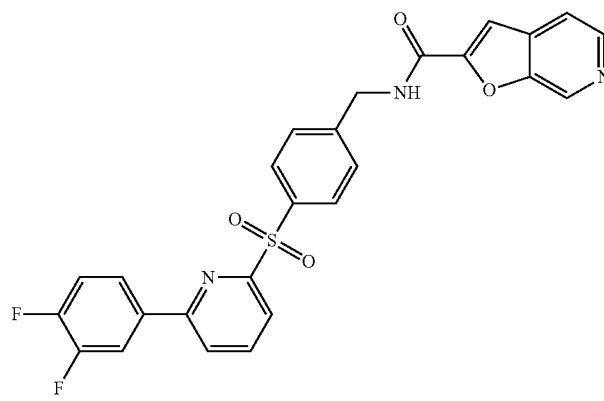
N-({4-[(3-methylbenzene)sulfonyl]phenyl}methyl)-1H-pyrrolo[3,2-c]pyridine-2-carboxamide
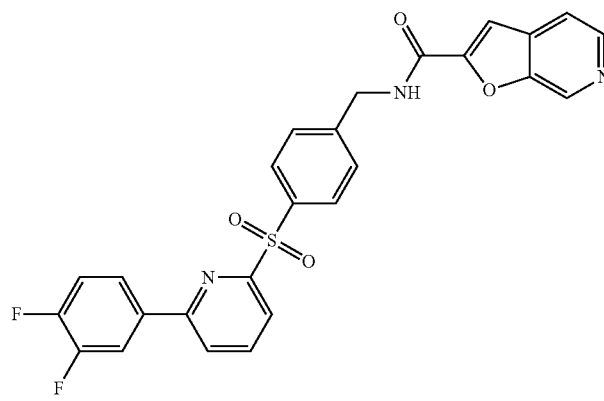
N-({4-[(3-fluoro-5-methylbenzene)sulfonyl]phenyl}methyl)imidazo[1,2-a]pyridine-6-carboxamide TABLE 2-continued
| | |
|---|---|
| 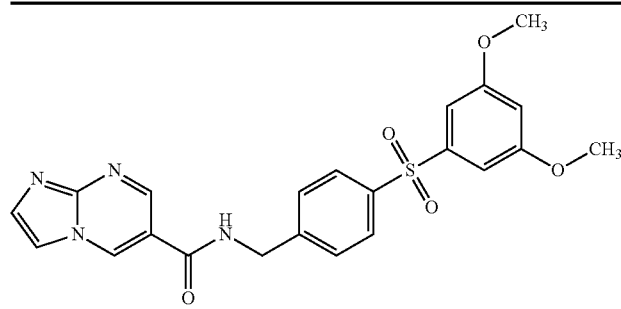 | N-({4-[(3,5-dimethoxybenzene)sulfonyl]phenyl}methyl)imidazo[1,2-a]pyrimidine-6-carboxamide |
| 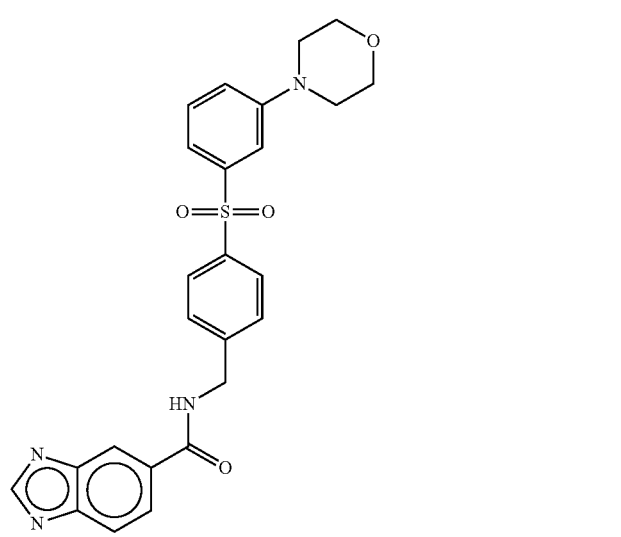 | N-[(4-{[3-(morpholin-4-yl)benzene]sulfonyl}phenyl)methyl]-1,3-benzothiazole-6-carboxamide |
| 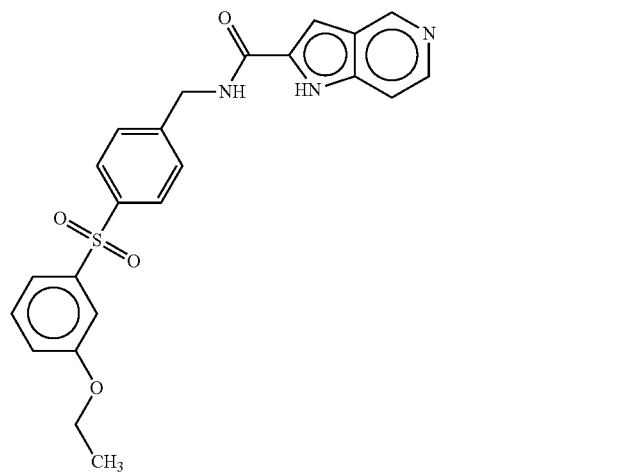 | N-({4-[(3-ethoxybenzene)sulfonyl]phenyl}methyl)-1H-pyrrolo[3,2-c]pyridine-2-carboxamide |

TABLE 2-continued
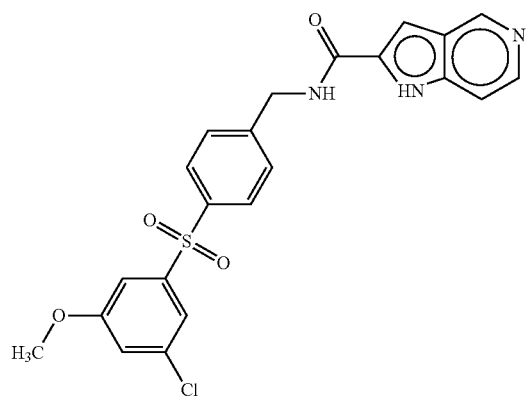
N-({4-[(3-chloro-5-methoxybenzene)sulfonyl]phenyl}methyl)-1H-pyrrolo[3,2-c]pyridine-2-carboxamide
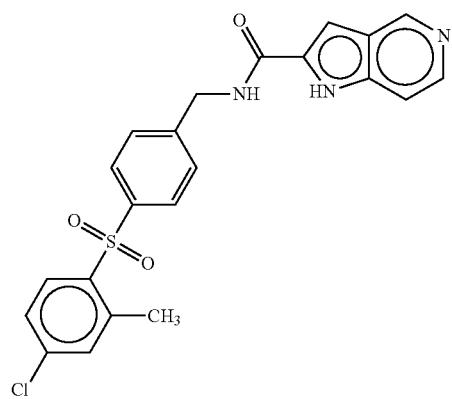
N-({4-[(4-chloro-2-methylbenzene)sulfonyl]phenyl}methyl)-1H-pyrrolo[3,2-c]pyridine-2-carboxamide
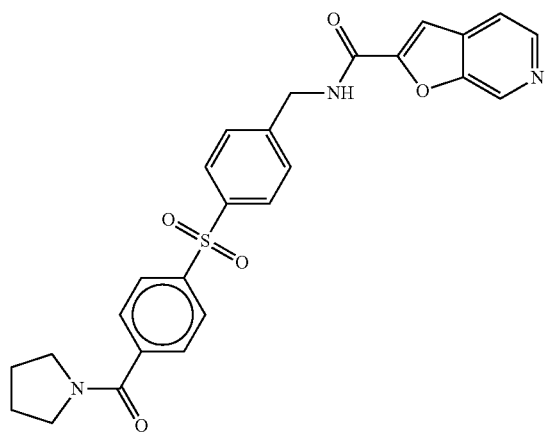
N-{[4-({4-[(pyrrolidin-1-yl)carbonyl]benzene]sulfonyl)phenyl]methyl}furo[2,3-c]pyridine-2-carboxamide
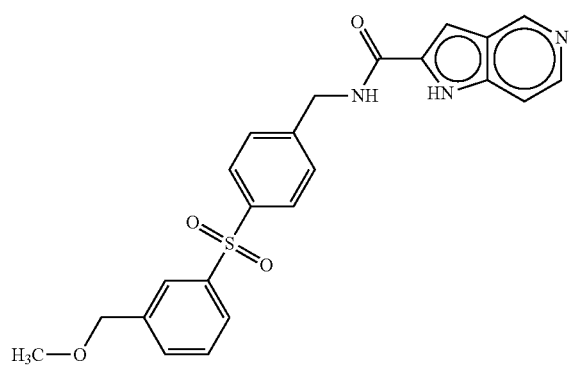
N-[(4-{[3-(methoxymethyl)benzene]sulfonyl}phenyl)methyl]-1H-pyrrolo[3,2-c]pyridine-2-carboxamide TABLE 2-continued
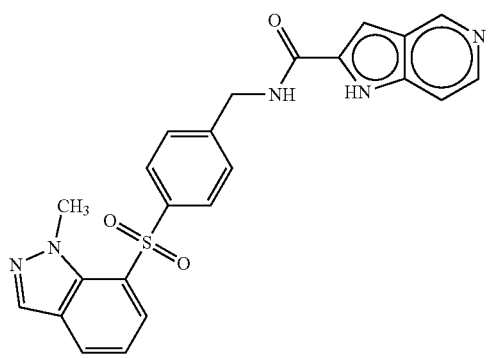
N-{[4-(1-methyl-1H-indazole-7-sulfonyl)phenyl]methyl}-1H-pyrrolo[3,2-c]pyridine-2-carboxamide
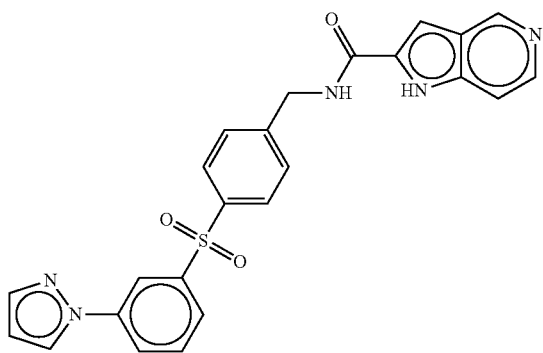
N-[(4-{[3-(1H-pyrazol-1-yl)benzene]sulfonyl}phenyl)methyl]-1H-pyrrolo[3,2-c]pyridine-2-carboxamide
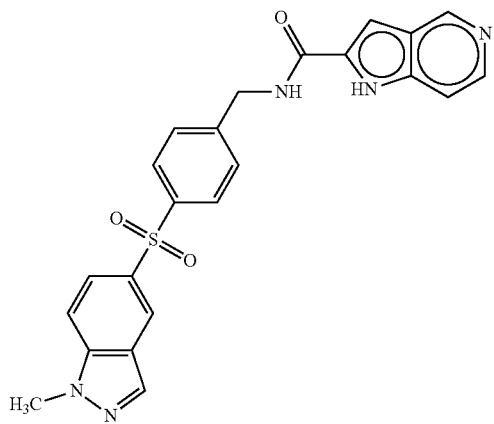
N-{[4-(1-methyl-1H-indazole-5-sulfonyl)phenyl]methyl}-1H-pyrrolo[3,2-c]pyridine-2-carboxamide
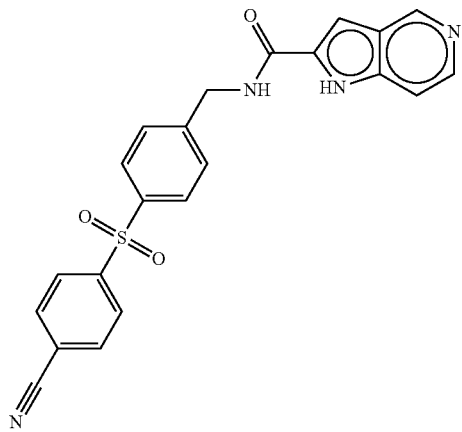
N-({4-[(4-cyanobenzene)sulfonyl]phenyl}methyl)-1H-pyrrolo[3,2-c]pyridine-2-carboxamide TABLE 2-continued
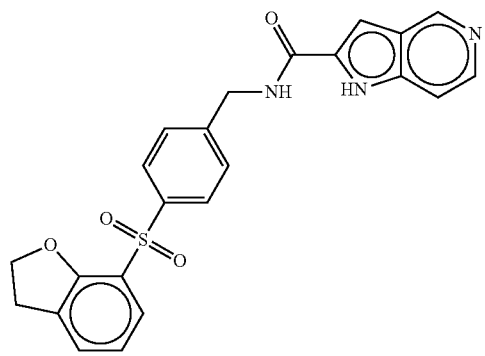
N-{[4-(2,3-dihydro-1-benzofuran-7-sulfonyl)phenyl]methyl)-1H-pyrrolo[3,2-c]pyridine-2-carboxamide
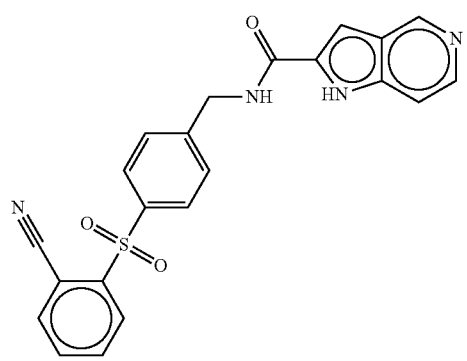
N-({4-[(2-cyanobenzene)sulfonyl]phenyl}methyl)-1H-pyrrolo[3,2-c]pyridine-2-carboxamide
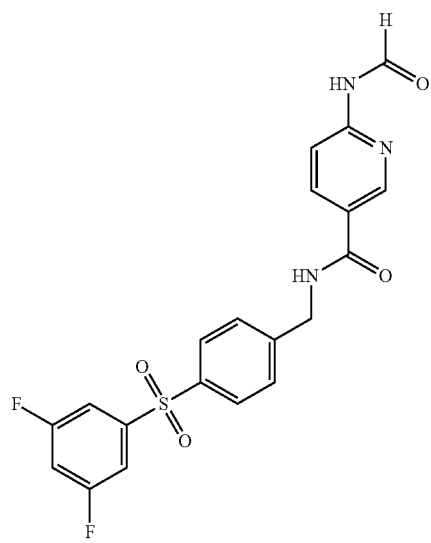 [SMILES: O=CNc1ccc(C(=O)NCc2ccc(S(=O)(=O)c3cc(F)cc(F)c3)cc2)cn1]
5-N-({4-[(3,5-difluorobenzene)sulfonyl]phenyl}methyl)pyridine-2,5-diamido
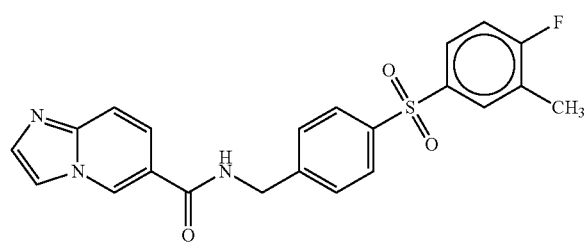
N-({4-[(4-fluoro-3-methylbenzene)sulfonyl]phenyl}methyl)imidazo[1,2-a]pyridine-6-carboxamide TABLE 2-continued

| | |
|---|---|
| 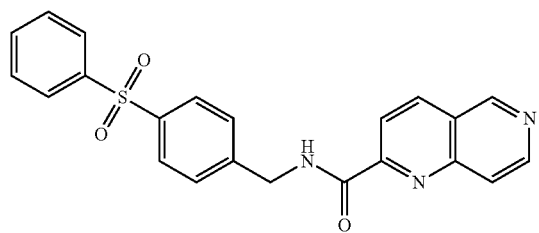 [SMILES: O=C(NCc1ccc(S(=O)(=O)c2ccccc2)cc1)c1ccc2cnccc2n1] | N-{[4-(benzenesulfonyl)phenyl]methyl}-1,6-naphthyridine-2-carboxamide |
| 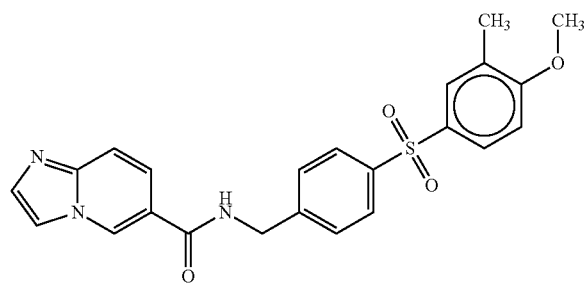 | N-({4-[(4-methoxy-3-methylbenzene)sulfonyl]phenyl}methyl)imidazo[1,2-a]pyridine-6-carboxamide |
| 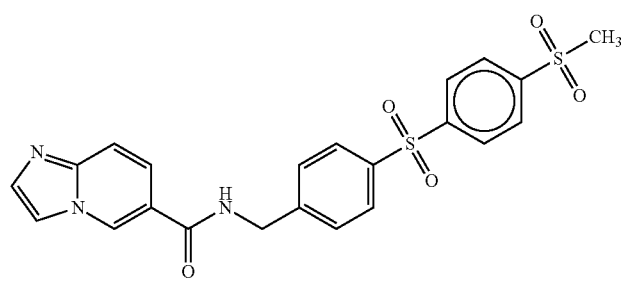 | N-({4-[(4-methanesulfonylbenzene)sulfonyl]phenyl}methyl)imidazo[1,2-a]pyridine-6-carboxamide |
| 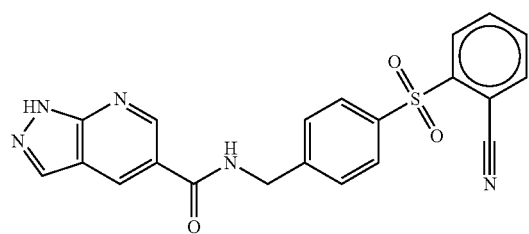 | N-({4-[(2-cyanobenzene)sulfonyl]phenyl}methyl)-1H-pyrazolo[3,4-b]pyridine-5-carboxamide |
| 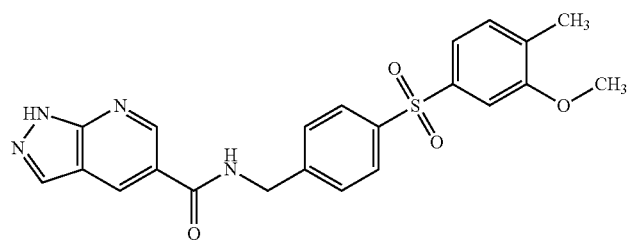 [SMILES: COc1cc(S(=O)(=O)c2ccc(CNC(=O)c3cnc4[nH]ncc4c3)cc2)ccc1C] | N-({4-[(3-methoxy-4-methylbenzene)sulfonyl]phenyl}methyl)-1H-pyrazolo[3,4-b]pyridine-5-carboxamide |
| 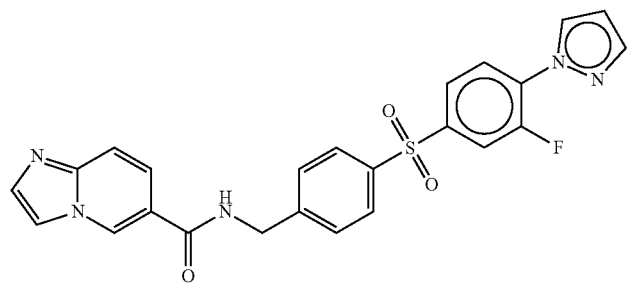 | N-[(4-{[3-fluoro-4-(1H-pyrazol-1-yl)benzene]sulfonyl}phenyl)methyl]imidazo[1,2-a]pyridine-6-carboxamide |

TABLE 2-continued

| 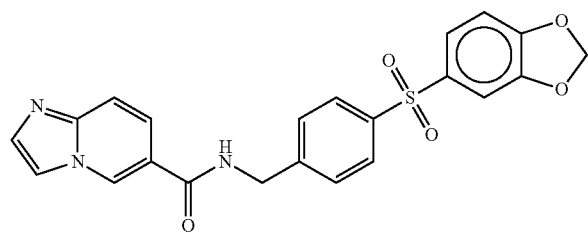 | N-{[4-(2H-1,3-benzodioxole-5-sulfonyl)phenyl]methyl}imidazo[1,2-a]pyridine-6-carboxamide |
| 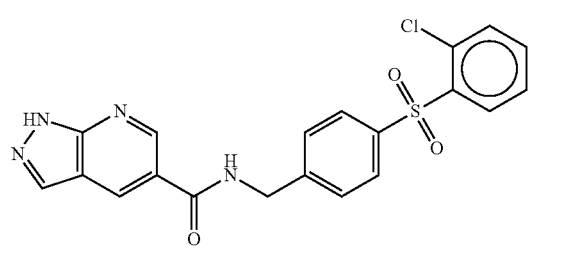 | N-({4-[(2-chlorobenzene)sulfonyl]phenyl}methyl)-1H-pyrazolo[3,4-b]pyridine-5-carboxamide |
| 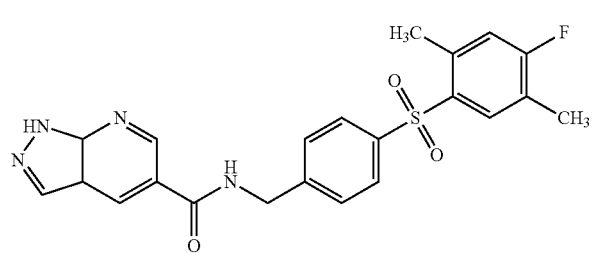 [SMILES: Cc1cc(S(=O)(=O)c2ccc(CNC(=O)C3=CC4C=NNC4N=C3)cc2)c(C)cc1F] | N-({4-[(4-fluoro-2,5-dimethylbenzene)sulfonyl]phenyl}methyl)-1H-pyrazolo[3,4-b]pyridine-5-carboxamide |
| 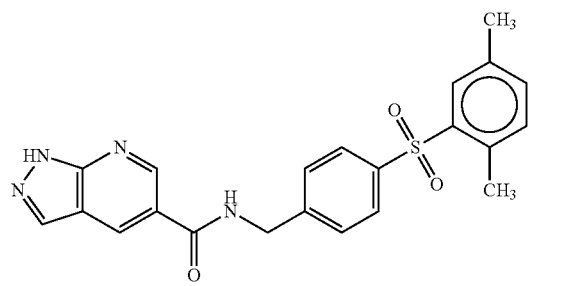 | N-({4-[(2,5-dimethylbenzene)sulfonyl]phenyl}methyl)-1H-pyrazolo[3,4-b]pyridine-5-carboxamide |
| 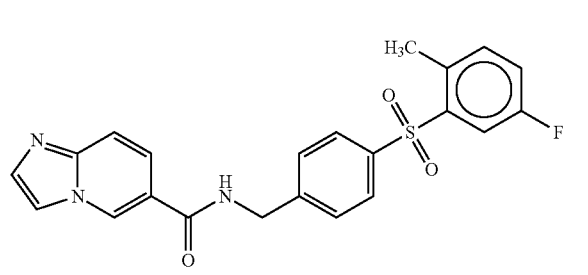 | N-({4-[(5-fluoro-2-methylbenzene)sulfonyl]phenyl}methyl)imidazo[1,2-a]pyridine-6-carboxamide |
| 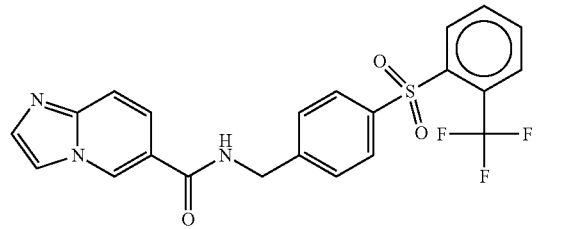 | N-[(4-{[2-(trifluoromethyl)benzene]sulfonyl}phenyl)methyl]imidazo[1,2-a]pyridine-6-carboxamide |

TABLE 2-continued

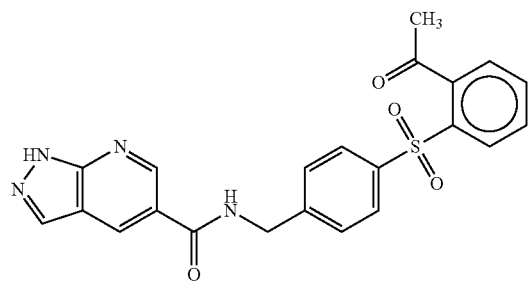
N-({4-[(2-acetylbenzene)sulfonyl]phenyl}methyl)-1H-pyrazolo[3,4-b]pyridine-5-carboxamide

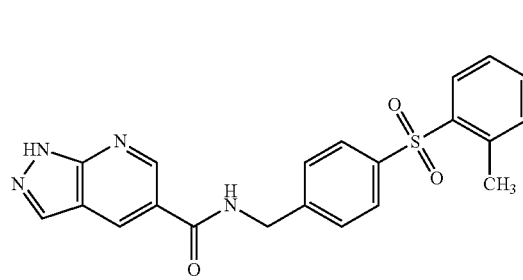
N-[(4-{[2-methyl-4-(trifluoromethyl)benzene]sulfonyl}phenyl)methyl]-1H-pyrazolo[3,4-b]pyridine-5-carboxamide

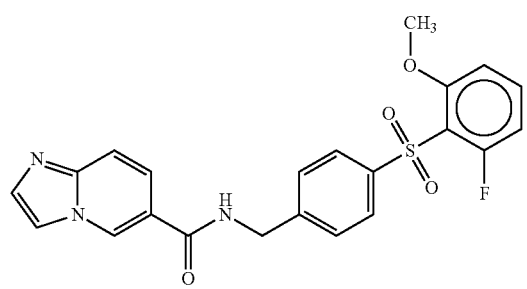
N-({4-[(2-fluoro-6-methoxybenzene)sulfonyl]phenyl}methyl)imidazo[1,2-a]pyridine-6-carboxamide

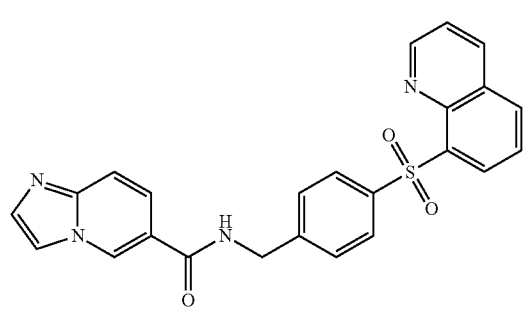 [SMILES: O=C(NCc1ccc(S(=O)(=O)c2cccc3cccnc23)cc1)c1ccc2nccn2c1]
N-{[4-(quinoline-8-sulfonyl)phenyl]methyl}imidazo[1,2-a]pyridine-6-carboxamide

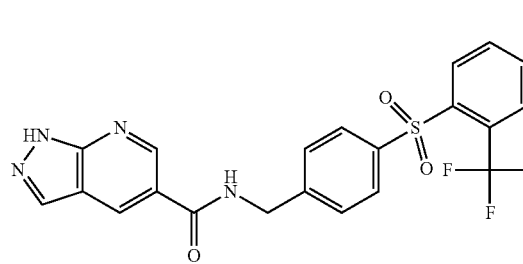
N-[(4-{[4-chloro-2-(trifluoromethyl)benzene]sulfonyl}phenyl)methyl]-1H-pyrazolo[3,4-b]pyridine-5-carboxamide TABLE 2-continued

| | |
|---|---|
| 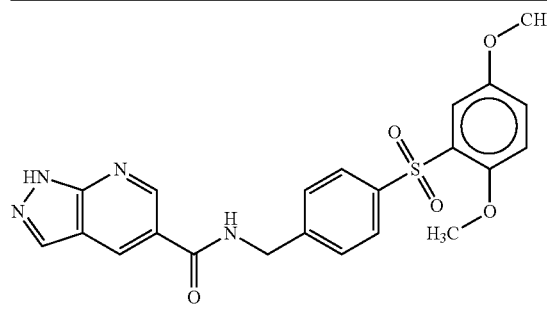 | N-({4-[(2,5-dimethoxybenzene)sulfonyl]phenyl}methyl)-1H-pyrazolo[3,4-b]pyridine-5-carboxamide |
| 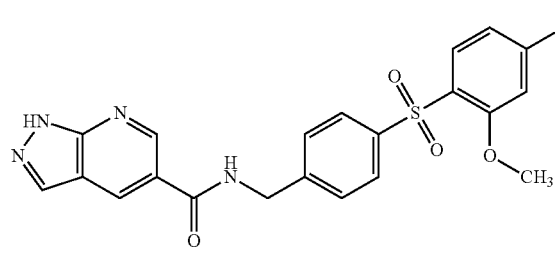 | N-({4-[(4-fluoro-2-methoxybenzene)sulfonyl]phenyl)methyl)-1H-pyrazolo[3,4-b]pyridine-5-carboxamide |
| 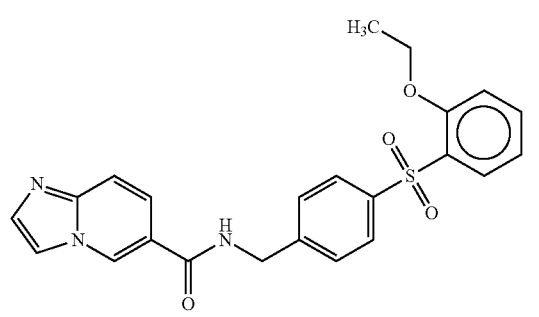 | N-({4-[(2-ethoxybenzene)sulfonyl]phenyl}methyl)imidazo[1,2-a]pyridine-6-carboxamide |
| 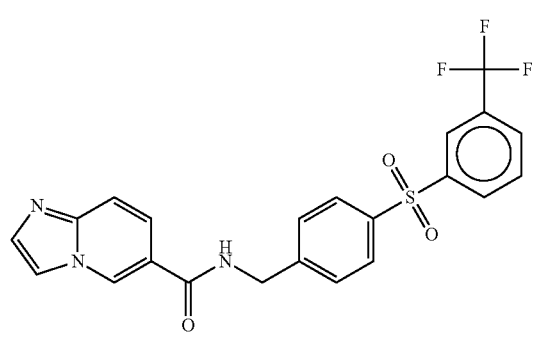 | N-[(4-{[3-(trifluoromethyl)benzene]sulfonyl}phenyl)methyl]imidazo[1,2-a]pyridine-6-carboxamide |
| 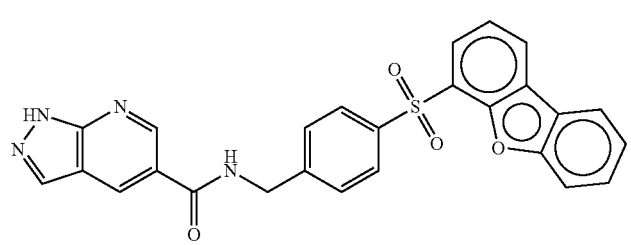 | N-[(4-{8-oxatricyclo[7.4.0.0$^{2,7}$]trideca-1(13),2,4,6,9,11-hexaene-6-sulfonyl}phenyl)methyl]-1H-pyrazolo[3,4-b]pyridine-5-carboxamide |

TABLE 2-continued
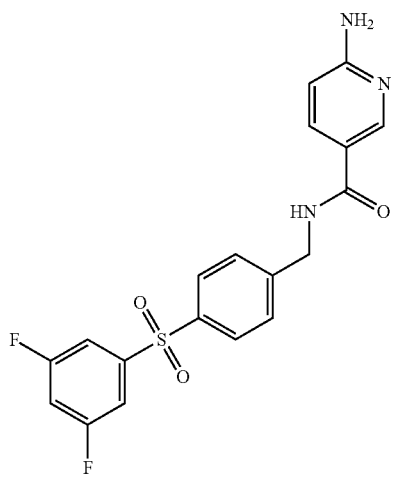 [SMILES: Nc1ccc(C(=O)NCc2ccc(S(=O)(=O)c3cc(F)cc(F)c3)cc2)cn1]
6-amino-N-({4-[(3,5-difluorobenzene)sulfonyl]phenyl}methyl)pyridine-3-carboxamide
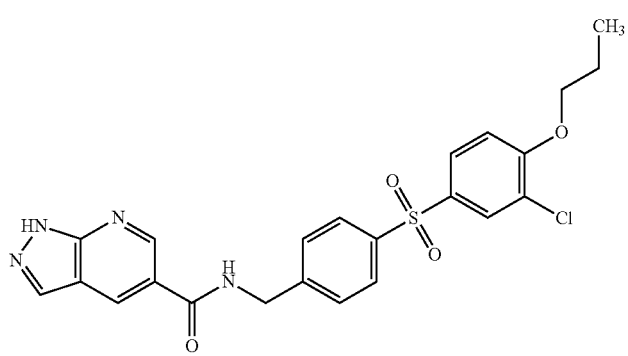
N-({4-[(3-chloro-4-propoxybenzene)sulfonyl]phenyl}methyl)-1H-pyrazolo[3,4-b]pyridine-5-carboxamide
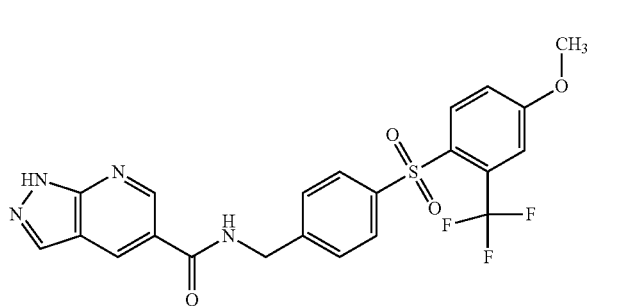 [SMILES: COc1ccc(S(=O)(=O)c2ccc(CNC(=O)c3cnc4[nH]ncc4c3)cc2)c(C(F)(F)F)c1]
N-[(4-{[4-methoxy-2-(trifluoromethyl)benzene]sulfonyl}phenyl)methyl]-1H-pyrazolo[3,4-b]pyridine-5-carboxamide
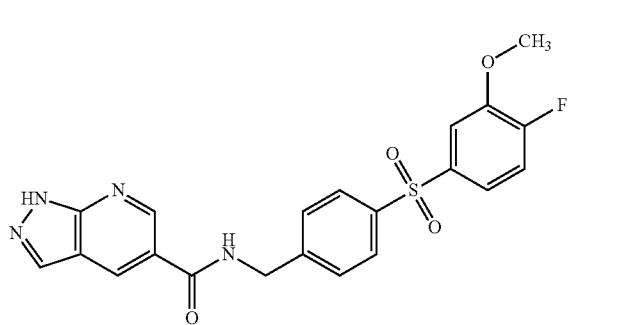 [SMILES: COc1cc(S(=O)(=O)c2ccc(CNC(=O)c3cnc4[nH]ncc4c3)cc2)ccc1F]
N-({4-[(4-fluoro-3-methoxybenzene)sulfonyl]phenyl}methyl)-1H-pyrazolo[3,4-b]pyridine-5-carboxamide TABLE 2-continued

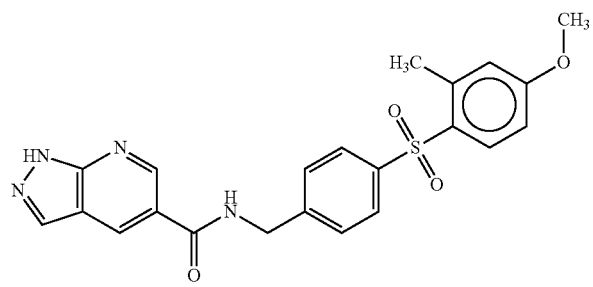

N-({4-[(4-methoxy-2-methylbenzene)sulfonyl]phenyl}methyl)-1H-pyrazolo[3,4-b]pyridine-5-carboxamide

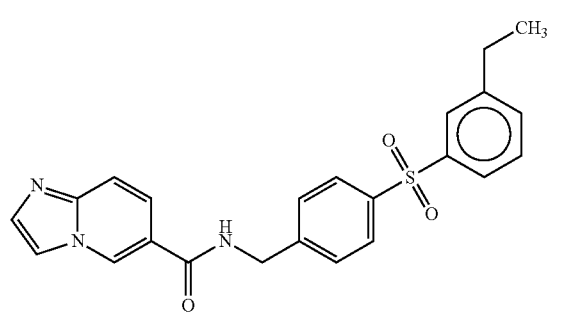

N-({4-[(3-ethylbenzene)sulfonyl]phenyl}methyl)imidazo[1,2-a]pyridine-6-carboxamide

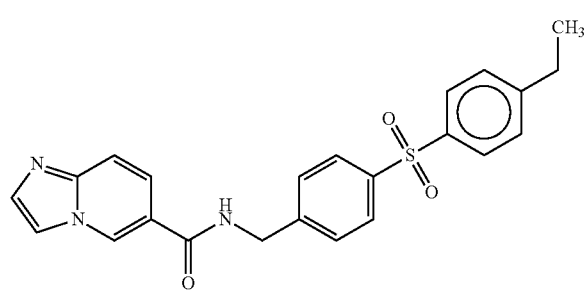

N-({4-[(4-ethylbenzene)sulfonyl]phenyl}methyl)imidazo[1,2-a]pyridine-6-carboxamide

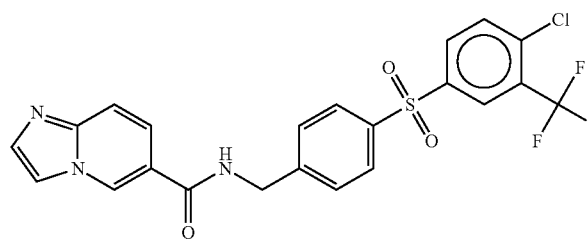

N-[(4-{[4-chloro-3-(trifluoromethyl)benzene]sulfonyl}phenyl)methyl]imidazo[1,2-a]pyridine-6-carboxamide

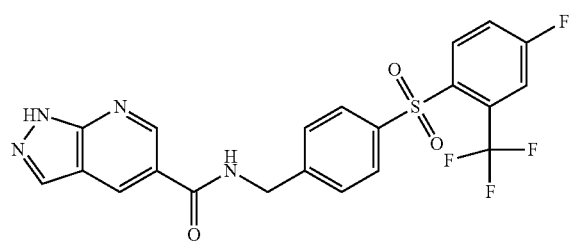 [SMILES: O=C(NCc1ccc(S(=O)(=O)c2ccc(F)cc2C(F)(F)F)cc1)c1cnc2[nH]ncc2c1]

N-[(4-{[4-fluoro-2-(trifluoromethyl)benzene]sulfonyl}phenyl)methyl]-1H-pyrazolo[3,4-b]pyridine-5-carboxamide TABLE 2-continued
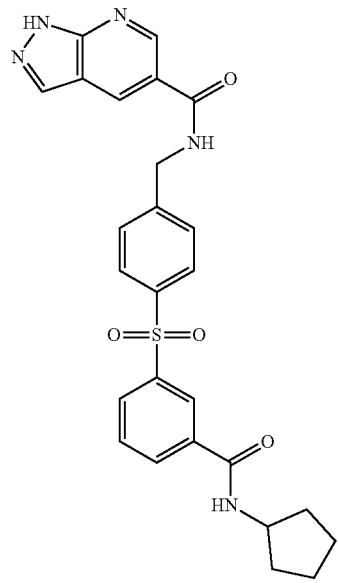 [SMILES: O=C(NCc1ccc(S(=O)(=O)c2cccc(C(=O)NC3CCCC3)c2)cc1)c1cnc2[nH]ncc2c1]
N-[(4-{[3-(cyclopentylcarbamoyl)benzene]sulfonyl}phenyl)methyl]-1H-pyrazolo[3,4-b]pyridine-5-carboxamide
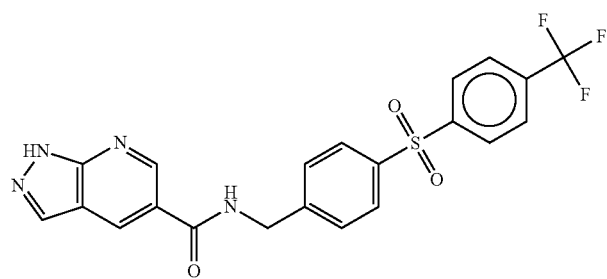
N-[(4-{[4-(trifluoromethyl)benzene]sulfonyl}phenyl)methyl]-1H-pyrazolo[3,4-b]pyridine-5-carboxamide
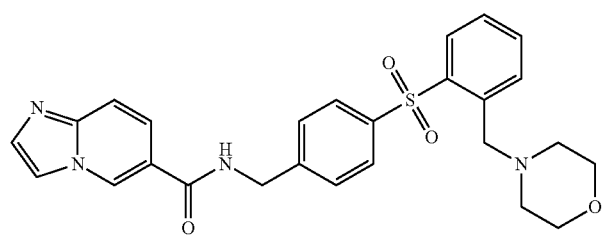 [SMILES: O=C(NCc1ccc(S(=O)(=O)c2ccccc2CN2CCOCC2)cc1)c1ccc2nccn2c1]
N-[(4-{[2-(morpholin-4-ylmethyl)benzene]sulfonyl}phenyl)methyl]imidazo[1,2-a]pyridine-6-carboxamide
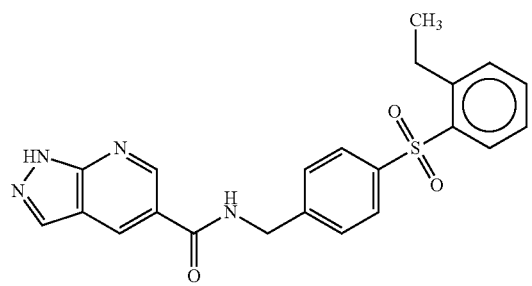
N-({4-[(2-ethylbenzene)sulfonyl]phenyl}methyl)-1H-pyrazolo[3,4-b]pyridine-5-carboxamide TABLE 2-continued

| | |
|---|---|
| 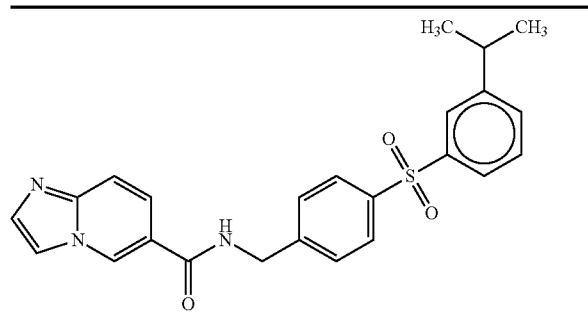 | N-[(4-{[3-(propan-2-yl)benzene]sulfonyl}phenyl)methyl]imidazo[1,2-a]pyridine-6-carboxamide |
| 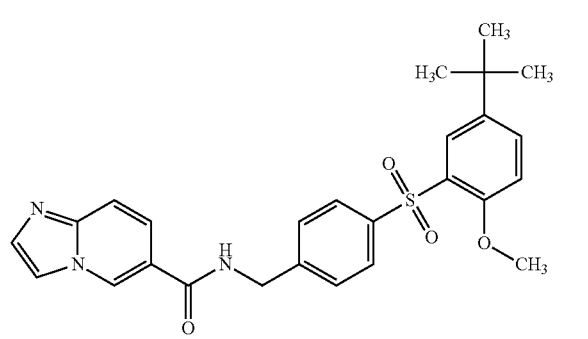 [SMILES: COc1ccc(C(C)(C)C)cc1S(=O)(=O)c1ccc(CNC(=O)c2ccc3nccn3c2)cc1] | N-({4-[(5-tert-butyl-2-methoxybenzene)sulfonyl]phenyl}methyl)imidazo[1,2-a]pyridine-6-carboxamide |
| 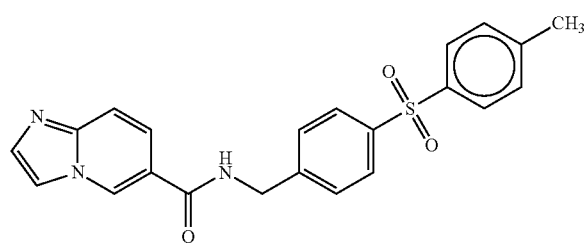 | N-({4-[(4-methylbenzene)sulfonyl]phenyl}methyl)imidazo[1,2-a]pyridine-6-carboxamide |
| 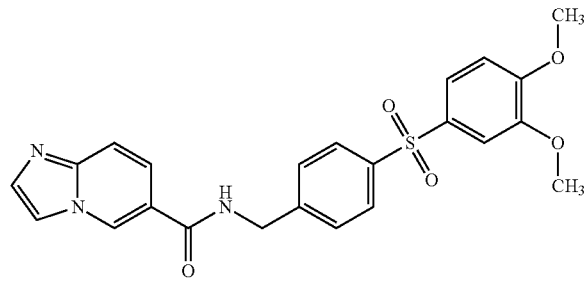 | N-({4-[(3,4-dimethoxybenzene)sulfonyl]phenyl}methyl)imidazo[1,2-a]pyridine-6-carboxamide |
| 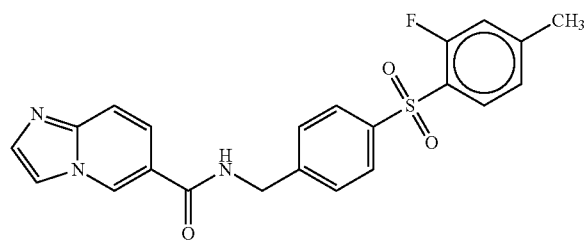 | N-({4-[(2-fluoro-4-methylbenzene)sulfonyl]phenyl}methyl)imidazo[1,2-a]pyridine-6-carboxamide |
| 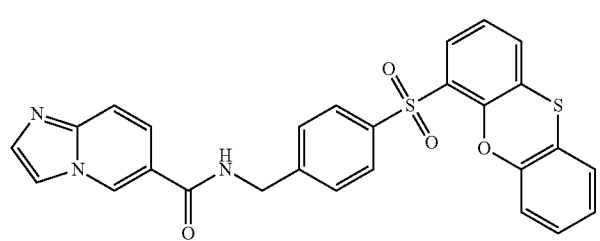 [SMILES: O=C(NCc1ccc(S(=O)(=O)c2cccc3c2Oc2ccccc2S3)cc1)c1ccc2nccn2c1] | N-{[4-(phenoxathiine-4-sulfonyl)phenyl]methyl}imidazo[1,2-a]pyridine-6-carboxamide |

TABLE 2-continued

| | |
|---|---|
| 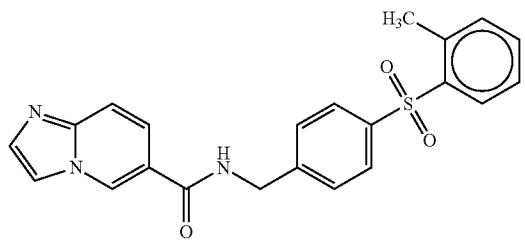 | N-({4-[(2-methylbenzene)sulfonyl]phenyl)methyl)imidazo[1,2-a]pyridine-6-carboxamide |
| 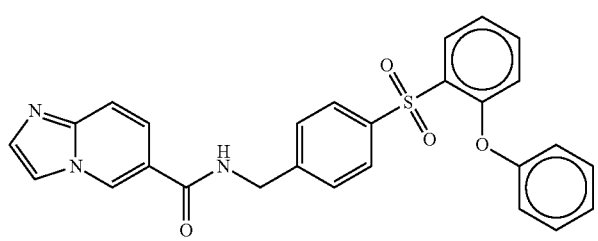 | N-({4-[(2-phenoxybenzene)sulfonyl]phenyl}methyl)imidazo[1,2-a]pyridine-6-carboxamide |
| 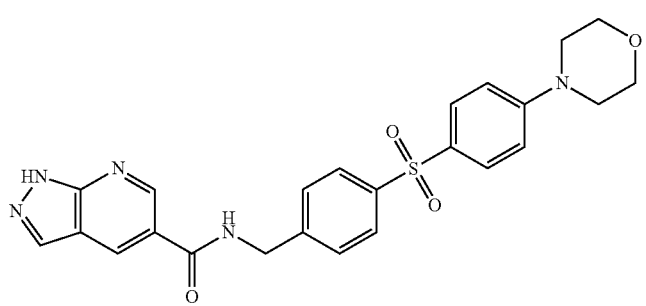 | N-[(4-{[4-(morpholin-4-yl)benzene]sulfonyl}phenyl)methyl]-1H-pyrazolo[3,4-b]pyridine-5-carboxamide |
| 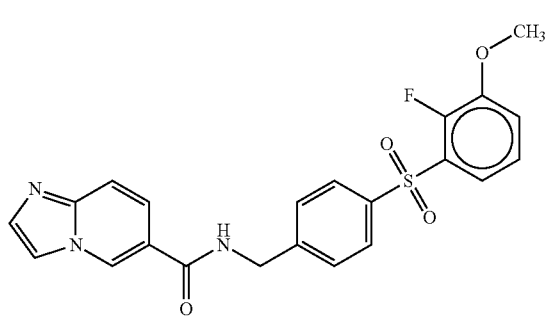 | N-({4-[(2-fluoro-3-methoxybenzene)sulfonyl]phenyl}methyl)imidazo[1,2-a]pyridine-6-carboxamide |
| 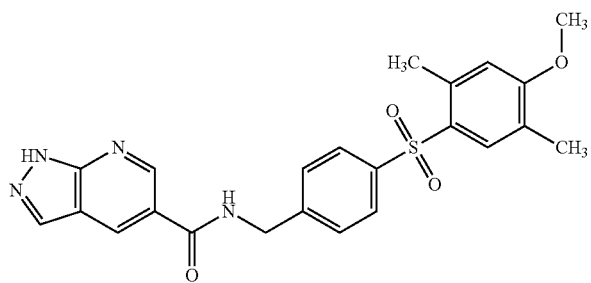 [SMILES: COc1cc(C)c(S(=O)(=O)c2ccc(CNC(=O)c3cnc4[nH]ncc4c3)cc2)cc1C] | N-({4-[(4-methoxy-2,5-dimethylbenzene)sulfonyl]phenyl}methyl)-1H-pyrazolo[3,4-b]pyridine-5-carboxamide |

TABLE 2-continued

| | |
|---|---|
| 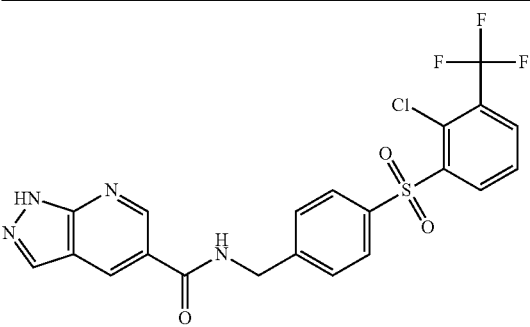 | N-[(4-{[2-chloro-3-(trifluoromethyl)benzene]sulfonyl}phenyl)methyl]-1H-pyrazolo[3,4-b]pyridine-5-carboxamide |
| 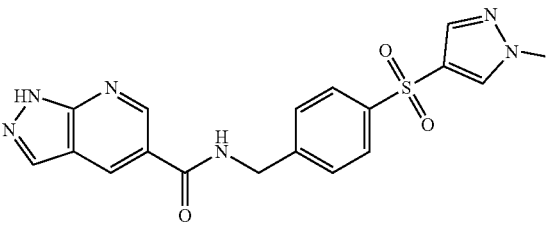 | N-{[4-(1-methyl-1H-pyrazole-4-sulfonyl)phenyl]methyl}-1H-pyrazolo[3,4-b]pyridine-5-carboxamide |
| 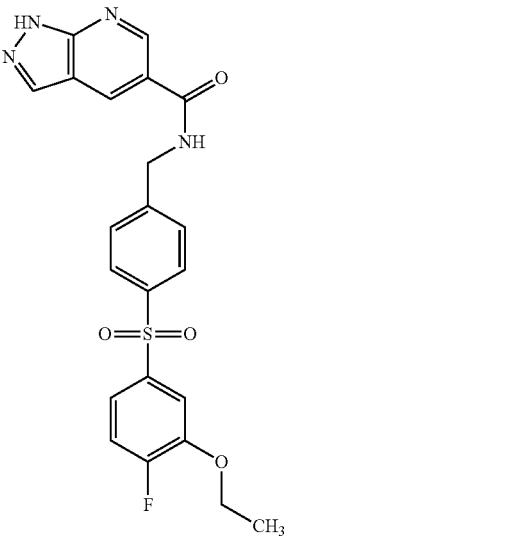 [SMILES: CCOc1cc(S(=O)(=O)c2ccc(CNC(=O)c3cnc4[nH]ncc4c3)cc2)ccc1F] | N-({4-[(3-ethoxy-4-fluorobenzene)sulfonyl]phenyl}methyl)-1H-pyrazolo[3,4-b]pyridine-5-carboxamide |
| 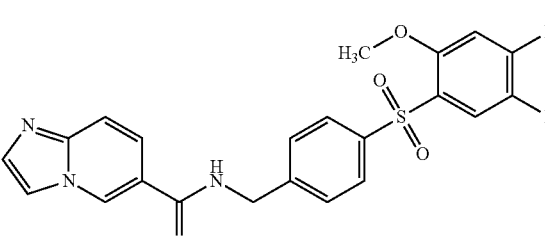 | N-({4-[(4,5-difluoro-2-methoxybenzene)sulfonyl]phenyl}methyl)imidazo[1,2-a]pyridine-6-carboxamide |
| 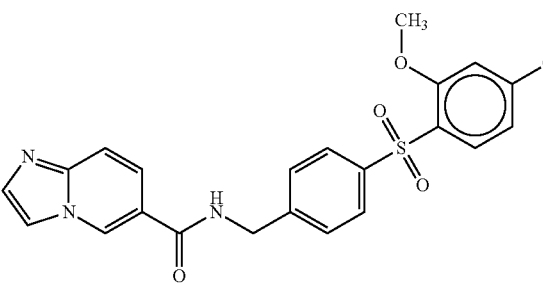 | N-({4-[(2,4-dimethoxybenzene)sulfonyl]phenyl}methyl)imidazo[1,2-a]pyridine-6-carboxamide |

TABLE 2-continued

| Structure | Name |
|---|---|
| (pyrazolo[1,5-a]pyridine-carboxamide linked via CH2NH to phenyl-SO2-2,4-difluorophenyl) | N-({4-[(2,4-difluorobenzene)sulfonyl]phenyl}methyl)imidazo[1,2-a]pyridine-6-carboxamide |
| (1H-pyrazolo[3,4-b]pyridine-5-carboxamide linked to phenyl-SO2-(5-methylthiophen-2-yl)) | N-{[4-(5-methylthiophene-2-sulfonyl)phenyl]methyl}-1H-pyrazolo[3,4-b]pyridine-5-carboxamide |
| (1H-pyrazolo[3,4-b]pyridine-5-carboxamide linked to phenyl-SO2-(2-ethyl-5-fluorophenyl)) | N-[(4-{[5-fluoro-2-(hydroxymethyl)benzene]sulfonyl}phenyl)methyl]-1H-pyrazolo[3,4-b]pyridine-5-carboxamide |
| (1H-pyrazolo[3,4-b]pyridine-5-carboxamide linked to phenyl-SO2-phenyl-C(O)NHEt) | N-[(4-{[4-(ethylcarbamoyl)benzene]sulfonyl}phenyl)methyl]-1H-pyrazolo[3,4-b]pyridine-5-carboxamide |
| (1H-pyrazolo[3,4-b]pyridine-5-carboxamide linked to phenyl-SO2-(4-methoxy-3,5-dimethylphenyl)) | N-({4-[(4-methoxy-3,5-dimethylbenzene)sulfonyl]phenyl}methyl)-1H-pyrazolo[3,4-b]pyridine-5-carboxamide |

TABLE 2-continued
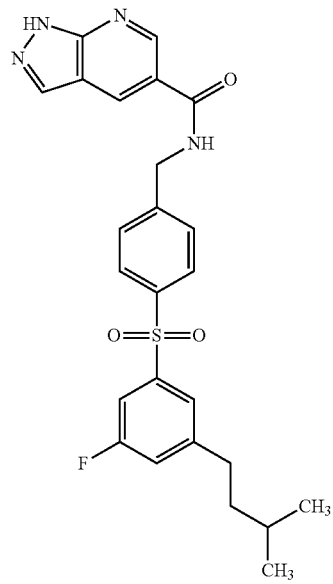 [SMILES: CC(C)CCc1cc(F)cc(S(=O)(=O)c2ccc(CNC(=O)c3cnc4[nH]ncc4c3)cc2)c1]
N-[(4-{[3-fluoro-5-(2-methylpropoxy)benzene]sulfonyl}phenyl)methyl]-1H-pyrazolo[3,4-b]pyridine-5-carboxamide
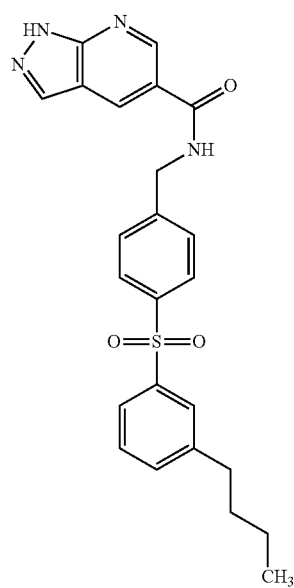 [SMILES: CCCCc1cccc(S(=O)(=O)c2ccc(CNC(=O)c3cnc4[nH]ncc4c3)cc2)c1]
N-({4-[(3-propoxybenzene)sulfonyl]phenyl}methyl)-1H-pyrazolo[3,4-b]pyridine-5-carboxamide
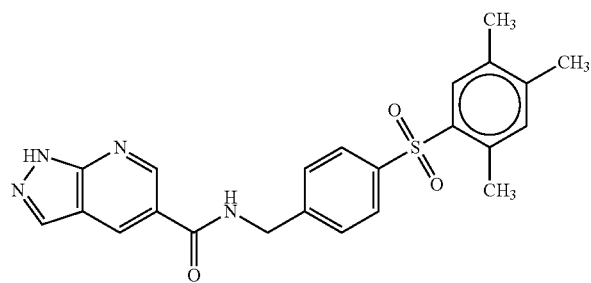
N-({4-[(2,4,5-trimethylbenzene)sulfonyl]phenyl}methyl)-1H-pyrazolo[3,4-b]pyridine-5-carboxamide TABLE 2-continued

| Structure | Name |
|---|---|
| (structure) | N-({4-[(2-chloro-4-methoxybenzene)sulfonyl]phenyl}methyl)-1H-pyrazolo[3,4-b]pyridine-5-carboxamide |
| (structure) | N-({4-[(2,3,6-trimethoxybenzene)sulfonyl]phenyl}methyl)-1H-pyrazolo[3,4-b]pyridine-5-carboxamide |
| (structure) | N-[(4-{[2-chloro-4-(trifluoromethyl)benzene]sulfonyl]phenyl)methyl]-1H-pyrazolo[3,4-b]pyridine-5-carboxamide |
| (structure) | N-({4-[(3-fluoro-2-methylbenzene)sulfonyl]phenyl}methyl)-1H-pyrazolo[3,4-b]pyridine-5-carboxamide |
| (structure) | N-({4-[(3-methylbenzene)sulfonyl]phenyl}methyl)imidazo[1,2-a]pyridine-6-carboxamide |

TABLE 2-continued

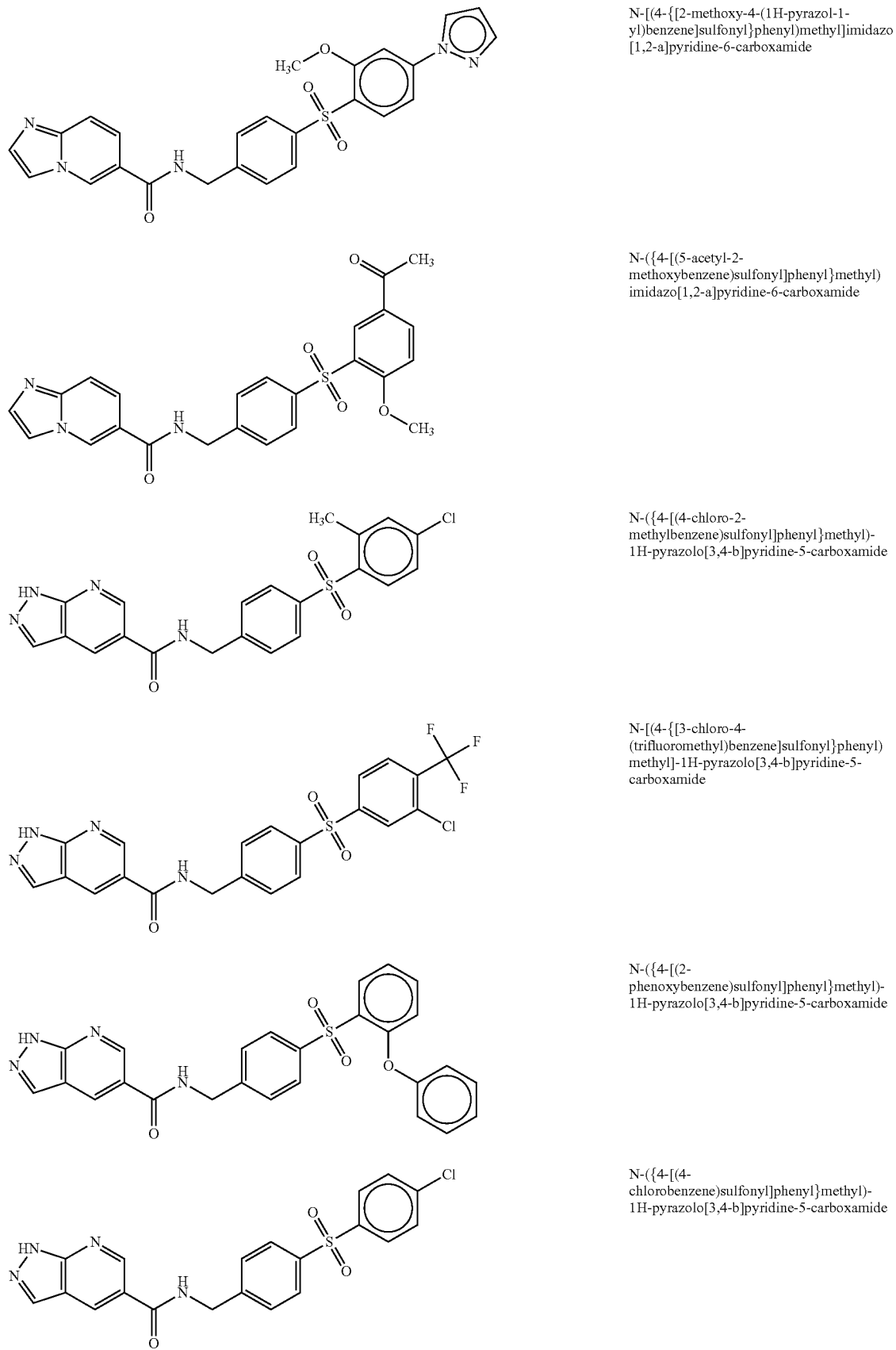

N-[(4-{[2-methoxy-4-(1H-pyrazol-1-yl)benzene]sulfonyl}phenyl)methyl]imidazo[1,2-a]pyridine-6-carboxamide N-({4-[(5-acetyl-2-methoxybenzene)sulfonyl]phenyl}methyl)imidazo[1,2-a]pyridine-6-carboxamide N-({4-[(4-chloro-2-methylbenzene)sulfonyl]phenyl}methyl)-1H-pyrazolo[3,4-b]pyridine-5-carboxamide N-[(4-{[3-chloro-4-(trifluoromethyl)benzene]sulfonyl}phenyl)methyl]-1H-pyrazolo[3,4-b]pyridine-5-carboxamide N-({4-[(2-phenoxybenzene)sulfonyl]phenyl}methyl)-1H-pyrazolo[3,4-b]pyridine-5-carboxamide N-({4-[(4-chlorobenzene)sulfonyl]phenyl}methyl)-1H-pyrazolo[3,4-b]pyridine-5-carboxamide TABLE 2-continued

| | |
|---|---|
| 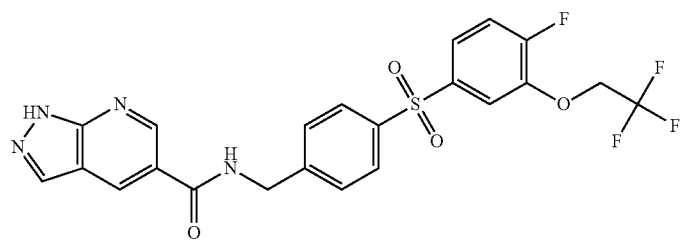 [SMILES: O=C(NCc1ccc(S(=O)(=O)c2ccc(F)c(OCC(F)(F)F)c2)cc1)c1cnc2[nH]ncc2c1] | N-[(4-{[4-fluoro-3-(2,2,2-trifluoroethoxy)benzene]sulfonyl}phenyl)methyl]-1H-pyrazolo[3,4-b]pyridine-5-carboxamide |
| 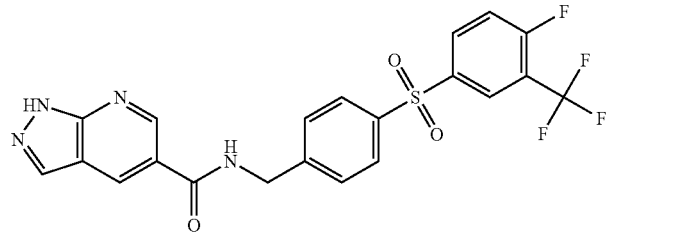 [SMILES: O=C(NCc1ccc(S(=O)(=O)c2ccc(F)c(C(F)(F)F)c2)cc1)c1cnc2[nH]ncc2c1] | N-[(4-{[4-fluoro-3-(trifluoromethyl)benzene]sulfonyl}phenyl)methyl]-1H-pyrazolo[3,4-b]pyridine-5-carboxamide |
| 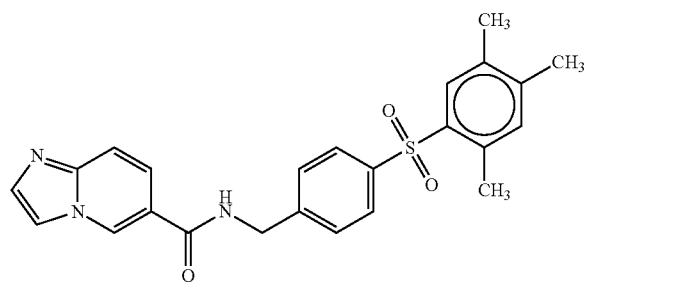 | N-({4-[(2,4,5-trimethylbenzene)sulfonyl]phenyl}methyl)imidazo[1,2-a]pyridine-6-carboxamide |
| 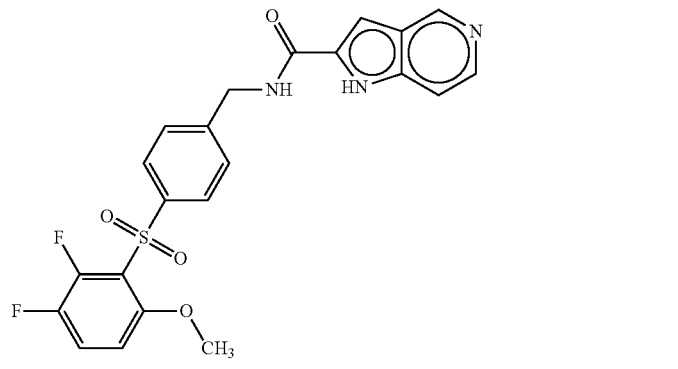 | N-({4-[(2,3-difluoro-6-methoxybenzene)sulfonyl]phenyl}methyl)-1H-pyrrolo[3,2-c]pyridine-2-carboxamide |
| 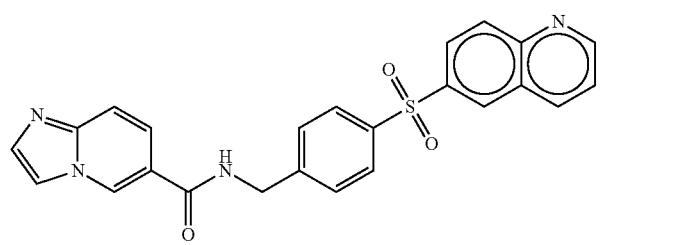 | N-{[4-(quinoline-6-sulfonyl)phenyl]methyl}imidazo[1,2-a]pyridine-6-carboxamide |

TABLE 2-continued

| | |
|---|---|
| 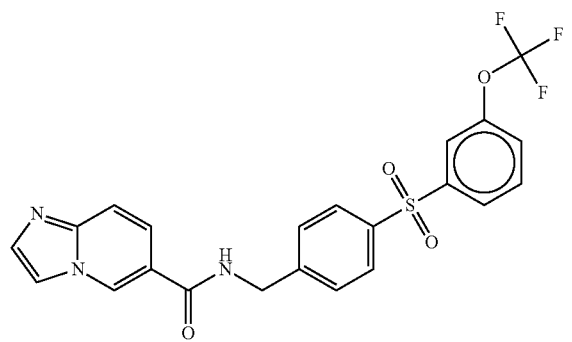 | N-[(4-{[3-(trifluoromethoxy)benzene]sulfonyl}phenyl)methyl]imidazo[1,2-a]pyridine-6-carboxamide |
| 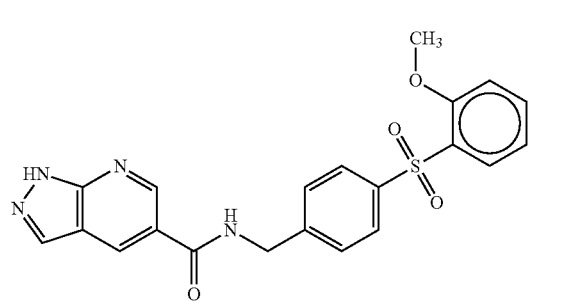 | N-({4-[(2-methoxybenzene)sulfonyl]phenyl}methyl)-1H-pyrazolo[3,4-b]pyridine-5-carboxamide |
| 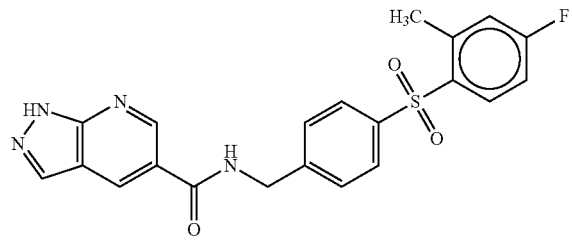 | N-({4-[(4-fluoro-2-methylbenzene)sulfonyl]phenyl}methyl)-1H-pyrazolo[3,4-b]pyridine-5-carboxamide |
| 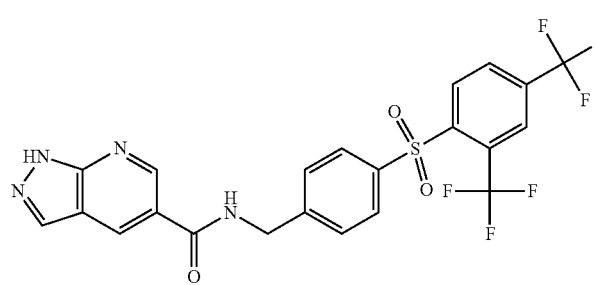 | N-[(4-{[2,4-bis(trifluoromethyl)benzene]sulfonyl}phenyl)methyl]-1H-pyrazolo[3,4-b]pyridine-5-carboxamide |
| 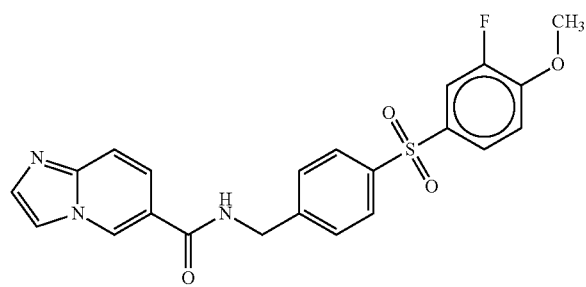 | N-({4-[(3-fluoro-4-methoxybenzene)sulfonyl]phenyl}methyl)imidazo[1,2-a]pyridine-6-carboxamide |

TABLE 2-continued

| | |
|---|---|
| 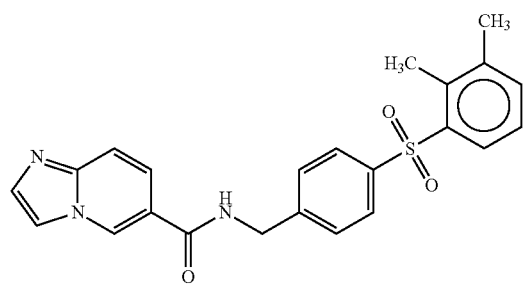 | N-({4-[(2,3-dimethylbenzene)sulfonyl]phenyl}methyl)imidazo[1,2-a]pyridine-6-carboxamide |
| 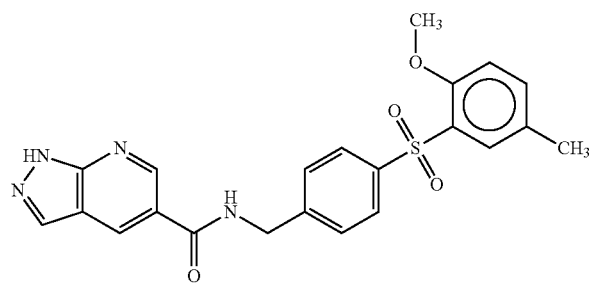 | N-({4-[(2-methoxy-5-methylbenzene)sulfonyl]phenyl}methyl)-1H-pyrazolo[3,4-b]pyridine-5-carboxamide |
| 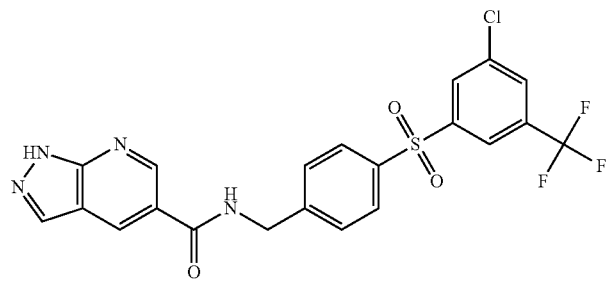 [SMILES: O=C(NCc1ccc(S(=O)(=O)c2cc(Cl)cc(C(F)(F)F)c2)cc1)c1cnc2[nH]ncc2c1] | N-[(4-{[3-chloro-5-(trifluoromethyl)benzene]sulfonyl}phenyl)methyl]-1H-pyrazolo[3,4-b]pyridine-5-carboxamide |
| 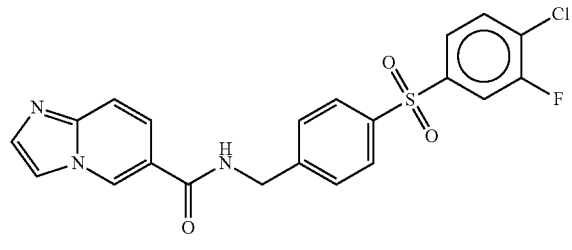 | N-({4-[(4-chloro-3-fluorobenzene)sulfonyl]phenyl}methyl)imidazo[1,2-a]pyridine-6-carboxamide |
| 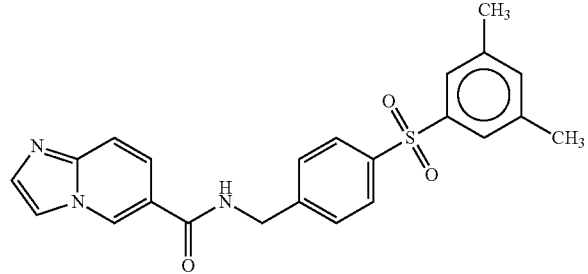 | N-({4-[(3,5-dimethylbenzene)sulfonyl]phenyl)methyl)imidazo[1,2-a]pyridine-6-carboxamide |

TABLE 2-continued

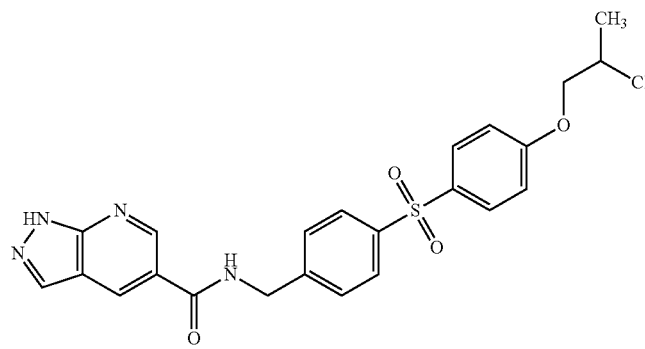
N-[(4-{[4-(2-methylpropoxy)benzene]sulfonyl}phenyl)methyl]-1H-pyrazolo[3,4-b]pyridine-5-carboxamide

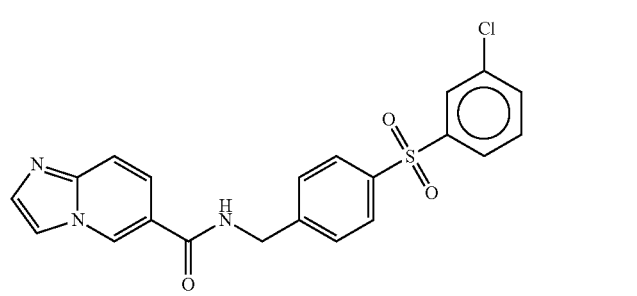
N-({4-[(3-chlorobenzene)sulfonyl]phenyl}methyl)imidazo[1,2-a]pyridine-6-carboxamide

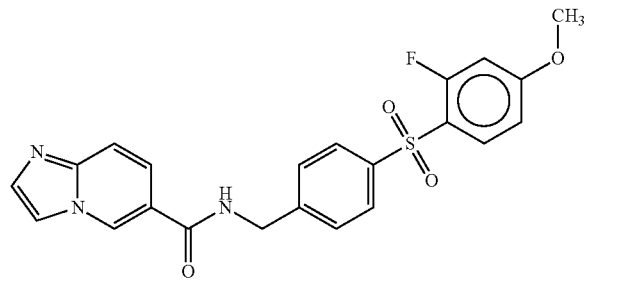
N-({4-[(2-fluoro-4-methoxybenzene)sulfonyl]phenyl}methyl)imidazo[1,2-a]pyridine-6-carboxamide

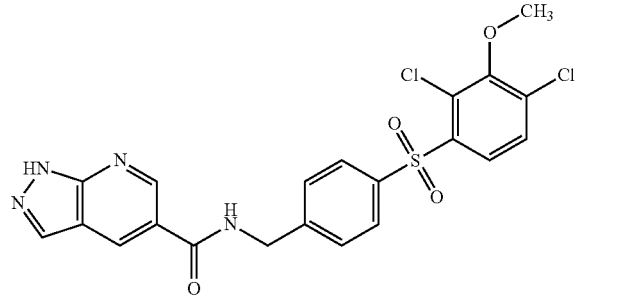 [SMILES: COc1c(Cl)ccc(S(=O)(=O)c2ccc(CNC(=O)c3cnc4[nH]ncc4c3)cc2)c1Cl]
N-({4-[(2,4-dichloro-3-methoxybenzene)sulfonyl]phenyl}methyl)-1H-pyrazolo[3,4-b]pyridine-5-carboxamide

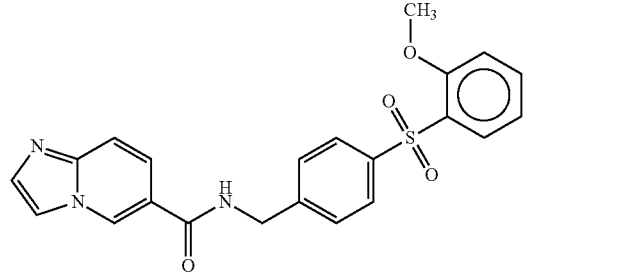
N-({4-[(2-methoxybenzene)sulfonyl]phenyl}methyl)imidazo[1,2-a]pyridine-6-carboxamide TABLE 2-continued

| | |
|---|---|
| 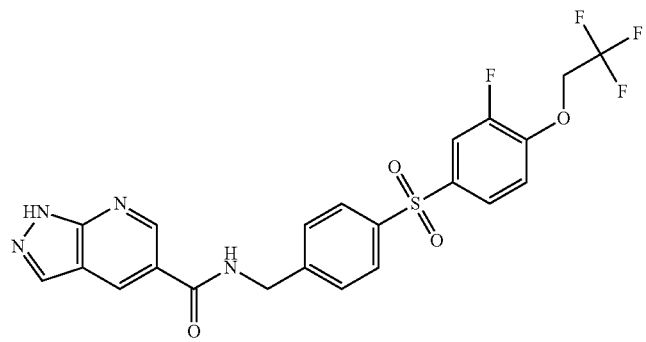 [SMILES: O=C(NCc1ccc(S(=O)(=O)c2ccc(OCC(F)(F)F)c(F)c2)cc1)c1cnc2[nH]ncc2c1] | N-[(4-{[3-fluoro-4-(2,2,2-trifluoroethoxy)benzene]sulfonyl}phenyl)methyl]-1H-pyrazolo[3,4-b]pyridine-5-carboxamide |
| 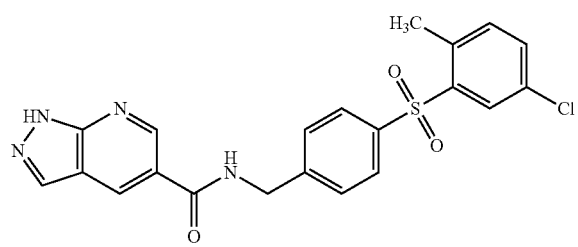 [SMILES: Cc1ccc(Cl)cc1S(=O)(=O)c1ccc(CNC(=O)c2cnc3[nH]ncc3c2)cc1] | N-({4-[(5-chloro-2-methylbenzene)sulfonyl]phenyl}methyl)-1H-pyrazolo[3,4-b]pyridine-5-carboxamide |
| 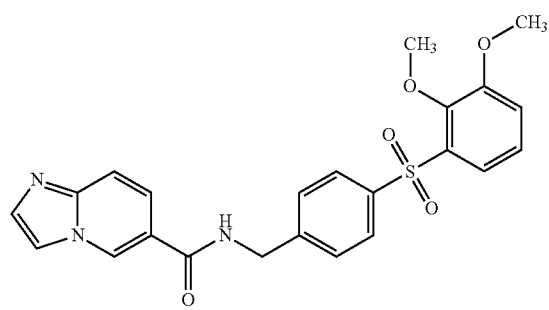 [SMILES: COc1cccc(S(=O)(=O)c2ccc(CNC(=O)c3ccc4nccn4c3)cc2)c1OC] | N-({4-[(2,3-dimethoxybenzene)sulfonyl]phenyl}methyl)imidazo[1,2-a]pyridine-6-carboxamide |
| 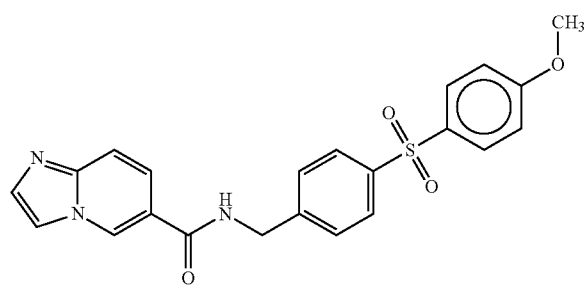 | N-({4-[(4-methoxybenzene)sulfonyl]phenyl}methyl)imidazo[1,2-a]pyridine-6-carboxamide |
| 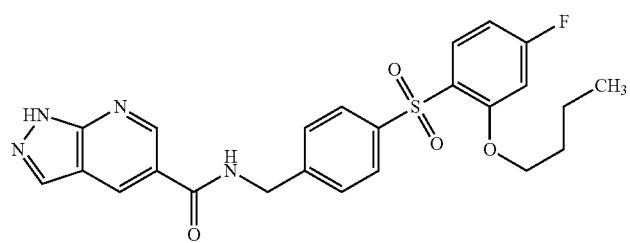 [SMILES: CCCCOc1cc(F)ccc1S(=O)(=O)c1ccc(CNC(=O)c2cnc3[nH]ncc3c2)cc1] | N-({4-[(2-butoxy-4-fluorobenzene)sulfonyl]phenyl}methyl)-1H-pyrazolo[3,4-b]pyridine-5-carboxamide |

TABLE 2-continued

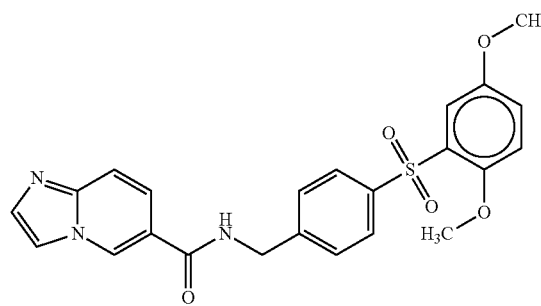
N-({4-[(2,5-dimethoxybenzene)sulfonyl]phenyl}methyl)imidazo[1,2-a]pyridine-6-carboxamide

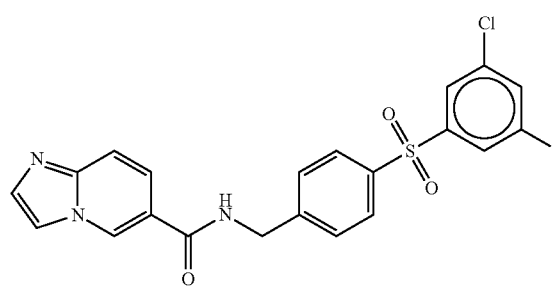
N-({4-[(3,5-dichlorobenzene)sulfonyl]phenyl}methyl)imidazo[1,2-a]pyridine-6-carboxamide

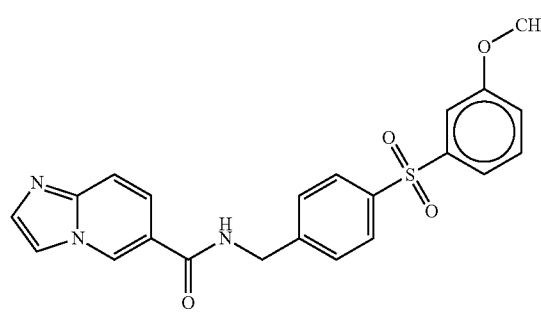
N-({4-[(3-methoxybenzene)sulfonyl]phenyl}methyl)imidazo[1,2-a]pyridine-6-carboxamide

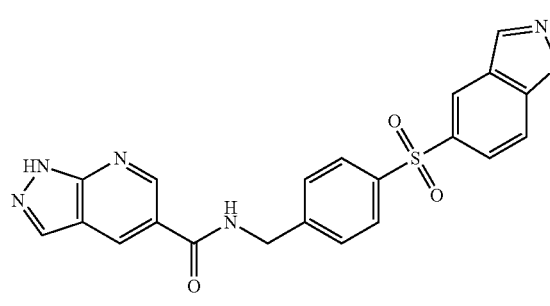
N-{[4-(1-methyl-1H-indazole-5-sulfonyl)phenyl]methyl}-1H-pyrazolo[3,4-b]pyridine-5-carboxamide

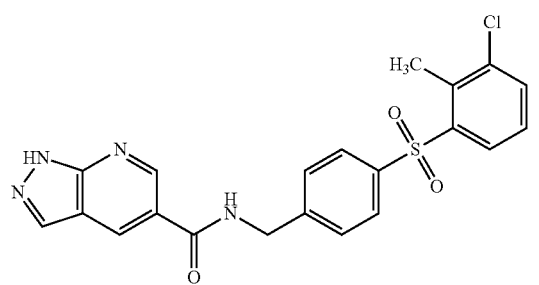 [SMILES: Cc1c(Cl)cccc1S(=O)(=O)c1ccc(CNC(=O)c2cnc3[nH]ncc3c2)cc1]
N-({4-[(3-chloro-2-methylbenzene)sulfonyl]phenyl}methyl)-1H-pyrazolo[3,4-b]pyridine-5-carboxamide TABLE 2-continued

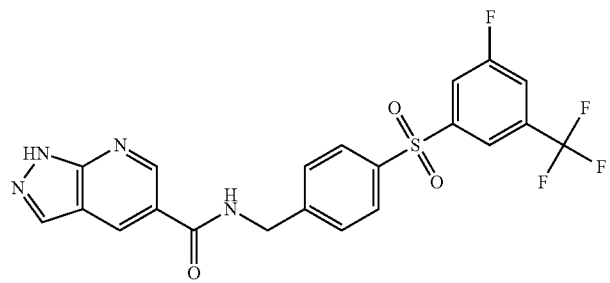

N-[(4-{[3-fluoro-5-(trifluoromethyl)benzene]sulfonyl}phenyl)methyl]-1H-pyrazolo[3,4-b]pyridine-5-carboxamide

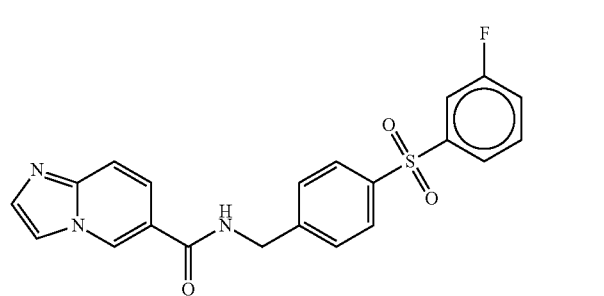

N-({4-[(3-fluorobenzene)sulfonyl]phenyl}methyl)imidazo[1,2-a]pyridine-6-carboxamide

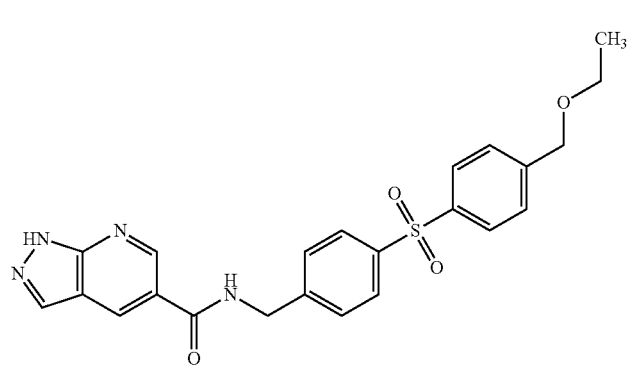 [SMILES: CCOCc1ccc(S(=O)(=O)c2ccc(CNC(=O)c3cnc4[nH]ncc4c3)cc2)cc1]

N-[(4-{[4-(ethoxymethyl)benzene]sulfonyl}phenyl)methyl]-1H-pyrazolo[3,4-b]pyridine-5-carboxamide

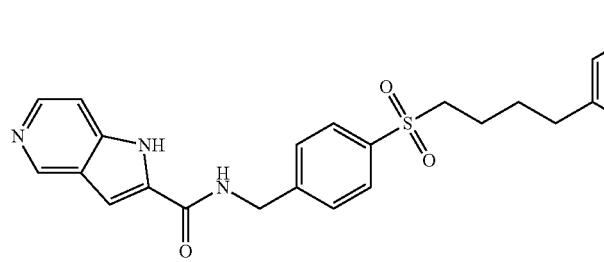

N-({4-[(4-phenylbutane)sulfonyl]phenyl}methyl)-1H-pyrrolo[3,2-c]pyridine-2-carboxamide

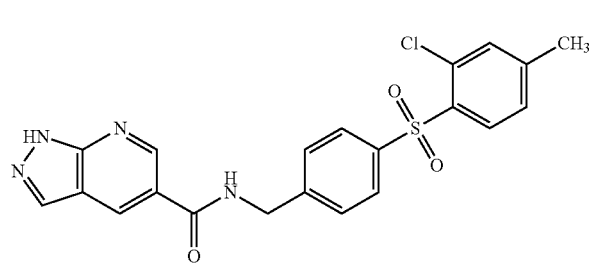 [SMILES: Cc1ccc(S(=O)(=O)c2ccc(CNC(=O)c3cnc4[nH]ncc4c3)cc2)c(Cl)c1]

N-({4-[(2-chloro-4-methylbenzene)sulfonyl]phenyl}methyl)-1H-pyrazolo[3,4-b]pyridine-5-carboxamide TABLE 2-continued

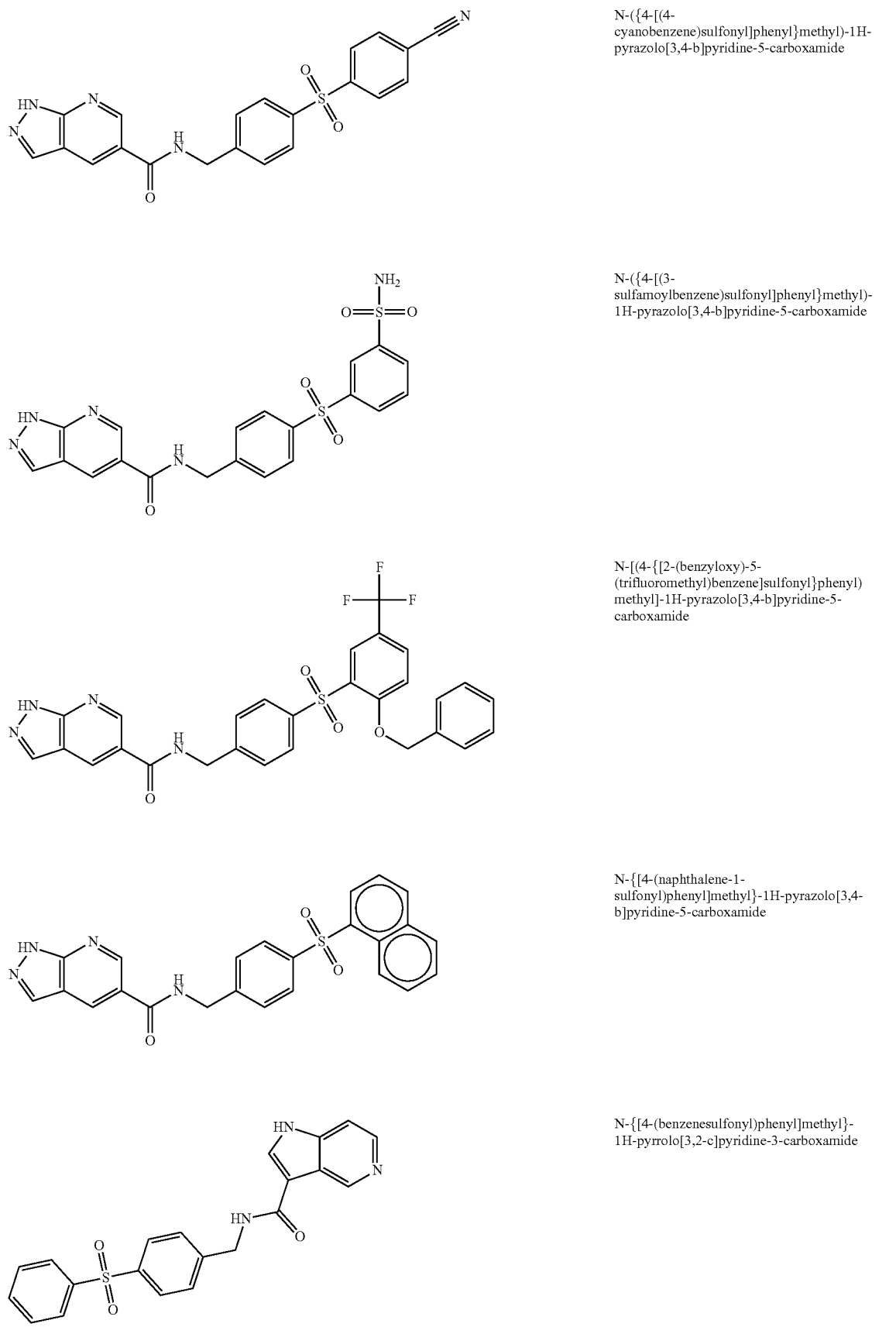

N-({4-[(4-cyanobenzene)sulfonyl]phenyl}methyl)-1H-pyrazolo[3,4-b]pyridine-5-carboxamide N-({4-[(3-sulfamoylbenzene)sulfonyl]phenyl}methyl)-1H-pyrazolo[3,4-b]pyridine-5-carboxamide N-[(4-{[2-(benzyloxy)-5-(trifluoromethyl)benzene]sulfonyl}phenyl)methyl]-1H-pyrazolo[3,4-b]pyridine-5-carboxamide N-{[4-(naphthalene-1-sulfonyl)phenyl]methyl}-1H-pyrazolo[3,4-b]pyridine-5-carboxamide N-{[4-(benzenesulfonyl)phenyl]methyl}-1H-pyrrolo[3,2-c]pyridine-3-carboxamide TABLE 2-continued

| | |
|---|---|
| 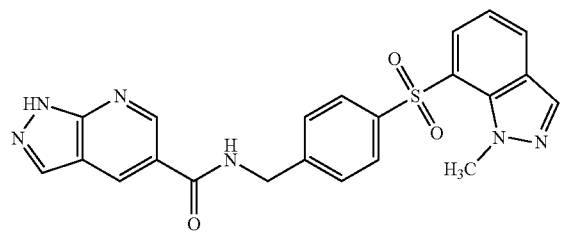 [SMILES: Cn1ncc2cccc(S(=O)(=O)c3ccc(CNC(=O)c4cnc5[nH]ncc5c4)cc3)c21] | N-{[4-(1-methyl-1H-indazole-7-sulfonyl)phenyl]methyl}-1H-pyrazolo[3,4-b]pyridine-5-carboxamide |
| 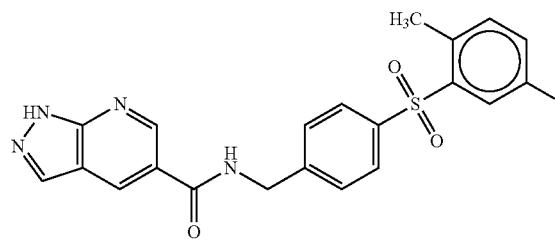 | N-({4-[(5-fluoro-2-methylbenzene)sulfonyl]phenyl}methyl)-1H-pyrazolo[3,4-b]pyridine-5-carboxamide |
| 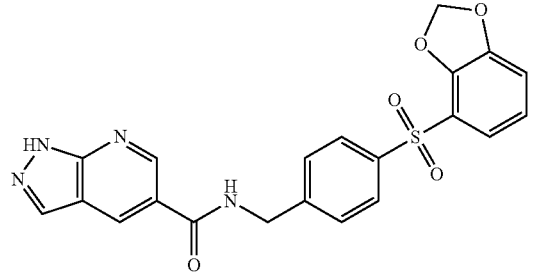 [SMILES: O=C(NCc1ccc(S(=O)(=O)c2cccc3c2OCO3)cc1)c1cnc2[nH]ncc2c1] | N-{[4-(2H-1,3-benzodioxole-4-sulfonyl)phenyl]methyl}-1H-pyrazolo[3,4-b]pyridine-5-carboxamide |
| 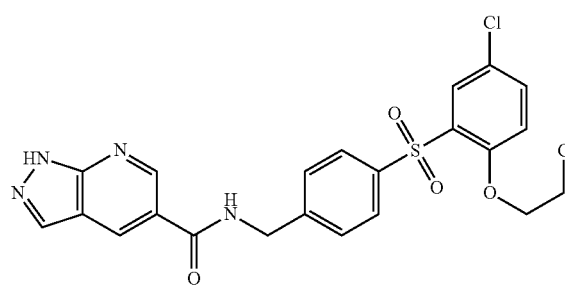 | N-({4-[(5-chloro-2-propoxybenzene)sulfonyl]phenyl}methyl)-1H-pyrazolo[3,4-b]pyridine-5-carboxamide |
| 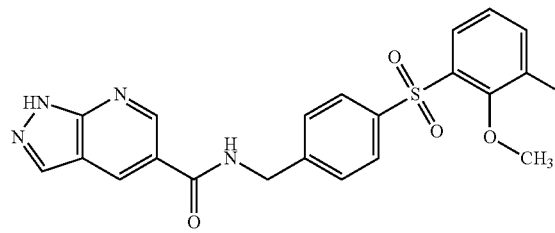 | N-({4-[(3-fluoro-2-methoxybenzene)sulfonyl]phenyl}methyl)-1H-pyrazolo[3,4-b]pyridine-5-carboxamide |
| 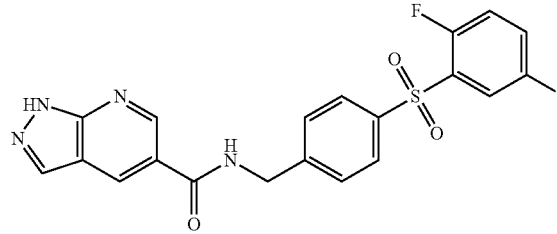 | N-({4-[(2-fluoro-5-methoxybenzene)sulfonyl]phenyl}methyl)-1H-pyrazolo[3,4-b]pyridine-5-carboxamide |

TABLE 2-continued

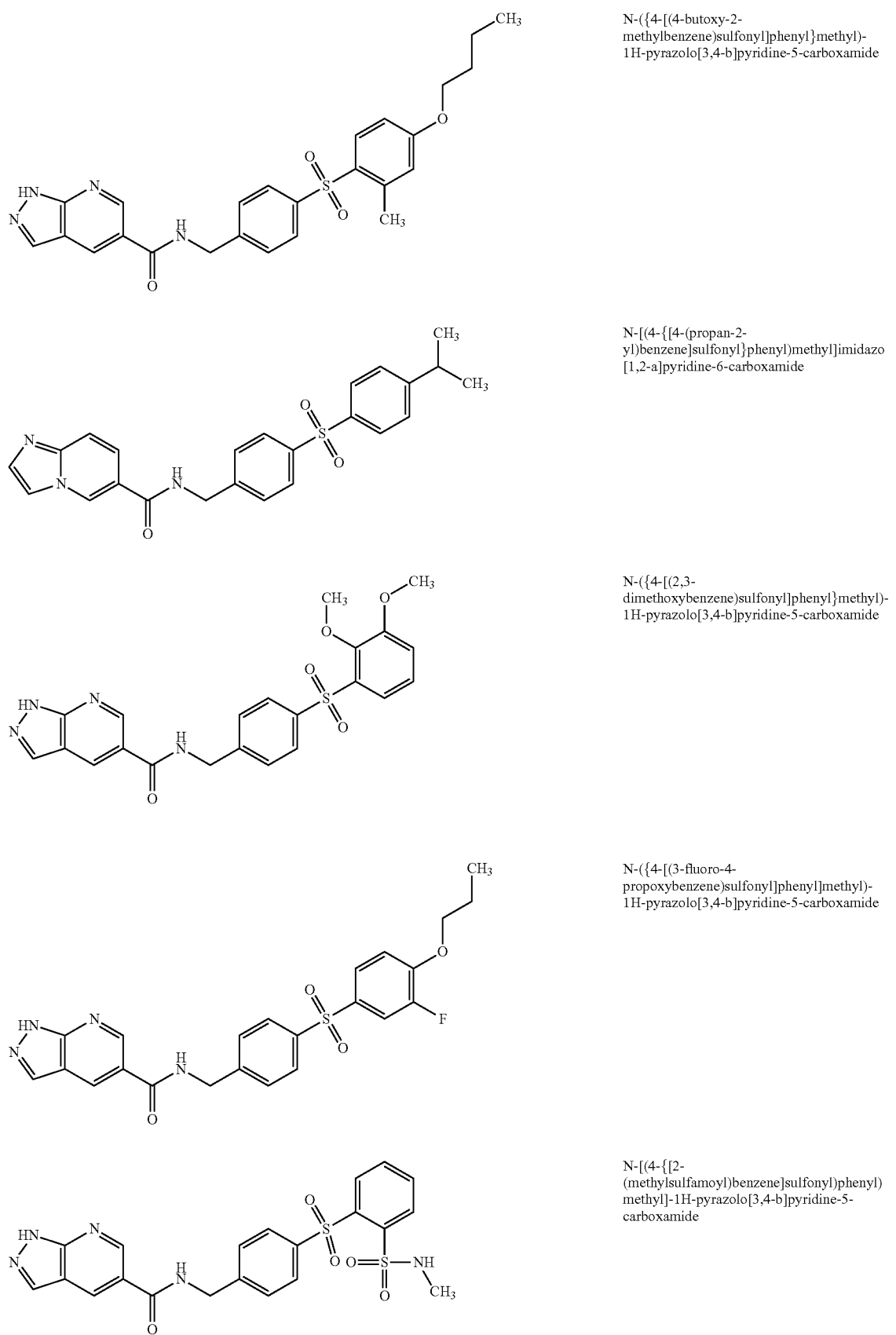

N-({4-[(4-butoxy-2-methylbenzene)sulfonyl]phenyl}methyl)-1H-pyrazolo[3,4-b]pyridine-5-carboxamide N-[(4-{[4-(propan-2-yl)benzene]sulfonyl}phenyl)methyl]imidazo[1,2-a]pyridine-6-carboxamide N-({4-[(2,3-dimethoxybenzene)sulfonyl]phenyl}methyl)-1H-pyrazolo[3,4-b]pyridine-5-carboxamide N-({4-[(3-fluoro-4-propoxybenzene)sulfonyl]phenyl]methyl)-1H-pyrazolo[3,4-b]pyridine-5-carboxamide N-[(4-{[2-(methylsulfamoyl)benzene]sulfonyl}phenyl)methyl]-1H-pyrazolo[3,4-b]pyridine-5-carboxamide TABLE 2-continued

| | |
|---|---|
| 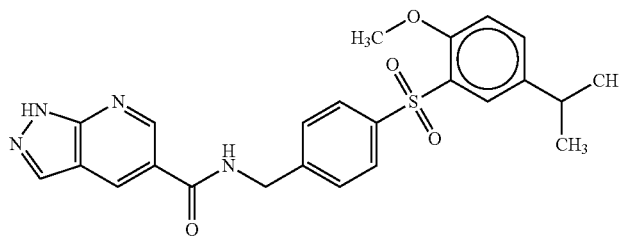 | N-[(4-{[2-methoxy-5-(propan-2-yl)benzene]sulfonyl}phenyl)methyl]-1H-pyrazolo[3,4-b]pyridine-5-carboxamide |
| 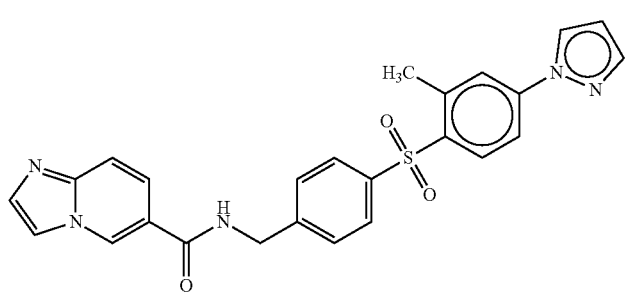 | N-[(4-{[2-methyl-4-(1H-pyrazol-1-yl)benzene]sulfonyl}phenyl)methyl]imidazo[1,2-a]pyridine-6-carboxamide |
| 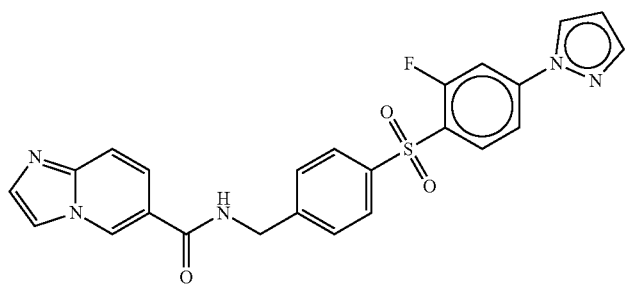 | N-[(4-{[2-fluoro-4-(1H-pyrazol-1-yl)benzene]sulfonyl}phenyl)methyl]imidazo[1,2-a]pyridine-6-carboxamide |
| 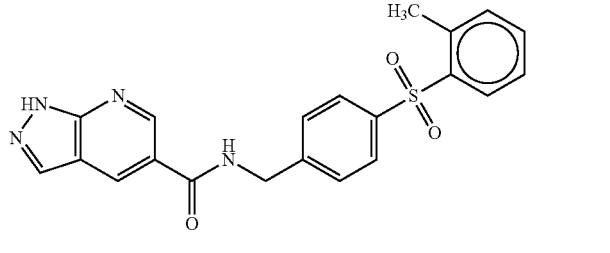 | N-({4-[(2-methylbenzene)sulfonyl]phenyl}methyl)-1H-pyrazolo[3,4-b]pyridine-5-carboxamide |
| 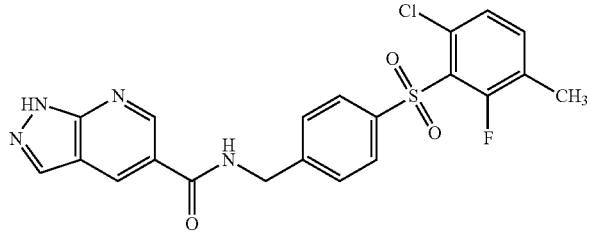 [SMILES: Cc1ccc(Cl)c(S(=O)(=O)c2ccc(CNC(=O)c3cnc4[nH]ncc4c3)cc2)c1F] | N-({4-[(6-chloro-2-fluoro-3-methylbenzene)sulfonyl]phenyl}methyl)-1H-pyrazolo[3,4-b]pyridine-5-carboxamide |

TABLE 2-continued
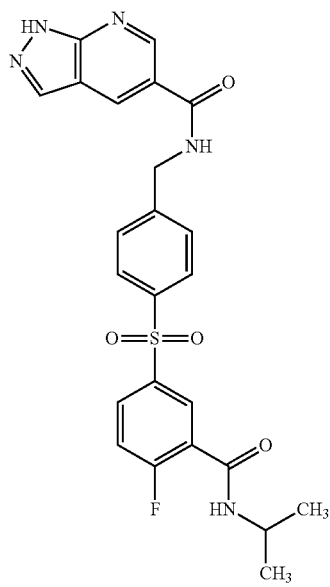 [SMILES: CC(C)NC(=O)c1cc(S(=O)(=O)c2ccc(CNC(=O)c3cnc4[nH]ncc4c3)cc2)ccc1F]
N-{[4-({4-fluoro-3-[(propan-2-yl)carbamoyl]benzene}sulfonyl)phenyl]methyl}-1H-pyrazolo[3,4-b]pyridine-5-carboxamide
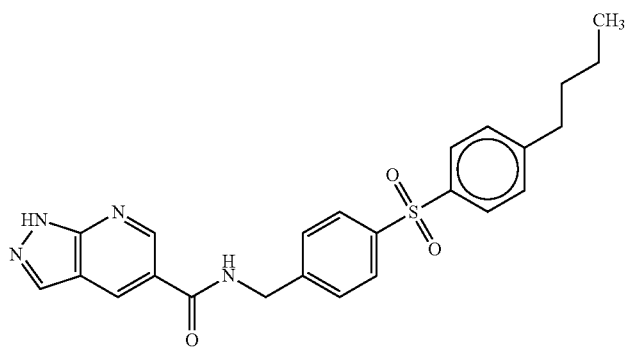
N-({4-[(4-butylbenzene)sulfonyl]phenyl}methyl)-1H-pyrazolo[3,4-b]pyridine-5-carboxamide
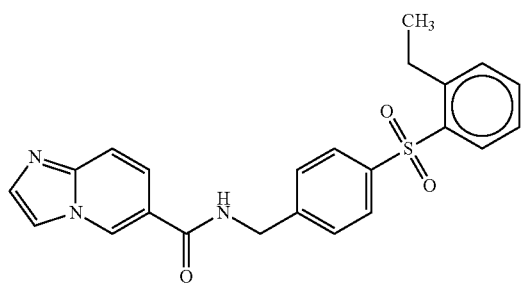
N-({4-[(2-ethylbenzene)sulfonyl]phenyl}methyl)imidazo[1,2-a]pyridine-6-carboxamide
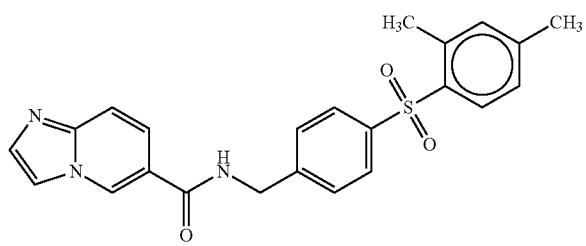
N-({4-[(2,4-dimethylbenzene)sulfonyl]phenyl}methyl)imidazo[1,2-a]pyridine-6-carboxamide TABLE 2-continued

| Structure | Name |
|---|---|
| (structure) | N-[(4-{[3-(methoxymethyl)benzene]sulfonyl}phenyl)methyl]-1H-pyrazolo[3,4-b]pyridine-5-carboxamide |
| (structure) | N-({4-[(2,5-dimethylbenzene)sulfonyl]phenyl}methyl)imidazo[1,2-a]pyridine-6-carboxamide |
| (structure) | N-[(4-{[5-chloro-2-(propan-2-yloxy)benzene]sulfonyl}phenyl)methyl]-1H-pyrazolo[3,4-b]pyridine-5-carboxamide |
| (structure) | N-({4-[(2-butoxy-5-chlorobenzene)sulfonyl]phenyl}methyl)-1H-pyrazolo[3,4-b]pyridine-5-carboxamide |
| (structure) | N-({4-[(4-chloro-2-methoxybenzene)sulfonyl]phenyl}methyl)imidazo[1,2-a]pyridine-6-carboxamide |

TABLE 2-continued
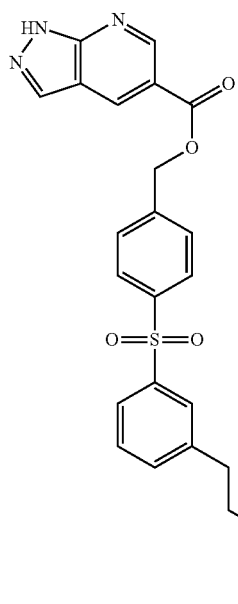
N-({4-[(3-butoxybenzene)sulfonyl]phenyl}methyl)-1H-pyrazolo[3,4-b]pyridine-5-carboxamide
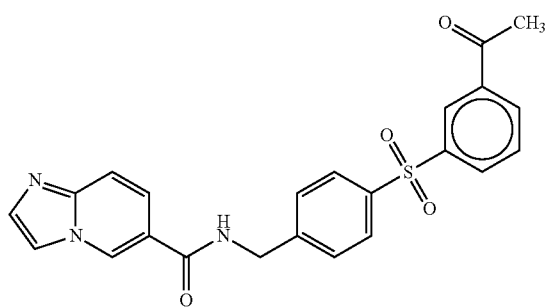
N-({4-[(3-acetylbenzene)sulfonyl]phenyl}methyl)imidazo[1,2-a]pyridine-6-carboxamide
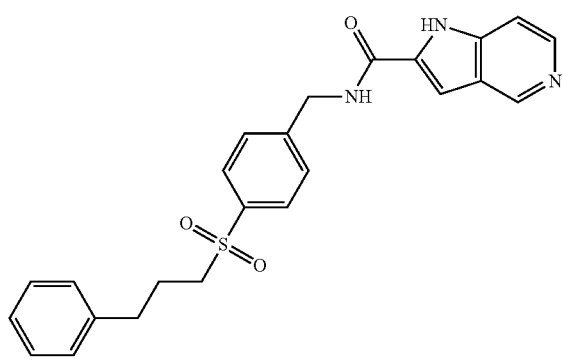 [SMILES: O=C(NCc1ccc(S(=O)(=O)CCCc2ccccc2)cc1)c1cc2cnccc2[nH]1]
N-({4-[(3-phenylpropane)sulfonyl]phenyl}methyl)-1H-pyrrolo[3,2-c]pyridine-2-carboxamide
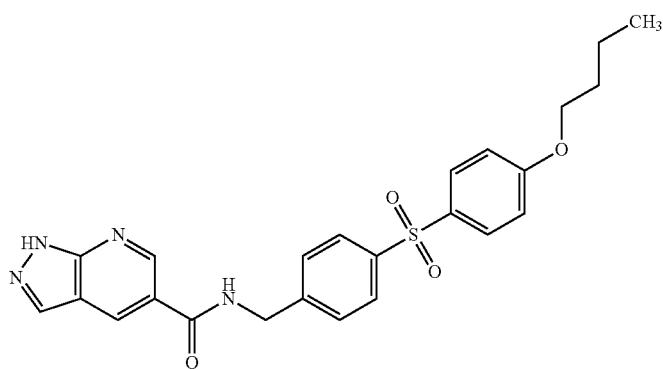 [SMILES: CCCCOc1ccc(S(=O)(=O)c2ccc(CNC(=O)c3cnc4[nH]ncc4c3)cc2)cc1]
N-({4-[(4-butoxybenzene)sulfonyl]phenyl}methyl)-1H-pyrazolo[3,4-b]pyridine-5-carboxamide TABLE 2-continued

| | |
|---|---|
| 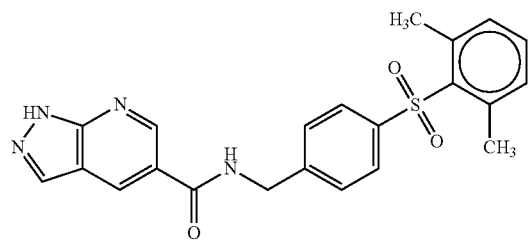 | N-({4-[(2,6-dimethylbenzene)sulfonyl]phenyl}methyl)-1H-pyrazolo[3,4-b]pyridine-5-carboxamide |
| 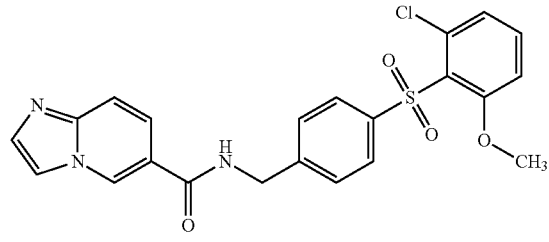 [SMILES: COc1cccc(Cl)c1S(=O)(=O)c1ccc(CNC(=O)c2ccc3nccn3c2)cc1] | N-({4-[(2-chloro-6-methoxybenzene)sulfonyl]phenyl}methyl)imidazo[1,2-a]pyridine-6-carboxamide |
| 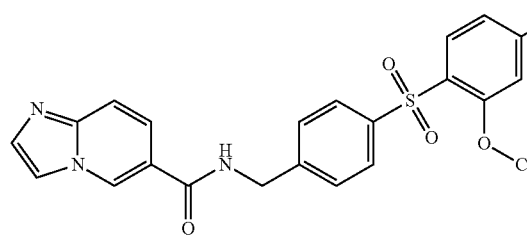 | N-({4-[(4-fluoro-2-methoxybenzene)sulfonyl]phenyl}methyl)imidazo[1,2-a]pyridine-6-carboxamide |
| 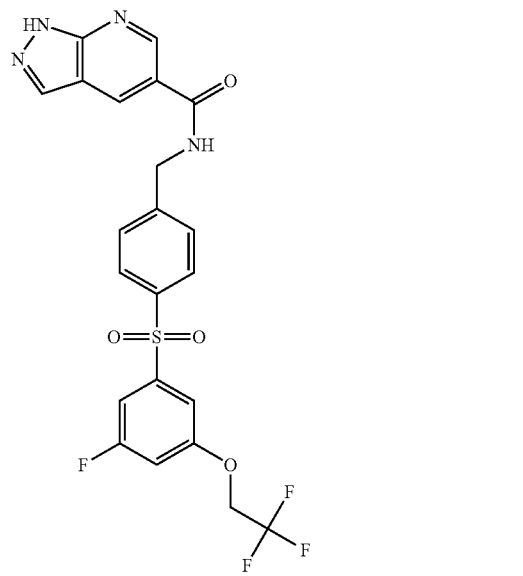 [SMILES: O=C(NCc1ccc(S(=O)(=O)c2cc(F)cc(OCC(F)(F)F)c2)cc1)c1cnc2[nH]ncc2c1] | N-[(4-{[3-fluoro-5-(2,2,2-trifluoroethoxy)benzene]sulfonyl}phenyl)methyl]-1H-pyrazolo[3,4-b]pyridine-5-carboxamide |
| 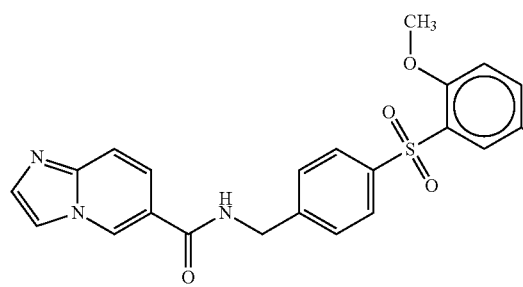 | N-({4-[(2-methoxy-5-methylbenzene)sulfonyl]phenyl}methyl)imidazo[1,2-a]pyridine-6-carboxamide |

TABLE 2-continued

| | |
|---|---|
| 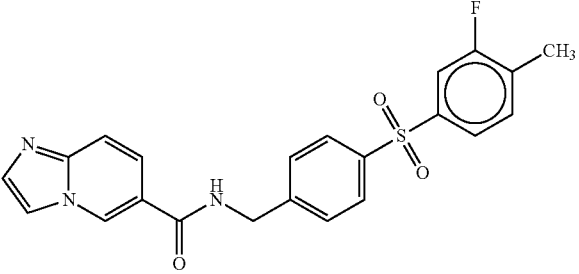 | N-({4-[(3-fluoro-4-methylbenzene)sulfonyl]phenyl}methyl)imidazo[1,2-a]pyridine-6-carboxamide |
| 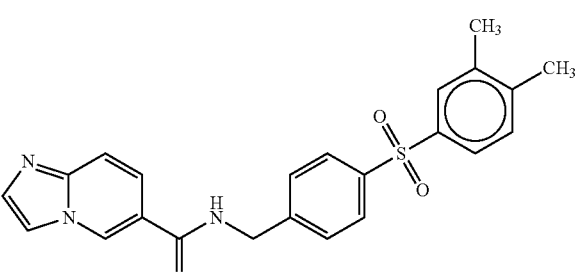 | N-({4-[(3,4-dimethylbenzene)sulfonyl]phenyl}methyl)imidazo[1,2-a]pyridine-6-carboxamide |
| 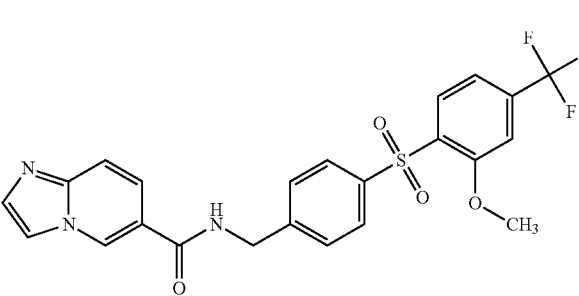 | N-[(4-{[2-methoxy-4-(trifluoromethyl)benzene]sulfonyl}phenyl)methyl]imidazo[1,2-a]pyridine-6-carboxamide |
| 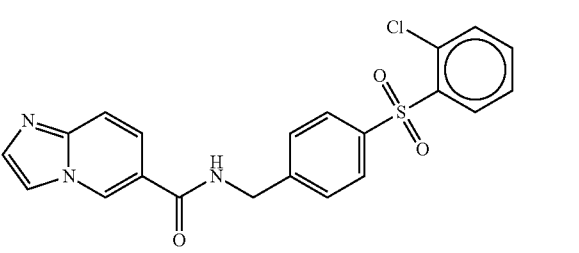 | N-({4-[(2-chlorobenzene)sulfonyl]phenyl}methyl)imidazo[1,2-a]pyridine-6-carboxamide |
| 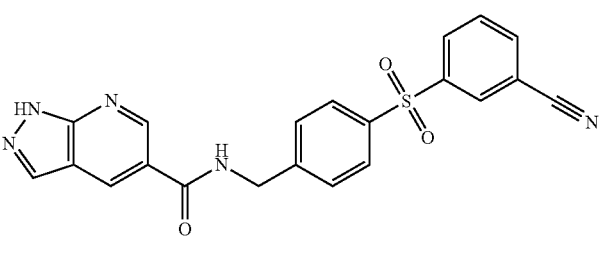 [SMILES: N#Cc1cccc(S(=O)(=O)c2ccc(CNC(=O)c3cnc4[nH]ncc4c3)cc2)c1] | N-({4-[(3-cyanobenzene)sulfonyl]phenyl}methyl)-1H-pyrazolo[3,4-b]pyridine-5-carboxamide |
| 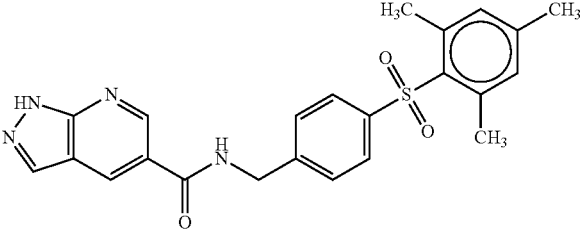 | N-({4-[(2,4,6-trimethylbenzene)sulfonyl]phenyl}methyl)-1H-pyrazolo[3,4-b]pyridine-5-carboxamide |

TABLE 2-continued

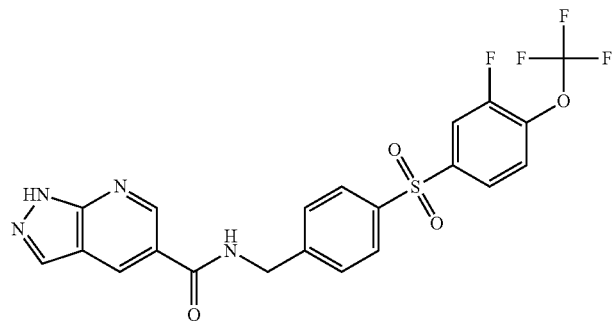 [SMILES: O=C(NCc1ccc(S(=O)(=O)c2ccc(OC(F)(F)F)c(F)c2)cc1)c1cnc2[nH]ncc2c1]

N-[(4-{[3-fluoro-4-(trifluoromethoxy)benzene]sulfonyl}phenyl)methyl]-1H-pyrazolo[3,4-b]pyridine-5-carboxamide

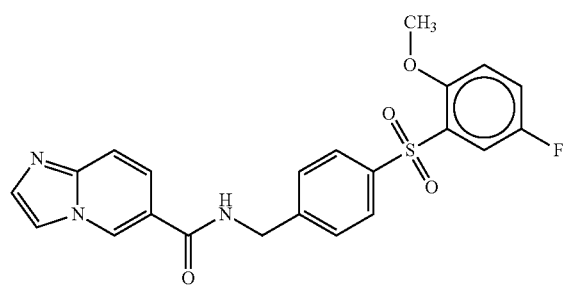

N-({4-[(5-fluoro-2-methoxybenzene)sulfonyl]phenyl}methyl)imidazo[1,2-a]pyridine-6-carboxamide

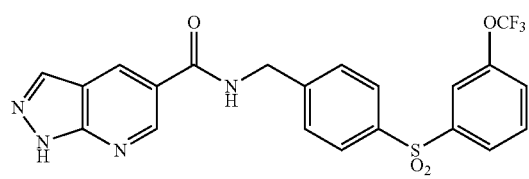 [SMILES: O=C(NCc1ccc(S(=O)(=O)c2cccc(OC(F)(F)F)c2)cc1)c1cnc2[nH]ncc2c1]

N-(4-(3-(trifluoromethoxy)phenylsulfonyl)benzyl)-1H-pyrazolo[3,4-b]pyridine-5-carboxamide

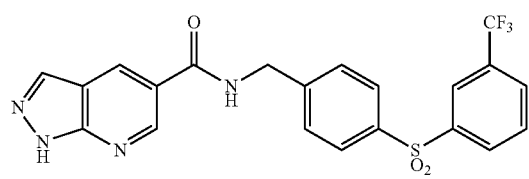 [SMILES: O=C(NCc1ccc(S(=O)(=O)c2cccc(C(F)(F)F)c2)cc1)c1cnc2[nH]ncc2c1]

N-(4-(3-(trifluoromethyl)phenylsulfonyl)benzyl)-1H-pyrazolo[3,4-b]pyridine-5-carboxamide

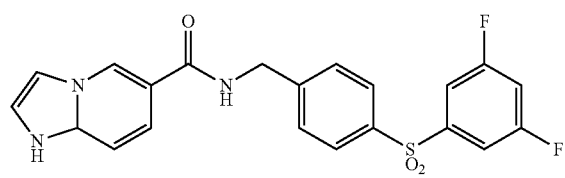 [SMILES: O=C(NCc1ccc(S(=O)(=O)c2cc(F)cc(F)c2)cc1)C1=CN2C=CNC2C=C1]

N-(4-(3,5-difluorophenylsulfonyl)benzyl)-1,8a-dihydroimidazo[1,2-a]pyridine-6-carboxamide

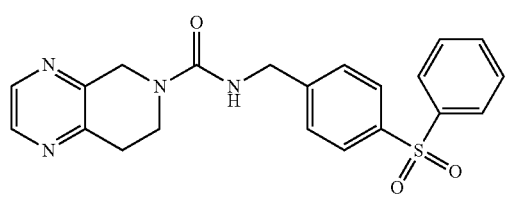 [SMILES: O=C(NCc1ccc(S(=O)(=O)c2ccccc2)cc1)N1CCc2nccnc2C1]

7,8-Dihydro-5H-pyrido[3,4-b]pyrazine-6-carboxylic acid 4-benzenesulfonyl-benzylamide

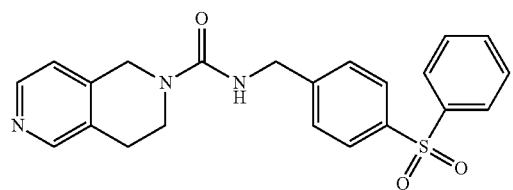 [SMILES: O=C(NCc1ccc(S(=O)(=O)c2ccccc2)cc1)N1CCc2cnccc2C1]

3,4-Dihydro-1H-[2,6]naphthyridine-2-carboxylic acid 4-benzenesulfonyl-benzylamide

| | |
|---|---|
| 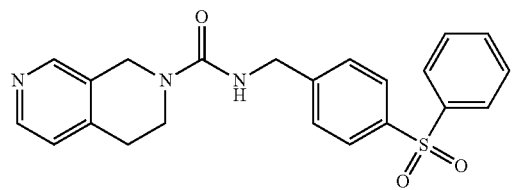 [SMILES: O=C(NCc1ccc(S(=O)(=O)c2ccccc2)cc1)N1CCc2ccncc2C1] | 3,4-Dihydro-1H-[2,7]naphthyridine-2-carboxylic acid 4-benzenesulfonyl-benzylamide |
| 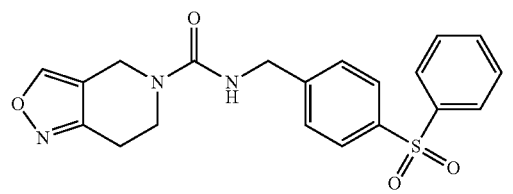 [SMILES: O=C(NCc1ccc(S(=O)(=O)c2ccccc2)cc1)N1CCc2nocc2C1] | 6,7-Dihydro-4H-isoxazolo[4,3-c]pyridine-5-carboxylic acid 4-benzenesulfonyl-benzylamide |
| 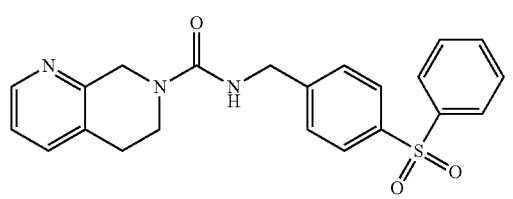 [SMILES: O=C(NCc1ccc(S(=O)(=O)c2ccccc2)cc1)N1CCc2cccnc2C1] | 5,8-Dihydro-6H-[1,7]naphthyridine-7-carboxylic acid 4-benzenesulfonyl-benzylamide |
| 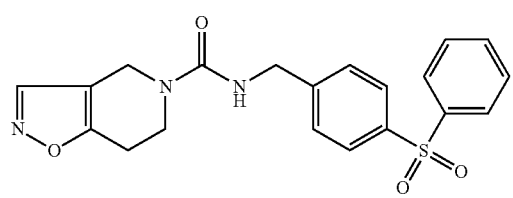 [SMILES: O=C(NCc1ccc(S(=O)(=O)c2ccccc2)cc1)N1CCc2oncc2C1] | 6,7-Dihydro-4H-isoxazolo[4,5-c]pyridine-5-carboxylic acid 4-benzenesulfonyl-benzylamide |
| 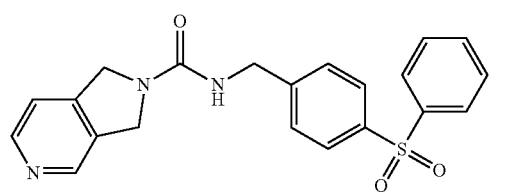 [SMILES: O=C(NCc1ccc(S(=O)(=O)c2ccccc2)cc1)N1Cc2ccncc2C1] | 1,3-Dihydro-pyrrolo[3,4-c]pyridine-2-carboxylic acid 4-benzenesulfonyl-benzylamide |
| 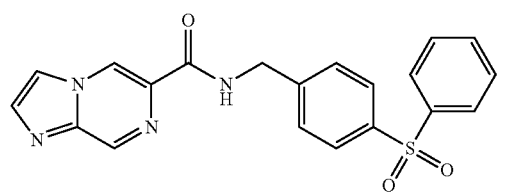 [SMILES: O=C(NCc1ccc(S(=O)(=O)c2ccccc2)cc1)c1cn2ccnc2cn1] | Imidazo[1,2-a]pyrazine-6-carboxylic acid 4-benzenesulfonyl-benzylamide |
| 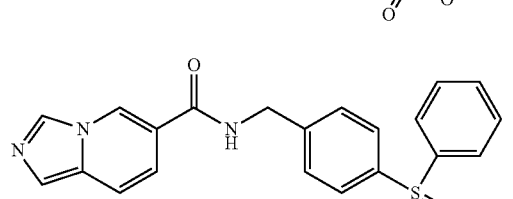 | Imidazo[1,5-a]pyridine-6-carboxylic acid 4-benzenesulfonyl-benzylamide |
| 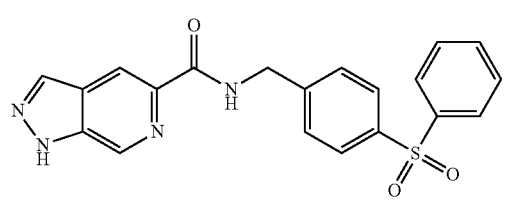 [SMILES: O=C(NCc1ccc(S(=O)(=O)c2ccccc2)cc1)c1cc2cn[nH]c2cn1] | 1H-Pyrazolo[3,4-c]pyridine-5-carboxylic acid 4-benzenesulfonyl-benzylamide |

TABLE 2-continued

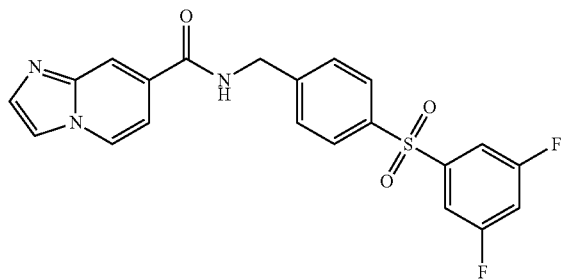 [SMILES: O=C(NCc1ccc(S(=O)(=O)c2cc(F)cc(F)c2)cc1)c1ccn2ccnc2c1]

Imidazo[1,2-a]pyridine-7-carboxylic acid 4-(3,5-difluoro-benzenesulfonyl)-benzylamide

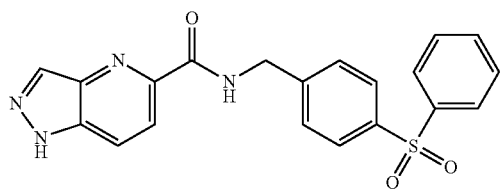 [SMILES: O=C(NCc1ccc(S(=O)(=O)c2ccccc2)cc1)c1ccc2[nH]ncc2n1]

1H-Pyrazolo[4,3-b]pyridine-5-carboxylic acid 4-benzenesulfonyl-benzylamide

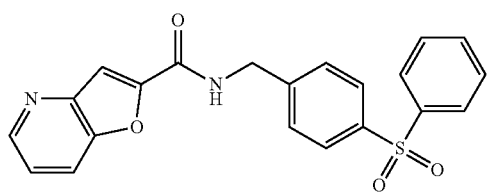 [SMILES: O=C(NCc1ccc(S(=O)(=O)c2ccccc2)cc1)c1cc2ncccc2o1]

Furo[3,2-b]pyridine-2-carboxylic acid 4-benzenesulfonyl-benzylamide

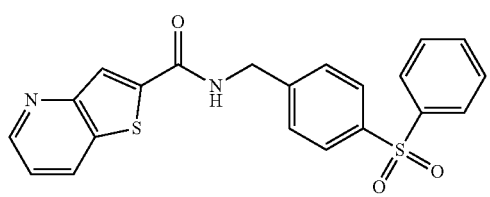 [SMILES: O=C(NCc1ccc(S(=O)(=O)c2ccccc2)cc1)c1cc2ncccc2s1]

N-{[4-(benzenesulfonyl)phenyl]methyl}thieno[3,2-b]pyridine-2-carboxamide

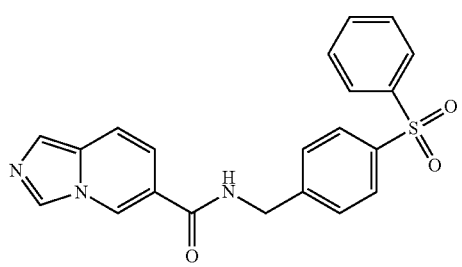 [SMILES: O=C(NCc1ccc(S(=O)(=O)c2ccccc2)cc1)c1ccc2cncn2c1]

N-{[4-(benzenesulfonyl)phenyl]methyl}imidazo[1,5-a]pyridine-6-carboxamide

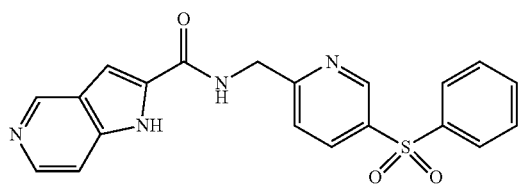 [SMILES: O=C(NCc1ccc(S(=O)(=O)c2ccccc2)cn1)c1cc2cnccc2[nH]1]

N-{[5-(benzenesulfonyl)pyridin-2-yl]methyl}-1H-pyrrolo[3,2-c]pyridine-2-carboxamide

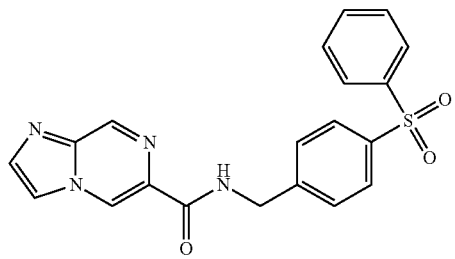 [SMILES: O=C(NCc1ccc(S(=O)(=O)c2ccccc2)cc1)c1cn2ccnc2cn1]

N-{[4-(benzenesulfonyl)phenyl]methyl}imidazo[1,2-a]pyrazine-6-carboxamide

TABLE 2-continued

| | |
|---|---|
| 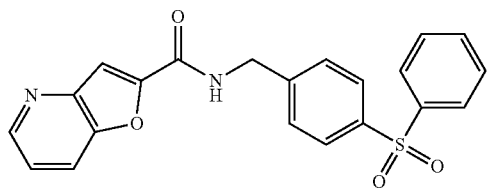 | N-{[4-(benzenesulfonyl)phenyl]methyl}furo[3,2-b]pyridine-2-carboxamide |
| 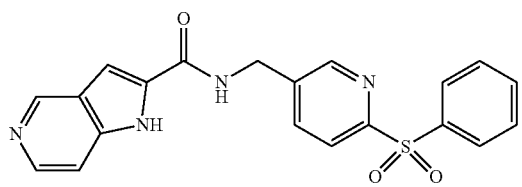 [SMILES: O=C(NCc1ccc(S(=O)(=O)c2ccccc2)nc1)c1cc2cnccc2[nH]1] | N-{[6-(benzenesulfonyl)pyridin-3-yl]methyl}-1H-pyrrolo[3,2-c]pyridine-2-carboxamide |
| 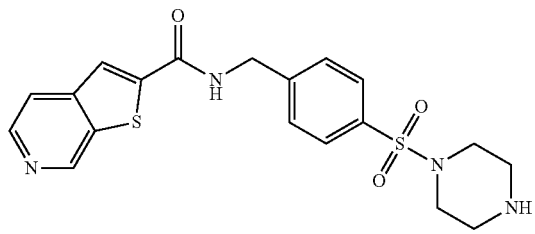 | N-{[4-(piperazine-1-sulfonyl)phenyl]methyl}thieno[2,3-c]pyridine-2-carboxamide |
| 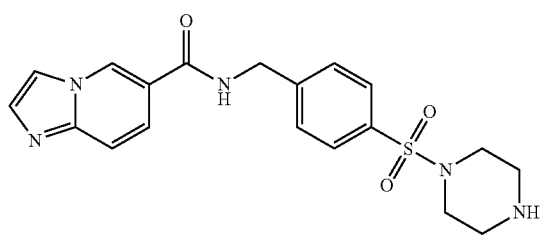 [SMILES: O=C(NCc1ccc(S(=O)(=O)N2CCNCC2)cc1)c1ccc2nccn2c1] | N-{[4-(piperazine-1-sulfonyl)phenyl]methyl}imidazo[1,2-a]pyridine-6-carboxamide |
| 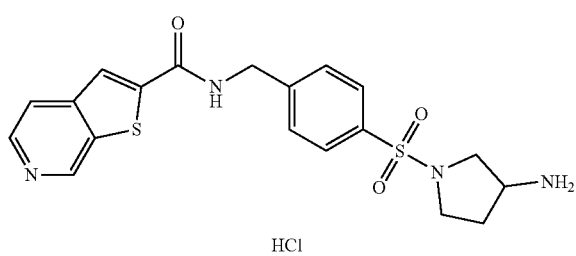 [SMILES: NC1CCN(S(=O)(=O)c2ccc(CNC(=O)c3cc4ccncc4s3)cc2)C1 ; Cl] | N-{[4-(3-aminopyrrolidine-1-sulfonyl)phenyl]methyl}thieno[2,3-c]pyridine-2-carboxamide hydrochloride |
| 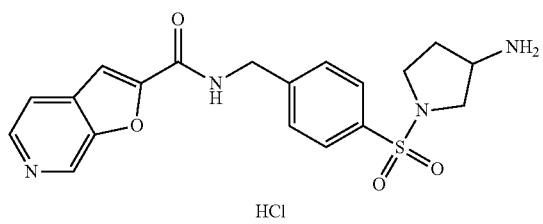 [SMILES: NC1CCN(S(=O)(=O)c2ccc(CNC(=O)c3cc4ccncc4o3)cc2)C1 ; Cl] | N-{[4-(3-aminopyrrolidine-1-sulfonyl)phenyl]methyl}furo[2,3-c]pyridine-2-carboxamide hydrochloride |
| 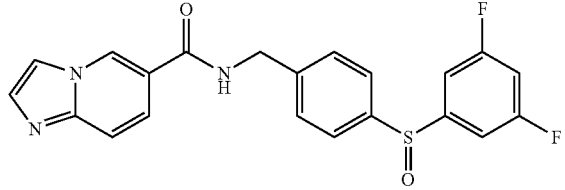 [SMILES: O=C(NCc1ccc(S(=O)c2cc(F)cc(F)c2)cc1)c1ccc2nccn2c1] | N-({4-[(3,5-difluorobenzene)sulfinyl]phenyl}methyl)imidazo[1,2-a]pyridine-6-carboxamide |

TABLE 2-continued

| Structure | Name |
|---|---|
| (structure) | N-{[4-(benzenesulfonyl)phenyl]methyl}-5,6,7,8-tetrahydro-1,6-naphthyridine-6-carboxamide |
| (structure) | N-{[4-(benzenesulfonyl)phenyl]methyl}-5H,6H,7H-pyrrolo[3,4-b]pyridine-6-carboxamide |
| (structure) | N-{[4-(benzenesulfonyl)phenyl]methyl}-1H,4H,5H,6H,7H-pyrazolo[4,3-c]pyridine-5-carboxamide |
| (structure) | N-{[4-(benzenesulfonyl)phenyl]methyl}-5H,6H,7H,8H-pyrido[4,3-d]pyrimidine-6-carboxamide |
| (structure) | N-{[4-(benzenesulfonyl)phenyl]methyl}-1H,4H,5H,6H,7H-imidazo[4,5-c]pyridine-5-carboxamide |
| (structure) | N-{[4-(benzenesulfonyl)phenyl]methyl}-4H,5H,6H,7H-[1,2]oxazolo[4,3-c]pyridine-5-carboxamide |

EXAMPLES

The following are illustrative, but non-limiting, examples of certain embodiments of the present invention.

The invention is illustrated further by the following examples, which are not to be construed as limiting the invention in scope or spirit to the specific procedures described in them. Those having skill in the art will recognize that the starting materials may be varied and additional steps employed to produce compounds encompassed by the present inventions, as demonstrated by the following examples. In some cases, protection of certain reactive functionalities may be necessary to achieve some of the above transformations. In general, such need for protecting groups, as well as the conditions necessary to attach and remove such groups, will be apparent to those skilled in the art of organic synthesis.

Compounds according to the invention may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-23, Wiley, N.Y. (1967-2006 ed.), or Beilsteins Handbuch der organischen Chemie, 4, Aufl. ed. Springer-Verlag, Berlin, including supplements (also available via the Beilstein online database).

Synthetic chemistry transformations and protecting group methodologies (protection and deprotection) useful in synthesizing compounds according to the invention and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, 3rd Ed., John Wiley and Sons (1999); and L. Paquette, ed., Encyclopedia of Reagents for Organic Synthesis, John Wiley and Sons (1995) and subsequent editions thereof.

Compounds according to the invention may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

The General Procedures and Examples provide exemplary methods for preparing compounds according to the invention. Those skilled in the art will appreciate that other synthetic routes may be used to synthesize the compounds according to the invention. Although specific starting materials and reagents are depicted and discussed in the schemes, General Procedures, and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds according to the invention, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

In the methods of preparing compounds according to the invention, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, a-methoxy-a-(trifluoromethyl)phenyl acetate of the racemic mixture and analyzing the 1H NMR spectrum for the presence of the two atropisomeric enantiomers or diastereomers (Jacob III. J. Org. Chem. (1982) 47:4165). Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Definitions Used in the Following Schemes and Elsewhere Herein are

BOP ammonium 4-(3-(pyridin-3-methyl)ureido)benzenesulfinate
$CDCl_3$ deuterated chloroform
δ chemical shift (ppm)
DCM dichloromethane or methylene chloride
DIEA N,N-diisopropylethylamine
DMA N,N-dimethylacetamide
DMF N,N-dimethylformamide
DMSO dimethylsulfoxide
DMSO-$d_6$ deuterated dimethylsulfoxide
EDCI N1-((ethylimino)methylene)-N3,N3-dimethylpropane-1,3-diamine hydrochloride
EtOAc ethyl acetate
EtOH ethanol
GF/F glass microfiber filter
$^1$H NMR proton nuclear magnetic resonance
HOAc acetic acid
HATU 2-(3H-[1,2,3]triazolo[4,5-b]pyridin-3-yl)-1,1,3,3-tetramethylisouronium hexafluorophosphate
HOBT 1H-benzo[d][1,2,3]triazol-1-ol hydrate
HPLC high pressure liquid chromatography
MHz megahertz
KOAc potassium acetate
i-PrOH isopropanol
LC-MS liquid chromatography/mass spectrometry
(M+1) mass+1
m-CPBA m-chloroperbenzoic acid
MeOH methanol
$N_2$ nitrogen
$NaHCO_3$ sodium bicarbonate
$MgSO_4$ magnesium sulfate
PTLC preparative thin layer chromatography
TEA triethylamine
THF tetrahydrofuran
TLC thin layer chromatography Amide-sulfonamide:

Scheme 1

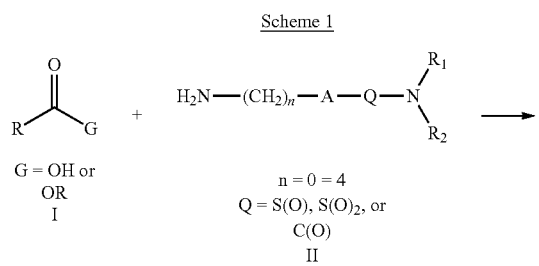

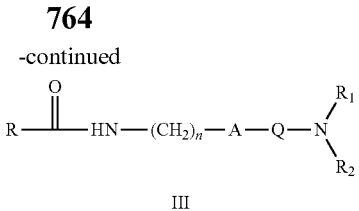

In Scheme 1, compound III can be obtained by treating II with I (G=OH) in the presence of a coupling reagent such as EDCI, HATU, or HOBt, and a base (e.g.: $K_2CO_3$, $Cs_2CO_3$, $NR_1R_2R_3$, NaOR, KOR) in an inert solvent such as dichloromethane, N,N-dialkylformamide, N,N-dialkylacetamide, dialkylethers, cyclic ethers, DMSO, N-methyl-2-pyrrolidinone at temperatures ranging from −78° C. to 200° C. Alternatively, compound I can be treated with I (G=OR) in the presence of trimethylaluminum in an inert solvent (such as toluene) at temperatures ranging from −78° C. to 200° C.

Those having skill in the art will recognize that the starting materials may be varied and additional steps employed to produce compounds encompassed by the present inventions, as demonstrated by the following examples. Unless otherwise specified, all reagents and solvents were of standard commercial grade and were used without further purification.

Amide Sulfone:

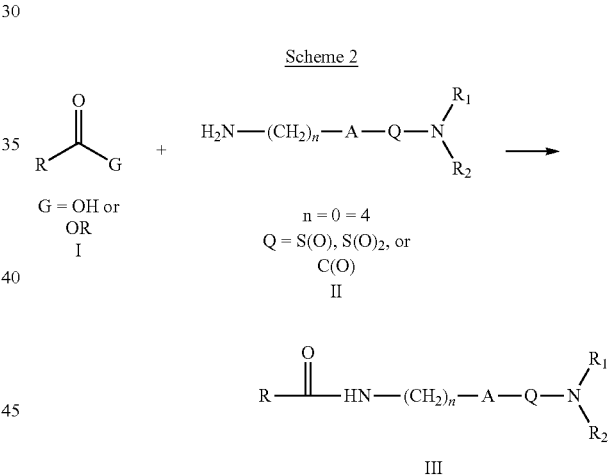

Compound III of scheme 2 can be obtained by treating II with I (G=OH) in the presence of a coupling reagent such as EDCI, HATU, BOP, or HOBt, and a base (eg: $K_2CO_3$, $Cs_2CO_3$, $NR_1R_2R_3$, NaOR, KOR) in an inert solvent such as dichloromethane, N,N-dialkylformamide, N,N-dialkylacetamide, dialkylethers, DMSO, or N-methyl-2-pyrrolidinone at temperatures ranging from −78° C. to 200° C. Alternatively, compound III can be obtained by treating I (G=OR) with I and trimethylaluminum in an inert solvent (such as toluene) at temperatures ranging from −78° C. to 200° C.

Those having skill in the art will recognize that the starting materials may be varied and additional steps employed to produce compounds encompassed by the present inventions, as demonstrated by the following examples. Unless otherwise specified all reagents and solvent are of standard commercial grade and are used without further purification.

Scheme 3

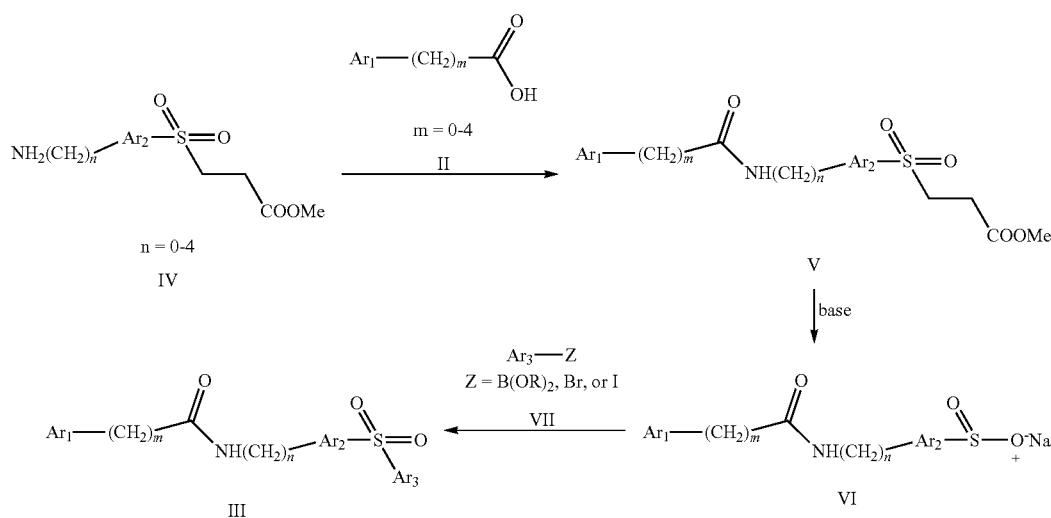

In Scheme 3, the compound of III present invention can also be synthesized by following the steps outlined in Scheme IV. Treating II with IV in the presence of a coupling reagent such as EDCI, HATU, BOP, or HOBt, and a base (eg: $K_2CO_3$, $Cs_2CO_3$, $NR_1R_2R_3$, NaOR, KOR) in an inert solvent such as dichloromethane, N,N-dialkylformamide, N,N-dialkylacetamide, dialkylethers, DMSO, or N-methyl-2-pyrrolidinone at temperatures ranging from −78° C. to 200° C. gives compound V. Compound V can be treated with a base such as sodium ethoxide in the present of a protonated solvent such as ethanol to afford compound VI. Treating compound VI with arylboronic acid or aryl halogens facilitated by palladium or copper to obtain the target compound III.

Example 1 Preparation of Representative Amide-Sulfonamide Analogues

These examples illustrate the preparation of representative substituted amide-sulfonamide analogues.

Example 1A

N-(4-(N-(2-(trifluoromethoxy)phenyl)sulfamoyl)benzyl)-1H-pyrrolo[3,2-c]pyridine-2-carboxamide

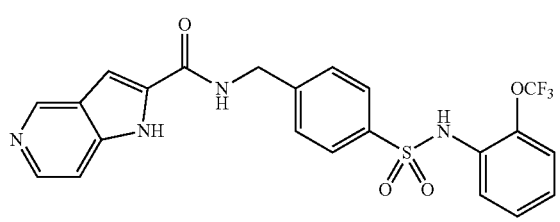 [SMILES: O=C(NCc1ccc(S(=O)(=O)Nc2ccccc2OC(F)(F)F)cc1)c1cc2cnccc2[nH]1]

A: 4-cyano-N-(2-(trifluoromethoxy)phenyl)benzene-sulfonamide

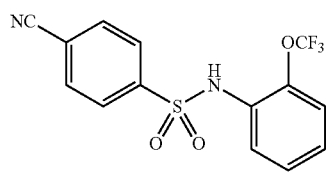 [SMILES: N#Cc1ccc(S(=O)(=O)Nc2ccccc2OC(F)(F)F)cc1]

2-(Trifluoromethoxy)aniline (10.902 g, 58.5 mmol) was dissolved in pyridine (100 mL) and cooled to 0° C. A solution of 4-cyanobenzene-1-sulfonyl chloride (11.573 g, 55.7 mmol) was added in pyridine (100 mL) over 10 minutes via addition funnel. The mixture was heated to 85° C. for 16 hours and the pyridine was removed under reduced pressure. The residue was diluted with DCM and washed with 1M HCl (×2), water (×1), brine (×1), and saturated $NaHCO_3$ (×1). The organic layer was dried over anhydrous $MgSO_4$, filtered, concentrated, and purified by Biotage SP1 (hexanes/DCM) to afford the title compound as a white solid.

$^1$H NMR (300 HMz; DMSO-$d_6$): δ 10.58 (s, 1H), 8.06 (d, 2H), 7.89 (d, 2H), 7.30 (s, 4H).

B: 4-(aminomethyl)-N-(2-(trifluoromethoxy)phenyl)benzenesulfonamide

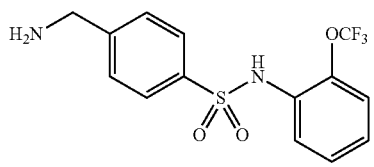 [SMILES: NCc1ccc(S(=O)(=O)Nc2ccccc2OC(F)(F)F)cc1]

4-Cyano-N-(2-(trifluoromethoxy)phenyl)benzenesulfonamide (2.0 g, 5.84 mmol) was dissolved in THF (30 mL) and borane tetrahydrofuran complex (14.61 mL of a 1M solution in THF) was added. The mixture was heated to 70° C. for 2 hours, then cooled to room temperature followed by the addition of MeOH (10 mL). The mixture was briefly warmed to 70° C. for 15 minutes, then the volatiles removed under reduced pressure and EtOAc (100 mL) and 1N NaOH (50 mL) were added to the residue. The layers were separated, and the organic layer washed with water and brine. The combined aqueous washes were extracted with EtOAc, combined with the previous organic extracts, and dried over $MgSO_4$. The residue was purified by Biotage SP1 (MeOH/DCM/$NH_3$ gradient) to afford the title compound as a pale yellow solid.

$^1$H NMR (300 HMz; DMSO-$d_6$): δ 7.70 (d, 2H), 7.41 (d, 2H), 7.19 (d, 1H), 7.00 (d, 1H), 6.89 (t, 1H), 6.58 (t, 1H), 3.84 (s, 2H).

C: N-(4-(N-(2-(trifluoromethoxy)phenyl)sulfamoyl)benzyl)-1H-pyrrolo[3,2-c]pyridine-2-carboxamide

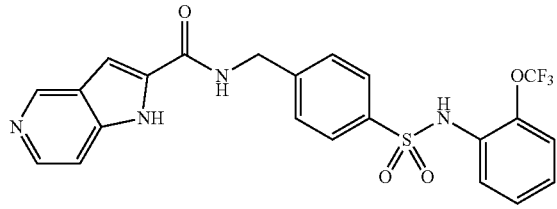 [SMILES: O=C(NCc1ccc(S(=O)(=O)Nc2ccccc2OC(F)(F)F)cc1)c1cc2cnccc2[nH]1]

A mixture of 1H-pyrrolo[3,2-c]pyridine-2-carboxylic acid (478 mg, 2.95 mmol), 4-(aminomethyl)-N-(2-(trifluoromethoxy)phenyl)benzenesulfonamide (973 mg, 2.81 mmol), HATU (1.122 g, 2.95 mmol), DIEA (1.082 mL, 6.20 mmol), and DMF (15 mL) at 25° C. were stirred for 16 hours at ambient temperature. The mixture was diluted with EtOAc and washed successively with saturated NaHCO₃ and brine. The organic extracts were separated and dried over MgSO₄, filtered, concentrated, and purified by Biotage SP1 (DCM/MeOH gradient). The combined fractions were triturated with Et₂O to afford the product as a white solid.

$^1$H NMR (300 HMz; DMSO-d₆): δ 12.10 (br s, 1H), 9.23 (t, 1H), 8.98 (s, 1H), 8.21 (d, 1H), 7.78 (d, 2H), 7.47 (d, 2H), 7.38 (d, 1H), 7.31-7.19 (m, 6H), 4.58 (d, 2H). LC-MS: 491.11 (M+1).

Example 1B

N-(4-(piperidin-1-ylsulfonyl)benzyl)thieno[3,2-c]pyridine-2-carboxamide

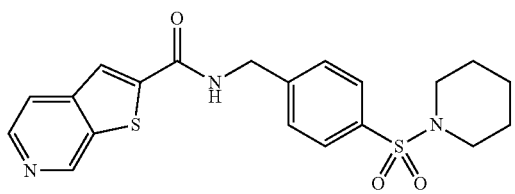 [SMILES: O=C(NCc1ccc(S(=O)(=O)N2CCCCC2)cc1)c1cc2ccncc2s1]

(4-(Piperidin-1-ylsulfonyl)phenyl)methanamine (155 mg, 0.609 mmol) and trimethylaluminum (0.30 mL, 0.600 mmol) were combined in toluene (2 mL) and stirred for 30 minutes at ambient temperature. A solution of methyl thieno[3,2-c]pyridine-2-carboxylate (100 mg, 0.518 mmol, prepared according to WO 2004/064836) in toluene (2 mL) was then added and the mixture heated to 110° C. for 16 hours. Upon cooling, a saturated solution of potassium sodium tartrate and EtOAc were added and the mixture stirred vigorously for 30 minutes and then filtered. The layers were separated, the organics dried over MgSO₄, and purified by Biotage SP1 (100% EtOAc) to afford the title compound as white foam.

$^1$H NMR (300 HMz; CDCl₃): δ 9.13 (s, 1H), 8.50 (d, 1H), 7.93 (s, 1H), 7.79 (t, 1H), 7.67 (d, 1H), 7.48 (d, 2H), 7.36 (d, 2H), 4.69 (d, 2H), 2.89 (t, 4H), 1.63-1.55 (m, 4H), 1.42-1.34 (m, 2H) LC-MS: 416.11 (M+1).

Example 1C

N-(4-(N-(2,5-dimethoxyphenyl)sulfamoyl)benzyl)-1H-pyrrolo[3,2-c]pyridine-2-carboxamide

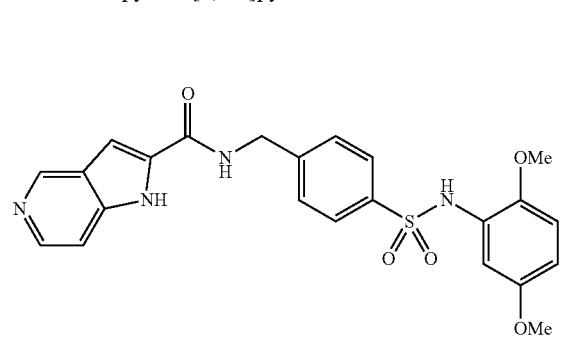

A: N-(4-(N-(2,5-dimethoxyphenyl)sulfamoyl)benzyl)acetamide

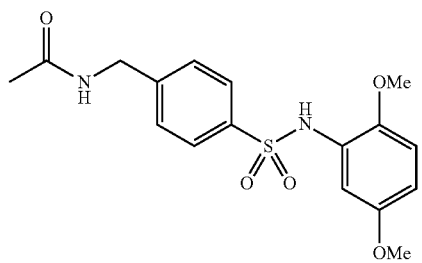 [SMILES: COc1ccc(OC)c(NS(=O)(=O)c2ccc(CNC(C)=O)cc2)c1]

A mixture of 4-(acetamidomethyl)benzene-1-sulfonyl chloride (25 mg, 0.1 mmol), 2,5-dimethoxyaniline (15.3 mg, 0.1 mmol), and pyridine (0.25 mL) in DMA (1 mL) were heated at 50° C. for 16 hours before being concentrated under reduced pressure. The residue was purified by PTLC (100% EtOAc) to afford the title compound as white solid.

$^1$H NMR (400 HMz; CDCl₃): δ 7.73 (d, J=8 Hz, 2H), 7.30 (d, J=8 Hz, 2H), 7.14 (d, J=3.2 Hz, 1H), 7.05 (s, 1H), 6.66 (d, J=8.8 Hz, 1H), 6.54 (dd, J=8.8 Hz, J'=3.2 Hz, 1H), 5.95 (br s, 1H), 4.46 (d, J=6 Hz, 2H), 3.74 (s, 3H), 3.61 (s, 3H), 2.07 (s, 3H). LC-MS: 364.99 (M+1).

B: (4-(N-(2,5-dimethoxyphenyl)sulfamoyl)phenyl)methanaminium chloride

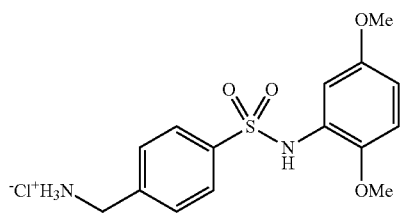

A mixture of N-(4-(N-(2,5-dimethoxyphenyl)sulfamoyl)benzyl)acetamide (28 mg, 0.077 mmol) and 3N HCl (0.5 mL, 1.5 mmol) in 70% i-PrOH (0.5 mL) was heated at 100° C. for 5 hours. The mixture was concentrated to dryness in vacuo to afford the title compound as off-white solid.

¹H NMR (400 HMz; CDCl₃): δ 7.84 (d, J=8.4 Hz, 2H), 7.56 (d, J=8.8 Hz, 2H), 7.04 (d, J=2.8 Hz, 1H), 6.74 (d, J=9.2 Hz, 1H), 6.60 (dd, J=9.2 Hz, J'=3.2 Hz, 1H), 5.95 (br s, 1H), 4.16 (s, 2H), 3.70 (s, 3H), 3.54 (s, 3H). LC-MS: 323.03 (M+1)

C: N-(4-(N-(2,5-dimethoxyphenyl)sulfamoyl)benzyl)-1H-pyrrolo[3,2-c]pyridine-2-carboxamide

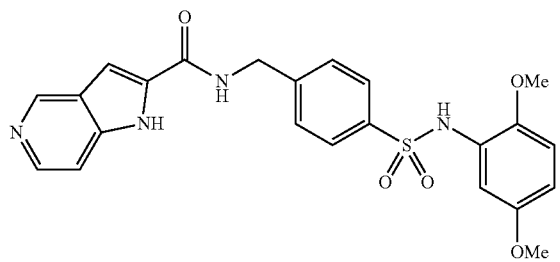 [SMILES: COc1ccc(OC)c(NS(=O)(=O)c2ccc(CNC(=O)c3cc4cnccc4[nH]3)cc2)c1]

The title compound was prepared following Example 1C, substituting BOP in place of HATU, and 4-(aminomethyl)-N-(2,5-dimethoxyphenyl)benzenesulfonamide in place of 4-(aminomethyl)-N-(2-(trifluoromethoxy)phenyl)benzenesulfonamide. The product was purified by PTLC.

¹H NMR (400 HMz; CD₃OD): δ 8.90 (d, J=0.8 Hz, 1H), 8.22 (d, J=5.6 Hz, 1H), 7.71 (d, J=8.4 Hz, 2H), 7.51 (d, J=6 Hz, 1H), 7.45 (d, J=8.8 Hz, 2H), 7.28 (d, J=0.8 Hz, 1H), 7.02 (d, J=3.2 Hz, 1H), 6.70 (d, J=9.2 Hz, 1H), 6.59 (dd, J=8.8 Hz, J'=3.2 Hz, 1H), 4.62 (s, 2H), 3.69 (s, 3H), 3.46 (s, 3H). LC-MS: 466.98 (M+1).

Example 2: Preparation of Representative Amide-sulfone Analogues

These examples illustrate the preparation of representative substituted amide-sulfonamide analogues.

Example 2 A

N-(4-(phenylsulfonyl)benzyl)-1H-pyrrolo[3,2-c]pyridine-2-carboxamide

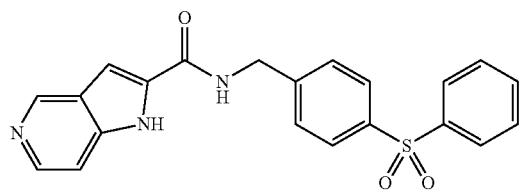 [SMILES: O=C(NCc1ccc(S(=O)(=O)c2ccccc2)cc1)c1cc2cnccc2[nH]1]

a: 4-(phenylsulfonyl) benzonitrile

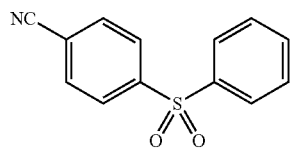 [SMILES: N#Cc1ccc(S(=O)(=O)c2ccccc2)cc1]

A mixture of 4-fluorobenzonitrile (5 g, 41.3 mmol) and sodium benzenesulfinate (7.45 g, 45.4 mmol) in DMSO (30 mL) was heated at 130° C. for 16 hours. The mixture was cooled to room temperature and poured onto 300 g of ice. The precipitate was collected, washed with water, and dried to afford the title compound.

¹H NMR (300 MHz, CDCl₃): δ 8.03-8.07 (m, 2H), 7.93-7.97 (m, 2H), 7.78-7.82 (m, 2H), 7.60 (m 7.65, 1H), 7.26-7.58 (m, 2H)

b: (4-[phenylsulfonyl]phenyl)methanamine

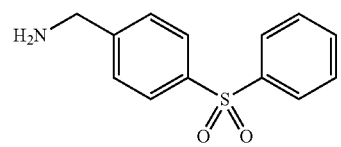 [SMILES: NCc1ccc(S(=O)(=O)c2ccccc2)cc1]

A mixture of 4-(phenylsulfonyl)benzonitrile (9.4 g, 38.64 mmol) and Raney Ni (500 mg) in 2N NH₃-MeOH (150 mL) was hydrogenated for 16 hours at 50 psi. Nitrogen gas was bubbled through the mixture, which was then filtered through a short Celite pad, and washed with methanol. The filtrate was concentrated and triturated with ether to afford the title compound.

¹H NMR (300 MHz, DMSO-d₆): δ 7.85-7.95 (m, 4H), 7.53-7.68 (m, 5H), 3.74 (s, 2H), 1.83 (br s, 2H)

c: N-(4-(phenylsulfonyl)benzyl)-1H-pyrrolo[3,2-c]pyridine-2-carboxamide

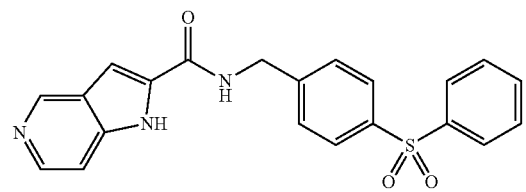 [SMILES: O=C(NCc1ccc(S(=O)(=O)c2ccccc2)cc1)c1cc2cnccc2[nH]1]

A mixture of 1H-pyrrolo[3,2-2]pyridine-2-carboxylic acid (1.0 g, 6.17 mmol), HATU (3.52 g, 9.25 mmol), diisopropylethylamine (2.69 mL, 15.42 mmol), and (4-(phenylsulfonyl)phenyl)methanamine (1.754 g, 7.09 mmol) in DMF (70 mL) was stirred at room temperature for 16 hours. The solvent was removed under reduced pressure, water (200 mL) was added, and the mixture was extracted with EtOAc (3×300 mL). The combined organic layers were successively washed with water, saturated sodium bicarbonate, and brine. The extracts were dried with sodium sulfate, concentrated in vacuo, and purified by Biotage with MeOH/DCM (0%-10%) to afford the title compound.

¹H NMR (300 MHz, DMSO-d₆) δ 4.56 (d, J=5.57 Hz, 2H), 7.29 (s, 1H), 7.34 (d, J=5.57 Hz, 1H), 7.56-7.66 (m, 5H), 7.91-7.94 (m, 4H), 8.20 (d, J=5.87 Hz, 1H), 8.91 (s, 1H), 9.245-9.28 (m, 1H). 12.03 (s, 1H) LC-MS: 392.13 (M+1).

Example 2 B 3-bromo-N-(4-(phenylsulfonyl)benzyl)-1H-Pyrrolo[3,2-c]pyridine-2-carboxamide

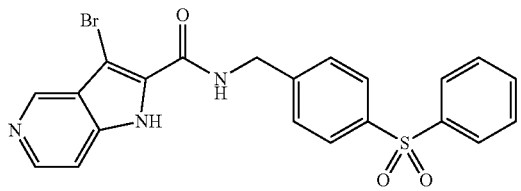 [SMILES: O=C(NCc1ccc(S(=O)(=O)c2ccccc2)cc1)c1[nH]c2ccncc2c1Br]

A mixture of N-(4-(phenylsulfonyl)benzyl)-1H-pyrrolo[3,2-c]pyridine-2-carboxamide (from Example 1; 200 mg, 0.511 mmol) and 1-bromopyrrolidine-2,5-dione (91 mg, 0.511 mmol) in DMF (10 mL) was stirred at room temperature for 16 hours. EtOAc (100 mL) was added to the mixture. The organic layer was washed with water and brine, dried with sodium sulfate, and concentrated in vacuo. The crude was purified by Biotage with MeOH/DCM (0%-10%) to afford the title compound.

$^1$H NMR (300 MHz, DMSO-d$_6$): δ 12.42 (br s, 1H), 8.78 (m, 2H), 8.30 (d, 1H), 7.93 (d, 4H), 7.59-7.69 (m, 5H), 7.38 (dd, 1H), 4.59 (d, 2H) LC-MS: 470.06 (M+1).

Example 2 C

N-({4-[(4-fluorobenzene)sulfonyl]phenyl}methyl)thieno[2,3-c]pyridine-2-carboxamide

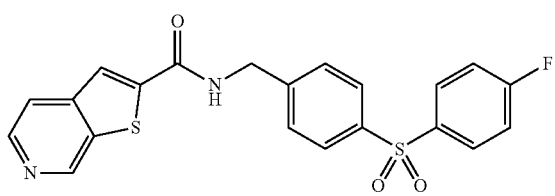 [SMILES: O=C(NCc1ccc(S(=O)(=O)c2ccc(F)cc2)cc1)c1cc2ccncc2s1]

a: 4-(4-fluorophenylsulfonyl)benzonitrile

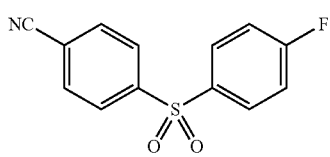 [SMILES: N#Cc1ccc(S(=O)(=O)c2ccc(F)cc2)cc1]

The title compound was prepared following Example 1A, substituting sodium 4-fluorobenzenesulfinate for sodium benzenesulfinate.

$^1$H NMR (300 MHz, DMSO-D$_6$) δ: 8.10-8.18 (m, 6H), 7.42-7.12 (t, 2H).

b: (4-[4-fluorophenylsulfonyl]phenyl)methanamine

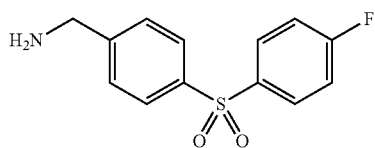 [SMILES: NCc1ccc(S(=O)(=O)c2ccc(F)cc2)cc1]

The title compound was prepared following Example 1B, substituting 4-(4-fluorophenylsulfonyl)benzonitrile for 4-(phenylsulfonyl)benzonitrile.

$^1$H NMR (300 MHz, (DMSO-d$_6$): δ 7.8-7.96 (m, 4H), 3.74 (s, 2H), 7.42-7.64 (m, 4H), 3.64 (m, 2H).

c: N-({4-[(4-fluorobenzene)sulfonyl]phenyl}methyl)thieno[2,3-c]pyridine-2-carboxamide

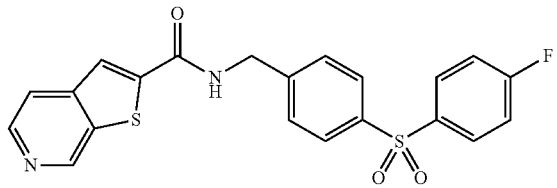 [SMILES: O=C(NCc1ccc(S(=O)(=O)c2ccc(F)cc2)cc1)c1cc2ccncc2s1]

(4-(4-Fluorophenylsulfonyl)phenyl)methanamine hydrochloride (1409 mg, 4.67 mmol) was mixed with toluene (20 mL) and cooled to 0° C. Trimethylaluminum (7.00 mL of a 2M solution in toluene) was added and the mixture was stirred for 40 minutes at ambient temperature. A solution of methyl thieno[2,3-c]pyridine-2-carboxylate (820 mg, 4.24 mmol, prepared according to WO 2004/064836) in toluene (10 mL) was added via syringe, and the mixture was heated to 80° C. for 4 hours. The mixture was diluted with saturated potassium sodium tartrate (25 mL) and EtOAc (25 mL), stirred vigorously for 1 hour, and then filtered through GF/F paper. The organic layer was separated, dried over MgSO$_4$, filtered, and concentrated to a yellow solid. The residue was triturated with DCM and the title compound was collected by vacuum filtration.

$^1$H NMR (300 MHz, DMSO-d$_6$) δ 9.59 (t, 1H), 9.30 (s, 1H), 9.50 (d, 1H), 8.15 (s, 1H), 8.04-7.98 (m, 2H), 7.96-7.90 (m, 3H), 7.56 (d, 2H), 7.47-7.40 (m, 2H), 4.55 (d, 2H) LC-MS: 427.03 (M+1).

Example 2 D

N-(4-(phenylsulfonyl)benzyl)-1H-pyrrolo[3,2-c]pyridine-2-carboxamide

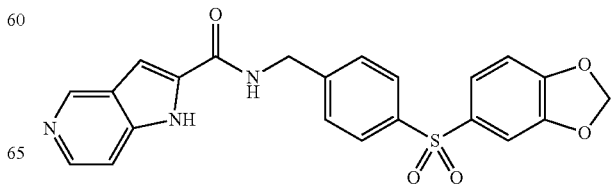

a: sodium 4-(acetamidomethyl)benzenesulfinate

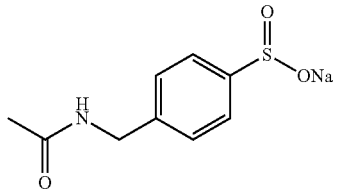

4-(Acetamidomethyl)benzene-1-sulfonyl chloride (1.24 g, 5 mmol) was added to a water-cooled solution of Na$_2$SO$_3$ (1.89 g, 15 mmol) in water (3.75 mL) then solid NaHCO$_3$ (850 mg, 10 mmol) was added in several small portions to keep the pH slightly basic. The mixture was stirred at ambient temperature for 2 hours, affording a thick white suspension. Brine (2 ml) was added and the mixture was stirred at ambient temperature for 15 minutes. The precipitate was collected by filtration and dried overnight under vacuum. The solid was ground up and stirred with 125 ml of MeOH for 30 min then the solid was filtered off, washing with MeOH (20 mL). The filtrate was concentrated to give the title compound as a white solid.

$^1$H NMR (400 MHz, CD$_3$OD): δ 7.61 (d, J=8.4 Hz, 2H), 7.34 (d, J=8.4 Hz, 2H), 4.38 (s, 2H), 1.98 (s, 3H).

b: N-(4-(benzo[d][1,3]dioxol-5-ylsulfonyl)benzyl)acetamide

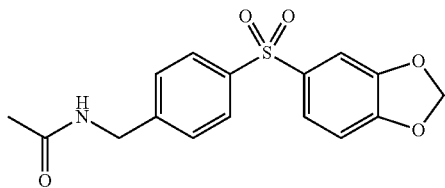 [SMILES: CC(=O)NCc1ccc(S(=O)(=O)c2ccc3c(c2)OCO3)cc1]

A mixture of sodium 4-(acetamidomethyl)benzenesulfinate (23.5 mg, 0.1 mmol), benzo[d][1,3]dioxol-5-ylboronic acid (20.7 mg, 0.125 mmol), copper(II) acetate (22.7 mg, 0.125 mmol), and TEA (0.063 mL, 0.45 mmol) in DMSO (1.5 mL) was heated at 60° C. for 16 hours. The mixture was cooled to room temperature and partitioned between EtOAc-brine. The organic layer was separated and concentrated in vacuo. The crude was purified by PTLC (100% EtOAc) to afford the title compound as white solid.

$^1$H NMR (400 MHz, CDCl$_3$): δ 7.85 (d, J=8 Hz, 2H), 7.52 (dd, J=8 Hz, J'=1.6 Hz, 1H), 7.39 (d, J=8.4 Hz, 2H), 7.29 (d, J=2 Hz, 1H), 6.87 (d, J=8 Hz, 1H), 6.05 (s, 2H), 5.87 (br s, 1H), 4.47 (d, J=6.4 Hz, 2H), 2.04 (s, 3H).

LC-MS: 333.97 (M+1)

c: (4-(benzo[d][1,3]dioxol-5-ylsulfonyl)phenyl)methanamine hydrochloride

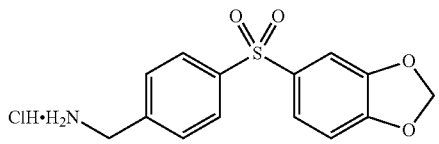

A mixture of N-(4-(benzo[d][1,3]dioxol-5-ylsulfonyl)benzyl)acetamide (10 mg, 0.03 mmol) and 3N HCl (0.36 mL, 1.08 mmol) in 70% i-PrOH (0.2 mL) was heated at 100° C. for 5 hours. The mixture was concentrated to dryness to afford the title compound as off-white solid.

$^1$H NMR (400 MHz, CD$_3$OD): δ 8.00 (d, J=8.4 Hz, 2H), 7.64 (d, J=8.4 Hz, 2H), 7.55 (dd, J=8.4 Hz, J'=2 Hz, 1H), 7.34 (d, J=2.4 Hz, 1H), 6.98 (d, J=8 Hz, 1H), 6.08 (s, 2H), 4.19 (s, 2H).

LC-MS: 219.99 (M+1)

d: N-(4-(phenylsulfonyl)benzyl)-1H-pyrrolo[3,2-c]pyridine-2-carboxamide

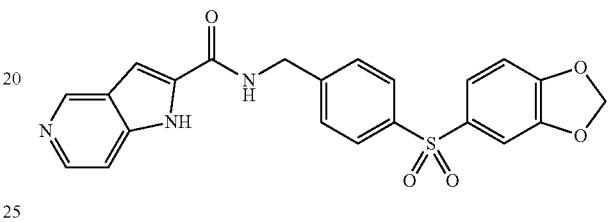

The title compound was prepared following Example IC, substituting (4-(benzo[d][1,3]dioxol-5-ylsulfonyl)phenyl)methanamine hydrochloride for (4-(phenylsulfonyl)phenyl)methanamine, and substituting BOP instead of HATU. The title compound was purified by PTLC.

$^1$H NMR (400 MHz, CD$_3$OD): δ 9.05 (s, 1H), 8.29 (d, J=6 Hz, 1H), 7.90 (d, J=8.4 Hz, 2H), 7.68 (d, J=6 Hz, 1H), 7.57 (d, J=8 Hz, 2H), 7.52 (dd, J=8 Hz, J'=2 Hz, 1H), 7.42 (s, 1H), 7.31 (d, J=2 Hz, 1H), 6.95 (d, J=8.4 Hz, 1H), 6.06 (s, 2H), 4.66 (s, 2H) LC-MS: 435.97 (M+1).

Example 2 E 1-methyl-N-(4-(phenylsulfonyl)benzyl)-1H-pyrazolo[3,4-b]pyridine-5-carboxamide

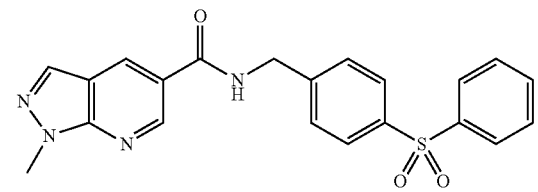 [SMILES: Cn1ncc2cc(C(=O)NCc3ccc(S(=O)(=O)c4ccccc4)cc3)cnc21]

Iodomethane (33.5 µL, 0.535 mmol) was added to a mixture of N-(4-(phenylsulfonyl)benzyl)-1H-pyrazolo[3,4-b]pyridine-5-carboxamide (Example 12; 100 mg, 0.255 mmol) and potassium carbonate (106 mg, 0.764 mmol) in DMF (1 mL) at room temperature. The reaction mixture was heated to 60° C. for 16 hours, whereupon the mixture was diluted with EtOAc and washed with brine (×3). The organic layer was dried over Na$_2$SO$_4$ and concentrated in vacuo. The residue was dissolved in DMSO (2 mL) and purified via HPLC to afford the title compound.

$^1$H NMR (DMSO-d$_6$): δ 9.31 (t, 1H), 9.02 (d, 1H), 8.72 (d, 1H), 8.28 (s, 1H), 7.94-7.90 (m, 4H), 7.66-7.55 (m, 5H), 4.56 (d, 2H), 4.07 (s, 3H). LC-MS: 407.07 (M+1).

Example 2 F 1-methyl-N-(4-(phenylsulfonyl)benzyl)-1H-pyrrolo[3,2-c]pyridine-2-carboxamide

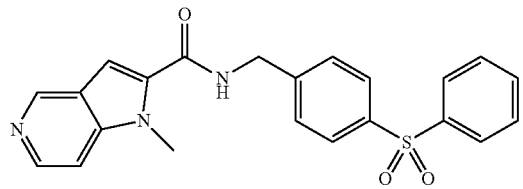 [SMILES: Cn1c(C(=O)NCc2ccc(S(=O)(=O)c3ccccc3)cc2)cc2cnccc21]

a: methyl 1-methyl-1H-pyrrolo[3,2-c]pyridine-2-carboxylate

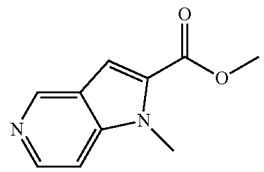

Sodium hydride (48 mg (60%), 1.226 mmol) was added to a ice-cold solution of 1H-pyrrolo[3,2-c]pyridine-2-carboxylate 9180 mg, 1.022 mmol) in THF (3 mL). The mixture was then warmed to room temperature over 10 minutes. Iodomethane (0.070 mL, 1.124 mmol) was added and the mixture stirred for 16 hours. The mixture was partitioned between EtOAc and water. The combined organic layers were dried over MgSO$_4$, filtered, and concentrated to dryness. The residue was purified by Biotage to afford the title compound.

$^1$H NMR (CDCl$_3$): δ 8.90 (s, 1H), 8.35 (d, 1H), 7.92 (s, 1H), 7.20 (d, 1H), 3.95 (s, 3H), 3.82 (s, 3H).

b: 1-methyl-N-(4-(phenylsulfonyl)benzyl)-1H-pyrrolo[3,2-c]pyridine-2-carboxamide

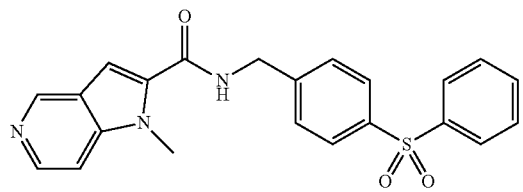 [SMILES: Cn1c(C(=O)NCc2ccc(S(=O)(=O)c3ccccc3)cc2)cc2cnccc21]

The title compound was prepared following Example 3C, substituting methyl 1-methyl-1H-pyrrolo[3,2-c]pyridine-2-carboxylate and (4-(phenylsulfonyl)phenyl)methanamine for methyl thieno[2,3-c]pyridine-2-carboxylate and (4-(4-fluorophenylsulfonyl)phenyl)methanamine, respectively. The title compound was purified by PTLC.

$^1$H NMR (DMSO-D$_6$): δ 9.27 (t, 1H), 8.91 (s, 1H), 8.28 (d, 1H), 7.92-7.95 (m, 4H). 7.53-7.67 (m, 6H), 7.27 (s, 1H), 4.52 (d, 2H), 3.95 (s, 3H). LC-MS: 406.01 (M+1).

Example 2 G

N-(4-(phenylsulfonyl)benzyl)-1H-imidazo[4,5-c]pyridine-2-carboxamide

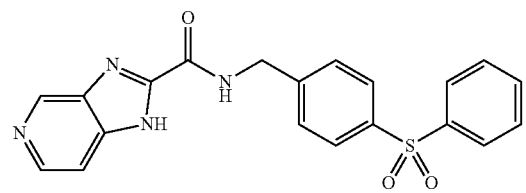 [SMILES: O=C(NCc1ccc(S(=O)(=O)c2ccccc2)cc1)c1nc2cnccc2[nH]1]

a: methyl 1H-imidazo[4,5-c]pyridine-2-carboxylate

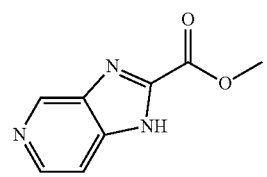

Methyl 2,2-dichloro-2-methoxyacetate (1.585 g, 9.16 mmol) was added to a solution of pyridine-3,4-diamine (0.5 g, 4.58 mmol) and DIEA (4.80 mL, 27.5 mmol) in DCM (20 mL). The mixture was stirred at room temperature for 16 hours, whereupon EtOAc was added and the mixture washed with saturated sodium bicarbonate and brine. The organic layer was dried over MgSO$_4$, filtered, concentrated, and purified by Biotage to afford the title compound.

$^1$H NMR (CD$_3$OD): δ 8.71 (s, 1H), 8.32 (d, 1H), 7.22 (d, 1H), 4.09 (s, 3H).

b: N-(4-(phenylsulfonyl)benzyl)-1H-imidazo[4,5-c]pyridine-2-carboxamide

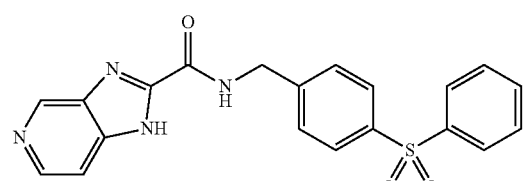

The title compound was prepared following Example 3C, substituting methyl 1H-imidazo[4,5-c]pyridine-2-carboxylate and (4-(phenylsulfonyl)phenyl)methanamine for methyl thieno[2,3-c]pyridine-2-carboxylate and (4-(4-fluorophenylsulfonyl)phenyl)methanamine, respectively. The title compound was purified by PTLC. $^1$H NMR (CD$_3$OD): δ 8.32 (s, 1H), 8.16 (d, 1H), 7.89-7.93 (m, 4H), 7.51-7.64 (m, 5H), 7.30 (d, 1H), 4.81 (s, 2H). LC-MS: 393.02 (M+1).

Example 2 H

N-(4-((3-chloro-5-fluorophenyl)sulfonyl)benzyl)furo[2,3-c]pyridine-2-carboxamide

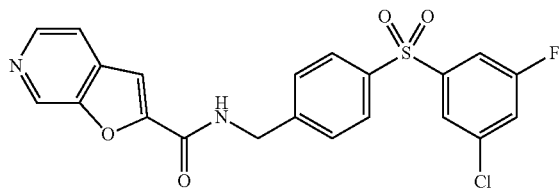 [SMILES: O=C(NCc1ccc(S(=O)(=O)c2cc(F)cc(Cl)c2)cc1)c1cc2ccncc2o1]

a: ethyl furo[2,3-c]pyridine-2-carboxylate

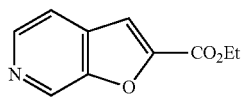

To a solution of ethyl 3-(trifluoromethylsulfonyloxy)furo[2,3-c]pyridine-2-carboxylate (524 mg, 1.545 mmol, prepared according to US 20070049603) in ethanol (15 mL) was added 10% Pd/C (50 mg) and triethylamine (0.5 mL, 3.59 mmol). The mixture was placed under an atmosphere of hydrogen (balloon) and stirred for 16 hours. The mixture was filtered, concentrated, and purified by silica gel chromatography to afford the title compound as an off-white solid (278 mg, 94%).
$^1$H NMR (CDCl$_3$): δ 9.03 (s, 1H), 8.51 (d, 1H), 7.63 (dd, 1H), 7.52 (d, 1H), 4.48 (q, 2H), 1.45 (t, 3H).
MS (ESI): 192.01 (M+H).

b: furo[2,3-c]pyridine-2-carboxylic acid

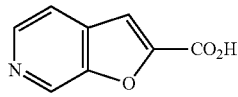

To a solution of ethyl furo[2,3-c]pyridine-2-carboxylate (3.82 g, 19.98 mmol) in water:THF:MeOH (1:1:1, 60 mL) was added potassium hydroxide (3.36 g, 59.9 mmol) and the resulting mixture was stirred at ambient temperature for 16 hours. The solvent volume was then reduced to ~20 mL and acetic acid was added until pH ~4. The solids were collected by vacuum filtration, washed twice with water, and dried in a vacuum oven overnight to afford the title compound (2.90 g, 89%).
$^1$H NMR (DMSO-d$_6$): δ 9.09 (s, 1H), 8.47 (d, 1H), 7.81 (dd, 1H), 7.71 (d, 1H), 3.36 (br s, 1H).

c: N-(4-((3-chloro-5-fluorophenyl)sulfonyl)benzyl)furo[2,3-c]pyridine-2-carboxamide

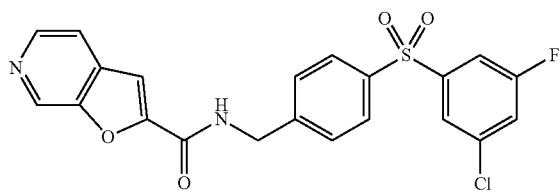 [SMILES: O=C(NCc1ccc(S(=O)(=O)c2cc(F)cc(Cl)c2)cc1)c1cc2ccncc2o1]

To a mixture of furo[2,3-c]pyridine-2-carboxylic acid (243 mg, 1.487 mmol), (4-(3-chloro-5-fluorophenylsulfonyl)phenyl)methanamine hydrochloride (500 mg, 1.487 mmol), and (benzotriazol-1-yloxy)tris(dimethylamino)phosphonium hexafluorophosphate (724 mg, 1.636 mmol) in DMF (8 mL) was added N,N-diisopropylethylamine (0.571 mL, 3.27 mmol). The homogeneous reaction mixture was stirred for 16 hours at ambient temperature, then the DMF was removed under reduced pressure. The residue was treated with EtOAc (10 mL) and 1N NaOH (5 mL) and the mixture was stirred vigorously until a precipitate emerged. The solids were collected by vacuum filtration, rinsing with water and EtOAc, to afford the title compound (440 mg, 67%).
$^1$H NMR (DMSO-d$_6$): δ 9.62 (t, 1H), 9.03 (s, 1H), 8.46 (d, 1H), 8.02 (dt, 2H), 7.87-7.80 (m, 4H), 7.62 (d, 1H), 7.58 (d, 2H), 4.56 (d, 2H).
MS (ESI): 444.82 (M+H).

Example 2 I

N-(4-(4-(ethylcarbamoyl)phenylsulfonyl)benzyl)imidazo[1,2-a]pyridine-6-carboxamide

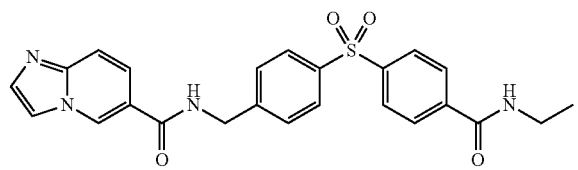 [SMILES: CCNC(=O)c1ccc(S(=O)(=O)c2ccc(CNC(=O)c3ccc4nccn4c3)cc2)cc1]

a. 4-((4-cyanophenylthio)benzoic acid

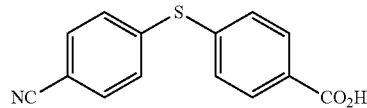

In a 250 mL round-bottomed flask was added 4-fluorobenzonitrile (2.121 g, 17.51 mmol), 4-mercaptobenzoic acid (3 g, 17.51 mmol), and potassium carbonate (7.26 g, 52.5 mmol) in DMF (Volume: 50 mL). The reaction was heated to 100° C. overnight and monitored by LCMS. When complete, the slurry was treated with 100 mL of water to give a clear solution. The solution was then treated with 6M aq. HCl slowly until pH<4 upon which a precipitate formed. The slurry was filtered and washed with water to give 14.8 g of crude product after drying briefly on filter. NMR showed product, an impurity and water. Dried in vacuum oven overnight to give 4.41 g of material which was adsorbed onto 50 g of silica gel and then plug filtered with 10% MeOH/CH$_2$Cl$_2$ to give 3.45 g of material which was used without further purification.
$^1$H NMR (300 MHz, DMSO-d6): δ 13.18 (br s, 1H), 7.96 (d, 2H), 7.80 (d, 2H), 7.52 (d, 2H), 7.42 (d, 2H).

b. 4-(4-cyanophenylthio)-N-ethylbenzamide

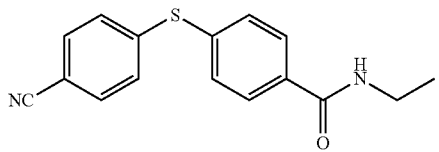 [SMILES: CCNC(=O)c1ccc(Sc2ccc(C#N)cc2)cc1]

In a 500 mL round-bottomed flask was added 4-(4-cyanophenylthio)benzoic acid (3.45 g, 13.51 mmol), HBTU (5.13 g, 13.51 mmol) and HOBT (2.070 g, 13.51 mmol) in DMF (Volume: 100 mL) followed by ethanamine (2M in THF, 20.27 mL, 40.5 mmol). The reaction was stirred overnight and then concentrated under reduced pressure. The residue was dissolved in ethyl acetate and washed with 2M aq. NaOH, water and brine. The organic layer was separated, dried with anhydrous sodium sulfate, filtered and concentrated to give 2.8 g of product. Material used without further purification.

$^1$H NMR (300 MHz, DMSO-d6): δ 8.57 (t, 1H), 7.89 (d, 2H), 7.75 (d, 2H), 7.55 (d, 2H), 7.31 (d, 2H), 3.30 (m, 2H), 1.10 (t, 3H).

c. 4-(4-cyanophenylsulfonyl)-N-ethylbenzamide

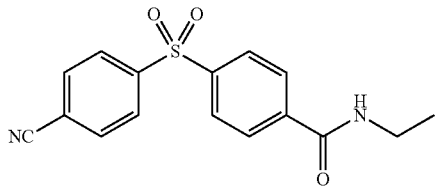 [SMILES: CCNC(=O)c1ccc(S(=O)(=O)c2ccc(C#N)cc2)cc1]

In a 500 mL round-bottomed flask was added 4-(4-cyanophenylthio)-N-ethylbenzamide (2.81 g, 9.95 mmol) in chloroform (Volume: 50 mL) which was cooled to 0° C. followed by the addition of mCPBA (6.87 g, 29.9 mmol). The reaction was stirred for 1 hour at 0° C. and then warmed to room temperature overnight. The reaction was diluted with chloroform and poured into a separatory funnel. The organic layer was washed with 10% aqueous sodium thiolsulfate, 2M NaOH, and saturated, aqueous sodium chloride. The bottom was separated, dried with anhydrous sodium sulfate, filtered and concentrated under reduced pressure to give 2.79 g of crude product. Material purified on Biotage to give 2.42 g of pure product (70% yield).

$^1$H NMR (300 MHz, DMSO-d6): δ 8.68 (t, 1H), 8.15 (d, 2H), 8.09 (m, 4H), 7.95 (d, 2H), 3.28 (m, 2H), 1.02 (t, 3H).

LC-MS (ESI): 314.92 (M+1).

d. 4-(4-(aminomethyl)phenylsulfonyl)-N-ethylbenzamide

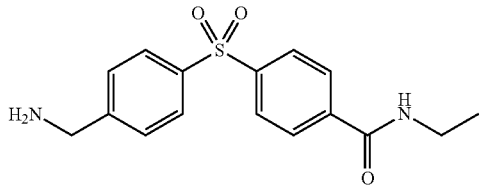 [SMILES: CCNC(=O)c1ccc(S(=O)(=O)c2ccc(CN)cc2)cc1]

A slurry of Raney Nickel (0.660 g, 7.70 mmol) was added to a Paar flask and washed with methanol. The MeOH was removed by pipette and the process repeated twice more. 4-(4-cyanophenylsulfonyl)-N-ethylbenzamide (2.42 g, 7.70 mmol) in MeOH (Volume: 50 mL)) was then added followed by potassium hydroxide (0.043 g, 0.770 mmol) and ammonia (7M, 11.00 mL, 77 mmol) in MeOH. The slurry was placed on the Paar shaker and hydrogenated at 35 psi overnight. Reaction monitored by LCMS. The solution was then filtered through celite and washed with MeOH. The solution was then concentrated under reduced pressure to give 2.56 g of product. Material purified on Biotage to give 2.03 g of product (83% yield).

$^1$H NMR (300 MHz, DMSO-d6): δ 8.65 (t, 1H), 7.98 (m, 4H), 7.88 (d, 2H), 7.55 (d, 2H), 3.76 (d, 2H), 3.24 (m, 2H), 2.10 (br s, 2H), 1.15 (t, 3H).

LC-MS (ESI): 318.95 (M+1).

e. N-(4-(4-(ethylcarbamoyl)phenylsulfonyl)benzyl)imidazo[1,2-a]pyridine-6-carboxamide

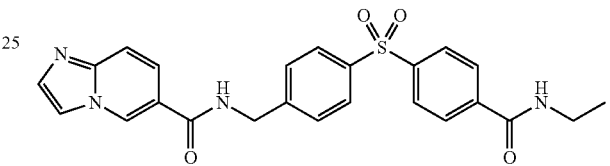

In a 250 mL round-bottomed flask was added 4-(4-(aminomethyl)phenylsulfonyl)-N-ethylbenzamide (1 g, 3.14 mmol), imidazo[1,2-a]pyridine-6-carboxylic acid (0.509 g, 3.14 mmol) and HATU (1.314 g, 3.45 mmol) in DMF (Volume: 50 mL) followed by DIEA (1.207 mL, 6.91 mmol). The reaction was stirred overnight and then concentrated under reduced pressure. The reaction was diluted with methylene chloride and poured into a separatory funnel. The organic layer was washed with 1M NaOH and water. The bottom was separated and concentrated and purified directly on the Biotage to give 514 mg of clean product (35% yield).

$^1$H NMR (300 MHz, DMSO-d6): δ 9.19 (t, 1H), 9.11 (t, 1H), 8.64 (t, 1H), 8.04-9.92 (m, 7H), 6.63 (m, 3H), 7.55 (d, 2H), 4.53 (d, 2H), 3.25 (m, 2H), 1.08 (t, 3H).

LC-MS (ESI): 463.05 (M+1).

Example 2 J

N-(4-((3-methoxyphenyl)sulfonyl)benzyl)imidazo[1,2-a]pyrimidine-6-carboxamide

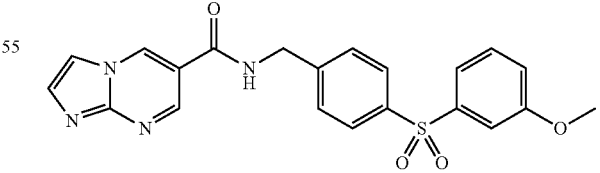

The title compound was prepared with 80% yield by following Example 4D.

$^1$H NMR δ (d$_6$-dmso) 9.47 (1H, d); 9.34 (1H, t); 8.92 (1H, d); 8.01 (1H, d); 7.95 (2H, d); 7.80 (1H, d); 7.58 (2H, d); 7.54-7.47 (2H, m); 7.42-7.41 (1H, m); 7.23 (1H, dt); 4.57 (2H, d and 3.81 (3H, s).

LC-MS (ESI): 422.9 (M+1).

Example 2 K

N-(4-(1-isopropyl-1H-pyrazol-4-ylsulfonyl)benzyl)imidazo[1,2-a]pyrimidine-6-carboxamide

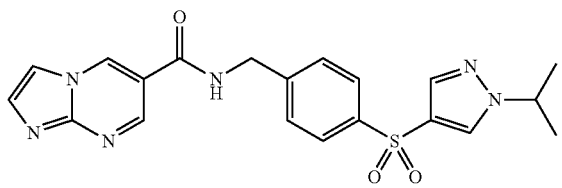 [SMILES: CC(C)n1cc(S(=O)(=O)c2ccc(CNC(=O)c3cnc4nccn4c3)cc2)cn1]

a. N-(4-((1-isopropyl-1H-Pyrazol-4-yl)sulfonyl)benzyl)acetamide

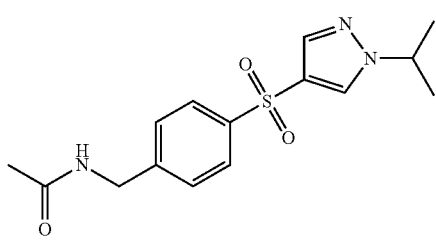 [SMILES: CC(=O)NCc1ccc(S(=O)(=O)c2cnn(C(C)C)c2)cc1]

In a 1 L round-bottomed flask were added sodium 4-(acetamidomethyl)benzenesulfinate (3.97 g, 16.89 mmol, 1.3 eq.), 1-isoproyl 1H-pyrazol-4-ylboronic acid (2 g, 12.99 mmol)] and COPPER (II) ACETATE (2.6 g, 14.29 mmol)), POTASSIUM CARBONATE (3.95 g, 28.6 mmol) in DMSO (50 ml) followed by 10 g of 4 Å molecular sieves. The reaction was stirred overnight. Added water and EtOAc, filtered through a short celite pad, added EtOAc, washed with water twice, dried and concentrated. The biotage column purification afforded 1.9 g of N-(4-((1-isopropyl-1H-Pyrazol-4-yl)sulfonyl)benzyl)acetamide (45%).

$^1$HNMR (DMSO-D$_6$): δ □□8.50 (s, 1H). 8.42 (t, 1H), 7.91 (s, 1H), 7.86 (d, 2H), 7.43 (d, 2H), 4.52 (m, 1H), 4.28 (d, 2H), 1.36 (d, 6H)

b. (4-(1-isopropyl-1H-pyrazol-4-ylsulfonyl)phenyl)methanamine HCl

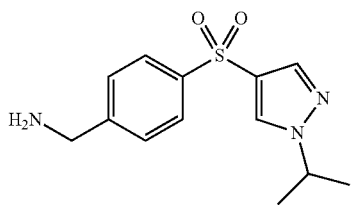 [SMILES: CC(C)n1cc(S(=O)(=O)c2ccc(CN)cc2)cn1]

The mixture of a 3M HCl solution (80 ml), and N-(4-(1-isopropyl-1H-pyrazol-4-ylsulfonyl)benzyl)acetamide (1.9 g, 5.91 mmol) in 2-Propanol (100 ml) was refluxed for over weekend, removed solvent, added ether, filtered and dried to afford 1.4 g of (4-(1-isopropyl-1H-pyrazol-4-ylsulfonyl)phenyl)methanamine HCl salt (75%) $^1$HNMR (DMSO-d$_6$): δ □□8.50 (s, 1H), 7.94-7.98 (m, 3H), 7.85 (dd, 1H), 7.69 (d, 2H), 4.52 (m, 1H), 4.08 (d, 2H), 1.37 (d, 6H).

c. N-(4-(1-isopropyl-1H-pyrazol-4-ylsulfonyl)benzyl)imidazo[1,2-a]pyridine-6-carboxamide

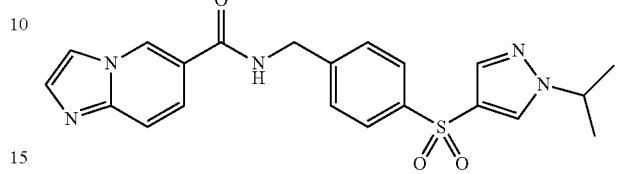

In a 250 mL round-bottomed flask were added imidazo[1,2-a]pyridine-6-carboxylic acid (0.719 g, 4.43 mmol), (4-(1-isopropyl-1H-pyrazol-4-ylsulfonyl)phenyl)methanamine, HCl (1.4 g, 4.43 mmol) and HBTU (1.849 g, 4.88 mmol), HOBT (0.747 g, 4.88 mmol) and DIEA (3.87 mL, 22.16 mmol) in DMF (Volume: 50 mL). The reaction was stirred overnight and then concentrated under reduced pressure. The residue was diluted with methylene chloride and washed with 1M aq. NaOH. The organic layer was separated and concentrated and directly purified in the Biotage to give 1.24 g of N-(4-(1-isopropyl-1H-pyrazol-4-ylsulfonyl)benzyl)imidazo[1,2-a]pyridine-6-carboxamide.

$^1$HNMR (DMSO-D$_6$): δ 9.20 (t, 1H), 9.13 (s, 2H), 8.51 (s, 1H), 8.05 (s, 1H), 7.88-7.91 (m, 3H), 7.53-7.67 (m, 4H), 4.42-4.55 (m, 3H), 1.37 (d, 6H).

LC-MS: 424.01 (M+1)

Example 2 L

N-(4-(phenylsulfonyl)benzyl)-1H-pyrazolo[3,4-b]pyridine-5-carboxamide

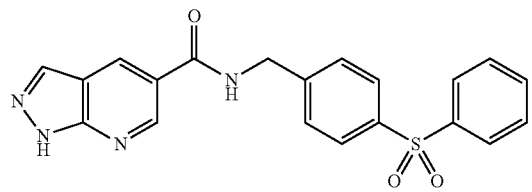 [SMILES: O=C(NCc1ccc(S(=O)(=O)c2ccccc2)cc1)c1cnc2[nH]ncc2c1]

The mixture of 1H-pyrazolo[3,4-b]pyridine-5-carboxylic acid (0.8 g, 4.90 mmol), HATU (1.87 g, 4.90 mmol), diisopropylethylamine (1.2 mL, 6.69 mmol), and (4-(phenylsulfonyl) phenyl)methanamine (1.10 g, 4.46 mmol) in DMF (50 mL) was stirred at room temperature for 16 h. The DMF was removed under reduced pressure. 150 mL of water was added to the residue and extracted with EtOAc (3×100 mL). The combined organic layers was washed with water, saturated sodium bicarbonate, brine, dried with sodium sulfate, and concentrated in vacuo. The crude was purified by Biotage with MeOH/DCM (0%-10%) to yield the title compound.

$^1$H NMR (DMSO-d6): δ 9.27 (t, 1H), 8.98 (d, 1H), 8.72 (d, 1H), 8.27 (s, 1H), 7.94-7.90 (m, 4H), 7.66-7.55 (m, 5H), 4.56 (d, 2H).

LC-MS: 393.01 (M+1).

Example 2 M

N-(4-(2,4-dimethylthiazol-5-ylsulfonyl)benzyl)imidazo[1,2-a]pyridine-6-carboxamide

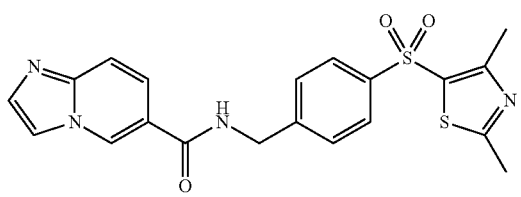 [SMILES: Cc1nc(C)c(S(=O)(=O)c2ccc(CNC(=O)c3ccc4nccn4c3)cc2)s1]

A mixture of copper iodide (0.2 M DMSO, 100 µL, 20 µmol), cesium (S)-pyrrolidine-2-carboxylate (0.2 M DMSO w/14% MeOH (v/v), 200 µL, 40 µmol), sodium 4-(acetamidomethyl)benzenesulfinate (0.2 M DMSO, 200 µL, 40 µmol) and 5-bromo-2,4-dimethylthiazole (0.2 M DMSO, 240 µL, 48 µmol) was heated at 90° C. with shaking over night. The reaction was treated with aqueous ammonia and extracted with EtOAc and the organic extract was concentrated to dryness and the resulting residue was dissolved in 70% i-PrOH (0.35 mL) and 3N HCl (0.35 mL, 1.05 mmol) and was heated at 90° C. for 4 hours then concentrated to dryness. The residue was treated with triethylamine (5% in ACN (v/v), 200 uL) and imidazo[1,2-a]pyridine-6-carboxylic acid (0.2 M in DMA w/10% TEA (v/v), 240 uL, 48 umol) and BOP (0.2 M DCE, 260 uL, 52 umol). The solution was heated to 40° C. for 4 h then cooled to room temperature and partitioned between NaOH and EtOAc. The organic layer was separated and concentrated in vacuo. The crude was purified by LC/MS to afford the title compound as white solid. $^1$H NMR (400 MHz, CDCl$_3$): δ 8.87 (dd, J=1.6 Hz, J'=0.8 Hz 1H), 7.89 (dt, J=8.4 Hz, J'=2 Hz, 2H), 7.71 (d, J=1.6 Hz, 1H), 7.67 (s, 1H), 7.60 (d, J=9.2 Hz, 1H), 7.50 (d, J=8.4 Hz 2H), 7.43 (dd, J=9.2 Hz, J'=2 Hz, 1H), 6.84 (bs, 1H), 4.73 (d, J=6 Hz, 2H), 2.65 (s, 3H), 2.57 (s, 3H).

LC-MS: 427.10 (M+1)

Example 2 N

N-(3-(naphthalen-2-ylsulfonyl)benzyl)imidazo[1,2-a]pyridine-6-carboxamide

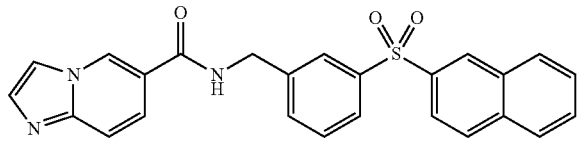 [SMILES: O=C(NCc1cccc(S(=O)(=O)c2ccc3ccccc3c2)c1)c1ccc2nccn2c1]

To a mixture of sodium 4-(acetamidomethyl)benzenesulfinate (0.2 M MeOH, 100 µL, 20 µmol) and zinc chloride (0.5 M THF, 40 µL, 20 µmol), cesium carbonate (1.43 M MeOH, 25 µL, 35 µmol) then 2-bromonapthelene (0.2 M Toluene, 110 µL, 22 µmol) were added. A toluene solution of XantPhos and Pd$_2$dba$_3$ (0.01 M XantPhos/0.005 M Pd$_2$dba$_3$, 50 µL, 2.5 mol %) was added and the reaction was heated for 4 h at 95° C. under nitrogen. The reaction was cooled to room temperature and 70% i-PrOH (0.35 mL) and 3N HCl (0.35 mL, 1.05 mmol) were added and was heated at 95° C. for 4 hours then concentrated to dryness. The residue was treated with triethylamine (5% in ACN (v/v), 100 µL) and imidazo[1,2-a]pyridine-6-carboxylic acid (0.2 M in DMA w/10% TEA (v/v), 120 µL, 24 µmol) and BOP (0.2 M DCE, 130 µL, 26 µmol). The solution was heated to 40° C. for 4 h then cooled to room temperature and partitioned between NaOH and EtOAc. The organic layer was separated and deposited on a SCX-SPE cartridge which was eluted to two fractions: the 1$^{st}$ with 25% MeOH/EtOAc (v/v), the 2$^{nd}$ with Et3N/MeOH/EtOAc (1:1:10 v/v/v). The second fraction was concentrated to dryness and was purified by LC/MS to afford the title compound as white solid.

$^1$H NMR (400 MHz, CDCl$_3$): δ 8.85 (s, 1H), 8.55 (s, 1H), 7.93 (m, 4H), 7.87 (d, J=8 Hz, 1H), 7.81 (dd, J=8.8 Hz, J'=1.6 Hz, 1H), 7.63 (m, 5H), 7.47 (d, J=8.4 Hz, 2H), 7.34 (m, 1H), 6.81 (m, 1H), 4.70 (d, J=5.6 Hz, 2H).

LC-MS: 442.13 (M+1)

Example 2 O

N-(4-(naphthalen-2-ylsulfonyl)benzyl)furo[2,3-c]pyridine-2-carboxamide

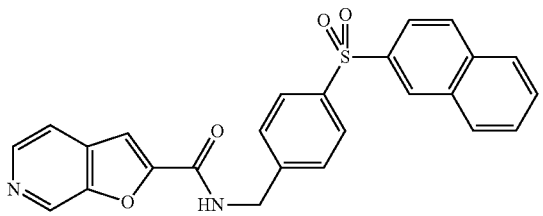 [SMILES: O=C(NCc1ccc(S(=O)(=O)c2ccc3ccccc3c2)cc1)c1cc2ccncc2o1]

a. tert-butyl 4-bromobenzylcarbamate

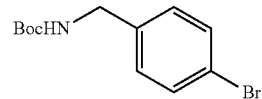

A 200-mL RBF equipped with a magnetic stir bar was charged with (4-bromophenyl)methanamine hydrochloride (5.23 g, 23.50 mmol), K$_2$CO$_3$ (3.90 g, 28.2 mmol), MeTHF (Ratio: 4.00, Volume: 50 ml), and Water (Ratio: 1.000, Volume: 12.5 ml). To the resulting mixture was added BOC$_2$O (6.00 ml, 25.9 mmol) in one portion at rt with stirring. LCMS after 1 h suggested clean, complete conversion. The mixture was diluted with additional MeTHF (50 mL) and water (10 mL), and the layers separated. The organic layer was washed with half-saturated brine (2×25 mL) and then concentrated under reduced pressure to 7.2 g of a white solid. The crude product was used without further purification in the next step.

$^1$H NMR (400 MHz, CDCl$_3$): δ 7.44 (d, J=8.4 Hz, 2H), 7.15 (d, J=8.3 Hz, 2H), 4.85 (br s, 1H), 4.26 (d, J=5.8 Hz, 2H), 1.45 (s, 9H) ppm.

b. methyl 3-(4-(((tert-butoxycarbonylamino)methyl)phenylthio)propanoate

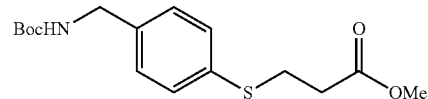 [SMILES: COC(=O)CCSc1ccc(CNC(=O)OC(C)(C)C)cc1]

A 200-mL RBF equipped with a magnetic stir bar and containing tert-butyl 4-bromobenzylcarbamate, crude (6.72 g, 23.5 mmol) was charged with Toluene (Volume: 50 ml), Hunig's Base (8.21 ml, 47.0 mmol), XANTPHOS (0.680 g, 1.175 mmol), Pd$_2$(dba)$_3$ (0.538 g, 0.588 mmol), and finally methyl 3-mercaptopropanoate (2.60 ml, 23.50 mmol). The mixture was then heated to 100° C. LCMS after 1 h suggested significant conversion, although starting bromide was still evident by 220 nm. LCMS after 2 h a little better. After 2.5 h, heating was discontinued. After cooling, the mixture was loaded directly on a short silica gel column. Elution with 5:1 hexanes-EtOAc, 4:1 hexanes-EtOAc, and finally 3:1 hexanes-EtOAc afforded methyl 3-(4-((tert-butoxycarbonylamino)methyl)phenylthio)propanoate (7.19 g, 22.09 mmol, 94% yield) as a nearly colorless oil.

$^1$H NMR (400 MHz, CDCl$_3$): δ 7.32 (d, J=8.3 Hz, 2H), 7.21 (d, J=8.2 Hz, 2H), 4.84 (br s, 1H), 4.28 (d, J=5.8 Hz, 2H), 3.67 (s, 3H), 3.14 (t, J=7.4 Hz, 2H), 2.61 (t, J=7.5 Hz, 2H), 1.45 (s, 9H) ppm.

ESMS: 348.15 (M+Na)

c. methyl 3-(4-((tert-butoxycarbonylamino)methyl)phenylsulfonyl)propanoate

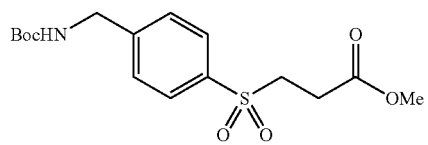 [SMILES: COC(=O)CCS(=O)(=O)c1ccc(CNC(=O)OC(C)(C)C)cc1]

A 500-mL RBF equipped with a magnetic stir bar was charged with OXONE (23.61 g, 38.4 mmol) and Water (Ratio: 1.822, Volume: 82 ml). The mixture was stirred at rt for 5 min in order to dissolve the Oxone. Next, a solution of methyl 3-(4-((tert-butoxycarbonylamino)methyl)phenylthio)propanoate (5.0 g, 15.36 mmol) in Acetonitrile (Ratio: 1.000, Volume: 45 ml) was added at rt with rapid stirring. The mixture was stirred at rt. After 2.5 h, an aliquot was removed, worked up, and analyzed by $^1$H NMR, which confirmed complete conversion to sulfone. LCMS also looked good. The reaction mixture was then extracted with EtOAc (100 mL). This extract was concentrated under reduced pressure. The aqueous layer was re-extracted once with fresh EtOAc. This extract was combined with the first, concentrated extract. The combined solution was washed twice with half-saturated brine (2×50 mL) and concentrated under reduced pressure to afford methyl 3-(4-((tert-butoxycarbonylamino)methyl)phenylsulfonyl)propanoate (5.17 g, 14.46 mmol, 94% yield) as a white solid.

$^1$H NMR (400 MHz, CDCl$_3$): δ 7.86 (d, J=8.4 Hz, 2H), 7.48 (d, J=8.6 Hz, 2H), 5.03 (br s, 1H), 4.41 (d, J=6.2 Hz, 2H), 3.64 (s, 3H), 3.41 (t, J=7.7 Hz, 2H), 2.74 (t, J=7.8 Hz, 2H), 1.46 (s, 9H) ppm.

ESMS: 380.07 (M+Na)

d. methyl 3-(4-(aminomethyl)phenylsulfonyl)propanoate hydrochlorid

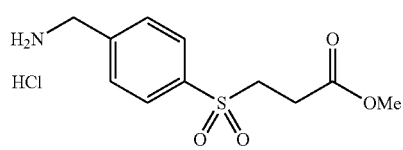 [SMILES: Cl ; COC(=O)CCS(=O)(=O)c1ccc(CN)cc1]

A 200-mL RBF equipped with a magnetic stir bar and containing methyl 3-(4-((tert-butoxycarbonylamino)methyl)phenylsulfonyl)propanoate (5.16 g, 14.44 mmol) was charged with MeOH (Volume: 50 ml) followed by HYDROCHLORIC ACID, conc (1.323 ml, 15.88 mmol). The solution was then heated to 50° C. LCMS after overnight indicated complete conversion. Heating was discontinued. After cooling, the slurry was concentrated partially under reduced pressure, removing 32 mL of MeOH. The resulting concentrated slurry was diluted with MTBE (50 mL). The slurry was stirred at rt for 30 min, then filtered on a glass, medium frit, 60-mL Buchner funnel. The filter cake was washed with MTBE and dried under suction and a positive pressure of nitrogen to afford methyl 3-(4-(aminomethyl)phenylsulfonyl)propanoate hydrochloride (4.10 g, 13.96 mmol, 97% yield) as a snow-white, crystalline, free-flowing solid.

$^1$H NMR (400 MHz, DMSO-d$_6$): δ 8.62 (br s, 2H), 7.92 (d, J=8.5 Hz, 2H), 7.77 (d, J=8.4 Hz, 2H), 4.14 (s, 2H), 3.58 (t, J=7.3 Hz, 2H), 3.52 (s, 3H), 2.59 (t, J=7.3 Hz, 2H) ppm.

ESMS: 258.10 (M+1).

e. methyl 3-(4-((furo[2,3-c]pyridine-2-carboxamido)methyl)phenylsulfonyl)propanoate

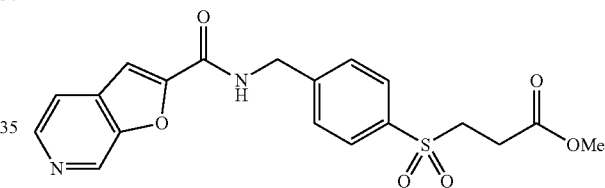

A 25-mL RBF equipped with a magnetic stir bar was charged with furo[2,3-c]pyridine-2-carboxylic acid (135 mg, 0.828 mmol), methyl 3-(4-(aminomethyl)phenylsulfonyl)propanoate hydrochloride (243 mg, 0.828 mmol), EtOH (Volume: 2.7 ml), N-METHYLMORPHOLINE (0.218 ml, 1.986 mmol), and finally EDC (190 mg, 0.993 mmol). The reaction mixture was stirred at rt. LCMS after 75 min shows some conversion, with longer-retaining by-product also forming. LCMS after 3 h shows some more conversion, but not significant. After 3.5 h, HOBT (6.34 mg, 0.041 mmol) was added. LCMS, 75 min after HOBT addition, not much different. LCMS after overnight not much different. The reaction mixture was slowly diluted with water (8.1 mL). The resulting slurry was stirred at rt for 1 h, then filtered on a 30-mL, medium frit, glass Buchner funnel. The solid was washed with water and dried under suction and a positive pressure of nitrogen to yield methyl 3-(4-((furo[2,3-c]pyridine-2-carboxamido)methyl)phenylsulfonyl)propanoate (0.12 g, 0.298 mmol, 36.0% yield) as a slightly off-white fluffy powder.

$^1$H NMR (400 MHz, DMSO-d$_6$): δ 9.67 (t, J=6.1 Hz, 1H), 9.05 (s, 1H), 8.47 (d, J=5.2 Hz, 1H), 7.85 (d, J=8.4 Hz, 2H), 7.82 (dd, J=5.3, 1.1 Hz, 1H), 7.65 (d, J=0.8 Hz, 1H), 7.60 (d, J=8.4 Hz, 2H), 4.59 (d, J=6.1 Hz, 2H), 3.53 (t, J=7.2 Hz, 2H), 3.49 (s, 3H), 2.59 (t, J=7.2 Hz, 2H) ppm.

ESMS: 403.03 (M+1)

f. sodium 4-((furo[2,3-c]pyridine-2-carboxamido)methyl)benzenesulfinate

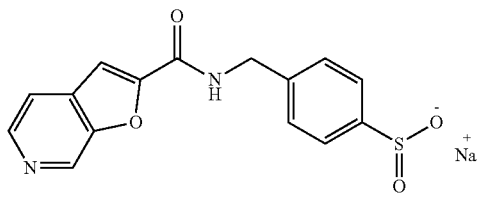

A 25-mL RBF equipped with a magnetic stir bar was charged with methyl 3-(4-((furo[2,3-c]pyridine-2-carboxamido)methyl)phenylsulfonyl)propanoate (113 mg, 0.281 mmol) followed by a solution of SODIUM ETHOXIDE (21 wt % in EtOH) (91 mg, 0.281 mmol) dissolved in MeOH (Volume: 2 ml). The mixture was stirred at rt. Over time, the solid dissolved. LCMS after 30 min shows ca 80-85% conversion. LCMS after 1 h shows essentially complete conversion. Note: no transient intermediate/by-product isomeric with the SM was observed as in the case with the analogous azaindole experiments. LCMS after 2 h shows complete, clean conversion. After 2.5 h, the solution was concentrated under a gentle stream of nitrogen overnight to afford sodium 4-((furo[2,3-c]pyridine-2-carboxamido)methyl)benzenesulfinate (0.102 g, 0.301 mmol, 107% yield) as an off-white/light tan solid.

$^1$H NMR (400 MHz, DMSO-$d_6$): δ 8.99 (s, 1H), 8.42 (d, J=5.2 Hz, 1H), 7.76 (dd, J=5.2, 1.1 Hz, 1H), 7.55 (d, J=0.6 Hz, 1H), 7.38 (d, J=8.0 Hz, 2H), 7.25 (d, J=8.1 Hz, 2H), 4.44 (s, 2H) ppm.

ESMS: 317.04 (M+1)

g. N-(4-(naphthalen-2-ylsulfonyl)benzyl)furo[2,3-c]pyridine-2-carboxamide

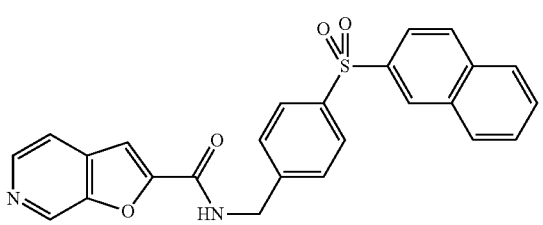 [SMILES: O=C(NCc1ccc(S(=O)(=O)c2ccc3ccccc3c2)cc1)c1cc2ccncc2o1]

To a mixture of naphthylen-2-boronic acid (0.2 M dioxane, 150 μL, 30 μmol) and diacetoxycopper (0.2 M DMSO, 150 μL, 30 μmol) and triethylamine (Neat, 9.3 μL, 67 μmol), sodium 4-((furo[2,3-c]pyridine-2-carboxamido)methyl)benzene sulfinate (0.2 M DMSO, 50 μL, 10 μmol) was added and the reaction was heated at 40° C. over night. The reaction was cooled to room temperature and partitioned between aqueous ammonia and EtOAc. The organic layer was separated and deposited on a SCX-SPE cartridge which was eluted to two fractions: the 1$^{st}$ with 25% MeOH/EtOAc (v/v), the 2$^{nd}$ with ammonia in methanol (2 N). The second fraction was concentrated to dryness and was purified by LC/MS to afford the title compound as white solid.

$^1$H NMR (400 MHz, CDCl$_3$): δ 8.89 (s, 1H), 8.56 (d, J=2 Hz, 1H), 8.50 (d, J=5.2 Hz, 1H), 7.99 (m, 3H), 7.92 (d, J=8.8 Hz, 1H), 7.87 (m, 2H), 7.62 (m, 3H), 7.51 (m, 3H), 7.08 (m, 1H), 4.72 (d, J=6.4 Hz, 2H).

LC-MS: 443.22 (M+1)

Example 2 P

N-(4-(5-(dimethylamino)pyrazin-2-ylsulfonyl)benzyl)imidazo[1,2-a]pyridine-6-carboxamide

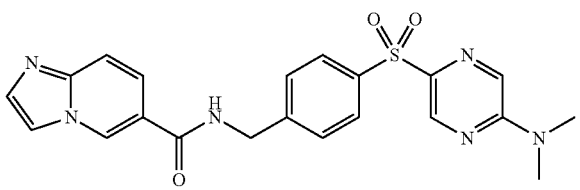 [SMILES: CN(C)c1cnc(S(=O)(=O)c2ccc(CNC(=O)c3ccc4nccn4c3)cc2)cn1]

a. N-(4-(5-(dimethylamino)pyrazin-2-ylsulfonyl)benzyl)acetamide

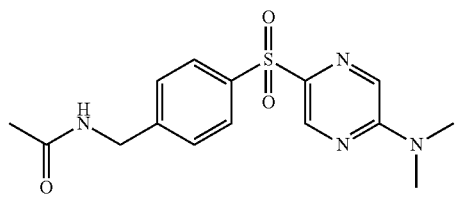 [SMILES: CC(=O)NCc1ccc(S(=O)(=O)c2cnc(N(C)C)cn2)cc1]

The mixture of XANTPHOS (0.573 g, 0.990 mmol), Cs$_2$CO$_3$ (6.45 g, 19.80 mmol), Pd2(dba)3 (0.453 g, 0.495 mmol),4-(acetamidomethyl)benzenesulfinic acid, sodium salt (3.51 g, 14.85 mmol), 5-bromo-N,N-dimethylpyrazin-2-amine (2 g, 9.90 mmol) in Toluene (50 ml) was degassed and heated to 120° C. for overnight. Cooled to RT, added EtOAc, washed with water, dried and concentrated, The Biotage purification afforded 1.6 g of the target compound (48%).

$^1$HNMR (CDCl$_3$): δ ☐ 8.75 (s, 1H). 8.03 (s, 1H), 7.87 (d, 2H), 7.38 (d, 2H), 6.11 (b, 1H), 4.45 (d, 2H), 3.21 (s, 6H), 2.16 (s, 3H).

b. 5-((4-(aminomethyl)phenyl)sulfonyl)-N,N-dimethylpyrazin-2-amine hydrochloride

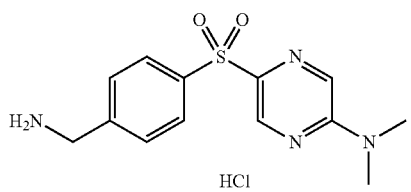 [SMILES: CN(C)c1cnc(S(=O)(=O)c2ccc(CN)cc2)cn1 ; Cl]

The mixture of a 3M HCl solution (80 ml) and, N-(4-(5-(dimethylamino)pyrazin-2-ylsulfonyl)benzyl)acetamide (1.6 g) in 2-Propanol (100 ml) was refluxed for over weekend, removed solvent, added ether, filtered and dried to afford 1.2 g of the target compound as a hydrochloride (76%).

¹HNMR (DMSO-D₆): δ □□8.71 (s, 1H), 8.14 (s, 1H), 7.92 (d, 2H), 7.45 (d, 2H), 4.08 (d, 2H), 3.13 (s, 6H).

c. N-(4-(5-(dimethylamino)pyrazin-2-ylsulfonyl)benzyl)imidazo[1,2-a]pyridine-6-carboxamide

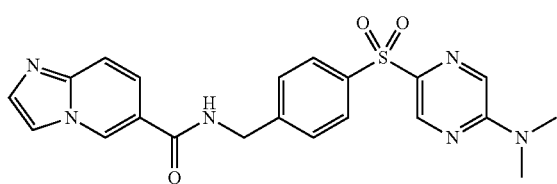 [SMILES: CN(C)c1cnc(S(=O)(=O)c2ccc(CNC(=O)c3ccc4nccn4c3)cc2)cn1]

In a 250 mL round-bottomed flask was added imidazo [1,2-a] pyridine-6-carboxylic acid (0.592 g, 3.65 mmol), 5-(4-(aminomethyl)phenylsulfonyl)-N,N-dimethylpyrazin-2-amine, HCl (1.2 g, 3.65 mmol) and HBTU (1.522 g, 4.01 mmol), HOBT (0.615 g, 4.01 mmol) and DIEA (3.19 mL, 18.25 mmol) in DMF (50 mL). The reaction was stirred overnight and then concentrated under reduced pressure. The residue was diluted with methylene chloride and washed with 1M aq. NaOH. The organic layer was separated and concentrated and directly purified in the Biotage to give 235 mg of N-(4-(5-(dimethylamino) pyrazin-2-ylsulfonyl)benzyl) imidazo [1, 2-a] pyridine-6-carboxamide (15%).

¹HNMR (DMSO-d₆): δ 9.21 (t, 1H), 9.13 (s, 1H), 8.67 (s, 1H), 8.12 (s, 1H), 8.95 (s, 1H), 7.86 (d, 2H), 7.63 (d, 2H), 7.54 (d, 2H), 4.53 (d, 2H), 3.11 (s, 6H).

LC-MS: 437.0 (M+1)

Example 2 Q

N-(4-((3-(trifluoromethoxy)phenyl)sulfonyl)benzyl)imidazo[1,2-a]pyrimidine-6-carboxamide

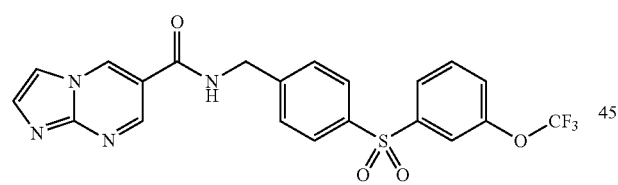

a: 4-((3-(trifluoromethoxy)phenyl)thio)benzonitrile

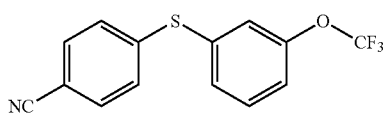 [SMILES: N#Cc1ccc(Sc2cccc(OC(F)(F)F)c2)cc1]

To a colorless solution of 3-(trifluoromethoxy)benzenethiol (5.0 g, 25.8 mmol) in DMF (80 mL) was added K₂CO₃ (4.21 g, 30.4 mmol) forming a yellow mixture. To this mixture was added 4-fluorobenzonitrile (2.84 g, 23.4 mmol). The mixture was heated to 120° C. for 16 h, cooled to room temperature, and diluted with 1N NaOH and Et20. The layers were separated. The organic layer was washed sequentially with 1N NaOH and brine, dried over Na₂SO₄, and concentrated in vacuo. The residue was purified by Biotage SP1 to afford the desired product as colorless oil (6.09 g, 88% yield).

¹H NMR (300 MHz, CDCl₃): δ 8.8-8.06 (m, 2H), 7.89-7.80 (m, 2H), 7.78-7.82 (m, 2H), 7.61 (t, 1H), 7.47 (d, 2H).

LC-MS: 295.93 (M+H).

b: 4-((3-(trifluoromethoxy)phenyl)sulfonyl)benzonitrile

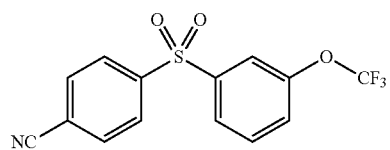 [SMILES: N#Cc1ccc(S(=O)(=O)c2cccc(OC(F)(F)F)c2)cc1]

To a solution of 4-(3-(trifluoromethoxy)phenylthio)benzonitrile (6.09 g, 20.6 mmol) in CHCl₃ (110 mL) at 0° C. was added mCPBA (20.88 g, 91.0 mmol). The mixture was stirred and warmed to room temperature slowly overnight. The solids were removed by vacuum filtration, rinsed with CHCl₃. The filtrate was washed with 1N NaOH (×2). The separated organic layer was washed with water and brine, dried over Na₂SO₄, filtered, concentrated to afford the product without further purification for next step (6.00 g, 89%).

¹H NMR (300 MHz, CDCl₃): δ 8.08 (d, 1H), 8.06 (d, 1H), 7.89-7.80 (m, 4H), 7.61 (t, 1H), 7.49-7.43 (m, 1H).

LC-MS: 349.90 (M+Na).

c: (4-((3-(trifluoromethoxy)phenyl)sulfonyl)phenyl)methanamine

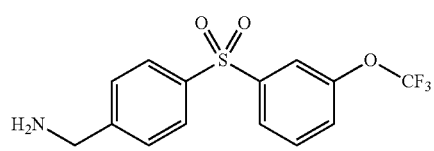 [SMILES: NCc1ccc(S(=O)(=O)c2cccc(OC(F)(F)F)c2)cc1]

To a small flask was added 3 pipette-full slurry of Raney Ni in water and then added methanol (2 mL). The wash solvent (MeOH) was removed via pipette. The wash was repeated twice more, affording about 7 equivalents of nickel. To a 500 mL Parr reaction cylinder was added 4-(3-(trifluoromethoxy)phenylsulfonyl)benzonitrile (6.00 g, 18.3 mmol) in MeOH (120 ml), followed by addition of the prewashed nickel, 7N ammonia (37.2 ml, 26.0 mmol) in MeOH and potassium hydroxide (0.329 g, 5.9 mmol). The mixture was vacuumed and purged with H₂ three times, then hydrogenated at 50 psi overnight. LC-MS analysis indicated the completion of the hydrogenation of nitrile. The mixture was filtered through celite. The filtrate was concentrated and purified by Biotage SP1 affording the product as light yellow oil (4.20 g, 93% yield).

¹H NMR (300 MHz, DMSO-d₆): δ 7.99-7.91 (m, 4H), 7.75-7.73 (m, 3H), 7.58 (d, 2H), 3.76 (s, 2H).

LC-MS: 331.97 (M+H).

d: N-(4-((3-(trifluoromethoxy)phenyl)sulfonyl)ben-zyl)imidazo[1,2-a]pyrimidine-6-carboxamide

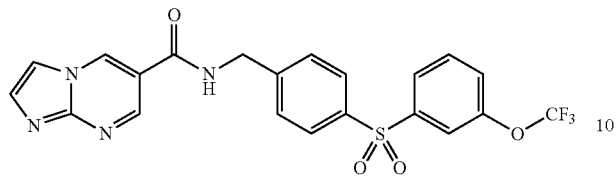

A mixture of imidazo[1,2-a]pyrimidine-6-carboxylic acid (0.739 g, 4.53 mmol), (4-(3-(trifluoromethoxy)phenylsulfonyl)phenyl)methanamine (1.5 g, 4.53 mmol), BOP (2.203 g, 4.98 mmol) and DIEA (0.949 mL, 5.43 mmol) in DMF (25 mL) was stirred at room temperature overnight. The reaction mixture was concentrated in vacuo to remove the DMF. The residue was diluted with EtOAc and then washed with 1N NaOH. The separated aqueous layer was back-extracted with EtOAc. The combined organic extracts were washed with 5% AcOH, water, brine and dried ($Na_2SO_4$), filtered and concentrated. Purification by Biotage SP1 of the crude afforded the title compound as off-white solids (980 mg, 45% yield).

$^1$H NMR (300 MHz, DMSO-$d_6$): δ 9.47 (d, 1H), 9.35 (t, 1H), 9.23 (d, 1H), 8.01-7.98 (m, 5H), 7.80-7.31 (m, 3H), 7.60 (d, 2H), 4.57 (d, 2H).

LC-MS: 476.87 (M+1).

Example 2 R

N-(4-(benzylsulfonyl)benzyl)-1H-pyrrolo[3,2-c]pyridine-2-carboxamide

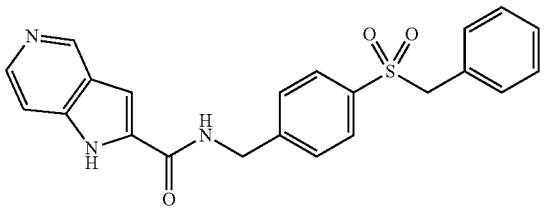 [SMILES: O=C(NCc1ccc(S(=O)(=O)Cc2ccccc2)cc1)c1cc2cnccc2[nH]1]

a: N-(4-(benzylsulfonyl)benzyl)acetamide

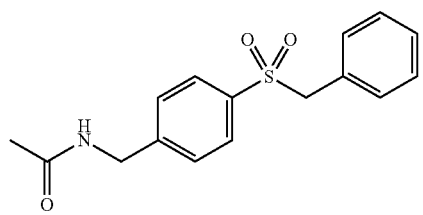 [SMILES: CC(=O)NCc1ccc(S(=O)(=O)Cc2ccccc2)cc1]

To a solution of sodium 4-(acetamidomethyl)benzenesulfinate (1 g, 4.25 mmol) in water (12 mL) were added TBAI (0.157 g, 0.425 mmol) and (bromomethyl)benzene (0.742 g, 4.34 mmol) under $N_2$ flow. The reaction mixture was heated to 70° C. for 2 h. The white solids were precipitated out. LC-MS analysis showed that the major peak was the desired product. The white solids were filtered and washed with water and ether to remove TBAI, then dried under reduced pressure to give 696 mg of desired product with 90% HPLC purity. The collected solids were used for next step without further purification. $^1$H NMR (300 MHz, $CDCl_3$): δ 7.55 (d, 2H), 7.33-7.23 (m, 5H), 7.08 (d, 2H), 5.94 (brs, 1H), 4.50 (d, 2H), 4.29 (s, 2H), 2.07 (s, 3H).

LC-MS: 304.12 (M+H).

b: (4-(benzylsulfonyl)phenyl)methanamine hydrochloride

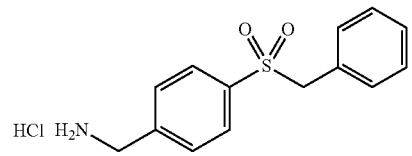 [SMILES: Cl ; NCc1ccc(S(=O)(=O)Cc2ccccc2)cc1]

A mixture of N-(4-(benzylsulfonyl)benzyl)acetamide (300 mg, 0.989 mmol) and 3N HCl (11.87 ml, 35.6 mmol) in $^i$PrOH (11 mL) was heated to 100° C. The cloudy mixture turned to a clear solution as temperature rose. The reaction mixture was stirred for 16 h at 100° C. LC-MS analysis indicated completion of hydrolysis. The reaction mixture was allowed to cool to room temperature. The white crystals were precipitated and filtered, rinsed with cold mixture of $^i$PrOH/ether to afford hydrochloride salt of the desired product (235 mg, 80% yield).

$^1$H NMR (300 MHz, DMSO-$d_6$): δ 8.44 (brs, 3H), 7.75, 7.65 (dd, 4H), 7.29-7.27 (m, 3H), 7.16-7.13 (m, 2H), 4.69 (s, 2H), 4.12 (s, 2H).

LC-MS: 262.11 (M+H).

c: N-(4-(benzylsulfonyl)benzyl)-1H-pyrrolo[3,2-c]pyridine-2-carboxamide

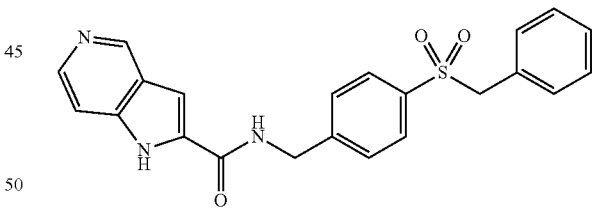

1H-pyrrolo[3,2-c]pyridine-2-carboxylic acid (57.2 mg, 0.353 mmol), 1H-benzo[d][1,2,3]triazol-1-ol (59.0 mg, 0.437 mmol) and EDC (86 mg, 0.450 mmol) were dissolved in anhydrous THF (4 mL), followed by addition of Hunig's base (0.12 mL, 0.7 mmol). The mixture formed a slurry solution. DMF (1 mL) was added. After stirring for 15 min., (4-(benzylsulfonyl) phenyl)methanamine hydrochloride (100 mg, 0.336 mmol) and Hunig's base (0.12 mL, 0.7 mmol) in THF (1 mL) was added. The reaction mixture was heated and stirred at 65° C. overnight, then diluted with ethyl acetate (×2). The combined organic layers were washed sequentially with 5% aqueous acetic acid (×1), saturated aqueous sodium bicarbonate (×2), and brine (×1). The organic layer was dried over anhydrous sodium sulfate, filtered and concentrated in vacuo to yield a crude product (65 mg). The crude was dissolved in DCM and a few drops of MeOH, and purified by Biotage to give the desired product (34 mg, 25% yield).

$^1$H NMR (300 MHz, DMSO-d$_6$): δ 12.05 (s, 1H), 9.31 (t, 1H), 8.93 (s, 1H), 8.21 (d, 1H), 7.68 (d, 2H), 7.51 (d, 2H), 7.36-7.26 (m, 5H), 7.16-7.13 (m, 2H), 4.63 (s, 2H), 4.59 (d, 2H).

LC-MS: 406.11 (M+H).

Example 2 S

N-(4-(cyclohexylsulfonyl)benzyl)-1H-pyrrolo[3,2-c]pyridine-2-carboxamide

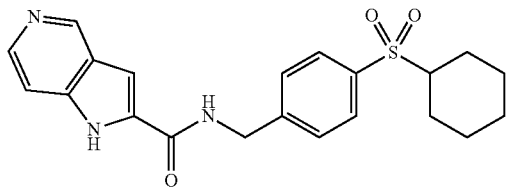 [SMILES: O=C(NCc1ccc(S(=O)(=O)C2CCCCC2)cc1)c1cc2cnccc2[nH]1]

a: N-(4-(cyclohexylsulfonyl)benzyl)acetamide

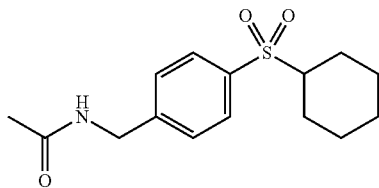 [SMILES: CC(=O)NCc1ccc(S(=O)(=O)C2CCCCC2)cc1]

To a solution of sodium 4-(acetamidomethyl)benzenesulfinate (500 mg, 2.126 mmol) in DMSO (8 mL) was added iodocyclohexane (670 mg, 3.19 mmol). The reaction was heated up to 100° C. for 48 h. The reaction mixture was diluted with EtOAc, and washed with water (×1) and brine (×2). The organic was dried over Na$_2$SO$_4$ and concentrated. The crude was purified by Biotage to yield the desired product (52 mg, 8% yield).

$^1$H NMR (300 MHz, CDCl$_3$): δ 7.66 (d, 2H), 7.36 (d, 2H), 6.72 (m, 1H), 4.46 (d, 2H), 2.83 (tt, 1H), 2.04 (s, 3H), 2.01-2.00 (m, 2H), 1.83-1.76 (m, 3H), 1.65 (d, 1H), 1.93-1.12 (m, 4H).

LC-MS: 296.06 (M+H).

b: (4-(cyclohexylsulfonyl)phenyl)methanamine

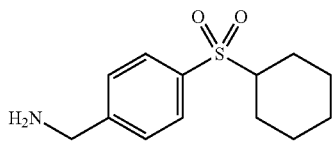 [SMILES: NCc1ccc(S(=O)(=O)C2CCCCC2)cc1]

A mixture of N-(4-(cyclohexylsulfonyl)benzyl)acetamide (52 mg, 0.176 mmol) and 3N HCl (2.11 mL, 6.34 mmol) in $^i$PrOH (2.5 mL) was heated to 100° C. The cloudy mixture turned to a clear solution as temperature rose. The reaction mixture was stirred and refluxed for 16 h at 100° C. LC-MS analysis indicated that no starting material was present and some other by-product was formed (the desired product showed as 22% in HPLC). The mixture was cooled to RT and the solvent was concentrated. The resulting slurry was treated with 1N NaOH and EtOAc. The combined organic extracts were washed with brine, dried and concentrated to yield a crude product (120 mg). The crude was purified by Biotage to yield the free amine (25 mg, 56% yield).

LC-MS: 254.08 (M+H).

c: N-(4-(cyclohexylsulfonyl)benzyl)-1H-pyrrolo[3,2-c]pyridine-2-carboxamide

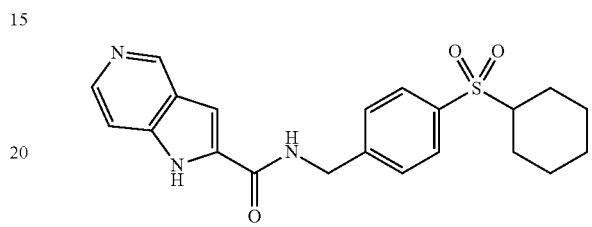

1H-pyrrolo[3,2-c]pyridine-2-carboxylic acid (16.80 mg, 0.104 mmol), 1H-benzo[d][1,2,3]triazol-1-ol (17.33 mg, 0.128 mmol) and EDC (25.3 mg, 0.132 mmol) were dissolved in anhydrous THF (3 mL), followed by addition of Hunig's base (0.7 mL, 0.7 mmol). The mixture formed a slurry solution. DMF (0.5 mL) was added. After stirring for 15 min at 65° C., (4-(cyclohexylsulfonyl)phenyl)methanamine (25 mg, 0.099 mmol) in THF/DMF (1.0/0.3 mL) was added. The reaction mixture was stirred at 65° C. overnight, then diluted with ethyl acetate. The organic layer was washed sequentially with 5% aqueous acetic acid (×2), saturated aqueous sodium bicarbonate (×2), and brine (×1). The organic layer was dried over anhydrous sodium sulfate, filtered and concentrated in vacuo to yield a crude product (40 mg). The crude was dissolved in DMSO and purified by reverse phase preparative HPLC to give the title compound (12.4 mg, 32% yield).

$^1$H NMR (300 MHz, DMSO-d$_6$): δ 12.05 (brs, 1H), 9.30 (t, 1H), 8.88 (s, 1H), 8.16 (d, 1H), 7.76 (d, 2H), 7.54 (d, 2H), 7.32 (d, 1H), 7.27 (s, 1H), 4.57 (d, 2H), 3.08 (m, 1H), 1.78-1.66 (m, 4H), 1.51 (d, 1H), 1.20-0.96 (m, 5H).

LC-MS: 398.0 (M+H).

It is understood that the person skilled in the art will be able to prepare the compounds of the present invention using methods known in the art along with the general method of synthesis described herein.

Assays

Assay Example 1

Biochemical Inhibition Assay
NAMPT Protein Purification

Recombinant His-tagged NAMPT was produced in *E. coli* cells, purified over a Ni column, and further purified over a size-exclusion column by XTAL Biostructures.

The NAMPT Enzymatic Reaction

The NAMPT enzymatic reactions were carried out in Buffer A (50 mM Hepes pH 7.5, 50 mM NaCl, 5 mM MgCl$_2$, and 1 mM THP) in 96-well V-bottom plates. The compound titrations were performed in a separate dilution plate by serially diluting the compounds in DMSO to make a 100× stock. Buffer A (89 μL) containing 33 nM of NAMPT protein was added to 1 µL of 100× compound plate containing controls (e.g. DMSO or blank). The compound and enzyme mix was incubated for 15 minutes at room temperature, then 10 µL of 10× substrate and co-factors in Buffer A were added to the test well to make a final concentration of 1 µM NAM, 100 µM 5-Phospho-D-ribose 1-diphosphate (PRPP), and 2.5 mM Adenosine 5'-triphosphate (ATP). The reaction was allowed to proceed for 30 minutes at room temperature, then was quenched with the addition of 11 µL of a solution of formic acid and L-Cystathionine to make a final concentration of 1% formic acid and 10 µM L-Cystathionine. Background and signal strength was determined by addition (or non-addition) of a serial dilution of NMN to a pre-quenched enzyme and cofactor mix.

Quantification of NMN

A mass spectrometry-based assay was used to measure the NAMPT reaction product (NMN) and the internal control (L-Cystathionine). NMN and L-Cystathionine were detected using the services of Biocius Lifesciences with the Rapid-Fire system. In short, the NMN and L-Cystathionine are bound to a graphitic carbon cartridge in 0.1% formic acid, eluted in 30% acetonitrile buffer, and injected into a Sciex 4000 mass spectrometer. The components of the sample were ionized with electrospray ionization and the positive ions were detected. The Q1 (parent ion) and Q3 (fragment ion) masses of NMN were 334.2 and 123.2, respectively. The Q1 and Q3 for L-Cystathionine were 223.1 and 134.1, respectively. The fragments are quantified and the analyzed by the following method.

% Inhibitions are Determined Using this Method.

First the NMN signal is normalized to the L-Cystathionine signal by dividing the NMN signal by the L-Cystathionine signal for each well. The signal from the background wells are averaged and subtracted from the test plates. The compound treated cells re then assayed for % inhibition by using this formula.

$$\% \text{ Inh} = 100 - 100 \cdot x/y$$

wherein x denotes the average signal of the compound treated wells and y denotes the average signal of the DMSO treated wells.

IC50s are Determined Using Excel and this Formula.

$$IC50 = 10^{\wedge}(\text{LOG }10(X) + (((50 - \% \text{ Inh at Cmpd Concentration }1)/(XX-YY) \cdot (\text{LOG }10(X) - \text{LOG }10(Y))))$$

wherein X denotes the compound concentration 1, Y denotes the compound concentration 2, XX denotes the % inhibition at compound concentration 1 (X), and YY denotes the % inhibition at compound concentration 2 (Y).

The NAMPT-inhibitor compounds of this invention have IC50 values that are preferably under 1 µM, more preferably under 0.1 µM, and most preferably under 0.01 µM. Results for the compounds are provided in Table 3.

Assay Example 2

In-Vitro Cell Proliferation Assay

A2780 cells were seeded in 96-well plates at 1×10³ cells/well in 180 µL of culture medium (10% FBS, 1% Pen/Strep Amphotecricin B, RPMI-1640) with and without the addition of either β-nicotinamide mononucleotide (NMN) or nicotinamide (NAM). After overnight incubation at 37° C. and 5% CO2, the compound titrations were performed in a separate dilution plate by serially diluting the compounds in DMSO to make a 1000× stock. The compounds were then further diluted to 10× final concentration in culture media, whereupon 20 µL of each dilution was added to the plated cells with controls (e.g. DMSO and blank) to make a final volume of 200 µL. The final DMSO concentration in each well was 0.1%. The plates were then incubated for 72 hours at 37° C. in a 5% $CO_2$ incubator. The number of viable cells was then assessed using sulforhodamine B (SRB) assay. Cells were fixed at 4° C. for 1 hour with the addition of 50 µL 30% trichloroacetic acid (TCA) to make a final concentration of 6% TCA. The plates were washed four times with $H_2O$ and allowed to dry for at least 1 hour, whereupon 100 µL of a 4% SRB in 1% acetic acid solution was added to each well and incubated at room temperature for at least 30 minutes. The plates were then washed three times with 1% acetic acid, dried, and treated with 100 µL of 10 mM Tris-Base solution. The plates were then read in a microplate reader at an absorbance of 570 nm. Background was generated on a separate plate with media only.

Method for Determining % Inhibition

First, the signals from the background plate are averaged, then the background was subtracted from the test plates. The compound-treated cells were then assayed for % inhibition by using the following formula:

$$\% \text{ Inh} = 100 - 100 \cdot x/y$$

wherein x denotes the average signal of the compound-treated cells and y denotes the average signal of the DMSO-treated cells.

Formula for Determining $IC_{50}$ Values:

$$IC50 = 10^{\wedge}(\text{LOG }10(X) + (((50 - \% \text{ Inh at Cmpd Concentration }1)/(XX-YY) \cdot (\text{LOG }10(X) - \text{LOG }10(Y))))$$

wherein X denotes the compound concentration 1, Y denotes the compound concentration 2, XX denotes the % inhibition at compound concentration 1 (X), and YY denotes the % inhibition at compound concentration 2 (Y).

Specificity of Cytotoxicity.

Inhibition of NAMPT could be reversed by the addition of NAM or NMN. The specificity of the compounds were determined via cell viability assay in the presence of the compound and either NAM or NMN. Percent inhibitions were determined using the method given above.

The NAMPT-inhibitor compounds of this invention have IC50 values that are preferably under 1 µM, more preferably under 0.1 µM, and most preferably under 0.01 µM. Most preferable compounds of this invention are compounds that have both the enzymatic IC50-value and the A2780 IC 50-value under 1 µM, more preferably both of the values are under 0.1 µM, and most preferably both of the values are under 0.01 µM. Results for the compounds are provided in Table 3.

TABLE 3

| IUPAC Name | Biochem IC50 uM | A2780 IC50 uM |
|---|---|---|
| (E)-2-cyano-3-({4-[(5-fluoro-2-methoxyphenyl)sulfamoyl]phenyl}methyl)-1-(pyridin-4-yl)guanidine | 0.0011 | 0.0030 |

TABLE 3-continued

| IUPAC Name | Biochem IC50 uM | A2780 IC50 uM |
|---|---|---|
| 5-hydroxy-N-({4-[(4-phenylbenzene)sulfonyl]phenyl}methyl)-1H-indole-2-carboxamide | 0.1-1 | 1-10 |
| 5-hydroxy-N-[(4-{[3-(morpholin-4-yl)benzene]sulfonyl}phenyl)methyl]-1H-indole-2-carboxamide | 0.1-1 | 1-10 |
| 5-hydroxy-N-[(4-{[3-(piperidin-1-yl)benzene]sulfonyl}phenyl)methyl]-1H-indole-2-carboxamide | 0.1-1 | 1-10 |
| 5-hydroxy-N-[(4-{[3-(pyrrolidin-1-yl)benzene]sulfonyl}phenyl)methyl]-1H-indole-2-carboxamide | 0.1442 | 0.1-1 |
| 5-hydroxy-N-{[4-(1-methyl-1H-indazole-4-sulfonyl)phenyl]methyl}-1H-indole-2-carboxamide | 0.1-1 | >1.0 |
| 5-N-({4-[(3,5-difluorobenzene)sulfonyl]phenyl}methyl)pyridine-2,5-diamido | 1-10 | 0.661 |
| 6-amino-N-({4-[(3,5-difluorobenzene)sulfonyl]phenyl}methyl)pyridine-3-carboxamide | 0.0142 | 0.275 |
| N-({4-[(2,3,6-trimethoxybenzene)sulfonyl]phenyl}methyl)-1H-pyrazolo[3,4-b]pyridine-5-carboxamide | 0.0797 | 0.0663 |
| N-({4-[(2,3,6-trimethoxybenzene)sulfonyl]phenyl}methyl)furo[2,3-c]pyridine-2-carboxamide | 0.0399 | 0.0667 |
| N-({4-[(2,3-difluoro-6-methoxybenzene)sulfonyl]phenyl}methyl)-1H-pyrrolo[3,2-c]pyridine-2-carboxamide | 0.204 | 0.0849 |
| N-({4-[(2,3-difluorobenzene)sulfonyl]phenyl}methyl)-1H-pyrazolo[3,4-b]pyridine-5-carboxamide | 0.0820 | 0.2786 |
| N-({4-[(2,3-dimethoxy-5-methylbenzene)sulfonyl]phenyl}methyl)-1H-pyrazolo[3,4-b]pyridine-5-carboxamide | 0.1462 | 0.0586 |
| N-({4-[(2,3-dimethoxy-5-methylbenzene)sulfonyl]phenyl}methyl)furo[2,3-c]pyridine-2-carboxamide | 0.0152 | 0.007 |
| N-({4-[(2,3-dimethoxy-5-methylbenzene)sulfonyl]phenyl}methyl)imidazo[1,2-a]pyrimidine-6-carboxamide | 0.0042 | 0.0156 |
| N-({4-[(2,3-dimethoxybenzene)sulfonyl]phenyl}methyl)-1H-pyrazolo[3,4-b]pyridine-5-carboxamide | 0.123 | 0.0833 |
| N-({4-[(2,3-dimethoxybenzene)sulfonyl]phenyl}methyl)-1H-pyrrolo[3,2-c]pyridine-2-carboxamide | 0.0117 | 0.0049 |
| N-({4-[(2,3-dimethoxybenzene)sulfonyl]phenyl}methyl)furo[2,3-c]pyridine-2-carboxamide | 0.0093 | 0.0136 |
| N-({4-[(2,3-dimethoxybenzene)sulfonyl]phenyl}methyl)imidazo[1,2-a]pyridine-6-carboxamide | 0.0687 | 0.0249 |
| N-({4-[(2,3-dimethoxybenzene)sulfonyl]phenyl}methyl)imidazo[1,2-a]pyrimidine-6-carboxamide | 0.0176 | 0.0776 |
| N-({4-[(2,3-dimethylbenzene)sulfonyl]phenyl}methyl)furo[2,3-c]pyridine-2-carboxamide | 0.0516 | 0.008 |
| N-({4-[(2,3-dimethylbenzene)sulfonyl]phenyl}methyl)imidazo[1,2-a]pyridine-6-carboxamide | 0.0433 | 0.00985 |
| N-({4-[(2,3-dimethylbenzene)sulfonyl]phenyl}methyl)imidazo[1,2-a]pyrimidine-6-carboxamide | 0.0041 | 0.0469 |
| N-({4-[(2,4,5-trimethylbenzene)sulfonyl]phenyl}methyl)-1H-pyrazolo[3,4-b]pyridine-5-carboxamide | 0.0313 | 0.0193 |
| N-({4-[(2,4,5-trimethylbenzene)sulfonyl]phenyl}methyl)furo[2,3-c]pyridine-2-carboxamide | 0.0091 | 0.0141 |
| N-({4-[(2,4,5-trimethylbenzene)sulfonyl]phenyl}methyl)imidazo[1,2-a]pyridine-6-carboxamide | 0.00934 | 0.0141 |
| N-({4-[(2,4,5-trimethylbenzene)sulfonyl]phenyl}methyl)imidazo[1,2-a]pyrimidine-6-carboxamide | 0.0069 | 0.0240 |
| N-({4-[(2,4,6-trimethylbenzene)sulfonyl]phenyl}methyl)-1H-pyrazolo[3,4-b]pyridine-5-carboxamide | 0.136 | 0.1-1 |
| N-({4-[(2,4,6-trimethylbenzene)sulfonyl]phenyl}methyl)furo[2,3-c]pyridine-2-carboxamide | 0.0592 | 0.1-1 |
| N-({4-[(2,4,6-trimethylbenzene)sulfonyl]phenyl}methyl)imidazo[1,2-a]pyrimidine-6-carboxamide | 0.0288 | 0.1-1 |
| N-({4-[(2,4-dichloro-3-methoxybenzene)sulfonyl]phenyl}methyl)-1H-pyrazolo[3,4-b]pyridine-5-carboxamide | 0.02 | 0.0147 |
| N-({4-[(2,4-dichloro-3-methoxybenzene)sulfonyl]phenyl}methyl)furo[2,3-c]pyridine-2-carboxamide | 0.0177 | 0.0162 |

TABLE 3-continued

| IUPAC Name | Biochem IC50 uM | A2780 IC50 uM |
|---|---|---|
| N-({4-[(2,4-dichloro-3-methoxybenzene)sulfonyl]phenyl}methyl)imidazo[1,2-a]pyridine-6-carboxamide | 0.0311 | 0.013 |
| N-({4-[(2,4-dichloro-3-methoxybenzene)sulfonyl]phenyl}methyl)imidazo[1,2-a]pyrimidine-6-carboxamide | 0.0066 | 0.0255 |
| N-({4-[(2,4-dichloro-3-methoxybenzene)sulfonyl]phenyl}methyl)thieno[2,3-c]pyridine-2-carboxamide | 0.0051 | 0.0067 |
| N-({4-[(2,4-difluorobenzene)sulfonyl]phenyl}methyl)imidazo[1,2-a]pyridine-6-carboxamide | 0.0283 | 0.0281 |
| N-({4-[(2,4-dimethoxybenzene)sulfonyl]phenyl}methyl)-1H-pyrazolo[3,4-b]pyridine-5-carboxamide | 0.1744 | 0.0447 |
| N-({4-[(2,4-dimethoxybenzene)sulfonyl]phenyl}methyl)imidazo[1,2-a]pyridine-6-carboxamide | 0.0582 | 0.0151 |
| N-({4-[(2,4-dimethoxybenzene)sulfonyl]phenyl}methyl)thieno[2,3-c]pyridine-2-carboxamide | 0.0045 | 0.0016 |
| N-({4-[(2,4-dimethylbenzene)sulfonyl]phenyl}methyl)-1H-pyrazolo[3,4-b]pyridine-5-carboxamide | 0.0612 | 0.0716 |
| N-({4-[(2,4-dimethylbenzene)sulfonyl]phenyl}methyl)furo[2,3-c]pyridine-2-carboxamide | 0.0218 | 0.024 |
| N-({4-[(2,4-dimethylbenzene)sulfonyl]phenyl}methyl)imidazo[1,2-a]pyridine-6-carboxamide | 0.0216 | 0.0321 |
| N-({4-[(2,4-dimethylbenzene)sulfonyl]phenyl}methyl)imidazo[1,2-a]pyrimidine-6-carboxamide | 0.0021 | 0.0492 |
| N-({4-[(2,5-difluorobenzene)sulfonyl]phenyl}methyl)-1H-pyrazolo[3,4-b]pyridine-5-carboxamide | 0.1-1 | 0.3921 |
| N-({4-[(2,5-dimethoxybenzene)sulfonyl]phenyl}methyl)-1H-pyrazolo[3,4-b]pyridine-5-carboxamide | 0.0398 | 0.0248 |
| N-({4-[(2,5-dimethoxybenzene)sulfonyl]phenyl}methyl)furo[2,3-c]pyridine-2-carboxamide | 0.0114 | 0.0063 |
| N-({4-[(2,5-dimethoxybenzene)sulfonyl]phenyl}methyl)imidazo[1,2-a]pyridine-6-carboxamide | 0.0202 | 0.0128 |
| N-({4-[(2,5-dimethoxybenzene)sulfonyl]phenyl}methyl)imidazo[1,2-a]pyrimidine-6-carboxamide | 0.0069 | 0.0457 |
| N-({4-[(2,5-dimethylbenzene)sulfonyl]phenyl}methyl)-1H-pyrazolo[3,4-b]pyridine-5-carboxamide | 0.0209 | 0.0172 |
| N-({4-[(2,5-dimethylbenzene)sulfonyl]phenyl}methyl)furo[2,3-c]pyridine-2-carboxamide | 0.0181 | 0.0239 |
| N-({4-[(2,5-dimethylbenzene)sulfonyl]phenyl}methyl)imidazo[1,2-a]pyrimidine-6-carboxamide | 0.0293 | 0.0154 |
| N-({4-[(2,6-dichloro-3-methylbenzene)sulfonyl]phenyl}methyl)furo[2,3-c]pyridine-2-carboxamide | 0.0108 | 0.0162 |
| N-({4-[(2,6-dichloro-3-methylbenzene)sulfonyl]phenyl}methyl)imidazo[1,2-a]pyrimidine-6-carboxamide | 0.0073 | 0.0560 |
| N-({4-[(2,6-dichloro-3-methylbenzene)sulfonyl]phenyl}methyl)thieno[2,3-c]pyridine-2-carboxamide | 0.0044 | 0.0082 |
| N-({4-[(2,6-dichlorobenzene)sulfonyl]phenyl}methyl)-1H-pyrazolo[3,4-b]pyridine-5-carboxamide | 0.1795 | 1-10 |
| N-({4-[(2,6-dichlorobenzene)sulfonyl]phenyl}methyl)-1H-pyrrolo[3,2-c]pyridine-2-carboxamide | 0.0447 | 0.0135 |
| N-({4-[(2,6-dichlorobenzene)sulfonyl]phenyl}methyl)furo[2,3-c]pyridine-2-carboxamide | 0.0124 | 0.0601 |
| N-({4-[(2,6-dichlorobenzene)sulfonyl]phenyl}methyl)imidazo[1,2-a]pyridine-6-carboxamide | 0.0012 | 0.0188 |
| N-({4-[(2,6-dichlorobenzene)sulfonyl]phenyl}methyl)imidazo[1,2-a]pyrimidine-6-carboxamide | 0.0134 | 0.1-1 |
| N-({4-[(2,6-dichlorobenzene)sulfonyl]phenyl}methyl)thieno[2,3-c]pyridine-2-carboxamide | 0.0076 | 0.0182 |
| N-({4-[(2,6-dimethoxy-4-methylbenzene)sulfonyl]phenyl}methyl)-1H-pyrazolo[3,4-b]pyridine-5-carboxamide | 0.1-1 | 0.1-1 |
| N-({4-[(2,6-dimethoxy-4-methylbenzene)sulfonyl]phenyl}methyl)furo[2,3-c]pyridine-2-carboxamide | 0.0050 | 0.0230 |

TABLE 3-continued

| IUPAC Name | Biochem IC50 uM | A2780 IC50 uM |
|---|---|---|
| N-({4-[(2,6-dimethylbenzene)sulfonyl]phenyl}methyl)-1H-pyrazolo[3,4-b]pyridine-5-carboxamide | 0.159 | 0.1-1 |
| N-({4-[(2,6-dimethylbenzene)sulfonyl]phenyl}methyl)furo[2,3-c]pyridine-2-carboxamide | 0.0323 | 0.1-1 |
| N-({4-[(2-acetylbenzene)sulfonyl]phenyl}methyl)-1H-pyrazolo[3,4-b]pyridine-5-carboxamide | 0.0036 | 0.0114 |
| N-({4-[(2-acetylbenzene)sulfonyl]phenyl}methyl)furo[2,3-c]pyridine-2-carboxamide | 0.0057 | 0.0065 |
| N-({4-[(2-acetylbenzene)sulfonyl]phenyl}methyl)imidazo[1,2-a]pyrimidine-6-carboxamide | 0.0025 | 0.0082 |
| N-({4-[(2-butoxy-4-fluorobenzene)sulfonyl]phenyl}methyl)-1H-pyrazolo[3,4-b]pyridine-5-carboxamide | 0.176 | 0.1-1 |
| N-({4-[(2-butoxy-4-fluorobenzene)sulfonyl]phenyl}methyl)-1H-pyrrolo[3,2-c]pyridine-2-carboxamide | 0.0311 | 0.0055 |
| N-({4-[(2-butoxy-4-fluorobenzene)sulfonyl]phenyl}methyl)furo[2,3-c]pyridine-2-carboxamide | 0.0335 | 0.0665 |
| N-({4-[(2-butoxy-4-fluorobenzene)sulfonyl]phenyl}methyl)imidazo[1,2-a]pyridine-6-carboxamide | 0.0512 | 0.0062 |
| N-({4-[(2-butoxy-4-fluorobenzene)sulfonyl]phenyl}methyl)imidazo[1,2-a]pyrimidine-6-carboxamide | 0.0073 | 0.0738 |
| N-({4-[(2-butoxy-4-fluorobenzene)sulfonyl]phenyl}methyl)thieno[2,3-c]pyridine-2-carboxamide | 0.0070 | 0.0063 |
| N-({4-[(2-butoxy-5-chlorobenzene)sulfonyl]phenyl}methyl)-1H-pyrazolo[3,4-b]pyridine-5-carboxamide | 0.117 | 0.0737 |
| N-({4-[(2-butoxy-5-chlorobenzene)sulfonyl]phenyl}methyl)-1H-pyrrolo[3,2-c]pyridine-2-carboxamide | 0.0156 | 0.0083 |
| N-({4-[(2-butoxy-5-chlorobenzene)sulfonyl]phenyl}methyl)furo[2,3-c]pyridine-2-carboxamide | 0.0243 | 0.0663 |
| N-({4-[(2-butoxy-5-chlorobenzene)sulfonyl]phenyl}methyl)imidazo[1,2-a]pyridine-6-carboxamide | 0.0110 | 0.0080 |
| N-({4-[(2-butoxy-5-chlorobenzene)sulfonyl]phenyl}methyl)imidazo[1,2-a]pyrimidine-6-carboxamide | 0.0037 | 0.0628 |
| N-({4-[(2-butoxy-5-chlorobenzene)sulfonyl]phenyl}methyl)thieno[2,3-c]pyridine-2-carboxamide | 0.0073 | 0.0100 |
| N-({4-[(2-butoxy-6-fluorobenzene)sulfonyl]phenyl}methyl)-1H-pyrrolo[3,2-c]pyridine-2-carboxamide | 0.0088 | 0.0056 |
| N-({4-[(2-butoxy-6-fluorobenzene)sulfonyl]phenyl}methyl)furo[2,3-c]pyridine-2-carboxamide | 0.0256 | 0.0698 |
| N-({4-[(2-butoxy-6-fluorobenzene)sulfonyl]phenyl}methyl)imidazo[1,2-a]pyridine-6-carboxamide | 0.0053 | 0.0069 |
| N-({4-[(2-chloro-3-fluorobenzene)sulfonyl]phenyl}methyl)-1H-pyrazolo[3,4-b]pyridine-5-carboxamide | 0.0736 | 0.1-1 |
| N-({4-[(2-chloro-3-fluorobenzene)sulfonyl]phenyl}methyl)furo[2,3-c]pyridine-2-carboxamide | 0.0170 | 0.0611 |
| N-({4-[(2-chloro-4-fluorobenzene)sulfonyl]phenyl}methyl)furo[2,3-c]pyridine-2-carboxamide | 0.0178 | 0.0634 |
| N-({4-[(2-chloro-4-fluorobenzene)sulfonyl]phenyl}methyl)imidazo[1,2-a]pyrimidine-6-carboxamide | 0.0144 | 0.1-1 |
| N-({4-[(2-chloro-4-methoxybenzene)sulfonyl]phenyl}methyl)-1H-pyrazolo[3,4-b]pyridine-5-carboxamide | 0.0516 | 0.0877 |
| N-({4-[(2-chloro-4-methoxybenzene)sulfonyl]phenyl}methyl)-1H-pyrrolo[3,2-c]pyridine-2-carboxamide | 0.0093 | 0.0145 |
| N-({4-[(2-chloro-4-methoxybenzene)sulfonyl]phenyl}methyl)imidazo[1,2-a]pyridine-6-carboxamide | 0.0167 | 0.0114 |
| N-({4-[(2-chloro-4-methoxybenzene)sulfonyl]phenyl}methyl)imidazo[1,2-a]pyrimidine-6-carboxamide | 0.0065 | 0.0669 |
| N-({4-[(2-chloro-4-methoxybenzene)sulfonyl]phenyl}methyl)thieno[2,3-c]pyridine-2-carboxamide | 0.0027 | 0.0055 |
| N-({4-[(2-chloro-4-methylbenzene)sulfonyl]phenyl}methyl)-1H-pyrazolo[3,4-b]pyridine-5-carboxamide | 0.05 | 0.00278 |

TABLE 3-continued

| IUPAC Name | Biochem IC50 uM | A2780 IC50 uM |
|---|---|---|
| N-({4-[(2-chloro-4-methylbenzene)sulfonyl]phenyl}methyl)-1H-pyrrolo[3,2-c]pyridine-2-carboxamide | 0.0080 | 0.0027 |
| N-({4-[(2-chloro-4-methylbenzene)sulfonyl]phenyl}methyl)furo[2,3-c]pyridine-2-carboxamide | 0.0141 | 0.0142 |
| N-({4-[(2-chloro-4-methylbenzene)sulfonyl]phenyl}methyl)imidazo[1,2-a]pyridine-6-carboxamide | 0.0011 | 0.0009 |
| N-({4-[(2-chloro-4-methylbenzene)sulfonyl]phenyl}methyl)imidazo[1,2-a]pyrimidine-6-carboxamide | 0.0015 | 0.0007 |
| N-({4-[(2-chloro-4-methylbenzene)sulfonyl]phenyl}methyl)thieno[2,3-c]pyridine-2-carboxamide | 0.0249 | 0.0016 |
| N-({4-[(2-chloro-5-fluorobenzene)sulfonyl]phenyl}methyl)-1H-pyrrolo[3,2-c]pyridine-2-carboxamide | 0.0281 | 0.0121 |
| N-({4-[(2-chloro-5-fluorobenzene)sulfonyl]phenyl}methyl)furo[2,3-c]pyridine-2-carboxamide | 0.0163 | 0.0248 |
| N-({4-[(2-chloro-5-fluorobenzene)sulfonyl]phenyl}methyl)imidazo[1,2-a]pyridine-6-carboxamide | 0.0210 | 0.0063 |
| N-({4-[(2-chloro-5-fluorobenzene)sulfonyl]phenyl}methyl)imidazo[1,2-a]pyrimidine-6-carboxamide | 0.0105 | 0.0530 |
| N-({4-[(2-chloro-5-fluorobenzene)sulfonyl]phenyl}methyl)thieno[2,3-c]pyridine-2-carboxamide | 0.0042 | 0.0057 |
| N-({4-[(2-chloro-5-methoxybenzene)sulfonyl]phenyl}methyl)-1H-pyrazolo[3,4-b]pyridine-5-carboxamide | 0.0247 | 0.0668 |
| N-({4-[(2-chloro-5-methoxybenzene)sulfonyl]phenyl}methyl)-1H-pyrrolo[3,2-c]pyridine-2-carboxamide | 0.0110 | 0.0097 |
| N-({4-[(2-chloro-5-methoxybenzene)sulfonyl]phenyl}methyl)furo[2,3-c]pyridine-2-carboxamide | 0.0026 | 0.0206 |
| N-({4-[(2-chloro-5-methoxybenzene)sulfonyl]phenyl}methyl)imidazo[1,2-a]pyridine-6-carboxamide | 0.0056 | 0.0027 |
| N-({4-[(2-chloro-5-methoxybenzene)sulfonyl]phenyl}methyl)imidazo[1,2-a]pyrimidine-6-carboxamide | 0.0061 | 0.0515 |
| N-({4-[(2-chloro-5-methoxybenzene)sulfonyl]phenyl}methyl)thieno[2,3-c]pyridine-2-carboxamide | 0.0049 | 0.0053 |
| N-({4-[(2-chloro-5-methylbenzene)sulfonyl]phenyl}methyl)-1H-pyrazolo[3,4-b]pyridine-5-carboxamide | 0.0602 | 0.0659 |
| N-({4-[(2-chloro-5-methylbenzene)sulfonyl]phenyl}methyl)-1H-pyrrolo[3,2-c]pyridine-2-carboxamide | 0.0188 | 0.0091 |
| N-({4-[(2-chloro-5-methylbenzene)sulfonyl]phenyl}methyl)furo[2,3-c]pyridine-2-carboxamide | 0.0178 | 0.0149 |
| N-({4-[(2-chloro-5-methylbenzene)sulfonyl]phenyl}methyl)imidazo[1,2-a]pyridine-6-carboxamide | 0.0056 | 0.0046 |
| N-({4-[(2-chloro-5-methylbenzene)sulfonyl]phenyl}methyl)imidazo[1,2-a]pyrimidine-6-carboxamide | 0.0057 | 0.0225 |
| N-({4-[(2-chloro-5-methylbenzene)sulfonyl]phenyl}methyl)thieno[2,3-c]pyridine-2-carboxamide | 0.0022 | 0.0049 |
| N-({4-[(2-chloro-6-fluorobenzene)sulfonyl]phenyl}methyl)-1H-pyrrolo[3,2-c]pyridine-2-carboxamide | 0.1142 | 0.0371 |
| N-({4-[(2-chloro-6-fluorobenzene)sulfonyl]phenyl}methyl)imidazo[1,2-a]pyridine-6-carboxamide | 0.1722 | 0.0766 |
| N-({4-[(2-chloro-6-methoxybenzene)sulfonyl]phenyl}methyl)furo[2,3-c]pyridine-2-carboxamide | 0.0167 | 0.0214 |
| N-({4-[(2-chloro-6-methoxybenzene)sulfonyl]phenyl}methyl)imidazo[1,2-a]pyridine-6-carboxamide | 0.0202 | 0.0258 |
| N-({4-[(2-chloro-6-methoxybenzene)sulfonyl]phenyl}methyl)thieno[2,3-c]pyridine-2-carboxamide | 0.0027 | 0.0029 |
| N-({4-[(2-chlorobenzene)sulfonyl]phenyl}methyl)-1H-pyrazolo[3,4-b]pyridine-5-carboxamide | 0.0925 | 1-0.1 |

TABLE 3-continued

| IUPAC Name | Biochem IC50 uM | A2780 IC50 uM |
|---|---|---|
| N-({4-[(2-chlorobenzene)sulfonyl]phenyl}methyl)imidazo[1,2-a]pyridine-6-carboxamide | 0.0241 | 0.0567 |
| N-({4-[(2-chlorobenzene)sulfonyl]phenyl}methyl)thieno[2,3-c]pyridine-2-carboxamide | 0.0024 | 0.0066 |
| N-({4-[(2-cyanobenzene)sulfonyl]phenyl}methyl)-1H-pyrazolo[3,4-b]pyridine-5-carboxamide | 0.131 | 0.1-1 |
| N-({4-[(2-cyanobenzene)sulfonyl]phenyl}methyl)-1H-pyrrolo[3,2-c]pyridine-2-carboxamide | 0.0253 | 0.0629 |
| N-({4-[(2-cyanobenzene)sulfonyl]phenyl}methyl)furo[2,3-c]pyridine-2-carboxamide | 0.0246 | 0.0635 |
| N-({4-[(2-cyanobenzene)sulfonyl]phenyl}methyl)imidazo[1,2-a]pyridine-6-carboxamide | 0.0156 | 0.0613 |
| N-({4-[(2-cyanobenzene)sulfonyl]phenyl}methyl)thieno[2,3-c]pyridine-2-carboxamide | 0.0146 | 0.0676 |
| N-({4-[(2-ethoxy-4-fluorobenzene)sulfonyl]phenyl}methyl)-1H-pyrazolo[3,4-b]pyridine-5-carboxamide | 0.0863 | 0.0670 |
| N-({4-[(2-ethoxy-4-fluorobenzene)sulfonyl]phenyl}methyl)-1H-pyrrolo[3,2-c]pyridine-2-carboxamide | 0.0034 | 0.0018 |
| N-({4-[(2-ethoxy-4-fluorobenzene)sulfonyl]phenyl}methyl)furo[2,3-c]pyridine-2-carboxamide | 0.0077 | 0.0069 |
| N-({4-[(2-ethoxy-4-fluorobenzene)sulfonyl]phenyl}methyl)imidazo[1,2-a]pyridine-6-carboxamide | 0.0314 | 0.0015 |
| N-({4-[(2-ethoxy-4-fluorobenzene)sulfonyl]phenyl}methyl)imidazo[1,2-a]pyrimidine-6-carboxamide | 0.0071 | 0.0143 |
| N-({4-[(2-ethoxy-4-fluorobenzene)sulfonyl]phenyl}methyl)thieno[2,3-c]pyridine-2-carboxamide | 0.0038 | 0.0009 |
| N-({4-[(2-ethoxy-6-fluorobenzene)sulfonyl]phenyl}methyl)furo[2,3-c]pyridine-2-carboxamide | 0.0170 | 0.0283 |
| N-({4-[(2-ethoxybenzene)sulfonyl]phenyl}methyl)-1H-pyrazolo[3,4-b]pyridine-5-carboxamide | 0.0493 | 0.0269 |
| N-({4-[(2-ethoxybenzene)sulfonyl]phenyl}methyl)furo[2,3-c]pyridine-2-carboxamide | 0.0659 | 0.006 |
| N-({4-[(2-ethoxybenzene)sulfonyl]phenyl}methyl)imidazo[1,2-a]pyridine-6-carboxamide | 0.0203 | 0.00339 |
| N-({4-[(2-ethoxybenzene)sulfonyl]phenyl}methyl)imidazo[1,2-a]pyrimidine-6-carboxamide | 0.0010 | 0.0071 |
| N-({4-[(2-ethylbenzene)sulfonyl]phenyl}methyl)-1H-pyrazolo[3,4-b]pyridine-5-carboxamide | 0.0084 | 0.013 |
| N-({4-[(2-ethylbenzene)sulfonyl]phenyl}methyl)furo[2,3-c]pyridine-2-carboxamide | 0.0054 | 0.0129 |
| N-({4-[(2-ethylbenzene)sulfonyl]phenyl}methyl)imidazo[1,2-a]pyridine-6-carboxamide | 0.0302 | 0.0129 |
| N-({4-[(2-ethylbenzene)sulfonyl]phenyl}methyl)imidazo[1,2-a]pyrimidine-6-carboxamide | 0.0025 | 0.0249 |
| N-({4-[(2-fluoro-3-methoxybenzene)sulfonyl]phenyl}methyl)-1H-pyrazolo[3,4-b]pyridine-5-carboxamide | 0.0086 | 0.0563 |
| N-({4-[(2-fluoro-3-methoxybenzene)sulfonyl]phenyl}methyl)imidazo[1,2-a]pyridine-6-carboxamide | 0.033 | 0.0135 |
| N-({4-[(2-fluoro-3-methylbenzene)sulfonyl]phenyl}methyl)-1H-pyrazolo[3,4-b]pyridine-5-carboxamide | 0.0197 | 0.0239 |
| N-({4-[(2-fluoro-3-methylbenzene)sulfonyl]phenyl}methyl)-1H-pyrrolo[3,2-c]pyridine-2-carboxamide | 0.0758 | 0.0070 |
| N-({4-[(2-fluoro-3-methylbenzene)sulfonyl]phenyl}methyl)furo[2,3-c]pyridine-2-carboxamide | 0.0063 | 0.0079 |
| N-({4-[(2-fluoro-3-methylbenzene)sulfonyl]phenyl}methyl)imidazo[1,2-a]pyridine-6-carboxamide | 0.0075 | 0.0033 |
| N-({4-[(2-fluoro-3-methylbenzene)sulfonyl]phenyl}methyl)imidazo[1,2-a]pyrimidine-6-carboxamide | 0.0032 | 0.0215 |
| N-({4-[(2-fluoro-3-methylbenzene)sulfonyl]phenyl}methyl)thieno[2,3-c]pyridine-2-carboxamide | 0.0107 | 0.0033 |
| N-({4-[(2-fluoro-4-methoxybenzene)sulfonyl]phenyl}methyl)-1H-pyrazolo[3,4-b]pyridine-5-carboxamide | 0.1203 | 0.2067 |
| N-({4-[(2-fluoro-4-methoxybenzene)sulfonyl]phenyl}methyl)imidazo[1,2-a]pyridine-6-carboxamide | 0.0413 | 0.0229 |

TABLE 3-continued

| IUPAC Name | Biochem IC50 uM | A2780 IC50 uM |
|---|---|---|
| N-({4-[(2-fluoro-4-methylbenzene)sulfonyl]phenyl}methyl)furo[2,3-c]pyridine-2-carboxamide | 0.0123 | 0.0253 |
| N-({4-[(2-fluoro-4-methylbenzene)sulfonyl]phenyl}methyl)imidazo[1,2-a]pyridine-6-carboxamide | 0.0214 | 0.0247 |
| N-({4-[(2-fluoro-4-methylbenzene)sulfonyl]phenyl}methyl)imidazo[1,2-a]pyrimidine-6-carboxamide | 0.0063 | 0.0614 |
| N-({4-[(2-fluoro-5-methoxybenzene)sulfonyl]phenyl}methyl)-1H-pyrazolo[3,4-b]pyridine-5-carboxamide | 0.139 | 0.1-1 |
| N-({4-[(2-fluoro-5-methoxybenzene)sulfonyl]phenyl}methyl)-1H-pyrrolo[3,2-c]pyridine-2-carboxamide | 0.0778 | 0.0144 |
| N-({4-[(2-fluoro-5-methoxybenzene)sulfonyl]phenyl}methyl)furo[2,3-c]pyridine-2-carboxamide | 0.0268 | 0.0637 |
| N-({4-[(2-fluoro-5-methoxybenzene)sulfonyl]phenyl}methyl)imidazo[1,2-a]pyridine-6-carboxamide | 0.0047 | 0.0128 |
| N-({4-[(2-fluoro-5-methoxybenzene)sulfonyl]phenyl}methyl)imidazo[1,2-a]pyrimidine-6-carboxamide | 0.0104 | 0.0629 |
| N-({4-[(2-fluoro-5-methoxybenzene)sulfonyl]phenyl}methyl)thieno[2,3-c]pyridine-2-carboxamide | 0.0023 | 0.0128 |
| N-({4-[(2-fluoro-5-methylbenzene)sulfonyl]phenyl}methyl)-1H-pyrazolo[3,4-b]pyridine-5-carboxamide | 0.0241 | 0.0716 |
| N-({4-[(2-fluoro-5-methylbenzene)sulfonyl]phenyl}methyl)furo[2,3-c]pyridine-2-carboxamide | 0.0059 | 0.0134 |
| N-({4-[(2-fluoro-5-methylbenzene)sulfonyl]phenyl}methyl)imidazo[1,2-a]pyrimidine-6-carboxamide | 0.0068 | 0.0275 |
| N-({4-[(2-fluoro-6-methoxybenzene)sulfonyl]phenyl}methyl)imidazo[1,2-a]pyridine-6-carboxamide | 0.0481 | 0.0264 |
| N-({4-[(2-fluoro-6-propoxybenzene)sulfonyl]phenyl}methyl)furo[2,3-c]pyridine-2-carboxamide | 0.0133 | 0.0142 |
| N-({4-[(2-fluoro-6-propoxybenzene)sulfonyl]phenyl}methyl)imidazo[1,2-a]pyridine-6-carboxamide | 0.0914 | 0.0010 |
| N-({4-[(2-fluoro-6-propoxybenzene)sulfonyl]phenyl}methyl)thieno[2,3-c]pyridine-2-carboxamide | 0.0115 | 0.0293 |
| N-({4-[(2-fluorobenzene)sulfonyl]phenyl}methyl)furo[2,3-c]pyridine-2-carboxamide | 0.0418 | 0.1-1 |
| N-({4-[(2-methanesulfonylbenzene)sulfonyl]phenyl}methyl)-1H-pyrazolo[3,4-b]pyridine-5-carboxamide | 0.2022 | 0.1-1 |
| N-({4-[(2-methanesulfonylbenzene)sulfonyl]phenyl}methyl)furo[2,3-c]pyridine-2-carboxamide | 0.0542 | 0.1-1 |
| N-({4-[(2-methoxy-5-methylbenzene)sulfonyl]phenyl}methyl)-1H-pyrazolo[3,4-b]pyridine-5-carboxamide | 0.0563 | 0.0244 |
| N-({4-[(2-methoxy-5-methylbenzene)sulfonyl]phenyl}methyl)furo[2,3-c]pyridine-2-carboxamide | 0.0133 | 0.0068 |
| N-({4-[(2-methoxy-5-methylbenzene)sulfonyl]phenyl}methyl)imidazo[1,2-a]pyridine-6-carboxamide | 0.0431 | 0.0117 |
| N-({4-[(2-methoxy-5-methylbenzene)sulfonyl]phenyl}methyl)imidazo[1,2-a]pyrimidine-6-carboxamide | 0.0039 | 0.0072 |
| N-({4-[(2-methoxybenzene)sulfonyl]phenyl}methyl)-1H-pyrazolo[3,4-b]pyridine-5-carboxamide | 0.0683 | 0.0618 |
| N-({4-[(2-methoxybenzene)sulfonyl]phenyl}methyl)furo[2,3-c]pyridine-2-carboxamide | 0.0189 | 0.0265 |
| N-({4-[(2-methoxybenzene)sulfonyl]phenyl}methyl)imidazo[1,2-a]pyridine-6-carboxamide | 0.0265 | 0.0153 |
| N-({4-[(2-methoxybenzene)sulfonyl]phenyl}methyl)imidazo[1,2-a]pyrimidine-6-carboxamide | 0.0039 | 0.0747 |
| N-({4-[(2-methyl-4-propoxybenzene)sulfonyl]phenyl}methyl)-1H-pyrazolo[3,4-b]pyridine-5-carboxamide | 0.0644 | 0.0794 |
| N-({4-[(2-methyl-4-propoxybenzene)sulfonyl]phenyl}methyl)-1H-pyrrolo[3,2-c]pyridine-2-carboxamide | 0.0305 | 0.0221 |

TABLE 3-continued

| IUPAC Name | Biochem IC50 uM | A2780 IC50 uM |
|---|---|---|
| N-({4-[(2-methyl-4-propoxybenzene)sulfonyl]phenyl}methyl)furo[2,3-c]pyridine-2-carboxamide | 0.0225 | 0.0596 |
| N-({4-[(2-methyl-4-propoxybenzene)sulfonyl]phenyl}methyl)imidazo[1,2-a]pyridine-6-carboxamide | 0.0092 | 0.0133 |
| N-({4-[(2-methyl-4-propoxybenzene)sulfonyl]phenyl}methyl)imidazo[1,2-a]pyrimidine-6-carboxamide | 0.0100 | 0.0518 |
| N-({4-[(2-methyl-4-propoxybenzene)sulfonyl]phenyl}methyl)thieno[2,3-c]pyridine-2-carboxamide | 0.0129 | 0.0017 |
| N-({4-[(2-methylbenzene)sulfonyl]phenyl}methyl)-1H-pyrazolo[3,4-b]pyridine-5-carboxamide | 0.0926 | 1-0.1 |
| N-({4-[(2-methylbenzene)sulfonyl]phenyl}methyl)furo[2,3-c]pyridine-2-carboxamide | 0.0152 | 0.0433 |
| N-({4-[(2-methylbenzene)sulfonyl]phenyl}methyl)imidazo[1,2-a]pyridine-6-carboxamide | 0.0669 | 0.0912 |
| N-({4-[(2-phenoxybenzene)sulfonyl]phenyl}methyl)-1H-pyrazolo[3,4-b]pyridine-5-carboxamide | 0.1-1 | 0.1-1 |
| N-({4-[(2-phenoxybenzene)sulfonyl]phenyl}methyl)furo[2,3-c]pyridine-2-carboxamide | 0.0204 | 1-10 |
| N-({4-[(2-phenoxybenzene)sulfonyl]phenyl}methyl)imidazo[1,2-a]pyridine-6-carboxamide | 0.0636 | 0.0607 |
| N-({4-[(2-phenoxybenzene)sulfonyl]phenyl}methyl)imidazo[1,2-a]pyrimidine-6-carboxamide | 0.0085 | 0.1-1 |
| N-({4-[(3,4-dichlorobenzene)sulfonyl]phenyl}methyl)-1H-pyrazolo[3,4-b]pyridine-5-carboxamide | 0.0067 | 0.0055 |
| N-({4-[(3,4-dichlorobenzene)sulfonyl]phenyl}methyl)furo[2,3-c]pyridine-2-carboxamide | 0.0104 | 0.0048 |
| N-({4-[(3,4-dichlorobenzene)sulfonyl]phenyl}methyl)imidazo[1,2-a]pyrimidine-6-carboxamide | 0.0015 | 0.0017 |
| N-({4-[(3,4-difluorobenzene)sulfonyl]phenyl}methyl)-1H-pyrazolo[3,4-b]pyridine-5-carboxamide | 0.0542 | 0.0289 |
| N-({4-[(3,4-difluorobenzene)sulfonyl]phenyl}methyl)furo[2,3-c]pyridine-2-carboxamide | 0.0168 | 0.013 |
| N-({4-[(3,4-difluorobenzene)sulfonyl]phenyl}methyl)imidazo[1,2-a]pyrimidine-6-carboxamide | 0.0041 | 0.0363 |
| N-({4-[(3,4-dimethoxybenzene)sulfonyl]phenyl}methyl)-1H-pyrazolo[3,4-b]pyridine-5-carboxamide | 0.0206 | 0.0056 |
| N-({4-[(3,4-dimethoxybenzene)sulfonyl]phenyl}methyl)furo[2,3-c]pyridine-2-carboxamide | 0.0062 | 0.0038 |
| N-({4-[(3,4-dimethoxybenzene)sulfonyl]phenyl}methyl)imidazo[1,2-a]pyridine-6-carboxamide | 0.012 | 0.00251 |
| N-({4-[(3,4-dimethoxybenzene)sulfonyl]phenyl}methyl)imidazo[1,2-a]pyrimidine-6-carboxamide | 0.0029 | 0.0073 |
| N-({4-[(3,4-dimethylbenzene)sulfonyl]phenyl}methyl)-1H-pyrazolo[3,4-b]pyridine-5-carboxamide | 0.0051 | 0.0034 |
| N-({4-[(3,4-dimethylbenzene)sulfonyl]phenyl}methyl)furo[2,3-c]pyridine-2-carboxamide | 0.0150 | 0.003 |
| N-({4-[(3,4-dimethylbenzene)sulfonyl]phenyl}methyl)imidazo[1,2-a]pyridine-6-carboxamide | 0.0111 | 0.00297 |
| N-({4-[(3,4-dimethylbenzene)sulfonyl]phenyl}methyl)imidazo[1,2-a]pyrimidine-6-carboxamide | 0.0011 | 0.0016 |
| N-({4-[(3,5-dichlorobenzene)sulfonyl]phenyl}methyl)-1H-pyrazolo[3,4-b]pyridine-5-carboxamide | 0.0067 | 0.0021 |
| N-({4-[(3,5-dichlorobenzene)sulfonyl]phenyl}methyl)-1H-pyrrolo[3,2-c]pyridine-2-carboxamide | 0.001 | 0.0004 |
| N-({4-[(3,5-dichlorobenzene)sulfonyl]phenyl}methyl)imidazo[1,2-a]pyridine-6-carboxamide | 0.00549 | 0.00128 |
| N-({4-[(3,5-difluorobenzene)sulfonyl]phenyl}methyl)-1H-pyrazolo[3,4-b]pyridine-5-carboxamide | 0.008 | 0.007 |
| N-({4-[(3,5-difluorobenzene)sulfonyl]phenyl}methyl)imidazo[1,2-a]pyridine-6-carboxamide | 0.006 | 0.0015 |
| N-({4-[(3,5-difluorobenzene)sulfonyl]phenyl}methyl)imidazo[1,2-a]pyrimidine-6-carboxamide | 0.002 | 0.003 |
| N-({4-[(3,5-dimethoxybenzene)sulfonyl]phenyl}methyl)-1H-pyrazolo[3,4-b]pyridine-5-carboxamide | 0.0026 | 0.0022 |
| N-({4-[(3,5-dimethoxybenzene)sulfonyl]phenyl}methyl)-1H-pyrrolo[3,2-c]pyridine-2-carboxamide | 0.0044 | 0.0015 |
| N-({4-[(3,5-dimethoxybenzene)sulfonyl]phenyl}methyl)furo[2,3-c]pyridine-2-carboxamide | 0.0027 | 0.0017 |

TABLE 3-continued

| IUPAC Name | Biochem IC50 uM | A2780 IC50 uM |
|---|---|---|
| N-({4-[(3,5-dimethoxybenzene)sulfonyl]phenyl}methyl)imidazo[1,2-a]pyridine-6-carboxamide | 0.0032 | 0.0015 |
| N-({4-[(3,5-dimethoxybenzene)sulfonyl]phenyl}methyl)imidazo[1,2-a]pyrimidine-6-carboxamide | 0.0024 | 0.0016 |
| N-({4-[(3,5-dimethoxybenzene)sulfonyl]phenyl}methyl)thieno[2,3-c]pyridine-2-carboxamide | 0.0013 | 0.0009 |
| N-({4-[(3,5-dimethylbenzene)sulfonyl]phenyl}methyl)-1H-pyrazolo[3,4-b]pyridine-5-carboxamide | 0.0104 | 0.0061 |
| N-({4-[(3,5-dimethylbenzene)sulfonyl]phenyl}methyl)furo[2,3-c]pyridine-2-carboxamide | 0.0167 | 0.0028 |
| N-({4-[(3,5-dimethylbenzene)sulfonyl]phenyl}methyl)imidazo[1,2-a]pyridine-6-carboxamide | 0.00676 | 0.00317 |
| N-({4-[(3,5-dimethylbenzene)sulfonyl]phenyl}methyl)imidazo[1,2-a]pyrimidine-6-carboxamide | 0.0017 | 0.0020 |
| N-({4-[(3-acetylbenzene)sulfonyl]phenyl}methyl)-1H-pyrazolo[3,4-b]pyridine-5-carboxamide | 0.0100 | 0.0129 |
| N-({4-[(3-acetylbenzene)sulfonyl]phenyl}methyl)furo[2,3-c]pyridine-2-carboxamide | 0.0176 | 0.008 |
| N-({4-[(3-acetylbenzene)sulfonyl]phenyl}methyl)imidazo[1,2-a]pyridine-6-carboxamide | 0.0125 | 0.00637 |
| N-({4-[(3-acetylbenzene)sulfonyl]phenyl}methyl)imidazo[1,2-a]pyrimidine-6-carboxamide | 0.0018 | 0.0105 |
| N-({4-[(3-butoxybenzene)sulfonyl]phenyl}methyl)-1H-pyrazolo[3,4-b]pyridine-5-carboxamide | 0.0384 | 0.0675 |
| N-({4-[(3-butoxybenzene)sulfonyl]phenyl}methyl)-1H-pyrrolo[3,2-c]pyridine-2-carboxamide | 0.0115 | 0.0216 |
| N-({4-[(3-butoxybenzene)sulfonyl]phenyl}methyl)furo[2,3-c]pyridine-2-carboxamide | 0.0123 | 0.0695 |
| N-({4-[(3-butoxybenzene)sulfonyl]phenyl}methyl)imidazo[1,2-a]pyridine-6-carboxamide | 0.0047 | 0.0180 |
| N-({4-[(3-butoxybenzene)sulfonyl]phenyl}methyl)thieno[2,3-c]pyridine-2-carboxamide | 0.0033 | 0.0387 |
| N-({4-[(3-chloro-2-fluorobenzene)sulfonyl]phenyl}methyl)furo[2,3-c]pyridine-2-carboxamide | 0.0109 | 0.0128 |
| N-({4-[(3-chloro-2-fluorobenzene)sulfonyl]phenyl}methyl)imidazo[1,2-a]pyrimidine-6-carboxamide | 0.0024 | 0.0176 |
| N-({4-[(3-chloro-2-methoxybenzene)sulfonyl]phenyl}methyl)furo[2,3-c]pyridine-2-carboxamide | 0.0192 | 0.0623 |
| N-({4-[(3-chloro-2-methylbenzene)sulfonyl]phenyl}methyl)-1H-pyrazolo[3,4-b]pyridine-5-carboxamide | 0.0369 | 0.0161 |
| N-({4-[(3-chloro-2-methylbenzene)sulfonyl]phenyl}methyl)-1H-pyrrolo[3,2-c]pyridine-2-carboxamide | 0.0625 | 0.0120 |
| N-({4-[(3-chloro-2-methylbenzene)sulfonyl]phenyl}methyl)furo[2,3-c]pyridine-2-carboxamide | 0.0026 | 0.0016 |
| N-({4-[(3-chloro-2-methylbenzene)sulfonyl]phenyl}methyl)imidazo[1,2-a]pyridine-6-carboxamide | 0.0257 | 0.0050 |
| N-({4-[(3-chloro-2-methylbenzene)sulfonyl]phenyl}methyl)imidazo[1,2-a]pyrimidine-6-carboxamide | 0.0043 | 0.0265 |
| N-({4-[(3-chloro-2-methylbenzene)sulfonyl]phenyl}methyl)thieno[2,3-c]pyridine-2-carboxamide | 0.0572 | 0.0071 |
| N-({4-[(3-chloro-4-methoxybenzene)sulfonyl]phenyl}methyl)-1H-pyrazolo[3,4-b]pyridine-5-carboxamide | 0.0040 | 0.0036 |
| N-({4-[(3-chloro-4-methoxybenzene)sulfonyl]phenyl}methyl)-1H-pyrrolo[3,2-c]pyridine-2-carboxamide | 0.0107 | 0.0021 |
| N-({4-[(3-chloro-4-methoxybenzene)sulfonyl]phenyl}methyl)furo[2,3-c]pyridine-2-carboxamide | 0.0073 | 0.0018 |
| N-({4-[(3-chloro-4-methoxybenzene)sulfonyl]phenyl}methyl)imidazo[1,2-a]pyrimidine-6-carboxamide | 0.0018 | 0.0018 |
| N-({4-[(3-chloro-4-methoxybenzene)sulfonyl]phenyl}methyl)thieno[2,3-c]pyridine-2-carboxamide | 0.0050 | 0.0016 |

TABLE 3-continued

| IUPAC Name | Biochem IC50 uM | A2780 IC50 uM |
|---|---|---|
| N-({4-[(3-chloro-4-methylbenzene)sulfonyl]phenyl}methyl)-1H-pyrazolo[3,4-b]pyridine-5-carboxamide | 0.0061 | 0.0019 |
| N-({4-[(3-chloro-4-methylbenzene)sulfonyl]phenyl}methyl)-1H-pyrrolo[3,2-c]pyridine-2-carboxamide | 0.0083 | 0.0025 |
| N-({4-[(3-chloro-4-methylbenzene)sulfonyl]phenyl}methyl)furo[2,3-c]pyridine-2-carboxamide | 0.0528 | 0.0017 |
| N-({4-[(3-chloro-4-methylbenzene)sulfonyl]phenyl}methyl)imidazo[1,2-a]pyrimidine-6-carboxamide | 0.0018 | 0.0012 |
| N-({4-[(3-chloro-4-methylbenzene)sulfonyl]phenyl}methyl)thieno[2,3-c]pyridine-2-carboxamide | 0.0051 | 0.0010 |
| N-({4-[(3-chloro-4-propoxybenzene)sulfonyl]phenyl}methyl)-1H-pyrazolo[3,4-b]pyridine-5-carboxamide | 0.0079 | 0.00958 |
| N-({4-[(3-chloro-4-propoxybenzene)sulfonyl]phenyl}methyl)-1H-pyrrolo[3,2-c]pyridine-2-carboxamide | 0.0740 | 0.0078 |
| N-({4-[(3-chloro-4-propoxybenzene)sulfonyl]phenyl}methyl)furo[2,3-c]pyridine-2-carboxamide | 0.0049 | 0.0119 |
| N-({4-[(3-chloro-4-propoxybenzene)sulfonyl]phenyl}methyl)imidazo[1,2-a]pyridine-6-carboxamide | 0.0065 | 0.0060 |
| N-({4-[(3-chloro-4-propoxybenzene)sulfonyl]phenyl}methyl)imidazo[1,2-a]pyrimidine-6-carboxamide | 0.0039 | 0.0024 |
| N-({4-[(3-chloro-4-propoxybenzene)sulfonyl]phenyl}methyl)thieno[2,3-c]pyridine-2-carboxamide | 0.0151 | 0.0174 |
| N-({4-[(3-chloro-5-fluorobenzene)sulfonyl]phenyl}methyl)-1H-pyrazolo[3,4-b]pyridine-5-carboxamide | 0.0133 | 0.0060 |
| N-({4-[(3-chloro-5-fluorobenzene)sulfonyl]phenyl}methyl)-1H-pyrrolo[3,2-c]pyridine-2-carboxamide | 0.0099 | 0.0014 |
| N-({4-[(3-chloro-5-fluorobenzene)sulfonyl]phenyl}methyl)furo[2,3-c]pyridine-2-carboxamide | 0.0178 | 0.0031 |
| N-({4-[(3-chloro-5-fluorobenzene)sulfonyl]phenyl}methyl)imidazo[1,2-a]pyridine-6-carboxamide | 0.0039 | 0.0003 |
| N-({4-[(3-chloro-5-fluorobenzene)sulfonyl]phenyl}methyl)imidazo[1,2-a]pyrimidine-6-carboxamide | 0.0024 | 0.0029 |
| N-({4-[(3-chloro-5-fluorobenzene)sulfonyl]phenyl}methyl)thieno[2,3-c]pyridine-2-carboxamide | 0.0014 | 0.0006 |
| N-({4-[(3-chloro-5-methoxybenzene)sulfonyl]phenyl}methyl)-1H-pyrazolo[3,4-b]pyridine-5-carboxamide | 0.0093 | 0.0025 |
| N-({4-[(3-chloro-5-methoxybenzene)sulfonyl]phenyl}methyl)-1H-pyrrolo[3,2-c]pyridine-2-carboxamide | 0.0170 | 0.0025 |
| N-({4-[(3-chloro-5-methoxybenzene)sulfonyl]phenyl}methyl)furo[2,3-c]pyridine-2-carboxamide | 0.0265 | 0.0015 |
| N-({4-[(3-chloro-5-methoxybenzene)sulfonyl]phenyl}methyl)imidazo[1,2-a]pyridine-6-carboxamide | 0.0092 | 0.0015 |
| N-({4-[(3-chloro-5-methoxybenzene)sulfonyl]phenyl}methyl)imidazo[1,2-a]pyrimidine-6-carboxamide | 0.0013 | 0.0008 |
| N-({4-[(3-chloro-5-methoxybenzene)sulfonyl]phenyl}methyl)thieno[2,3-c]pyridine-2-carboxamide | 0.0041 | 0.0011 |
| N-({4-[(3-chloro-5-methylbenzene)sulfonyl]phenyl}methyl)-1H-pyrazolo[3,4-b]pyridine-5-carboxamide | 0.0062 | 0.0026 |
| N-({4-[(3-chloro-5-methylbenzene)sulfonyl]phenyl}methyl)furo[2,3-c]pyridine-2-carboxamide | 0.0269 | 0.0018 |
| N-({4-[(3-chloro-5-methylbenzene)sulfonyl]phenyl}methyl)furo[2,3-c]pyridine-2-carboxamide | 0.0013 | 0.0008 |
| N-({4-[(3-chloro-5-methylbenzene)sulfonyl]phenyl}methyl)imidazo[1,2-a]pyridine-6-carboxamide | 0.0064 | 0.002 |
| N-({4-[(3-chloro-5-methylbenzene)sulfonyl]phenyl}methyl)imidazo[1,2-a]pyrimidine-6-carboxamide | 0.0048 | 0.0023 |

TABLE 3-continued

| IUPAC Name | Biochem IC50 uM | A2780 IC50 uM |
|---|---|---|
| N-({4-[(3-chloro-5-methylbenzene)sulfonyl]phenyl}methyl)thieno[2,3-c]pyridine-2-carboxamide | 0.0045 | 0.0016 |
| N-({4-[(3-chlorobenzene)sulfonyl]phenyl}methyl)-1H-pyrazolo[3,4-b]pyridine-5-carboxamide | 0.007 | 0.006 |
| N-({4-[(3-chlorobenzene)sulfonyl]phenyl}methyl)-1H-pyrrolo[3,2-b]pyridine-2-carboxamide | 0.0039 | 0.013 |
| N-({4-[(3-chlorobenzene)sulfonyl]phenyl}methyl)furo[2,3-c]pyridine-2-carboxamide | 0.0060 | 0.0033 |
| N-({4-[(3-chlorobenzene)sulfonyl]phenyl}methyl)imidazo[1,2-a]pyridine-6-carboxamide | 0.00908 | 0.00307 |
| N-({4-[(3-chlorobenzene)sulfonyl]phenyl}methyl)imidazo[1,2-a]pyrimidine-6-carboxamide | 0.0013 | 0.0012 |
| N-({4-[(3-cyanobenzene)sulfonyl]phenyl}methyl)-1H-pyrazolo[3,4-b]pyridine-5-carboxamide | 0.0185 | 0.00954 |
| N-({4-[(3-cyanobenzene)sulfonyl]phenyl}methyl)-1H-pyrrolo[3,2-c]pyridine-2-carboxamide | 0.0121 | 0.0113 |
| N-({4-[(3-cyanobenzene)sulfonyl]phenyl}methyl)furo[2,3-c]pyridine-2-carboxamide | 0.0154 | 0.0126 |
| N-({4-[(3-cyanobenzene)sulfonyl]phenyl}methyl)imidazo[1,2-a]pyrimidine-6-carboxamide | 0.0059 | 0.0192 |
| N-({4-[(3-cyanobenzene)sulfonyl]phenyl}methyl)thieno[2,3-c]pyridine-2-carboxamide | 0.0035 | 0.0056 |
| N-({4-[(3-ethoxy-2-fluorobenzene)sulfonyl]phenyl}methyl)-1H-pyrrolo[3,2-c]pyridine-2-carboxamide | 0.0312 | 0.0116 |
| N-({4-[(3-ethoxy-2-fluorobenzene)sulfonyl]phenyl}methyl)furo[2,3-c]pyridine-2-carboxamide | 0.0175 | 0.0227 |
| N-({4-[(3-ethoxy-2-fluorobenzene)sulfonyl]phenyl}methyl)imidazo[1,2-a]pyridine-6-carboxamide | 0.0050 | 0.0062 |
| N-({4-[(3-ethoxy-2-fluorobenzene)sulfonyl]phenyl}methyl)imidazo[1,2-a]pyrimidine-6-carboxamide | 0.0040 | 0.0197 |
| N-({4-[(3-ethoxy-2-fluorobenzene)sulfonyl]phenyl}methyl)thieno[2,3-c]pyridine-2-carboxamide | 0.0037 | 0.0129 |
| N-({4-[(3-ethoxy-4-fluorobenzene)sulfonyl]phenyl}methyl)-1H-pyrazolo[3,4-b]pyridine-5-carboxamide | 0.0261 | 0.012 |
| N-({4-[(3-ethoxy-4-fluorobenzene)sulfonyl]phenyl}methyl)-1H-pyrrolo[3,2-c]pyridine-2-carboxamide | 0.0824 | 0.0044 |
| N-({4-[(3-ethoxy-4-fluorobenzene)sulfonyl]phenyl}methyl)furo[2,3-c]pyridine-2-carboxamide | 0.0110 | 0.0072 |
| N-({4-[(3-ethoxy-4-fluorobenzene)sulfonyl]phenyl}methyl)imidazo[1,2-a]pyridine-6-carboxamide | 0.0170 | 0.006 |
| N-({4-[(3-ethoxy-4-fluorobenzene)sulfonyl]phenyl}methyl)imidazo[1,2-a]pyrimidine-6-carboxamide | 0.0003 | 0.0078 |
| N-({4-[(3-ethoxy-4-fluorobenzene)sulfonyl]phenyl}methyl)thieno[2,3-c]pyridine-2-carboxamide | 0.0033 | 0.0031 |
| N-({4-[(3-ethoxybenzene)sulfonyl]phenyl}methyl)-1H-pyrazolo[3,4-b]pyridine-5-carboxamide | 0.0146 | 0.0190 |
| N-({4-[(3-ethoxybenzene)sulfonyl]phenyl}methyl)-1H-pyrrolo[3,2-c]pyridine-2-carboxamide | 0.0077 | 0.0035 |
| N-({4-[(3-ethoxybenzene)sulfonyl]phenyl}methyl)furo[2,3-c]pyridine-2-carboxamide | 0.0068 | 0.0110 |
| N-({4-[(3-ethoxybenzene)sulfonyl]phenyl}methyl)imidazo[1,2-a]pyridine-6-carboxamide | 0.0050 | 0.0031 |
| N-({4-[(3-ethoxybenzene)sulfonyl]phenyl}methyl)imidazo[1,2-a]pyrimidine-6-carboxamide | 0.0021 | 0.0067 |
| N-({4-[(3-ethoxybenzene)sulfonyl]phenyl}methyl)thieno[2,3-c]pyridine-2-carboxamide | 0.0032 | 0.0029 |
| N-({4-[(3-ethylbenzene)sulfonyl]phenyl}methyl)-1H-pyrazolo[3,4-b]pyridine-5-carboxamide | 0.0070 | 0.0071 |
| N-({4-[(3-ethylbenzene)sulfonyl]phenyl}methyl)furo[2,3-c]pyridine-2-carboxamide | 0.0087 | 0.0065 |
| N-({4-[(3-ethylbenzene)sulfonyl]phenyl}methyl)imidazo[1,2-a]pyridine-6-carboxamide | 0.00483 | 0.00323 |
| N-({4-[(3-ethylbenzene)sulfonyl]phenyl}methyl)imidazo[1,2-a]pyrimidine-6-carboxamide | 0.0038 | 0.0041 |
| N-({4-[(3-fluoro-2-methoxybenzene)sulfonyl]phenyl}methyl)-1H-pyrazolo[3,4-b]pyridine-5-carboxamide | 0.121 | 0.1-1 |

TABLE 3-continued

| IUPAC Name | Biochem IC50 uM | A2780 IC50 uM |
|---|---|---|
| N-({4-[(3-fluoro-2-methoxybenzene)sulfonyl]phenyl}methyl)-1H-pyrrolo[3,2-c]pyridine-2-carboxamide | 0.0324 | 0.0063 |
| N-({4-[(3-fluoro-2-methoxybenzene)sulfonyl]phenyl}methyl)furo[2,3-c]pyridine-2-carboxamide | 0.0166 | 0.0309 |
| N-({4-[(3-fluoro-2-methoxybenzene)sulfonyl]phenyl}methyl)imidazo[1,2-a]pyridine-6-carboxamide | 0.0769 | 0.0650 |
| N-({4-[(3-fluoro-2-methoxybenzene)sulfonyl]phenyl}methyl)imidazo[1,2-a]pyrimidine-6-carboxamide | 0.0289 | 0.1-1 |
| N-({4-[(3-fluoro-2-methoxybenzene)sulfonyl]phenyl}methyl)thieno[2,3-c]pyridine-2-carboxamide | 0.0133 | 0.0125 |
| N-({4-[(3-fluoro-2-methylbenzene)sulfonyl]phenyl}methyl)-1H-pyrazolo[3,4-b]pyridine-5-carboxamide | 0.0469 | 0.0718 |
| N-({4-[(3-fluoro-2-methylbenzene)sulfonyl]phenyl}methyl)-1H-pyrrolo[3,2-c]pyridine-2-carboxamide | 0.0576 | 0.0132 |
| N-({4-[(3-fluoro-2-methylbenzene)sulfonyl]phenyl}methyl)furo[2,3-c]pyridine-2-carboxamide | 0.0132 | 0.0307 |
| N-({4-[(3-fluoro-2-methylbenzene)sulfonyl]phenyl}methyl)imidazo[1,2-a]pyridine-6-carboxamide | 0.0469 | 0.0132 |
| N-({4-[(3-fluoro-2-methylbenzene)sulfonyl]phenyl}methyl)imidazo[1,2-a]pyrimidine-6-carboxamide | 0.0081 | 0.0656 |
| N-({4-[(3-fluoro-2-methylbenzene)sulfonyl]phenyl}methyl)thieno[2,3-c]pyridine-2-carboxamide | 0.0071 | 0.0214 |
| N-({4-[(3-fluoro-4-methoxybenzene)sulfonyl]phenyl}methyl)-1H-pyrazolo[3,4-b]pyridine-5-carboxamide | 0.0430 | 0.0060 |
| N-({4-[(3-fluoro-4-methoxybenzene)sulfonyl]phenyl}methyl)furo[2,3-c]pyridine-2-carboxamide | 0.0022 | 0.0068 |
| N-({4-[(3-fluoro-4-methoxybenzene)sulfonyl]phenyl}methyl)imidazo[1,2-a]pyridine-6-carboxamide | 0.00595 | 0.00289 |
| N-({4-[(3-fluoro-4-methoxybenzene)sulfonyl]phenyl}methyl)imidazo[1,2-a]pyrimidine-6-carboxamide | 0.0017 | 0.0083 |
| N-({4-[(3-fluoro-4-methylbenzene)sulfonyl]phenyl}methyl)-1H-pyrazolo[3,4-b]pyridine-5-carboxamide | 0.0117 | 0.0056 |
| N-({4-[(3-fluoro-4-methylbenzene)sulfonyl]phenyl}methyl)furo[2,3-c]pyridine-2-carboxamide | 0.0140 | 0.0033 |
| N-({4-[(3-fluoro-4-methylbenzene)sulfonyl]phenyl}methyl)imidazo[1,2-a]pyridine-6-carboxamide | 0.0133 | 0.00378 |
| N-({4-[(3-fluoro-4-methylbenzene)sulfonyl]phenyl}methyl)imidazo[1,2-a]pyrimidine-6-carboxamide | 0.0023 | 0.0063 |
| N-({4-[(3-fluoro-4-propoxybenzene)sulfonyl]phenyl}methyl)-1H-pyrazolo[3,4-b]pyridine-5-carboxamide | 0.0116 | 0.0065 |
| N-({4-[(3-fluoro-4-propoxybenzene)sulfonyl]phenyl}methyl)-1H-pyrrolo[3,2-c]pyridine-2-carboxamide | 0.0309 | 0.0104 |
| N-({4-[(3-fluoro-4-propoxybenzene)sulfonyl]phenyl}methyl)furo[2,3-c]pyridine-2-carboxamide | 0.0068 | 0.0118 |
| N-({4-[(3-fluoro-4-propoxybenzene)sulfonyl]phenyl}methyl)imidazo[1,2-a]pyridine-6-carboxamide | 0.0221 | 0.0044 |
| N-({4-[(3-fluoro-4-propoxybenzene)sulfonyl]phenyl}methyl)imidazo[1,2-a]pyrimidine-6-carboxamide | 0.0027 | 0.0033 |
| N-({4-[(3-fluoro-4-propoxybenzene)sulfonyl]phenyl}methyl)thieno[2,3-c]pyridine-2-carboxamide | 0.0037 | 0.0081 |
| N-({4-[(3-fluoro-5-methoxybenzene)sulfonyl]phenyl}methyl)-1H-pyrazolo[3,4-b]pyridine-5-carboxamide | 0.0044 | 0.0063 |
| N-({4-[(3-fluoro-5-methoxybenzene)sulfonyl]phenyl}methyl)furo[2,3-c]pyridine-2-carboxamide | 0.0174 | 0.0033 |
| N-({4-[(3-fluoro-5-methoxybenzene)sulfonyl]phenyl}methyl)imidazo[1,2-a]pyrimidine-6-carboxamide | 0.0016 | 0.0033 |

TABLE 3-continued

| IUPAC Name | Biochem IC50 uM | A2780 IC50 uM |
|---|---|---|
| N-({4-[(3-fluoro-5-methylbenzene)sulfonyl]phenyl}methyl)-1H-pyrazolo[3,4-b]pyridine-5-carboxamide | 0.0095 | 0.0056 |
| N-({4-[(3-fluoro-5-methylbenzene)sulfonyl]phenyl}methyl)-1H-pyrrolo[3,2-c]pyridine-2-carboxamide | 0.0083 | 0.0018 |
| N-({4-[(3-fluoro-5-methylbenzene)sulfonyl]phenyl}methyl)furo[2,3-c]pyridine-2-carboxamide | 0.0034 | 0.0032 |
| N-({4-[(3-fluoro-5-methylbenzene)sulfonyl]phenyl}methyl)imidazo[1,2-a]pyridine-6-carboxamide | 0.0027 | 0.0006 |
| N-({4-[(3-fluoro-5-methylbenzene)sulfonyl]phenyl}methyl)imidazo[1,2-a]pyrimidine-6-carboxamide | 0.0015 | 0.0054 |
| N-({4-[(3-fluoro-5-methylbenzene)sulfonyl]phenyl}methyl)thieno[2,3-c]pyridine-2-carboxamide | 0.0010 | 0.0006 |
| N-({4-[(3-fluorobenzene)sulfonyl]phenyl}methyl)-1H-pyrazolo[3,4-b]pyridine-5-carboxamide | 0.0339 | 0.0253 |
| N-({4-[(3-fluorobenzene)sulfonyl]phenyl}methyl)furo[2,3-c]pyridine-2-carboxamide | 0.0058 | 0.0145 |
| N-({4-[(3-fluorobenzene)sulfonyl]phenyl}methyl)imidazo[1,2-a]pyridine-6-carboxamide | 0.0221 | 0.0122 |
| N-({4-[(3-fluorobenzene)sulfonyl]phenyl}methyl)imidazo[1,2-a]pyrimidine-6-carboxamide | 0.0019 | 0.0221 |
| N-({4-[(3-hydroxybenzene)sulfonyl]phenyl}methyl)imidazo[1,2-a]pyridine-6-carboxamide | 0.005 | 0.0070 |
| N-({4-[(3-methanesulfonylbenzene)sulfonyl]phenyl}methyl)furo[2,3-c]pyridine-2-carboxamide | 0.0060 | 0.0068 |
| N-({4-[(3-methanesulfonylbenzene)sulfonyl]phenyl}methyl)imidazo[1,2-a]pyridine-6-carboxamide | 0.0256 | 0.016 |
| N-({4-[(3-methanesulfonylbenzene)sulfonyl]phenyl}methyl)thieno[2,3-c]pyridine-2-carboxamide | 0.0017 | 0.0035 |
| N-({4-[(3-methoxy-4-methylbenzene)sulfonyl]phenyl}methyl)-1H-pyrazolo[3,4-b]pyridine-5-carboxamide | 0.0036 | 0.0034 |
| N-({4-[(3-methoxy-4-methylbenzene)sulfonyl]phenyl}methyl)-1H-pyrrolo[3,2-c]pyridine-2-carboxamide | 0.0079 | 0.0030 |
| N-({4-[(3-methoxy-4-methylbenzene)sulfonyl]phenyl}methyl)furo[2,3-c]pyridine-2-carboxamide | 0.0046 | 0.0031 |
| N-({4-[(3-methoxy-4-methylbenzene)sulfonyl]phenyl}methyl)imidazo[1,2-a]pyrimidine-6-carboxamide | 0.0013 | 0.0017 |
| N-({4-[(3-methoxy-4-methylbenzene)sulfonyl]phenyl}methyl)thieno[2,3-c]pyridine-2-carboxamide | 0.0027 | 0.0015 |
| N-({4-[(3-methoxy-5-methylbenzene)sulfonyl]phenyl}methyl)-1H-pyrrolo[3,2-c]pyridine-2-carboxamide | 0.0096 | 0.0028 |
| N-({4-[(3-methoxy-5-methylbenzene)sulfonyl]phenyl}methyl)furo[2,3-c]pyridine-2-carboxamide | 0.0022 | 0.0016 |
| N-({4-[(3-methoxy-5-methylbenzene)sulfonyl]phenyl}methyl)imidazo[1,2-a]pyridine-6-carboxamide | 0.0053 | 0.0016 |
| N-({4-[(3-methoxy-5-methylbenzene)sulfonyl]phenyl}methyl)imidazo[1,2-a]pyrimidine-6-carboxamide | 0.0016 | 0.0013 |
| N-({4-[(3-methoxy-5-methylbenzene)sulfonyl]phenyl}methyl)thieno[2,3-c]pyridine-2-carboxamide | 0.0024 | 0.0008 |
| N-({4-[(3-methoxybenzene)sulfonyl]phenyl}methyl)-1H-pyrazolo[3,4-b]pyridine-5-carboxamide | 0.0209 | 0.0100 |
| N-({4-[(3-methoxybenzene)sulfonyl]phenyl}methyl)furo[2,3-c]pyridine-2-carboxamide | 0.0035 | 0.0069 |
| N-({4-[(3-methoxybenzene)sulfonyl]phenyl}methyl)imidazo[1,2-a]pyridine-6-carboxamide | 0.00497 | 0.00245 |
| N-({4-[(3-methoxybenzene)sulfonyl]phenyl}methyl)imidazo[1,2-a]pyrimidine-6-carboxamide | 0.0020 | 0.0124 |
| N-({4-[(3-methylbenzene)sulfonyl]phenyl}methyl)furo[2,3-c]pyridine-2-carboxamide | 0.0023 | 0.0053 |
| N-({4-[(3-methylbenzene)sulfonyl]phenyl}methyl)imidazo[1,2-a]pyridine-6-carboxamide | 0.00812 | 0.00639 |
| N-({4-[(3-methylbenzene)sulfonyl]phenyl}methyl)imidazo[1,2-a]pyrimidine-6-carboxamide | 0.0019 | 0.0091 |

TABLE 3-continued

| IUPAC Name | Biochem IC50 uM | A2780 IC50 uM |
|---|---|---|
| N-({4-[(3-phenylbenzene)sulfonyl]phenyl}methyl)-1,3-benzothiazole-6-carboxamide | 0.0185 | 1-10 |
| N-({4-[(3-phenylbenzene)sulfonyl]phenyl}methyl)-1H-pyrrolo[3,2-c]pyridine-2-carboxamide | 0.0023 | 0.0119 |
| N-({4-[(3-phenylbenzene)sulfonyl]phenyl}methyl)furo[2,3-c]pyridine-2-carboxamide | 0.0137 | 0.0234 |
| N-({4-[(3-phenylbenzene)sulfonyl]phenyl}methyl)imidazo[1,2-a]pyridine-6-carboxamide | 0.0122 | 0.0068 |
| N-({4-[(3-phenylbenzene)sulfonyl]phenyl}methyl)imidazo[1,2-a]pyrimidine-6-carboxamide | 0.0009 | 0.0033 |
| N-({4-[(3-phenylbenzene)sulfonyl]phenyl}methyl)thieno[2,3-c]pyridine-2-carboxamide | 0.0045 | 0.0100 |
| N-({4-[(3-phenylpropane)sulfonyl]phenyl}methyl)-1H-pyrrolo[3,2-c]pyridine-2-carboxamide | 0.014 | 0.078 |
| N-({4-[(3-propoxybenzene)sulfonyl]phenyl}methyl)-1H-pyrazolo[3,4-b]pyridine-5-carboxamide | 0.0304 | 0.041 |
| N-({4-[(3-propoxybenzene)sulfonyl]phenyl}methyl)-1H-pyrrolo[3,2-c]pyridine-2-carboxamide | 0.0102 | 0.0122 |
| N-({4-[(3-propoxybenzene)sulfonyl]phenyl}methyl)furo[2,3-c]pyridine-2-carboxamide | 0.0101 | 0.0252 |
| N-({4-[(3-propoxybenzene)sulfonyl]phenyl}methyl)imidazo[1,2-a]pyridine-6-carboxamide | 0.0042 | 0.0063 |
| N-({4-[(3-propoxybenzene)sulfonyl]phenyl}methyl)imidazo[1,2-a]pyrimidine-6-carboxamide | 0.0048 | 0.0075 |
| N-({4-[(3-propoxybenzene)sulfonyl]phenyl}methyl)thieno[2,3-c]pyridine-2-carboxamide | 0.0040 | 0.0122 |
| N-({4-[(3-sulfamoylbenzene)sulfonyl]phenyl}methyl)-1H-pyrazolo[3,4-b]pyridine-5-carboxamide | 0.0301 | 0.1-1 |
| N-({4-[(3-sulfamoylbenzene)sulfonyl]phenyl}methyl)imidazo[1,2-a]pyridine-6-carboxamide | 0.0103 | 0.0546 |
| N-({4-[(3-sulfamoylbenzene)sulfonyl]phenyl}methyl)thieno[2,3-c]pyridine-2-carboxamide | 0.0020 | 0.0121 |
| N-({4-[(3-tert-butylbenzene)sulfonyl]phenyl}methyl)furo[2,3-c]pyridine-2-carboxamide | 0.0093 | 0.0070 |
| N-({4-[(3-tert-butylbenzene)sulfonyl]phenyl}methyl)imidazo[1,2-a]pyridine-6-carboxamide | 0.0097 | 0.0032 |
| N-({4-[(3-tert-butylbenzene)sulfonyl]phenyl}methyl)imidazo[1,2-a]pyrimidine-6-carboxamide | <0.00065 | 0.0012 |
| N-({4-[(3-tert-butylbenzene)sulfonyl]phenyl}methyl)thieno[2,3-c]pyridine-2-carboxamide | 0.0105 | 0.0091 |
| N-({4-[(4,5-difluoro-2-methoxybenzene)sulfonyl]phenyl}methyl)furo[2,3-c]pyridine-2-carboxamide | 0.0281 | 0.0259 |
| N-({4-[(4,5-difluoro-2-methoxybenzene)sulfonyl]phenyl}methyl)imidazo[1,2-a]pyridine-6-carboxamide | 0.0281 | 0.0068 |
| N-({4-[(4,5-difluoro-2-methoxybenzene)sulfonyl]phenyl}methyl)imidazo[1,2-a]pyrimidine-6-carboxamide | 0.0119 | 0.0249 |
| N-({4-[(4-acetylbenzene)sulfonyl]phenyl}methyl)-1H-pyrazolo[3,4-b]pyridine-5-carboxamide | 0.0289 | 0.0037 |
| N-({4-[(4-acetylbenzene)sulfonyl]phenyl}methyl)imidazo[1,2-a]pyrimidine-6-carboxamide | 0.0052 | 0.0065 |
| N-({4-[(4-butoxy-2-methylbenzene)sulfonyl]phenyl}methyl)-1H-pyrazolo[3,4-b]pyridine-5-carboxamide | 0.0709 | 0.0688 |
| N-({4-[(4-butoxy-2-methylbenzene)sulfonyl]phenyl}methyl)-1H-pyrrolo[3,2-c]pyridine-2-carboxamide | 0.0800 | 0.0625 |
| N-({4-[(4-butoxy-2-methylbenzene)sulfonyl]phenyl}methyl)furo[2,3-c]pyridine-2-carboxamide | 0.0160 | 0.0648 |
| N-({4-[(4-butoxy-2-methylbenzene)sulfonyl]phenyl}methyl)imidazo[1,2-a]pyridine-6-carboxamide | 0.0100 | 0.0224 |
| N-({4-[(4-butoxy-2-methylbenzene)sulfonyl]phenyl}methyl)thieno[2,3-c]pyridine-2-carboxamide | 0.0033 | 1.0-0.1 |
| N-({4-[(4-butoxy-3-chlorobenzene)sulfonyl]phenyl}methyl)-1H-pyrazolo[3,4-b]pyridine-5-carboxamide | 0.0045 | 0.0111 |
| N-({4-[(4-butoxy-3-chlorobenzene)sulfonyl]phenyl}methyl)-1H-pyrrolo[3,2-c]pyridine-2-carboxamide | 0.0178 | 0.0124 |
| N-({4-[(4-butoxy-3-chlorobenzene)sulfonyl]phenyl}methyl)furo[2,3-c]pyridine-2-carboxamide | 0.0047 | 0.0100 |
| N-({4-[(4-butoxy-3-chlorobenzene)sulfonyl]phenyl}methyl)imidazo[1,2-a]pyridine-6-carboxamide | 0.0041 | 0.0076 |

TABLE 3-continued

| IUPAC Name | Biochem IC50 uM | A2780 IC50 uM |
|---|---|---|
| N-({4-[(4-butoxy-3-chlorobenzene)sulfonyl]phenyl}methyl)thieno[2,3-c]pyridine-2-carboxamide | 0.0048 | 0.0125 |
| N-({4-[(4-butoxy-3-fluorobenzene)sulfonyl]phenyl}methyl)-1H-pyrrolo[3,2-c]pyridine-2-carboxamide | 0.0536 | 0.0134 |
| N-({4-[(4-butoxy-3-fluorobenzene)sulfonyl]phenyl}methyl)furo[2,3-c]pyridine-2-carboxamide | 0.0123 | 0.0139 |
| N-({4-[(4-butoxy-3-fluorobenzene)sulfonyl]phenyl}methyl)imidazo[1,2-a]pyridine-6-carboxamide | 0.0062 | 0.0031 |
| N-({4-[(4-butoxy-3-fluorobenzene)sulfonyl]phenyl}methyl)imidazo[1,2-a]pyrimidine-6-carboxamide | 0.0012 | 0.0031 |
| N-({4-[(4-butoxy-3-fluorobenzene)sulfonyl]phenyl}methyl)thieno[2,3-c]pyridine-2-carboxamide | 0.0047 | 0.0126 |
| N-({4-[(4-butoxybenzene)sulfonyl]phenyl}methyl)-1H-pyrazolo[3,4-b]pyridine-5-carboxamide | 0.0275 | 0.0225 |
| N-({4-[(4-butoxybenzene)sulfonyl]phenyl}methyl)-1H-pyrrolo[3,2-c]pyridine-2-carboxamide | 0.0084 | 0.0171 |
| N-({4-[(4-butoxybenzene)sulfonyl]phenyl}methyl)furo[2,3-c]pyridine-2-carboxamide | 0.0062 | 0.0130 |
| N-({4-[(4-butoxybenzene)sulfonyl]phenyl}methyl)imidazo[1,2-a]pyridine-6-carboxamide | 0.0038 | 0.0028 |
| N-({4-[(4-butoxybenzene)sulfonyl]phenyl}methyl)thieno[2,3-c]pyridine-2-carboxamide | 0.0036 | 0.0103 |
| N-({4-[(4-butylbenzene)sulfonyl]phenyl}methyl)-1H-pyrazolo[3,4-b]pyridine-5-carboxamide | 0.0712 | 0.0684 |
| N-({4-[(4-butylbenzene)sulfonyl]phenyl}methyl)-1H-pyrrolo[3,2-c]pyridine-2-carboxamide | 0.0146 | 0.0358 |
| N-({4-[(4-butylbenzene)sulfonyl]phenyl}methyl)furo[2,3-c]pyridine-2-carboxamide | 0.0181 | 0.0265 |
| N-({4-[(4-butylbenzene)sulfonyl]phenyl}methyl)imidazo[1,2-a]pyridine-6-carboxamide | 0.0057 | 0.0076 |
| N-({4-[(4-butylbenzene)sulfonyl]phenyl}methyl)imidazo[1,2-a]pyrimidine-6-carboxamide | 0.0053 | 0.0107 |
| N-({4-[(4-butylbenzene)sulfonyl]phenyl}methyl)thieno[2,3-c]pyridine-2-carboxamide | 0.0029 | 0.0260 |
| N-({4-[(4-chloro-2-ethoxybenzene)sulfonyl]phenyl}methyl)-1H-pyrrolo[3,2-c]pyridine-2-carboxamide | 0.0112 | 0.0004 |
| N-({4-[(4-chloro-2-ethoxybenzene)sulfonyl]phenyl}methyl)furo[2,3-c]pyridine-2-carboxamide | 0.0072 | 0.0051 |
| N-({4-[(4-chloro-2-ethoxybenzene)sulfonyl]phenyl}methyl)imidazo[1,2-a]pyridine-6-carboxamide | 0.0041 | 0.0007 |
| N-({4-[(4-chloro-2-ethoxybenzene)sulfonyl]phenyl}methyl)imidazo[1,2-a]pyrimidine-6-carboxamide | 0.0020 | 0.0045 |
| N-({4-[(4-chloro-2-ethoxybenzene)sulfonyl]phenyl}methyl)thieno[2,3-c]pyridine-2-carboxamide | 0.0024 | <0.0004 |
| N-({4-[(4-chloro-2-methoxybenzene)sulfonyl]phenyl}methyl)furo[2,3-c]pyridine-2-carboxamide | 0.0085 | 0.0248 |
| N-({4-[(4-chloro-2-methoxybenzene)sulfonyl]phenyl}methyl)imidazo[1,2-a]pyridine-6-carboxamide | 0.0187 | 0.0126 |
| N-({4-[(4-chloro-2-methoxybenzene)sulfonyl]phenyl}methyl)imidazo[1,2-a]pyrimidine-6-carboxamide | 0.0033 | 0.0247 |
| N-({4-[(4-chloro-2-methylbenzene)sulfonyl]phenyl}methyl)-1H-pyrazolo[3,4-b]pyridine-5-carboxamide | 0.0775 | 0.0587 |
| N-({4-[(4-chloro-2-methylbenzene)sulfonyl]phenyl}methyl)furo[2,3-c]pyridine-2-carboxamide | 0.0249 | 0.0647 |
| N-({4-[(4-chloro-2-methylbenzene)sulfonyl]phenyl}methyl)imidazo[1,2-a]pyrimidine-6-carboxamide | 0.0066 | 0.0539 |
| N-({4-[(4-chloro-3-fluorobenzene)sulfonyl]phenyl}methyl)furo[2,3-c]pyridine-2-carboxamide | 0.0185 | 0.0065 |
| N-({4-[(4-chloro-3-fluorobenzene)sulfonyl]phenyl}methyl)imidazo[1,2-a]pyridine-6-carboxamide | 0.00722 | 0.00724 |

TABLE 3-continued

| IUPAC Name | Biochem IC50 uM | A2780 IC50 uM |
|---|---|---|
| N-({4-[(4-chloro-3-fluorobenzene)sulfonyl]phenyl}methyl)imidazo[1,2-a]pyrimidine-6-carboxamide | 0.0019 | 0.0089 |
| N-({4-[(4-chloro-3-methoxybenzene)sulfonyl]phenyl}methyl)-1H-pyrazolo[3,4-b]pyridine-5-carboxamide | 0.0127 | 0.0130 |
| N-({4-[(4-chloro-3-methoxybenzene)sulfonyl]phenyl}methyl)-1H-pyrrolo[3,2-c]pyridine-2-carboxamide | 0.0055 | 0.0036 |
| N-({4-[(4-chloro-3-methoxybenzene)sulfonyl]phenyl}methyl)furo[2,3-c]pyridine-2-carboxamide | 0.0059 | 0.0060 |
| N-({4-[(4-chloro-3-methoxybenzene)sulfonyl]phenyl}methyl)imidazo[1,2-a]pyridine-6-carboxamide | 0.0135 | 0.006 |
| N-({4-[(4-chloro-3-methoxybenzene)sulfonyl]phenyl}methyl)imidazo[1,2-a]pyrimidine-6-carboxamide | 0.0027 | 0.0052 |
| N-({4-[(4-chloro-3-methoxybenzene)sulfonyl]phenyl}methyl)thieno[2,3-c]pyridine-2-carboxamide | 0.0026 | 0.0023 |
| N-({4-[(4-chlorobenzene)sulfonyl]phenyl}methyl)-1H-pyrazolo[3,4-b]pyridine-5-carboxamide | 0.0288 | 0.022 |
| N-({4-[(4-chlorobenzene)sulfonyl]phenyl}methyl)furo[2,3-c]pyridine-2-carboxamide | 0.0049 | 0.0142 |
| N-({4-[(4-chlorobenzene)sulfonyl]phenyl}methyl)imidazo[1,2-a]pyrimidine-6-carboxamide | 0.0025 | 0.0236 |
| N-({4-[(4-cyanobenzene)sulfonyl]phenyl}methyl)-1H-pyrazolo[3,4-b]pyridine-5-carboxamide | 0.0284 | 0.0208 |
| N-({4-[(4-cyanobenzene)sulfonyl]phenyl}methyl)-1H-pyrrolo[3,2-c]pyridine-2-carboxamide | 0.0111 | 0.0251 |
| N-({4-[(4-cyanobenzene)sulfonyl]phenyl}methyl)furo[2,3-c]pyridine-2-carboxamide | 0.0053 | 0.0309 |
| N-({4-[(4-cyanobenzene)sulfonyl]phenyl}methyl)imidazo[1,2-a]pyridine-6-carboxamide | 0.0160 | 0.0141 |
| N-({4-[(4-cyclohexylbenzene)sulfonyl]phenyl}methyl)imidazo[1,2-a]pyridine-6-carboxamide | 0.0178 | 0.0117 |
| N-({4-[(4-cyclohexylbenzene)sulfonyl]phenyl}methyl)imidazo[1,2-a]pyrimidine-6-carboxamide | 0.0058 | 0.0077 |
| N-({4-[(4-cyclohexylbenzene)sulfonyl]phenyl}methyl)thieno[2,3-c]pyridine-2-carboxamide | 0.0034 | 0.0129 |
| N-({4-[(4-ethoxy-2-methylbenzene)sulfonyl]phenyl}methyl)-1H-pyrazolo[3,4-b]pyridine-5-carboxamide | 0.1083 | 0.0667 |
| N-({4-[(4-ethoxy-2-methylbenzene)sulfonyl]phenyl}methyl)-1H-pyrrolo[3,2-c]pyridine-2-carboxamide | 0.0092 | 0.0126 |
| N-({4-[(4-ethoxy-2-methylbenzene)sulfonyl]phenyl}methyl)furo[2,3-c]pyridine-2-carboxamide | 0.0216 | 0.0274 |
| N-({4-[(4-ethoxy-2-methylbenzene)sulfonyl]phenyl}methyl)imidazo[1,2-a]pyridine-6-carboxamide | 0.0066 | 0.0111 |
| N-({4-[(4-ethoxy-2-methylbenzene)sulfonyl]phenyl}methyl)imidazo[1,2-a]pyrimidine-6-carboxamide | 0.0117 | 0.0607 |
| N-({4-[(4-ethoxy-2-methylbenzene)sulfonyl]phenyl}methyl)thieno[2,3-c]pyridine-2-carboxamide | 0.0012 | 0.0132 |
| N-({4-[(4-ethoxy-3-fluorobenzene)sulfonyl]phenyl}methyl)-1H-pyrazolo[3,4-b]pyridine-5-carboxamide | 0.0095 | 0.0052 |
| N-({4-[(4-ethoxy-3-fluorobenzene)sulfonyl]phenyl}methyl)-1H-pyrrolo[3,2-c]pyridine-2-carboxamide | 0.0205 | 0.0054 |
| N-({4-[(4-ethoxy-3-fluorobenzene)sulfonyl]phenyl}methyl)imidazo[1,2-a]pyridine-6-carboxamide | 0.0127 | 0.0018 |
| N-({4-[(4-ethoxy-3-fluorobenzene)sulfonyl]phenyl}methyl)imidazo[1,2-a]pyrimidine-6-carboxamide | 0.0009 | 0.0031 |
| N-({4-[(4-ethoxy-3-fluorobenzene)sulfonyl]phenyl}methyl)thieno[2,3-c]pyridine-2-carboxamide | 0.0089 | 0.0036 |
| N-({4-[(4-ethoxybenzene)sulfonyl]phenyl}methyl)-1H-pyrazolo[3,4-b]pyridine-5-carboxamide | 0.0151 | 0.0084 |
| N-({4-[(4-ethoxybenzene)sulfonyl]phenyl}methyl)furo[2,3-c]pyridine-2-carboxamide | 0.0025 | 0.0071 |
| N-({4-[(4-ethoxybenzene)sulfonyl]phenyl}methyl)imidazo[1,2-a]pyridine-6-carboxamide | 0.0045 | 0.0029 |
| N-({4-[(4-ethoxybenzene)sulfonyl]phenyl}methyl)imidazo[1,2-a]pyrimidine-6-carboxamide | 0.0020 | 0.0061 |

TABLE 3-continued

| IUPAC Name | Biochem IC50 uM | A2780 IC50 uM |
|---|---|---|
| N-({4-[(4-ethoxybenzene)sulfonyl]phenyl}methyl)thieno[2,3-c]pyridine-2-carboxamide | 0.0021 | 0.0040 |
| N-({4-[(4-ethylbenzene)sulfonyl]phenyl}methyl)furo[2,3-c]pyridine-2-carboxamide | 0.0050 | 0.007 |
| N-({4-[(4-ethylbenzene)sulfonyl]phenyl}methyl)imidazo[1,2-a]pyridine-6-carboxamide | 0.0165 | 0.00736 |
| N-({4-[(4-ethylbenzene)sulfonyl]phenyl}methyl)imidazo[1,2-a]pyrimidine-6-carboxamide | 0.0012 | 0.0062 |
| N-({4-[(4-fluoro-2,5-dimethylbenzene)sulfonyl]phenyl}methyl)-1H-pyrazolo[3,4-b]pyridine-5-carboxamide | 0.0373 | 0.0459 |
| N-({4-[(4-fluoro-2,5-dimethylbenzene)sulfonyl]phenyl}methyl)-1H-pyrrolo[3,2-c]pyridine-2-carboxamide | 0.0514 | 0.0128 |
| N-({4-[(4-fluoro-2,5-dimethylbenzene)sulfonyl]phenyl}methyl)furo[2,3-c]pyridine-2-carboxamide | 0.0176 | 0.0242 |
| N-({4-[(4-fluoro-2,5-dimethylbenzene)sulfonyl]phenyl}methyl)imidazo[1,2-a]pyridine-6-carboxamide | 0.0440 | 0.011 |
| N-({4-[(4-fluoro-2,5-dimethylbenzene)sulfonyl]phenyl}methyl)imidazo[1,2-a]pyrimidine-6-carboxamide | 0.0058 | 0.0294 |
| N-({4-[(4-fluoro-2,5-dimethylbenzene)sulfonyl]phenyl}methyl)thieno[2,3-c]pyridine-2-carboxamide | 0.0042 | 0.0136 |
| N-({4-[(4-fluoro-2-methoxybenzene)sulfonyl]phenyl}methyl)-1H-pyrazolo[3,4-b]pyridine-5-carboxamide | 0.159 | 0.0742 |
| N-({4-[(4-fluoro-2-methoxybenzene)sulfonyl]phenyl}methyl)furo[2,3-c]pyridine-2-carboxamide | 0.0127 | 0.0160 |
| N-({4-[(4-fluoro-2-methoxybenzene)sulfonyl]phenyl}methyl)imidazo[1,2-a]pyridine-6-carboxamide | 0.0193 | 0.00705 |
| N-({4-[(4-fluoro-2-methoxybenzene)sulfonyl]phenyl}methyl)imidazo[1,2-a]pyrimidine-6-carboxamide | 0.0191 | 0.0736 |
| N-({4-[(4-fluoro-2-methylbenzene)sulfonyl]phenyl}methyl)-1H-pyrazolo[3,4-b]pyridine-5-carboxamide | 0.0788 | 0.0983 |
| N-({4-[(4-fluoro-2-methylbenzene)sulfonyl]phenyl}methyl)furo[2,3-c]pyridine-2-carboxamide | 0.0187 | 0.0651 |
| N-({4-[(4-fluoro-2-methylbenzene)sulfonyl]phenyl}methyl)imidazo[1,2-a]pyrimidine-6-carboxamide | 0.0130 | 0.1-1 |
| N-({4-[(4-fluoro-3-methoxybenzene)sulfonyl]phenyl}methyl)-1H-pyrazolo[3,4-b]pyridine-5-carboxamide | 0.0239 | 0.0115 |
| N-({4-[(4-fluoro-3-methoxybenzene)sulfonyl]phenyl}methyl)-1H-pyrrolo[3,2-c]pyridine-2-carboxamide | 0.0278 | 0.0054 |
| N-({4-[(4-fluoro-3-methoxybenzene)sulfonyl]phenyl}methyl)furo[2,3-c]pyridine-2-carboxamide | 0.0078 | 0.0070 |
| N-({4-[(4-fluoro-3-methoxybenzene)sulfonyl]phenyl}methyl)imidazo[1,2-a]pyridine-6-carboxamide | 0.0197 | 0.0067 |
| N-({4-[(4-fluoro-3-methoxybenzene)sulfonyl]phenyl}methyl)imidazo[1,2-a]pyrimidine-6-carboxamide | 0.0049 | 0.0108 |
| N-({4-[(4-fluoro-3-methoxybenzene)sulfonyl]phenyl}methyl)thieno[2,3-c]pyridine-2-carboxamide | 0.0090 | 0.0031 |
| N-({4-[(4-fluoro-3-methylbenzene)sulfonyl]phenyl}methyl)-1H-pyrazolo[3,4-b]pyridine-5-carboxamide | 0.0050 | 0.0083 |
| N-({4-[(4-fluoro-3-methylbenzene)sulfonyl]phenyl}methyl)furo[2,3-c]pyridine-2-carboxamide | 0.0132 | 0.006 |
| N-({4-[(4-fluoro-3-methylbenzene)sulfonyl]phenyl}methyl)imidazo[1,2-a]pyridine-6-carboxamide | 0.0235 | 0.00714 |
| N-({4-[(4-fluoro-3-methylbenzene)sulfonyl]phenyl}methyl)imidazo[1,2-a]pyrimidine-6-carboxamide | 0.0022 | 0.0096 |
| N-({4-[(4-methanesulfonylbenzene)sulfonyl]phenyl}methyl)-1H-pyrazolo[3,4-b]pyridine-5-carboxamide | 0.0293 | 0.0238 |
| N-({4-[(4-methanesulfonylbenzene)sulfonyl]phenyl}methyl)imidazo[1,2-a]pyridine-6-carboxamide | 0.105 | 0.0247 |

TABLE 3-continued

| IUPAC Name | Biochem IC50 uM | A2780 IC50 uM |
|---|---|---|
| N-({4-[(4-methoxy-2,5-dimethylbenzene)sulfonyl]phenyl}methyl)-1H-pyrazolo[3,4-b]pyridine-5-carboxamide | 0.0368 | 0.0236 |
| N-({4-[(4-methoxy-2,5-dimethylbenzene)sulfonyl]phenyl}methyl)furo[2,3-c]pyridine-2-carboxamide | 0.0123 | 0.0128 |
| N-({4-[(4-methoxy-2,5-dimethylbenzene)sulfonyl]phenyl}methyl)imidazo[1,2-a]pyridine-6-carboxamide | 0.0281 | 0.006 |
| N-({4-[(4-methoxy-2,5-dimethylbenzene)sulfonyl]phenyl}methyl)imidazo[1,2-a]pyrimidine-6-carboxamide | 0.0052 | 0.0130 |
| N-({4-[(4-methoxy-2-methylbenzene)sulfonyl]phenyl}methyl)-1H-pyrazolo[3,4-b]pyridine-5-carboxamide | 0.029 | 0.0555 |
| N-({4-[(4-methoxy-2-methylbenzene)sulfonyl]phenyl}methyl)furo[2,3-c]pyridine-2-carboxamide | 0.0216 | 0.0351 |
| N-({4-[(4-methoxy-2-methylbenzene)sulfonyl]phenyl}methyl)imidazo[1,2-a]pyrimidine-6-carboxamide | 0.0024 | 0.0679 |
| N-({4-[(4-methoxy-3,5-dimethylbenzene)sulfonyl]phenyl}methyl)-1H-pyrazolo[3,4-b]pyridine-5-carboxamide | 0.005 | 0.00185 |
| N-({4-[(4-methoxy-3,5-dimethylbenzene)sulfonyl]phenyl}methyl)-1H-pyrrolo[3,2-c]pyridine-2-carboxamide | 0.0516 | 0.0017 |
| N-({4-[(4-methoxy-3,5-dimethylbenzene)sulfonyl]phenyl}methyl)furo[2,3-c]pyridine-2-carboxamide | 0.0056 | 0.0018 |
| N-({4-[(4-methoxy-3,5-dimethylbenzene)sulfonyl]phenyl}methyl)imidazo[1,2-a]pyridine-6-carboxamide | 0.0146 | 0.0014 |
| N-({4-[(4-methoxy-3,5-dimethylbenzene)sulfonyl]phenyl}methyl)imidazo[1,2-a]pyrimidine-6-carboxamide | 0.0027 | 0.0013 |
| N-({4-[(4-methoxy-3,5-dimethylbenzene)sulfonyl]phenyl}methyl)thieno[2,3-c]pyridine-2-carboxamide | 0.0098 | 0.0009 |
| N-({4-[(4-methoxy-3-methylbenzene)sulfonyl]phenyl}methyl)imidazo[1,2-a]pyridine-6-carboxamide | 0.0141 | 0.00532 |
| N-({4-[(4-methoxy-3-methylbenzene)sulfonyl]phenyl}methyl)imidazo[1,2-a]pyrimidine-6-carboxamide | 0.0022 | 0.0055 |
| N-({4-[(4-methoxybenzene)sulfonyl]phenyl}methyl)-1H-pyrazolo[3,4-b]pyridine-5-carboxamide | 0.0209 | 0.0143 |
| N-({4-[(4-methoxybenzene)sulfonyl]phenyl}methyl)furo[2,3-c]pyridine-2-carboxamide | 0.0055 | 0.006 |
| N-({4-[(4-methoxybenzene)sulfonyl]phenyl}methyl)imidazo[1,2-a]pyridine-6-carboxamide | 0.00974 | 0.00866 |
| N-({4-[(4-methoxybenzene)sulfonyl]phenyl}methyl)imidazo[1,2-a]pyrimidine-6-carboxamide | 0.0027 | 0.0207 |
| N-({4-[(4-methylbenzene)sulfonyl]phenyl}methyl)furo[2,3-c]pyridine-2-carboxamide | 0.1208 | 0.006 |
| N-({4-[(4-methylbenzene)sulfonyl]phenyl}methyl)imidazo[1,2-a]pyridine-6-carboxamide | 0.0176 | 0.012 |
| N-({4-[(4-methylbenzene)sulfonyl]phenyl}methyl)imidazo[1,2-a]pyrimidine-6-carboxamide | 0.0043 | 0.0194 |
| N-({4-[(4-phenylbenzene)sulfonyl]phenyl}methyl)-1,3-benzothiazole-6-carboxamide | 0.0207 | 0.1-1 |
| N-({4-[(4-phenylbenzene)sulfonyl]phenyl}methyl)-1H-pyrazolo[3,4-b]pyridine-5-carboxamide | 0.0320 | 0.0117 |
| N-({4-[(4-phenylbenzene)sulfonyl]phenyl}methyl)-1H-pyrrolo[3,2-c]pyridine-2-carboxamide | 0.0310 | 0.0133 |
| N-({4-[(4-phenylbenzene)sulfonyl]phenyl}methyl)furo[2,3-c]pyridine-2-carboxamide | 0.0037 | 0.0069 |
| N-({4-[(4-phenylbenzene)sulfonyl]phenyl}methyl)imidazo[1,2-a]pyrimidine-6-carboxamide | 0.0032 | 0.0076 |
| N-({4-[(4-phenylbenzene)sulfonyl]phenyl}methyl)thieno[2,3-c]pyridine-2-carboxamide | 0.0030 | 0.0106 |
| N-({4-[(4-phenylbutane)sulfonyl]phenyl}methyl)-1H-pyrrolo[3,2-c]pyridine-2-carboxamide | 0.216 | 0.0715 |
| N-({4-[(4-propoxybenzene)sulfonyl]phenyl}methyl)-1H-pyrrolo[3,2-c]pyridine-2-carboxamide | 0.0053 | 0.0067 |
| N-({4-[(4-propoxybenzene)sulfonyl]phenyl}methyl)furo[2,3-c]pyridine-2-carboxamide | 0.0495 | 0.012 |

TABLE 3-continued

| IUPAC Name | Biochem IC50 uM | A2780 IC50 uM |
|---|---|---|
| N-({4-[(4-propoxybenzene)sulfonyl]phenyl}methyl)imidazo[1,2-a]pyridine-6-carboxamide | 0.0061 | 0.0019 |
| N-({4-[(4-propoxybenzene)sulfonyl]phenyl}methyl)imidazo[1,2-a]pyrimidine-6-carboxamide | 0.0022 | 0.0061 |
| N-({4-[(4-propoxybenzene)sulfonyl]phenyl}methyl)thieno[2,3-c]pyridine-2-carboxamide | 0.0043 | 0.0081 |
| N-({4-[(5-acetyl-2-methoxybenzene)sulfonyl]phenyl}methyl)-1H-pyrazolo[3,4-b]pyridine-5-carboxamide | 0.0277 | 0.0275 |
| N-({4-[(5-acetyl-2-methoxybenzene)sulfonyl]phenyl}methyl)furo[2,3-c]pyridine-2-carboxamide | 0.0072 | 0.0038 |
| N-({4-[(5-acetyl-2-methoxybenzene)sulfonyl]phenyl}methyl)imidazo[1,2-a]pyridine-6-carboxamide | 0.0379 | 0.0127 |
| N-({4-[(5-acetyl-2-methoxybenzene)sulfonyl]phenyl}methyl)imidazo[1,2-a]pyrimidine-6-carboxamide | 0.0172 | 0.0548 |
| N-({4-[(5-chloro-2-ethoxybenzene)sulfonyl]phenyl}methyl)imidazo[1,2-a]pyridine-6-carboxamide | 0.0022 | 0.0005 |
| N-({4-[(5-chloro-2-ethoxybenzene)sulfonyl]phenyl}methyl)imidazo[1,2-a]pyrimidine-6-carboxamide | 0.0019 | 0.0033 |
| N-({4-[(5-chloro-2-ethoxybenzene)sulfonyl]phenyl}methyl)thieno[2,3-c]pyridine-2-carboxamide | 0.0027 | 0.0005 |
| N-({4-[(5-chloro-2-hydroxybenzene)sulfonyl]phenyl}methyl)imidazo[1,2-a]pyridine-6-carboxamide | 0.014 | 0.1682 |
| N-({4-[(5-chloro-2-methoxybenzene)sulfonyl]phenyl}methyl)-1H-pyrazolo[3,4-b]pyridine-5-carboxamide | 0.0492 | 0.0081 |
| N-({4-[(5-chloro-2-methoxybenzene)sulfonyl]phenyl}methyl)imidazo[1,2-a]pyridine-6-carboxamide | 0.0191 | 0.0032 |
| N-({4-[(5-chloro-2-methoxybenzene)sulfonyl]phenyl}methyl)imidazo[1,2-a]pyrimidine-6-carboxamide | 0.0055 | 0.0061 |
| N-({4-[(5-chloro-2-methylbenzene)sulfonyl]phenyl}methyl)-1H-pyrazolo[3,4-b]pyridine-5-carboxamide | 0.0227 | 0.0139 |
| N-({4-[(5-chloro-2-methylbenzene)sulfonyl]phenyl}methyl)furo[2,3-c]pyridine-2-carboxamide | 0.0058 | 0.0078 |
| N-({4-[(5-chloro-2-methylbenzene)sulfonyl]phenyl}methyl)imidazo[1,2-a]pyridine-6-carboxamide | 0.0019 | 0.0037 |
| N-({4-[(5-chloro-2-methylbenzene)sulfonyl]phenyl}methyl)imidazo[1,2-a]pyrimidine-6-carboxamide | 0.0031 | 0.0043 |
| N-({4-[(5-chloro-2-methylbenzene)sulfonyl]phenyl}methyl)thieno[2,3-c]pyridine-2-carboxamide | 0.0048 | 0.0066 |
| N-({4-[(5-chloro-2-propoxybenzene)sulfonyl]phenyl}methyl)-1H-pyrazolo[3,4-b]pyridine-5-carboxamide | 0.0492 | 0.0251 |
| N-({4-[(5-chloro-2-propoxybenzene)sulfonyl]phenyl}methyl)-1H-pyrrolo[3,2-c]pyridine-2-carboxamide | 0.0075 | 0.0012 |
| N-({4-[(5-chloro-2-propoxybenzene)sulfonyl]phenyl}methyl)furo[2,3-c]pyridine-2-carboxamide | 0.0080 | 0.0093 |
| N-({4-[(5-chloro-2-propoxybenzene)sulfonyl]phenyl}methyl)imidazo[1,2-a]pyridine-6-carboxamide | 0.0080 | 0.0032 |
| N-({4-[(5-chloro-2-propoxybenzene)sulfonyl]phenyl}methyl)thieno[2,3-c]pyridine-2-carboxamide | 0.0057 | 0.0012 |
| N-({4-[(5-cyano-2-methoxybenzene)sulfonyl]phenyl}methyl)imidazo[1,2-a]pyridine-6-carboxamide | 0.0146 | 0.0119 |
| N-({4-[(5-fluoro-2-methoxybenzene)sulfonyl]phenyl}methyl)-1H-pyrazolo[3,4-b]pyridine-5-carboxamide | 0.0390 | 0.0151 |
| N-({4-[(5-fluoro-2-methoxybenzene)sulfonyl]phenyl}methyl)furo[2,3-c]pyridine-2-carboxamide | 0.0022 | 0.0124 |
| N-({4-[(5-fluoro-2-methoxybenzene)sulfonyl]phenyl}methyl)imidazo[1,2-a]pyridine-6-carboxamide | 0.022 | 0.00665 |

TABLE 3-continued

| IUPAC Name | Biochem IC50 uM | A2780 IC50 uM |
|---|---|---|
| N-({4-[(5-fluoro-2-methoxybenzene)sulfonyl]phenyl}methyl)imidazo[1,2-a]pyrimidine-6-carboxamide | 0.0073 | 0.0261 |
| N-({4-[(5-fluoro-2-methoxybenzene)sulfonyl]phenyl}methyl)thieno[2,3-c]pyridine-2-carboxamide | 0.0020 | 0.0008 |
| N-({4-[(5-fluoro-2-methylbenzene)sulfonyl]phenyl}methyl)-1H-pyrazolo[3,4-b]pyridine-5-carboxamide | 0.0204 | 0.0597 |
| N-({4-[(5-fluoro-2-methylbenzene)sulfonyl]phenyl}methyl)furo[2,3-c]pyridine-2-carboxamide | 0.0143 | 0.0249 |
| N-({4-[(5-fluoro-2-methylbenzene)sulfonyl]phenyl}methyl)imidazo[1,2-a]pyridine-6-carboxamide | 0.0126 | 0.0229 |
| N-({4-[(5-fluoro-2-methylbenzene)sulfonyl]phenyl}methyl)imidazo[1,2-a]pyrimidine-6-carboxamide | 0.0027 | 0.0351 |
| N-({4-[(5-tert-butyl-2-methoxybenzene)sulfonyl]phenyl}methyl)-1H-pyrazolo[3,4-b]pyridine-5-carboxamide | 0.0456 | 0.0216 |
| N-({4-[(5-tert-butyl-2-methoxybenzene)sulfonyl]phenyl}methyl)furo[2,3-c]pyridine-2-carboxamide | 0.0218 | 0.0101 |
| N-({4-[(5-tert-butyl-2-methoxybenzene)sulfonyl]phenyl}methyl)imidazo[1,2-a]pyridine-6-carboxamide | 0.029 | 0.00677 |
| N-({4-[(5-tert-butyl-2-methoxybenzene)sulfonyl]phenyl}methyl)imidazo[1,2-a]pyrimidine-6-carboxamide | 0.0098 | 0.0077 |
| N-({4-[(6-chloro-2-fluoro-3-methylbenzene)sulfonyl]phenyl}methyl)-1H-pyrazolo[3,4-b]pyridine-5-carboxamide | 0.112 | 0.1-1 |
| N-({4-[(6-chloro-2-fluoro-3-methylbenzene)sulfonyl]phenyl}methyl)-1H-pyrrolo[3,2-c]pyridine-2-carboxamide | 0.0065 | 0.0071 |
| N-({4-[(6-chloro-2-fluoro-3-methylbenzene)sulfonyl]phenyl}methyl)furo[2,3-c]pyridine-2-carboxamide | 0.0219 | 0.0293 |
| N-({4-[(6-chloro-2-fluoro-3-methylbenzene)sulfonyl]phenyl}methyl)thieno[2,3-c]pyridine-2-carboxamide | 0.0077 | 0.0068 |
| N-({4-[1-(3-chlorophenyl)-1H-pyrazole-4-sulfonyl]phenyl}methyl)-1H-pyrazolo[3,4-b]pyridine-5-carboxamide | 0.0282 | 0.0556 |
| N-({4-[1-(3-chlorophenyl)-1H-pyrazole-4-sulfonyl]phenyl}methyl)-1H-pyrrolo[3,2-c]pyridine-2-carboxamide | 0.0169 | 0.0131 |
| N-({4-[1-(3-chlorophenyl)-1H-pyrazole-4-sulfonyl]phenyl}methyl)furo[2,3-c]pyridine-2-carboxamide | 0.0116 | 0.0140 |
| N-({4-[1-(3-chlorophenyl)-1H-pyrazole-4-sulfonyl]phenyl}methyl)imidazo[1,2-a]pyridine-6-carboxamide | 0.0140 | 0.0064 |
| N-({4-[1-(3-chlorophenyl)-1H-pyrazole-4-sulfonyl]phenyl}methyl)imidazo[1,2-a]pyrimidine-6-carboxamide | 0.0022 | 0.0115 |
| N-({4-[1-(3-chlorophenyl)-1H-pyrazole-4-sulfonyl]phenyl}methyl)thieno[2,3-c]pyridine-2-carboxamide | 0.0041 | 0.0139 |
| N-({4-[1-(4-fluorophenyl)-1H-pyrazole-4-sulfonyl]phenyl}methyl)-1H-pyrrolo[3,2-c]pyridine-2-carboxamide | 0.0184 | 0.0066 |
| N-({4-[1-(4-fluorophenyl)-1H-pyrazole-4-sulfonyl]phenyl}methyl)furo[2,3-c]pyridine-2-carboxamide | 0.0069 | 0.0074 |
| N-({4-[1-(4-fluorophenyl)-1H-pyrazole-4-sulfonyl]phenyl}methyl)thieno[2,3-c]pyridine-2-carboxamide | 0.0045 | 0.0062 |
| N-({4-[1-(propan-2-yl)-1H-pyrazole-4-sulfonyl]phenyl}methyl)imidazo[1,2-a]pyridine-6-carboxamide | 0.008 | 0.0027 |
| N-({4-[1-methyl-3-(trifluoromethyl)-1H-pyrazole-4-sulfonyl]phenyl}methyl)imidazo[1,2-a]pyridine-6-carboxamide | 0.0299 | 0.0278 |
| N-({4-[1-methyl-5-(trifluoromethyl)-1H-pyrazole-4-sulfonyl]phenyl}methyl)-1H-pyrazolo[3,4-b]pyridine-5-carboxamide | 0.0534 | 0.0434 |
| N-({4-[1-methyl-5-(trifluoromethyl)-1H-pyrazole-4-sulfonyl]phenyl}methyl)imidazo[1,2-a]pyrimidine-6-carboxamide | 0.0040 | 0.0679 |
| N-({4-[2-(3-fluorophenyl)-1,3-thiazole-4-sulfonyl]phenyl}methyl)-1H-pyrazolo[3,4-b]pyridine-5-carboxamide | 0.0271 | 0.0609 |
| N-({4-[2-(3-fluorophenyl)-1,3-thiazole-4-sulfonyl]phenyl}methyl)-1H-pyrrolo[3,2-c]pyridine-2-carboxamide | 0.0192 | 0.0232 |
| N-({4-[2-(3-fluorophenyl)-1,3-thiazole-4-sulfonyl]phenyl}methyl)furo[2,3-c]pyridine-2-carboxamide | 0.0119 | 0.0504 |
| N-({4-[2-(3-fluorophenyl)-1,3-thiazole-4-sulfonyl]phenyl}methyl)imidazo[1,2-a]pyridine-6-carboxamide | 0.0229 | 0.0128 |

TABLE 3-continued

| IUPAC Name | Biochem IC50 uM | A2780 IC50 uM |
|---|---|---|
| N-({4-[2-(3-fluorophenyl)-1,3-thiazole-4-sulfonyl]phenyl}methyl)imidazo[1,2-a]pyrimidine-6-carboxamide | 0.0010 | 0.0069 |
| N-({4-[2-(3-fluorophenyl)-1,3-thiazole-4-sulfonyl]phenyl}methyl)thieno[2,3-c]pyridine-2-carboxamide | 0.0066 | 0.0244 |
| N-({4-[2-(benzenesulfonyl)ethyl]phenyl}methyl)-1H-pyrrolo[3,2-c]pyridine-2-carboxamide | 0.023 | 0.166 |
| N-({4-[2-(dimethylamino)pyrimidine-5-sulfonyl]phenyl}methyl)-1H-pyrazolo[3,4-b]pyridine-5-carboxamide | 0.0079 | 0.0059 |
| N-({4-[2-(dimethylamino)pyrimidine-5-sulfonyl]phenyl}methyl)-1H-pyrrolo[3,2-c]pyridine-2-carboxamide | 0.0190 | 0.0035 |
| N-({4-[2-(dimethylamino)pyrimidine-5-sulfonyl]phenyl}methyl)furo[2,3-c]pyridine-2-carboxamide | 0.0258 | 0.012 |
| N-({4-[2-(dimethylamino)pyrimidine-5-sulfonyl]phenyl}methyl)imidazo[1,2-a]pyridine-6-carboxamide | 0.0229 | 0.0036 |
| N-({4-[2-(dimethylamino)pyrimidine-5-sulfonyl]phenyl}methyl)thieno[2,3-c]pyridine-2-carboxamide | 0.0080 | 0.0017 |
| N-({4-[2-(morpholin-4-yl)pyridine-3-sulfonyl]phenyl}methyl)furo[2,3-c]pyridine-2-carboxamide | 0.0325 | 0.0605 |
| N-({4-[2-(morpholin-4-yl)pyridine-3-sulfonyl]phenyl}methyl)imidazo[1,2-a]pyrimidine-6-carboxamide | 0.0312 | 0.1-1 |
| N-({4-[2-(pyrrolidin-1-yl)-1,3-thiazole-5-sulfonyl]phenyl}methyl)-1H-pyrazolo[3,4-b]pyridine-5-carboxamide | 0.0028 | 0.0009 |
| N-({4-[2-(pyrrolidin-1-yl)-1,3-thiazole-5-sulfonyl]phenyl}methyl)-1H-pyrrolo[3,2-c]pyridine-2-carboxamide | 0.0060 | 0.0005 |
| N-({4-[2-(pyrrolidin-1-yl)-1,3-thiazole-5-sulfonyl]phenyl}methyl)imidazo[1,2-a]pyridine-6-carboxamide | 0.0024 | 0.0004 |
| N-({4-[2-(pyrrolidin-1-yl)-1,3-thiazole-5-sulfonyl]phenyl}methyl)imidazo[1,2-a]pyrimidine-6-carboxamide | 0.0029 | 0.0009 |
| N-({4-[2-(pyrrolidin-1-yl)-1,3-thiazole-5-sulfonyl]phenyl}methyl)thieno[2,3-c]pyridine-2-carboxamide | 0.0015 | 0.0007 |
| N-({4-[2-(trifluoromethyl)imidazo[1,2-a]pyridine-6-sulfonyl]phenyl}methyl)-1H-pyrazolo[3,4-b]pyridine-5-carboxamide | 0.0497 | 0.0330 |
| N-({4-[2-(trifluoromethyl)imidazo[1,2-a]pyridine-6-sulfonyl]phenyl}methyl)furo[2,3-c]pyridine-2-carboxamide | 0.0212 | 0.0119 |
| N-({4-[2-(trifluoromethyl)imidazo[1,2-a]pyridine-6-sulfonyl]phenyl}methyl)imidazo[1,2-a]pyridine-6-carboxamide | 0.0362 | 0.0070 |
| N-({4-[2-(trifluoromethyl)imidazo[1,2-a]pyridine-6-sulfonyl]phenyl}methyl)thieno[2,3-c]pyridine-2-carboxamide | 0.0031 | 0.0039 |
| N-({4-[2-(trifluoromethyl)pyridine-3-sulfonyl]phenyl}methyl)furo[2,3-c]pyridine-2-carboxamide | 0.0304 | 0.0279 |
| N-({4-[3-chloro-2-(morpholin-4-yl)pyridine-4-sulfonyl]phenyl}methyl)thieno[2,3-c]pyridine-2-carboxamide | 0.0085 | 0.0018 |
| N-({4-[4-(trifluoromethyl)pyridine-2-sulfonyl]phenyl}methyl)-1H-pyrazolo[3,4-b]pyridine-5-carboxamide | 0.0283 | 0.0118 |
| N-({4-[4-(trifluoromethyl)pyridine-2-sulfonyl]phenyl}methyl)furo[2,3-c]pyridine-2-carboxamide | 0.0139 | 0.0061 |
| N-({4-[4-(trifluoromethyl)pyridine-2-sulfonyl]phenyl}methyl)imidazo[1,2-a]pyridine-6-carboxamide | 0.0197 | 0.0032 |
| N-({4-[4-(trifluoromethyl)pyridine-2-sulfonyl]phenyl}methyl)imidazo[1,2-a]pyrimidine-6-carboxamide | 0.0087 | 0.0130 |
| N-({4-[4-(trifluoromethyl)pyridine-2-sulfonyl]phenyl}methyl)thieno[2,3-c]pyridine-2-carboxamide | 0.0036 | 0.0030 |
| N-({4-[5-(dimethylamino)pyrazine-2-sulfonyl]phenyl}methyl)imidazo[1,2-a]pyridine-6-carboxamide | 0.016 | 0.0036 |
| N-({4-[5-(pyrrolidin-1-yl)pyridine-3-sulfonyl]phenyl}methyl)-1,3-benzothiazole-6-carboxamide | 0.0092 | 0.1-1 |
| N-({4-[5-(pyrrolidin-1-yl)pyridine-3-sulfonyl]phenyl}methyl)-1H-pyrazolo[3,4-b]pyridine-5-carboxamide | 0.0179 | 0.0040 |
| N-({4-[5-(pyrrolidin-1-yl)pyridine-3-sulfonyl]phenyl}methyl)-1H-pyrrolo[3,2-c]pyridine-2-carboxamide | 0.0139 | 0.0020 |
| N-({4-[5-(pyrrolidin-1-yl)pyridine-3-sulfonyl]phenyl}methyl)furo[2,3-c]pyridine-2-carboxamide | 0.0228 | 0.0049 |
| N-({4-[5-(pyrrolidin-1-yl)pyridine-3-sulfonyl]phenyl}methyl)imidazo[1,2-a]pyridine-6-carboxamide | 0.004 | 0.0005 |
| N-({4-[5-(trifluoromethyl)pyridine-2-sulfonyl]phenyl}methyl)-1H-pyrazolo[3,4-b]pyridine-5-carboxamide | 0.1-1 | 0.1-1 |
| N-({4-[5-(trifluoromethyl)pyridine-2-sulfonyl]phenyl}methyl)furo[2,3-c]pyridine-2-carboxamide | 0.0370 | 0.1-1 |
| N-({4-[5-(trifluoromethyl)pyridine-2-sulfonyl]phenyl}methyl)imidazo[1,2-a]pyridine-6-carboxamide | 0.0463 | 0.0326 |
| N-({4-[5-(trifluoromethyl)pyridine-2-sulfonyl]phenyl}methyl)imidazo[1,2-a]pyrimidine-6-carboxamide | 0.0059 | 0.0708 |
| N-({4-[5-(trifluoromethyl)pyridine-2-sulfonyl]phenyl}methyl)thieno[2,3-c]pyridine-2-carboxamide | 0.0235 | 0.1-1 |

TABLE 3-continued

| IUPAC Name | Biochem IC50 uM | A2780 IC50 uM |
|---|---|---|
| N-({4-[5-(trifluoromethyl)pyridine-3-sulfonyl]phenyl}methyl)-1H-pyrazolo[3,4-b]pyridine-5-carboxamide | 0.011 | 0.004 |
| N-({4-[5-(trifluoromethyl)pyridine-3-sulfonyl]phenyl}methyl)imidazo[1,2-a]pyridine-6-carboxamide | 0.009 | 0.0013 |
| N-({4-[6-(1H-pyrazol-1-yl)pyridine-3-sulfonyl]phenyl}methyl)imidazo[1,2-a]pyridine-6-carboxamide | 0.004 | 0.0019 |
| N-({4-[6-(3,4-difluorophenyl)pyridine-2-sulfonyl]phenyl}methyl)-1H-pyrazolo[3,4-b]pyridine-5-carboxamide | 0.0178 | 0.0410 |
| N-({4-[6-(3,4-difluorophenyl)pyridine-2-sulfonyl]phenyl}methyl)-1H-pyrrolo[3,2-c]pyridine-2-carboxamide | 0.0160 | 0.0127 |
| N-({4-[6-(3,4-difluorophenyl)pyridine-2-sulfonyl]phenyl}methyl)furo[2,3-c]pyridine-2-carboxamide | 0.0050 | 0.0427 |
| N-({4-[6-(3,4-difluorophenyl)pyridine-2-sulfonyl]phenyl}methyl)imidazo[1,2-a]pyridine-6-carboxamide | 0.0043 | 0.0057 |
| N-({4-[6-(3,4-difluorophenyl)pyridine-2-sulfonyl]phenyl}methyl)thieno[2,3-c]pyridine-2-carboxamide | 0.0022 | 0.0132 |
| N-({4-[6-(4-methylpiperazin-1-yl)pyridine-3-sulfonyl]phenyl}methyl)-1H-pyrrolo[3,2-c]pyridine-2-carboxamide | 0.006 | 0.0006 |
| N-({4-[6-(dimethylamino)pyridine-3-sulfonyl]phenyl}methyl)-1H-pyrazolo[3,4-b]pyridine-5-carboxamide | 0.0305 | 0.0033 |
| N-({4-[6-(dimethylamino)pyridine-3-sulfonyl]phenyl}methyl)-1H-pyrrolo[3,2-c]pyridine-2-carboxamide | 0.0209 | 0.0034 |
| N-({4-[6-(dimethylamino)pyridine-3-sulfonyl]phenyl}methyl)furo[2,3-c]pyridine-2-carboxamide | 0.003 | 0.0018 |
| N-({4-[6-(dimethylamino)pyridine-3-sulfonyl]phenyl}methyl)imidazo[1,2-a]pyridine-6-carboxamide | 0.0449 | 0.0027 |
| N-({4-[6-(dimethylamino)pyridine-3-sulfonyl]phenyl}methyl)imidazo[1,2-a]pyrimidine-6-carboxamide | 0.0027 | 0.0059 |
| N-({4-[6-(dimethylamino)pyridine-3-sulfonyl]phenyl}methyl)thieno[2,3-c]pyridine-2-carboxamide | 0.001 | 0.0006 |
| N-({4-[6-(morpholin-4-yl)pyridine-3-sulfonyl]phenyl}methyl)-1H-pyrazolo[3,4-b]pyridine-5-carboxamide | 0.0057 | 0.0032 |
| N-({4-[6-(morpholin-4-yl)pyridine-3-sulfonyl]phenyl}methyl)-1H-pyrrolo[3,2-c]pyridine-2-carboxamide | 0.0096 | 0.0015 |
| N-({4-[6-(morpholin-4-yl)pyridine-3-sulfonyl]phenyl}methyl)furo[2,3-c]pyridine-2-carboxamide | 0.002 | 0.0009 |
| N-({4-[6-(morpholin-4-yl)pyridine-3-sulfonyl]phenyl}methyl)imidazo[1,2-a]pyridine-6-carboxamide | 0.0090 | 0.0015 |
| N-({4-[6-(morpholin-4-yl)pyridine-3-sulfonyl]phenyl}methyl)imidazo[1,2-a]pyrimidine-6-carboxamide | 0.0011 | 0.0033 |
| N-({4-[6-(morpholin-4-yl)pyridine-3-sulfonyl]phenyl}methyl)thieno[2,3-c]pyridine-2-carboxamide | 0.0041 | 0.0007 |
| N-({4-[6-(trifluoromethyl)pyridine-2-sulfonyl]phenyl}methyl)-1H-pyrazolo[3,4-b]pyridine-5-carboxamide | 0.0242 | 0.0111 |
| N-({4-[6-(trifluoromethyl)pyridine-2-sulfonyl]phenyl}methyl)furo[2,3-c]pyridine-2-carboxamide | 0.0050 | 0.0031 |
| N-({4-[6-(trifluoromethyl)pyridine-2-sulfonyl]phenyl}methyl)imidazo[1,2-a]pyridine-6-carboxamide | 0.0087 | 0.0015 |
| N-({4-[6-(trifluoromethyl)pyridine-2-sulfonyl]phenyl}methyl)imidazo[1,2-a]pyrimidine-6-carboxamide | 0.0114 | 0.0204 |
| N-({4-[6-(trifluoromethyl)pyridine-2-sulfonyl]phenyl}methyl)thieno[2,3-c]pyridine-2-carboxamide | 0.0021 | 0.0022 |
| N-({4-[6-(trifluoromethyl)pyridine-3-sulfonyl]phenyl}methyl)thieno[2,3-c]pyridine-2-carboxamide | 0.0076 | 0.0067 |
| N-(1,3-benzothiazol-6-ylmethyl)-4-[(3-chlorobenzene)sulfonyl]benzamide | 0.0100 | >10 |
| N-[(4-{[2-(2,2,2-trifluoroethoxy)-4-(trifluoromethyl)benzene]sulfonyl}phenyl)methyl]-1H-pyrrolo[3,2-c]pyridine-2-carboxamide | 0.009 | 0.0010 |
| N-[(4-{[2-(2,2,2-trifluoroethoxy)-4-(trifluoromethyl)benzene]sulfonyl}phenyl)methyl]imidazo[1,2-a]pyridine-6-carboxamide | 0.007 | 0.0012 |
| N-[(4-{[2-(benzyloxy)-5-(trifluoromethyl)benzene]sulfonyl}phenyl)methyl]-1H-pyrazolo[3,4-b]pyridine-5-carboxamide | 0.1-1 | 0.1-1 |
| N-[(4-{[2-(benzyloxy)-5-(trifluoromethyl)benzene]sulfonyl}phenyl)methyl]-1H-pyrrolo[3,2-c]pyridine-2-carboxamide | 0.1303 | 0.0259 |
| N-[(4-{[2-(benzyloxy)-5-(trifluoromethyl)benzene]sulfonyl}phenyl)methyl]imidazo[1,2-a]pyrimidine-6-carboxamide | 0.0332 | 0.1-1 |
| N-[(4-{[2-(dimethylcarbamoyl)benzene]sulfonyl}phenyl)methyl]-1H-pyrrolo[3,2-c]pyridine-2-carboxamide | 0.1-1 | 0.1-1 |

TABLE 3-continued

| IUPAC Name | Biochem IC50 uM | A2780 IC50 uM |
|---|---|---|
| N-[(4-{2-(dimethylcarbamoyl)benzene]sulfonyl}phenyl)methyl]furo[2,3-c]pyridine-2-carboxamide | 0.1-1 | 1-10 |
| N-[(4-{2-(dimethylcarbamoyl)benzene]sulfonyl}phenyl)methyl]imidazo[1,2-a]pyridine-6-carboxamide | >0.1667 | 0.1-1 |
| N-[(4-{2-(dimethylcarbamoyl)benzene]sulfonyl}phenyl)methyl]imidazo[1,2-a]pyrimidine-6-carboxamide | 0.1-1 | 1-10 |
| N-[(4-{2-(dimethylcarbamoyl)benzene]sulfonyl}phenyl)methyl]thieno[2,3-c]pyridine-2-carboxamide | 0.1-1 | 0.1-1 |
| N-[(4-{[2-(ethoxymethyl)benzene]sulfonyl}phenyl)methyl]-1H-pyrazolo[3,4-b]pyridine-5-carboxamide | 0.0520 | 0.0612 |
| N-[(4-{[2-(ethoxymethyl)benzene]sulfonyl}phenyl)methyl]-1H-pyrrolo[3,2-c]pyridine-2-carboxamide | 0.0185 | 0.0067 |
| N-[(4-{2-(ethoxymethyl)benzene]sulfonyl}phenyl)methyl]furo[2,3-c]pyridine-2-carboxamide | 0.0133 | 0.0260 |
| N-[(4-{2-(ethoxymethyl)benzene]sulfonyl}phenyl)methyl]imidazo[1,2-a]pyrimidine-6-carboxamide | 0.0037 | 0.0396 |
| N-[(4-{[2-(methylsulfamoyl)benzene]sulfonyl}phenyl)methyl]-1H-pyrazolo[3,4-b]pyridine-5-carboxamide | >0.167 | >10 |
| N-[(4-{2-(methylsulfamoyl)benzene]sulfonyl}phenyl)methyl]furo[2,3-c]pyridine-2-carboxamide | 0.0513 | 0.0740 |
| N-[(4-{2-(methylsulfamoyl)benzene]sulfonyl}phenyl)methyl]imidazo[1,2-a]pyrimidine-6-carboxamide | 0.0304 | 1-10 |
| N-[(4-{[2-(morpholin-4-ylmethyl)benzene]sulfonyl}phenyl)methyl]-1H-pyrazolo[3,4-b]pyridine-5-carboxamide | 0.0694 | 0.0465 |
| N-[(4-{[2-(morpholin-4-ylmethyl)benzene]sulfonyl}phenyl)methyl]imidazo[1,2-a]pyridine-6-carboxamide | 0.136 | 0.0342 |
| N-[(4-{[2-(morpholin-4-ylmethyl)benzene]sulfonyl}phenyl)methyl]imidazo[1,2-a]pyrimidine-6-carboxamide | 0.0145 | 0.1-1 |
| N-[(4-{[2-(trifluoromethoxy)benzene]sulfonyl}phenyl)methyl]furo[2,3-c]pyridine-2-carboxamide | 0.0086 | 0.0146 |
| N-[(4-{[2-(trifluoromethoxy)benzene]sulfonyl}phenyl)methyl]imidazo[1,2-a]pyrimidine-6-carboxamide | 0.0024 | 0.0115 |
| N-[(4-{[2-(trifluoromethyl)benzene]sulfonyl}phenyl)methyl]furo[2,3-c]pyridine-2-carboxamide | 0.0194 | 0.0593 |
| N-[(4-{[2-(trifluoromethyl)benzene]sulfonyl}phenyl)methyl]imidazo[1,2-a]pyridine-6-carboxamide | 0.0341 | 0.0579 |
| N-[(4-{[2-(trifluoromethyl)benzene]sulfonyl}phenyl)methyl]imidazo[1,2-a]pyrimidine-6-carboxamide | 0.0100 | 0.1-1 |
| N-[(4-{[2,4-bis(trifluoromethyl)benzene]sulfonyl}phenyl)methyl]-1H-pyrazolo[3,4-b]pyridine-5-carboxamide | 0.0816 | 0.0562 |
| N-[(4-{[2,4-bis(trifluoromethyl)benzene]sulfonyl}phenyl)methyl]-1H-pyrrolo[3,2-c]pyridine-2-carboxamide | 0.0401 | 0.0140 |
| N-[(4-{[2,4-bis(trifluoromethyl)benzene]sulfonyl}phenyl)methyl]furo[2,3-c]pyridine-2-carboxamide | 0.0530 | 0.0637 |
| N-[(4-{[2,4-bis(trifluoromethyl)benzene]sulfonyl}phenyl)methyl]imidazo[1,2-a]pyridine-6-carboxamide | 0.2202 | 0.0532 |
| N-[(4-{[2,4-bis(trifluoromethyl)benzene]sulfonyl}phenyl)methyl]imidazo[1,2-a]pyrimidine-6-carboxamide | 0.0188 | 0.0964 |
| N-[(4-{[2,4-bis(trifluoromethyl)benzene]sulfonyl}phenyl)methyl]thieno[2,3-c]pyridine-2-carboxamide | 0.0215 | 0.0043 |
| N-[(4-{[2-chloro-3-(trifluoromethyl)benzene]sulfonyl}phenyl)methyl]-1H-pyrazolo[3,4-b]pyridine-5-carboxamide | 0.0365 | 0.0384 |
| N-[(4-{[2-chloro-3-(trifluoromethyl)benzene]sulfonyl}phenyl)methyl]-1H-pyrrolo[3,2-c]pyridine-2-carboxamide | 0.0364 | 0.0088 |

TABLE 3-continued

| IUPAC Name | Biochem IC50 uM | A2780 IC50 uM |
|---|---|---|
| N-[(4-{[2-chloro-3-(trifluoromethyl)benzene]sulfonyl}phenyl)methyl]furo[2,3-c]pyridine-2-carboxamide | 0.0184 | 0.0279 |
| N-[(4-{[2-chloro-3-(trifluoromethyl)benzene]sulfonyl}phenyl)methyl]imidazo[1,2-a]pyrimidine-6-carboxamide | 0.0024 | 0.0246 |
| N-[(4-{[2-chloro-4-(trifluoromethyl)benzene]sulfonyl}phenyl)methyl]-1H-pyrazolo[3,4-b]pyridine-5-carboxamide | 0.114 | 0.0869 |
| N-[(4-{[2-chloro-4-(trifluoromethyl)benzene]sulfonyl}phenyl)methyl]-1H-pyrrolo[3,2-c]pyridine-2-carboxamide | 0.1269 | 0.0254 |
| N-[(4-{[2-chloro-4-(trifluoromethyl)benzene]sulfonyl}phenyl)methyl]imidazo[1,2-a]pyrimidine-6-carboxamide | 0.0184 | 0.0644 |
| N-[(4-{[2-chloro-5-(hydroxymethyl)benzene]sulfonyl}phenyl)methyl]-1H-pyrrolo[3,2-c]pyridine-2-carboxamide | 0.0083 | 0.0262 |
| N-[(4-{[2-chloro-5-(trifluoromethoxy)benzene]sulfonyl}phenyl)methyl]-1H-pyrrolo[3,2-c]pyridine-2-carboxamide | 0.0531 | 0.0120 |
| N-[(4-{[2-chloro-5-(trifluoromethoxy)benzene]sulfonyl}phenyl)methyl]imidazo[1,2-a]pyrimidine-6-carboxamide | 0.0080 | 0.0125 |
| N-[(4-{[2-chloro-5-(trifluoromethyl)benzene]sulfonyl}phenyl)methyl]furo[2,3-c]pyridine-2-carboxamide | 0.0139 | 0.0141 |
| N-[(4-{[2-chloro-5-(trifluoromethyl)benzene]sulfonyl}phenyl)methyl]imidazo[1,2-a]pyrimidine-6-carboxamide | 0.0070 | 0.0141 |
| N-[(4-{[2-fluoro-3-(propan-2-yloxy)benzene]sulfonyl}phenyl)methyl]imidazo[1,2-a]pyridine-6-carboxamide | 0.0078 | 0.0040 |
| N-[(4-{[2-fluoro-3-(propan-2-yloxy)benzene]sulfonyl}phenyl)methyl]imidazo[1,2-a]pyrimidine-6-carboxamide | 0.0018 | 0.0070 |
| N-[(4-{[2-fluoro-3-(propan-2-yloxy)benzene]sulfonyl}phenyl)methyl]thieno[2,3-c]pyridine-2-carboxamide | 0.0047 | 0.0066 |
| N-[(4-{[2-fluoro-3-(trifluoromethoxy)benzene]sulfonyl}phenyl)methyl]thieno[2,3-c]pyridine-2-carboxamide | 0.0098 | 0.0133 |
| N-[(4-{[2-fluoro-4-(1H-pyrazol-1-yl)benzene]sulfonyl}phenyl)methyl]-1H-pyrazolo[3,4-b]pyridine-5-carboxamide | 0.0389 | 0.0344 |
| N-[(4-{[2-fluoro-4-(1H-pyrazol-1-yl)benzene]sulfonyl}phenyl)methyl]furo[2,3-c]pyridine-2-carboxamide | 0.0184 | 0.008 |
| N-[(4-{[2-fluoro-4-(1H-pyrazol-1-yl)benzene]sulfonyl}phenyl)methyl]imidazo[1,2-a]pyridine-6-carboxamide | 0.00844 | 0.0128 |
| N-[(4-{[2-fluoro-4-(1H-pyrazol-1-yl)benzene]sulfonyl}phenyl)methyl]imidazo[1,2-a]pyrimidine-6-carboxamide | 0.0022 | 0.0190 |
| N-[(4-{[2-fluoro-4-(trifluoromethyl)benzene]sulfonyl}phenyl)methyl]-1H-pyrrolo[3,2-c]pyridine-2-carboxamide | 0.0802 | 0.0281 |
| N-[(4-{[2-fluoro-4-(trifluoromethyl)benzene]sulfonyl}phenyl)methyl]imidazo[1,2-a]pyridine-6-carboxamide | 0.0156 | 0.0157 |
| N-[(4-{[2-fluoro-4-(trifluoromethyl)benzene]sulfonyl}phenyl)methyl]thieno[2,3-c]pyridine-2-carboxamide | 0.0202 | 0.0423 |
| N-[(4-{[2-methoxy-3-(trifluoromethyl)benzene]sulfonyl}phenyl)methyl]imidazo[1,2-a]pyridine-6-carboxamide | 0.0219 | 0.0148 |
| N-[(4-{[2-methoxy-3-(trifluoromethyl)benzene]sulfonyl}phenyl)methyl]thieno[2,3-c]pyridine-2-carboxamide | 0.0094 | 0.0128 |
| N-[(4-{[2-methoxy-4-(1H-pyrazol-1-yl)benzene]sulfonyl}phenyl)methyl]-1H-pyrazolo[3,4-b]pyridine-5-carboxamide | 0.0242 | 0.0094 |
| N-[(4-{[2-methoxy-4-(1H-pyrazol-1-yl)benzene]sulfonyl}phenyl)methyl]furo[2,3-c]pyridine-2-carboxamide | 0.0065 | 0.006 |

TABLE 3-continued

| IUPAC Name | Biochem IC50 uM | A2780 IC50 uM |
|---|---|---|
| N-[(4-{[2-methoxy-4-(1H-pyrazol-1-yl)benzene]sulfonyl}phenyl)methyl]imidazo[1,2-a]pyridine-6-carboxamide | 0.021 | 0.00359 |
| N-[(4-{[2-methoxy-4-(1H-pyrazol-1-yl)benzene]sulfonyl}phenyl)methyl]imidazo[1,2-a]pyrimidine-6-carboxamide | 0.0032 | 0.0087 |
| N-[(4-{[2-methoxy-4-(trifluoromethyl)benzene]sulfonyl}phenyl)methyl]-1H-pyrazolo[3,4-b]pyridine-5-carboxamide | 0.1200 | 0.0281 |
| N-[(4-{[2-methoxy-4-(trifluoromethyl)benzene]sulfonyl}phenyl)methyl]imidazo[1,2-a]pyridine-6-carboxamide | 0.0264 | 0.00984 |
| N-[(4-{[2-methoxy-4-(trifluoromethyl)benzene]sulfonyl}phenyl)methyl]imidazo[1,2-a]pyrimidine-6-carboxamide | 0.0044 | 0.0224 |
| N-[(4-{[2-methoxy-4-(trifluoromethyl)benzene]sulfonyl}phenyl)methyl]thieno[2,3-c]pyridine-2-carboxamide | 0.01 | 0.0022 |
| N-[(4-{[2-methoxy-5-(propan-2-yl)benzene]sulfonyl}phenyl)methyl]-1H-pyrazolo[3,4-b]pyridine-5-carboxamide | 0.0892 | 0.0294 |
| N-[(4-{[2-methoxy-5-(propan-2-yl)benzene]sulfonyl}phenyl)methyl]furo[2,3-c]pyridine-2-carboxamide | 0.0154 | 0.0124 |
| N-[(4-{[2-methoxy-5-(propan-2-yl)benzene]sulfonyl}phenyl)methyl]imidazo[1,2-a]pyridine-6-carboxamide | 0.0352 | 0.0064 |
| N-[(4-{[2-methoxy-5-(trifluoromethoxy)benzene]sulfonyl}phenyl)methyl]-1H-pyrazolo[3,4-b]pyridine-5-carboxamide | 0.0926 | 0.0246 |
| N-[(4-{[2-methoxy-5-(trifluoromethoxy)benzene]sulfonyl}phenyl)methyl]-1H-pyrrolo[3,2-c]pyridine-2-carboxamide | 0.0481 | 0.0066 |
| N-[(4-{[2-methoxy-5-(trifluoromethoxy)benzene]sulfonyl}phenyl)methyl]imidazo[1,2-a]pyridine-6-carboxamide | 0.0677 | 0.0144 |
| N-[(4-{[2-methoxy-5-(trifluoromethoxy)benzene]sulfonyl}phenyl)methyl]imidazo[1,2-a]pyrimidine-6-carboxamide | <0.00065 | 0.0058 |
| N-[(4-{[2-methoxy-5-(trifluoromethyl)benzene]sulfonyl}phenyl)methyl]imidazo[1,2-a]pyrimidine-6-carboxamide | 0.0068 | 0.0036 |
| N-[(4-{[2-methyl-4-(1H-pyrazol-1-yl)benzene]sulfonyl}phenyl)methyl]-1H-pyrazolo[3,4-b]pyridine-5-carboxamide | 0.0271 | 0.0235 |
| N-[(4-{[2-methyl-4-(1H-pyrazol-1-yl)benzene]sulfonyl}phenyl)methyl]furo[2,3-c]pyridine-2-carboxamide | 0.0062 | 0.006 |
| N-[(4-{[2-methyl-4-(1H-pyrazol-1-yl)benzene]sulfonyl}phenyl)methyl]imidazo[1,2-a]pyridine-6-carboxamide | 0.00799 | 0.0036 |
| N-[(4-{[2-methyl-4-(1H-pyrazol-1-yl)benzene]sulfonyl}phenyl)methyl]thieno[2,3-c]pyridine-2-carboxamide | 0.0015 | 0.0031 |
| N-[(4-{[2-methyl-4-(trifluoromethyl)benzene]sulfonyl}phenyl)methyl]-1H-pyrazolo[3,4-b]pyridine-5-carboxamide | 0.1-1 | 0.0746 |
| N-[(4-{[2-methyl-4-(trifluoromethyl)benzene]sulfonyl}phenyl)methyl]-1H-pyrrolo[3,2-c]pyridine-2-carboxamide | 0.0305 | 0.0253 |
| N-[(4-{[2-methyl-4-(trifluoromethyl)benzene]sulfonyl}phenyl)methyl]furo[2,3-c]pyridine-2-carboxamide | 0.0345 | 0.0631 |
| N-[(4-{[2-methyl-4-(trifluoromethyl)benzene]sulfonyl}phenyl)methyl]imidazo[1,2-a]pyridine-6-carboxamide | 0.0247 | 0.0166 |
| N-[(4-{[2-methyl-4-(trifluoromethyl)benzene]sulfonyl}phenyl)methyl]imidazo[1,2-a]pyrimidine-6-carboxamide | 0.0071 | 0.0511 |
| N-[(4-{[2-methyl-4-(trifluoromethyl)benzene]sulfonyl}phenyl)methyl]thieno[2,3-c]pyridine-2-carboxamide | 0.0103 | 0.0242 |
| N-[(4-{[3-(1H-pyrazol-1-yl)benzene]sulfonyl}phenyl)methyl]-1H-pyrrolo[3,2-c]pyridine-2-carboxamide | 0.0097 | 0.0074 |

TABLE 3-continued

| IUPAC Name | Biochem IC50 uM | A2780 IC50 uM |
|---|---|---|
| N-[(4-{3-(1H-pyrazol-1-yl)benzene]sulfonyl}phenyl)methyl]furo[2,3-c]pyridine-2-carboxamide | 0.0075 | 0.0091 |
| N-[(4-{[3-(1H-pyrazol-1-yl)benzene]sulfonyl}phenyl)methyl]imidazo[1,2-a]pyridine-6-carboxamide | 0.0048 | 0.0062 |
| N-[(4-{[3-(1H-pyrazol-1-yl)benzene]sulfonyl}phenyl)methyl]thieno[2,3-c]pyridine-2-carboxamide | 0.0015 | 0.0001 |
| N-[(4-{[3-(2,2,2-trifluoroethoxy)benzene]sulfonyl}phenyl)methyl]furo[2,3-c]pyridine-2-carboxamide | 0.0072 | 0.0120 |
| N-[(4-{[3-(2,2,2-trifluoroethoxy)benzene]sulfonyl}phenyl)methyl]imidazo[1,2-a]pyridine-6-carboxamide | 0.0150 | 0.0059 |
| N-[(4-{[3-(2,2,2-trifluoroethoxy)benzene]sulfonyl}phenyl)methyl]imidazo[1,2-a]pyrimidine-6-carboxamide | 0.0055 | 0.0114 |
| N-[(4-{[3-(2-methylpropoxy)benzene]sulfonyl}phenyl)methyl]-1H-pyrazolo[3,4-b]pyridine-5-carboxamide | 0.0285 | 0.0342 |
| N-[(4-{[3-(2-methylpropoxy)benzene]sulfonyl}phenyl)methyl]-1H-pyrrolo[3,2-c]pyridine-2-carboxamide | 0.0322 | 0.0143 |
| N-[(4-{[3-(2-methylpropoxy)benzene]sulfonyl}phenyl)methyl]furo[2,3-c]pyridine-2-carboxamide | 0.0148 | 0.0677 |
| N-[(4-{[3-(2-methylpropoxy)benzene]sulfonyl}phenyl)methyl]imidazo[1,2-a]pyridine-6-carboxamide | 0.0157 | 0.0106 |
| N-[(4-{[3-(2-methylpropoxy)benzene]sulfonyl}phenyl)methyl]imidazo[1,2-a]pyrimidine-6-carboxamide | 0.0039 | 0.0132 |
| N-[(4-{[3-(2-methylpropoxy)benzene]sulfonyl}phenyl)methyl]thieno[2,3-c]pyridine-2-carboxamide | 0.0032 | 0.0252 |
| N-[(4-{[3-(3,5-dimethyl-1H-pyrazol-1-yl)benzene]sulfonyl}phenyl)methyl]-1,3-benzothiazole-6-carboxamide | 0.0179 | 0.1-1 |
| N-[(4-{[3-(3,5-dimethyl-1H-pyrazol-1-yl)benzene]sulfonyl}phenyl)methyl]-1H-pyrazolo[3,4-b]pyridine-5-carboxamide | 0.0253 | 0.0053 |
| N-[(4-{[3-(3,5-dimethyl-1H-pyrazol-1-yl)benzene]sulfonyl}phenyl)methyl]-1H-pyrrolo[3,2-c]pyridine-2-carboxamide | 0.0132 | 0.0016 |
| N-[(4-{[3-(3,5-dimethyl-1H-pyrazol-1-yl)benzene]sulfonyl}phenyl)methyl]-5-hydroxy-1H-indole-2-carboxamide | 0.1-1 | 0.1-1 |
| N-[(4-{[3-(3,5-dimethyl-1H-pyrazol-1-yl)benzene]sulfonyl}phenyl)methyl]furo[2,3-c]pyridine-2-carboxamide | 0.0071 | 0.0035 |
| N-[(4-{[3-(3,5-dimethyl-1H-pyrazol-1-yl)benzene]sulfonyl}phenyl)methyl]imidazo[1,2-a]pyridine-6-carboxamide | 0.0072 | 0.0008 |
| N-[(4-{[3-(3,5-dimethyl-1H-pyrazol-1-yl)benzene]sulfonyl}phenyl)methyl]imidazo[1,2-a]pyrimidine-6-carboxamide | 0.0018 | 0.0041 |
| N-[(4-{[3-(3,5-dimethyl-1H-pyrazol-1-yl)benzene]sulfonyl}phenyl)methyl]thieno[2,3-c]pyridine-2-carboxamide | 0.0031 | 0.0015 |
| N-[(4-{[3-(4-fluorophenoxy)benzene]sulfonyl}phenyl)methyl]imidazo[1,2-a]pyridine-6-carboxamide | 0.0151 | 0.0340 |
| N-[(4-{[3-(4-fluorophenoxy)benzene]sulfonyl}phenyl)methyl]thieno[2,3-c]pyridine-2-carboxamide | 0.0026 | 0.0656 |
| N-[(4-{[3-(5-methyl-1,2,4-oxadiazol-3-yl)benzene]sulfonyl}phenyl)methyl]furo[2,3-c]pyridine-2-carboxamide | 0.0079 | 0.0032 |
| N-[(4-{[3-(5-methyl-1,2,4-oxadiazol-3-yl)benzene]sulfonyl}phenyl)methyl]imidazo[1,2-a]pyrimidine-6-carboxamide | 0.0028 | 0.0023 |
| N-[(4-{[3-(5-methyl-1,2,4-oxadiazol-3-yl)benzene]sulfonyl}phenyl)methyl]thieno[2,3-c]pyridine-2-carboxamide | 0.0033 | 0.0010 |
| N-[(4-{[3-(cyclopentylcarbamoyl)benzene]sulfonyl}phenyl)methyl]-1H-pyrazolo[3,4-b]pyridine-5-carboxamide | 0.0333 | 0.033 |

TABLE 3-continued

| IUPAC Name | Biochem IC50 uM | A2780 IC50 uM |
|---|---|---|
| N-[(4-{3-(cyclopentylcarbamoyl)benzene]sulfonyl}phenyl)methyl]furo[2,3-c]pyridine-2-carboxamide | 0.0066 | 0.0226 |
| N-[(4-{3-(cyclopentylcarbamoyl)benzene]sulfonyl}phenyl)methyl]imidazo[1,2-a]pyridine-6-carboxamide | 0.0103 | 0.0162 |
| N-[(4-{3-(cyclopentylcarbamoyl)benzene]sulfonyl}phenyl)methyl]imidazo[1,2-a]pyrimidine-6-carboxamide | 0.0047 | 0.0483 |
| N-[(4-{3-(cyclopentylcarbamoyl)benzene]sulfonyl}phenyl)methyl]thieno[2,3-c]pyridine-2-carboxamide | 0.0048 | 0.0138 |
| N-[(4-{[3-(diethylcarbamoyl)-5-fluorobenzene]sulfonyl}phenyl)methyl]-1H-pyrrolo[3,2-c]pyridine-2-carboxamide | 0.0093 | 0.0033 |
| N-[(4-{[3-(diethylcarbamoyl)-5-fluorobenzene]sulfonyl}phenyl)methyl]furo[2,3-c]pyridine-2-carboxamide | 0.0103 | 0.0038 |
| N-[(4-{[3-(diethylcarbamoyl)-5-fluorobenzene]sulfonyl}phenyl)methyl]imidazo[1,2-a]pyrimidine-6-carboxamide | 0.0047 | 0.0168 |
| N-[(4-{[3-(difluoromethoxy)benzene]sulfonyl}phenyl)methyl]furo[2,3-c]pyridine-2-carboxamide | 0.0028 | 0.0030 |
| N-[(4-{[3-(difluoromethoxy)benzene]sulfonyl}phenyl)methyl]imidazo[1,2-a]pyrimidine-6-carboxamide | 0.0021 | 0.0050 |
| N-[(4-{[3-(dimethylsulfamoyl)benzene]sulfonyl}phenyl)methyl]furo[2,3-c]pyridine-2-carboxamide | 0.0020 | 0.0032 |
| N-[(4-{[3-(dimethylsulfamoyl)benzene]sulfonyl}phenyl)methyl]imidazo[1,2-a]pyrimidine-6-carboxamide | 0.0020 | 0.0112 |
| N-[(4-{[3-(ethanesulfonyl)benzene]sulfonyl}phenyl)methyl]-1H-pyrrolo[3,2-c]pyridine-2-carboxamide | 0.0170 | 0.0155 |
| N-[(4-{[3-(ethanesulfonyl)benzene]sulfonyl}phenyl)methyl]furo[2,3-c]pyridine-2-carboxamide | 0.0027 | 0.0032 |
| N-[(4-{[3-(ethanesulfonyl)benzene]sulfonyl}phenyl)methyl]imidazo[1,2-a]pyridine-6-carboxamide | 0.0135 | 0.0060 |
| N-[(4-{[3-(ethanesulfonyl)benzene]sulfonyl}phenyl)methyl]imidazo[1,2-a]pyrimidine-6-carboxamide | 0.0027 | 0.0645 |
| N-[(4-{[3-(ethanesulfonyl)benzene]sulfonyl}phenyl)methyl]thieno[2,3-c]pyridine-2-carboxamide | 0.0028 | 0.0054 |
| N-[(4-{[3-(ethylcarbamoyl)benzene]sulfonyl}phenyl)methyl]furo[2,3-c]pyridine-2-carboxamide | 0.0060 | 0.0064 |
| N-[(4-{[3-(ethylcarbamoyl)benzene]sulfonyl}phenyl)methyl]imidazo[1,2-a]pyrimidine-6-carboxamide | 0.0031 | 0.0655 |
| N-[(4-{[3-(methoxymethyl)benzene]sulfonyl}phenyl)methyl]-1H-pyrazolo[3,4-b]pyridine-5-carboxamide | 0.0387 | 0.0394 |
| N-[(4-{[3-(methoxymethyl)benzene]sulfonyl}phenyl)methyl]-1H-pyrrolo[3,2-c]pyridine-2-carboxamide | 0.0202 | 0.0128 |
| N-[(4-{[3-(methoxymethyl)benzene]sulfonyl}phenyl)methyl]furo[2,3-c]pyridine-2-carboxamide | 0.0185 | 0.0134 |
| N-[(4-{[3-(methoxymethyl)benzene]sulfonyl}phenyl)methyl]imidazo[1,2-a]pyridine-6-carboxamide | 0.0067 | 0.0068 |
| N-[(4-{[3-(methoxymethyl)benzene]sulfonyl}phenyl)methyl]imidazo[1,2-a]pyrimidine-6-carboxamide | 0.0032 | 0.0138 |
| N-[(4-{[3-(methoxymethyl)benzene]sulfonyl}phenyl)methyl]thieno[2,3-c]pyridine-2-carboxamide | 0.0026 | 0.0067 |
| N-[(4-{[3-(methylcarbamoyl)benzene]sulfonyl}phenyl)methyl]furo[2,3-c]pyridine-2-carboxamide | 0.0081 | 0.0143 |
| N-[(4-{[3-(methylcarbamoyl)benzene]sulfonyl}phenyl)methyl]imidazo[1,2-a]pyrimidine-6-carboxamide | 0.0037 | 0.1-1 |

TABLE 3-continued

| IUPAC Name | Biochem IC50 uM | A2780 IC50 uM |
|---|---|---|
| N-[(4-{3-(morpholin-4-yl)benzene]sulfonyl}phenyl)methyl]-1,3-benzothiazole-6-carboxamide | 0.0401 | 1-10 |
| N-[(4-{3-(morpholin-4-yl)benzene]sulfonyl}phenyl)methyl]-1H-pyrazolo[3,4-b]pyridine-5-carboxamide | 0.0167 | 0.0130 |
| N-[(4-{3-(morpholin-4-yl)benzene]sulfonyl}phenyl)methyl]-1H-pyrrolo[3,2-c]pyridine-2-carboxamide | 0.0207 | 0.0106 |
| N-[(4-{3-(morpholin-4-yl)benzene]sulfonyl}phenyl)methyl]-1H-pyrrolo[3,2-c]pyridine-2-carboxamide | 0.0084 | 0.0017 |
| N-[(4-{[3-(morpholin-4-yl)benzene]sulfonyl}phenyl)methyl]furo[2,3-c]pyridine-2-carboxamide | 0.0050 | 0.0056 |
| N-[(4-{[3-(morpholin-4-yl)benzene]sulfonyl}phenyl)methyl]imidazo[1,2-a]pyridine-6-carboxamide | 0.0077 | 0.0033 |
| N-[(4-{[3-(morpholin-4-yl)benzene]sulfonyl}phenyl)methyl]imidazo[1,2-a]pyrimidine-6-carboxamide | 0.0027 | 0.0135 |
| N-[(4-{[3-(morpholin-4-yl)benzene]sulfonyl}phenyl)methyl]thieno[2,3-c]pyridine-2-carboxamide | 0.0040 | 0.0019 |
| N-[(4-{[3-(morpholin-4-yl)benzene]sulfonyl}phenyl)methyl]thieno[2,3-c]pyridine-2-carboxamide | 0.0036 | 0.0032 |
| N-[(4-{[3-(piperidin-1-yl)benzene]sulfonyl}phenyl)methyl]-1,3-benzothiazole-6-carboxamide | 0.0210 | 0.1-1 |
| N-[(4-{[3-(piperidin-1-yl)benzene]sulfonyl}phenyl)methyl]-1H-pyrazolo[3,4-b]pyridine-5-carboxamide | 0.0536 | 0.0140 |
| N-[(4-{[3-(piperidin-1-yl)benzene]sulfonyl}phenyl)methyl]-1H-pyrrolo[3,2-c]pyridine-2-carboxamide | 0.0144 | 0.0033 |
| N-[(4-{[3-(piperidin-1-yl)benzene]sulfonyl}phenyl)methyl]furo[2,3-c]pyridine-2-carboxamide | 0.0113 | 0.0127 |
| N-[(4-{[3-(piperidin-1-yl)benzene]sulfonyl}phenyl)methyl]imidazo[1,2-a]pyridine-6-carboxamide | 0.0114 | 0.0034 |
| N-[(4-{[3-(piperidin-1-yl)benzene]sulfonyl}phenyl)methyl]imidazo[1,2-a]pyrimidine-6-carboxamide | 0.0051 | 0.0114 |
| N-[(4-{[3-(piperidin-1-yl)benzene]sulfonyl}phenyl)methyl]imidazo[1,2-a]pyrimidine-6-carboxamide | 0.0012 | 0.0057 |
| N-[(4-{[3-(piperidin-1-yl)benzene]sulfonyl}phenyl)methyl]thieno[2,3-c]pyridine-2-carboxamide | 0.0167 | 0.0136 |
| N-[(4-{[3-(piperidin-1-ylmethyl)benzene]sulfonyl}phenyl)methyl]imidazo[1,2-a]pyridine-6-carboxamide | 0.0091 | 0.0035 |
| N-[(4-{[3-(piperidin-1-ylmethyl)benzene]sulfonyl}phenyl)methyl]imidazo[1,2-a]pyrimidine-6-carboxamide | 0.0019 | 0.0306 |
| N-[(4-{[3-(propan-2-yl)benzene]sulfonyl}phenyl)methyl]-1H-pyrazolo[3,4-b]pyridine-5-carboxamide | 0.0139 | 0.0063 |
| N-[(4-{[3-(propan-2-yl)benzene]sulfonyl}phenyl)methyl]furo[2,3-c]pyridine-2-carboxamide | 0.0045 | 0.007 |
| N-[(4-{[3-(propan-2-yl)benzene]sulfonyl}phenyl)methyl]imidazo[1,2-a]pyridine-6-carboxamide | 0.0124 | 0.00349 |
| N-[(4-{[3-(propan-2-yl)benzene]sulfonyl}phenyl)methyl]imidazo[1,2-a]pyrimidine-6-carboxamide | 0.0029 | 0.0053 |
| N-[(4-{[3-(propan-2-yloxy)benzene]sulfonyl}phenyl)methyl]-1H-pyrazolo[3,4-b]pyridine-5-carboxamide | 0.0461 | 0.0245 |
| N-[(4-{[3-(propan-2-yloxy)benzene]sulfonyl}phenyl)methyl]furo[2,3-c]pyridine-2-carboxamide | 0.0126 | 0.0144 |
| N-[(4-{[3-(propan-2-yloxy)benzene]sulfonyl}phenyl)methyl]imidazo[1,2-a]pyrimidine-6-carboxamide | 0.0023 | 0.0105 |
| N-[(4-{[3-(propane-1-sulfonamido)benzene]sulfonyl}phenyl)methyl]imidazo[1,2-a]pyrimidine-6-carboxamide | 0.0023 | 0.0862 |
| N-[(4-{[3-(propane-1-sulfonamido)benzene]sulfonyl}phenyl)methyl]thieno[2,3-c]pyridine-2-carboxamide | 0.0015 | 0.0032 |

TABLE 3-continued

| IUPAC Name | Biochem IC50 uM | A2780 IC50 uM |
|---|---|---|
| N-[(4-{3-(pyrimidin-2-yl)benzene]sulfonyl}phenyl)methyl]imidazo[1,2-a]pyridine-6-carboxamide | 0.0219 | 0.0038 |
| N-[(4-{3-(pyrimidin-2-yl)benzene]sulfonyl}phenyl)methyl]imidazo[1,2-a]pyrimidine-6-carboxamide | 0.0032 | 0.0130 |
| N-[(4-{3-(pyrrolidin-1-yl)benzene]sulfonyl}phenyl)methyl]-1,3-benzothiazole-6-carboxamide | 0.0088 | 1-10 |
| N-[(4-{3-(pyrrolidin-1-yl)benzene]sulfonyl}phenyl)methyl]-1H-pyrazolo[3,4-b]pyridine-5-carboxamide | 0.0171 | 0.0128 |
| N-[(4-{3-(pyrrolidin-1-yl)benzene]sulfonyl}phenyl)methyl]-1H-pyrrolo[3,2-c]pyridine-2-carboxamide | 0.0134 | 0.0028 |
| N-[(4-{3-(pyrrolidin-1-yl)benzene]sulfonyl}phenyl)methyl]furo[2,3-c]pyridine-2-carboxamide | 0.0082 | 0.0074 |
| N-[(4-{3-(pyrrolidin-1-yl)benzene]sulfonyl}phenyl)methyl]imidazo[1,2-a]pyridine-6-carboxamide | 0.0136 | 0.0016 |
| N-[(4-{3-(pyrrolidin-1-yl)benzene]sulfonyl}phenyl)methyl]imidazo[1,2-a]pyrimidine-6-carboxamide | 0.0025 | 0.0041 |
| N-[(4-{3-(pyrrolidin-1-yl)benzene]sulfonyl}phenyl)methyl]thieno[2,3-c]pyridine-2-carboxamide | 0.0019 | 0.0025 |
| N-[(4-{3-(trifluoromethoxy)benzene]sulfonyl}phenyl)methyl]-1H-pyrazolo[3,4-b]pyridine-5-carboxamide | 0.0204 | 0.0071 |
| N-[(4-{3-(trifluoromethoxy)benzene]sulfonyl}phenyl)methyl]furo[2,3-c]pyridine-2-carboxamide | 0.0034 | 0.0067 |
| N-[(4-{3-(trifluoromethoxy)benzene]sulfonyl}phenyl)methyl]imidazo[1,2-a]pyridine-6-carboxamide | 0.00873 | 0.00318 |
| N-[(4-{3-(trifluoromethoxy)benzene]sulfonyl}phenyl)methyl]imidazo[1,2-a]pyrimidine-6-carboxamide | 0.0025 | 0.0027 |
| N-[(4-{3-(trifluoromethyl)benzene]sulfonyl}phenyl)methyl]-1,3-benzothiazole-6-carboxamide | 0.006 | 0.5481 |
| N-[(4-{3-(trifluoromethyl)benzene]sulfonyl}phenyl)methyl]-1H-pyrazolo[3,4-b]pyridine-5-carboxamide | 0.0607 | 0.0104 |
| N-[(4-{3-(trifluoromethyl)benzene]sulfonyl}phenyl)methyl]furo[2,3-c]pyridine-2-carboxamide | 0.0054 | 0.0048 |
| N-[(4-{3-(trifluoromethyl)benzene]sulfonyl}phenyl)methyl]imidazo[1,2-a]pyridine-6-carboxamide | 0.00842 | 0.00172 |
| N-[(4-{3-(trifluoromethyl)benzene]sulfonyl}phenyl)methyl]imidazo[1,2-a]pyrimidine-6-carboxamide | 0.0027 | 0.0030 |
| N-[(4-{3-chloro-4-(trifluoromethyl)benzene]sulfonyl}phenyl)methyl]-1H-pyrazolo[3,4-b]pyridine-5-carboxamide | 0.0843 | 0.0264 |
| N-[(4-{3-chloro-4-(trifluoromethyl)benzene]sulfonyl}phenyl)methyl]-1H-pyrrolo[3,2-c]pyridine-2-carboxamide | 0.0133 | 0.0077 |
| N-[(4-{3-chloro-4-(trifluoromethyl)benzene]sulfonyl}phenyl)methyl]furo[2,3-c]pyridine-2-carboxamide | 0.0079 | 0.0062 |
| N-[(4-{3-chloro-4-(trifluoromethyl)benzene]sulfonyl}phenyl)methyl]imidazo[1,2-a]pyridine-6-carboxamide | 0.0029 | 0.0012 |
| N-[(4-{3-chloro-4-(trifluoromethyl)benzene]sulfonyl}phenyl)methyl]imidazo[1,2-a]pyrimidine-6-carboxamide | 0.0028 | 0.0018 |
| N-[(4-{3-chloro-4-(trifluoromethyl)benzene]sulfonyl}phenyl)methyl]thieno[2,3-c]pyridine-2-carboxamide | 0.0030 | 0.0023 |
| N-[(4-{3-chloro-5-(diethylcarbamoyl)benzene]sulfonyl}phenyl)methyl]furo[2,3-c]pyridine-2-carboxamide | 0.0084 | 0.0017 |
| N-[(4-{3-chloro-5-(diethylcarbamoyl)benzene]sulfonyl}phenyl)methyl]imidazo[1,2-a]pyrimidine-6-carboxamide | 0.0009 | 0.0012 |
| N-[(4-{3-chloro-5-(diethylcarbamoyl)benzene]sulfonyl}phenyl)methyl]thieno[2,3-c]pyridine-2-carboxamide | 0.0023 | 0.0008 |

TABLE 3-continued

| IUPAC Name | Biochem IC50 uM | A2780 IC50 uM |
|---|---|---|
| N-[(4-{[3-chloro-5-(hydroxymethyl)benzene]sulfonyl}phenyl)methyl]imidazo[1,2-a]pyridine-6-carboxamide | 0.0058 | 0.0014 |
| N-[(4-{[3-chloro-5-(hydroxymethyl)benzene]sulfonyl}phenyl)methyl]imidazo[1,2-a]pyrimidine-6-carboxamide | 0.0034 | 0.0114 |
| N-[(4-{[3-chloro-5-(hydroxymethyl)benzene]sulfonyl}phenyl)methyl]thieno[2,3-c]pyridine-2-carboxamide | 0.0033 | 0.0008 |
| N-[(4-{[3-chloro-5-(trifluoromethyl)benzene]sulfonyl}phenyl)methyl]-1H-pyrazolo[3,4-b]pyridine-5-carboxamide | 0.0078 | 0.00273 |
| N-[(4-{[3-chloro-5-(trifluoromethyl)benzene]sulfonyl}phenyl)methyl]-1H-pyrrolo[3,2-c]pyridine-2-carboxamide | 0.0199 | 0.0027 |
| N-[(4-{[3-chloro-5-(trifluoromethyl)benzene]sulfonyl}phenyl)methyl]imidazo[1,2-a]pyrimidine-6-carboxamide | 0.0044 | 0.0004 |
| N-[(4-{[3-fluoro-4-(1H-pyrazol-1-yl)benzene]sulfonyl}phenyl)methyl]-1H-pyrazolo[3,4-b]pyridine-5-carboxamide | 0.0131 | 0.0033 |
| N-[(4-{[3-fluoro-4-(1H-pyrazol-1-yl)benzene]sulfonyl}phenyl)methyl]furo[2,3-c]pyridine-2-carboxamide | 0.0173 | 0.005 |
| N-[(4-{[3-fluoro-4-(1H-pyrazol-1-yl)benzene]sulfonyl}phenyl)methyl]imidazo[1,2-a]pyridine-6-carboxamide | 0.00537 | 0.00341 |
| N-[(4-{[3-fluoro-4-(2,2,2-trifluoroethoxy)benzene]sulfonyl}phenyl)methyl]-1H-pyrazolo[3,4-b]pyridine-5-carboxamide | 0.0103 | 0.0223 |
| N-[(4-{[3-fluoro-4-(2,2,2-trifluoroethoxy)benzene]sulfonyl}phenyl)methyl]furo[2,3-c]pyridine-2-carboxamide | 0.0069 | 0.0238 |
| N-[(4-{[3-fluoro-4-(2,2,2-trifluoroethoxy)benzene]sulfonyl}phenyl)methyl]imidazo[1,2-a]pyridine-6-carboxamide | 0.0150 | 0.008 |
| N-[(4-{[3-fluoro-4-(2,2,2-trifluoroethoxy)benzene]sulfonyl}phenyl)methyl]imidazo[1,2-a]pyrimidine-6-carboxamide | 0.0044 | 0.0073 |
| N-[(4-{[3-fluoro-4-(2,2,2-trifluoroethoxy)benzene]sulfonyl}phenyl)methyl]thieno[2,3-c]pyridine-2-carboxamide | 0.0046 | 0.0235 |
| N-[(4-{[3-fluoro-4-(methylsulfanyl)benzene]sulfonyl}phenyl)methyl]furo[2,3-c]pyridine-2-carboxamide | 0.0123 | 0.0112 |
| N-[(4-{[3-fluoro-4-(methylsulfanyl)benzene]sulfonyl}phenyl)methyl]imidazo[1,2-a]pyridine-6-carboxamide | 0.0056 | 0.0027 |
| N-[(4-{[3-fluoro-4-(methylsulfanyl)benzene]sulfonyl}phenyl)methyl]thieno[2,3-c]pyridine-2-carboxamide | 0.0022 | 0.0020 |
| N-[(4-{[3-fluoro-4-(trifluoromethoxy)benzene]sulfonyl}phenyl)methyl]-1H-pyrazolo[3,4-b]pyridine-5-carboxamide | 0.0174 | 0.0137 |
| N-[(4-{[3-fluoro-4-(trifluoromethoxy)benzene]sulfonyl}phenyl)methyl]-1H-pyrrolo[3,2-c]pyridine-2-carboxamide | 0.0262 | 0.0205 |
| N-[(4-{[3-fluoro-4-(trifluoromethoxy)benzene]sulfonyl}phenyl)methyl]furo[2,3-c]pyridine-2-carboxamide | 0.0100 | 0.0156 |
| N-[(4-{[3-fluoro-4-(trifluoromethoxy)benzene]sulfonyl}phenyl)methyl]imidazo[1,2-a]pyridine-6-carboxamide | 0.0084 | 0.0063 |
| N-[(4-{[3-fluoro-4-(trifluoromethoxy)benzene]sulfonyl}phenyl)methyl]imidazo[1,2-a]pyrimidine-6-carboxamide | 0.0040 | 0.0118 |
| N-[(4-{[3-fluoro-4-(trifluoromethoxy)benzene]sulfonyl}phenyl)methyl]thieno[2,3-c]pyridine-2-carboxamide | 0.0115 | 0.0115 |
| N-[(4-{[3-fluoro-4-(trifluoromethyl)benzene]sulfonyl}phenyl)methyl]-1H-pyrrolo[3,2-c]pyridine-2-carboxamide | 0.0103 | 0.0130 |
| N-[(4-{[3-fluoro-4-(trifluoromethyl)benzene]sulfonyl}phenyl)methyl]furo[2,3-c]pyridine-2-carboxamide | 0.0092 | 0.0137 |

TABLE 3-continued

| IUPAC Name | Biochem IC50 uM | A2780 IC50 uM |
|---|---|---|
| N-[(4-{[3-fluoro-4-(trifluoromethyl)benzene]sulfonyl}phenyl)methyl]imidazo[1,2-a]pyridine-6-carboxamide | 0.0402 | 0.0044 |
| N-[(4-{[3-fluoro-4-(trifluoromethyl)benzene]sulfonyl}phenyl)methyl]imidazo[1,2-a]pyrimidine-6-carboxamide | 0.0041 | 0.0069 |
| N-[(4-{[3-fluoro-4-(trifluoromethyl)benzene]sulfonyl}phenyl)methyl]thieno[2,3-c]pyridine-2-carboxamide | 0.0088 | 0.0072 |
| N-[(4-{[3-fluoro-5-(2,2,2-trifluoroethoxy)benzene]sulfonyl}phenyl)methyl]-1H-pyrazolo[3,4-b]pyridine-5-carboxamide | 0.008 | 0.00482 |
| N-[(4-{[3-fluoro-5-(2,2,2-trifluoroethoxy)benzene]sulfonyl}phenyl)methyl]-1H-pyrrolo[3,2-c]pyridine-2-carboxamide | 0.0056 | 0.0019 |
| N-[(4-{[3-fluoro-5-(2,2,2-trifluoroethoxy)benzene]sulfonyl}phenyl)methyl]furo[2,3-c]pyridine-2-carboxamide | 0.0074 | 0.0061 |
| N-[(4-{[3-fluoro-5-(2,2,2-trifluoroethoxy)benzene]sulfonyl}phenyl)methyl]imidazo[1,2-a]pyrimidine-6-carboxamide | 0.0019 | 0.0015 |
| N-[(4-{[3-fluoro-5-(2,2,2-trifluoroethoxy)benzene]sulfonyl}phenyl)methyl]thieno[2,3-c]pyridine-2-carboxamide | 0.0029 | 0.0035 |
| N-[(4-{[3-fluoro-5-(2-methylpropoxy)benzene]sulfonyl}phenyl)methyl]-1H-pyrazolo[3,4-b]pyridine-5-carboxamide | 0.0112 | 0.00949 |
| N-[(4-{[3-fluoro-5-(2-methylpropoxy)benzene]sulfonyl}phenyl)methyl]-1H-pyrrolo[3,2-c]pyridine-2-carboxamide | 0.0132 | 0.0070 |
| N-[(4-{[3-fluoro-5-(2-methylpropoxy)benzene]sulfonyl}phenyl)methyl]furo[2,3-c]pyridine-2-carboxamide | 0.0103 | 0.0129 |
| N-[(4-{[3-fluoro-5-(2-methylpropoxy)benzene]sulfonyl}phenyl)methyl]imidazo[1,2-a]pyridine-6-carboxamide | 0.0113 | 0.003 |
| N-[(4-{[3-fluoro-5-(2-methylpropoxy)benzene]sulfonyl}phenyl)methyl]imidazo[1,2-a]pyrimidine-6-carboxamide | 0.0031 | 0.0034 |
| N-[(4-{[3-fluoro-5-(2-methylpropoxy)benzene]sulfonyl}phenyl)methyl]thieno[2,3-c]pyridine-2-carboxamide | 0.0048 | 0.0075 |
| N-[(4-{[3-fluoro-5-(morpholin-4-yl)benzene]sulfonyl}phenyl)methyl]-1H-pyrrolo[3,2-c]pyridine-2-carboxamide | 0.004 | 0.0008 |
| N-[(4-{[3-fluoro-5-(morpholin-4-yl)benzene]sulfonyl}phenyl)methyl]imidazo[1,2-a]pyridine-6-carboxamide | 0.003 | 0.0006 |
| N-[(4-{[3-fluoro-5-(pyrrolidin-1-yl)benzene]sulfonyl}phenyl)methyl]imidazo[1,2-a]pyridine-6-carboxamide | 0.0039 | 0.0022 |
| N-[(4-{[3-fluoro-5-(pyrrolidin-1-yl)benzene]sulfonyl}phenyl)methyl]imidazo[1,2-a]pyrimidine-6-carboxamide | 0.0031 | 0.0020 |
| N-[(4-{[3-fluoro-5-(pyrrolidin-1-yl)benzene]sulfonyl}phenyl)methyl]thieno[2,3-c]pyridine-2-carboxamide | 0.0012 | 0.0027 |
| N-[(4-{[3-fluoro-5-(trifluoromethyl)benzene]sulfonyl}phenyl)methyl]-1H-pyrazolo[3,4-b]pyridine-5-carboxamide | 0.0112 | 0.00345 |
| N-[(4-{[3-fluoro-5-(trifluoromethyl)benzene]sulfonyl}phenyl)methyl]-1H-pyrrolo[3,2-c]pyridine-2-carboxamide | 0.0262 | 0.0036 |
| N-[(4-{[3-fluoro-5-(trifluoromethyl)benzene]sulfonyl}phenyl)methyl]furo[2,3-c]pyridine-2-carboxamide | 0.0074 | 0.0050 |
| N-[(4-{[3-fluoro-5-(trifluoromethyl)benzene]sulfonyl}phenyl)methyl]imidazo[1,2-a]pyrimidine-6-carboxamide | 0.0059 | 0.0011 |
| N-[(4-{[3-fluoro-5-(trifluoromethyl)benzene]sulfonyl}phenyl)methyl]thieno[2,3-c]pyridine-2-carboxamide | 0.0102 | 0.0031 |
| N-[(4-{[4-(1-cyanocyclopentyl)benzene]sulfonyl}phenyl)methyl]-1H-pyrrolo[3,2-c]pyridine-2-carboxamide | 0.0601 | 0.0189 |

TABLE 3-continued

| IUPAC Name | Biochem IC50 uM | A2780 IC50 uM |
|---|---|---|
| N-[(4-{[4-(1-cyanocyclopentyl)benzene]sulfonyl}phenyl)methyl]furo[2,3-c]pyridine-2-carboxamide | 0.0080 | 0.0060 |
| N-[(4-{[4-(1-cyanocyclopentyl)benzene]sulfonyl}phenyl)methyl]imidazo[1,2-a]pyridine-6-carboxamide | 0.0107 | 0.0030 |
| N-[(4-{[4-(1-cyanocyclopentyl)benzene]sulfonyl}phenyl)methyl]imidazo[1,2-a]pyrimidine-6-carboxamide | 0.0032 | 0.0047 |
| N-[(4-{[4-(1H-imidazol-1-yl)benzene]sulfonyl}phenyl)methyl]imidazo[1,2-a]pyrimidine-6-carboxamide | <0.00065 | 0.0122 |
| N-[(4-{[4-(1H-imidazol-1-ylmethyl)benzene]sulfonyl}phenyl)methyl]furo[2,3-c]pyridine-2-carboxamide | 0.0190 | 0.0137 |
| N-[(4-{[4-(1H-imidazol-1-ylmethyl)benzene]sulfonyl}phenyl)methyl]thieno[2,3-c]pyridine-2-carboxamide | 0.0053 | 0.0122 |
| N-[(4-{[4-(1H-pyrazol-1-yl)benzene]sulfonyl}phenyl)methyl]-1H-pyrazolo[3,4-b]pyridine-5-carboxamide | 0.0123 | 0.0075 |
| N-[(4-{[4-(1H-pyrazol-1-yl)benzene]sulfonyl}phenyl)methyl]furo[2,3-c]pyridine-2-carboxamide | 0.0041 | 0.0073 |
| N-[(4-{[4-(2-methylpropoxy)benzene]sulfonyl}phenyl)methyl]-1H-pyrazolo[3,4-b]pyridine-5-carboxamide | 0.0263 | 0.0162 |
| N-[(4-{[4-(2-methylpropoxy)benzene]sulfonyl}phenyl)methyl]-1H-pyrrolo[3,2-c]pyridine-2-carboxamide | 0.0127 | 0.0094 |
| N-[(4-{[4-(2-methylpropoxy)benzene]sulfonyl}phenyl)methyl]furo[2,3-c]pyridine-2-carboxamide | 0.0094 | 0.0116 |
| N-[(4-{[4-(2-methylpropoxy)benzene]sulfonyl}phenyl)methyl]imidazo[1,2-a]pyridine-6-carboxamide | 0.0022 | 0.0027 |
| N-[(4-{[4-(2-methylpropoxy)benzene]sulfonyl}phenyl)methyl]imidazo[1,2-a]pyrimidine-6-carboxamide | 0.0055 | 0.0052 |
| N-[(4-{[4-(2-methylpropoxy)benzene]sulfonyl}phenyl)methyl]thieno[2,3-c]pyridine-2-carboxamide | 0.0040 | 0.0103 |
| N-[(4-{[4-(4-ethoxyphenyl)benzene]sulfonyl}phenyl)methyl]-1H-pyrrolo[3,2-c]pyridine-2-carboxamide | 0.009 | 0.0090 |
| N-[(4-{[4-(4-methylpiperazin-1-yl)benzene]sulfonyl}phenyl)methyl]-1H-pyrazolo[3,4-b]pyridine-5-carboxamide | 0.004 | 0.0013 |
| N-[(4-{[4-(4-methylpiperazin-1-yl)benzene]sulfonyl}phenyl)methyl]-1H-pyrrolo[3,2-c]pyridine-2-carboxamide | 0.003 | 0.0008 |
| N-[(4-{[4-(4-methylpiperazin-1-yl)benzene]sulfonyl}phenyl)methyl]furo[2,3-c]pyridine-2-carboxamide | 0.001 | 0.0005 |
| N-[(4-{[4-(4-methylpiperazin-1-yl)benzene]sulfonyl}phenyl)methyl]imidazo[1,2-a]pyridine-6-carboxamide | 0.001 | 0.0002 |
| N-[(4-{[4-(4-methylpiperazin-1-yl)benzene]sulfonyl}phenyl)methyl]thieno[2,3-c]pyridine-2-carboxamide | 0.001 | 0.0003 |
| N-[(4-{[4-(difluoromethyl)-3-fluorobenzene]sulfonyl}phenyl)methyl]imidazo[1,2-a]pyrimidine-6-carboxamide | 0.0082 | 0.0279 |
| N-[(4-{[4-(ethoxymethyl)benzene]sulfonyl}phenyl)methyl]-1H-pyrazolo[3,4-b]pyridine-5-carboxamide | 0.0266 | 0.0128 |
| N-[(4-{[4-(ethoxymethyl)benzene]sulfonyl}phenyl)methyl]-1H-pyrrolo[3,2-c]pyridine-2-carboxamide | 0.0225 | 0.0068 |
| N-[(4-{[4-(ethoxymethyl)benzene]sulfonyl}phenyl)methyl]furo[2,3-c]pyridine-2-carboxamide | 0.0049 | 0.0066 |
| N-[(4-{[4-(ethoxymethyl)benzene]sulfonyl}phenyl)methyl]imidazo[1,2-a]pyrimidine-6-carboxamide | 0.0027 | 0.0052 |
| N-[(4-{[4-(ethylcarbamoyl)benzene]sulfonyl}phenyl)methyl]-1H-pyrazolo[3,4-b]pyridine-5-carboxamide | 0.103 | 0.0968 |
| N-[(4-{[4-(ethylcarbamoyl)benzene]sulfonyl}phenyl)methyl]-1H-pyrrolo[3,2-c]pyridine-2-carboxamide | 0.0145 | 0.0141 |
| N-[(4-{[4-(ethylcarbamoyl)benzene]sulfonyl}phenyl)methyl]furo[2,3-c]pyridine-2-carboxamide | 0.0045 | 0.0067 |

TABLE 3-continued

| IUPAC Name | Biochem IC50 uM | A2780 IC50 uM |
|---|---|---|
| N-[(4-{4-(ethylcarbamoyl)benzene]sulfonyl}phenyl)methyl]imidazo[1,2-a]pyridine-6-carboxamide | 0.0120 | 0.0063 |
| N-[(4-{4-(ethylcarbamoyl)benzene]sulfonyl}phenyl)methyl]imidazo[1,2-a]pyrimidine-6-carboxamide | 0.0226 | 0.0878 |
| N-[(4-{4-(ethylcarbamoyl)benzene]sulfonyl}phenyl)methyl]thieno[2,3-c]pyridine-2-carboxamide | 0.0015 | 0.0033 |
| N-[(4-{4-(hydroxymethyl)benzene]sulfonyl}phenyl)methyl]furo[2,3-c]pyridine-2-carboxamide | 0.0049 | 0.0062 |
| N-[(4-{4-(hydroxymethyl)benzene]sulfonyl}phenyl)methyl]imidazo[1,2-a]pyridine-6-carboxamide | 0.0142 | 0.0129 |
| N-[(4-{4-(hydroxymethyl)benzene]sulfonyl}phenyl)methyl]thieno[2,3-c]pyridine-2-carboxamide | 0.0038 | 0.0066 |
| N-(4-{[4-(morpholin-4-yl)benzene]sulfonyl}phenyl)methyl]-1H-pyrazolo[3,4-b]pyridine-5-carboxamide | 0.00445 | 0.00247 |
| N-(4-{[4-(morpholin-4-yl)benzene]sulfonyl}phenyl)methyl]furo[2,3-c]pyridine-2-carboxamide | 0.0046 | 0.0025 |
| N-[(4-{[4-(morpholin-4-yl)benzene]sulfonyl}phenyl)methyl]imidazo[1,2-a]pyridine-6-carboxamide | 0.0035 | 0.0009 |
| N-[(4-{[4-(morpholin-4-yl)benzene]sulfonyl}phenyl)methyl]imidazo[1,2-a]pyrimidine-6-carboxamide | 0.0017 | 0.0040 |
| N-[(4-{[4-(morpholin-4-yl)benzene]sulfonyl}phenyl)methyl]thieno[2,3-c]pyridine-2-carboxamide | 0.0016 | 0.0015 |
| N-(4-{[4-(propan-2-yl)benzene]sulfonyl}phenyl)methyl]furo[2,3-c]pyridine-2-carboxamide | 0.0119 | 0.0080 |
| N-[(4-{[4-(propan-2-yl)benzene]sulfonyl}phenyl)methyl]imidazo[1,2-a]pyridine-6-carboxamide | 0.0146 | 0.00666 |
| N-[(4-{[4-(propan-2-yl)benzene]sulfonyl}phenyl)methyl]imidazo[1,2-a]pyrimidine-6-carboxamide | 0.0017 | 0.0081 |
| N-(4-{[4-(propan-2-yloxy)benzene]sulfonyl}phenyl)methyl]-1H-pyrazolo[3,4-b]pyridine-5-carboxamide | 0.0080 | 0.0066 |
| N-[(4-{[4-(propan-2-yloxy)benzene]sulfonyl}phenyl)methyl]furo[2,3-c]pyridine-2-carboxamide | 0.0068 | 0.0057 |
| N-[(4-{[4-(propan-2-yloxy)benzene]sulfonyl}phenyl)methyl]imidazo[1,2-a]pyrimidine-6-carboxamide | 0.0043 | 0.0032 |
| N-[(4-{[4-(pyrrolidin-1-yl)benzene]sulfonyl}phenyl)methyl]-1H-pyrazolo[3,4-b]pyridine-6-carboxamide | 0.006 | 0.0045 |
| N-[(4-{[4-(pyrrolidin-1-yl)benzene]sulfonyl}phenyl)methyl]imidazo[1,2-a]pyridine-6-carboxamide | 0.003 | 0.0014 |
| N-(4-{[4-(trifluoromethoxy)benzene]sulfonyl}phenyl)methyl]-1H-pyrazolo[3,4-b]pyridine-5-carboxamide | 0.0346 | 0.0223 |
| N-[(4-{4-(trifluoromethoxy)benzene]sulfonyl}phenyl)methyl]furo[2,3-c]pyridine-2-carboxamide | 0.0094 | 0.0277 |
| N-[(4-{4-(trifluoromethoxy)benzene]sulfonyl}phenyl)methyl]imidazo[1,2-a]pyrimidine-6-carboxamide | 0.0050 | 0.0176 |
| N-(4-{[4-(trifluoromethyl)benzene]sulfonyl}phenyl)methyl]-1H-pyrazolo[3,4-b]pyridine-5-carboxamide | 0.0199 | 0.0194 |
| N-[(4-{4-(trifluoromethyl)benzene]sulfonyl}phenyl)methyl]furo[2,3-c]pyridine-2-carboxamide | 0.0087 | 0.0198 |
| N-[(4-{4-(trifluoromethyl)benzene]sulfonyl}phenyl)methyl]imidazo[1,2-a]pyrimidine-6-carboxamide | 0.0060 | 0.0235 |
| N-[(4-{[4-chloro-2-(trifluoromethyl)benzene]sulfonyl}phenyl)methyl]-1H-pyrazolo[3,4-b]pyridine-5-carboxamide | 0.147 | 0.0783 |
| N-[(4-{[4-chloro-2-(trifluoromethyl)benzene]sulfonyl}phenyl)methyl]-1H-pyrrolo[3,2-c]pyridine-2-carboxamide | 0.0422 | 0.0174 |

TABLE 3-continued

| IUPAC Name | Biochem IC50 uM | A2780 IC50 uM |
|---|---|---|
| N-[(4-{[4-chloro-2-(trifluoromethyl)benzene]sulfonyl}phenyl)methyl]furo[2,3-c]pyridine-2-carboxamide | 0.0098 | 0.0254 |
| N-[(4-{[4-chloro-2-(trifluoromethyl)benzene]sulfonyl}phenyl)methyl]imidazo[1,2-a]pyridine-6-carboxamide | 0.0198 | 0.0085 |
| N-[(4-{[4-chloro-2-(trifluoromethyl)benzene]sulfonyl}phenyl)methyl]imidazo[1,2-a]pyrimidine-6-carboxamide | 0.0079 | 0.0684 |
| N-[(4-{[4-chloro-2-(trifluoromethyl)benzene]sulfonyl}phenyl)methyl]thieno[2,3-c]pyridine-2-carboxamide | 0.0070 | 0.0096 |
| N-[(4-{[4-chloro-3-(trifluoromethyl)benzene]sulfonyl}phenyl)methyl]furo[2,3-c]pyridine-2-carboxamide | 0.0060 | 0.0069 |
| N-[(4-{[4-chloro-3-(trifluoromethyl)benzene]sulfonyl}phenyl)methyl]imidazo[1,2-a]pyridine-6-carboxamide | 0.00984 | 0.00357 |
| N-[(4-{[4-chloro-3-(trifluoromethyl)benzene]sulfonyl}phenyl)methyl]imidazo[1,2-a]pyrimidine-6-carboxamide | 0.0028 | 0.0043 |
| N-[(4-{[4-fluoro-2-(propan-2-yloxy)benzene]sulfonyl}phenyl)methyl]-1H-pyrrolo[3,2-c]pyridine-2-carboxamide | 0.0254 | 0.0033 |
| N-[(4-{[4-fluoro-2-(propan-2-yloxy)benzene]sulfonyl}phenyl)methyl]furo[2,3-c]pyridine-2-carboxamide | 0.0156 | 0.0139 |
| N-[(4-{[4-fluoro-2-(propan-2-yloxy)benzene]sulfonyl}phenyl)methyl]imidazo[1,2-a]pyridine-6-carboxamide | 0.0222 | 0.0021 |
| N-[(4-{[4-fluoro-2-(propan-2-yloxy)benzene]sulfonyl}phenyl)methyl]imidazo[1,2-a]pyrimidine-6-carboxamide | 0.0035 | 0.0150 |
| N-[(4-{[4-fluoro-2-(propan-2-yloxy)benzene]sulfonyl}phenyl)methyl]thieno[2,3-c]pyridine-2-carboxamide | 0.0050 | 0.0016 |
| N-[(4-{[4-fluoro-2-(trifluoromethyl)benzene]sulfonyl}phenyl)methyl]-1H-pyrazolo[3,4-b]pyridine-5-carboxamide | 0.112 | 0.109 |
| N-[(4-{[4-fluoro-2-(trifluoromethyl)benzene]sulfonyl}phenyl)methyl]-1H-pyrrolo[3,2-c]pyridine-2-carboxamide | 0.0270 | 0.0141 |
| N-[(4-{[4-fluoro-2-(trifluoromethyl)benzene]sulfonyl}phenyl)methyl]imidazo[1,2-a]pyridine-6-carboxamide | 0.0040 | 0.0150 |
| N-[(4-{[4-fluoro-2-(trifluoromethyl)benzene]sulfonyl}phenyl)methyl]imidazo[1,2-a]pyrimidine-6-carboxamide | 0.0187 | 0.1-1 |
| N-[(4-{[4-fluoro-2-(trifluoromethyl)benzene]sulfonyl}phenyl)methyl]thieno[2,3-c]pyridine-2-carboxamide | 0.0064 | 0.0143 |
| N-[(4-{[4-fluoro-3-(2,2,2-trifluoroethoxy)benzene]sulfonyl}phenyl)methyl]-1H-pyrazolo[3,4-b]pyridine-5-carboxamide | 0.01 | 0.0147 |
| N-[(4-{[4-fluoro-3-(2,2,2-trifluoroethoxy)benzene]sulfonyl}phenyl)methyl]-1H-pyrrolo[3,2-c]pyridine-2-carboxamide | 0.0103 | 0.0065 |
| N-[(4-{[4-fluoro-3-(2,2,2-trifluoroethoxy)benzene]sulfonyl}phenyl)methyl]furo[2,3-c]pyridine-2-carboxamide | 0.0087 | 0.0255 |
| N-[(4-{[4-fluoro-3-(2,2,2-trifluoroethoxy)benzene]sulfonyl}phenyl)methyl]imidazo[1,2-a]pyrimidine-6-carboxamide | 0.0024 | 0.0065 |
| N-[(4-{[4-fluoro-3-(2,2,2-trifluoroethoxy)benzene]sulfonyl}phenyl)methyl]thieno[2,3-c]pyridine-2-carboxamide | 0.0033 | 0.0118 |
| N-[(4-{[4-fluoro-3-(trifluoromethyl)benzene]sulfonyl}phenyl)methyl]-1H-pyrazolo[3,4-b]pyridine-5-carboxamide | 0.0394 | 0.0138 |
| N-[(4-{[4-fluoro-3-(trifluoromethyl)benzene]sulfonyl}phenyl)methyl]-1H-pyrrolo[3,2-c]pyridine-2-carboxamide | 0.0164 | 0.0043 |
| N-[(4-{[4-fluoro-3-(trifluoromethyl)benzene]sulfonyl}phenyl)methyl]furo[2,3-c]pyridine-2-carboxamide | 0.0082 | 0.0072 |

TABLE 3-continued

| IUPAC Name | Biochem IC50 uM | A2780 IC50 uM |
|---|---|---|
| N-[(4-{[4-fluoro-3-(trifluoromethyl)benzene]sulfonyl}phenyl)methyl]imidazo[1,2-a]pyridine-6-carboxamide | 0.0040 | 0.0017 |
| N-[(4-{[4-fluoro-3-(trifluoromethyl)benzene]sulfonyl}phenyl)methyl]imidazo[1,2-a]pyrimidine-6-carboxamide | 0.0080 | 0.0032 |
| N-[(4-{[4-fluoro-3-(trifluoromethyl)benzene]sulfonyl}phenyl)methyl]thieno[2,3-c]pyridine-2-carboxamide | 0.0040 | 0.0028 |
| N-[(4-{[4-methoxy-2-(trifluoromethyl)benzene]sulfonyl}phenyl)methyl]-1H-pyrazolo[3,4-b]pyridine-5-carboxamide | 0.0868 | 0.0628 |
| N-[(4-{[4-methoxy-2-(trifluoromethyl)benzene]sulfonyl}phenyl)methyl]-1H-pyrrolo[3,2-c]pyridine-2-carboxamide | 0.0804 | 0.0130 |
| N-[(4-{[4-methoxy-2-(trifluoromethyl)benzene]sulfonyl}phenyl)methyl]furo[2,3-c]pyridine-2-carboxamide | 0.0146 | 0.0152 |
| N-[(4-{[4-methoxy-2-(trifluoromethyl)benzene]sulfonyl}phenyl)methyl]imidazo[1,2-a]pyrimidine-6-carboxamide | 0.0070 | 0.0657 |
| N-[(4-{[4-methoxy-2-(trifluoromethyl)benzene]sulfonyl}phenyl)methyl]thieno[2,3-c]pyridine-2-carboxamide | 0.0217 | 0.0130 |
| N-(4-{[5-(diethylcarbamoyl)-2-fluorobenzene]sulfonyl}phenyl)methyl]-1H-pyrrolo[3,2-c]pyridine-2-carboxamide | 0.0384 | 0.0262 |
| N-[(4-{[5-chloro-2-(2,2,2-trifluoroethoxy)benzene]sulfonyl}phenyl)methyl]imidazo[1,2-a]pyridine-6-carboxamide | 0.001 | 0.0003 |
| N-[(4-{[5-chloro-2-(2,2-difluoroethoxy)benzene]sulfonyl}phenyl)methyl]-1H-pyrrolo[3,2-c]pyridine-2-carboxamide | 0.005 | 0.0005 |
| N-[(4-{[5-chloro-2-(2,2-difluoroethoxy)benzene]sulfonyl}phenyl)methyl]imidazo[1,2-a]pyridine-6-carboxamide | 0.002 | 0.0003 |
| N-[(4-{[5-chloro-2-(prop-2-yn-1-yloxy)benzene]sulfonyl}phenyl)methyl]imidazo[1,2-a]pyridine-6-carboxamide | 0.007 | 0.0014 |
| N-[(4-{[5-chloro-2-(propan-2-yloxy)benzene]sulfonyl}phenyl)methyl]-1H-pyrazolo[3,4-b]pyridine-5-carboxamide | 0.0678 | 0.0271 |
| N-[(4-{[5-chloro-2-(propan-2-yloxy)benzene]sulfonyl}phenyl)methyl]furo[2,3-c]pyridine-2-carboxamide | 0.0091 | 0.0121 |
| N-[(4-{[5-chloro-2-(propan-2-yloxy)benzene]sulfonyl}phenyl)methyl]imidazo[1,2-a]pyrimidine-6-carboxamide | 0.0047 | 0.0146 |
| N-[(4-{[5-fluoro-2-(hydroxymethyl)benzene]sulfonyl}phenyl)methyl]-1H-pyrazolo[3,4-b]pyridine-5-carboxamide | 0.109 | 0.1-1 |
| N-[(4-{[5-fluoro-2-(hydroxymethyl)benzene]sulfonyl}phenyl)methyl]-1H-pyrrolo[3,2-c]pyridine-2-carboxamide | 0.0169 | 0.0675 |
| N-[(4-{[5-fluoro-2-(hydroxymethyl)benzene]sulfonyl}phenyl)methyl]furo[2,3-c]pyridine-2-carboxamide | 0.0229 | 0.0670 |
| N-[(4-{[5-fluoro-2-(hydroxymethyl)benzene]sulfonyl}phenyl)methyl]imidazo[1,2-a]pyridine-6-carboxamide | 0.0104 | 0.0650 |
| N-[(4-{[5-fluoro-2-(hydroxymethyl)benzene]sulfonyl}phenyl)methyl]imidazo[1,2-a]pyrimidine-6-carboxamide | 0.0129 | 0.1-1 |
| N-[(4-{[5-fluoro-2-(hydroxymethyl)benzene]sulfonyl}phenyl)methyl]thieno[2,3-c]pyridine-2-carboxamide | 0.0077 | 0.0249 |
| N-[(4-{[5-hydroxy-2-(trifluoromethoxy)benzene]sulfonyl}phenyl)methyl]-1H-pyrazolo[3,4-b]pyridine-5-carboxamide | 0.0219 | 0.0679 |
| N-[(4-{[5-hydroxy-2-(trifluoromethoxy)benzene]sulfonyl}phenyl)methyl]furo[2,3-c]pyridine-2-carboxamide | 0.0064 | 0.0115 |
| N-[(4-{2-[ethyl(methyl)amino]-1,3-thiazole-5-sulfonyl}phenyl)methyl]-1H-pyrazolo[3,4-b]pyridine-5-carboxamide | 0.0036 | 0.0015 |

TABLE 3-continued

| IUPAC Name | Biochem IC50 uM | A2780 IC50 uM |
|---|---|---|
| N-[(4-{2-[ethyl(methyl)amino]-1,3-thiazole-5-sulfonyl}phenyl)methyl]furo[2,3-c]pyridine-2-carboxamide | 0.0048 | 0.0009 |
| N-[(4-{2-[ethyl(methyl)amino]-1,3-thiazole-5-sulfonyl}phenyl)methyl]imidazo[1,2-a]pyridine-6-carboxamide | 0.0033 | 0.0004 |
| N-[(4-{2-[ethyl(methyl)amino]-1,3-thiazole-5-sulfonyl}phenyl)methyl]imidazo[1,2-a]pyrimidine-6-carboxamide | 0.0018 | 0.0009 |
| N-[(4-{2-[ethyl(methyl)amino]-1,3-thiazole-5-sulfonyl}phenyl)methyl]thieno[2,3-c]pyridine-2-carboxamide | 0.0029 | 0.0012 |
| N-[(4-{5H,6H,7H,8H,9H-imidazo[1,2-a]azepine-3-sulfonyl}phenyl)methyl]-1H-pyrazolo[3,4-b]pyridine-5-carboxamide | 0.0316 | 0.0123 |
| N-[(4-{5H,6H,7H,8H,9H-imidazo[1,2-a]azepine-3-sulfonyl}phenyl)methyl]furo[2,3-c]pyridine-2-carboxamide | 0.0060 | 0.0057 |
| N-[(4-{5H,6H,7H,8H,9H-imidazo[1,2-a]azepine-3-sulfonyl}phenyl)methyl]imidazo[1,2-a]pyrimidine-6-carboxamide | 0.0011 | 0.0287 |
| N-[(4-{5H,6H,7H,8H,9H-imidazo[1,2-a]azepine-3-sulfonyl}phenyl)methyl]thieno[2,3-c]pyridine-2-carboxamide | 0.0030 | 0.0008 |
| N-[(4-{6-chloroimidazo[1,2-a]pyridine-3-sulfonyl}phenyl)methyl]-1H-pyrazolo[3,4-b]pyridine-5-carboxamide | 0.0033 | 0.0008 |
| N-[(4-{6-chloroimidazo[1,2-a]pyridine-3-sulfonyl}phenyl)methyl]-1H-pyrrolo[3,2-c]pyridine-2-carboxamide | 0.0132 | 0.0014 |
| N-[(4-{6-chloroimidazo[1,2-a]pyridine-3-sulfonyl}phenyl)methyl]furo[2,3-c]pyridine-2-carboxamide | 0.0012 | 0.0004 |
| N-[(4-{6-chloroimidazo[1,2-a]pyridine-3-sulfonyl}phenyl)methyl]imidazo[1,2-a]pyridine-6-carboxamide | 0.0053 | 0.0004 |
| N-[(4-{6-chloroimidazo[1,2-a]pyridine-3-sulfonyl}phenyl)methyl]imidazo[1,2-a]pyrimidine-6-carboxamide | 0.0016 | 0.0004 |
| N-[(4-{6-chloroimidazo[1,2-a]pyridine-3-sulfonyl}phenyl)methyl]thieno[2,3-c]pyridine-2-carboxamide | 0.0012 | 0.0004 |
| N-[(4-{8-oxatricyclo[7.4.0.0$^{2,7}$]trideca-1(13),2,4,6,9,11-hexaene-6-sulfonyl}phenyl)methyl]-1H-pyrazolo[3,4-b]pyridine-5-carboxamide | 0.021 | 0.00752 |
| N-[(4-{8-oxatricyclo[7.4.0.0$^{2,7}$]trideca-1(13),2,4,6,9,11-hexaene-6-sulfonyl}phenyl)methyl]furo[2,3-c]pyridine-2-carboxamide | 0.0124 | 0.0128 |
| N-[(4-{8-oxatricyclo[7.4.0.0$^{2,7}$]trideca-1(13),2,4,6,9,11-hexaene-6-sulfonyl}phenyl)methyl]imidazo[1,2-a]pyrimidine-6-carboxamide | 0.0017 | 0.0029 |
| N-[(4-{8-thiatricyclo[7.4.0.0$^{2,7}$]trideca-1(13),2,4,6,9,11-hexaene-6-sulfonyl}phenyl)methyl]-1H-pyrrolo[3,2-c]pyridine-2-carboxamide | 0.0035 | 0.0032 |
| N-[(4-{8-thiatricyclo[7.4.0.0$^{2,7}$]trideca-1(13),2,4,6,9,11-hexaene-6-sulfonyl}phenyl)methyl]furo[2,3-c]pyridine-2-carboxamide | 0.0087 | 0.012 |
| N-[(4-{8-thiatricyclo[7.4.0.0$^{2,7}$]trideca-1(13),2,4,6,9,11-hexaene-6-sulfonyl}phenyl)methyl]imidazo[1,2-a]pyrimidine-6-carboxamide | 0.0018 | 0.0020 |
| N-[(4-{8-thiatricyclo[7.4.0.0$^{2,7}$]trideca-1(13),2,4,6,9,11-hexaene-6-sulfonyl}phenyl)methyl]thieno[2,3-c]pyridine-2-carboxamide | 0.0014 | 0.0043 |
| N-{[4-({3-[(2-methylpropyl)carbamoyl]benzene}sulfonyl)phenyl]methyl}-1H-pyrrolo[3,2-c]pyridine-2-carboxamide | 0.0193 | 0.0458 |
| N-{[4-({3-[(2-methylpropyl)carbamoyl]benzene}sulfonyl)phenyl]methyl}furo[2,3-c]pyridine-2-carboxamide | 0.0169 | 0.0263 |
| N-{[4-({3-[(2-methylpropyl)carbamoyl]benzene}sulfonyl)phenyl]methyl}imidazo[1,2-a]pyrimidine-6-carboxamide | 0.0070 | 0.0456 |
| N-{[4-({3-[(2-methylpropyl)carbamoyl]benzene}sulfonyl)phenyl]methyl}thieno[2,3-c]pyridine-2-carboxamide | 0.0052 | 0.0145 |
| N-{[4-({3-[(dimethylamino)methyl]benzene}sulfonyl)phenyl]methyl}furo[2,3-c]pyridine-2-carboxamide | 0.0047 | 0.0062 |
| N-{[4-({3-[(dimethylamino)methyl]benzene}sulfonyl)phenyl]methyl}imidazo[1,2-a]pyrimidine-6-carboxamide | 0.0044 | 0.0660 |
| N-{[4-({3-[(morpholin-4-yl)carbonyl]benzene}sulfonyl)phenyl]methyl}-1H-pyrazolo[3,4-b]pyridine-5-carboxamide | 0.1235 | 0.1-1 |
| N-{[4-({3-[(propan-2-yl)carbamoyl]benzene}sulfonyl)phenyl]methyl}furo[2,3-c]pyridine-2-carboxamide | 0.0151 | 0.0157 |
| N-{[4-({3-[(propan-2-yl)carbamoyl]benzene}sulfonyl)phenyl]methyl}imidazo[1,2-a]pyridine-6-carboxamide | 0.0222 | 0.0504 |
| N-{[4-({3-[(propan-2-yl)carbamoyl]benzene}sulfonyl)phenyl]methyl}imidazo[1,2-a]pyrimidine-6-carboxamide | 0.0070 | 0.0658 |

TABLE 3-continued

| IUPAC Name | Biochem IC50 uM | A2780 IC50 uM |
|---|---|---|
| N-{[4-({3-[(propan-2-yl)carbamoyl]benzene}sulfonyl)phenyl]methyl}thieno[2,3-c]pyridine-2-carboxamide | 0.0027 | 0.0067 |
| N-{[4-({3-[2-(dimethylamino)ethoxy]benzene}sulfonyl)phenyl]methyl}furo[2,3-c]pyridine-2-carboxamide | 0.0118 | 0.0058 |
| N-{[4-({3-[2-(dimethylamino)ethyl]benzene}sulfonyl)phenyl]methyl}-1H-pyrrolo[3,2-c]pyridine-2-carboxamide | 0.0292 | 0.0223 |
| N-{[4-({3-[2-(dimethylamino)ethyl]benzene}sulfonyl)phenyl]methyl}imidazo[1,2-a]pyrimidine-6-carboxamide | 0.0035 | 0.1-1 |
| N-{[4-({3-[2-(dimethylamino)ethyl]benzene}sulfonyl)phenyl]methyl}thieno[2,3-c]pyridine-2-carboxamide | 0.0025 | 0.0016 |
| N-{[4-({3-[2-(morpholin-4-yl)ethoxy]benzene}sulfonyl)phenyl]methyl}-1H-pyrrolo[3,2-c]pyridine-2-carboxamide | 0.0649 | 0.0126 |
| N-{[4-({3-[2-(morpholin-4-yl)ethoxy]benzene}sulfonyl)phenyl]methyl}imidazo[1,2-a]pyridine-6-carboxamide | 0.0068 | 0.0034 |
| N-{[4-({3-[2-(morpholin-4-yl)ethoxy]benzene}sulfonyl)phenyl]methyl}imidazo[1,2-a]pyrimidine-6-carboxamide | 0.0031 | 0.0247 |
| N-{[4-({3-[2-(morpholin-4-yl)ethoxy]benzene}sulfonyl)phenyl]methyl}thieno[2,3-c]pyridine-2-carboxamide | 0.0030 | 0.0015 |
| N-{[4-({4-[(1R)-1-hydroxybutyl]benzene}sulfonyl)phenyl]methyl}furo[2,3-c]pyridine-2-carboxamide | 0.0285 | 0.0122 |
| N-{[4-({4-[(1R)-1-hydroxybutyl]benzene}sulfonyl)phenyl]methyl}imidazo[1,2-a]pyrimidine-6-carboxamide | 0.0048 | 0.0142 |
| N-{[4-({4-[(dimethylamino)methyl]benzene}sulfonyl)phenyl]methyl}imidazo[1,2-a]pyrimidine-6-carboxamide | 0.0033 | 0.0246 |
| N-{[4-({4-[(pyrrolidin-1-yl)carbonyl]benzene}sulfonyl)phenyl]methyl}-1H-pyrazolo[3,4-b]pyridine-5-carboxamide | 0.0158 | 0.0093 |
| N-{[4-({4-[(pyrrolidin-1-yl)carbonyl]benzene}sulfonyl)phenyl]methyl}furo[2,3-c]pyridine-2-carboxamide | 0.0015 | 0.0014 |
| N-{[4-({4-[(pyrrolidin-1-yl)carbonyl]benzene}sulfonyl)phenyl]methyl}thieno[2,3-c]pyridine-2-carboxamide | 0.0037 | 0.0017 |
| N-{[4-({4-[2-(dimethylamino)ethyl]benzene}sulfonyl)phenyl]methyl}imidazo[1,2-a]pyridine-6-carboxamide | 0.0021 | 0.0008 |
| N-{[4-({4-[2-(dimethylamino)ethyl]benzene}sulfonyl)phenyl]methyl}imidazo[1,2-a]pyrimidine-6-carboxamide | 0.0020 | 0.0181 |
| N-{[4-({4-[2-(pyrrolidin-1-yl)ethoxy]benzene}sulfonyl)phenyl]methyl}-1H-pyrrolo[3,2-c]pyridine-2-carboxamide | 0.003 | 0.0023 |
| N-{[4-({4-fluoro-3-[(propan-2-yl)carbamoyl]benzene}sulfonyl)phenyl]methyl}-1H-pyrazolo[3,4-b]pyridine-5-carboxamide | 0.0852 | 0.0631 |
| N-{[4-({4-fluoro-3-[(propan-2-yl)carbamoyl]benzene}sulfonyl)phenyl]methyl}imidazo[1,2-a]pyrimidine-6-carboxamide | 0.0077 | 0.0854 |
| N-{[4-({4-fluoro-3-[(propan-2-yl)carbamoyl]benzene}sulfonyl)phenyl]methyl}thieno[2,3-c]pyridine-2-carboxamide | 0.0213 | 0.0068 |
| N-{[4-(1,3-thiazole-2-sulfonyl)phenyl]methyl}furo[2,3-c]pyridine-2-carboxamide | 0.0198 | 0.0786 |
| N-{[4-(1,3-thiazole-2-sulfonyl)phenyl]methyl}imidazo[1,2-a]pyridine-6-carboxamide | 0.021 | 0.0994 |
| N-{[4-(1,3-thiazole-2-sulfonyl)phenyl]methyl}thieno[2,3-c]pyridine-2-carboxamide | 0.0144 | 0.0751 |
| N-{[4-(1,4-dimethyl-1H-imidazole-2-sulfonyl)phenyl]methyl}furo[2,3-c]pyridine-2-carboxamide | 0.0607 | 0.1-1 |
| N-{[4-(1,4-dimethyl-1H-imidazole-2-sulfonyl)phenyl]methyl}imidazo[1,2-a]pyridine-6-carboxamide | 0.1-1 | 0.0954 |
| N-{[4-(1,4-dimethyl-1H-imidazole-2-sulfonyl)phenyl]methyl}imidazo[1,2-a]pyrimidine-6-carboxamide | 0.0316 | 1-10 |

TABLE 3-continued

| IUPAC Name | Biochem IC50 uM | A2780 IC50 uM |
|---|---|---|
| N-{[4-(1,5-dimethyl-1H-imidazole-2-sulfonyl)phenyl]methyl}furo[2,3-c]pyridine-2-carboxamide | 0.0574 | 0.0659 |
| N-{[4-(1,5-dimethyl-1H-imidazole-2-sulfonyl)phenyl]methyl}imidazo[1,2-a]pyridine-6-carboxamide | 0.0309 | 0.0731 |
| N-{[4-(1,5-dimethyl-1H-imidazole-2-sulfonyl)phenyl]methyl}imidazo[1,2-a]pyrimidine-6-carboxamide | 0.0329 | 1-10 |
| N-{[4-(1-benzothiophene-7-sulfonyl)phenyl]methyl}-1H-pyrazolo[3,4-b]pyridine-5-carboxamide | 0.0099 | 0.0128 |
| N-{[4-(1-benzothiophene-7-sulfonyl)phenyl]methyl}furo[2,3-c]pyridine-2-carboxamide | 0.0049 | 0.0139 |
| N-{[4-(1-benzothiophene-7-sulfonyl)phenyl]methyl}thieno[2,3-c]pyridine-2-carboxamide | 0.0015 | 0.0015 |
| N-{[4-(1H-indole-7-sulfonyl)phenyl]methyl}-1H-pyrazolo[3,4-b]pyridine-5-carboxamide | 0.0147 | 0.0432 |
| N-{[4-(1-methyl-1H-1,3-benzodiazole-6-sulfonyl)phenyl]methyl}imidazo[1,2-a]pyrimidine-6-carboxamide | 0.0040 | 0.0338 |
| N-{[4-(1-methyl-1H-indazole-4-sulfonyl)phenyl]methyl}-1,3-benzothiazole-6-carboxamide | 0.0098 | 1-10 |
| N-{[4-(1-methyl-1H-indazole-4-sulfonyl)phenyl]methyl}-1H-pyrazolo[3,4-b]pyridine-5-carboxamide | 0.0203 | 0.0064 |
| N-{[4-(1-methyl-1H-indazole-4-sulfonyl)phenyl]methyl}-1H-pyrrolo[3,2-c]pyridine-2-carboxamide | 0.0031 | 0.0015 |
| N-{[4-(1-methyl-1H-indazole-4-sulfonyl)phenyl]methyl}furo[2,3-c]pyridine-2-carboxamide | 0.0092 | 0.0036 |
| N-{[4-(1-methyl-1H-indazole-4-sulfonyl)phenyl]methyl}imidazo[1,2-a]pyridine-6-carboxamide | 0.0125 | 0.0030 |
| N-{[4-(1-methyl-1H-indazole-4-sulfonyl)phenyl]methyl}imidazo[1,2-a]pyrimidine-6-carboxamide | 0.0042 | 0.0103 |
| N-{[4-(1-methyl-1H-indazole-4-sulfonyl)phenyl]methyl}thieno[2,3-c]pyridine-2-carboxamide | 0.0011 | 0.0008 |
| N-{[4-(1-methyl-1H-indazole-5-sulfonyl)phenyl]methyl}-1H-pyrazolo[3,4-b]pyridine-5-carboxamide | 0.0054 | 0.00273 |
| N-{[4-(1-methyl-1H-indazole-5-sulfonyl)phenyl]methyl}-1H-pyrrolo[3,2-c]pyridine-2-carboxamide | 0.0057 | 0.0031 |
| N-{[4-(1-methyl-1H-indazole-5-sulfonyl)phenyl]methyl}furo[2,3-c]pyridine-2-carboxamide | 0.0033 | 0.0035 |
| N-{[4-(1-methyl-1H-indazole-5-sulfonyl)phenyl]methyl}imidazo[1,2-a]pyridine-6-carboxamide | 0.0040 | 0.0016 |
| N-{[4-(1-methyl-1H-indazole-5-sulfonyl)phenyl]methyl}imidazo[1,2-a]pyrimidine-6-carboxamide | 0.0017 | 0.0049 |
| N-{[4-(1-methyl-1H-indazole-5-sulfonyl)phenyl]methyl}thieno[2,3-c]pyridine-2-carboxamide | 0.0015 | 0.0016 |
| N-{[4-(1-methyl-1H-indazole-6-sulfonyl)phenyl]methyl}-1H-pyrazolo[3,4-b]pyridine-5-carboxamide | 0.004 | 0.0030 |
| N-{[4-(1-methyl-1H-indazole-6-sulfonyl)phenyl]methyl}-1H-pyrrolo[3,2-c]pyridine-2-carboxamide | 0.0051 | 0.0033 |
| N-{[4-(1-methyl-1H-indazole-6-sulfonyl)phenyl]methyl}furo[2,3-c]pyridine-2-carboxamide | 0.0047 | 0.0034 |
| N-{[4-(1-methyl-1H-indazole-6-sulfonyl)phenyl]methyl}imidazo[1,2-a]pyridine-6-carboxamide | 0.0050 | 0.0039 |
| N-{[4-(1-methyl-1H-indazole-6-sulfonyl)phenyl]methyl}imidazo[1,2-a]pyrimidine-6-carboxamide | 0.0016 | 0.0050 |
| N-{[4-(1-methyl-1H-indazole-6-sulfonyl)phenyl]methyl}thieno[2,3-c]pyridine-2-carboxamide | 0.0023 | 0.0011 |
| N-{[4-(1-methyl-1H-indazole-7-sulfonyl)phenyl]methyl}-1H-pyrazolo[3,4-b]pyridine-5-carboxamide | 0.0918 | 0.0869 |
| N-{[4-(1-methyl-1H-indazole-7-sulfonyl)phenyl]methyl}-1H-pyrrolo[3,2-c]pyridine-2-carboxamide | 0.0371 | 0.0111 |
| N-{[4-(1-methyl-1H-indazole-7-sulfonyl)phenyl]methyl}furo[2,3-c]pyridine-2-carboxamide | 0.0115 | 0.0275 |
| N-{[4-(1-methyl-1H-indazole-7-sulfonyl)phenyl]methyl}imidazo[1,2-a]pyridine-6-carboxamide | 0.0287 | 0.0275 |
| N-{[4-(1-methyl-1H-indazole-7-sulfonyl)phenyl]methyl}imidazo[1,2-a]pyrimidine-6-carboxamide | 0.0233 | 0.1-1 |
| N-{[4-(1-methyl-1H-indazole-7-sulfonyl)phenyl]methyl}thieno[2,3-c]pyridine-2-carboxamide | 0.0045 | 0.0104 |
| N-{[4-(1-methyl-1H-indole-2-sulfonyl)phenyl]methyl}-1H-pyrazolo[3,4-b]pyridine-5-carboxamide | 0.0140 | 0.0132 |
| N-{[4-(1-methyl-1H-indole-2-sulfonyl)phenyl]methyl}thieno[2,3-c]pyridine-2-carboxamide | 0.0052 | 0.0034 |
| N-{[4-(1-methyl-1H-pyrazole-4-sulfonyl)phenyl]methyl}-1H-pyrazolo[3,4-b]pyridine-5-carboxamide | 0.182 | 0.1-1 |
| N-{[4-(1-methyl-1H-pyrazole-4-sulfonyl)phenyl]methyl}furo[2,3-c]pyridine-2-carboxamide | 0.0168 | 0.0654 |
| N-{[4-(1-methyl-1H-pyrazole-4-sulfonyl)phenyl]methyl}imidazo[1,2-a]pyrimidine-6-carboxamide | 0.0082 | 0.1-1 |

TABLE 3-continued

| IUPAC Name | Biochem IC50 uM | A2780 IC50 uM |
|---|---|---|
| N-{[4-(1-propyl-1H-pyrazole-4-sulfonyl)phenyl]methyl}-1H-pyrazolo[3,4-b]pyridine-5-carboxamide | 0.008 | 0.0070 |
| N-{[4-(1-propyl-1H-pyrazole-4-sulfonyl)phenyl]methyl}-1H-pyrrolo[3,2-c]pyridine-2-carboxamide | 0.0149 | 0.0059 |
| N-{[4-(1-propyl-1H-pyrazole-4-sulfonyl)phenyl]methyl}furo[2,3-c]pyridine-2-carboxamide | 0.0057 | 0.0064 |
| N-{[4-(1-propyl-1H-pyrazole-4-sulfonyl)phenyl]methyl}imidazo[1,2-a]pyridine-6-carboxamide | 0.0049 | 0.0052 |
| N-{[4-(1-propyl-1H-pyrazole-4-sulfonyl)phenyl]methyl}thieno[2,3-c]pyridine-2-carboxamide | 0.0019 | 0.0016 |
| N-{[4-(2,3-dihydro-1,4-benzodioxine-6-sulfonyl)phenyl]methyl}furo[2,3-c]pyridine-2-carboxamide | 0.0055 | 0.0062 |
| N-{[4-(2,3-dihydro-1,4-benzodioxine-6-sulfonyl)phenyl]methyl}imidazo[1,2-a]pyrimidine-6-carboxamide | 0.0002 | 0.0005 |
| N-{[4-(2,3-dihydro-1-benzofuran-7-sulfonyl)phenyl]methyl}-1H-pyrazolo[3,4-b]pyridine-5-carboxamide | 0.0248 | 0.0147 |
| N-{[4-(2,3-dihydro-1-benzofuran-7-sulfonyl)phenyl]methyl}-1H-pyrrolo[3,2-c]pyridine-2-carboxamide | 0.0140 | 0.0038 |
| N-{[4-(2,3-dihydro-1-benzofuran-7-sulfonyl)phenyl]methyl}furo[2,3-c]pyridine-2-carboxamide | 0.0060 | 0.0071 |
| N-{[4-(2,3-dihydro-1-benzofuran-7-sulfonyl)phenyl]methyl}imidazo[1,2-a]pyridine-6-carboxamide | 0.0125 | 0.0064 |
| N-{[4-(2,3-dihydro-1-benzofuran-7-sulfonyl)phenyl]methyl}imidazo[1,2-a]pyrimidine-6-carboxamide | 0.0021 | 0.0258 |
| N-{[4-(2,3-dihydro-1-benzofuran-7-sulfonyl)phenyl]methyl}thieno[2,3-c]pyridine-2-carboxamide | 0.0022 | 0.0030 |
| N-{[4-(2,6-dimethoxypyridine-3-sulfonyl)phenyl]methy}-1H-pyrazolo[3,4-b]pyridine-5-carboxamide | 0.0307 | 0.0020 |
| N-{[4-(2,6-dimethoxypyridine-3-sulfonyl)phenyl]methyl}furo[2,3-c]pyridine-2-carboxamide | 0.0066 | 0.011 |
| N-{[4-(2,6-dimethoxypyridine-3-sulfonyl)phenyl]methyl}imidazo[1,2-a]pyridine-6-carboxamide | 0.0433 | 0.0092 |
| N-{[4-(2H-1,3-benzodioxole-4-sulfonyl)phenyl]methyl}-1H-pyrazolo[3,4-b]pyridine-5-carboxamide | 0.047 | 0.0884 |
| N-{[4-(2H-1,3-benzodioxole-4-sulfonyl)phenyl]methyl}-1H-pyrrolo[3,2-c]pyridine-2-carboxamide | 0.0205 | 0.0118 |
| N-{[4-(2H-1,3-benzodioxole-4-sulfonyl)phenyl]methyl}furo[2,3-c]pyridine-2-carboxamide | 0.0258 | 0.0266 |
| N-{[4-(2H-1,3-benzodioxole-4-sulfonyl)phenyl]methyl}imidazo[1,2-a]pyridine-6-carboxamide | 0.0071 | 0.0130 |
| N-{[4-(2H-1,3-benzodioxole-4-sulfonyl)phenyl]methyl}imidazo[1,2-a]pyrimidine-6-carboxamide | 0.0029 | 0.0933 |
| N-{[4-(2H-1,3-benzodioxole-4-sulfonyl)phenyl]methyl}thieno[2,3-c]pyridine-2-carboxamide | 0.0033 | 0.0072 |
| N-{[4-(2H-1,3-benzodioxole-5-sulfonyl)phenyl]methyl}-1H-pyrazolo[3,4-b]pyridine-5-carboxamide | 0.0482 | 0.0074 |
| N-{[4-(2H-1,3-benzodioxole-5-sulfonyl)phenyl]methyl}furo[2,3-c]pyridine-2-carboxamide | 0.0053 | 0.0087 |
| N-{[4-(2H-1,3-benzodioxole-5-sulfonyl)phenyl]methyl}imidazo[1,2-a]pyridine-6-carboxamide | 0.0107 | 0.00533 |
| N-{[4-(2H-1,3-benzodioxole-5-sulfonyl)phenyl]methyl}imidazo[1,2-a]pyrimidine-6-carboxamide | 0.0030 | 0.0117 |
| N-{[4-(2-methyl-1,3-thiazole-4-sulfonyl)phenyl]methyl}-1H-pyrazolo[3,4-b]pyridine-5-carboxamide | 0.0828 | 0.0207 |
| N-{[4-(2-methyl-1,3-thiazole-4-sulfonyl)phenyl]methyl}furo[2,3-c]pyridine-2-carboxamide | 0.0367 | 0.0690 |
| N-{[4-(2-methyl-1,3-thiazole-4-sulfonyl)phenyl]methyl}imidazo[1,2-a]pyrimidine-6-carboxamide | 0.0286 | 1-10 |
| N-{[4-(2-methyl-2H-indazole-5-sulfonyl)phenyl]methyl}imidazo[1,2-a]pyridine-6-carboxamide | 0.0133 | 0.0058 |
| N-{[4-(2-methyl-2H-indazole-5-sulfonyl)phenyl]methyl}imidazo[1,2-a]pyrimidine-6-carboxamide | 0.0012 | 0.0082 |
| N-{[4-(2-methyl-2H-indazole-5-sulfonyl)phenyl]methyl}thieno[2,3-c]pyridine-2-carboxamide | 0.0055 | 0.0033 |
| N-{[4-(2-methyl-2H-indazole-6-sulfonyl)phenyl]methyl}-1H-pyrazolo[3,4-b]pyridine-5-carboxamide | 0.0147 | 0.0070 |
| N-{[4-(2-methyl-2H-indazole-6-sulfonyl)phenyl]methyl}-1H-pyrrolo[3,2-c]pyridine-2-carboxamide | 0.0025 | 0.0032 |
| N-{[4-(2-methyl-2H-indazole-6-sulfonyl)phenyl]methyl}furo[2,3-c]pyridine-2-carboxamide | 0.0034 | 0.0028 |
| N-{[4-(2-methyl-2H-indazole-6-sulfonyl)phenyl]methyl}imidazo[1,2-a]pyridine-6-carboxamide | 0.0019 | 0.0017 |
| N-{[4-(2-methyl-2H-indazole-6-sulfonyl)phenyl]methyl}imidazo[1,2-a]pyrimidine-6-carboxamide | 0.0012 | 0.0061 |
| N-{[4-(2-methyl-2H-indazole-6-sulfonyl)phenyl]methyl}thieno[2,3-c]pyridine-2-carboxamide | 0.0014 | 0.0015 |

TABLE 3-continued

| IUPAC Name | Biochem IC50 uM | A2780 IC50 uM |
|---|---|---|
| N-{[4-(2-methylpyridine-3-sulfonyl)phenyl]methyl}-1H-pyrazolo[3,4-b]pyridine-5-carboxamide | 0.1045 | 0.1356 |
| N-{[4-(2-methylpyridine-3-sulfonyl)phenyl]methyl}-1H-pyrrolo[3,2-c]pyridine-2-carboxamide | 0.1803 | 0.0240 |
| N-{[4-(2-methylpyridine-3-sulfonyl)phenyl]methyl}imidazo[1,2-a]pyrimidine-6-carboxamide | 0.0208 | 0.1-1 |
| N-{[4-(2-methylpyridine-3-sulfonyl)phenyl]methyl}thieno[2,3-c]pyridine-2-carboxamide | 0.0154 | 0.0119 |
| N-{[4-(4-methylpyridine-2-sulfonyl)phenyl]methyl}furo[2,3-c]pyridine-2-carboxamide | 0.0192 | 0.0114 |
| N-{[4-(4-methylpyridine-3-sulfonyl)phenyl]methyl}-1H-pyrazolo[3,4-b]pyridine-5-carboxamide | 0.1-1 | 0.2714 |
| N-{[4-(4-methylpyridine-3-sulfonyl)phenyl]methyl}-1H-pyrrolo[3,2-c]pyridine-2-carboxamide | 0.2599 | 0.0258 |
| N-{[4-(4-methylpyridine-3-sulfonyl)phenyl]methyl}furo[2,3-c]pyridine-2-carboxamide | 0.0252 | 0.062 |
| N-{[4-(4-methylpyridine-3-sulfonyl)phenyl]methyl}imidazo[1,2-a]pyridine-6-carboxamide | 0.0665 | 0.0658 |
| N-{[4-(4-methylpyridine-3-sulfonyl)phenyl]methyl}imidazo[1,2-a]pyrimidine-6-carboxamide | 0.0191 | 0.1-1 |
| N-{[4-(4-methylpyridine-3-sulfonyl)phenyl]methyl}thieno[2,3-c]pyridine-2-carboxamide | 0.0292 | 0.0225 |
| N-{[4-(4-methylthiophene-2-sulfonyl)phenyl]methyl}imidazo[1,2-a]pyridine-6-carboxamide | 0.0124 | 0.0125 |
| N-{[4-(5-chloro-3-methylpyridine-2-sulfonyl)phenyl]methyl}-1H-pyrazolo[3,4-b]pyridine-5-carboxamide | 0.0625 | 0.0753 |
| N-{[4-(5-chloro-3-methylpyridine-2-sulfonyl)phenyl]methyl}furo[2,3-c]pyridine-2-carboxamide | 0.0099 | 0.0165 |
| N-{[4-(5-chloro-3-methylpyridine-2-sulfonyl)phenyl]methyl}imidazo[1,2-a]pyridine-6-carboxamide | 0.0188 | 0.0080 |
| N-{[4-(5-chloro-3-methylpyridine-2-sulfonyl)phenyl]methyl}imidazo[1,2-a]pyrimidine-6-carboxamide | 0.0022 | 0.0220 |
| N-{[4-(5-chloro-3-methylpyridine-2-sulfonyl)phenyl]methyl}thieno[2,3-c]pyridine-2-carboxamide | 0.0039 | 0.0072 |
| N-{[4-(5-chloropyridine-3-sulfonyl)phenyl]methyl}-1H-pyrazolo[3,4-b]pyridine-5-carboxamide | 0.0238 | 0.0062 |
| N-{[4-(5-chloropyridine-3-sulfonyl)phenyl]methyl}-1H-pyrrolo[3,2-c]pyridine-2-carboxamide | 0.0200 | 0.0036 |
| N-{[4-(5-chloropyridine-3-sulfonyl)phenyl]methyl}imidazo[1,2-a]pyridine-6-carboxamide | 0.0244 | 0.0032 |
| N-{[4-(5-fluoro-6-methylpyridine-2-sulfonyl)phenyl]methyl}furo[2,3-c]pyridine-2-carboxamide | 0.0062 | 0.0124 |
| N-{[4-(5-fluoro-6-methylpyridine-2-sulfonyl)phenyl]methyl}thieno[2,3-c]pyridine-2-carboxamide | 0.0083 | 0.0071 |
| N-{[4-(5-fluoropyridine-3-sulfonyl)phenyl]methyl}-1H-pyrazolo[3,4-b]pyridine-5-carboxamide | 0.0792 | 0.0254 |
| N-{[4-(5-fluoropyridine-3-sulfonyl)phenyl]methyl}-1H-pyrrolo[3,2-c]pyridine-2-carboxamide | 0.0713 | 0.0136 |
| N-{[4-(5-fluoropyridine-3-sulfonyl)phenyl]methyl}imidazo[1,2-a]pyridine-6-carboxamide | 0.0278 | 0.0137 |
| N-{[4-(5-fluoropyridine-3-sulfonyl)phenyl]methyl}imidazo[1,2-a]pyrimidine-6-carboxamide | 0.0067 | 0.0564 |
| N-{[4-(5-fluoropyridine-3-sulfonyl)phenyl]methyl}thieno[2,3-c]pyridine-2-carboxamide | 0.0097 | 0.0064 |
| N-{[4-(5-methoxypyridine-2-sulfonyl)phenyl]methyl}furo[2,3-c]pyridine-2-carboxamide | 0.0079 | 0.0316 |
| N-{[4-(5-methoxypyridine-2-sulfonyl)phenyl]methyl}imidazo[1,2-a]pyridine-6-carboxamide | 0.0229 | 0.0173 |
| N-{[4-(5-methoxypyridine-2-sulfonyl)phenyl]methyl}thieno[2,3-c]pyridine-2-carboxamide | 0.0071 | 0.0193 |
| N-{[4-(5-methoxypyridine-3-sulfonyl)phenyl]methyl}-1H-pyrazolo[3,4-b]pyridine-5-carboxamide | 0.0414 | 0.0167 |
| N-{[4-(5-methoxypyridine-3-sulfonyl)phenyl]methyl}imidazo[1,2-a]pyridine-6-carboxamide | 0.0090 | 0.0034 |
| N-{[4-(5-methoxypyridine-3-sulfonyl)phenyl]methyl}imidazo[1,2-a]pyrimidine-6-carboxamide | 0.0016 | 0.0258 |
| N-{[4-(5-methoxypyridine-3-sulfonyl)phenyl]methyl}thieno[2,3-c]pyridine-2-carboxamide | 0.0090 | 0.0016 |
| N-{[4-(5-methylpyridine-3-sulfonyl)phenyl]methyl}imidazo[1,2-a]pyridine-6-carboxamide | 0.0368 | 0.0071 |
| N-{[4-(5-methylpyridine-3-sulfonyl)phenyl]methyl}imidazo[1,2-a]pyrimidine-6-carboxamide | 0.0022 | 0.0124 |
| N-{[4-(5-methylpyridine-3-sulfonyl)phenyl]methyl}thieno[2,3-c]pyridine-2-carboxamide | 0.0060 | 0.0025 |
| N-{[4-(5-methylthiophene-2-sulfonyl)phenyl]methyl}-1H-pyrazolo[3,4-b]pyridine-5-carboxamide | 0.0223 | 0.0347 |

TABLE 3-continued

| IUPAC Name | Biochem IC50 uM | A2780 IC50 uM |
|---|---|---|
| N-{[4-(6-methoxynaphthalene-2-sulfonyl)phenyl]methyl}-1H-pyrrolo[3,2-c]pyridine-2-carboxamide | 0.0099 | 0.0051 |
| N-{[4-(6-methoxynaphthalene-2-sulfonyl)phenyl]methyl}furo[2,3-c]pyridine-2-carboxamide | 0.0030 | 0.0036 |
| N-{[4-(6-methoxynaphthalene-2-sulfonyl)phenyl]methyl}imidazo[1,2-a]pyridine-6-carboxamide | 0.0027 | 0.0018 |
| N-{[4-(6-methoxynaphthalene-2-sulfonyl)phenyl]methyl}thieno[2,3-c]pyridine-2-carboxamide | 0.0015 | 0.0033 |
| N-{[4-(6-methoxypyridine-2-sulfonyl)phenyl]methyl}furo[2,3-c]pyridine-2-carboxamide | 0.0025 | 0.0032 |
| N-{[4-(6-methoxypyridine-2-sulfonyl)phenyl]methyl}imidazo[1,2-a]pyridine-6-carboxamide | 0.0052 | 0.0013 |
| N-{[4-(6-methoxypyridine-2-sulfonyl)phenyl]methyl}imidazo[1,2-a]pyrimidine-6-carboxamide | 0.0022 | 0.0059 |
| N-{[4-(6-methylpyrazine-2-sulfonyl)phenyl]methyl}-1H-pyrazolo[3,4-b]pyridine-5-carboxamide | 0.0349 | 0.0312 |
| N-{[4-(6-methylpyrazine-2-sulfonyl)phenyl]methyl}furo[2,3-c]pyridine-2-carboxamide | 0.0209 | 0.0097 |
| N-{[4-(6-methylpyrazine-2-sulfonyl)phenyl]methyl}imidazo[1,2-a]pyrimidine-6-carboxamide | 0.0010 | 0.0525 |
| N-{[4-(6-methylpyrazine-2-sulfonyl)phenyl]methyl}thieno[2,3-c]pyridine-2-carboxamide | 0.0048 | 0.0051 |
| N-{[4-(6-methylpyridine-2-sulfonyl)phenyl]methyl}furo[2,3-c]pyridine-2-carboxamide | 0.0128 | 0.0125 |
| N-{[4-(6-methylpyridine-3-sulfonyl)phenyl]methyl}-1H-pyrazolo[3,4-b]pyridine-5-carboxamide | 0.0241 | 0.0213 |
| N-{[4-(6-methylpyridine-3-sulfonyl)phenyl]methyl}-1H-pyrrolo[3,2-c]pyridine-2-carboxamide | 0.0557 | 0.0130 |
| N-{[4-(6-methylpyridine-3-sulfonyl)phenyl]methyl}imidazo[1,2-a]pyridine-6-carboxamide | 0.0215 | 0.0139 |
| N-{[4-(6-methylpyridine-3-sulfonyl)phenyl]methyl}imidazo[1,2-a]pyrimidine-6-carboxamide | 0.0059 | 0.0555 |
| N-{[4-(6-methylpyridine-3-sulfonyl)phenyl]methyl}thieno[2,3-c]pyridine-2-carboxamide | 0.0220 | 0.0063 |
| N-{[4-(benzenesulfonyl)phenyl]methyl}-[1,3]thiazolo[5,4-c]pyridine-2-carboxamide | 0.220 | >10 |
| N-{[4-(benzenesulfonyl)phenyl]methyl}-1,6-naphthyridine-2-carboxamide | 2.85 | >10 |
| N-{[4-(benzenesulfonyl)phenyl]methyl}-1H-pyrrolo[3,2-c]pyridine-3-carboxamide | 1.91 | 2.06 |
| N-{[4-(benzenesulfonyl)phenyl]methyl}furo[2,3-c]pyridine-2-carboxamide | 0.007 | 0.0088 |
| N-{[4-(benzenesulfonyl)phenyl]methyl}imidazo[1,2-a]pyrimidine-6-carboxamide | 0.002 | 0.057 |
| N-{[4-(benzenesulfonyl)phenyl]methyl}quinoline-6-carboxamide | 0.108 | >10 |
| N-{[4-(cyclohexanesulfonyl)phenyl]methyl}-1H-pyrrolo[3,2-c]pyridine-2-carboxamide | 0.005 | 0.0176 |
| N-{[4-(dimethyl-1,3-thiazole-5-sulfonyl)phenyl]methyl}-1H-pyrazolo[3,4-b]pyridine-5-carboxamide | 0.0386 | 0.0164 |
| N-{[4-(dimethyl-1,3-thiazole-5-sulfonyl)phenyl]methyl}furo[2,3-c]pyridine-2-carboxamide | 0.0083 | 0.0103 |
| N-{[4-(dimethyl-1,3-thiazole-5-sulfonyl)phenyl]methyl}imidazo[1,2-a]pyridine-6-carboxamide | 0.009 | 0.0037 |
| N-{[4-(dimethyl-1,3-thiazole-5-sulfonyl)phenyl]methyl}imidazo[1,2-a]pyrimidine-6-carboxamide | 0.0037 | 0.0495 |
| N-{[4-(dimethyl-1,3-thiazole-5-sulfonyl)phenyl]methyl}thieno[2,3-c]pyridine-2-carboxamide | 0.0013 | 0.0030 |
| N-{[4-(furan-2-sulfonyl)phenyl]methyl}imidazo[1,2-a]pyridine-6-carboxamide | 0.0762 | 0.1-1 |
| N-{[4-(isoquinoline-4-sulfonyl)phenyl]methyl}-1H-pyrazolo[3,4-b]pyridine-5-carboxamide | 0.0037 | 0.0025 |
| N-{[4-(isoquinoline-4-sulfonyl)phenyl]methyl}-1H-pyrrolo[3,2-c]pyridine-2-carboxamide | 0.0109 | 0.0016 |
| N-{[4-(isoquinoline-4-sulfonyl)phenyl]methyl}furo[2,3-c]pyridine-2-carboxamide | 0.0190 | 0.003 |
| N-{[4-(isoquinoline-4-sulfonyl)phenyl]methyl}imidazo[1,2-a]pyridine-6-carboxamide | 0.0224 | 0.0041 |
| N-{[4-(isoquinoline-4-sulfonyl)phenyl]methyl}imidazo[1,2-a]pyrimidine-6-carboxamide | 0.0016 | 0.0032 |
| N-{[4-(isoquinoline-4-sulfonyl)phenyl]methyl}thieno[2,3-c]pyridine-2-carboxamide | 0.0067 | 0.0008 |
| N-{[4-(naphthalene-1-sulfonyl)phenyl]methyl}-1H-pyrazolo[3,4-b]pyridine-5-carboxamide | 0.0091 | 0.00368 |
| N-{[4-(naphthalene-1-sulfonyl)phenyl]methyl}furo[2,3-c]pyridine-2-carboxamide | 0.0049 | 0.0031 |

TABLE 3-continued

| IUPAC Name | Biochem IC50 uM | A2780 IC50 uM |
|---|---|---|
| N-{[4-(naphthalene-1-sulfonyl)phenyl]methyl}imidazo[1,2-a]pyrimidine-6-carboxamide | 0.0029 | 0.0036 |
| N-{[4-(phenoxathiine-4-sulfonyl)phenyl]methyl}-1H-pyrazolo[3,4-b]pyridine-5-carboxamide | 0.0148 | 0.0204 |
| N-{[4-(phenoxathiine-4-sulfonyl)phenyl]methyl}furo[2,3-c]pyridine-2-carboxamide | 0.0056 | 0.0131 |
| N-{[4-(phenoxathiine-4-sulfonyl)phenyl]methyl}imidazo[1,2-a]pyridine-6-carboxamide | 0.00215 | 0.00218 |
| N-{[4-(phenoxathiine-4-sulfonyl)phenyl]methyl}imidazo[1,2-a]pyrimidine-6-carboxamide | 0.0021 | 0.0042 |
| N-{[4-(pyridine-2-sulfonyl)phenyl]methyl}furo[2,3-c]pyridine-2-carboxamide | 0.0551 | 0.0870 |
| N-{[4-(pyridine-3-sulfonyl)phenyl]methyl}furo[2,3-c]pyridine-2-carboxamide | 0.0090 | 0.0664 |
| N-{[4-(pyridine-3-sulfonyl)phenyl]methyl}imidazo[1,2-a]pyrimidine-6-carboxamide | 0.0059 | 0.1-1 |
| N-{[4-(quinoline-3-sulfonyl)phenyl]methyl}-1H-pyrazolo[3,4-b]pyridine-5-carboxamide | 0.0052 | 0.0044 |
| N-{[4-(quinoline-3-sulfonyl)phenyl]methyl}-1H-pyrrolo[3,2-c]pyridine-2-carboxamide | 0.0163 | 0.0029 |
| N-{[4-(quinoline-3-sulfonyl)phenyl]methyl}furo[2,3-c]pyridine-2-carboxamide | 0.0042 | 0.0032 |
| N-{[4-(quinoline-3-sulfonyl)phenyl]methyl}imidazo[1,2-a]pyridine-6-carboxamide | 0.014 | 0.001 |
| N-{[4-(quinoline-3-sulfonyl)phenyl]methyl}imidazo[1,2-a]pyrimidine-6-carboxamide | 0.0025 | 0.0036 |
| N-{[4-(quinoline-3-sulfonyl)phenyl]methyl}thieno[2,3-c]pyridine-2-carboxamide | 0.0044 | 0.0009 |
| N-{[4-(quinoline-6-sulfonyl)phenyl]methyl}-1H-pyrazolo[3,4-b]pyridine-5-carboxamide | 0.0101 | 0.0041 |
| N-{[4-(quinoline-6-sulfonyl)phenyl]methyl}furo[2,3-c]pyridine-2-carboxamide | 0.0073 | 0.005 |
| N-{[4-(quinoline-6-sulfonyl)phenyl]methyl}imidazo[1,2-a]pyridine-6-carboxamide | 0.00516 | 0.00083 |
| N-{[4-(quinoline-6-sulfonyl)phenyl]methyl}imidazo[1,2-a]pyrimidine-6-carboxamide | 0.0033 | 0.0056 |
| N-{[4-(quinoline-8-sulfonyl)phenyl]methyl}-1H-pyrazolo[3,4-b]pyridine-5-carboxamide | 0.0455 | 0.0236 |
| N-{[4-(quinoline-8-sulfonyl)phenyl]methyl}furo[2,3-c]pyridine-2-carboxamide | 0.0076 | 0.0060 |
| N-{[4-(quinoline-8-sulfonyl)phenyl]methyl}imidazo[1,2-a]pyridine-6-carboxamide | 0.0098 | 0.0055 |
| N-{[4-(quinoline-8-sulfonyl)phenyl]methyl}imidazo[1,2-a]pyrimidine-6-carboxamide | 0.0030 | 0.0277 |
| N-({4-[(2,4-dimethoxyphenyl)sulfamoyl]phenyl}methyl)-1H-pyrrolo[3,2-c]pyridine-2-carboxamide | 0.0058 | 0.0069 |
| N-[(4-{[2-(2-hydroxyethyl)phenyl]sulfamoyl}phenyl)methyl]-1H-pyrrolo[3,2-c]pyridine-2-carboxamide | 0.0188 | 0.0199 |
| N-({4-[(5-fluoro-2-methoxyphenyl)sulfamoyl]phenyl}methyl)quinoline-6-carboxamide | 0.0660 | 1-10 |
| N-({4-[(2,3,6-trimethoxybenzene)sulfonyl]phenyl}methyl)thieno[2,3-c]pyridine-2-carboxamide | 0.012 | 0.0055 |
| N-({4-[(2,3-dimethoxy-5-methylbenzene)sulfonyl]phenyl}methyl)-1H-pyrrolo[3,2-c]pyridine-2-carboxamide | 0.010 | 0.002 |
| N-({4-[(2,3-dimethoxy-5-methylbenzene)sulfonyl]phenyl}methyl)thieno[2,3-c]pyridine-2-carboxamide | 0.006 | 0.0027 |
| N-({4-[(2,3-dimethoxybenzene)sulfonyl]phenyl}methyl)thieno[2,3-c]pyridine-2-carboxamide | 0.009 | 0.0034 |
| N-({4-[(2,3-dimethylbenzene)sulfonyl]phenyl}methyl)-1H-pyrrolo[3,2-c]pyridine-2-carboxamide | 0.014 | 0.007 |
| N-({4-[(2,3-dimethylbenzene)sulfonyl]phenyl}methyl)thieno[2,3-c]pyridine-2-carboxamide | 0.011 | 0.0044 |
| N-({4-[(2,4,5-trimethylbenzene)sulfonyl]phenyl}methyl)thieno[2,3-c]pyridine-2-carboxamide | 0.008 | 0.0081 |
| N-({4-[(2,4,6-trimethylbenzene)sulfonyl]phenyl}methyl)-1H-pyrrolo[3,2-c]pyridine-2-carboxamide | 0.076 | 0.046 |
| N-({4-[(2,4-dimethoxybenzene)sulfonyl]phenyl}methyl)-1H-pyrrolo[3,2-c]pyridine-2-carboxamide | 0.027 | 0.007 |
| N-({4-[(2,4-dimethylbenzene)sulfonyl]phenyl}methyl)-1H-pyrrolo[3,2-c]pyridine-2-carboxamide | 0.021 | 0.012 |

TABLE 3-continued

| IUPAC Name | Biochem IC50 uM | A2780 IC50 uM |
|---|---|---|
| N-({4-[(2,4-dimethylbenzene)sulfonyl]phenyl}methyl)thieno[2,3-c]pyridine-2-carboxamide | 0.012 | 0.0222 |
| N-({4-[(2,5-dimethoxybenzene)sulfonyl]phenyl}methyl)-1H-pyrrolo[3,2-c]pyridine-2-carboxamide | 0.017 | 0.006 |
| N-({4-[(2,5-dimethoxybenzene)sulfonyl]phenyl}methyl)thieno[2,3-c]pyridine-2-carboxamide | 0.004 | 0.0023 |
| N-({4-[(2,5-dimethylbenzene)sulfonyl]phenyl}methyl)-1H-pyrrolo[3,2-c]pyridine-2-carboxamide | 0.011 | 0.014 |
| N-({4-[(2,5-dimethylbenzene)sulfonyl]phenyl}methyl)thieno[2,3-c]pyridine-2-carboxamide | 0.011 | 0.0086 |
| N-({4-[(2,6-dimethoxy-4-methylbenzene)sulfonyl]phenyl}methyl)-1H-pyrrolo[3,2-c]pyridine-2-carboxamide | 0.016 | 0.010 |
| N-({4-[(2,6-dimethoxy-4-methylbenzene)sulfonyl]phenyl}methyl)thieno[2,3-c]pyridine-2-carboxamide | 0.007 | 0.0030 |
| N-({4-[(2-acetylbenzene)sulfonyl]phenyl}methyl)-1H-pyrrolo[3,2-c]pyridine-2-carboxamide | 0.006 | 0.004 |
| N-({4-[(2-acetylbenzene)sulfonyl]phenyl}methyl)thieno[2,3-c]pyridine-2-carboxamide | 0.001 | 0.0010 |
| N-({4-[(2-chloro-6-methoxybenzene)sulfonyl]phenyl}methyl)-1H-pyrrolo[3,2-c]pyridine-2-carboxamide | 0.013 | 0.003 |
| N-({4-[(2-chlorobenzene)sulfonyl]phenyl}methyl)-1H-pyrrolo[3,2-c]pyridine-2-carboxamide | 0.006 | 0.117 |
| N-({4-[(2-ethoxybenzene)sulfonyl]phenyl}methyl)-1H-pyrrolo[3,2-c]pyridine-2-carboxamide | 0.011 | 0.002 |
| N-({4-[(2-ethoxybenzene)sulfonyl]phenyl}methyl)thieno[2,3-c]pyridine-2-carboxamide | 0.002 | 0.0008 |
| N-({4-[(2-ethylbenzene)sulfonyl]phenyl}methyl)-1H-pyrrolo[3,2-c]pyridine-2-carboxamide | 0.005 | 0.003 |
| N-({4-[(2-ethylbenzene)sulfonyl]phenyl}methyl)thieno[2,3-c]pyridine-2-carboxamide | 0.005 | 0.0029 |
| N-({4-[(2-fluoro-3-methoxybenzene)sulfonyl]phenyl}methyl)-1H-pyrrolo[3,2-c]pyridine-2-carboxamide | 0.010 | 0.007 |
| N-({4-[(2-fluoro-4-methylbenzene)sulfonyl]phenyl}methyl)-1H-pyrrolo[3,2-c]pyridine-2-carboxamide | 0.011 | 0.021 |
| N-({4-[(2-fluoro-4-methylbenzene)sulfonyl]phenyl}methyl)thieno[2,3-c]pyridine-2-carboxamide | 0.008 | 0.0207 |
| N-({4-[(2-fluoro-5-methylbenzene)sulfonyl]phenyl}methyl)-1H-pyrrolo[3,2-c]pyridine-2-carboxamide | 0.025 | 0.024 |
| N-({4-[(2-methanesulfonamidobenzene)sulfonyl]phenyl}methyl)-1H-pyrrolo[3,2-c]pyridine-2-carboxamide | 0.284 | >1 |
| N-({4-[(2-methoxy-5-methylbenzene)sulfonyl]phenyl}methyl)-1H-pyrrolo[3,2-c]pyridine-2-carboxamide | 0.012 | 0.003 |
| N-({4-[(2-methoxy-5-methylbenzene)sulfonyl]phenyl}methyl)thieno[2,3-c]pyridine-2-carboxamide | 0.006 | 0.0025 |
| N-({4-[(2-methoxybenzene)sulfonyl]phenyl}methyl)-1H-pyrrolo[3,2-c]pyridine-2-carboxamide | 0.009 | 0.007 |
| N-({4-[(2-methoxybenzene)sulfonyl]phenyl}methyl)thieno[2,3-c]pyridine-2-carboxamide | 0.007 | 0.0053 |
| N-({4-[(2-methylbenzene)sulfonyl]phenyl}methyl)-1H-pyrrolo[3,2-c]pyridine-2-carboxamide | 0.014 | 0.013 |
| N-({4-[(2-methylbenzene)sulfonyl]phenyl}methyl)thieno[2,3-c]pyridine-2-carboxamide | 0.010 | 0.0222 |
| N-({4-[(2-phenoxybenzene)sulfonyl]phenyl}methyl)-1H-pyrrolo[3,2-c]pyridine-2-carboxamide | 0.011 | 0.007 |
| N-({4-[(2-phenoxybenzene)sulfonyl]phenyl}methyl)thieno[2,3-c]pyridine-2-carboxamide | 0.011 | 0.0697 |
| N-({4-[(2-phenylethane)sulfonyl]phenyl}methyl)-1H-pyrrolo[3,2-c]pyridine-2-carboxamide | 0.011 | 0.022 |
| N-({4-[(3,4-difluorobenzene)sulfonyl]phenyl}methyl)-1H-pyrrolo[3,2-c]pyridine-2-carboxamide | 0.013 | 0.014 |
| N-({4-[(3,4-difluorobenzene)sulfonyl]phenyl}methyl)thieno[2,3-c]pyridine-2-carboxamide | 0.009 | 0.0081 |
| N-({4-[(3,4-dimethoxybenzene)sulfonyl]phenyl}methyl)-1H-pyrrolo[3,2-c]pyridine-2-carboxamide | 0.014 | 0.003 |
| N-({4-[(3,4-dimethoxybenzene)sulfonyl]phenyl}methyl)thieno[2,3-c]pyridine-2-carboxamide | 0.003 | 0.0009 |
| N-({4-[(3,4-dimethylbenzene)sulfonyl]phenyl}methyl)thieno[2,3-c]pyridine-2-carboxamide | 0.006 | 0.0023 |
| N-({4-[(3,5-dichlorobenzene)sulfonyl]phenyl}methyl)thieno[2,3-c]pyridine-2-carboxamide | 0.006 | 0.0007 |

TABLE 3-continued

| IUPAC Name | Biochem IC50 uM | A2780 IC50 uM |
|---|---|---|
| N-({4-[(3,5-difluorobenzene)sulfonyl]phenyl}methyl)-1H-pyrrolo[3,2-c]pyridine-2-carboxamide | 0.011 | 0.007 |
| N-({4-[(3,5-difluorobenzene)sulfonyl]phenyl}methyl)thieno[2,3-c]pyridine-2-carboxamide | 0.004 | 0.0027 |
| N-({4-[(3,5-dimethylbenzene)sulfonyl]phenyl}methyl)-1H-pyrrolo[3,2-c]pyridine-2-carboxamide | 0.009 | 0.002 |
| N-({4-[(3,5-dimethylbenzene)sulfonyl]phenyl}methyl)thieno[2,3-c]pyridine-2-carboxamide | 0.005 | 0.0018 |
| N-({4-[(3-acetylbenzene)sulfonyl]phenyl}methyl)-1H-pyrrolo[3,2-c]pyridine-2-carboxamide | 0.012 | 0.006 |
| N-({4-[(3-acetylbenzene)sulfonyl]phenyl}methyl)thieno[2,3-c]pyridine-2-carboxamide | 0.004 | 0.0026 |
| N-({4-[(3-chlorobenzene)sulfonyl]phenyl}methyl)-1H-pyrrolo[3,2-c]pyridine-2-carboxamide | 0.005 | 0.003 |
| N-({4-[(3-chlorobenzene)sulfonyl]phenyl}methyl)thieno[2,3-c]pyridine-2-carboxamide | 0.005 | 0.003 |
| N-({4-[(3-ethylbenzene)sulfonyl]phenyl}methyl)thieno[2,3-c]pyridine-2-carboxamide | 0.006 | 0.0027 |
| N-({4-[(3-fluoro-4-methoxybenzene)sulfonyl]phenyl}methyl)-1H-pyrrolo[3,2-c]pyridine-2-carboxamide | 0.005 | 0.004 |
| N-({4-[(3-fluoro-4-methoxybenzene)sulfonyl]phenyl}methyl)thieno[2,3-c]pyridine-2-carboxamide | 0.005 | 0.0025 |
| N-({4-[(3-fluoro-4-methylbenzene)sulfonyl]phenyl}methyl)-1H-pyrrolo[3,2-c]pyridine-2-carboxamide | 0.008 | 0.006 |
| N-({4-[(3-fluoro-4-methylbenzene)sulfonyl]phenyl}methyl)thieno[2,3-c]pyridine-2-carboxamide | 0.003 | 0.0028 |
| N-({4-[(3-fluorobenzene)sulfonyl]phenyl}methyl)-1H-pyrrolo[3,2-c]pyridine-2-carboxamide | 0.009 | 0.01 |
| N-({4-[(3-fluorobenzene)sulfonyl]phenyl}methyl)thieno[2,3-c]pyridine-2-carboxamide | 0.003 | 0.0033 |
| N-({4-[(3-methoxybenzene)sulfonyl]phenyl}methyl)-1H-pyrrolo[3,2-c]pyridine-2-carboxamide | 0.007 | 0.004 |
| N-({4-[(3-methoxybenzene)sulfonyl]phenyl}methyl)thieno[2,3-c]pyridine-2-carboxamide | 0.005 | 0.0026 |
| N-({4-[(3-methylbenzene)sulfonyl]phenyl}methyl)-1H-pyrrolo[3,2-c]pyridine-2-carboxamide | 0.009 | 0.004 |
| N-({4-[(3-methylbenzene)sulfonyl]phenyl}methyl)thieno[2,3-c]pyridine-2-carboxamide | 0.004 | 0.0023 |
| N-({4-[(4,5-difluoro-2-methoxybenzene)sulfonyl]phenyl}methyl)-1H-pyrrolo[3,2-c]pyridine-2-carboxamide | 0.014 | 0.006 |
| N-({4-[(4,5-difluoro-2-methoxybenzene)sulfonyl]phenyl}methyl)thieno[2,3-c]pyridine-2-carboxamide | 0.005 | 0.0029 |
| N-({4-[(4-acetylbenzene)sulfonyl]phenyl}methyl)-1H-pyrrolo[3,2-c]pyridine-2-carboxamide | 0.007 | 0.003 |
| N-({4-[(4-acetylbenzene)sulfonyl]phenyl}methyl)thieno[2,3-c]pyridine-2-carboxamide | 0.004 | 0.0025 |
| N-({4-[(4-chloro-2-methoxybenzene)sulfonyl]phenyl}methyl)-1H-pyrrolo[3,2-c]pyridine-2-carboxamide | 0.022 | 0.003 |
| N-({4-[(4-chloro-2-methoxybenzene)sulfonyl]phenyl}methyl)thieno[2,3-c]pyridine-2-carboxamide | 0.010 | 0.0038 |
| N-({4-[(4-chloro-2-methylbenzene)sulfonyl]phenyl}methyl)-1H-pyrrolo[3,2-c]pyridine-2-carboxamide | 0.027 | 0.025 |
| N-({4-[(4-chloro-3-fluorobenzene)sulfonyl]phenyl}methyl)-1H-pyrrolo[3,2-c]pyridine-2-carboxamide | 0.008 | 0.013 |
| N-({4-[(4-chloro-3-fluorobenzene)sulfonyl]phenyl}methyl)thieno[2,3-c]pyridine-2-carboxamide | 0.003 | 0.0071 |
| N-({4-[(4-chlorobenzene)sulfonyl]phenyl}methyl)-1H-pyrrolo[3,2-c]pyridine-2-carboxamide | 0.009 | 0.025 |
| N-({4-[(4-ethylbenzene)sulfonyl]phenyl}methyl)-1H-pyrrolo[3,2-c]pyridine-2-carboxamide | 0.008 | 0.012 |
| N-({4-[(4-ethylbenzene)sulfonyl]phenyl}methyl)thieno[2,3-c]pyridine-2-carboxamide | 0.006 | 0.0078 |
| N-({4-[(4-fluoro-2-methoxybenzene)sulfonyl]phenyl}methyl)-1H-pyrrolo[3,2-c]pyridine-2-carboxamide | 0.031 | 0.007 |
| N-({4-[(4-fluoro-2-methoxybenzene)sulfonyl]phenyl}methyl)thieno[2,3-c]pyridine-2-carboxamide | 0.009 | 0.0065 |
| N-({4-[(4-fluoro-2-methylbenzene)sulfonyl]phenyl}methyl)-1H-pyrrolo[3,2-c]pyridine-2-carboxamide | 0.019 | 0.027 |
| N-({4-[(4-fluoro-3-methylbenzene)sulfonyl]phenyl}methyl)-1H-pyrrolo[3,2-c]pyridine-2-carboxamide | 0.009 | 0.007 |

TABLE 3-continued

| IUPAC Name | Biochem IC50 uM | A2780 IC50 uM |
|---|---|---|
| N-({4-[(4-fluoro-3-methylbenzene)sulfonyl]phenyl}methyl)thieno[2,3-c]pyridine-2-carboxamide | 0.007 | 0.0029 |
| N-({4-[(4-fluorobenzene)sulfonyl]phenyl}methyl)-1H-pyrrolo[3,2-c]pyridine-2-carboxamide | 0.038 | 0.008 |
| N-({4-[(4-fluorobenzene)sulfonyl]phenyl}methyl)imidazo[1,2-a]pyridine-6-carboxamide | 0.023 | 0.011 |
| N-({4-[(4-fluorobenzene)sulfonyl]phenyl}methyl)thieno[2,3-c]pyridine-2-carboxamide | 0.003 | 0.010 |
| N-({4-[(4-methanesulfonylbenzene)sulfonyl]phenyl}methyl)-1H-pyrrolo[3,2-c]pyridine-2-carboxamide | 0.024 | 0.012 |
| N-({4-[(4-methoxy-2-methylbenzene)sulfonyl]phenyl}methyl)-1H-pyrrolo[3,2-c]pyridine-2-carboxamide | 0.024 | 0.024 |
| N-({4-[(4-methoxy-3-methylbenzene)sulfonyl]phenyl}methyl)-1H-pyrrolo[3,2-c]pyridine-2-carboxamide | 0.01 | 0.002 |
| N-({4-[(4-methoxy-3-methylbenzene)sulfonyl]phenyl}methyl)thieno[2,3-c]pyridine-2-carboxamide | 0.003 | 0.0024 |
| N-({4-[(4-methoxybenzene)sulfonyl]phenyl}methyl)-1H-pyrrolo[3,2-c]pyridine-2-carboxamide | 0.011 | 0.009 |
| N-({4-[(4-methoxybenzene)sulfonyl]phenyl}methyl)thieno[2,3-c]pyridine-2-carboxamide | 0.005 | 0.0027 |
| N-({4-[(4-methylbenzene)sulfonyl]phenyl}methyl)-1H-pyrrolo[3,2-c]pyridine-2-carboxamide | 0.006 | 0.009 |
| N-({4-[(4-methylbenzene)sulfonyl]phenyl}methyl)thieno[2,3-c]pyridine-2-carboxamide | 0.005 | 0.0050 |
| N-({4-[(5-acetyl-2-methoxybenzene)sulfonyl]phenyl}methyl)-1H-pyrrolo[3,2-c]pyridine-2-carboxamide | 0.02 | 0.006 |
| N-({4-[(5-chloro-2-methoxybenzene)sulfonyl]phenyl}methyl)-1H-pyrrolo[3,2-c]pyridine-2-carboxamide | 0.006 | 0.002 |
| N-({4-[(5-chloro-2-methoxybenzene)sulfonyl]phenyl}methyl)thieno[2,3-c]pyridine-2-carboxamide | 0.004 | 0.0013 |
| N-({4-[(5-fluoro-2-methoxybenzene)sulfonyl]phenyl}methyl)-1H-pyrrolo[3,2-c]pyridine-2-carboxamide | 0.005 | 0.003 |
| N-({4-[(5-fluoro-2-methylbenzene)sulfonyl]phenyl}methyl)-1H-pyrrolo[3,2-c]pyridine-2-carboxamide | 0.011 | 0.007 |
| N-({4-[(5-fluoro-2-methylbenzene)sulfonyl]phenyl}methyl)thieno[2,3-c]pyridine-2-carboxamide | 0.003 | 0.0094 |
| N-({4-[(5-tert-butyl-2-methoxybenzene)sulfonyl]phenyl}methyl)-1H-pyrrolo[3,2-c]pyridine-2-carboxamide | 0.647 | 0.006 |
| N-({4-[(5-tert-butyl-2-methoxybenzene)sulfonyl]phenyl}methyl)thieno[2,3-c]pyridine-2-carboxamide | 0.015 | 0.0046 |
| N-(4-(2-(trifluoromethoxy)phenylsulfonyl)benzyl)imidazo[1,2-a]pyridine-6-carboxamide | 0.008 | |
| N-(4-(phenylsulfonyl)benzyl)-1H-imidazo[4,5-b]pyridine-6-carboxamide | 5.780 | >10 |
| N-(4-(phenylsulfonyl)benzyl)benzo[d]thiazole-5-carboxamide | 0.047 | 3.872 |
| N-[(4-{[2-(benzyloxy)benzene]sulfonyl}phenyl)methyl]-1H-pyrrolo[3,2-c]pyridine-2-carboxamide | 0.018 | 0.033 |
| N-[(4-{[2-(dimethylcarbamoyl)benzene]sulfonyl}phenyl)methyl]-1H-pyrrolo[3,2-c]pyridine-2-carboxamide | 0.951 | 0.484 |
| N-[(4-{[2-(methylsulfamoyl)benzene]sulfonyl}phenyl)methyl]-1H-pyrrolo[3,2-c]pyridine-2-carboxamide | 0.076 | 0.202 |
| N-[(4-{[2-(morpholin-4-ylmethyl)benzene]sulfonyl}phenyl)methyl]-1H-pyrrolo[3,2-c]pyridine-2-carboxamide | 0.034 | 0.006 |
| N-[(4-{[2-(morpholin-4-ylmethyl)benzene]sulfonyl}phenyl)methyl]thieno[2,3-c]pyridine-2-carboxamide | 0.013 | 0.0036 |
| N-[(4-{[2-(trifluoromethoxy)benzene]sulfonyl}phenyl)methyl]-1H-pyrrolo[3,2-c]pyridine-2-carboxamide | 0.016 | 0.003 |
| N-[(4-{[2-(trifluoromethoxy)benzene]sulfonyl}phenyl)methyl]thieno[2,3-c]pyridine-2-carboxamide | 0.004 | 0.0028 |
| N-[(4-{[2-(trifluoromethyl)benzene]sulfonyl}phenyl)methyl]-1H-pyrrolo[3,2-c]pyridine-2-carboxamide | 0.022 | 0.025 |
| N-[(4-{[2-(trifluoromethyl)benzene]sulfonyl}phenyl)methyl]thieno[2,3-c]pyridine-2-carboxamide | 0.013 | 0.0260 |
| N-[(4-{[2-fluoro-4-(1H-pyrazol-1-yl)benzene]sulfonyl}phenyl)methyl]thieno[2,3-c]pyridine-2-carboxamide | 0.006 | 0.0080 |

TABLE 3-continued

| IUPAC Name | Biochem IC50 uM | A2780 IC50 uM |
|---|---|---|
| N-[(4-{[2-methoxy-4-(1H-pyrazol-1-yl)benzene]sulfonyl}phenyl)methyl]-1H-pyrrolo[3,2-c]pyridine-2-carboxamide | 0.016 | 0.002 |
| N-[(4-{[2-methoxy-4-(1H-pyrazol-1-yl)benzene]sulfonyl}phenyl)methyl]thieno[2,3-c]pyridine-2-carboxamide | 0.005 | 0.0026 |
| N-[(4-{[2-methoxy-4-(trifluoromethyl)benzene]sulfonyl}phenyl)methyl]-1H-pyrrolo[3,2-c]pyridine-2-carboxamide | 0.022 | 0.005 |
| N-[(4-{[2-methoxy-4-(trifluoromethyl)benzene]sulfonyl}phenyl)methyl]thieno[2,3-c]pyridine-2-carboxamide | 0.009 | 0.0075 |
| N-[(4-{[2-methoxy-5-(propan-2-yl)benzene]sulfonyl}phenyl)methyl]-1H-pyrrolo[3,2-c]pyridine-2-carboxamide | 0.061 | 0.012 |
| N-[(4-{[2-methoxy-5-(propan-2-yl)benzene]sulfonyl}phenyl)methyl]thieno[2,3-c]pyridine-2-carboxamide | 0.009 | 0.0062 |
| N-[(4-{[2-methoxy-6-(propan-2-yloxy)benzene]sulfonyl}phenyl)methyl]-1H-pyrrolo[3,2-c]pyridine-2-carboxamide | 0.036 | 0.022 |
| N-[(4-{[2-methyl-4-(1H-pyrazol-1-yl)benzene]sulfonyl}phenyl)methyl]-1H-pyrrolo[3,2-c]pyridine-2-carboxamide | 0.004 | 0.004 |
| N-[(4-{[3-(propan-2-yl)benzene]sulfonyl}phenyl)methyl]-1H-pyrrolo[3,2-c]pyridine-2-carboxamide | 0.006 | 0.004 |
| N-[(4-{[3-(propan-2-yl)benzene]sulfonyl}phenyl)methyl]thieno[2,3-c]pyridine-2-carboxamide | 0.009 | 0.0026 |
| N-[(4-{[3-(trifluoromethoxy)benzene]sulfonyl}phenyl)methyl]-1H-pyrrolo[3,2-c]pyridine-2-carboxamide | 0.005 | 0.003 |
| N-[(4-{[3-(trifluoromethoxy)benzene]sulfonyl}phenyl)methyl]thieno[2,3-c]pyridine-2-carboxamide | 0.002 | 0.0024 |
| N-[(4-{[3-(trifluoromethyl)benzene]sulfonyl}phenyl)methyl]-1H-pyrrolo[3,2-c]pyridine-2-carboxamide | 0.009 | 0.003 |
| N-[(4-{[3-(trifluoromethyl)benzene]sulfonyl}phenyl)methyl]thieno[2,3-c]pyridine-2-carboxamide | 0.003 | 0.0010 |
| N-[(4-{[3-fluoro-4-(1H-pyrazol-1-yl)benzene]sulfonyl}phenyl)methyl]-1H-pyrrolo[3,2-c]pyridine-2-carboxamide | 0.011 | 0.004 |
| N-[(4-{[4-(dimethylcarbamoyl)benzene]sulfonyl}phenyl)methyl]-1H-pyrrolo[3,2-c]pyridine-2-carboxamide | 0.027 | 0.014 |
| N-[(4-{[4-(propan-2-yl)benzene]sulfonyl}phenyl)methyl]thieno[2,3-c]pyridine-2-carboxamide | 0.006 | 0.0071 |
| N-[(4-{[4-(trifluoromethyl)benzene]sulfonyl}phenyl)methyl]-1H-pyrrolo[3,2-c]pyridine-2-carboxamide | 0.024 | 0.026 |
| N-[(4-{[4-chloro-3-(trifluoromethyl)benzene]sulfonyl}phenyl)methyl]-1H-pyrrolo[3,2-c]pyridine-2-carboxamide | 0.008 | 0.005 |
| N-[(4-{[4-chloro-3-(trifluoromethyl)benzene]sulfonyl}phenyl)methyl]thieno[2,3-c]pyridine-2-carboxamide | 0.010 | 0.0034 |
| N-[4-(benzenesulfonyl)phenyl]pyridine-3-carboxamide | 12.038 | >30 |
| N-{[3-(benzenesulfonyl)phenyl]methyl}-1H-pyrrolo[3,2-c]pyridine-2-carboxamide | >30 | >30 |
| N-{[4-(1H-indole-7-sulfonyl)phenyl]methyl}thieno[2,3-c]pyridine-2-carboxamide | 0.003 | 0.0027 |
| N-{[4-(1-methyl-1H-pyrazole-4-sulfonyl)phenyl]methyl}-1H-pyrrolo[3,2-c]pyridine-2-carboxamide | 0.048 | 0.123 |
| N-{[4-(2,3-dihydro-1,4-benzodioxine-6-sulfonyl)phenyl]methyl}thieno[2,3-c]pyridine-2-carboxamide | 0.004 | 0.0027 |
| N-{[4-(2H-1,3-benzodioxole-5-sulfonyl)phenyl]methyl}-1H-pyrrolo[3,2-c]pyridine-2-carboxamide | 0.008 | 0.007 |
| N-{[4-(2H-1,3-benzodioxole-5-sulfonyl)phenyl]methyl}thieno[2,3-c]pyridine-2-carboxamide | 0.003 | 0.0025 |
| N-{[4-(5-methylthiophene-2-sulfonyl)phenyl]methyl}-1H-pyrrolo[3,2-c]pyridine-2-carboxamide | 0.007 | 0.013 |
| N-{[4-(5-methylthiophene-2-sulfonyl)phenyl]methyl}thieno[2,3-c]pyridine-2-carboxamide | 0.005 | 0.0077 |
| N-{[4-(benzenesulfonyl)phenyl]methyl}-[1,2,3,4]tetrazolo[1,5-a]pyridine-6-carboxamide | 0.447 | >30 |
| N-{[4-(benzenesulfonyl)phenyl]methyl}-[1,2,4]triazolo[4,3-a]pyridine-6-carboxamide | 0.301 | >10 |

TABLE 3-continued

| IUPAC Name | Biochem IC50 uM | A2780 IC50 uM |
|---|---|---|
| N-{[4-(benzenesulfonyl)phenyl]methyl}-1,5-naphthyridine-2-carboxamide | 0.875 | >10 |
| N-{[4-(benzenesulfonyl)phenyl]methyl}-1H-imidazo[4,5-c]pyridine-2-carboxamide | 7.062 | 5.37 |
| N-{[4-(benzenesulfonyl)phenyl]methyl}-1H-pyrazolo[3,4-b]pyridine-3-carboxamide | 1.271 | >10 |
| N-{[4-(benzenesulfonyl)phenyl]methyl}-1H-pyrazolo[3,4-b]pyridine-5-carboxamide | 0.070 | 0.051 |
| N-{[4-(benzenesulfonyl)phenyl]methyl}-1H-pyrrolo[2,3-b]pyridine-5-carboxamide | 1.906 | >30 |
| N-{[4-(benzenesulfonyl)phenyl]methyl}-1H-pyrrolo[2,3-c]pyridine-3-carboxamide | >10 | >10 |
| N-{[4-(benzenesulfonyl)phenyl]methyl}-1-methyl-1H-pyrazolo[3,4-b]pyridine-5-carboxamide | 1.725 | >30 |
| N-{[4-(benzenesulfonyl)phenyl]methyl}-1-methyl-1H-pyrrolo[3,2-c]pyridine-2-carboxamide | >10 | >30 |
| N-{[4-(benzenesulfonyl)phenyl]methyl}-3-(pyridin-2-yl)-1H-pyrazole-5-carboxamide | 7.429 | 23.371 |
| N-{[4-(benzenesulfonyl)phenyl]methyl}-3-(pyridin-3-yl)-1,2-oxazole-5-carboxamide | 0.033 | >30 |
| N-{[4-(benzenesulfonyl)phenyl]methyl}-3-(pyridin-4-yl)-1H-pyrazole-5-carboxamide | 3.176 | 21.554 |
| N-{[4-(benzenesulfonyl)phenyl]methyl}-3-bromo-1H-pyrrolo[3,2-c]pyridine-2-carboxamide | 0.306 | 7.390 |
| N-{[4-(benzenesulfonyl)phenyl]methyl}-5-(pyridin-3-yl)-1,2,4-oxadiazole-3-carboxamide | 0.312 | >30 |
| N-{[4-(benzenesulfonyl)phenyl]methyl}-5-(pyridin-3-yl)-1H-pyrazole-3-carboxamide | 0.023 | 11.825 |
| N-{[4-(benzenesulfonyl)phenyl]methyl}imidazo[1,2-a]pyrazine-2-carboxamide | 1.491 | >30 |
| N-{[4-(benzenesulfonyl)phenyl]methyl}imidazo[1,2-a]pyridine-6-carboxamide | 0.021 | 0.011 |
| N-{[4-(benzenesulfonyl)phenyl]methyl}isoquinoline-6-carboxamide | 16.082 | 21.303 |
| N-{[4-(benzenesulfonyl)phenyl]methyl}isoquinoline-7-carboxamide | 0.219 | 24.000 |
| N-{[4-(benzenesulfonyl)phenyl]methyl}quinazoline-6-carboxamide | 16.082 | 21.303 |
| N-{[4-(benzenesulfonyl)phenyl]methyl}thieno[2,3-b]pyrazine-6-carboxamide | 0.052 | >30 |
| N-{[4-(benzenesulfonyl)phenyl]methyl}thieno[2,3-c]pyridine-2-carboxamide | 0.011 | 0.012 |
| N-{[4-(isoquinoline-4-sulfonyl)phenyl]methyl}thieno[2,3-c]pyridine-2-carboxamide | 0.003 | 0.0007 |
| N-{[4-(naphthalene-1-sulfonyl)phenyl]methyl}thieno[2,3-c]pyridine-2-carboxamide | 0.002 | 0.0005 |
| N-{[4-(phenoxathiine-4-sulfonyl)phenyl]methyl}-1H-pyrrolo[3,2-c]pyridine-2-carboxamide | 0.005 | 0.0009 |
| N-{[4-(phenoxathiine-4-sulfonyl)phenyl]methyl}thieno[2,3-c]pyridine-2-carboxamide | 0.004 | 0.0017 |
| N-{[4-(phenylmethane)sulfonylphenyl]methyl}-1H-pyrrolo[3,2-c]pyridine-2-carboxamide | 0.029 | 0.3015 |
| N-{[4-(pyridine-3-sulfonyl)phenyl]methyl}-1H-pyrrolo[3,2-c]pyridine-2-carboxamide | 0.021 | 0.048 |
| N-{[4-(quinoline-3-sulfonyl)phenyl]methyl}thieno[2,3-c]pyridine-2-carboxamide | 0.003 | 0.0008 |
| N-{[4-(quinoline-6-sulfonyl)phenyl]methyl}thieno[2,3-c]pyridine-2-carboxamide | 0.003 | 0.0009 |
| N-{[4-(quinoline-8-sulfonyl)phenyl]methyl}thieno[2,3-c]pyridine-2-carboxamide | 0.006 | 0.0025 |
| N-{2-[4-(benzenesulfonyl)phenyl]ethyl}-1H-pyrrolo[3,2-c]pyridine-2-carboxamide | 0.410 | 9.1 |
| N-({4-[(1H-indazol-6-yl)sulfamoyl]phenyl}methyl)-1H-pyrrolo[3,2-c]pyridine-2-carboxamide | 0.135 | 5.44 |
| N-({4-[(1-oxo-1H-isochromen-5-yl)sulfamoyl]phenyl}methyl)-1H-pyrrolo[3,2-c]pyridine-2-carboxamide | 0.008 | 2.27 |
| N-({4-[(2,3-dihydro-1,4-benzodioxin-6-yl)sulfamoyl]phenyl}methyl)-1H-pyrrolo[3,2-c]pyridine-2-carboxamide | >10 | >10 |
| N-({4-[(2-acetylphenyl)sulfamoyl]phenyl}methyl)-1H-pyrrolo[3,2-c]pyridine-2-carboxamide | 0.005 | 0.005 |
| N-({4-[(2-methoxy-6-methylphenyl)sulfamoyl]phenyl}methyl)-1H-pyrrolo[3,2-c]pyridine-2-carboxamide | 0.006 | 12.4 |
| N-({4-[(2-methoxyphenyl)sulfamoyl]phenyl}methyl)-1H-pyrrolo[3,2-c]pyridine-2-carboxamide | 0.089 | 2.150 |

TABLE 3-continued

| IUPAC Name | Biochem IC50 uM | A2780 IC50 uM |
|---|---|---|
| N-({4-[(2-phenoxyphenyl)sulfamoyl]phenyl}methyl)-1H-pyrrolo[3,2-c]pyridine-2-carboxamide | 4.019 | 12.000 |
| N-({4-[(2-propoxyphenyl)sulfamoyl]phenyl}methyl)-1H-pyrrolo[3,2-c]pyridine-2-carboxamide | 0.052 | 0.100 |
| N-({4-[(3-methoxy-2-methylphenyl)sulfamoyl]phenyl}methyl)-1H-pyrrolo[3,2-c]pyridine-2-carboxamide | 0.030 | 0.006 |
| N-({4-[(4-chloro-2-methoxy-5-methylphenyl)sulfamoyl]phenyl}methyl-1H-pyrrolo[3,2-c]pyridine-2-carboxamide | 7.835 | 18.322 |
| N-({4-[(4-ethoxy-2-fluorophenyl)sulfamoyl]phenyl}methyl)-1H-pyrrolo[3,2-c]pyridine-2-carboxamide | 0.154 | 1.600 |
| N-({4-[(4-fluoro-2-methoxyphenyl)sulfamoyl]phenyl}methyl)-1H-pyrrolo[3,2-c]pyridine-2-carboxamide | 3.138 | >30 |
| N-({4-[(4-methoxy-2-methylphenyl)sulfamoyl]phenyl}methyl)-1H-pyrrolo[3,2-c]pyridine-2-carboxamide | 1.451 | >30 |
| N-({4-[(5,6,7,8-tetrahydronaphthalen-1-yl)sulfamoyl]phenyl}methyl)-1H-pyrrolo[3,2-c]pyridine-2-carboxamide | >30 | >30 |
| N-({4-[(5-chloro-2-methoxyphenyl)sulfamoyl]phenyl}methyl)-1H-pyrrolo[3,2-c]pyridine-2-carboxamide | 0.197 | 17.984 |
| N-({4-[(5-fluoro-2-methoxyphenyl)sulfamoyl]phenyl}methyl)-1H-pyrrolo[3,2-c]pyridine-2-carboxamide | 0.232 | >30 |
| N-({4-[(5-methoxy-2-methylphenyl)sulfamoyl]phenyl}methyl)-1H-pyrrolo[3,2-c]pyridine-2-carboxamide | 0.051 | 13.018 |
| N-({4-[(quinolin-8-yl)sulfamoyl]phenyl}methyl)-1H-pyrrolo[3,2-c]pyridine-2-carboxamide | 0.075 | 1.478 |
| N-[(4-{[2-(2-hydroxyethoxy)phenyl]sulfamoyl}phenyl)methyl]-1H-pyrrolo[3,2-c]pyridine-2-carboxamide | 19.611 | 23.854 |
| N-[(4-{[2-(hydroxymethyl)phenyl]sulfamoyl}phenyl)methyl)-1H-pyrrolo[3,2-c]pyridine-2-carboxamide | 0.030 | 0.006 |
| N-[(4-{[2-(morpholin-4-yl)phenyl]sulfamoyl}phenyl)methyl]-1H-pyrrolo[3,2-c]pyridine-2-carboxamide | 0.019 | 0.017 |
| N-[(4-{[2-(piperidin-1-yl)phenyl]sulfamoyl}phenyl)methyl]-1H-pyrrolo[3,2-c]pyridine-2-carboxamide | 0.072 | 0.008 |
| N-[(4-{[2-(propan-2-yloxy)phenyl]sulfamoyl}phenyl)methyl]-1H-pyrrolo[3,2-c]pyridine-2-carboxamide | 0.003 | 0.001 |
| N-[(4-{[2-(trifluoromethoxy)benzene]sulfonamido}phenyl)methyl]-1H-pyrrolo[3,2-c]pyridine-2-carboxamide | 0.003 | 0.001 |
| N-[(4-{[2-(trifluoromethoxy)phenyl]sulfamoyl}phenyl)methyl]-1H-pyrrolo[3,2-c]pyridine-2-carboxamide | 0.006 | 0.001 |
| N-[(4-{[2-methoxy-5-(trifluoromethyl)phenyl]sulfamoyl}phenyl)methyl]-1H-pyrrolo[3,2-c]pyridine-2-carboxamide | 0.0005 | 0.0016 |
| N-[(4-{[4-chloro-2-(trifluoromethoxy)phenyl]sulfamoyl}phenyl)methyl]-1H-pyrrolo[3,2-c]pyridine-2-carboxamide | 0.002 | 0.002 |
| N-[(4-{8-oxa-3-azabicyclo[3.2.1]octane-3-sulfonyl}phenyl)methyl]-1H-pyrrolo[3,2-c]pyridine-2-carboxamide | 0.008 | 0.003 |
| N-[(4-{8-oxa-3-azabicyclo[3.2.1]octane-3-sulfonyl}phenyl)methyl]imidazo[1,2-a]pyridine-6-carboxamide | 0.004 | 0.003 |
| N-[(4-{8-oxa-3-azabicyclo[3.2.1]octane-3-sulfonyl}phenyl)methyl]thieno[2,3-c]pyridine-2-carboxamide | 0.015 | 0.003 |
| N-[(4-benzamidophenyl)methyl]-1H-pyrrolo[3,2-c]pyridine-2-carboxamide | 0.019 | 0.004 |
| N-[(4-benzenesulfonamidophenyl)methyl]-1H-pyrrolo[3,2-c]pyridine-2-carboxamide | 0.011 | 0.005 |
| N-[4-(piperidine-1-sulfonyl)phenyl]-1H-pyrrolo[3,2-c]pyridine-2-carboxamide | 0.008 | 0.006 |
| N-[4-(piperidine-1-sulfonyl)phenyl]-2-(pyridin-3-yloxy)acetamide | 0.0011 | 0.0066 |
| N-[4-(piperidine-1-sulfonyl)phenyl]-3-(pyridin-3-yl)propanamide | 0.003 | 0.007 |
| N-{[1-(benzenesulfonyl)piperidin-4-yl]methyl}-1H-pyrrolo[3,2-c]pyridine-2-carboxamide | 0.015 | 0.009 |
| N-{[4-(piperidine-1-sulfonyl)phenyl]methyl}-[1,2,3,4]tetrazolo[1,5-a]pyridine-7-carboxamide | 0.003 | 0.009 |
| N-{[4-(piperidine-1-sulfonyl)phenyl]methyl}-1,3-benzothiazole-6-carboxamide | 0.009 | 0.010 |
| N-{[4-(piperidine-1-sulfonyl)phenyl]methyl}-1,6-naphthyridine-2-carboxamide | 0.012 | 0.010 |
| N-{[4-(piperidine-1-sulfonyl)phenyl]methyl}-1H-1,3-benzodiazole-5-carboxamide | 0.021 | 0.010 |
| N-{[4-(piperidine-1-sulfonyl)phenyl]methyl}-1H-imidazo[1,2-b]pyrazole-5-carboxamide | 0.0008 | 0.0110 |
| N-{[4-(piperidine-1-sulfonyl)phenyl]methyl}-1H-indazole-5-carboxamide | 0.018 | 0.016 |

TABLE 3-continued

| IUPAC Name | Biochem IC50 uM | A2780 IC50 uM |
|---|---|---|
| N-{[4-(piperidine-1-sulfonyl)phenyl]methyl}-1H-pyrazolo[3,4-b]pyridine-5-carboxamide | 0.017 | 0.033 |
| N-{[4-(piperidine-1-sulfonyl)phenyl]methyl}-1H-pyrrolo[2,3-c]pyridine-2-carboxamide | 0.004 | 0.054 |
| N-{[4-(piperidine-1-sulfonyl)phenyl]methyl}-1H-pyrrolo[3,2-c]pyridine-2-carboxamide | 0.023 | 0.200 |
| N-{[4-(piperidine-1-sulfonyl)phenyl]methyl}furo[3,2-c]pyridine-2-carboxamide | 0.017 | 0.286 |
| N-{[4-(piperidine-1-sulfonyl)phenyl]methyl}imidazo[1,2-a]pyridine-6-carboxamide | 0.018 | 1.160 |
| N-{[4-(piperidine-1-sulfonyl)phenyl]methyl}imidazo[1,2-a]pyridine-7-carboxamide | >0.1 | >0.5 |
| N-{[4-(piperidine-1-sulfonyl)phenyl]methyl}pyridine-3-carboxamide | 0.039 | 0.64 |
| N-{[4-(piperidine-1-sulfonyl)phenyl]methyl}thieno[2,3-b]pyridine-2-carboxamide | 6.146 | 14.000 |
| N-{[4-(piperidine-1-sulfonyl)phenyl]methyl}thieno[3,2-c]pyridine-2-carboxamide | 0.886 | 10 |
| N-{1-[4-(piperidine-1-sulfonyl)phenyl]ethyl}-1H-pyrrolo[3,2-c]pyridine-2-carboxamide | 0.020 | 0.007 |

Assay Example 3

In-Vitro Cell Proliferation Assay

U251 cells were seeded in 96-well plates at 1.25×103 cells/well in 180 μL of culture medium (10% FBS, 1% Pen/Strep Amphotecricin B, RPMI-5 1640) with and without the addition of either—nicotinamide mononucleotide (NMN) or nicotinamide (NAM). After overnight incubation at 37° C. and 5% CO2, the compound titrations were performed in a separate dilution plate by serially diluting the compounds in DMSO to make a 1000× stock. The compounds were then further diluted to 10× final concentration in culture media, whereupon 20 μL of each dilution was added to the plated cells with controls (e.g. DMSO and blank) to make a final volume of 5 200 μL. The final DMSO concentration in each well was 0.1%. The plates were then incubated for 72 hours at 37° C. in a 5% CO2 incubator. The number of viable cells was then assessed using sulforhodamine B (SRB) assay. Cells were fixed at 4° C. for 1 hour with the addition of 50 μL 30% trichloroacetic acid (TCA) to make a final concentration of 6% 10 TCA. The plates were washed four times with H2O and allowed to dry for at least 1 hour, whereupon 100 μL of a 4% SRB in 1% acetic acid solution was added to each well and incubated at room temperature for at least 30 minutes. The plates were then washed three times with 1% acetic acid, dried, and treated with 100 μL of 10 mM Tris-Base solution. The plates were then read in a microplate reader at an absorbance of 570 nm. 15 Background was generated on a separate plate with media only.

Method for Determining % Inhibition

First, the signals from the background plate are averaged, then the background was subtracted from the test plates. The compound-treated cells were then assayed for % 20 inhibition by using the following formula:

% Inh=100−100*x/y wherein x denotes the average signal of the compound-treated cells and y denotes the average signal of the DMSO-treated cells.

25 Formula for Determining IC50 Values:

IC50=10^(LOG 10(X)+(((50−% Inh at Cmpd Concentration 1)/(XXYY)*(LOG 10(X)−LOG 10(Y))))

wherein X denotes the compound concentration 1, Y denotes the compound concentration 2, XX denotes the % inhibition at compound concentration 1 (X), and YY 30 denotes the % inhibition at compound concentration 2 (Y).

Table 4 below shows U251-values for some compounds.

| Chemical name | U251 IC50 (uM) |
|---|---|
| N-{[4-(benzenesulfonyl)phenyl]methyl}thieno[3,2-b]pyridine-2-carboxamide | >2 |
| N-{[4-(benzenesulfonyl)phenyl]methyl}imidazo[1,5-a]pyridine-6-carboxamide | >2 |
| N-{[4-(benzenesulfonyl)phenyl]methyl}-1H-pyrrolo[3,2-c]pyridine-2-carboxamide | 0.040 |
| N-{[5-(benzenesulfonyl)pyridin-2-yl]methyl}-1H-pyrrolo[3,2-c]pyridine-2-carboxamide | 0.035 |
| N-{[4-(benzenesulfonyl)phenyl]methyl}imidazo[1,2-a]pyrazine-6-carboxamide | >2 |
| N-{[4-(benzenesulfonyl)phenyl]methyl}furo[3,2-b]pyridine-2-carboxamide | 0.545 |
| N-{[6-(benzenesulfonyl)pyridin-3-yl]methyl}-1H-pyrrolo[3,2-c]pyridine-2-carboxamide | >2 |
| N-{[4-(piperazine-1-sulfonyl)phenyl]methyl}thieno[2,3-c]pyridine-2-carboxamide | 0.405 |
| N-{[4-(piperazine-1-sulfonyl)phenyl]methyl}imidazo[1,2-a]pyridine-6-carboxamide | 0.556 |
| N-{[4-(3-aminopyrrolidine-1-sulfonyl)phenyl]methyl}thieno[2,3-c]pyridine-2-carboxamide hydrochloride | 0.31 |
| N-{[4-(3-aminopyrrolidine-1-sulfonyl)phenyl]methyl}furo[2,3-c]pyridine-2-carboxamide hydrochloride | 1.85 |
| N-({4-[(3,5-difluorobenzene)sulfinyl]phenyl}methyl)imidazo[1,2-a]pyridine-6-carboxamide | 0.0066 |

Xenograft Studies:

C.B-17-Igh-1b-Prkdc$^{scid}$ mice (female) were injected s.c. with 5×10$^6$ A2780 cells (NCI) in the left flank. 10-12 days later when tumors reached 100-200 mm3 in size, mice were randomized into treatment groups of 8 mice per group including vehicle control and reference standard groups. The compounds were formulated in 60:30:10 PEG-400:D5W: Ethanol and administered p.o., at the dose volume of 10 ml/kg BID for a duration of 5 or 10 days. The dose used for efficacy was selected from the MTD (Maximum Tolerated Dose) study. Mice were weighed and tumors measured using vernier calipers every alternate day. Tumor volume was calculated according to the formula (length×width$^2$)/2. All animal work was approved by the Institutional Animal Care and Use Committee of Biological Resource Centre, Singapore.

The compound N-[(4-{[2-(trifluoromethoxy)phenyl]sulfamoyl}phenyl)methyl]-1H-pyrrolo[3,2-c]pyridine-2-carboxamide produced tumor stasis.

The following compounds produced tumor regression:
N-{[4-(benzenesulfonyl)phenyl]methyl}imidazo[1,2-a]pyridine-6-carboxamide;
N-{[4-(benzenesulfonyl)phenyl]methyl}thieno[2,3-c]pyridine-2-carboxamide;
N-{[4-(benzenesulfonyl)phenyl]methyl}-1H-pyrrolo[3,2-c]pyridine-2-carboxamide
N-({4-[(4-fluorobenzene)sulfonyl]phenyl}methyl)-1H-pyrrolo[3,2-c]pyridine-2-carboxamide;
N-({4-[(4-fluorobenzene)sulfonyl]phenyl}methyl)imidazo[1,2-a]pyridine-6-carboxamide;
N-({4-[(4-acetylbenzene)sulfonyl]phenyl}methyl)-1H-pyrrolo[3,2-c]pyridine-2-carboxamide;
N-[(4-{[2-(trifluoromethoxy)benzene]sulfonyl}phenyl)methyl]-1H-pyrrolo[3,2-c]pyridine-2-carboxamide;
N-({4-[(3-chlorobenzene)sulfonyl]phenyl}methyl)-1H-pyrrolo[3,2-c]pyridine-2-carboxamide.

The following compounds delayed tumor growth;
N-{[4-(pyridine-3-sulfonyl)phenyl]methyl}-1H-pyrrolo[3,2-c]pyridine-2-carboxamide.
N-[(4-{[2-methoxy-4-(1H-pyrazol-1-yl)benzene]sulfonyl}phenyl)methyl]-1H-pyrrolo[3,2-c]pyridine-2-carboxamide While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

We claim:

1. A compound of formula IIB or a pharmaceutically acceptable salt thereof:

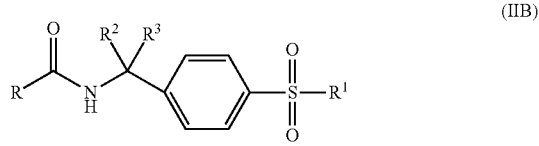

(IIB)

wherein:
R is bicyclic heteroaryl comprising 1, 2, 3, or 4 heteroatom(s) independently selected from N, S, and O, wherein said heteroaryl may be substituted by one or more substituents selected from the group consisting of amino, oxo, and halo; and wherein said heteroaryl can comprise one or more N-oxide(s) formed with a N atom member of said heteroaryl;
R$^1$ is aryl,
wherein:
(i) said aryl is unsubstituted or substituted with 1, 2, 3, 4, or 5 substituents which can be the same or different and are independently selected from the group consisting of:
deuterium, halo, hydroxy, hydroxyalkyl, cyano, —(CH$_2$)$_m$NR$^a$R$^b$, oxo, alkyl, cyanoalkyl, haloalkyl, alkoxy, haloalkoxy, alkoxyalkyl-, alkenyl, alkynyl, alkynylalkoxy, —CONH$_2$, —S-alkyl, —C(O)NH(alkyl), —C(O)N(alkyl)$_2$, —C(O)NH(cycloalkyl), —C(O)NH(aryl), —C(O)N(aryl)$_2$, arylalkyl-, arylalkoxy-, aryloxy-, cycloalkyl, heterocycloalkyl, aryl, (heterocycloalkyl)alkyl-, (heterocycloalkyl)alkoxy, —C(O)heterocycloalkyl, heteroaryl, (heteroaryl)alkyl-, —S(O)$_2$-alkyl, —S(O)$_2$-aryl, —S(O)$_2$—CH$_z$F$_{3-z}$, —C(O)alkyl, —N(R$^5$)—C(O)-alkyl, —N(R$^5$)—C(O)-aryl, —S(O$_2$)NH$_2$, —S(O$_2$)NH(alkyl), —S(O$_2$)N(alkyl)$_2$, —N(H)(SO$_2$)(alkyl), and methylenedioxy, wherein each of said cycloalkyl, heterocycloalkyl, aryl, or heteroaryl may be substituted by one or more halo, cyano, alkyl, and alkoxy; and
(ii) said aryl may optionally additionally be fused with independently selected aryl, heterocycloalkyl or cycloalkyl to form a bicyclic or tricyclic group that may be substituted by one or more halo, cyano, alkyl, and alkoxy;
R$^2$ and R$^3$ can be independently selected from the group consisting of H and deuterium;
R$^5$ is H, alkyl, or arylalkyl;
R$^a$ and R$^b$ are independently selected from the group consisting of H, alkyl, alkoxy, alkoxyalkyl, and haloalkyl;
m is 0, 1, 2, 3, 4, 5, or 6; and
z is 0, 1, or 2.

2. The compound of claim 1, wherein R is selected from 9-to 10-membered bicyclic heteroaryl groups containing 1, 2, 3, or 4 heteroatoms independently selected from N, S, and O.

3. The compound of claim 1, wherein R is selected from the group consisting of: benzothiazole, dihydronaphthyridine, dihydropyridopyrimidine, dihydropyrrolopyridine, furopyridine, imidazopyrazine, imidazopyrazole, imidazopyridine, imidazopyrimidine, indazole, indole, isoquinoline, naphthyridine, pyrazolopyridine, pyrrolopyridine, tetrazolopyridine, tetrahydroimidazopyridine, tetrahydropyrazolopyridine, thiazolopyridine, and thienopyridine.

4. The compound of claim 1, wherein R is selected from the group consisting of: 1H-pyrazolo[3,4-b]pyridine; 1,4,6,7-Tetrahydro-pyrazolo[4,3-c]pyridine; 7,8-Dihydro-5H-pyrido[4,3-d]pyrimidine; 5,7-Dihydro-pyrrolo[3,4-b]pyridine; 7,8-Dihydro-5H-[1,6]naphthyridine; 1,4,6,7-Tetrahydro-imidazo[4,5-c]pyridine; 1,8a-dihydroimidazo[1,2-a]pyridine; thieno[3,2-c]pyridine; 1H-imidazo[1,2-b]pyrazole; furo[2,3-c]pyridine; 1H-pyrrolo[3,2-c]pyridine; thieno[2,3-b]pyridine; imidazo[1,2-a]pyrimidine; furo[2,3-c]pyridine; isoquinoline; 1H-indazole; imidazo[1,2-a]pyridine; thieno[2,3-c]pyridine; furo[2,3-c]pyridine; 1H-pyrrolo[2,3-c]pyridine; imidazo[1,2-a]pyrazine; 1,3-benzothiazole; benzo[d]thiazole; 1H-pyrrolo[2,3-b]pyridine; [1,3]thiazolo[5,4-c]pyridine; [1,2,3,4]tetrazolo[1,5-a]pyridine; 1,5-naphthyridine; 1H-indole; 1H-imidazo[4,5-c]pyridine; and 1,6-naphthyridine.

5. The compound of claim 1, wherein R is substituted at a position adjacent to a nitrogen atom on its cycle.

6. The compound of claim 1, wherein R$^1$ is substituted aryl.

7. The compound of claim 1, wherein R$^1$ is selected from the group consisting of: 2-ethoxy-4-fluorophenyl; 3,4-difluorophenyl; 3,4-dimethoxyphenyl; 3-chloro-5-fluorophenyl; 3-fluoro-4-methoxyphenyl; 4-chloro-2-methylphenyl; 4-fluoro-2-methoxyphenyl; 4-methoxy-2,5-dimethylphenyl; 4-methylphenyl; 5-chloro-2-ethoxyphenyl; 5-fluoro-2- methoxyphenyl; 2-(2,2,2-trifluoroethoxy)-4-(trifluoromethyl)phenyl; 2-(benzyloxy)-5-(trifluoromethyl)phenyl; 2-(benzyloxy)phenyl; 2-(dimethylcarbamoyl)phenyl; 2-(ethoxymethyl)phenyl; 2-(methylsulfamoyl)phenyl; 2-(morpholin-4-ylmethyl)phenyl; 2-(trifluoromethoxy)phenyl; 2-(trifluoromethyl)phenyl; 2,3,6-trimethoxyphenyl; 2,3-difluoro-6-methoxyphenyl; 2,3-difluorophenyl; 2,3-dihydro-1,4-benzodioxine; 2,3-dihydro-1-benzofuran; 2,3-dihydro-1-benzofuranphenyl; 2,3-dimethoxy-5-methylphenyl; 2,3-dimethoxyphenyl; 2,3-dimethylphenyl; 2,4,5-trimethylphenyl; 2,4-bis(trifluoromethyl)phenyl; 2,4-dichloro-3-methoxyphenyl; 2,4-difluorophenyl; 2,4-dimethoxyphenyl; 2,4-dimethylphenyl; 2,5-difluorophenyl; 2,5-dimethoxyphenyl; 2,5-dimethylphenyl; 2,6-dichloro-3-methylphenyl; 2,6-dichlorophenyl; 2,6-dimethoxy-4-methylphenyl; 2,6-dimethylphenyl; 2-acetylphenyl; 2-butoxy-4-fluorophenyl; 2-butoxy-5-chlorophenyl; 2-butoxy-6-fluorophenyl; 2-chloro-3-(trifluoromethyl)phenyl; 2-chloro-3-fluorophenyl; 2-chloro-4-(trifluoromethyl)phenyl; 2-chloro-4-fluorophenyl; 2-chloro-4-methoxyphenyl; 2-chloro-4-methylphenyl; 2-chloro-5-(hydroxymethyl)phenyl; 2-chloro-5-(trifluoromethoxy)phenyl; 2-chloro-5-(trifluoromethyl)phenyl; 2-chloro-5-fluorophenyl; 2-chloro-5-methoxyphenyl; 2-chloro-5-methylphenyl; 2-chloro-6-fluorophenyl; 3-trifluoromethylphenyl; 2-chloro-6-methoxyphenyl; 2-chlorophenyl; 2-cyanophenyl; 2-ethoxy-4-fluorophenyl; 2-ethoxy-6-fluorophenyl; 2-ethoxyphenyl; 2-ethylphenyl; 2-fluoro-3-(propan-2-yloxy)phenyl; 2-fluoro-3-(trifluoromethoxy)phenyl; 2-fluoro-3-methoxyphenyl; 2-fluoro-3-methylphenyl; 2-fluoro-4-(1H-pyrazol-1-yl)phenyl; 2-fluoro-4-(trifluoromethyl)phenyl; 2-fluoro-4-methoxyphenyl; 2-fluoro-4-methylphenyl; 2-fluoro-5-methoxyphenyl; 2-fluoro-5-methylphenyl; 2-fluoro-6-methoxyphenyl; 2-fluoro-6-propoxyphenyl; 2-fluorophenyl; 2H-1,3-benzodioxole; 2-methanesulfonamidophenyl; 2-methanesulfonylphenyl; 2-methoxy-3-(trifluoromethyl)phenyl; 2-methoxy-4-(1H-pyrazol-1-yl)phenyl; 2-methoxy-4-(trifluoromethyl)phenyl; 2-methoxy-5-(propan-2-yl)phenyl; 2-methoxy-5-(trifluoromethoxy)phenyl; 2-methoxy-5-methylphenyl; 2-methoxy-6-(propan-2-yloxy)phenyl; 2-methoxyphenyl; 2-methyl-4-(1H-pyrazol-1-yl)phenyl; 2-methyl-4-(trifluoromethyl)phenyl; 2-methyl-4-propoxyphenyl; 2-methylphenyl; 2-phenoxyphenyl; 2-phenylethane; 3-(1H-pyrazol-1-yl)phenyl; 3-(2,2,2-trifluoroethoxy)phenyl; 3-(2-methylpropoxy)phenyl; 3-(3,5-dimethyl-1H-pyrazol-1-yl)phenyl; 3-(4-fluorophenoxy)phenyl; 3-(5-methyl-1,2,4-oxadiazol-3-yl)phenyl; 3-(cyclopentylcarbamoyl)phenyl; 3-(diethylcarbamoyl)-5-fluorophenyl; 3-(difluoromethoxy)phenyl; 3-(dimethylsulfamoyl)phenyl; 3-(ethanesulfonyl)phenyl; 3-(ethylcarbamoyl)phenyl; 3-(methoxymethyl)phenyl, 3-(methylcarbamoyl)phenyl; 3-(morpholin-4-yl)phenyl; 3-(piperidin-1-yl)phenyl; 3-(piperidin-1-ylmethyl)phenyl; 3-(piperidin-1-yl)phenyl; 3-(propan-2-yl)phenyl; 3-(propan-2-yloxy)phenyl; 3-(propane-1-sulfonamido)phenyl; 3-(pyrimidin-2-yl)phenyl; 3-(trifluoromethoxy)phenyl; 3-(trifluoromethyl)phenyl; 3,4-dichlorophenyl; 3,4-dimethoxyphenyl; 3,4-dimethylphenyl; 3,5-dichlorophenyl; 3,5-difluorophenyl; 3,5-dimethoxyphenyl; 3,5-dimethylphenyl; 3-[(2-methylpropyl)carbamoyl]phenyl; 3-[(dimethylamino)methyl]phenyl; 3-[(morpholin-4-yl)carbonyl]phenyl; 3-[(propan-2-yl)carbamoyl]phenyl; 3-[2-(dimethylamino)ethoxy]phenyl; 3-[2-(dimethylamino)ethyl]phenyl; 3-[2-(morpholin-4-yl)ethoxy]phenyl; 3-acetylphenyl; 3-butoxyphenyl; 3-chloro-2-fluorophenyl; 3-chloro-2-methoxyphenyl; 3-chloro-2-methylphenyl; 3-chloro-4-(trifluoromethyl)phenyl; 3-chloro-4-methoxyphenyl; 3-chloro-4-methylphenyl; 3-chloro-4-propoxyphenyl; 3-chloro-5-(diethylcarbamoyl)phenyl; 3-chloro-5-(hydroxymethyl)phenyl; 3-chloro-5-fluorophenyl; 3-chloro-5-methoxyphenyl; 3-chloro-5-methylphenyl; 3-chlorophenyl; 3-cyanophenyl; 3-ethoxy-2-fluorophenyl; 3-ethoxy-4-fluorophenyl; 3-ethoxyphenyl; 3-ethylphenyl; 3-fluoro-2-methoxyphenyl; 3-fluoro-2-methylphenyl; 3-fluoro-4-(1H-pyrazol-1-yl)phenyl; 3-fluoro-4-(2,2,2-trifluoroethoxy)phenyl; 3-fluoro-4-(methylsulfanyl)phenyl; 3-fluoro-4-(trifluoromethoxy)phenyl; 3-fluoro-4-(trifluoromethyl)phenyl; 3-fluoro-4-methoxyphenyl; 3-fluoro-4-methylphenyl; 3-fluoro-4-propoxyphenyl; 3-fluoro-5-(2,2,2-trifluoroethoxy)phenyl; 3-fluoro-5-(2-methylpropoxy)phenyl; 3-fluoro-5-(morpholin-4-yl)phenyl; 3-fluoro-5-(pyrrolidin-1-yl)phenyl; 3-fluoro-5-(trifluoromethyl)phenyl; 3-fluoro-5-methoxyphenyl; 3-fluoro-5-methylphenyl; 3-fluorophenyl; 3-hydroxyphenyl; 3-methanesulfonylphenyl; 3-methoxy-4-methylphenyl; 3-methoxy-5-methylphenyl; 3-methoxyphenyl; 3-methylphenyl; 3-phenylphenyl; 3-phenylpropane; 3-propoxyphenyl; 3-sulfamoylphenyl; 3-tert-butylphenyl; 4-(1-cyanocyclopentyl)phenyl; 4-(1H-imidazol-1-yl)phenyl; 4-(1H-imidazol-1-ylmethyl)phenyl; 4-(1H-pyrazol-1-yl)phenyl; 4-(2-methylpropoxy)phenyl; 4-(4-ethoxyphenyl)phenyl; 4-(4-methylpiperazin-1-yl)phenyl; 4-(difluoromethyl)-3-fluorophenyl; 4-(dimethylcarbamoyl)phenyl; 4-(ethoxymethyl)phenyl; 4-(ethylcarbamoyl)phenyl; 4-(hydroxymethyl)phenyl; 4-(morpholin-4-yl)phenyl; 4-(propan-2-yl)phenyl; 4-(propan-2-yloxy)phenyl; 4-(pyrrolidin-1-yl)phenyl; 4-(trifluoromethoxy)phenyl; 4-(trifluoromethyl)phenyl; 4,5-difluoro-2-methoxyphenyl; 4-[(1R)-1-hydroxybutyl]phenyl; (dimethylamino)methylphenyl; 4-[(pyrrolidin-1-yl)carbonyl]phenyl; 4-[2-(dimethylamino)ethyl]phenyl; 4-[2-(pyrrolidin-1-yl)ethoxy]phenyl; 4-acetylphenyl; 4-butoxy-2-methylphenyl; 4-butoxy-3-chlorophenyl; 4-butoxy-3-fluorophenyl; 4-butoxyphenyl; 4-butylphenyl; 4-chloro-2-(trifluoromethyl)phenyl; 4-chloro-2-ethoxyphenyl; 4-chloro-2-methoxyphenyl; 4-chloro-2-methylphenyl; 4-chloro-3-(trifluoromethyl)phenyl; 4-chloro-3-fluorophenyl; 4-chloro-3-methoxyphenyl; 4-chlorophenyl; 4-cyanophenyl; 4-cyclohexylphenyl; 4-ethoxy-2-methylphenyl; 4-ethoxy-3-fluorophenyl; 4-ethoxyphenyl; 4-ethylphenyl; 4-fluoro-2-(propan-2-yloxy)phenyl; 4-fluoro-2,5-dimethylphenyl; 4-fluoro-2-methoxyphenyl; 4-fluoro-2-methylphenyl; 4-fluoro-3-(2,2,2-trifluoroethoxy)phenyl; 4-fluoro-3-(trifluoromethyl)phenyl; 4-fluoro-3-[(propan-2-yl)carbamoyl]phenyl; 4-fluoro-3-methoxyphenyl; 4-fluoro-3-methylphenyl; 4-fluorophenyl; 4-methanesulfonylphenyl; 4-methoxy-2-(trifluoromethyl)phenyl; 4-methoxy-2,5-dimethylphenyl; 4-methoxy-2-methylphenyl; 4-methoxy-3,5-dimethylphenyl; 4-methoxy-3-methylphenyl; 4-methoxyphenyl; 4-methylphenyl; 4-phenylbutane; 4-phenylphenyl; 4-propoxyphenyl; 5-(diethylcarbamoyl)-2-fluorophenyl; 5-acetyl-2-methoxyphenyl; 5-chloro-2-(2,2,2-trifluoroethoxy)phenyl; 5-chloro-2-(2,2-difluoroethoxy)phenyl; 5-chloro-2-(prop-2-yn-1-yloxy)phenyl; 5-chloro-2-(propan-2-yloxy)phenyl; 5-chloro-2-ethoxyphenyl; 5-chloro-2-hydroxyphenyl; 5-chloro-2-methoxyphenyl; 5-chloro-2-methylphenyl; 5-chloro-2-propoxyphenyl; 5-cyano-2-methoxyphenyl; 5-fluoro-2-(hydroxymethyl)phenyl; 5-fluoro-2-methoxyphenyl; 5-fluoro-2-methylphenyl; 5H,6H,7H,8H,9H-imidazo[1,2-a]azepinephenyl; 5-hydroxy-(4-phenylphenyl); 5-hydroxy-2-(trifluoromethoxy)phenyl; 5-hydroxy-3-(morpholin-4-yl)phenyl; 5-hydroxy-3-(piperidin-1-yl)phenyl; 5-hydroxy-3-(pyrrolidin-1-yl)phenyl; 5-tert-butyl-2-methoxyphenyl; 6-chloro-2-fluoro-3-methylphenyl; 6-chloroimidazo[1,2-a]pyridinephenyl; 6-methoxynaphthalene;

8-thiatricyclo[7.4.0.0²,⁷]trideca-1(13),2,4,6,9,11-hexaene; naphthalene; naphthalenephenyl; phenoxathiine; phenyl; and quinolone.

8. The compound of claim 1 wherein R¹ is aryl wherein said aryl is unsubstituted or substituted with 1, 2, 3, 4, or 5 substituents which can be the same or different and are independently selected from the group consisting of:

halo, hydroxy, hydroxyalkyl, cyano, alkyl, alkynyl, alkynylalkoxy, alkoxyalkyl, alkoxy, haloalkyl, haloalkoxy, —C(O)NH(alkyl), —C(O)NH(cycloalkyl), —C(O)N(alkyl)₂, arylalkoxy-, aryloxy-, cycloalkyl, heterocycloalkyl, aryl, (heterocycloalkyl)alkyl-, (heterocycloalkyl)alkoxy-, —C(O)heterocycloalkyl, heteroaryl, (heteroaryl)alkyl-, —S(O)₂-alkyl, —S-alkyl, —C(O)alkyl, —S(O₂)NH₂, —S(O₂)NH(alkyl), —S(O₂)N(alkyl)₂, and —N(H)(SO₂)(alkyl), wherein each of said cycloalkyl, heterocycloalkyl, aryl, or heteroaryl may be substituted by one or more halo, cyano, alkyl, and alkoxy.

9. The compound of claim 1, wherein R¹ is aryl wherein said aryl is unsubstituted or substituted with 1, 2, 3, 4, or 5 substituents which can be the same or different and are independently selected from the group consisting of: halo, haloalkyl, and haloalkoxy.

10. The compound of claim 9, wherein haloalkyl is —CH$_z$F$_{3-z}$ or —CH₂CH$_z$F$_{3-z}$, and z is 0, 1 or 2.

11. The compound of claim 9, wherein haloalkoxy is —OCH$_z$F$_{3-z}$, and z is 0, 1 or 2.

12. The of claim 9, wherein halo is F.

13. A compound selected from the group consisting of:
N-({4-[(4-chloro-2-ethoxybenzene)sulfonyl]phenyl}methyl)-1H-pyrrolo[3,2-c]pyridine-2-carboxamide,
N-[(4-{[2-fluoro-4-(1H-pyrazol-1-yl)benzene]sulfonyl}phenyl)methyl]imidazo[1,2-a]pyrimidine-6-carboxamide,
N-({4-[(2-chloro-5-methylbenzene)sulfonyl]phenyl}methyl)-1H-pyrazolo[3,4-b]pyridine-5-carboxamide,
N-({4-[(5-acetyl-2-methoxybenzene)sulfonyl]phenyl}methyl)imidazo[1,2-a]pyrimidine-6-carboxamide,
N-({4-[(2-fluoro-4-methylbenzene)sulfonyl]phenyl}methyl)furo[2,3-c]pyridine-2-carboxamide,
N-[(4-{[3-fluoro-5-(2,2,2-trifluoroethoxy)benzene]sulfonyl}phenyl)methyl]imidazo[1,2-a]pyrimidine-6-carboxamide,
N-{[4-(benzenesulfonyl)phenyl]methyl}isoquinoline-6-carboxamide,
N-[(4-{[3-(trifluoromethyl)benzene]sulfonyl}phenyl)methyl]imidazo[1,2-a]pyrimidine-6-carboxamide,
N-[(4-{[3-(piperidin-1-ylmethyl)benzene]sulfonyl}phenyl)methyl]imidazo[1,2-a]pyridine-6-carboxamide,
N-({4-[(4-butylbenzene)sulfonyl]phenyl}methyl)imidazo[1,2-a]pyridine-6-carboxamide,
N-{[4-(2-methylpyridine-3-sulfonyl)phenyl]methyl}-1H-pyrrolo[3,2-c]pyridine-2-carboxamide,
N-({4-[(4-methoxy-3,5-dimethylbenzene)sulfonyl]phenyl}methyl)furo[2,3-c]pyridine-2-carboxamide,
N-({4-[(4-butoxy-3-chlorobenzene)sulfonyl]phenyl}methyl)-1H-pyrrolo[3,2-c]pyridine-2-carboxamide,
N-({4-[(2-methanesulfonylbenzene)sulfonyl]phenyl}methyl)-1H-pyrazolo[3,4-b]pyridine-5-carboxamide,
N-[(4-{[3-chloro-5-(hydroxymethyl)benzene]sulfonyl}phenyl)methyl]imidazo[1,2-a]pyrimidine-6-carboxamide,
N-[(4-{[3-(diethylcarbamoyl)-5-fluorobenzene]sulfonyl}phenyl)methyl]furo[2,3-c]pyridine-2-carboxamide,
N-({4-[(2-chloro-6-methoxybenzene)sulfonyl]phenyl}methyl)thieno[2,3-c]pyridine-2-carboxamide,
N-({4-[(3-chloro-4-propoxybenzene)sulfonyl]phenyl}methyl)imidazo[1,2-a]pyrimidine-6-carboxamide,
N-({4-[(2,3-dimethylbenzene)sulfonyl]phenyl}methyl)-1H-pyrrolo[3,2-c]pyridine-2-carboxamide,
N-[(4-{[3-(propan-2-yloxy)benzene]sulfonyl}phenyl)methyl]imidazo[1,2-a]pyrimidine-6-carboxamide,
N-({4-[(4-acetylbenzene)sulfonyl]phenyl}methyl)imidazo[1,2-a]pyrimidine-6-carboxamide,
N-{[4-({3-[(2-methylpropyl)carbamoyl]benzene}sulfonyl)phenyl]methyl}-1H-pyrrolo[3,2-c]pyridine-2-carboxamide,
N-({4-[(2-chloro-6-fluorobenzene)sulfonyl]phenyl}methyl)imidazo[1,2-a]pyridine-6-carboxamide,
N-({4-[(3-fluoro-5-methylbenzene)sulfonyl]phenyl}methyl)furo[2,3-c]pyridine-2-carboxamide,
N-{[4-({4-[2-(pyrrolidin-1-yl)ethoxy]benzene}sulfonyl)phenyl]methyl}-1H-pyrrolo[3,2-c]pyridine-2-carboxamide,
N-[(4-{[3-(morpholin-4-yl)benzene]sulfonyl}phenyl)methyl]-1H-pyrrolo[3,2-c]pyridine-2-carboxamide,
N-({4-[(4-butoxy-2-methylbenzene)sulfonyl]phenyl}methyl)imidazo[1,2-a]pyridine-6-carboxamide,
N-({4-[(4-fluoro-2,5-dimethylbenzene)sulfonyl]phenyl}methyl)imidazo[1,2-a]pyrimidine-6-carboxamide,
N-[(4-{[2-methyl-4-(trifluoromethyl)benzene]sulfonyl}phenyl)methyl]imidazo[1,2-a]pyrimidine-6-carboxamide,
N-({4-[(3-ethylbenzene)sulfonyl]phenyl}methyl)-1H-pyrazolo[3,4-b]pyridine-5-carboxamide,
N-({4-[(3-phenylbenzene)sulfonyl]phenyl}methyl)imidazo[1,2-a]pyridine-6-carboxamide,
N-({4-[(2-chloro-5-methylbenzene)sulfonyl]phenyl}methyl)imidazo[1,2-a]pyridine-6-carboxamide,
N-({4-[(2-chloro-3-fluorobenzene)sulfonyl]phenyl}methyl)-1H-pyrazolo[3,4-b]pyridine-5-carboxamide,
N-[(4-{[5-chloro-2-(2,2,2-trifluoroethoxy)benzene]sulfonyl}phenyl)methyl]imidazo[1,2-a]pyridine-6-carboxamide,
N-({4-[(4-butoxybenzene)sulfonyl]phenyl}methyl)imidazo[1,2-a]pyridine-6-carboxamide,
N-({4-[(2,5-dimethylbenzene)sulfonyl]phenyl}methyl)-1H-pyrrolo[3,2-c]pyridine-2-carboxamide,
N-({4-[(5-fluoro-2-methoxybenzene)sulfonyl]phenyl}methyl)furo[2,3-c]pyridine-2-carboxamide,
N-{[4-({3-[2-(morpholin-4-yl)ethoxy]benzene}sulfonyl)phenyl]methyl}thieno[2,3-c]pyridine-2-carboxamide,
N-({4-[(3-chloro-5-methylbenzene)sulfonyl]phenyl}methyl)furo[2,3-c]pyridine-2-carboxamide,
N-({4-[(4-ethoxy-3-fluorobenzene)sulfonyl]phenyl}methyl)thieno[2,3-c]pyridine-2-carboxamide,
N-({4-[(4-chlorobenzene)sulfonyl]phenyl}methyl)furo[2,3-c]pyridine-2-carboxamide, N-({4-[(4-ethylbenzene)sulfonyl]phenyl}methyl)thieno[2,3-c]pyridine-2-carboxamide,
N-({4-[(4-ethoxy-2-methylbenzene)sulfonyl]phenyl}methyl)imidazo[1,2-a]pyridine-6-carboxamide,
N-({4-[(3-chloro-5-fluorobenzene)sulfonyl]phenyl}methyl)imidazo[1,2-a]pyridine-6-carboxamide,
N-[(4-{[4-(1-cyanocyclopentyl)benzene]sulfonyl}phenyl)methyl]imidazo[1,2-a]pyrimidine-6-carboxamide,
N-({4-[(3-propoxybenzene)sulfonyl]phenyl}methyl)thieno[2,3-c]pyridine-2-carboxamide,
N-[(4-{[3-fluoro-4-(trifluoromethoxy)benzene]sulfonyl}phenyl)methyl]imidazo[1,2-a]pyrimidine-6-carboxamide,
N-({4-[(4-fluoro-2-methoxybenzene)sulfonyl]phenyl}methyl)-1H-pyrrolo[3,2-c]pyridine-2-carboxamide,
N-({4-[(3-fluorobenzene)sulfonyl]phenyl}methyl)-1H-pyrazolo[3,4-b]pyridine-5-carboxamide,
N-[(4-{8-thiatricyclo[7.4.0.0$^{2,7}$]trideca-1(13),2,4,6,9,11-hexaene-6-sulfonyl}phenyl)methyl]furo[2,3-c]pyridine-2-carboxamide,
N-({4-[(5-chloro-2-ethoxybenzene)sulfonyl]phenyl}methyl)thieno[2,3-c]pyridine-2-carboxamide,
N-({4-[(3-fluoro-4-methoxybenzene)sulfonyl]phenyl}methyl)-1H-pyrrolo[3,2-c]pyridine-2-carboxamide,
N-[(4-{[3-chloro-5-(diethylcarbamoyl)benzene]sulfonyl}phenyl)methyl]imidazo[1,2-a]pyrimidine-6-carboxamide,
N-({4-[(3,4-difluorobenzene)sulfonyl]phenyl}methyl)furo[2,3-c]pyridine-2-carboxamide,
N-[(4-{[3-(trifluoromethyl)benzene]sulfonyl}phenyl)methyl]thieno[2,3-c]pyridine-2-carboxamide,
N-[(4-{[4-(4-methylpiperazin-1-yl)benzene]sulfonyl}phenyl)methyl]imidazo[1,2-a]pyridine-6-carboxamide,
N-[(4-{[2-(ethoxymethyl)benzene]sulfonyl}phenyl)methyl]-1H-pyrazolo[3,4-b]pyridine-5-carboxamide,
N-{[4-(benzenesulfonyl)phenyl]methyl}-1H-pyrrolo[2,3-c]pyridine-3-carboxamide,
N-[(4-{[3-fluoro-4-(2,2,2-trifluoroethoxy)benzene]sulfonyl}phenyl)methyl]imidazo[1,2-a]pyrimidine-6-carboxamide,
N-({4-[(3-fluoro-2-methylbenzene)sulfonyl]phenyl}methyl)thieno[2,3-c]pyridine-2-carboxamide,
N-({4-[(2-chloro-4-methylbenzene)sulfonyl]phenyl}methyl)-1H-pyrrolo[3,2-c]pyridine-2-carboxamide,
N-({4-[(5-fluoro-2-methylbenzene)sulfonyl]phenyl}methyl)furo[2,3-c]pyridine-2-carboxamide,
N-({4-[(3,4-dimethoxybenzene)sulfonyl]phenyl}methyl)thieno[2,3-c]pyridine-2-carboxamide,
N-({4-[(3-fluoro-5-methoxybenzene)sulfonyl]phenyl}methyl)-1H-pyrazolo[3,4-b]pyridine-5-carboxamide,
N-({4-[(4-ethylbenzene)sulfonyl]phenyl}methyl)furo[2,3-c]pyridine-2-carboxamide,
N-({4-[(2,4,5-trimethylbenzene)sulfonyl]phenyl}methyl)thieno[2,3-c]pyridine-2-carboxamide,
N-[(4-{[3-(propan-2-yl)benzene]sulfonyl}phenyl)methyl]thieno[2,3-c]pyridine-2-carboxamide,
N-({4-[(4-methylbenzene)sulfonyl]phenyl}methyl)thieno[2,3-c]pyridine-2-carboxamide, N-[(4-{[2-fluoro-4-(1H-pyrazol-1-yl)benzene]sulfonyl}phenyl)methyl]thieno[2,3-c]pyridine-2-carboxamide,
N-({4-[(2-chlorobenzene)sulfonyl]phenyl}methyl)-1H-pyrrolo[3,2-c]pyridine-2-carboxamide,
N-({4-[(3-chloro-4-propoxybenzene)sulfonyl]phenyl}methyl)furo[2,3-c]pyridine-2-carboxamide,
N-({4-[(2-fluoro-6-propoxybenzene)sulfonyl]phenyl}methyl)furo[2,3-c]pyridine-2-carboxamide,
N-[(4-{[2-(morpholin-4-ylmethyl)benzene]sulfonyl}phenyl)methyl]thieno[2,3-c]pyridine-2-carboxamide,
N-({4-[(5-fluoro-2-methoxybenzene)sulfonyl]phenyl}methyl)imidazo[1,2-a]pyrimidine-6-carboxamide,
N-[(4-{[2-(2,2,2-trifluoroethoxy)-4-(trifluoromethyl)benzene]sulfonyl}phenyl)methyl]-1H-pyrrolo[3,2-c]pyridine-2-carboxamide,
N-({4-[(2-fluoro-3-methylbenzene)sulfonyl]phenyl}methyl)-1H-pyrrolo[3,2-c]pyridine-2-carboxamide,
N-[(4-{[3-(trifluoromethoxy)benzene]sulfonyl}phenyl)methyl]thieno[2,3-c]pyridine-2-carboxamide,
N-[(4-{[4-(propan-2-yl)benzene]sulfonyl}phenyl)methyl]furo[2,3-c]pyridine-2-carboxamide,
N-({4-[(3-chlorobenzene)sulfonyl]phenyl}methyl)-1H-pyrrolo[3,2-c]pyridine-2-carboxamide,
N-[(4-{[4-(2-methylpropoxy)benzene]sulfonyl}phenyl)methyl]-1H-pyrrolo[3,2-c]pyridine-2-carboxamide,
N-({4-[(3-ethylbenzene)sulfonyl]phenyl}methyl)thieno[2,3-c]pyridine-2-carboxamide,
N-({4-[(3-chlorobenzene)sulfonyl]phenyl}methyl)-1H-pyrrolo[3,2-b]pyridine-2-carboxamide,
N-({4-[(4-fluoro-3-methylbenzene)sulfonyl]phenyl}methyl)-1H-pyrazolo[3,4-b]pyridine-5-carboxamide,
N-[(4-{[3-(methoxymethyl)benzene]sulfonyl}phenyl)methyl]imidazo[1,2-a]pyridine-6-carboxamide,
N-({4-[(2-butoxy-4-fluorobenzene)sulfonyl]phenyl}methyl)imidazo[1,2-a]pyridine-6-carboxamide,
N-({4-[(3-hydroxybenzene)sulfonyl]phenyl}methyl)imidazo[1,2-a]pyridine-6-carboxamide,
N-({4-[(3-fluoro-2-methoxybenzene)sulfonyl]phenyl}methyl)furo[2,3-c]pyridine-2-carboxamide,
N-[(4-{[2-(ethoxymethyl)benzene]sulfonyl}phenyl)methyl]imidazo[1,2-a]pyrimidine-6-carboxamide,
N-({4-[(5-chloro-2-methoxybenzene)sulfonyl]phenyl}methyl)imidazo[1,2-a]pyridine-6-carboxamide,
N-({4-[(3-ethoxy-2-fluorobenzene)sulfonyl]phenyl}methyl)thieno[2,3-c]pyridine-2-carboxamide,
N-({4-[(2-ethylbenzene)sulfonyl]phenyl}methyl)-1H-pyrrolo[3,2-c]pyridine-2-carboxamide,
N-({4-[(4-fluoro-3-methoxybenzene)sulfonyl]phenyl}methyl)imidazo[1,2-a]pyridine-6-carboxamide,
N-({4-[(4-ethoxy-3-fluorobenzene)sulfonyl]phenyl}methyl)-1H-pyrrolo[3,2-c]pyridine-2-carboxamide,
N-[(4-{[3-fluoro-5-(morpholin-4-yl)benzene]sulfonyl}phenyl)methyl]-1H-pyrrolo[3,2-c]pyridine-2-carboxamide,
N-({4-[(2-fluoro-6-propoxybenzene)sulfonyl]phenyl}methyl)thieno[2,3-c]pyridine-2-carboxamide, N-[(4-{[2-methoxy-4-(trifluoromethyl)benzene]sulfonyl}phenyl)methyl]imidazo[1,2-a]pyrimidine-6-carboxamide,
N-[(4-{8-oxatricyclo[7.4.0.0²,⁷]trideca-1(13),2,4,6,9,11-hexaene-6-sulfonyl}phenyl)methyl]furo[2,3-c]pyridine-2-carboxamide,
N-({4-[(4-phenylbenzene)sulfonyl]phenyl}methyl)thieno[2,3-c]pyridine-2-carboxamide,
N-({4-[(2-ethoxy-4-fluorobenzene)sulfonyl]phenyl}methyl)furo[2,3-c]pyridine-2-carboxamide,
N-[(4-{[2-fluoro-4-(trifluoromethyl)benzene]sulfonyl}phenyl)methyl]thieno[2,3-c]pyridine-2-carboxamide,
N-({4-[(5-chloro-2-propoxybenzene)sulfonyl]phenyl}methyl)-1H-pyrrolo[3,2-c]pyridine-2-carboxamide,
N-{[4-(2H-1,3-benzodioxole-5-sulfonyl)phenyl]methyl}-1H-pyrazolo[3,4-b]pyridine-5-carboxamide,
N-{[4-({4-[(1R)-1-hydroxybutyl]benzene}sulfonyl)phenyl]methyl}imidazo[1,2-a]pyrimidine-6-carboxamide,
N-({4-[(3-methoxybenzene)sulfonyl]phenyl}methyl)furo[2,3-c]pyridine-2-carboxamide,
N-{[4-({3-[2-(morpholin-4-yl)ethoxy]benzene}sulfonyl)phenyl]methyl}imidazo[1,2-a]pyridine-6-carboxamide,
N-{[4-(benzenesulfonyl)phenyl]methyl}imidazo[1,2-a]pyrazine-2-carboxamide,
N-({4-[(4-ethoxybenzene)sulfonyl]phenyl}methyl)imidazo[1,2-a]pyridine-6-carboxamide,
N-[(4-{[3-(morpholin-4-yl)benzene]sulfonyl}phenyl)methyl]-1H-pyrazolo[3,4-b]pyridine-5-carboxamide,
N-({4-[(2-fluoro-3-methylbenzene)sulfonyl]phenyl}methyl)-1H-pyrazolo[3,4-b]pyridine-5-carboxamide,
N-({4-[(3,4-dichlorobenzene)sulfonyl]phenyl}methyl)furo[2,3-c]pyridine-2-carboxamide,
N-{[4-({4-fluoro-3-[(propan-2-yl)carbamoyl]benzene}sulfonyl)phenyl]methyl}imidazo[1,2-a]pyrimidine-6-carboxamide,
N-[(4-{[2,4-bis(trifluoromethyl)benzene]sulfonyl}phenyl)methyl]imidazo[1,2-a]pyridine-6-carboxamide,
N-[(4-{[3-fluoro-4-(trifluoromethyl)benzene]sulfonyl}phenyl)methyl]furo[2,3-c]pyridine-2-carboxamide,
N-({4-[(2-fluoro-3-methoxybenzene)sulfonyl]phenyl}methyl)-1H-pyrrolo[3,2-c]pyridine-2-carboxamide,
N-[(4-{[2,4-bis(trifluoromethyl)benzene]sulfonyl}phenyl)methyl]-1H-pyrrolo[3,2-c]pyridine-2-carboxamide,
N-({4-[(2-methyl-4-propoxybenzene)sulfonyl]phenyl}methyl)imidazo[1,2-a]pyridine-6-carboxamide,
N-({4-[(3-phenylbenzene)sulfonyl]phenyl}methyl)-1,3-benzothiazole-6-carboxamide,
N-[(4-{[4-(ethylcarbamoyl)benzene]sulfonyl}phenyl)methyl]furo[2,3-c]pyridine-2-carboxamide,
N-({4-[(4-methoxybenzene)sulfonyl]phenyl}methyl)imidazo[1,2-a]pyrimidine-6-carboxamide,
N-[(4-{[3-(cyclopentylcarbamoyl)benzene]sulfonyl}phenyl)methyl]thieno[2,3-c]pyridine-2-carboxamide,
N-({4-[(3-chloro-4-methylbenzene)sulfonyl]phenyl}methyl)thieno[2,3-c]pyridine-2-carboxamide,
N-({4-[(4,5-difluoro-2-methoxybenzene)sulfonyl]phenyl}methyl)imidazo[1,2-a]pyrimidine-6-carboxamide,
N-[(4-{[3-(methoxymethyl)benzene]sulfonyl}phenyl)methyl]imidazo[1,2-a]pyrimidine-6-carboxamide,
N-[(4-{[3-fluoro-4-(2,2,2-trifluoroethoxy)benzene]sulfonyl}phenyl)methyl]thieno[2,3-c]pyridine-2-carboxamide,
N-{[4-(2H-1,3-benzodioxole-4-sulfonyl)phenyl]methyl}thieno[2,3-c]pyridine-2-carboxamide,
N-[(4-{[5-chloro-2-(prop-2-yn-1-yloxy)benzene]sulfonyl}phenyl)methyl]imidazo[1,2-a]pyrimidine-6-carboxamide,
N-({4-[(3-phenylbenzene)sulfonyl]phenyl}methyl)furo[2,3-c]pyridine-2-carboxamide,
N-({4-[(4-fluoro-2-methoxybenzene)sulfonyl]phenyl}methyl)furo[2,3-c]pyridine-2-carboxamide,
N-[(4-{[3-(propan-2-yloxy)benzene]sulfonyl}phenyl)methyl]furo[2,3-c]pyridine-2-carboxamide,
N-({4-[(3-methylbenzene)sulfonyl]phenyl}methyl)furo[2,3-c]pyridine-2-carboxamide,
N-({4-[(5-chloro-2-propoxybenzene)sulfonyl]phenyl}methyl)thieno[2,3-c]pyridine-2-carboxamide,
N-({4-[(4-methoxy-3,5-dimethylbenzene)sulfonyl]phenyl}methyl)imidazo[1,2-a]pyrimidine-6-carboxamide,
N-({4-[(3-cyanobenzene)sulfonyl]phenyl}methyl)furo[2,3-c]pyridine-2-carboxamide,
N-({4-[(3-fluoro-4-propoxybenzene)sulfonyl]phenyl}methyl)furo[2,3-c]pyridine-2-carboxamide,
N-({4-[(2,6-dichloro-3-methylbenzene)sulfonyl]phenyl}methyl)furo[2,3-c]pyridine-2-carboxamide,
N-({4-[(3-propoxybenzene)sulfonyl]phenyl}methyl)imidazo[1,2-a]pyrimidine-6-carboxamide,
N-({4-[(4-fluoro-2-methylbenzene)sulfonyl]phenyl}methyl)furo[2,3-c]pyridine-2-carboxamide,
N-({4-[(3-methanesulfonylbenzene)sulfonyl]phenyl}methyl)furo[2,3-c]pyridine-2-carboxamide,
N-[(4-{[4-chloro-3-(trifluoromethyl)benzene]sulfonyl}phenyl)methyl]thieno[2,3-c]pyridine-2-carboxamide,
N-({4-[(3-fluoro-2-methylbenzene)sulfonyl]phenyl}methyl)furo[2,3-c]pyridine-2-carboxamide,
N-({4-[(2-chloro-4-methoxybenzene)sulfonyl]phenyl}methyl)imidazo[1,2-a]pyridine-6-carboxamide,
N-({4-[(2-methanesulfonamidobenzene)sulfonyl]phenyl}methyl)-1H-pyrrolo[3,2-c]pyridine-2-carboxamide,
N-{[4-(2,3-dihydro-1,4-benzodioxine-6-sulfonyl)phenyl]methyl}imidazo[1,2-a]pyrimidine-6-carboxamide,
N-({4-[(2-methyl-4-propoxybenzene)sulfonyl]phenyl}methyl)imidazo[1,2-a]pyrimidine-6-carboxamide,
N-({4-[(2-methoxy-5-methylbenzene)sulfonyl]phenyl}methyl)-1H-pyrrolo[3,2-c]pyridine-2-carboxamide,
N-({4-[(2,4-dimethoxybenzene)sulfonyl]phenyl}methyl)-1H-pyrrolo[3,2-c]pyridine-2-carboxamide,
N-[(4-{[3-(morpholin-4-yl)benzene]sulfonyl}phenyl)methyl]thieno[2,3-c]pyridine-2-carboxamide,
N-[(4-{[4-methoxy-2-(trifluoromethyl)benzene]sulfonyl}phenyl)methyl]-1H-pyrrolo[3,2-c]pyridine-2-carboxamide, N-({4-[(4-ethoxy-3-fluorobenzene)sulfonyl]
phenyl}methyl)-1H-pyrazolo[3,4-b]pyridine-5-carbox-
amide,
N-{[4-({3-[2-(morpholin-4-yl)ethoxy]benzene}sulfonyl)
phenyl]methyl}imidazo[1,2-a]pyrimidine-6-carbox-
amide,
N-({4-[(4-fluoro-3-methoxybenzene)sulfonyl]
phenyl}methyl)imidazo[1,2-a]pyrimidine-6-carbox-
amide,
N-[(4-{[3-(5-methyl-1,2,4-oxadiazol-3-yl)benzene]
sulfonyl}phenyl)methyl]thieno[2,3-c]pyridine-2-car-
boxamide,
N-({4-[(3-fluoro-4-methylbenzene)sulfonyl]
phenyl}methyl)furo[2,3-c]pyridine-2-carboxamide,
N-(4-(2-(trifluoromethoxy)phenylsulfonyl)benzyl)imi-
dazo[1,2-a]pyridine-6-carboxamide,
N-({4-[(3-fluoro-2-methoxybenzene)sulfonyl]
phenyl}methyl)imidazo[1,2-a]pyrimidine-6-carbox-
amide,
N-({4-[(4,5-difluoro-2-methoxybenzene)sulfonyl]
phenyl}methyl)-1H-pyrrolo[3,2-c]pyridine-2-carbox-
amide,
N-[(4-{[2-(methylsulfamoyl)benzene]sulfonyl}phenyl)
methyl]imidazo[1,2-a]pyrimidine-6-carboxamide,
N-[(4-{[3-fluoro-4-(methylsulfanyl)benzene]
sulfonyl}phenyl)methyl]thieno[2,3-c]pyridine-2-car-
boxamide,
N-[(4-{[3-(2-methylpropoxy)benzene]sulfonyl}phenyl)
methyl]thieno[2,3-c]pyridine-2-carboxamide,
N-[(4-{[4-(pyrrolidin-1-yl)benzene]sulfonyl}phenyl)
methyl]imidazo[1,2-a]pyridine-6-carboxamide,
N-({4-[(3-methoxy-4-methylbenzene)sulfonyl]
phenyl}methyl)imidazo[1,2-a]pyrimidine-6-carbox-
amide,
N-{[4-(benzenesulfonyl)phenyl]methyl}-1-methyl-1H-
pyrrolo[3,2-c]pyridine-2-carboxamide,
N-({4-[(3-fluoro-4-methylbenzene)sulfonyl]
phenyl}methyl)thieno[2,3-c]pyridine-2-carboxamide,
N-[(4-{[2-(ethoxymethyl)benzene]sulfonyl}phenyl)
methyl]-1H-pyrrolo[3,2-c]pyridine-2-carboxamide,
N-({4-[(3-methoxy-4-methylbenzene)sulfonyl]
phenyl}methyl)furo[2,3-c]pyridine-2-carboxamide,
N-[(4-{[3-(piperidin-1-ylmethyl)benzene]
sulfonyl}phenyl)methyl]imidazo[1,2-a]pyrimidine-6-
carboxamide,
N-[(4-{[3-fluoro-5-(2-methylpropoxy)benzene]
sulfonyl}phenyl)methyl]imidazo[1,2-a]pyrimidine-6-
carboxamide,
N-({4-[(4-methoxybenzene)sulfonyl]phenyl}methyl)-
1H-pyrazolo[3,4-b]pyridine-5-carboxamide,
N-({4-[(3-fluoro-2-methylbenzene)sulfonyl]
phenyl}methyl)-1H-pyrrolo[3,2-c]pyridine-2-carbox-
amide,
N-[(4-{[2-(trifluoromethyl)benzene]sulfonyl}phenyl)
methyl]thieno[2,3-c]pyridine-2-carboxamide,
N-({4-[(3-chloro-4-propoxybenzene)sulfonyl]
phenyl}methyl)imidazo[1,2-a]pyrimidine-6-carboxam-
ide,
N-({4-[(2,4-dichloro-3-methoxybenzene)sulfonyl]
phenyl}methyl)furo[2,3-c]pyridine-2-carboxamide,
N-({4-[(2-chloro-5-fluorobenzene)sulfonyl]
phenyl}methyl)imidazo[1,2-a]pyrimidine-6-carbox-
amide,
N-(4-(phenylsulfonyl)benzyl)benzo[d]thiazole-5-carbox-
amide,
N-({4-[(3,4-dimethylbenzene)sulfonyl]phenyl}methyl)
furo[2,3-c]pyridine-2-carboxamide,
N-({4-[(3-fluoro-4-methoxybenzene)sulfonyl]
phenyl}methyl)furo[2,3-c]pyridine-2-carboxamide,
N-({4-[(4-chloro-2-methylbenzene)sulfonyl]
phenyl}methyl)imidazo[1,2-a]pyrimidine-6-carbox-
amide,
N-({4-[(4-ethoxy-3-fluorobenzene)sulfonyl]
phenyl}methyl)imidazo[1,2-a]pyrimidine-6-carbox-
amide,
N-[(4-{[3-(2,2,2-trifluoroethoxy)benzene]
sulfonyl}phenyl)methyl]imidazo[1,2-a]pyrimidine-6-
carboxamide,
N-{[4-(2H-1,3-benzodioxole-5-sulfonyl)phenyl]
methyl}imidazo[1,2-a]pyrimidine-6-carboxamide,
N-{[4-(2H-1,3-benzodioxole-4-sulfonyl)phenyl]
methyl}imidazo[1,2-a]pyrimidine-6-carboxamide,
N-({4-[(5-tert-butyl-2-methoxybenzene)sulfonyl]
phenyl}methyl)-1H-pyrrolo[3,2-c]pyridine-2-carbox-
amide,
N-[(4-{[3-(ethanesulfonyl)benzene]sulfonyl}phenyl)
methyl]furo[2,3-c]pyridine-2-carboxamide,
N-({4-[(4-methoxy-3-methylbenzene)sulfonyl]
phenyl}methyl)thieno[2,3-c]pyridine-2-carboxamide,
N-({4-[(3-chloro-2-methoxybenzene)sulfonyl]
phenyl}methyl)furo[2,3-c]pyridine-2-carboxamide,
N-({4-[(3-methoxy-5-methylbenzene)sulfonyl]
phenyl}methyl)imidazo[1,2-a]pyrimidine-6-carboxam-
ide,
N-[(4-{[2-methoxy-4-(trifluoromethyl)benzene]
sulfonyl}phenyl)methyl]thieno[2,3-c]pyridine-2-car-
boxamide,
N-[(4-{[3-(pyrimidin-2-yl)benzene]sulfonyl}phenyl)
methyl]imidazo[1,2-a]pyridine-6-carboxamide,
N-({4-[(6-chloro-2-fluoro-3-methylbenzene)sulfonyl]
phenyl}methyl)thieno[2,3-c]pyridine-2-carboxamide,
N-({4-[(5-fluoro-2-methylbenzene)sulfonyl]
phenyl}methyl)thieno[2,3-c]pyridine-2-carboxamide,
N-({4-[(3-sulfamoylbenzene)sulfonyl]phenyl}methyl)
thieno[2,3-c]pyridine-2-carboxamide,
N-({4-[(5-cyano-2-methoxybenzene)sulfonyl]
phenyl}methyl)imidazo[1,2-a]pyrimidine-6-carboxam-
ide,
N-[(4-{[4-fluoro-3-(2,2,2-trifluoroethoxy)benzene]
sulfonyl}phenyl)methyl]furo[2,3-c]pyridine-2-carbox-
amide,
N-({4-[(3-cyanobenzene)sulfonyl]phenyl}methyl)thieno
[2,3-c]pyridine-2-carboxamide,
N-[(4-{[3-(3,5-dimethyl-1H-pyrazol-1-yl)benzene]
sulfonyl}phenyl)methyl]imidazo[1,2-a]pyrimidine-6-
carboxamide,
N-({4-[(3-chlorobenzene)sulfonyl]phenyl}methyl)thieno
[2,3-c]pyridine-2-carboxamide,
N-({4-[(2,6-dichlorobenzene)sulfonyl]phenyl}methyl)
imidazo[1,2-a]pyrimidine-6-carboxamide,
N-[(4-{[2-fluoro-4-(trifluoromethyl)benzene]
sulfonyl}phenyl)methyl]imidazo[1,2-a]pyridine-6-car-
boxamide,
N-[(4-{[3-chloro-5-(trifluoromethyl)benzene]
sulfonyl}phenyl)methyl]imidazo[1,2-a]pyrimidine-6-
carboxamide,
N-({4-[(2-phenoxybenzene)sulfonyl]phenyl}methyl)imi-
dazo[1,2-a]pyrimidine-6-carboxamide,
N-({4-[(2-methylbenzene)sulfonyl]phenyl}methyl)-1H-
pyrrolo[3,2-c]pyridine-2-carboxamide,
N-({4-[(2-chloro-4-methoxybenzene)sulfonyl]
phenyl}methyl)-1H-pyrrolo[3,2-c]pyridine-2-carbox-
amide, N-[(4-{[2-methoxy-4-(1H-pyrazol-1-yl)benzene]
sulfonyl}phenyl)methyl]furo[2,3-c]pyridine-2-carbox-
amide,
N-({4-[(4-ethylbenzene)sulfonyl]phenyl}methyl)-1H-
pyrrolo[3,2-c]pyridine-2-carboxamide,
N-[(4-{[3-(cyclopentylcarbamoyl)benzene]
sulfonyl}phenyl)methyl]furo[2,3-c]pyridine-2-carbox-
amide,
5-hydroxy-N-({4-[(4-phenylbenzene)sulfonyl]
phenyl}methyl)-1H-indole-2-carboxamide,
N-[(4-{[4-(morpholin-4-yl)benzene]sulfonyl}phenyl)
methyl]furo[2,3-c]pyridine-2-carboxamide,
N-[(4-{[4-(ethoxymethyl)benzene]sulfonyl}phenyl)
methyl]imidazo[1,2-a]pyrimidine-6-carboxamide,
N-({4-[(3-chloro-5-fluorobenzene)sulfonyl]
phenyl}methyl)imidazo[1,2-a]pyrimidine-6-carbox-
amide,
N-[(4-{[4-(morpholin-4-yl)benzene]sulfonyl}phenyl)
methyl]imidazo[1,2-a]pyridine-6-carboxamide,
N-({4-[(4-ethoxy-2-methylbenzene)sulfonyl]
phenyl}methyl)-1H-pyrazolo[3,4-b]pyridine-5-carbox-
amide,
N-({4-[(4-butoxy-3-chlorobenzene)sulfonyl]
phenyl}methyl)imidazo[1,2-a]pyridine-6-carboxam-
ide,
N-({4-[(4-methanesulfonylbenzene)sulfonyl]
phenyl}methyl)-1H-pyrrolo[3,2-c]pyridine-2-carbox-
amide,
N-[(4-{8-oxatricyclo[7.4.0.0$^{2,7}$]trideca-1(13),2,4,6,9,11-
hexaene-6-sulfonyl}phenyl)methyl]imidazo[1,2-a]py-
rimidine-6-carboxamide,
N-[(4-{[2-(ethoxymethyl)benzene]sulfonyl}phenyl)
methyl]furo[2,3-c]pyridine-2-carboxamide,
N-{[4-(naphthalene-1-sulfonyl)phenyl]methyl}imidazo
[1,2-a]pyrimidine-6-carboxamide,
N-({4-[(4-chloro-3-methoxybenzene)sulfonyl]
phenyl}methyl)-1H-pyrazolo[3,4-b]pyridine-5-carbox-
amide,
N-{[4-(5-chloropyridine-3-sulfonyl)phenyl]methyl}-1H-
pyrrolo[3,2-c]pyridine-2-carboxamide,
N-({4-[(3-fluoro-5-methylbenzene)sulfonyl]
phenyl}methyl)-1H-pyrazolo[3,4-b]pyridine-5-carbox-
amide,
N-({4-[(4-butylbenzene)sulfonyl]phenyl}methyl)-1H-
pyrrolo[3,2-c]pyridine-2-carboxamide,
N-({4-[(2,6-dichlorobenzene)sulfonyl]phenyl}methyl)-
1H-pyrazolo[3,4-b]pyridine-5-carboxamide,
N-[(4-{[3-(piperidin-1-yl)benzene]sulfonyl}phenyl)
methyl]-1H-pyrazolo[3,4-b]pyridine-5-carboxamide,
N-({4-[(3-methoxy-5-methylbenzene)sulfonyl]
phenyl}methyl)furo[2,3-c]pyridine-2-carboxamide,
N-[(4-{[3-fluoro-4-(trifluoromethoxy)benzene]
sulfonyl}phenyl)methyl]thieno[2,3-c]pyridine-2-car-
boxamide,
N-[(4-{[2-methoxy-5-(trifluoromethoxy)benzene]
sulfonyl}phenyl)methyl]-1H-pyrrolo[3,2-c]pyridine-2-
carboxamide,
N-({4-[(4-fluoro-3-methoxybenzene)sulfonyl]
phenyl}methyl)furo[2,3-c]pyridine-2-carboxamide,
N-{[4-(phenoxathiine-4-sulfonyl)phenyl]
methyl}imidazo[1,2-a]pyrimidine-6-carboxamide,
N-[(4-{[3-(4-fluorophenoxy)benzene]sulfonyl}phenyl)
methyl]imidazo[1,2-a]pyridine-6-carboxamide,
N-({4-[(5-chloro-2-methylbenzene)sulfonyl]
phenyl}methyl)furo[2,3-c]pyridine-2-carboxamide,
N-[(4-{[4-methoxy-2-(trifluoromethyl)benzene]
sulfonyl}phenyl)methyl]imidazo[1,2-a]pyrimidine-6-
carboxamide,
N-[(4-{[3-fluoro-4-(trifluoromethoxy)benzene]
sulfonyl}phenyl)methyl]furo[2,3-c]pyridine-2-carbox-
amide,
N-[(4-{[3-(5-methyl-1,2,4-oxadiazol-3-yl)benzene]
sulfonyl}phenyl)methyl]furo[2,3-c]pyridine-2-carbox-
amide,
N-({4-[(3-acetylbenzene)sulfonyl]phenyl}methyl)thieno
[2,3-c]pyridine-2-carboxamide,
N-({4-[(4-butoxy-2-methylbenzene)sulfonyl]
phenyl}methyl)furo[2,3-c]pyridine-2-carboxamide,
N-({4-[(2-butoxy-4-fluorobenzene)sulfonyl]
phenyl}methyl)imidazo[1,2-a]pyrimidine-6-carbox-
amide,
N-{[4-({3-[(propan-2-yl)carbamoyl]benzene}sulfonyl)
phenyl]methyl}imidazo[1,2-a]pyrimidine-6-carbox-
amide,
N-({4-[(4,5-difluoro-2-methoxybenzene)sulfonyl]
phenyl}methyl)thieno[2,3-c]pyridine-2-carboxamide,
N-({4-[(3,4-dichlorobenzene)sulfonyl]phenyl}methyl)
imidazo[1,2-a]pyrimidine-6-carboxamide,
N-({4-[(3-chloro-5-fluorobenzene)sulfonyl]
phenyl}methyl)thieno[2,3-c]pyridine-2-carboxamide,
N-[(4-{[3-chloro-4-(trifluoromethyl)benzene]
sulfonyl}phenyl)methyl]imidazo[1,2-a]pyridine-6-car-
boxamide,
N-({4-[(4-ethoxybenzene)sulfonyl]phenyl}methyl)furo
[2,3-c]pyridine-2-carboxamide,
N-({4-[(2,3-dimethylbenzene)sulfonyl]phenyl}methyl)
imidazo[1,2-a]pyrimidine-6-carboxamide,
N-({4-[(3-chloro-4-methoxybenzene)sulfonyl]
phenyl}methyl)-1H-pyrrolo[3,2-c]pyridine-2-carbox-
amide,
N-({4-[(2-chloro-4-methylbenzene)sulfonyl]
phenyl}methyl)thieno[2,3-c]pyridine-2-carboxamide,
N-({4-[(4-propoxybenzene)sulfonyl]phenyl}methyl)-1H-
pyrrolo[3,2-c]pyridine-2-carboxamide,
N-({4-[(2-fluoro-6-propoxybenzene)sulfonyl]
phenyl}methyl)imidazo[1,2-a]pyridine-6-carboxam-
ide,
N-{[4-(benzenesulfonyl)phenyl]methyl}-1H-pyrrolo[2,3-
b]pyridine-5-carboxamide,
N-({4-[(3-chloro-4-methoxybenzene)sulfonyl]
phenyl}methyl)imidazo[1,2-a]pyrimidine-6-carbox-
amide,
N-({4-[(2-methoxybenzene)sulfonyl]phenyl}methyl)-
1H-pyrrolo[3,2-c]pyridine-2-carboxamide,
N-({4-[(2-chloro-5-methylbenzene)sulfonyl]
phenyl}methyl)thieno[2,3-c]pyridine-2-carboxamide,
N-[(4-{[4-(1-cyanocyclopentyl)benzene]
sulfonyl}phenyl)methyl]furo[2,3-c]pyridine-2-carbox-
amide,
N-({4-[(4,5-difluoro-2-methoxybenzene)sulfonyl]
phenyl}methyl)furo[2,3-c]pyridine-2-carboxamide,
N-[(4-{[4-(ethylcarbamoyl)benzene]sulfonyl}phenyl)
methyl]imidazo[1,2-a]pyridine-6-carboxamide,
N-({4-[(3-fluorobenzene)sulfonyl]phenyl}methyl)-1H-
pyrrolo[3,2-c]pyridine-2-carboxamide,
N-({4-[(2-ethylbenzene)sulfonyl]phenyl}methyl)thieno
[2,3-c]pyridine-2-carboxamide,
N-({4-[(2-ethoxybenzene)sulfonyl]phenyl}methyl)furo
[2,3-c]pyridine-2-carboxamide,
N-({4-[(4-fluoro-2,5-dimethylbenzene)sulfonyl]
phenyl}methyl)imidazo[1,2-a]pyridine-6-carboxam-
ide, N-{[4-(benzenesulfonyl)phenyl]methyl}-[1,2,4]triazolo[4,3-a]pyridine-6-carboxamide,
N-[(4-{[3-(5-methyl-1,2,4-oxadiazol-3-yl)benzene]sulfonyl}phenyl)methyl]imidazo[1,2-a]pyrimidine-6-carboxamide,
N-({4-[(3-ethoxybenzene)sulfonyl]phenyl}methyl)furo[2,3-c]pyridine-2-carboxamide,
N-({4-[(2-methoxy-5-methylbenzene)sulfonyl]phenyl}methyl)furo[2,3-c]pyridine-2-carboxamide,
N-({4-[(2,3-dimethoxy-5-methylbenzene)sulfonyl]phenyl}methyl)-1H-pyrrolo[3,2-c]pyridine-2-carboxamide,
N-[(4-{[3-fluoro-5-(pyrrolidin-1-yl)benzene]sulfonyl}phenyl)methyl]imidazo[1,2-a]pyridine-6-carboxamide,
N-({4-[(2,6-dimethoxy-4-methylbenzene)sulfonyl]phenyl}methyl)-1H-pyrazolo[3,4-b]pyridine-5-carboxamide,
N-{[4-(benzenesulfonyl)phenyl]methyl}thieno[2,3-c]pyridine-2-carboxamide,
N-[(4-{[4-(ethylcarbamoyl)benzene]sulfonyl}phenyl)methyl]-1H-pyrrolo[3,2-c]pyridine-2-carboxamide,
N-[(4-{[3-(methylcarbamoyl)benzene]sulfonyl}phenyl)methyl]furo[2,3-c]pyridine-2-carboxamide,
N-({4-[(6-chloro-2-fluoro-3-methylbenzene)sulfonyl]phenyl}methyl)-1H-pyrrolo[3,2-c]pyridine-2-carboxamide,
N-({4-[(3-chloro-4-methylbenzene)sulfonyl]phenyl}methyl)-1H-pyrrolo[3,2-c]pyridine-2-carboxamide,
N-{[4-(2H-1,3-benzodioxole-4-sulfonyl)phenyl]methyl}imidazo[1,2-a]pyrimidine-6-carboxamide,
N-[(4-{[3-(pyrrolidin-1-yl)benzene]sulfonyl}phenyl)methyl]imidazo[1,2-a]pyridine-6-carboxamide,
N-[(4-{[4-fluoro-2-(trifluoromethyl)benzene]sulfonyl}phenyl)methyl]thieno[2,3-c]pyridine-2-carboxamide,
N-({4-[(2,4,5-trimethylbenzene)sulfonyl]phenyl}methyl)furo[2,3-c]pyridine-2-carboxamide,
N-({4-[(2,4-dichloro-3-methoxybenzene)sulfonyl]phenyl}methyl)imidazo[1,2-a]pyrimidine-6-carboxamide,
N-[(4-{[2-fluoro-3-(propan-2-yloxy)benzene]sulfonyl}phenyl)methyl]thieno[2,3-c]pyridine-2-carboxamide,
N-({4-[(4-methoxy-3-methylbenzene)sulfonyl]phenyl}methyl)imidazo[1,2-a]pyrimidine-6-carboxamide,
N-[(4-{[4-methoxy-2-(trifluoromethyl)benzene]sulfonyl}phenyl)methyl]thieno[2,3-c]pyridine-2-carboxamide,
N-[(4-{[3-(piperidin-1-yl)benzene]sulfonyl}phenyl)methyl]-1,3-benzothiazole-6-carboxamide,
N-[(4-{[3-(piperidin-1-yl)benzene]sulfonyl}phenyl)methyl]imidazo[1,2-a]pyrimidine-6-carboxamide,
N-({4-[(4-fluoro-2-methylbenzene)sulfonyl]phenyl}methyl)-1H-pyrrolo[3,2-c]pyridine-2-carboxamide,
N-[(4-{[3-fluoro-5-(2,2,2-trifluoroethoxy)benzene]sulfonyl}phenyl)methyl]-1H-pyrrolo[3,2-c]pyridine-2-carboxamide,
N-({4-[(2-chloro-5-methoxybenzene)sulfonyl]phenyl}methyl)-1H-pyrrolo[3,2-c]pyridine-2-carboxamide,
N-[(4-{[4-(1-cyanocyclopentyl)benzene]sulfonyl}phenyl)methyl]-1H-pyrrolo[3,2-c]pyridine-2-carboxamide,
N-({4-[(4-ethoxybenzene)sulfonyl]phenyl}methyl)thieno[2,3-c]pyridine-2-carboxamide,
N-{[4-(2-methylpyridine-3-sulfonyl)phenyl]methyl}imidazo[1,2-a]pyrimidine-6-carboxamide,
N-[(4-{[4-fluoro-2-(propan-2-yloxy)benzene]sulfonyl}phenyl)methyl]furo[2,3-c]pyridine-2-carboxamide,
N-[(4-{[2-fluoro-3-(trifluoromethoxy)benzene]sulfonyl}phenyl)methyl]thieno[2,3-c]pyridine-2-carboxamide,
N-[(4-{[2-methoxy-4-(trifluoromethyl)benzene]sulfonyl}phenyl)methyl]-1H-pyrazolo[3,4-b]pyridine-5-carboxamide,
N-({4-[(4-propoxybenzene)sulfonyl]phenyl}methyl)furo[2,3-c]pyridine-2-carboxamide,
N-({4-[(4-methoxy-2,5-dimethylbenzene)sulfonyl]phenyl}methyl)imidazo[1,2-a]pyrimidine-6-carboxamide,
N-({4-[(5-chloro-2-methoxybenzene)sulfonyl]phenyl}methyl)-1H-pyrrolo[3,2-c]pyridine-2-carboxamide,
N-[(4-{[2-methyl-4-(trifluoromethyl)benzene]sulfonyl}phenyl)methyl]furo[2,3-c]pyridine-2-carboxamide,
N-[(4-{[4-(trifluoromethoxy)benzene]sulfonyl}phenyl)methyl]-1H-pyrazolo[3,4-b]pyridine-5-carboxamide,
N-({4-[(3,4-difluorobenzene)sulfonyl]phenyl}methyl)-1H-pyrrolo[3,2-c]pyridine-2-carboxamide,
N-({4-[(3,5-dimethoxybenzene)sulfonyl]phenyl}methyl)thieno[2,3-c]pyridine-2-carboxamide,
N-[(4-{[4-chloro-2-(trifluoromethyl)benzene]sulfonyl}phenyl)methyl]thieno[2,3-c]pyridine-2-carboxamide,
N-{[4-(benzenesulfonyl)phenyl]methyl}-[1,3]thiazolo[5,4-c]pyridine-2-carboxamide,
N-[(4-{[2-methyl-4-(trifluoromethyl)benzene]sulfonyl}phenyl)methyl]thieno[2,3-c]pyridine-2-carboxamide,
N-[(4-{[3-(3,5-dimethyl-1H-pyrazol-1-yl)benzene]sulfonyl}phenyl)methyl]-1H-pyrazolo[3,4-b]pyridine-5-carboxamide,
N-[(4-{[3-chloro-4-(trifluoromethyl)benzene]sulfonyl}phenyl)methyl]-1H-pyrrolo[3,2-c]pyridine-2-carboxamide,
N-({4-[(2-chloro-4-methoxybenzene)sulfonyl]phenyl}methyl)imidazo[1,2-a]pyrimidine-6-carboxamide,
N-({4-[(3-chloro-5-methoxybenzene)sulfonyl]phenyl}methyl)imidazo[1,2-a]pyrimidine-6-carboxamide,
N-[(4-{[2-(dimethylcarbamoyl)benzene]sulfonyl}phenyl)methyl]furo[2,3-c]pyridine-2-carboxamide,
N-[(4-{[4-(pyrrolidin-1-yl)benzene]sulfonyl}phenyl)methyl]-1H-pyrazolo[3,4-b]pyridine-6-carboxamide,
N-[(4-{[4-(morpholin-4-yl)benzene]sulfonyl}phenyl)methyl]thieno[2,3-c]pyridine-2-carboxamide,
N-({4-[(4-chloro-2-methoxybenzene)sulfonyl]phenyl}methyl)thieno[2,3-c]pyridine-2-carboxamide,
N-[(4-{[2-methoxy-5-(trifluoromethoxy)benzene]sulfonyl}phenyl)methyl]imidazo[1,2-a]pyrimidine-6-carboxamide,
N-({4-[(4-methoxy-2,5-dimethylbenzene)sulfonyl]phenyl}methyl)furo[2,3-c]pyridine-2-carboxamide,
N-[(4-{[3-fluoro-4-(trifluoromethyl)benzene]sulfonyl}phenyl)methyl]imidazo[1,2-a]pyrimidine-6-carboxamide, N-[(4-{[3-(propan-2-yloxy)benzene]sulfonyl}phenyl)methyl]-1H-pyrazolo[3,4-b]pyridine-5-carboxamide,
N-{[4-({4-[(pyrrolidin-1-yl)carbonyl]benzene}sulfonyl)phenyl]methyl}thieno[2,3-c]pyridine-2-carboxamide,
N-({4-[(2,4,6-trimethylbenzene)sulfonyl]phenyl}methyl)furo[2,3-c]pyridine-2-carboxamide,
N-({4-[(2-chloro-5-methylbenzene)sulfonyl]phenyl}methyl)imidazo[1,2-a]pyrimidine-6-carboxamide,
N-[(4-{[2-(benzyloxy)-5-(trifluoromethyl)benzene]sulfonyl}phenyl)methyl]imidazo[1,2-a]pyrimidine-6-carboxamide,
N-[(4-{[2-methoxy-4-(1H-pyrazol-1-yl)benzene]sulfonyl}phenyl)methyl]-1H-pyrrolo[3,2-c]pyridine-2-carboxamide,
N-[(4-{[3-(propan-2-yl)benzene]sulfonyl}phenyl)methyl]-1H-pyrazolo[3,4-b]pyridine-5-carboxamide,
N-(1,3-benzothiazol-6-ylmethyl)-4-[(3-chlorobenzene)sulfonyl]benzamide,
N-({4-[(2,4-dichloro-3-methoxybenzene)sulfonyl]phenyl}methyl)thieno[2,3-c]pyridine-2-carboxamide,
N-({4-[(4-ethoxy-3-fluorobenzene)sulfonyl]phenyl}methyl)imidazo[1,2-a]pyridine-6-carboxamide,
N-{[4-(phenoxathiine-4-sulfonyl)phenyl]methyl}-1H-pyrrolo[3,2-c]pyridine-2-carboxamide,
N-[(4-{[2-methoxy-4-(1H-pyrazol-1-yl)benzene]sulfonyl}phenyl)methyl]-1H-pyrazolo[3,4-b]pyridine-5-carboxamide,
N-({4-[(2-chloro-5-methoxybenzene)sulfonyl]phenyl}methyl)thieno[2,3-c]pyridine-2-carboxamide,
N-[(4-{[3-(cyclopentylcarbamoyl)benzene]sulfonyl}phenyl)methyl]imidazo[1,2-a]pyrimidine-6-carboxamide,
N-{[4-({3-[2-(morpholin-4-yl)ethoxy]benzene}sulfonyl)phenyl]methyl}-1H-pyrrolo[3,2-c]pyridine-2-carboxamide,
N-[(4-{[4-fluoro-2-(propan-2-yloxy)benzene]sulfonyl}phenyl)methyl]imidazo[1,2-a]pyridine-6-carboxamide,
N-[(4-{[4-fluoro-3-(trifluoromethyl)benzene]sulfonyl}phenyl)methyl]thieno[2,3-c]pyridine-2-carboxamide,
N-({4-[(2-fluoro-5-methoxybenzene)sulfonyl]phenyl}methyl)furo[2,3-c]pyridine-2-carboxamide,
N-{[4-({3-[(morpholin-4-yl)carbonyl]benzene}sulfonyl)phenyl]methyl}-1H-pyrazolo[3,4-b]pyridine-5-carboxamide,
N-[(4-{[3-(pyrimidin-2-yl)benzene]sulfonyl}phenyl)methyl]imidazo[1,2-a]pyrimidine-6-carboxamide,
N-({4-[(2-fluoro-3-methylbenzene)sulfonyl]phenyl}methyl)thieno[2,3-c]pyridine-2-carboxamide,
N-[(4-{[4-fluoro-2-(trifluoromethyl)benzene]sulfonyl}phenyl)methyl]-1H-pyrrolo[3,2-c]pyridine-2-carboxamide,
N-({4-[(2,3-dimethylbenzene)sulfonyl]phenyl}methyl)furo[2,3-c]pyridine-2-carboxamide,
N-({4-[(3-chloro-5-methoxybenzene)sulfonyl]phenyl}methyl)imidazo[1,2-a]pyridine-6-carboxamide,
N-({4-[(2-chloro-6-methoxybenzene)sulfonyl]phenyl}methyl)furo[2,3-c]pyridine-2-carboxamide,
N-({4-[(3,4-dimethoxybenzene)sulfonyl]phenyl}methyl)imidazo[1,2-a]pyrimidine-6-carboxamide,
N-({4-[(3,5-difluorobenzene)sulfonyl]phenyl}methyl)-1H-pyrazolo[3,4-b]pyridine-5-carboxamide,
N-[(4-{[3-fluoro-4-(trifluoromethyl)benzene]sulfonyl}phenyl)methyl]imidazo[1,2-a]pyridine-6-carboxamide,
N-({4-[(4-chloro-2-methoxybenzene)sulfonyl]phenyl}methyl)furo[2,3-c]pyridine-2-carboxamide,
N-({4-[(5-fluoro-2-methylbenzene)sulfonyl]phenyl}methyl)-1H-pyrrolo[3,2-c]pyridine-2-carboxamide,
N-({4-[(2-chloro-4-methoxybenzene)sulfonyl]phenyl}methyl)thieno[2,3-c]pyridine-2-carboxamide,
N-({4-[(4-butylbenzene)sulfonyl]phenyl}methyl)imidazo[1,2-a]pyrimidine-6-carboxamide,
N-({4-[(3-chlorobenzene)sulfonyl]phenyl}methyl)imidazo[1,2-a]pyrimidine-6-carboxamide,
N-[(4-{[3-(propan-2-yl)benzene]sulfonyl}phenyl)methyl]furo[2,3-c]pyridine-2-carboxamide,
N-[(4-{[3-(4-fluorophenoxy)benzene]sulfonyl}phenyl)methyl]thieno[2,3-c]pyridine-2-carboxamide,
N-[(4-{[5-chloro-2-(2,2-difluoroethoxy)benzene]sulfonyl}phenyl)methyl]-1H-pyrrolo[3,2-c]pyridine-2-carboxamide,
N-[(4-{[3-(piperidin-1-yl)benzene]sulfonyl}phenyl)methyl]thieno[2,3-c]pyridine-2-carboxamide,
N-({4-[(5-acetyl-2-methoxybenzene)sulfonyl]phenyl}methyl)-1H-pyrazolo[3,4-b]pyridine-5-carboxamide,
N-[(4-{8-thiatricyclo[7.4.0.0$^{2,7}$]trideca-1(13),2,4,6,9,11-hexaene-6-sulfonyl}phenyl)methyl]imidazo[1,2-a]pyrimidine-6-carboxamide,
N-({4-[(4-butoxybenzene)sulfonyl]phenyl}methyl)thieno[2,3-c]pyridine-2-carboxamide,
N-[(4-{[4-(propan-2-yloxy)benzene]sulfonyl}phenyl)methyl]furo[2,3-c]pyridine-2-carboxamide,
N-({4-[(3-fluoro-4-methylbenzene)sulfonyl]phenyl}methyl)imidazo[1,2-a]pyrimidine-6-carboxamide,
N-({4-[(2-acetylbenzene)sulfonyl]phenyl}methyl)thieno[2,3-c]pyridine-2-carboxamide,
N-({4-[(4-acetylbenzene)sulfonyl]phenyl}methyl)thieno[2,3-c]pyridine-2-carboxamide,
N-({4-[(2-acetylbenzene)sulfonyl]phenyl}methyl)imidazo[1,2-a]pyrimidine-6-carboxamide,
N-[(4-{[3-(3,5-dimethyl-1H-pyrazol-1-yl)benzene]sulfonyl}phenyl)methyl]imidazo[1,2-a]pyrimidine-6-carboxamide,
N-({4-[(2-chloro-5-methylbenzene)sulfonyl]phenyl}methyl)furo[2,3-c]pyridine-2-carboxamide,
N-[(4-{[4-chloro-2-(trifluoromethyl)benzene]sulfonyl}phenyl)methyl]imidazo[1,2-a]pyrimidine-6-carboxamide,
N-({4-[(2-methoxy-5-methylbenzene)sulfonyl]phenyl}methyl)imidazo[1,2-a]pyrimidine-6-carboxamide,
N-({4-[(3-phenylbenzene)sulfonyl]phenyl}methyl)imidazo[1,2-a]pyrimidine-6-carboxamide,
N-{[4-(6-methoxynaphthalene-2-sulfonyl)phenyl]methyl}imidazo[1,2-a]pyrimidine-6-carboxamide,
N-[(4-{[4-(morpholin-4-yl)benzene]sulfonyl}phenyl)methyl]imidazo[1,2-a]pyrimidine-6-carboxamide,
N-[(4-{[3-chloro-5-(hydroxymethyl)benzene]sulfonyl}phenyl)methyl]thieno[2,3-c]pyridine-2-carboxamide,
N-({4-[(4-fluoro-2-methylbenzene)sulfonyl]phenyl}methyl)imidazo[1,2-a]pyrimidine-6-carboxamide,
N-({4-[(4-ethoxy-2-methylbenzene)sulfonyl]phenyl}methyl)thieno[2,3-c]pyridine-2-carboxamide, N-[(4-{[4-(ethylcarbamoyl)benzene]sulfonyl}phenyl)
methyl]thieno[2,3-c]pyridine-2-carboxamide,
N-[(4-{[3-(piperidin-1-yl)benzene]sulfonyl}phenyl)
methyl]-1H-pyrrolo[3,2-c]pyridine-2-carboxamide,
N-({4-[(3-chloro-4-methylbenzene)sulfonyl]
phenyl}methyl)furo[2,3-c]pyridine-2-carboxamide,
N-[(4-{[2-(dimethylcarbamoyl)benzene]
sulfonyl}phenyl)methyl]-1H-pyrrolo[3,2-c]pyridine-2-
carboxamide,
N-[(4-{[3-(dimethylsulfamoyl)benzene]sulfonyl}phenyl)
methyl]imidazo[1,2-a]pyrimidine-6-carboxamide,
N-{[4-(2,3-dihydro-1-benzofuran-7-sulfonyl)phenyl]
methyl}imidazo[1,2-a]pyridine-6-carboxamide,
N-[(4-{[2-methoxy-5-(propan-2-yl)benzene]
sulfonyl}phenyl)methyl]-1H-pyrrolo[3,2-c]pyridine-2-
carboxamide,
N-({4-[(3,5-difluorobenzene)sulfonyl]phenyl}methyl)
thieno[2,3-c]pyridine-2-carboxamide,
N-({4-[(4-chloro-3-fluorobenzene)sulfonyl]
phenyl}methyl)thieno[2,3-c]pyridine-2-carboxamide,
N-({4-[(2,4,5-trimethylbenzene)sulfonyl]phenyl}methyl)
imidazo[1,2-a]pyrimidine-6-carboxamide,
N-({4-[(2,4-dimethylbenzene)sulfonyl]phenyl}methyl)
furo[2,3-c]pyridine-2-carboxamide,
N-[(4-{[2-chloro-3-(trifluoromethyl)benzene]
sulfonyl}phenyl)methyl]furo[2,3-c]pyridine-2-carbox-
amide,
N-[(4-{[3-(3,5-dimethyl-1H-pyrazol-1-yl)benzene]
sulfonyl}phenyl)methyl]-1H-pyrrolo[3,2-c]pyridine-2-
carboxamide,
N-({4-[(2-chloro-4-methylbenzene)sulfonyl]
phenyl}methyl)furo[2,3-c]pyridine-2-carboxamide,
N-({4-[(4-fluoro-3-methoxybenzene)sulfonyl]
phenyl}methyl)-1H-pyrrolo[3,2-c]pyridine-2-carbox-
amide,
N-[(4-{[3-(difluoromethoxy)benzene]sulfonyl}phenyl)
methyl]furo[2,3-c]pyridine-2-carboxamide,
N-[(4-{[2-methoxy-6-(propan-2-yloxy)benzene]
sulfonyl}phenyl)methyl]-1H-pyrrolo[3,2-c]pyridine-2-
carboxamide,
N-({4-[(4-chloro-3-methoxybenzene)sulfonyl]
phenyl}methyl)imidazo[1,2-a]pyridine-6-carboxam-
ide,
N-({4-[(2,3-dimethylbenzene)sulfonyl]phenyl}methyl)
thieno[2,3-c]pyridine-2-carboxamide,
N-({4-[(5-tert-butyl-2-methoxybenzene)sulfonyl]
phenyl}methyl)furo[2,3-c]pyridine-2-carboxamide,
N-({4-[(4-methoxy-2-methylbenzene)sulfonyl]
phenyl}methyl)imidazo[1,2-a]pyrimidine-6-carbox-
amide,
N-({4-[(2,5-dimethylbenzene)sulfonyl]phenyl}methyl)
thieno[2,3-c]pyridine-2-carboxamide,
N-({4-[(2-fluoro-5-methylbenzene)sulfonyl]
phenyl}methyl)-1H-pyrazolo[3,4-b]pyridine-5-carbox-
amide,
N-[(4-{[2-chloro-5-(hydroxymethyl)benzene]
sulfonyl}phenyl)methyl]-1H-pyrrolo[3,2-c]pyridine-2-
carboxamide,
N-({4-[(4-fluoro-2,5-dimethylbenzene)sulfonyl]
phenyl}methyl)-1H-pyrrolo[3,2-c]pyridine-2-carbox-
amide,
N-({4-[(4-butoxy-3-fluorobenzene)sulfonyl]
phenyl}methyl)furo[2,3-c]pyridine-2-carboxamide,
N-({4-[(2-fluoro-5-methoxybenzene)sulfonyl]
phenyl}methyl)imidazo[1,2-a]pyrimidine-6-carbox-
amide,
N-[(4-{[2-(trifluoromethyl)benzene]sulfonyl}phenyl)
methyl]furo[2,3-c]pyridine-2-carboxamide,
N-[(4-{[5-chloro-2-(2,2-difluoroethoxy)benzene]
sulfonyl}phenyl)methyl]imidazo[1,2-a]pyridine-6-car-
boxamide,
N-({4-[(2-butoxy-5-chlorobenzene)sulfonyl]
phenyl}methyl)imidazo[1,2-a]pyridine-6-carboxam-
ide,
N-[(4-{[2-chloro-3-(trifluoromethyl)benzene]
sulfonyl}phenyl)methyl]-1H-pyrrolo[3,2-c]pyridine-2-
carboxamide,
N-({4-[(2-chloro-3-fluorobenzene)sulfonyl]
phenyl}methyl)furo[2,3-c]pyridine-2-carboxamide,
N-[(4-{[3-(pyrrolidin-1-yl)benzene]sulfonyl}phenyl)
methyl]thieno[2,3-c]pyridine-2-carboxamide,
N-[(4-{[3-fluoro-5-(2-methylpropoxy)benzene]
sulfonyl}phenyl)methyl]imidazo[1,2-a]pyridine-6-car-
boxamide,
N-({4-[(2-fluoro-5-methoxybenzene)sulfonyl]
phenyl}methyl)-1H-pyrrolo[3,2-c]pyridine-2-carbox-
amide,
N-({4-[(3-chloro-4-propoxybenzene)sulfonyl]
phenyl}methyl)thieno[2,3-c]pyridine-2-carboxamide,
N-[(4-{[2,4-bis(trifluoromethyl)benzene]
sulfonyl}phenyl)methyl]imidazo[1,2-a]pyrimidine-6-
carboxamide,
N-({4-[(4-propoxybenzene)sulfonyl]phenyl}methyl)imi-
dazo[1,2-a]pyrimidine-6-carboxamide,
N-({4-[(2-ethoxybenzene)sulfonyl]phenyl}methyl)thieno
[2,3-c]pyridine-2-carboxamide,
N-({4-[(3-phenylbenzene)sulfonyl]phenyl}methyl)thieno
[2,3-c]pyridine-2-carboxamide,
N-[(4-{[2-methoxy-4-(1H-pyrazol-1-yl)benzene]
sulfonyl}phenyl)methyl]imidazo[1,2-a]pyrimidine-6-
carboxamide,
N-[(4-{[2-methoxy-3-(trifluoromethyl)benzene]
sulfonyl}phenyl)methyl]thieno[2,3-c]pyridine-2-car-
boxamide,
N-({4-[(4-fluoro-3-methylbenzene)sulfonyl]
phenyl}methyl)-1H-pyrrolo[3,2-c]pyridine-2-carbox-
amide,
N-({4-[(2-ethoxy-4-fluorobenzene)sulfonyl]
phenyl}methyl)imidazo[1,2-a]pyrimidine-6-carbox-
amide,
N-[(4-{[2-chloro-5-(trifluoromethyl)benzene]
sulfonyl}phenyl)methyl]furo[2,3-c]pyridine-2-carbox-
amide,
N-[(4-{[5-(diethylcarbamoyl)-2-fluorobenzene]
sulfonyl}phenyl)methyl]-1H-pyrrolo[3,2-c]pyridine-2-
carboxamide,
N-({4-[(2-chloro-6-fluorobenzene)sulfonyl]
phenyl}methyl)-1H-pyrrolo[3,2-c]pyridine-2-carbox-
amide,
N-({4-[(3-chloro-2-methylbenzene)sulfonyl]
phenyl}methyl)imidazo[1,2-a]pyrimidine-6-carbox-
amide,
N-({4-[(4-butoxybenzene)sulfonyl]phenyl}methyl)furo
[2,3-c]pyridine-2-carboxamide,
N-({4-[(3,5-dimethylbenzene)sulfonyl]phenyl}methyl)
imidazo[1,2-a]pyrimidine-6-carboxamide,
N-({4-[(5-chloro-2-methylbenzene)sulfonyl]
phenyl}methyl)imidazo[1,2-a]pyrimidine-6-carbox-
amide,
N-[(4-{[3-fluoro-4-(methylsulfanyl)benzene]
sulfonyl}phenyl)methyl]furo[2,3-c]pyridine-2-carbox-
amide, N-({4-[(4-fluoro-3-methylbenzene)sulfonyl]
  phenyl}methyl)imidazo[1,2-a]pyrimidine-6-carbox-
  amide,
N-({4-[(3-tert-butylbenzene)sulfonyl]phenyl}methyl)
  furo[2,3-c]pyridine-2-carboxamide,
N-[(4-{[3-fluoro-4-(trifluoromethoxy)benzene]
  sulfonyl}phenyl)methyl]imidazo[1,2-a]pyridine-6-car-
  boxamide,
N-({4-[(5-tert-butyl-2-methoxybenzene)sulfonyl]
  phenyl}methyl)-1H-pyrazolo[3,4-b]pyridine-5-carbox-
  amide,
N-[(4-{[4-fluoro-2-(trifluoromethyl)benzene]
  sulfonyl}phenyl)methyl]imidazo[1,2-a]pyridine-6-car-
  boxamide,
N-({4-[(3-ethoxy-4-fluorobenzene)sulfonyl]
  phenyl}methyl)thieno[2,3-c]pyridine-2-carboxamide,
N-({4-[(3-fluoro-2-methylbenzene)sulfonyl]
  phenyl}methyl)imidazo[1,2-a]pyridine-6-carboxam-
  ide,
N-({4-[(4-butoxy-3-fluorobenzene)sulfonyl]
  phenyl}methyl)imidazo[1,2-a]pyrimidine-6-carbox-
  amide,
N-({4-[(3-methoxy-4-methylbenzene)sulfonyl]
  phenyl}methyl)-1H-pyrrolo[3,2-c]pyridine-2-carbox-
  amide,
N-{[4-(phenoxathiine-4-sulfonyl)phenyl]methyl}furo[2,
  3-c]pyridine-2-carboxamide,
N-({4-[(3,4-dimethylbenzene)sulfonyl]phenyl}methyl)
  imidazo[1,2-a]pyrimidine-6-carboxamide,
N-[(4-{[2-methyl-4-(1H-pyrazol-1-yl)benzene]
  sulfonyl}phenyl)methyl]-1H-pyrrolo[3,2-c]pyridine-2-
  carboxamide,
N-({4-[(3-chloro-5-methoxybenzene)sulfonyl]
  phenyl}methyl)-1H-pyrazolo[3,4-b]pyridine-5-carbox-
  amide,
N-[(4-{[2-(methylsulfamoyl)benzene]sulfonyl}phenyl)
  methyl]-1H-pyrrolo[3,2-c]pyridine-2-carboxamide,
N-({4-[(4-methylbenzene)sulfonyl]phenyl}methyl)-1H-
  pyrrolo[3,2-c]pyridine-2-carboxamide,
N-({4-[(3-propoxybenzene)sulfonyl]phenyl}methyl)-1H-
  pyrrolo[3,2-c]pyridine-2-carboxamide,
N-[(4-{[2-(methylsulfamoyl)benzene]sulfonyl}phenyl)
  methyl]furo[2,3-c]pyridine-2-carboxamide,
N-({4-[(4-ethoxybenzene)sulfonyl]phenyl}methyl)-1H-
  pyrazolo[3,4-b]pyridine-5-carboxamide,
N-({4-[(3-fluoro-2-methoxybenzene)sulfonyl]
  phenyl}methyl)-1H-pyrrolo[3,2-c]pyridine-2-carbox-
  amide,
N-[(4-{[4-(1-cyanocyclopentyl)benzene]
  sulfonyl}phenyl)methyl]imidazo[1,2-a]pyridine-6-car-
  boxamide,
N-[(4-{[2-methoxy-4-(trifluoromethyl)benzene]
  sulfonyl}phenyl)methyl]-1H-pyrrolo[3,2-c]pyridine-2-
  carboxamide,
N-[(4-{[4-(hydroxymethyl)benzene]sulfonyl}phenyl)
  methyl]furo[2,3-c]pyridine-2-carboxamide,
N-({4-[(4-cyclohexylbenzene)sulfonyl]phenyl}methyl)
  imidazo[1,2-a]pyridine-6-carboxamide,
N-[(4-{[3-(piperidin-1-yl)benzene]sulfonyl}phenyl)
  methyl]imidazo[1,2-a]pyridine-6-carboxamide,
N-{[4-({4-[2-(dimethylamino)ethyl]benzene}sulfonyl)
  phenyl]methyl}imidazo[1,2-a]pyridine-6-carboxam-
  ide,
N-({4-[(5-fluoro-2-methylbenzene)sulfonyl]
  phenyl}methyl)imidazo[1,2-a]pyrimidine-6-carbox-
  amide,
N-{[4-(benzenesulfonyl)phenyl]methyl}quinazoline-6-
  carboxamide,
N-[(4-{[4-fluoro-3-(2,2,2-trifluoroethoxy)benzene]
  sulfonyl}phenyl)methyl]-1H-pyrrolo[3,2-c]pyridine-2-
  carboxamide,
N-[(4-{[3-(pyrrolidin-1-yl)benzene]sulfonyl}phenyl)
  methyl]-1,3-benzothiazole-6-carboxamide,
N-({4-[(3,5-dimethylbenzene)sulfonyl]phenyl}methyl)-
  1H-pyrazolo[3,4-b]pyridine-5-carboxamide,
N-({4-[(3-chloro-4-methylbenzene)sulfonyl]
  phenyl}methyl)-1H-pyrazolo[3,4-b]pyridine-5-carbox-
  amide,
N-[(4-{[4-(1H-pyrazol-1-yl)benzene]sulfonyl}phenyl)
  methyl]-1H-pyrazolo[3,4-b]pyridine-5-carboxamide,
N-({4-[(4-butoxy-3-chlorobenzene)sulfonyl]
  phenyl}methyl)furo[2,3-c]pyridine-2-carboxamide,
N-({4-[(4-fluorobenzene)sulfonyl]phenyl}methyl)thieno
  [2,3-c]pyridine-2-carboxamide,
N-{[4-({3-[(propan-2-yl)carbamoyl]benzene}sulfonyl)
  phenyl]methyl}imidazo[1,2-a]pyridine-6-carboxam-
  ide,
N-({4-[(2,4-dimethoxybenzene)sulfonyl]
  phenyl}methyl)-1H-pyrazolo[3,4-b]pyridine-5-carbox-
  amide,
N-({4-[(2,3-dimethoxy-5-methylbenzene)sulfonyl]
  phenyl}methyl)thieno[2,3-c]pyridine-2-carboxamide,
N-[(4-{[2-fluoro-3-(propan-2-yloxy)benzene]
  sulfonyl}phenyl)methyl]imidazo[1,2-a]pyridine-6-car-
  boxamide,
N-[(4-{[3-(pyrrolidin-1-yl)benzene]sulfonyl}phenyl)
  methyl]-1H-pyrazolo[3,4-b]pyridine-5-carboxamide,
N-({4-[(3-chloro-2-fluorobenzene)sulfonyl]
  phenyl}methyl)imidazo[1,2-a]pyrimidine-6-carbox-
  amide,
N-[(4-{[5-hydroxy-2-(trifluoromethoxy)benzene]
  sulfonyl}phenyl)methyl]furo[2,3-c]pyridine-2-carbox-
  amide,
N-({4-[(3,4-dimethylbenzene)sulfonyl]phenyl}methyl)
  thieno[2,3-c]pyridine-2-carboxamide,
N-[(4-{[4-chloro-3-(trifluoromethyl)benzene]
  sulfonyl}phenyl)methyl]-1H-pyrrolo[3,2-c]pyridine-2-
  carboxamide,
N-[(4-{[3-(morpholin-4-yl)benzene]sulfonyl}phenyl)
  methyl]imidazo[1,2-a]pyrimidine-6-carboxamide,
N-({4-[(2-butoxy-4-fluorobenzene)sulfonyl]
  phenyl}methyl)-1H-pyrrolo[3,2-c]pyridine-2-carbox-
  amide,
N-({4-[(4-propoxybenzene)sulfonyl]phenyl}methyl)
  thieno[2,3-c]pyridine-2-carboxamide,
N-({4-[(3,4-dimethylbenzene)sulfonyl]phenyl}methyl)-
  1H-pyrazolo[3,4-b]pyridine-5-carboxamide,
N-({4-[(2,6-dimethylbenzene)sulfonyl]phenyl}methyl)
  furo[2,3-c]pyridine-2-carboxamide,
N-({4-[(4-methoxy-3,5-dimethylbenzene)sulfonyl]
  phenyl}methyl)-1H-pyrrolo[3,2-c]pyridine-2-carbox-
  amide,
N-{[4-(benzenesulfonyl)phenyl]methyl}-[1,2,3,4]tetra-
  zolo[1,5-a]pyridine-6-carboxamide,
N-({4-[(4-cyanobenzene)sulfonyl]phenyl}methyl)imi-
  dazo[1,2-a]pyridine-6-carboxamide,
N-{[4-({3-[(propan-2-yl)carbamoyl]benzene}sulfonyl)
  phenyl]methyl}furo[2,3-c]pyridine-2-carboxamide,
N-({4-[(2,4-dimethylbenzene)sulfonyl]phenyl}methyl)
  imidazo[1,2-a]pyrimidine-6-carboxamide,
N-({4-[(4-butoxy-3-fluorobenzene)sulfonyl]
  phenyl}methyl)-1H-pyrrolo[3,2-c]pyridine-2-carbox-
  amide, N-[(4-{[2-(trifluoromethoxy)benzene]sulfonyl}phenyl)methyl]-1H-pyrrolo[3,2-c]pyridine-2-carboxamide,
N-({4-[(4-ethoxybenzene)sulfonyl]phenyl}methyl)imidazo[1,2-a]pyrimidine-6-carboxamide,
N-[(4-{[4-(2-methylpropoxy)benzene]sulfonyl}phenyl)methyl]imidazo[1,2-a]pyrimidine-6-carboxamide,
N-({4-[(3-chloro-2-methylbenzene)sulfonyl]phenyl}methyl)furo[2,3-c]pyridine-2-carboxamide,
N-({4-[(4-chloro-3-methoxybenzene)sulfonyl]phenyl}methyl)imidazo[1,2-a]pyrimidine-6-carboxamide,
N-({4-[(3-cyanobenzene)sulfonyl]phenyl}methyl)-1H-pyrrolo[3,2-c]pyridine-2-carboxamide,
N-{[4-(2,3-dihydro-1-benzofuran-7-sulfonyl)phenyl]methyl}imidazo[1,2-a]pyrimidine-6-carboxamide,
N-({4-[(3-fluorobenzene)sulfonyl]phenyl}methyl)imidazo[1,2-a]pyrimidine-6-carboxamide,
N-({4-[(2-chloro-5-methoxybenzene)sulfonyl]phenyl}methyl)imidazo[1,2-a]pyridine-6-carboxamide,
N-({4-[(4-ethoxy-2-methylbenzene)sulfonyl]phenyl}methyl)furo[2,3-c]pyridine-2-carboxamide,
N-[(4-{[2-(benzyloxy)benzene]sulfonyl}phenyl)methyl]-1H-pyrrolo[3,2-c]pyridine-2-carboxamide,
N-({4-[(5-acetyl-2-methoxybenzene)sulfonyl]phenyl}methyl)furo[2,3-c]pyridine-2-carboxamide,
N-[(4-{[4-chloro-3-(trifluoromethyl)benzene]sulfonyl}phenyl)methyl]furo[2,3-c]pyridine-2-carboxamide,
N-({4-[(2-butoxy-4-fluorobenzene)sulfonyl]phenyl}methyl)thieno[2,3-c]pyridine-2-carboxamide,
N-[(4-{[2-methoxy-5-(trifluoromethoxy)benzene]sulfonyl}phenyl)methyl]-1H-pyrazolo[3,4-b]pyridine-5-carboxamide,
N-({4-[(4-ethylbenzene)sulfonyl]phenyl}methyl)imidazo[1,2-a]pyrimidine-6-carboxamide,
N-({4-[(4-chloro-3-methoxybenzene)sulfonyl]phenyl}methyl)-1H-pyrrolo[3,2-c]pyridine-2-carboxamide,
N-({4-[(2-chloro-5-methoxybenzene)sulfonyl]phenyl}methyl)imidazo[1,2-a]pyrimidine-6-carboxamide,
N-{[4-(benzenesulfonyl)phenyl]methyl}thieno[2,3-b]pyrazine-6-carboxamide,
N-({4-[(2-butoxy-5-chlorobenzene)sulfonyl]phenyl}methyl)thieno[2,3-c]pyridine-2-carboxamide,
N-[(4-{[2-chloro-3-(trifluoromethyl)benzene]sulfonyl}phenyl)methyl]imidazo[1,2-a]pyrimidine-6-carboxamide,
N-({4-[(3-ethoxy-2-fluorobenzene)sulfonyl]phenyl}methyl)-1H-pyrrolo[3,2-c]pyridine-2-carboxamide,
N-[(4-{[2-(morpholin-4-ylmethyl)benzene]sulfonyl}phenyl)methyl]-1H-pyrrolo[3,2-c]pyridine-2-carboxamide,
N-({4-[(4-methoxy-3-methylbenzene)sulfonyl]phenyl}methyl)-1H-pyrrolo[3,2-c]pyridine-2-carboxamide,
N-({4-[(3-fluoro-4-methoxybenzene)sulfonyl]phenyl}methyl)thieno[2,3-c]pyridine-2-carboxamide,
N-{[4-(2,3-dihydro-1-benzofuran-7-sulfonyl)phenyl]methyl}-1H-pyrazolo[3,4-b]pyridine-5-carboxamide,
N-[(4-{[3-(propane-1-sulfonamido)benzene]sulfonyl}phenyl)methyl]imidazo[1,2-a]pyrimidine-6-carboxamide,
N-({4-[(3-methoxybenzene)sulfonyl]phenyl}methyl)-1H-pyrazolo[3,4-b]pyridine-5-carboxamide,
N-({4-[(3-fluoro-4-methylbenzene)sulfonyl]phenyl}methyl)-1H-pyrrolo[3,2-c]pyridine-2-carboxamide,
N-({4-[(4-methylbenzene)sulfonyl]phenyl}methyl)furo[2,3-c]pyridine-2-carboxamide,
N-({4-[(4-chloro-3-methoxybenzene)sulfonyl]phenyl}methyl)thieno[2,3-c]pyridine-2-carboxamide,
N-{[4-({3-[2-(dimethylamino)ethoxy]benzene}sulfonyl)phenyl]methyl}furo[2,3-c]pyridine-2-carboxamide,
N-[(4-{[3-(2,2,2-trifluoroethoxy)benzene]sulfonyl}phenyl)methyl]imidazo[1,2-a]pyridine-6-carboxamide,
N-[(4-{[3-(cyclopentylcarbamoyl)benzene]sulfonyl}phenyl)methyl]imidazo[1,2-a]pyridine-6-carboxamide,
N-[(4-{[4-fluoro-3-(trifluoromethyl)benzene]sulfonyl}phenyl)methyl]-1H-pyrrolo[3,2-c]pyridine-2-carboxamide,
N-({4-[(2-cyanobenzene)sulfonyl]phenyl}methyl)imidazo[1,2-a]pyridine-6-carboxamide,
N-({4-[(2,4-dimethylbenzene)sulfonyl]phenyl}methyl)-1H-pyrrolo[3,2-c]pyridine-2-carboxamide,
N-[(4-{[2-chloro-5-(trifluoromethyl)benzene]sulfonyl}phenyl)methyl]imidazo[1,2-a]pyrimidine-6-carboxamide,
N-[(4-{[2-chloro-4-(trifluoromethyl)benzene]sulfonyl}phenyl)methyl]-1H-pyrrolo[3,2-c]pyridine-2-carboxamide,
N-({4-[(3-chloro-5-fluorobenzene)sulfonyl]phenyl}methyl)furo[2,3-c]pyridine-2-carboxamide,
N-[(4-{[3-(pyrrolidin-1-yl)benzene]sulfonyl}phenyl)methyl]furo[2,3-c]pyridine-2-carboxamide,
N-[(4-{[3-(trifluoromethoxy)benzene]sulfonyl}phenyl)methyl]furo[2,3-c]pyridine-2-carboxamide,
N-({4-[(2-acetylbenzene)sulfonyl]phenyl}methyl)-1H-pyrrolo[3,2-c]pyridine-2-carboxamide,
N-({4-[(4-chloro-3-fluorobenzene)sulfonyl]phenyl}methyl)furo[2,3-c]pyridine-2-carboxamide,
N-({4-[(2-butoxy-6-fluorobenzene)sulfonyl]phenyl}methyl)-1H-pyrrolo[3,2-c]pyridine-2-carboxamide,
N-({4-[(3-fluoro-2-methylbenzene)sulfonyl]phenyl}methyl)imidazo[1,2-a]pyrimidine-6-carboxamide,
N-{[4-(naphthalene-1-sulfonyl)phenyl]methyl}furo[2,3-c]pyridine-2-carboxamide,
N-({4-[(3,5-difluorobenzene)sulfonyl]phenyl}methyl)-1H-pyrrolo[3,2-c]pyridine-2-carboxamide,
N-{[4-(benzenesulfonyl)phenyl]methyl}-1-methyl-1H-pyrazolo[3,4-b]pyridine-5-carboxamide,
N-[(4-{8-thiatricyclo[7.4.0.0$^{2,7}$]trideca-1(13),2,4,6,9,11-hexaene-6-sulfonyl}phenyl)methyl]-1H-pyrrolo[3,2-c]pyridine-2-carboxamide,
N-({4-[(3-ethoxybenzene)sulfonyl]phenyl}methyl)-1H-pyrazolo[3,4-b]pyridine-5-carboxamide,
N-({4-[(3-ethoxybenzene)sulfonyl]phenyl}methyl)imidazo[1,2-a]pyridine-6-carboxamide,
N-[(4-{[3-chloro-5-(hydroxymethyl)benzene]sulfonyl}phenyl)methyl]imidazo[1,2-a]pyridine-6-carboxamide,
N-[(4-{[2-(dimethylcarbamoyl)benzene]sulfonyl}phenyl)methyl]thieno[2,3-c]pyridine-2-carboxamide,
N-({4-[(4-chloro-3-fluorobenzene)sulfonyl]phenyl}methyl)imidazo[1,2-a]pyrimidine-6-carboxamide, N-({4-[(3-fluoro-5-methoxybenzene)sulfonyl]
phenyl}methyl)imidazo[1,2-a]pyrimidine-6-carboxamide,
N-[(4-{[4-fluoro-2-(propan-2-yloxy)benzene]
sulfonyl}phenyl)methyl]thieno[2,3-c]pyridine-2-carboxamide,
N-({4-[(2,6-dichlorobenzene)sulfonyl]phenyl}methyl)-1H-pyrrolo[3,2-c]pyridine-2-carboxamide,
N-({4-[(4-acetylbenzene)sulfonyl]phenyl}methyl)-1H-pyrrolo[3,2-c]pyridine-2-carboxamide,
N-({4-[(3,5-dimethoxybenzene)sulfonyl]phenyl}methyl)imidazo[1,2-a]pyridine-6-carboxamide,
N-{[4-({4-[(1R)-1-hydroxybutyl]benzene}sulfonyl)phenyl]methyl}furo[2,3-c]pyridine-2-carboxamide,
N-({4-[(4-fluoro-3-methylbenzene)sulfonyl]
phenyl}methyl)furo[2,3-c]pyridine-2-carboxamide,
N-{[4-({3-[2-(dimethylamino)ethyl]benzene}sulfonyl)
phenyl]methyl}-1H-pyrrolo[3,2-c]pyridine-2-carboxamide,
N-({4-[(2-ethoxybenzene)sulfonyl]phenyl}methyl)-1H-pyrazolo[3,4-b]pyridine-5-carboxamide,
N-({4-[(2-ethylbenzene)sulfonyl]phenyl}methyl)imidazo[1,2-a]pyrimidine-6-carboxamide,
N-({4-[(3,4-dimethoxybenzene)sulfonyl]phenyl}methyl)furo[2,3-c]pyridine-2-carboxamide,
N-[(4-{[3-(3,5-dimethyl-1H-pyrazol-1-yl)benzene]
sulfonyl}phenyl)methyl]-5-hydroxy-1H-indole-2-carboxamide,
N-({4-[(5-chloro-2-methoxybenzene)sulfonyl]
phenyl}methyl)thieno[2,3-c]pyridine-2-carboxamide,
N-({4-[(2,3-dimethoxy-5-methylbenzene)sulfonyl]
phenyl}methyl)-1H-pyrazolo[3,4-b]pyridine-5-carboxamide,
N-({4-[(3-chloro-4-methoxybenzene)sulfonyl]
phenyl}methyl)-1H-pyrazolo[3,4-b]pyridine-5-carboxamide,
N-[(4-{[2-(trifluoromethyl)benzene]sulfonyl}phenyl)
methyl]imidazo[1,2-a]pyrimidine-6-carboxamide,
N-[(4-{[3-(trifluoromethyl)benzene]sulfonyl}phenyl)
methyl]furo[2,3-c]pyridine-2-carboxamide,
N-({4-[(2-butoxy-6-fluorobenzene)sulfonyl]
phenyl}methyl)imidazo[1,2-a]pyridine-6-carboxamide,
N-[(4-{[3-(ethanesulfonyl)benzene]sulfonyl}phenyl)
methyl]imidazo[1,2-a]pyridine-6-carboxamide,
N-[(4-{[2-methoxy-4-(1H-pyrazol-1-yl)benzene]
sulfonyl}phenyl)methyl]thieno[2,3-c]pyridine-2-carboxamide,
N-[(4-{[3-(1H-pyrazol-1-yl)benzene]sulfonyl}phenyl)
methyl]imidazo[1,2-a]pyridine-6-carboxamide,
N-({4-[(3-chloro-4-propoxybenzene)sulfonyl]
phenyl}methyl)-1H-pyrrolo[3,2-c]pyridine-2-carboxamide,
N-({4-[(5-chloro-2-propoxybenzene)sulfonyl]
phenyl}methyl)furo[2,3-c]pyridine-2-carboxamide,
N-[(4-{[3-fluoro-5-(trifluoromethyl)benzene]
sulfonyl}phenyl)methyl]-1H-pyrrolo[3,2-c]pyridine-2-carboxamide,
N-[(4-{[3-(ethylcarbamoyl)benzene]sulfonyl}phenyl)
methyl]imidazo[1,2-a]pyrimidine-6-carboxamide,
N-({4-[(5-tert-butyl-2-methoxybenzene)sulfonyl]
phenyl}methyl)imidazo[1,2-a]pyrimidine-6-carboxamide,
N-({4-[(3-ethoxy-4-fluorobenzene)sulfonyl]
phenyl}methyl)-1H-pyrrolo[3,2-c]pyridine-2-carboxamide,
N-({4-[(4-cyanobenzene)sulfonyl]phenyl}methyl)furo[2,3-c]pyridine-2-carboxamide,
N-[(4-{[4-fluoro-2-(trifluoromethyl)benzene]
sulfonyl}phenyl)methyl]imidazo[1,2-a]pyrimidine-6-carboxamide,
N-({4-[(4-methoxybenzene)sulfonyl]phenyl}methyl)
thieno[2,3-c]pyridine-2-carboxamide,
N-({4-[(3,5-dimethylbenzene)sulfonyl]phenyl}methyl)-1H-pyrrolo[3,2-c]pyridine-2-carboxamide,
N-({4-[(4-acetylbenzene)sulfonyl]phenyl}methyl)-1H-pyrazolo[3,4-b]pyridine-5-carboxamide,
N-({4-[(5-chloro-2-methoxybenzene)sulfonyl]
phenyl}methyl)imidazo[1,2-a]pyrimidine-6-carboxamide,
N-[(4-{[3-fluoro-5-(trifluoromethyl)benzene]
sulfonyl}phenyl)methyl]imidazo[1,2-a]pyrimidine-6-carboxamide,
N-({4-[(2,3-dimethoxybenzene)sulfonyl]
phenyl}methyl)-1H-pyrrolo[3,2-c]pyridine-2-carboxamide,
N-({4-[(3-acetylbenzene)sulfonyl]phenyl}methyl)-1H-pyrazolo[3,4-b]pyridine-5-carboxamide,
N-[(4-{[2,4-bis(trifluoromethyl)benzene]
sulfonyl}phenyl)methyl]furo[2,3-c]pyridine-2-carboxamide,
N-[(4-{[4-(ethoxymethyl)benzene]sulfonyl}phenyl)
methyl]furo[2,3-c]pyridine-2-carboxamide,
N-({4-[(2-fluoro-5-methylbenzene)sulfonyl]
phenyl}methyl)-1H-pyrrolo[3,2-c]pyridine-2-carboxamide,
N-({4-[(3-fluoro-5-methylbenzene)sulfonyl]
phenyl}methyl)thieno[2,3-c]pyridine-2-carboxamide,
N-({4-[(4-fluorobenzene)sulfonyl]phenyl}methyl)-1H-pyrrolo[3,2-c]pyridine-2-carboxamide,
N-[(4-{[2-methoxy-5-(propan-2-yl)benzene]
sulfonyl}phenyl)methyl]furo[2,3-c]pyridine-2-carboxamide,
N-[(4-{[3-(trifluoromethyl)benzene]sulfonyl}phenyl)
methyl]-1,3-benzothiazole-6-carboxamide,
N-({4-[(3-propoxybenzene)sulfonyl]phenyl}methyl)imidazo[1,2-a]pyrimidine-6-carboxamide,
N-({4-[(2-fluoro-4-methylbenzene)sulfonyl]
phenyl}methyl)imidazo[1,2-a]pyrimidine-6-carboxamide,
N-({4-[(2,5-dimethylbenzene)sulfonyl]phenyl}methyl)
furo[2,3-c]pyridine-2-carboxamide,
N-({4-[(2-chloro-5-methylbenzene)sulfonyl]
phenyl}methyl)-1H-pyrrolo[3,2-c]pyridine-2-carboxamide,
N-[(4-{[3-fluoro-5-(trifluoromethyl)benzene]
sulfonyl}phenyl)methyl]furo[2,3-c]pyridine-2-carboxamide,
N-({4-[(3,5-dimethylbenzene)sulfonyl]phenyl}methyl)
furo[2,3-c]pyridine-2-carboxamide,
N-({4-[(2,3-dimethoxybenzene)sulfonyl]phenyl}methyl)
imidazo[1,2-a]pyrimidine-6-carboxamide,
N-({4-[(3-ethylbenzene)sulfonyl]phenyl}methyl)imidazo[1,2-a]pyrimidine-6-carboxamide,
N-{[4-(2H-1,3-benzodioxole-5-sulfonyl)phenyl]
methyl}furo[2,3-c]pyridine-2-carboxamide,
N-[(4-{[2-methyl-4-(1H-pyrazol-1-yl)benzene]
sulfonyl}phenyl)methyl]thieno[2,3-c]pyridine-2-carboxamide,
N-({4-[(3-sulfamoylbenzene)sulfonyl]phenyl}methyl)
imidazo[1,2-a]pyridine-6-carboxamide,
N-[(4-{[3-(pyrrolidin-1-yl)benzene]sulfonyl}phenyl)
methyl]imidazo[1,2-a]pyrimidine-6-carboxamide, N-[(4-{[4-(trifluoromethoxy)benzene]sulfonyl}phenyl)methyl]imidazo[1,2-a]pyrimidine-6-carboxamide, N-{[4-({3-[(2-methylpropyl)carbamoyl]benzene}sulfonyl)phenyl]methyl}imidazo[1,2-a]pyrimidine-6-carboxamide, N-({4-[(2,3,6-trimethoxybenzene)sulfonyl]phenyl}methyl)thieno[2,3-c]pyridine-2-carboxamide, N-({4-[(2-fluoro-5-methylbenzene)sulfonyl]phenyl}methyl)imidazo[1,2-a]pyrimidine-6-carboxamide, N-({4-[(3-methoxy-5-methylbenzene)sulfonyl]phenyl}methyl)-1H-pyrrolo[3,2-c]pyridine-2-carboxamide, N-{[4-(benzenesulfonyl)phenyl]methyl}imidazo[1,2-a]pyridine-6-carboxamide, N-({4-[(2-chloro-4-methylbenzene)sulfonyl]phenyl}methyl)imidazo[1,2-a]pyridine-6-carboxamide, N-({4-[(4-butoxy-3-chlorobenzene)sulfonyl]phenyl}methyl)-1H-pyrazolo[3,4-b]pyridine-5-carboxamide, N-({4-[(3-ethoxy-2-fluorobenzene)sulfonyl]phenyl}methyl)imidazo[1,2-a]pyridine-6-carboxamide, N-[(4-{[4-(4-methylpiperazin-1-yl)benzene]sulfonyl}phenyl)methyl]-1H-pyrrolo[3,2-c]pyridine-2-carboxamide, N-({4-[(4-chloro-2-methoxybenzene)sulfonyl]phenyl}methyl)-1H-pyrrolo[3,2-c]pyridine-2-carboxamide, N-({4-[(5-chloro-2-methoxybenzene)sulfonyl]phenyl}methyl)-1H-pyrazolo[3,4-b]pyridine-5-carboxamide, N-[(4-{[3-fluoro-4-(trifluoromethyl)benzene]sulfonyl}phenyl)methyl]thieno[2,3-c]pyridine-2-carboxamide, N-{[4-(benzenesulfonyl)phenyl]methyl}imidazo[1,2-a]pyrimidine-6-carboxamide, N-({4-[(3-propoxybenzene)sulfonyl]phenyl}methyl)furo[2,3-c]pyridine-2-carboxamide, N-{[4-(2H-1,3-benzodioxole-4-sulfonyl)phenyl]methyl}-1H-pyrrolo[3,2-c]pyridine-2-carboxamide, N-[(4-{[4-(trifluoromethyl)benzene]sulfonyl}phenyl)methyl]imidazo[1,2-a]pyrimidine-6-carboxamide, N-[(4-{[3-fluoro-4-(1H-pyrazol-1-yl)benzene]sulfonyl}phenyl)methyl]-1H-pyrrolo[3,2-c]pyridine-2-carboxamide, N-{[4-(6-methoxynaphthalene-2-sulfonyl)phenyl]methyl}furo[2,3-c]pyridine-2-carboxamide, N-({4-[(2-methylbenzene)sulfonyl]phenyl}methyl)thieno[2,3-c]pyridine-2-carboxamide, N-({4-[(2,4-dichloro-3-methoxybenzene)sulfonyl]phenyl}methyl)imidazo[1,2-a]pyridine-6-carboxamide, N-({4-[(5-fluoro-2-methoxybenzene)sulfonyl]phenyl}methyl)-1H-pyrrolo[3,2-c]pyridine-2-carboxamide, N-{[4-(naphthalene-1-sulfonyl)phenyl]methyl}thieno[2,3-c]pyridine-2-carboxamide, N-{[4-({4-[2-(dimethylamino)ethyl]benzene}sulfonyl)phenyl]methyl}imidazo[1,2-a]pyrimidine-6-carboxamide, N-[(4-{[2-methyl-4-(trifluoromethyl)benzene]sulfonyl}phenyl)methyl]-1H-pyrrolo[3,2-c]pyridine-2-carboxamide, N-({4-[(2,3,6-trimethoxybenzene)sulfonyl]phenyl}methyl)furo[2,3-c]pyridine-2-carboxamide, N-({4-[(3-butoxybenzene)sulfonyl]phenyl}methyl)imidazo[1,2-a]pyridine-6-carboxamide, N-({4-[(3,5-dimethoxybenzene)sulfonyl]phenyl}methyl)furo[2,3-c]pyridine-2-carboxamide, N-({4-[(3-chloro-2-fluorobenzene)sulfonyl]phenyl}methyl)furo[2,3-c]pyridine-2-carboxamide, N-({4-[(3-methylbenzene)sulfonyl]phenyl}methyl)thieno[2,3-c]pyridine-2-carboxamide, N-[(4-{[4-(dimethylcarbamoyl)benzene]sulfonyl}phenyl)methyl]-1H-pyrrolo[3,2-c]pyridine-2-carboxamide, N-[(4-{[4-(hydroxymethyl)benzene]sulfonyl}phenyl)methyl]imidazo[1,2-a]pyridine-6-carboxamide, N-({4-[(3,4-dimethoxybenzene)sulfonyl]phenyl}methyl)-1H-pyrazolo[3,4-b]pyridine-5-carboxamide, N-{[4-(2,3-dihydro-1-benzofuran-7-sulfonyl)phenyl]methyl}thieno[2,3-c]pyridine-2-carboxamide, N-({4-[(3-tert-butylbenzene)sulfonyl]phenyl}methyl)imidazo[1,2-a]pyrimidine-6-carboxamide, N-[(4-{[4-(propan-2-yloxy)benzene]sulfonyl}phenyl)methyl]imidazo[1,2-a]pyrimidine-6-carboxamide, N-{[4-({3-[(propan-2-yl)carbamoyl]benzene}sulfonyl)phenyl]methyl}thieno[2,3-c]pyridine-2-carboxamide, N-({4-[(2,3-dimethoxy-5-methylbenzene)sulfonyl]phenyl}methyl)furo[2,3-c]pyridine-2-carboxamide, N-{[4-(benzenesulfonyl)phenyl]methyl}-1,5-naphthyridine-2-carboxamide, 5-hydroxy-N-[(4-{[3-(pyrrolidin-1-yl)benzene]sulfonyl}phenyl)methyl]-1H-indole-2-carboxamide, N-[(4-{[3-(1H-pyrazol-1-yl)benzene]sulfonyl}phenyl)methyl]furo[2,3-c]pyridine-2-carboxamide, N-({4-[(2-methyl-4-propoxybenzene)sulfonyl]phenyl}methyl)-1H-pyrrolo[3,2-c]pyridine-2-carboxamide, N-{[4-({3-[(dimethylamino)methyl]benzene}sulfonyl)phenyl]methyl}furo[2,3-c]pyridine-2-carboxamide, N-({4-[(3-chlorobenzene)sulfonyl]phenyl}methyl)furo[2,3-c]pyridine-2-carboxamide, N-[(4-{[3-(2-methylpropoxy)benzene]sulfonyl}phenyl)methyl]-1H-pyrazolo[3,4-b]pyridine-5-carboxamide, N-{[4-(2,3-dihydro-1,4-benzodioxine-6-sulfonyl)phenyl]methyl}thieno[2,3-c]pyridine-2-carboxamide, N-({4-[(4-methoxy-3,5-dimethylbenzene)sulfonyl]phenyl}methyl)imidazo[1,2-a]pyridine-6-carboxamide, N-[(4-{[3-(3,5-dimethyl-1H-pyrazol-1-yl)benzene]sulfonyl}phenyl)methyl]thieno[2,3-c]pyridine-2-carboxamide, N-({4-[(2,5-dimethoxybenzene)sulfonyl]phenyl}methyl)furo[2,3-c]pyridine-2-carboxamide, N-({4-[(2,4,6-trimethylbenzene)sulfonyl]phenyl}methyl)imidazo[1,2-a]pyrimidine-6-carboxamide, N-[(4-{[4-(4-methylpiperazin-1-yl)benzene]sulfonyl}phenyl)methyl]thieno[2,3-c]pyridine-2-carboxamide, N-[(4-{[2-methoxy-5-(trifluoromethyl)benzene]sulfonyl}phenyl)methyl]imidazo[1,2-a]pyrimidine-6-carboxamide, N-({4-[(4-chloro-2-ethoxybenzene)sulfonyl]phenyl}methyl)imidazo[1,2-a]pyrimidine-6-carboxamide, N-[(4-{[3-(ethanesulfonyl)benzene]sulfonyl}phenyl)methyl]imidazo[1,2-a]pyrimidine-6-carboxamide, N-{[4-({3-[2-(dimethylamino)ethyl]benzene}sulfonyl)phenyl]methyl}thieno[2,3-c]pyridine-2-carboxamide, N-({4-[(4-methoxy-3,5-dimethylbenzene)sulfonyl]
phenyl}methyl)thieno[2,3-c]pyridine-2-carboxamide,
N-({4-[(3,4-difluorobenzene)sulfonyl]phenyl}methyl)
imidazo[1,2-a]pyrimidine-6-carboxamide,
N-[(4-{[3-fluoro-4-(2,2,2-trifluoroethoxy)benzene]
sulfonyl}phenyl)methyl]furo[2,3-c]pyridine-2-carboxamide,
N-({4-[(2-ethoxybenzene)sulfonyl]phenyl}methyl)-1H-pyrrolo[3,2-c]pyridine-2-carboxamide,
N-[(4-{[2-methoxy-5-(propan-2-yl)benzene]
sulfonyl}phenyl)methyl]imidazo[1,2-a]pyridine-6-carboxamide,
N-({4-[(2,6-dichlorobenzene)sulfonyl]phenyl}methyl)
imidazo[1,2-a]pyridine-6-carboxamide,
N-({4-[(2-fluoro-5-methoxybenzene)sulfonyl]
phenyl}methyl)thieno[2,3-c]pyridine-2-carboxamide,
N-({4-[(2-methoxy-5-methylbenzene)sulfonyl]
phenyl}methyl)thieno[2,3-c]pyridine-2-carboxamide,
N-({4-[(3-chloro-5-methoxybenzene)sulfonyl]
phenyl}methyl)furo[2,3-c]pyridine-2-carboxamide,
N-({4-[(3,5-difluorobenzene)sulfonyl]phenyl}methyl)
imidazo[1,2-a]pyrimidine-6-carboxamide,
N-({4-[(2-ethylbenzene)sulfonyl]phenyl}methyl)furo[2,3-c]pyridine-2-carboxamide,
N-({4-[(4-phenylbenzene)sulfonyl]phenyl}methyl)-1,3-benzothiazole-6-carboxamide,
N-[(4-{[3-(3,5-dimethyl-1H-pyrazol-1-yl)benzene]
sulfonyl}phenyl)methyl]-1,3-benzothiazole-6-carboxamide,
N-[(4-{[4-(ethoxymethyl)benzene]sulfonyl}phenyl)
methyl]-1H-pyrrolo[3,2-c]pyridine-2-carboxamide,
N-({4-[(2-chloro-5-fluorobenzene)sulfonyl]
phenyl}methyl)imidazo[1,2-a]pyridine-6-carboxamide,
N-[(4-{[3-chloro-5-(diethylcarbamoyl)benzene]
sulfonyl}phenyl)methyl]thieno[2,3-c]pyridine-2-carboxamide,
N-[(4-{[4-(2-methylpropoxy)benzene]sulfonyl}phenyl)
methyl]thieno[2,3-c]pyridine-2-carboxamide,
N-({4-[(3-butoxybenzene)sulfonyl]phenyl}methyl)furo
[2,3-c]pyridine-2-carboxamide,
N-({4-[(4-methylbenzene)sulfonyl]phenyl}methyl)imidazo[1,2-a]pyrimidine-6-carboxamide,
N-({4-[(3-methanesulfonylbenzene)sulfonyl]
phenyl}methyl)imidazo[1,2-a]pyridine-6-carboxamide,
N-({4-[(2,6-dimethoxy-4-methylbenzene)sulfonyl]
phenyl}methyl)thieno[2,3-c]pyridine-2-carboxamide,
N-{[4-({4-fluoro-3-[(propan-2-yl)carbamoyl]
benzene}sulfonyl)phenyl]methyl}thieno[2,3-c]pyridine-2-carboxamide,
N-({4-[(5-chloro-2-ethoxybenzene)sulfonyl]
phenyl}methyl)imidazo[1,2-a]pyridine-6-carboxamide,
N-({4-[(3,5-dichlorobenzene)sulfonyl]phenyl}methyl)-1H-pyrazolo[3,4-b]pyridine-5-carboxamide,
N-[(4-{[2-methoxy-3-(trifluoromethyl)benzene]
sulfonyl}phenyl)methyl]imidazo[1,2-a]pyridine-6-carboxamide,
N-[(4-{[4-(4-methylpiperazin-1-yl)benzene]
sulfonyl}phenyl)methyl]-1H-pyrazolo[3,4-b]pyridine-5-carboxamide,
N-({4-[(2-fluoro-3-methoxybenzene)sulfonyl]
phenyl}methyl)-1H-pyrazolo[3,4-b]pyridine-5-carboxamide,
N-({4-[(4-chloro-3-fluorobenzene)sulfonyl]
phenyl}methyl)-1H-pyrrolo[3,2-c]pyridine-2-carboxamide,
N-[(4-{[2-fluoro-4-(1H-pyrazol-1-yl)benzene]
sulfonyl}phenyl)methyl]furo[2,3-c]pyridine-2-carboxamide,
N-[(4-{[4-fluoro-3-(2,2,2-trifluoroethoxy)benzene]
sulfonyl}phenyl)methyl]imidazo[1,2-a]pyrimidine-6-carboxamide,
N-[(4-{[3-(trifluoromethoxy)benzene]sulfonyl}phenyl)
methyl]-1H-pyrrolo[3,2-c]pyridine-2-carboxamide,
N-({4-[(3-chloro-5-methylbenzene)sulfonyl]
phenyl}methyl)-1H-pyrazolo[3,4-b]pyridine-5-carboxamide,
N-({4-[(2-chloro-5-fluorobenzene)sulfonyl]
phenyl}methyl)furo[2,3-c]pyridine-2-carboxamide,
N-{[4-({3-[(2-methylpropyl)carbamoyl]
benzene}sulfonyl)phenyl]methyl}furo[2,3-c]pyridine-2-carboxamide,
N-{[4-(benzenesulfonyl)phenyl]methyl}-1H-pyrazolo[3,4-b]pyridine-5-carboxamide,
N-{[4-(2H-1,3-benzodioxole-5-sulfonyl)phenyl]methyl}-1H-pyrrolo[3,2-c]pyridine-2-carboxamide,
N-({4-[(3,5-dimethoxybenzene)sulfonyl]
phenyl}methyl)-1H-pyrazolo[3,4-b]pyridine-5-carboxamide,
N-[(4-{[2-(morpholin-4-ylmethyl)benzene]
sulfonyl}phenyl)methyl]imidazo[1,2-a]pyrimidine-6-carboxamide,
N-({4-[(2,6-dichloro-3-methylbenzene)sulfonyl]
phenyl}methyl)imidazo[1,2-a]pyrimidine-6-carboxamide,
N-({4-[(2-fluoro-5-methylbenzene)sulfonyl]
phenyl}methyl)furo[2,3-c]pyridine-2-carboxamide,
N-({4-[(3-fluorobenzene)sulfonyl]phenyl}methyl)furo[2,3-c]pyridine-2-carboxamide,
N-[(4-{[5-fluoro-2-(hydroxymethyl)benzene]
sulfonyl}phenyl)methyl]thieno[2,3-c]pyridine-2-carboxamide,
N-({4-[(3-methoxy-4-methylbenzene)sulfonyl]
phenyl}methyl)thieno[2,3-c]pyridine-2-carboxamide,
N-({4-[(2-chloro-4-methylbenzene)sulfonyl]
phenyl}methyl)imidazo[1,2-a]pyrimidine-6-carboxamide,
N-[(4-{[2-(trifluoromethoxy)benzene]sulfonyl}phenyl)
methyl]furo[2,3-c]pyridine-2-carboxamide,
N-[(4-{[3-chloro-4-(trifluoromethyl)benzene]
sulfonyl}phenyl)methyl]thieno[2,3-c]pyridine-2-carboxamide,
N-[(4-{[5-hydroxy-2-(trifluoromethoxy)benzene]
sulfonyl}phenyl)methyl]-1H-pyrazolo[3,4-b]pyridine-5-carboxamide,
N-[(4-{[4-(1H-imidazol-1-yl)benzene]sulfonyl}phenyl)
methyl]imidazo[1,2-a]pyrimidine-6-carboxamide,
N-{[4-(benzenesulfonyl)phenyl]methyl}-1H-pyrazolo[3,4-b]pyridine-3-carboxamide,
N-({4-[(4-fluorobenzene)sulfonyl]phenyl}methyl)imidazo[1,2-a]pyridine-6-carboxamide,
N-({4-[(3,4-difluorobenzene)sulfonyl]phenyl}methyl)-1H-pyrazolo[3,4-b]pyridine-5-carboxamide,
N-({4-[(4-butoxy-3-chlorobenzene)sulfonyl]
phenyl}methyl)thieno[2,3-c]pyridine-2-carboxamide,
N-({4-[(3-methanesulfonylbenzene)sulfonyl]
phenyl}methyl)thieno[2,3-c]pyridine-2-carboxamide,
N-({4-[(3-chloro-4-methylbenzene)sulfonyl]
phenyl}methyl)imidazo[1,2-a]pyrimidine-6-carboxamide, N-({4-[(2-ethoxy-4-fluorobenzene)sulfonyl]
phenyl}methyl)imidazo[1,2-a]pyridine-6-carboxamide,
N-[(4-{[4-chloro-2-(trifluoromethyl)benzene]
sulfonyl}phenyl)methyl]imidazo[1,2-a]pyridine-6-carboxamide,
N-({4-[(4-butoxy-2-methylbenzene)sulfonyl]
phenyl}methyl)-1H-pyrrolo[3,2-c]pyridine-2-carboxamide,
N-{[4-(6-methoxynaphthalene-2-sulfonyl)phenyl]
methyl}-1H-pyrrolo[3,2-c]pyridine-2-carboxamide,
N-[(4-{[3-(propane-1-sulfonamido)benzene]
sulfonyl}phenyl)methyl]thieno[2,3-c]pyridine-2-carboxamide,
N-[(4-{[4-chloro-3-(trifluoromethyl)benzene]
sulfonyl}phenyl)methyl]imidazo[1,2-a]pyrimidine-6-carboxamide,
N-[(4-{[3-fluoro-5-(2-methylpropoxy)benzene]
sulfonyl}phenyl)methyl]thieno[2,3-c]pyridine-2-carboxamide,
N-[(4-{[2-methyl-4-(1H-pyrazol-1-yl)benzene]
sulfonyl}phenyl)methyl]-1H-pyrazolo[3,4-b]pyridine-5-carboxamide,
N-({4-[(3-chloro-5-fluorobenzene)sulfonyl]
phenyl}methyl)-1H-pyrazolo[3,4-b]pyridine-5-carboxamide,
N-({4-[(3-methylbenzene)sulfonyl]phenyl}methyl)imidazo[1,2-a]pyrimidine-6-carboxamide,
N-({4-[(2-cyanobenzene)sulfonyl]phenyl}methyl)furo[2,3-c]pyridine-2-carboxamide,
N-{[4-(benzenesulfonyl)phenyl]methyl}-1H-pyrrolo[3,2-c]pyridine-2-carboxamide,
N-[(4-{[3-(ethylcarbamoyl)benzene]sulfonyl}phenyl)
methyl]furo[2,3-c]pyridine-2-carboxamide,
N-({4-[(3-acetylbenzene)sulfonyl]phenyl}methyl)furo[2,3-c]pyridine-2-carboxamide,
N-({4-[(2-chloro-5-methoxybenzene)sulfonyl]
phenyl}methyl)furo[2,3-c]pyridine-2-carboxamide,
N-[(4-{[4-fluoro-3-(trifluoromethyl)benzene]
sulfonyl}phenyl)methyl]furo[2,3-c]pyridine-2-carboxamide,
N-({4-[(4-butoxy-2-methylbenzene)sulfonyl]
phenyl}methyl)thieno[2,3-c]pyridine-2-carboxamide,
N-({4-[(3-ethoxybenzene)sulfonyl]phenyl}methyl)imidazo[1,2-a]pyrimidine-6-carboxamide,
N-({4-[(3-fluoro-4-methylbenzene)sulfonyl]
phenyl}methyl)-1H-pyrazolo[3,4-b]pyridine-5-carboxamide,
N-[(4-{[4-chloro-2-(trifluoromethyl)benzene]
sulfonyl}phenyl)methyl]furo[2,3-c]pyridine-2-carboxamide,
N-({4-[(4-chloro-2-ethoxybenzene)sulfonyl]
phenyl}methyl)furo[2,3-c]pyridine-2-carboxamide,
N-{[4-(2,3-dihydro-1-benzofuran-7-sulfonyl)phenyl]
methyl}furo[2,3-c]pyridine-2-carboxamide,
N-[(4-{[3-(trifluoromethoxy)benzene]sulfonyl}phenyl)
methyl]imidazo[1,2-a]pyrimidine-6-carboxamide,
N-[(4-{[5-chloro-2-(propan-2-yloxy)benzene]
sulfonyl}phenyl)methyl]furo[2,3-c]pyridine-2-carboxamide,
N-({4-[(2-chloro-6-methoxybenzene)sulfonyl]
phenyl}methyl)-1H-pyrrolo[3,2-c]pyridine-2-carboxamide,
N-{[3-(benzenesulfonyl)phenyl]methyl}-1H-pyrrolo[3,2-c]pyridine-2-carboxamide,
N-[(4-{[4-fluoro-3-(trifluoromethyl)benzene]
sulfonyl}phenyl)methyl]imidazo[1,2-a]pyridine-6-carboxamide,
N-({4-[(2-ethoxybenzene)sulfonyl]phenyl}methyl)imidazo[1,2-a]pyrimidine-6-carboxamide,
N-[(4-{[2-methoxy-5-(propan-2-yl)benzene]
sulfonyl}phenyl)methyl]thieno[2,3-c]pyridine-2-carboxamide,
N-[(4-{[2-methyl-4-(trifluoromethyl)benzene]
sulfonyl}phenyl)methyl]imidazo[1,2-a]pyridine-6-carboxamide,
N-({4-[(2-methoxybenzene)sulfonyl]phenyl}methyl)
thieno[2,3-c]pyridine-2-carboxamide,
N-({4-[(2-phenoxybenzene)sulfonyl]phenyl}methyl)furo
[2,3-c]pyridine-2-carboxamide,
N-({4-[(4-chlorobenzene)sulfonyl]phenyl}methyl)imidazo[1,2-a]pyrimidine-6-carboxamide,
N-({4-[(3-fluoro-5-methylbenzene)sulfonyl]
phenyl}methyl)imidazo[1,2-a]pyrimidine-6-carboxamide,
N-({4-[(3-chloro-2-methylbenzene)sulfonyl]
phenyl}methyl)-1H-pyrrolo[3,2-c]pyridine-2-carboxamide,
N-[(4-{[3-(trifluoromethoxy)benzene]sulfonyl}phenyl)
methyl]-1H-pyrazolo[3,4-b]pyridine-5-carboxamide,
N-({4-[(2-butoxy-5-chlorobenzene)sulfonyl]
phenyl}methyl)-1H-pyrrolo[3,2-c]pyridine-2-carboxamide,
N-({4-[(2-ethoxy-4-fluorobenzene)sulfonyl]
phenyl}methyl)-1H-pyrazolo[3,4-b]pyridine-5-carboxamide,
N-({4-[(2-chloro-5-fluorobenzene)sulfonyl]
phenyl}methyl)thieno[2,3-c]pyridine-2-carboxamide,
N-({4-[(3-methoxy-5-methylbenzene)sulfonyl]
phenyl}methyl)imidazo[1,2-a]pyrimidine-6-carboxamide,
N-[(4-{[3-(ethanesulfonyl)benzene]sulfonyl}phenyl)
methyl]thieno[2,3-c]pyridine-2-carboxamide,
N-({4-[(2-fluorobenzene)sulfonyl]phenyl}methyl)furo[2,3-c]pyridine-2-carboxamide,
N-({4-[(3,4-dimethoxybenzene)sulfonyl]
phenyl}methyl)-1H-pyrrolo[3,2-c]pyridine-2-carboxamide
N-[(4-{[3-(2-methylpropoxy)benzene]sulfonyl}phenyl)
methyl]imidazo[1,2-a]pyridine-6-carboxamide,
N-[(4-{[2-chloro-4-(trifluoromethyl)benzene]
sulfonyl}phenyl)methyl]imidazo[1,2-a]pyrimidine-6-carboxamide,
N-({4-[(3-butoxybenzene)sulfonyl]phenyl}methyl)
thieno[2,3-c]pyridine-2-carboxamide,
N-({4-[(2,4-dimethylbenzene)sulfonyl]phenyl}methyl)
thieno[2,3-c]pyridine-2-carboxamide,
N-({4-[(4-methoxybenzene)sulfonyl]phenyl}methyl)-1H-pyrrolo[3,2-c]pyridine-2-carboxamide,
N-[(4-{[4-(propan-2-yl)benzene]sulfonyl}phenyl)
methyl]thieno[2,3-c]pyridine-2-carboxamide,
N-[(4-{[2-(trifluoromethyl)benzene]sulfonyl}phenyl)
methyl]-1H-pyrrolo[3,2-c]pyridine-2-carboxamide,
N-({4-[(3-acetylbenzene)sulfonyl]phenyl}methyl)-1H-pyrrolo[3,2-c]pyridine-2-carboxamide,
N-({4-[(2-ethoxy-4-fluorobenzene)sulfonyl]
phenyl}methyl)thieno[2,3-c]pyridine-2-carboxamide,
N-({4-[(3,5-dichlorobenzene)sulfonyl]phenyl}methyl)-1H-pyrrolo[3,2-c]pyridine-2-carboxamide,
N-[(4-{[3-(3,5-dimethyl-1H-pyrazol-1-yl)benzene]
sulfonyl}phenyl)methyl]furo[2,3-c]pyridine-2-carboxamide, N-[(4-{[2-fluoro-4-(1H-pyrazol-1-yl)benzene]
sulfonyl}phenyl)methyl]-1H-pyrazolo[3,4-b]pyridine-
5-carboxamide,
N-[(4-{[4-chloro-2-(trifluoromethyl)benzene]
sulfonyl}phenyl)methyl]-1H-pyrrolo[3,2-c]pyridine-2-
carboxamide,
N-(4-(phenylsulfonyl)benzyl)-1H-imidazo[4,5-b]pyri-
dine-6-carboxamide,
N-[(4-{[4-(trifluoromethoxy)benzene]sulfonyl}phenyl)
methyl]furo[2,3-c]pyridine-2-carboxamide,
N-({4-[(3-ethoxy-2-fluorobenzene)sulfonyl]
phenyl}methyl)imidazo[1,2-a]pyrimidine-6-carbox-
amide,
N-({4-[(3-fluoro-4-propoxybenzene)sulfonyl]
phenyl}methyl)imidazo[1,2-a]pyridine-6-carboxam-
ide,
N-[(4-{[3-chloro-4-(trifluoromethyl)benzene]
sulfonyl}phenyl)methyl]imidazo[1,2-a]pyrimidine-6-
carboxamide,
N-({4-[(3,5-dimethoxybenzene)sulfonyl]
phenyl}methyl)-1H-pyrrolo[3,2-c]pyridine-2-carbox-
amide,
N-({4-[(2-chloro-4-fluorobenzene)sulfonyl]
phenyl}methyl)imidazo[1,2-a]pyrimidine-6-carbox-
amide,
N-({4-[(3-acetylbenzene)sulfonyl]phenyl}methyl)imi-
dazo[1,2-a]pyrimidine-6-carboxamide,
N-[(4-{[3-fluoro-5-(morpholin-4-yl)benzene]
sulfonyl}phenyl)methyl]imidazo[1,2-a]pyridine-6-car-
boxamide,
N-[(4-{[2-(morpholin-4-ylmethyl)benzene]
sulfonyl}phenyl)methyl]-1H-pyrazolo[3,4-b]pyridine-
5-carboxamide,
N-[(4-{[4-(1H-imidazol-1-ylmethyl)benzene]
sulfonyl}phenyl)methyl]furo[2,3-c]pyridine-2-carbox-
amide,
N-({4-[(4-methoxy-2,5-dimethylbenzene)sulfonyl]
phenyl}methyl)imidazo[1,2-a]pyridine-6-carboxam-
ide,
N-[(4-{[4-fluoro-3-(2,2,2-trifluoroethoxy)benzene]
sulfonyl}phenyl)methyl]thieno[2,3-c]pyridine-2-car-
boxamide,
N-[(4-{[3-fluoro-5-(2-methylpropoxy)benzene]
sulfonyl}phenyl)methyl]-1H-pyrrolo[3,2-c]pyridine-2-
carboxamide,
N-({4-[(2,5-dimethoxybenzene)sulfonyl]
phenyl}methyl)-1H-pyrrolo[3,2-c]pyridine-2-carbox-
amide,
N-({4-[(2-fluoro-4-methylbenzene)sulfonyl]
phenyl}methyl)thieno[2,3-c]pyridine-2-carboxamide,
N-({4-[(3-phenylbenzene)sulfonyl]phenyl}methyl)-1H-
pyrrolo[3,2-c]pyridine-2-carboxamide,
N-{[4-({4-[(dimethylamino)methyl]benzene}sulfonyl)
phenyl]methyl}imidazo[1,2-a]pyrimidine-6-carbox-
amide,
N-[(4-{[3-(diethylcarbamoyl)-5-fluorobenzene]
sulfonyl}phenyl)methyl]-1H-pyrrolo[3,2-c]pyridine-2-
carboxamide,
N-({4-[(5-chloro-2-methylbenzene)sulfonyl]
phenyl}methyl)thieno[2,3-c]pyridine-2-carboxamide,
N-({4-[(5-chloro-2-propoxybenzene)sulfonyl]
phenyl}methyl)imidazo[1,2-a]pyridine-6-carboxam-
ide,
N-[(4-{[4-(1H-imidazol-1-ylmethyl)benzene]
sulfonyl}phenyl)methyl]thieno[2,3-c]pyridine-2-car-
boxamide, N-({4-[(4-chloro-2-ethoxybenzene)sulfonyl]
phenyl}methyl)thieno[2,3-c]pyridine-2-carboxamide,
N-({4-[(3-chloro-5-methylbenzene)sulfonyl]
phenyl}methyl)imidazo[1,2-a]pyrimidine-6-carbox-
amide,
N-[(4-{[4-(2-methylpropoxy)benzene]sulfonyl}phenyl)
methyl]furo[2,3-c]pyridine-2-carboxamide,
N-[(4-{[4-fluoro-2-(propan-2-yloxy)benzene]
sulfonyl}phenyl)methyl]-1H-pyrrolo[3,2-c]pyridine-2-
carboxamide,
N-({4-[(2-methylbenzene)sulfonyl]phenyl}methyl)furo
[2,3-c]pyridine-2-carboxamide,
N-({4-{[3-(propan-2-yl)benzene]sulfonyl}phenyl)
methyl]-1H-pyrrolo[3,2-c]pyridine-2-carboxamide,
N-({4-[(3-methoxy-5-methylbenzene)sulfonyl]
phenyl}methyl)thieno[2,3-c]pyridine-2-carboxamide,
N-({4-[(3-chloro-5-fluorobenzene)sulfonyl]
phenyl}methyl)-1H-pyrrolo[3,2-c]pyridine-2-carbox-
amide,
N-({4-[(4-fluoro-2,5-dimethylbenzene)sulfonyl]
phenyl}methyl)furo[2,3-c]pyridine-2-carboxamide,
N-({4-[(2,3-dimethoxy-5-methylbenzene)sulfonyl]
phenyl}methyl)imidazo[1,2-a]pyrimidine-6-carbox-
amide,
N-({4-[(2-methanesulfonylbenzene)sulfonyl]
phenyl}methyl)furo[2,3-c]pyridine-2-carboxamide,
N-[(4-{[4-(propan-2-yl)benzene]sulfonyl}phenyl)
methyl]imidazo[1,2-a]pyrimidine-6-carboxamide,
N-({4-[(4-cyclohexylbenzene)sulfonyl]phenyl}methyl)
thieno[2,3-c]pyridine-2-carboxamide,
N-({4-[(2-chloro-5-fluorobenzene)sulfonyl]
phenyl}methyl)-1H-pyrrolo[3,2-c]pyridine-2-carbox-
amide,
N-({4-[(2-butoxy-6-fluorobenzene)sulfonyl]
phenyl}methyl)furo[2,3-c]pyridine-2-carboxamide,
N-{[4-({3-[2-(dimethylamino)ethyl]benzene}sulfonyl)
phenyl]methyl}imidazo[1,2-a]pyrimidine-6-carbox-
amide,
N-({4-[(2,6-dimethoxy-4-methylbenzene)sulfonyl]
phenyl}methyl)-1H-pyrrolo[3,2-c]pyridine-2-carbox-
amide,
N-[(4-{[3-(morpholin-4-yl)benzene]sulfonyl}phenyl)
methyl]furo[2,3-c]pyridine-2-carboxamide,
N-({4-[(3-tert-butylbenzene)sulfonyl]phenyl}methyl)
thieno[2,3-c]pyridine-2-carboxamide,
N-[(4-{[3-(trifluoromethyl)benzene]sulfonyl}phenyl)
methyl]-1H-pyrazolo[3,4-b]pyridine-5-carboxamide,
N-[(4-{[3-fluoro-4-(methylsulfanyl)benzene]
sulfonyl}phenyl)methyl]imidazo[1,2-a]pyridine-6-car-
boxamide,
N-{[4-(2,3-dihydro-1,4-benzodioxine-6-sulfonyl)phenyl]
methyl}furo[2,3-c]pyridine-2-carboxamide,
N-({4-[(4-butylbenzene)sulfonyl]phenyl}methyl)furo[2,
3-c]pyridine-2-carboxamide,
N-[(4-{[3-fluoro-4-(1H-pyrazol-1-yl)benzene]
sulfonyl}phenyl)methyl]furo[2,3-c]pyridine-2-carbox-
amide,
N-({4-[(4-phenylbenzene)sulfonyl]phenyl}methyl)-1H-
pyrazolo[3,4-b]pyridine-5-carboxamide,
N-({4-[(4-ethoxy-2-methylbenzene)sulfonyl]
phenyl}methyl)-1H-pyrrolo[3,2-c]pyridine-2-carbox-
amide,
N-[(4-{[4-(ethylcarbamoyl)benzene]sulfonyl}phenyl)
methyl]imidazo[1,2-a]pyrimidine-6-carboxamide,
N-[(4-{[3-(methoxymethyl)benzene]sulfonyl}phenyl)
methyl]thieno[2,3-c]pyridine-2-carboxamide, N-({4-[(2-butoxy-5-chlorobenzene)sulfonyl]
  phenyl}methyl)furo[2,3-c]pyridine-2-carboxamide,
N-({4-[(3-fluoro-4-propoxybenzene)sulfonyl]
  phenyl}methyl)-1H-pyrrolo[3,2-c]pyridine-2-carboxamide,
N-({4-[(2-methyl-4-propoxybenzene)sulfonyl]
  phenyl}methyl)furo[2,3-c]pyridine-2-carboxamide,
N-[(4-{[5-fluoro-2-(hydroxymethyl)benzene]
  sulfonyl}phenyl)methyl]imidazo[1,2-a]pyrimidine-6-carboxamide,
N-[(4-{[3-(methoxymethyl)benzene]sulfonyl}phenyl)
  methyl]furo[2,3-c]pyridine-2-carboxamide,
N-[(4-{[4-(2-methylpropoxy)benzene]sulfonyl}phenyl)
  methyl]imidazo[1,2-a]pyridine-6-carboxamide,
N-[(4-{[2-(benzyloxy)-5-(trifluoromethyl)benzene]
  sulfonyl}phenyl)methyl]-1H-pyrrolo[3,2-c]pyridine-2-carboxamide,
N-[(4-{8-thiatricyclo[7.4.0.0$^{2,7}$]trideca-1(13),2,4,6,9,11-hexaene-6-sulfonyl}phenyl)methyl]thieno[2,3-c]pyridine-2-carboxamide,
N-({4-[(3,4-difluorobenzene)sulfonyl]phenyl}methyl)
  thieno[2,3-c]pyridine-2-carboxamide,
N-{[4-(benzenesulfonyl)phenyl]methyl}isoquinoline-7-carboxamide,
N-[(4-{[3-fluoro-4-(2,2,2-trifluoroethoxy)benzene]
  sulfonyl}phenyl)methyl]imidazo[1,2-a]pyridine-6-carboxamide,
N-({4-[(2-butoxy-5-chlorobenzene)sulfonyl]
  phenyl}methyl)imidazo[1,2-a]pyrimidine-6-carboxamide,
N-[(4-{[4-fluoro-3-(trifluoromethyl)benzene]
  sulfonyl}phenyl)methyl]imidazo[1,2-a]pyrimidine-6-carboxamide,
N-({4-[(2,6-dichlorobenzene)sulfonyl]phenyl}methyl)
  thieno[2,3-c]pyridine-2-carboxamide,
N-[(4-{[2-methyl-4-(1H-pyrazol-1-yl)benzene]
  sulfonyl}phenyl)methyl]furo[2,3-c]pyridine-2-carboxamide,
N-{[4-({4-[(pyrrolidin-1-yl)carbonyl]benzene}sulfonyl)
  phenyl]methyl}-1H-pyrazolo[3,4-b]pyridine-5-carboxamide,
N-({4-[(4-butoxy-3-fluorobenzene)sulfonyl]
  phenyl}methyl)imidazo[1,2-a]pyridine-6-carboxamide,
N-({4-[(3-ethoxy-4-fluorobenzene)sulfonyl]
  phenyl}methyl)imidazo[1,2-a]pyridine-6-carboxamide,
N-[(4-{[3-fluoro-5-(pyrrolidin-1-yl)benzene]
  sulfonyl}phenyl)methyl]thieno[2,3-c]pyridine-2-carboxamide,
N-({4-[(4-chlorobenzene)sulfonyl]phenyl}methyl)-1H-pyrrolo[3,2-c]pyridine-2-carboxamide,
N-[(4-{[3-(difluoromethoxy)benzene]sulfonyl}phenyl)
  methyl]imidazo[1,2-a]pyrimidine-6-carboxamide,
N-({4-[(3-fluoro-5-methylbenzene)sulfonyl]
  phenyl}methyl)-1H-pyrrolo[3,2-c]pyridine-2-carboxamide,
N-({4-[(5-acetyl-2-methoxybenzene)sulfonyl]
  phenyl}methyl)-1H-pyrrolo[3,2-c]pyridine-2-carboxamide,
N-({4-[(4-propoxybenzene)sulfonyl]phenyl}methyl)imidazo[1,2-a]pyridine-6-carboxamide,
N-({4-[(2,3-dimethoxybenzene)sulfonyl]phenyl}methyl)
  furo[2,3-c]pyridine-2-carboxamide,
N-[(4-{[5-fluoro-2-(hydroxymethyl)benzene]
  sulfonyl}phenyl)methyl]imidazo[1,2-a]pyrimidine-6-carboxamide,
N-({4-[(5-tert-butyl-2-methoxybenzene)sulfonyl]
  phenyl}methyl)thieno[2,3-c]pyridine-2-carboxamide,
N-[(4-{[3-(pyrrolidin-1-yl)benzene]sulfonyl}phenyl)
  methyl]-1H-pyrrolo[3,2-c]pyridine-2-carboxamide,
N-[(4-{[3-fluoro-4-(1H-pyrazol-1-yl)benzene]
  sulfonyl}phenyl)methyl]-1H-pyrazolo[3,4-b]pyridine-5-carboxamide,
N-({4-[(2-chloro-4-fluorobenzene)sulfonyl]
  phenyl}methyl)furo[2,3-c]pyridine-2-carboxamide,
N-({4-[(2-fluoro-3-methylbenzene)sulfonyl]
  phenyl}methyl)imidazo[1,2-a]pyridine-6-carboxamide,
N-{[4-(2H-1,3-benzodioxole-4-sulfonyl)phenyl]
  methyl}furo[2,3-c]pyridine-2-carboxamide,
N-({4-[(2,3-difluorobenzene)sulfonyl]phenyl}methyl)-1H-pyrazolo[3,4-b]pyridine-5-carboxamide,
N-[(4-{[3-(2-methylpropoxy)benzene]sulfonyl}phenyl)
  methyl]imidazo[1,2-a]pyrimidine-6-carboxamide,
N-[(4-{[3-fluoro-5-(pyrrolidin-1-yl)benzene]
  sulfonyl}phenyl)methyl]imidazo[1,2-a]pyrimidine-6-carboxamide,
N-({4-[(3-fluoro-4-propoxybenzene)sulfonyl]
  phenyl}methyl)imidazo[1,2-a]pyrimidine-6-carboxamide,
N-[(4-{[4-(4-methylpiperazin-1-yl)benzene]
  sulfonyl}phenyl)methyl]furo[2,3-c]pyridine-2-carboxamide,
N-({4-[(3-ethoxy-2-fluorobenzene)sulfonyl]
  phenyl}methyl)furo[2,3-c]pyridine-2-carboxamide,
N-({4-[(4-butylbenzene)sulfonyl]phenyl}methyl)thieno[2,3-c]pyridine-2-carboxamide,
N-{[4-(benzenesulfonyl)phenyl]methyl}-3-bromo-1H-pyrrolo[3,2-c]pyridine-2-carboxamide,
N-({4-[(2,6-dichlorobenzene)sulfonyl]phenyl}methyl)
  furo[2,3-c]pyridine-2-carboxamide,
N-{[4-({3-[(dimethylamino)methyl]benzene}sulfonyl)
  phenyl]methyl}imidazo[1,2-a]pyrimidine-6-carboxamide,
N-({4-[(2-fluoro-5-methoxybenzene)sulfonyl]
  phenyl}methyl)imidazo[1,2-a]pyridine-6-carboxamide,
N-[(4-{[2-methoxy-5-(trifluoromethoxy)benzene]
  sulfonyl}phenyl)methyl]imidazo[1,2-a]pyridine-6-carboxamide,
N-{[4-(phenoxathiine-4-sulfonyl)phenyl]methyl}thieno[2,3-c]pyridine-2-carboxamide,
N-[(4-{[3-(2-methylpropoxy)benzene]sulfonyl}phenyl)
  methyl]furo[2,3-c]pyridine-2-carboxamide,
N-({4-[(5-fluoro-2-methoxybenzene)sulfonyl]
  phenyl}methyl)thieno[2,3-c]pyridine-2-carboxamide,
N-({4-[(3-methoxybenzene)sulfonyl]phenyl}methyl)-1H-pyrrolo[3,2-c]pyridine-2-carboxamide,
N-({4-[(2-methyl-4-propoxybenzene)sulfonyl]
  phenyl}methyl)-1H-pyrazolo[3,4-b]pyridine-5-carboxamide,
N-({4-[(3-fluoro-2-methoxybenzene)sulfonyl]
  phenyl}methyl)thieno[2,3-c]pyridine-2-carboxamide,
N-({4-[(4-chloro-2-methoxybenzene)sulfonyl]
  phenyl}methyl)imidazo[1,2-a]pyrimidine-6-carboxamide,
N-({4-[(2,3-dimethoxybenzene)sulfonyl]phenyl}methyl)
  thieno[2,3-c]pyridine-2-carboxamide,
N-({4-[(4-fluoro-2-methoxybenzene)sulfonyl]
  phenyl}methyl)imidazo[1,2-a]pyrimidine-6-carboxamide, N-({4-[(5-chloro-2-ethoxybenzene)sulfonyl]phenyl}methyl)imidazo[1,2-a]pyrimidine-6-carboxamide,
N-[(4-{[2-chloro-5-(trifluoromethoxy)benzene]sulfonyl}phenyl)methyl]imidazo[1,2-a]pyrimidine-6-carboxamide,
N-({4-[(4-phenylbenzene)sulfonyl]phenyl}methyl)imidazo[1,2-a]pyrimidine-6-carboxamide,
N-({4-[(2-butoxy-4-fluorobenzene)sulfonyl]phenyl}methyl)furo[2,3-c]pyridine-2-carboxamide,
N-{[4-(2H-1,3-benzodioxole-5-sulfonyl)phenyl]methyl}thieno[2,3-c]pyridine-2-carboxamide,
N-({4-[(2,5-difluorobenzene)sulfonyl]phenyl}methyl)-1H-pyrazolo[3,4-b]pyridine-5-carboxamide,
N-[(4-{[4-(1H-pyrazol-1-yl)benzene]sulfonyl}phenyl)methyl]furo[2,3-c]pyridine-2-carboxamide,
N-({4-[(2,5-dimethoxybenzene)sulfonyl]phenyl}methyl)thieno[2,3-c]pyridine-2-carboxamide,
N-[(4-{[4-(trifluoromethyl)benzene]sulfonyl}phenyl)methyl]furo[2,3-c]pyridine-2-carboxamide,
N-({4-[(3-chloro-2-methylbenzene)sulfonyl]phenyl}methyl)thieno[2,3-c]pyridine-2-carboxamide,
N-({4-[(3,5-dimethylbenzene)sulfonyl]phenyl}methyl)thieno[2,3-c]pyridine-2-carboxamide,
N-[(4-{[4-(trifluoromethyl)benzene]sulfonyl}phenyl)methyl]-1H-pyrrolo[3,2-c]pyridine-2-carboxamide,
N-[(4-{[3-chloro-4-(trifluoromethyl)benzene]sulfonyl}phenyl)methyl]furo[2,3-c]pyridine-2-carboxamide,
N-[(4-{[3-(dimethylsulfamoyl)benzene]sulfonyl}phenyl)methyl]furo[2,3-c]pyridine-2-carboxamide,
5-hydroxy-N-[(4-{[3-(morpholin-4-yl)benzene]sulfonyl}phenyl)methyl]-1H-indole-2-carboxamide,
N-({4-[(2-chlorobenzene)sulfonyl]phenyl}methyl)thieno[2,3-c]pyridine-2-carboxamide,
N-({4-[(3-tert-butylbenzene)sulfonyl]phenyl}methyl)imidazo[1,2-a]pyridine-6-carboxamide,
N-({4-[(3-chloro-5-methoxybenzene)sulfonyl]phenyl}methyl)thieno[2,3-c]pyridine-2-carboxamide,
N-[(4-{[3-(propan-2-yl)benzene]sulfonyl}phenyl)methyl]imidazo[1,2-a]pyrimidine-6-carboxamide,
N-({4-[(4-chloro-2-ethoxybenzene)sulfonyl]phenyl}methyl)imidazo[1,2-a]pyridine-6-carboxamide,
N-({4-[(3-methoxybenzene)sulfonyl]phenyl}methyl)thieno[2,3-c]pyridine-2-carboxamide,
N-({4-[(3-cyanobenzene)sulfonyl]phenyl}methyl)imidazo[1,2-a]pyrimidine-6-carboxamide,
N-({4-[(3-chloro-5-methylbenzene)sulfonyl]phenyl}methyl)imidazo[1,2-a]pyridine-6-carboxamide,
N-[(4-{[5-fluoro-2-(hydroxymethyl)benzene]sulfonyl}phenyl)methyl]-1H-pyrrolo[3,2-c]pyridine-2-carboxamide,
N-({4-[(3-chloro-2-methylbenzene)sulfonyl]phenyl}methyl)imidazo[1,2-a]pyridine-6-carboxamide,
N-({4-[(3,5-dichlorobenzene)sulfonyl]phenyl}methyl)thieno[2,3-c]pyridine-2-carboxamide,
N-({4-[(2-fluoro-4-methoxybenzene)sulfonyl]phenyl}methyl)-1H-pyrazolo[3,4-b]pyridine-5-carboxamide,
N-{[4-(benzenesulfonyl)phenyl]methyl}furo[2,3-c]pyridine-2-carboxamide,
N-[(4-{[3-(morpholin-4-yl)benzene]sulfonyl}phenyl)methyl]imidazo[1,2-a]pyridine-6-carboxamide,
N-({4-[(5-fluoro-2-methoxybenzene)sulfonyl]phenyl}methyl)-1H-pyrazolo[3,4-b]pyridine-5-carboxamide,
N-[(4-{[3-(methylcarbamoyl)benzene]sulfonyl}phenyl)methyl]imidazo[1,2-a]pyrimidine-6-carboxamide,
N-[(4-{[4-methoxy-2-(trifluoromethyl)benzene]sulfonyl}phenyl)methyl]furo[2,3-c]pyridine-2-carboxamide,
N-({4-[(4-cyclohexylbenzene)sulfonyl]phenyl}methyl)imidazo[1,2-a]pyrimidine-6-carboxamide,
N-({4-[(4-butoxybenzene)sulfonyl]phenyl}methyl)-1H-pyrrolo[3,2-c]pyridine-2-carboxamide,
N-({4-[(4-phenylbenzene)sulfonyl]phenyl}methyl)-1H-pyrrolo[3,2-c]pyridine-2-carboxamide,
N-[(4-{[3-(diethylcarbamoyl)-5-fluorobenzene]sulfonyl}phenyl)methyl]imidazo[1,2-a]pyrimidine-6-carboxamide,
N-[(4-{[3-fluoro-5-(2,2,2-trifluoroethoxy)benzene]sulfonyl}phenyl)methyl]furo[2,3-c]pyridine-2-carboxamide,
N-[(4-{[2-(2,2,2-trifluoroethoxy)-4-(trifluoromethyl)benzene]sulfonyl}phenyl)methyl]imidazo[1,2-a]pyridine-6-carboxamide,
N-[(4-{[3-chloro-5-(trifluoromethyl)benzene]sulfonyl}phenyl)methyl]-1H-pyrrolo[3,2-c]pyridine-2-carboxamide,
N-[(4-{[4-(4-ethoxyphenyl)benzene]sulfonyl}phenyl)methyl]-1H-pyrrolo[3,2-c]pyridine-2-carboxamide,
N-({4-[(3-chlorobenzene)sulfonyl]phenyl}methyl)-1H-pyrazolo[3,4-b]pyridine-5-carboxamide,
N-({4-[(5-chloro-2-hydroxybenzene)sulfonyl]phenyl}methyl)imidazo[1,2-a]pyridine-6-carboxamide,
N-({4-[(3-fluoro-4-methoxybenzene)sulfonyl]phenyl}methyl)-1H-pyrazolo[3,4-b]pyridine-5-carboxamide,
N-({4-[(3-fluoro-4-propoxybenzene)sulfonyl]phenyl}methyl)thieno[2,3-c]pyridine-2-carboxamide,
N-({4-[(4-methoxy-2-methylbenzene)sulfonyl]phenyl}methyl)-1H-pyrrolo[3,2-c]pyridine-2-carboxamide,
N-({4-[(2-phenoxybenzene)sulfonyl]phenyl}methyl)thieno[2,3-c]pyridine-2-carboxamide,
N-[(4-{[3-fluoro-5-(2,2,2-trifluoroethoxy)benzene]sulfonyl}phenyl)methyl]thieno[2,3-c]pyridine-2-carboxamide,
N-({4-[(3-ethoxybenzene)sulfonyl]phenyl}methyl)thieno[2,3-c]pyridine-2-carboxamide,
N-[(4-{[3-(1H-pyrazol-1-yl)benzene]sulfonyl}phenyl)methyl]thieno[2,3-c]pyridine-2-carboxamide,
N-{[4-({3-[(2-methylpropyl)carbamoyl]benzene}sulfonyl)phenyl]methyl}thieno[2,3-c]pyridine-2-carboxamide,
N-({4-[(4-methoxybenzene)sulfonyl]phenyl}methyl)furo[2,3-c]pyridine-2-carboxamide,
N-[(4-{[5-chloro-2-(propan-2-yloxy)benzene]sulfonyl}phenyl)methyl]imidazo[1,2-a]pyrimidine-6-carboxamide,
N-({4-[(2,4-dimethylbenzene)sulfonyl]phenyl}methyl)-1H-pyrazolo[3,4-b]pyridine-5-carboxamide,
N-[(4-{[3-(2-methylpropoxy)benzene]sulfonyl}phenyl)methyl]-1H-pyrrolo[3,2-c]pyridine-2-carboxamide,
N-({4-[(4-fluoro-2,5-dimethylbenzene)sulfonyl]phenyl}methyl)thieno[2,3-c]pyridine-2-carboxamide,
N-[(4-{[2-chloro-5-(trifluoromethoxy)benzene]sulfonyl}phenyl)methyl]-1H-pyrrolo[3,2-c]pyridine-2-carboxamide, N-({4-[(2-methoxybenzene)sulfonyl]phenyl}methyl)furo[2,3-c]pyridine-2-carboxamide,
N-[(4-{[3-(piperidin-1-yl)benzene]sulfonyl}phenyl)methyl]furo[2,3-c]pyridine-2-carboxamide,
N-({4-[(4-phenylbenzene)sulfonyl]phenyl}methyl)furo[2,3-c]pyridine-2-carboxamide,
N-({4-[(2-methoxybenzene)sulfonyl]phenyl}methyl)imidazo[1,2-a]pyrimidine-6-carboxamide,
N-({4-[(3-ethoxy-4-fluorobenzene)sulfonyl]phenyl}methyl)imidazo[1,2-a]pyrimidine-6-carboxamide,
N-({4-[(2-fluoro-4-methylbenzene)sulfonyl]phenyl}methyl)-1H-pyrrolo[3,2-c]pyridine-2-carboxamide,
N-({4-[(2-fluoro-3-methylbenzene)sulfonyl]phenyl}methyl)imidazo[1,2-a]pyrimidine-6-carboxamide,
N-({4-[(3-butoxybenzene)sulfonyl]phenyl}methyl)-1H-pyrrolo[3,2-c]pyridine-2-carboxamide,
N-({4-[(3,4-dichlorobenzene)sulfonyl]phenyl}methyl)-1H-pyrazolo[3,4-b]pyridine-5-carboxamide,
N-({4-[(2,4-dimethoxybenzene)sulfonyl]phenyl}methyl)thieno[2,3-c]pyridine-2-carboxamide,
N-[(4-{[2-fluoro-4-(trifluoromethyl)benzene]sulfonyl}phenyl)methyl]-1H-pyrrolo[3,2-c]pyridine-2-carboxamide,
N-[(4-{[2-(dimethylcarbamoyl)benzene]sulfonyl}phenyl)methyl]imidazo[1,2-a]pyridine-6-carboxamide,
N-({4-[(2-chloro-5-methoxybenzene)sulfonyl]phenyl}methyl)-1H-pyrazolo[3,4-b]pyridine-5-carboxamide,
N-({4-[(4-butoxy-3-fluorobenzene)sulfonyl]phenyl}methyl)thieno[2,3-c]pyridine-2-carboxamide,
N-({4-[(3-ethylbenzene)sulfonyl]phenyl}methyl)furo[2,3-c]pyridine-2-carboxamide,
N-[(4-{[3-fluoro-5-(2-methylpropoxy)benzene]sulfonyl}phenyl)methyl]furo[2,3-c]pyridine-2-carboxamide,
N-({4-[(3-chloro-4-methoxybenzene)sulfonyl]phenyl}methyl)thieno[2,3-c]pyridine-2-carboxamide,
N-({4-[(3-chloro-4-methoxybenzene)sulfonyl]phenyl}methyl)furo[2,3-c]pyridine-2-carboxamide,
N-[(4-{[2-(trifluoromethoxy)benzene]sulfonyl}phenyl)methyl]imidazo[1,2-a]pyrimidine-6-carboxamide,
N-({4-[(2-ethoxy-6-fluorobenzene)sulfonyl]phenyl}methyl)furo[2,3-c]pyridine-2-carboxamide,
N-({4-[(3,5-difluorobenzene)sulfonyl]phenyl}methyl)imidazo[1,2-a]pyridine-6-carboxamide,
N-[(4-{[4-fluoro-2-(propan-2-yloxy)benzene]sulfonyl}phenyl)methyl]imidazo[1,2-a]pyrimidine-6-carboxamide,
N-({4-[(2-phenoxybenzene)sulfonyl]phenyl}methyl)-1H-pyrrolo[3,2-c]pyridine-2-carboxamide,
N-[(4-{[3-chloro-5-(diethylcarbamoyl)benzene]sulfonyl}phenyl)methyl]furo[2,3-c]pyridine-2-carboxamide,
N-({4-[(2-fluoro-3-methylbenzene)sulfonyl]phenyl}methyl)furo[2,3-c]pyridine-2-carboxamide,
N-({4-[(3-fluoro-2-methoxybenzene)sulfonyl]phenyl}methyl)imidazo[1,2-a]pyridine-6-carboxamide,
N-[(4-{[3-(ethanesulfonyl)benzene]sulfonyl}phenyl)methyl]-1H-pyrrolo[3,2-c]pyridine-2-carboxamide,
N-[(4-{[4-(propan-2-yloxy)benzene]sulfonyl}phenyl)methyl]-1H-pyrazolo[3,4-b]pyridine-5-carboxamide,
N-({4-[(3-methoxybenzene)sulfonyl]phenyl}methyl)imidazo[1,2-a]pyrimidine-6-carboxamide,
N-({4-[(4-fluoro-3-methoxybenzene)sulfonyl]phenyl}methyl)thieno[2,3-c]pyridine-2-carboxamide,
N-[(4-{[5-fluoro-2-(hydroxymethyl)benzene]sulfonyl}phenyl)methyl]furo[2,3-c]pyridine-2-carboxamide,
N-({4-[(4-chloro-2-methylbenzene)sulfonyl]phenyl}methyl)furo[2,3-c]pyridine-2-carboxamide,
N-({4-[(2,6-dichloro-3-methylbenzene)sulfonyl]phenyl}methyl)thieno[2,3-c]pyridine-2-carboxamide,
N-({4-[(2,5-dimethoxybenzene)sulfonyl]phenyl}methyl)imidazo[1,2-a]pyrimidine-6-carboxamide,
N-({4-[(3-fluorobenzene)sulfonyl]phenyl}methyl)thieno[2,3-c]pyridine-2-carboxamide,
N-({4-[(4-fluoro-2-methoxybenzene)sulfonyl]phenyl}methyl)thieno[2,3-c]pyridine-2-carboxamide,
N-[(4-{[3-(2,2,2-trifluoroethoxy)benzene]sulfonyl}phenyl)methyl]furo[2,3-c]pyridine-2-carboxamide,
N-[(4-{[3-fluoro-4-(trifluoromethyl)benzene]sulfonyl}phenyl)methyl]-1H-pyrrolo[3,2-c]pyridine-2-carboxamide,
N-({4-[(2,4,6-trimethylbenzene)sulfonyl]phenyl}methyl)-1H-pyrrolo[3,2-c]pyridine-2-carboxamide,
N-({4-[(4-chloro-3-methoxybenzene)sulfonyl]phenyl}methyl)furo[2,3-c]pyridine-2-carboxamide,
N-({4-[(3-chloro-5-methylbenzene)sulfonyl]phenyl}methyl)thieno[2,3-c]pyridine-2-carboxamide,
N-[(4-{[3-(trifluoromethyl)benzene]sulfonyl}phenyl)methyl]-1H-pyrrolo[3,2-c]pyridine-2-carboxamide,
N-({4-[(2-cyanobenzene)sulfonyl]phenyl}methyl)thieno[2,3-c]pyridine-2-carboxamide,
N-[(4-{[2-fluoro-3-(propan-2-yloxy)benzene]sulfonyl}phenyl)methyl]imidazo[1,2-a]pyrimidine-6-carboxamide,
N-[(4-{[4-(difluoromethyl)-3-fluorobenzene]sulfonyl}phenyl)methyl]imidazo[1,2-a]pyrimidine-6-carboxamide,
N-{[4-(phenoxathiine-4-sulfonyl)phenyl]methyl}-1H-pyrazolo[3,4-b]pyridine-5-carboxamide,
N-[(4-{[2-(dimethylcarbamoyl)benzene]sulfonyl}phenyl)methyl]imidazo[1,2-a]pyrimidine-6-carboxamide,
N-({4-[(3-fluoro-5-methoxybenzene)sulfonyl]phenyl}methyl)furo[2,3-c]pyridine-2-carboxamide,
N-({4-[(4-methoxy-2-methylbenzene)sulfonyl]phenyl}methyl)furo[2,3-c]pyridine-2-carboxamide,
N-({4-[(2-methyl-4-propoxybenzene)sulfonyl]phenyl}methyl)thieno[2,3-c]pyridine-2-carboxamide,
N-({4-[(3-ethoxy-4-fluorobenzene)sulfonyl]phenyl}methyl)furo[2,3-c]pyridine-2-carboxamide,
N-{[4-(benzenesulfonyl)phenyl]methyl}-1H-imidazo[4,5-c]pyridine-2-carboxamide,
N-[(4-{[2,4-bis(trifluoromethyl)benzene]sulfonyl}phenyl)methyl]thieno[2,3-c]pyridine-2-carboxamide,
N-{[4-(6-methoxynaphthalene-2-sulfonyl)phenyl]methyl}thieno[2,3-c]pyridine-2-carboxamide,
N-({4-[(2-acetylbenzene)sulfonyl]phenyl}methyl)furo[2,3-c]pyridine-2-carboxamide,
N-({4-[(4-methanesulfonylbenzene)sulfonyl]phenyl}methyl)-1H-pyrazolo[3,4-b]pyridine-5-carboxamide, N-({4-[(3-fluoro-4-methoxybenzene)sulfonyl] phenyl}methyl)imidazo[1,2-a]pyrimidine-6-carboxamide,
N-[(4-{[3-fluoro-4-(trifluoromethoxy)benzene] sulfonyl}phenyl)methyl]-1H-pyrrolo[3,2-c]pyridine-2-carboxamide,
N-({4-[(2-ethoxy-4-fluorobenzene)sulfonyl] phenyl}methyl)-1H-pyrrolo[3,2-c]pyridine-2-carboxamide,
N-[(4-{[2-(trifluoromethoxy)benzene]sulfonyl}phenyl) methyl]thieno[2,3-c]pyridine-2-carboxamide,
N-({4-[(4-ethoxy-2-methylbenzene)sulfonyl] phenyl}methyl)imidazo[1,2-a]pyrimidine-6-carboxamide,
N-({4-[(6-chloro-2-fluoro-3-methylbenzene)sulfonyl] phenyl}methyl)furo[2,3-c]pyridine-2-carboxamide,
N-({4-[(5-chloro-2-methylbenzene)sulfonyl] phenyl}methyl)imidazo[1,2-a]pyridine-6-carboxamide,
N-({4-[(2,6-dimethoxy-4-methylbenzene)sulfonyl] phenyl}methyl)furo[2,3-c]pyridine-2-carboxamide,
N-({4-[(4-fluoro-3-methylbenzene)sulfonyl] phenyl}methyl)thieno[2,3-c]pyridine-2-carboxamide,
N-[(4-{[3-fluoro-5-(trifluoromethyl)benzene] sulfonyl}phenyl)methyl]thieno[2,3-c]pyridine-2-carboxamide,
N-[(4-{[4-(hydroxymethyl)benzene]sulfonyl}phenyl) methyl]thieno[2,3-c]pyridine-2-carboxamide,
N-({4-[(3-methylbenzene)sulfonyl]phenyl}methyl)-1H-pyrrolo[3,2-c]pyridine-2-carboxamide,
N-({4-[(3-fluoro-5-methylbenzene)sulfonyl] phenyl}methyl)imidazo[,2-a]pyridine-6-carboxamide,
N-({4-[(3,5-dimethoxybenzene)sulfonyl]phenyl}methyl) imidazo[1,2-a]pyrimidine-6-carboxamide,
N-[(4-{[3-(morpholin-4-yl)benzene]sulfonyl}phenyl) methyl]-1,3-benzothiazole-6-carboxamide,
N-({4-[(3-ethoxybenzene)sulfonyl]phenyl}methyl)-1H-pyrrolo[3,2-c]pyridine-2-carboxamide,
N-({4-[(3-chloro-5methoxybenzene)sulfonyl] phenyl}methyl)-1H-pyrrolo[3,2-c]pyridine-2-carboxamide,
N-({4-[(4-chloro-2-methylbenzene)sulfonyl] phenyl}methyl)-1H-pyrrolo[3,2-c]pyridine-2-carboxamide,
N-{[4-({4-[(pyrrolidin-1-yl)carbonyl]benzene}sulfonyl) phenyl]methyl}furo[2,3-c]pyridine-2-carboxamide,
N-[(4-{[3-(methoxymethyl)benzene]sulfonyl}phenyl) methyl]-1H-pyrrolo[3,2-c]pyridine-2-carboxamide,
N-[(4-{[3-(1H-pyrazol-1-yl)benzene]sulfonyl}phenyl) methyl]-1H-pyrrolo[3,2-c]pyridine-2-carboxamide,
N-({4-[(4-cyanobenzene)sulfonyl]phenyl}methyl)-1H-pyrrolo[3,2-c]pyridine-2-carboxamide,
N-{[4-(2,3-dihydro-1-benzofuran-7-sulfonyl)phenyl] methyl}-1H-pyrrolo[3,2-c]pyridine-2-carboxamide,
N-({4-[(2-cyanobenzene)sulfonyl]phenyl}methyl)-1H-pyrrolo[3,2-c]pyridine-2-carboxamide,
N-({4-[(4-fluoro-3-methylbenzene)sulfonyl] phenyl}methyl)imidazo[1,2-a]pyridine-6-carboxamide,
N-{[4-(benzenesulfonyl)phenyl]methyl}-1,6-naphthyridine-2-carboxamide,
N-({4-[(4-methoxy-3-methylbenzene)sulfonyl] phenyl}methyl)imidazo[1,2-a]pyridine-6-carboxamide,
N-({4-[(4-methanesulfonylbenzene)sulfonyl] phenyl}methyl)imidazo[1,2-a]pyridine-6-carboxamide,
N-({4-[(2-cyanobenzene)sulfonyl]phenyl}methyl)-1H-pyrazolo[3,4-b]pyridine-5-carboxamide,
N-({4-[(3-methoxy-4-methylbenzene)sulfonyl] phenyl}methyl)-1H-pyrazolo[3,4-b]pyridine-5-carboxamide,
N-[(4-{[3-fluoro-4-(1H-pyrazol-1-yl)benzene] sulfonyl}phenyl)methyl]imidazo[1,2-a]pyridine-6-carboxamide,
N-{[4-(2H-1,3-benzodioxole-5-sulfonyl)phenyl] methyl}imidazo[1,2-a]pyridine-6-carboxamide,
N-({4-[(2-chlorobenzene)sulfonyl]phenyl}methyl)-1H-pyrazolo[3,4-b]pyridine-5-carboxamide,
N-({4-[(4-fluoro-2,5-dimethylbenzene)sulfonyl] phenyl}methyl)-1H-pyrazolo[3,4-b]pyridine-5-carboxamide,
N-({4-[(2,5-dimethylbenzene)sulfonyl]phenyl}methyl)-1H-pyrazolo[3,4-b]pyridine-5-carboxamide,
N-({4-[(5-fluoro-2-methylbenzene)sulfonyl] phenyl}methyl)imidazo[1,2-a]pyridine-6-carboxamide,
N-[(4-{[2-(trifluoromethyl)benzene]sulfonyl}phenyl) methyl]imidazo[1,2-a]pyridine-6-carboxamide,
N-({4-[(2-acetylbenzene)sulfonyl]phenyl}methyl)-1H-pyrazolo[3,4-b]pyridine-5-carboxamide,
N-[(4-{[2-methyl-4-(trifluoromethyl)benzene] sulfonyl}phenyl)methyl]-1H-pyrazolo[3,4-b]pyridine-5-carboxamide,
N-({4-[(2-fluoro-6-methoxybenzene)sulfonyl] phenyl}methyl)imidazo[1,2-a]pyridine-6-carboxamide,
N-[(4-{[4-chloro-2-(trifluoromethyl)benzene] sulfonyl}phenyl)methyl]-1H-pyrazolo[3,4-b]pyridine-5-carboxamide,
N-({4-[(2,5-dimethoxybenzene)sulfonyl] phenyl}methyl)-1H-pyrazolo[3,4-b]pyridine-5-carboxamide,
N-({4-[(4-fluoro-2-methoxybenzene)sulfonyl] phenyl}methyl)-1H-pyrazolo[3,4-b]pyridine-5-carboxamide,
N-({4-[(2-ethoxybenzene)sulfonyl]phenyl}methyl)imidazo[1,2-a]pyridine-6-carboxamide,
N-[(4-{[3-(trifluoromethyl)benzene]sulfonyl}phenyl) methyl]imidazo[1,2-a]pyridine-6-carboxamide,
N-[(4-{8-oxatricyclo[7.4.0.0$^{2,7}$]trideca-1(13),2,4,6,9,11-hexaene-6-sulfonyl}phenyl)methyl]-1H-pyrazolo[3,4-b]pyridine-5-carboxamide,
N-({4-[(3-chloro-4-propoxybenzene)sulfonyl] phenyl}methyl)-1H-pyrazolo[3,4-b]pyridine-5-carboxamide,
N-[(4-{[4-methoxy-2-(trifluoromethyl)benzene] sulfonyl}phenyl)methyl]-1H-pyrazolo[3,4-b]pyridine-5-carboxamide,
N-({4-[(4-fluoro-3-methoxybenzene)sulfonyl] phenyl}methyl)-1H-pyrazolo[3,4-b]pyridine-5-carboxamide,
N-({4-[(4-methoxy-2-methylbenzene)sulfonyl] phenyl}methyl)-1H-pyrazolo[3,4-b]pyridine-5-carboxamide,
N-({4-[(3-ethylbenzene)sulfonyl]phenyl}methyl)imidazo [1,2-a]pyridine-6-carboxamide,
N-({4-[(4-ethylbenzene)sulfonyl]phenyl}methyl)imidazo [1,2-a]pyridine-6-carboxamide,
N-[(4-{[4-chloro-3-(trifluoromethyl)benzene] sulfonyl}phenyl)methyl]imidazo[1,2-a]pyridine-6-carboxamide, N-[(4-{[4-fluoro-2-(trifluoromethyl)benzene]
sulfonyl}phenyl)methyl]-1H-pyrazolo[3,4-b]pyridine-5-carboxamide,
N-[(4-{[3-(cyclopentylcarbamoyl)benzene]
sulfonyl}phenyl)methyl]-1H-pyrazolo[3,4-b]pyridine-5-carboxamide,
N-[(4-{[4-(trifluoromethyl)benzene]sulfonyl}phenyl)methyl]-1H-pyrazolo[3,4-b]pyridine-5-carboxamide,
N-[(4-{[2-(morpholin-4-ylmethyl)benzene]
sulfonyl}phenyl)methyl]imidazo[1,2-a]pyridine-6-carboxamide,
N-({4-[(2-ethylbenzene)sulfonyl]phenyl}methyl)-1H-pyrazolo[3,4-b]pyridine-5-carboxamide,
N-[(4-{[3-(propan-2-yl)benzene]sulfonyl}phenyl)methyl]imidazo[1,2-a]pyridine-6-carboxamide,
N-({4-[(5-tert-butyl-2-methoxybenzene)sulfonyl]
phenyl}methyl)imidazo[1,2-a]pyridine-6-carboxamide,
N-({4-[(4-methylbenzene)sulfonyl]phenyl}methyl)imidazo[1,2-a]pyridine-6-carboxamide,
N-({4-[(3,4-dimethoxybenzene)sulfonyl]phenyl}methyl)imidazo[1,2-a]pyridine-6-carboxamide,
N-({4-[(2-fluoro-4-methylbenzene)sulfonyl]
phenyl}methyl)imidazo[1,2-a]pyridine-6-carboxamide,
N-{[4-(phenoxathiine-4-sulfonyl)phenyl]
methyl}imidazo[1,2-a]pyridine-6-carboxamide,
N-({4-[(2-methylbenzene)sulfonyl]phenyl}methyl)imidazo[1,2-a]pyridine-6-carboxamide,
N-({4-[(2-phenoxybenzene)sulfonyl]phenyl}methyl)imidazo[1,2-a]pyridine-6-carboxamide,
N-[(4-{[4-(morpholin-4-yl)benzene]sulfonyl}phenyl)methyl]-1H-pyrazolo[3,4-b]pyridine-5-carboxamide,
N-({4-[(2-fluoro-3-methoxybenzene)sulfonyl]
phenyl}methyl)imidazo[1,2-a]pyridine-6-carboxamide,
N-({4-[(4-methoxy-2,5-dimethylbenzene)sulfonyl]
phenyl}methyl)-1H-pyrazolo[3,4-b]pyridine-5-carboxamide,
N-[(4-{[2-chloro-3-(trifluoromethyl)benzene]
sulfonyl}phenyl)methyl]-1H-pyrazolo[3,4-b]pyridine-5-carboxamide,
N-({4-[(3-ethoxy-4-fluorobenzene)sulfonyl]
phenyl}methyl)-1H-pyrazolo[3,4-b]pyridine-5-carboxamide,
N-({4-[(4,5-difluoro-2-methoxybenzene)sulfonyl]
phenyl}methyl)imidazo[1,2-a]pyridine-6-carboxamide,
N-({4-[(2,4-dimethoxybenzene)sulfonyl]phenyl}methyl)imidazo[1,2-a]pyridine-6-carboxamide,
N-({4-[(2,4-difluorobenzene)sulfonyl]phenyl}methyl)imidazo[1,2-a]pyridine-6-carboxamide,
N-[(4-{[5-fluoro-2-(hydroxymethyl)benzene]
sulfonyl}phenyl)methyl]-1H-pyrazolo[3,4-b]pyridine-5-carboxamide,
N-[(4-{[4-(ethylcarbamoyl)benzene]sulfonyl}phenyl)methyl]-1H-pyrazolo[3,4-b]pyridine-5-carboxamide,
N-({4-[(4-methoxy-3,5-dimethylbenzene)sulfonyl]
phenyl}methyl)-1H-pyrazolo[3,4-b]pyridine-5-carboxamide,
N-[(4-{[3-fluoro-5-(2-methylpropoxy)benzene]
sulfonyl}phenyl)methyl]-1H-pyrazolo[3,4-b]pyridine-5-carboxamide,
N-({4-[(3-propoxybenzene)sulfonyl]phenyl}methyl)-1H-pyrazolo[3,4-b]pyridine-5-carboxamide,
N-({4-[(2,4,5-trimethylbenzene)sulfonyl]
phenyl}methyl)-1H-pyrazolo[3,4-b]pyridine-5-carboxamide,
N-({4-[(2-chloro-4-methoxybenzene)sulfonyl]
phenyl}methyl)-1H-pyrazolo[3,4-b]pyridine-5-carboxamide,
N-({4-[(2,3,6-trimethoxybenzene)sulfonyl]
phenyl}methyl)-1H-pyrazolo[3,4-b]pyridine-5-carboxamide,
N-[(4-{[2-chloro-4-(trifluoromethyl)benzene]
sulfonyl}phenyl)methyl]-1H-pyrazolo[3,4-b]pyridine-5-carboxamide,
N-({4-[(3-fluoro-2-methylbenzene)sulfonyl]
phenyl}methyl)-1H-pyrazolo[3,4-b]pyridine-5-carboxamide,
N-({4-[(3-methylbenzene)sulfonyl]phenyl}methyl)imidazo[1,2-a]pyridine-6-carboxamide,
N-[(4-{[2-methoxy-4-(1H-pyrazol-1-yl)benzene]
sulfonyl}phenyl)methyl]imidazo[1,2-a]pyridine-6-carboxamide,
N-({4-[(5-acetyl-2-methoxybenzene)sulfonyl]
phenyl}methyl)imidazo[1,2-a]pyridine-6-carboxamide,
N-({4-[(4-chloro-2-methylbenzene)sulfonyl]
phenyl}methyl)-1H-pyrazolo[3,4-b]pyridine-5-carboxamide,
N-[(4-{[3-chloro-4-(trifluoromethyl)benzene]
sulfonyl}phenyl)methyl]-1H-pyrazolo[3,4-b]pyridine-5-carboxamide,
N-({4-[(2-phenoxybenzene)sulfonyl]phenyl}methyl)-1H-pyrazolo[3,4-b]pyridine-5-carboxamide,
N-({4-[(4-chlorobenzene)sulfonyl]phenyl}methyl)-1H-pyrazolo[3,4-b]pyridine-5-carboxamide,
N-[(4-{[4-fluoro-3-(2,2,2-trifluoroethoxy)benzene]
sulfonyl}phenyl)methyl]-1H-pyrazolo[3,4-b]pyridine-5-carboxamide,
N-[(4-{[4-fluoro-3-(trifluoromethyl)benzene]
sulfonyl}phenyl)methyl]-1H-pyrazolo[3,4-b]pyridine-5-carboxamide,
N-({4-[(2,4,5-trimethylbenzene)sulfonyl]phenyl}methyl)imidazo[1,2-a]pyridine-6-carboxamide,
N-({4-[(2,3-difluoro-6-methoxybenzene)sulfonyl]
phenyl}methyl)-1H-pyrrolo[3,2-c]pyridine-2-carboxamide,
N-[(4-{[3-(trifluoromethoxy)benzene]sulfonyl}phenyl)methyl]imidazo[1,2-a]pyridine-6-carboxamide,
N-({4-[(2-methoxybenzene)sulfonyl]phenyl}methyl)-1H-pyrazolo[3,4-b]pyridine-5-carboxamide,
N-({4-[(4-fluoro-2-methylbenzene)sulfonyl]
phenyl}methyl)-1H-pyrazolo[3,4-b]pyridine-5-carboxamide,
N-[(4-{[2,4-bis(trifluoromethyl)benzene]
sulfonyl}phenyl)methyl]-1H-pyrazolo[3,4-b]pyridine-5-carboxamide,
N-({4-[(3-fluoro-4-methoxybenzene)sulfonyl]
phenyl}methyl)imidazo[1,2-a]pyridine-6-carboxamide,
N-({4-[(2,3-dimethylbenzene)sulfonyl]phenyl}methyl)imidazo[1,2-a]pyridine-6-carboxamide,
N-({4-[(2-methoxy-5-methylbenzene)sulfonyl]
phenyl}methyl)-1H-pyrazolo[3,4-b]pyridine-5-carboxamide,
N-[(4-{[3-chloro-5-(trifluoromethyl)benzene]
sulfonyl}phenyl)methyl]-1H-pyrazolo[3,4-b]pyridine-5-carboxamide, N-({4-[(4-chloro-3-fluorobenzene)sulfonyl]phenyl}methyl)imidazo[1,2-a]pyridine-6-carboxamide,
N-({4-[(3,5-dimethylbenzene)sulfonyl]phenyl}methyl)imidazo[1,2-a]pyridine-6-carboxamide,
N-[(4-{[4-(2-methylpropoxy)benzene]sulfonyl}phenyl)methyl]-1H-pyrazolo[3,4-b]pyridine-5-carboxamide,
N-({4-[(3-chlorobenzene)sulfonyl]phenyl}methyl)imidazo[1,2-a]pyridine-6-carboxamide,
N-({4-[(2-fluoro-4-methoxybenzene)sulfonyl]phenyl}methyl)imidazo[1,2-a]pyridine-6-carboxamide,
N-({4-[(2,4-dichloro-3-methoxybenzene)sulfonyl]phenyl}methyl)-1H-pyrazolo[3,4-b]pyridine-5-carboxamide,
N-({4-[(2-methoxybenzene)sulfonyl]phenyl}methyl)imidazo[1,2-a]pyridine-6-carboxamide,
N-[(4-{[3-fluoro-4-(2,2,2-trifluoroethoxy)benzene]sulfonyl}phenyl)methyl]-1H-pyrazolo[3,4-b]pyridine-5-carboxamide,
N-({4-[(5-chloro-2-methylbenzene)sulfonyl]phenyl}methyl)-1H-pyrazolo[3,4-b]pyridine-5-carboxamide,
N-({4-[(2,3-dimethoxybenzene)sulfonyl]phenyl}methyl)imidazo[1,2-a]pyridine-6-carboxamide,
N-({4-[(4-methoxybenzene)sulfonyl]phenyl}methyl)imidazo[1,2-a]pyridine-6-carboxamide,
N-({4-[(2-butoxy-4-fluorobenzene)sulfonyl]phenyl}methyl)-1H-pyrazolo[3,4-b]pyridine-5-carboxamide,
N-({4-[(2,5-dimethoxybenzene)sulfonyl]phenyl}methyl)imidazo[1,2-a]pyridine-6-carboxamide,
N-({4-[(3,5-dichlorobenzene)sulfonyl]phenyl}methyl)imidazo[1,2-a]pyridine-6-carboxamide,
N-({4-[(3-methoxybenzene)sulfonyl]phenyl}methyl)imidazo[1,2-a]pyridine-6-carboxamide,
N-({4-[(3-chloro-2-methylbenzene)sulfonyl]phenyl}methyl)-1H-pyrazolo[3,4-b]pyridine-5-carboxamide,
N-[(4-{[3-fluoro-5-(trifluoromethyl)benzene]sulfonyl}phenyl)methyl]-1H-pyrazolo[3,4-b]pyridine-5-carboxamide,
N-({4-[(3-fluorobenzene)sulfonyl]phenyl}methyl)imidazo[1,2-a]pyridine-6-carboxamide,
N-[(4-{[4-(ethoxymethyl)benzene]sulfonyl}phenyl)methyl]-1H-pyrazolo[3,4-b]pyridine-5-carboxamide,
N-({4-[(2-chloro-4-methylbenzene)sulfonyl]phenyl}methyl)-1H-pyrazolo[3,4-b]pyridine-5-carboxamide,
N-({4-[(4-cyanobenzene)sulfonyl]phenyl}methyl)-1H-pyrazolo[3,4-b]pyridine-5-carboxamide,
N-({4-[(3-sulfamoylbenzene)sulfonyl]phenyl}methyl)-1H-pyrazolo[3,4-b]pyridine-5-carboxamide,
N-[(4-{[2-(benzyloxy)-5-(trifluoromethyl)benzene]sulfonyl}phenyl)methyl]-1H-pyrazolo[3,4-b]pyridine-5-carboxamide,
N-{[4-(naphthalene-1-sulfonyl)phenyl]methyl}-1H-pyrazolo[3,4-b]pyridine-5-carboxamide,
N-{[4-(benzenesulfonyl)phenyl]methyl}-1H-pyrrolo[3,2-c]pyridine-3-carboxamide,
N-({4-[(5-fluoro-2-methylbenzene)sulfonyl]phenyl}methyl)-1H-pyrazolo[3,4-b]pyridine-5-carboxamide,
N-{[4-(2H-1,3-benzodioxole-4-sulfonyl)phenyl]methyl}-1H-pyrazolo[3,4-b]pyridine-5-carboxamide,
N-({4-[(5-chloro-2-propoxybenzene)sulfonyl]phenyl}methyl)-1H-pyrazolo[3,4-b]pyridine-5-carboxamide,
N-({4-[(3-fluoro-2-methoxybenzene)sulfonyl]phenyl}methyl)-1H-pyrazolo[3,4-b]pyridine-5-carboxamide,
N-({4-[(2-fluoro-5-methoxybenzene)sulfonyl]phenyl}methyl)-1H-pyrazolo[3,4-b]pyridine-5-carboxamide,
N-({4-[(4-butoxy-2-methylbenzene)sulfonyl]phenyl}methyl)-1H-pyrazolo[3,4-b]pyridine-5-carboxamide,
N-[(4-{[4-(propan-2-yl)benzene]sulfonyl}phenyl)methyl]imidazo[1,2-a]pyridine-6-carboxamide,
N-({4-[(2,3-dimethoxybenzene)sulfonyl]phenyl}methyl)-1H-pyrazolo[3,4-b]pyridine-5-carboxamide,
N-({4-[(3-fluoro-4-propoxybenzene)sulfonyl]phenyl}methyl)-1H-pyrazolo[3,4-b]pyridine-5-carboxamide,
N-[(4-{[2-(methylsulfamoyl)benzene]sulfonyl}phenyl)methyl]-1H-pyrazolo[3,4-b]pyridine-5-carboxamide,
N-[(4-{[2-methoxy-5-(propan-2-yl)benzene]sulfonyl}phenyl)methyl]-1H-pyrazolo[3,4-b]pyridine-5-carboxamide,
N-[(4-{[2-methyl-4-(1H-pyrazol-1-yl)benzene]sulfonyl}phenyl)methyl]imidazo[1,2-a]pyridine-6-carboxamide,
N-[(4-{[2-fluoro-4-(1H-pyrazol-1-yl)benzene]sulfonyl}phenyl)methyl]imidazo[1,2-a]pyridine-6-carboxamide,
N-({4-[(2-methylbenzene)sulfonyl]phenyl}methyl)-1H-pyrazolo[3,4-b]pyridine-5-carboxamide,
N-({4-[(6-chloro-2-fluoro-3-methylbenzene)sulfonyl]phenyl}methyl)-1H-pyrazol[3,4-b]pyridine-5-carboxamide,
N-{[4-({4-fluoro-3-[(propan-2-yl)carbamoyl]benzene}sulfonyl)phenyl]methyl}-1H-pyrazolo[3,4-b]pyridine-5-carboxamide,
N-({4-[(4-butylbenzene)sulfonyl]phenyl}methyl)-1H-pyrazolo[3,4-b]pyridine-5-carboxamide,
N-({4-[(2-ethylbenzene)sulfonyl]phenyl}methyl)imidazo[1,2-a]pyridine-6-carboxamide,
N-({4-[(2,4-dimethylbenzene)sulfonyl]phenyl}methyl)imidazo[1,2-a]pyridine-6-carboxamide,
N-[(4-{[3-(methoxymethyl)benzene]sulfonyl}phenyl)methyl]-1H-pyrazolo[3,4-b]pyridine-5-carboxamide,
N-({4-[(2,5-dimethylbenzene)sulfonyl]phenyl}methyl)imidazo[1,2-a]pyridine-6-carboxamide,
N-[(4-{[5-chloro-2-(propan-2-yloxy)benzene]sulfonyl}phenyl)methyl]-1H-pyrazolo[3,4-b]pyridine-5-carboxamide,
N-({4-[(2-butoxy-5-chlorobenzene)sulfonyl]phenyl}methyl)-1H-pyrazolo[3,4-b]pyridine-5-carboxamide,
N-({4-[(4-chloro-2-methoxybenzene)sulfonyl]phenyl}methyl)imidazo[1,2-a]pyridine-6-carboxamide,
N-({4-[(3-butoxybenzene)sulfonyl]phenyl}methyl)-1H-pyrazolo[3,4-b]pyridine-5-carboxamide,
N-({4-[(3-acetylbenzene)sulfonyl]phenyl}methyl)imidazo[1,2-a]pyridine-6-carboxamide,
N-({4-[(4-butoxybenzene)sulfonyl]phenyl}methyl)-1H-pyrazolo[3,4-b]pyridine-5-carboxamide,
N-({4-[(2,6-dimethylbenzene)sulfonyl]phenyl}methyl)-1H-pyrazolo[3,4-b]pyridine-5-carboxamide, N-({4-[(2-chloro-6-methoxybenzene)sulfonyl]phenyl}methyl)imidazo[1,2-a]pyridine-6-carboxamide,
N-({4-[(4-fluoro-2-methoxybenzene)sulfonyl]phenyl}methyl)imidazo[1,2-a]pyridine-6-carboxamide,
N-[(4-{[3-fluoro-5-(2,2,2-trifluoroethoxy)benzene]sulfonyl}phenyl)methyl]-1H-pyrazolo[3,4-b]pyridine-5-carboxamide,
N-({4-[(2-methoxy-5-methylbenzene)sulfonyl]phenyl}methyl)imidazo[1,2-a]pyridine-6-carboxamide,
N-({4-[(3-fluoro-4-methylbenzene)sulfonyl]phenyl}methyl)imidazo[1,2-a]pyridine-6-carboxamide,
N-({4-[(3,4-dimethylbenzene)sulfonyl]phenyl}methyl)imidazo[1,2-a]pyridine-6-carboxamide,
N-[(4-{[2-methoxy-4-(trifluoromethyl)benzene]sulfonyl}phenyl)methyl]imidazo[1,2-a]pyridine-6-carboxamide,
N-({4-[(2-chlorobenzene)sulfonyl]phenyl}methyl)imidazo[1,2-a]pyridine-6-carboxamide,
N-({4-[(3-cyanobenzene)sulfonyl]phenyl}methyl)-1H-pyrazolo[3,4-b]pyridine-5-carboxamide,
N-({4-[(2,4,6-trimethylbenzene)sulfonyl]phenyl}methyl)-1H-pyrazolo[3,4-b]pyridine-5-carboxamide,
N-[(4-{[3-fluoro-4-(trifluoromethoxy)benzene]sulfonyl}phenyl)methyl]-1H-pyrazolo[3,4-b]pyridine-5-carboxamide,
N-({4-[(5-fluoro-2-methoxybenzene)sulfonyl]phenyl}methyl)imidazo[1,2-a]pyridine-6-carboxamide,
N-(4-(3-(trifluoromethoxy)phenylsulfonyl)benzyl)-1H-pyrazolo[3,4-b]pyridine-5-carboxamide,
N-(4-(3-(trifluoromethyl)phenylsulfonyl)benzyl)-1H-pyrazolo[3,4-b]pyridine-5-carboxamide,
N-(4-(3,5-difluorophenylsulfonyl)benzyl)-1,8a-dihydroimidazo[1,2-a]pyridine-6-carboxamide,
7,8-Dihydro-5H-pyrido[3,4-b]pyrazine-6-carboxylic acid 4-benzenesulfonyl-benzylamide,
3,4-Dihydro-1H-[2,6]naphthyridine-2-carboxylic acid 4-benzenesulfonyl-benzylamide,
3,4-Dihydro-1H-[2,7]naphthyridine-2-carboxylic acid 4-benzenesulfonyl-benzylamide,
6,7-Dihydro-4H-isoxazolo[4,3-c]pyridine-5-carboxylic acid 4-benzenesulfonyl-benzylamide,
5,8-Dihydro-6H-[1,7]naphthyridine-7-carboxylic acid 4-benzenesulfonyl-benzylamide,
6,7-Dihydro-4H-isoxazolo[4,5-c]pyridine-5-carboxylic acid 4-benzenesulfonyl-benzylamide,
1,3-Dihydro-pyrrolo[3,4-c]pyridine-2-carboxylic acid 4-benzenesulfonyl-benzylamide,
Imidazo[1,2-a]pyrazine-6-carboxylic acid 4-benzenesulfonyl-benzylamide,
Imidazo[1,5-a]pyridine-6-carboxylic acid 4-benzenesulfonyl-benzylamide,
1H-Pyrazolo[3,4-c]pyridine-5-carboxylic acid 4-benzenesulfonyl-benzylamide,
Imidazo[1,2-a]pyridine-7-carboxylic acid 4-(3,5-difluoro-benzenesulfonyl)-benzylamide,
1H-Pyrazolo[4,3-b]pyridine-5-carboxylic acid 4-benzenesulfonyl-benzylamide,
Furo[3,2-b]pyridine-2-carboxylic acid 4-benzenesulfonyl-benzylamide,
N-{[4-(benzenesulfonyl)phenyl]methyl}thieno[3,2-b]pyridine-2-carboxamide,
N-{[4-(benzenesulfonyl)phenyl]methyl}imidazo[1,5-a]pyridine-6-carboxamide,
N-{[4-(benzenesulfonyl)phenyl]methyl}imidazo[1,2-a]pyrazine-6-carboxamide,
N-{[4-(benzenesulfonyl)phenyl]methyl}furo[3,2-b]pyridine-2-carboxamide,
N-{[4-(benzenesulfonyl)phenyl]methyl}-5,6,7,8-tetrahydro-1,6-naphthyridine-6-carboxamide,
N-{[4-(benzenesulfonyl)phenyl]methyl}-5H,6H,7H-pyrrolo[3,4-b]pyridine-6-carboxamide,
N-{[4-(benzenesulfonyl)phenyl]methyl}-1H,4H,5H,6H,7H-pyrazolo[4,3-c]pyridine-5-carboxamide,
N-{[4-(benzenesulfonyl)phenyl]methyl}-5H,6H,7H,8H-pyrido[4,3-d]pyrimidine-6-carboxamide,
N-{[4-(benzenesulfonyl)phenyl]methyl}-1H,4H,5H,6H,7H-imidazo[4,5-c]pyridine-5-carboxamide; and
N-{[4-(benzenesulfonyl)phenyl]methyl}-4H,5H,6H,7H-[1,2]oxazolo[4,3-c]pyridine-5-carboxamide;
or a pharmaceutically acceptable salt thereof.

14. A pharmaceutical composition comprising a compound of claim 1 and a pharmaceutically acceptable carrier.

15. A compound of formula IIB:

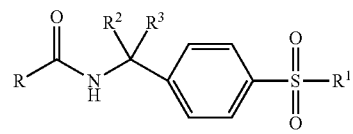

(IIB)

or pharmaceutically acceptable salt thereof
wherein:
R is 9-to 10-membered bicyclic heteroaryl groups containing 1, 2, 3, or 4 heteroatoms independently selected from N, S, and O, wherein said heteroaryl may be substituted by one or more substituents selected from the group consisting of amino, oxo, and halo; and wherein said heteroaryl can comprise one or more N-oxide(s) formed with a N atom member of said heteroaryl;
$R^1$ is aryl,
wherein:
said aryl is unsubstituted or substituted with 1, 2, 3, 4, or 5 substituents which can be the same or different and are independently selected from the group consisting of:
halo, hydroxy, hydroxyalkyl, cyano, alkyl, alkynyl, alkynylalkoxy, alkoxyalkyl, alkoxy, haloalkyl, haloalkoxy, —C(O)NH(alkyl), —C(O)NH(cycloalkyl), —C(O)N(alkyl)$_2$, arylalkoxy-, aryloxy-, cycloalkyl, heterocycloalkyl, aryl, (heterocycloalkyl)alkyl-, (heterocycloalkyl)alkoxy-, —C(O)heterocycloalkyl, heteroaryl, (heteroaryl)alkyl-, —S(O)$_2$-alkyl, —S-alkyl, —C(O)alkyl, —S(O)$_2$NH$_2$, —S(O$_2$)NH(alkyl), —S(O)$_2$N(alkyl)$_2$, and —N(H)(SO$_2$)(alkyl), wherein each of said cycloalkyl, heterocycloalkyl, aryl, or heteroaryl may be substituted by one or more halo, cyano, alkyl, and alkoxy; and
said aryl may optionally additionally be fused with independently selected aryl, heterocycloalkyl or cycloalkyl to form a bicyclic or tricyclic group that may be substituted by one or more halo, cyano, alkyl, and alkoxy;

$R^2$ and $R^3$ can be independently selected from the group consisting of H and deuterium;

$R^5$ is H, alkyl, or arylalkyl;

$R^a$ and $R^b$ are independently selected from the group consisting of H, alkyl, alkoxy, alkoxyalkyl, and haloalkyl;

m is 0, 1, 2, 3, 4, 5, or 6; and z is 0, 1, or 2.

16. The compound of claim 15, wherein $R^1$ is aryl, wherein said aryl is unsubstituted or substituted with 1, 2, 3, 4, or 5 substituents which can be the same or different and are independently selected from the group consisting of: halo, haloalkyl, and haloalkoxy.

17. The compound of claim 16, wherein haloalkyl is —$CH_zF_{3-z}$ or —$CH_2CH_zF_{3-z}$, and z is 0, 1 or 2.

18. The compound of claim 16, wherein haloalkoxy is —$OCH_zF_{3-z}$, and z is 0, 1 or 2.

19. The compound of claim 16, wherein halo is F.

* * * * *

UNITED STATES PATENT AND TRADEMARK OFFICE
CERTIFICATE OF CORRECTION

PATENT NO. : 10,272,072 B2
APPLICATION NO. : 15/352184
DATED : April 30, 2019
INVENTOR(S) : Kenneth W. Bair et al.

Page 1 of 1

It is certified that error appears in the above-identified patent and that said Letters Patent is hereby corrected as shown below:

In the Claims

In Claim 13, Column 908, beginning at Line 3 and ending at Line 4, please delete:
"N-{[4-(2-methylpyridine-3-sulfonyl)phenyl]methyl}imidazo[1,2-a]pyrimidine-6-carboxamide,"

In Claim 13, Column 933, beginning at Line 39 and ending at Line 41, please delete:
"N-({4-[(3-chloro-5methoxybenzene)sulfonyl]phenyl}methyl)-1H-pyrrolo[3,2-c]pyridine-2-carboxamide,"
And insert:
--N-({4-[(3-chloro-5-methoxybenzene)sulfonyl]phenyl}methyl)-1H-pyrrolo[3,2-c]pyridine-2-carboxamide,--

Signed and Sealed this
Tenth Day of September, 2019

Andrei Iancu
*Director of the United States Patent and Trademark Office*